(12) United States Patent
Pham et al.

(10) Patent No.: US 11,028,058 B2
(45) Date of Patent: Jun. 8, 2021

(54) HETEROCYCLIC COMPOUNDS AS ADENOSINE ANTAGONISTS

(71) Applicant: NUVATION BIO INC., New York, NY (US)

(72) Inventors: Son Minh Pham, San Francisco, CA (US); Jiyun Chen, Moraga, CA (US); Amantullah Ansari, Noida (IN); Pradeep S. Jadhavar, Noida (IN); Varshavekumar S. Patil, Greater Noida (IN); Farha Khan, Greater Noida (IN); Sreekanth A. Ramachandran, New Delhi (IN); Anil Kumar Agarwal, Greater Noida (IN); Sarvajit Chakravarty, Edmond, OK (US)

(73) Assignee: NUVATION BIO INC., New York, NY (US)

( * ) Notice: Subject to any disclaimer, the term of this patent is extended or adjusted under 35 U.S.C. 154(b) by 0 days.

(21) Appl. No.: 16/039,307

(22) Filed: Jul. 18, 2018

(65) Prior Publication Data

US 2019/0023666 A1  Jan. 24, 2019

Related U.S. Application Data

(60) Provisional application No. 62/534,176, filed on Jul. 18, 2017.

(51) Int. Cl.

| | | |
|---|---|---|
| *C07D 241/20* | (2006.01) |
| *C07D 403/04* | (2006.01) |
| *C07D 407/04* | (2006.01) |
| *C07D 401/04* | (2006.01) |
| *C07D 413/04* | (2006.01) |
| *C07D 405/14* | (2006.01) |
| *C07D 409/14* | (2006.01) |
| *C07D 413/14* | (2006.01) |
| *C07D 417/04* | (2006.01) |
| *C07D 417/14* | (2006.01) |
| *C07D 403/14* | (2006.01) |
| *C07D 401/14* | (2006.01) |
| *A61P 35/00* | (2006.01) |

(52) U.S. Cl.
CPC ............ *C07D 241/20* (2013.01); *A61P 35/00* (2018.01); *C07D 401/04* (2013.01); *C07D 401/14* (2013.01); *C07D 403/04* (2013.01); *C07D 403/14* (2013.01); *C07D 405/14* (2013.01); *C07D 407/04* (2013.01); *C07D 409/14* (2013.01); *C07D 413/04* (2013.01); *C07D 413/14* (2013.01); *C07D 417/04* (2013.01); *C07D 417/14* (2013.01)

(58) Field of Classification Search
CPC .. C07D 241/20; C07D 403/04; C07D 407/04; C07D 401/04; C07D 413/04; C07D 405/14; C07D 409/14; C07D 413/14; C07D 417/04; C07D 417/14; C07D 403/14; C07D 401/14
See application file for complete search history.

(56) References Cited

U.S. PATENT DOCUMENTS

| | | | |
|---|---|---|---|
| 6,992,087 B2 | 1/2006 | Verhoest |
| 7,407,961 B2 | 8/2008 | Yonishi |
| 7,728,141 B2 | 6/2010 | Debenham |
| 7,790,728 B2 | 9/2010 | Vidal |
| 8,754,085 B2 | 6/2014 | Charlton |
| 9,132,127 B2 | 9/2015 | Charlton |
| 10,112,923 B2 | 10/2018 | Congreve |
| RE47,351 E | 4/2019 | Zablocki |
| 10,253,044 B2 | 4/2019 | Wang |
| 10,292,968 B2 | 5/2019 | Brown |
| 10,307,407 B2 | 6/2019 | Wang |
| 10,328,074 B2 | 6/2019 | Engelhardt |
| 10,336,697 B2 | 7/2019 | Ujjinamatada |
| 10,336,722 B2 | 7/2019 | Bair |
| 10,363,257 B2 | 7/2019 | Quinn |
| 10,370,356 B2 | 8/2019 | Atkinson |
| 10,370,374 B2 | 8/2019 | Ibrahim |
| 10,377,769 B2 | 8/2019 | Bair |
| 10,391,175 B2 | 8/2019 | Wang |
| 10,399,962 B2 | 9/2019 | Beatty |
| 10,472,347 B2 | 11/2019 | Kuang |
| 2006/0293339 A1 | 12/2006 | Chakravarty |
| 2007/0072874 A1 | 3/2007 | Cui |
| 2009/0247567 A1 | 10/2009 | Do |
| 2011/0288090 A1 | 11/2011 | Armstrong |

(Continued)

FOREIGN PATENT DOCUMENTS

| | | | |
|---|---|---|---|
| AU | 2019205984 A1 | | 8/2019 |
| CN | 104341386 A | * | 2/2015 |

(Continued)

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface (Year: 2005).*
Ex parte Cao, Decision rendered by the Board of Patent Appeals and Interferences in U.S. Appl. No. 10/696,862 on Sep. 21, 2011 (Year: 2011).*
Allard, B. et al. (2013; e-pub. Aug. 27, 2013). "Targeting CD73 Enhances the Antitumor Activity of Anti-PD-1and Anti-CTLA-4 mAbs," Clinical Cancer Research 19(20):1-10.
Allard, B. et al. (2016). "Immunosuppressive Activities of Adenosine in Cancer," Current Opinion in Pharmacology 29:7-16.
Allard, D. et al. (Apr. 2017; e-published Feb. 8, 2017). "Targeting A2 Adenosine Receptors in Cancer," Immunology and Cell Biology 95(4):333-339; 34 pages.

(Continued)

*Primary Examiner* — Matthew P Coughlin
(74) *Attorney, Agent, or Firm* — Morris & Foerster LLP

(57) ABSTRACT

Aminopyrazine compounds as modulators of an adenosine receptor are provided. The compounds may find use as therapeutic agents for the treatment of diseases mediated through a G-protein-coupled receptor signaling pathway and may find particular use in oncology.

52 Claims, 2 Drawing Sheets

(56) References Cited

U.S. PATENT DOCUMENTS

| | | |
|---|---|---|
| 2013/0203774 A1 | 8/2013 | Jensen |
| 2014/0174537 A1* | 6/2014 | Fadhel ............... C07D 471/16 136/263 |
| 2014/0243346 A1 | 8/2014 | Charlton |
| 2015/0094312 A1 | 4/2015 | Adcock |
| 2016/0130253 A1 | 5/2016 | Arancio |
| 2016/0311784 A1 | 10/2016 | Leach |
| 2019/0023702 A1 | 1/2019 | Pham |
| 2019/0135784 A1 | 5/2019 | Strum |
| 2019/0135811 A1 | 5/2019 | Strum |
| 2019/0135820 A1 | 5/2019 | Smith |
| 2019/0248795 A1 | 8/2019 | Burkamp |
| 2019/0276473 A1 | 9/2019 | Crosignani |
| 2019/0292188 A1 | 9/2019 | Wang |
| 2019/0337957 A1 | 11/2019 | Wang |
| 2020/0231570 A1 | 7/2020 | Pham |
| 2020/0231589 A1 | 7/2020 | Pham |
| 2020/0330458 A1 | 10/2020 | Qi et al. |
| 2020/0331918 A1 | 10/2020 | Zeng et al. |

FOREIGN PATENT DOCUMENTS

| | | | |
|---|---|---|---|
| CN | 104341386 A | 2/2015 | |
| CN | 107221611 A | 9/2017 | |
| EP | 3230277 B1 | 9/2019 | |
| WO | WO-03030909 A1 * | 4/2003 | ........... C07D 231/12 |
| WO | WO2005040151 A1 | 5/2005 | |
| WO | WO2007017096 A1 | 2/2007 | |
| WO | WO2011095625 A1 | 8/2011 | |
| WO | WO2012168358 A1 | 12/2012 | |
| WO | WO2014145485 A2 | 9/2014 | |
| WO | WO2014145485 A3 | 11/2014 | |
| WO | WO2015017335 A1 | 2/2015 | |
| WO | WO2016081290 A1 | 5/2016 | |
| WO | WO2017025918 A1 | 2/2017 | |
| WO | WO2017112917 A1 | 6/2017 | |
| WO | WO2018081863 A1 | 5/2018 | |
| WO | WO2018178338 A1 | 10/2018 | |
| WO | WO2019002606 A1 | 1/2019 | |
| WO | WO2019090347 A1 | 5/2019 | |
| WO | WO2019096322 A1 | 5/2019 | |
| WO | WO2019118313 A1 | 6/2019 | |
| WO | WO2019120234 A2 | 6/2019 | |
| WO | WO2019134539 A1 | 7/2019 | |
| WO | WO2019141131 A1 | 7/2019 | |
| WO | WO2019148161 A1 | 8/2019 | |
| WO | WO2019154294 A1 | 8/2019 | |
| WO | WO2019158070 A1 | 8/2019 | |
| WO | WO2019160829 A1 | 8/2019 | |
| WO | WO2019165204 A1 | 8/2019 | |
| WO | WO2019169065 A2 | 9/2019 | |
| WO | WO2019173082 A1 | 9/2019 | |

OTHER PUBLICATIONS

Allard, D. et al. (Feb. 2016; e-pub. Jan. 25, 2016). "CD73-Adenosine: A Next-Generation Target in Immuno-Oncology," Immunotherapy 8(2):143-163, 19 pages.
Allard, D. et al. (Jan. 2019; e-pub. May 24, 2018). "Targeting the CD73-Adenosine Axis in Immuno-Oncology," Immunology Letters 205:31-39.
Arab, S. et al. (Mar. 2017). "Increased Efficacy of a Dendritic Cell-based Therapeutic Cancer Vaccine with Adenosine Receptor Antagonist and CD73 Inhibitor," Tumor Biology, pp. 1-8.
Azambuja, J.H. et al. (May 2019; e-pub. Aug. 16, 2018). "CD73 Downregulation Decreases In Vitro and In Vivo Glioblastoma Growth," Molecular Neurobiology 56(5):3260-3279, 20 pages.
Badawneh, M. et al. (Sep. 2003). "Synthesis of 3- or 4-Phenyl-1,8-Naphthyridine Derivatives and Evaluation of Antimycobacterial and Antimicrobial Activity," II Farmaco 58(9):859-866.
Banuelos, J. et al. (Feb. 18-22, 2019). "Targeting Innate Immune Cells for the Treatment of Cancer," #1008, Poster presented at Keystone Conference, Uncovering Mechanisms of Immune-Based Therapy in Cancer and Autoimmunity, Breckenridge, CO, 1 page.
Barbosa, R.S.S. et al. (2019). "Sequential Combination of Bortezomib and WEE1 Inhibitor, MK-1775, Induced Apoptosis in Multiple Myeloma Cell Lines," Biochemical and Biophysical Research Communication pp. 1-8.
Bastid, J. et al. (Mar. 3, 2015, e-pub. Nov. 17, 2014). "Inhibition of CD39 Enzymatic Function at the Surface of Tumor Cells Alleviates Their Immunosuppressive Activity," Cancer Immunology Research 3(3):254-265.
Beavis, P.A. et al. (Mar. 2017). "Targeting the Adenosine 2A Receptor Enhances Chimeric Antigen Receptor T Cell Efficacy," The Journal of Clinical Investigation 127(3):929-941.
Beavis, P.A. et al. (May 2015; e-pub. Feb. 11, 2015). "Adenosine Receptor 2A Blockade Increases the Efficacy of Anti-PD-1 through Enhanced Antitumor T-cell Responses," Cancer Immunology Research 3(5):506-517.
Beavis, P.A. et al. (Nov. 2015). "CD73: A Potential Biomarker for Anti-PD-1 Therapy," OncoImmunology 4(11): e1046675, 3 pages.
Beavis, P.V. et al. (Sep. 3, 2013). "Blockade of A2A Receptors Potently Suppresses the Metabolism of CD73+ Tumors," Proc. Natl. Acad. Sci. 110(36):14711-14716.
Becker, A. et al. (2018). "CD73 Inhibitors (CD73i) Reverse the AMP/Adenosine-Mediated Impairment of Immune Effector Cell Activation by Immune Checkpoint Inhibitors (ICI)," Abstract No. 3501, Poster present at Annual Meeting of the American Association of Cancer Research, Chicago, IL,1 page.
Bendell, J. et al. (Mar. 29-Apr. 4, 2019). "Evidence of Immune Activation in the First-in-Human Phase Ia Dose Escalation Study of the Adenosine 2a Receptor Antagonist, AZD4635, in Patients with Advanced Solid Tumors," Poster presented at the American Association for Cancer Research Annual Meeting, Atlanta, GA, 1 page.
Blay, J. et al. (Jul. 1, 1997). "The Extracellular Fluid of Solid Carcinomas Contains Immunosuppressive Concentrations of Adenosine," Cancer Research 57(13):2602-2605.
Borodovsky, A. et al. (Apr. 17, 2018). "Inhibition of A2AR by AZD4635 Induces Anti-tumor Immunity Alone and in Combination with Anti-PD-L1 in Preclinical Models," Poster Presented at the AACR Annual Meeting, Chicago, IL, 1 page.
Borodovsky, A. et al. (Apr. 5, 2017). "Preclinical Pharmacodynamics and Antitumor Activity of AZD4635, a Novel Adenosine 2A Receptor Inhibitor that Reverses Adenosine Mediated T Cell Suppression," Poster Presented at the AACR Annual Meeting, Wahington, D.C., 1 page.
Borodovsky, A. et al. (Apr. 5, 2017). "Preclinical Pharmacodynamics and Antitumor Activity of AZD4635, A Novel Adenosine 2A Receptor Inhibitor That Reverses Adenosine Mediated T Cell Suppression," AACR 2017 Annual Meeting, Washington, D.C, Poster 5580, 1 page.
Burkholder, B. et al. (2014; e-pub. Jan. 17, 2014). "Tumor-induced Perturbations of Cytokines and Immune Cell Networks," Biochimica Biophysica Acta 1845:182-201.
Cekic, C. et al. (2011). Adenosine A2B Receptor Blockade Slows Growth of Bladder and Breast Tumors, J. Immunol. 188(1):198-205.
Cekic, C. et al. (Mar. 2016). "Purinergic Regulation of the Immune System," Nature Reviews 16:177-192.
Chen, J.-F. et al. (Apr. 2013). "Adenosine Receptors as Drug Targets—What are the Challenges?," Nature Reviews 12:265-286.
Chen, X.-W. (Nov. 6, 2017; e-pub. Sep. 19, 2017). "Hydrogen-Transfer-Mediated α-Functionalization of 1,8-Naphthyridines by a Strategy Overcoming the Over-Hydrogenation Barrier," Anger Chem Int Ed. 56 (45):14232-14236.
Congreve, M. et al. (2012). "Discovery of 1,2,4-Triazine Derivatives as Adenosine A2A Antagonists using Structure Based Drug Design," Journal of Medicinal Chemistry 55:1898-1903, (with Supplementary material, 18 pages).
Congreve, M. et al. (Nov. 2018; e-pub. Oct. 18, 2018). "Targeting Adenosine A2A Receptor Antagonism for Treatment of Cancer," Expert Opinion on Drug Discovery 13(11):997-1003, 8 pages.
Corvus Pharmaceuticals. (Oct. 2, 2018). Corporate Presentation at Cantor Global Healthcare Conference, 25 pages.

(56) References Cited

OTHER PUBLICATIONS

Cretella, D. et al. (2019, e-pub. Sep. 10, 2019). "Pre-Treatment With the CDK4/6 Inhibitor Palbociclib Improves the Efficacy of Paclitaxel in TNBC Cells," Scientific Reports 9(13014)1-11.

Dastjerdi, N. eta l. (2016). "Adenosine A1 Receptor Modifies PTE Expression and Apoptosis in Breast Cancer Cell Line Mcf-7," Bratisl. Med. J. 117(4):242-246.

De Lera Ruiz, M. et al. (May 8, 2014; e-pub. Nov. 15, 2013). "Adenosine A2A Receptor as a Drug Discovery Target," J. Med. Chem. 57(9):3623-3650, 28 pages.

De Mendonca, A. et al. (2000). "Adenosine: Does it have a Neuroprotective Role After All?," Brain Research Reviews 33:258-274.

Debenham, J.S. et al. (Feb. 1, 2006, e-pub. Nov. 2, 2005). "Synthesis of Functionalized 1,8-Naphthyridinones and their Evaluation as Novel, Orally Active CB1 Receptor Inverse Agonists," Bioorg & Med Chem Lett 16(3):681-685.

Di Sante, G. et al. (2019). "Recent Advances With Cyclin-Dependent Kinase Inhibitors: Therapeutic Agents for Breast Cancer and Their Role in Immuno-Oncology," Expert Review of Anticancer Therapy 19(7):569-587.

Dosa, P.I. et al. (Feb. 11, 2016; e-pub. Sep. 21, 2015). "Tactical Approaches to Interconverting GPCR Agonists and Antagonists," Journal of Medicinal Chemistry 59(3):810-840, 31 pages.

Draper-Joyce, C.J. et al. (2018). "Structure of the Adenosine-bound Human Adenosine A1 Receptor-Gi Complex," Nature 558:559-563, 21 pages.

Eastwood, P. et al. (2010; e-pub. Jan. 20, 2010). "Discovery of N-(5,6-diarylpyridin-2-yl)amide Derivatives as Potent and Selective A2B Adenosine Receptor Antagonists," Bioorganic & Medicinal Chemistry Letters 20:1697-1700.

Eastwood, P. et al. (2011; e-pub. Dec. 20, 2010). "Discovery of LAS101057: A Potent, Selective, and Orally Efficacious A2B Adenosine Receptor Antagonist," Bioorganic & Medicinal Chemistry Letters 2:213-218.

Fang, Y. et al. (Jun. 10, 2019). "Sequential Therapy with PARP and WEE1 Inhibitors Minimizes Toxicity while Maintaining Efficacy," Cancer Cell 35:851-867.

Ferrarini, P.L. et al. (Nov. 23, 2000). "Synthesis and Antiplatelet Activity of Some 3-Phenyl-1,8-Naphthyridine Derivatives," II Farmaco 55(9-10):603-610.

Garapaty, S. et al. (Jun. 2018). "Novel, Heterocyclic Small Molecule Inhibitors of PD-1/PD-L1 Pathway," Jubilant Biosys Ltd., Poster presented at AACR, 1 page.

Gessi, S. et al. (Dec. 1, 2017). "Inhibition of A2A Adenosine Receptor Signaling in Cancer Cells Proliferation by the Novel Antagonist TP455," Frontiers in Pharmacology 8(Article 888), 13 pages.

Gessi, S. et al. (May 2011; e-pub. Oct. 1, 2010). "Adenosine Receptors and Cancer," Biochim Biophys Acta 1808 (5):1400-1412.

Glukhova, A. et al. (Feb. 23, 2017). "Structure of the Adenosine A1 Receptor Reveals the Basis for Subtype Selectivity," Cell 168:867-877.

Goulding, J. et al. (2018; e-pub. Oct. 26, 2017). "Characterisation of Endogenous A2A and A2B Receptor-mediated Cyclic AMP Responses in HEK 293 Cells Using the GloSensorTM Biosensor: Evidence for an Allosteric Mechanism of Action for the A2B-Selective Antagonist PSB 603," Biochemical Pharmacology 147:55-66.

Gutierrez-De-Teran, H. et al. (2017). "Structure-Based Rational Design of Adenosine Receptor Ligands," Current Topics in Medicinal Chemistry 17(1):40-58.

Hafner, M. et al. (Aug. 15, 2019). "Multiomics Profiling Establishes the Polypharmacology of FDA-Approved CDK4/6 Inhibitors and the Potential for Differential Clinical Activity," Cell Chemical Biology 26:1-14.

Harter, M. et al. (2019). "Novel non-xanthine antagonist of the A2B adenosine receptor: From HTS hit to lead structure," European Journal of Medicinal Chemistry 163:763-778.

Hausler, S. et al. (2014). "Anti-CD39 and Anti-CD73 Antibodies A1 and 7G2 Improve Targeted Therapy in Ovarian Cancer by Blocking Adenosine-Dependent Immune Evasion," Am J Transl Res 6(2):129-139.

Hinz, S. et al. (2018). "Adenosine A2A Receptor Ligand Recognition and Signaling is Blockedby A2B Receptors," Oncotarget 9(17):13593-13611.

Hocher, B. (2010; e-pub. Jun. 30, 2010). "Adenosine A1 Receptor Antagonists in Clinical Research and Development," Kidney International 78:438-445.

Houthuys, E. et al. (Sep. 2017). "A Novel Non-Competitive and Non-Brain Penetrant Adenosine A2A Receptor Antagonist Designed to Reverse Adenosinemediated Suppression of Anti-tumor Immunity," Poster prepsented at ICIC, 1 page.

Hu, Y. et al. (2018, e-pub. Dec. 24, 2018). "Pharmacophore Modeling, Multiple Docking, and Molecular Dynamics Studies on Wee1 Kinase Inhibitors," Journal of Biomolecular Structure and Dynamics 1-14.

Huang, S. et al. (Aug. 15, 1997). "Role of A2a Extracellular Adenosine Receptor-Mediated Signaling in Adenosine-Mediated Inhibition of T-Cell Activation and Expansion," Blood 90(4):1600-1610.

Iannone, R. et al. (Dec. 2013). Blockade of A2B Adenosine Receptor Reduces Tumor Growth and Immune Suppression Mediated by Myeloid-Derived Suppressor Cells in a Mouse Model of Melanoma, Neoplasia, 15 (12):1400-1409.

Iannone, R. et al. (Mar. 15, 2014; e-pub. Mar. 1, 2014). "Adenosine Limits the Therapeutic Effectiveness of Anti-CTLA4 mAb in a Mouse Melanoma Model," Am J Cancer Res 4(2):172-181.

International Search Report and Written Opinion dated Nov. 1, 2018 for PCT Application No. PCT/US2018/042777 filed on Jul. 18, 2018, 10 pages.

Invitrogen. (Dec. 1, 2010). "GeneBLAzer ADORA2A CHO-K1 DA Cell-Based Assay" 12 pages.

Invitrogen. (Sep. 1, 2008). "GeneBLAzer ADORA2A CHO-K1 DA Assay Kit," 5 pages.

Ismayilova, N. et al. (2004). "Effects of Adenosine A1, Dopamine D1 and Metabotropic Glutamate 5 Receptors-modulating Agents on Locomotion of the Reserpinised Rats," European Journal of Pharmacology 497:187-195.

Jaakola, V.-P. et al. (Nov. 21, 2008). "The 2.6 Angstrom Crystal Structure of a Human A2A Adenosine Receptor Bound to an Antagonist," Science 322:1211-1217.

Jajoo, S. et al. (Nov. 2009). "Adenosine A3 Receptor Suppresses Prostate Cancer Metastasis by Inhibiting NADPH Oxidase Activity," Neoplasia 11(11):1132-1145.

Jazayeri, A. et al. (Jan. 11, 2017; e-pub. Jun. 22, 2016). "Structurally Enabled Discovery of Adenosine A2A Receptor Antagonists," Chemical Reviews 117(1):21-37, 17 pages.

Jiang, J. et al. (2019). "A2B Adenosione Receptor Antagonists With Picomolar Potency," 62:4032-4055.

Jin, M.H. et al. (2019). "Therapeutic Co-Targeting of WEE1 and ATM Downregulates PD-L1 Expression in Pancreatic Cancer," Cancer Research and Treatment (CRT) pp. 1-40.

Kang, N.S. et al. (Jun. 1, 2009, e-pub. Apr. 17, 2009). "Predictive Models of Cannabinoid-1 Receptor Antagonists Derived from Diverse Classes," Bioorg & Med Chem Lett 19(11):2990-2996.

Katritch, V. et al. (Feb. 25, 2010). "Structure-Based Discovery of Novel Chemotypes for Adenosine A2A Receptor Antagonists," J Med Chem. 53(4):1799-1809, 30 pages.

Kjaergaard, J. et al. (Jul. 15, 2018; e-pub. May 25, 2018). "A2A Adenosine Receptor Gene Deletion or Synthetic A2A Antagonist Liberate Tumor-Reactive CD8+ T Cells from Tumor-Induced Immunosuppression," The Journal of Immunology 201(2):782-791, 10 pages.

Koszalka, P. et al. (2014). "Inhibition of CD73 Stimulates the Migration and Invasion of B16F10 Melanoma Cells In Vitro, but Results in Impaired Angiogenesis and Reduced Melanoma Growth In Vivo," Oncology Reports 31:819-827.

Kumar, V. (2013; e-pub. Dec. 28, 2012). "Adenosine as an Endogenous Immunoregulator in Cancer Pathogenesis: Where to go?," Purinergic Signalling 9(2):145-165.

(56) References Cited

OTHER PUBLICATIONS

Kuzu, O.F. et al. (2017). "improving Pharmacological targeting of AKT in Melanoma," Cancer Letters 404:29-36.
Köse, M. et al. (May 24, 2018; e-pub. May 15, 2018). "Fluorescent-Labeled Selective Adenosine A2B Receptor Antagonist Enables Competition Binding Assay by Flow Cytometry," Journal of Medicinal Chemistry 61(10):4301-4316, 16 pages.
Lappas, C.M. et al. (2005). "A2A Adenosine Receptor Induction Inhibits IFN-γ Productionin Murine CD4+ T Cells," The Journal of Immunology 174:1073-1080.
Leclerc, B.G. et al. (Jan. 1, 2016; e-pub. Aug. 7, 2015). "CD73 Expression Is an Independent Prognostic Factor in Prostate Cancer," Clinical Cancer Research 22(1):158-166.
Leone, R.D. et al. (2015; e-pub. Apr. 8, 2015). "A2aR Antagonists: Next Generation Checkpoint Blockade for Cancer Immunotherapy," Computational and Structural Biotechnology Journal 13:265-272.
Leone, R.D. et al. (2018). "Targeting Adenosine for Cancer Immunotherapy," Journal for ImmunoTherapy of Cancer 6:57, 9 pages.
Leone, R.D. et al. (Aug. 2018; e-pub. Jun. 19, 2018). "Inhibition of the Adenosine A2a Receptor Modulates Expression of T Cell Coinhibitory Receptors and Improves Effector Function for Enhanced Checkpoint Blockade and ACT in Murine Cancer Models," Cancer Immunology Immunotherapy 67(8):1271-1284, 14 pages.
Lertsuwan, K. et al. (2017). "Purinergic Receptor Expression and Cellular Responses to Purinergic Agonists in Human Prostate Cancer Cells," Anticancer Research 37:529-538.
Li, Q.-X. et al. (May 2017; e-pub. Feb. 4, 2017). "Experimental Animal Modeling for Immuno-Oncology," Pharmacology & Therapeutics 173:34-46, 13 pages.
Liang, J. et al. (Sep. 24, 2019). "Genome-Wide CRIPSR-cas9 Screen Reveals Selective Vulnerability of ATRX-Mutant Cancers to WEE1 Inhibition," State Key Laboratory of Medical Molecular Biology, Institute of Basic Medical Sciences, Chinese Academy of Medical Sciences, Peking Union Medical School, Manuscript, 42 pages.
Lin, C.A. (2013). "Structural Characteristics of Cannabinoid Type 1 Receptor Antagonists," 160:536900 Abstract 34 (5):1240-1245, 1 page.
Lin, Z. et al. (Feb. 25, 2010). "Adenosine A1 Receptor, a Target and Regulator of ERα Action, Mediates the Proliferative Effects of Estradiol in Breast Cancer," Oncogene 29(8):1114-1122, 18 pages.
Linden, J. et al. (1999). "Characterization of Human A2B Adenosine Receptors: Radioligand Binding, Western Blotting, and Coupling to Gq in Human Embryonic Kidney 293 Cells and HMC-1 Mast Cells," Molecular Pharmacology 56:705-713.
Lingam, V.S. et al. (Oct. 22, 2015; e-pub. Sep. 30, 2015). "Design, Synthesis and Pharmacological Evaluation of 5,6-Disubstituted Pyridin-2(1H)-one Derivatives as Phosphodiesterase 10A (PDE10A) Antagonists," J. Med. Chem 58(20):8292-8308.
Liu, D. et al. (2019). "Enhancement of Chemosensitivity by WEE1 Inhibition in EGFR-TKIs Resistant Non-Small Cell Lung Cancer," Biomedicine & Pharmacotherapy 117(109185):1-8.
Liu, W. et al. (2019, e-pub. Jun. 13, 2019). "Targeting the WEE1 kinase strengthens the antitumor activity of imatinib via promoting KIT autophagic degradation in gastrointestinal stromal tumors," Gastric Cancer pp. 1-13.
Lübbehüsen, c. et al. (2019, e-pub. Apr. 23, 2019). "Characterization of Three Novel H3F3A-mutated Giant Cell Tumor Cell Lines and Targeting of Their Wee1 Pathway," Scientific Reports 9(6458):1-10.
Ma, S.-R. et al. (2017). "Blockade of Adenosine A2A Receptor Enhances CD8+ T Cells Response and Decreases Regulatory T Cells in Head and Neck Squamous Cell Carcinoma," Molecular Cancer 16:99, 15 pages.
Madsen-Duggen, C.B. et al. (Jun. 15, 2010, e-pub. Apr. 21, 2010). "Dihydro-Pyrano[2,3-B]Pyridines and Tetrahydro-1,8-Naphthyridines as CB1 Receptor Inverse Agonists: Synthesis, SAR and Biological Evaluation," Bioorg & Med Chem Lett 20(12):3750-3754.

Maemoto, T. et al. (2004). "Pharmacological Characterization of FR194921, a New Potent, Selective, and Orally Active Antagonist for Central Adenosine A1 Receptors," J Pharmacol 96:42-52.
Mantri, M. et al. (2008; e-pub. Jul. 19, 2008). "2-Amino-6-furan-2-yl-4-substituted Nicotinonitriles as A2A Adenosine Receptor Antagonists," J. Med. Chem. 51(15):4449-4455.
Massie, B.M. et al. (Oct. 7, 2010). "Rolofylline, an Adenosine A1-Receptor Antagonist, in Acute Heart Failure," The New England Journal of Medicine 363(15):1419-1428.
Mastracchio, A. et al. (2019). "Investigation of Biaryl Heterocycles as Inhibitors of Wee1 Kinase," Bioorganic & Medicinal Chemistry Letters 29:1481-1486.
McCoull, A. et al. (2018). "Development of a Novel B-Cell Lymphoma 6 (BCL6) PROTAC to Provide Insight into Small Molecule Targeting of BCL6," ACS Chemical Biology 11 pages.
McCoull, W. et al. (Nov. 16, 2018; e-pub. Oct. 17, 2018). "Development of a Novel B-Cell Lymphoma 6 (BCL6) PROTAC to Provide Insight into Small Molecule Targeting of BCL6," ACS Chem. Biol. 13(11):3131-3141, 11 pages.
Medialvilla-Varela, M. et al. (Jul. 2017). "A Novel Antagonist of the Immune Checkpoint Protein Adenosine A2a Receptor Restores Tumor-Infiltrating Lymphocyte Activity in the Context of the Tumor Microenvironment," Neoplasia 19(7):530-536.
Medialvilla-Varela, M. et al. (Sep. 2013; e-pub. Jul. 17, 2013). "Antagonism of Adenosine A2A Receptor Expressed by Lung Adenocarcinoma Tumor Cells and Cancer Associated Fibroblasts Inhibits Their Growth," Cancer Biology & Therapy 14(9):860-868.
Mendonca, A.D. et al. (2000). "Adenosine: Does it Have a Neuroprotective Role After All?," Brain Research Reviews 33:258-274.
Mihara, T. et al. (2007). "Pharmacological Characterization of a Novel, Potent Adenosine A1 and A2A Receptor Dual Antagonist, 5-[5-Amino-3-(4-fluorophenyl)pyrazin-2-yl]-1-isopropylpyridine-2(1H)-one (ASP5854), in Models of Parkinson's Disease and Cognition," The Journal of Pharmacology and Experimental Therapeutics 323(2):708-719.
Mittal, D. et al. (Aug. 1, 2016; e-pub. May 24, 2016). "Adenosine 2B Receptor Expression on Cancer Cells Promotes Metastasis," Cancer Research 76(15):1-11.
Mittal, D. et al. (Jul. 15, 2014; e-pub. Jul. 1, 2014). "Antimetastatic Effects of Blocking PD-1 and the Adenosine A2A Receptor," Cancer Research 74(14):3652-3658.
Mokyr, M.B. et al. (Dec. 1, 1998). "Realization of the Therapeutic Potential of CTLA-4 Blockade in Low-Dose Chemotherapy-treated Tumor-bearing Mice," Cancer Research 58:5301-5304.
Moriyama, K. et al. (Dec. 10, 2010). "Adenosine A2A Receptor Is Involved in Cell Surface Expression of A2B Receptor," The Journal of Biology Chemistry 285(50):39271-39288.
Mousavi, S. et al. (2015; e-pub. Feb. 20, 2015). "Expression of Adenosine Receptor Subclasses in Malignant and Adjacent Normal Human Prostate Tissues," The Prostate 75:735-747.
Nikbakht, D.M. et al. (2016). "Adenosine A1 Receptor Modifies P53 Expression and Apoptosis in Breast Cancer Cell Line Mcf-7," Bratisl Med J 117(4):242-246.
Novío, S. et al. (2017; e-pub. Mar. 30, 2017). "Adenosine Signaling Pathways as Potential Therapeutic Targets in Prostate Cancer Disease," Molecular Oncology: Underlying Mechanisms and Translational Advancements pp. 93-107.
Ohana, G. et al. (2001; e-pub. Nov. 30, 2000). "Differential Effect of Adenosine on Tumor and Normal Cell Growth: Focus on the A3 Adenosine Receptor," Journal of Cellular Physiology 186:19-23.
Ohta, A. (Mar. 29, 2016). "A Metabolic Immune Checkpoint: Adenosine in Tumor Microenvironment," Frontiers in Immunology 7(Article 109), 11 pages.
Palmer, B.D. et al. (2006, e-pub. Jul. 15, 2006). "4-Phenylpyrrolo[3,4-c]carbazole-1,3(2H,6H)-dione Inhibitors of the Checkpoint Kinase Wee1. Structure-Activity Relationships for Chromophore Modification and Phenyl Ring Substitution," J. Med. Chem. 49:4896-4911.
Pandey, K. et al. (2019). "Molecular Mechanisms of Resistance to CDK4/6 Inhibitors in Breast Cancer: A review," International Journal of Cancer 145:1179-1188.
Panjehpour, M. et al. (Summer 2010). "Adenosine Receptor Expression in Two Different Human Cancer Cell Lines at Molecular Level," Iran J Cancer Prev 3(3):111-116.

(56) References Cited

OTHER PUBLICATIONS

Pinna, A. et al. (2014; e-pub. Apr. 1, 2014). "Adenosine A2A Receptor Antagonists in Parkinson's Disease: Progress in Clinical Trials from the Newly Approved Istradefylline to Drugs in Early Development and Those Already Discontinued," CNS Drugs 28:455-474.

Popoli, P. et al. (Mar. 1, 2002). "Blockade of Striatal Adenosine A2A Receptor Reduces, Through a Presynaptic Mechanism, Quinolinic Acid-Induced Excitotoxicity: Possible Relevance to Neuroprotective Interventions in Neurodegenerative Diseases of the Striatum," J. Neurosci 22(5):1967-1975.

Powderly, J. et al. (May 2019). "AB928, a Novel Dual Adenosine Receptor Antagonist, Combined With Chemotherapy or AB122 (anti-PD-1) in Patients With Advanced Tumors: Preliminary Results From Ongoing Phase I Studies," ASCO 2019, Abstract No. 2604, 1 page.

Preti, D. et al. (Jul. 2015; e-pub. Mar. 27, 2015). "History and Perspectives of A2A Adenosine Receptor Antagonists as Potential Therapeutic Agents," Med. Res. Rev. 35(4):790-848, 59 pages.

PUBCHEM. CID 66665902 (Nov. 30, 2012). Located at https://pubchem.ncbi.nlm.nih.gov/compound/66665902, last visited on Sep. 1, 2018, 13 pages.

Rahimova, R. et al. (Jan. 29, 2018). "Identification of Allosteric Inhibitors of the Ecto-5'-Nucleotidase (CD73) Targeting the Dimer Interface," PLoS Comput Biol 14(1):e1005943, 23 pages.

Remington's Pharmaceutical Sciences, Mack Publishing Company, Philadelphia, PA, 21th ed. (2000) TOC, 4 Pages.

Restelli, V. et al. (2019, e-pub. May 7, 2019). "DNA Damage Response Inhibitor Combinations Exert Synergistic Antitumor Activity in Aggressive B Cell Lymphomas," American Association for Cancer Research Manuscript pp. 1-25.

Rosse, G. (Dec. 8, 2016; e-pub. Nov. 2, 2016); "Quinazoline Carboxamides as Selective Antagonists of Adenosine 2A Receptor," ACS Med. Chem. Lett. 7(12):1014-1015.

Rusinov, V.L. et al., (Dec. 2005). "Synthesis and Antiviral Activity of 2-Amino-3-Ethoxycarbonylpyrazine Derivatives," Pharmaceutical Chemistry Journal 39(12):630-635.

Schuler, P.J. et al. (2014). "Human CD4+CD39+ Regulatory T Cells Produce Adenosine Upon Co-Expression of Surface CD73 or Contact with CD73+ Exosomes or CD73+ Cells," Clinical and Experimental Immunology 177:531-543.

Segala, E. et al. (Jul. 14, 2016; e-published Jul. 1, 2016). "Controlling the Dissociation of Ligands from the Adenosine A2A Receptor Through Modulation of Salt Bridge Strength," J. Med. Chem. 59(13):6470-6479, 41 pages.

Sek, K. et al. (Dec. 2, 2018). "Targeting Adenosine Receptor Signaling inCancer Immunotherapy," Int. J. Mol. Sci. 19:3837, 23 pages.

Serpico, A.F. et al. (2019, e-pub. Jun. 13, 2019). "Wee1 Rather Than Plk1 Is Inhibited by AZD1775 at Therapeutically Relevant Concentrations," Cancers 11:1-10.

Shook, B.C. et al. (2010; e-pub. Oct. 25, 2010). "In Vivo Characterization of a Dual Adenosine A2A/A1 Receptor Antagonist in Animal Models of Parkinson's Disease," J. Med. Chem. 53(22):8104-8115.

Sitkowsky, M. et al. (Jul. 2014). "Hostile, Hypoxia-A2-Adenosinergic Tumor Biology as the Next Barrier to Overcome for Tumor Immunologists," Cancer Immunol. Res. 2(7):598-605, 15 pages.

Sivakumar, P.M. et al. (Jun. 2012). "QSAR Studies on Substituted 3- or 4-Phenyl-1,8-Naphthyridine Derivatives as Antimicrobial Agents," Med Chem Res 21(6):788-795.

Sorrentino, C. et al. (Jul. 17, 2017). "Role of Adenosine in Tumor Progression: Focus on A2B Receptor as Potential Therapeutic Target," Journal of Cancer Metastasis and Treatment 3:127-138.

Sorrentino, C. et al. (Sep. 29, 2015; e-pub. Jul. 25, 2015). "Myeloid-Derived Suppressor Cells Contribute to A2B Adenosine Receptor-Induced VEGF Production and Angiogenesis in a Mouse Melanoma Model," Oncotarget 6 (29):27478-27489.

Takashima, Y. et al. (2019). "Bromodomain and Extraterminal Domain Inhibition Synergizes with WEE1-Inhibitor AZD1775 Effect by Impairing Non-Homologous End Joining and Enhancing DNA Damage in Non-Small Cell Lung Cancer," Department of Respiratory Medicine, Faculty of Medicine and Graduate School of Medicine, Hokkaido University pp. 1-33.

Tarkhov, et al. (2005). "Photoluminescence of Some Indolylpyrazines." Materialovedenie 4:16-22. with English Translation.

Tarkhov, et al., (2005). "Analysis of Electronic Transitions During Photoluminescence for some Indolylpyrazines," Materialovedenie 10:18-21. with English Translation.

Thomas, A. et al. (Oct. 4, 2015, e-pub. Sep. 30, 2015). "Design, Synthesis and Pharmacological Evaluation of 5,6-Disubstituted Pyridin-2(1H)-one Derivatives as Phosphodiesterase 10A (PDE10A) Antagonists," Journal of Medicinal Chemistry 62 pages.

Tuite, P. et al. (Aug. 2003). "Recent Developments in the Pharmacological Treatment of Parkinson's Disease," Expert Opin. Investig. Drugs 12(8):1335-1352.

Van Waarde, A. et al. (Jan. 2018; e-pub. Jan. 27, 2017). "Potential Therapeutic Applications of Adenosine A2A Receptor Ligands and Opportunities for A2A Receptor Imaging," Med. Res. Rev. 38(1):1-56, 52 pages.

Varani, K. et al. (1997). "Characterization of A2A Adenosine Receptors in Human Lymphocyte Membranes by [3H]-SCH 58261 Binding," British Journal of Pharmacology 122:386-392.

Vaupel, P. et al. (Dec. 21, 2017). "Accomplices of the Hypoxic Tumor Microenvironment Compromising Antitumor immunity: Adenosine, Lactate, Acidosis, Vascular Endothelial Growth Factor, Potassium Ions, and Phosphatidylserine," Frontiers in Immunology 8(Article 1887), 6 pages.

Vecchio, E. A. et al. (Apr. 2016). "Ligand-Independent Adenosine A2B Receptor Constitutive Activity as a Promoter of Prostate Cancer Cell Proliferation," J Pharmacol Exp Ther 357:36-44.

Vecchio, E.A. et al. (Jun. 2019). "The Adenosine A2B G Protein-Coupled Receptor: Recent Advances and Therapeutic Implications," Pharmacology and Therapeutics 198:20-33, 50 pages.

Vijayan, D. et al. (Dec. 2017; e-pub. Oct. 23, 2017). "Targeting Immunosuppressive Adenosine in Cancer," Nature Rev Cancer 17(12):709-724.

Vilgelm, A.E. (2019). "MDM2 Antagonists Overcome Intrinsic resistance to CDK4/6 Inhibition by Inducing p21," Sci. Transl. Med. 11(3aav7171):1-15.

Virgilio, F.D. et al. (2017; e-pub. Jun. 20, 2016). "Extracellular Purines, Purinergic Receptors and Tumor Growth," Oncogene 36:293-303.

Voors, A.A. et al. (May 10, 2011). "Effects of the Adenosine A1 Receptor Antagonist Rolofylline on Renal Function in Patients With Acute Heart Failure and Renal Dysfunction," J Am Coll Cardiol 57(19):1899-1907.

Waickman, A.T. et al. (Jun. 2012). "Enhancement of Tumor Immunotherapy by Deletion of the A2A Adenosine Receptor," Cancer Immunol Immunother. 61(6):917-926, 17 pages.

Walters, M.J. et al. (2017). "Characterization of AB928, an A2R Antagonist for the Treatment of Cancer," Poster presented at AACR, 1 page.

Walters, M.J. et al. (2018). "Combining Adenosine Receptor Inhibition, with AB928, and Chemotherapy Results in Greater Immune Activation and Tumor Control," Abstract 5556, Poster presented at AACR, 1 page.

Walters, M.J. et al. (2018). "Combining Adenosine Receptor Inhibition, With AB928, and Chemotherapy Results in greater Immune Activation and Tumor Control," AACR 2018, Abstract 5556, 1 page.

Wang, J. et al. (Sep. 2018; e-pub. Aug. 1, 2018). "Adenosinergic Signaling as a Target for Natural Killer Cell Immunotherapy," Journal of Molecular Medicine 96(9):903-913, 11 pages.

Wei, Q. et al. (2013; e-pub. Jan. 15, 2013). "A2B Adenosine Receptor Blockade Inhibits Growth of Prostate Cancer Cells," Purinergic Signalling 9:271-280.

Whiteside, T.L. et al. (Jun. 2017; e-pub. Apr. 27, 2017). "Targeting Adenosine in Cancer Immunotherapy: A Review of Recent Progress," Expert Review of Anticancer Therapy 17(6):527-535, 36 pages.

(56) References Cited

OTHER PUBLICATIONS

Wichapong, K. et al. (2009, e-pub. Sep. 20, 2008). "Receptor-based 3D-QSAR studies of checkpoint Wee1 kinase inhibitors," European Journal of Medicinal Chemistry 44:1383-1395.

Willingham, S.B. et al. (Oct. 2018; e-pub. Aug. 21, 2018). "A2AR Antagonism with CPI-444 Induces Antitumor Responses and Augments Efficacy to Anti-PD-(L)1 and Anti-CTLA-4 in Preclinical Models," Cancer Immunol Res. 6(10):1-14.

Willingham, S.B. et al. (Oct. 2018; e-pub. Aug. 21, 2018). "A2AR Antagonism with CPI-444 Induces Antitumor Responses and Augments Efficacy to Anti-PD-(L)1 and Anti-CTLA-4 in Preclinical Models," Cancer Immunol Res. 6(10):1136-1149, (with Supplementary material, 30 pages).

Yang, Q. et al. (2013, e-pub. May 8, 2013). "Overexpression of CD73 in Prostate Cancer is Associated with Lymph Node Metastasis," Pathol. Oncol. Res. 4 pages.

Yang, X. et al. (2017). "Tiamulin Inhibits Breast Cancer Growth and Pulmonary Metastasis by Decreasing the Activity of CD73," BMC Cancer 17:255, 12 pages.

Yang_X. et al. (2018; e-pub. Aug. 6, 2018). "An Affinity-Based Probe for the Human Adenosine A2A Receptor," J. Med. Chem. 61:7892-7901.

Young, A. et al. (Sep. 12, 2016). "Co-inhibition of CD73 and A2AR Adenosine Signaling improves Anti-tumor Immune Responses," Cancer Cell 30:391-403.

Yuan, G. et al. (2014). "Towards Next Generation Adenosine A2A Receptor Antagonists," Current Medicinal Chemistry 21(34):3918-3935.

Zhang, P. et al. (2019, e-pub. Jul. 21, 2019). "BRD4 Inhibitor AZD5153 Suppresses the Proliferation of Colorectal Cancer Cells and Sensitizes the Anticancer Effect of PARP Inhibitor," Int. J. Biol. Sci. 15(9):1942-1954.

Zhou, J.Z. et al. (Apr. 2, 2015). "Differential Impact of Adenosine Nucleotides Released by Osteocytes on Breast Cancer Growth and Bone Metastasis," Oncogene 34(14):1831-1842, 31 pages.

International Preliminary Report on Patentability, dated Jan. 21, 2020, for PCT Application No. PCT/US2018/042777, 6 pages.

PUBCHEM. CID 66665561 (Nov. 30, 2012). "2,3-Diphenyl-5,6,7,8-Tetrahydropyrido[3,2-b]pyrazine," Located at https://pubchem.ncbi.nlm.nih.gov/compound/66665561, last visited on Sep. 1, 2018, 9 pages.

* cited by examiner

HETEROCYCLIC COMPOUNDS AS ADENOSINE ANTAGONISTS

CROSS-REFERENCE TO RELATED APPLICATIONS

This application claims priority to U.S. Provisional Application No. 62/534,176, filed Jul. 18, 2017, the contents of which are incorporated by reference in their entirety.

FIELD OF THE INVENTION

This disclosure relates generally to therapeutics for treatment mediated through a G-protein-coupled receptor (GPCR) signaling pathway and, more particularly, to compounds that inhibit an adenosine receptor (such as an $A_{2A}$ antagonist). The disclosure also provides pharmaceutically acceptable compositions comprising such compounds and methods of using the compounds or compositions in the treatment of a disease associated with a GPCR signaling pathway.

BACKGROUND OF THE INVENTION

Adenosine receptors (ARs) are distributed throughout the body and are responsible for numerous biological functions. The seven trans-membrane G-protein-coupled receptors (GPCRs) have been divided into four different subtypes: $A_1$, $A_{2A}$, $A_{2B}$, and $A_3$. The $A_{2A}$ and $A_{2B}$ ARs stimulate activity of the adenylyl cyclase, inducing an increase of cAMP levels. $A_{2A}$ ARs have a distinct tissue localization, different biochemical pathways, and specific pharmacological profiles.

Adenosine is one of the human body's most important neuromodulators in both the central and the peripheral nervous systems. Adenosine is released from tumor cells and its concentration in the extracellular fluid of tumors can reach immunosuppressive levels (Blay et al. (1997), Cancer Res., 57(13), pp. 2602-5). The extracellular fluid of solid carcinomas contains immunosuppressive concentrations of adenosine. Id. This increase in adenosine concentration is a result of increases in CD73 (ecto-5'-nucleotidase) and CD39 (nucleoside triphosphate dephosphorylase) enzymes, which are responsible for directly catabolizing ATP into adenosine. These upregulations are triggered by hypoxia and the generation of HIF-1α. High levels of adenosine around tumor cells act to regulate multiple immune cells (e.g., CD4+ T-cells and cytotoxic CD8+ T-cells) via activation of multiple adenosine receptor subtypes, but particularly $A_{2A}$ receptors, resulting the suppressing of pro-inflammatory activities and upregulation of anti-inflammatory molecules and immunoregulatory cells (Kumar et al. (2013), Adenosine as an endogenous immunoregulator in cancer pathogenesis: where to go? Purinergic Signal., 9(2), pp 145-65 and Sitkowsky et al., Hostile, hypoxia-A2-adenosinergic tumor biology as the next barrier to overcome for tumor immunologists. Cancer Immunol. Res. 2(7), pp 598-605; Ohta (2016), A Metabolic Immune Checkpoint: Adenosine in Tumor Microenvironment. Frontiers in Immunology., 7 article #109, pp 1-11). It was demonstrated that chimeric antigen receptor (CAR) T cells upregulate A2ARs upon antigen-specific stimulation in vitro and in vivo (Beavls (2017), Targeting the Adenosine 2A Receptor Enhances Chimeric Antigen Receptor T Cell Efficacy. J of Clin Invest. 127 (3): pp 929-941).

Survival of cancer cells is dependent on their ability to avoid attack by the immune system. In addition, tumor cells can overtake the immune system to facilitate tumor survival and metastasis. Adenosine, whose concentration increases within hypoxic regions of solid tumors, has been recognized as being able to interfere with the recognition of tumor cells by cytolytic effector cells of the immune system. (Tuite and Riss (2013). Recent developments in the pharmacological treatment of Parkinson's disease. Expert Opin. Investig. Drugs, 12(8) pp 1335-52, Popoli et al. (2002). Blockade of striatal adenosine $A_{2A}$ receptor reduces, through a presynaptic mechanism, quinolinic acid-induced excitotoxicity: possible relevance to neuroprotective interventions in neurodegenerative diseases of the striatum, J. Neurosci, 22(5) pp. 1967-75, Gessi et al. (2011). Adenosine receptors and cancer. Biochim Biophys Acta, 1808(5), pp. 1400-12).

Although all adenosine receptors now have an increasing number of recognized biological roles in tumors, the $A_{2A}$ and $A_3$ subtypes appear promising targets for therapeutic development. In particular, activation of $A_{2A}$ receptors leads to immunosuppressive effects, which decreases anti-tumoral immunity and thereby encourages tumor growth.

The $A_{2B}$ receptor is another potential target for therapeutic development. Autocrine/paracrine stimulation of $A_{2B}$ expressed on tumor cells is believed to enhance their metastatic potential and $A_{2B}$ blockade may reduce tumor metastasis in an immune-independent manner (Beavis et al. (2013). Blockade of $A_{2A}$ receptors potently suppresses the metabolism of CD73+ Tumors. Proc. Natl. Acad. Sci., 110 (36) pp. 14711-6). $A_{2B}$ expression also correlates with relapse-free survival (RFS) in triple negative breast cancer suggesting that this pathway may be clinically relevant. $A_{2B}$ blockade also has the potential to modulate the immunosuppressive properties of tumor-associated immune cells including dendritic cells and myeloid-derived suppressor cells (MDSCs) (Cekic et al. (2011). Adenosine A2B receptor blockade slows growth of bladder and breast tumors. J. Immunol. 188(1), pp. 198-205; Sorrentino et al. (2015). Myeloid-derived suppressor cells contribute to $A_{2B}$ adenosine receptor-induced VEGF production and angiogenesis in a mouse melanoma model. Oncotarget 6(29), pp. 27478-89; Iannone et al. (2013). Blockade of $A_{2B}$ adenosine receptor reduces tumor growth and immune suppression mediated by myeloid-derived suppressor cells in a mouse model of melanoma. Neoplasia, 15(12), pp. 1400-9.

There remains a continuing need for new therapies for the treatment of diseases and disorders related to the adenosine signaling pathway.

BRIEF SUMMARY OF THE INVENTION

In one aspect, provided is a compound of the formula (I):

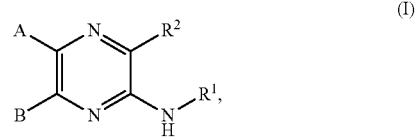

or a tautomer or isomer thereof, or a pharmaceutically acceptable salt of any of the foregoing, wherein A, B, $R^1$ and $R^2$ are as detailed herein. In some embodiments, provided is a compound of formula (I), or a salt thereof.

In some embodiments, the compound of the formula (I), or a tautomer or isomer thereof, or a pharmaceutically acceptable salt of any of the foregoing, is of the formula (II), (III) or (IV) or a tautomer or isomer thereof, or a pharmaceutically acceptable salt of any of the foregoing, as detailed herein. In some embodiments, the compound of the formula (I), or a salt thereof, is of the formula (II), (III) or (IV) or a salt of the foregoing, as detailed herein.

In another aspect, provided is a method for any one or more of: (a) treating a disease, such as a proliferative disease, in an individual in need thereof; (b) enhancing an immune response in an individual in need thereof; (c) inhibiting tumor metastasis in an individual in need thereof; (d) modulating the activity of a G protein coupled receptor signaling pathway in an individual in need thereof; (e) modulating the activity of an adenosine receptor, such as an $A_{2A}$ receptor, in an individual in need thereof; and (f) increasing the activity of a natural killer cell in an individual in need thereof, wherein the method comprises administering to the individual an effective amount of a compound of formula (I), or a tautomer or isomer thereof, or a pharmaceutically acceptable salt of any of the foregoing. In some embodiments, provided is a method for any one or more of: (a) treating a disease, such as a proliferative disease, in an individual in need thereof; (b) enhancing an immune response in an individual in need thereof; (c) inhibiting tumor metastasis in an individual in need thereof; (d) modulating the activity of a G protein coupled receptor signaling pathway in an individual in need thereof; (e) modulating the activity of an adenosine receptor, such as an $A_{2A}$ receptor, in an individual in need thereof; and (f) increasing the activity of a natural killer cell in an individual in need thereof, wherein the method comprises administering to the individual an effective amount of a compound of formula (I), or a salt thereof. In one aspect, the compound of formula (I) or a salt thereof is administered to the individual in combination with another therapeutic agent. In some embodiments, the compound of formula (I) or a tautomer or isomer thereof, or a pharmaceutically acceptable salt of any of the foregoing is administered to the individual in combination with another therapeutic agent. In a further aspect of the methods, the compound of formula (I) or a salt thereof is a compound of the formula (II), (III) or (IV) or a salt of the foregoing. In some embodiments, the compound of formula (I) or a tautomer or isomer thereof, or a pharmaceutically acceptable salt of any of the foregoing is a compound of the formula (II), (III) or (IV), or a tautomer or isomer thereof, or a pharmaceutically acceptable salt of any of the foregoing.

Also provided are pharmaceutical compositions comprising (A) a compound detailed herein, such as a compound of formula (I) or a tautomer or isomer thereof, or a pharmaceutically acceptable salt of any of the foregoing, or a compound of formula (II) or a tautomer or isomer thereof, or a pharmaceutically acceptable salt of any of the foregoing, or a compound of formula (III) or a tautomer or isomer thereof, or a pharmaceutically acceptable salt of any of the foregoing, or a compound of formula (IV) or a tautomer or isomer thereof, or a pharmaceutically acceptable salt of any of the foregoing, and (B) a pharmaceutically acceptable carrier or excipient. In some embodiments, provided are pharmaceutical compositions comprising (A) a compound detailed herein, such as a compound of formula (I) or a salt thereof, or a compound of formula (II) or a salt thereof, or a compound of formula (III) or a salt thereof, or a compound of formula (IV) or a salt thereof, and (B) a pharmaceutically acceptable carrier or excipient. Kits comprising a compound detailed herein or a tautomer or isomer thereof, or a pharmaceutically acceptable salt of any of the foregoing and instructions for use are also provided. Kits comprising a compound detailed herein or a salt thereof and instructions for use are also provided. A compound detailed herein or a tautomer or isomer thereof, or a pharmaceutically acceptable salt of any of the foregoing is also provided for the manufacture of a medicament for the treatment of cancer. Compounds as detailed herein or a pharmaceutically acceptable salt thereof are also provided for the manufacture of a medicament for the treatment of cancer.

DETAILED DESCRIPTION OF THE INVENTION

Definitions

Figure 1:
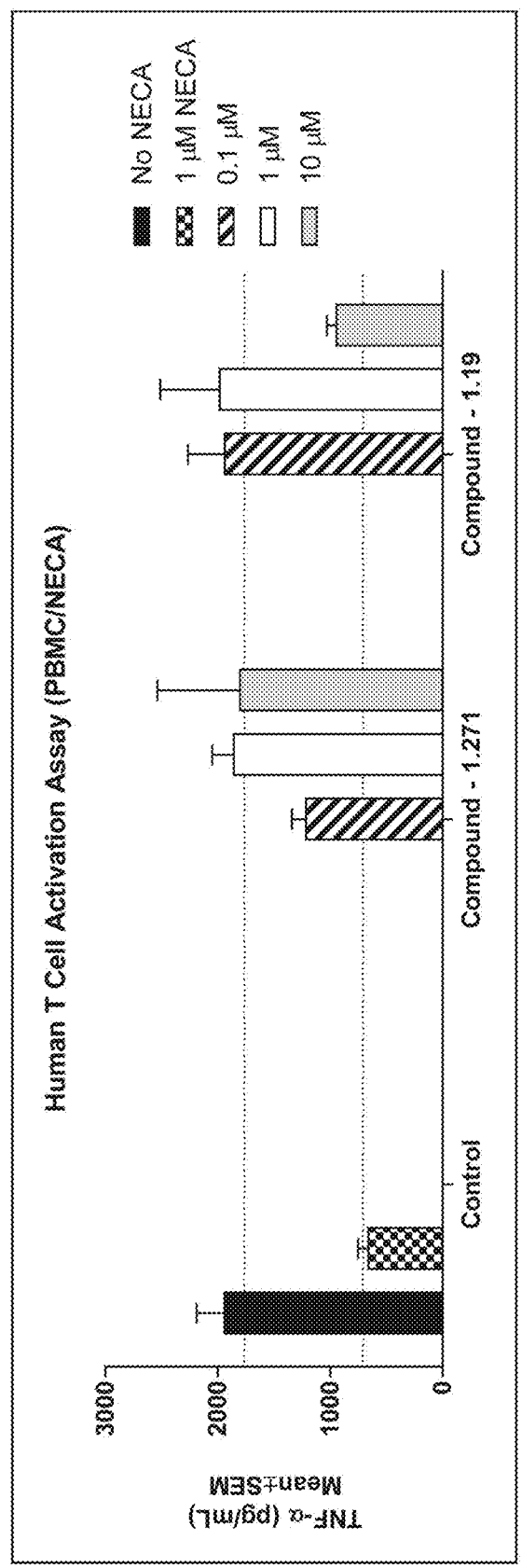
FIG. 1 shows the effects of certain compounds on TNF-α production in activated human PBMCs.

For use herein, unless clearly indicated otherwise, use of the terms "a", "an" and the like refers to one or more.

"Alkenyl" as used herein refers to an unsaturated linear or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

The term "alkyl" refers to and includes saturated linear and branched univalent hydrocarbon structures and combination thereof, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), butylene (—$CH_2CH_2CH_2CH_2$—), and the like.

"Alkynyl" as used herein refers to an unsaturated linear or branched univalent hydrocarbon chain or combination thereof, having at least one site of acetylenic unsaturation (i.e., having at least one moiety of the formula CC) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

The term "aryl" refers to and includes polyunsaturated aromatic hydrocarbon groups. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

The term "cycloalkyl" refers to and includes cyclic univalent hydrocarbon structures, which may be fully saturated, mono- or polyunsaturated, but which are non-aromatic, having the number of carbon atoms designated (e.g., $C_1$-$C_{10}$ means one to ten carbons). Cycloalkyl can consist of one ring, such as cyclohexyl, or multiple rings, such as adamantyl, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

"Halo" or "halogen" refers to elements of the Group 17 series having atomic number 9 to 85. Preferred halo groups include fluoro, chloro, bromo and iodo. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

The term "heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, thiophenyl, furanyl, thiazolyl, and the like. Examples of heteroaryl groups also include, but are not limited to, pyridyl, pyrimidyl, thiophenyl, furanyl, thiazolyl, oxazolyl, isoxazolyl, thiophenyl, pyrrolyl, pyrazolyl, 1,3,4-oxadiazolyl, imidazolyl, isothiazolyl, triazolyl, 1,3,4-thiadiazolyl, tetrazolyl, benzofuranyl, benzothiophenyl, pyrazolopyridinyl, indazolyl, benzothiazolyl, benzooxazolyl or benzoimidazolyl and the like.

In one variation, a heteroaryl containing at least one additional fused ring that is nonaromatic (e.g., cycloakyl or heterocyclyl) is attached to the parent structure at an annular atom of the additional ring. In another variation, a heteroaryl containing at least one additional ring that is nonaromatic (e.g., cycloakyl or heterocyclyl) is attached to the parent structure at an annular atom of the aromatic ring.

The term "heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl, cycloalyl or heterocyclyl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1(2H)-yl, and the like.

In one variation, a heterocyclyl containing at least one additional ring (such as a fused additional ring) that does not contain a heteroatom is attached to the parent structure at an annular atom of the additional ring. In another variation, a heterocyclyl containing at least one additional ring (such as a fused additional ring) that does not contain a heteroatom is attached to the parent structure at an annular atom of the ring containing a heteroatom.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" or "treating" is an approach for obtaining beneficial or desired results including clinical results. For example, beneficial or desired results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals. In reference to cancers or other unwanted cell proliferation, beneficial or desired results include shrinking a tumor (reducing tumor size); decreasing the growth rate of the tumor (such as to suppress tumor growth); reducing the number of cancer cells; inhibiting, retarding or slowing to some extent and preferably stopping cancer cell infiltration into peripheral organs; inhibiting (slowing to some extent and preferably stopping) tumor metastasis; inhibiting tumor growth; preventing or delaying occurrence and/or recurrence of tumor; and/or relieving to some extent one or more of the symptoms associated with the cancer. In some embodiments, beneficial or desired results include preventing or delaying occurrence and/or recurrence, such as of unwanted cell proliferation.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, an "effective dosage" or "effective amount" of compound or salt thereof or pharmaceutical composition is an amount sufficient to effect beneficial or desired results. For prophylactic use, beneficial or desired results include results such as eliminating or reducing the risk, lessening the severity of, or delaying the onset of the disease, including biochemical, histological and/or behavioral symptoms of the disease, its complications and intermediate pathological phenotypes presenting during development of the disease. For therapeutic use, beneficial or desired results include ameliorating, palliating, lessening, delaying or decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more administrations, in the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective dosage can be administered in one or more administrations. For purposes of this disclosure, an effective dosage of compound or a salt thereof, or pharmaceutical composition is an amount sufficient to accomplish prophylactic or therapeutic treatment either directly or indirectly. It is intended and understood that an effective dosage of a compound or salt thereof, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "individual" is a mammal, including humans. An individual includes, but is not limited to, human, bovine, horse, feline, canine, rodent, or primate. In some embodiments, the individual is human. The individual (such as a human) may have advanced disease or lesser extent of disease, such as low tumor burden. In some embodiments, the individual is at an early stage of a proliferative disease (such as cancer). In some embodiments, the individual is at an advanced stage of a proliferative disease (such as an advanced cancer).

Reference to "about" a value or parameter herein includes (and describes) embodiments that are directed to that value or parameter per se. For example, description referring to "about X" includes description of "X".

It is understood that aspects and variations described herein also include "consisting" and/or "consisting essentially of" aspects and variations.

Compounds

In one aspect, provided is a compound of the formula (I):

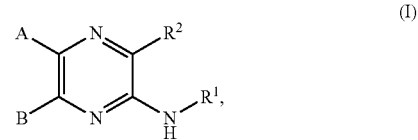

or a tautomer or isomer thereof, or a pharmaceutically acceptable salt of any of the foregoing, wherein:

A is 4-hydroxyphenyl optionally further substituted by $R^3$, 4-hydroxy-2-pyridyl optionally further substituted by $R^4$, a naphthyl substituted by $R^4$, a 9- or 10-membered bicylic heterocylyl optionally substituted by $R^4$, or a 9- or 10-membered bicyclic heteroaryl optionally substituted by $R^4$;

B is a phenyl optionally substituted by $R^3$, $C_3$-$C_6$ cycloalkyl optionally substituted by $R^4$, 3- to 6-membered heterocyclyl optionally substituted by $R^4$ or a 5- to 10-membered heteroaryl optionally substituted by $R^4$;

$R^1$ is a hydrogen, $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, 5- to 10-membered heteroaryl, —($C_1$-$C_3$ alkylene)($C_3$-$C_6$ cycloalkyl), —($C_1$-$C_3$ alkylene)(3-6-membered heterocyclyl), —($C_1$-$C_3$ alkylene)(5-6-membered heteroaryl), —($C_1$-$C_3$ alkylene)($C_6$ aryl), —C(O)$R^{1a}$, —C(O)O$R^{1a}$, —C(O)NR$^{1b}$R$^{1c}$, —S(O)$_2$R$^{1a}$, —($C_1$-$C_3$ alkylene)C(O)NR$^{1b}$R$^{1c}$, —($C_1$-$C_3$ alkylene)C(O)R$^{1a}$ or —($C_1$-$C_3$ alkylene)NR$^{1b}$R$^{1c}$, wherein the $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, 5- to 10-membered heteroaryl, —($C_1$-$C_3$ alkylene)($C_3$-$C_6$ cycloalkyl), —($C_1$-$C_3$ alkylene)(3-6-membered heterocyclyl), —($C_1$-$C_3$ alkylene)(5-6-membered heteroaryl), and —($C_1$-$C_3$ alkylene)($C_6$ aryl) of $R^1$ are independently optionally substituted by $R^4$;

each $R^{1a}$ is independently hydrogen, $C_1$-$C_6$ alkyl, $C_3$-$C_6$ cycloalkyl, 3-6-membered heterocyclyl, $C_6$ aryl, 5-6-membered heteroaryl, —($C_1$-$C_3$ alkylene)($C_3$-$C_6$ cycloalkyl), —($C_1$-$C_3$ alkylene)(3-6-membered heterocyclyl), —($C_1$-$C_3$ alkylene)($C_6$ aryl) or —($C_1$-$C_3$ alkylene)(5-6-membered heteroaryl), wherein each of which is optionally substituted by methyl, ethyl, halogen, oxo, —CF$_3$, —OH, —OCH$_3$, —CN, —C(O)OCH$_3$, —C(O)OC$_2$H$_5$, —NH$_2$ or —NHCH$_3$;

each $R^{1b}$ and $R^{1c}$ is independently hydrogen, $C_1$-$C_6$ alkyl, $C_3$-$C_6$ cycloalkyl, 3-6-membered heterocyclyl, $C_6$ aryl, 5-6-membered heteroaryl, —($C_1$-$C_3$ alkylene)($C_3$-$C_6$ cycloalkyl), —($C_1$-$C_3$ alkylene)(3-6-membered heterocyclyl), —($C_1$-$C_3$ alkylene)($C_6$ aryl) or —($C_1$-$C_3$ alkylene)(5-6-membered heteroaryl), wherein each of which is optionally substituted by methyl, ethyl, halogen, oxo, —CF$_3$, —OH, —OCH$_3$, —CN, —C(O)OCH$_3$, —C(O)OC$_2$H$_5$, —NH$_2$ or —NHCH$_3$;

or R$^{1b}$ and R$^{1c}$ are taken together with the nitrogen atom to which they are attached to form a 3- to 6-membered heterocyclyl; R$^2$ is hydrogen, C$_1$-C$_6$ alkyl, C$_2$-C$_6$ alkenyl, C$_2$-C$_6$ alkynyl, C$_6$-C$_{14}$ aryl, C$_5$-C$_{14}$ heteroaryl, C$_3$-C$_6$ cycloalkyl, 3- to 6-membered heterocyclyl, —CN, halogen, —OR$^{2a}$, —SR$^{2a}$, —NR$^{2b}$R$^{2c}$, —C(O)R$^{2a}$, —NR$^{2b}$C(O)R$^{2c}$, —NR$^{2a}$C(O)NR$^{2b}$R$^{2c}$, —C(O)OR$^{2a}$, —C(O)ONR$^{2b}$R$^{2c}$ or —C(O)NR$^{2b}$R$^{2c}$, wherein the C$_1$-C$_6$ alkyl, C$_2$-C$_6$ alkenyl, C$_2$-C$_6$ alkynyl, C$_6$-C$_{14}$ aryl, C$_3$-C$_6$ cycloalkyl and 3- to 6-membered heterocyclyl of R$^2$ are independently optionally substituted by R$^4$;

each R$^{2a}$ is independently hydrogen, C$_1$-C$_6$ alkyl, C$_3$-C$_6$ cycloalkyl, 3- to 6-membered heterocyclyl, C$_6$-aryl, 5- to 6-membered heteroaryl, —(C$_1$-C$_3$ alkylene)N(C$_2$H$_5$)$_2$, —(C$_1$-C$_3$ alkylene)(C$_3$-C$_6$ cycloalkyl), —(C$_1$-C$_3$ alkylene)(3-6-membered heterocyclyl), —(C$_1$-C$_3$ alkylene)(5-6-membered heteroaryl) or —(C$_1$-C$_3$ alkylene)(C$_6$ aryl), wherein each of which is optionally substituted by methyl, ethyl, halogen, oxo, —CF$_3$, —OH, —OCH$_3$, —CN, —C(O)OCH$_3$, —C(O)OC$_2$H$_5$, —NH$_2$ or —NHCH$_3$;

each R$^{2b}$ and R$^{2c}$ is independently hydrogen, C$_1$-C$_6$ alkyl, C$_3$-C$_6$ cycloalkyl, 3- to 6-membered heterocyclyl, C$_6$-aryl, 5- to 6-membered heteroaryl, —(C$_1$-C$_3$ alkylene)N(C$_2$H$_5$)$_2$, —(C$_1$-C$_3$ alkylene)(C$_3$-C$_6$ cycloalkyl), —(C$_1$-C$_3$ alkylene)(3-6-membered heterocyclyl), —(C$_1$-C$_3$ alkylene)(C$_6$ aryl) or —(C$_1$-C$_3$ alkylene)(5-6-membered heteroaryl), wherein each of which is optionally substituted by methyl, ethyl, halogen, oxo, —CF$_3$, —OH, —OCH$_3$, —CN, —C(O)OCH$_3$, —C(O)OC$_2$H$_5$, —NH$_2$ or —NHCH$_3$;

or R$^{2b}$ and R$^{2c}$ are taken together with the nitrogen atom to which they are attached to form a 3- to 6-membered heterocyclyl;

each R$^3$ is independently C$_1$-C$_6$ alkyl, C$_2$-C$_6$ alkenyl, C$_2$-C$_6$ alkynyl, halogen, —CN, —OR$^5$, —SR$^5$, —NR$^6$R$^7$, —NO$_2$, —C=NH(OR$^5$), —C(O)R$^5$, —OC(O)R$^5$, —C(O)OR$^5$, —C(O)NR$^6$R$^7$, —OC(O)NR$^6$R$^7$, —NR$^5$C(O)R$^6$, —NR$^5$C(O)OR$^6$, —NR$^5$C(O)NR$^6$R$^7$, —S(O)R$^5$, —S(O)$_2$R$^5$, —NR$^5$S(O)R$^6$, —C(O)NR$^5$S(O)R$^6$, —NR$^5$S(O)$_2$R$^6$, —C(O)NR$^5$S(O)$_2$R$^6$, —S(O)NR$^6$R$^7$, —S(O)$_2$NR$^6$R$^7$, —P(O)(OR$^6$) (OR$^7$), C$_3$-C$_6$ cycloalkyl, 3-12-membered heterocyclyl, 5- to 10-membered heteroaryl, C$_6$-C$_{14}$ aryl, —(C$_1$-C$_3$ alkylene)CN, —(C$_1$-C$_3$ alkylene)OR$^5$, —(C$_1$-C$_3$ alkylene)SR$^5$, —(C$_1$-C$_3$ alkylene)NR$^6$R$^7$, —(C$_1$-C$_3$ alkylene)CF$_3$, —(C$_1$-C$_3$ alkylene)NO$_2$, —C=NH(OR$^5$), —(C$_1$-C$_3$ alkylene)C(O)R$^5$, —(C$_1$-C$_3$ alkylene)OC(O)R$^5$, —(C$_1$-C$_3$ alkylene)C(O)OR$^5$, —(C$_1$-C$_3$ alkylene)C(O)NR$^6$R$^7$, —(C$_1$-C$_3$ alkylene)OC(O)NR$^6$R$^7$, —(C$_1$-C$_3$ alkylene)NR$^5$C(O)R$^6$, —(C$_1$-C$_3$ alkylene)NR$^5$C(O)OR$^6$, —(C$_1$-C$_3$ alkylene)NR$^5$C(O)NR$^6$R$^7$, —(C$_1$-C$_3$ alkylene)S(O)R$^5$, —(C$_1$-C$_3$ alkylene)S(O)$_2$R$^5$, —(C$_1$-C$_3$ alkylene)NR$^5$S(O)R$^6$, —C(O)(C$_1$-C$_3$ alkylene)NR$^5$S(O)R$^6$, —(C$_1$-C$_3$ alkylene)NR$^5$S(O)$_2$R$^6$, —(C$_1$-C$_3$ alkylene)C(O)NR$^5$S(O)$_2$R$^6$, —(C$_1$-C$_3$ alkylene)S(O)NR$^6$R$^7$, —(C$_1$-C$_3$ alkylene)S(O)$_2$NR$^6$R$^7$, —(C$_1$-C$_3$ alkylene)P(O)(OR$^6$)(OR$^7$), —(C$_1$-C$_3$ alkylene)(C$_3$-C$_6$ cycloalkyl), —(C$_1$-C$_3$ alkylene)(3-12-membered heterocyclyl), —(C$_1$-C$_3$ alkylene)(5-10-membered heteroaryl) or —(C$_1$-C$_3$ alkylene)(C$_6$-C$_{14}$ aryl), wherein each R$^3$ is independently optionally substituted by halogen, oxo, —OR$^8$, —NR$^8$R$^9$, —C(O)R$^8$, —CN, —S(O)R$^8$, —S(O)$_2$R$^8$, —P(O)(OR$^8$)(OR$^9$), —(C$_1$-C$_3$ alkylene)OR$^8$, —(C$_1$-C$_3$ alkylene)NR$^8$R$^9$, —(C$_1$-C$_3$ alkylene)C(O)R$^8$, —(C$_1$-C$_3$ alkylene)S(O)R$^8$, —(C$_1$-C$_3$ alkylene)S(O)$_2$R$^8$, —(C$_1$-C$_3$ alkylene)P(O)(OR$^8$)(OR$^9$), C$_3$-C$_8$ cycloalkyl, or C$_1$-C$_6$ alkyl optionally substituted by oxo, —OH or halogen;

each R$^4$ is independently oxo or R$^3$;

R$^5$ is independently hydrogen, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl or 3-6-membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl and 3-6-membered heterocyclyl of R$^5$ are independently optionally substituted by halogen, oxo, —CN, —OR$^9$, —NR$^9$R$^{10}$, —P(O)(OR$^9$)(OR$^{10}$), phenyl optionally substituted by halogen, or C$_1$-C$_6$ alkyl optionally substituted by halogen, —OH or oxo;

R$^6$ and R$^7$ are each independently hydrogen, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl, —(C$_1$-C$_3$ alkylene)(C$_6$ aryl) or 3-6 membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl, —(C$_1$-C$_3$ alkylene)(C$_6$ aryl) and 3-6 membered heterocyclyl of R$^6$ and R$^7$ are independently optionally substituted by halogen, oxo, —CN, —OR$^9$, —NR$^9$R$^{10}$ or C$_1$-C$_6$ alkyl optionally substituted by halogen, —OH or oxo;

or R$^6$ and R$^7$ are taken together with the atom to which they attached to form a 3-6 membered heterocyclyl optionally substituted by halogen, oxo, —OR$^9$, —NR$^9$R$^{10}$ or C$_1$-C$_6$ alkyl optionally substituted by halogen, oxo or —OH;

R$^8$ and R$^9$ in R$^3$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo;

or R$^8$ and R$^9$ in R$^3$ are taken together with the atom to which they attached to form a 3-6 membered heterocyclyl optionally substituted by halogen, oxo or C$_1$-C$_6$ alkyl optionally substituted by halogen or oxo; and R$^9$ and R$^{10}$ in R$^5$, R$^6$ and R$^7$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo;

or R$^9$ and R$^{10}$ in R$^5$, R$^6$ and R$^7$ are taken together with the atom to which they attached to form a 3-6 membered heterocyclyl optionally substituted by halogen, oxo or C$_1$-C$_6$ alkyl optionally substituted by oxo or halogen.

In some embodiments, provided is a compound of the formula (I):

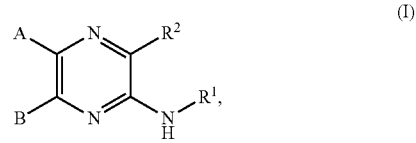

or a salt thereof, wherein:

A is 4-hydroxyphenyl optionally further substituted by R$^3$, 4-hydroxy-2-pyridyl optionally further substituted by R$^4$, or a 9- or 10-membered bicyclic heteroaryl optionally substituted by R$^4$;

B is a phenyl optionally substituted by R$^3$, or a 5- to 6-membered heteroaryl optionally substituted by R$^4$;

R$^1$ is a hydrogen, C$_1$-C$_6$ alkyl, C$_2$-C$_6$ alkenyl, C$_2$-C$_6$ alkynyl, C$_3$-C$_6$ cycloalkyl, 3- to 6-membered heterocyclyl, —C(O)R$^{1a}$, —C(O)OR$^{1a}$, —C(O)NR$^{1b}$R$^{1c}$, or wherein the C$_1$-C$_6$ alkyl, C$_2$-C$_6$ alkenyl, C$_2$-C$_6$ alkynyl, C$_3$-C$_6$ cycloalkyl and 3- to 6-membered heterocyclyl of R$^1$ are independently optionally substituted by R$^4$;

each $R^{1a}$ is independently hydrogen, $C_1$-$C_6$ alkyl, or $C_3$-$C_6$ cycloalkyl;

each $R^{1b}$ and $R^{1c}$ is independently hydrogen, $C_1$-$C_6$ alkyl, or $C_3$-$C_6$ cycloalkyl;

or $R^{1b}$ and $R^{1c}$ are taken together with the nitrogen atom to which they are attached to form a 3- to 6-membered heterocyclyl;

$R^2$ is hydrogen, $C_1$-$C_6$ alkyl, $C_2$-$C_6$ alkenyl, $C_2$-$C_6$ alkynyl, $C_6$-$C_{14}$ aryl, —CN, halogen, —OR$^{2a}$, —NR$^{2b}$R$^{2c}$, —C(O)R$^{2a}$, —C(O)OR$^{2a}$, or —C(O)NR$^{2b}$R$^{2c}$, wherein the $C_1$-$C_6$ alkyl, $C_2$-$C_6$ alkenyl, $C_2$-$C_6$ alkynyl and $C_6$-$C_{14}$ aryl of $R^2$ are independently optionally substituted by $R^4$;

each $R^{2a}$ is independently hydrogen, $C_1$-$C_6$ alkyl, or $C_3$-$C_6$ cycloalkyl;

each $R^{2b}$ and $R^{2c}$ is independently hydrogen, $C_1$-$C_6$ alkyl, or $C_3$-$C_6$ cycloalkyl;

or $R^{2b}$ and $R^{2c}$ are taken together with the nitrogen atom to which they are attached to form a 3- to 6-membered heterocyclyl;

each $R^3$ is independently $C_1$-$C_6$ alkyl, $C_2$-$C_6$ alkenyl, $C_2$-$C_6$ alkynyl, halogen, —CN, —OR$^5$, —SR$^5$, —NR$^6$R$^7$, —NO$_2$, —C=NH(OR$^5$), —C(O)R$^5$, —OC(O)R$^5$, —C(O)OR$^5$, —C(O)NR$^6$R$^7$, —OC(O)NR$^6$R$^7$, —NR$^5$C(O)R$^6$, —NR$^5$C(O)OR$^6$, —NR$^5$C(O)NR$^6$R$^7$, —S(O)R$^5$, —S(O)$_2$R$^5$, —NR$^5$S(O)R$^6$, —C(O)NR$^5$S(O)R$^6$, —NR$^5$S(O)$_2$R$^6$, —C(O)NR$^5$S(O)$_2$R$^6$, —S(O)NR$^6$R$^7$, —S(O)$_2$NR$^6$R$^7$, —P(O)(OR$^6$)(OR$^7$), $C_3$-$C_6$ cycloalkyl, 3-12-membered heterocyclyl, 5- to 10-membered heteroaryl, $C_6$-$C_{14}$ aryl, —($C_1$-$C_3$ alkylene)CN, —($C_1$-$C_3$ alkylene)OR$^5$, —($C_1$-$C_3$ alkylene)SR$^5$, —($C_1$-$C_3$ alkylene)NR$^6$R$^7$, —($C_1$-$C_3$ alkylene)CF$_3$, —($C_1$-$C_3$ alkylene)NO$_2$, —C=NH(OR$^5$), —($C_1$-$C_3$ alkylene)C(O)R$^5$, —($C_1$-$C_3$ alkylene)OC(O)R$^5$, —($C_1$-$C_3$ alkylene)C(O)OR$^5$, —($C_1$-$C_3$ alkylene)C(O)NR$^6$R$^7$, —($C_1$-$C_3$ alkylene)OC(O)NR$^6$R$^7$, —($C_1$-$C_3$ alkylene)NR$^5$C(O)R$^6$, —($C_1$-$C_3$ alkylene)NR$^5$C(O)OR$^6$, —($C_1$-$C_3$ alkylene)NR$^5$C(O)NR$^6$R$^7$, —($C_1$-$C_3$ alkylene)S(O)R$^5$, —($C_1$-$C_3$ alkylene)S(O)$_2$R$^5$, —($C_1$-$C_3$ alkylene)NR$^5$S(O)R$^6$, —C(O)($C_1$-$C_3$ alkylene)NR$^5$S(O)R$^6$, —($C_1$-$C_3$ alkylene)NR$^5$S(O)$_2$R$^6$, —($C_1$-$C_3$ alkylene)C(O)NR$^5$S(O)$_2$R$^6$, —($C_1$-$C_3$ alkylene)S(O)NR$^6$R$^7$, —($C_1$-$C_3$ alkylene)S(O)$_2$NR$^6$R$^7$, —($C_1$-$C_3$ alkylene)P(O)(OR$^6$)(OR$^7$), —($C_1$-$C_3$ alkylene)($C_3$-$C_6$ cycloalkyl), —($C_1$-$C_3$ alkylene)(3-12-membered heterocyclyl), —($C_1$-$C_3$ alkylene)(5-10-membered heteroaryl) or —($C_1$-$C_3$ alkylene)($C_6$-$C_{14}$ aryl), wherein each $R^3$ is independently optionally substituted by halogen, oxo, —OR$^8$, —NR$^8$R$^9$, —C(O)R$^8$, —CN, —S(O)R$^8$, —S(O)$_2$R$^8$, —P(O)(OR$^8$)(OR$^9$), —($C_1$-$C_3$ alkylene)OR$^8$, —($C_1$-$C_3$ alkylene)NR$^8$R$^9$, —($C_1$-$C_3$ alkylene)C(O)R$^8$, —($C_1$-$C_3$ alkylene)S(O)R$^8$, —($C_1$-$C_3$ alkylene)S(O)$_2$R$^8$, —($C_1$-$C_3$ alkylene)P(O)(OR$^8$)(OR$^9$), $C_3$-$C_5$ cycloalkyl, or $C_1$-$C_6$ alkyl optionally substituted by oxo, —OH or halogen;

each $R^4$ is independently oxo or $R^3$;

$R^5$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6-membered heterocyclyl of $R^5$ are independently optionally substituted by halogen, oxo, —CN, —OR$^9$, —NR$^9$R$^{10}$, —P(O)(OR$^9$)(OR$^{10}$), phenyl optionally substituted by halogen, or $C_1$-$C_6$ alkyl optionally substituted by halogen, —OH or oxo;

$R^6$ and $R^7$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6 membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6 membered heterocyclyl of $R^6$ and $R^7$ are independently optionally substituted by halogen, oxo, —CN, —OR$^9$, —NR$^9$R$^{10}$ or $C_1$-$C_6$ alkyl optionally substituted by halogen, —OH or oxo;

or $R^6$ and $R^7$ are taken together with the atom to which they attached to form a 3-6 membered heterocyclyl optionally substituted by halogen, oxo, —OR$^9$—NR$^9$R$^{10}$ or $C_1$-$C_6$, alkyl optionally substituted by halogen, oxo or —OH;

$R^8$ and $R^9$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or $R^8$ and $R^9$ are taken together with the atom to which they attached to form a 3-6 membered heterocyclyl optionally substituted by halogen, oxo or $C_1$-$C_6$ alkyl optionally substituted by halogen or oxo; and $R^9$ and $R^{10}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or $R^9$ and $R^{10}$ are taken together with the atom to which they attached to form a 3-6 membered heterocyclyl optionally substituted by halogen, oxo or $C_1$-$C_6$ alkyl optionally substituted by oxo or halogen.

In some embodiments, the compound of formula (I) or a salt thereof is other than a compound selected from Table 1 or a salt thereof. In some embodiments, the compound of formula (I) or a tautomer or isomer thereof, or a pharmaceutically acceptable salt of any of the foregoing is other than a compound seletec from Table 1 or a tautomer or isomer thereof, or a pharmaceutically acceptable salt of any of the foregoing.

TABLE 1

| Compound No. | Compound Name |
|---|---|
| 1x | 5-(1-ethyl-1H-indol-5-yl)-6-(3-pyridinyl)-2-pyrazinamine |
| 2x | 5-(1-ethyl-1H-indol-5-yl)-6-(2H-tetrazol-5-yl)-2-pyrazinamine |
| 3x | 2-[6-amino-3-(1-ethyl-2-fluoro-1H-indol-5-yl)-2-pyrazinyl]-4-fluorophenol |
| 4x | 5-(1-ethyl-1H-indol-5-yl)-6-(3-thienyl)-2-pyrazinamine |
| 5x | 2-[6-amino-3-(1-ethyl-1H-indol-5-yl)-2-pyrazinyl]-6-fluorophenol |
| 6x | 5-(1-ethyl-1H-indol-5-yl)-6-(1H-pyrazol-3-yl)-2-pyrazinamine |
| 7x | 2-[6-amino-3-(1-ethyl-2-methyl-1H-indol-5-yl)-2-pyrazinyl]-4-fluorophenol |
| 8x | 5-[6-amino-3-(1-ethyl-1H-indol-5-yl)-2-pyrazinyl]-4(3H)-pyrimidinone |
| 9x | 5-(2-benzofuranyl)-6-(4-pyridinyl)-2,3-pyrazinediamine |
| 10x | 2-[6-amino-3-(1-ethyl-2-methyl-1H-benzimidazol-5-yl)-2-pyrazinyl]-4-fluorophenol |
| 11x | 5-(1-ethyl-1H-indol-5-yl)-6-(1H-pyrrol-2-yl)-2-pyrazinamine |
| 12x | 2-[6-amino-3-(1-ethyl-1H-indol-5-yl)-2-pyrazinyl]-4-fluorophenol |

TABLE 1-continued

| Compound No. | Compound Name |
|---|---|
| 13x | 3-[6-amino-3-(1-ethyl-1H-indol-5-yl)-2-pyrazinyl]-2(1H)-pyridinone |
| 14x | 5-(1-ethyl-1H-indol-5-yl)-6-[5-fluoro-2-(phenylmethoxy)phenyl]-2-pyrazinamine |
| 15x | 2-[6-amino-3-(1-ethyl-1H-benzimidazol-5-yl)-2-pyrazinyl]-4-fluorophenol |
| 16x | 5-(1-ethyl-1H-indol-5-yl)-6-(2-thienyl)-2-pyrazinamine |
| 17x | 2-[6-amino-3-(1-ethyl-1H-indol-5-yl)-2-pyrazinyl]phenol |
| 18x | 5,6-bis(1-phenyl-1H-benzimidazol-2-yl)-2,3-pyrazinediamine |

In some embodiments, $R^1$ is a hydrogen, $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, 5- to 10-membered heteroaryl, —C(O)$R^{1a}$, —C(O)O$R^{1a}$, —C(O)N$R^{1b}R^{1c}$, or x or —S(O)$_2R^{1a}$, wherein the $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, and 5- to 10-membered heteroaryl are optionally substituted with $R^4$. In some embodiments, $R^1$ is hydrogen, $C_1$-$C_6$ alkyl or —C(O)$R^{1a}$. In certain embodiments, $R^1$ is hydrogen. In certain embodiments, $R^1$ is —C(O)$R^{1a}$ where $R^{1a}$ is $C_1$-$C_6$ alkyl (e.g., methyl) or $C_3$-$C_6$ cycloalkyl. It is understood that each $R^1$ may be combined with each $R^2$, A and/or B the same as if each and every combination of $R^1$ with $R^2$, A and/or B were specifically and individually listed.

In some embodiments $R^2$ is selected from the group consisting of: hydrogen, fluoro, chloro, bromo, —CN, methyl, ethyl, isopropyl, propyl, tert-butyl, isopropenyl, —OCH$_3$, —C(O)OCH$_3$, —C(O)OH, —C(O)ONH$_2$, —CH$_2$NH$_2$, —NH$_2$, —NHCH$_3$, —N(CH$_3$)$_2$, —OH, —CF$_3$, —OCF$_3$,

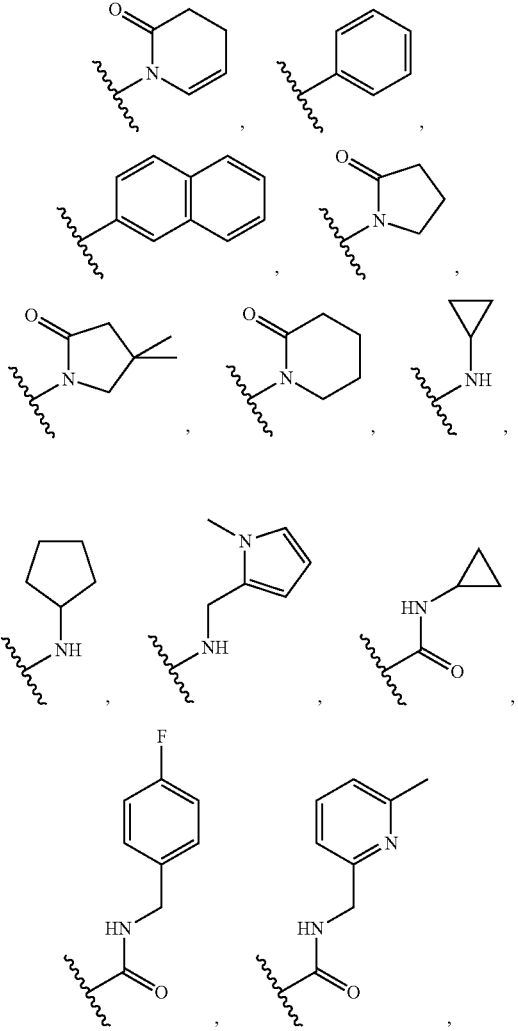

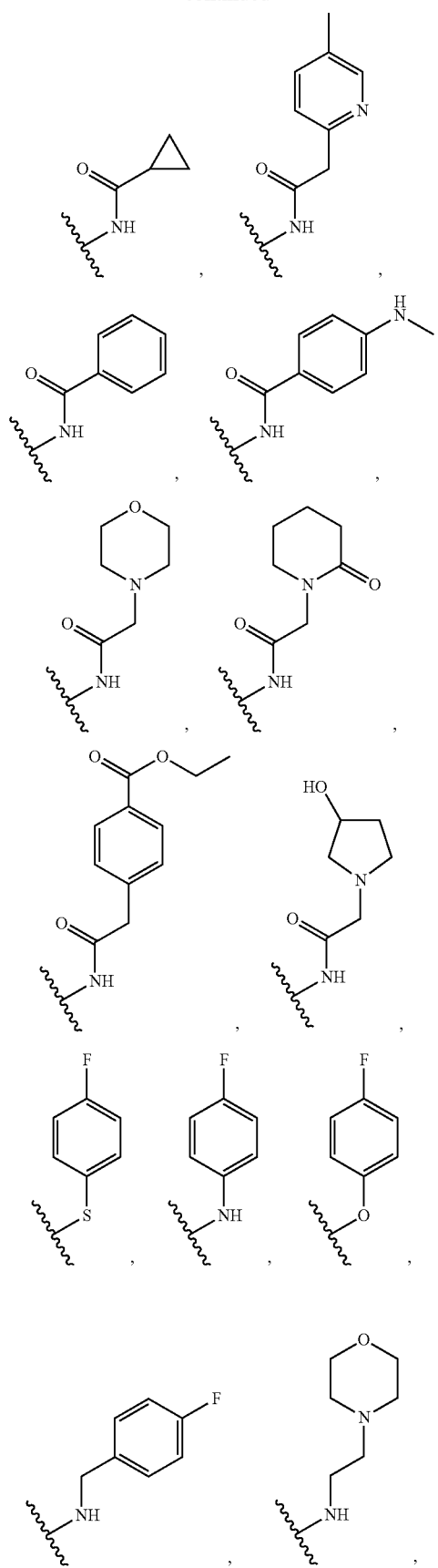
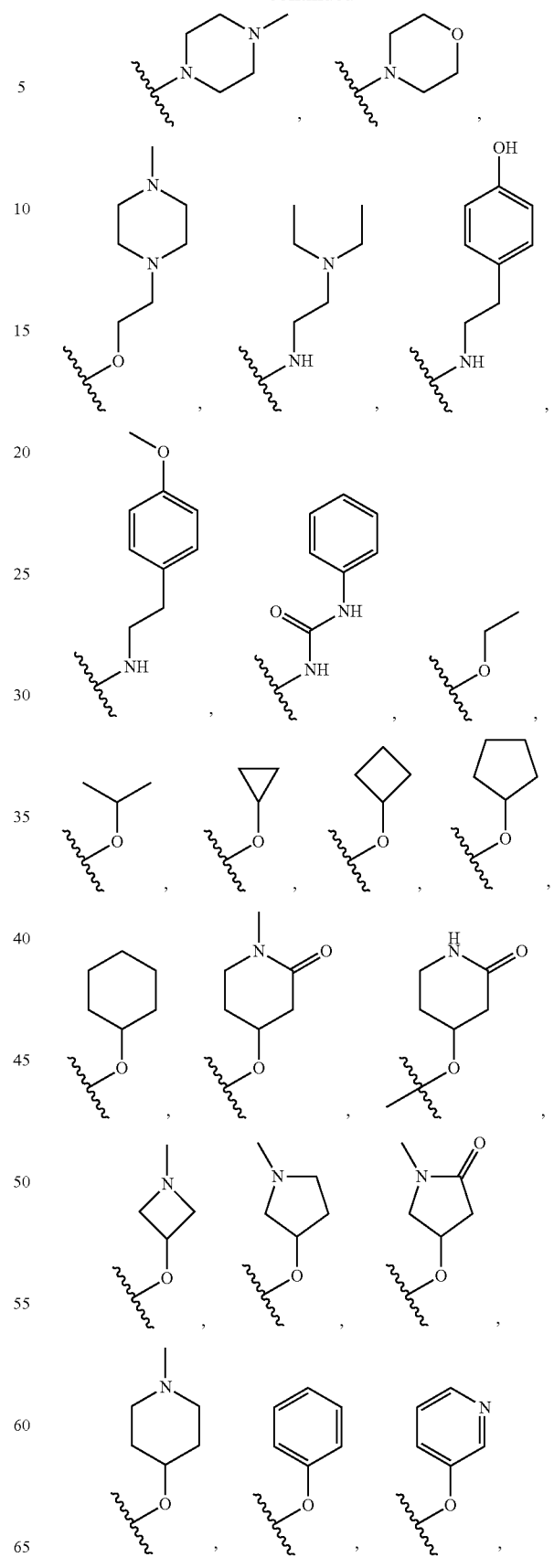

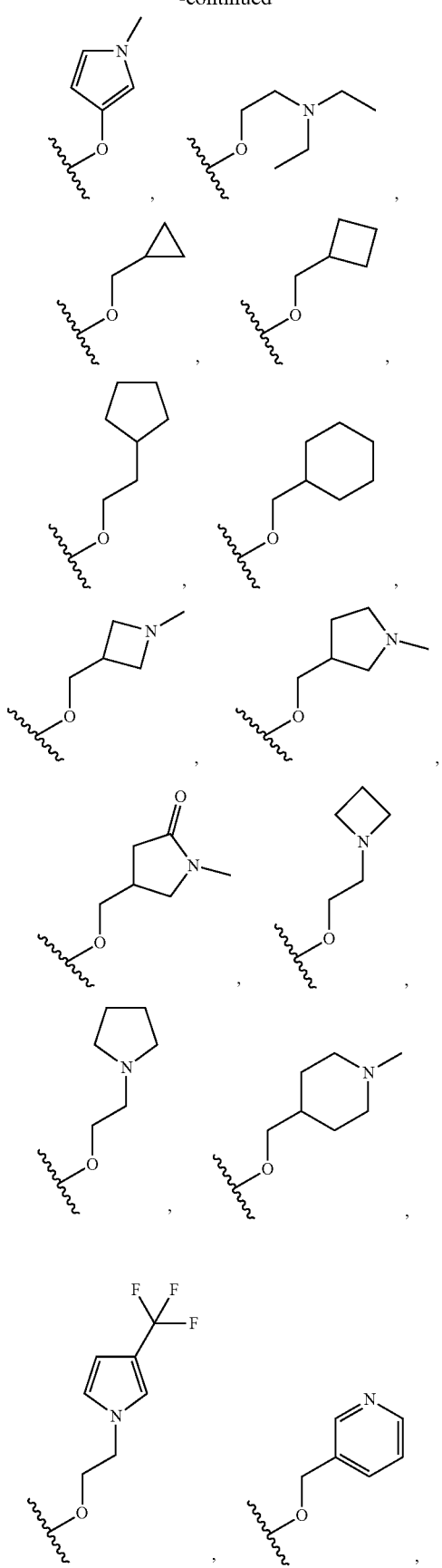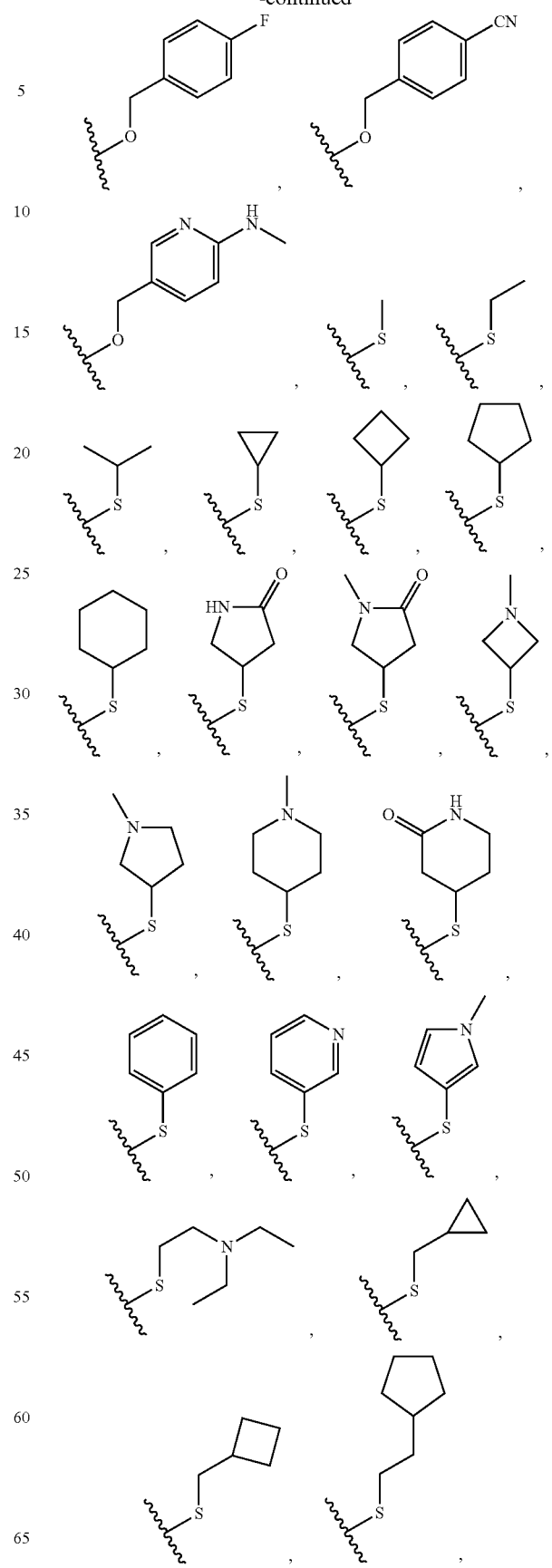

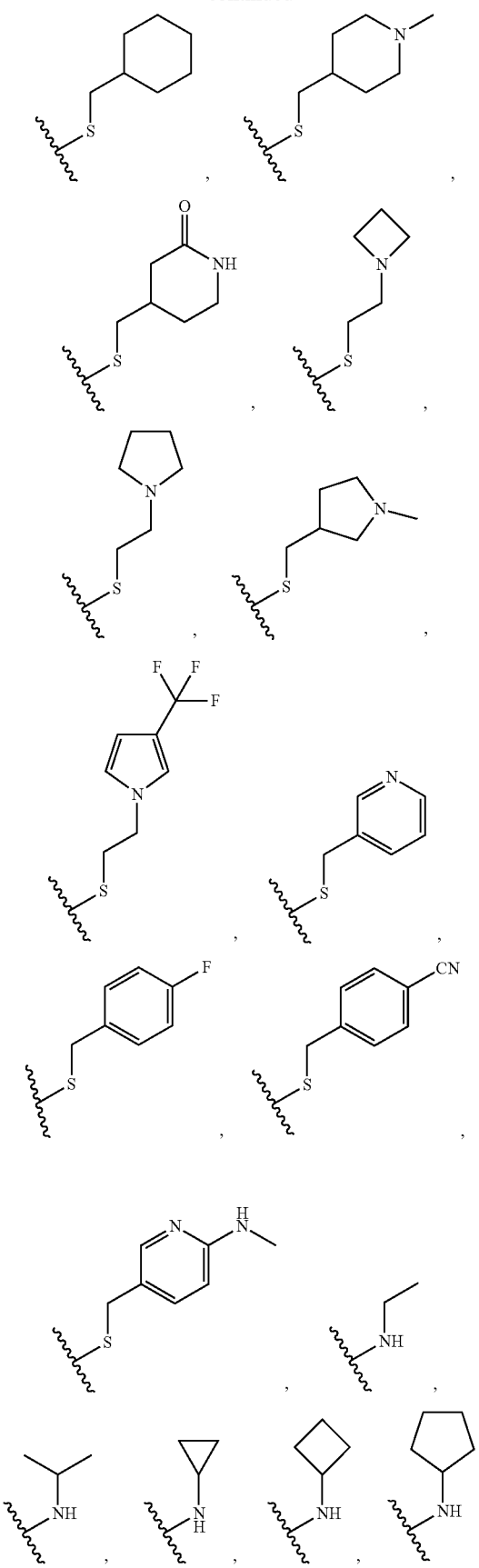
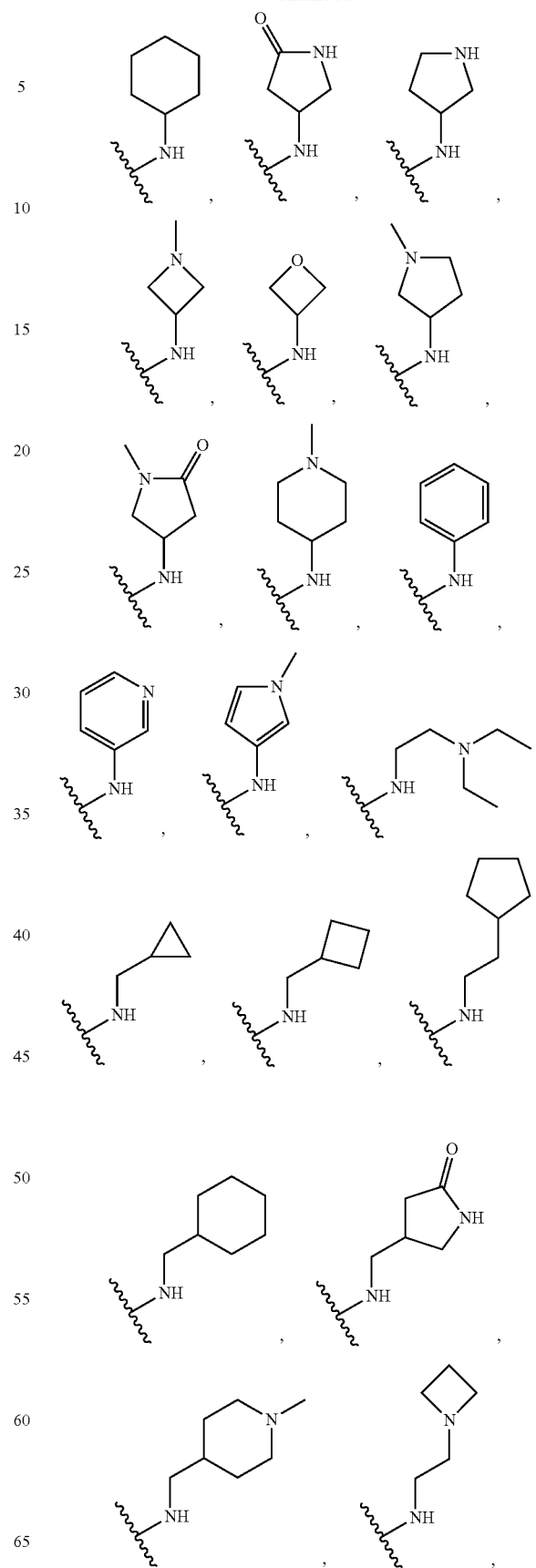

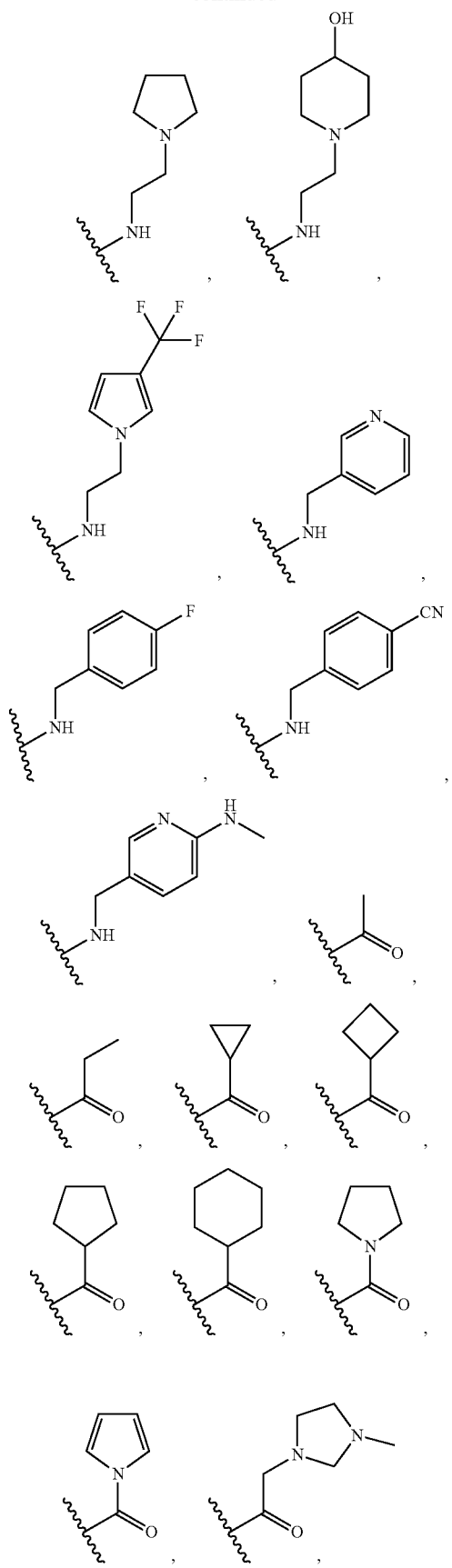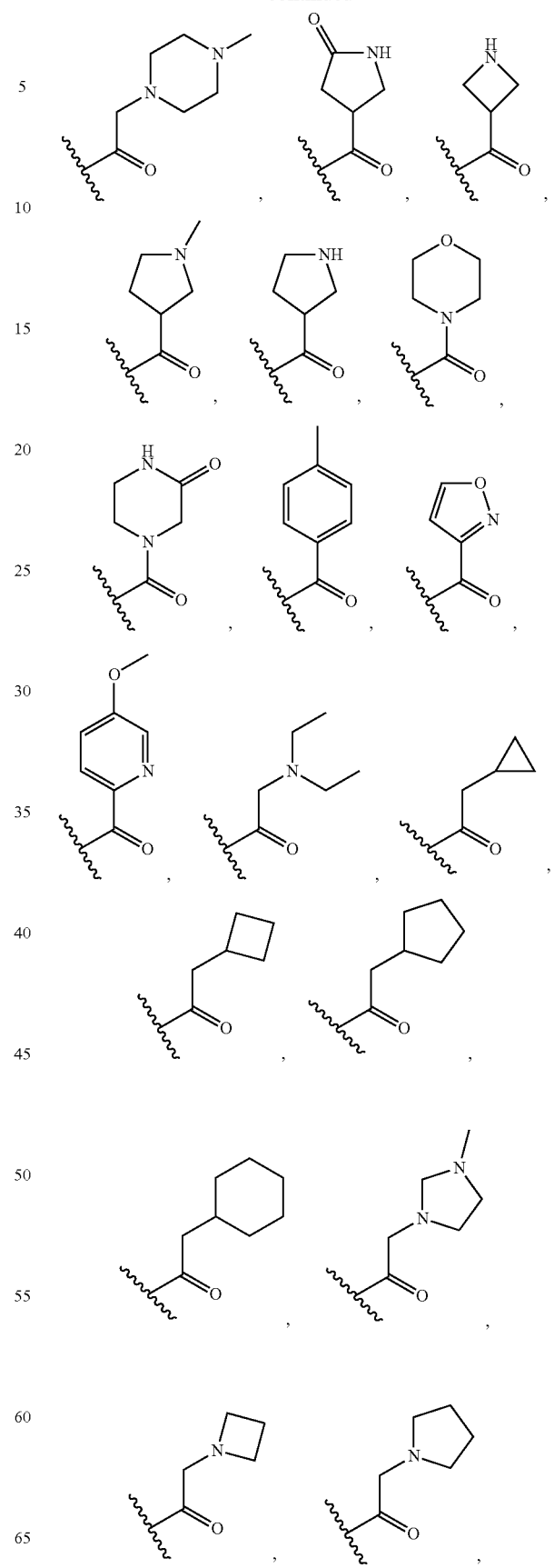

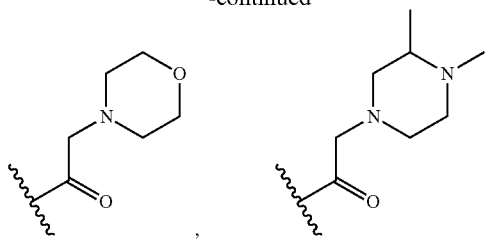
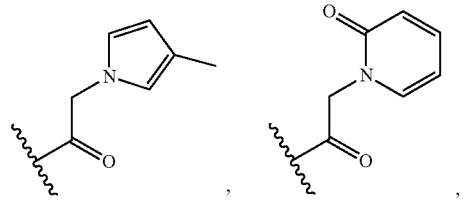
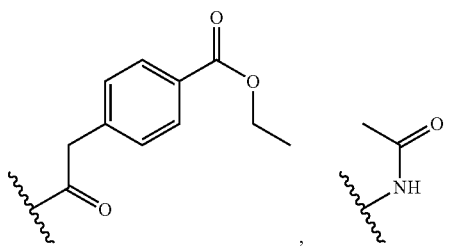
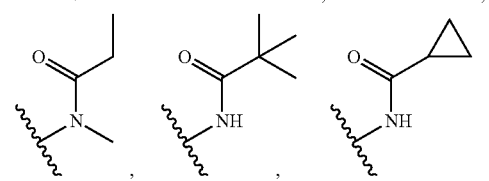
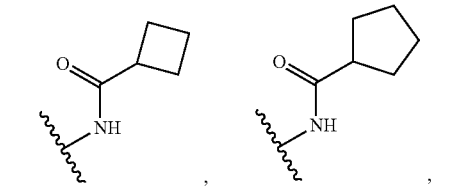
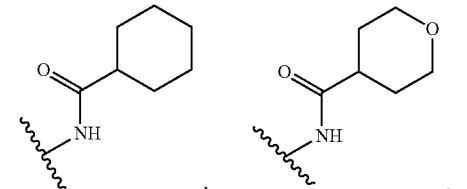
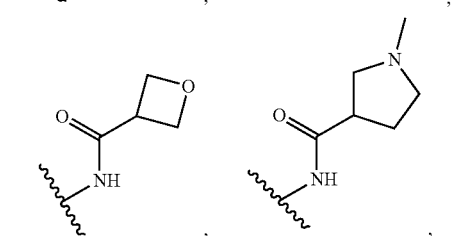
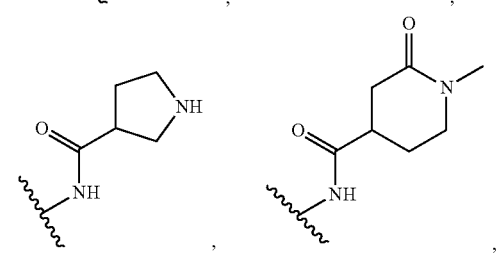
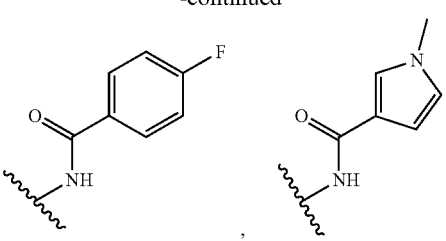
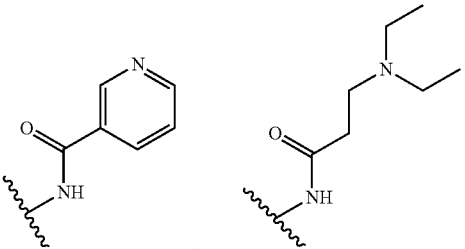
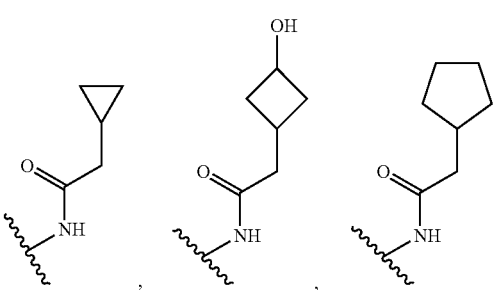
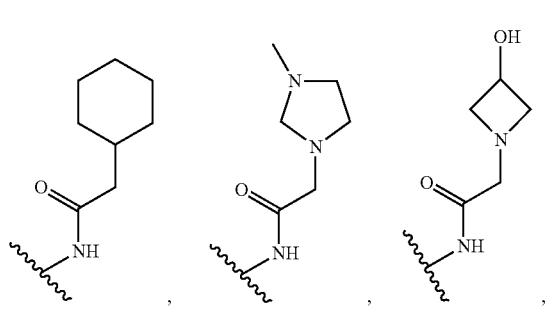
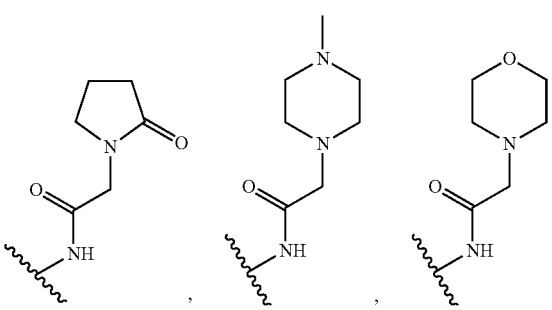

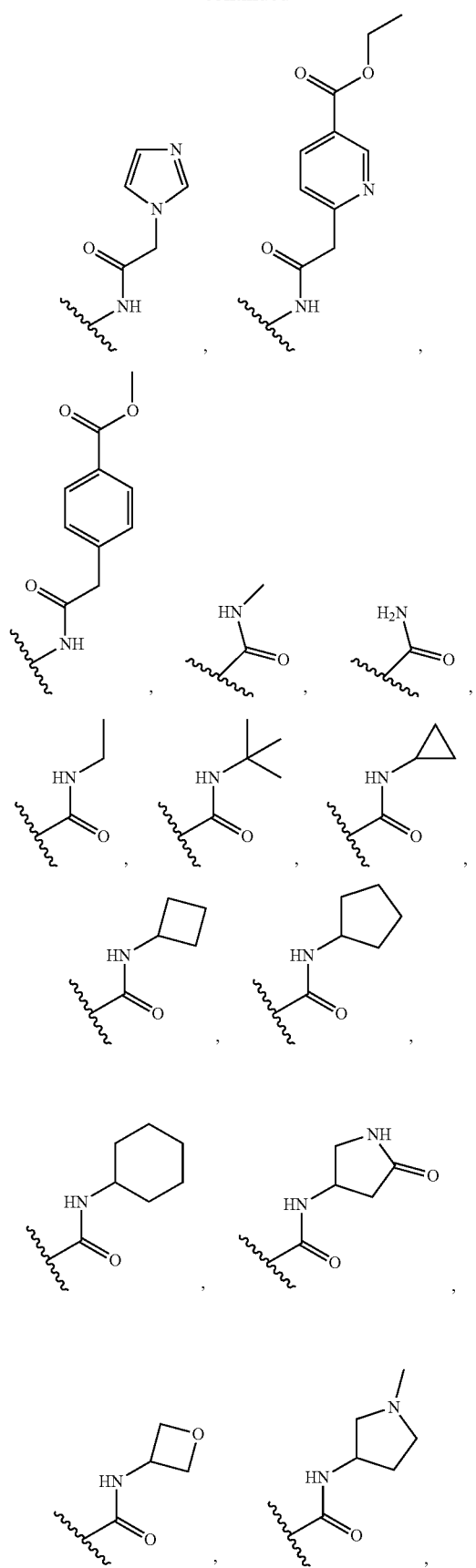
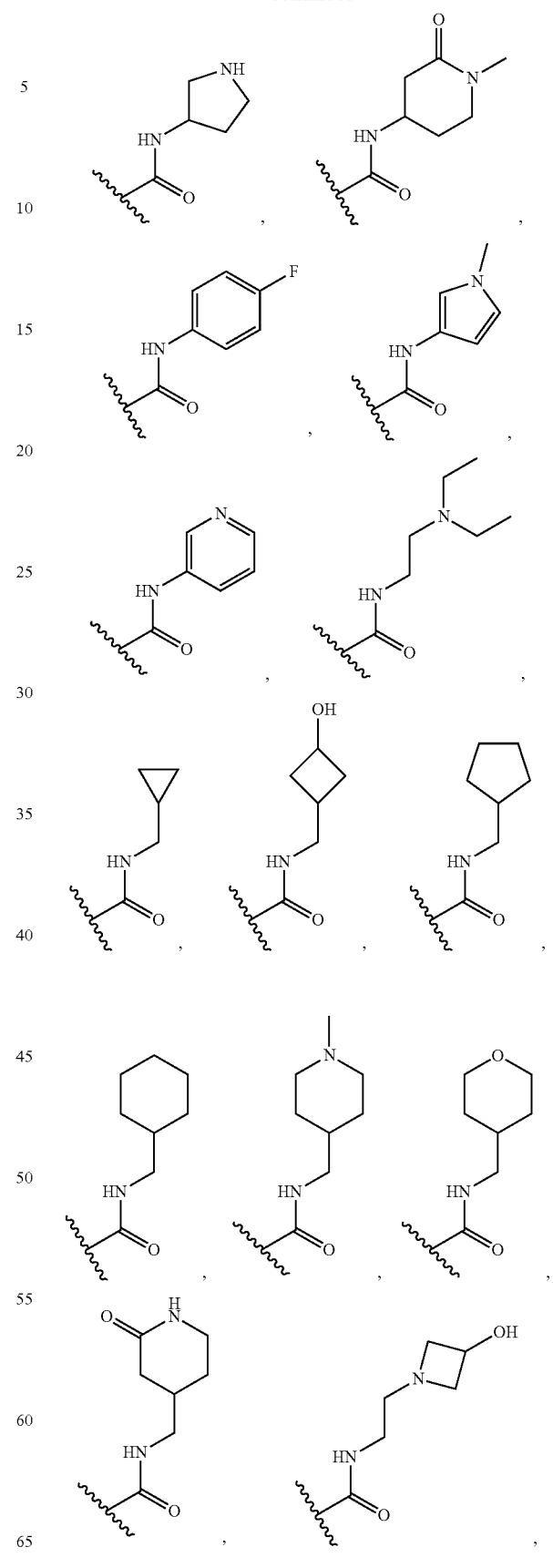

27
-continued
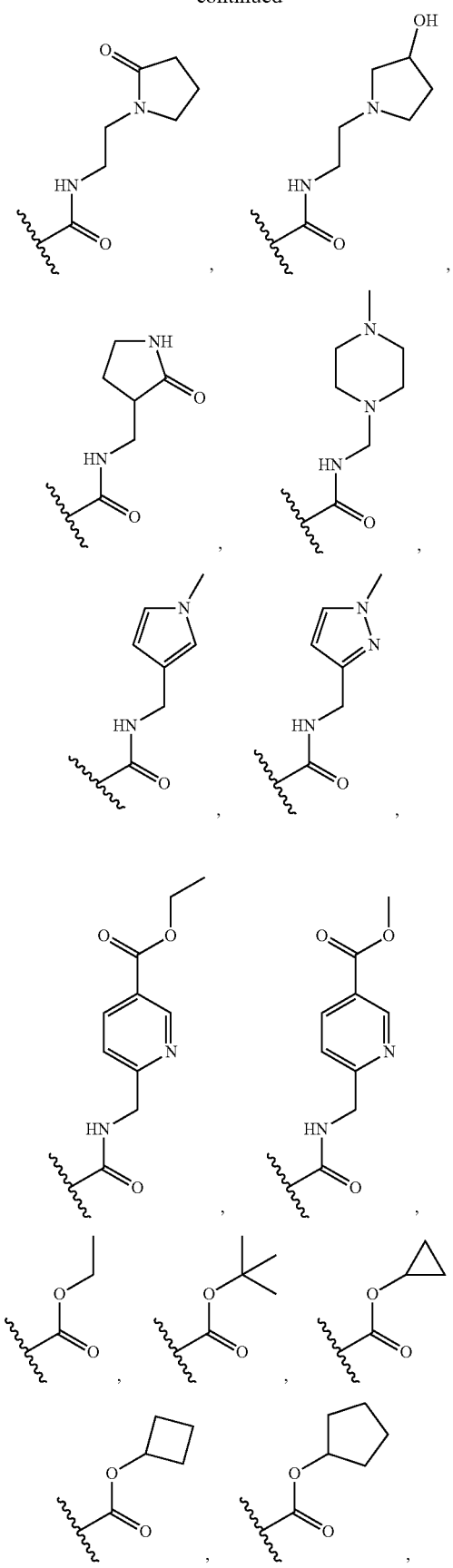
28
-continued
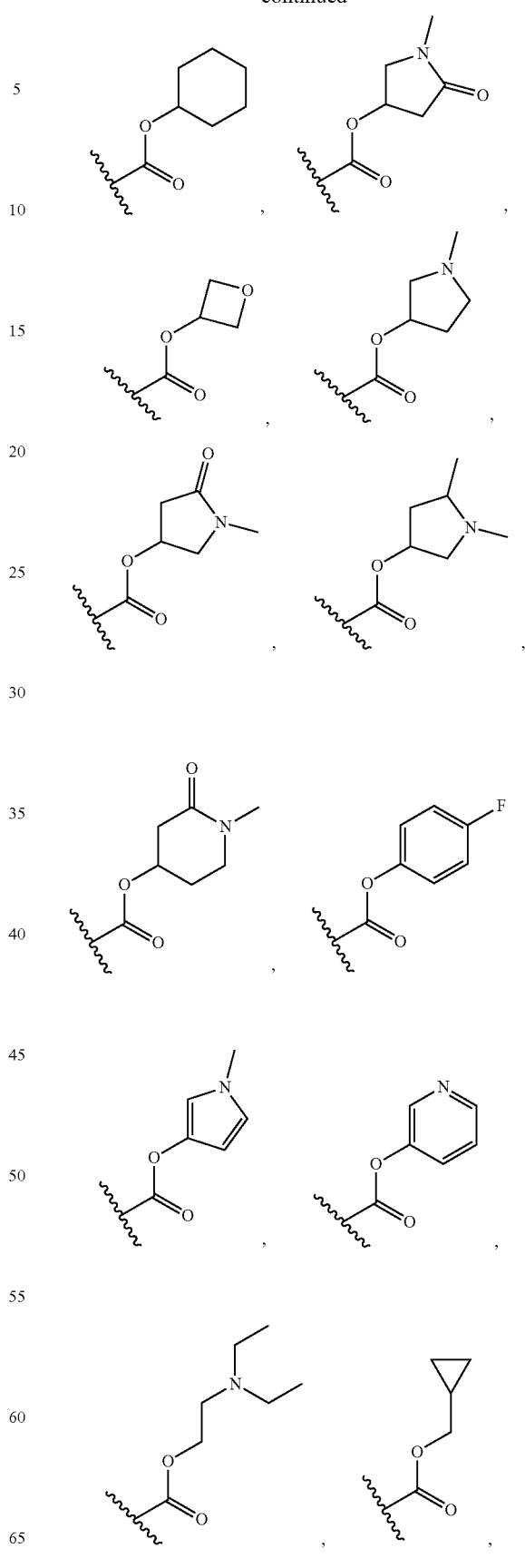

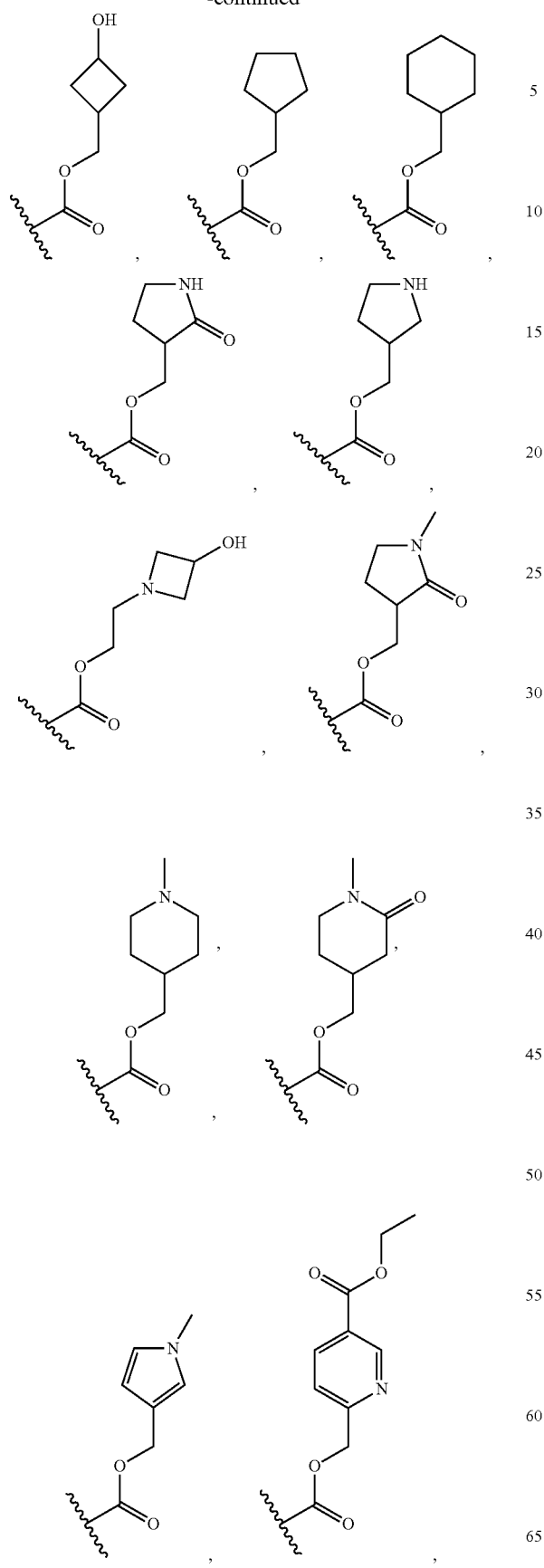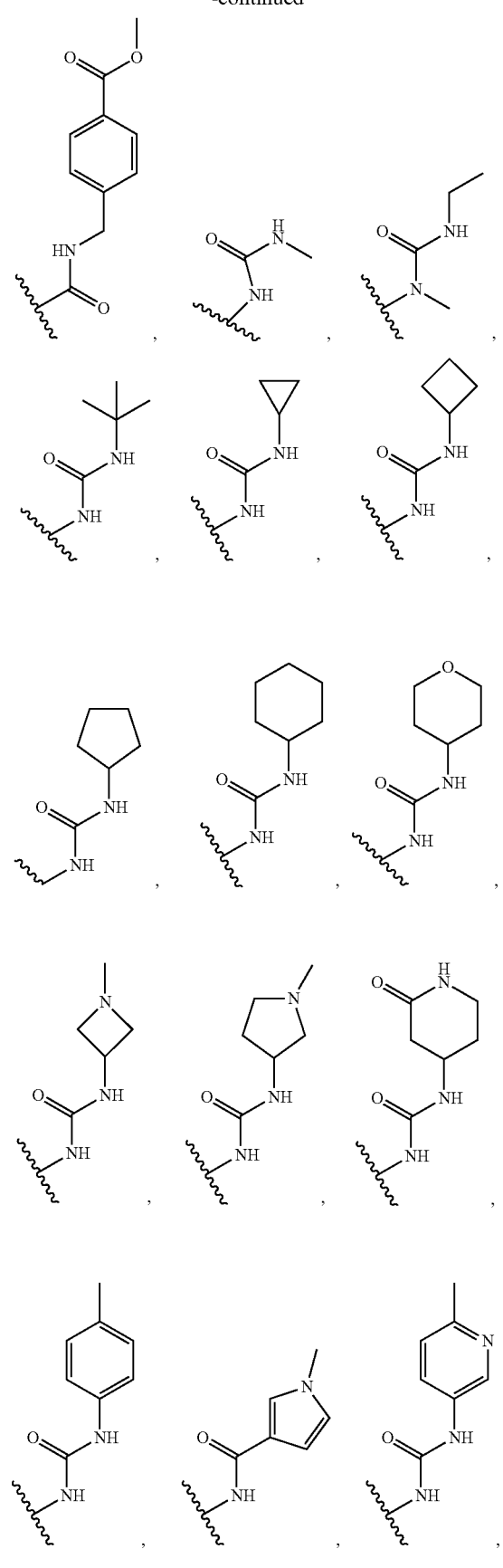

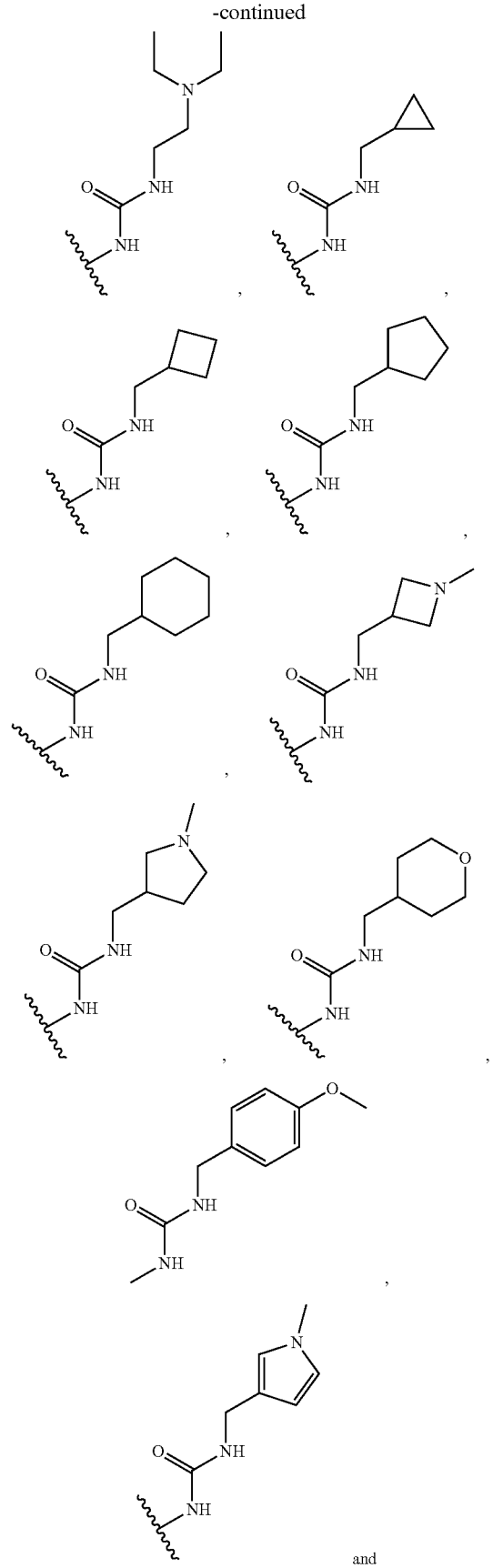

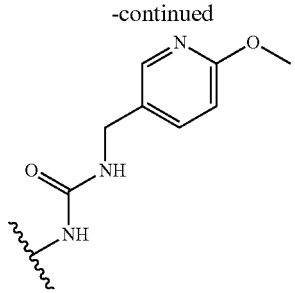

;

wherein the wavy lines denote attachment points to the parent molecule.

In some embodiments $R^2$ is selected from the group consisting of: hydrogen, fluoro, chloro, bromo, —CN, methyl, ethyl, isopropyl, propyl, tert-butyl, isopropenyl, —OCH$_3$, —C(O)OCH$_3$, —C(O)OH, —C(O)ONH$_2$, —CH$_2$NH$_2$, —NH$_2$, —NHCH$_3$, —N(CH$_3$)$_2$, —OH, —CF$_3$, —OCF$_3$,

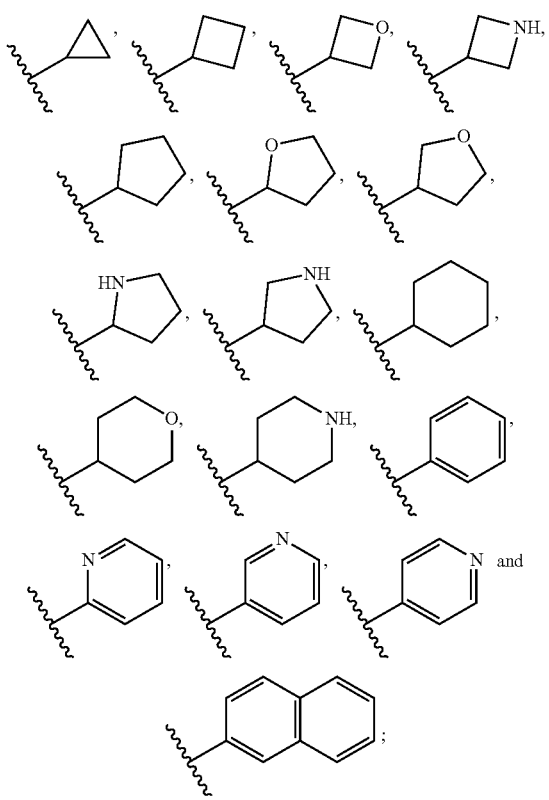

wherein the wavy lines denote attachment points to the parent molecule.

In some embodiments $R^2$ is selected from the group consisting of: hydrogen, fluoro, chloro, bromo, —CN, methyl, ethyl, isopropyl, propyl, tert-butyl, isopropenyl, —OCH$_3$, —C(O)OCH$_3$, —C(O)OH, —C(O)ONH$_2$, —CH$_2$NH$_2$, —NH$_2$, —NHCH$_3$, —N(CH$_3$)$_2$, —OH, —CF$_3$, —OCF$_3$,

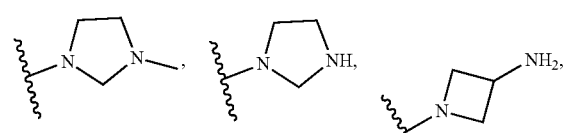
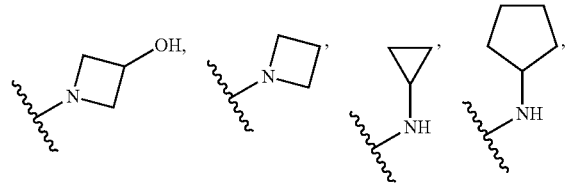
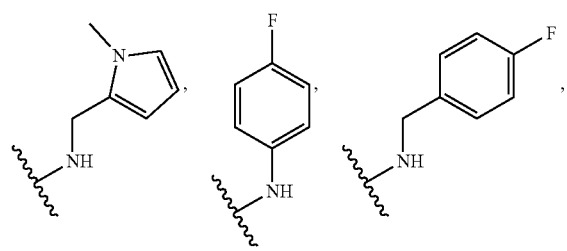
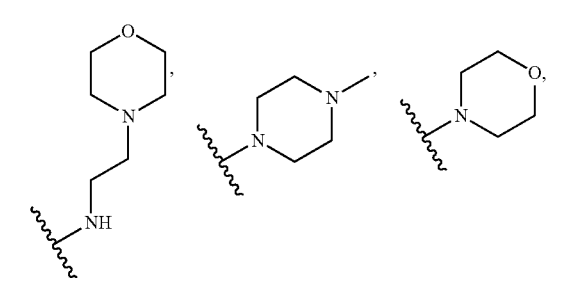
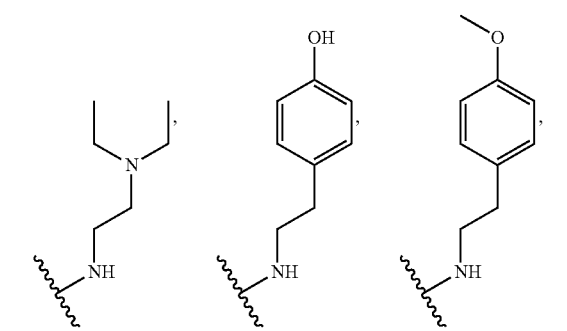
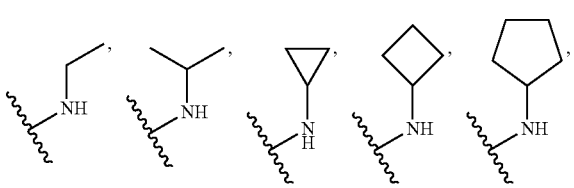
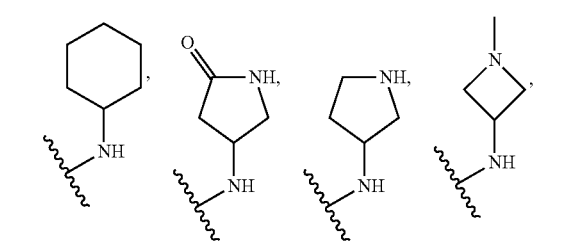
-continued
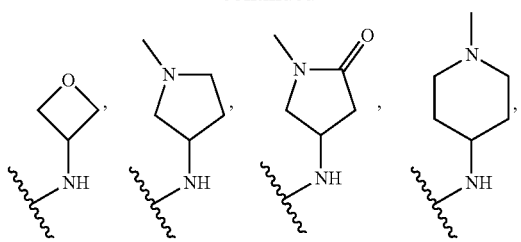
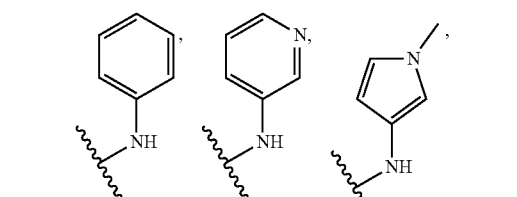
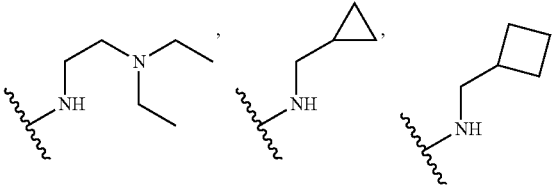
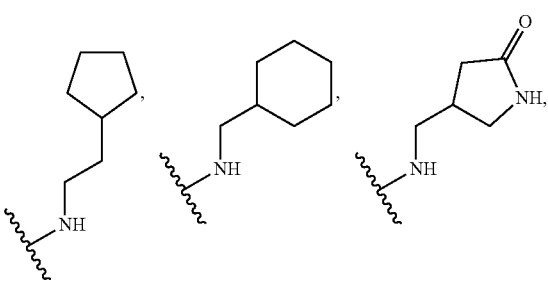
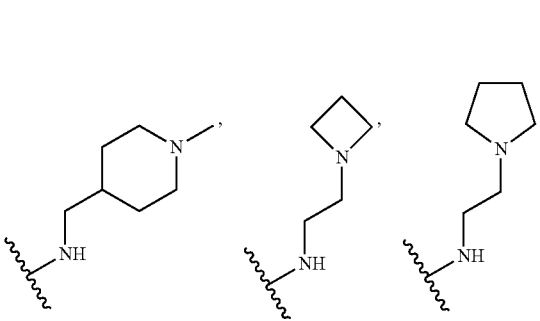
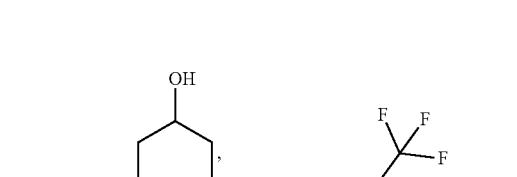
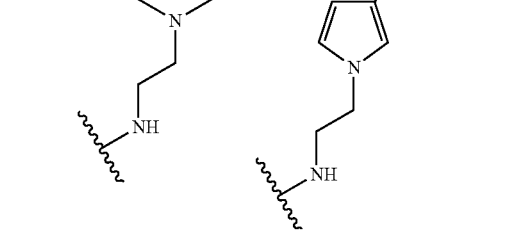

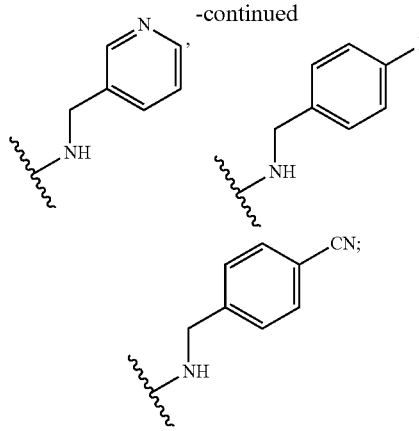
wherein the wavy lines denote attachment points to the parent molecule.
In some embodiments $R^2$ is selected from the group consisting of: hydrogen, fluoro, chloro, bromo, —CN, methyl, ethyl, isopropyl, propyl, tert-butyl, isopropenyl —OCH$_3$, —C(O)OCH$_3$, —C(O)OH, —C(O)ONH$_2$, —CH$_2$NH$_2$, —NHCH$_3$, —N(CH$_3$)$_2$, —OH, —CF$_3$, —OCF$_3$,
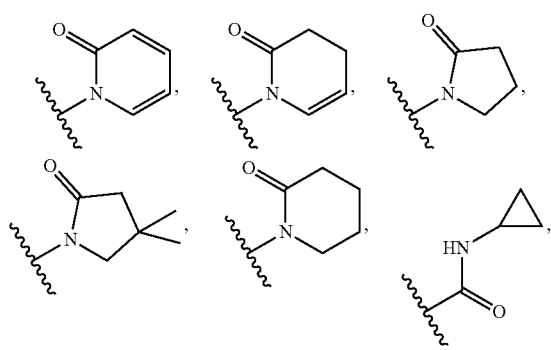
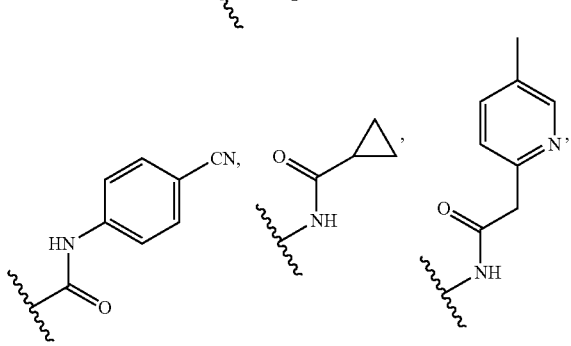
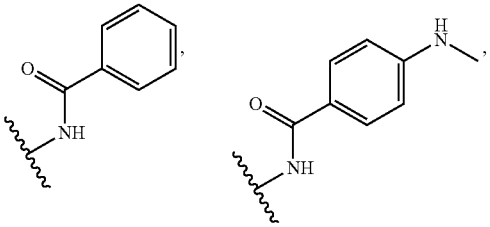
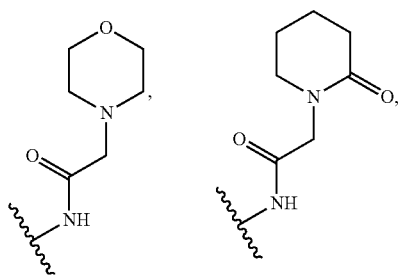
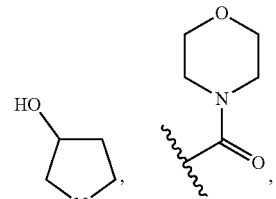
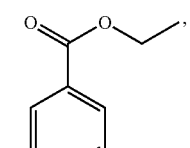
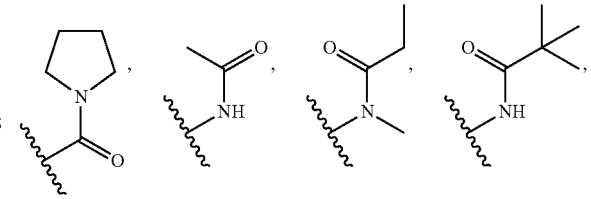
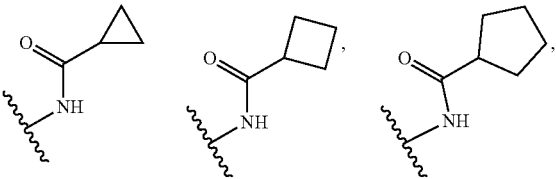
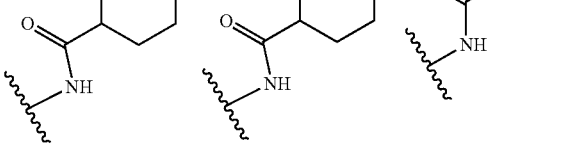

37
-continued
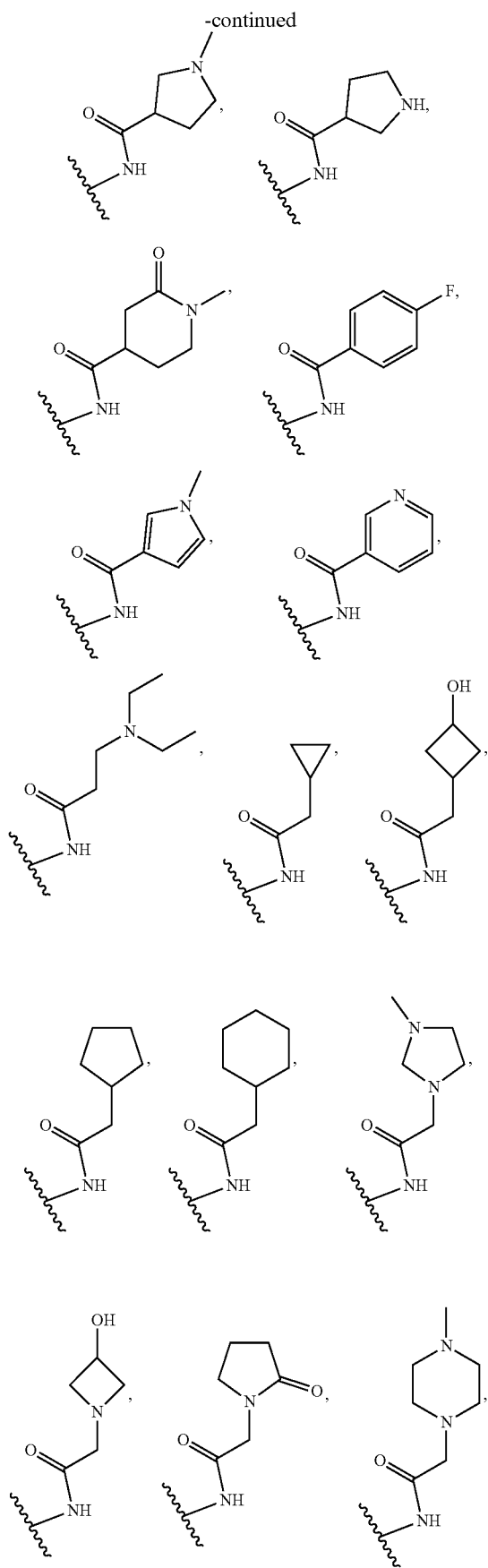
38
-continued
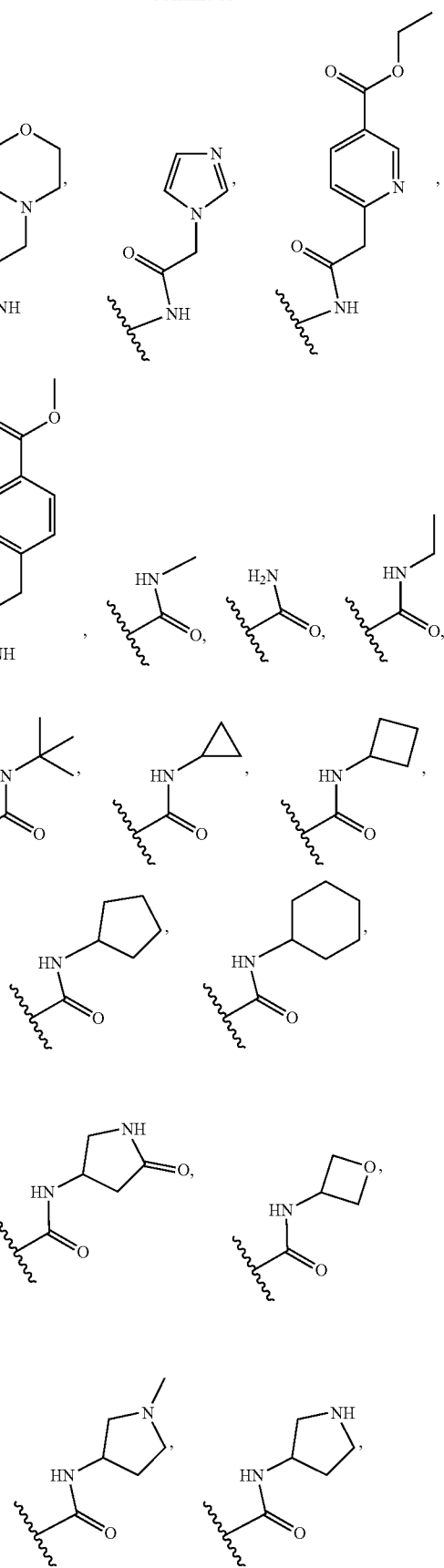

-continued
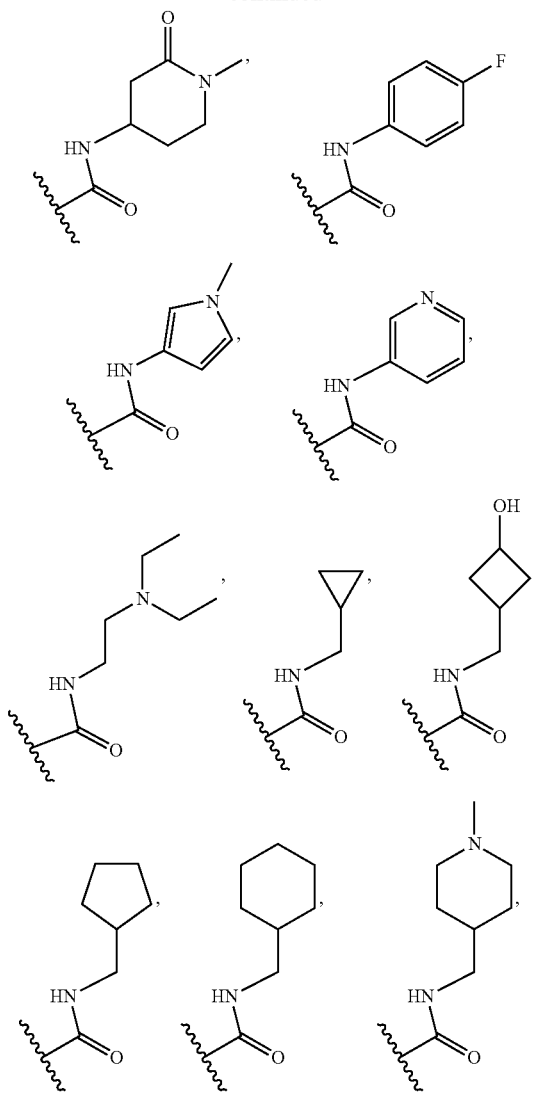
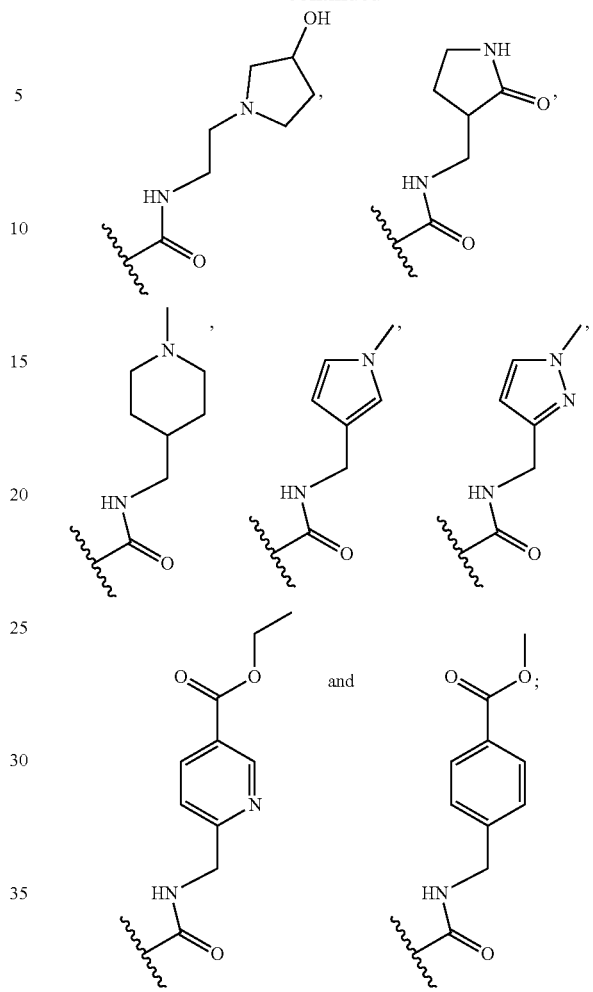
wherein the wavy lines denote attachment points to the parent molecule.
In some embodiments $R^2$ is selected from the group consisting of: hydrogen, fluoro, chloro, bromo, —CN, methyl, ethyl, isopropyl, propyl, tert-butyl, isopropenyl, —OCH$_3$, —C(O)OCH$_3$, —C(O)OH, —C(O)ONH$_2$, —CH$_2$NH$_2$, —NH$_2$, —NHCH$_3$, —N(CH$_3$)$_2$, —OH, —CF$_3$, —OCF$_3$,
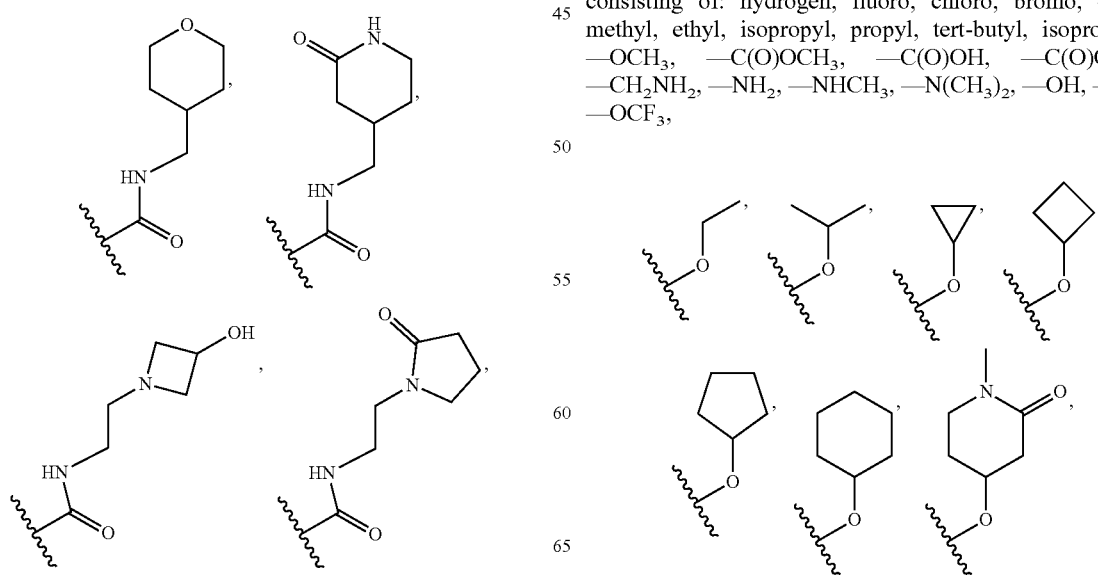

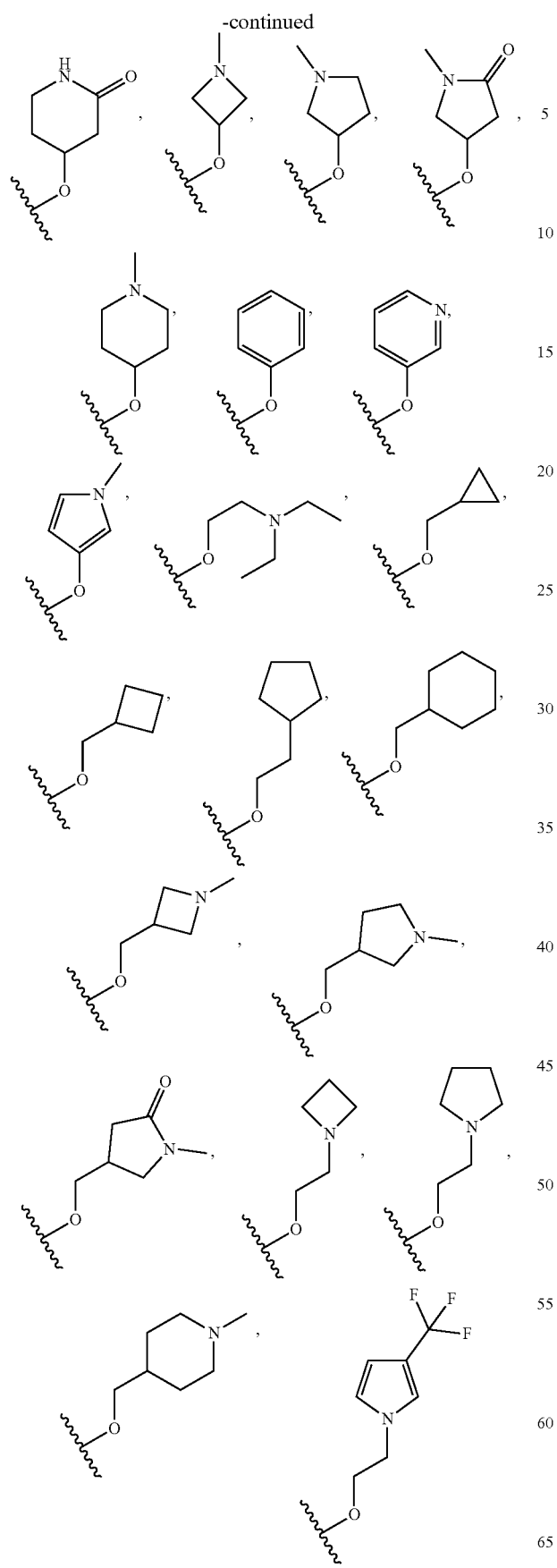
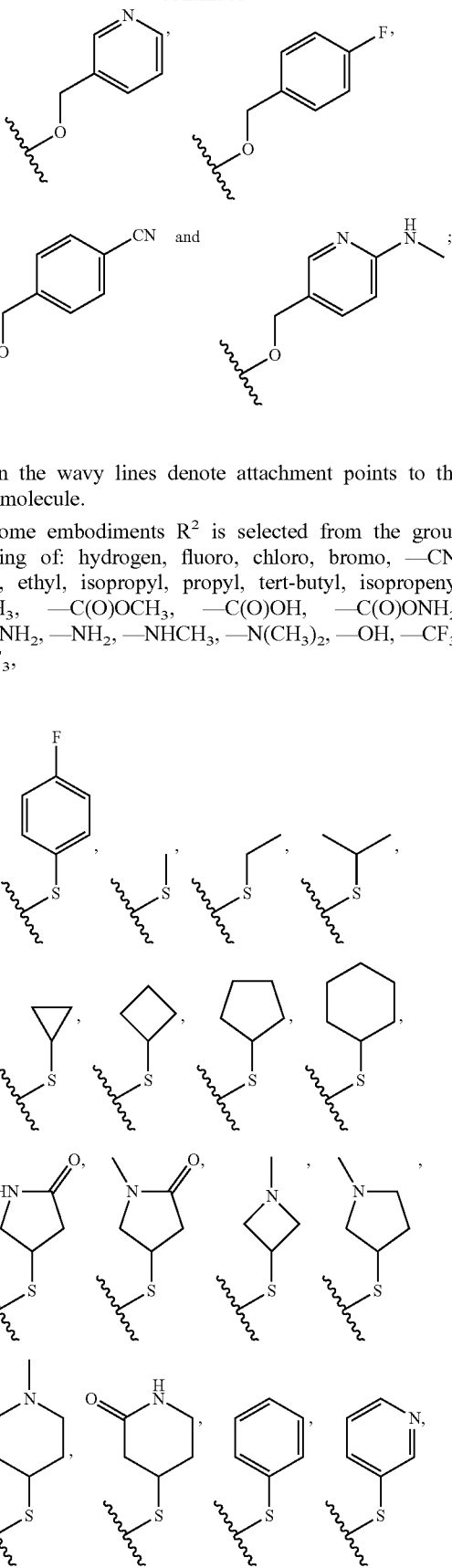
wherein the wavy lines denote attachment points to the parent molecule.
In some embodiments $R^2$ is selected from the group consisting of: hydrogen, fluoro, chloro, bromo, —CN, methyl, ethyl, isopropyl, propyl, tert-butyl, isopropenyl —OCH$_3$, —C(O)OCH$_3$, —C(O)OH, —C(O)ONH$_2$, —CH$_2$NH$_2$, —NH$_2$, —NHCH$_3$, —N(CH$_3$)$_2$, —OH, —CF$_3$, —OCF$_3$, -continued
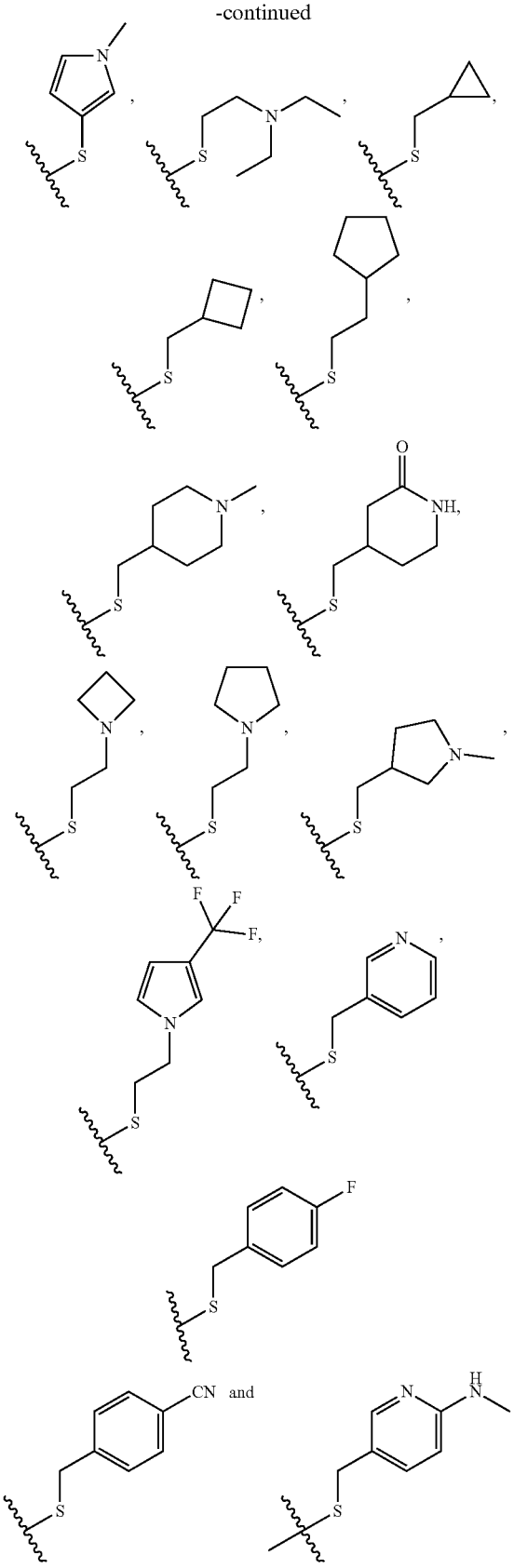
wherein the wavy lines denote attachment points to the parent molecule.
In some embodiments $R^2$ is selected from the group consisting of: hydrogen, fluoro, chloro, bromo, —CN, methyl, ethyl, isopropyl, propyl, tert-butyl, isopropenyl, —OCH$_3$, —C(O)OCH$_3$, —C(O)OH, —C(O)ONH$_2$, —CH$_2$NH$_2$, —NH$_2$, —NHCH$_3$, —N(CH$_3$)$_2$, —OH, —CF$_3$, —OCF$_3$,
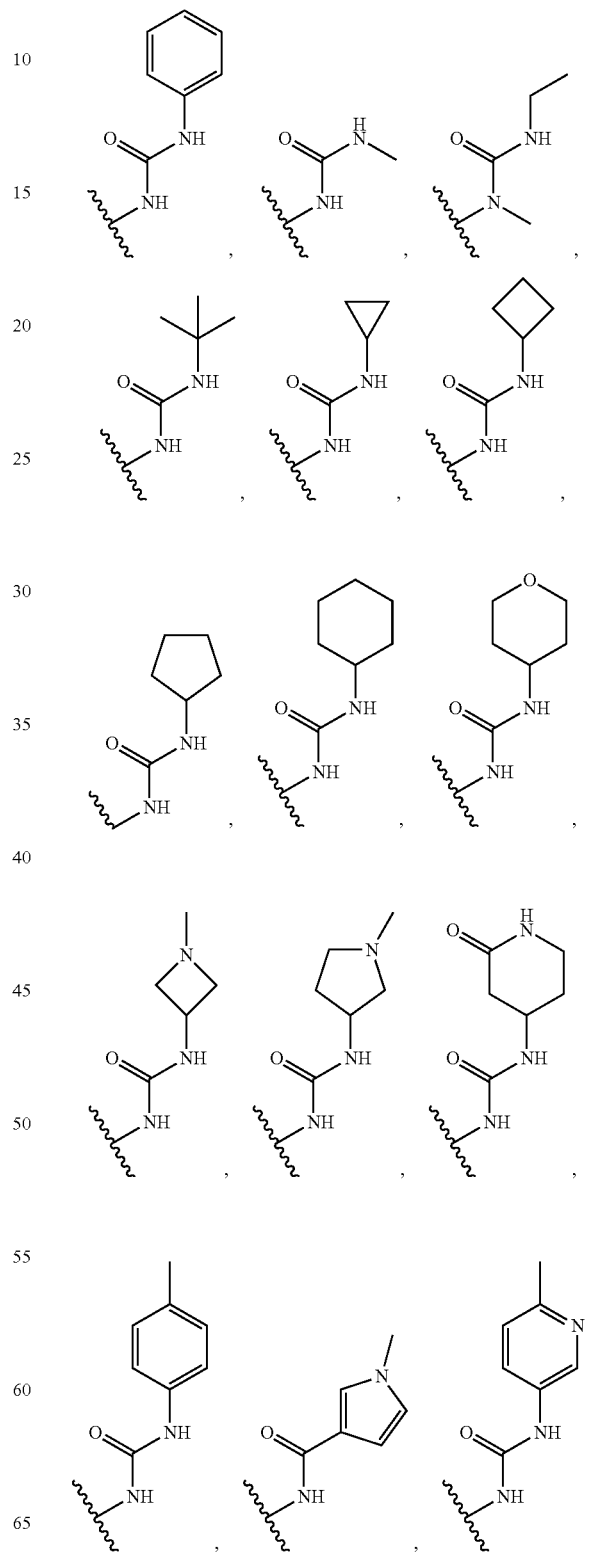

-continued
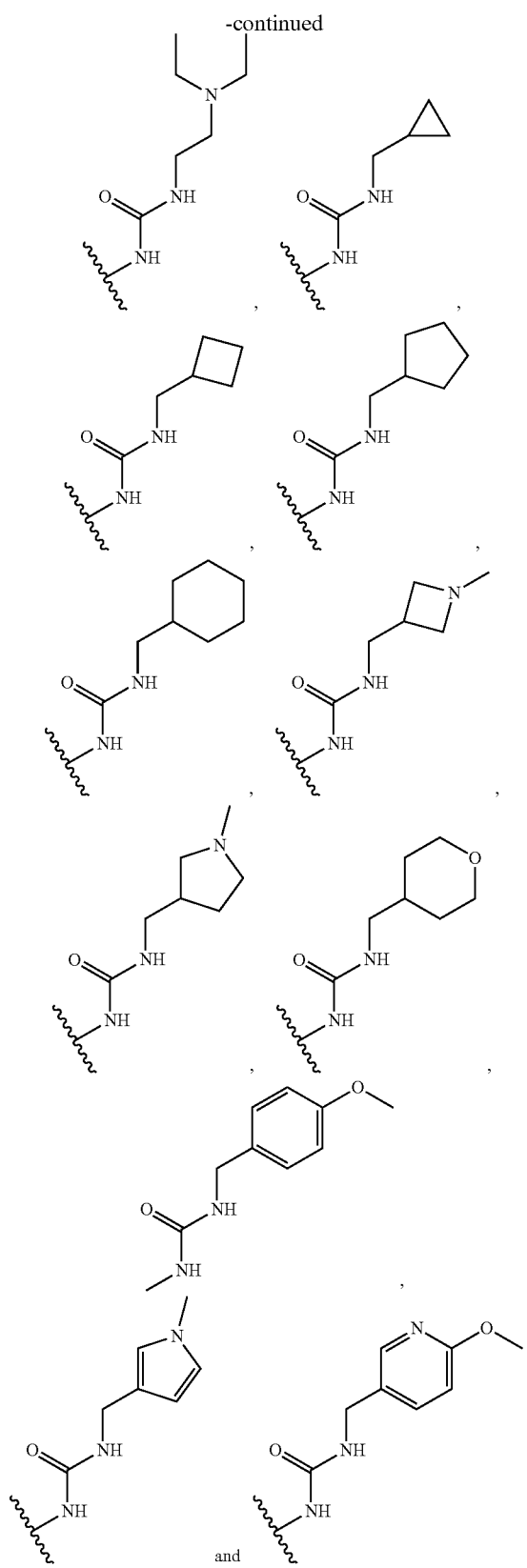
wherein the wavy lines denote attachment points to the parent molecule.
In some embodiments R² is selected from the group consisting of: hydrogen, fluoro, chloro, bromo, —CN, methyl, ethyl, isopropyl, propyl, tert-butyl, isopropenyl, —OCH₃, —C(O)OCH₃, —C(O)OH, —C(O)ONH₂, —CH₂NH₂, —NH₂, —NHCH₃, —N(CH₃)₂, —OH, —CF₃, —OCF₃,
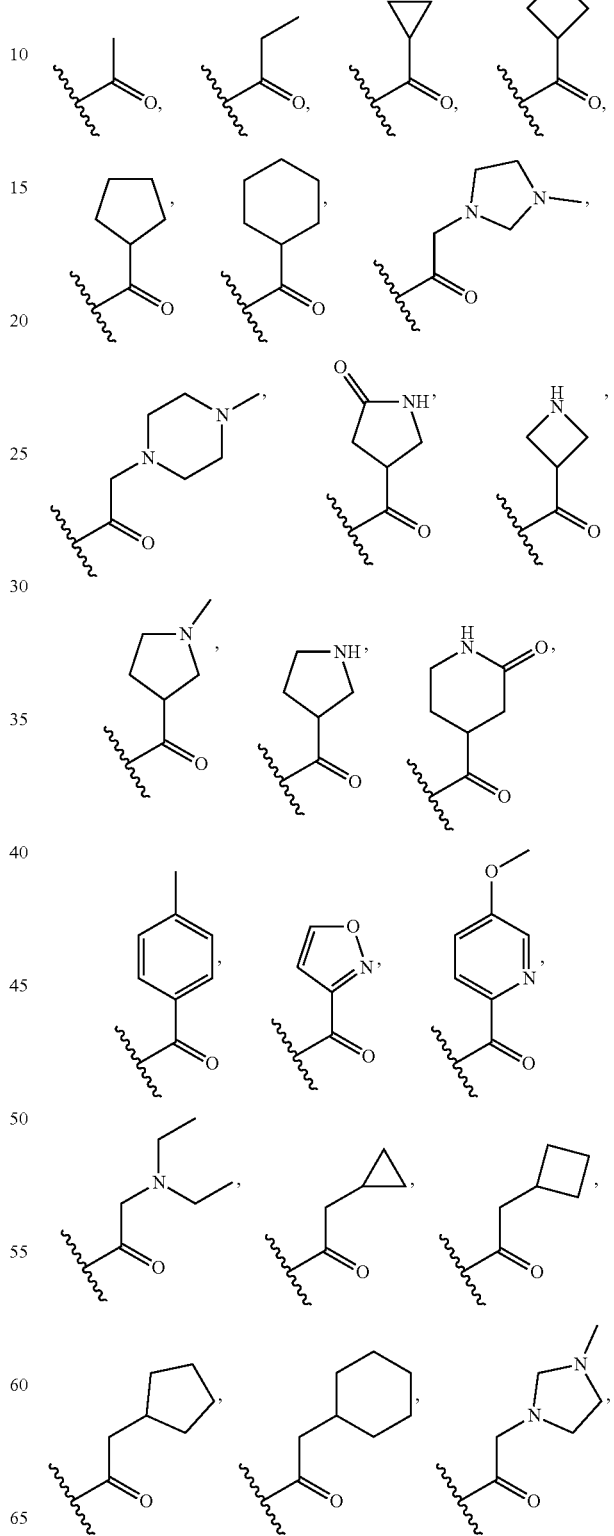

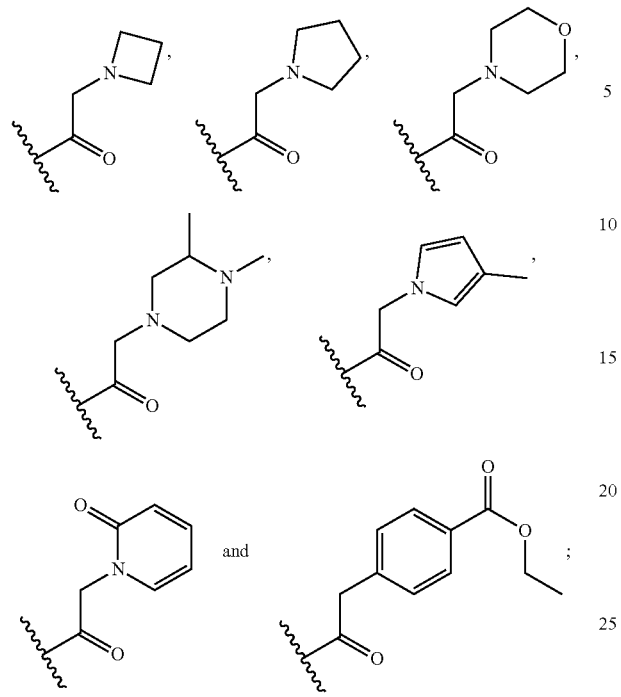
wherein the wavy lines denote attachment points to the parent molecule.
In some embodiments R² is selected from the groups consisting of: hydrogen, fluoro, chloro, bromo, —CN, methyl, ethyl, isopropyl, propyl, tert-butyl, isopropenyl, —OCH₃, —C(O)OCH₃, —C(O)OH, —C(O)ONH₂, —CH₂NH₂, —NHCH₃, —N(CH₃)₂, —OH, —CF₃, —OCF₃,
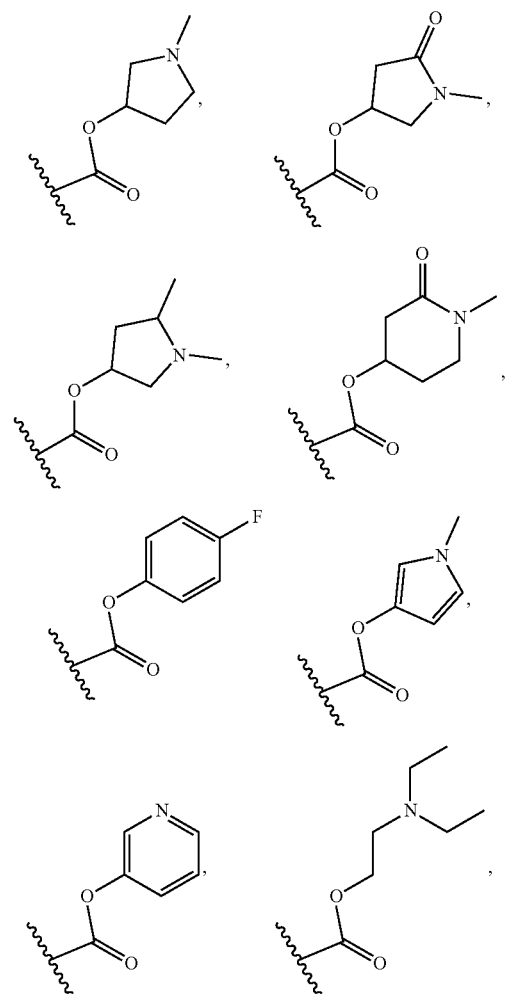
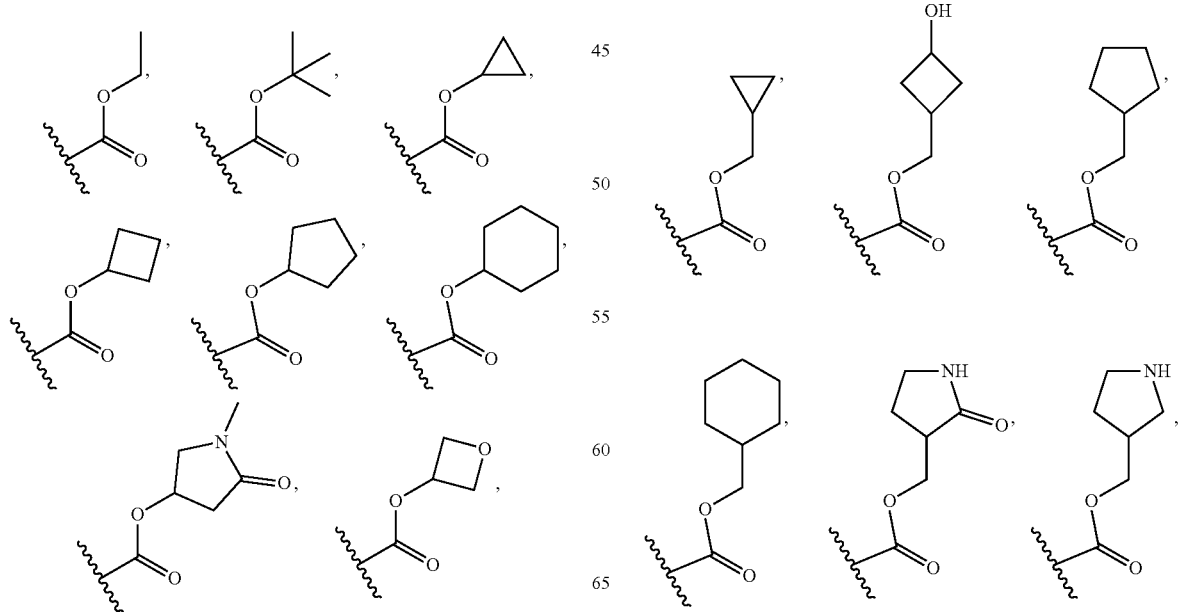

-continued

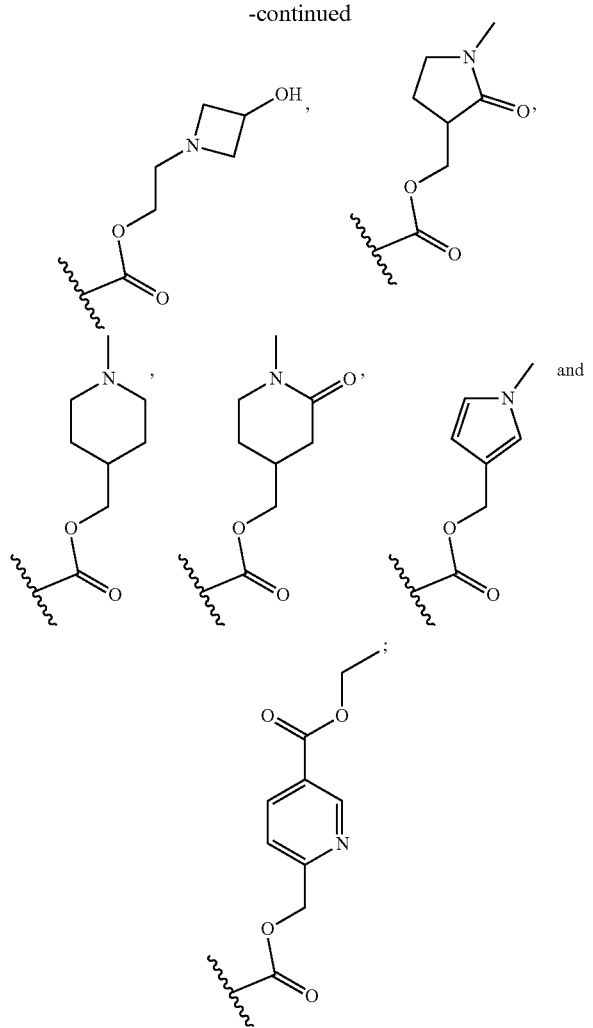

wherein the wavy lines denote attachment points to the parent molecule.

It is understood that each $R^2$ may be combined with each R', A and/or B the same as if each and every combination of $R^2$ with R', A and/or B were specifically and individually listed. In some embodiments $R^2$ is hydrogen, $C_1$-$C_6$ alkyl, —CN, halogen, —$OR^{2a}$, —$C(O)R^{2a}$, —$C(O)ONR^{2b}R^{2c}$, —$C(O)NR^{2b}R^{2c}$, —$NR^{2b}R^{2c}$, —$NR^{2b}C(O)R^{2c}$, —$NR^{2a}C(O)NR^{2b}R^{2c}$, —$SR^{2a}$ or —$C(O)OR^{2a}$. In some embodiments, $R^2$ is hydrogen. In some embodiments, $R^2$ is $C_1$-$C_6$ alkyl (e.g., methyl). In some embodiments, $R^2$ is —CN. In some embodiments, $R^2$ is halogen (e.g., bromo). In some embodiments, $R^2$ is —$OR^{2a}$ and in certain aspects $R^{2a}$ is $C_1$-$C_6$ alkyl (e.g., methyl). In some embodiments, $R^2$ is $C(O)R^{2a}$ and in certain aspects $R^{2a}$ is $C_1$-$C_6$ alkyl (e.g., methyl) or $C_3$-$C_6$ cycloalkyl. In some embodiments, $R^2$ is $C(O)OR^{2a}$ and in certain aspects $R^{2a}$ is hydrogen or $C_1$-$C_6$ alkyl (e.g., methyl). In some embodiments, $R^2$ is —$C(O)NR^{2b}R^{2c}$ and in certain aspects $R^{2b}$ and $R^{2c}$ are independently hydrogen or $C_1$-$C_6$ alkyl (e.g., methyl) or $C_3$-$C_6$ cycloalkyl. In some embodiments, $R^2$ is —$NR^{2b}C(O)R^{2c}$ and in certain aspects $R^{2b}$ and $R^{2c}$ are independently hydrogen or $C_1$-$C_6$ alkyl (e.g., methyl) or $C_3$-$C_6$ cycloalkyl. In some embodiments, $R^2$ is —$NR^{2a}C(O)NR^{2b}R^{2c}$ and in certain aspects $R^{2a}$ is hydrogen or $C_1$-$C_6$ alkyl (e.g., methyl) and $R^{2b}$ and $R^{2c}$ are independently hydrogen or $C_1$-$C_6$ alkyl (e.g., methyl) or $C_3$-$C_6$ cycloalkyl. In some embodiments, $R^2$ is —$SR^{2a}$ and in certain aspects $R^{2a}$ is $C_1$-$C_6$ alkyl (e.g., methyl).

In some embodiments $R^2$ is hydrogen, $C_1$-$C_6$ alkyl, —CN, halogen, —$OR^{2a}$, —$C(O)R^{2a}$, or —$C(O)OR^{2a}$. In some embodiments, $R^2$ is hydrogen. In some embodiments, $R^2$ is $C_1$-$C_6$ alkyl (e.g., methyl). In some embodiments, $R^2$ is —CN or halogen (e.g., bromo). In some embodiments, $R^2$ is —$OR^{2a}$ and in certain aspects $R^{2a}$ is $C_1$-$C_6$ alkyl (e.g., methyl). In some embodiments, $R^2$ is $C(O)R^{2a}$ and in certain aspects $R^{2a}$ is $C_1$-$C_6$ alkyl (e.g., methyl) or $C_3$-$C_6$ cycloalkyl. In some embodiments, $R^2$ is $C(O)OR^{2a}$ and in certain aspects $R^{2a}$ is hydrogen or $C_1$-$C_6$ alkyl (e.g., methyl).

In some embodiments, $R^1$ and $R^2$ are each hydrogen. In one such variation, $R^1$ and $R^2$ are each hydrogen and A is 4-hydroxyphenyl optionally further substituted by $R^3$ or 4-hydroxy-2-pyridyl optionally further substituted by $R^4$. In another variation, $R^1$ and $R^2$ are each hydrogen and B is unsubstituted phenyl. In another variation, $R^1$ and $R^2$ are each hydrogen and B is a 5- to 10-membered heteroaryl substituted by 1 to 3 $R^4$ wherein each $R^4$ is independently oxo or $R^3$. In a further variation, $R^1$ and $R^2$ are each hydrogen and A is an unsubstituted 9- or 10-membered bicyclic heteroaryl containing at least one annular nitrogen atom. In a further variation, $R^1$ and $R^2$ are each hydrogen, A is a 9- or 10-membered bicyclic heteroaryl containing at least one annular nitrogen atom and which is optionally substituted by $R^4$ and B is unsubstituted phenyl or a 5- to 10-membered heteroaryl substituted by 1 to 3 $R^4$ wherein each $R^4$ is independently oxo or $R^3$. In another embodiment, $R^1$ is hydrogen and $R^2$ is $C_1$-$C_6$ alkyl, —CN, halogen or —$OR^{2a}$. In one aspect, $R^1$ is hydrogen and $R^2$ is bromo, methyl, —CN, —OH, —$CONH_2$, —COOH or methoxy.

In some embodiments, $R^1$ and $R^2$ are hydrogen. In one such variation, $R^1$ and $R^2$ are hydrogen and A is 4-hydroxyphenyl optionally further substituted by $R^3$ or 4-hydroxy-2-pyridyl optionally further substituted by $R^4$. In another variation, $R^1$ and $R^2$ are hydrogen and B is unsubstituted phenyl. In another variation, $R^1$ and $R^2$ are hydrogen and B is a 5- to 6-membered heteroaryl substituted by 1 to 3 $R^4$ wherein each $R^4$ is independently $R^3$. In a further variation, $R^1$ and $R^2$ are hydrogen and A is an unsubstituted 9- or 10-membered bicyclic heteroaryl containing at least one annular nitrogen atom. In a further variation, $R^1$ and $R^2$ are hydrogen, A is a 9- or 10-membered bicyclic heteroaryl containing at least one annular nitrogen atom and which is optionally substituted by $R^4$ and B is unsubstituted phenyl or a 5- to 6-membered heteroaryl substituted by 1 to 3 $R^4$ wherein each $R^4$ is independently $R^3$. In another embodiment, $R^1$ is hydrogen and $R^2$ is $C_1$-$C_6$ alkyl, —CN, halogen or —$OR^{2a}$. In one aspect, $R^1$ is hydrogen and $R^2$ is bromo, methyl, —CN or methoxy.

In some embodiments, $R^1$ is hydrogen and $R^2$ is —CN. In one such variation, $R^1$ is hydrogen, $R^2$ is —CN, A is a 9- or 10-membered bicyclic heteroaryl containing at least one annular nitrogen atom (e.g., quinolinyl or indazolyl) and which is optionally substituted by $R^4$ and B is unsubstituted phenyl or a 5- to 6-membered heteroaryl (e.g., pyrazolyl, pyridyl or pyridone) substituted by 1 to 3 $R^4$ wherein each $R^4$ is independently oxo or $R^3$. In some embodiments, $R^1$ is hydrogen, $R^2$ is Br, A is a 9- or 10-membered bicyclic heteroaryl containing at least one annular nitrogen atom (e.g., quinolinyl or indazolyl) and which is optionally substituted by $R^4$ and B is unsubstituted phenyl or a 5- to 6-membered heteroaryl (e.g., pyrazolyl, pyridyl or pyridone) substituted by 1 to 3 $R^4$ wherein each $R^4$ is independently oxo or $R^3$. In some embodiments, both $R^1$ and $R^2$ are hydrogen, A is a 9- or 10-membered bicyclic heteroaryl containing at least one annular nitrogen atom (e.g., quinolinyl or indazolyl) and which is optionally substituted by $R^4$ and B is unsubstituted phenyl or a 5- to 6-membered heteroaryl (e.g., pyrazolyl, pyridyl or pyridone) substituted by 1 to 3 $R^4$ wherein each $R^4$ is independently oxo or $R^3$. In these variations $R^4$ is independently oxo, methyl, methoxy, chloro or —CN.

In some embodiments, A is 4-hydroxyphenyl optionally further substituted by $R^3$, 4-hydroxy-2-pyridyl optionally further substituted by $R^4$, or a 9- or 10-membered bicyclic heteroaryl optionally substituted by $R^4$.

In some embodiments, A is 4-hydroxyphenyl optionally further substituted by $R^3$ or 4-hydroxy-2-pyridyl optionally further substituted by $R^4$. In some embodiments, A is 4-hydroxyphenyl optionally further substituted by $R^3$. In some embodiments, A is 4-hydroxy-2-pyridyl optionally further substituted by $R^4$. In some embodiments, A is a 9- or 10-membered bicyclic heteroaryl optionally substituted by $R^4$. In some embodiments, A is a 9- or 10-membered bicyclic heteroaryl optionally substituted by $R^4$, wherein one ring is saturated. In some embodiments, A is a 9- or 10-membered bicyclic heteroaryl optionally substituted by $R^4$, wherein both rings are unsaturated. In some embodiments, A is selected from the group consisting of benzimidazolyl, benzoxazolyl, benzothiazolyl, quinolinyl, isoquinolinyl, indazolyl, quinoxalinyl, quinazolinyl, cinnolinyl, naphthyridinyl and naphthyl. In some embodiments, A is selected from the group consisting of benzimidazolyl, benzoxazolyl, benzothiazolyl, quinolinyl, isoquinolinyl, indazolyl, quinoxalinyl, quinazolinyl, cinnolinyl, naphthyridinyl and naphthyl, each of which is optionally substituted by $R^4$. In yet further embodiments, A is a 9- or 10-membered bicyclic heteroaryl optionally substituted by $R^4$, comprising a first and second ring, wherein the first ring has a greater number of ring atoms than the second ring. In certain embodiments, the point of attachment of A to the parent molecule is on the first ring having a greater number of ring atoms. In other embodiments, the point of attachment of A to the parent molecule is on the second ring having a smaller number of ring atoms. In some embodiments, A is a 9- or 10-membered bicyclic heteroaryl optionally substituted by $R^4$, wherein the two rings are selected from the group consisting of: a 5-membered ring and a 6-membered ring or two 6-membered rings.

In one aspect, when A is a 9- or 10-membered bicyclic heteroaryl optionally substituted by $R^4$, A is an unsubstituted 9- or 10-membered bicyclic heteroaryl containing at least one annular nitrogen atom, a 9- or 10-membered bicyclic heteroaryl containing at least two annular nitrogen atoms and optionally substituted by $R^4$ which $R^4$ groups are connected to the parent structure via a carbon atom, or a 10-membered bicyclic heteroaryl optionally substituted by $R^4$.

In some embodiments, A is 4-hydroxyphenyl optionally further substituted by $R^3$ where $R^3$ is selected from the group consisting of halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl and $C_1$-$C_6$ alkyl optionally substituted by halogen. In some embodiments, A is 4-hydroxyphenyl further substituted by 1 to 3 $R^3$ where each $R^3$ is independently selected from the group consisting of halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl and $C_1$-$C_6$ alkyl optionally substituted by halogen. In some embodiments, A is 4-hydroxyphenyl optionally further substituted by $R^3$ where $R^3$ is selected from the group consisting of halogen, —$OR^5$ and $C_1$-$C_6$ alkyl optionally substituted by halogen. In some embodiments, A is 4-hydroxyphenyl further substituted by 1 to 3 $R^3$ where each $R^3$ is independently selected from the group consisting of halogen, —$OR^5$ and $C_1$-$C_6$ alkyl optionally substituted by halogen. In some embodiments, A is 4-hydroxyphenyl further substituted by 1 to 3 $R^3$ where each $R^3$ is independently selected from the group consisting of fluoro, chloro, —O—$C_1$-$C_6$alkyl and $C_1$-$C_6$ alkyl optionally substituted by halogen.

In some embodiments, A is 4-hydroxy-2-pyridyl optionally further substituted by $R^4$ where $R^4$ is selected from the group consisting of halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl and $C_1$-$C_6$ alkyl optionally substituted by halogen. In some embodiments, A is 4-hydroxy-2-pyridyl optionally further substituted by 1 to 3 $R^4$, where each $R^4$ is independently selected from the group consisting of halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl and $C_1$-$C_6$ alkyl optionally substituted by halogen. In some embodiments, A is 4-hydroxy-2-pyridyl further substituted by 1 to 3 $R^4$ where each $R^4$ is independently selected from the group consisting of halogen, —$OR^5$ and $C_1$-$C_6$ alkyl optionally substituted by halogen. In some embodiments, A is 4-hydroxyphenyl further substituted by 1 to 3 $R^4$ where each $R^4$ is independently selected from the group consisting of fluoro, chloro, —O—$C_1$-$C_6$alkyl and $C_1$-$C_6$ alkyl optionally substituted by halogen.

In some embodiments, A is a 4-hydroxyphenyl or a 4-hydroxy-2-pyridyl substituted with 1 to 3 $R^3$ groups, which may be the same or different. In some of these embodiments, A is selected from the group consisting of:

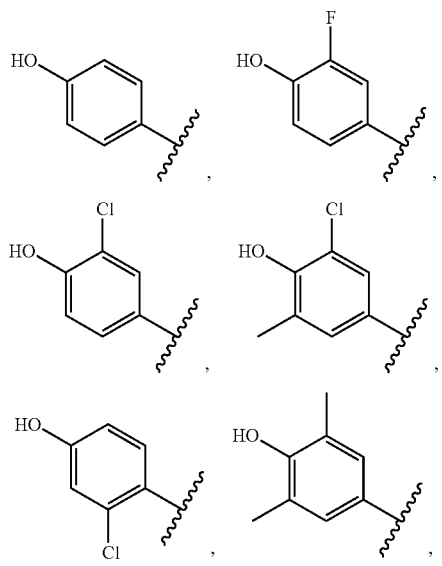

-continued

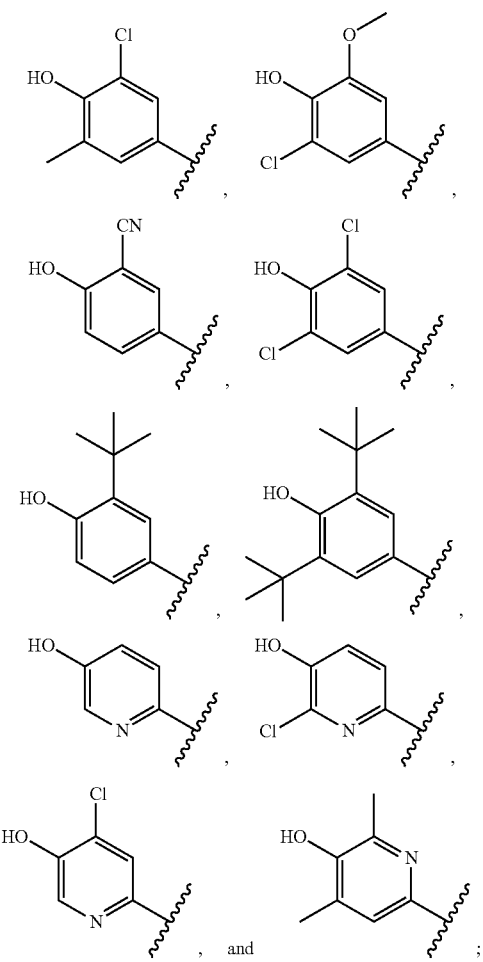

, and ;

wherein the wavy lines denote attachment points to the parent molecule.

In some embodiments, A is a 9- or 10-membered bicyclic heteroaryl substituted with 0 to 3 $R^4$ groups which may be the same or different, and which may be present on either one ring or both rings. In one such aspect, A is a 9- or 10-membered bicyclic heteroaryl substituted with 0 to 3 $R^3$ groups which may be the same or different, and which may be present on either one ring or both rings. In one such aspect, A is a 9- or 10-membered bicyclic heteroaryl substituted with 1 $R^3$ group. In another such aspect, A is a 9- or 10-membered bicyclic heteroaryl substituted with 2 $R^3$ groups, which may be the same or different. In another such aspect, A is a 9- or 10-membered bicyclic heteroaryl substituted with 3 $R^3$ groups, which may be the same or different. In some embodiments, A is selected from the group consisting of:

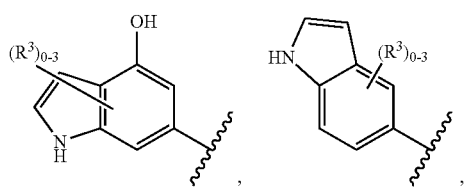

-continued

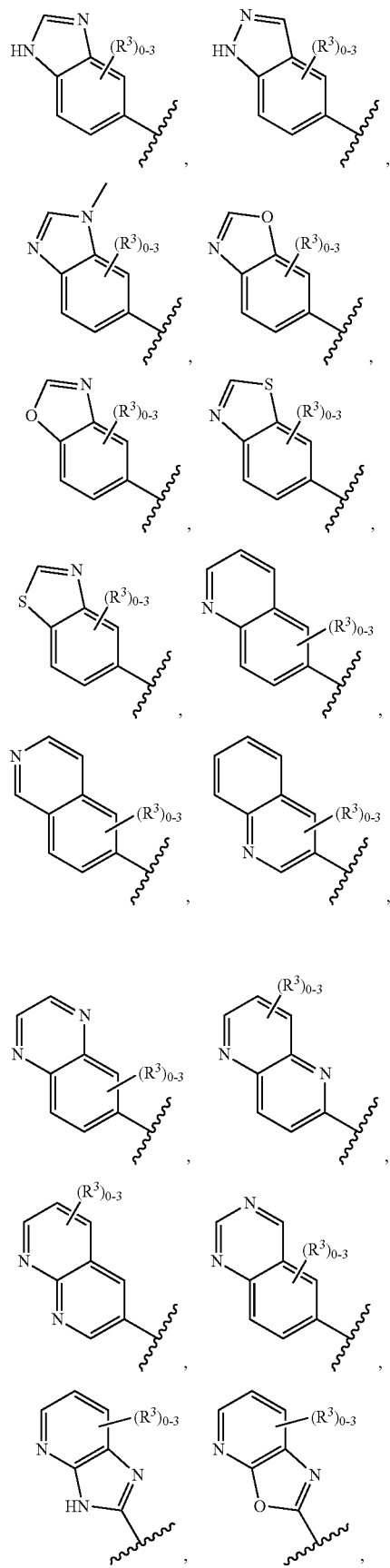

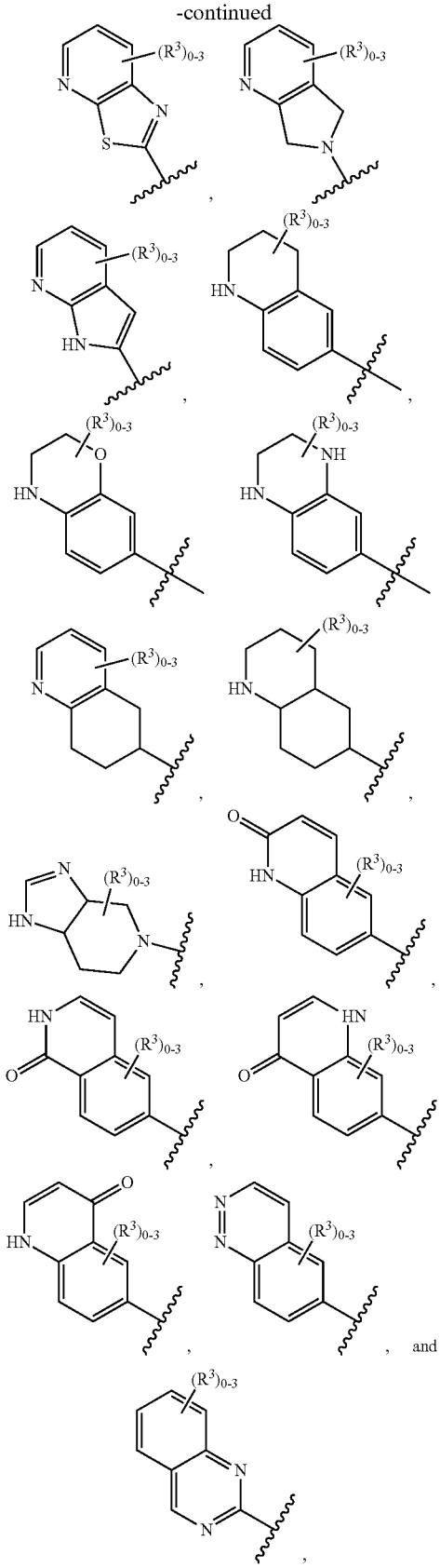

where R³, if present, is attached at any available position on the bicyclic ring system. In one aspect, at least one R³ is present and is attached at a position on the ring bearing the wavy line (on the ring that is the attachment point of the bicyclic ring to the parent molecule). In one aspect, at least one R³ is present and is attached at a position on the ring that does not bear the wavy line (on the ring that is fused to the ring which is the attachment point of the bicyclic ring to the parent molecule).

In some embodiments, A is a 9- or 10-membered bicyclic heteroaryl substituted with 0 to 3 R³ groups which may be the same or different, and which may be present on either one ring or both rings. In some embodiments, A is selected from the group consisting of:

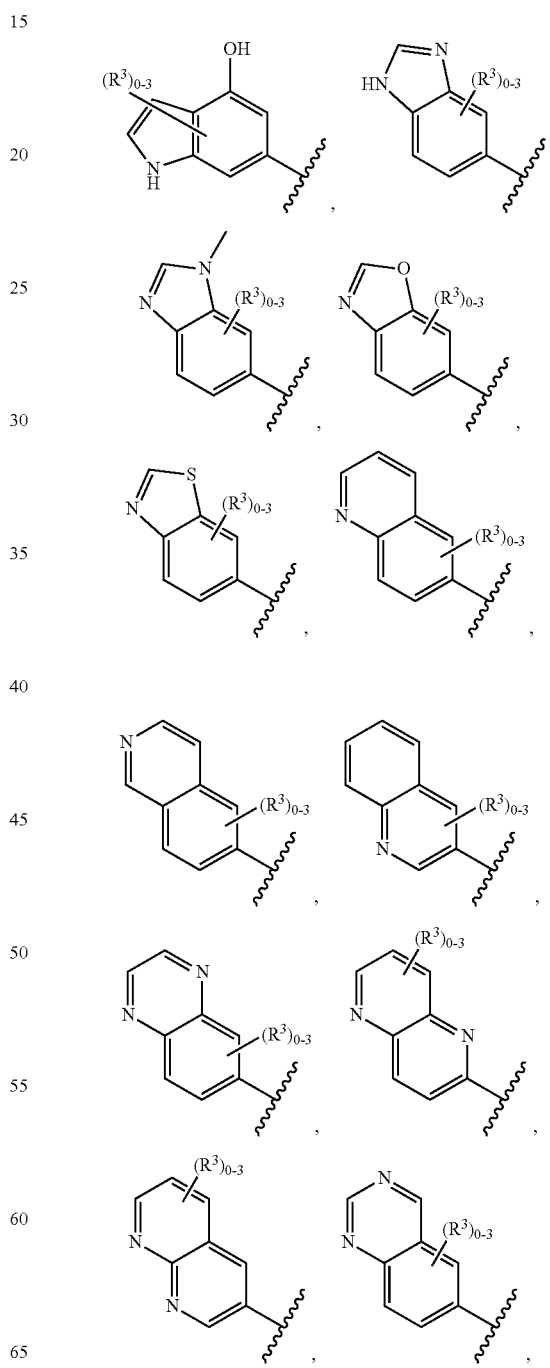

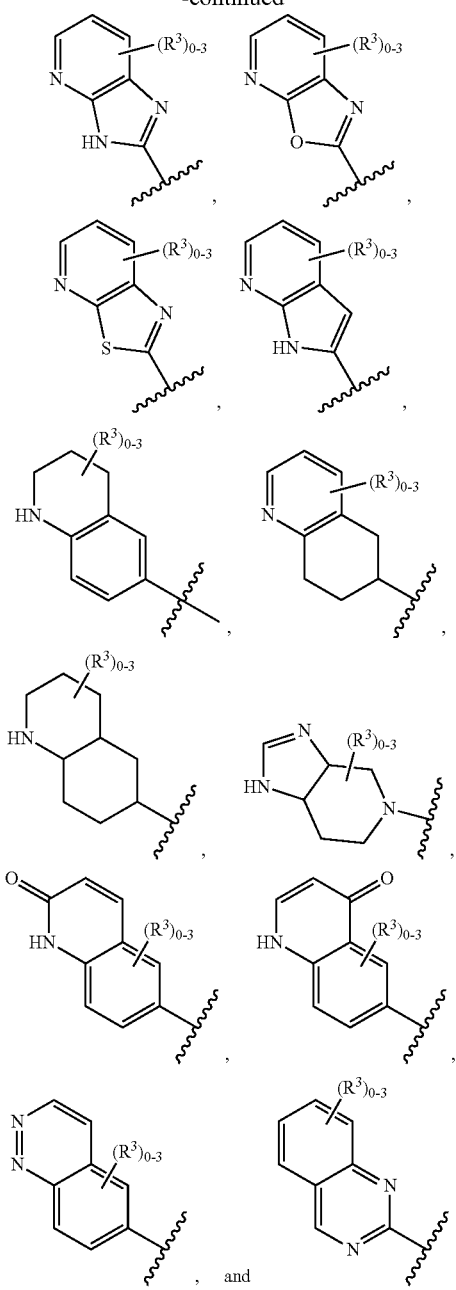

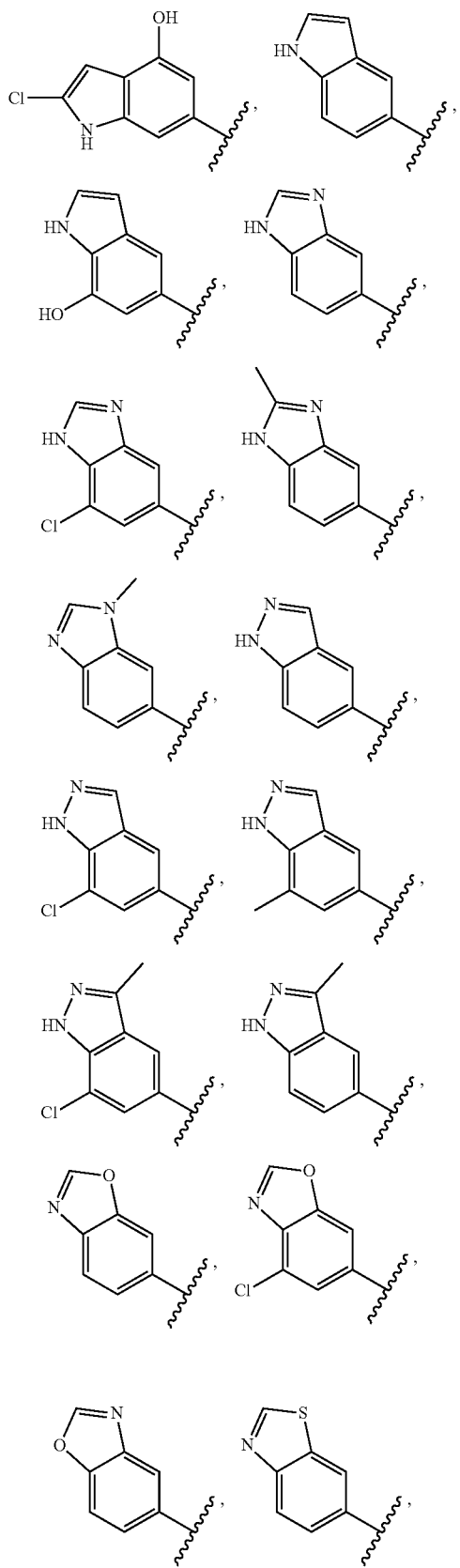

where R³, if present, is attached at any available position on the bicyclic ring system. In one aspect, at least one R³ is present and is attached at a position on the ring bearing the wavy line (on the ring that is the attachment point of the bicyclic ring to the parent molecule). In one aspect, at least one R³ is present and is attached at a position on the ring that does not bear the wavy line (on the ring that is fused to the ring which is the attachment point of the bicyclic ring to the parent molecule).

In some embodiments, A is selected from the group consisting of:

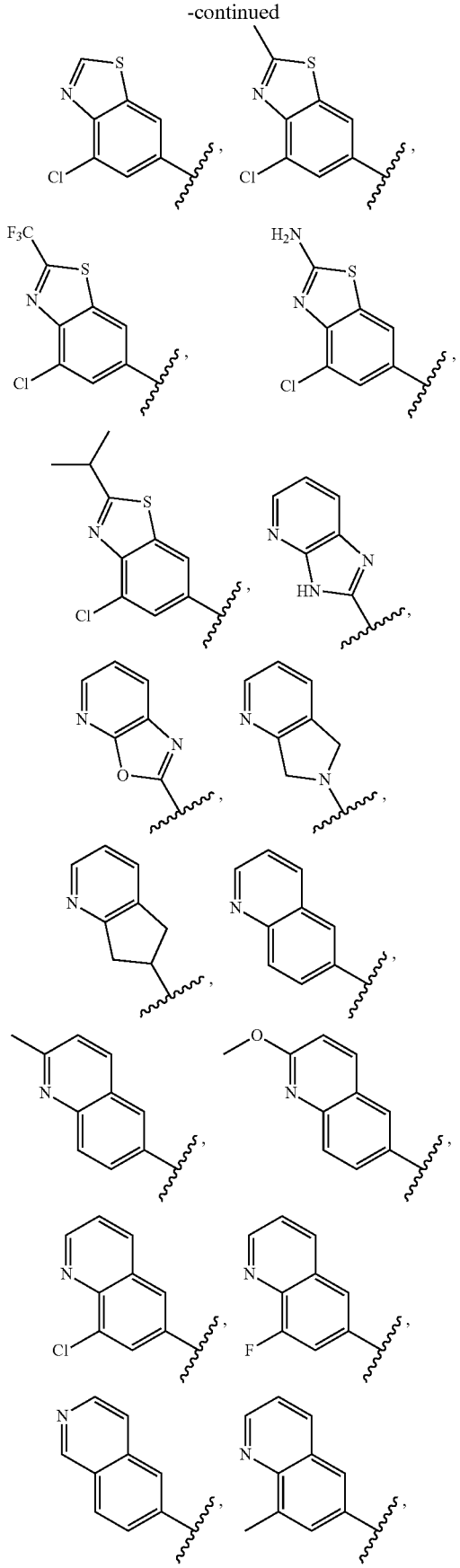
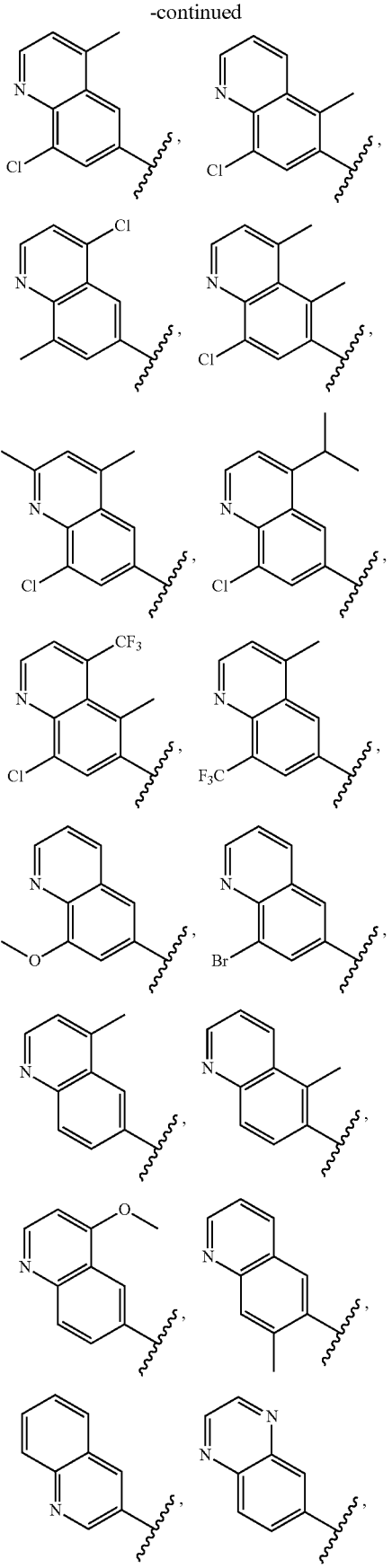

-continued
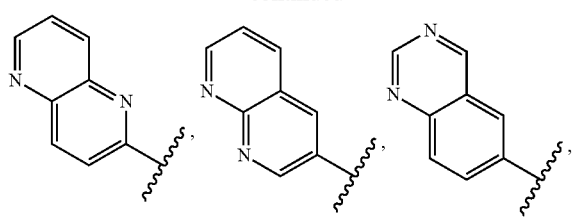
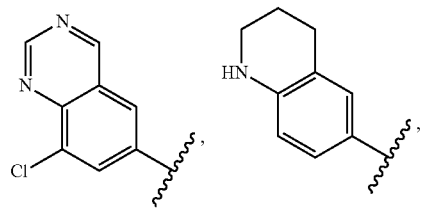
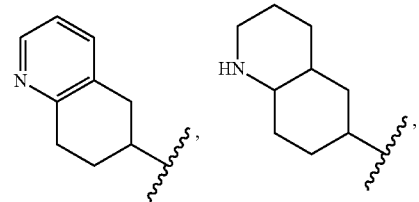
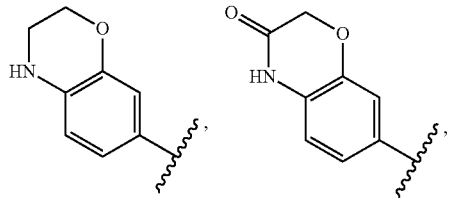
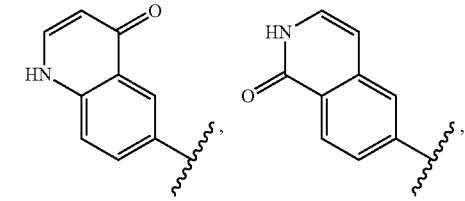
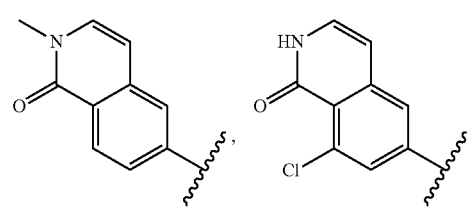
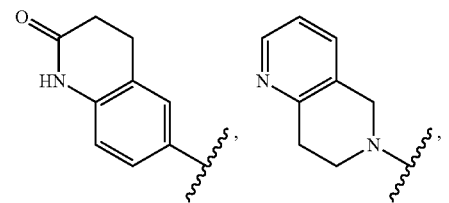
-continued
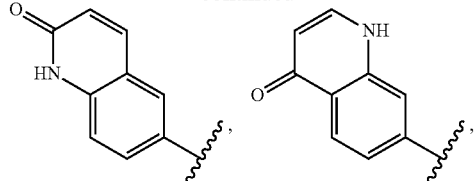
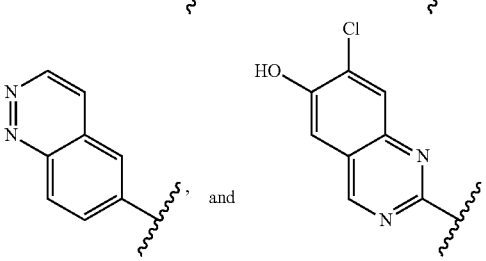
and
In some embodiments, A is selected from the group consisting of:
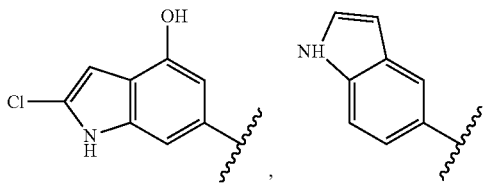
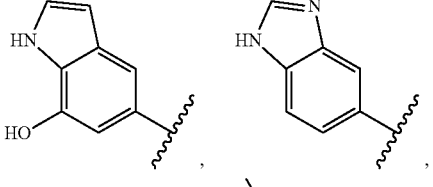
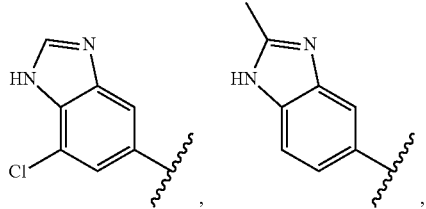
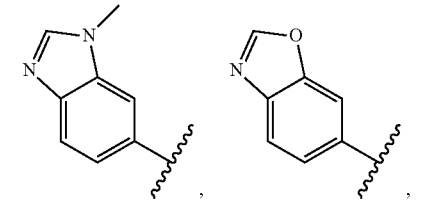
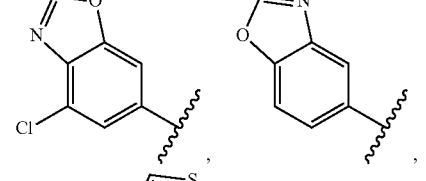
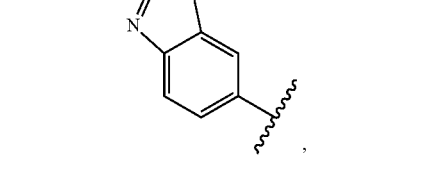

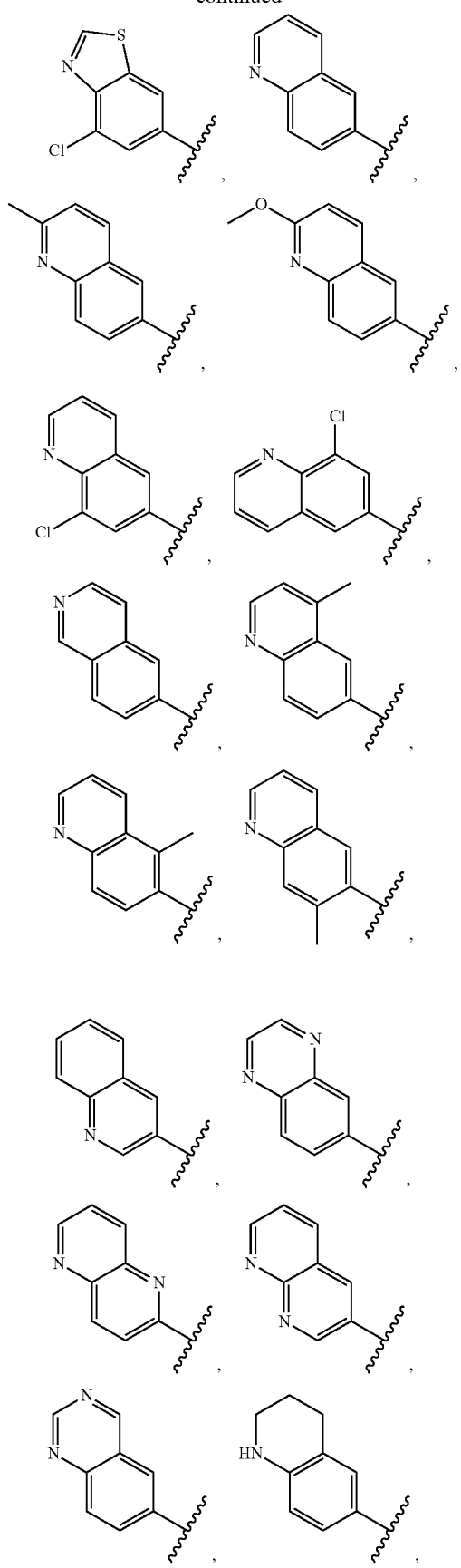
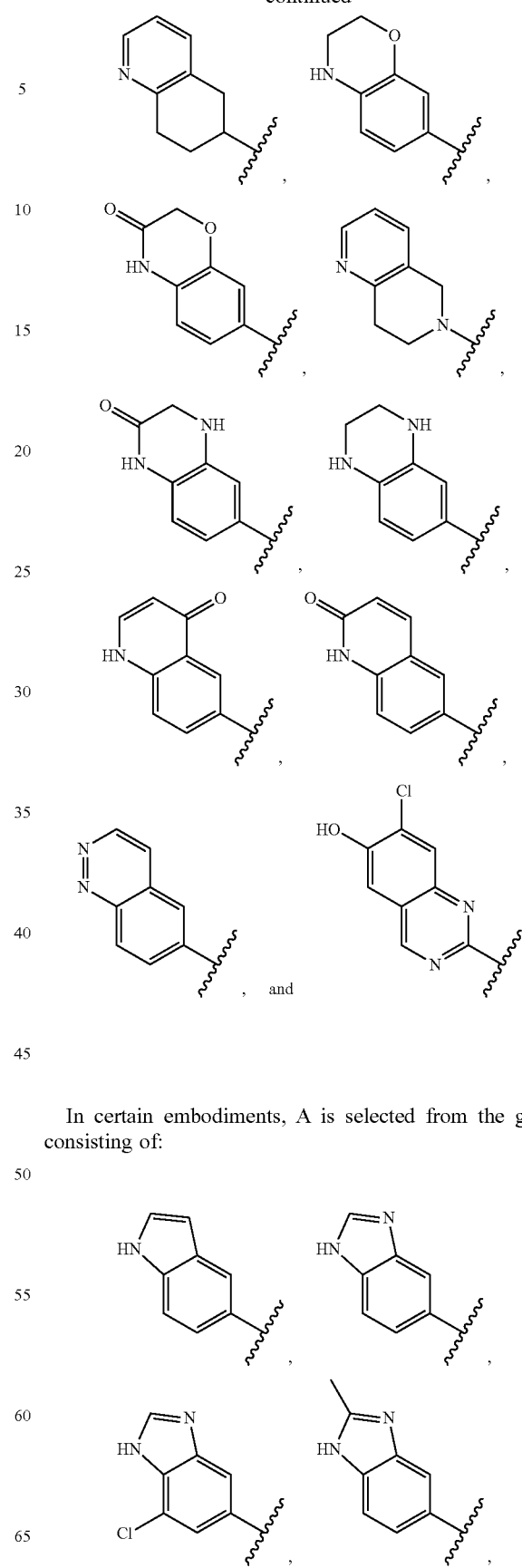
In certain embodiments, A is selected from the group consisting of:

-continued
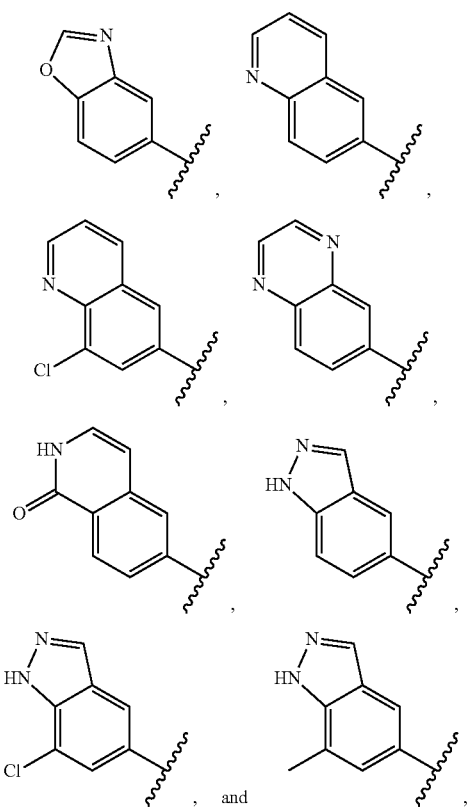
wherein the wavy lines denote attachment points to the parent molecule.
In certain embodiments, A is selected from the group consisting of:
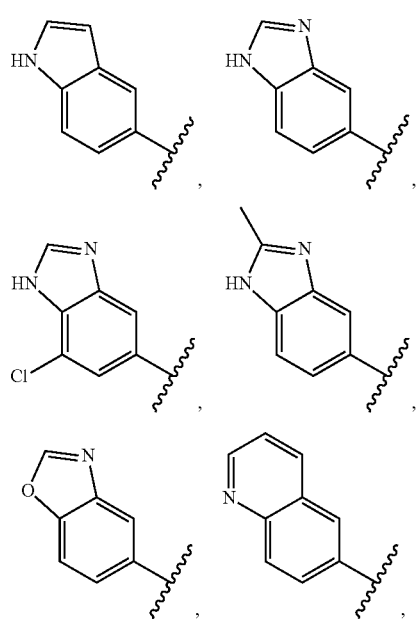
-continued
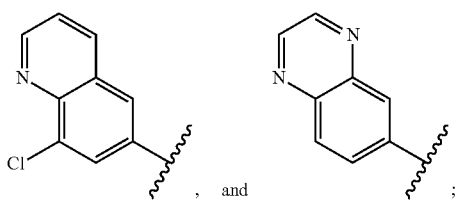
wherein the wavy lines denote attachment points to the parent molecule.
In some embodiments, A is
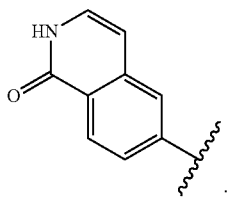 [SMILES: *c1ccc2c(=O)[nH]ccc2c1]
In some embodiments, A is
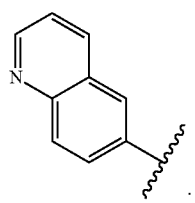
In some embodiments, A is
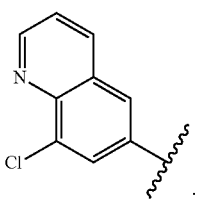 [SMILES: *c1cc(Cl)c2ncccc2c1]
In some embodiments, A is
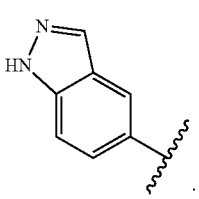

In some embodiments, A is

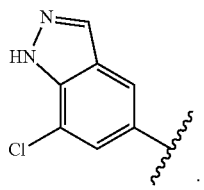 [SMILES: *c1cc(Cl)c2[nH]ncc2c1]

In some embodiments, A is naphthyl substituted with halogen, —CN, or hydroxy.

It is understood that each description of A may be combined with each description of $R^1$ and/or $R^2$ the same as if each and every combination were specifically and individually listed. For example, in one embodiment, A is as described in any of the embodiments, aspects or variations herein and $R^1$ and $R^2$ are each H. It is similarly understood that each description of A may be combined with each description of B (and further with each description of $R^1$ and $R^2$) the same as if each and every combination were specifically and individually listed. For example, in one aspect, it is understood that each description of A may be combined in one aspect with a variation in which $R^1$ and $R^2$ are each hydrogen. In one aspect, it is understood that each description of A may be combined in one aspect with a variation in which $R^1$ and $R^2$ are each hydrogen and B is a 5- to 10-membered heteroaryl optionally substituted by $R^4$.

In some embodiments, B is an unsubstituted phenyl. In some embodiments, B is a phenyl optionally substituted by $R^3$. In some embodiments, B is a phenyl substituted by 1 to 3 $R^3$ which $R^3$ groups may be the same or different. In other embodiments, B is a 5- to 10-membered heteroaryl optionally substituted by $R^4$. In other embodiments, B is a 5- to 10-membered heteroaryl substituted by 1 to 3 $R^4$ which $R^4$ may be the same or different. In some embodiments, the 5- to 10-membered heteroaryl of B is a 5-membered heteroaryl selected from the group consisting of furanyl, oxazolyl, thiophenyl, pyrazolyl, isoxazolyl, 1,3,4-oxadiazolyl, imidazolyl, thiazolyl, isothiazolyl, triazolyl, 1,3,4-thiadiazolyl and tetrazolyl, which 5-membered heteroaryl is optionally substituted by 1 to 3 $R^4$ which $R^4$ groups may be the same or different. In other embodiments, the 5- to 10-membered heteroaryl of B is a 6-membered heteroaryl selected from the group consisting of pyridyl, pyridazinyl and pyrimidinyl which 6-membered heteroaryl is optionally substituted to 1 to 3 $R^4$ which $R^4$ groups may be the same or different. In some embodiments, the 5- to 10-membered heteroaryl of B is a bicyclic heteroaryl selected from the group consisting of benzofuranyl, benzothiophenyl, pyrazolopyridinyl, indazolyl, benzothiazolyl, benzooxazolyl or benzoimidazolyl, each of bicyclic heteroaryl is optionally substituted by 1 to 3 $R^4$ which $R^4$ groups may be the same or different.

In some embodiments, B is an unsubstituted phenyl. In some embodiments, B is a phenyl optionally substituted by $R^3$. In some embodiments, B is a phenyl substituted by 1 to 3 $R^3$ which $R^3$ groups may be the same or different. In other embodiments, B is a 5- to 6-membered heteroaryl optionally substituted by $R^4$. In other embodiments, B is a 5- to 6-membered heteroaryl substituted by 1 to 3 $R^4$ which $R^4$ may be the same or different. In some embodiments, the 5- to 6-membered heteroaryl of B is a 5-membered heteroaryl selected from the group consisting of furanyl, oxazolyl, thiophenyl, pyrazolyl, isoxazolyl, 1,3,4-oxadiazolyl, imidazolyl, thiazolyl, isothiazolyl, triazolyl, 1,3,4-thiadiazolyl and tetrazolyl, which 5-membered heteroaryl is optionally substituted by 1 to 3 $R^4$ which $R^4$ groups may be the same or different. In other embodiments, the 5- to 6-membered heteroaryl of B is a 6-membered heteroaryl selected from the group consisting of pyridyl and pyrimidinyl which 6-membered heteroaryl is optionally substituted to 1 to 3 $R^4$ which $R^4$ groups may be the same or different.

In some embodiments of B in which B is a phenyl substituted by $R^3$, such as when B is a phenyl substituted by 1 to 3 $R^3$ which may be the same or different, each $R^3$ of B in one aspect is independently selected from the group consisting of halogen, —$OR^5$, —$NR^6R^7$, —$C(O)R^5$, $C_3$-$C_6$ cycloalkyl and $C_1$-$C_6$ alkyl optionally substituted by halogen. In other embodiments, each $R^3$ of B is independently selected from the group consisting of halogen and $C_1$-$C_6$ alkyl optionally substituted by halogen (e.g., $CF_3$).

In some embodiments, B is a phenyl substituted with 1 to 3 halo groups which may be the same or different. In some embodiments, B is phenyl, fluoro-phenyl, di-fluoro-phenyl, chloro-phenyl, di-chloro-phenyl or (fluoro)(chloro)-phenyl. In some embodiments, B is selected from the group consisting of:

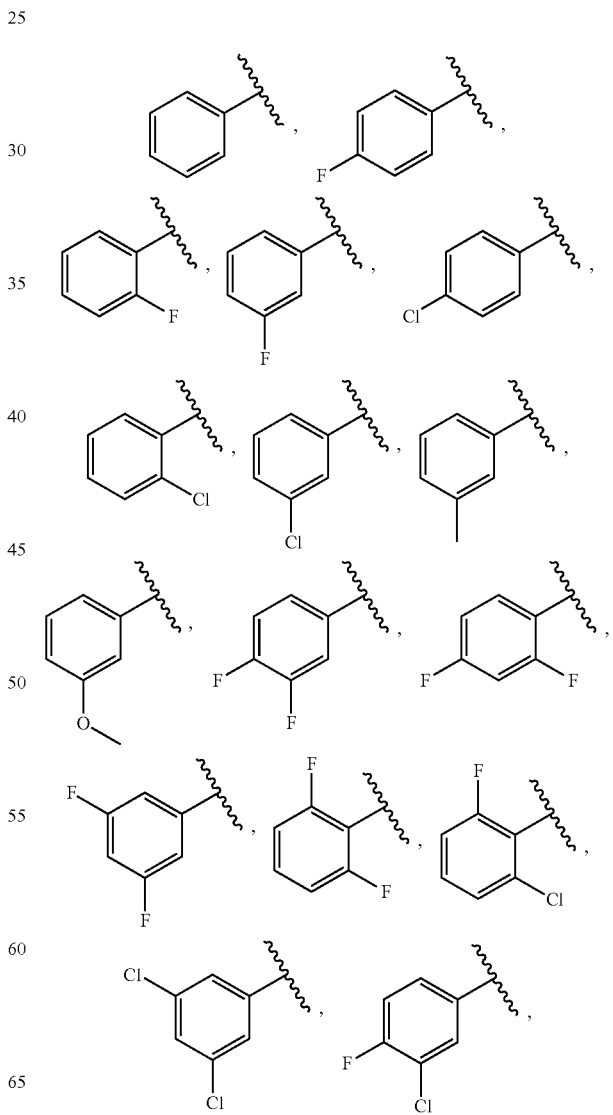

-continued

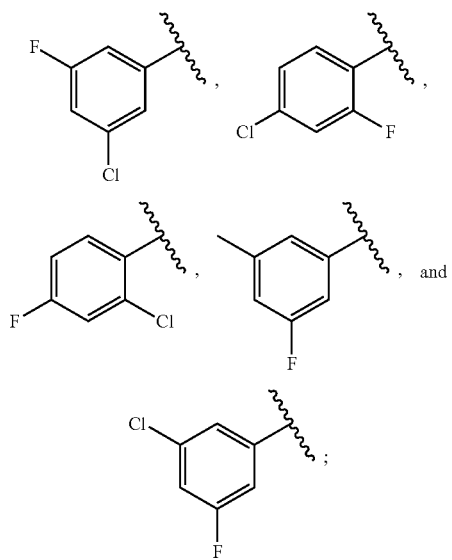

wherein the wavy lines denote attachment points to the parent molecule.

In some embodiments, B is a phenyl substituted with 1 to 3 halo groups which may be the same or different. In some embodiments, B is phenyl, fluoro-phenyl, di-fluoro-phenyl, chloro-phenyl, di-chloro-phenyl or (fluoro)(chloro)-phenyl. In some embodiments, B is selected from the group consisting of:

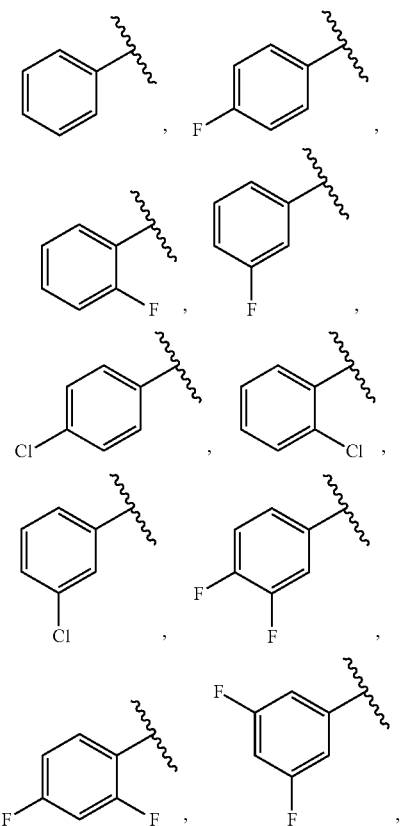

-continued

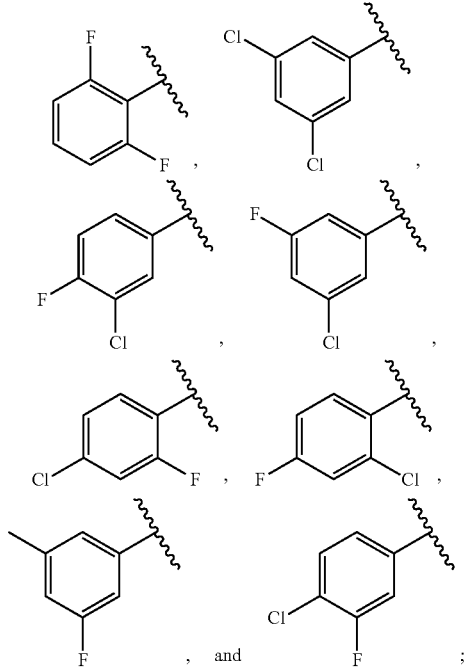

wherein the wavy lines denote attachment points to the parent molecule.

In some embodiments, B is a 5-membered heteroaryl substituted with 0 to 3 $R^4$ groups which may be the same or different. In some embodiments, B is a 5-membered heteroaryl substituted with 0 to 3 $R^3$ groups which may be the same or different. In one such aspect, B is a 5-membered heteroaryl substituted with 1 $R^3$ group. In another such aspect, B is a 5-membered heteroaryl substituted with 2 $R^3$ groups, which may be the same or different. In another such aspect, B is a 5-membered heteroaryl substituted with 3 $R^3$ groups, which may be the same or different. In some embodiments, B is a 5-membered heteroaryl selected from the group consisting of:

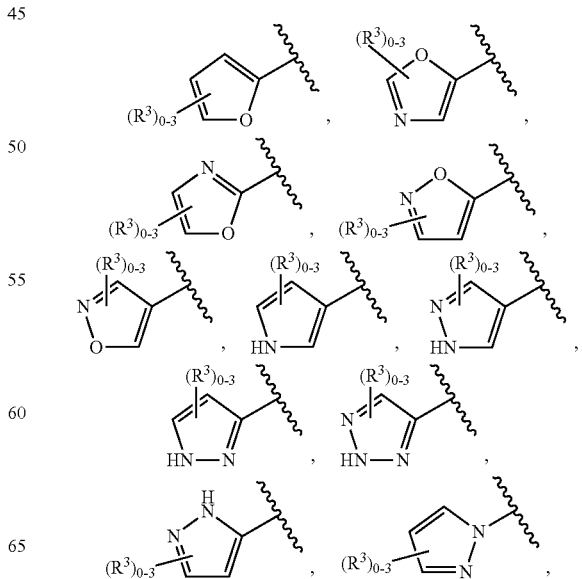

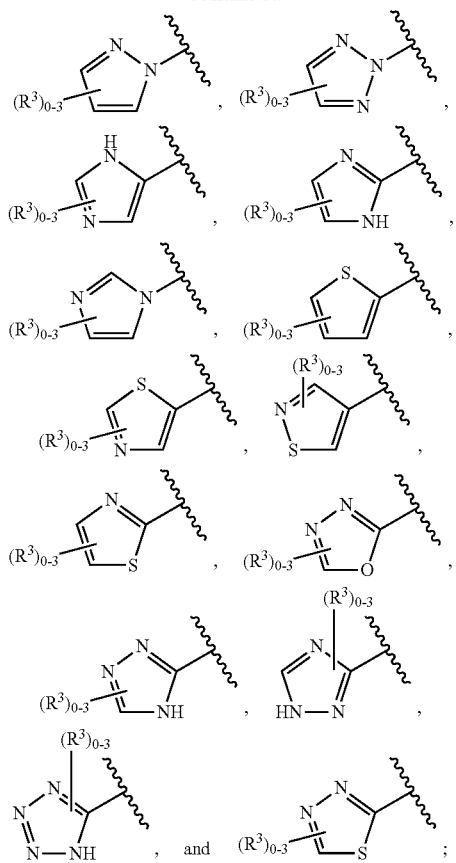

wherein the wavy lines denote attachment points to the parent molecule.

In some embodiments, B is a 5-membered heteroaryl substituted with 0 to 3 R³ groups which may be the same or different. In some embodiments, B is a 5-membered heteroaryl selected from the group consisting of:

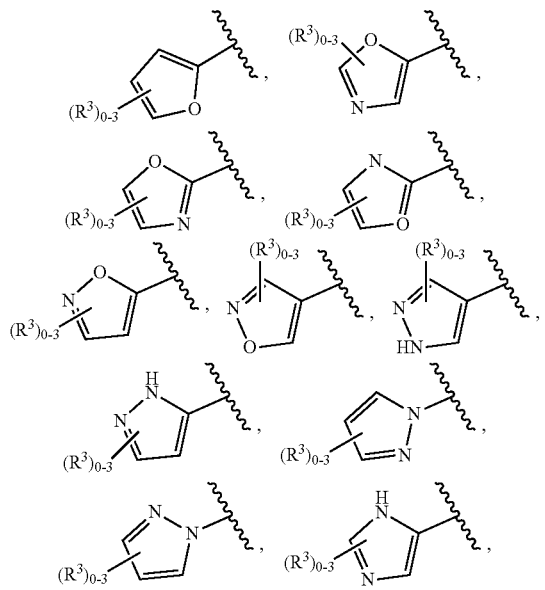

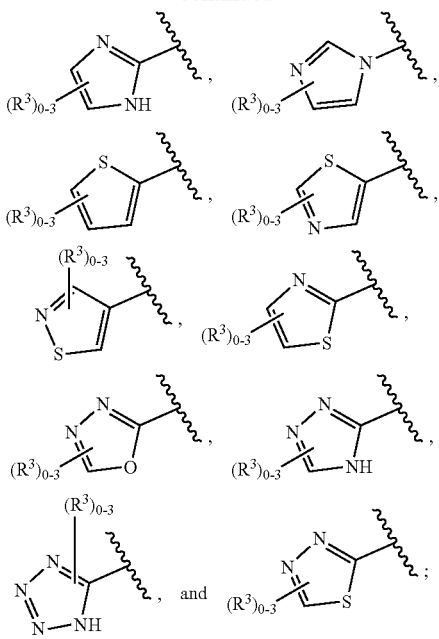

wherein the wavy lines denote attachment points to the parent molecule.

In some embodiments, B is a 5-membered heteroaryl selected from the group consisting of:

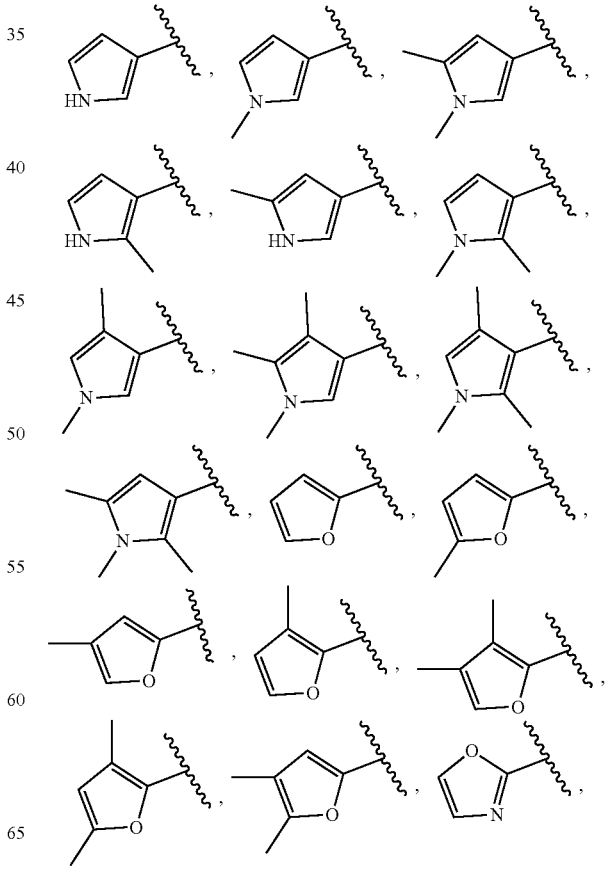

-continued
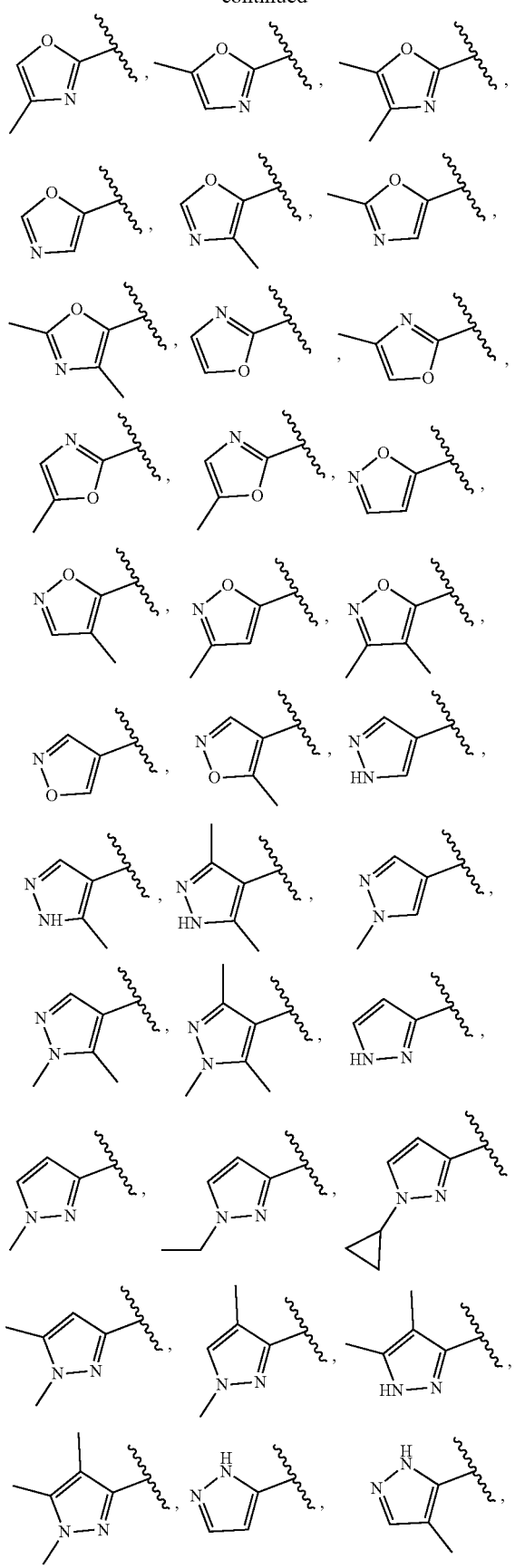
-continued
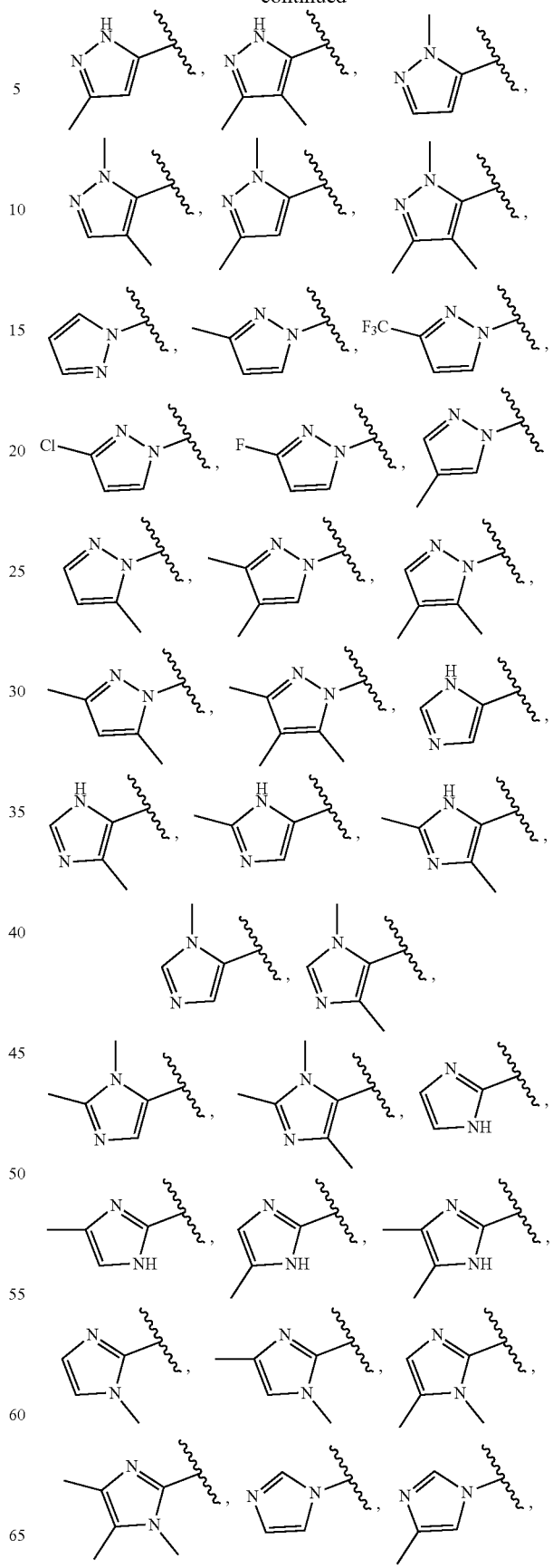

-continued
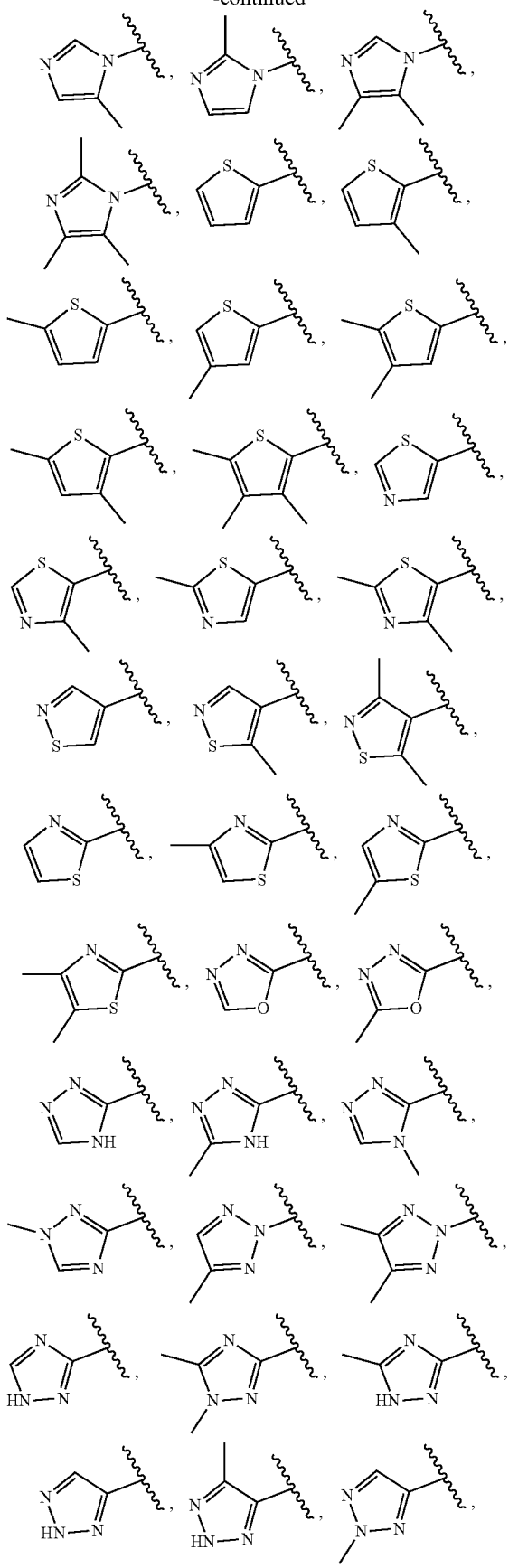
-continued
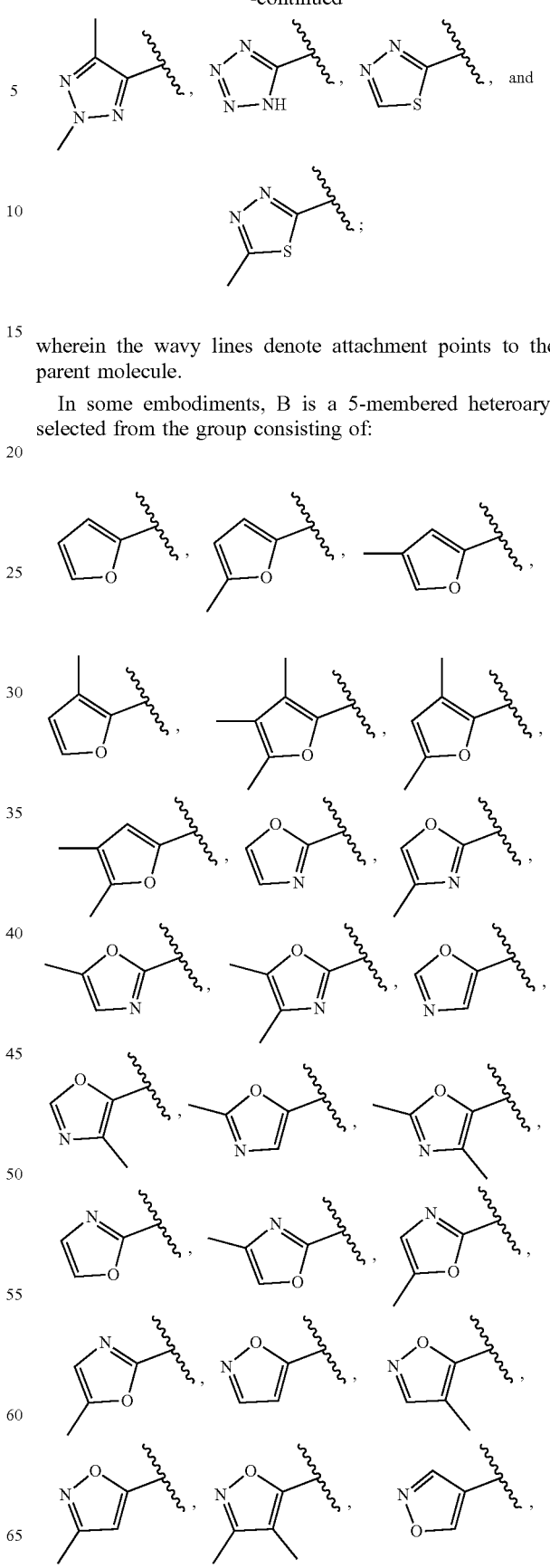
wherein the wavy lines denote attachment points to the parent molecule.
In some embodiments, B is a 5-membered heteroaryl selected from the group consisting of:

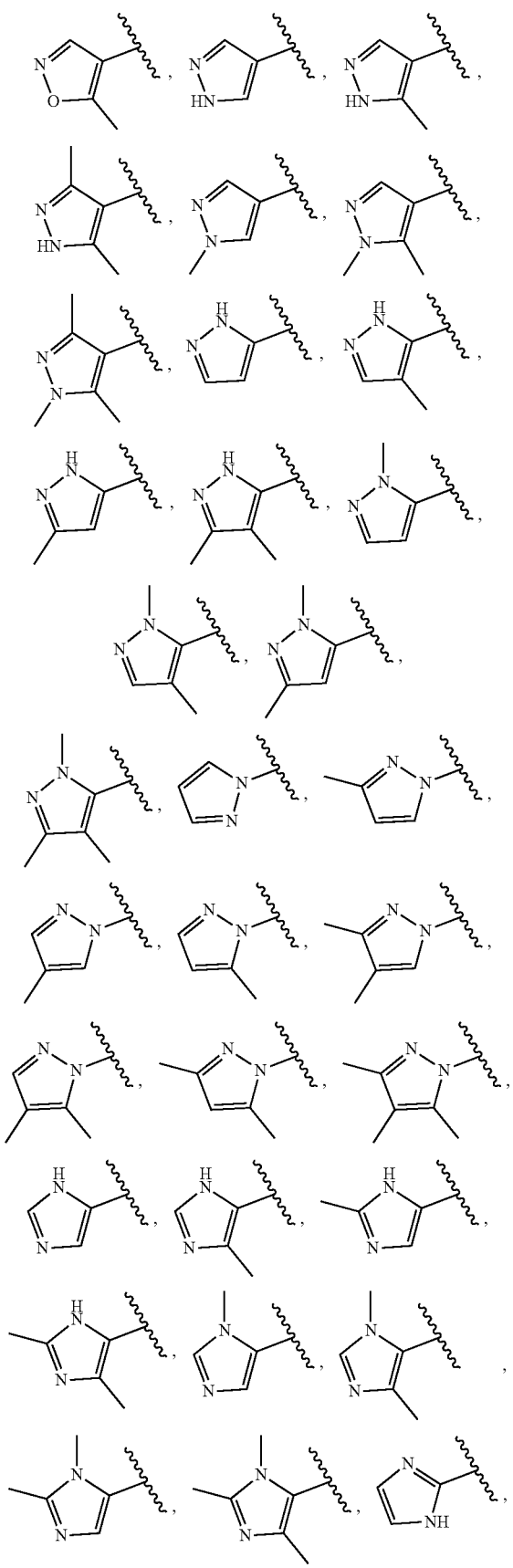
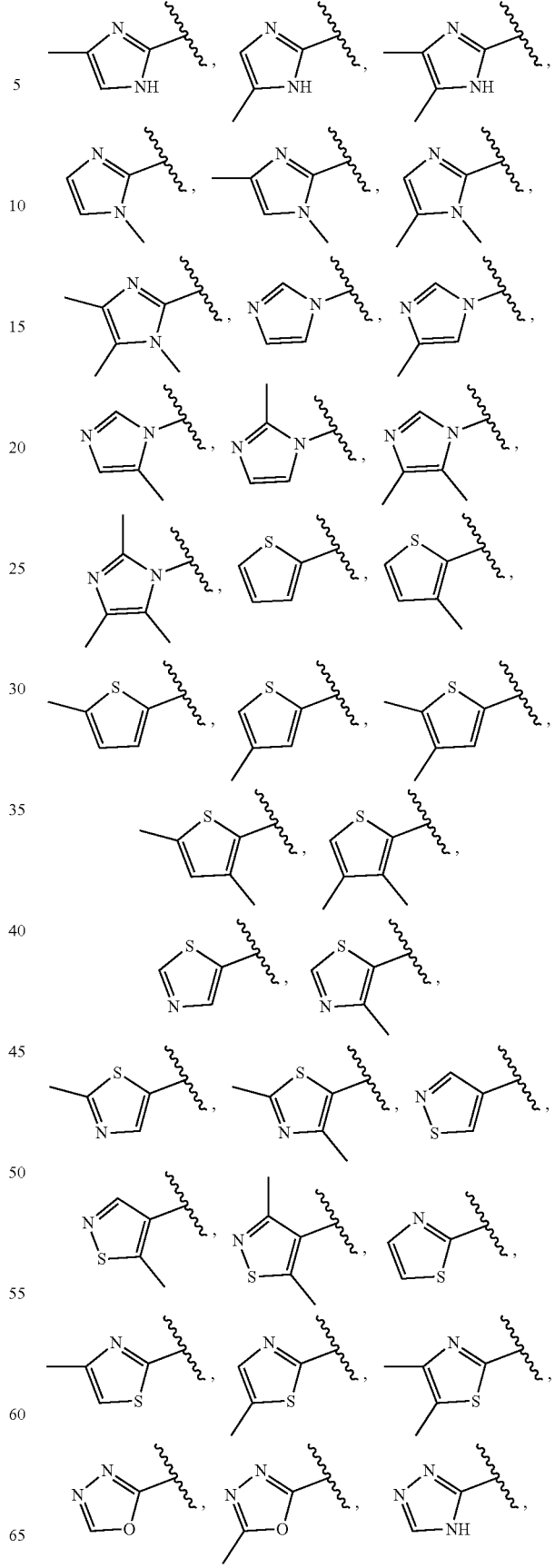

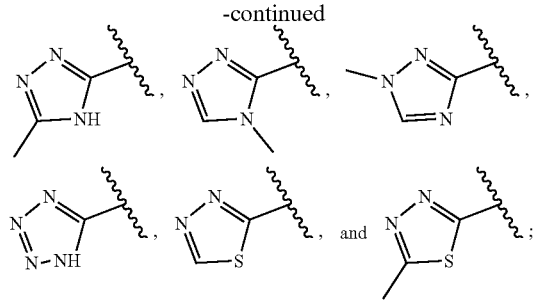

wherein the wavy lines denote attachment points to the parent molecule.

In some embodiments, B is a pyridyl or pyrimidyl optionally substituted by 1 to 3 R⁴, which R⁴ may be the same or different. In some embodiments, B is a pyridyl or pyrimidyl optionally substituted by 1 to 3 halo groups which may be the same or different. In some embodiments, B is a 6-membered heteroaryl selected from the group consisting of:

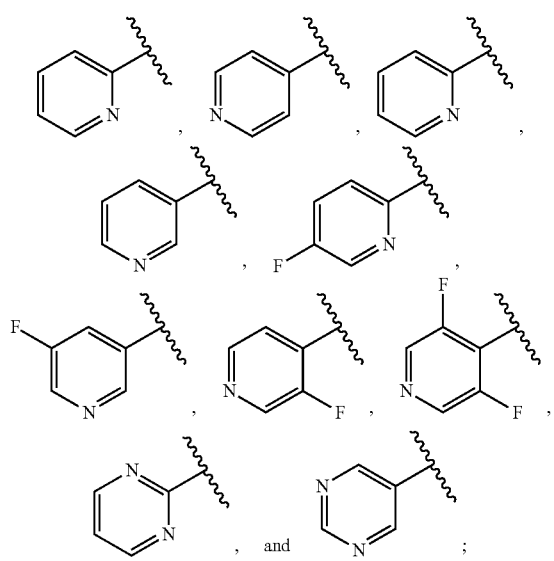

wherein the wavy lines denote attachment points to the parent molecule.

In some embodiments, B is a pyridyl or pyrimidyl optionally substituted by 1 to 3 R⁴, which R⁴ may be the same or different. In some embodiments, B is a pyridyl or pyrimidyl optionally substituted by 1 to 3 R³, which R³ may be the same or different. In some embodiments, B is a pyridyl or pyrimidyl optionally substituted by 1 to 3 halo groups which may be the same or different. In some embodiments, B is a 6-membered heteroaryl selected from the group consisting of:

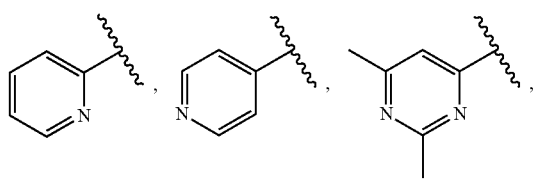

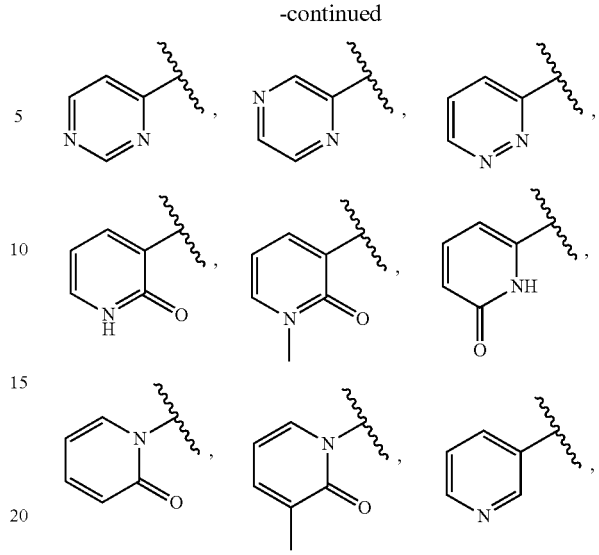

wherein the wavy lines denote attachment points to the parent molecule.

In some embodiments, B is selected from the group consisting of:

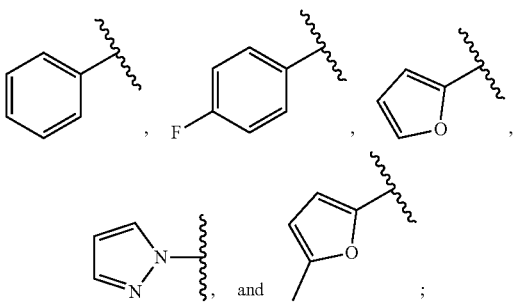

wherein the wavy lines denote attachment points to the parent molecule.

In some embodiments, B is a bicycle heteroaryl optionally substituted by 1 to 3 R⁴, which may be the same or different, and which may be present on either one ring or both rings. In some embodiments, B is a bicylic heteroaryl selected from the group consisting of:

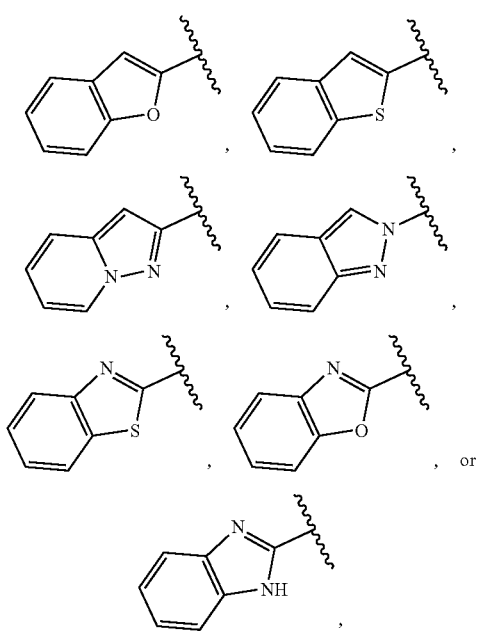

wherein the wavy lines denote attachment points to the parent molecule.

In some embodiments, B is selected from the group consisting of:

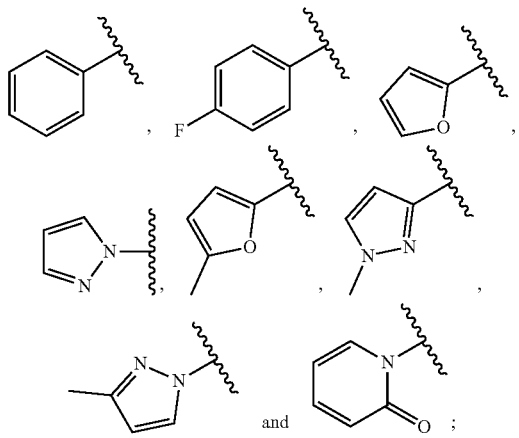

wherein the wavy lines denote attachment points to the parent molecule.

In some embodiments, B is

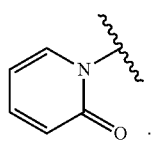 [SMILES: *n1ccccc1=O]

In some embodiments, B is

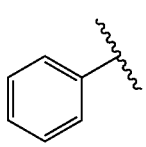

In some embodiments, B is

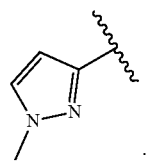

In some embodiments, B is

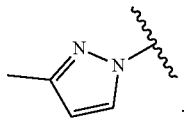

It is understood that each description of B may be combined with each description of $R^1$ and/or $R^2$ the same as if each and every combination were specifically and individually listed. It is similarly understood that each description of B may be combined with each description of A (and further with each description of $R^1$ and $R^2$) the same as if each and every combination were specifically and individually listed. For example, in one aspect, it is understood that each description of B may be combined in one aspect with a variation in which $R^1$ and $R^2$ are each hydrogen. In one such variation, B is as defined in any variation herein, $R^1$ and $R^2$ are each hydrogen and A is 4-hydroxyphenyl optionally further substituted by $R^3$ or 4-hydroxy-2-pyridyl optionally further substituted by $R^4$. In another variation, B is as defined in any variation herein, $R^1$ and $R^2$ are as defined in any variation herein and A is 4-hydroxyphenyl optionally further substituted by $R^3$ or 4-hydroxy-2-pyridyl optionally further substituted by $R^4$. In another variation, B is as defined in any variation herein, $R^1$ and $R^2$ are each hydrogen and A is 9- or 10-membered bicyclic heteroaryl (eg., quinolinyl or indazolyl) optionally substituted by $R^4$. In another variation, B is as defined in any variation herein, $R^1$ and $R^2$ are as defined in any variation herein and A is 9- or 10-membered bicyclic heteroaryl (eg., quinolinyl or indazolyl) optionally substituted by $R^4$.

In some embodiments, the compound of formula (I) is of the formula (II):

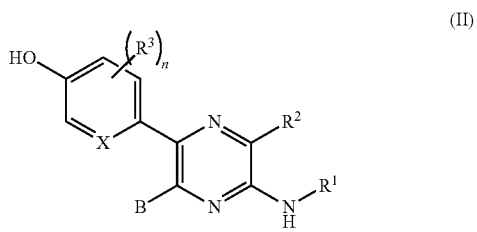

(II)

or a salt thereof, wherein $R^1$, $R^2$ and B are as defined for formula (I) or any embodiment or aspect or other variation thereof, X is N, CH or $CR^3$;

each $R^3$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen;

each $R^5$ is independently hydrogen, $C_1$-$C_6$ alkyl, or $C_3$-$C_6$ cycloalkyl;

$R^6$ and $R^7$ are each independently hydrogen, $C_1$-$C_6$ alkyl, or $C_3$-$C_6$ cycloalkyl;

or $R^6$ and $R^7$ are taken together with the atom to which they attached to form a 3-6 membered heterocyclyl; and n is 0, 1, 2 or 3.

In some embodiments, provided is a compound of formula (II), or a tautomer or isomer thereof, or a pharmaceutically acceptable salt of any of the foregoing.

In some embodiments of the compound of formula (II), $R^3$ is selected from the group consisting of halogen, —$OR^5$ and $C_1$-$C_6$ alkyl optionally substituted by halogen.

In some embodiments, the compound of formula (I) is a compound of formula (IIIa):

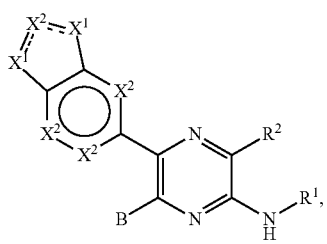

(IIIa)

or a salt thereof, wherein $R^1$, $R^2$ and B are as defined for formula (I);

each $X^1$ is independently O, S, NH, $NR^{4a}$, $CH_2$, $CHR^{4b}$, $CR^{4b}R^{4b}$, N, CH or $CR^{4b}$;

each $X^2$ is independently NH, $NR^{4a}$, $CHR^{4b}$, $CR^{4b}R^{4b}$, CH, $CR^{4b}$ or N;

each ═ is a single or double bond, provided that when $X^{2═}X^1$ is a double bond, $X^{2═}X^1$ is a single bond and when $X^{2═}X^1$ is a double bond, $X^{2═}X^1$ is a single bond;

$R^{4a}$ is $C_1$-$C_6$ alkyl;

each $R^{4b}$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen;

where each $R^5$ is independently hydrogen, $C_1$-$C_6$ alkyl, or $C_3$-$C_6$ cycloalkyl; and $R^6$ and $R^7$ are each independently hydrogen, $C_1$-$C_6$ alkyl, or $C_3$-$C_6$ cycloalkyl;

or $R^6$ and $R^7$ are taken together with the atom to which they attached to form a 3-6 membered heterocyclyl, provided the compound is other than a compound selected from Table 1 or a salt thereof.

In some embodiments, provided is a compound of formula (IIIa), or a tautomer or isomer thereof, or a pharmaceutically acceptable salt of any of the foregoing.

In some embodiments, the compound of formula (I) is a compound of formula (IIIb):

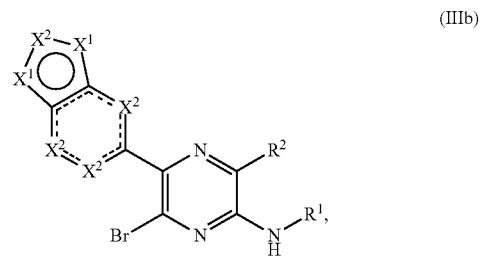

(IIIb)

or a salt thereof, wherein $R^1$, $R^2$ and B are as defined for formula (I);

each $X^1$ is independently O, S, NH, $NR^{4a}$, $CH_2$, $CHR^{4b}$, $CR^{4b}R^{4b}$, N, CH or $CR^{4b}$;

each $X^2$ is independently NH, $NR^{4a}$, $CH_2$, $CHR^{4b}$, $CR^{4b}R^{4b}$, CH, $CR^{4b}$ or N;

each ═ is a single or double bond;

$R^{4a}$ is $C_1$-$C_6$ alkyl;

each $R^{4b}$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen;

where each $R^5$ is independently hydrogen, $C_1$-$C_6$ alkyl, or $C_3$-$C_6$ cycloalkyl; and $R^6$ and $R^7$ are each independently hydrogen, $C_1$-$C_6$ alkyl, or $C_3$-$C_6$ cycloalkyl;

or $R^6$ and $R^7$ are taken together with the atom to which they attached to form a 3-6 membered heterocyclyl, provided the compound is other than a compound selected from Table 1 or a salt thereof.

In some embodiments, provided is a compound of formula (IIIb), or a tautomer or isomer thereof, or a pharmaceutically acceptable salt of any of the foregoing.

In some embodiments, the compound of formula (I) is a compound of formula (IIIc):

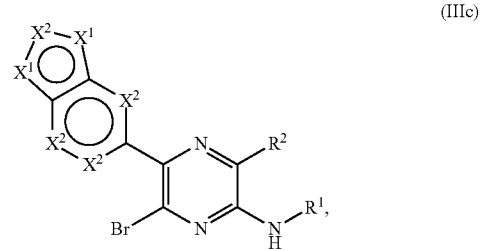

(IIIc)

or a salt thereof, wherein $R^1$, $R^2$ and B are as defined for formula (I);

each $X^1$ is independently O, S, NH, $NR^{4a}$, $CH_2$, $CHR^{4b}$, $CR^{4b}R^{4b}$, N, CH or $CR^{4b}$;

each $X^2$ is independently CH, $CR^{4b}$ or N;

$R^{4a}$ is $C_1$-$C_6$ alkyl;

each $R^{4b}$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen;

where each $R^5$ is independently hydrogen, $C_1$-$C_6$ alkyl, or $C_3$-$C_6$ cycloalkyl; and $R^6$ and $R^7$ are each independently hydrogen, $C_1$-$C_6$ alkyl, or $C_3$-$C_6$ cycloalkyl;

or $R^6$ and $R^7$ are taken together with the atom to which they attached to form a 3-6 membered heterocyclyl, provided the compound is other than a compound selected from Table 1 or a salt thereof.

In some embodiments, provided is a compound of formula (IIIc), or a tautomer or isomer thereof, or a pharmaceutically acceptable salt of any of the foregoing.

In some embodiments, the compound of formula (I) is a compound of formula (IIIc-1):

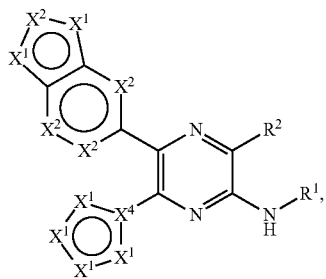

(IIIc-1)

or a salt thereof, wherein $R^1$ and $R^2$ are as defined for formula (I);
each $X^1$ and $X^2$ are as defined for formula (Inc);
$X^4$ is C or N;
provided the compound is other than a compound selected from Table 1 or a salt thereof.

In some embodiments, provided is a compound of formula (IIIc-1), or a tautomer or isomer thereof, or a pharmaceutically acceptable salt of any of the foregoing.

In some embodiments, the compound of formula (I) is a compound of formula (IIIc-2):

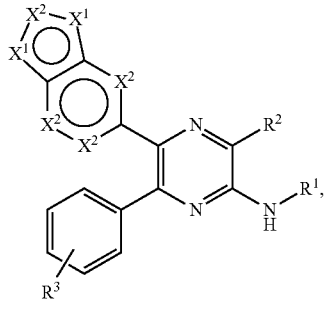

(IIIc-2)

or a salt thereof, wherein $R^1$, $R^2$ and $R^3$ are as defined for formula (I);
each $X^1$ and $X^2$ are as defined for formula (IIIc);
provided the compound is other than a compound selected from Table 1 or a salt thereof.

In some embodiments, provided is a compound of formula (IIIc-2), or a tautomer or isomer thereof, or a pharmaceutically acceptable salt of any of the foregoing.

In some embodiments, the compound of formula (I) is a compound of formula (IIId):

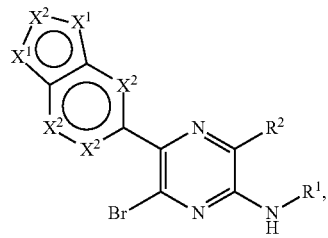

(IIId)

or a salt thereof, wherein $R^1$, $R^2$ and B are as defined for formula (I);
each $X^1$ is independently O, S, NH, $CH_2$, $CHR^{4b}$, $CR^{4b}R^{4b}$, N, CH or $CR^{4b}$;
each $X^2$ is independently CH, $CR^{4b}$ or N;
each $R^{4b}$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen;
where each $R^5$ is independently hydrogen, $C_1$-$C_6$ alkyl, or $C_3$-$C_6$ cycloalkyl; and
$R^6$ and $R^7$ are each independently hydrogen, $C_1$-$C_6$ alkyl, or $C_3$-$C_6$ cycloalkyl;
or $R^6$ and $R^7$ are taken together with the atom to which they attached to form a 3-6 membered heterocyclyl.

In some embodiments, provided is a compound of formula (IIId), or a tautomer or isomer thereof, or a pharmaceutically acceptable salt of any of the foregoing.

In some embodiments, the compound of formula (I) is a compound of formula (IIIe):

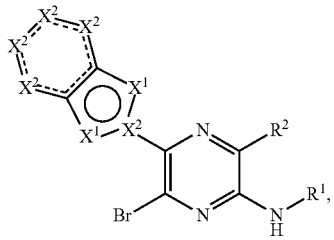

(IIIe)

or a salt thereof, wherein $R^1$, $R^2$ and B are as defined for formula (I);
each $X^1$ is independently O, S, NH, $NR^{4a}$, $CH_2$, $CHR^{4b}$, $CR^{4b}R^{4b}$, N, CH or $CR^{4b}$;
each $X^2$ is independently 0, $CH_2$, $CHR^{4b}$, $CR^{4b}R^{4b}$, CH, $CR^{4b}$ or N;
each = is a single or double bond;
$R^{4a}$ is $C_1$-$C_6$ alkyl;
each $R^{4b}$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen;
where each $R^5$ is independently hydrogen, $C_1$-$C_6$ alkyl, or $C_3$-$C_6$ cycloalkyl; and
$R^6$ and $R^7$ are each independently hydrogen, $C_1$-$C_6$ alkyl, or $C_3$-$C_6$ cycloalkyl;

or $R^6$ and $R^7$ are taken together with the atom to which they attached to form a 3-6 membered heterocyclyl,
provided the compound is other than a compound selected from Table 1 or a salt thereof.

In some embodiments, provided is a compound of formula (IIIe), or a tautomer or isomer thereof, or a pharmaceutically acceptable salt of any of the foregoing.

In some embodiments, the compound of formula (I) is a compound of formula (IIIf):

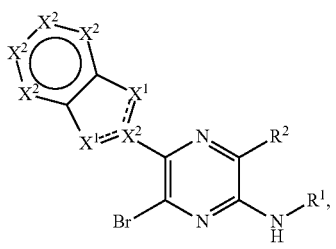

(IIIf)

or a salt thereof, wherein $R^1$, $R^2$ and B are as defined for formula (I);
each $X^1$ is independently O, S, NH, $NR^{4a}$, $CH_2$, $CHR^{4b}$, $CR^{4b}R^{4b}$, N, CH or $CR^{4b}$;
each $X^2$ is independently C, CH, $CR^{4b}$ or N;
each $=\!=$ is a single or double bond, provided that when $X^{2}\!=\!\!X^1$ is a double bond, $X^{2}\!=\!\!X^1$ is a single bond and when $X^{2}\!=\!\!X^1$ is a double bond, $X^{2}\!=\!\!X^1$ is a single bond;
$R^{4a}$ is $C_1$-$C_6$ alkyl;
each $R^{4b}$ is independently halogen, —CN, —$OR^5$, —$SR^5$, —$NR^6R^7$, —$NO_2$, —C(O)$R^5$, —C(O)O$R^5$, —C(O)$NR^6R^7$, —C(O)$NR^5$S(O)$_2R^6$, —OC(O)$R^5$, —OC(O)$NR^6R^7$, —$NR^5$C(O)$R^6$, —$NR^5$C(O)$NR^6R^7$, —S(O)$R^5$, —S(O)$_2R^5$, $C_3$-$C_6$ cycloalkyl, or $C_1$-$C_6$ alkyl optionally substituted by halogen;
where each $R^5$ is independently hydrogen, $C_1$-$C_6$ alkyl, or $C_3$-$C_6$ cycloalkyl; and
$R^6$ and $R^7$ are each independently hydrogen, $C_1$-$C_6$ alkyl, or $C_3$-$C_6$ cycloalkyl;
or $R^6$ and $R^7$ are taken together with the atom to which they attached to form a 3-6 membered heterocyclyl, provided the compound is other than a compound selected from Table 1 or a salt thereof.

In some embodiments, provided is a compound of formula (IIIf), or a tautomer or isomer thereof, or a pharmaceutically acceptable salt of any of the foregoing.

In some embodiments, the compound of formula (I) is a compound of formula (IIIg):

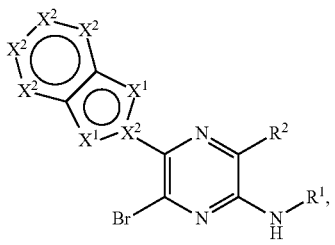

(IIIg)

or a salt thereof, wherein $R^1$, $R^2$ and B are as defined for formula (I);

each $X^1$ is independently O, S, NH, $NR^{4a}$, N, CH or $CR^{4b}$;
each $X^2$ is independently C, CH, $CR^{4b}$ or N;
$R^{4a}$ is $C_1$-$C_6$ alkyl;
each $R^{4b}$ is independently halogen, —CN, —$OR^5$, —$SR^5$, —$NR^6R^7$, —$NO_2$, —C(O)$R^5$, —C(O)O$R^5$, —C(O)$NR^6R^7$, —C(O)$NR^5$S(O)$_2R^6$, —OC(O)$R^5$, —OC(O)$NR^6R^7$, —$NR^5$C(O)$R^6$, —$NR^5$C(O)$NR^6R^7$, —S(O)$R^5$, —S(O)$_2R^5$, $C_3$-$C_6$ cycloalkyl, or $C_1$-$C_6$ alkyl optionally substituted by halogen;
where each $R^5$ is independently hydrogen, $C_1$-$C_6$ alkyl, or $C_3$-$C_6$ cycloalkyl; and
$R^6$ and $R^7$ are each independently hydrogen, $C_1$-$C_6$ alkyl, or $C_3$-$C_6$ cycloalkyl;
or $R^6$ and $R^7$ are taken together with the atom to which they attached to form a 3-6 membered heterocyclyl, provided the compound is other than a compound selected from Table 1 or a salt thereof.

In some embodiments, provided is a compound of formula (IIIg), or a tautomer or isomer thereof, or a pharmaceutically acceptable salt of any of the foregoing.

In some embodiments of the compound of formula (III), $R^{4b}$ is selected from the group consisting of halogen, —$OR^5$ and $C_1$-$C_6$ alkyl optionally substituted by halogen.

In some embodiments of the compound of formula (III), one of $X^1$ is N, and the other one of $X^1$ is $NR^{4a}$, and each $X^2$ is CH or $CR^{4b}$. In other embodiments of the compound of formula (III), one of $X^1$ is N, and the other one of $X^1$ is O or S, and each $X^2$ is CH or $CR^{4b}$.

In some embodiments, the compound of formula (I) is a compound of formula (IVa):

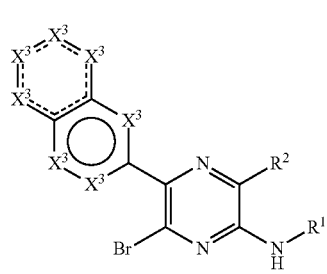

(IVa)

or a salt thereof, wherein $R^1$, $R^2$ and B are as defined for formula (I);
each $X^3$ is independently NH, $NR^4$, $CH_2$, $CHR^4$, $CR^4R^4$, $CR^4$, CH, C=O, O or N;
each $=\!=$ is a single or double bond;
each $R^4$ is independently halogen, —CN, —$OR^5$, —$SR^5$, —$NR^6R^7$, —$NO_2$, —C(O)$R^5$, —C(O)O$R^5$, —C(O)$NR^6R^7$, —C(O)$NR^5$S(O)$_2R^6$, —OC(O)$R^5$, —OC(O)$NR^6R^7$, —$NR^5$C(O)$R^6$, —$NR^5$C(O)$NR^6R^7$, —S(O)$R^5$, —S(O)$_2R^5$, $C_3$-$C_6$ cycloalkyl, —($C_1$-$C_3$ alkylene)(6-membered aryl) optionally substituted by halogen or $C_1$-$C_6$ alkyl optionally substituted by halogen;
where each $R^5$ is independently hydrogen, $C_1$-$C_6$ alkyl, or $C_3$-$C_6$ cycloalkyl; and
$R^6$ and $R^7$ are each independently hydrogen, $C_1$-$C_6$ alkyl, or $C_3$-$C_6$ cycloalkyl;
or $R^6$ and $R^7$ are taken together with the atom to which they attached to form a 3-6 membered heterocyclyl.

In some embodiments, the compound of formula (I) is a compound of formula (IVa):

(IVa)

or a salt thereof, wherein $R^1$, $R^2$ and B are as defined for formula (I);
each $X^3$ is independently NH, $NR^4$, $CH_2$, $CHR^4$, $CR^4R^4$, $CR^4$, CH or N;
each $=\!\!=$ is a single or double bond;
each $R^4$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen;
where each $R^5$ is independently hydrogen, $C_1$-$C_6$ alkyl, or $C_3$-$C_6$ cycloalkyl; and
$R^6$ and $R^7$ are each independently hydrogen, $C_1$-$C_6$ alkyl, or $C_3$-$C_6$ cycloalkyl;
or $R^6$ and $R^7$ are taken together with the atom to which they attached to form a 3-6 membered heterocyclyl.

In some embodiments, provided is a compound of formula (IVa), or a tautomer or isomer thereof, or a pharmaceutically acceptable salt of any of the foregoing.

In some embodiments, the compound of formula (I) is a compound of formula (IVb):

(IVb)

or a salt thereof, wherein $R^1$, $R^2$ and B are as defined for formula (I);
each $X^3$ is independently NH, $NR^4$, $CH_2$, $CHR^4$, $CR^4R^4$, $CR^4$, CH or N;
each $=\!\!=$ is a single or double bond;
each $R^4$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen;
where each $R^5$ is independently hydrogen, $C_1$-$C_6$ alkyl, or $C_3$-$C_6$ cycloalkyl; and
$R^6$ and $R^7$ are each independently hydrogen, $C_1$-$C_6$ alkyl, or $C_3$-$C_6$ cycloalkyl;
or $R^6$ and $R^7$ are taken together with the atom to which they attached to form a 3-6 membered heterocyclyl.

In some embodiments, provided is a compound of formula (IVb), or a tautomer or isomer thereof, or a pharmaceutically acceptable salt of any of the foregoing.

In some embodiments, the compound of formula (I) is a compound of formula (IVc):

(IVc)

or a salt thereof, wherein $R^1$, $R^2$ and B are as defined for formula (I);
each $X^3$ is independently $CR^4$, CH or N;
each $R^4$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen;
where each $R^5$ is independently hydrogen, $C_1$-$C_6$ alkyl, or $C_3$-$C_6$ cycloalkyl; and
$R^6$ and $R^7$ are each independently hydrogen, $C_1$-$C_6$ alkyl, or $C_3$-$C_6$ cycloalkyl;
or $R^6$ and $R^7$ are taken together with the atom to which they attached to form a 3-6 membered heterocyclyl.

In some embodiments, provided is a compound of formula (IVc), or a tautomer or isomer thereof, or a pharmaceutically acceptable salt of any of the foregoing.

In some embodiments of formula (IV), $R^4$ is selected from the group consisting of halogen, —$OR^5$ and $C_1$-$C_6$ alkyl optionally substituted by halogen.

In some embodiments, one $X^3$ is N, and the remaining $X^3$ are each $CR^4$. In some embodiments, two of the $X^3$ are N, and the remaining $X^3$ are each $CR^4$.

In some embodiments, the compound of formula (I) is a compound of formula (IVc-1):

(IVc-1)

or a salt thereof, wherein $R^1$ and $R^2$ are as defined for formula (I);
each $X^1$ is independently O, S, NH, $NR^{4a}$, N, CH or $CR^{4b}$;
$X^4$ is C or N;
each $X^3$ is as defined for formula (IVc)
$R^{4a}$ is $C_1$-$C_6$ alkyl;

each $R^{4b}$ is independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, $C_3$-$C_6$ cycloalkyl, or $C_1$-$C_6$ alkyl optionally substituted by halogen;

where each $R^5$ is independently hydrogen, $C_1$-$C_6$ alkyl, or $C_3$-$C_6$ cycloalkyl; and $R^6$ and $R^7$ are each independently hydrogen, $C_1$-$C_6$ alkyl, or $C_3$-$C_6$ cycloalkyl;

or $R^6$ and $R^7$ are taken together with the atom to which they attached to form a 3-6 membered heterocyclyl.

In some embodiments, provided is a compound of formula (IVc-1), or a tautomer or isomer thereof, or a pharmaceutically acceptable salt of any of the foregoing.

In some embodiments, the compound of formula (I) is a compound of formula (IVc-2):

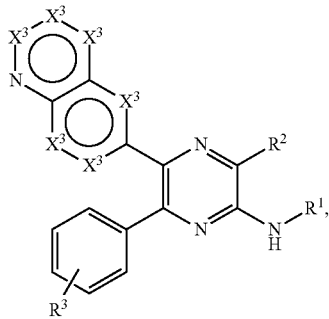

(IVc-2)

or a salt thereof, wherein $R^1$, $R^2$ and $R^3$ are as defined for formula (I);

each $X_3$ is as defined for formula (IVc);

In some embodiments, provided is a compound of formula (IVc-2), or a tautomer or isomer thereof, or a pharmaceutically acceptable salt of any of the foregoing.

In some embodiments of a compound of formula (I), (IVa), (IVb), or (IVc), A is

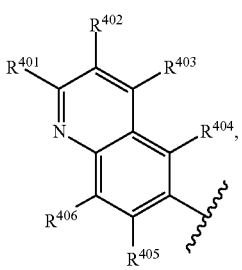

wherein $R^{401}$, $R^{402}$, $R^{403}$, $R^{404}$, $R^{405}$, and $R^{406}$ are each independently $R^4$. In some embodiments, $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, $C_3$-$C_6$ cycloalkyl, or $C_1$-$C_6$ alkyl optionally substituted by halogen.

In some embodiments of a compound of formula (I), (IVa), (IVb), or (IVc), A is

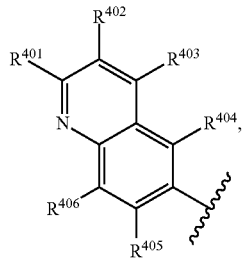

wherein $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, $C_3$-$C_6$ cycloalkyl, or $C_1$-$C_6$ alkyl optionally substituted by halogen; and B is phenyl, optionally substituted with $R^3$.

In some embodiments of a compound of formula (I), (IVa), (IVb), or (IVc), A is

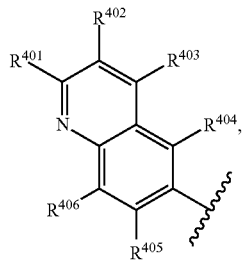

wherein $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, $C_3$-$C_6$ cycloalkyl, or $C_1$-$C_6$ alkyl optionally substituted by halogen; and B is 5- to 6-membered heteroaryl, optionally substituted with $R^4$.

In some embodiments of a compound of formula (I), (IVa), (IVb), or (IVc), A is

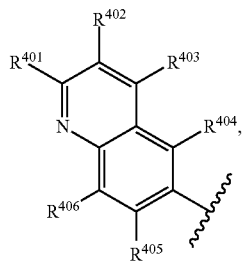

wherein $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, $C_3$-$C_6$ cycloalkyl, or $C_1$-$C_6$ alkyl optionally substituted by halogen; and B is 5-membered heteroaryl such as furanyl, oxazolyl, thiophenyl, pyrazolyl, isoxazolyl, 1,3,4-oxadiazolyl, imidazolyl, thiazolyl, isothiazolyl, triazolyl, 1,3,4-thiadiazolyl and tetrazolyl, each of which optionally substituted with $R^4$.

In some embodiments of a compound of formula (I), (IVa), (IVb), or (IVc), A is

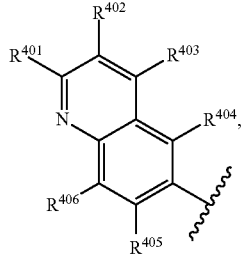

wherein $R^{401}$, $R^{402}$, $R^{403}$, $R^{404}$, $R^{405}$, and $R^{406}$ are each independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen; and B is selected from the group consisting of:

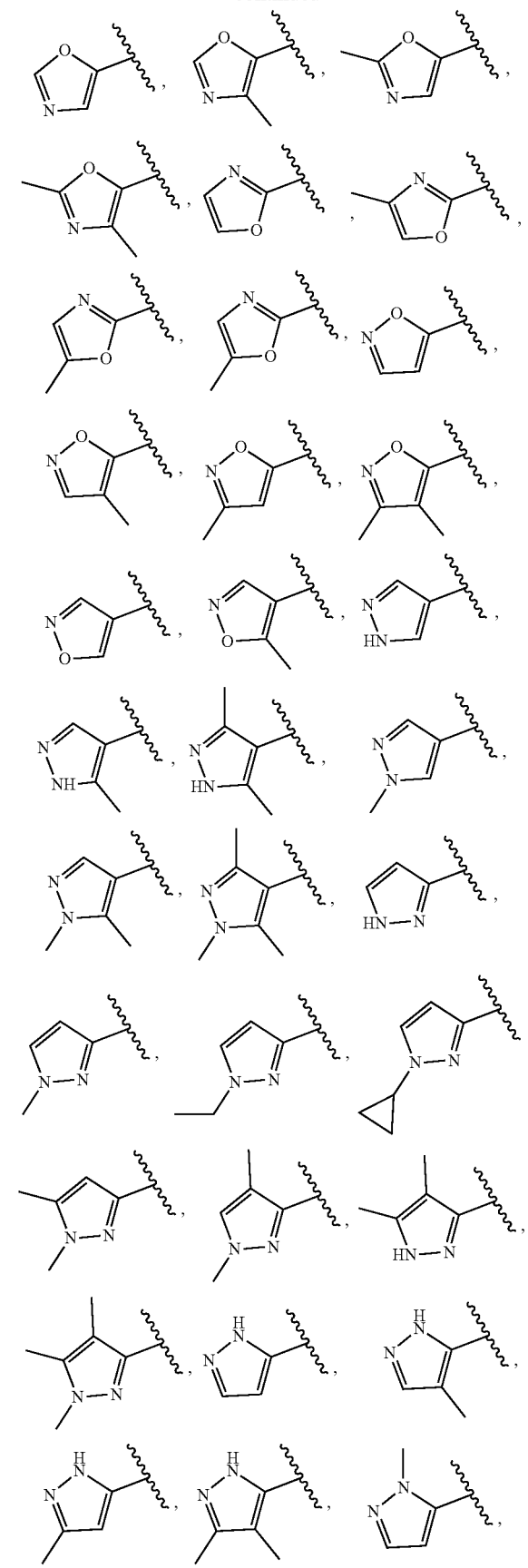

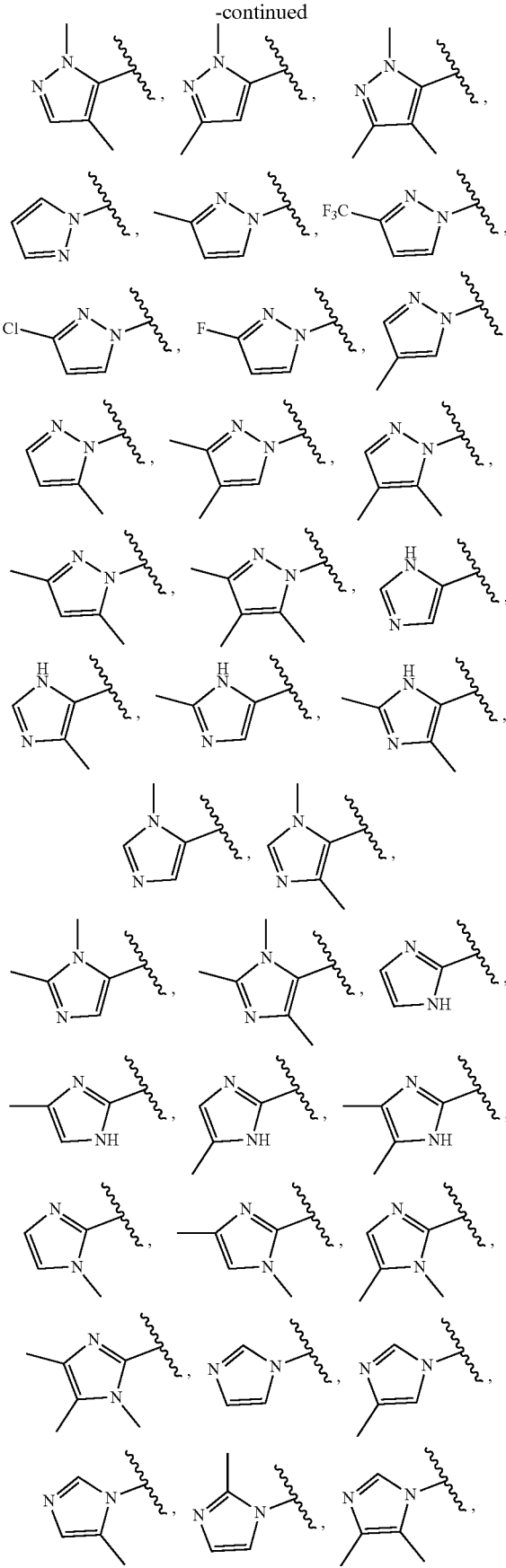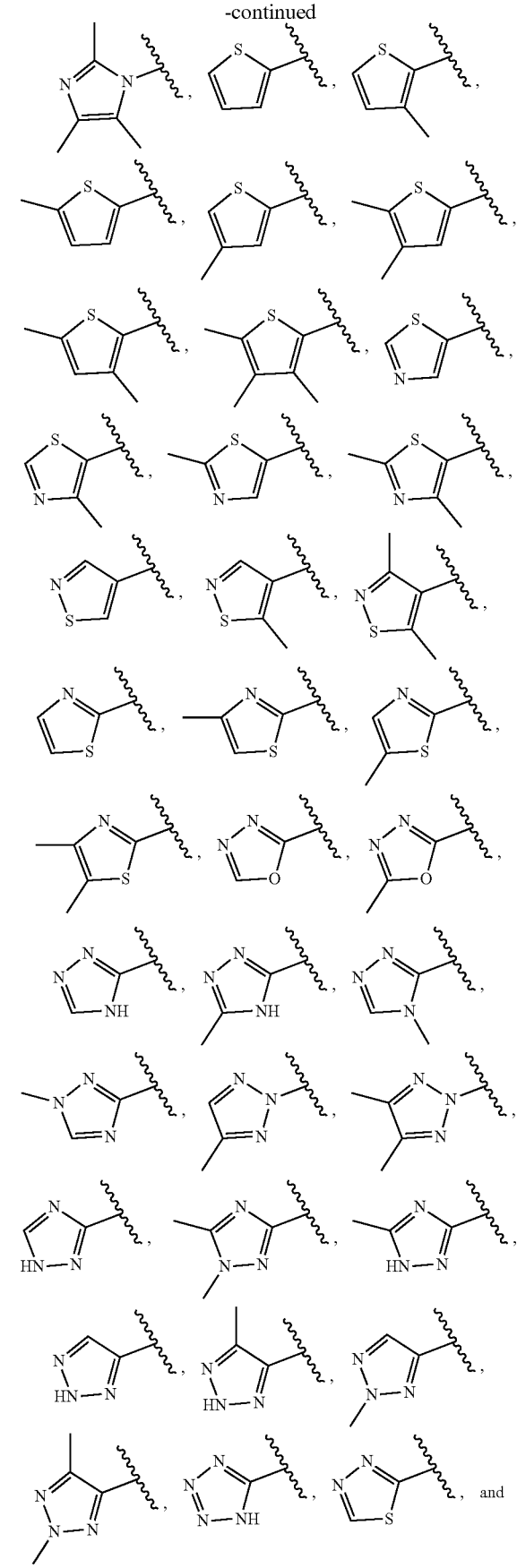

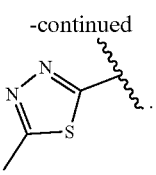

In some embodiments of a compound of formula (I), (IVa), (IVb), or (IVc), A is

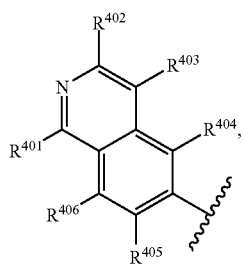

wherein $R^{401}$, $R^{402}$, $R^{403}$, $R^{404}$, $R^{405}$, and $R^{406}$ are each independently $R^4$. In some embodiments, $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, C$_3$-C$_6$ cycloalkyl, or C$_1$-C$_6$ alkyl optionally substituted by halogen.

In some embodiments of a compound of formula (I), (IVa), (IVb), or (IVc), A is

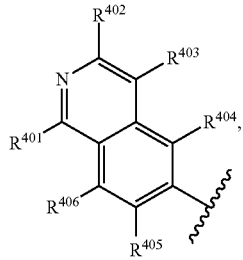

wherein $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, C$_3$-C$_6$ cycloalkyl, or C$_1$-C$_6$ alkyl optionally substituted by halogen; and B is phenyl, optionally substituted with $R^3$.

In some embodiments of a compound of formula (I), (IVa), (IVb), or (IVc), A is

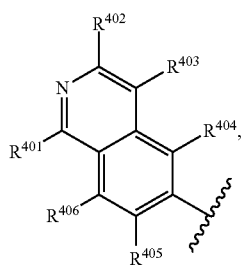

wherein $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, C$_3$-C$_6$ cycloalkyl, or C$_1$-C$_6$ alkyl optionally substituted by halogen; and B is 5- to 6-membered heteroaryl, optionally substituted with $R^4$.

In some embodiments of a compound of formula (I), (IVa), (IVb), or (IVc), A is

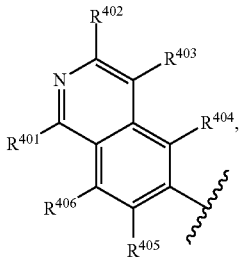

wherein $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, C$_3$-C$_6$ cycloalkyl, or C$_1$-C$_6$ alkyl optionally substituted by halogen; and B is 5-membered heteroaryl such as furanyl, oxazolyl, thiophenyl, pyrazolyl, isoxazolyl, 1,3,4-oxadiazolyl, imidazolyl, thiazolyl, isothiazolyl, triazolyl, 1,3,4-thiadiazolyl and tetrazolyl, each of which optionally substituted with $R^4$.

In some embodiments of a compound of formula (I), (IVa), (IVb), or (IVc), A is

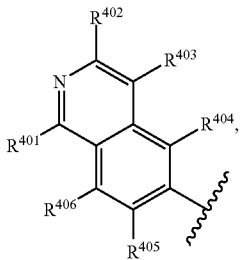

wherein $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, C$_3$-C$_6$ cycloalkyl, or C$_1$-C$_6$ alkyl optionally substituted by halogen; and B is selected from the group consisting of:

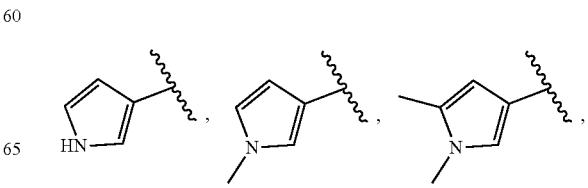

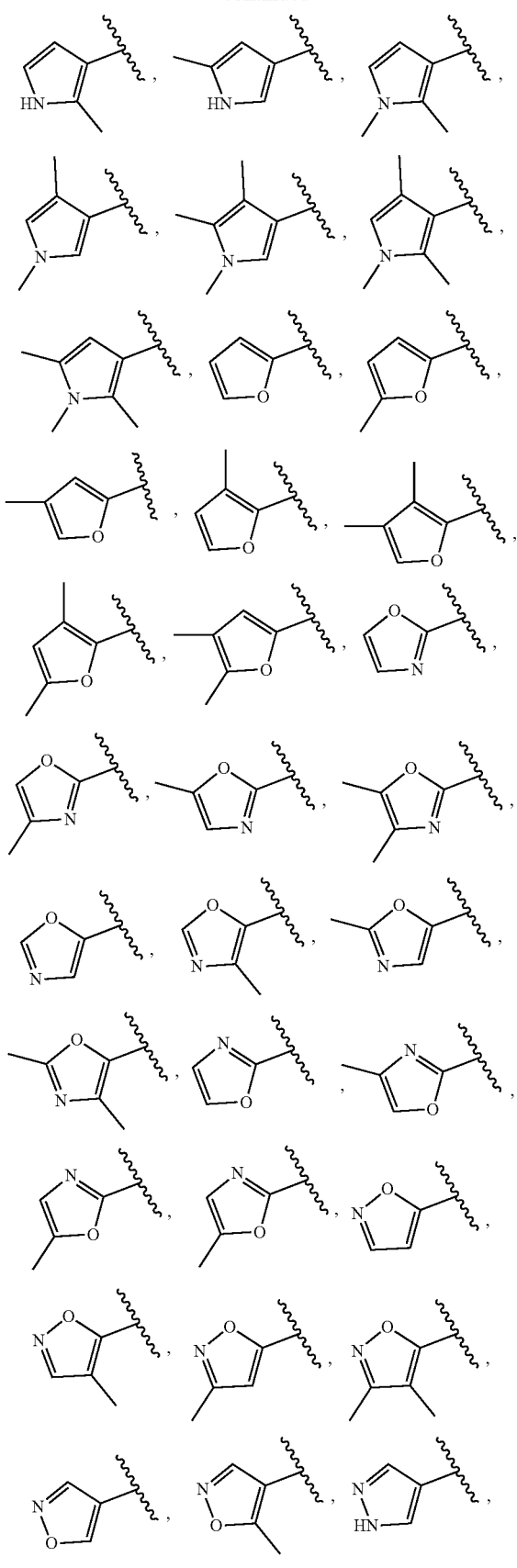
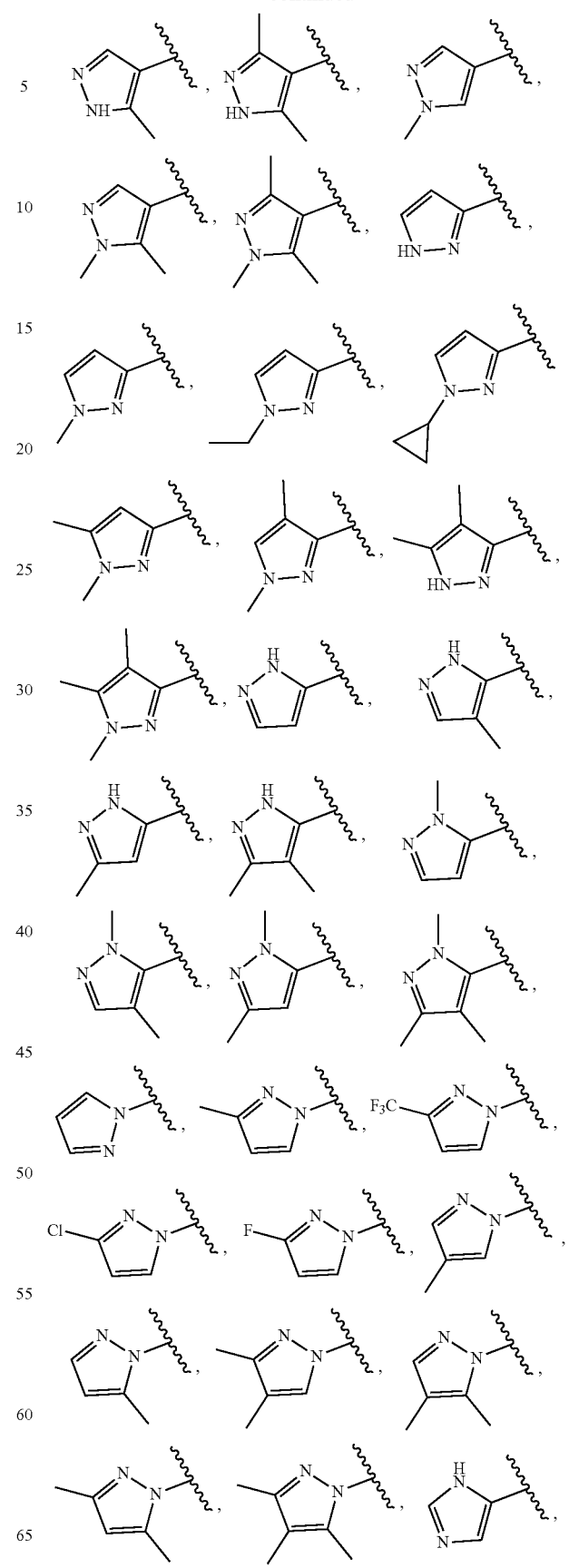

-continued

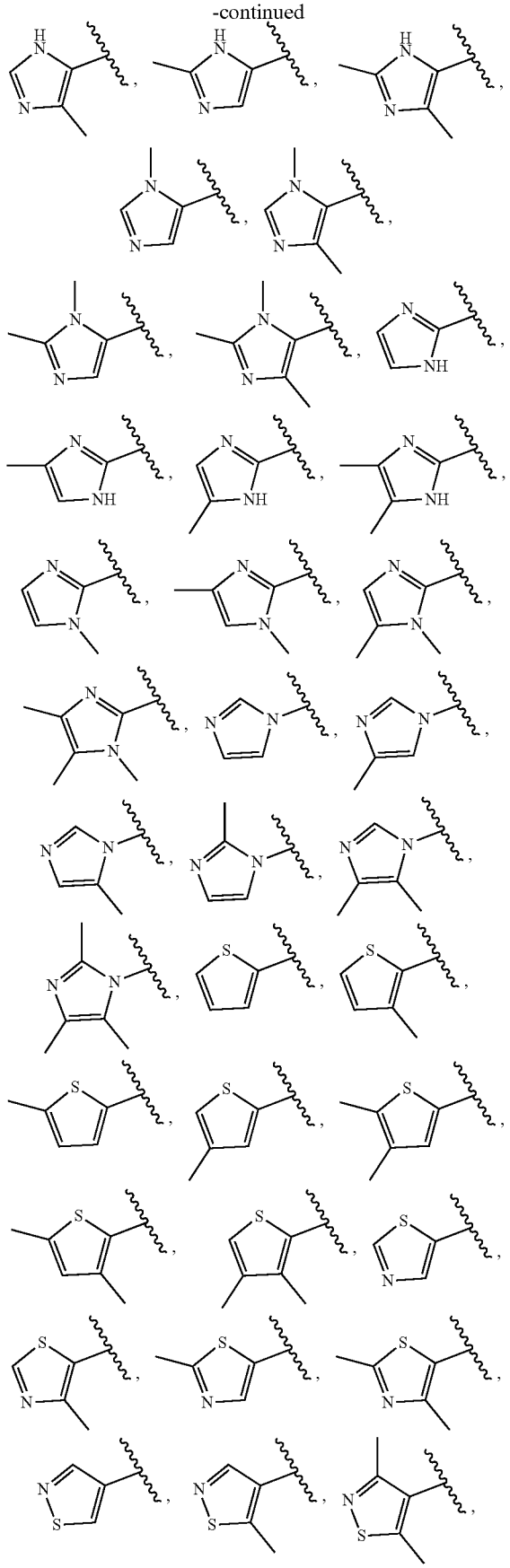

-continued

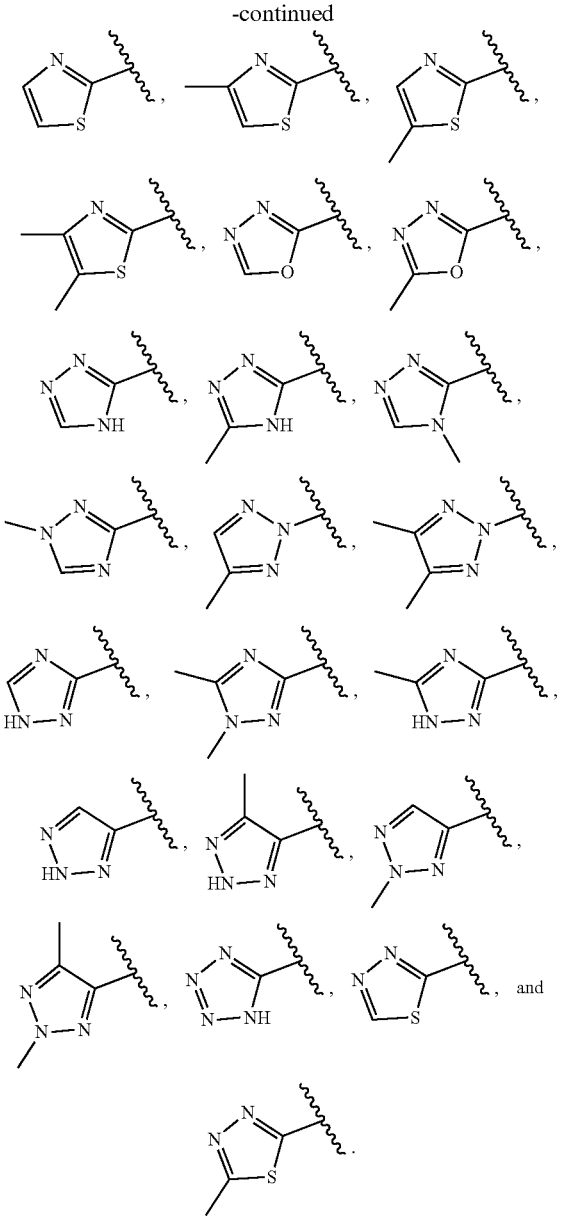

Also provided are salts of compounds referred to herein, such as pharmaceutically acceptable salts. The invention also includes any or all of the stereochemical forms, including any enantiomeric or diastereomeric forms, and any tautomers or other forms of the compounds described.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Representative compounds are listed in Table 2. It is understood that individual enantiomers and diastereomers if not depicted and their corresponding structures can be readily determined therefrom. Compounds 1.180-1.185 are provided as reference compounds.

TABLE 2

| Compound No. | Structure |
|---|---|
| 1.1 | 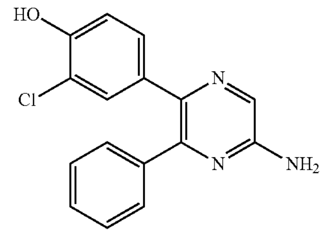 [SMILES: Nc1cnc(-c2ccc(O)c(Cl)c2)c(-c2ccccc2)n1] |
| 1.2 | 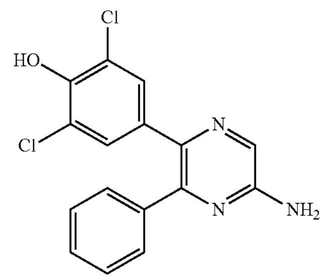 [SMILES: Nc1cnc(-c2cc(Cl)c(O)c(Cl)c2)c(-c2ccccc2)n1] |
| 1.3 | 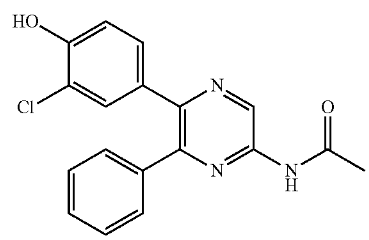 [SMILES: CC(=O)Nc1cnc(-c2ccc(O)c(Cl)c2)c(-c2ccccc2)n1] |
| 1.4 | 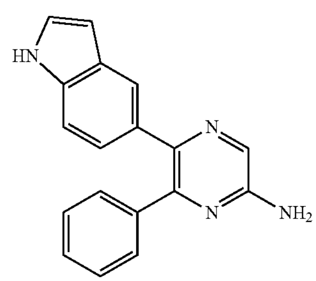 [SMILES: Nc1cnc(-c2ccc3[nH]ccc3c2)c(-c2ccccc2)n1] |
| 1.5 | 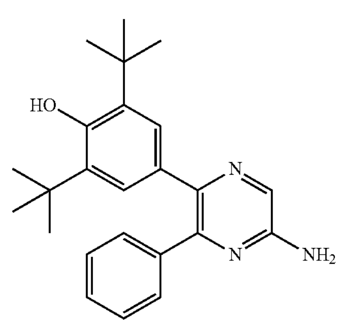 [SMILES: CC(C)(C)c1cc(-c2ncc(N)nc2-c2ccccc2)cc(C(C)(C)C)c1O] |

TABLE 2-continued
| Compound No. | Structure |
|---|---|
| 1.6 | 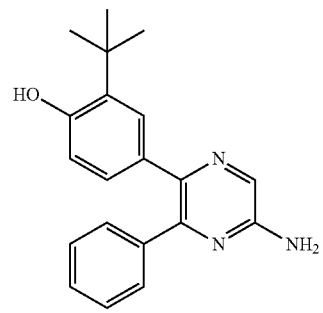 [SMILES: CC(C)(C)c1cc(-c2ncc(N)nc2-c2ccccc2)ccc1O] |
| 1.7 | 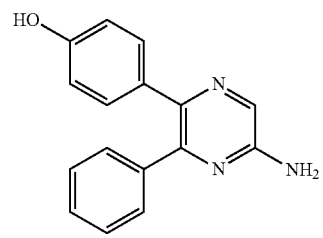 [SMILES: Nc1cnc(-c2ccc(O)cc2)c(-c2ccccc2)n1] |
| 1.8 | 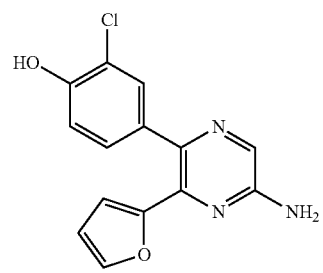 [SMILES: Nc1cnc(-c2ccc(O)c(Cl)c2)c(-c2ccco2)n1] |
| 1.9 | 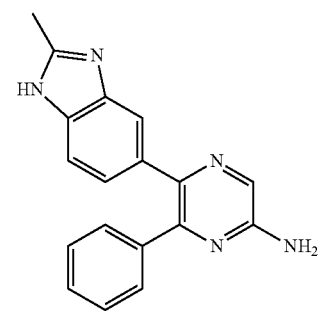 [SMILES: Cc1nc2cc(-c3ncc(N)nc3-c3ccccc3)ccc2[nH]1] |
| 1.10 | 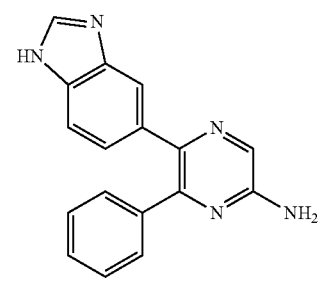 [SMILES: Nc1cnc(-c2ccc3[nH]cnc3c2)c(-c2ccccc2)n1] |

TABLE 2-continued

| Compound No. | Structure |
| --- | --- |
| 1.11 | 5-(5-amino-3-phenylpyrazin-2-yl)-2-hydroxybenzonitrile |
| 1.12 | 5-phenyl-6-(quinolin-6-yl)pyrazin-2-amine |
| 1.13 | 6-(5-amino-3-phenylpyrazin-2-yl)-7-chloro-1H-benzimidazole |
| 1.14 | 3-bromo-5-phenyl-6-(quinolin-6-yl)pyrazin-2-amine |
| 1.15 | 5-(4-fluorophenyl)-6-(quinolin-6-yl)pyrazin-2-amine |

TABLE 2-continued
| Compound No. | Structure |
|---|---|
| 1.16 | 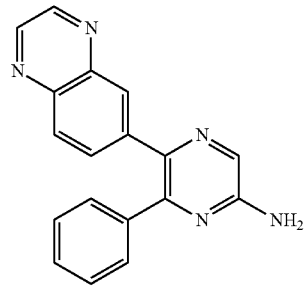 [SMILES: Nc1cnc(-c2ccc3nccnc3c2)c(-c2ccccc2)n1] |
| 1.17 | 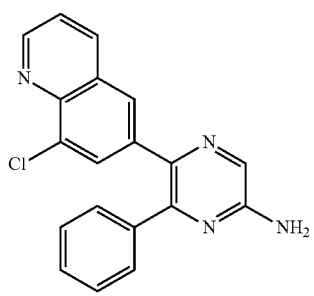 [SMILES: Nc1cnc(-c2cc(Cl)c3ncccc3c2)c(-c2ccccc2)n1] |
| 1.18 | 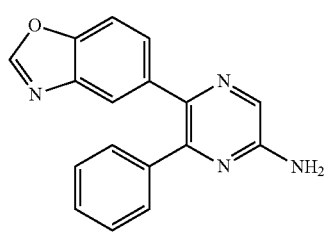 [SMILES: Nc1cnc(-c2ccc3ocnc3c2)c(-c2ccccc2)n1] |
| 1.19 | 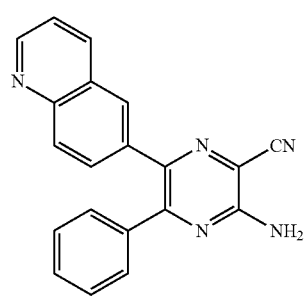 |
| 1.20 | 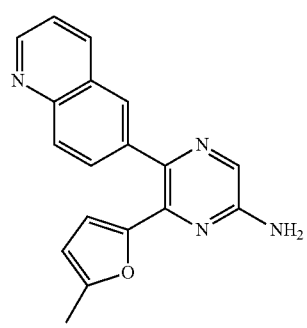 [SMILES: Cc1ccc(-c2nc(N)cnc2-c2ccc3ncccc3c2)o1] |

TABLE 2-continued
| Compound No. | Structure |
| --- | --- |
| 1.21 | 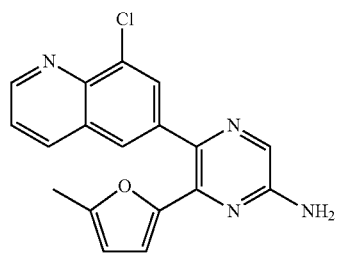 [SMILES: Cc1ccc(-c2nc(N)cnc2-c2cc(Cl)c3ncccc3c2)o1] |
| 1.22 | 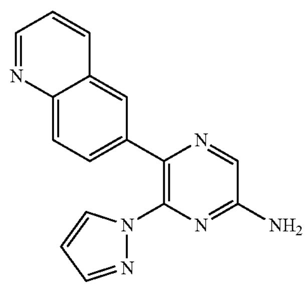 [SMILES: Nc1cnc(-c2ccc3ncccc3c2)c(-n2cccn2)n1] |
| 1.23 | 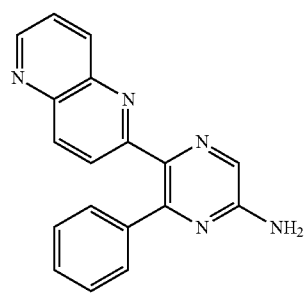 [SMILES: Nc1cnc(-c2ccc3ncccc3n2)c(-c2ccccc2)n1] |
| 1.24 | 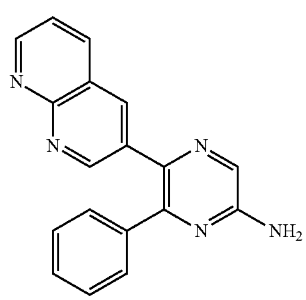 [SMILES: Nc1cnc(-c2cnc3ncccc3c2)c(-c2ccccc2)n1] |
| 1.25 | 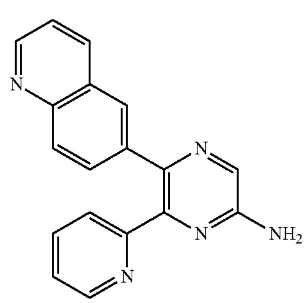 [SMILES: Nc1cnc(-c2ccc3ncccc3c2)c(-c2ccccn2)n1] |

TABLE 2-continued
| Compound No. | Structure |
|---|---|
| 1.26 | 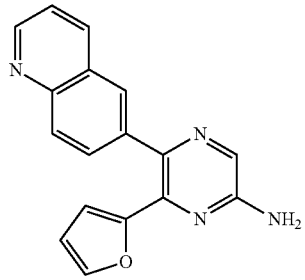 [SMILES: Nc1cnc(-c2ccc3ncccc3c2)c(-c2ccco2)n1] |
| 1.27 | 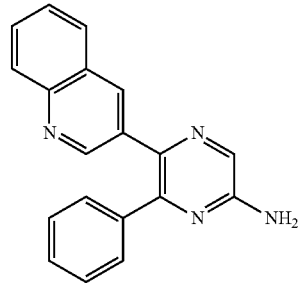 [SMILES: Nc1cnc(-c2cnc3ccccc3c2)c(-c2ccccc2)n1] |
| 1.28 | 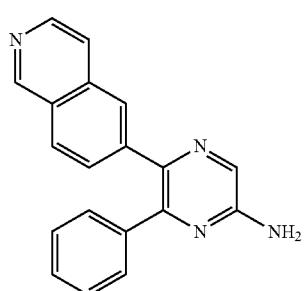 |
| 1.29 | 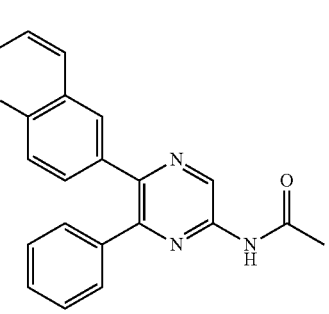 |
| 1.30 | 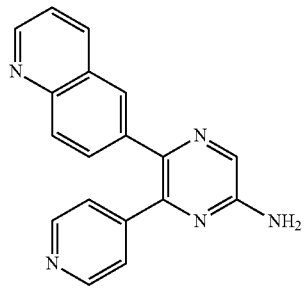 |

TABLE 2-continued
| Compound No. | Structure |
|---|---|
| 1.31 | 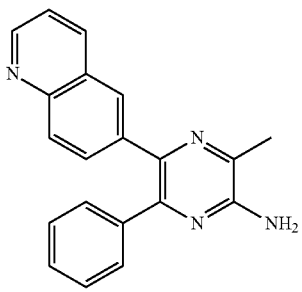 [SMILES: Cc1nc(-c2ccc3ncccc3c2)c(-c2ccccc2)nc1N] |
| 1.32 | 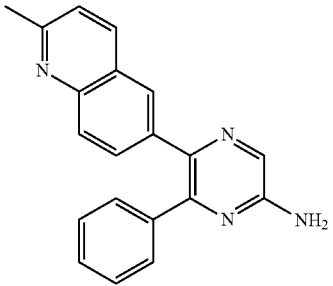 [SMILES: Cc1ccc2cc(-c3ncc(N)nc3-c3ccccc3)ccc2n1] |
| 1.33 | 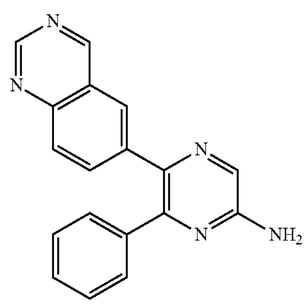 [SMILES: Nc1cnc(-c2ccc3ncncc3c2)c(-c2ccccc2)n1] |
| 1.34 | 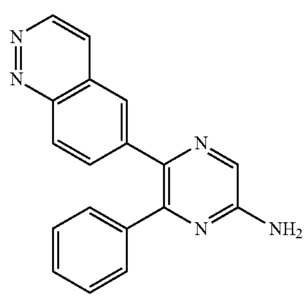 [SMILES: Nc1cnc(-c2ccc3nnccc3c2)c(-c2ccccc2)n1] |
| 1.35 | 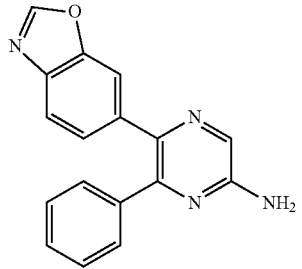 [SMILES: Nc1cnc(-c2ccc3ncoc3c2)c(-c2ccccc2)n1] |

TABLE 2-continued
| Compound No. | Structure |
|---|---|
| 1.36 | 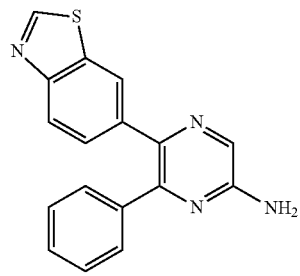 [SMILES: Nc1cnc(-c2ccc3ncsc3c2)c(-c2ccccc2)n1] |
| 1.37 | 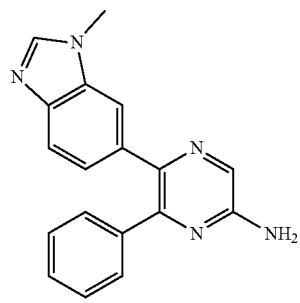 [SMILES: Cn1cnc2ccc(-c3ncc(N)nc3-c3ccccc3)cc21] |
| 1.38 | 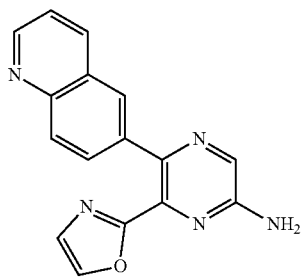 [SMILES: Nc1cnc(-c2ccc3ncccc3c2)c(-c2ncco2)n1] |
| 1.39 | 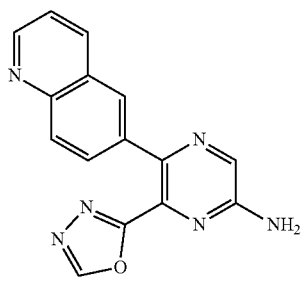 [SMILES: Nc1cnc(-c2ccc3ncccc3c2)c(-c2nnco2)n1] |
| 1.40 | 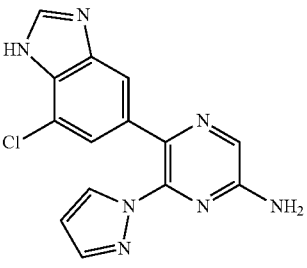 [SMILES: Nc1cnc(-c2cc(Cl)c3[nH]cnc3c2)c(-n2cccn2)n1] |

TABLE 2-continued

| Compound No. | Structure |
|---|---|
| 1.41 | [structure: 4-chlorobenzoxazole-6-yl substituted aminopyrazine with phenyl] |
| 1.42 | [structure: 4-chlorobenzothiazole-6-yl substituted aminopyrazine with phenyl] |
| 1.43 | [structure: 2-methoxyquinolin-6-yl substituted aminopyrazine with phenyl] |
| 1.44 | [structure: quinolin-6-yl substituted methoxy-aminopyrazine with phenyl] |
| 1.45 | [structure: 4-chloro-1H-benzimidazol-6-yl substituted aminopyrazine with 5-methylfuran-2-yl] |

TABLE 2-continued
| Compound No. | Structure |
|---|---|
| 1.46 | 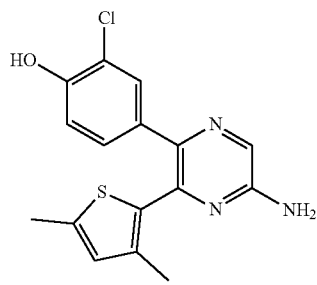 [SMILES: Cc1cc(C)c(-c2nc(N)cnc2-c2ccc(O)c(Cl)c2)s1] |
| 1.47 | 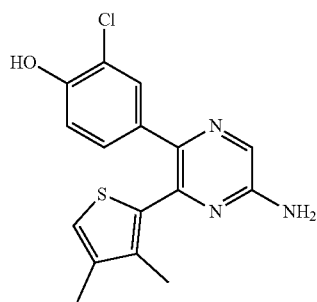 [SMILES: Cc1csc(-c2nc(N)cnc2-c2ccc(O)c(Cl)c2)c1C] |
| 1.48 | 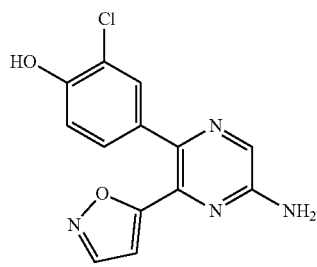 [SMILES: Nc1cnc(-c2ccc(O)c(Cl)c2)c(-c2ccno2)n1] |
| 1.49 | 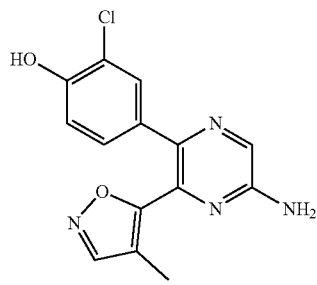 [SMILES: Cc1cnoc1-c1nc(N)cnc1-c1ccc(O)c(Cl)c1] |
| 1.50 | 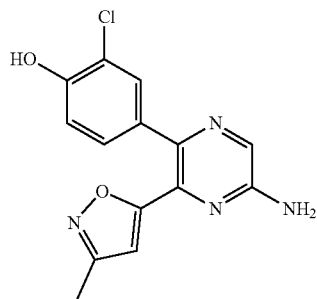 [SMILES: Cc1cc(-c2nc(N)cnc2-c2ccc(O)c(Cl)c2)on1] |

TABLE 2-continued

| Compound No. | Structure |
|---|---|
| 1.51 | 3-chloro-4-hydroxyphenyl pyrazine with 3,4-dimethylisoxazole and NH₂ |
| 1.52 | 3-chloro-4-hydroxyphenyl pyrazine with oxazole and NH₂ |
| 1.53 | 3-chloro-4-hydroxyphenyl pyrazine with 5-methyloxazole and NH₂ |
| 1.54 | 3-chloro-4-hydroxyphenyl pyrazine with 4-methyloxazole and NH₂ |
| 1.55 | 3-chloro-4-hydroxyphenyl pyrazine with 4,5-dimethyloxazole and NH₂ |

TABLE 2-continued
| Compound No. | Structure |
|---|---|
| 1.56 | 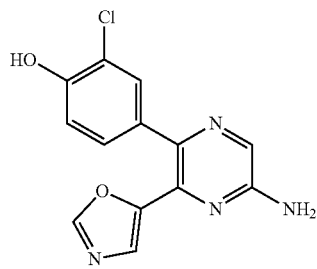 [SMILES: Nc1cnc(-c2ccc(O)c(Cl)c2)c(-c2cnco2)n1] |
| 1.57 | 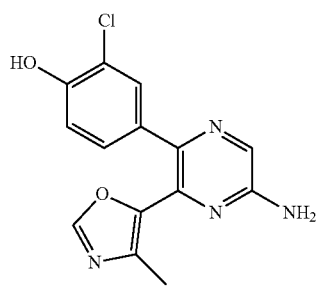 [SMILES: Cc1ncoc1-c1nc(N)cnc1-c1ccc(O)c(Cl)c1] |
| 1.58 | 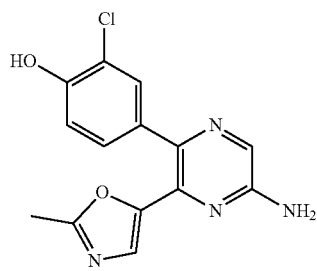 [SMILES: Cc1ncc(-c2nc(N)cnc2-c2ccc(O)c(Cl)c2)o1] |
| 1.59 | 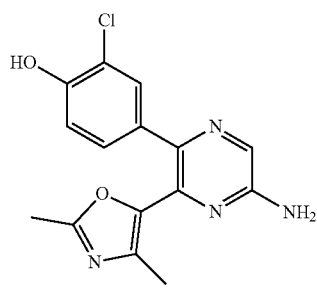 [SMILES: Cc1nc(C)c(-c2nc(N)cnc2-c2ccc(O)c(Cl)c2)o1] |
| 1.60 | 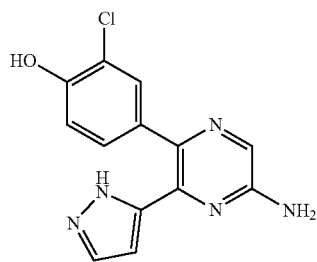 |

TABLE 2-continued
| Compound No. | Structure |
|---|---|
| 1.61 | 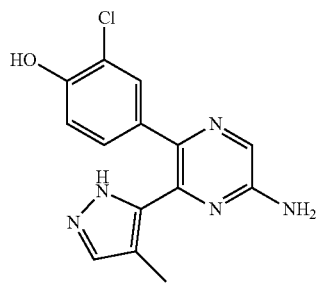 [SMILES: Cc1cn[nH]c1-c1nc(N)cnc1-c1ccc(O)c(Cl)c1] |
| 1.62 | 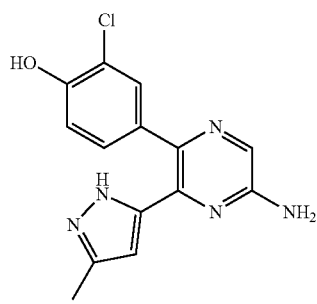 [SMILES: Cc1cc(-c2nc(N)cnc2-c2ccc(O)c(Cl)c2)[nH]n1] |
| 1.63 | 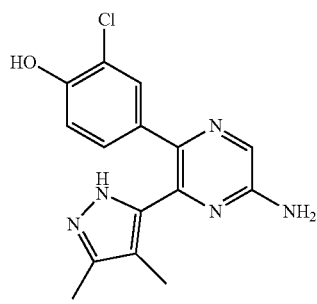 [SMILES: Cc1n[nH]c(-c2nc(N)cnc2-c2ccc(O)c(Cl)c2)c1C] |
| 1.64 | 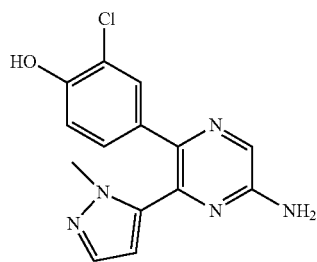 [SMILES: Cn1nccc1-c1nc(N)cnc1-c1ccc(O)c(Cl)c1] |
| 1.65 | 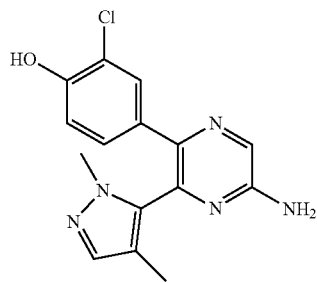 [SMILES: Cc1cnn(C)c1-c1nc(N)cnc1-c1ccc(O)c(Cl)c1] |

TABLE 2-continued
| Compound No. | Structure |
|---|---|
| 1.66 | 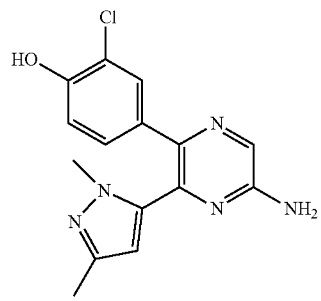 [SMILES: Cc1cc(-c2nc(N)cnc2-c2ccc(O)c(Cl)c2)n(C)n1] |
| 1.67 | 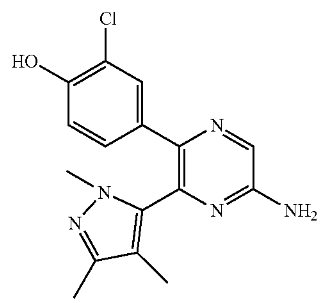 [SMILES: Cc1nn(C)c(-c2nc(N)cnc2-c2ccc(O)c(Cl)c2)c1C] |
| 1.68 | 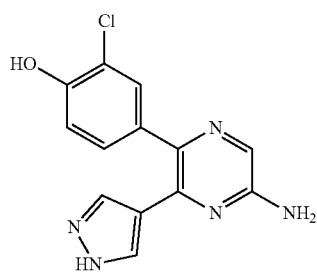 [SMILES: Nc1cnc(-c2ccc(O)c(Cl)c2)c(-c2cn[nH]c2)n1] |
| 1.69 | 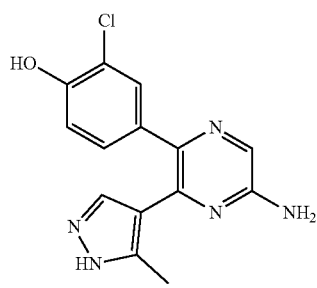 [SMILES: Cc1[nH]ncc1-c1nc(N)cnc1-c1ccc(O)c(Cl)c1] |
| 1.70 | 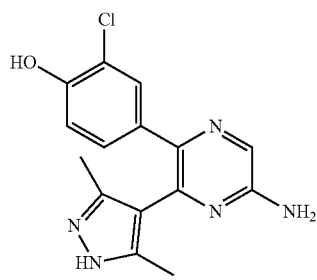 [SMILES: Cc1n[nH]c(C)c1-c1nc(N)cnc1-c1ccc(O)c(Cl)c1] |

TABLE 2-continued

| Compound No. | Structure |
|---|---|
| 1.71 | (3-chloro-4-hydroxyphenyl)-(1-methyl-1H-pyrazol-4-yl)-pyrazin-2-amine |
| 1.72 | (3-chloro-4-hydroxyphenyl)-(1,5-dimethyl-1H-pyrazol-4-yl)-pyrazin-2-amine |
| 1.73 | (3-chloro-4-hydroxyphenyl)-(1,3,5-trimethyl-1H-pyrazol-4-yl)-pyrazin-2-amine |
| 1.74 | (3-chloro-4-hydroxyphenyl)-(3-methyl-1H-pyrazol-1-yl)-pyrazin-2-amine |
| 1.75 | (3-chloro-4-hydroxyphenyl)-(4-methyl-1H-pyrazol-1-yl)-pyrazin-2-amine |

TABLE 2-continued

| Compound No. | Structure |
| --- | --- |
| 1.76 | 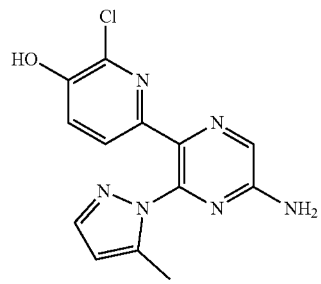 [SMILES: Cc1ccnn1-c1nc(N)cnc1-c1ccc(O)c(Cl)n1] |
| 1.77 | 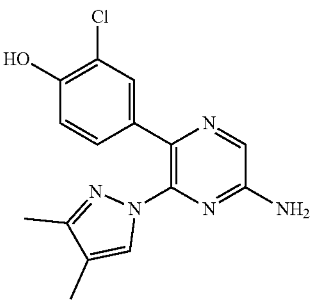 [SMILES: Cc1cn(-c2nc(N)cnc2-c2ccc(O)c(Cl)c2)nc1C] |
| 1.78 | 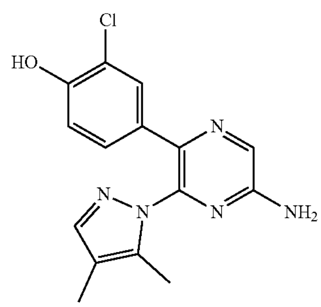 [SMILES: Cc1cnn(-c2nc(N)cnc2-c2ccc(O)c(Cl)c2)c1C] |
| 1.79 | 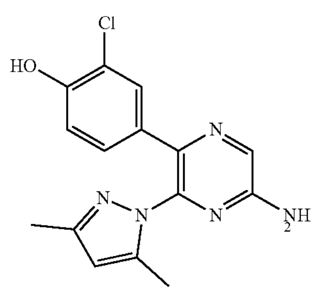 [SMILES: Cc1cc(C)n(-c2nc(N)cnc2-c2ccc(O)c(Cl)c2)n1] |
| 1.80 | 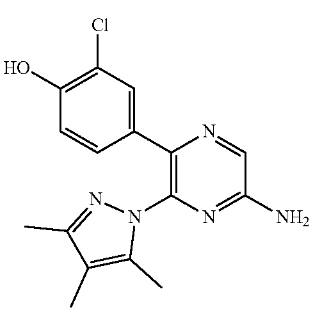 [SMILES: Cc1nn(-c2nc(N)cnc2-c2ccc(O)c(Cl)c2)c(C)c1C] |

TABLE 2-continued

| Compound No. | Structure |
|---|---|
| 1.81 | 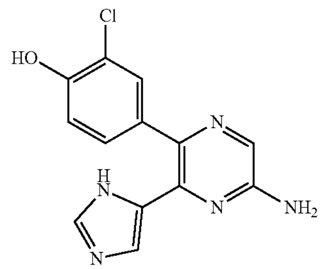 [SMILES: Nc1cnc(-c2ccc(O)c(Cl)c2)c(-c2cnc[nH]2)n1] |
| 1.82 | 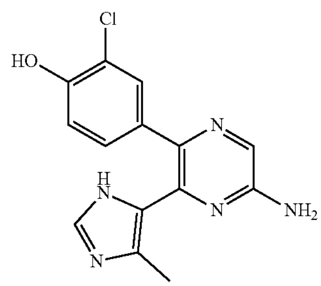 |
| 1.83 | 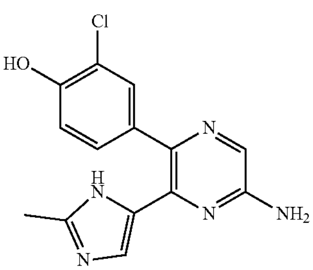 [SMILES: Cc1ncc(-c2nc(N)cnc2-c2ccc(O)c(Cl)c2)[nH]1] |
| 1.84 | 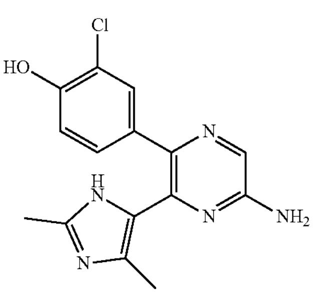 [SMILES: Cc1nc(C)c(-c2nc(N)cnc2-c2ccc(O)c(Cl)c2)[nH]1] |
| 1.85 | 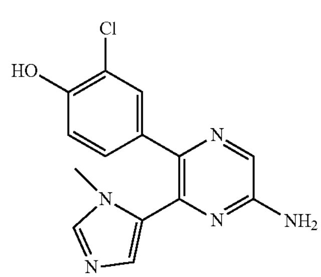 [SMILES: Cn1cncc1-c1nc(N)cnc1-c1ccc(O)c(Cl)c1] |

TABLE 2-continued
| Compound No. | Structure |
|---|---|
| 1.86 | 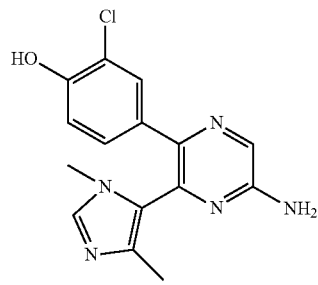 [SMILES: Cc1ncn(C)c1-c1nc(N)cnc1-c1ccc(O)c(Cl)c1] |
| 1.87 | 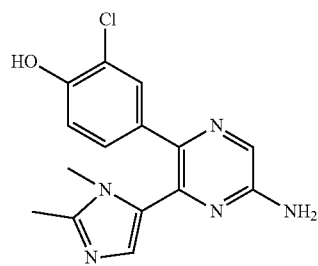 [SMILES: Cc1ncc(-c2nc(N)cnc2-c2ccc(O)c(Cl)c2)n1C] |
| 1.88 | 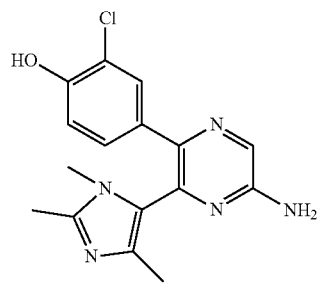 [SMILES: Cc1nc(C)n(C)c1-c1nc(N)cnc1-c1ccc(O)c(Cl)c1] |
| 1.89 | 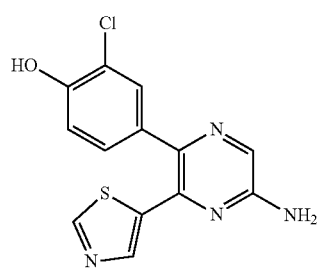 [SMILES: Nc1cnc(-c2ccc(O)c(Cl)c2)c(-c2cncs2)n1] |
| 1.90 | 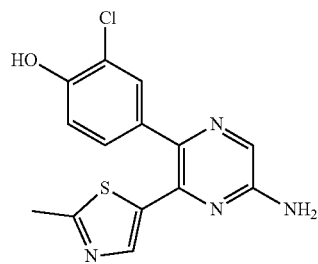 [SMILES: Cc1ncc(-c2nc(N)cnc2-c2ccc(O)c(Cl)c2)s1] |

TABLE 2-continued
| Compound No. | Structure |
| --- | --- |
| 1.91 | 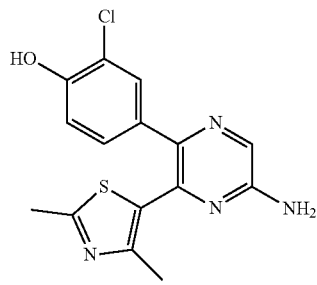 [SMILES: Cc1nc(C)c(-c2nc(N)cnc2-c2ccc(O)c(Cl)c2)s1] |
| 1.92 | 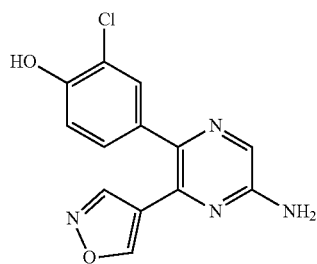 [SMILES: Nc1cnc(-c2ccc(O)c(Cl)c2)c(-c2cnoc2)n1] |
| 1.93 | 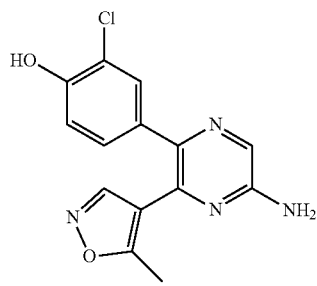 [SMILES: Cc1oncc1-c1nc(N)cnc1-c1ccc(O)c(Cl)c1] |
| 1.94 | 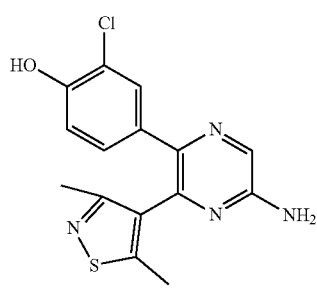 [SMILES: Cc1nsc(C)c1-c1nc(N)cnc1-c1ccc(O)c(Cl)c1] |
| 1.95 | 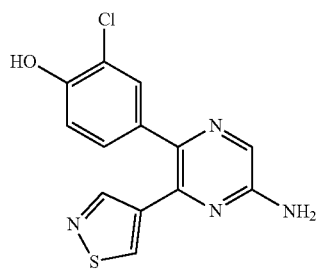 [SMILES: Nc1cnc(-c2ccc(O)c(Cl)c2)c(-c2cnsc2)n1] |

141
TABLE 2-continued
| Compound No. | Structure |
|---|---|
| 1.96 | 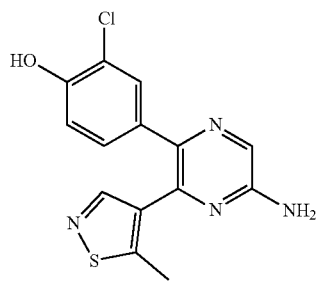 [SMILES: Cc1sncc1-c1nc(N)cnc1-c1ccc(O)c(Cl)c1] |
| 1.97 | 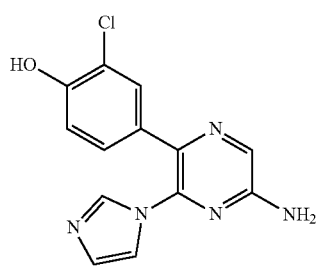 [SMILES: Nc1cnc(-c2ccc(O)c(Cl)c2)c(-n2ccnc2)n1] |
| 1.98 | 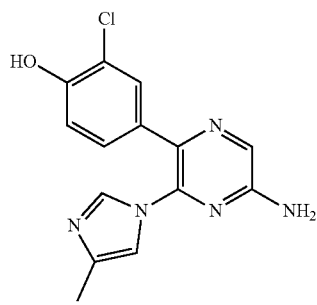 [SMILES: Cc1cn(-c2nc(N)cnc2-c2ccc(O)c(Cl)c2)cn1] |
| 1.99 | 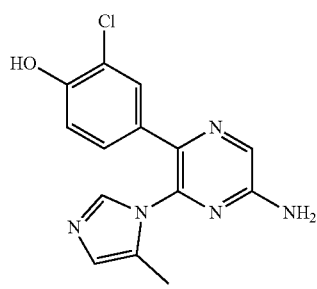 [SMILES: Cc1cncn1-c1nc(N)cnc1-c1ccc(O)c(Cl)c1] |
| 1.100 | 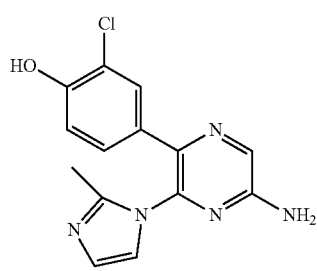 [SMILES: Cc1nccn1-c1nc(N)cnc1-c1ccc(O)c(Cl)c1] |

TABLE 2-continued
| Compound No. | Structure |
|---|---|
| 1.101 | 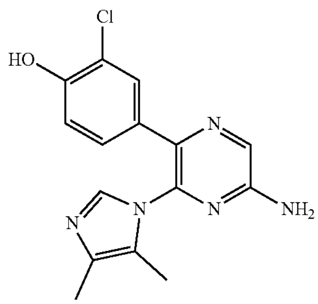 [SMILES: Cc1ncn(-c2nc(N)cnc2-c2ccc(O)c(Cl)c2)c1C] |
| 1.102 | 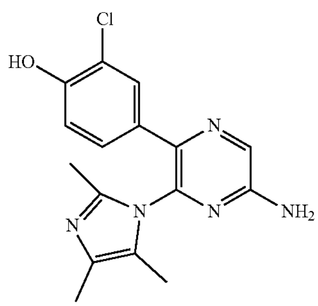 [SMILES: Cc1nc(C)n(-c2nc(N)cnc2-c2ccc(O)c(Cl)c2)c1C] |
| 1.103 | 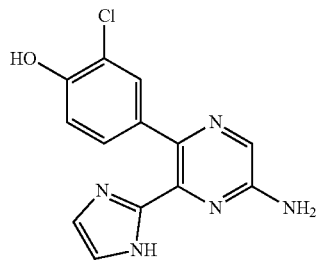 [SMILES: Nc1cnc(-c2ccc(O)c(Cl)c2)c(-c2ncc[nH]2)n1] |
| 1.104 | 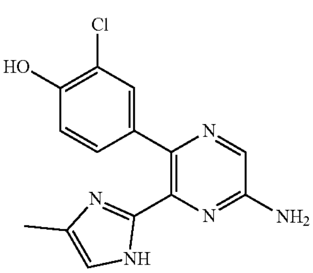 [SMILES: Cc1c[nH]c(-c2nc(N)cnc2-c2ccc(O)c(Cl)c2)n1] |
| 1.105 | 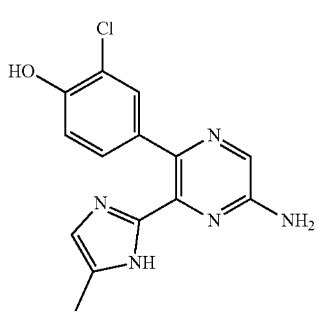 [SMILES: Cc1cnc(-c2nc(N)cnc2-c2ccc(O)c(Cl)c2)[nH]1] |

TABLE 2-continued
| Compound No. | Structure |
|---|---|
| 1.106 | 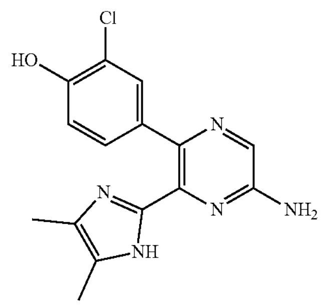 [SMILES: Cc1nc(-c2nc(N)cnc2-c2ccc(O)c(Cl)c2)[nH]c1C] |
| 1.107 | 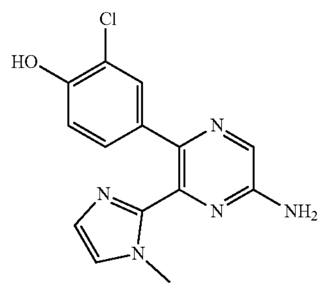 [SMILES: Cn1ccnc1-c1nc(N)cnc1-c1ccc(O)c(Cl)c1] |
| 1.108 | 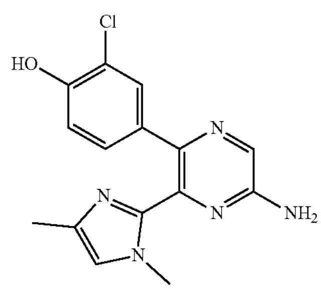 [SMILES: Cc1cn(C)c(-c2nc(N)cnc2-c2ccc(O)c(Cl)c2)n1] |
| 1.109 | 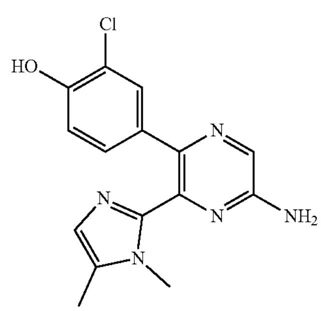 [SMILES: Cc1cnc(-c2nc(N)cnc2-c2ccc(O)c(Cl)c2)n1C] |
| 1.110 | 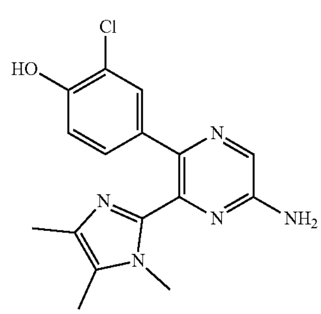 [SMILES: Cc1nc(-c2nc(N)cnc2-c2ccc(O)c(Cl)c2)n(C)c1C] |

TABLE 2-continued
| Compound No. | Structure |
| --- | --- |
| 1.111 | 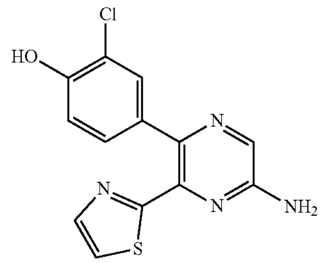 [SMILES: Nc1cnc(-c2ccc(O)c(Cl)c2)c(-c2nccs2)n1] |
| 1.112 | 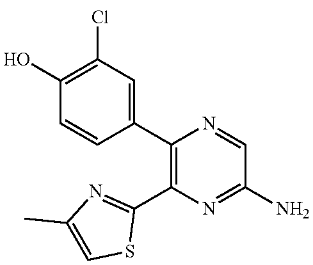 [SMILES: Cc1csc(-c2nc(N)cnc2-c2ccc(O)c(Cl)c2)n1] |
| 1.113 | 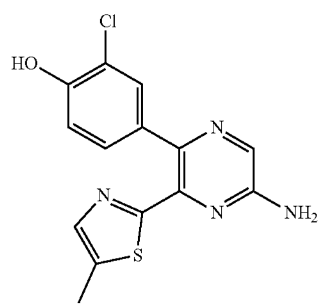 [SMILES: Cc1cnc(-c2nc(N)cnc2-c2ccc(O)c(Cl)c2)s1] |
| 1.114 | 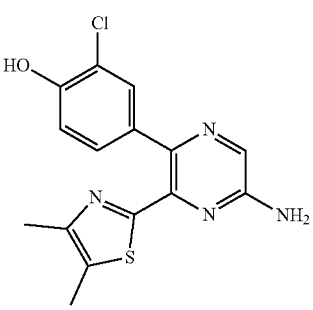 [SMILES: Cc1nc(-c2nc(N)cnc2-c2ccc(O)c(Cl)c2)sc1C] |
| 1.115 | 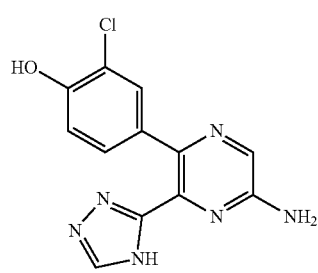 [SMILES: Nc1cnc(-c2ccc(O)c(Cl)c2)c(-c2nnc[nH]2)n1] |

TABLE 2-continued
| Compound No. | Structure |
|---|---|
| 1.116 | 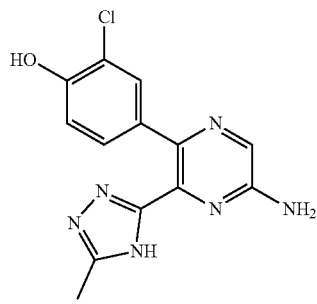 |
| 1.117 | 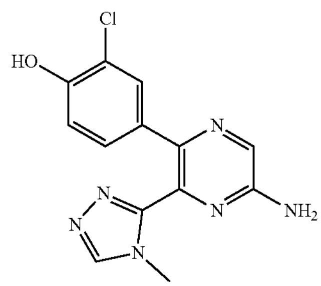 [SMILES: Cn1cnnc1-c1nc(N)cnc1-c1ccc(O)c(Cl)c1] |
| 1.118 | 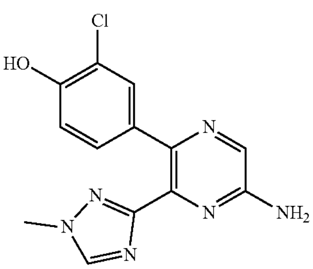 [SMILES: Cn1cnc(-c2nc(N)cnc2-c2ccc(O)c(Cl)c2)n1] |
| 1.119 | 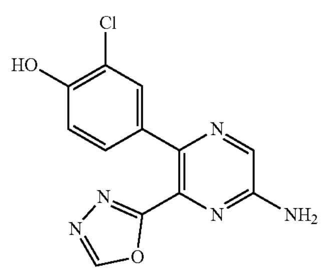 [SMILES: Nc1cnc(-c2ccc(O)c(Cl)c2)c(-c2nnco2)n1] |
| 1.120 | 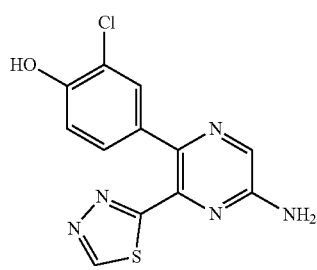 |

TABLE 2-continued

| Compound No. | Structure |
|---|---|
| 1.121 | 3-chloro-4-hydroxyphenyl pyrazine with 5-methyl-1,3,4-oxadiazol-2-yl substituent and NH₂ |
| 1.122 | 3-chloro-4-hydroxyphenyl pyrazine with 5-methyl-1,3,4-thiadiazol-2-yl substituent and NH₂ |
| 1.123 | 3-chloro-4-hydroxyphenyl pyrazine with 1H-tetrazol-5-yl substituent and NH₂ |
| 1.124 | 3-chloro-4-hydroxyphenyl pyrazine with 2-fluorophenyl substituent and NH₂ |
| 1.125 | 3-chloro-4-hydroxyphenyl pyrazine with 3-fluorophenyl substituent and NH₂ |

TABLE 2-continued
| Compound No. | Structure |
|---|---|
| 1.126 | 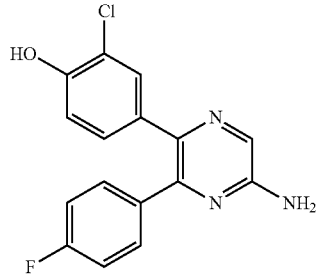 [SMILES: Nc1cnc(-c2ccc(O)c(Cl)c2)c(-c2ccc(F)cc2)n1] |
| 1.127 | 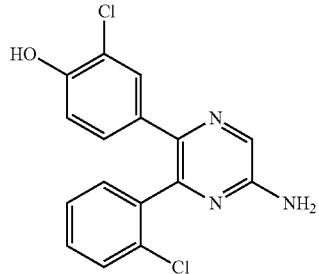 [SMILES: Nc1cnc(-c2ccc(O)c(Cl)c2)c(-c2ccccc2Cl)n1] |
| 1.128 | 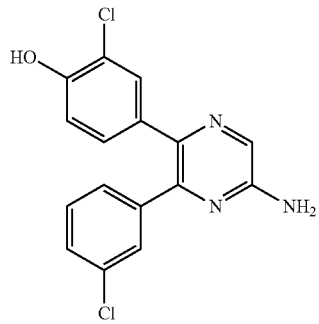 [SMILES: Nc1cnc(-c2ccc(O)c(Cl)c2)c(-c2cccc(Cl)c2)n1] |
| 1.129 | 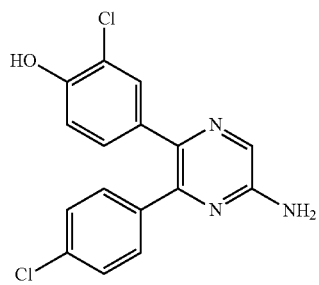 [SMILES: Nc1cnc(-c2ccc(O)c(Cl)c2)c(-c2ccc(Cl)cc2)n1] |
| 1.130 | 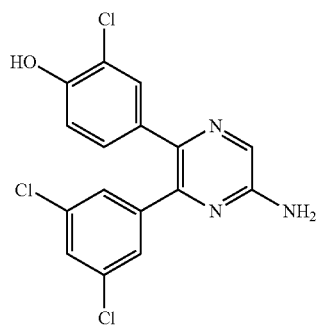 [SMILES: Nc1cnc(-c2ccc(O)c(Cl)c2)c(-c2cc(Cl)cc(Cl)c2)n1] |

TABLE 2-continued

| Compound No. | Structure |
|---|---|
| 1.131 | 3-chloro-4-hydroxyphenyl and 3,4-difluorophenyl substituted aminopyrazine |
| 1.132 | 3-chloro-4-hydroxyphenyl and 3,5-difluorophenyl substituted aminopyrazine |
| 1.133 | 3-chloro-4-hydroxyphenyl and 2,6-difluorophenyl substituted aminopyrazine |
| 1.134 | 3-chloro-4-hydroxyphenyl and 3-chloro-4-fluorophenyl substituted aminopyrazine |
| 1.135 | 3-chloro-4-hydroxyphenyl and 4-chloro-3-fluorophenyl substituted aminopyrazine |

TABLE 2-continued
| Compound No. | Structure |
|---|---|
| 1.136 | 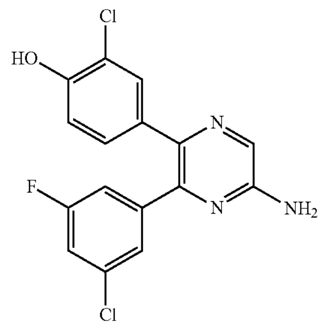 [SMILES: Nc1cnc(-c2ccc(O)c(Cl)c2)c(-c2cc(F)cc(Cl)c2)n1] |
| 1.137 | 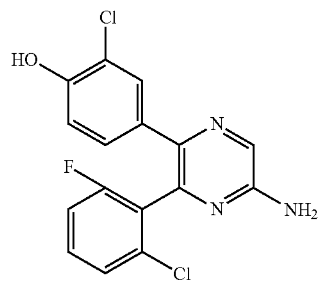 [SMILES: Nc1cnc(-c2ccc(O)c(Cl)c2)c(-c2c(F)cccc2Cl)n1] |
| 1.138 | 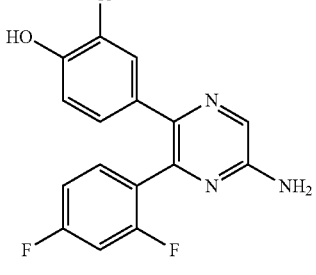 |
| 1.139 | 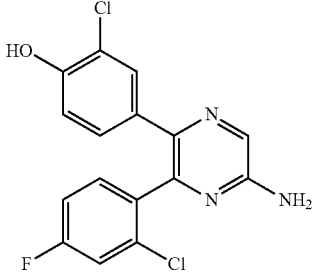 [SMILES: Nc1cnc(-c2ccc(O)c(Cl)c2)c(-c2ccc(F)cc2Cl)n1] |
| 1.140 | 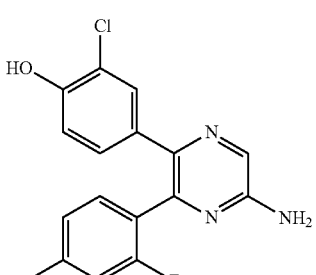 |

TABLE 2-continued
| Compound No. | Structure |
|---|---|
| 1.141 | 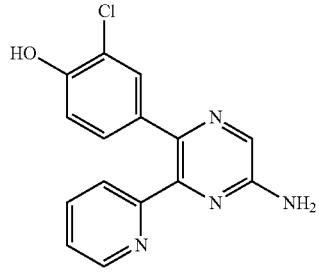 [SMILES: Nc1cnc(-c2ccc(O)c(Cl)c2)c(-c2ccccn2)n1] |
| 1.142 | 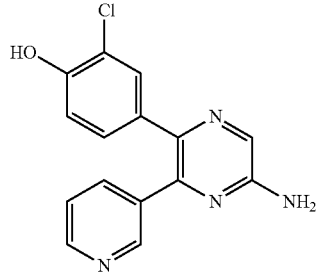 [SMILES: Nc1cnc(-c2ccc(O)c(Cl)c2)c(-c2cccnc2)n1] |
| 1.143 | 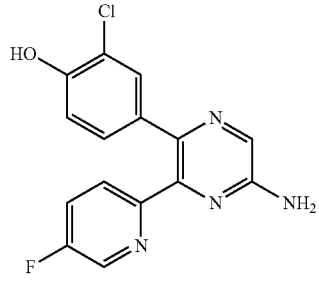 [SMILES: Nc1cnc(-c2ccc(O)c(Cl)c2)c(-c2ccc(F)cn2)n1] |
| 1.144 | 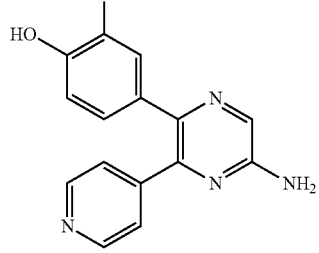 |
| 1.145 | 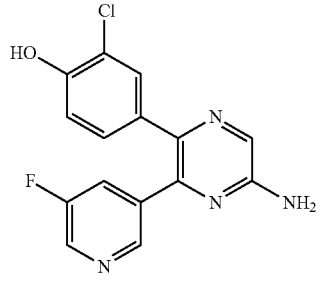 [SMILES: Nc1cnc(-c2ccc(O)c(Cl)c2)c(-c2cncc(F)c2)n1] |

TABLE 2-continued

| Compound No. | Structure |
|---|---|
| 1.146 | 5-(3-chloro-4-hydroxyphenyl)-6-(pyrimidin-2-yl)pyrazin-2-amine |
| 1.147 | 3-bromo-6-(3-chloro-4-hydroxyphenyl)-5-phenylpyrazin-2-amine |
| 1.148 | 5-(3-chloro-4-hydroxyphenyl)-3-methoxy-6-phenylpyrazin-2-amine |
| 1.149 | 5-(3-chloro-4-hydroxyphenyl)-3-methyl-6-phenylpyrazin-2-amine |
| 1.150 | 5-(3-chloro-4-hydroxyphenyl)-N-methyl-6-phenylpyrazin-2-amine |
| 1.151 | 5-(3-chloro-4-hydroxy-5-methylphenyl)-6-phenylpyrazin-2-amine |

TABLE 2-continued
| Compound No. | Structure |
|---|---|
| 1.152 | 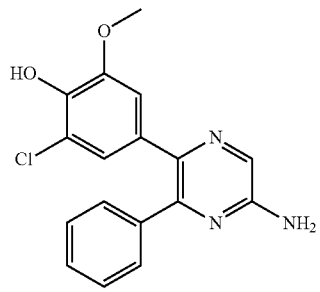 [SMILES: COc1cc(-c2ncc(N)nc2-c2ccccc2)cc(Cl)c1O] |
| 1.153 | 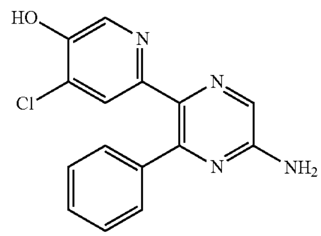 [SMILES: Nc1cnc(-c2cc(Cl)c(O)cn2)c(-c2ccccc2)n1] |
| 1.154 | 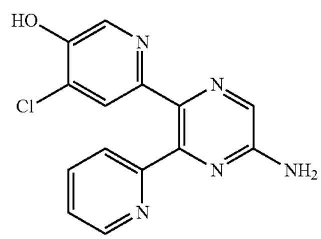 [SMILES: Nc1cnc(-c2cc(Cl)c(O)cn2)c(-c2ccccn2)n1] |
| 1.155 | 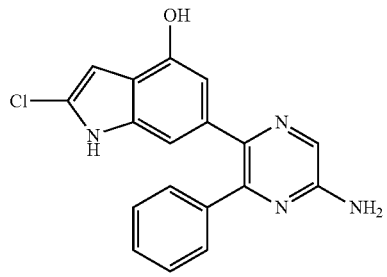 [SMILES: Nc1cnc(-c2cc(O)c3cc(Cl)[nH]c3c2)c(-c2ccccc2)n1] |
| 1.156 | 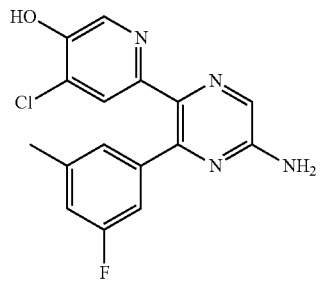 [SMILES: Cc1cc(F)cc(-c2nc(N)cnc2-c2cc(Cl)c(O)cn2)c1] |

TABLE 2-continued

| Compound No. | Structure |
|---|---|
| 1.157 | 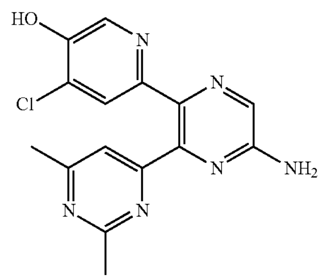 [SMILES: Cc1cc(-c2nc(N)cnc2-c2cc(Cl)c(O)cn2)nc(C)n1] |
| 1.158 | 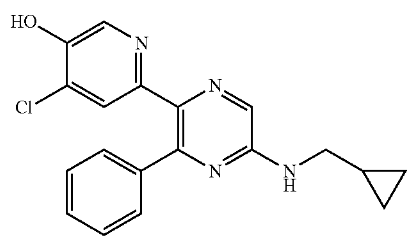 |
| 1.159 | 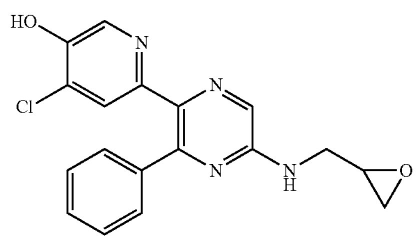 [SMILES: Oc1cnc(-c2ncc(NCC3CO3)nc2-c2ccccc2)cc1Cl] |
| 1.160 | 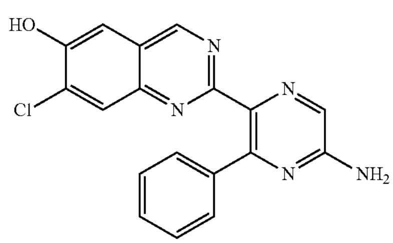 [SMILES: Nc1cnc(-c2ncc3cc(O)c(Cl)cc3n2)c(-c2ccccc2)n1] |
| 1.161 | 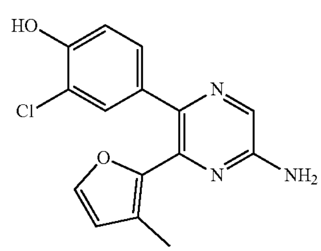 [SMILES: Cc1ccoc1-c1nc(N)cnc1-c1ccc(O)c(Cl)c1] |
| 1.162 | 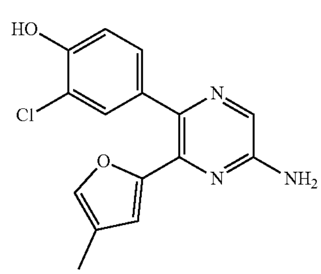 [SMILES: Cc1coc(-c2nc(N)cnc2-c2ccc(O)c(Cl)c2)c1] |

TABLE 2-continued

| Compound No. | Structure |
|---|---|
| 1.163 | 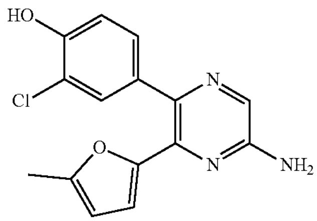 [SMILES: Cc1ccc(-c2nc(N)cnc2-c2ccc(O)c(Cl)c2)o1] |
| 1.164 | 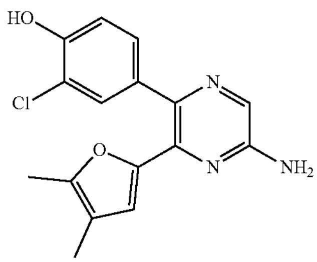 [SMILES: Cc1cc(-c2nc(N)cnc2-c2ccc(O)c(Cl)c2)oc1C] |
| 1.165 | 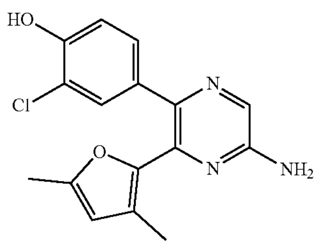 [SMILES: Cc1cc(C)c(-c2nc(N)cnc2-c2ccc(O)c(Cl)c2)o1] |
| 1.166 | 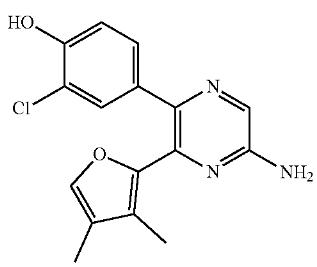 [SMILES: Cc1coc(-c2nc(N)cnc2-c2ccc(O)c(Cl)c2)c1C] |
| 1.167 | 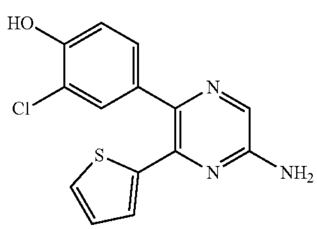 [SMILES: Nc1cnc(-c2ccc(O)c(Cl)c2)c(-c2cccs2)n1] |
| 1.168 | 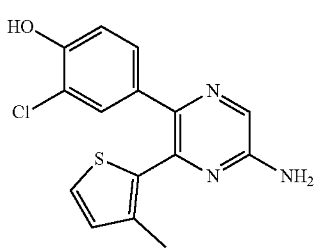 [SMILES: Cc1ccsc1-c1nc(N)cnc1-c1ccc(O)c(Cl)c1] |

TABLE 2-continued
| Compound No. | Structure |
|---|---|
| 1.169 | 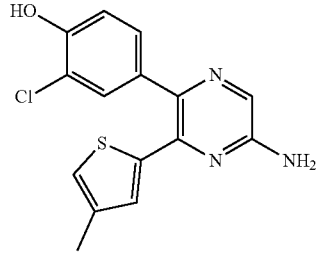 [SMILES: Cc1csc(-c2nc(N)cnc2-c2ccc(O)c(Cl)c2)c1] |
| 1.170 | 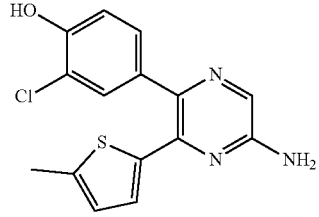 [SMILES: Cc1ccc(-c2nc(N)cnc2-c2ccc(O)c(Cl)c2)s1] |
| 1.171 | 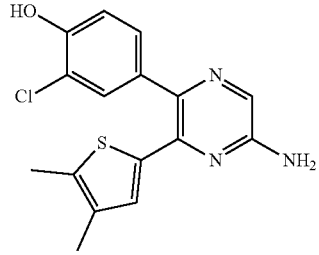 |
| 1.172 | 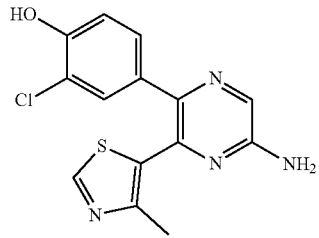 [SMILES: Cc1ncsc1-c1nc(N)cnc1-c1ccc(O)c(Cl)c1] |
| 1.173 | 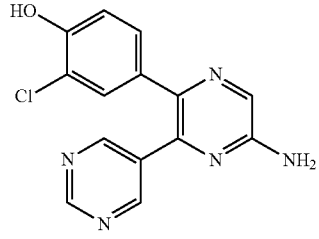 [SMILES: Nc1cnc(-c2ccc(O)c(Cl)c2)c(-c2cncnc2)n1] |
| 1.174 | 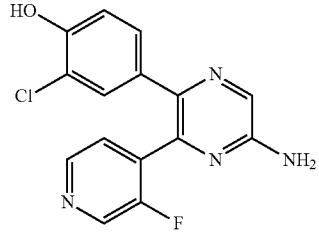 [SMILES: Nc1cnc(-c2ccc(O)c(Cl)c2)c(-c2ccncc2F)n1] |

TABLE 2-continued

| Compound No. | Structure |
|---|---|
| 1.175 | 3-chloro-4-hydroxyphenyl / 3,5-difluoropyridin-4-yl / aminopyrazine |
| 1.176 | 3-chloro-4-hydroxyphenyl / phenyl / 3-amino-6-cyanopyrazine |
| 1.177 | 3,5-dimethyl-4-hydroxyphenyl / phenyl / aminopyrazine |
| 1.178 | 3-hydroxy-2-methyl-4-methylpyridin-6-yl / phenyl / aminopyrazine |
| 1.179 | 6-hydroxy-1H-indol-5-yl / pyridin-3-yl / aminopyrazine |
| 1.180 | 3-chlorophenyl / phenyl / aminopyrazine |

TABLE 2-continued

| Compound No. | Structure |
|---|---|
| 1.181 | 5-(3-chloro-4-methoxyphenyl)-6-phenylpyrazin-2-amine |
| 1.182 | 5-(3-chloro-5-methylphenyl)-6-phenylpyrazin-2-amine |
| 1.183 | 5-(2,6-dimethylmorpholino)-6-phenylpyrazin-2-amine |
| 1.184 | 5-(2,6-dimethylpyridin-4-yl)-6-phenylpyrazin-2-amine |
| 1.185 | 5-(naphthalen-2-yl)-6-phenylpyrazin-2-amine |

TABLE 2-continued
| Compound No. | Structure |
|---|---|
| 1.186 | 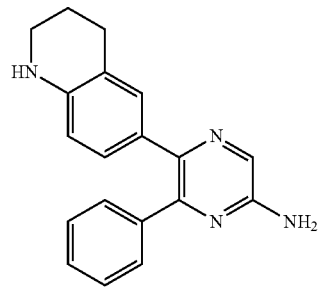 [SMILES: Nc1cnc(-c2ccc3c(c2)CCCN3)c(-c2ccccc2)n1] |
| 1.187 | 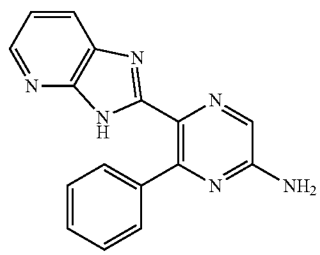 [SMILES: Nc1cnc(-c2nc3cccnc3[nH]2)c(-c2ccccc2)n1] |
| 1.188 | 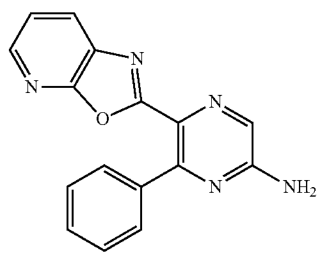 [SMILES: Nc1cnc(-c2nc3cccnc3o2)c(-c2ccccc2)n1] |
| 1.189 | 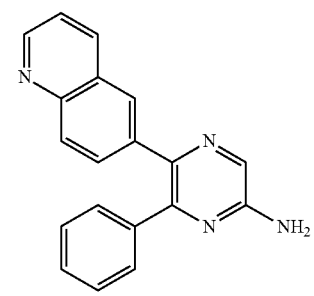 |
| 1.190 | 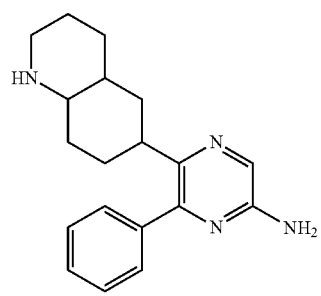 [SMILES: Nc1cnc(C2CCC3NCCCC3C2)c(-c2ccccc2)n1] |

TABLE 2-continued
| Compound No. | Structure |
|---|---|
| 1.191 | 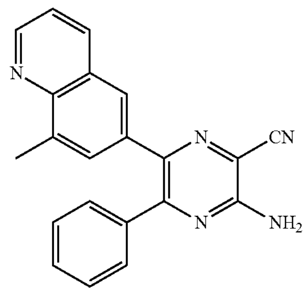 [SMILES: Cc1cc(-c2nc(C#N)c(N)nc2-c2ccccc2)cc2cccnc12] |
| 1.192 | 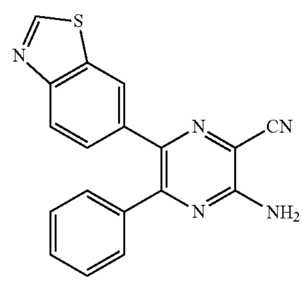 [SMILES: N#Cc1nc(-c2ccc3ncsc3c2)c(-c2ccccc2)nc1N] |
| 1.193 | 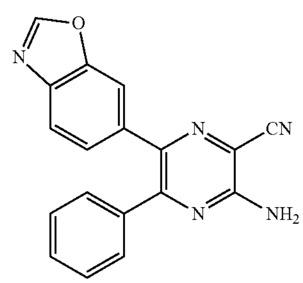 [SMILES: N#Cc1nc(-c2ccc3ncoc3c2)c(-c2ccccc2)nc1N] |
| 1.194 | 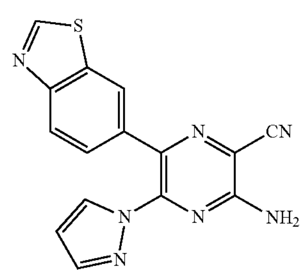 [SMILES: N#Cc1nc(-c2ccc3ncsc3c2)c(-n2cccn2)nc1N] |
| 1.195 | 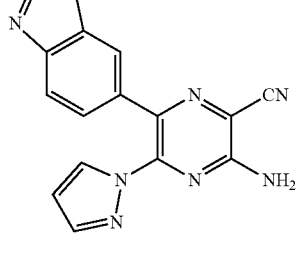 |

TABLE 2-continued

| Compound No. | Structure |
|---|---|
| 1.196 | 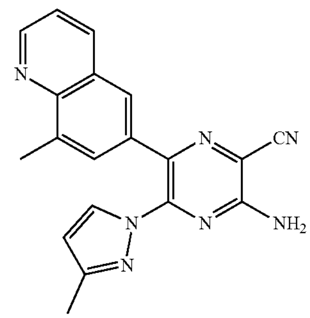 [SMILES: Cc1ccn(-c2nc(N)c(C#N)nc2-c2cc(C)c3ncccc3c2)n1] |
| 1.197 | 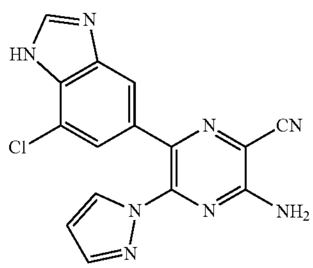 [SMILES: N#Cc1nc(-c2cc(Cl)c3[nH]cnc3c2)c(-n2cccn2)nc1N] |
| 1.198 | 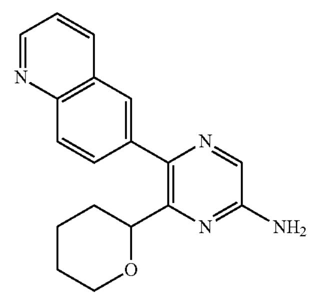 [SMILES: Nc1cnc(-c2ccc3ncccc3c2)c(C2CCCCO2)n1] |
| 1.199 | 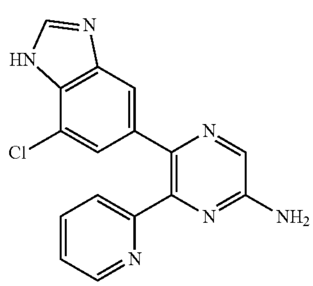 [SMILES: Nc1cnc(-c2cc(Cl)c3[nH]cnc3c2)c(-c2ccccn2)n1] |
| 1.200 | 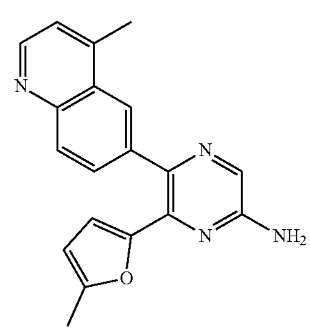 [SMILES: Cc1ccc(-c2nc(N)cnc2-c2ccc3nccc(C)c3c2)o1] |

TABLE 2-continued
| Compound No. | Structure |
|---|---|
| 1.201 | 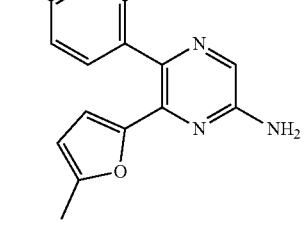 |
| 1.202 | 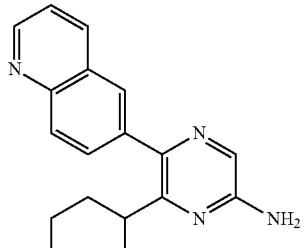 |
| 1.203 | 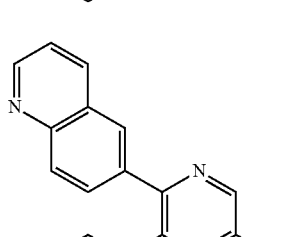 |
| 1.204 | 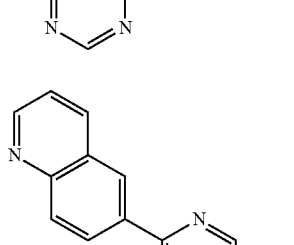 |
| 1.205 | 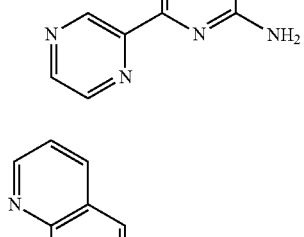 |

TABLE 2-continued

| Compound No. | Structure |
|---|---|
| 1.206 | (2-oxo-1H-quinolin-6-yl) phenyl pyrazin-2-amine |
| 1.207 | (4-oxo-1H-quinolin-6-yl) phenyl pyrazin-2-amine |
| 1.208 | quinolin-6-yl (1H-pyrazol-5-yl) pyrazin-2-amine |
| 1.209 | quinolin-6-yl (pyrazol-1-yl) pyrazin-2-amine |
| 1.210 | quinolin-6-yl (5-methylthiophen-2-yl) pyrazin-2-amine |

TABLE 2-continued

| Compound No. | Structure |
|---|---|
| 1.211 | 6-(quinolin-6-yl)-5-(thiazol-5-yl)pyrazin-2-amine |
| 1.212 | 6-(quinolin-6-yl)-5-(1,3,4-thiadiazol-2-yl)pyrazin-2-amine |
| 1.213 | 6-(quinolin-6-yl)-5-(oxazol-5-yl)pyrazin-2-amine |
| 1.214 | 6-(quinolin-6-yl)-5-(isoxazol-5-yl)pyrazin-2-amine |
| 1.215 | 6-(quinolin-6-yl)-5-(1H-imidazol-1-yl)pyrazin-2-amine |

TABLE 2-continued
| Compound No. | Structure |
|---|---|
| 1.216 | 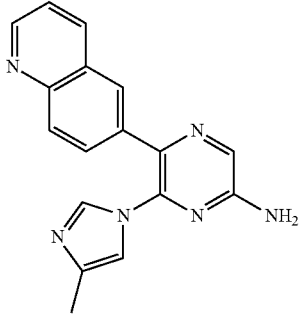 [SMILES: Cc1cn(-c2nc(N)cnc2-c2ccc3ncccc3c2)cn1] |
| 1.217 | 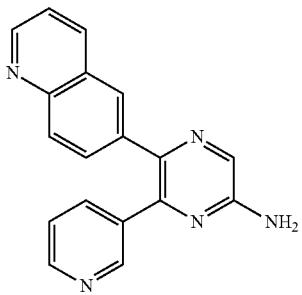 [SMILES: Nc1cnc(-c2ccc3ncccc3c2)c(-c2cccnc2)n1] |
| 1.218 | 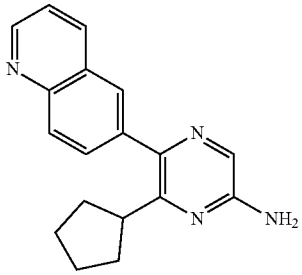 [SMILES: Nc1cnc(-c2ccc3ncccc3c2)c(C2CCCC2)n1] |
| 1.219 | 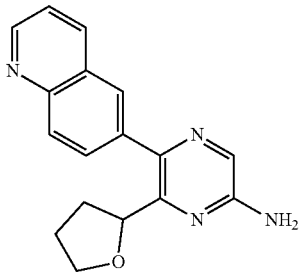 [SMILES: Nc1cnc(-c2ccc3ncccc3c2)c(C2CCCO2)n1] |
| 1.220 | 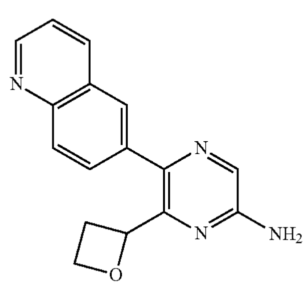 [SMILES: Nc1cnc(-c2ccc3ncccc3c2)c(C2CCO2)n1] |

TABLE 2-continued
| Compound No. | Structure |
|---|---|
| 1.221 | 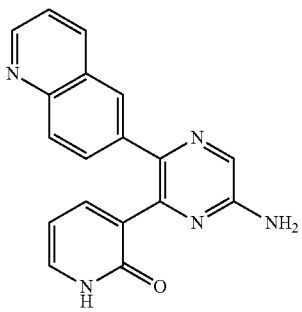 [SMILES: Nc1cnc(-c2ccc3ncccc3c2)c(-c2ccc[nH]c2=O)n1] |
| 1.222 | 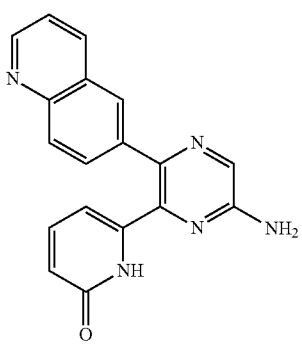 [SMILES: Nc1cnc(-c2ccc3ncccc3c2)c(-c2cccc(=O)[nH]2)n1] |
| 1.223 | 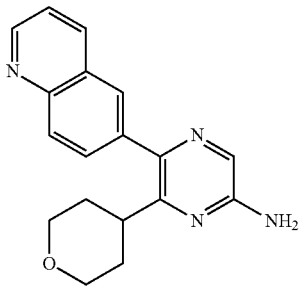 [SMILES: Nc1cnc(-c2ccc3ncccc3c2)c(C2CCOCC2)n1] |
| 1.224 | 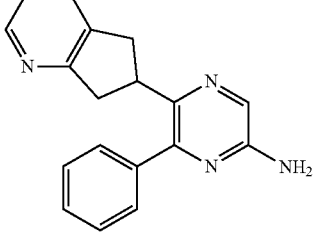 |
| 1.225 | 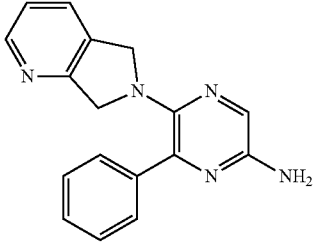 [SMILES: Nc1cnc(N2Cc3cccnc3C2)c(-c2ccccc2)n1] |

TABLE 2-continued
| Compound No. | Structure |
|---|---|
| 1.226 | 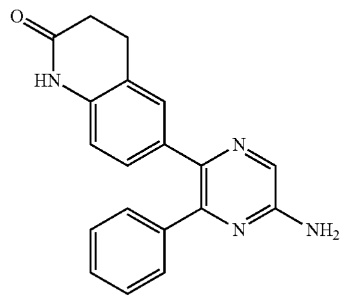 [SMILES: Nc1cnc(-c2ccc3c(c2)CCC(=O)N3)c(-c2ccccc2)n1] |
| 1.227 | 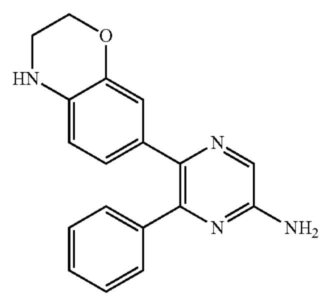 [SMILES: Nc1cnc(-c2ccc3c(c2)OCCN3)c(-c2ccccc2)n1] |
| 1.228 | 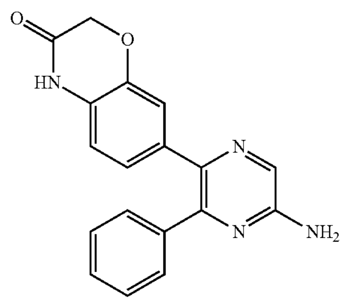 [SMILES: Nc1cnc(-c2ccc3c(c2)OCC(=O)N3)c(-c2ccccc2)n1] |
| 1.229 | 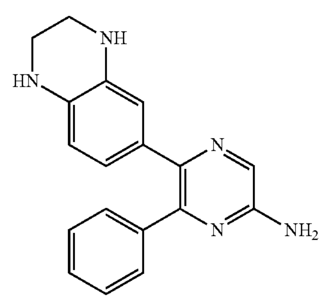 [SMILES: Nc1cnc(-c2ccc3c(c2)NCCN3)c(-c2ccccc2)n1] |
| 1.230 | 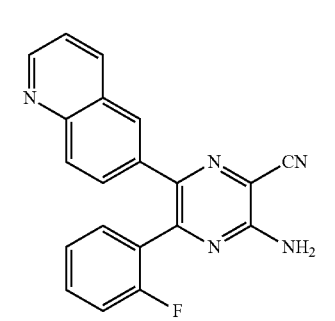 [SMILES: N#Cc1nc(-c2ccc3ncccc3c2)c(-c2ccccc2F)nc1N] |

TABLE 2-continued
| Compound No. | Structure |
|---|---|
| 1.231 | 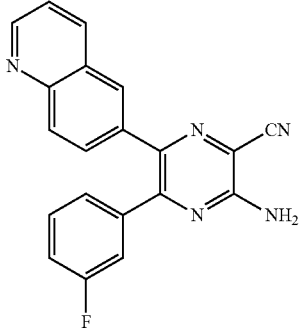 [SMILES: N#Cc1nc(-c2ccc3ncccc3c2)c(-c2cccc(F)c2)nc1N] |
| 1.232 | 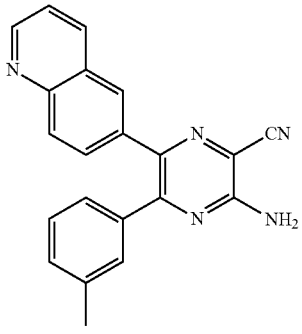 [SMILES: Cc1cccc(-c2nc(N)c(C#N)nc2-c2ccc3ncccc3c2)c1] |
| 1.233 | 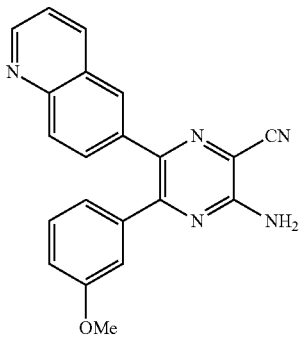 [SMILES: COc1cccc(-c2nc(N)c(C#N)nc2-c2ccc3ncccc3c2)c1] |
| 1.234 | 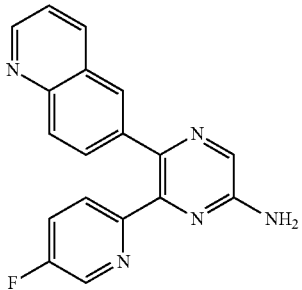 [SMILES: Nc1cnc(-c2ccc3ncccc3c2)c(-c2ccc(F)cn2)n1] |

TABLE 2-continued

| Compound No. | Structure |
| --- | --- |
| 1.235 | (quinolin-6-yl)-(5-methylfuran-2-yl)-pyrazinyl-NH-C(=O)-cyclopropyl |
| 1.236 | (quinolin-6-yl)-(5-methylfuran-2-yl)-pyrazine with NH₂ and NHC(=O)CH₃ substituents |
| 1.237 | (quinolin-6-yl)-phenyl-pyrazine with CN and NHMe substituents |
| 1.238 | (quinolin-6-yl)-phenyl-pyrazine with COOH and NH₂ substituents |
| 1.239 | (quinolin-6-yl)-phenyl-pyrazine with C(=O)OMe and NH₂ substituents |

TABLE 2-continued
| Compound No. | Structure |
|---|---|
| 1.240 | 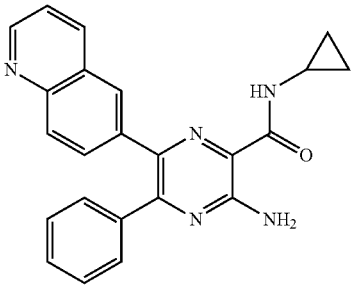 [SMILES: Nc1nc(-c2ccccc2)c(-c2ccc3ncccc3c2)nc1C(=O)NC1CC1] |
| 1.241 | 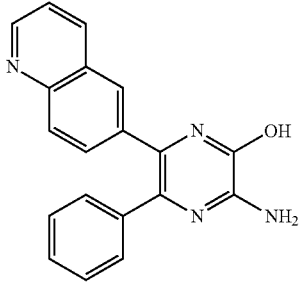 [SMILES: Nc1nc(-c2ccccc2)c(-c2ccc3ncccc3c2)nc1O] |
| 1.242 | 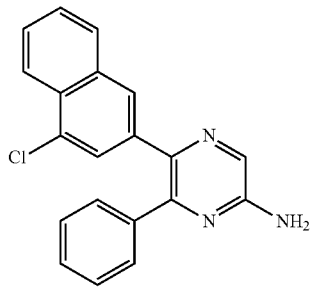 |
| 1.243 | 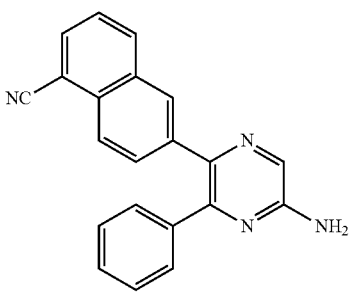 |
| 1.244 | 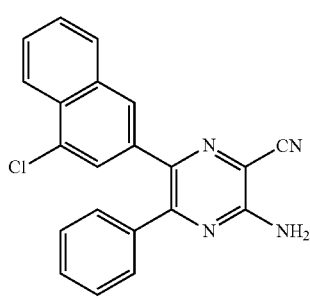 [SMILES: N#Cc1nc(-c2cc(Cl)c3ccccc3c2)c(-c2ccccc2)nc1N] |

TABLE 2-continued

| Compound No. | Structure |
| --- | --- |
| 1.245 | 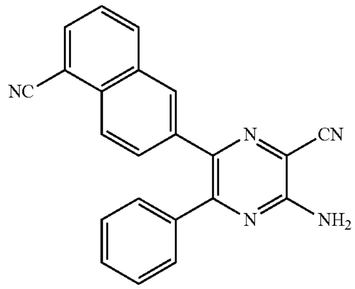 |
| 1.246 | 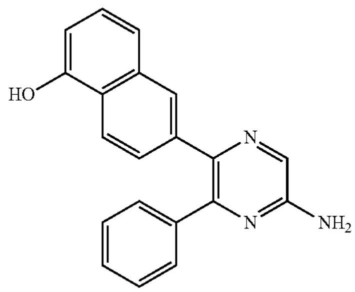 [SMILES: Nc1cnc(-c2ccc3c(O)cccc3c2)c(-c2ccccc2)n1] |
| 1.247 | 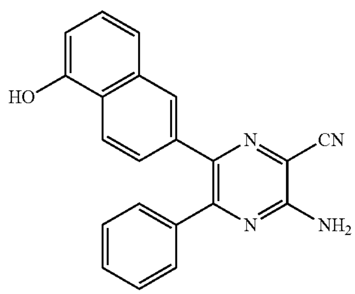 [SMILES: N#Cc1nc(-c2ccc3c(O)cccc3c2)c(-c2ccccc2)nc1N] |
| 1.248 | 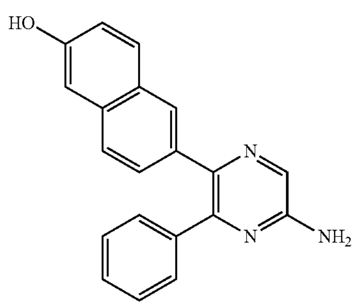 [SMILES: Nc1cnc(-c2ccc3cc(O)ccc3c2)c(-c2ccccc2)n1] |
| 1.249 | 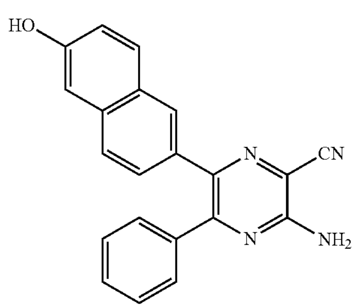 [SMILES: N#Cc1nc(-c2ccc3cc(O)ccc3c2)c(-c2ccccc2)nc1N] |

TABLE 2-continued
| Compound No. | Structure |
| --- | --- |
| 1.250 | 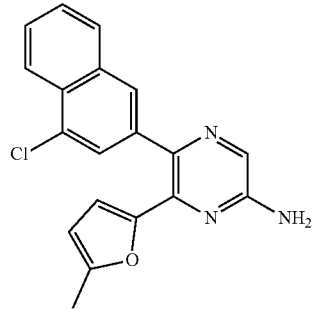 [SMILES: Cc1ccc(-c2nc(N)cnc2-c2cc(Cl)c3ccccc3c2)o1] |
| 1.251 | 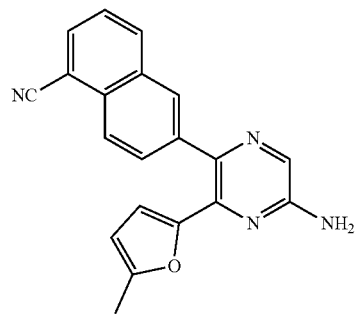 [SMILES: Cc1ccc(-c2nc(N)cnc2-c2ccc3c(C#N)cccc3c2)o1] |
| 1.252 | 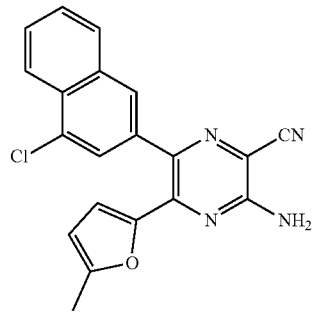 [SMILES: Cc1ccc(-c2nc(N)c(C#N)nc2-c2cc(Cl)c3ccccc3c2)o1] |
| 1.253 | 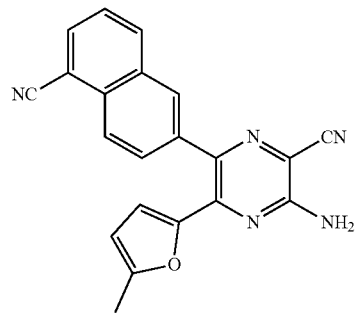 [SMILES: Cc1ccc(-c2nc(N)c(C#N)nc2-c2ccc3c(C#N)cccc3c2)o1] |

TABLE 2-continued
| Compound No. | Structure |
|---|---|
| 1.254 | 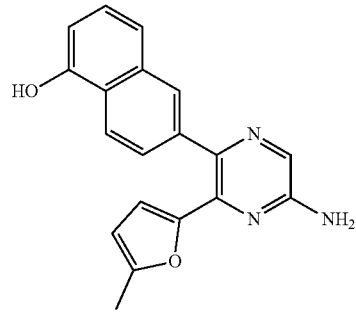 [SMILES: Cc1ccc(-c2nc(N)cnc2-c2ccc3c(O)cccc3c2)o1] |
| 1.255 | 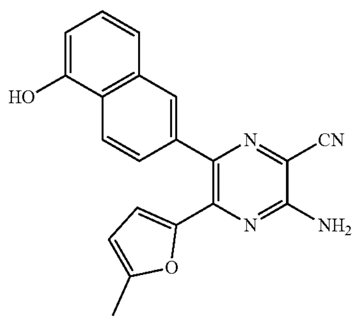 [SMILES: Cc1ccc(-c2nc(N)c(C#N)nc2-c2ccc3c(O)cccc3c2)o1] |
| 1.256 | 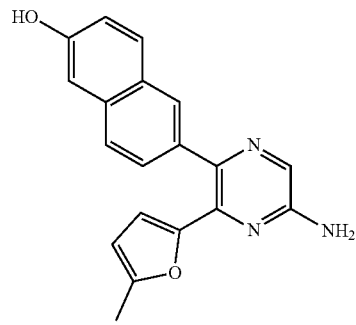 [SMILES: Cc1ccc(-c2nc(N)cnc2-c2ccc3cc(O)ccc3c2)o1] |
| 1.257 | 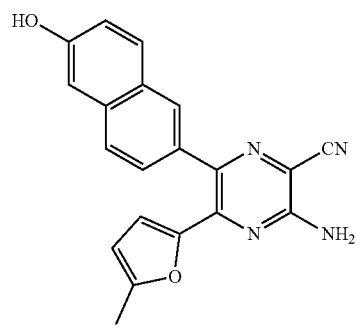 [SMILES: Cc1ccc(-c2nc(N)c(C#N)nc2-c2ccc3cc(O)ccc3c2)o1] |

TABLE 2-continued
| Compound No. | Structure |
|---|---|
| 1.258 | 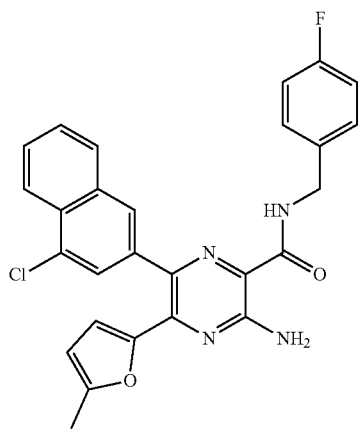 [SMILES: Cc1ccc(-c2nc(N)c(C(=O)NCc3ccc(F)cc3)nc2-c2cc(Cl)c3ccccc3c2)o1] |
| 1.259 | 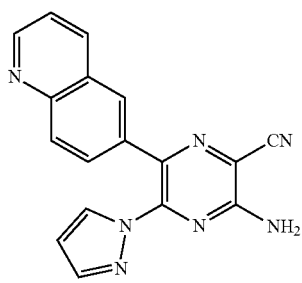 [SMILES: N#Cc1nc(-c2ccc3ncccc3c2)c(-n2cccn2)nc1N] |
| 1.260 | 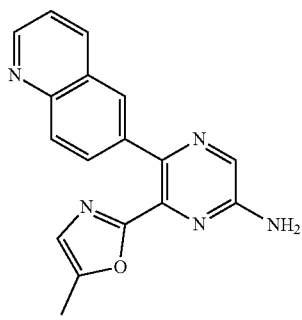 [SMILES: Cc1cnc(-c2nc(N)cnc2-c2ccc3ncccc3c2)o1] |
| 1.261 | 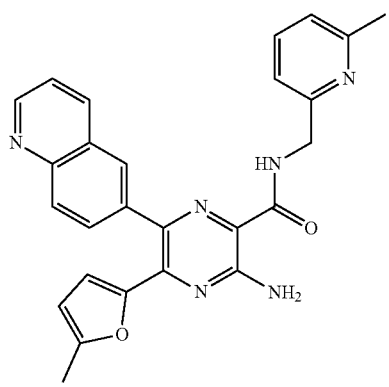 [SMILES: Cc1cccc(CNC(=O)c2nc(-c3ccc4ncccc4c3)c(-c3ccc(C)o3)nc2N)n1] |

TABLE 2-continued
| Compound No. | Structure |
|---|---|
| 1.262 | 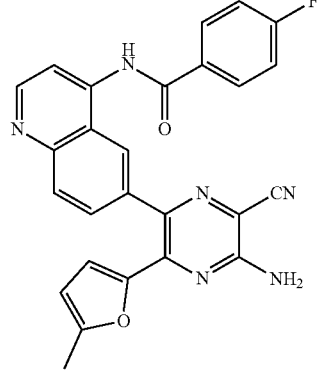 |
| 1.263 | 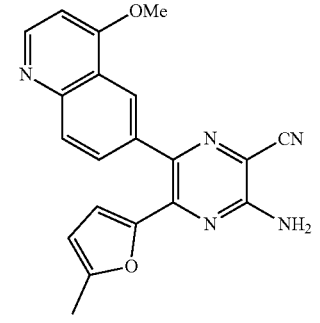 [SMILES: COc1ccnc2ccc(-c3nc(C#N)c(N)nc3-c3ccc(C)o3)cc12] |
| 1.264 | 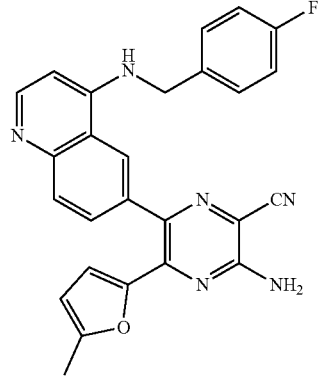 [SMILES: Cc1ccc(-c2nc(N)c(C#N)nc2-c2ccc3nccc(NCc4ccc(F)cc4)c3c2)o1] |
| 1.265 | 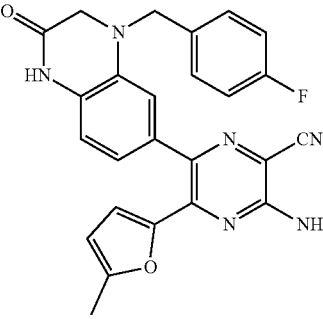 |

TABLE 2-continued
| Compound No. | Structure |
|---|---|
| 1.266 | 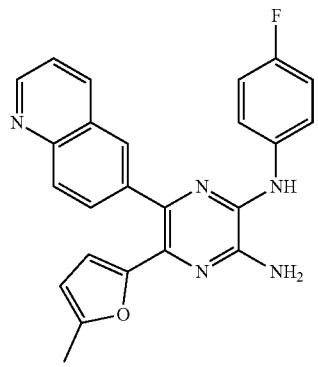 [SMILES: Cc1ccc(-c2nc(N)c(Nc3ccc(F)cc3)nc2-c2ccc3ncccc3c2)o1] |
| 1.267 | 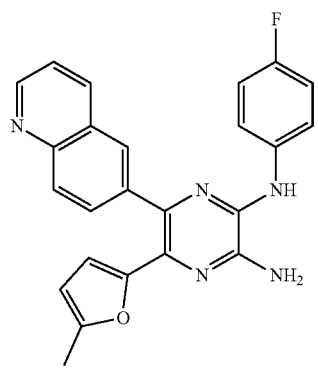 [SMILES: Cc1ccc(-c2nc(N)c(Nc3ccc(F)cc3)nc2-c2ccc3ncccc3c2)o1] |
| 1.268 | 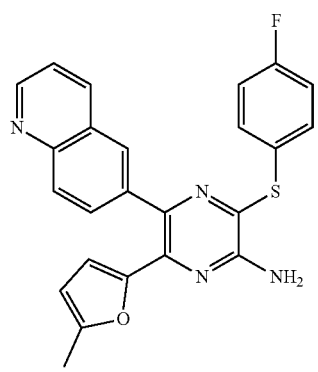 [SMILES: Cc1ccc(-c2nc(N)c(Sc3ccc(F)cc3)nc2-c2ccc3ncccc3c2)o1] |
| 1.269 | 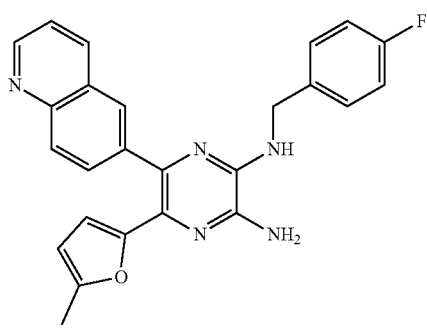 [SMILES: Cc1ccc(-c2nc(N)c(NCc3ccc(F)cc3)nc2-c2ccc3ncccc3c2)o1] |

TABLE 2-continued

| Compound No. | Structure |
|---|---|
| 1.270 | 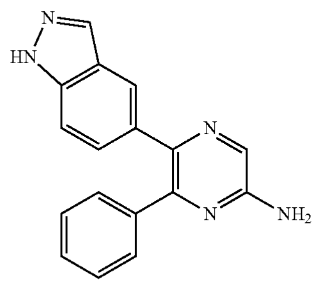 [SMILES: Nc1cnc(-c2ccc3[nH]ncc3c2)c(-c2ccccc2)n1] |
| 1.271 | 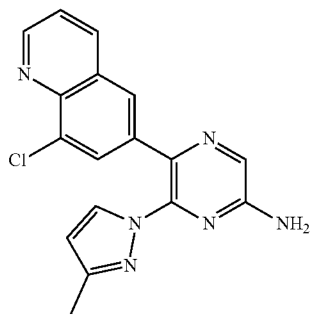 [SMILES: Cc1ccn(-c2nc(N)cnc2-c2cc(Cl)c3ncccc3c2)n1] |
| 1.272 | 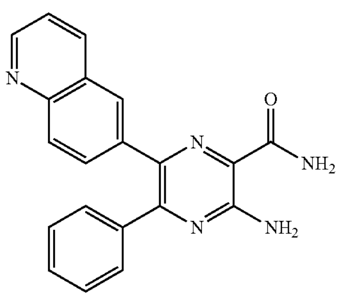 [SMILES: NC(=O)c1nc(-c2ccc3ncccc3c2)c(-c2ccccc2)nc1N] |
| 1.273 | 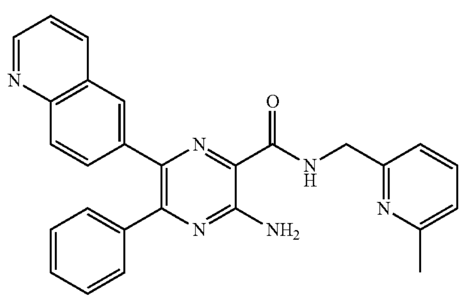 [SMILES: Cc1cccc(CNC(=O)c2nc(-c3ccc4ncccc4c3)c(-c3ccccc3)nc2N)n1] |
| 1.274 | 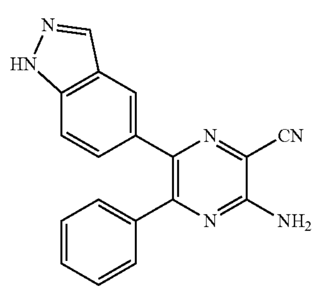 [SMILES: N#Cc1nc(-c2ccc3[nH]ncc3c2)c(-c2ccccc2)nc1N] |

TABLE 2-continued
| Compound No. | Structure |
|---|---|
| 1.275 | 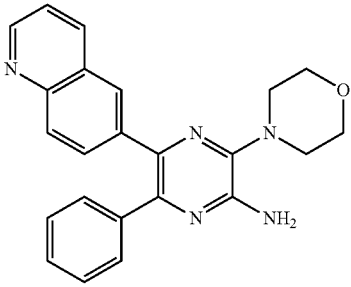 [SMILES: Nc1nc(-c2ccccc2)c(-c2ccc3ncccc3c2)nc1N1CCOCC1] |
| 1.276 | 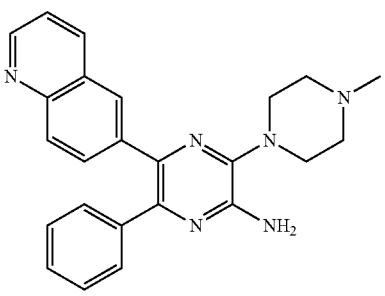 [SMILES: CN1CCN(c2nc(-c3ccc4ncccc4c3)c(-c3ccccc3)nc2N)CC1] |
| 1.277 | 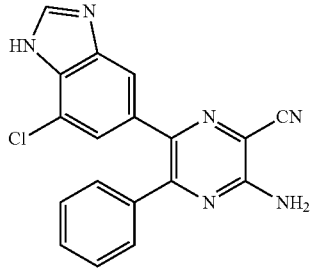 [SMILES: N#Cc1nc(-c2cc(Cl)c3[nH]cnc3c2)c(-c2ccccc2)nc1N] |
| 1.278 | 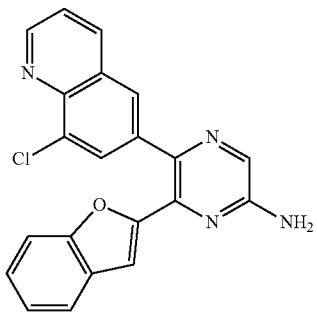 [SMILES: Nc1cnc(-c2cc(Cl)c3ncccc3c2)c(-c2cc3ccccc3o2)n1] |
| 1.279 | 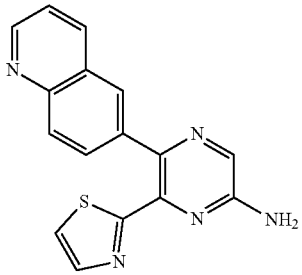 [SMILES: Nc1cnc(-c2ccc3ncccc3c2)c(-c2nccs2)n1] |

TABLE 2-continued

| Compound No. | Structure |
| --- | --- |
| 1.280 | 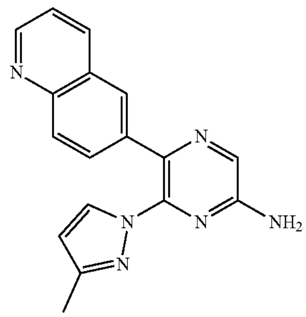 [SMILES: Cc1ccn(-c2nc(N)cnc2-c2ccc3ncccc3c2)n1] |
| 1.281 | 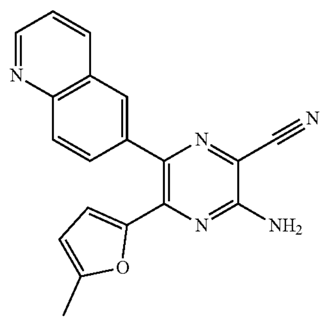 [SMILES: Cc1ccc(-c2nc(N)c(C#N)nc2-c2ccc3ncccc3c2)o1] |
| 1.282 | 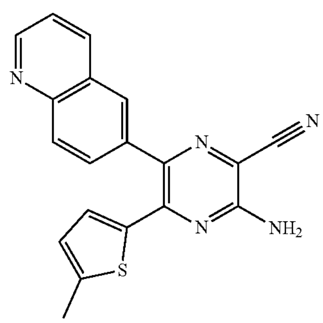 [SMILES: Cc1ccc(-c2nc(N)c(C#N)nc2-c2ccc3ncccc3c2)s1] |
| 1.283 | 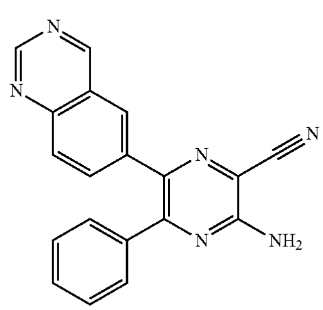 [SMILES: N#Cc1nc(-c2ccc3ncncc3c2)c(-c2ccccc2)nc1N] |
| 1.284 | 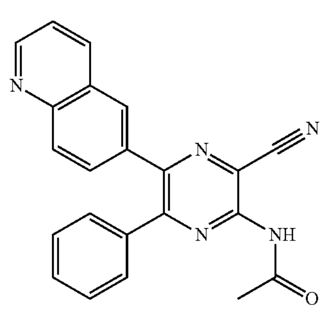 [SMILES: CC(=O)Nc1nc(-c2ccccc2)c(-c2ccc3ncccc3c2)nc1C#N] |

TABLE 2-continued

| Compound No. | Structure |
|---|---|
| 1.285 | 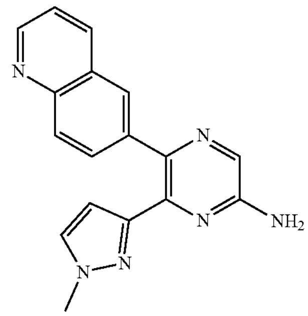 [SMILES: Cn1ccc(-c2nc(N)cnc2-c2ccc3ncccc3c2)n1] |
| 1.286 | 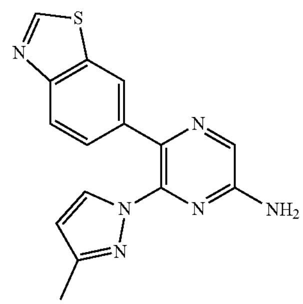 [SMILES: Cc1ccn(-c2nc(N)cnc2-c2ccc3ncsc3c2)n1] |
| 1.287 | 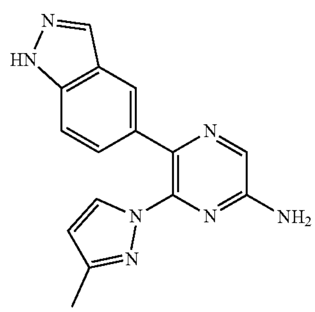 [SMILES: Cc1ccn(-c2nc(N)cnc2-c2ccc3[nH]ncc3c2)n1] |
| 1.288 | 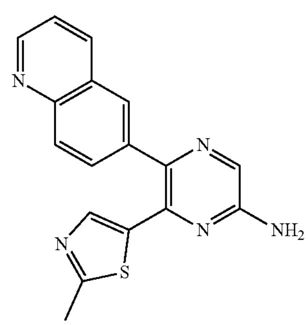 [SMILES: Cc1ncc(-c2nc(N)cnc2-c2ccc3ncccc3c2)s1] |
| 1.289 | 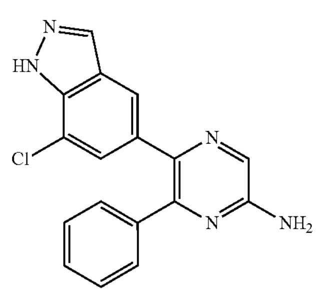 [SMILES: Nc1cnc(-c2cc(Cl)c3[nH]ncc3c2)c(-c2ccccc2)n1] |

TABLE 2-continued

| Compound No. | Structure |
| --- | --- |
| 1.290 | 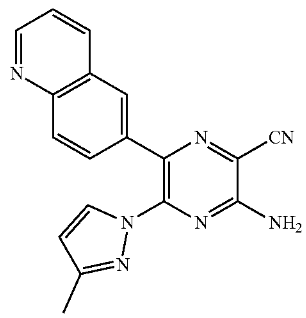 [SMILES: Cc1ccn(-c2nc(N)c(C#N)nc2-c2ccc3ncccc3c2)n1] |
| 1.291 | 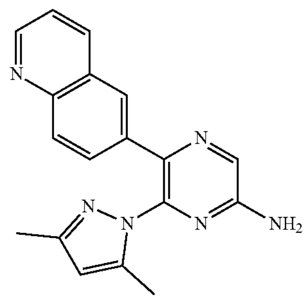 [SMILES: Cc1cc(C)n(-c2nc(N)cnc2-c2ccc3ncccc3c2)n1] |
| 1.292 | 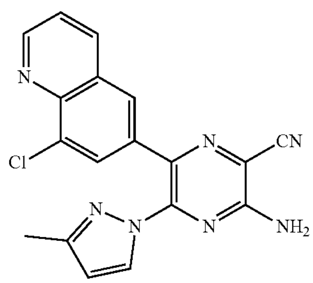 [SMILES: Cc1ccn(-c2nc(N)c(C#N)nc2-c2cc(Cl)c3ncccc3c2)n1] |
| 1.293 | 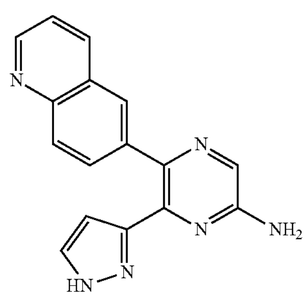 [SMILES: Nc1cnc(-c2ccc3ncccc3c2)c(-c2cc[nH]n2)n1] |
| 1.294 | 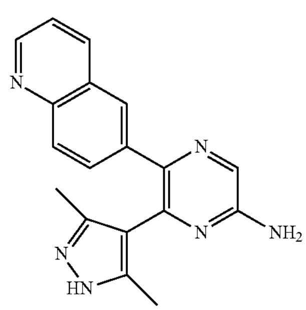 [SMILES: Cc1n[nH]c(C)c1-c1nc(N)cnc1-c1ccc2ncccc2c1] |

TABLE 2-continued

| Compound No. | Structure |
|---|---|
| 1.295 | 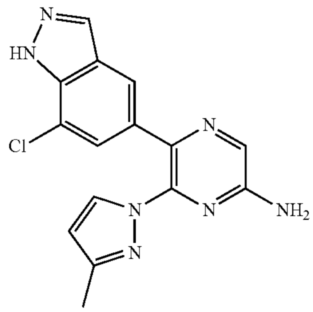 [SMILES: Cc1ccn(-c2nc(N)cnc2-c2cc(Cl)c3[nH]ncc3c2)n1] |
| 1.296 | 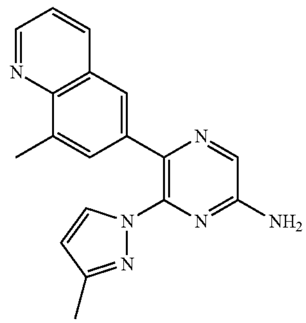 [SMILES: Cc1ccn(-c2nc(N)cnc2-c2cc(C)c3ncccc3c2)n1] |
| 1.297 | 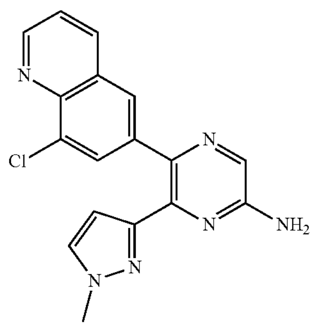 [SMILES: Cn1ccc(-c2nc(N)cnc2-c2cc(Cl)c3ncccc3c2)n1] |
| 1.298 | 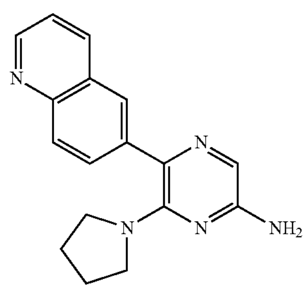 [SMILES: Nc1cnc(-c2ccc3ncccc3c2)c(N2CCCC2)n1] |
| 1.299 | 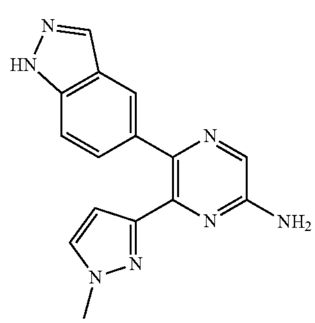 [SMILES: Cn1ccc(-c2nc(N)cnc2-c2ccc3[nH]ncc3c2)n1] |

TABLE 2-continued

| Compound No. | Structure |
|---|---|
| 1.300 | 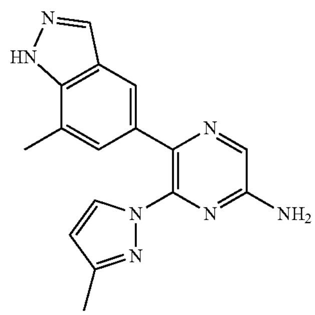 [SMILES: Cc1ccn(-c2nc(N)cnc2-c2cc(C)c3[nH]ncc3c2)n1] |
| 1.301 | 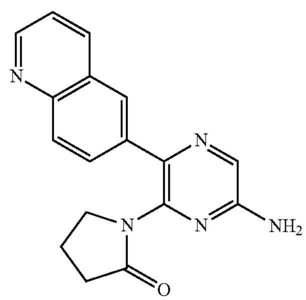 [SMILES: Nc1cnc(-c2ccc3ncccc3c2)c(N2CCCC2=O)n1] |
| 1.302 | 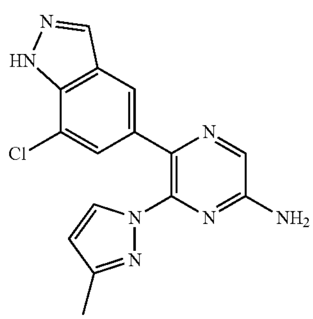 [SMILES: Cc1ccn(-c2nc(N)cnc2-c2cc(Cl)c3[nH]ncc3c2)n1] |
| 1.303 | 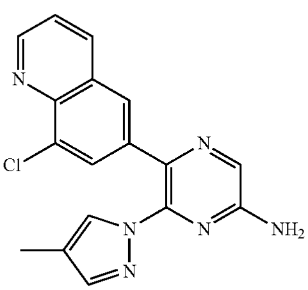 [SMILES: Cc1cnn(-c2nc(N)cnc2-c2cc(Cl)c3ncccc3c2)c1] |
| 1.304 | 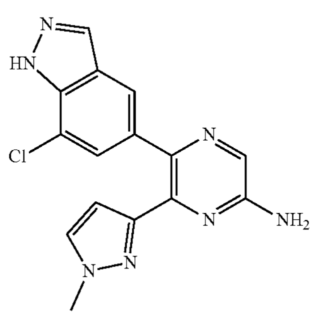 [SMILES: Cn1ccc(-c2nc(N)cnc2-c2cc(Cl)c3[nH]ncc3c2)n1] |

TABLE 2-continued
| Compound No. | Structure |
| --- | --- |
| 1.305 | 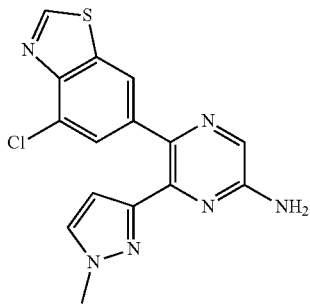 [SMILES: Cn1ccc(-c2nc(N)cnc2-c2cc(Cl)c3ncsc3c2)n1] |
| 1.306 | 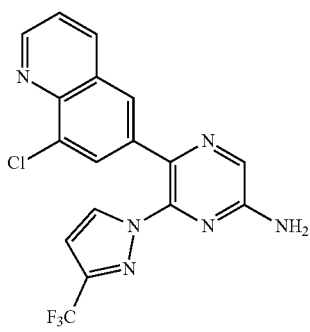 [SMILES: Nc1cnc(-c2cc(Cl)c3ncccc3c2)c(-n2ccc(C(F)(F)F)n2)n1] |
| 1.307 | 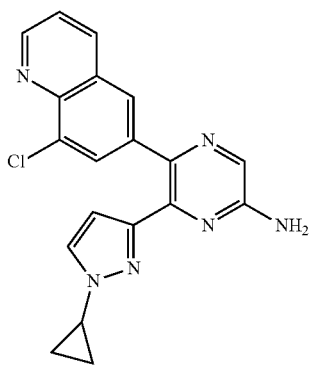 [SMILES: Nc1cnc(-c2cc(Cl)c3ncccc3c2)c(-c2ccn(C3CC3)n2)n1] |
| 1.308 | 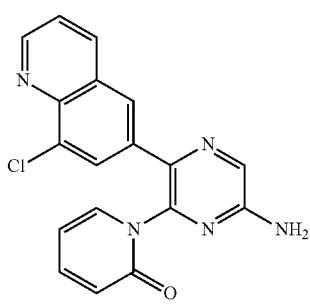 [SMILES: Nc1cnc(-c2cc(Cl)c3ncccc3c2)c(-n2ccccc2=O)n1] |

TABLE 2-continued
| Compound No. | Structure |
|---|---|
| 1.309 | 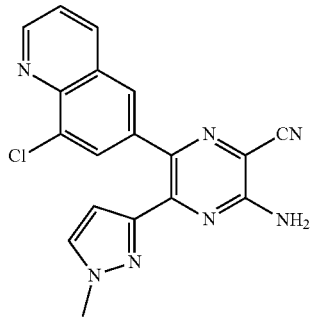 [SMILES: Cn1ccc(-c2nc(N)c(C#N)nc2-c2cc(Cl)c3ncccc3c2)n1] |
| 1.310 | 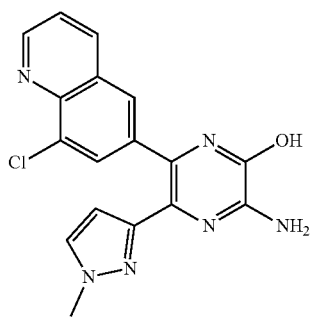 [SMILES: Cn1ccc(-c2nc(N)c(O)nc2-c2cc(Cl)c3ncccc3c2)n1] |
| 1.311 | 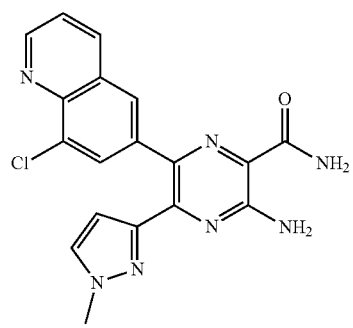 [SMILES: Cn1ccc(-c2nc(N)c(C(N)=O)nc2-c2cc(Cl)c3ncccc3c2)n1] |
| 1.312 | 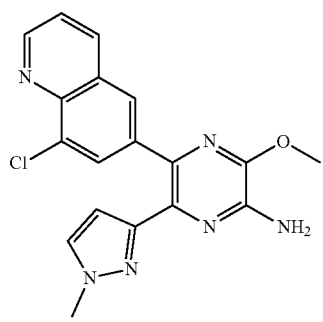 [SMILES: COc1nc(-c2cc(Cl)c3ncccc3c2)c(-c2ccn(C)n2)nc1N] |

TABLE 2-continued

| Compound No. | Structure |
|---|---|
| 1.313 | 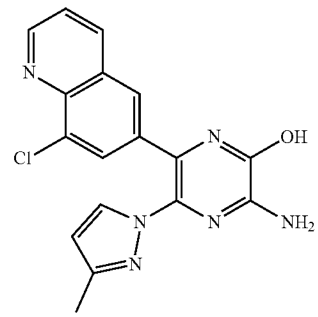 [SMILES: Cc1ccn(-c2nc(N)c(O)nc2-c2cc(Cl)c3ncccc3c2)n1] |
| 1.314 | 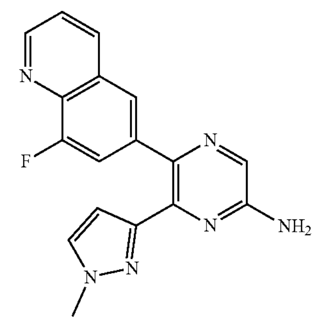 [SMILES: Cn1ccc(-c2nc(N)cnc2-c2cc(F)c3ncccc3c2)n1] |
| 1.315 | 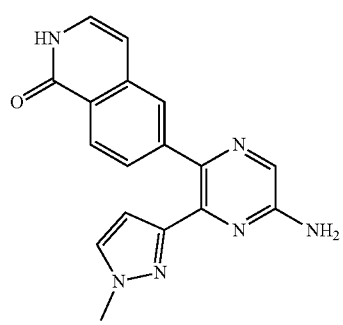 [SMILES: Cn1ccc(-c2nc(N)cnc2-c2ccc3c(=O)[nH]ccc3c2)n1] |
| 1.316 | 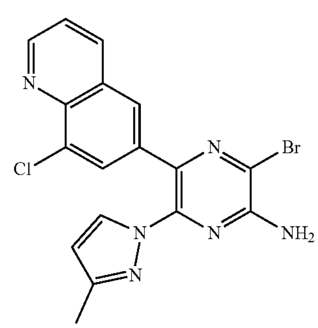 [SMILES: Cc1ccn(-c2nc(N)c(Br)nc2-c2cc(Cl)c3ncccc3c2)n1] |

TABLE 2-continued

| Compound No. | Structure |
|---|---|
| 1.317 | 3-amino-6-(8-chloroquinolin-6-yl)-5-(3-methyl-1H-pyrazol-1-yl)pyrazine-2-carboxamide |
| 1.318 | 6-(8-chloroquinolin-6-yl)-5-(2-methylthiazol-5-yl)pyrazin-2-amine |
| 1.319 | 6-(8-chloroquinolin-6-yl)-5-(3-ethyl-1H-pyrazol-1-yl)pyrazin-2-amine |
| 1.320 | 1-(6-amino-3-(7-chloro-1H-indazol-5-yl)pyrazin-2-yl)pyridin-2(1H)-one |

TABLE 2-continued

| Compound No. | Structure |
|---|---|
| 1.321 | 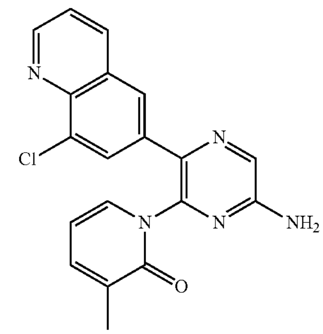 [SMILES: Cc1cccn(-c2nc(N)cnc2-c2cc(Cl)c3ncccc3c2)c1=O] |
| 1.322 | 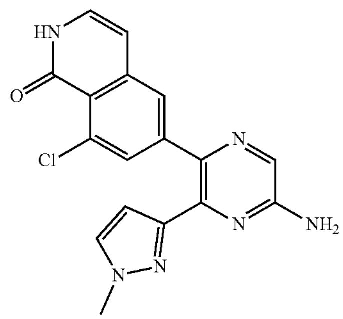 [SMILES: Cn1ccc(-c2nc(N)cnc2-c2cc(Cl)c3c(=O)[nH]ccc3c2)n1] |
| 1.323 | 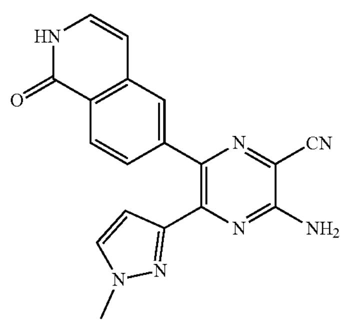 [SMILES: Cn1ccc(-c2nc(N)c(C#N)nc2-c2ccc3c(=O)[nH]ccc3c2)n1] |
| 1.324 | 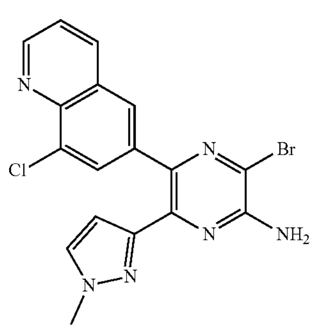 [SMILES: Cn1ccc(-c2nc(N)c(Br)nc2-c2cc(Cl)c3ncccc3c2)n1] |

TABLE 2-continued

| Compound No. | Structure |
|---|---|
| 1.325 | 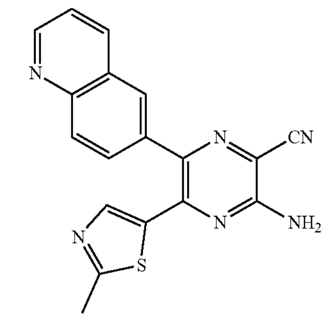 [SMILES: Cc1ncc(-c2nc(N)c(C#N)nc2-c2ccc3ncccc3c2)s1] |
| 1.326 | 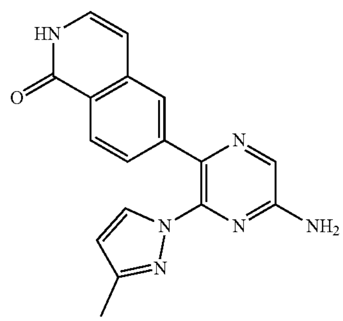 [SMILES: Cc1ccn(-c2nc(N)cnc2-c2ccc3c(=O)[nH]ccc3c2)n1] |
| 1.327 | 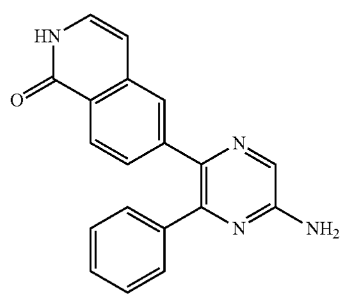 [SMILES: Nc1cnc(-c2ccc3c(=O)[nH]ccc3c2)c(-c2ccccc2)n1] |
| 1.328 | 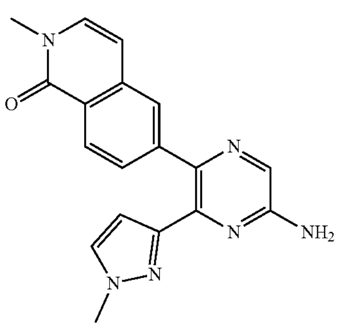 [SMILES: Cn1ccc(-c2nc(N)cnc2-c2ccc3c(=O)n(C)ccc3c2)n1] |
| 1.329 | 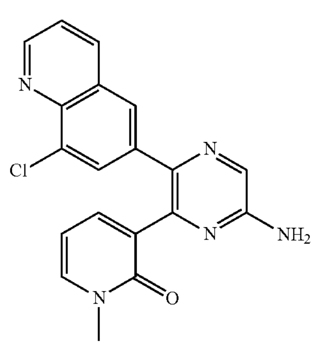 [SMILES: Cn1cccc(-c2nc(N)cnc2-c2cc(Cl)c3ncccc3c2)c1=O] |

TABLE 2-continued
| Compound No. | Structure |
|---|---|
| 1.330 | 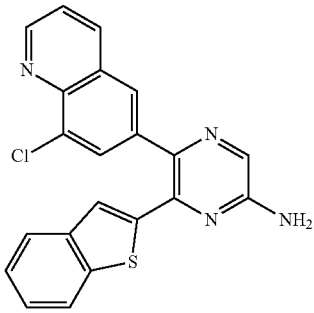 [SMILES: Nc1cnc(-c2cc(Cl)c3ncccc3c2)c(-c2cc3ccccc3s2)n1] |
| 1.331 | 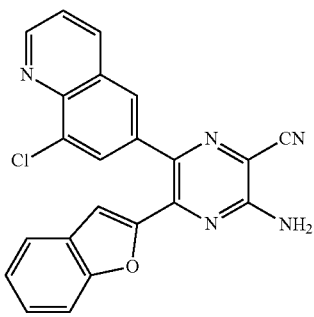 [SMILES: N#Cc1nc(-c2cc(Cl)c3ncccc3c2)c(-c2cc3ccccc3o2)nc1N] |
| 1.332 | 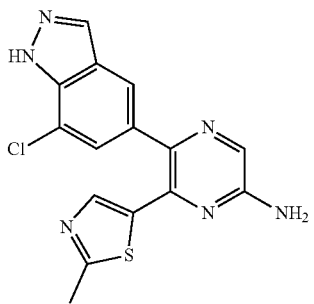 [SMILES: Cc1ncc(-c2nc(N)cnc2-c2cc(Cl)c3[nH]ncc3c2)s1] |
| 1.333 | 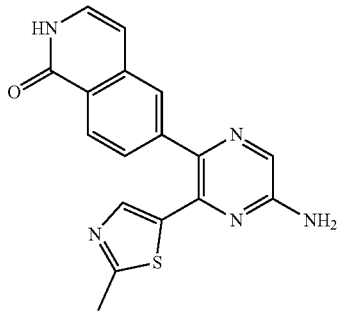 [SMILES: Cc1ncc(-c2nc(N)cnc2-c2ccc3c(=O)[nH]ccc3c2)s1] |

TABLE 2-continued

| Compound No. | Structure |
|---|---|
| 1.334 | 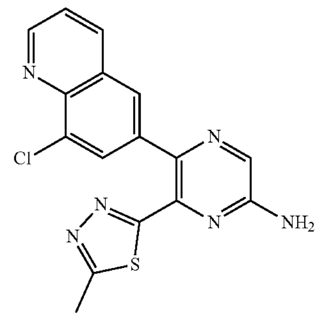 |
| 1.335 | 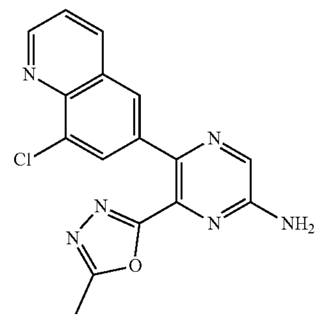 [SMILES: Cc1nnc(-c2nc(N)cnc2-c2cc(Cl)c3ncccc3c2)o1] |
| 1.336 | 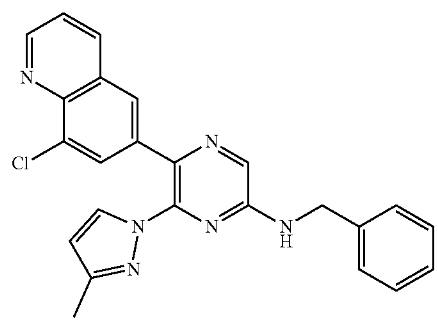 [SMILES: Cc1ccn(-c2nc(NCc3ccccc3)cnc2-c2cc(Cl)c3ncccc3c2)n1] |
| 1.337 | 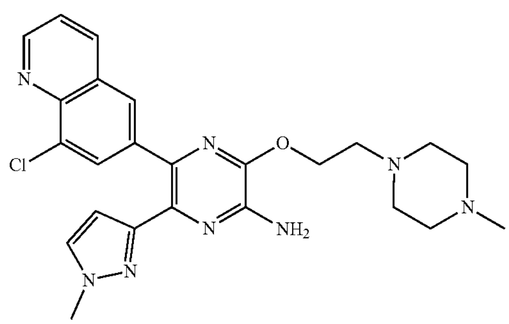 [SMILES: CN1CCN(CCOc2nc(-c3cc(Cl)c4ncccc4c3)c(-c3ccn(C)n3)nc2N)CC1] |
| 1.338 | 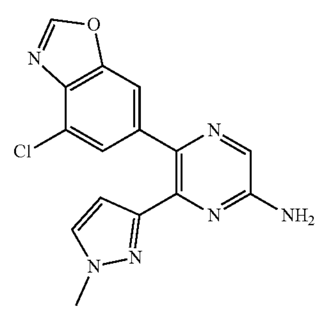 [SMILES: Cn1ccc(-c2nc(N)cnc2-c2cc(Cl)c3ncoc3c2)n1] |

TABLE 2-continued

| Compound No. | Structure |
|---|---|
| 1.339 | *(structure image)* |
| 1.340 | *(structure image)* |
| 1.341 | *(structure image)* |
| 1.342 | *(structure image)* |
| 1.343 | *(structure image)* |

TABLE 2-continued
| Compound No. | Structure |
|---|---|
| 1.344 | 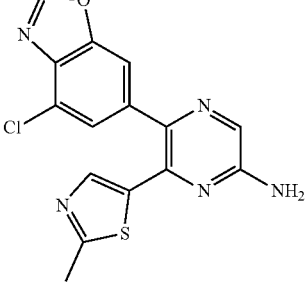 |
| 1.345 | 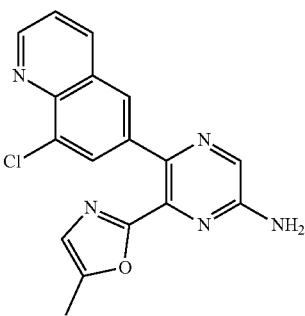 |
| 1.346 | 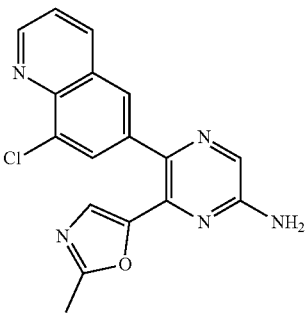 |
| 1.347 | 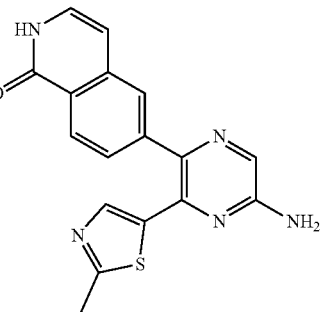 |
| 1.348 | 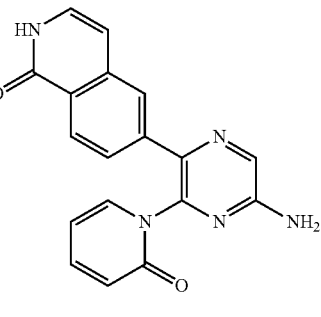 |

TABLE 2-continued
| Compound No. | Structure |
|---|---|
| 1.349 | 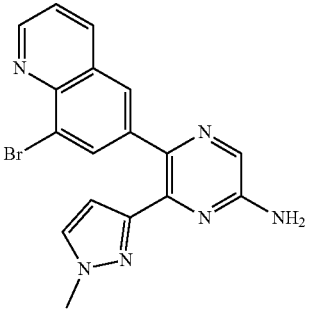 |
| 1.350 | 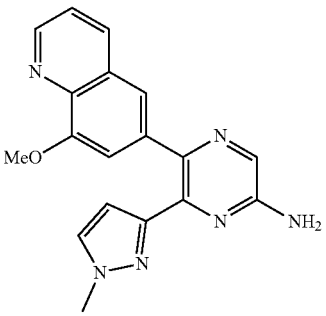 [SMILES: COc1cc(-c2ncc(N)nc2-c2ccn(C)n2)cc2cccnc12] |
| 1.351 | 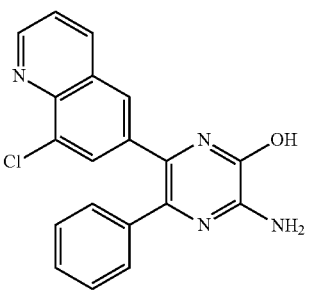 [SMILES: Nc1nc(-c2ccccc2)c(-c2cc(Cl)c3ncccc3c2)nc1O] |
| 1.352 | 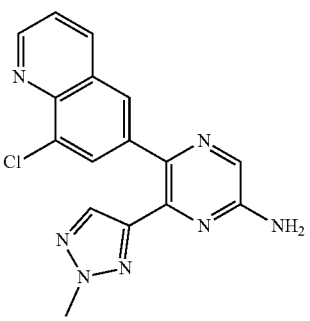 [SMILES: Cn1ncc(-c2nc(N)cnc2-c2cc(Cl)c3ncccc3c2)n1] |
| 1.353 | 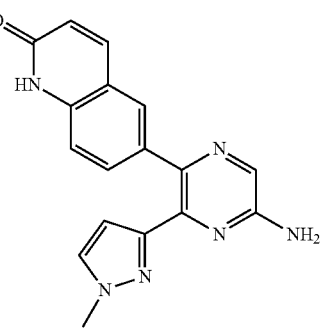 |

TABLE 2-continued

| Compound No. | Structure |
|---|---|
| 1.354 | 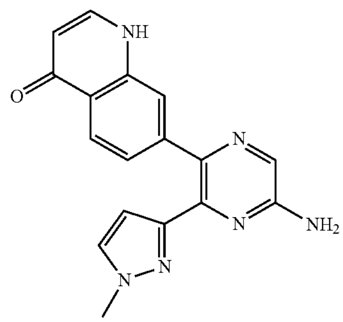 [SMILES: Cn1ccc(-c2nc(N)cnc2-c2ccc3c(=O)cc[nH]c3c2)n1] |
| 1.355 | 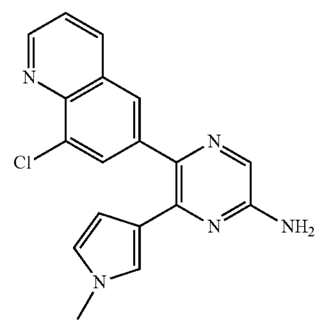 [SMILES: Cn1ccc(-c2nc(N)cnc2-c2cc(Cl)c3ncccc3c2)c1] |
| 1.356 | 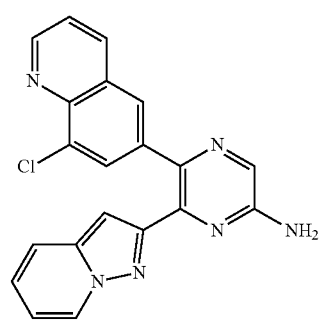 [SMILES: Nc1cnc(-c2cc(Cl)c3ncccc3c2)c(-c2cc3ccccn3n2)n1] |
| 1.357 | 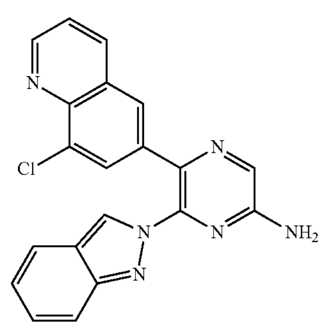 [SMILES: Nc1cnc(-c2cc(Cl)c3ncccc3c2)c(-n2cc3ccccc3n2)n1] |

TABLE 2-continued
| Compound No. | Structure |
|---|---|
| 1.358 | 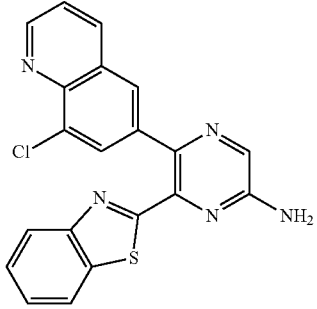 [SMILES: Nc1cnc(-c2cc(Cl)c3ncccc3c2)c(-c2nc3ccccc3s2)n1] |
| 1.359 | 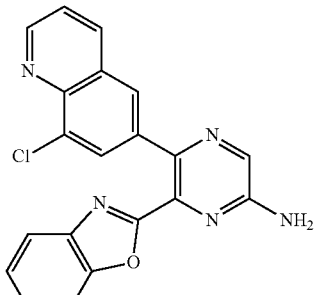 |
| 1.360 | 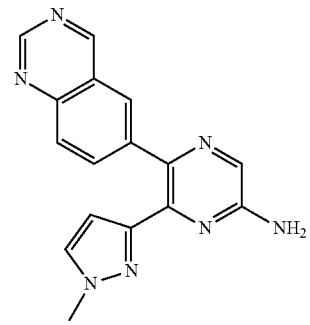 [SMILES: Cn1ccc(-c2nc(N)cnc2-c2ccc3ncncc3c2)n1] |
| 1.361 | 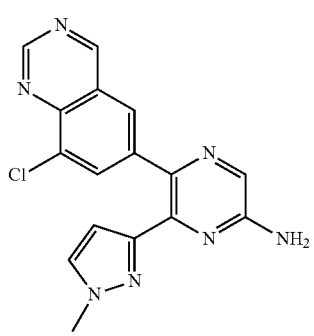 [SMILES: Cn1ccc(-c2nc(N)cnc2-c2cc(Cl)c3ncncc3c2)n1] |

TABLE 2-continued

| Compound No. | Structure |
|---|---|
| 1.362 | (quinazoline-pyrazine with CN, NH₂, and 1-methylpyrazole substituents) |
| 1.363 | (8-chloroquinoline-pyrazine with NH₂ and benzimidazole substituents) |
| 1.364 | (8-chloroquinoline-pyrazine with NH₂ and pyrazine substituents) |
| 1.365 | (8-chloro-4-methylquinoline-pyrazine with Br, NH₂, and 1-methylpyrazole substituents) |
| 1.366 | (8-chloro-4-methylquinoline-pyrazine with CN, NH₂, and 1-methylpyrazole substituents) |

TABLE 2-continued

| Compound No. | Structure |
|---|---|
| 1.367 | 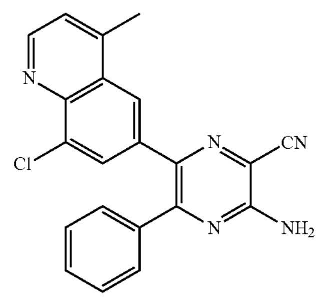 [SMILES: Cc1ccnc2c(Cl)cc(-c3nc(C#N)c(N)nc3-c3ccccc3)cc12] |
| 1.368 | 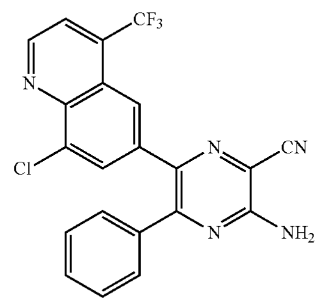 [SMILES: N#Cc1nc(-c2cc(Cl)c3nccc(C(F)(F)F)c3c2)c(-c2ccccc2)nc1N] |
| 1.369 | 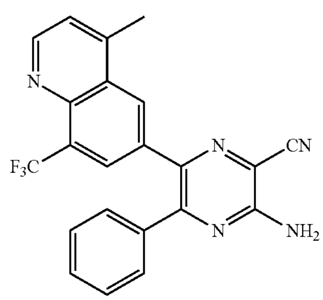 [SMILES: Cc1ccnc2c(C(F)(F)F)cc(-c3nc(C#N)c(N)nc3-c3ccccc3)cc12] |
| 1.370 | 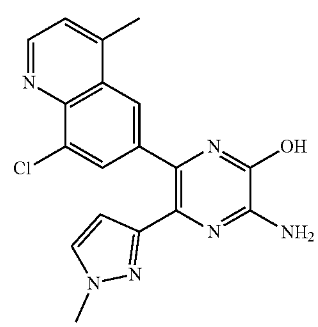 [SMILES: Cc1ccnc2c(Cl)cc(-c3nc(O)c(N)nc3-c3ccn(C)n3)cc12] |
| 1.371 | 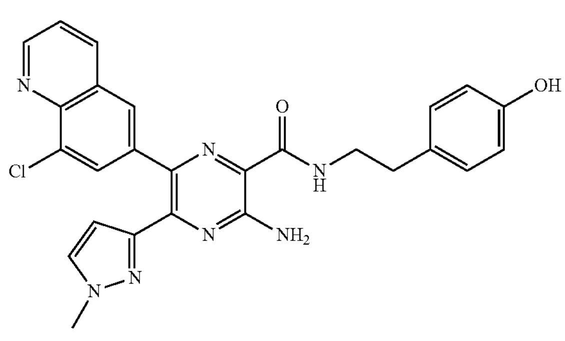 [SMILES: Cn1ccc(-c2nc(N)c(C(=O)NCCc3ccc(O)cc3)nc2-c2cc(Cl)c3ncccc3c2)n1] |

TABLE 2-continued
| Compound No. | Structure |
|---|---|
| 1.372 | 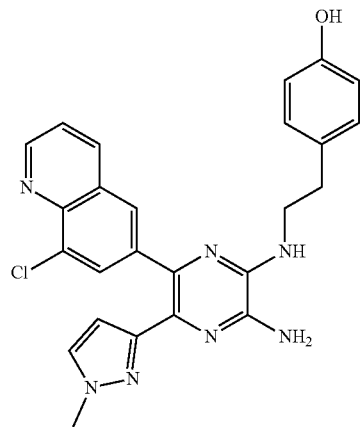 [SMILES: Cn1ccc(-c2nc(N)c(NCCc3ccc(O)cc3)nc2-c2cc(Cl)c3ncccc3c2)n1] |
| 1.373 | 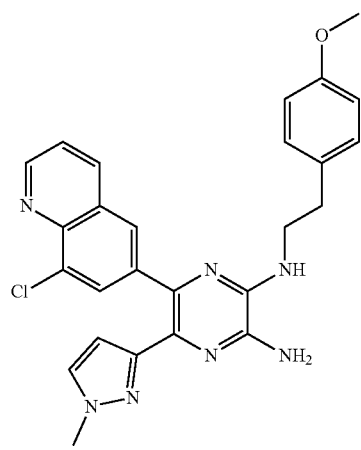 [SMILES: COc1ccc(CCNc2nc(-c3cc(Cl)c4ncccc4c3)c(-c3ccn(C)n3)nc2N)cc1] |
| 1.374 | 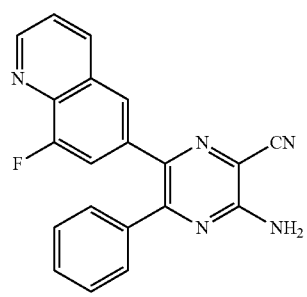 |
| 1.375 | 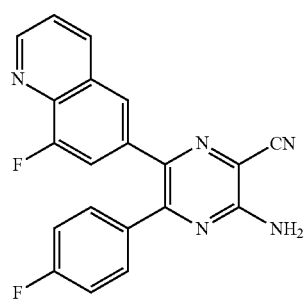 [SMILES: N#Cc1nc(-c2cc(F)c3ncccc3c2)c(-c2ccc(F)cc2)nc1N] |

TABLE 2-continued
| Compound No. | Structure |
|---|---|
| 1.376 | 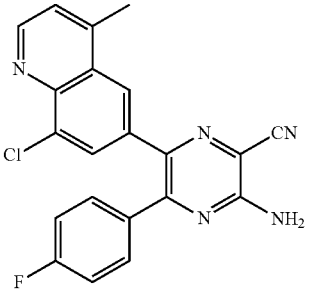 [SMILES: Cc1ccnc2c(Cl)cc(-c3nc(C#N)c(N)nc3-c3ccc(F)cc3)cc12] |
| 1.377 | 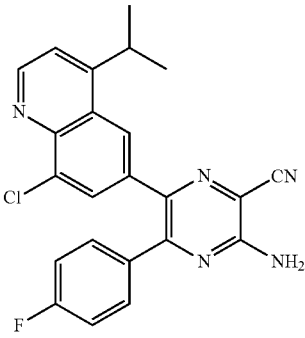 [SMILES: CC(C)c1ccnc2c(Cl)cc(-c3nc(C#N)c(N)nc3-c3ccc(F)cc3)cc12] |
| 1.378 | 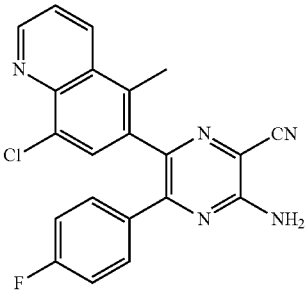 [SMILES: Cc1c(-c2nc(C#N)c(N)nc2-c2ccc(F)cc2)cc(Cl)c2ncccc12] |
| 1.379 | 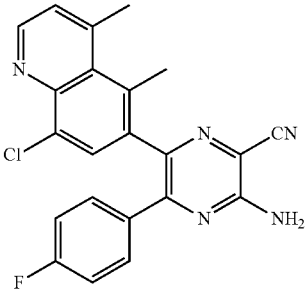 [SMILES: Cc1ccnc2c(Cl)cc(-c3nc(C#N)c(N)nc3-c3ccc(F)cc3)c(C)c12] |
| 1.380 | 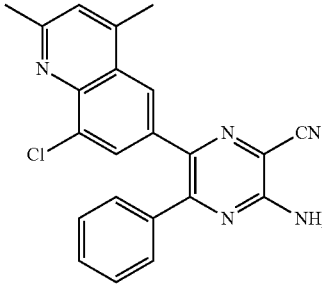 |

TABLE 2-continued

| Compound No. | Structure |
|---|---|
| 1.381 | 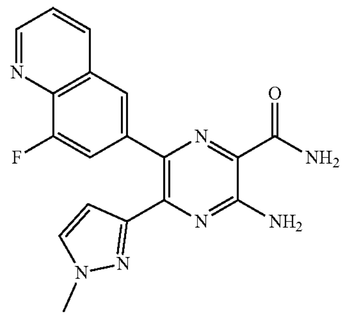 [SMILES: Cn1ccc(-c2nc(N)c(C(N)=O)nc2-c2cc(F)c3ncccc3c2)n1] |
| 1.382 | 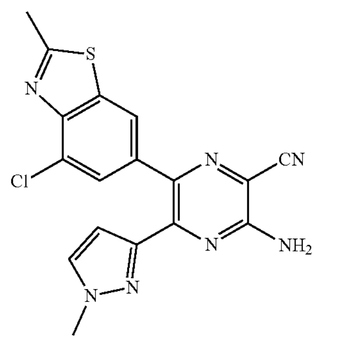 [SMILES: Cc1nc2c(Cl)cc(-c3nc(C#N)c(N)nc3-c3ccn(C)n3)cc2s1] |
| 1.383 | 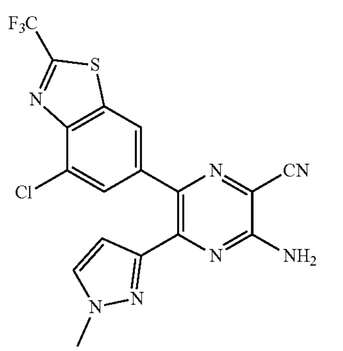 [SMILES: Cn1ccc(-c2nc(N)c(C#N)nc2-c2cc(Cl)c3nc(C(F)(F)F)sc3c2)n1] |
| 1.384 | 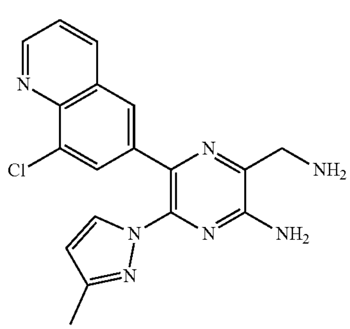 [SMILES: Cc1ccn(-c2nc(N)c(CN)nc2-c2cc(Cl)c3ncccc3c2)n1] |

TABLE 2-continued

| Compound No. | Structure |
|---|---|
| 1.385 | 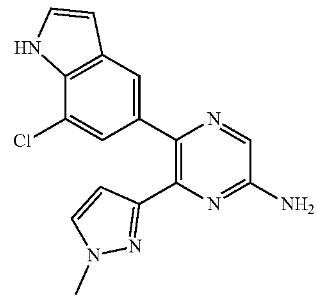 [SMILES: Cn1ccc(-c2nc(N)cnc2-c2cc(Cl)c3[nH]ccc3c2)n1] |
| 1.386 | 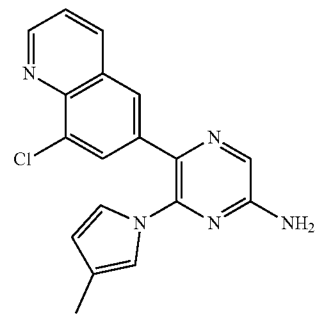 [SMILES: Cc1ccn(-c2nc(N)cnc2-c2cc(Cl)c3ncccc3c2)c1] |
| 1.387 | 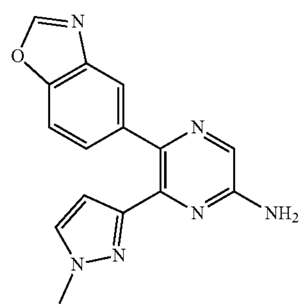 [SMILES: Cn1ccc(-c2nc(N)cnc2-c2ccc3ocnc3c2)n1] |
| 1.388 | 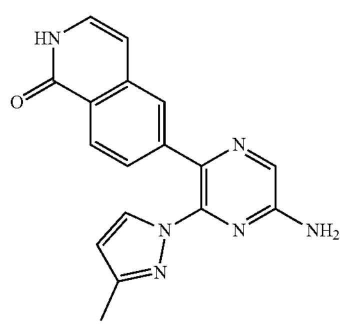 [SMILES: Cc1ccn(-c2nc(N)cnc2-c2ccc3c(=O)[nH]ccc3c2)n1] |
| 1.389 | 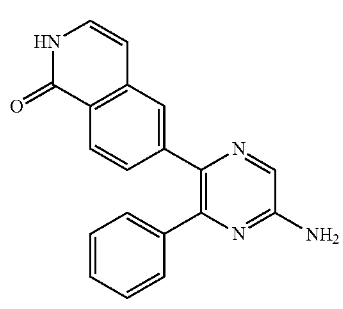 [SMILES: Nc1cnc(-c2ccc3c(=O)[nH]ccc3c2)c(-c2ccccc2)n1] |

TABLE 2-continued

| Compound No. | Structure |
| --- | --- |
| 1.390 | 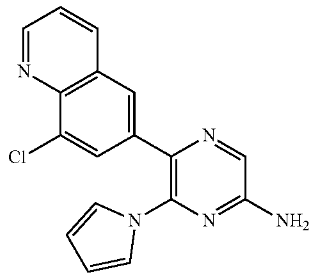 [SMILES: Nc1cnc(-c2cc(Cl)c3ncccc3c2)c(-n2cccc2)n1] |
| 1.391 | 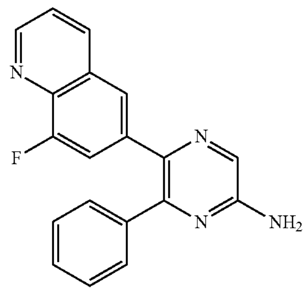 [SMILES: Nc1cnc(-c2cc(F)c3ncccc3c2)c(-c2ccccc2)n1] |
| 1.392 | 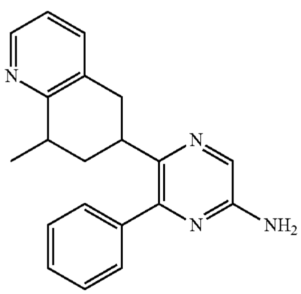 [SMILES: CC1CC(c2ncc(N)nc2-c2ccccc2)Cc2cccnc21] |
| 1.393 | 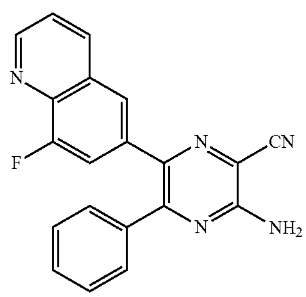 [SMILES: N#Cc1nc(-c2cc(F)c3ncccc3c2)c(-c2ccccc2)nc1N] |
| 1.394 | 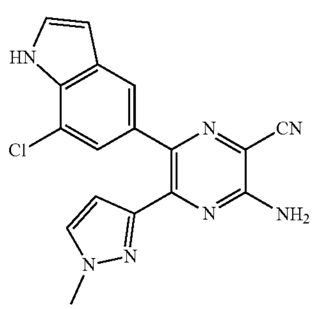 [SMILES: Cn1ccc(-c2nc(N)c(C#N)nc2-c2cc(Cl)c3[nH]ccc3c2)n1] |

TABLE 2-continued
| Compound No. | Structure |
|---|---|
| 1.395 | 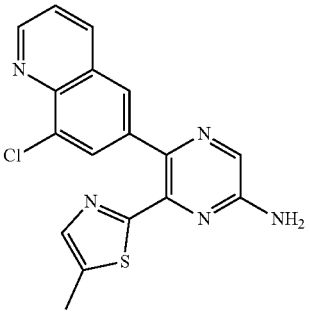 |
| 1.396 | 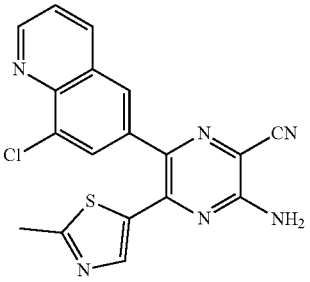 [SMILES: Cc1ncc(-c2nc(N)c(C#N)nc2-c2cc(Cl)c3ncccc3c2)s1] |
| 1.397 | 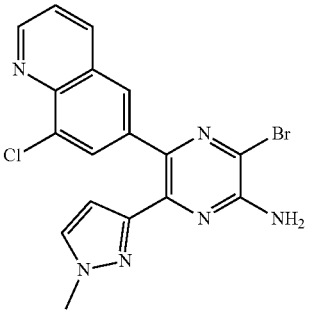 [SMILES: Cn1ccc(-c2nc(N)c(Br)nc2-c2cc(Cl)c3ncccc3c2)n1] |
| 1.398 | 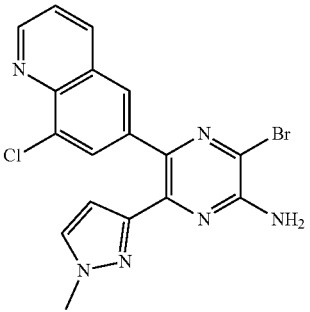 |
| 1.399 | 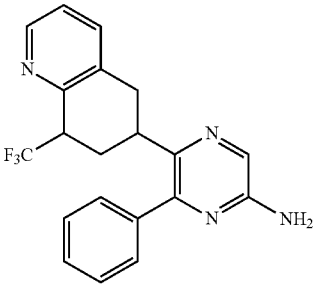 [SMILES: Nc1cnc(C2Cc3cccnc3C(C(F)(F)F)C2)c(-c2ccccc2)n1] |

TABLE 2-continued
| Compound No. | Structure |
|---|---|
| 1.400 | 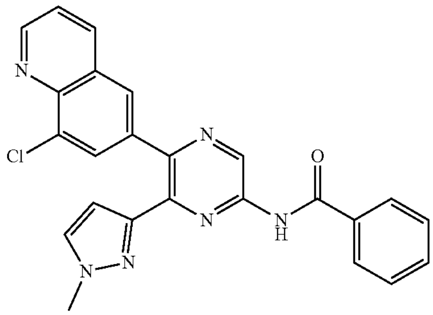 [SMILES: Cn1ccc(-c2nc(NC(=O)c3ccccc3)cnc2-c2cc(Cl)c3ncccc3c2)n1] |
| 1.401 | 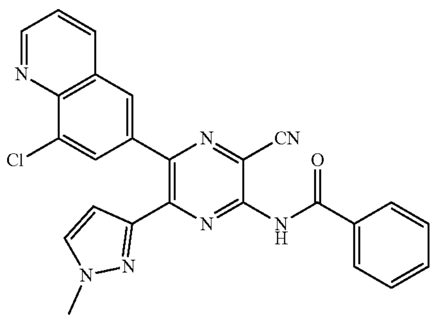 [SMILES: Cn1ccc(-c2nc(NC(=O)c3ccccc3)c(C#N)nc2-c2cc(Cl)c3ncccc3c2)n1] |
| 1.402 | 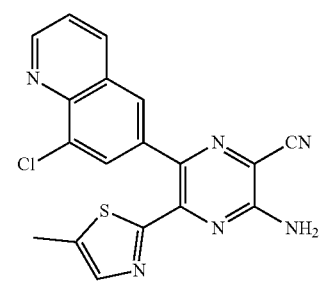 [SMILES: Cc1cnc(-c2nc(N)c(C#N)nc2-c2cc(Cl)c3ncccc3c2)s1] |
| 1.403 | 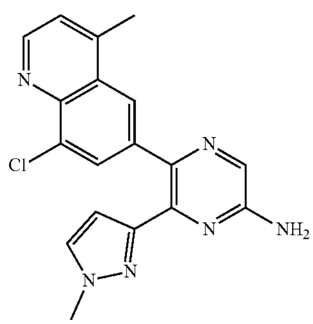 [SMILES: Cc1ccnc2c(Cl)cc(-c3ncc(N)nc3-c3ccn(C)n3)cc12] |
| 1.404 | 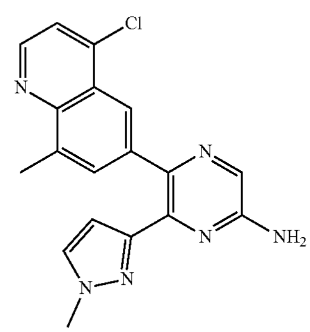 [SMILES: Cc1cc(-c2ncc(N)nc2-c2ccn(C)n2)cc2c(Cl)ccnc12] |

TABLE 2-continued

| Compound No. | Structure |
| --- | --- |
| 1.405 | 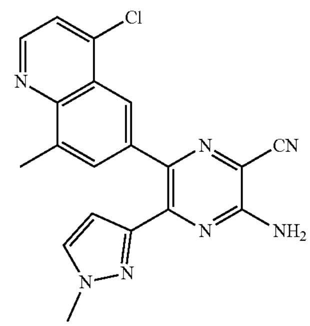 [SMILES: Cc1cc(-c2nc(C#N)c(N)nc2-c2ccn(C)n2)cc2c(Cl)ccnc12] |
| 1.406 | 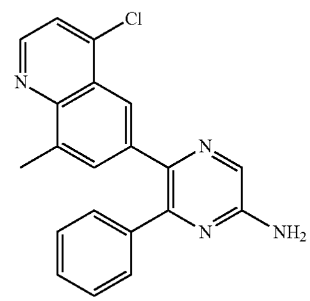 [SMILES: Cc1cc(-c2ncc(N)nc2-c2ccccc2)cc2c(Cl)ccnc12] |
| 1.407 | 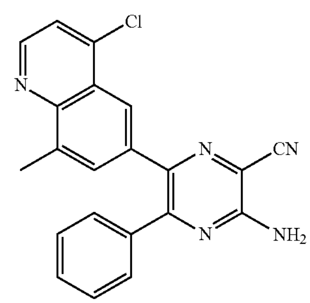 [SMILES: Cc1cc(-c2nc(C#N)c(N)nc2-c2ccccc2)cc2c(Cl)ccnc12] |
| 1.408 | 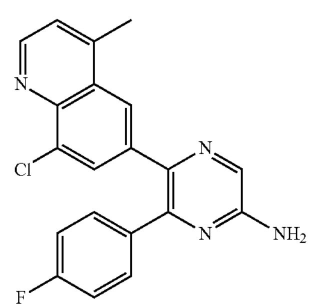 [SMILES: Cc1ccnc2c(Cl)cc(-c3ncc(N)nc3-c3ccc(F)cc3)cc12] |
| 1.409 | 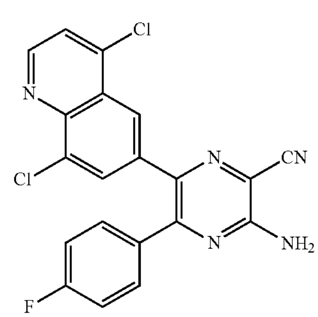 [SMILES: N#Cc1nc(-c2cc(Cl)c3nccc(Cl)c3c2)c(-c2ccc(F)cc2)nc1N] |

TABLE 2-continued

| Compound No. | Structure |
|---|---|
| 1.410 | (3-methyl-1H-indazol-5-yl / pyrazine-2-amine / 1-methyl-1H-pyrazol-3-yl structure) |
| 1.411 | (7-chloro-3-methyl-1H-indazol-5-yl / pyrazine-2-amine / 1-methyl-1H-pyrazol-3-yl structure) |
| 1.412 | (7-chloro-3-methyl-1H-indazol-5-yl / phenyl / pyrazine-2-amine structure) |
| 1.413 | (7-chloro-3-methyl-1H-indazol-5-yl / phenyl / 3-amino-pyrazine-2-carbonitrile structure) |
| 1.414 | (7-chloro-3-methyl-1H-indazol-5-yl / 4-fluorophenyl / pyrazine-2-amine structure) |

TABLE 2-continued

| Compound No. | Structure |
|---|---|
| 1.415 | 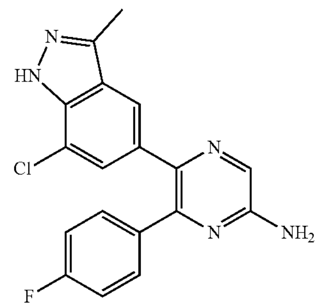 [SMILES: Cc1n[nH]c2c(Cl)cc(-c3ncc(N)nc3-c3ccc(F)cc3)cc12] |
| 1.416 | 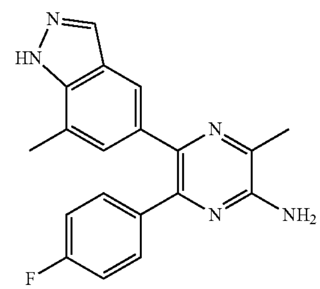 |
| 1.417 | 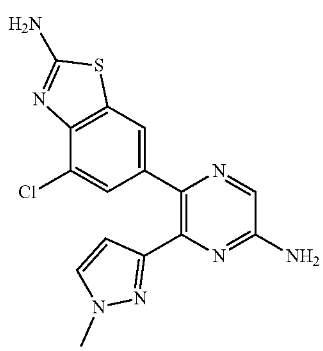 [SMILES: Cn1ccc(-c2nc(N)cnc2-c2cc(Cl)c3nc(N)sc3c2)n1] |
| 1.418 | 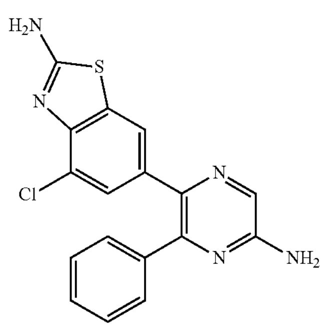 [SMILES: Nc1cnc(-c2cc(Cl)c3nc(N)sc3c2)c(-c2ccccc2)n1] |
| 1.419 | 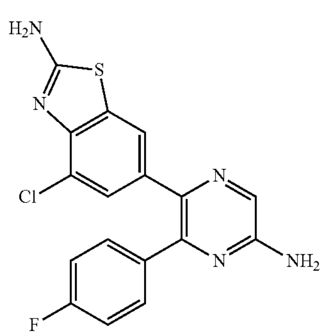 [SMILES: Nc1cnc(-c2cc(Cl)c3nc(N)sc3c2)c(-c2ccc(F)cc2)n1] |

TABLE 2-continued
| Compound No. | Structure |
| --- | --- |
| 1.420 | 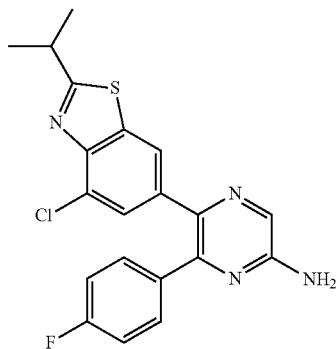 [SMILES: CC(C)c1nc2c(Cl)cc(-c3ncc(N)nc3-c3ccc(F)cc3)cc2s1] |
| 1.421 | 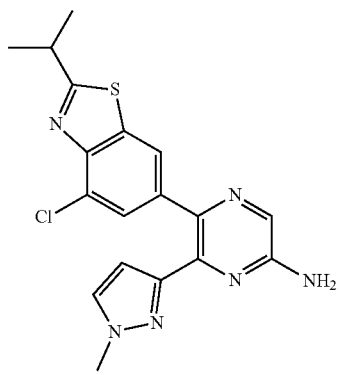 [SMILES: CC(C)c1nc2c(Cl)cc(-c3ncc(N)nc3-c3ccn(C)n3)cc2s1] |
| 1.422 | 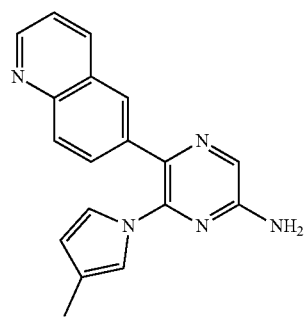 |
| 1.423 | 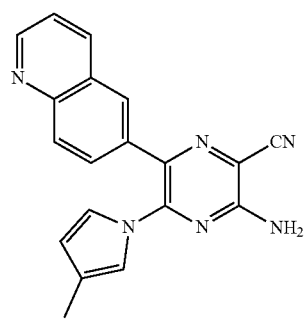 [SMILES: Cc1ccn(-c2nc(N)c(C#N)nc2-c2ccc3ncccc3c2)c1] |

TABLE 2-continued

| Compound No. | Structure |
|---|---|
| 1.424 | 8-chloroquinolin-6-yl pyrazine with 3-fluoropyrazol-1-yl and NH₂ substituents |
| 1.425 | 8-chloroquinolin-6-yl pyrazine with 3-chloropyrazol-1-yl and NH₂ substituents |
| 1.426 | quinolin-6-yl, phenyl, CN-substituted pyrazine with NH-CH₂-C(O)-NH-C₆H₄-C(O)O-ethyl |
| 1.427 | quinolin-6-yl, phenyl, methyl-substituted pyrazine with NH₂ |

TABLE 2-continued

| Compound No. | Structure |
|---|---|
| 1.428 | 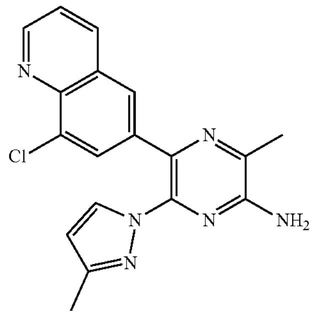 [SMILES: Cc1ccn(-c2nc(N)c(C)nc2-c2cc(Cl)c3ncccc3c2)n1] |
| 1.429 | 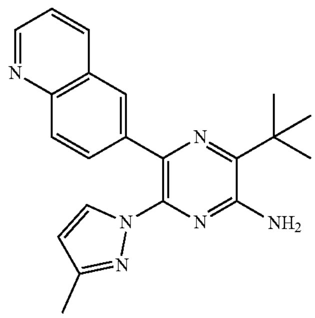 [SMILES: Cc1ccn(-c2nc(N)c(C(C)(C)C)nc2-c2ccc3ncccc3c2)n1] |
| 1.430 | 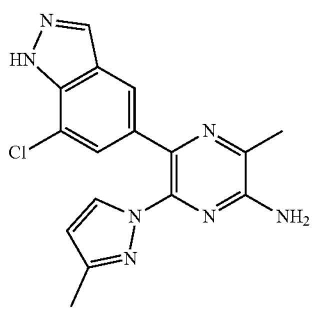 [SMILES: Cc1ccn(-c2nc(N)c(C)nc2-c2cc(Cl)c3[nH]ncc3c2)n1] |
| 1.431 | 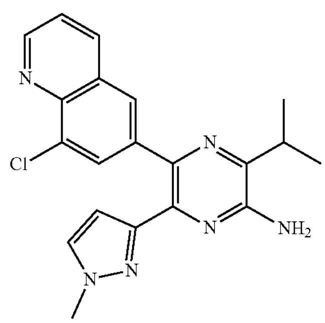 |
| 1.432 | 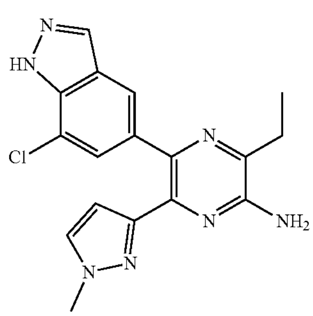 [SMILES: CCc1nc(-c2cc(Cl)c3[nH]ncc3c2)c(-c2ccn(C)n2)nc1N] |

TABLE 2-continued
| Compound No. | Structure |
|---|---|
| 1.433 | 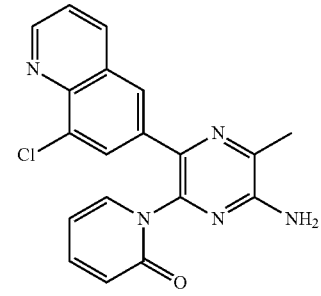 [SMILES: Cc1nc(-c2cc(Cl)c3ncccc3c2)c(-n2ccccc2=O)nc1N] |
| 1.434 | 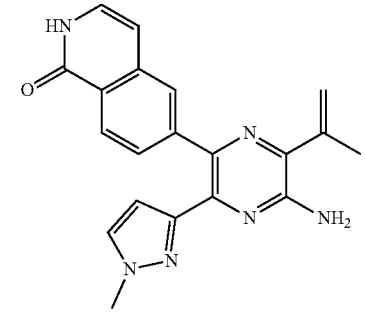 [SMILES: C=C(C)c1nc(-c2ccc3c(=O)[nH]ccc3c2)c(-c2ccn(C)n2)nc1N] |
| 1.435 | 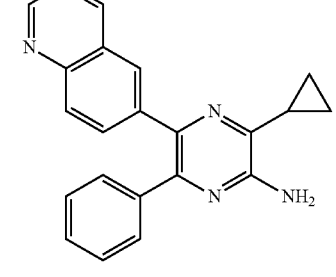 |
| 1.436 | 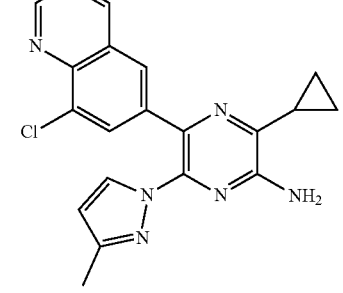 |
| 1.437 | 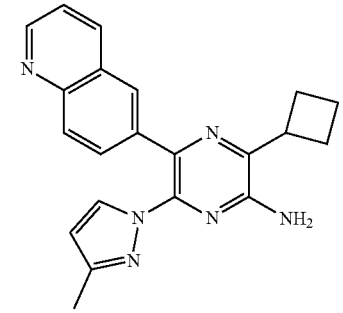 [SMILES: Cc1ccn(-c2nc(N)c(C3CCC3)nc2-c2ccc3ncccc3c2)n1] |

TABLE 2-continued
| Compound No. | Structure |
|---|---|
| 1.438 | 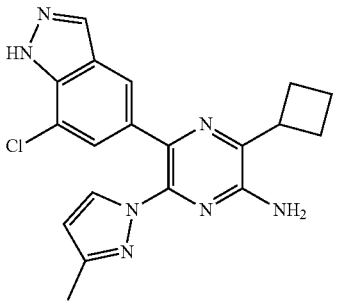 [SMILES: Cc1ccn(-c2nc(N)c(C3CCC3)nc2-c2cc(Cl)c3[nH]ncc3c2)n1] |
| 1.439 | 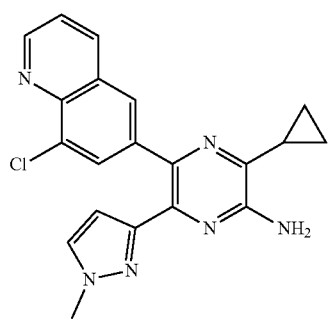 [SMILES: Cn1ccc(-c2nc(N)c(C3CC3)nc2-c2cc(Cl)c3ncccc3c2)n1] |
| 1.440 | 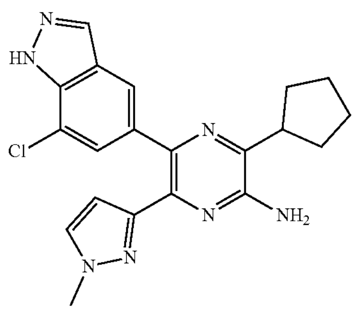 [SMILES: Cn1ccc(-c2nc(N)c(C3CCCC3)nc2-c2cc(Cl)c3[nH]ncc3c2)n1] |
| 1.441 | 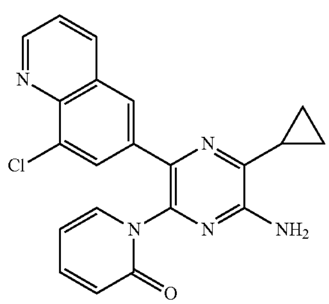 [SMILES: Nc1nc(-n2ccccc2=O)c(-c2cc(Cl)c3ncccc3c2)nc1C1CC1] |
| 1.442 | 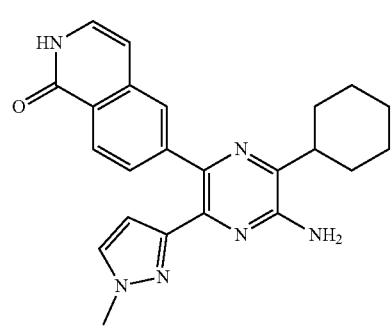 [SMILES: Cn1ccc(-c2nc(N)c(C3CCCCC3)nc2-c2ccc3c(=O)[nH]ccc3c2)n1] |

TABLE 2-continued

| Compound No. | Structure |
|---|---|
| 1.443 | 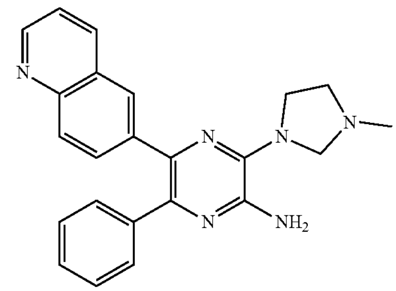 [SMILES: CN1CCN(c2nc(-c3ccc4ncccc4c3)c(-c3ccccc3)nc2N)C1] |
| 1.444 | 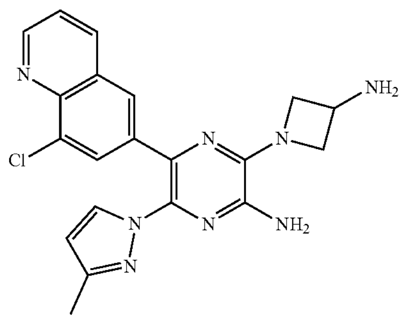 [SMILES: Cc1ccn(-c2nc(N)c(N3CC(N)C3)nc2-c2cc(Cl)c3ncccc3c2)n1] |
| 1.445 | 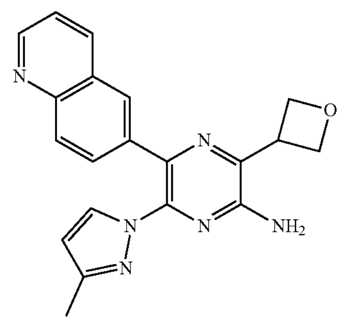 [SMILES: Cc1ccn(-c2nc(N)c(C3COC3)nc2-c2ccc3ncccc3c2)n1] |
| 1.446 | 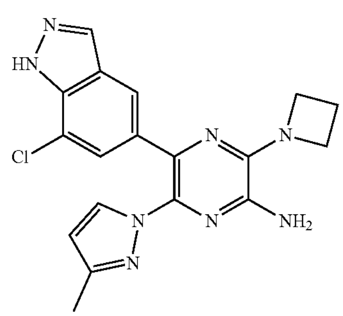 [SMILES: Cc1ccn(-c2nc(N)c(N3CCC3)nc2-c2cc(Cl)c3[nH]ncc3c2)n1] |
| 1.447 | 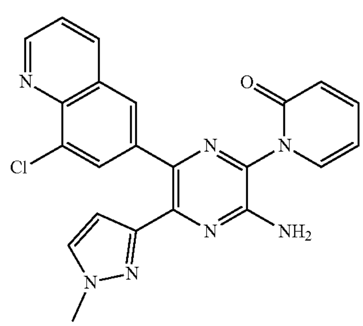 [SMILES: Cn1ccc(-c2nc(N)c(-n3ccccc3=O)nc2-c2cc(Cl)c3ncccc3c2)n1] |

TABLE 2-continued

| Compound No. | Structure |
|---|---|
| 1.448 | 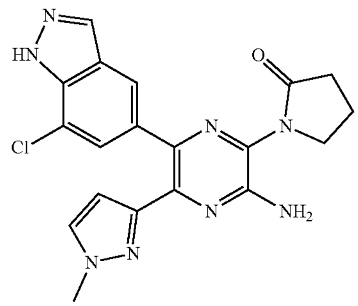 [SMILES: Cn1ccc(-c2nc(N)c(N3CCCC3=O)nc2-c2cc(Cl)c3[nH]ncc3c2)n1] |
| 1.449 | 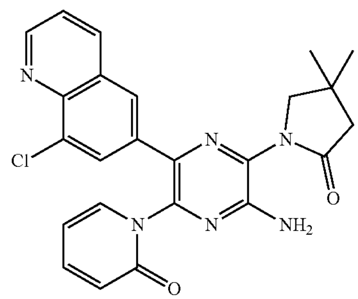 [SMILES: CC1(C)CC(=O)N(c2nc(-c3cc(Cl)c4ncccc4c3)c(-n3ccccc3=O)nc2N)C1] |
| 1.450 | 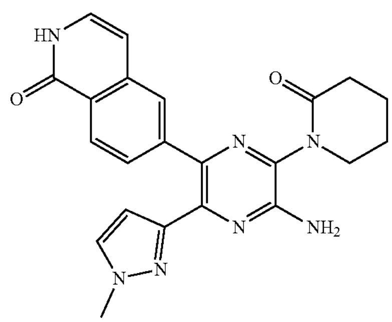 [SMILES: Cn1ccc(-c2nc(N)c(N3CCCCC3=O)nc2-c2ccc3c(=O)[nH]ccc3c2)n1] |
| 1.451 | 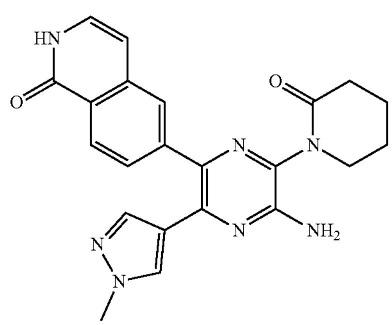 [SMILES: Cn1cc(-c2nc(N)c(N3CCCCC3=O)nc2-c2ccc3c(=O)[nH]ccc3c2)cn1] |
| 1.452 | 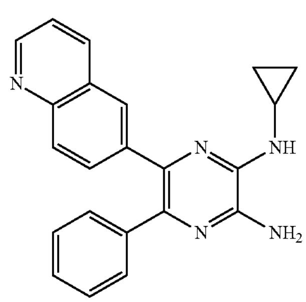 [SMILES: Nc1nc(-c2ccccc2)c(-c2ccc3ncccc3c2)nc1NC1CC1] |

TABLE 2-continued

| Compound No. | Structure |
|---|---|
| 1.453 | 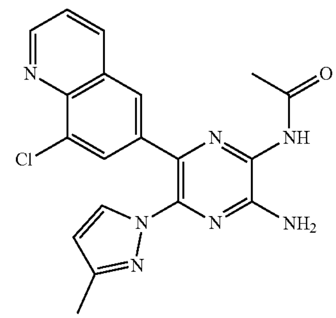 [SMILES: CC(=O)Nc1nc(-c2cc(Cl)c3ncccc3c2)c(-n2ccc(C)n2)nc1N] |
| 1.454 | 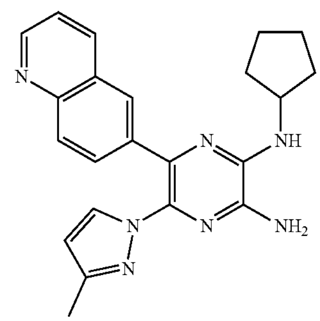 [SMILES: Cc1ccn(-c2nc(N)c(NC3CCCC3)nc2-c2ccc3ncccc3c2)n1] |
| 1.455 | 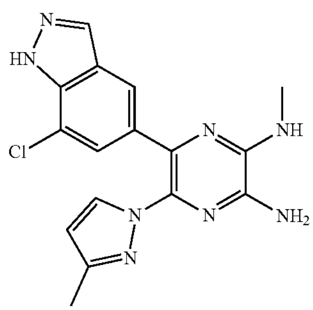 [SMILES: CNc1nc(-c2cc(Cl)c3[nH]ncc3c2)c(-n2ccc(C)n2)nc1N] |
| 1.456 | 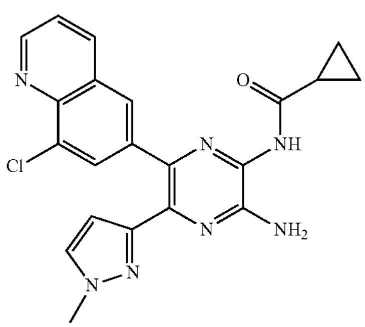 [SMILES: Cn1ccc(-c2nc(N)c(NC(=O)C3CC3)nc2-c2cc(Cl)c3ncccc3c2)n1] |
| 1.457 | 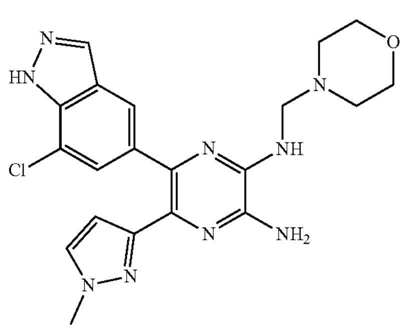 [SMILES: Cn1ccc(-c2nc(N)c(NCN3CCOCC3)nc2-c2cc(Cl)c3[nH]ncc3c2)n1] |

TABLE 2-continued
| Compound No. | Structure |
|---|---|
| 1.458 | 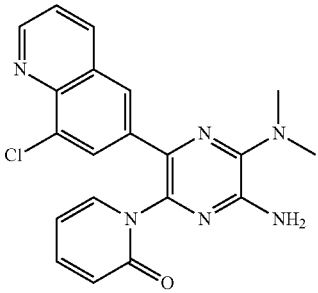 [SMILES: CN(C)c1nc(-c2cc(Cl)c3ncccc3c2)c(-n2ccccc2=O)nc1N] |
| 1.459 | 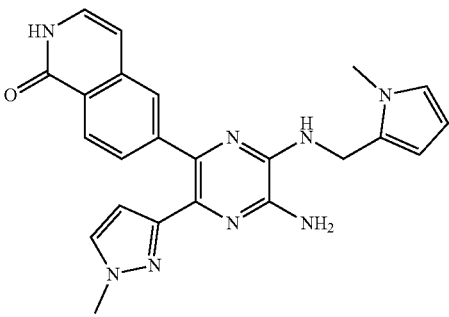 [SMILES: Cn1ccc(-c2nc(N)c(NCc3cccn3C)nc2-c2ccc3c(=O)[nH]ccc3c2)n1] |
| 1.460 | 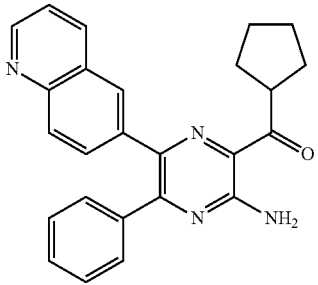 [SMILES: Nc1nc(-c2ccccc2)c(-c2ccc3ncccc3c2)nc1C(=O)C1CCCC1] |
| 1.461 | 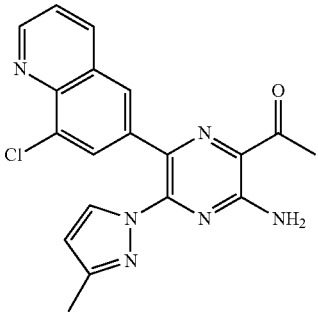 [SMILES: CC(=O)c1nc(-c2cc(Cl)c3ncccc3c2)c(-n2ccc(C)n2)nc1N] |
| 1.462 | 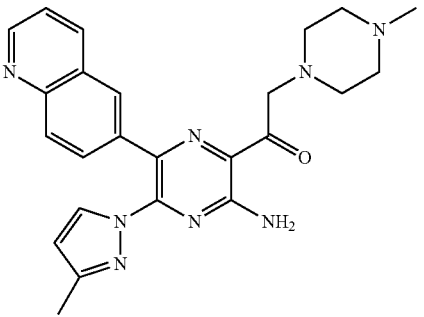 [SMILES: Cc1ccn(-c2nc(N)c(C(=O)CN3CCN(C)CC3)nc2-c2ccc3ncccc3c2)n1] |

TABLE 2-continued

| Compound No. | Structure |
|---|---|
| 1.463 | 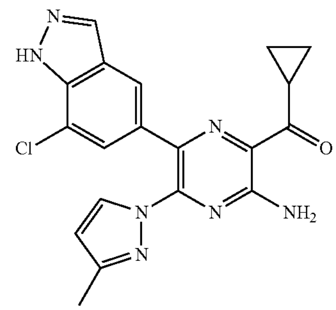 [SMILES: Cc1ccn(-c2nc(N)c(C(=O)C3CC3)nc2-c2cc(Cl)c3[nH]ncc3c2)n1] |
| 1.464 | 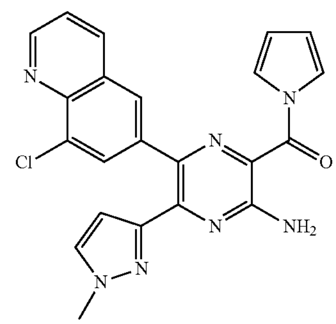 [SMILES: Cn1ccc(-c2nc(N)c(C(=O)n3cccc3)nc2-c2cc(Cl)c3ncccc3c2)n1] |
| 1.465 | 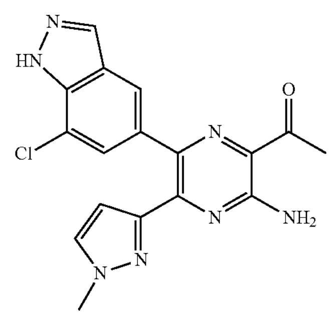 [SMILES: CC(=O)c1nc(-c2cc(Cl)c3[nH]ncc3c2)c(-c2ccn(C)n2)nc1N] |
| 1.466 | 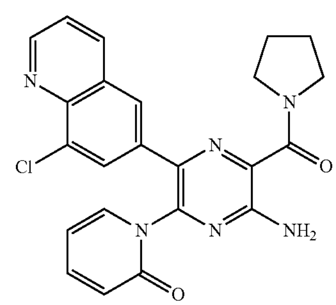 [SMILES: Nc1nc(-n2ccccc2=O)c(-c2cc(Cl)c3ncccc3c2)nc1C(=O)N1CCCC1] |
| 1.467 | 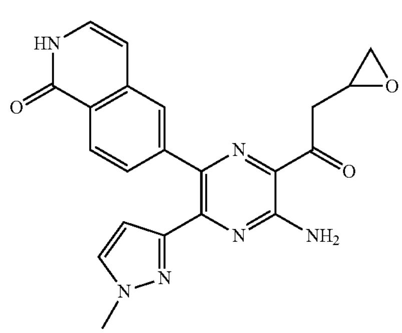 [SMILES: Cn1ccc(-c2nc(N)c(C(=O)CC3CO3)nc2-c2ccc3c(=O)[nH]ccc3c2)n1] |

TABLE 2-continued
| Compound No. | Structure |
|---|---|
| 1.468 | 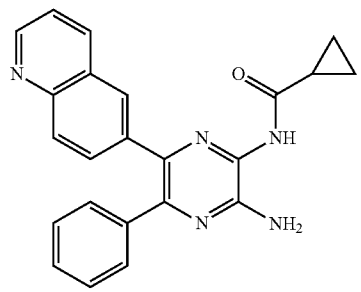 [SMILES: Nc1nc(-c2ccccc2)c(-c2ccc3ncccc3c2)nc1NC(=O)C1CC1] |
| 1.469 | 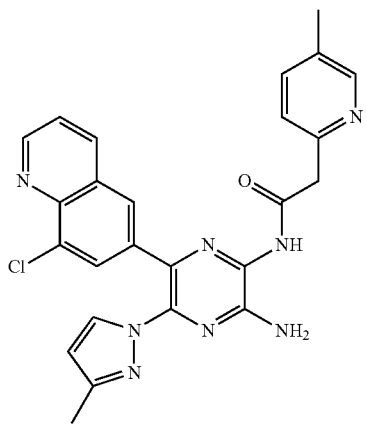 [SMILES: Cc1ccc(CC(=O)Nc2nc(-c3cc(Cl)c4ncccc4c3)c(-n3ccc(C)n3)nc2N)nc1] |
| 1.470 | 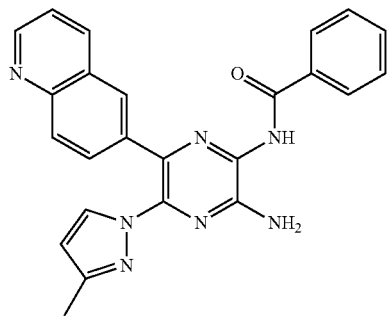 [SMILES: Cc1ccn(-c2nc(N)c(NC(=O)c3ccccc3)nc2-c2ccc3ncccc3c2)n1] |
| 1.471 | 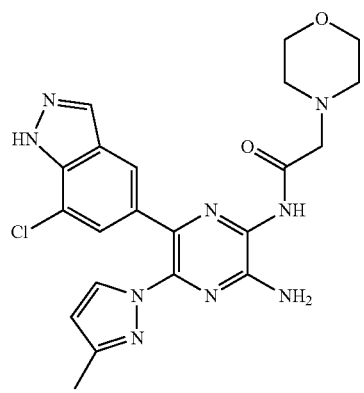 [SMILES: Cc1ccn(-c2nc(N)c(NC(=O)CN3CCOCC3)nc2-c2cc(Cl)c3[nH]ncc3c2)n1] |

TABLE 2-continued

| Compound No. | Structure |
|---|---|
| 1.472 | 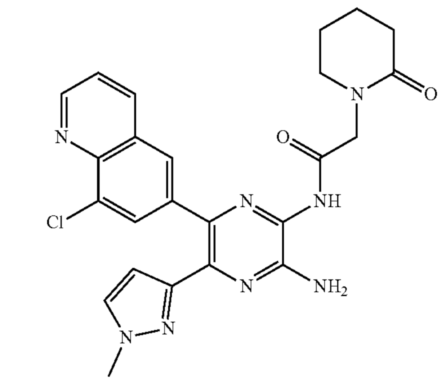 [SMILES: Cn1ccc(-c2nc(N)c(NC(=O)CN3CCCCC3=O)nc2-c2cc(Cl)c3ncccc3c2)n1] |
| 1.473 | 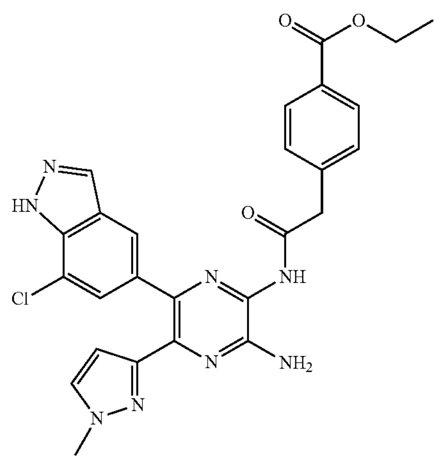 [SMILES: CCOC(=O)c1ccc(CC(=O)Nc2nc(-c3cc(Cl)c4[nH]ncc4c3)c(-c3ccn(C)n3)nc2N)cc1] |
| 1.474 | 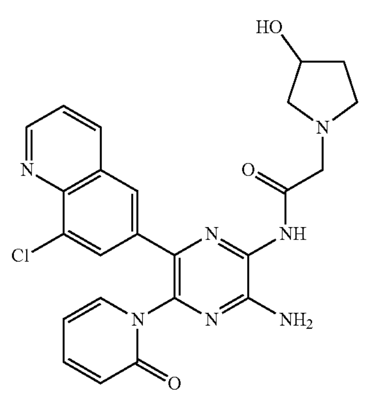 [SMILES: Nc1nc(-n2ccccc2=O)c(-c2cc(Cl)c3ncccc3c2)nc1NC(=O)CN1CCC(O)C1] |
| 1.475 | 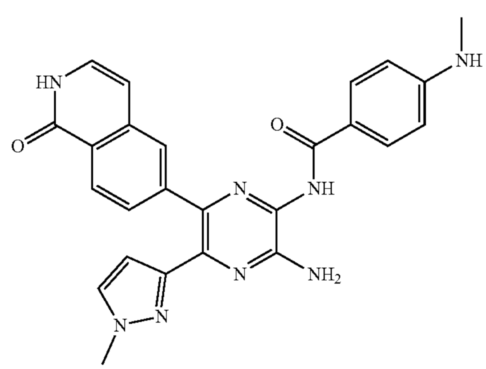 [SMILES: CNc1ccc(C(=O)Nc2nc(-c3ccc4c(=O)[nH]ccc4c3)c(-c3ccn(C)n3)nc2N)cc1] |

TABLE 2-continued

| Compound No. | Structure |
|---|---|
| 1.476 | (quinolin-6-yl)(phenyl)-substituted pyrazine with F and NH₂ |
| 1.477 | (8-chloroquinolin-6-yl)- and (3-methylpyrazol-1-yl)-substituted pyrazine with Cl and NH₂ |
| 1.478 | (quinolin-6-yl)- and (3-methylpyrazol-1-yl)-substituted pyrazine with CF₃ and NH₂ |
| 1.479 | (7-chloro-1H-indazol-5-yl)- and (3-methylpyrazol-1-yl)-substituted pyrazine with OCF₃ and NH₂ |
| 1.480 | (8-chloroquinolin-6-yl)- and (1-methylpyrazol-5-yl)-substituted pyrazine with Cl and NH₂ |

TABLE 2-continued
| Compound No. | Structure |
|---|---|
| 1.481 | 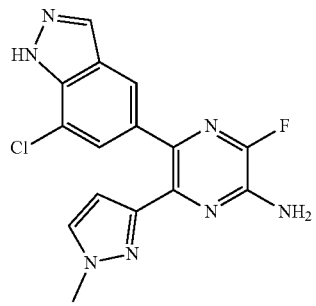 [SMILES: Cn1ccc(-c2nc(N)c(F)nc2-c2cc(Cl)c3[nH]ncc3c2)n1] |
| 1.482 | 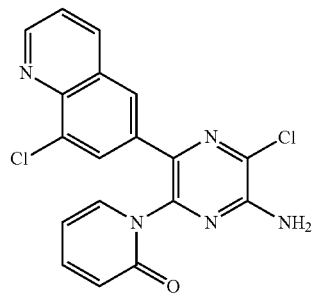 |
| 1.483 | 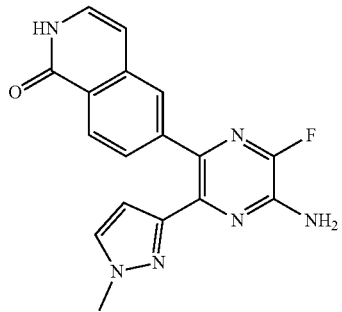 [SMILES: Cn1ccc(-c2nc(N)c(F)nc2-c2ccc3c(=O)[nH]ccc3c2)n1] |
| 1.484 | 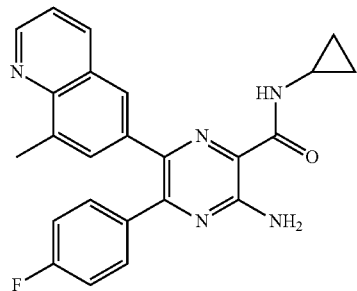 [SMILES: Cc1cc(-c2nc(C(=O)NC3CC3)c(N)nc2-c2ccc(F)cc2)cc2cccnc12] |

TABLE 2-continued

| Compound No. | Structure |
|---|---|
| 1.485 | 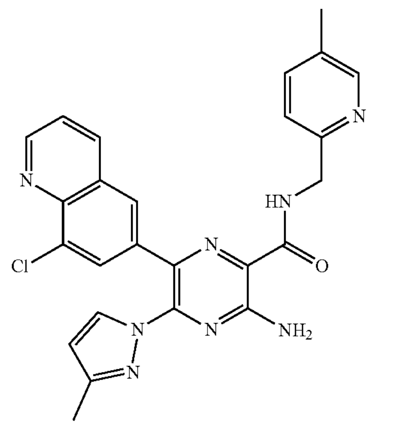 [SMILES: Cc1ccc(CNC(=O)c2nc(-c3cc(Cl)c4ncccc4c3)c(-n3ccc(C)n3)nc2N)nc1] |
| 1.486 | 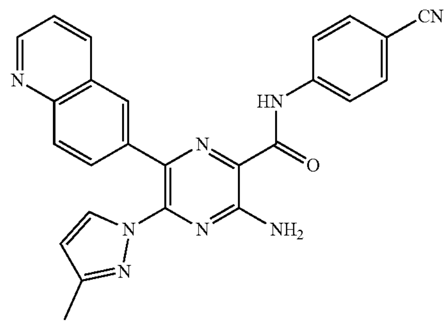 [SMILES: Cc1ccn(-c2nc(N)c(C(=O)Nc3ccc(C#N)cc3)nc2-c2ccc3ncccc3c2)n1] |
| 1.487 | 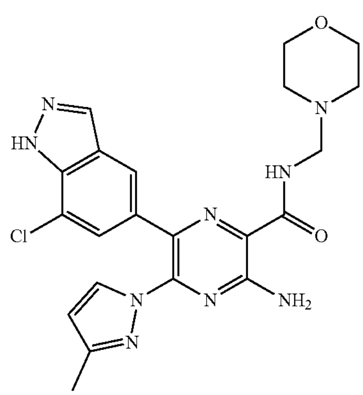 [SMILES: Cc1ccn(-c2nc(N)c(C(=O)NCN3CCOCC3)nc2-c2cc(Cl)c3[nH]ncc3c2)n1] |
| 1.488 | 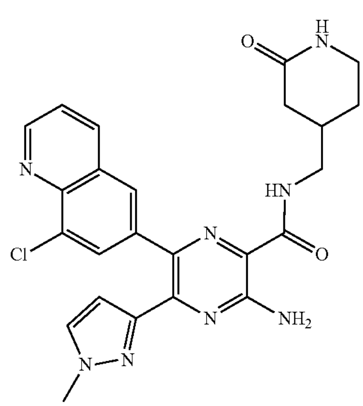 [SMILES: Cn1ccc(-c2nc(N)c(C(=O)NCC3CCNC(=O)C3)nc2-c2cc(Cl)c3ncccc3c2)n1] |

TABLE 2-continued

| Compound No. | Structure |
|---|---|
| 1.489 | 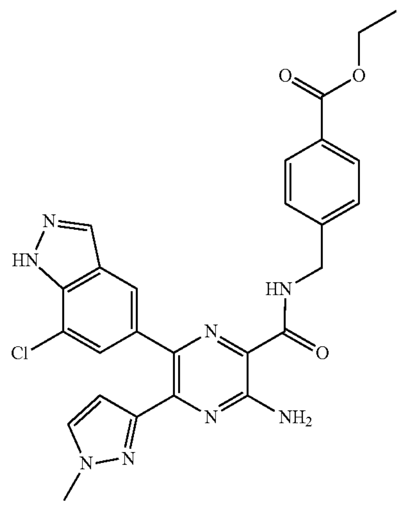 [SMILES: CCOC(=O)c1ccc(CNC(=O)c2nc(-c3cc(Cl)c4[nH]ncc4c3)c(-c3ccn(C)n3)nc2N)cc1] |
| 1.490 | 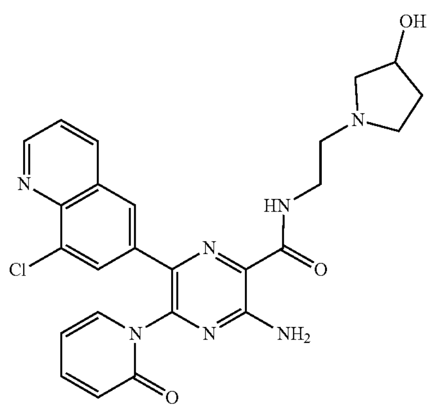 [SMILES: Nc1nc(-n2ccccc2=O)c(-c2cc(Cl)c3ncccc3c2)nc1C(=O)NCCN1CCC(O)C1] |
| 1.491 | 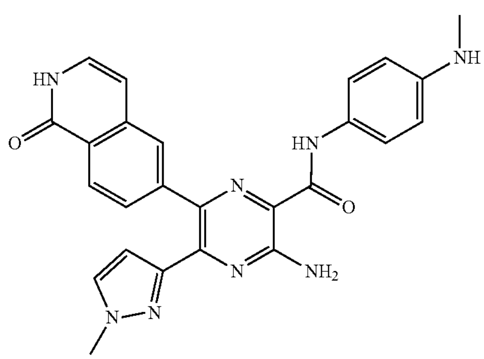 [SMILES: CNc1ccc(NC(=O)c2nc(-c3ccc4c(=O)[nH]ccc4c3)c(-c3ccn(C)n3)nc2N)cc1] |
| 1.492 | 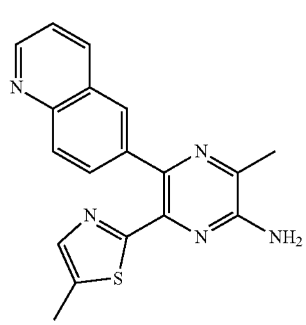 [SMILES: Cc1cnc(-c2nc(N)c(C)nc2-c2ccc3ncccc3c2)s1] |

TABLE 2-continued

| Compound No. | Structure |
| --- | --- |
| 1.493 | 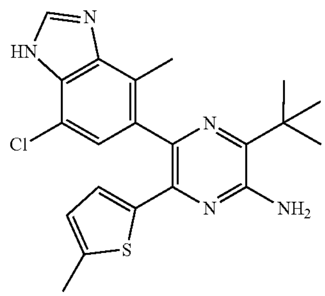 [SMILES: Cc1ccc(-c2nc(N)c(C(C)(C)C)nc2-c2cc(Cl)c3[nH]cnc3c2C)s1] |
| 1.494 | 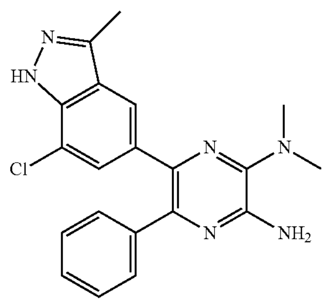 [SMILES: Cc1n[nH]c2c(Cl)cc(-c3nc(N(C)C)c(N)nc3-c3ccccc3)cc12] |
| 1.495 | 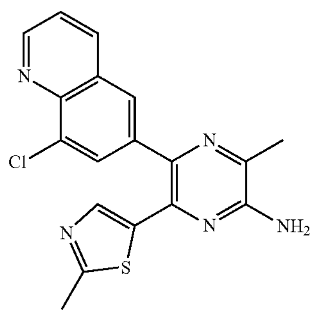 [SMILES: Cc1ncc(-c2nc(N)c(C)nc2-c2cc(Cl)c3ncccc3c2)s1] |
| 1.496 | 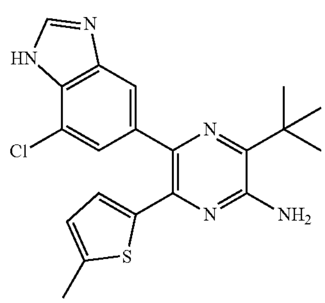 [SMILES: Cc1ccc(-c2nc(N)c(C(C)(C)C)nc2-c2cc(Cl)c3[nH]cnc3c2)s1] |
| 1.497 | 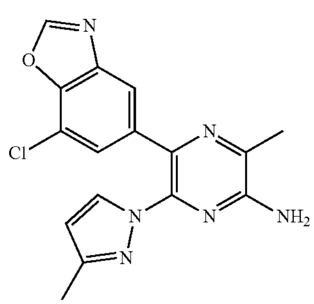 [SMILES: Cc1ccn(-c2nc(N)c(C)nc2-c2cc(Cl)c3ocnc3c2)n1] |

TABLE 2-continued

| Compound No. | Structure |
|---|---|
| 1.498 | 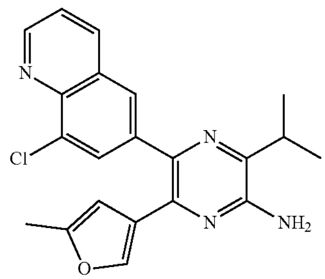 [SMILES: Cc1cc(-c2nc(N)c(C(C)C)nc2-c2cc(Cl)c3ncccc3c2)co1] |
| 1.499 | 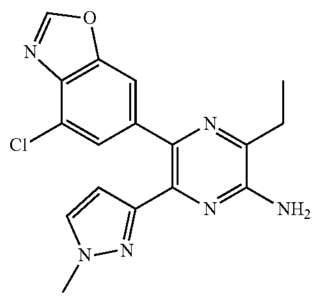 [SMILES: CCc1nc(-c2cc(Cl)c3ncoc3c2)c(-c2ccn(C)n2)nc1N] |
| 1.500 | 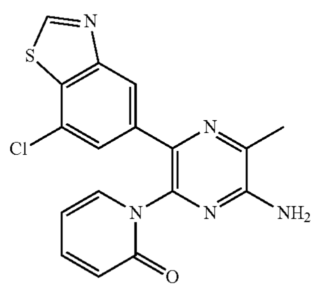 [SMILES: Cc1nc(-c2cc(Cl)c3scnc3c2)c(-n2ccccc2=O)nc1N] |
| 1.501 | 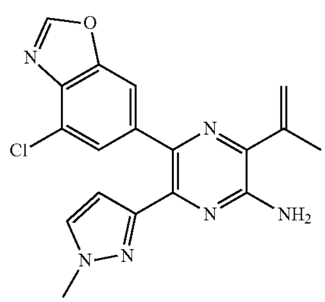 [SMILES: C=C(C)c1nc(-c2cc(Cl)c3ncoc3c2)c(-c2ccn(C)n2)nc1N] |
| 1.502 | 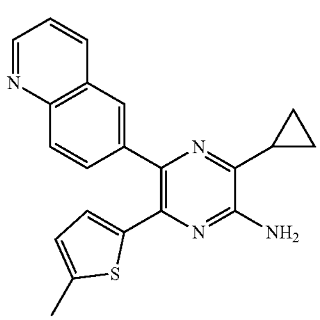 [SMILES: Cc1ccc(-c2nc(N)c(C3CC3)nc2-c2ccc3ncccc3c2)s1] |

TABLE 2-continued
| Compound No. | Structure |
|---|---|
| 1.503 | 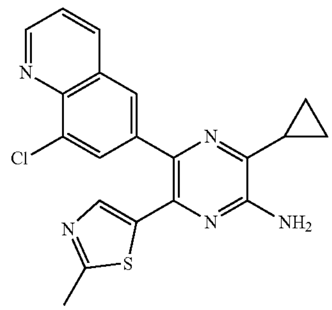 |
| 1.504 | 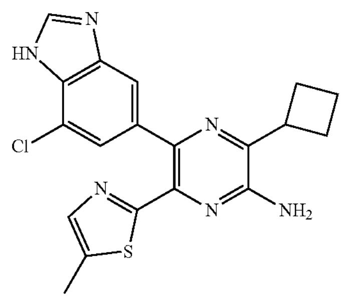 [SMILES: Cc1cnc(-c2nc(N)c(C3CCC3)nc2-c2cc(Cl)c3[nH]cnc3c2)s1] |
| 1.505 | 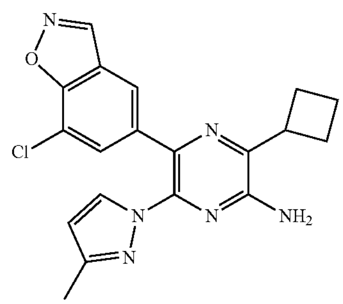 [SMILES: Cc1ccn(-c2nc(N)c(C3CCC3)nc2-c2cc(Cl)c3oncc3c2)n1] |
| 1.506 | 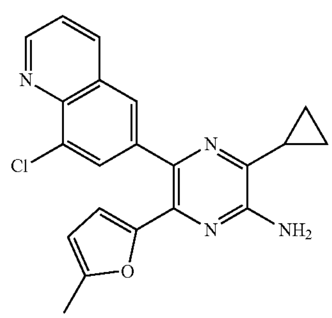 [SMILES: Cc1ccc(-c2nc(N)c(C3CC3)nc2-c2cc(Cl)c3ncccc3c2)o1] |
| 1.507 | 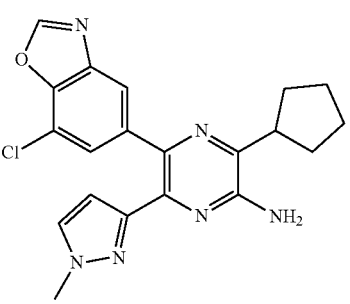 [SMILES: Cn1ccc(-c2nc(N)c(C3CCCC3)nc2-c2cc(Cl)c3ocnc3c2)n1] |

TABLE 2-continued

| Compound No. | Structure |
|---|---|
| 1.508 | 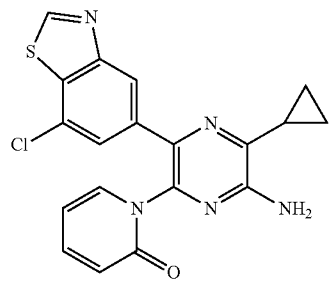 [SMILES: Nc1nc(-n2ccccc2=O)c(-c2cc(Cl)c3scnc3c2)nc1C1CC1] |
| 1.509 | 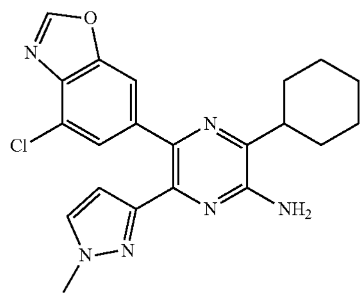 [SMILES: Cn1ccc(-c2nc(N)c(C3CCCCC3)nc2-c2cc(Cl)c3ncoc3c2)n1] |
| 1.510 | 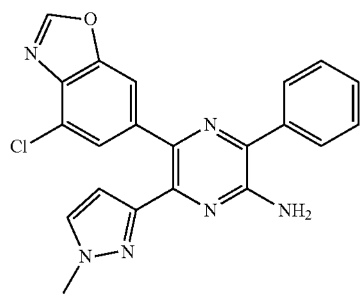 [SMILES: Cn1ccc(-c2nc(N)c(-c3ccccc3)nc2-c2cc(Cl)c3ncoc3c2)n1] |
| 1.511 | 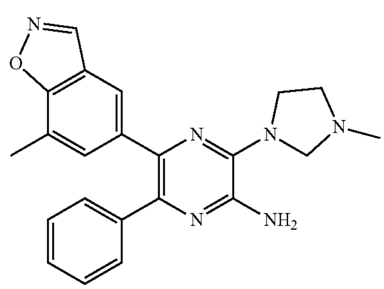 |
| 1.512 | 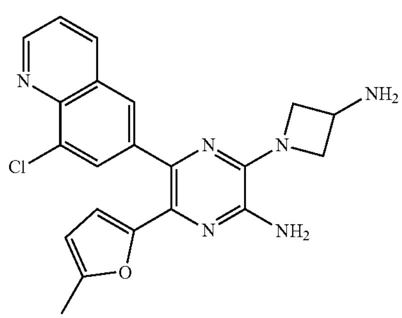 [SMILES: Cc1ccc(-c2nc(N)c(N3CC(N)C3)nc2-c2cc(Cl)c3ncccc3c2)o1] |

TABLE 2-continued

| Compound No. | Structure |
|---|---|
| 1.513 | 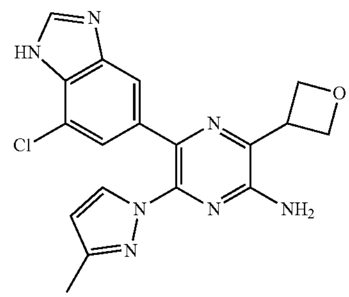 [SMILES: Cc1ccn(-c2nc(N)c(C3COC3)nc2-c2cc(Cl)c3[nH]cnc3c2)n1] |
| 1.514 | 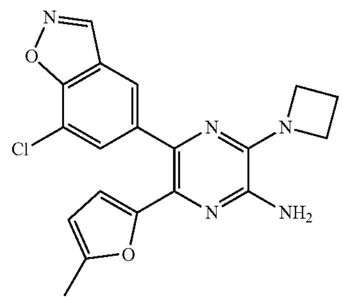 [SMILES: Cc1ccc(-c2nc(N)c(N3CCC3)nc2-c2cc(Cl)c3oncc3c2)o1] |
| 1.515 | 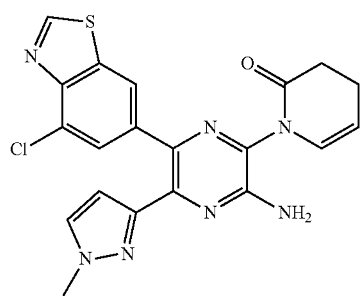 [SMILES: Cn1ccc(-c2nc(N)c(N3C=CCCC3=O)nc2-c2cc(Cl)c3ncsc3c2)n1] |
| 1.516 | 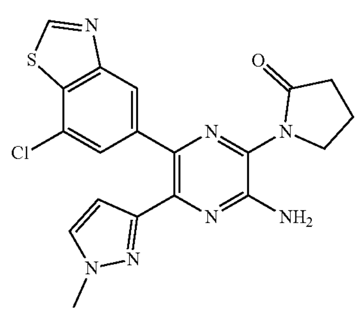 [SMILES: Cn1ccc(-c2nc(N)c(N3CCCC3=O)nc2-c2cc(Cl)c3scnc3c2)n1] |
| 1.517 | 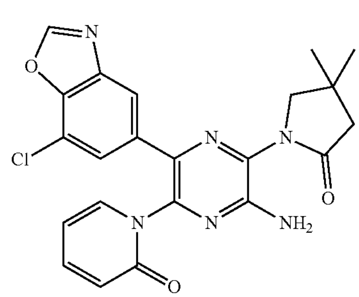 [SMILES: CC1(C)CC(=O)N(c2nc(-c3cc(Cl)c4ocnc4c3)c(-n3ccccc3=O)nc2N)C1] |

TABLE 2-continued
| Compound No. | Structure |
| --- | --- |
| 1.518 | 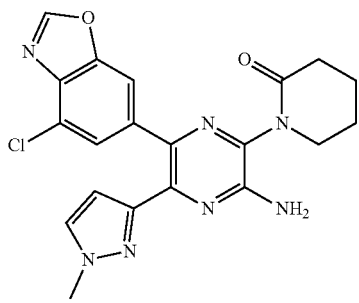 [SMILES: Cn1ccc(-c2nc(N)c(N3CCCCC3=O)nc2-c2cc(Cl)c3ncoc3c2)n1] |
| 1.519 | 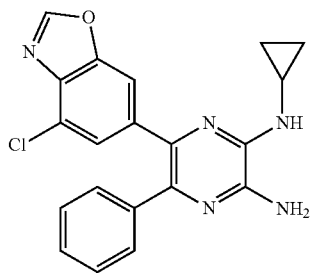 [SMILES: Nc1nc(-c2ccccc2)c(-c2cc(Cl)c3ncoc3c2)nc1NC1CC1] |
| 1.520 | 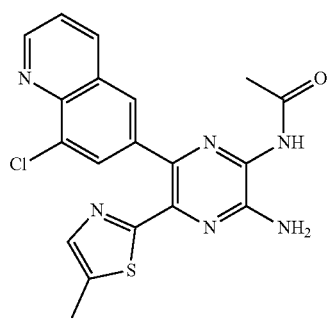 [SMILES: CC(=O)Nc1nc(-c2cc(Cl)c3ncccc3c2)c(-c2ncc(C)s2)nc1N] |
| 1.521 | 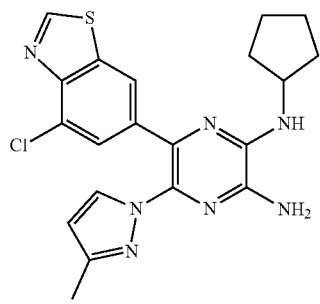 [SMILES: Cc1ccn(-c2nc(N)c(NC3CCCC3)nc2-c2cc(Cl)c3ncsc3c2)n1] |
| 1.522 | 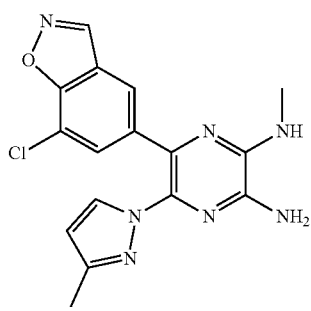 [SMILES: CNc1nc(-c2cc(Cl)c3oncc3c2)c(-n2ccc(C)n2)nc1N] |

TABLE 2-continued

| Compound No. | Structure |
|---|---|
| 1.523 | 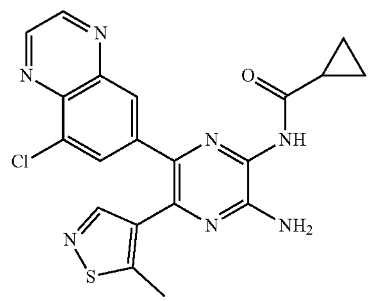 [SMILES: Cc1sncc1-c1nc(N)c(NC(=O)C2CC2)nc1-c1cc(Cl)c2nccnc2c1] |
| 1.524 | 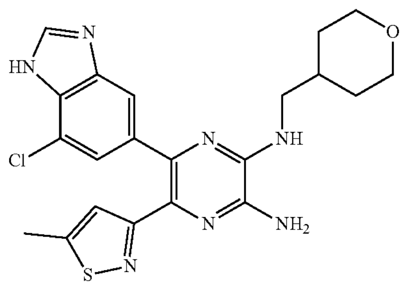 [SMILES: Cc1cc(-c2nc(N)c(NCC3CCOCC3)nc2-c2cc(Cl)c3[nH]cnc3c2)ns1] |
| 1.525 | 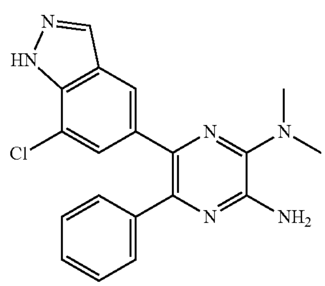 [SMILES: CN(C)c1nc(-c2cc(Cl)c3[nH]ncc3c2)c(-c2ccccc2)nc1N] |
| 1.526 | 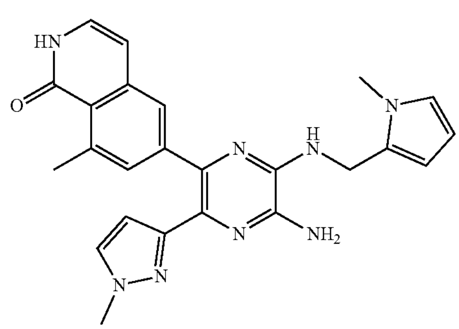 [SMILES: Cc1cc(-c2nc(NCc3cccn3C)c(N)nc2-c2ccn(C)n2)cc2cc[nH]c(=O)c12] |
| 1.527 | 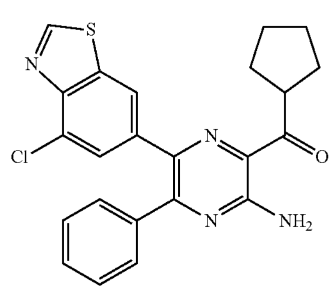 [SMILES: Nc1nc(-c2ccccc2)c(-c2cc(Cl)c3ncsc3c2)nc1C(=O)C1CCCC1] |

TABLE 2-continued

| Compound No. | Structure |
|---|---|
| 1.528 | 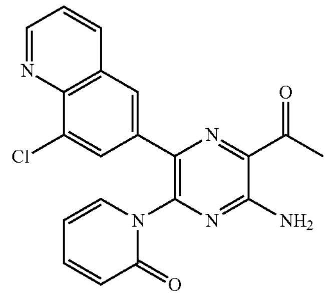 [SMILES: CC(=O)c1nc(-c2cc(Cl)c3ncccc3c2)c(-n2ccccc2=O)nc1N] |
| 1.529 | 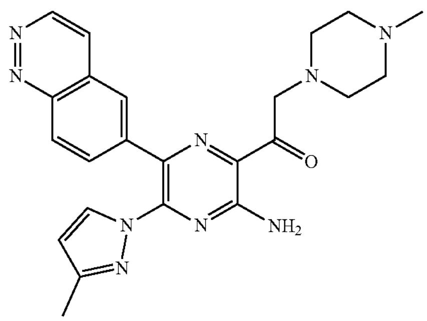 [SMILES: Cc1ccn(-c2nc(N)c(C(=O)CN3CCN(C)CC3)nc2-c2ccc3nnccc3c2)n1] |
| 1.530 | 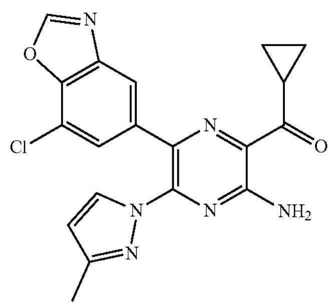 [SMILES: Cc1ccn(-c2nc(N)c(C(=O)C3CC3)nc2-c2cc(Cl)c3ocnc3c2)n1] |
| 1.531 | 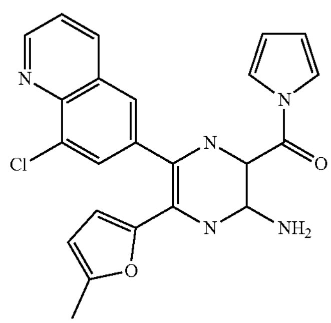 [SMILES: Cc1ccc(C2=C(c3cc(Cl)c4ncccc4c3)NC(C(=O)n3cccc3)C(N)N2)o1] |
| 1.532 | 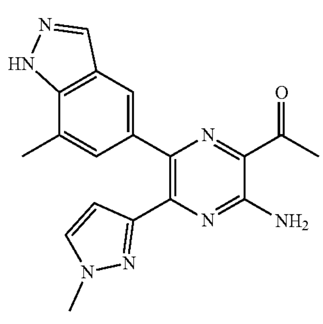 [SMILES: CC(=O)c1nc(-c2cc(C)c3[nH]ncc3c2)c(-c2ccn(C)n2)nc1N] |

TABLE 2-continued

| Compound No. | Structure |
|---|---|
| 1.533 | 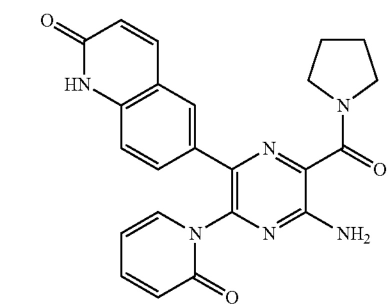 [SMILES: Nc1nc(-n2ccccc2=O)c(-c2ccc3[nH]c(=O)ccc3c2)nc1C(=O)N1CCCC1] |
| 1.534 | 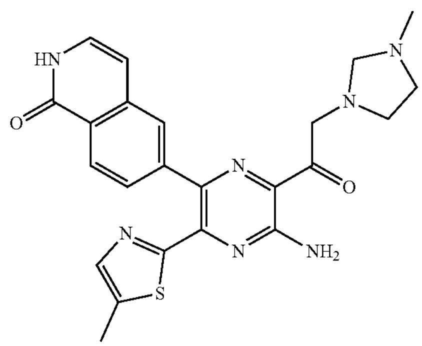 [SMILES: Cc1cnc(-c2nc(N)c(C(=O)CN3CCN(C)C3)nc2-c2ccc3c(=O)[nH]ccc3c2)s1] |
| 1.535 | 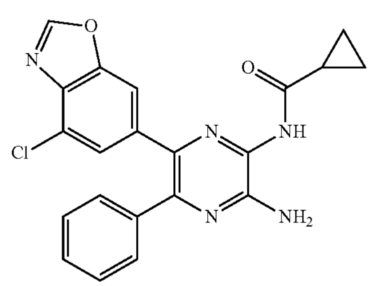 [SMILES: Nc1nc(-c2ccccc2)c(-c2cc(Cl)c3ncoc3c2)nc1NC(=O)C1CC1] |
| 1.536 | 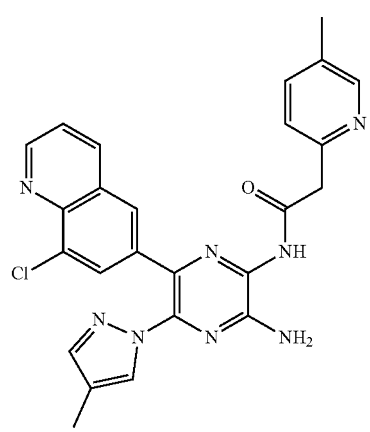 [SMILES: Cc1ccc(CC(=O)Nc2nc(-c3cc(Cl)c4ncccc4c3)c(-n3cc(C)cn3)nc2N)nc1] |

TABLE 2-continued

| Compound No. | Structure |
|---|---|
| 1.537 | (chemical structure) |
| 1.538 | (chemical structure) |
| 1.539 | (chemical structure) |
| 1.540 | (chemical structure) |

TABLE 2-continued
| Compound No. | Structure |
|---|---|
| 1.541 | 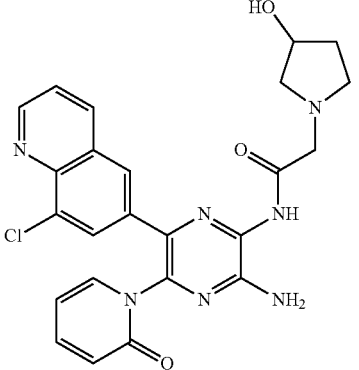 [SMILES: Nc1nc(-n2ccccc2=O)c(-c2cc(Cl)c3ncccc3c2)nc1NC(=O)CN1CCC(O)C1] |
| 1.542 | 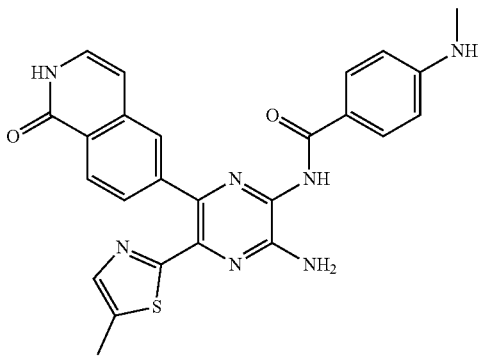 [SMILES: CNc1ccc(C(=O)Nc2nc(-c3ccc4c(=O)[nH]ccc4c3)c(-c3ncc(C)s3)nc2N)cc1] |
| 1.543 | 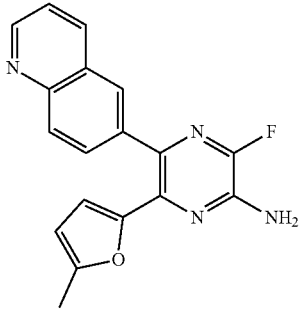 [SMILES: Cc1ccc(-c2nc(N)c(F)nc2-c2ccc3ncccc3c2)o1] |
| 1.544 | 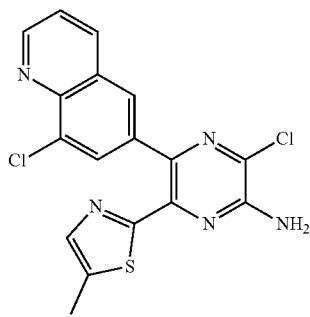 [SMILES: Cc1cnc(-c2nc(N)c(Cl)nc2-c2cc(Cl)c3ncccc3c2)s1] |

TABLE 2-continued

| Compound No. | Structure |
|---|---|
| 1.545 | 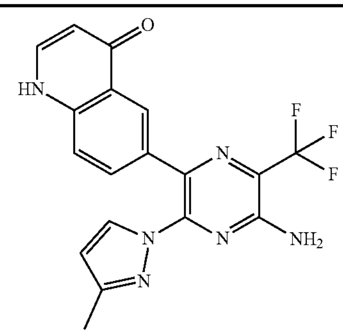 |
| 1.546 | 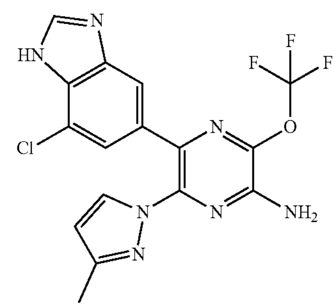 [SMILES: Cc1ccn(-c2nc(N)c(OC(F)(F)F)nc2-c2cc(Cl)c3[nH]cnc3c2)n1] |
| 1.547 | 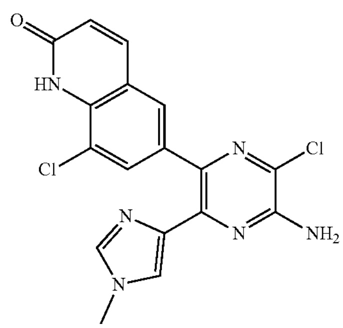 [SMILES: Cn1cnc(-c2nc(N)c(Cl)nc2-c2cc(Cl)c3[nH]c(=O)ccc3c2)c1] |
| 1.548 | 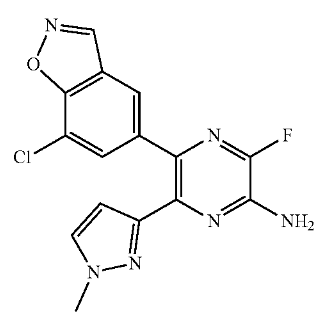 [SMILES: Cn1ccc(-c2nc(N)c(F)nc2-c2cc(Cl)c3oncc3c2)n1] |
| 1.549 | 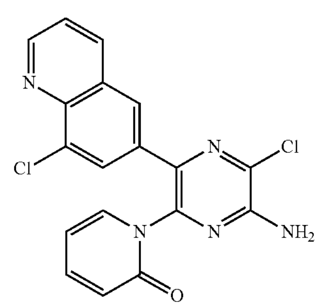 [SMILES: Nc1nc(-n2ccccc2=O)c(-c2cc(Cl)c3ncccc3c2)nc1Cl] |

TABLE 2-continued

| Compound No. | Structure |
|---|---|
| 1.550 | 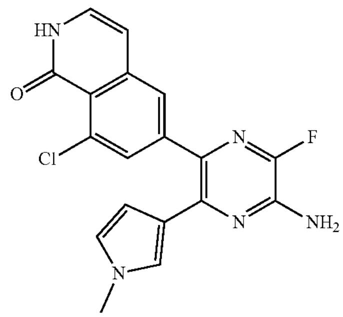 [SMILES: Cn1ccc(-c2nc(N)c(F)nc2-c2cc(Cl)c3c(=O)[nH]ccc3c2)c1] |
| 1.551 | 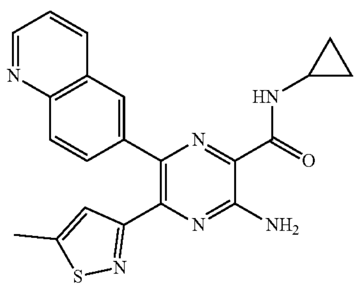 [SMILES: Cc1cc(-c2nc(N)c(C(=O)NC3CC3)nc2-c2ccc3ncccc3c2)ns1] |
| 1.552 | 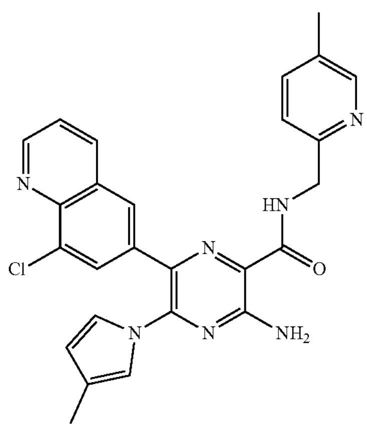 [SMILES: Cc1ccc(CNC(=O)c2nc(-c3cc(Cl)c4ncccc4c3)c(-n3ccc(C)c3)nc2N)nc1] |
| 1.553 | 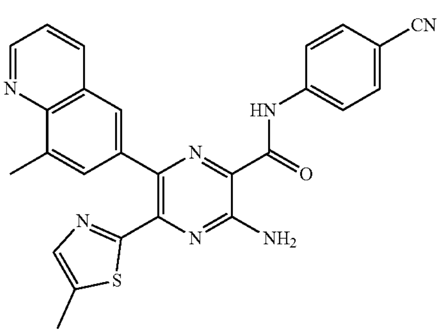 [SMILES: Cc1cnc(-c2nc(N)c(C(=O)Nc3ccc(C#N)cc3)nc2-c2cc(C)c3ncccc3c2)s1] |

TABLE 2-continued

| Compound No. | Structure |
|---|---|
| 1.554 | 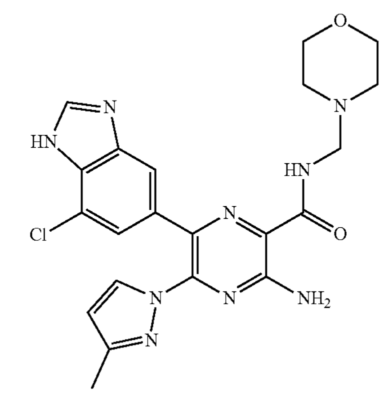 |
| 1.555 | 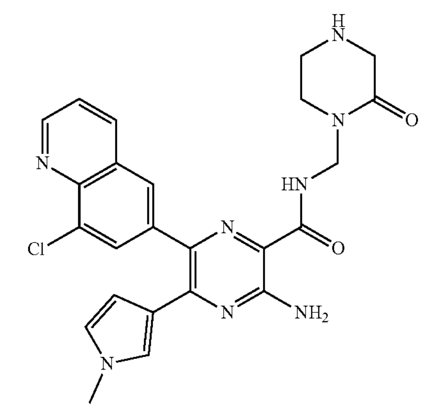 [SMILES: Cn1ccc(-c2nc(N)c(C(=O)NCN3CCNCC3=O)nc2-c2cc(Cl)c3ncccc3c2)c1] |
| 1.556 | 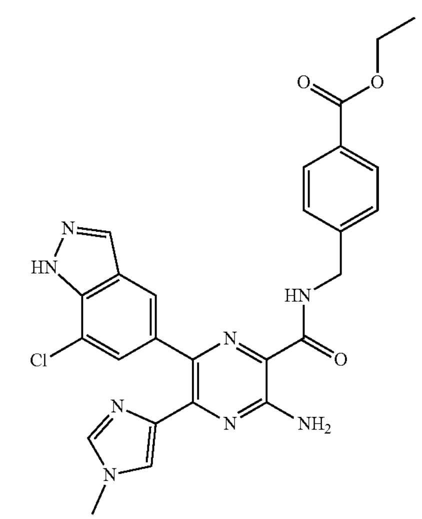 [SMILES: CCOC(=O)c1ccc(CNC(=O)c2nc(-c3cc(Cl)c4[nH]ncc4c3)c(-c3cn(C)cn3)nc2N)cc1] |

TABLE 2-continued
| Compound No. | Structure |
|---|---|
| 1.557 | 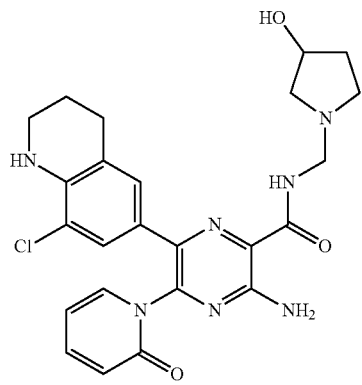 [SMILES: Nc1nc(-n2ccccc2=O)c(-c2cc(Cl)c3c(c2)CCCN3)nc1C(=O)NCN1CCC(O)C1] |
| 1.558 | 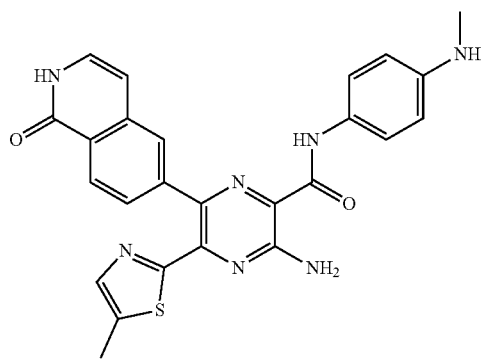 [SMILES: CNc1ccc(NC(=O)c2nc(-c3ccc4c(=O)[nH]ccc4c3)c(-c3ncc(C)s3)nc2N)cc1] |
| 1.559 | 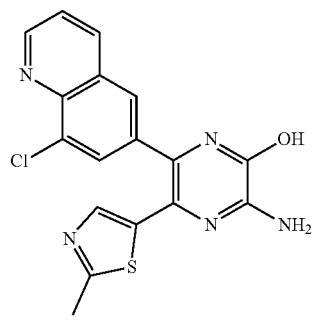 [SMILES: Cc1ncc(-c2nc(N)c(O)nc2-c2cc(Cl)c3ncccc3c2)s1] |
| 1.560 | 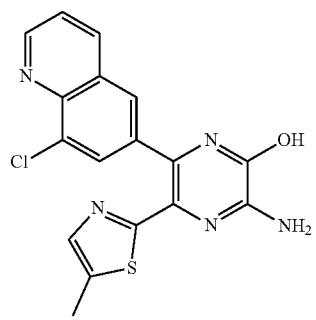 [SMILES: Cc1cnc(-c2nc(N)c(O)nc2-c2cc(Cl)c3ncccc3c2)s1] |

TABLE 2-continued

| Compound No. | Structure |
|---|---|
| 1.561 | 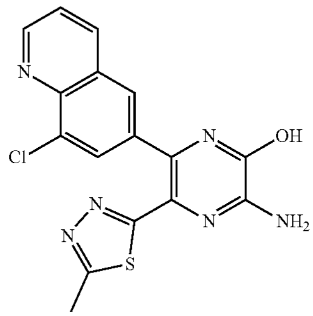 [SMILES: Cc1nnc(-c2nc(N)c(O)nc2-c2cc(Cl)c3ncccc3c2)s1] |
| 1.562 | 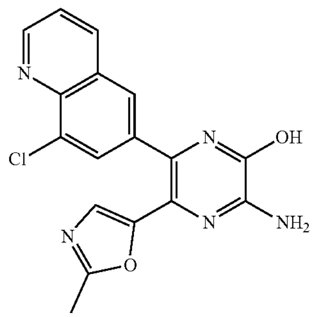 [SMILES: Cc1ncc(-c2nc(N)c(O)nc2-c2cc(Cl)c3ncccc3c2)o1] |
| 1.563 | 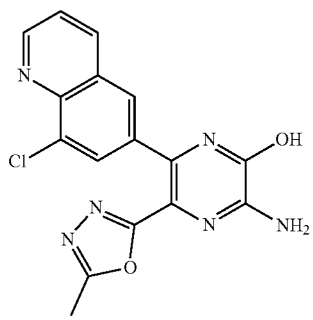 [SMILES: Cc1nnc(-c2nc(N)c(O)nc2-c2cc(Cl)c3ncccc3c2)o1] |
| 1.564 | 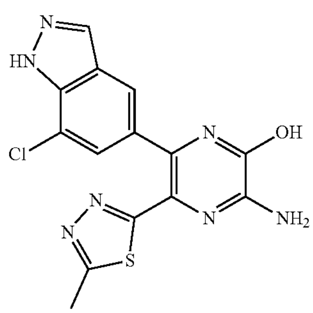 [SMILES: Cc1nnc(-c2nc(N)c(O)nc2-c2cc(Cl)c3[nH]ncc3c2)s1] |
| 1.565 | 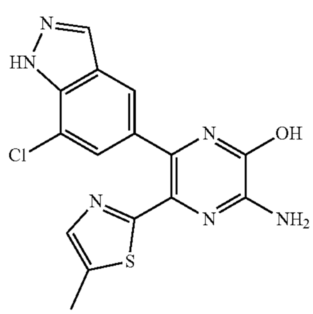 [SMILES: Cc1cnc(-c2nc(N)c(O)nc2-c2cc(Cl)c3[nH]ncc3c2)s1] |

TABLE 2-continued

| Compound No. | Structure |
|---|---|
| 1.566 | 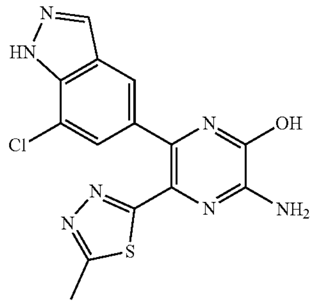 [SMILES: Cc1nnc(-c2nc(N)c(O)nc2-c2cc(Cl)c3[nH]ncc3c2)s1] |
| 1.567 | 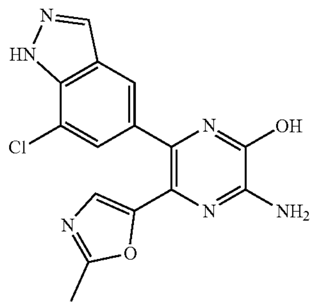 [SMILES: Cc1ncc(-c2nc(N)c(O)nc2-c2cc(Cl)c3[nH]ncc3c2)o1] |
| 1.568 | 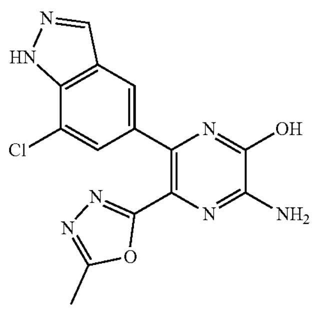 [SMILES: Cc1nnc(-c2nc(N)c(O)nc2-c2cc(Cl)c3[nH]ncc3c2)o1] |
| 1.569 | 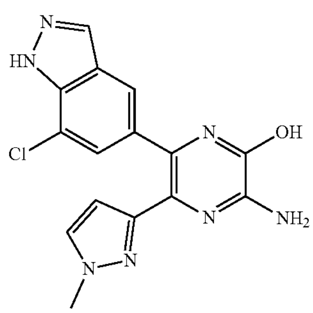 |
| 1.570 | 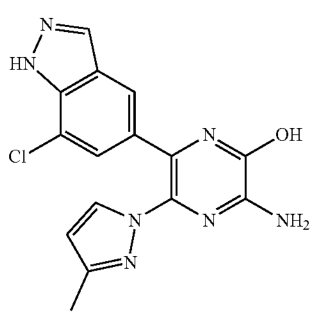 [SMILES: Cc1ccn(-c2nc(N)c(O)nc2-c2cc(Cl)c3[nH]ncc3c2)n1] |

TABLE 2-continued

| Compound No. | Structure |
| --- | --- |
| 1.571 | 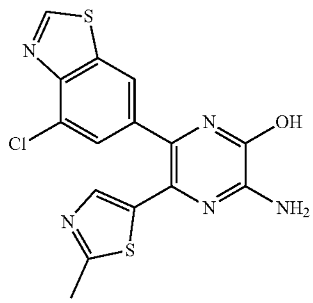 [SMILES: Cc1ncc(-c2nc(N)c(O)nc2-c2cc(Cl)c3ncsc3c2)s1] |
| 1.572 | 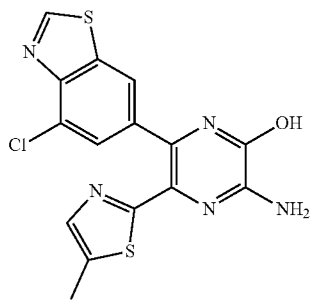 |
| 1.573 | 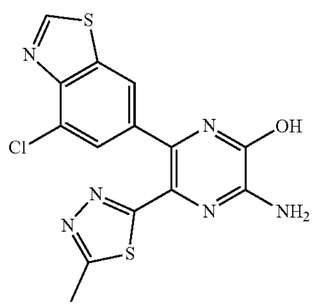 |
| 1.574 | 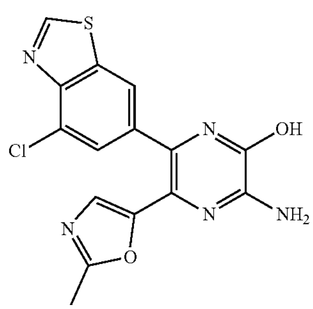 [SMILES: Cc1ncc(-c2nc(N)c(O)nc2-c2cc(Cl)c3ncsc3c2)o1] |
| 1.575 | 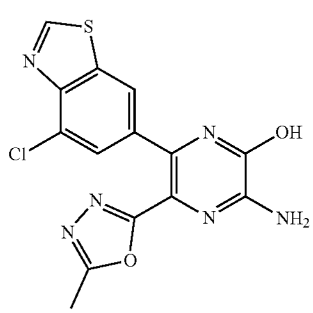 [SMILES: Cc1nnc(-c2nc(N)c(O)nc2-c2cc(Cl)c3ncsc3c2)o1] |

TABLE 2-continued

| Compound No. | Structure |
|---|---|
| 1.576 | 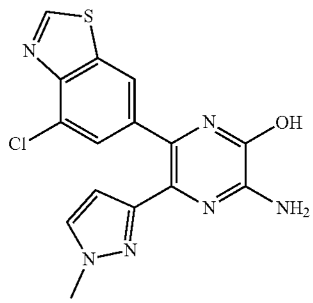 [SMILES: Cn1ccc(-c2nc(N)c(O)nc2-c2cc(Cl)c3ncsc3c2)n1] |
| 1.577 | 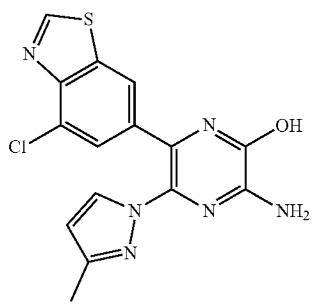 |
| 1.578 | 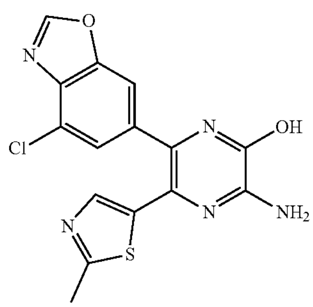 [SMILES: Cc1ncc(-c2nc(N)c(O)nc2-c2cc(Cl)c3ncoc3c2)s1] |
| 1.579 | 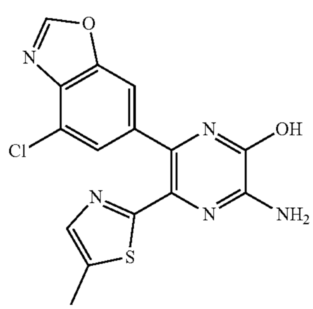 [SMILES: Cc1cnc(-c2nc(N)c(O)nc2-c2cc(Cl)c3ncoc3c2)s1] |
| 1.580 | 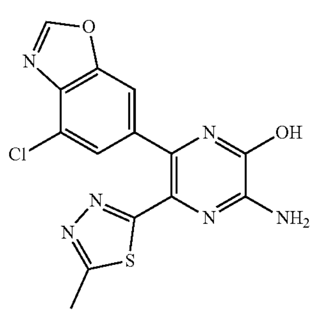 [SMILES: Cc1nnc(-c2nc(N)c(O)nc2-c2cc(Cl)c3ncoc3c2)s1] |

TABLE 2-continued

| Compound No. | Structure |
|---|---|
| 1.581 | 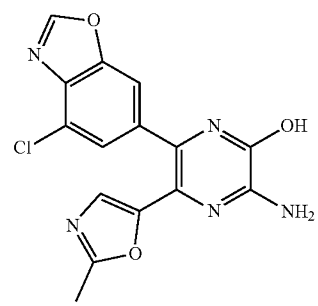 [SMILES: Cc1ncc(-c2nc(N)c(O)nc2-c2cc(Cl)c3ncoc3c2)o1] |
| 1.582 | 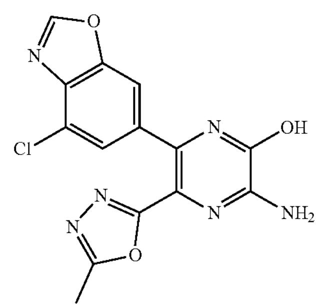 [SMILES: Cc1nnc(-c2nc(N)c(O)nc2-c2cc(Cl)c3ncoc3c2)o1] |
| 1.583 | 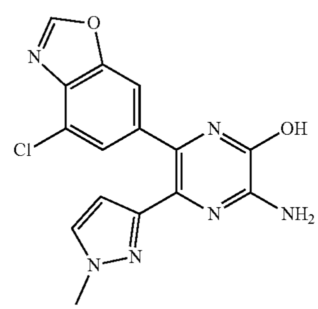 [SMILES: Cn1ccc(-c2nc(N)c(O)nc2-c2cc(Cl)c3ncoc3c2)n1] |
| 1.584 | 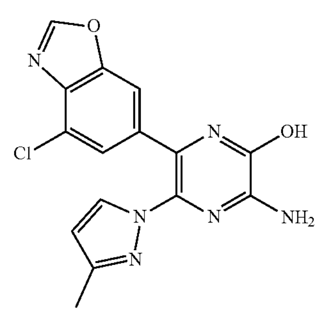 [SMILES: Cc1ccn(-c2nc(N)c(O)nc2-c2cc(Cl)c3ncoc3c2)n1] |
| 1.585 | 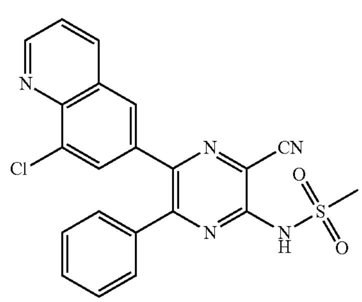 [SMILES: CS(=O)(=O)Nc1nc(-c2ccccc2)c(-c2cc(Cl)c3ncccc3c2)nc1C#N] |

TABLE 2-continued

| Compound No. | Structure |
|---|---|
| 1.586 | (8-chloroquinolin-6-yl / 3-methylpyrazol-1-yl / hydroxy / methanesulfonamido pyrazine) |
| 1.587 | (7-chlorobenzothiazol-5-yl / 3-methylpyrazol-1-yl / cyano / methanesulfonamido pyrazine) |
| 1.588 | (7-chlorobenzothiazol-5-yl / 3-methylpyrazol-1-yl / cyano / benzylamino pyrazine) |
| 1.589 | (7-chloro-1H-indazol-5-yl / 3-methylpyrazol-1-yl / amino / benzylamino pyrazine) |
| 1.590 | (4-chloronaphthalen-2-yl / phenyl / carboxamide / benzylamino pyrazine) |

TABLE 2-continued

| Compound No. | Structure |
|---|---|
| 1.591 | 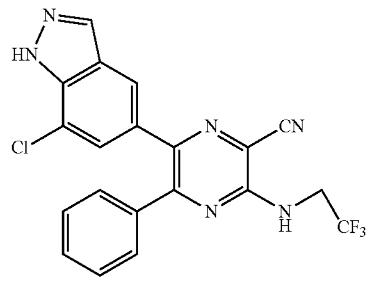 [SMILES: N#Cc1nc(-c2cc(Cl)c3[nH]ncc3c2)c(-c2ccccc2)nc1NCC(F)(F)F] |
| 1.592 | 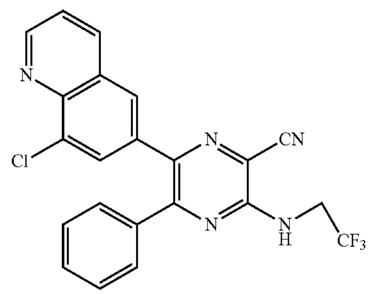 [SMILES: N#Cc1nc(-c2cc(Cl)c3ncccc3c2)c(-c2ccccc2)nc1NCC(F)(F)F] |
| 1.593 | 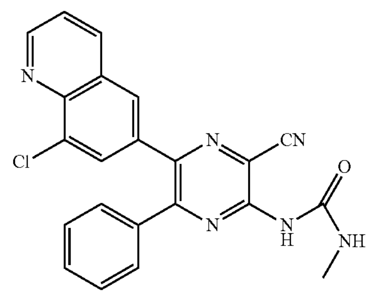 [SMILES: CNC(=O)Nc1nc(-c2ccccc2)c(-c2cc(Cl)c3ncccc3c2)nc1C#N] |
| 1.594 | 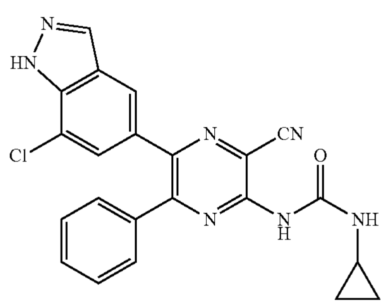 [SMILES: N#Cc1nc(-c2cc(Cl)c3[nH]ncc3c2)c(-c2ccccc2)nc1NC(=O)NC1CC1] |
| 1.595 | 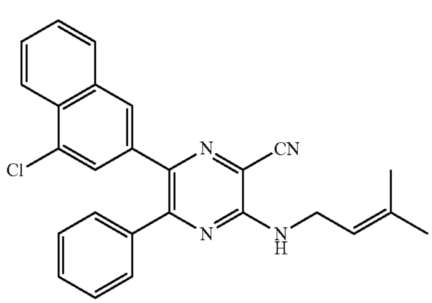 [SMILES: CC(C)=CCNc1nc(-c2ccccc2)c(-c2cc(Cl)c3ccccc3c2)nc1C#N] |

US 11,028,058 B2
351                                                     352
TABLE 2-continued
| Compound No. | Structure |
|---|---|
| 1.596 | 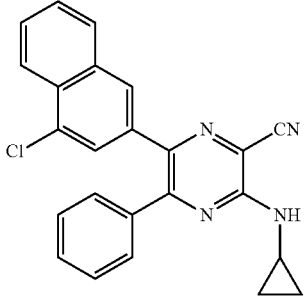 [SMILES: N#Cc1nc(-c2cc(Cl)c3ccccc3c2)c(-c2ccccc2)nc1NC1CC1] |
| 1.597 | 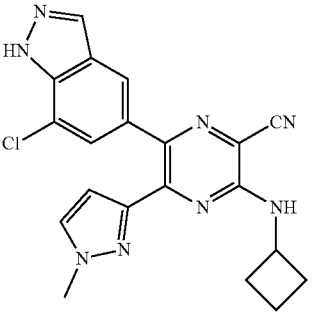 [SMILES: Cn1ccc(-c2nc(NC3CCC3)c(C#N)nc2-c2cc(Cl)c3[nH]ncc3c2)n1] |
| 1.598 | 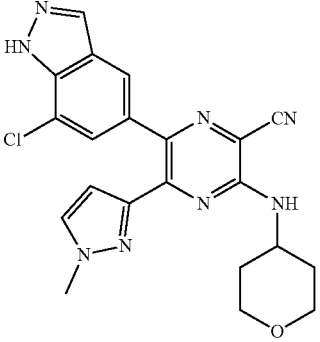 [SMILES: Cn1ccc(-c2nc(NC3CCOCC3)c(C#N)nc2-c2cc(Cl)c3[nH]ncc3c2)n1] |
| 1.599 | 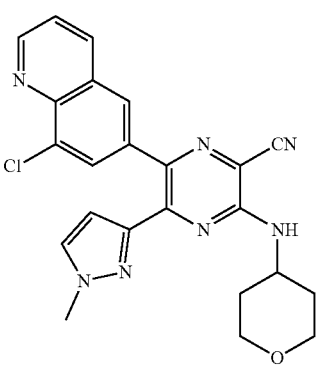 [SMILES: Cn1ccc(-c2nc(NC3CCOCC3)c(C#N)nc2-c2cc(Cl)c3ncccc3c2)n1] |

TABLE 2-continued

| Compound No. | Structure |
|---|---|
| 1.600 | 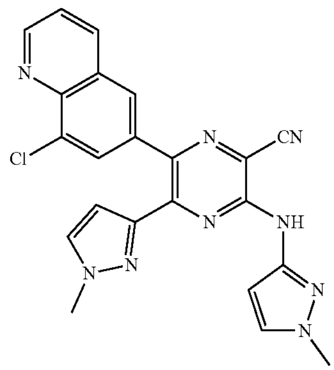 [SMILES: Cn1ccc(Nc2nc(-c3ccn(C)n3)c(-c3cc(Cl)c4ncccc4c3)nc2C#N)n1] |
| 1.601 | 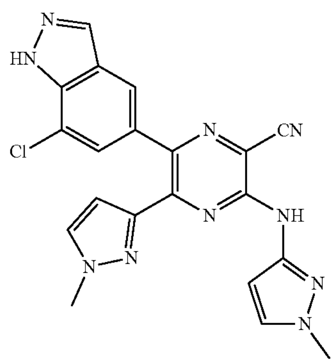 [SMILES: Cn1ccc(Nc2nc(-c3ccn(C)n3)c(-c3cc(Cl)c4[nH]ncc4c3)nc2C#N)n1] |
| 1.602 | 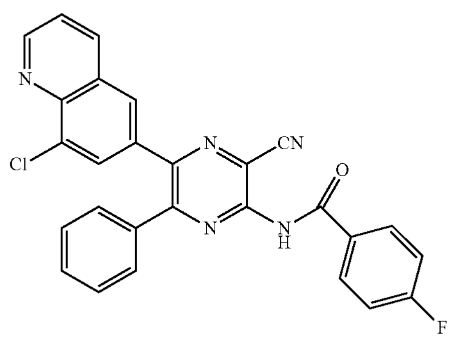 [SMILES: N#Cc1nc(-c2cc(Cl)c3ncccc3c2)c(-c2ccccc2)nc1NC(=O)c1ccc(F)cc1] |
| 1.603 | 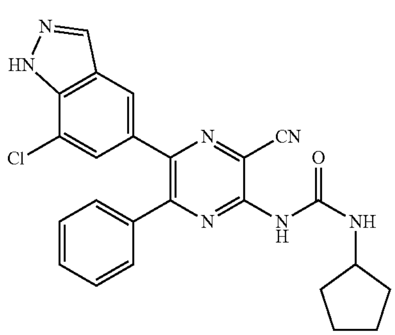 [SMILES: N#Cc1nc(-c2cc(Cl)c3[nH]ncc3c2)c(-c2ccccc2)nc1NC(=O)NC1CCCC1] |

TABLE 2-continued

| Compound No. | Structure |
| --- | --- |
| 1.604 | 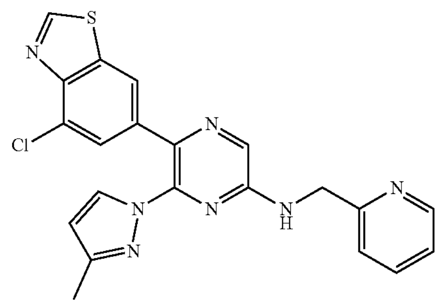 [SMILES: Cc1ccn(-c2nc(NCc3ccccn3)cnc2-c2cc(Cl)c3ncsc3c2)n1] |
| 1.605 | 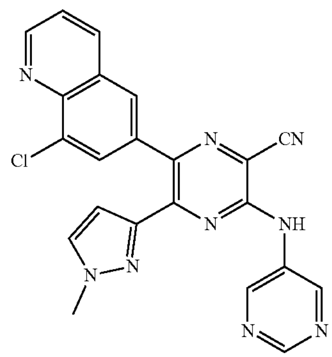 [SMILES: Cn1ccc(-c2nc(Nc3cncnc3)c(C#N)nc2-c2cc(Cl)c3ncccc3c2)n1] |
| 1.606 | 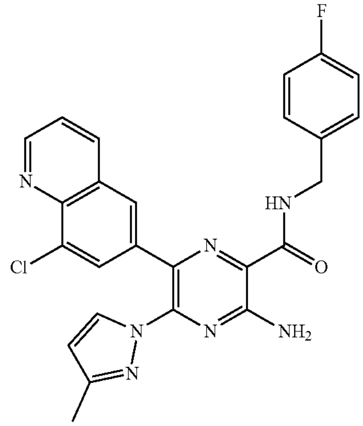 [SMILES: Cc1ccn(-c2nc(N)c(C(=O)NCc3ccc(F)cc3)nc2-c2cc(Cl)c3ncccc3c2)n1] |
| 1.607 | 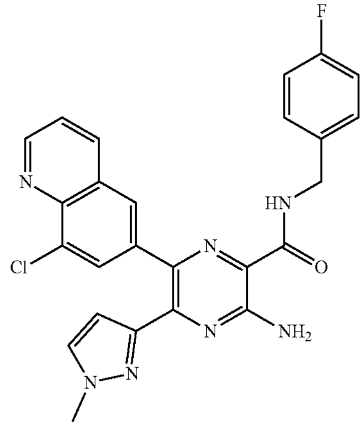 [SMILES: Cn1ccc(-c2nc(N)c(C(=O)NCc3ccc(F)cc3)nc2-c2cc(Cl)c3ncccc3c2)n1] |

TABLE 2-continued
| Compound No. | Structure |
|---|---|
| 1.608 | 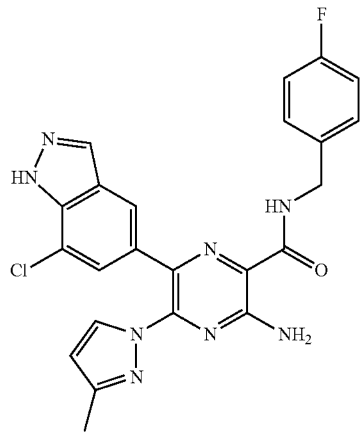 [SMILES: Cc1ccn(-c2nc(N)c(C(=O)NCc3ccc(F)cc3)nc2-c2cc(Cl)c3[nH]ncc3c2)n1] |
| 1.609 | 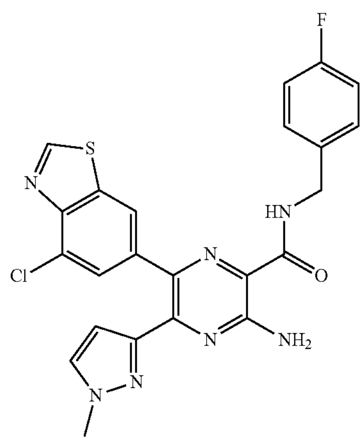 [SMILES: Cn1ccc(-c2nc(N)c(C(=O)NCc3ccc(F)cc3)nc2-c2cc(Cl)c3ncsc3c2)n1] |
| 1.610 | 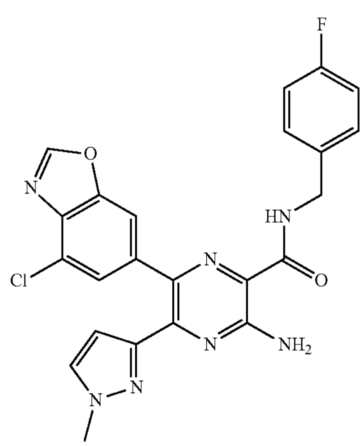 [SMILES: Cn1ccc(-c2nc(N)c(C(=O)NCc3ccc(F)cc3)nc2-c2cc(Cl)c3ncoc3c2)n1] |

TABLE 2-continued

| Compound No. | Structure |
|---|---|
| 1.611 | (structure) |
| 1.612 | (structure) |
| 1.613 | (structure) |
| 1.614 | (structure) |

TABLE 2-continued

| Compound No. | Structure |
| --- | --- |
| 1.615 | 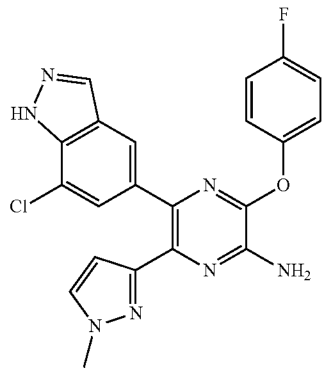 [SMILES: Cn1ccc(-c2nc(N)c(Oc3ccc(F)cc3)nc2-c2cc(Cl)c3[nH]ncc3c2)n1] |
| 1.616 | 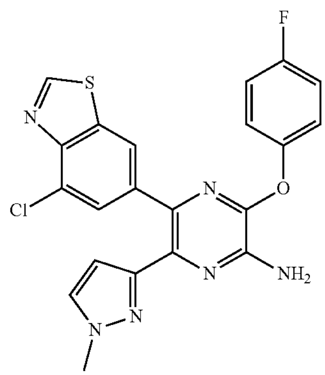 [SMILES: Cn1ccc(-c2nc(N)c(Oc3ccc(F)cc3)nc2-c2cc(Cl)c3ncsc3c2)n1] |
| 1.617 | 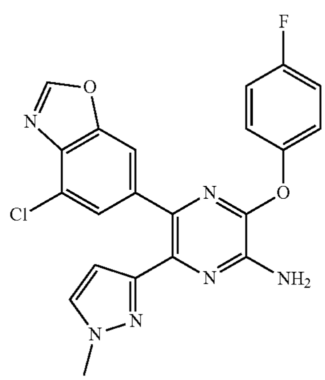 [SMILES: Cn1ccc(-c2nc(N)c(Oc3ccc(F)cc3)nc2-c2cc(Cl)c3ncoc3c2)n1] |
| 1.618 | 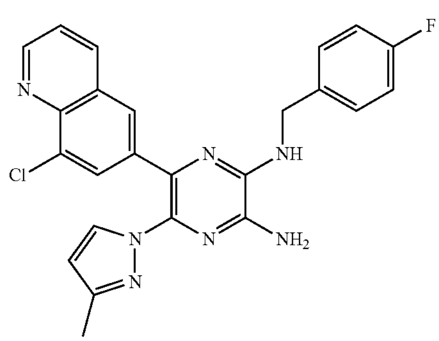 [SMILES: Cc1ccn(-c2nc(N)c(NCc3ccc(F)cc3)nc2-c2cc(Cl)c3ncccc3c2)n1] |

TABLE 2-continued

| Compound No. | Structure |
| --- | --- |
| 1.619 | 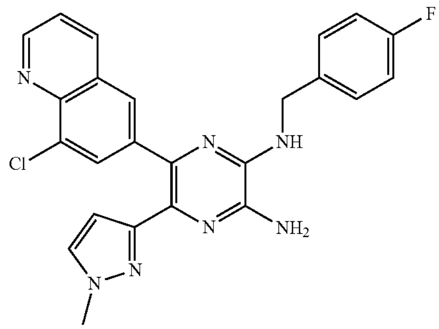 [SMILES: Cn1ccc(-c2nc(N)c(NCc3ccc(F)cc3)nc2-c2cc(Cl)c3ncccc3c2)n1] |
| 1.620 | 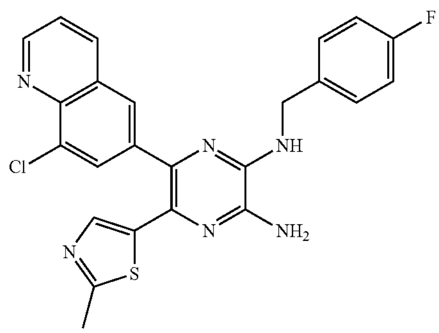 [SMILES: Cc1ncc(-c2nc(N)c(NCc3ccc(F)cc3)nc2-c2cc(Cl)c3ncccc3c2)s1] |
| 1.621 | 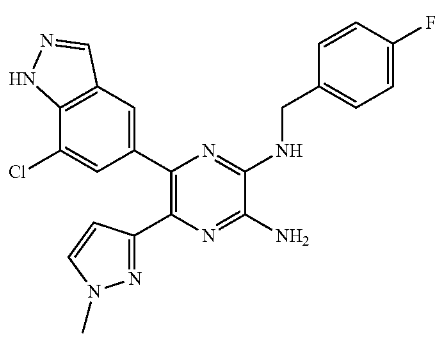 [SMILES: Cn1ccc(-c2nc(N)c(NCc3ccc(F)cc3)nc2-c2cc(Cl)c3[nH]ncc3c2)n1] |
| 1.622 | 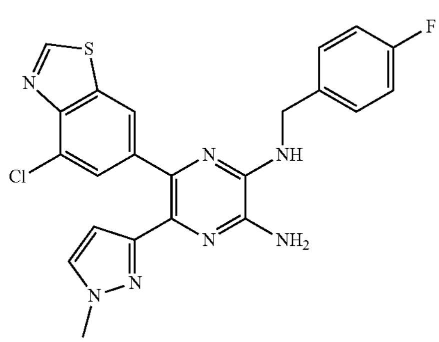 [SMILES: Cn1ccc(-c2nc(N)c(NCc3ccc(F)cc3)nc2-c2cc(Cl)c3ncsc3c2)n1] |

TABLE 2-continued

| Compound No. | Structure |
|---|---|
| 1.623 | 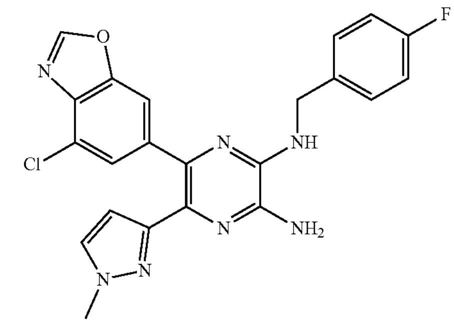 [SMILES: Cn1ccc(-c2nc(N)c(NCc3ccc(F)cc3)nc2-c2cc(Cl)c3ncoc3c2)n1] |
| 1.624 | 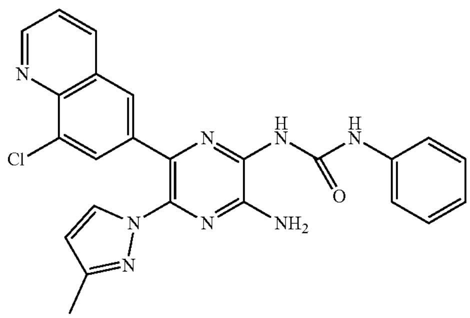 [SMILES: Cc1ccn(-c2nc(N)c(NC(=O)Nc3ccccc3)nc2-c2cc(Cl)c3ncccc3c2)n1] |
| 1.625 | 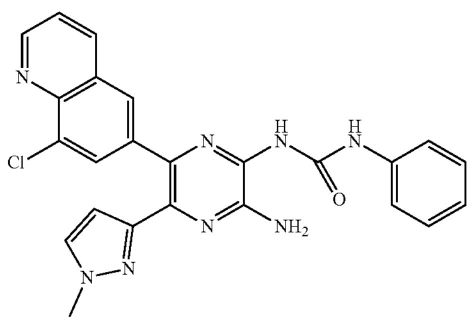 [SMILES: Cn1ccc(-c2nc(N)c(NC(=O)Nc3ccccc3)nc2-c2cc(Cl)c3ncccc3c2)n1] |
| 1.626 | 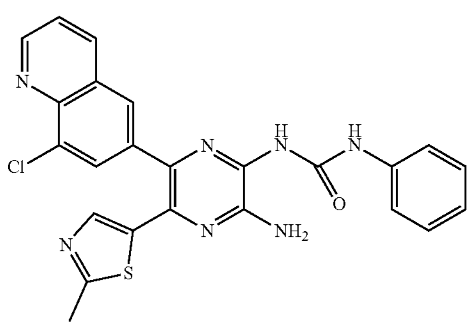 [SMILES: Cc1ncc(-c2nc(N)c(NC(=O)Nc3ccccc3)nc2-c2cc(Cl)c3ncccc3c2)s1] |
| 1.627 | 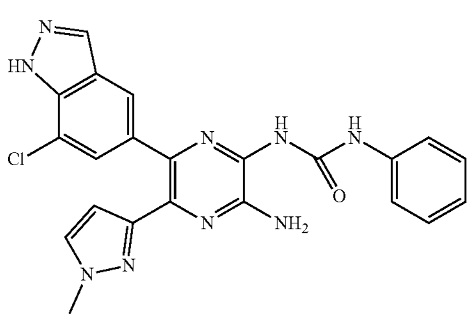 [SMILES: Cn1ccc(-c2nc(N)c(NC(=O)Nc3ccccc3)nc2-c2cc(Cl)c3[nH]ncc3c2)n1] |

TABLE 2-continued
| Compound No. | Structure |
|---|---|
| 1.628 | 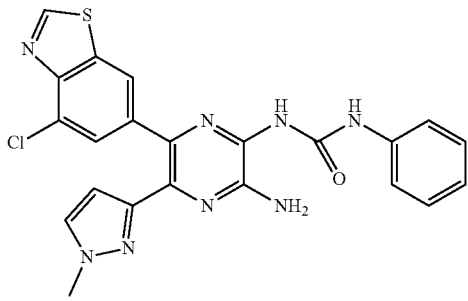 [SMILES: Cn1ccc(-c2nc(N)c(NC(=O)Nc3ccccc3)nc2-c2cc(Cl)c3ncsc3c2)n1] |
| 1.629 | 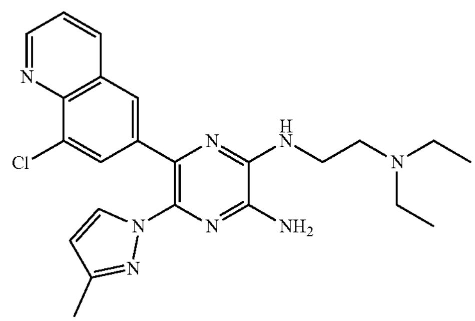 [SMILES: CCN(CC)CCNc1nc(-c2cc(Cl)c3ncccc3c2)c(-n2ccc(C)n2)nc1N] |
| 1.630 | 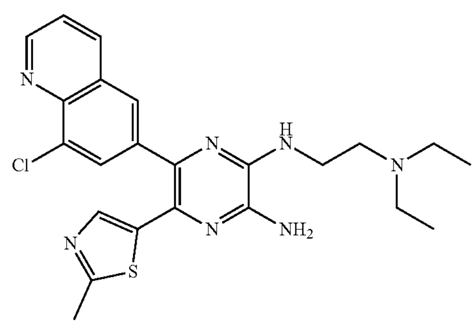 [SMILES: CCN(CC)CCNc1nc(-c2cc(Cl)c3ncccc3c2)c(-c2cnc(C)s2)nc1N] |
| 1.631 | 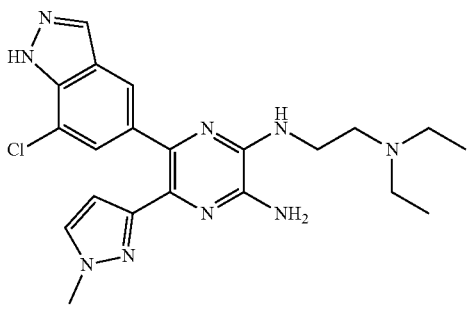 [SMILES: CCN(CC)CCNc1nc(-c2cc(Cl)c3[nH]ncc3c2)c(-c2ccn(C)n2)nc1N] |
| 1.632 | 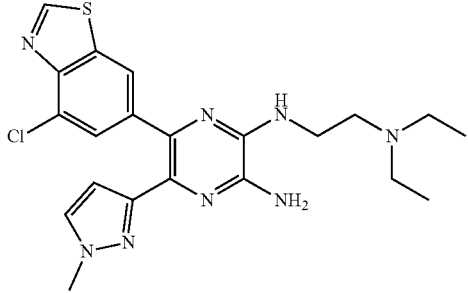 [SMILES: CCN(CC)CCNc1nc(-c2cc(Cl)c3ncsc3c2)c(-c2ccn(C)n2)nc1N] |

TABLE 2-continued

| Compound No. | Structure |
|---|---|
| 1.633 | 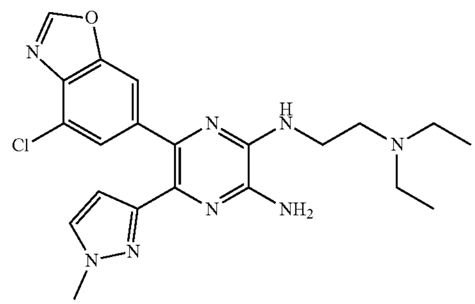 [SMILES: CCN(CC)CCNc1nc(-c2cc(Cl)c3ncoc3c2)c(-c2ccn(C)n2)nc1N] |
| 1.634 | 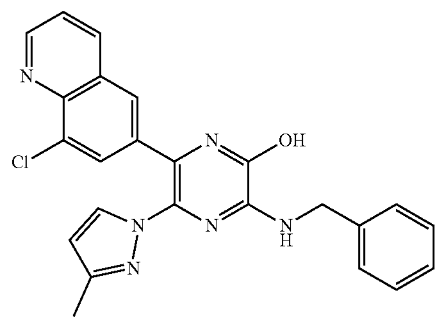 [SMILES: Cc1ccn(-c2nc(NCc3ccccc3)c(O)nc2-c2cc(Cl)c3ncccc3c2)n1] |
| 1.635 | 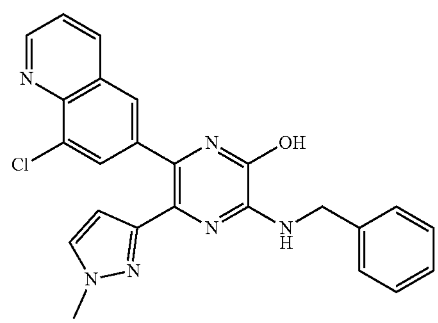 [SMILES: Cn1ccc(-c2nc(NCc3ccccc3)c(O)nc2-c2cc(Cl)c3ncccc3c2)n1] |
| 1.636 | 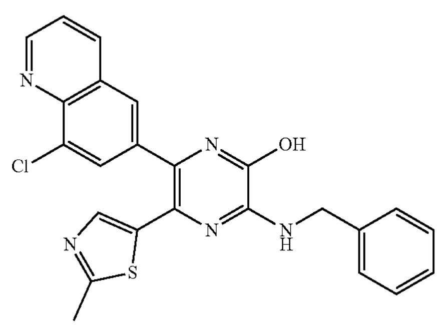 [SMILES: Cc1ncc(-c2nc(NCc3ccccc3)c(O)nc2-c2cc(Cl)c3ncccc3c2)s1] |
| 1.637 | 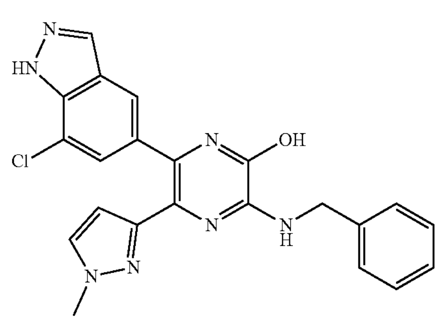 [SMILES: Cn1ccc(-c2nc(NCc3ccccc3)c(O)nc2-c2cc(Cl)c3[nH]ncc3c2)n1] |

TABLE 2-continued

| Compound No. | Structure |
|---|---|
| 1.638 | 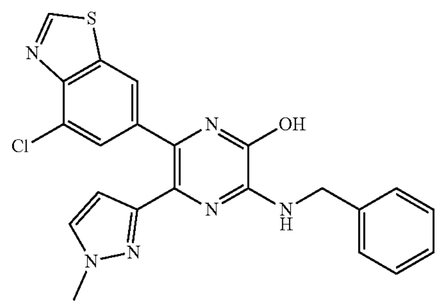 [SMILES: Cn1ccc(-c2nc(NCc3ccccc3)c(O)nc2-c2cc(Cl)c3ncsc3c2)n1] |
| 1.639 | 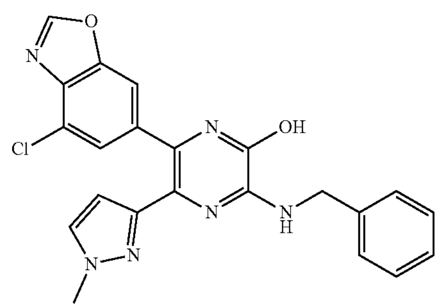 [SMILES: Cn1ccc(-c2nc(NCc3ccccc3)c(O)nc2-c2cc(Cl)c3ncoc3c2)n1] |
| 1.640 | 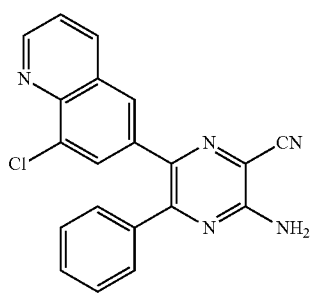 [SMILES: N#Cc1nc(-c2cc(Cl)c3ncccc3c2)c(-c2ccccc2)nc1N] |
| 1.641 | 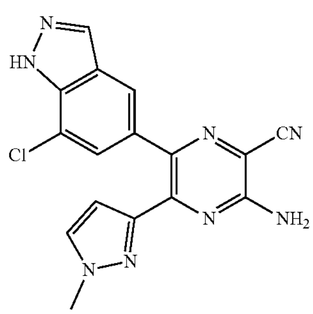 [SMILES: Cn1ccc(-c2nc(N)c(C#N)nc2-c2cc(Cl)c3[nH]ncc3c2)n1] |
| 1.642 | 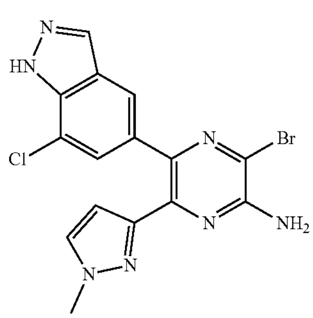 [SMILES: Cn1ccc(-c2nc(N)c(Br)nc2-c2cc(Cl)c3[nH]ncc3c2)n1] |

TABLE 2-continued
| Compound No. | Structure |
|---|---|
| 1.643 | 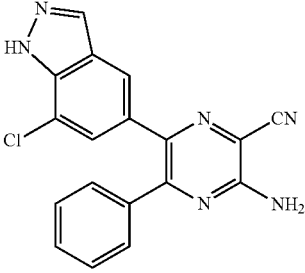 |
| 1.644 | 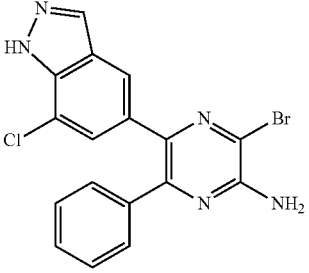 [SMILES: Nc1nc(-c2ccccc2)c(-c2cc(Cl)c3[nH]ncc3c2)nc1Br] |
| 1.645 | 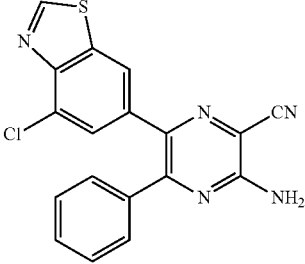 [SMILES: N#Cc1nc(-c2cc(Cl)c3ncsc3c2)c(-c2ccccc2)nc1N] |
| 1.646 | 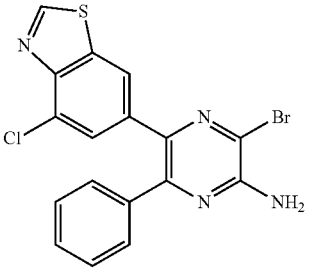 [SMILES: Nc1nc(-c2ccccc2)c(-c2cc(Cl)c3ncsc3c2)nc1Br] |
| 1.647 | 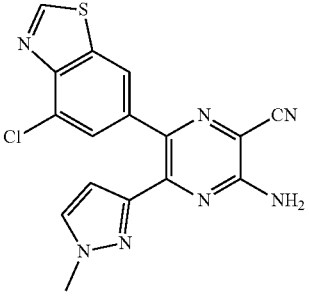 |

TABLE 2-continued

| Compound No. | Structure |
|---|---|
| 1.648 | 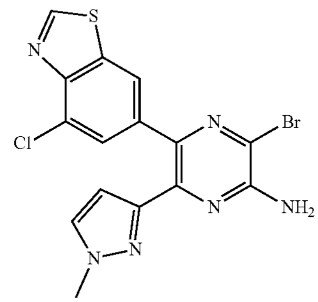 [SMILES: Cn1ccc(-c2nc(N)c(Br)nc2-c2cc(Cl)c3ncsc3c2)n1] |
| 1.649 | 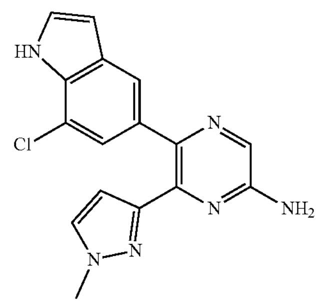 [SMILES: Cn1ccc(-c2nc(N)cnc2-c2cc(Cl)c3[nH]ccc3c2)n1] |
| 1.650 | 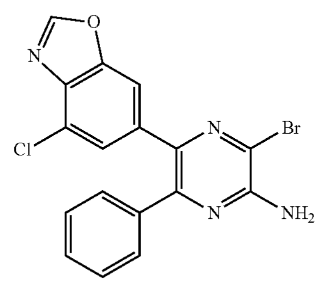 |
| 1.651 | 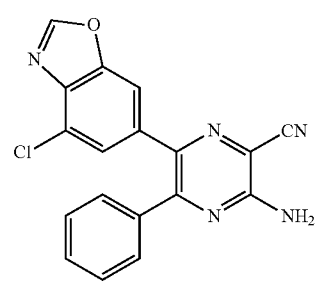 [SMILES: N#Cc1nc(-c2cc(Cl)c3ncoc3c2)c(-c2ccccc2)nc1N] |
| 1.652 | 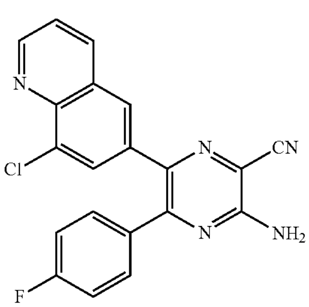 [SMILES: N#Cc1nc(-c2cc(Cl)c3ncccc3c2)c(-c2ccc(F)cc2)nc1N] |

TABLE 2-continued

| Compound No. | Structure |
|---|---|
| 1.653 | (structure) |
| 1.654 | (structure) |
| 1.655 | (structure) |
| 1.656 | (structure) |
| 1.657 | (structure) |

TABLE 2-continued

| Compound No. | Structure |
|---|---|
| 1.658 | 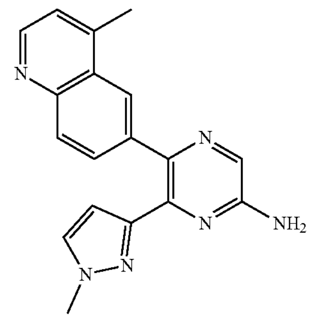 [SMILES: Cc1ccnc2ccc(-c3ncc(N)nc3-c3ccn(C)n3)cc12] |
| 1.659 | 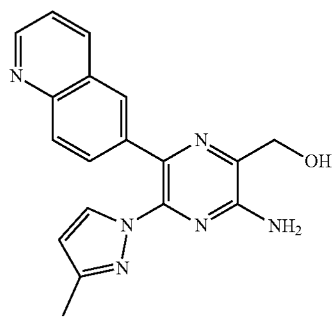 [SMILES: Cc1ccn(-c2nc(N)c(CO)nc2-c2ccc3ncccc3c2)n1] |
| 1.660 | 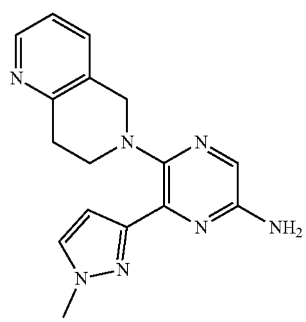 [SMILES: Cn1ccc(-c2nc(N)cnc2N2CCc3ncccc3C2)n1] |
| 1.661 | 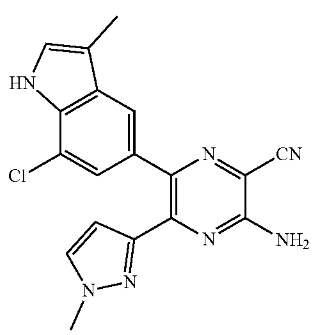 [SMILES: Cc1c[nH]c2c(Cl)cc(-c3nc(C#N)c(N)nc3-c3ccn(C)n3)cc12] |
| 1.662 | 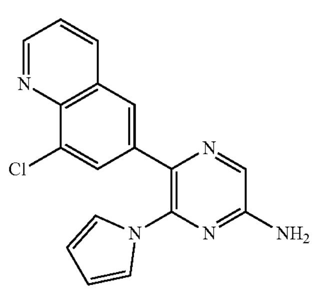 [SMILES: Nc1cnc(-c2cc(Cl)c3ncccc3c2)c(-n2cccc2)n1] |

TABLE 2-continued

| Compound No. | Structure |
| --- | --- |
| 1.663 | 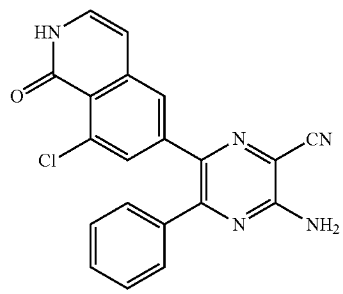 [SMILES: N#Cc1nc(-c2cc(Cl)c3c(=O)[nH]ccc3c2)c(-c2ccccc2)nc1N] |
| 1.664 | 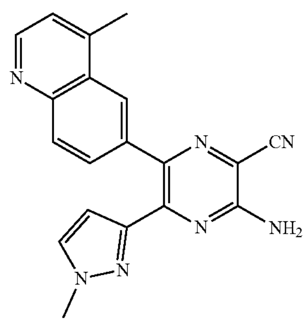 [SMILES: Cc1ccnc2ccc(-c3nc(C#N)c(N)nc3-c3ccn(C)n3)cc12] |
| 1.665 | 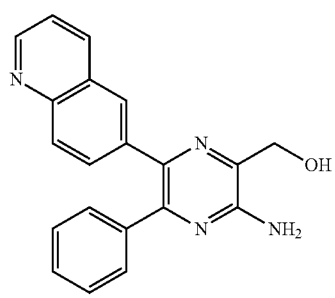 [SMILES: Nc1nc(-c2ccccc2)c(-c2ccc3ncccc3c2)nc1CO] |
| 1.666 | 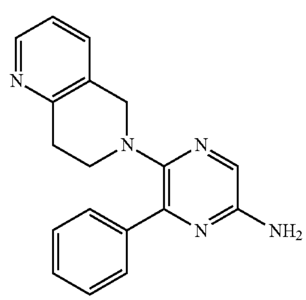 [SMILES: Nc1cnc(N2CCc3ncccc3C2)c(-c2ccccc2)n1] |
| 1.667 | 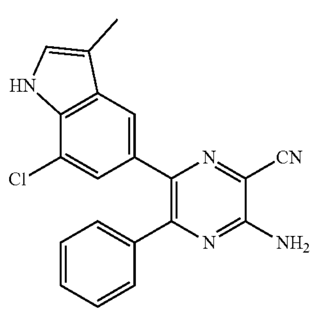 [SMILES: Cc1c[nH]c2c(Cl)cc(-c3nc(C#N)c(N)nc3-c3ccccc3)cc12] |

TABLE 2-continued

| Compound No. | Structure |
|---|---|
| 1.668 | 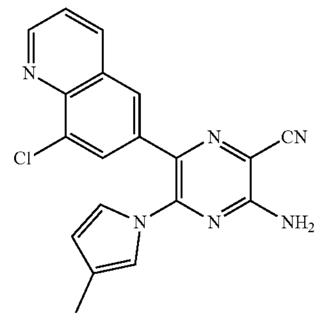 [SMILES: Cc1ccn(-c2nc(N)c(C#N)nc2-c2cc(Cl)c3ncccc3c2)c1] |
| 1.669 | 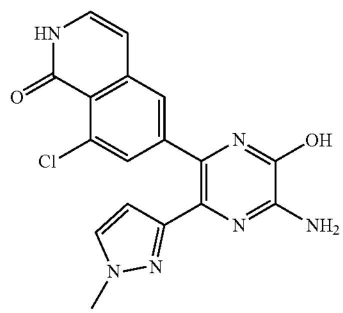 [SMILES: Cn1ccc(-c2nc(N)c(O)nc2-c2cc(Cl)c3c(=O)[nH]ccc3c2)n1] |
| 1.670 | 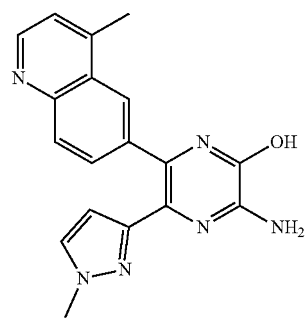 [SMILES: Cc1ccnc2ccc(-c3nc(O)c(N)nc3-c3ccn(C)n3)cc12] |
| 1.671 | 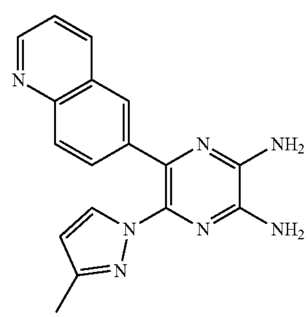 [SMILES: Cc1ccn(-c2nc(N)c(N)nc2-c2ccc3ncccc3c2)n1] |
| 1.672 | 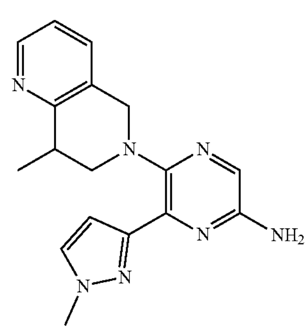 [SMILES: CC1CN(c2ncc(N)nc2-c2ccn(C)n2)Cc2cccnc21] |

TABLE 2-continued

| Compound No. | Structure |
|---|---|
| 1.673 | 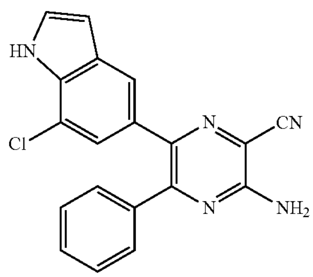 [SMILES: N#Cc1nc(-c2cc(Cl)c3[nH]ccc3c2)c(-c2ccccc2)nc1N] |
| 1.674 | 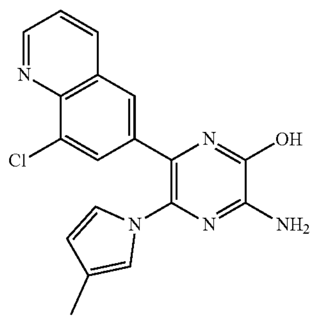 [SMILES: Cc1ccn(-c2nc(N)c(O)nc2-c2cc(Cl)c3ncccc3c2)c1] |
| 1.675 | 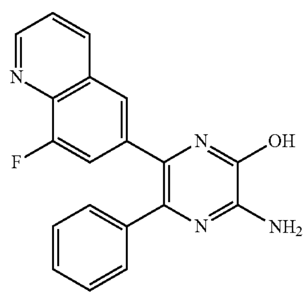 [SMILES: Nc1nc(-c2ccccc2)c(-c2cc(F)c3ncccc3c2)nc1O] |
| 1.676 | 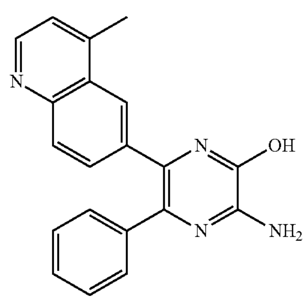 [SMILES: Cc1ccnc2ccc(-c3nc(O)c(N)nc3-c3ccccc3)cc12] |
| 1.677 | 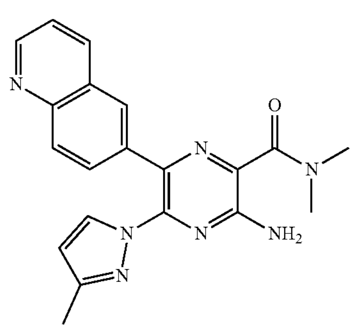 [SMILES: Cc1ccn(-c2nc(N)c(C(=O)N(C)C)nc2-c2ccc3ncccc3c2)n1] |

TABLE 2-continued

| Compound No. | Structure |
|---|---|
| 1.678 | 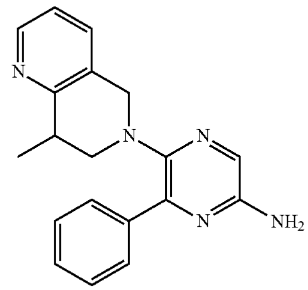 [SMILES: CC1CN(c2ncc(N)nc2-c2ccccc2)Cc2cccnc21] |
| 1.679 | 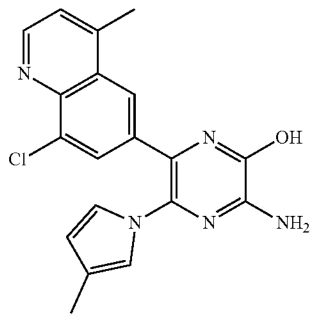 [SMILES: Cc1ccn(-c2nc(N)c(O)nc2-c2cc(Cl)c3nccc(C)c3c2)c1] |
| 1.680 | 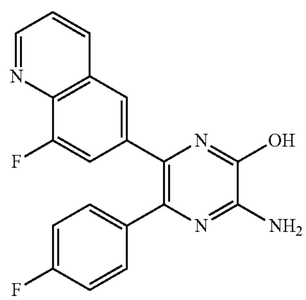 [SMILES: Nc1nc(-c2ccc(F)cc2)c(-c2cc(F)c3ncccc3c2)nc1O] |
| 1.681 | 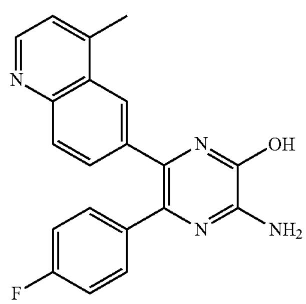 [SMILES: Cc1ccnc2ccc(-c3nc(O)c(N)nc3-c3ccc(F)cc3)cc12] |
| 1.682 | 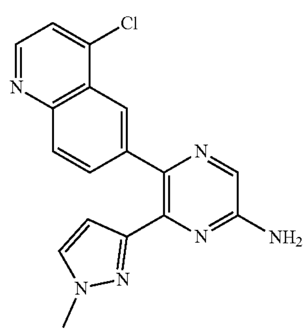 [SMILES: Cn1ccc(-c2nc(N)cnc2-c2ccc3nccc(Cl)c3c2)n1] |

TABLE 2-continued

| Compound No. | Structure |
|---|---|
| 1.683 | 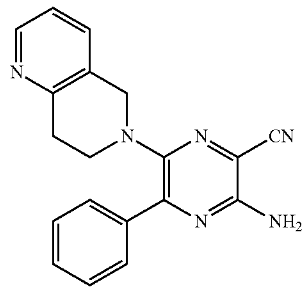 [SMILES: N#Cc1nc(N2CCc3ncccc3C2)c(-c2ccccc2)nc1N] |
| 1.684 | 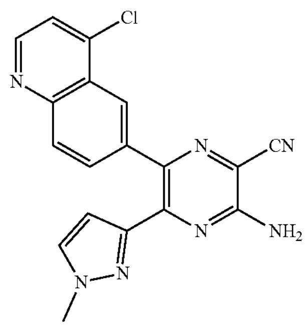 [SMILES: Cn1ccc(-c2nc(N)c(C#N)nc2-c2ccc3nccc(Cl)c3c2)n1] |
| 1.685 | 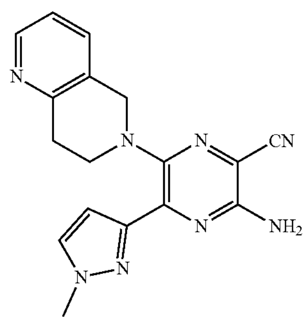 [SMILES: Cn1ccc(-c2nc(N)c(C#N)nc2N2CCc3ncccc3C2)n1] |
| 1.686 | 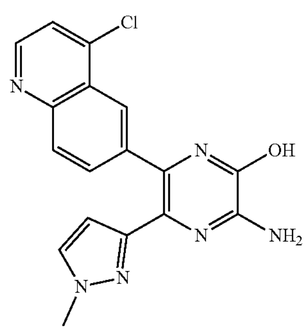 [SMILES: Cn1ccc(-c2nc(N)c(O)nc2-c2ccc3nccc(Cl)c3c2)n1] |
| 1.687 | 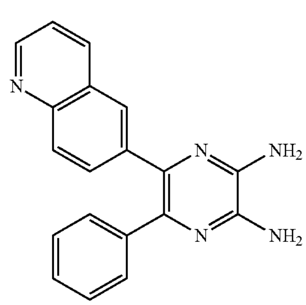 [SMILES: Nc1nc(-c2ccccc2)c(-c2ccc3ncccc3c2)nc1N] |

TABLE 2-continued
| Compound No. | Structure |
|---|---|
| 1.688 | 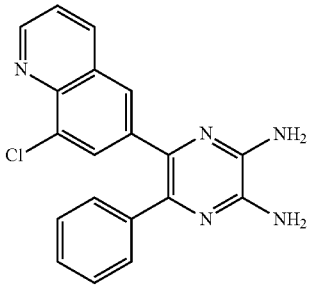 [SMILES: Nc1nc(-c2ccccc2)c(-c2cc(Cl)c3ncccc3c2)nc1N] |
| 1.689 | 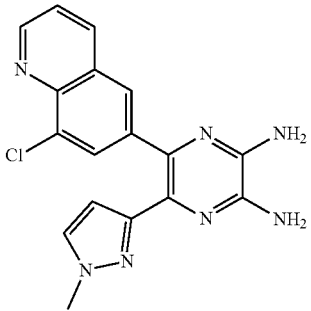 [SMILES: Cn1ccc(-c2nc(N)c(N)nc2-c2cc(Cl)c3ncccc3c2)n1] |
| 1.690 | 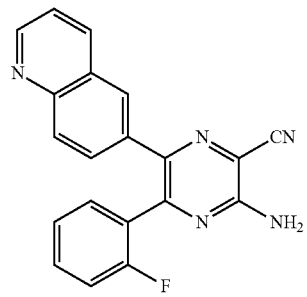 [SMILES: N#Cc1nc(-c2ccc3ncccc3c2)c(-c2ccccc2F)nc1N] |
| 1.691 | 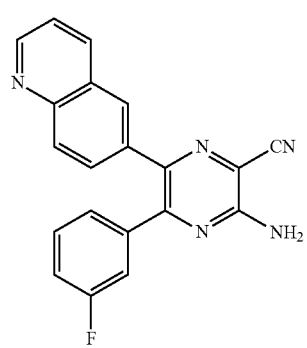 [SMILES: N#Cc1nc(-c2ccc3ncccc3c2)c(-c2cccc(F)c2)nc1N] |
| 1.692 | 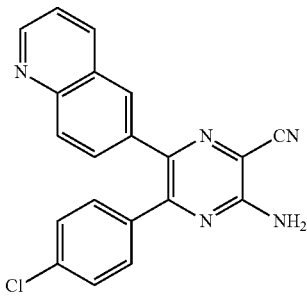 [SMILES: N#Cc1nc(-c2ccc3ncccc3c2)c(-c2ccc(Cl)cc2)nc1N] |

TABLE 2-continued

| Compound No. | Structure |
| --- | --- |
| 1.693 | 3-amino-5-(2-chlorophenyl)-6-(quinolin-6-yl)pyrazine-2-carbonitrile |
| 1.694 | 3-amino-5-(3-chlorophenyl)-6-(quinolin-6-yl)pyrazine-2-carbonitrile |
| 1.695 | 3-amino-5-(m-tolyl)-6-(quinolin-6-yl)pyrazine-2-carbonitrile |
| 1.696 | 3-amino-5-(3-methoxyphenyl)-6-(quinolin-6-yl)pyrazine-2-carbonitrile |

TABLE 2-continued
| Compound No. | Structure |
|---|---|
| 1.697 | 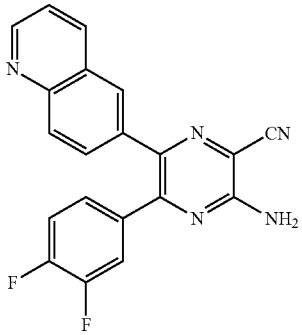 [SMILES: N#Cc1nc(-c2ccc3ncccc3c2)c(-c2ccc(F)c(F)c2)nc1N] |
| 1.698 | 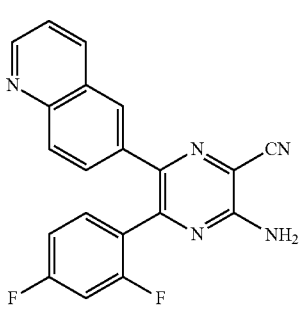 [SMILES: N#Cc1nc(-c2ccc3ncccc3c2)c(-c2ccc(F)cc2F)nc1N] |
| 1.699 | 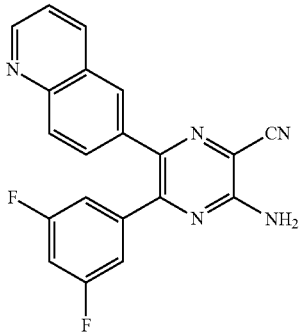 [SMILES: N#Cc1nc(-c2ccc3ncccc3c2)c(-c2cc(F)cc(F)c2)nc1N] |
| 1.700 | 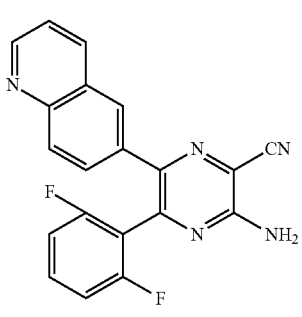 [SMILES: N#Cc1nc(-c2ccc3ncccc3c2)c(-c2c(F)cccc2F)nc1N] |
| 1.701 | 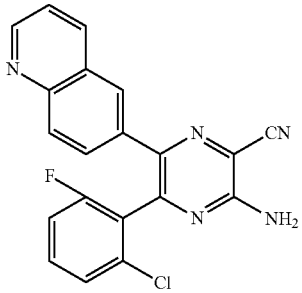 [SMILES: N#Cc1nc(-c2ccc3ncccc3c2)c(-c2c(F)cccc2Cl)nc1N] |

TABLE 2-continued
| Compound No. | Structure |
|---|---|
| 1.702 | 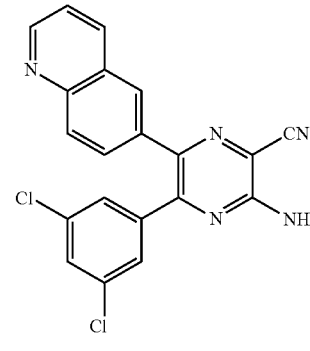 |
| 1.703 | 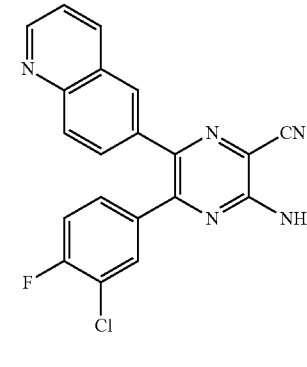 |
| 1.704 | 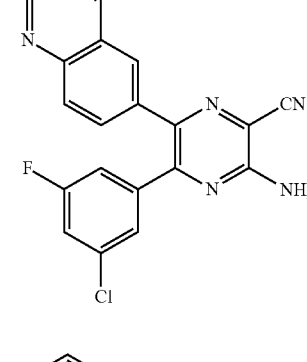 |
| 1.705 | 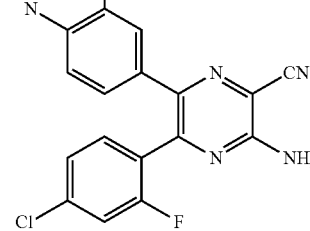 |

TABLE 2-continued

| Compound No. | Structure |
|---|---|
| 1.706 | (quinolin-6-yl, 4-fluoro-2-chlorophenyl, 3-amino-pyrazine-2-carbonitrile) |
| 1.707 | (quinolin-6-yl, 3,5-...fluoro-methylphenyl, 3-amino-pyrazine-2-carbonitrile) |
| 1.708 | (quinolin-6-yl, 4-chloro-3-fluorophenyl, 3-amino-pyrazine-2-carbonitrile) |
| 1.709 | (7-chloro-1H-indazol-5-yl, 2-fluorophenyl, 3-amino-pyrazine-2-carbonitrile) |

TABLE 2-continued

| Compound No. | Structure |
|---|---|
| 1.710 | 3-amino-5-(7-chloro-1H-indazol-5-yl)-6-(3-fluorophenyl)pyrazine-2-carbonitrile |
| 1.711 | 3-amino-5-(7-chloro-1H-indazol-5-yl)-6-(4-chlorophenyl)pyrazine-2-carbonitrile |
| 1.712 | 3-amino-5-(7-chloro-1H-indazol-5-yl)-6-(2-chlorophenyl)pyrazine-2-carbonitrile |
| 1.713 | 3-amino-5-(7-chloro-1H-indazol-5-yl)-6-(3-chlorophenyl)pyrazine-2-carbonitrile |
| 1.714 | 3-amino-6-(7-chloro-1H-indazol-5-yl)-5-(m-tolyl)pyrazine-2-carbonitrile |

TABLE 2-continued
| Compound No. | Structure |
|---|---|
| 1.715 | 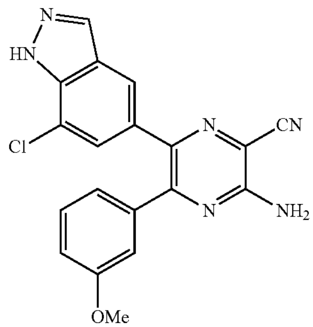 [SMILES: COc1cccc(-c2nc(N)c(C#N)nc2-c2cc(Cl)c3[nH]ncc3c2)c1] |
| 1.716 | 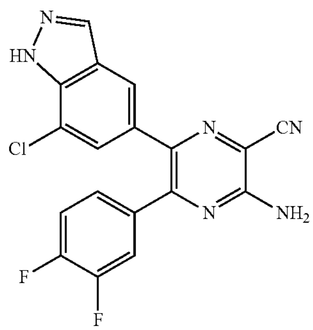 [SMILES: N#Cc1nc(-c2cc(Cl)c3[nH]ncc3c2)c(-c2ccc(F)c(F)c2)nc1N] |
| 1.717 | 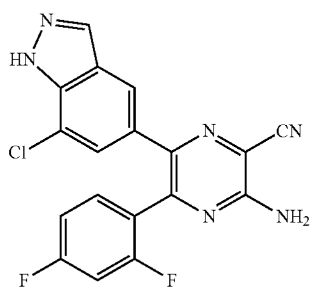 [SMILES: N#Cc1nc(-c2cc(Cl)c3[nH]ncc3c2)c(-c2ccc(F)cc2F)nc1N] |
| 1.718 | 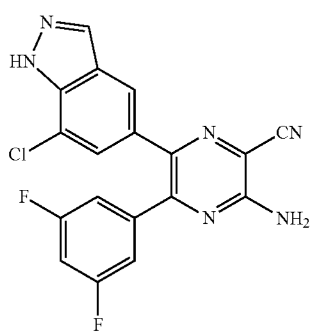 [SMILES: N#Cc1nc(-c2cc(Cl)c3[nH]ncc3c2)c(-c2cc(F)cc(F)c2)nc1N] |
| 1.719 | 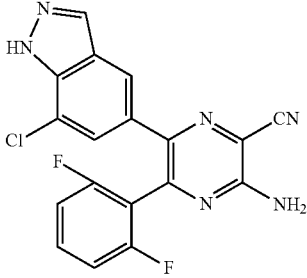 [SMILES: N#Cc1nc(-c2cc(Cl)c3[nH]ncc3c2)c(-c2c(F)cccc2F)nc1N] |

TABLE 2-continued

| Compound No. | Structure |
|---|---|
| 1.720 | 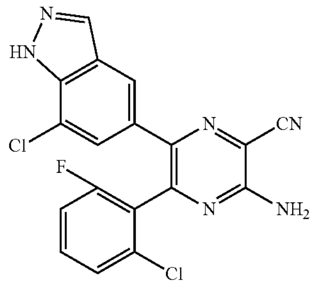 [SMILES: N#Cc1nc(-c2cc(Cl)c3[nH]ncc3c2)c(-c2c(F)cccc2Cl)nc1N] |
| 1.721 | 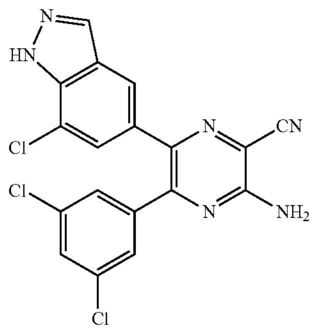 [SMILES: N#Cc1nc(-c2cc(Cl)c3[nH]ncc3c2)c(-c2cc(Cl)cc(Cl)c2)nc1N] |
| 1.722 | 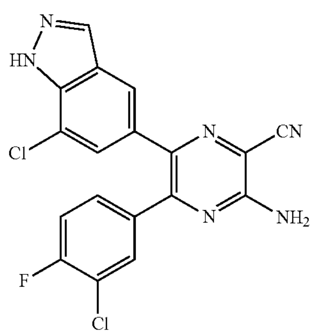 [SMILES: N#Cc1nc(-c2cc(Cl)c3[nH]ncc3c2)c(-c2ccc(F)c(Cl)c2)nc1N] |
| 1.723 | 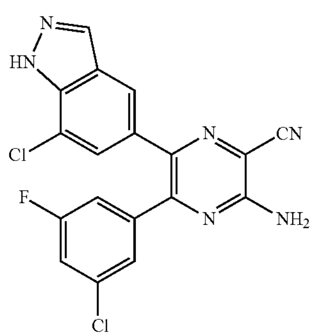 [SMILES: N#Cc1nc(-c2cc(Cl)c3[nH]ncc3c2)c(-c2cc(F)cc(Cl)c2)nc1N] |
| 1.724 | 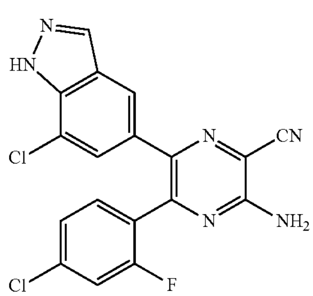 [SMILES: N#Cc1nc(-c2cc(Cl)c3[nH]ncc3c2)c(-c2ccc(Cl)cc2F)nc1N] |

TABLE 2-continued

| Compound No. | Structure |
|---|---|
| 1.725 | 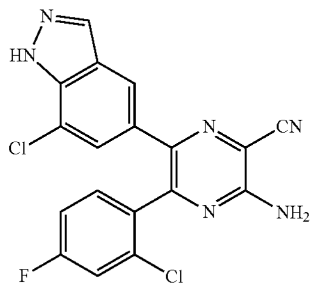 [SMILES: N#Cc1nc(-c2cc(Cl)c3[nH]ncc3c2)c(-c2ccc(F)cc2Cl)nc1N] |
| 1.726 | 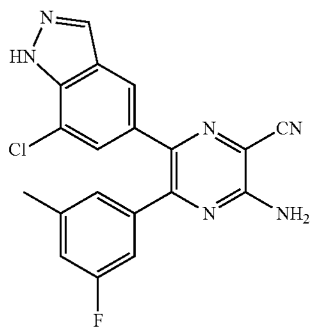 [SMILES: Cc1cc(F)cc(-c2nc(N)c(C#N)nc2-c2cc(Cl)c3[nH]ncc3c2)c1] |
| 1.727 | 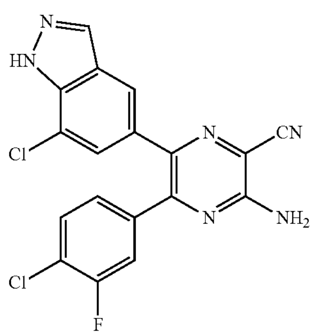 [SMILES: N#Cc1nc(-c2cc(Cl)c3[nH]ncc3c2)c(-c2ccc(Cl)c(F)c2)nc1N] |
| 1.728 | 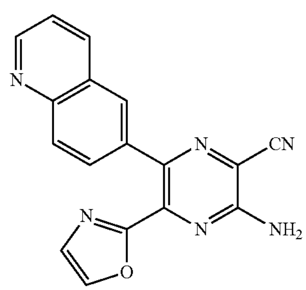 [SMILES: N#Cc1nc(-c2ccc3ncccc3c2)c(-c2ncco2)nc1N] |
| 1.729 | 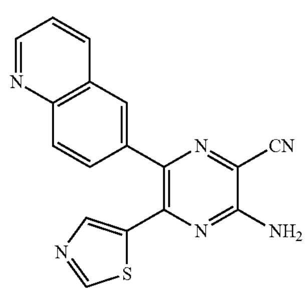 [SMILES: N#Cc1nc(-c2ccc3ncccc3c2)c(-c2cncs2)nc1N] |

TABLE 2-continued

| Compound No. | Structure |
|---|---|
| 1.730 | 3-amino-5-(1H-imidazol-5-yl)-6-(quinolin-6-yl)pyrazine-2-carbonitrile |
| 1.731 | 3-amino-5-(isoxazol-5-yl)-6-(quinolin-6-yl)pyrazine-2-carbonitrile |
| 1.732 | 3-amino-5-(isothiazol-5-yl)-6-(quinolin-6-yl)pyrazine-2-carbonitrile |
| 1.733 | 3-amino-5-(1H-pyrazol-5-yl)-6-(quinolin-6-yl)pyrazine-2-carbonitrile |
| 1.734 | 3-amino-5-(1-methyl-1H-pyrazol-5-yl)-6-(quinolin-6-yl)pyrazine-2-carbonitrile |

TABLE 2-continued
| Compound No. | Structure |
|---|---|
| 1.735 | 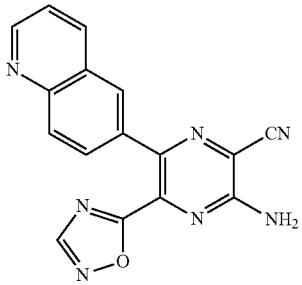 [SMILES: N#Cc1nc(-c2ccc3ncccc3c2)c(-c2ncno2)nc1N] |
| 1.736 | 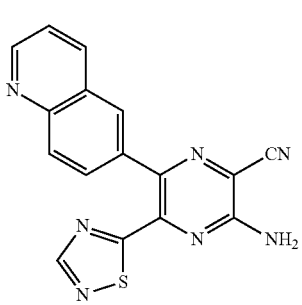 [SMILES: N#Cc1nc(-c2ccc3ncccc3c2)c(-c2ncns2)nc1N] |
| 1.737 | 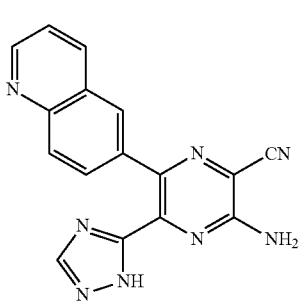 [SMILES: N#Cc1nc(-c2ccc3ncccc3c2)c(-c2ncn[nH]2)nc1N] |
| 1.738 | 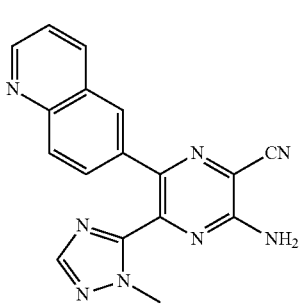 [SMILES: Cn1ncnc1-c1nc(N)c(C#N)nc1-c1ccc2ncccc2c1] |
| 1.739 | 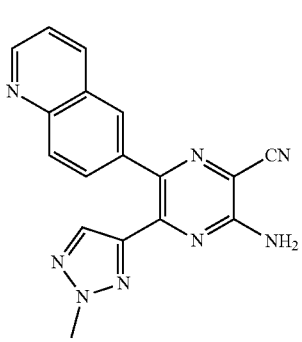 [SMILES: Cn1ncc(-c2nc(N)c(C#N)nc2-c2ccc3ncccc3c2)n1] |

TABLE 2-continued

| Compound No. | Structure |
|---|---|
| 1.740 | (quinolin-6-yl)-pyrazine with CN, NH₂, and 1H-pyrazol-4-yl substituents |
| 1.741 | (quinolin-6-yl)-pyrazine with CN, NH₂, and 4H-1,2,4-triazol-4-yl substituents |
| 1.742 | (quinolin-6-yl)-pyrazine with CN, NH₂, and 1H-imidazol-1-yl substituents |
| 1.743 | (quinolin-6-yl)-pyrazine with CN, NH₂, and 1H-tetrazol-5-yl substituents |
| 1.744 | (quinolin-6-yl)-pyrazine with CN, NH₂, and 1-methyl-1H-tetrazol-5-yl substituents |

TABLE 2-continued

| Compound No. | Structure |
|---|---|
| 1.745 | (quinolin-6-yl and 1H-pyrrol-2-yl substituted 3-amino-pyrazine-2-carbonitrile) |
| 1.746 | (quinolin-6-yl and 1H-pyrazol-5-yl substituted 3-amino-pyrazine-2-carbonitrile) |
| 1.747 | (quinolin-6-yl and 2H-1,2,3-triazol-4-yl substituted 3-amino-pyrazine-2-carbonitrile) |
| 1.748 | (8-fluoroquinolin-6-yl and 1H-1,2,4-triazol-5-yl substituted 3-amino-pyrazine-2-carbonitrile) |
| 1.749 | (7-chloro-1H-indazol-5-yl and oxazol-5-yl substituted 3-amino-pyrazine-2-carbonitrile) |

TABLE 2-continued

| Compound No. | Structure |
|---|---|
| 1.750 | 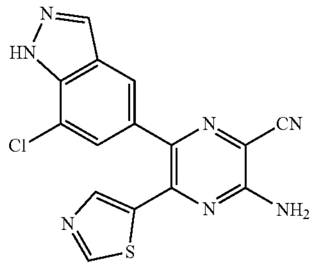 [SMILES: N#Cc1nc(-c2cc(Cl)c3[nH]ncc3c2)c(-c2cncs2)nc1N] |
| 1.751 | 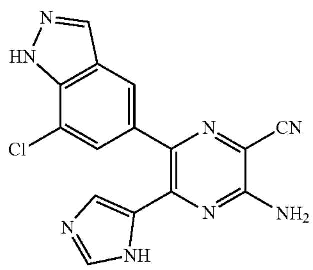 [SMILES: N#Cc1nc(-c2cc(Cl)c3[nH]ncc3c2)c(-c2cnc[nH]2)nc1N] |
| 1.752 | 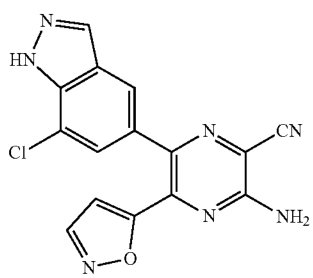 [SMILES: N#Cc1nc(-c2cc(Cl)c3[nH]ncc3c2)c(-c2ccno2)nc1N] |
| 1.753 | 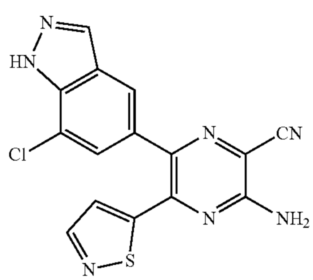 [SMILES: N#Cc1nc(-c2cc(Cl)c3[nH]ncc3c2)c(-c2ccns2)nc1N] |
| 1.754 | 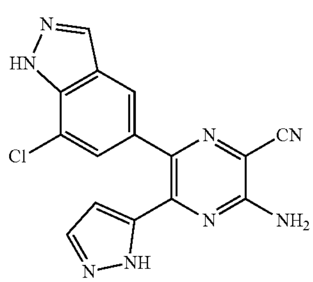 [SMILES: N#Cc1nc(-c2cc(Cl)c3[nH]ncc3c2)c(-c2ccn[nH]2)nc1N] |

TABLE 2-continued

| Compound No. | Structure |
|---|---|
| 1.755 | 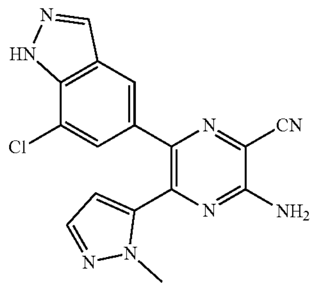 [SMILES: Cn1nccc1-c1nc(N)c(C#N)nc1-c1cc(Cl)c2[nH]ncc2c1] |
| 1.756 | 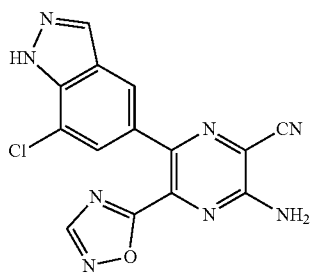 [SMILES: N#Cc1nc(-c2cc(Cl)c3[nH]ncc3c2)c(-c2ncno2)nc1N] |
| 1.757 | 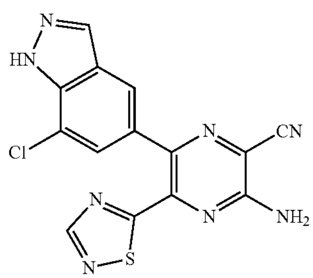 [SMILES: N#Cc1nc(-c2cc(Cl)c3[nH]ncc3c2)c(-c2ncns2)nc1N] |
| 1.758 | 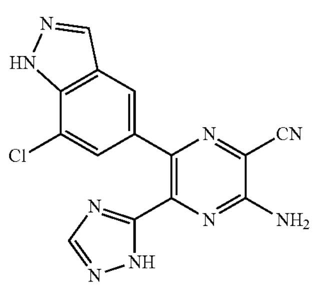 [SMILES: N#Cc1nc(-c2cc(Cl)c3[nH]ncc3c2)c(-c2ncn[nH]2)nc1N] |
| 1.759 | 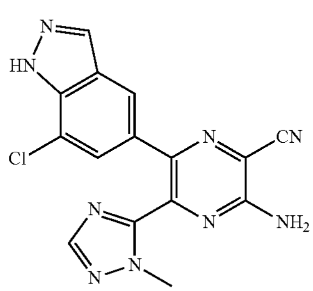 [SMILES: Cn1ncnc1-c1nc(N)c(C#N)nc1-c1cc(Cl)c2[nH]ncc2c1] |

TABLE 2-continued

| Compound No. | Structure |
| --- | --- |
| 1.760 | 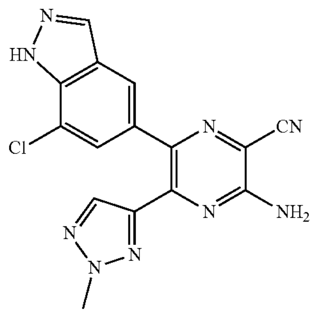 [SMILES: Cn1ncc(-c2nc(N)c(C#N)nc2-c2cc(Cl)c3[nH]ncc3c2)n1] |
| 1.761 | 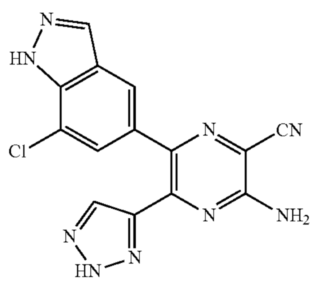 [SMILES: N#Cc1nc(-c2cc(Cl)c3[nH]ncc3c2)c(-c2cn[nH]n2)nc1N] |
| 1.762 | 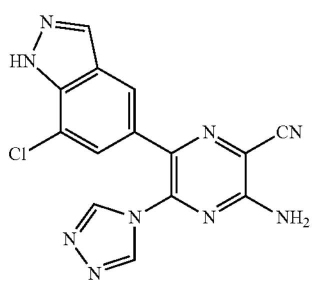 [SMILES: N#Cc1nc(-c2cc(Cl)c3[nH]ncc3c2)c(-n2cnnc2)nc1N] |
| 1.763 | 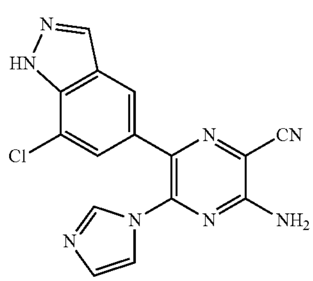 [SMILES: N#Cc1nc(-c2cc(Cl)c3[nH]ncc3c2)c(-n2ccnc2)nc1N] |
| 1.764 | 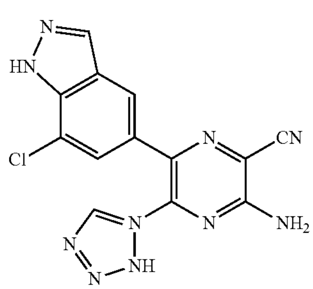 |

TABLE 2-continued

| Compound No. | Structure |
|---|---|
| 1.765 | (structure: 7-chloro-1H-indazol-5-yl and 1-methyl-1H-tetrazol-5-yl substituted 3-amino-pyrazine-2-carbonitrile) |
| 1.766 | (structure: 7-chloro-1H-indazol-5-yl and 1H-pyrrol-2-yl substituted 3-amino-pyrazine-2-carbonitrile) |
| 1.767 | (structure: 7-chloro-1H-indazol-5-yl and 1H-pyrazol-3-yl substituted 3-amino-pyrazine-2-carbonitrile) |
| 1.768 | (structure: 7-chloro-1H-indazol-5-yl and 1H-1,2,3-triazol-4-yl substituted 3-amino-pyrazine-2-carbonitrile) |
| 1.769 | (structure: 7-fluoro-1H-indazol-5-yl and 1H-1,2,4-triazol-3-yl substituted 3-amino-pyrazine-2-carbonitrile) |

TABLE 2-continued

| Compound No. | Structure |
|---|---|
| 1.770 | 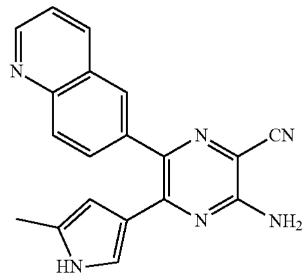 [SMILES: Cc1cc(-c2nc(N)c(C#N)nc2-c2ccc3ncccc3c2)c[nH]1] |
| 1.771 | 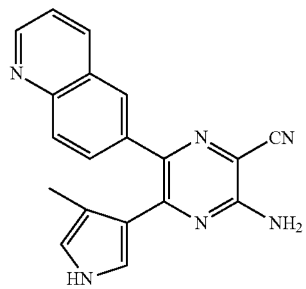 [SMILES: Cc1c[nH]cc1-c1nc(N)c(C#N)nc1-c1ccc2ncccc2c1] |
| 1.772 | 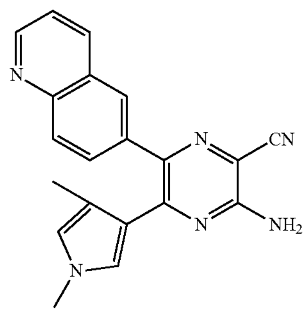 [SMILES: Cc1cn(C)cc1-c1nc(N)c(C#N)nc1-c1ccc2ncccc2c1] |
| 1.773 | 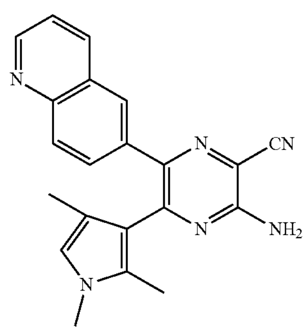 [SMILES: Cc1cn(C)c(C)c1-c1nc(N)c(C#N)nc1-c1ccc2ncccc2c1] |
| 1.774 | 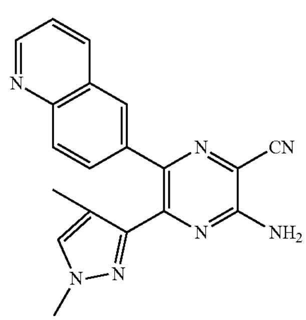 [SMILES: Cc1cn(C)nc1-c1nc(N)c(C#N)nc1-c1ccc2ncccc2c1] |

TABLE 2-continued

| Compound No. | Structure |
| --- | --- |
| 1.775 | 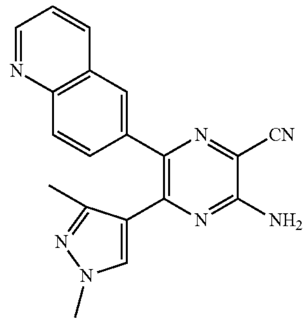 [SMILES: Cc1nn(C)cc1-c1nc(N)c(C#N)nc1-c1ccc2ncccc2c1] |
| 1.776 | 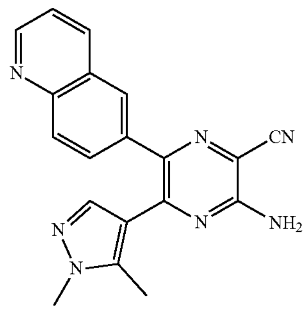 [SMILES: Cc1c(-c2nc(N)c(C#N)nc2-c2ccc3ncccc3c2)cnn1C] |
| 1.777 | 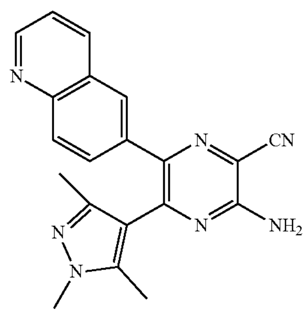 [SMILES: Cc1nn(C)c(C)c1-c1nc(N)c(C#N)nc1-c1ccc2ncccc2c1] |
| 1.778 | 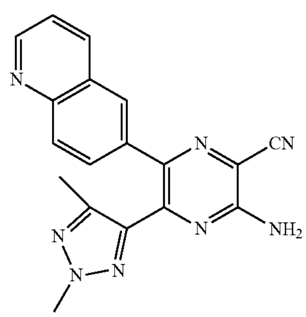 [SMILES: Cc1nn(C)nc1-c1nc(N)c(C#N)nc1-c1ccc2ncccc2c1] |
| 1.779 | 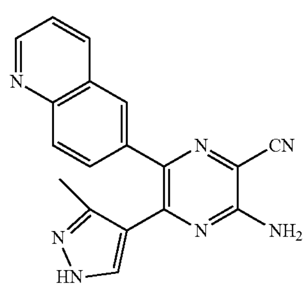 [SMILES: Cc1n[nH]cc1-c1nc(N)c(C#N)nc1-c1ccc2ncccc2c1] |

TABLE 2-continued

| Compound No. | Structure |
|---|---|
| 1.780 | 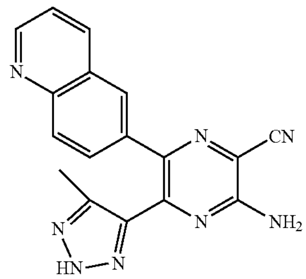 [SMILES: Cc1n[nH]nc1-c1nc(N)c(C#N)nc1-c1ccc2ncccc2c1] |
| 1.781 | 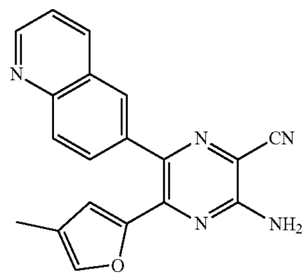 [SMILES: Cc1coc(-c2nc(N)c(C#N)nc2-c2ccc3ncccc3c2)c1] |
| 1.782 | 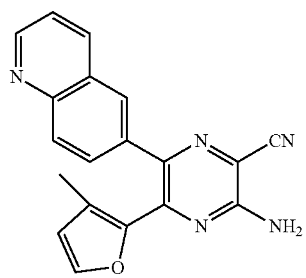 [SMILES: Cc1ccoc1-c1nc(N)c(C#N)nc1-c1ccc2ncccc2c1] |
| 1.783 | 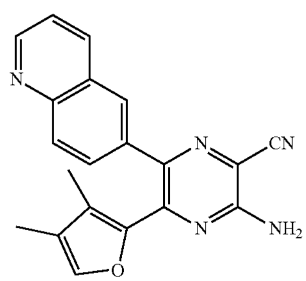 [SMILES: Cc1coc(-c2nc(N)c(C#N)nc2-c2ccc3ncccc3c2)c1C] |
| 1.784 | 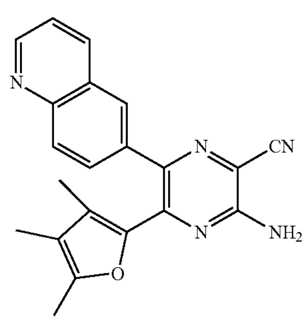 [SMILES: Cc1oc(-c2nc(N)c(C#N)nc2-c2ccc3ncccc3c2)c(C)c1C] |

TABLE 2-continued
| Compound No. | Structure |
|---|---|
| 1.785 | 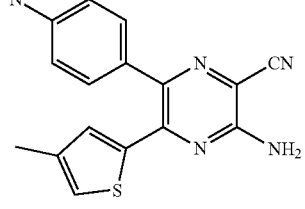 |
| 1.786 | 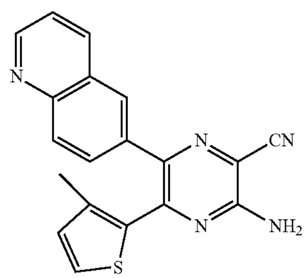 [SMILES: Cc1ccsc1-c1nc(N)c(C#N)nc1-c1ccc2ncccc2c1] |
| 1.787 | 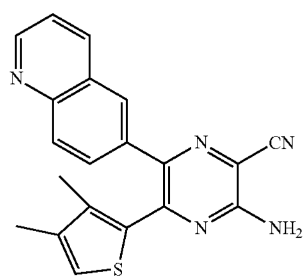 [SMILES: Cc1csc(-c2nc(N)c(C#N)nc2-c2ccc3ncccc3c2)c1C] |
| 1.788 | 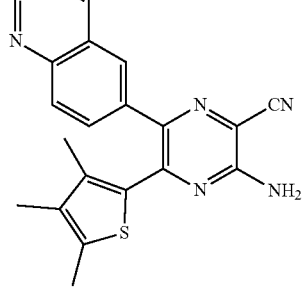 |
| 1.789 | 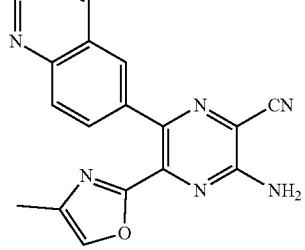 |

TABLE 2-continued

| Compound No. | Structure |
|---|---|
| 1.790 | (quinolin-6-yl, 4,5-dimethyloxazol-2-yl substituted 3-amino-6-cyanopyrazine) |
| 1.791 | (quinolin-6-yl, 4-methylthiazol-2-yl substituted 3-amino-6-cyanopyrazine) |
| 1.792 | (quinolin-6-yl, 4,5-dimethylthiazol-2-yl substituted 3-amino-6-cyanopyrazine) |
| 1.793 | (quinolin-6-yl, 3-methylisoxazol-5-yl substituted 3-amino-6-cyanopyrazine) |
| 1.794 | (quinolin-6-yl, 3,4-dimethylisoxazol-5-yl substituted 3-amino-6-cyanopyrazine) |

TABLE 2-continued
| Compound No. | Structure |
|---|---|
| 1.795 | 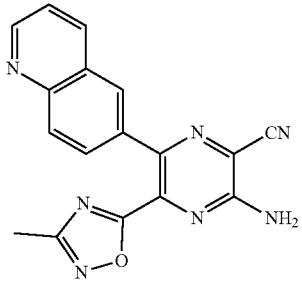 |
| 1.796 | 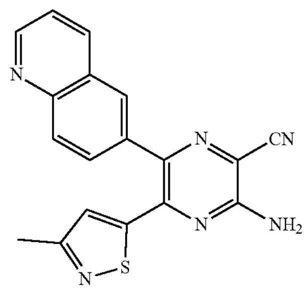 [SMILES: Cc1cc(-c2nc(N)c(C#N)nc2-c2ccc3ncccc3c2)sn1] |
| 1.797 | 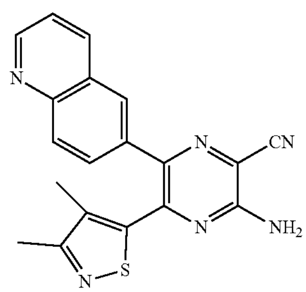 [SMILES: Cc1nsc(-c2nc(N)c(C#N)nc2-c2ccc3ncccc3c2)c1C] |
| 1.798 | 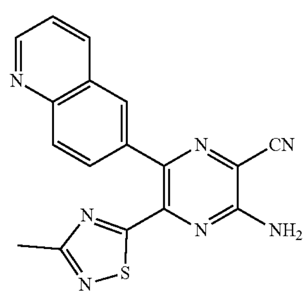 [SMILES: Cc1nsc(-c2nc(N)c(C#N)nc2-c2ccc3ncccc3c2)n1] |
| 1.799 | 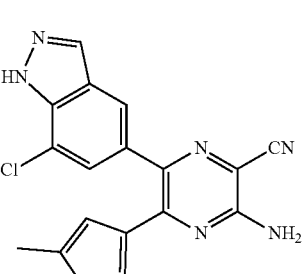 |

TABLE 2-continued

| Compound No. | Structure |
|---|---|
| 1.800 | 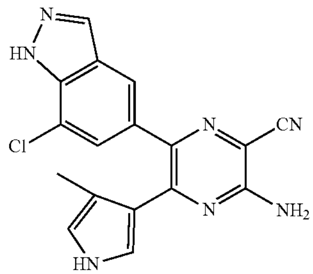 [SMILES: Cc1c[nH]cc1-c1nc(N)c(C#N)nc1-c1cc(Cl)c2[nH]ncc2c1] |
| 1.801 | 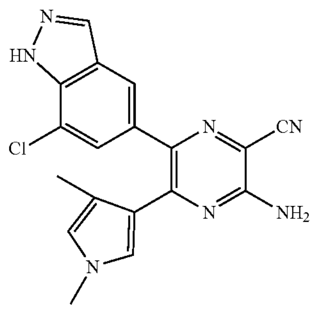 [SMILES: Cc1cn(C)cc1-c1nc(N)c(C#N)nc1-c1cc(Cl)c2[nH]ncc2c1] |
| 1.802 | 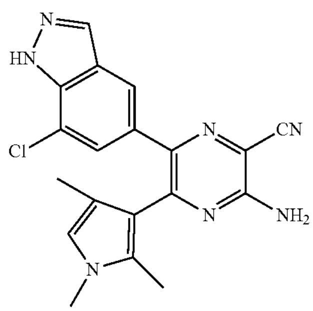 [SMILES: Cc1cn(C)c(C)c1-c1nc(N)c(C#N)nc1-c1cc(Cl)c2[nH]ncc2c1] |
| 1.803 | 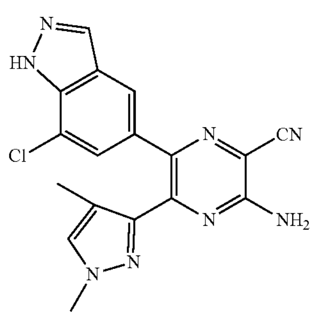 [SMILES: Cc1cn(C)nc1-c1nc(N)c(C#N)nc1-c1cc(Cl)c2[nH]ncc2c1] |
| 1.804 | 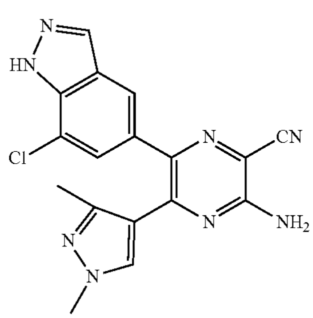 [SMILES: Cc1nn(C)cc1-c1nc(N)c(C#N)nc1-c1cc(Cl)c2[nH]ncc2c1] |

TABLE 2-continued

| Compound No. | Structure |
|---|---|
| 1.805 | 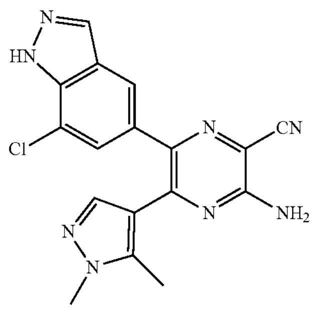 [SMILES: Cc1c(-c2nc(N)c(C#N)nc2-c2cc(Cl)c3[nH]ncc3c2)cnn1C] |
| 1.806 | 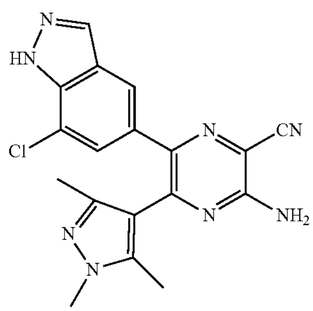 [SMILES: Cc1nn(C)c(C)c1-c1nc(N)c(C#N)nc1-c1cc(Cl)c2[nH]ncc2c1] |
| 1.807 | 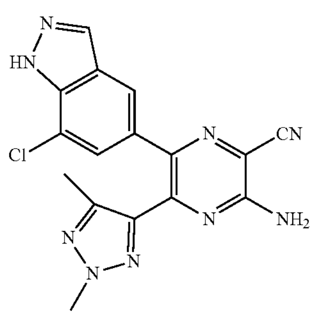 [SMILES: Cc1nn(C)nc1-c1nc(N)c(C#N)nc1-c1cc(Cl)c2[nH]ncc2c1] |
| 1.808 | 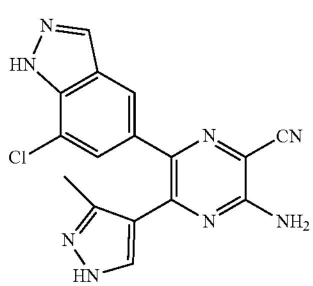 [SMILES: Cc1n[nH]cc1-c1nc(N)c(C#N)nc1-c1cc(Cl)c2[nH]ncc2c1] |
| 1.809 | 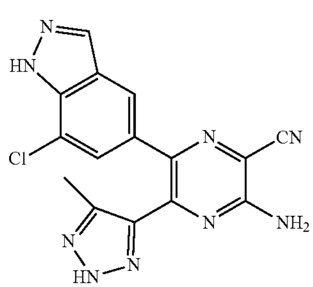 [SMILES: Cc1n[nH]nc1-c1nc(N)c(C#N)nc1-c1cc(Cl)c2[nH]ncc2c1] |

TABLE 2-continued

| Compound No. | Structure |
|---|---|
| 1.810 | 5-(7-chloro-1H-indazol-5-yl)-6-(5-methylfuran-2-yl)-3-aminopyrazine-2-carbonitrile |
| 1.811 | 5-(7-chloro-1H-indazol-5-yl)-6-(3-methylfuran-2-yl)-3-aminopyrazine-2-carbonitrile |
| 1.812 | 5-(7-chloro-1H-indazol-5-yl)-6-(3,4-dimethylfuran-2-yl)-3-aminopyrazine-2-carbonitrile |
| 1.813 | 5-(7-chloro-1H-indazol-5-yl)-6-(3,4,5-trimethylfuran-2-yl)-3-aminopyrazine-2-carbonitrile |
| 1.814 | 5-(7-chloro-1H-indazol-5-yl)-6-(4-methylthiophen-2-yl)-3-aminopyrazine-2-carbonitrile |

TABLE 2-continued

| Compound No. | Structure |
|---|---|
| 1.815 | 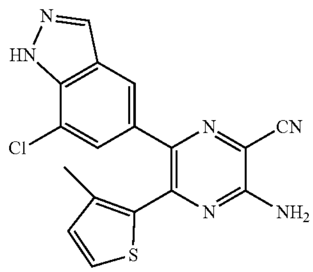 [SMILES: Cc1ccsc1-c1nc(N)c(C#N)nc1-c1cc(Cl)c2[nH]ncc2c1] |
| 1.816 | 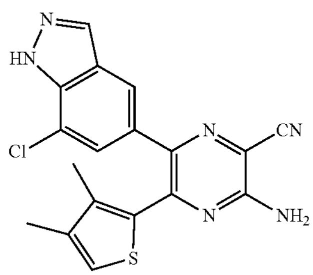 [SMILES: Cc1csc(-c2nc(N)c(C#N)nc2-c2cc(Cl)c3[nH]ncc3c2)c1C] |
| 1.817 | 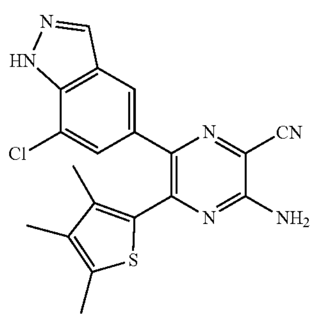 [SMILES: Cc1sc(-c2nc(N)c(C#N)nc2-c2cc(Cl)c3[nH]ncc3c2)c(C)c1C] |
| 1.818 | 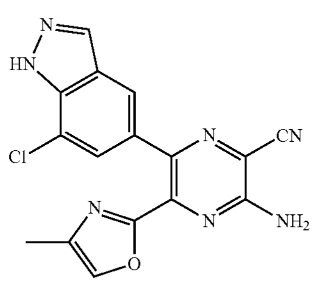 [SMILES: Cc1coc(-c2nc(N)c(C#N)nc2-c2cc(Cl)c3[nH]ncc3c2)n1] |
| 1.819 | 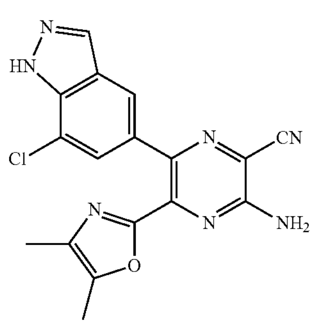 [SMILES: Cc1nc(-c2nc(N)c(C#N)nc2-c2cc(Cl)c3[nH]ncc3c2)oc1C] |

TABLE 2-continued
| Compound No. | Structure |
|---|---|
| 1.820 | 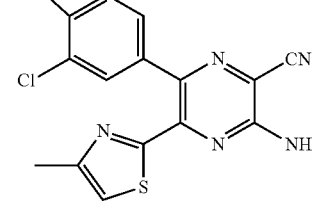 |
| 1.821 | 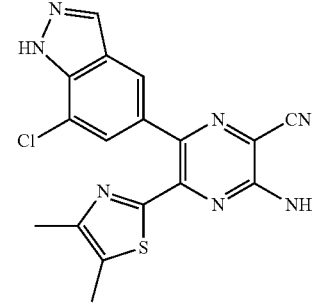 |
| 1.822 | 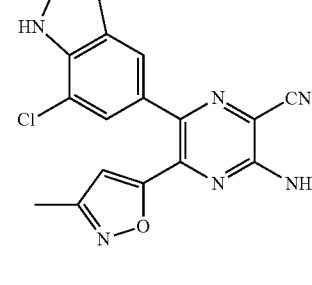 |
| 1.823 | 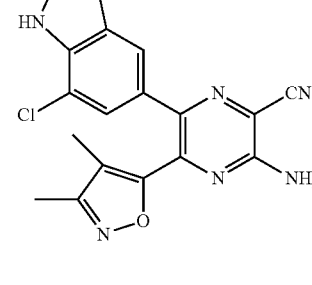 |
| 1.824 | 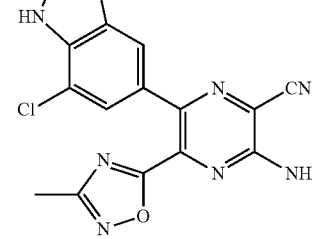 |

TABLE 2-continued

| Compound No. | Structure |
|---|---|
| 1.825 | 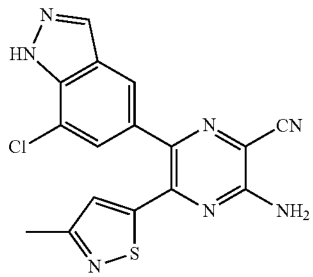 [SMILES: Cc1cc(-c2nc(N)c(C#N)nc2-c2cc(Cl)c3[nH]ncc3c2)sn1] |
| 1.826 | 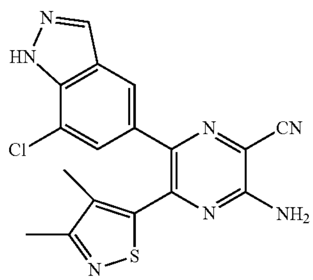 [SMILES: Cc1nsc(-c2nc(N)c(C#N)nc2-c2cc(Cl)c3[nH]ncc3c2)c1C] |
| 1.827 | 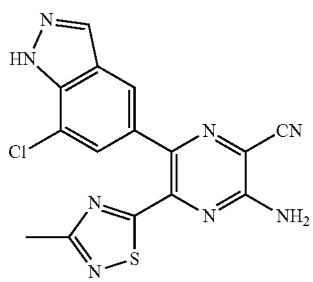 [SMILES: Cc1nsc(-c2nc(N)c(C#N)nc2-c2cc(Cl)c3[nH]ncc3c2)n1] |
| 1.828 | 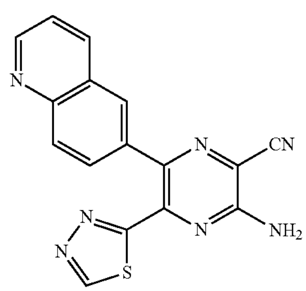 [SMILES: N#Cc1nc(-c2ccc3ncccc3c2)c(-c2nncs2)nc1N] |
| 1.829 | 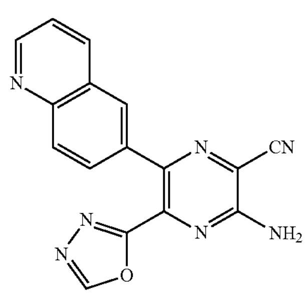 [SMILES: N#Cc1nc(-c2ccc3ncccc3c2)c(-c2nnco2)nc1N] |

TABLE 2-continued

| Compound No. | Structure |
|---|---|
| 1.830 | 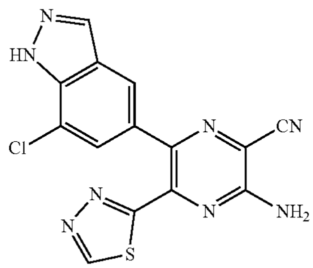 [SMILES: N#Cc1nc(-c2cc(Cl)c3[nH]ncc3c2)c(-c2nncs2)nc1N] |
| 1.831 | 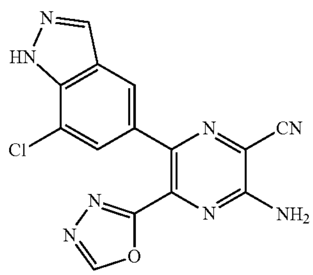 [SMILES: N#Cc1nc(-c2cc(Cl)c3[nH]ncc3c2)c(-c2nnco2)nc1N] |
| 1.832 | 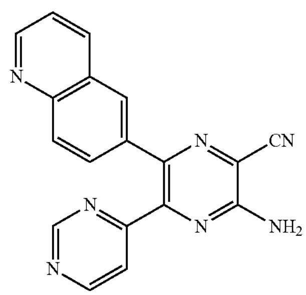 [SMILES: N#Cc1nc(-c2ccc3ncccc3c2)c(-c2ccncn2)nc1N] |
| 1.833 | 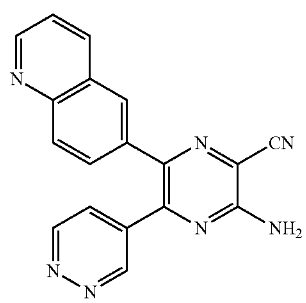 [SMILES: N#Cc1nc(-c2ccc3ncccc3c2)c(-c2ccnnc2)nc1N] |
| 1.834 | 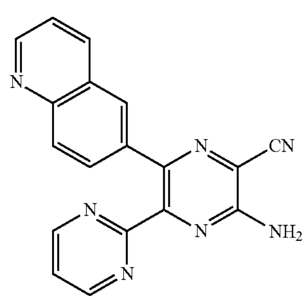 [SMILES: N#Cc1nc(-c2ccc3ncccc3c2)c(-c2ncccn2)nc1N] |

TABLE 2-continued

| Compound No. | Structure |
|---|---|
| 1.835 | 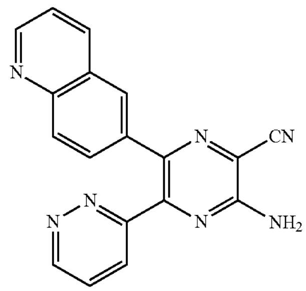 [SMILES: N#Cc1nc(-c2ccc3ncccc3c2)c(-c2cccnn2)nc1N] |
| 1.836 | 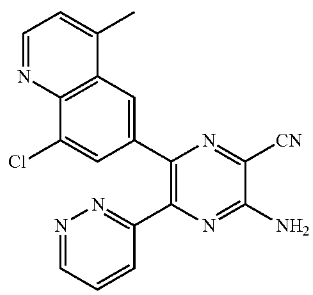 [SMILES: Cc1ccnc2c(Cl)cc(-c3nc(C#N)c(N)nc3-c3cccnn3)cc12] |
| 1.837 | 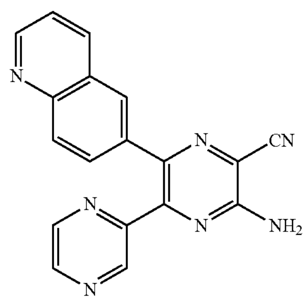 [SMILES: N#Cc1nc(-c2ccc3ncccc3c2)c(-c2cnccn2)nc1N] |
| 1.838 | 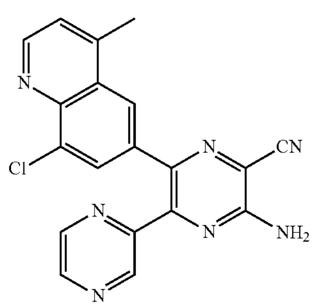 [SMILES: Cc1ccnc2c(Cl)cc(-c3nc(C#N)c(N)nc3-c3cnccn3)cc12] |
| 1.839 | 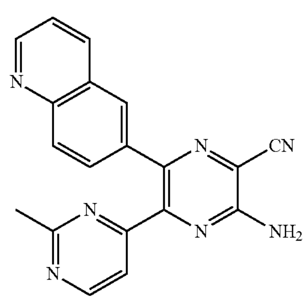 [SMILES: Cc1nccc(-c2nc(N)c(C#N)nc2-c2ccc3ncccc3c2)n1] |

TABLE 2-continued

| Compound No. | Structure |
|---|---|
| 1.840 | 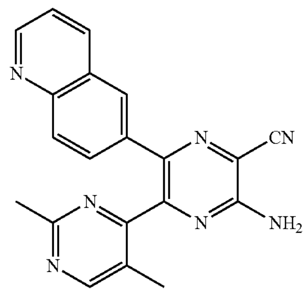 [SMILES: Cc1ncc(C)c(-c2nc(N)c(C#N)nc2-c2ccc3ncccc3c2)n1] |
| 1.841 | 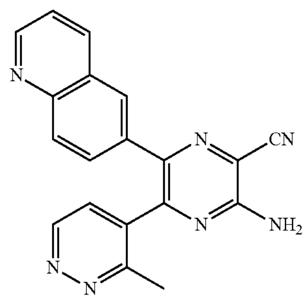 [SMILES: Cc1nnccc1-c1nc(N)c(C#N)nc1-c1ccc2ncccc2c1] |
| 1.842 | 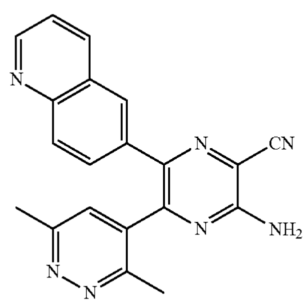 [SMILES: Cc1cc(-c2nc(N)c(C#N)nc2-c2ccc3ncccc3c2)c(C)nn1] |
| 1.843 | 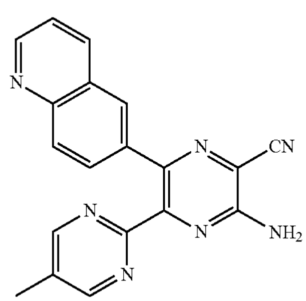 [SMILES: Cc1cnc(-c2nc(N)c(C#N)nc2-c2ccc3ncccc3c2)nc1] |
| 1.844 | 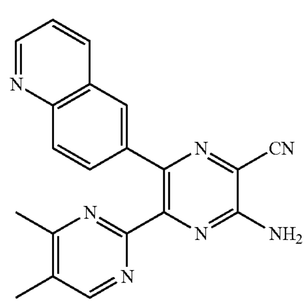 [SMILES: Cc1cnc(-c2nc(N)c(C#N)nc2-c2ccc3ncccc3c2)nc1C] |

TABLE 2-continued

| Compound No. | Structure |
|---|---|
| 1.845 | 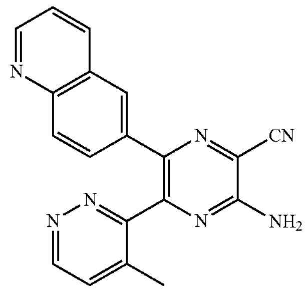 [SMILES: Cc1ccnnc1-c1nc(N)c(C#N)nc1-c1ccc2ncccc2c1] |
| 1.846 | 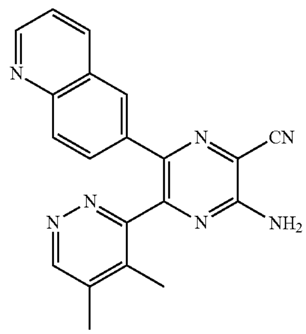 [SMILES: Cc1cnnc(-c2nc(N)c(C#N)nc2-c2ccc3ncccc3c2)c1C] |
| 1.847 | 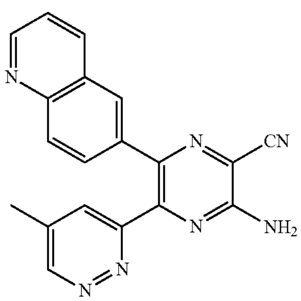 [SMILES: Cc1cnnc(-c2nc(N)c(C#N)nc2-c2ccc3ncccc3c2)c1] |
| 1.848 | 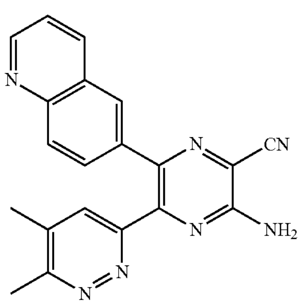 [SMILES: Cc1cc(-c2nc(N)c(C#N)nc2-c2ccc3ncccc3c2)nnc1C] |
| 1.849 | 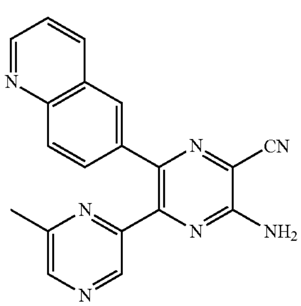 [SMILES: Cc1cncc(-c2nc(N)c(C#N)nc2-c2ccc3ncccc3c2)n1] |

TABLE 2-continued

| Compound No. | Structure |
|---|---|
| 1.850 | 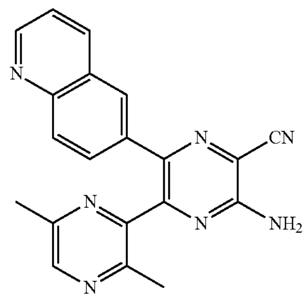 [SMILES: Cc1cnc(C)c(-c2nc(N)c(C#N)nc2-c2ccc3ncccc3c2)n1] |
| 1.851 | 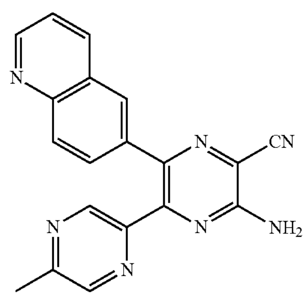 [SMILES: Cc1cnc(-c2nc(N)c(C#N)nc2-c2ccc3ncccc3c2)cn1] |
| 1.852 | 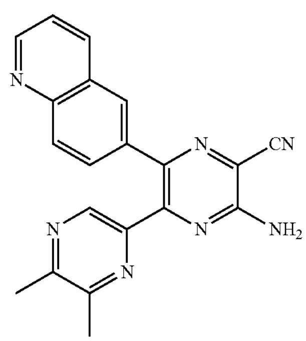 [SMILES: Cc1ncc(-c2nc(N)c(C#N)nc2-c2ccc3ncccc3c2)nc1C] |
| 1.853 | 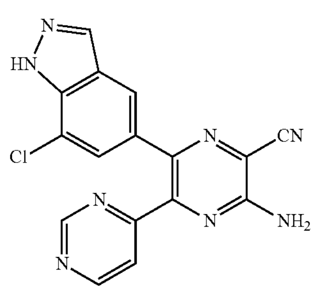 [SMILES: N#Cc1nc(-c2cc(Cl)c3[nH]ncc3c2)c(-c2ccncn2)nc1N] |
| 1.854 | 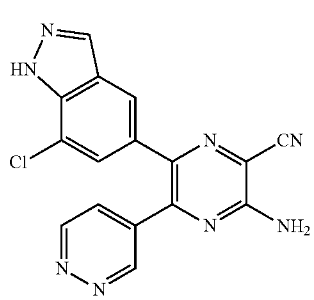 [SMILES: N#Cc1nc(-c2cc(Cl)c3[nH]ncc3c2)c(-c2ccnnc2)nc1N] |

TABLE 2-continued

| Compound No. | Structure |
|---|---|
| 1.855 | *7-chloro-1H-indazol-5-yl and pyrimidin-2-yl substituted 3-amino-pyrazine-2-carbonitrile* |
| 1.856 | *7-chloro-1H-indazol-5-yl and pyridazin-3-yl substituted 3-amino-pyrazine-2-carbonitrile* |
| 1.857 | *7-methyl-1H-indazol-5-yl and pyridazin-3-yl substituted 3-amino-pyrazine-2-carbonitrile* |
| 1.858 | *7-chloro-1H-indazol-5-yl and pyrazin-2-yl substituted 3-amino-pyrazine-2-carbonitrile* |
| 1.859 | *7-methyl-1H-indazol-5-yl and pyrazin-2-yl substituted 3-amino-pyrazine-2-carbonitrile* |

TABLE 2-continued

| Compound No. | Structure |
| --- | --- |
| 1.860 | 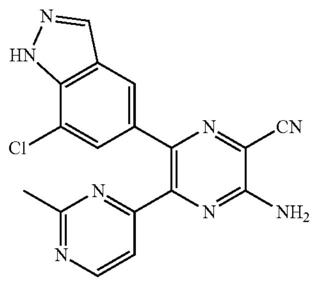 [SMILES: Cc1nccc(-c2nc(N)c(C#N)nc2-c2cc(Cl)c3[nH]ncc3c2)n1] |
| 1.861 | 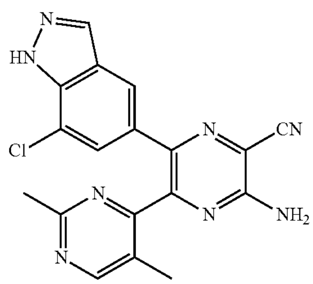 [SMILES: Cc1ncc(C)c(-c2nc(N)c(C#N)nc2-c2cc(Cl)c3[nH]ncc3c2)n1] |
| 1.862 | 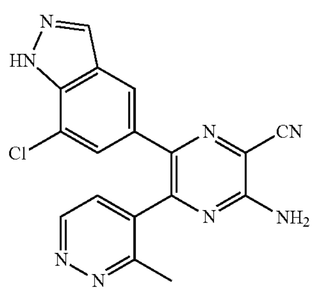 [SMILES: Cc1nnccc1-c1nc(N)c(C#N)nc1-c1cc(Cl)c2[nH]ncc2c1] |
| 1.863 | 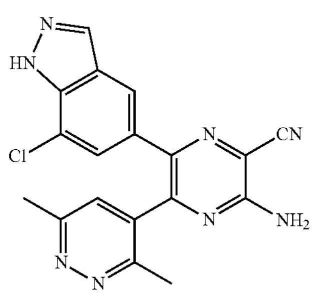 [SMILES: Cc1cc(-c2nc(N)c(C#N)nc2-c2cc(Cl)c3[nH]ncc3c2)c(C)nn1] |
| 1.864 | 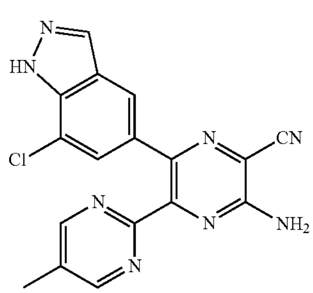 [SMILES: Cc1cnc(-c2nc(N)c(C#N)nc2-c2cc(Cl)c3[nH]ncc3c2)nc1] |

TABLE 2-continued

| Compound No. | Structure |
|---|---|
| 1.865 | 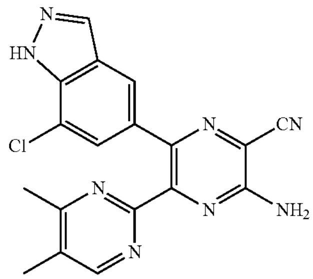 [SMILES: Cc1cnc(-c2nc(N)c(C#N)nc2-c2cc(Cl)c3[nH]ncc3c2)nc1C] |
| 1.866 | 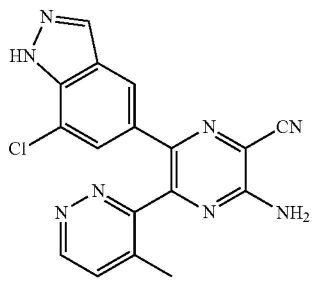 [SMILES: Cc1ccnnc1-c1nc(N)c(C#N)nc1-c1cc(Cl)c2[nH]ncc2c1] |
| 1.867 | 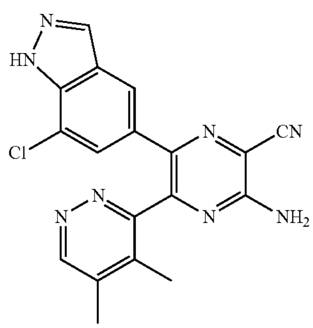 [SMILES: Cc1cnnc(-c2nc(N)c(C#N)nc2-c2cc(Cl)c3[nH]ncc3c2)c1C] |
| 1.868 | 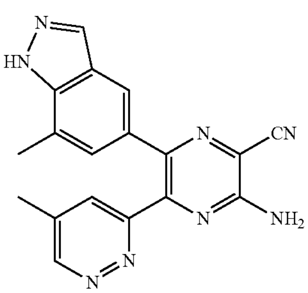 [SMILES: Cc1cnnc(-c2nc(N)c(C#N)nc2-c2cc(C)c3[nH]ncc3c2)c1] |
| 1.869 | 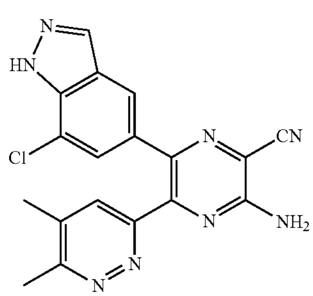 [SMILES: Cc1cc(-c2nc(N)c(C#N)nc2-c2cc(Cl)c3[nH]ncc3c2)nnc1C] |

TABLE 2-continued

| Compound No. | Structure |
|---|---|
| 1.870 | (structure) |
| 1.871 | (structure) |
| 1.872 | (structure) |
| 1.873 | (structure) |
| 1.874 | (structure) |

TABLE 2-continued
| Compound No. | Structure |
|---|---|
| 1.875 | 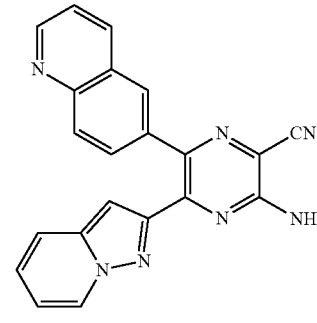 |
| 1.876 | 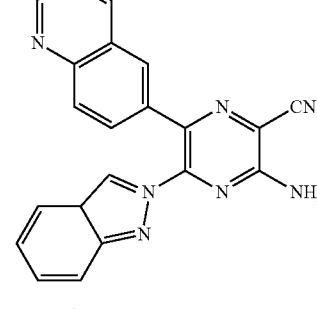 |
| 1.877 | 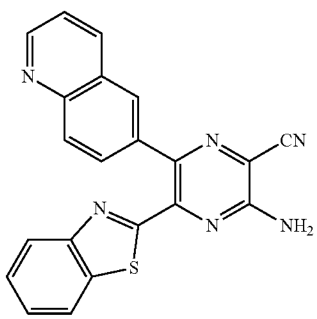 [SMILES: N#Cc1nc(-c2ccc3ncccc3c2)c(-c2nc3ccccc3s2)nc1N] |
| 1.878 | 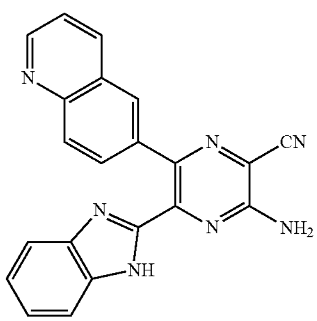 [SMILES: N#Cc1nc(-c2ccc3ncccc3c2)c(-c2nc3ccccc3[nH]2)nc1N] |
| 1.879 | 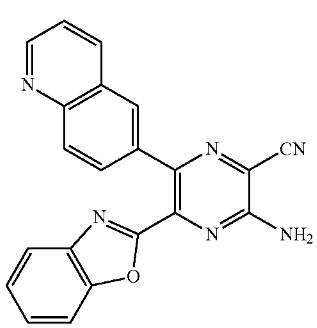 |

TABLE 2-continued

| Compound No. | Structure |
|---|---|
| 1.880 | (structure) |
| 1.881 | (structure) |
| 1.882 | (structure) |
| 1.883 | (structure) |
| 1.884 | (structure) |

TABLE 2-continued

| Compound No. | Structure |
| --- | --- |
| 1.885 | 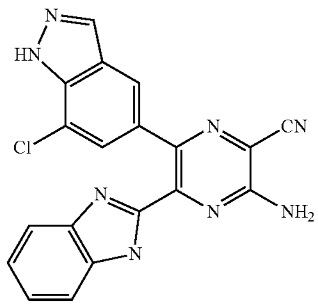 [SMILES: N#Cc1nc(-c2cc(Cl)c3[nH]ncc3c2)c(-c2nc3ccccc3s2)nc1N] |
| 1.886 | 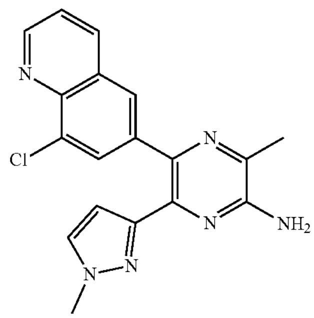 [SMILES: Cc1nc(-c2cc(Cl)c3ncccc3c2)c(-c2ccn(C)n2)nc1N] |
| 1.887 | 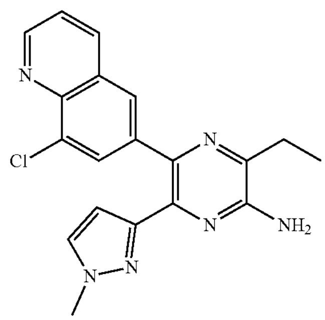 |
| 1.888 | 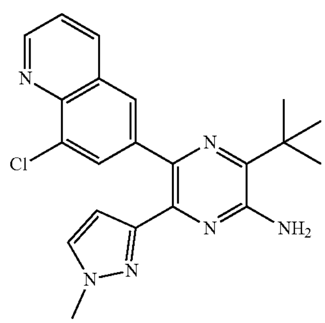 [SMILES: Cn1ccc(-c2nc(N)c(C(C)(C)C)nc2-c2cc(Cl)c3ncccc3c2)n1] |
| 1.889 | 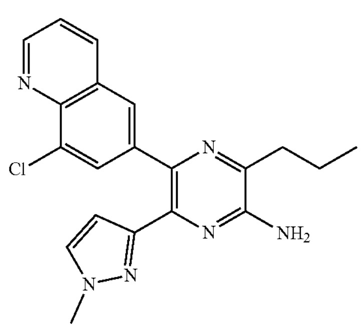 [SMILES: CCCc1nc(-c2cc(Cl)c3ncccc3c2)c(-c2ccn(C)n2)nc1N] |

TABLE 2-continued

| Compound No. | Structure |
|---|---|
| 1.890 | 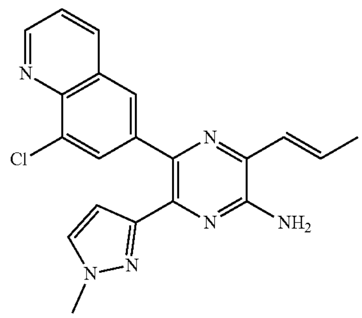 [SMILES: C/C=C/c1nc(-c2cc(Cl)c3ncccc3c2)c(-c2ccn(C)n2)nc1N] |
| 1.891 | 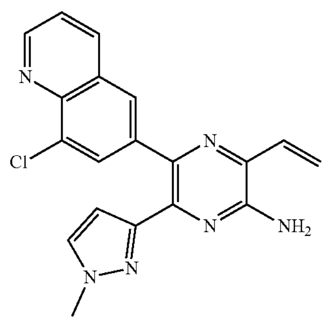 [SMILES: C=Cc1nc(-c2cc(Cl)c3ncccc3c2)c(-c2ccn(C)n2)nc1N] |
| 1.892 | 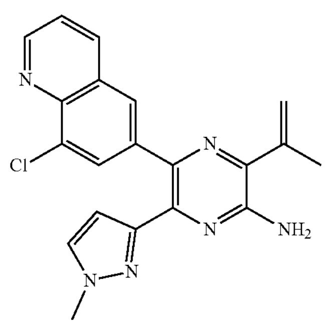 [SMILES: C=C(C)c1nc(-c2cc(Cl)c3ncccc3c2)c(-c2ccn(C)n2)nc1N] |
| 1.893 | 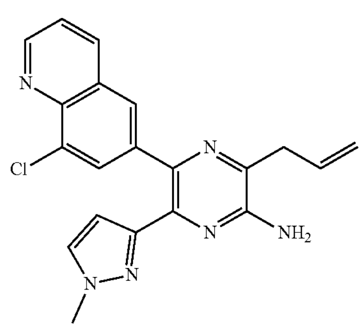 [SMILES: C=CCc1nc(-c2cc(Cl)c3ncccc3c2)c(-c2ccn(C)n2)nc1N] |

TABLE 2-continued
| Compound No. | Structure |
|---|---|
| 1.894 | 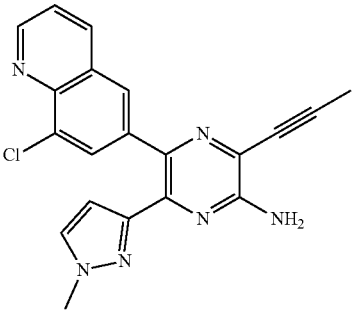 [SMILES: CC#Cc1nc(-c2cc(Cl)c3ncccc3c2)c(-c2ccn(C)n2)nc1N] |
| 1.895 | 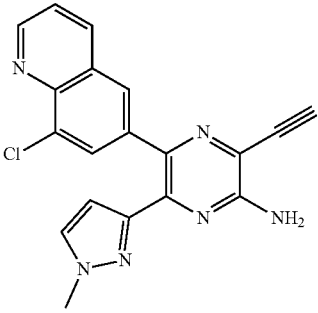 [SMILES: C#Cc1nc(-c2cc(Cl)c3ncccc3c2)c(-c2ccn(C)n2)nc1N] |
| 1.896 | 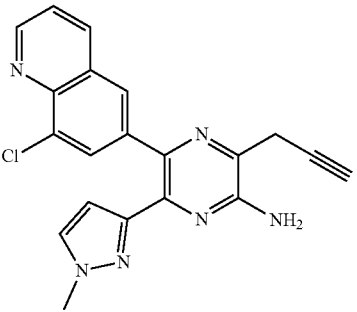 [SMILES: C#CCc1nc(-c2cc(Cl)c3ncccc3c2)c(-c2ccn(C)n2)nc1N] |
| 1.897 | 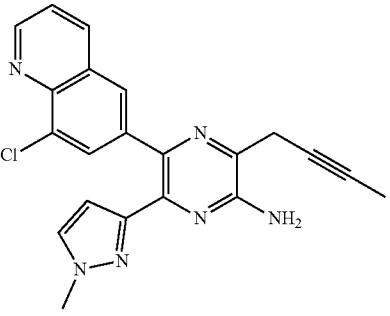 [SMILES: CC#CCc1nc(-c2cc(Cl)c3ncccc3c2)c(-c2ccn(C)n2)nc1N] |
| 1.898 | 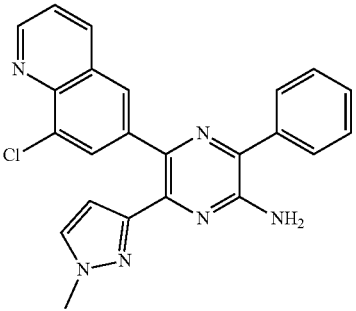 [SMILES: Cn1ccc(-c2nc(N)c(-c3ccccc3)nc2-c2cc(Cl)c3ncccc3c2)n1] |

TABLE 2-continued
| Compound No. | Structure |
|---|---|
| 1.899 | 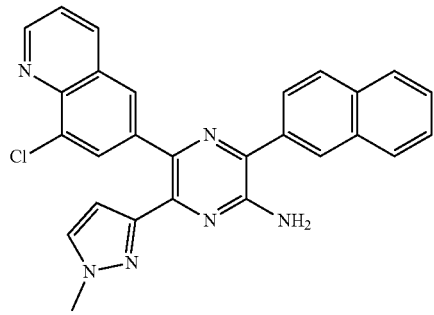 [SMILES: Cn1ccc(-c2nc(N)c(-c3ccc4ccccc4c3)nc2-c2cc(Cl)c3ncccc3c2)n1] |
| 1.900 | 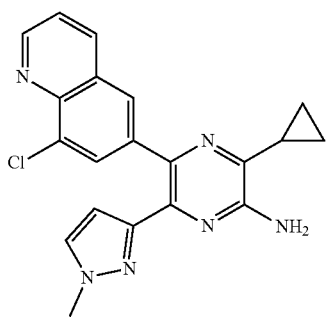 [SMILES: Cn1ccc(-c2nc(N)c(C3CC3)nc2-c2cc(Cl)c3ncccc3c2)n1] |
| 1.901 | 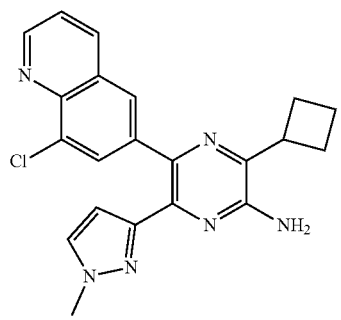 [SMILES: Cn1ccc(-c2nc(N)c(C3CCC3)nc2-c2cc(Cl)c3ncccc3c2)n1] |
| 1.902 | 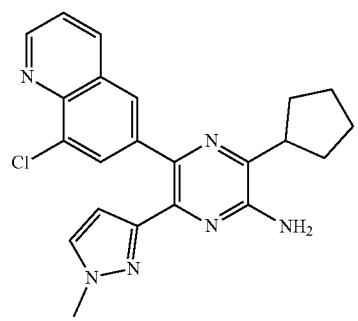 |

TABLE 2-continued

| Compound No. | Structure |
|---|---|
| 1.903 | 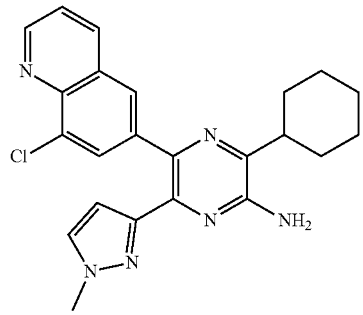 [SMILES: Cn1ccc(-c2nc(N)c(C3CCCCC3)nc2-c2cc(Cl)c3ncccc3c2)n1] |
| 1.904 | 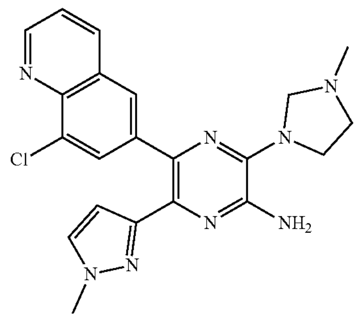 [SMILES: CN1CCN(c2nc(-c3cc(Cl)c4ncccc4c3)c(-c3ccn(C)n3)nc2N)C1] |
| 1.905 | 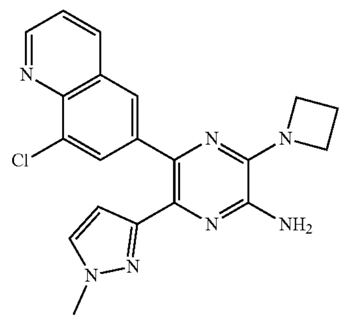 [SMILES: Cn1ccc(-c2nc(N)c(N3CCC3)nc2-c2cc(Cl)c3ncccc3c2)n1] |
| 1.906 | 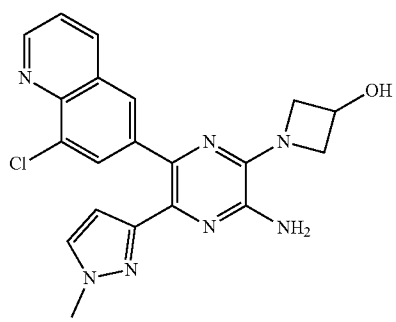 [SMILES: Cn1ccc(-c2nc(N)c(N3CC(O)C3)nc2-c2cc(Cl)c3ncccc3c2)n1] |
| 1.907 | 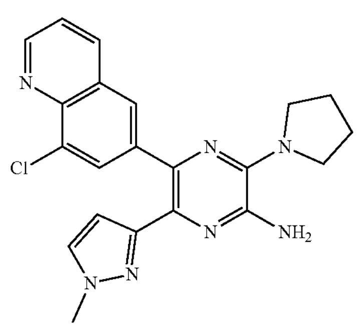 [SMILES: Cn1ccc(-c2nc(N)c(N3CCCC3)nc2-c2cc(Cl)c3ncccc3c2)n1] |

TABLE 2-continued
| Compound No. | Structure |
|---|---|
| 1.908 | 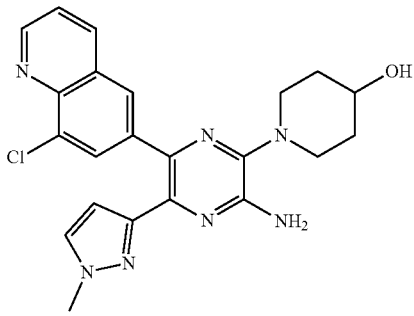 [SMILES: Cn1ccc(-c2nc(N)c(N3CCC(O)CC3)nc2-c2cc(Cl)c3ncccc3c2)n1] |
| 1.909 | 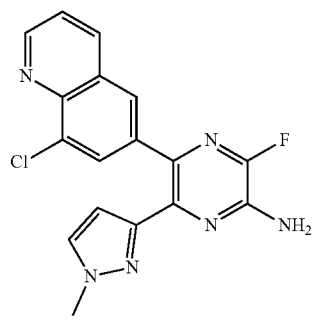 |
| 1.910 | 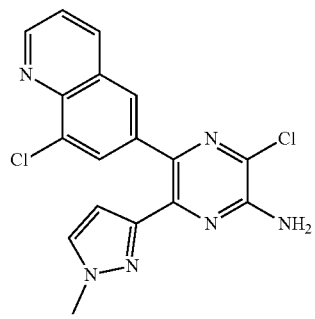 |
| 1.911 | 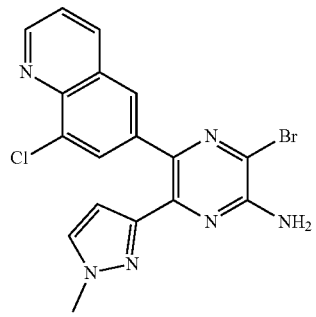 |

TABLE 2-continued

| Compound No. | Structure |
|---|---|
| 1.912 | 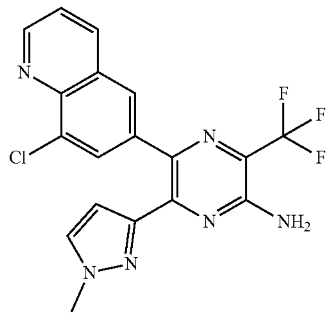 [SMILES: Cn1ccc(-c2nc(N)c(C(F)(F)F)nc2-c2cc(Cl)c3ncccc3c2)n1] |
| 1.913 | 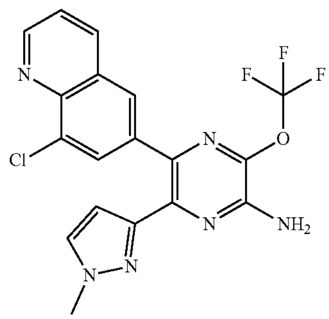 [SMILES: Cn1ccc(-c2nc(N)c(OC(F)(F)F)nc2-c2cc(Cl)c3ncccc3c2)n1] |
| 1.914 | 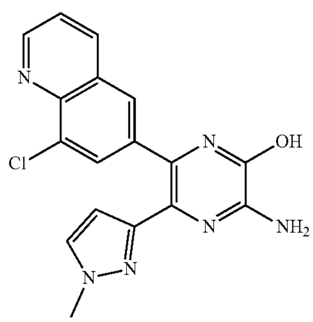 |
| 1.915 | 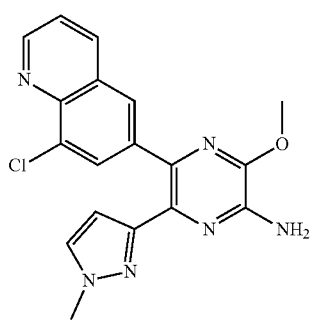 |

TABLE 2-continued

| Compound No. | Structure |
|---|---|
| 1.916 | 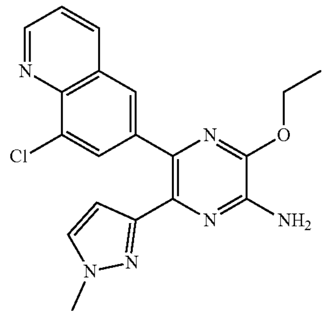 |
| 1.917 | 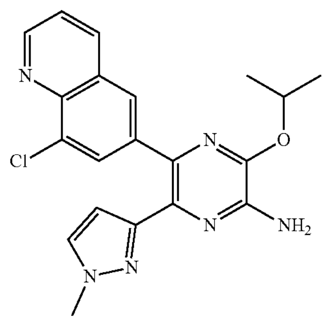 |
| 1.918 | 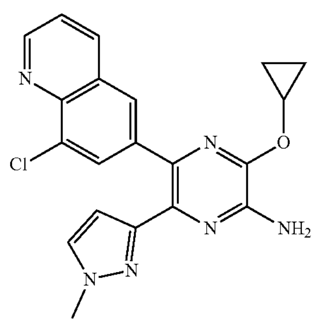 |
| 1.919 | 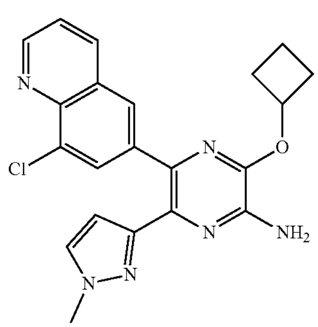 |

TABLE 2-continued

| Compound No. | Structure |
|---|---|
| 1.920 | 8-chloroquinolin-6-yl linked to pyrazine with cyclopentyloxy, NH₂, and 1-methylpyrazol-3-yl substituents |
| 1.921 | 8-chloroquinolin-6-yl linked to pyrazine with cyclohexyloxy, NH₂, and 1-methylpyrazol-3-yl substituents |
| 1.922 | 8-chloroquinolin-6-yl linked to pyrazine with (1-methyl-2-oxopiperidin-4-yl)oxy, NH₂, and 1-methylpyrazol-3-yl substituents |
| 1.923 | 8-chloroquinolin-6-yl linked to pyrazine with (1-methylazetidin-3-yl)oxy, NH₂, and 1-methylpyrazol-3-yl substituents |

TABLE 2-continued

| Compound No. | Structure |
|---|---|
| 1.924 | (8-chloroquinolin-6-yl, (1-methylpyrrolidin-3-yl)oxy, 1-methylpyrazol-3-yl, NH₂-substituted pyrazine) |
| 1.925 | (8-chloroquinolin-6-yl, (1-methylpiperidin-4-yl)oxy, 1-methylpyrazol-3-yl, NH₂-substituted pyrazine) |
| 1.926 | (8-chloroquinolin-6-yl, phenoxy, 1-methylpyrazol-3-yl, NH₂-substituted pyrazine) |
| 1.927 | (8-chloroquinolin-6-yl, pyridin-3-yloxy, 1-methylpyrazol-3-yl, NH₂-substituted pyrazine) |

TABLE 2-continued

| Compound No. | Structure |
| --- | --- |
| 1.928 | 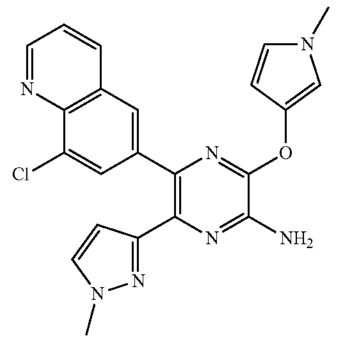 [SMILES: Cn1ccc(Oc2nc(-c3cc(Cl)c4ncccc4c3)c(-c3ccn(C)n3)nc2N)c1] |
| 1.929 | 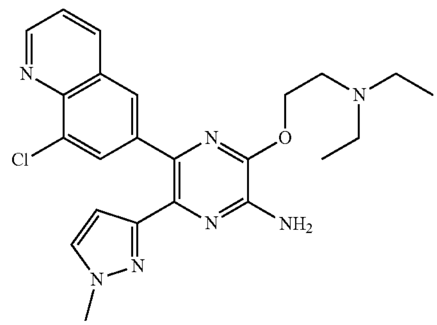 [SMILES: CCN(CC)CCOc1nc(-c2cc(Cl)c3ncccc3c2)c(-c2ccn(C)n2)nc1N] |
| 1.930 | 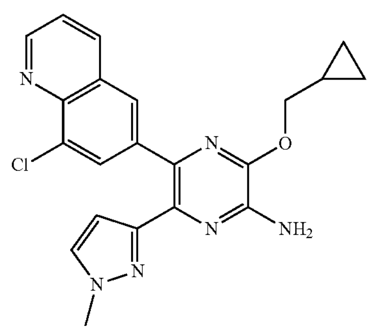 [SMILES: Cn1ccc(-c2nc(N)c(OCC3CC3)nc2-c2cc(Cl)c3ncccc3c2)n1] |
| 1.931 | 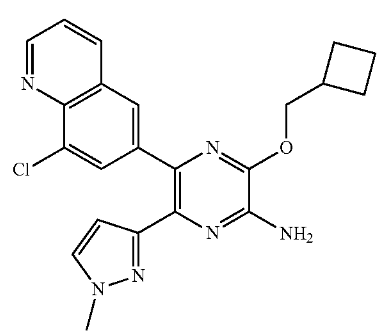 [SMILES: Cn1ccc(-c2nc(N)c(OCC3CCC3)nc2-c2cc(Cl)c3ncccc3c2)n1] |

TABLE 2-continued
| Compound No. | Structure |
|---|---|
| 1.932 | 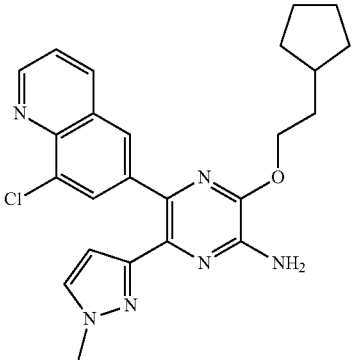 [SMILES: Cn1ccc(-c2nc(N)c(OCCC3CCCC3)nc2-c2cc(Cl)c3ncccc3c2)n1] |
| 1.933 | 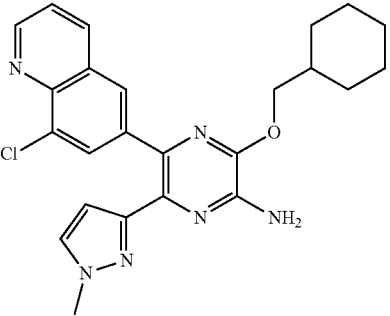 [SMILES: Cn1ccc(-c2nc(N)c(OCC3CCCCC3)nc2-c2cc(Cl)c3ncccc3c2)n1] |
| 1.934 | 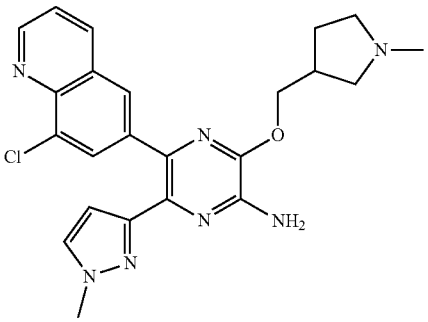 [SMILES: CN1CCC(COc2nc(-c3cc(Cl)c4ncccc4c3)c(-c3ccn(C)n3)nc2N)C1] |
| 1.935 | 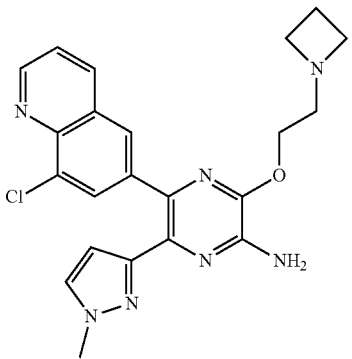 [SMILES: Cn1ccc(-c2nc(N)c(OCCN3CCC3)nc2-c2cc(Cl)c3ncccc3c2)n1] |

TABLE 2-continued
| Compound No. | Structure |
|---|---|
| 1.936 | 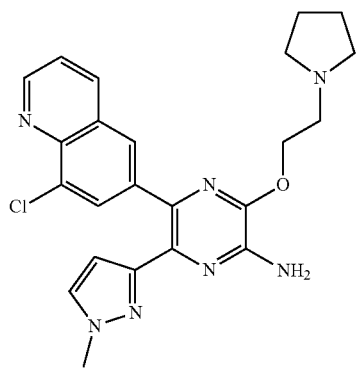 [SMILES: Cn1ccc(-c2nc(N)c(OCCN3CCCC3)nc2-c2cc(Cl)c3ncccc3c2)n1] |
| 1.937 | 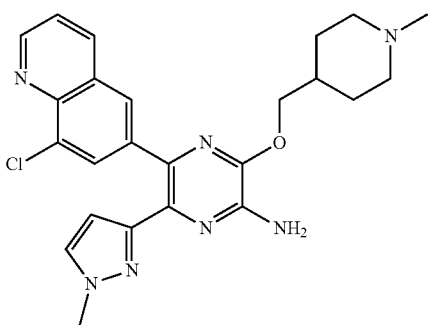 [SMILES: CN1CCC(COc2nc(-c3cc(Cl)c4ncccc4c3)c(-c3ccn(C)n3)nc2N)CC1] |
| 1.938 | 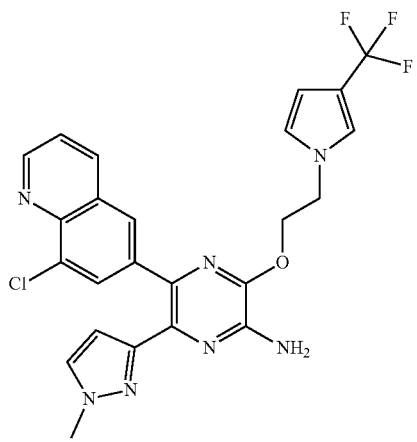 [SMILES: Cn1ccc(-c2nc(N)c(OCCn3ccc(C(F)(F)F)c3)nc2-c2cc(Cl)c3ncccc3c2)n1] |
| 1.939 | 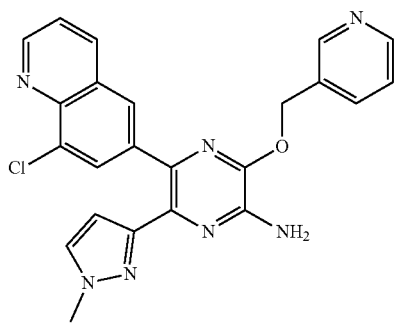 [SMILES: Cn1ccc(-c2nc(N)c(OCc3cccnc3)nc2-c2cc(Cl)c3ncccc3c2)n1] |

TABLE 2-continued

| Compound No. | Structure |
|---|---|
| 1.940 | (8-chloroquinolin-6-yl)-pyrazine with 4-fluorobenzyloxy, 1-methylpyrazol-3-yl, and NH₂ substituents |
| 1.941 | (8-chloroquinolin-6-yl)-pyrazine with 4-cyanobenzyloxy, 1-methylpyrazol-3-yl, and NH₂ substituents |
| 1.942 | (8-chloroquinolin-6-yl)-pyrazine with (6-(methylamino)pyridin-3-yl)methoxy, 1-methylpyrazol-3-yl, and NH₂ substituents |
| 1.943 | (8-chloroquinolin-6-yl)-pyrazine with methylthio, 1-methylpyrazol-3-yl, and NH₂ substituents |

TABLE 2-continued

| Compound No. | Structure |
|---|---|
| 1.944 | (8-chloroquinolin-6-yl, ethylthio, 1-methylpyrazol-3-yl, amino pyrazine) |
| 1.945 | (8-chloroquinolin-6-yl, isopropylthio, 1-methylpyrazol-3-yl, amino pyrazine) |
| 1.946 | (8-chloroquinolin-6-yl, cyclopropylthio, 1-methylpyrazol-3-yl, amino pyrazine) |
| 1.947 | (8-chloroquinolin-6-yl, cyclobutylthio, 1-methylpyrazol-3-yl, amino pyrazine) |
| 1.948 | (8-chloroquinolin-6-yl, cyclopentylthio, 1-methylpyrazol-3-yl, amino pyrazine) |

TABLE 2-continued

| Compound No. | Structure |
|---|---|
| 1.949 | 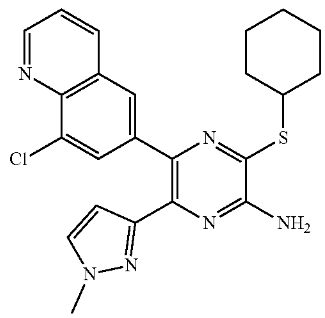 [SMILES: Cn1ccc(-c2nc(N)c(SC3CCCCC3)nc2-c2cc(Cl)c3ncccc3c2)n1] |
| 1.950 | 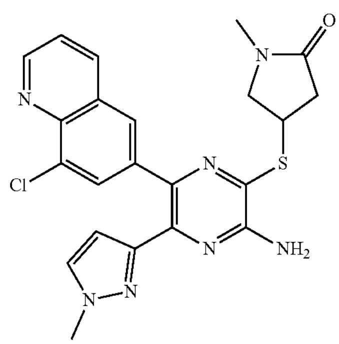 [SMILES: CN1CC(Sc2nc(-c3cc(Cl)c4ncccc4c3)c(-c3ccn(C)n3)nc2N)CC1=O] |
| 1.951 | 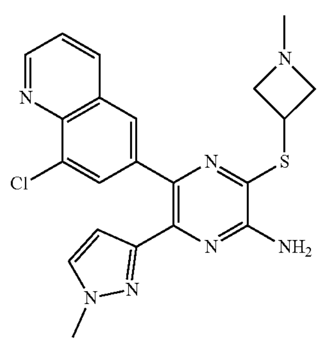 [SMILES: CN1CC(Sc2nc(-c3cc(Cl)c4ncccc4c3)c(-c3ccn(C)n3)nc2N)C1] |
| 1.952 | 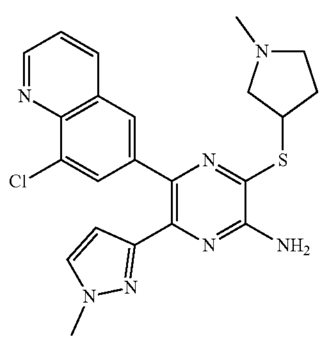 [SMILES: CN1CCC(Sc2nc(-c3cc(Cl)c4ncccc4c3)c(-c3ccn(C)n3)nc2N)C1] |

TABLE 2-continued

| Compound No. | Structure |
|---|---|
| 1.953 | 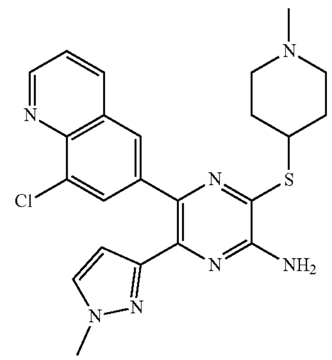 [SMILES: CN1CCC(Sc2nc(-c3cc(Cl)c4ncccc4c3)c(-c3ccn(C)n3)nc2N)CC1] |
| 1.954 | 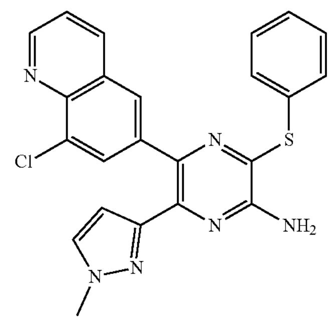 [SMILES: Cn1ccc(-c2nc(N)c(Sc3ccccc3)nc2-c2cc(Cl)c3ncccc3c2)n1] |
| 1.955 | 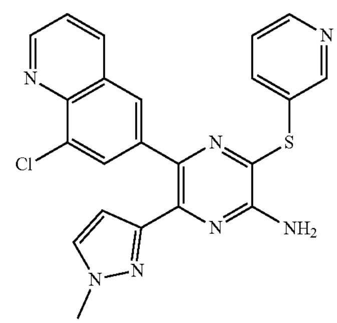 [SMILES: Cn1ccc(-c2nc(N)c(Sc3cccnc3)nc2-c2cc(Cl)c3ncccc3c2)n1] |
| 1.956 | 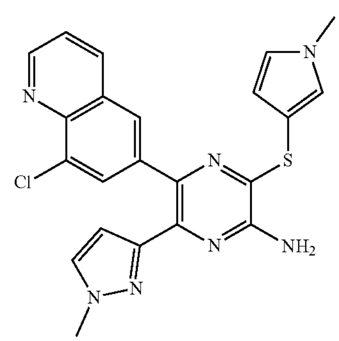 [SMILES: Cn1ccc(Sc2nc(-c3cc(Cl)c4ncccc4c3)c(-c3ccn(C)n3)nc2N)c1] |

TABLE 2-continued
| Compound No. | Structure |
|---|---|
| 1.957 | 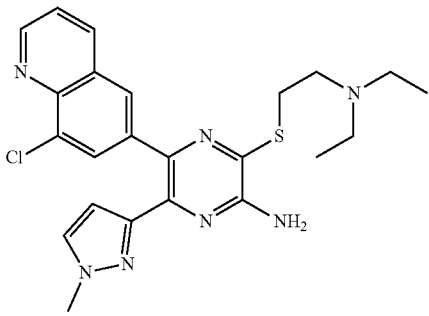 [SMILES: CCN(CC)CCSc1nc(-c2cc(Cl)c3ncccc3c2)c(-c2ccn(C)n2)nc1N] |
| 1.958 | 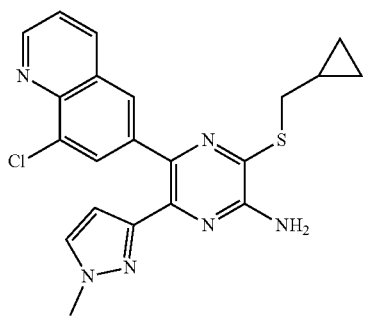 [SMILES: Cn1ccc(-c2nc(N)c(SCC3CC3)nc2-c2cc(Cl)c3ncccc3c2)n1] |
| 1.959 | 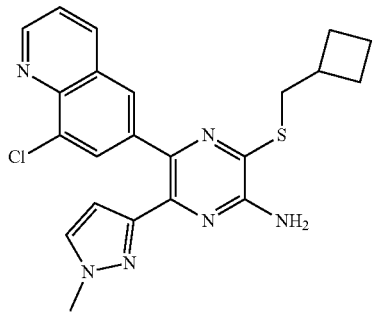 [SMILES: Cn1ccc(-c2nc(N)c(SCC3CCC3)nc2-c2cc(Cl)c3ncccc3c2)n1] |
| 1.960 | 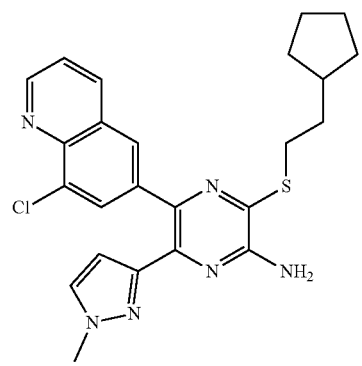 [SMILES: Cn1ccc(-c2nc(N)c(SCCC3CCCC3)nc2-c2cc(Cl)c3ncccc3c2)n1] |

TABLE 2-continued

| Compound No. | Structure |
|---|---|
| 1.961 | 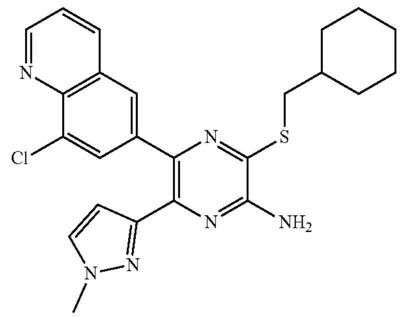 [SMILES: Cn1ccc(-c2nc(N)c(SCC3CCCCC3)nc2-c2cc(Cl)c3ncccc3c2)n1] |
| 1.962 | 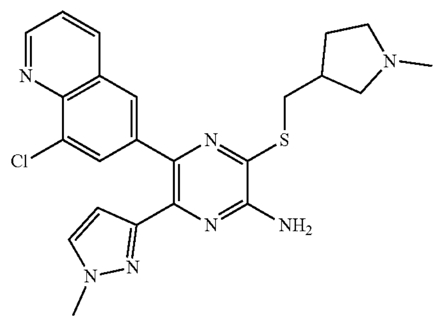 [SMILES: CN1CCC(CSc2nc(-c3cc(Cl)c4ncccc4c3)c(-c3ccn(C)n3)nc2N)C1] |
| 1.963 | 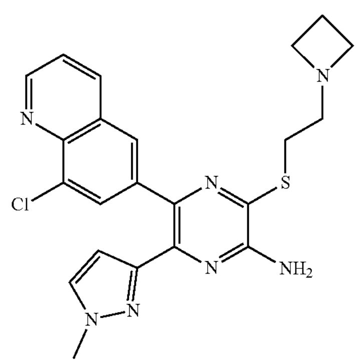 [SMILES: Cn1ccc(-c2nc(N)c(SCCN3CCC3)nc2-c2cc(Cl)c3ncccc3c2)n1] |
| 1.964 | 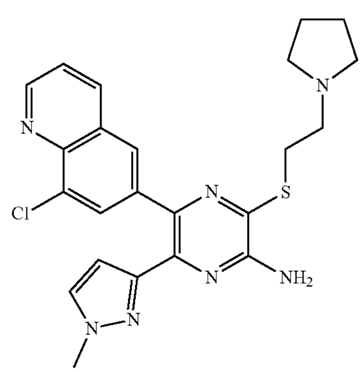 [SMILES: Cn1ccc(-c2nc(N)c(SCCN3CCCC3)nc2-c2cc(Cl)c3ncccc3c2)n1] |

TABLE 2-continued

| Compound No. | Structure |
|---|---|
| 1.965 | 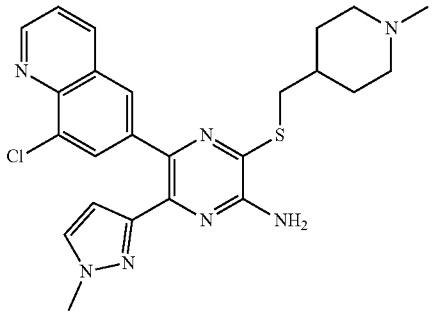 [SMILES: CN1CCC(CSc2nc(-c3cc(Cl)c4ncccc4c3)c(-c3ccn(C)n3)nc2N)CC1] |
| 1.966 | 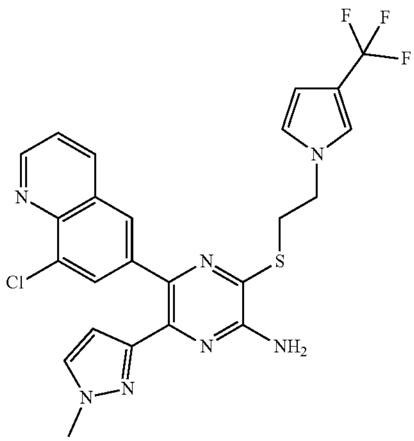 [SMILES: Cn1ccc(-c2nc(N)c(SCCn3ccc(C(F)(F)F)c3)nc2-c2cc(Cl)c3ncccc3c2)n1] |
| 1.967 | 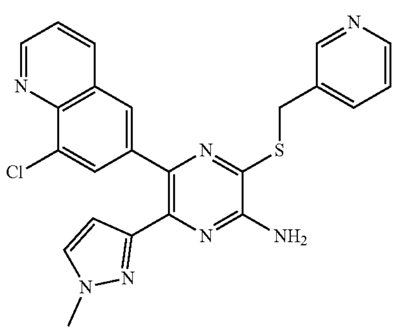 [SMILES: Cn1ccc(-c2nc(N)c(SCc3cccnc3)nc2-c2cc(Cl)c3ncccc3c2)n1] |
| 1.968 | 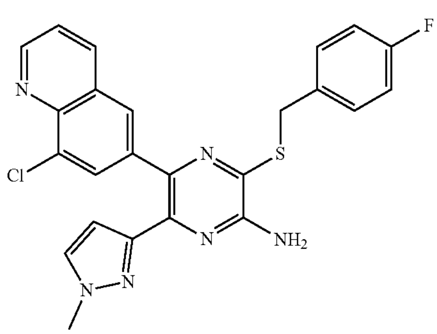 [SMILES: Cn1ccc(-c2nc(N)c(SCc3ccc(F)cc3)nc2-c2cc(Cl)c3ncccc3c2)n1] |

TABLE 2-continued
| Compound No. | Structure |
|---|---|
| 1.969 | 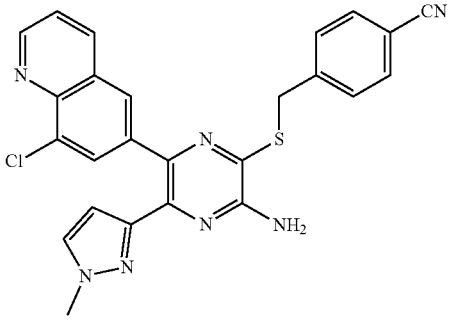 |
| 1.970 | 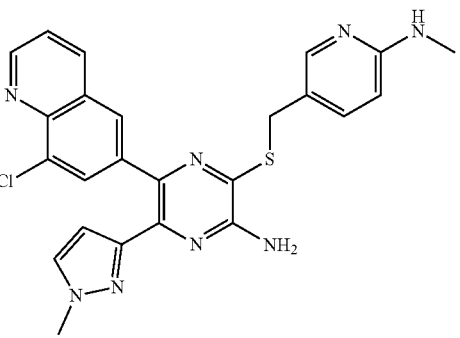 |
| 1.971 | 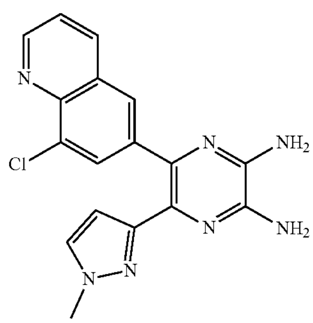 [SMILES: Cn1ccc(-c2nc(N)c(N)nc2-c2cc(Cl)c3ncccc3c2)n1] |
| 1.972 | 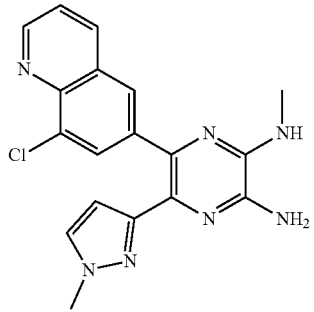 [SMILES: CNc1nc(-c2cc(Cl)c3ncccc3c2)c(-c2ccn(C)n2)nc1N] |

TABLE 2-continued

| Compound No. | Structure |
|---|---|
| 1.973 | 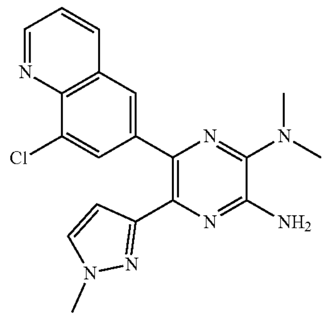 [SMILES: CN(C)c1nc(-c2cc(Cl)c3ncccc3c2)c(-c2ccn(C)n2)nc1N] |
| 1.974 | 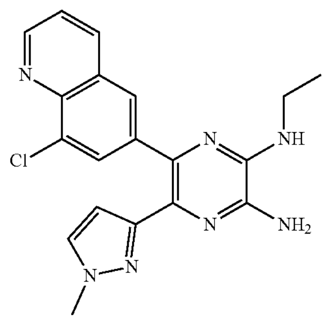 [SMILES: CCNc1nc(-c2cc(Cl)c3ncccc3c2)c(-c2ccn(C)n2)nc1N] |
| 1.975 | 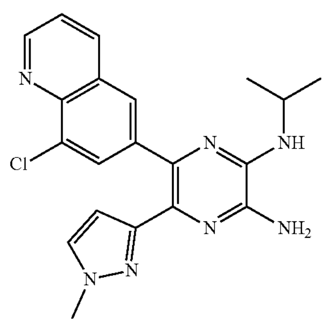 [SMILES: CC(C)Nc1nc(-c2cc(Cl)c3ncccc3c2)c(-c2ccn(C)n2)nc1N] |
| 1.976 | 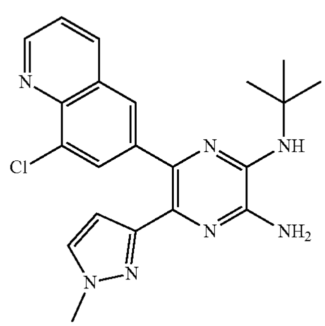 [SMILES: Cn1ccc(-c2nc(N)c(NC(C)(C)C)nc2-c2cc(Cl)c3ncccc3c2)n1] |

TABLE 2-continued

| Compound No. | Structure |
|---|---|
| 1.977 | 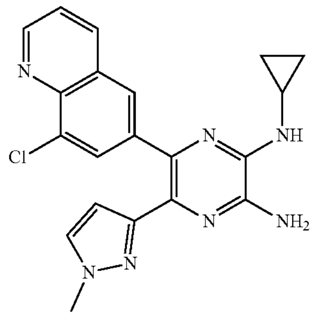 [SMILES: Cn1ccc(-c2nc(N)c(NC3CC3)nc2-c2cc(Cl)c3ncccc3c2)n1] |
| 1.978 | 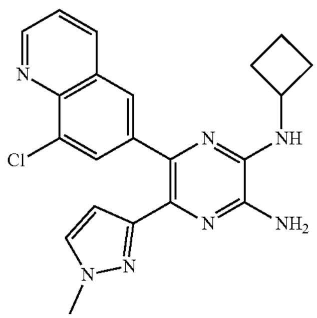 [SMILES: Cn1ccc(-c2nc(N)c(NC3CCC3)nc2-c2cc(Cl)c3ncccc3c2)n1] |
| 1.979 | 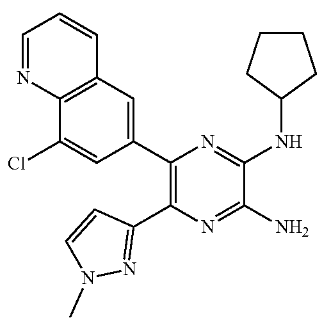 [SMILES: Cn1ccc(-c2nc(N)c(NC3CCCC3)nc2-c2cc(Cl)c3ncccc3c2)n1] |
| 1.980 | 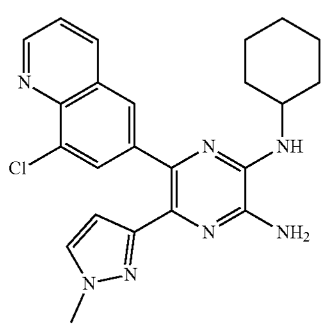 [SMILES: Cn1ccc(-c2nc(N)c(NC3CCCCC3)nc2-c2cc(Cl)c3ncccc3c2)n1] |

TABLE 2-continued

| Compound No. | Structure |
| --- | --- |
| 1.981 | 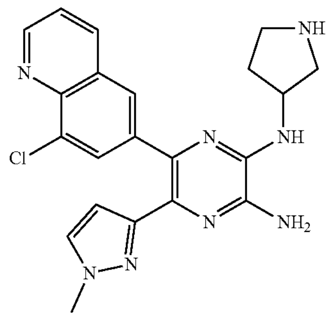 [SMILES: Cn1ccc(-c2nc(N)c(NC3CCNC3)nc2-c2cc(Cl)c3ncccc3c2)n1] |
| 1.982 | 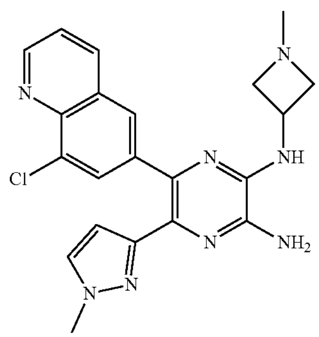 [SMILES: CN1CC(Nc2nc(-c3cc(Cl)c4ncccc4c3)c(-c3ccn(C)n3)nc2N)C1] |
| 1.983 | 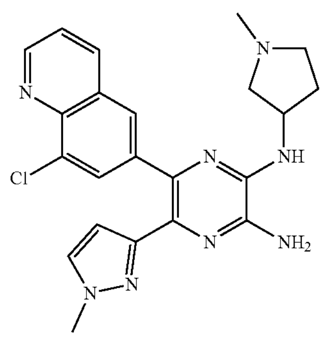 [SMILES: CN1CCC(Nc2nc(-c3cc(Cl)c4ncccc4c3)c(-c3ccn(C)n3)nc2N)C1] |
| 1.984 | 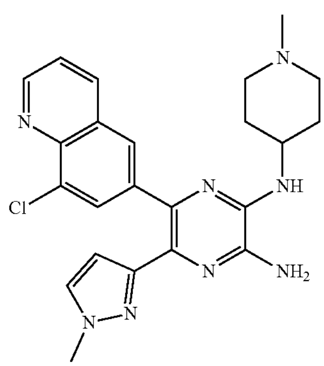 [SMILES: CN1CCC(Nc2nc(-c3cc(Cl)c4ncccc4c3)c(-c3ccn(C)n3)nc2N)CC1] |

TABLE 2-continued
| Compound No. | Structure |
|---|---|
| 1.985 | 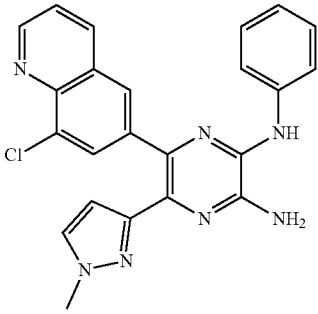 [SMILES: Cn1ccc(-c2nc(N)c(Nc3ccccc3)nc2-c2cc(Cl)c3ncccc3c2)n1] |
| 1.986 | 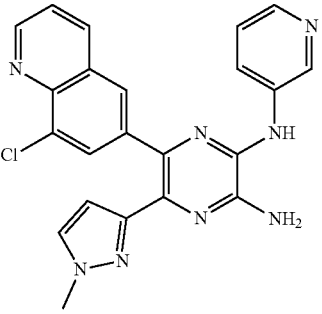 [SMILES: Cn1ccc(-c2nc(N)c(Nc3cccnc3)nc2-c2cc(Cl)c3ncccc3c2)n1] |
| 1.987 | 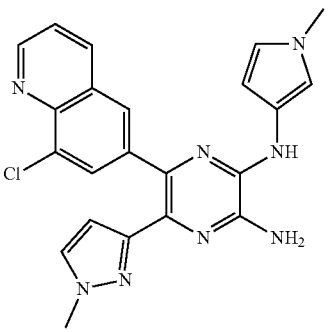 [SMILES: Cn1ccc(Nc2nc(-c3cc(Cl)c4ncccc4c3)c(-c3ccn(C)n3)nc2N)c1] |
| 1.988 | 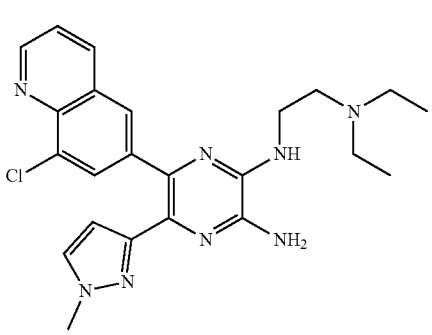 [SMILES: CCN(CC)CCNc1nc(-c2cc(Cl)c3ncccc3c2)c(-c2ccn(C)n2)nc1N] |

TABLE 2-continued
| Compound No. | Structure |
|---|---|
| 1.989 | 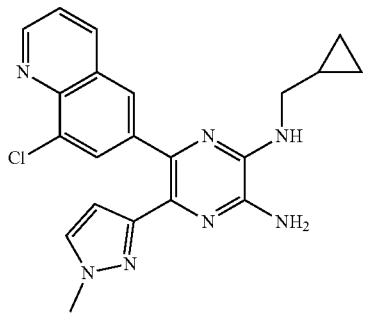 [SMILES: Cn1ccc(-c2nc(N)c(NCC3CC3)nc2-c2cc(Cl)c3ncccc3c2)n1] |
| 1.990 | 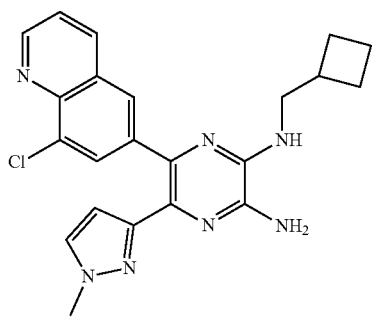 [SMILES: Cn1ccc(-c2nc(N)c(NCC3CCC3)nc2-c2cc(Cl)c3ncccc3c2)n1] |
| 1.991 | 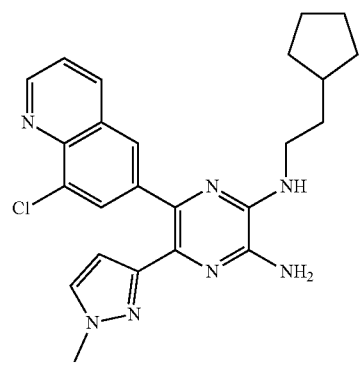 [SMILES: Cn1ccc(-c2nc(N)c(NCCC3CCCC3)nc2-c2cc(Cl)c3ncccc3c2)n1] |
| 1.992 | 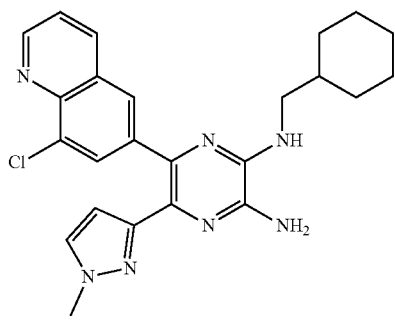 [SMILES: Cn1ccc(-c2nc(N)c(NCC3CCCCC3)nc2-c2cc(Cl)c3ncccc3c2)n1] |

TABLE 2-continued
| Compound No. | Structure |
|---|---|
| 1.993 | 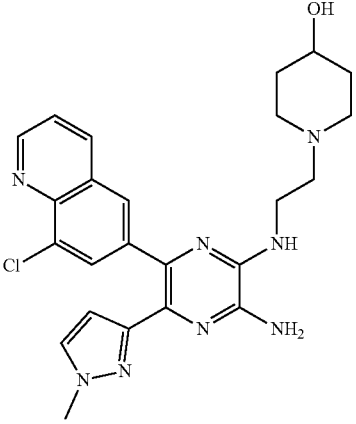 [SMILES: Cn1ccc(-c2nc(N)c(NCCN3CCC(O)CC3)nc2-c2cc(Cl)c3ncccc3c2)n1] |
| 1.994 | 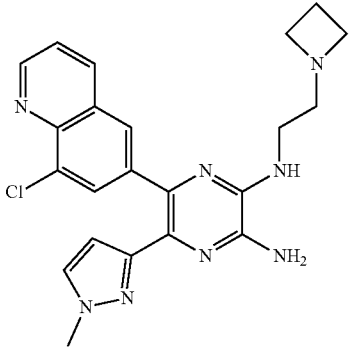 [SMILES: Cn1ccc(-c2nc(N)c(NCCN3CCC3)nc2-c2cc(Cl)c3ncccc3c2)n1] |
| 1.995 | 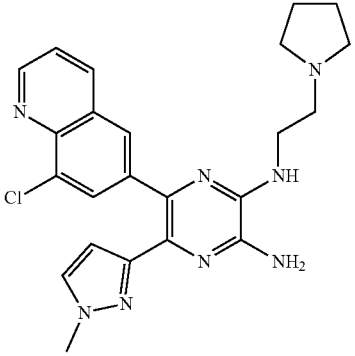 [SMILES: Cn1ccc(-c2nc(N)c(NCCN3CCCC3)nc2-c2cc(Cl)c3ncccc3c2)n1] |
| 1.996 | 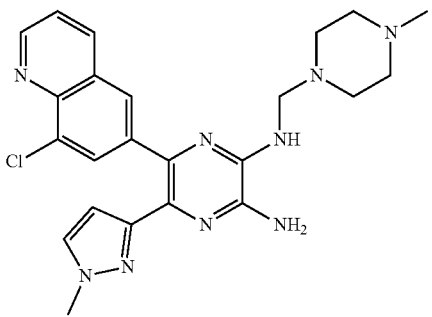 [SMILES: CN1CCN(CNc2nc(-c3cc(Cl)c4ncccc4c3)c(-c3ccn(C)n3)nc2N)CC1] |

TABLE 2-continued

| Compound No. | Structure |
|---|---|
| 1.997 | 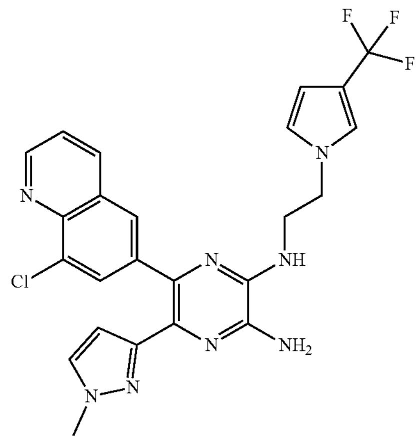 [SMILES: Cn1ccc(-c2nc(N)c(NCCn3ccc(C(F)(F)F)c3)nc2-c2cc(Cl)c3ncccc3c2)n1] |
| 1.998 | 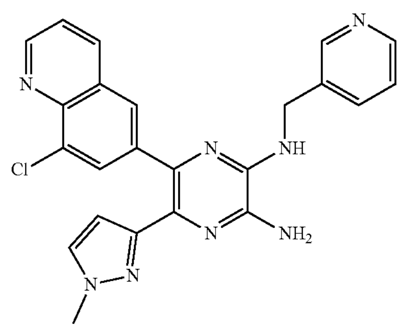 [SMILES: Cn1ccc(-c2nc(N)c(NCc3cccnc3)nc2-c2cc(Cl)c3ncccc3c2)n1] |
| 1.999 | 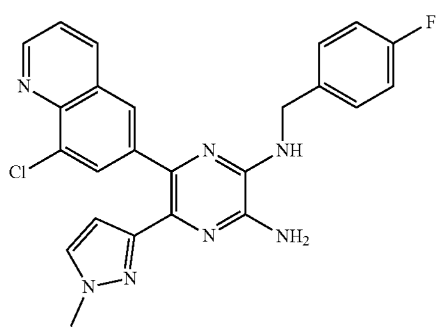 [SMILES: Cn1ccc(-c2nc(N)c(NCc3ccc(F)cc3)nc2-c2cc(Cl)c3ncccc3c2)n1] |
| 2.000 | 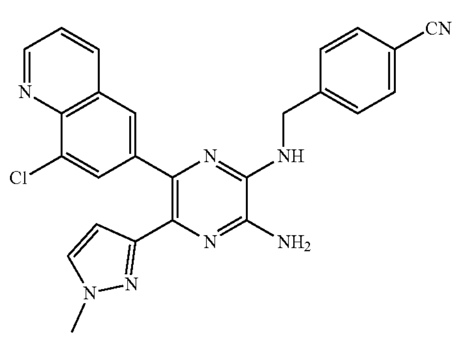 [SMILES: Cn1ccc(-c2nc(N)c(NCc3ccc(C#N)cc3)nc2-c2cc(Cl)c3ncccc3c2)n1] |

TABLE 2-continued

| Compound No. | Structure |
|---|---|
| 2.001 | 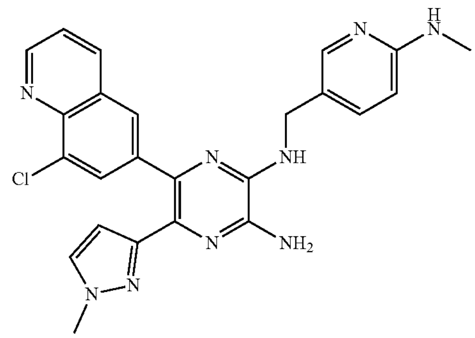 [SMILES: CNc1ccc(CNc2nc(-c3cc(Cl)c4ncccc4c3)c(-c3ccn(C)n3)nc2N)cn1] |
| 2.002 | 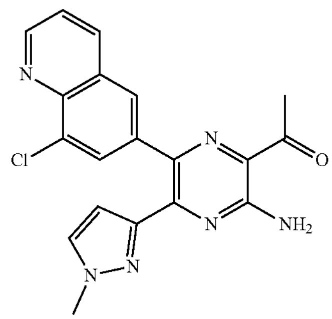 [SMILES: CC(=O)c1nc(-c2cc(Cl)c3ncccc3c2)c(-c2ccn(C)n2)nc1N] |
| 2.003 | 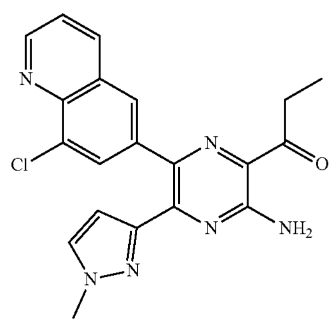 [SMILES: CCC(=O)c1nc(-c2cc(Cl)c3ncccc3c2)c(-c2ccn(C)n2)nc1N] |
| 2.004 | 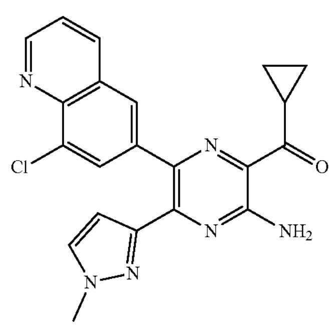 [SMILES: Cn1ccc(-c2nc(N)c(C(=O)C3CC3)nc2-c2cc(Cl)c3ncccc3c2)n1] |

TABLE 2-continued
| Compound No. | Structure |
|---|---|
| 2.005 | 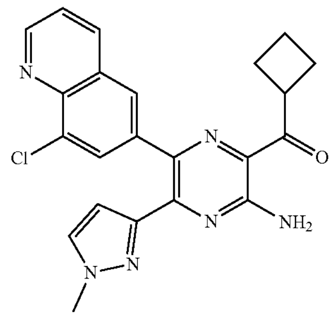 [SMILES: Cn1ccc(-c2nc(N)c(C(=O)C3CCC3)nc2-c2cc(Cl)c3ncccc3c2)n1] |
| 2.006 | 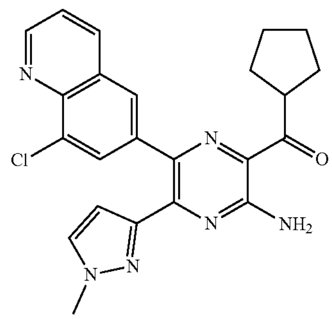 [SMILES: Cn1ccc(-c2nc(N)c(C(=O)C3CCCC3)nc2-c2cc(Cl)c3ncccc3c2)n1] |
| 2.007 | 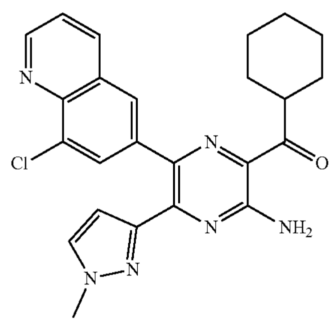 [SMILES: Cn1ccc(-c2nc(N)c(C(=O)C3CCCCC3)nc2-c2cc(Cl)c3ncccc3c2)n1] |
| 2.008 | 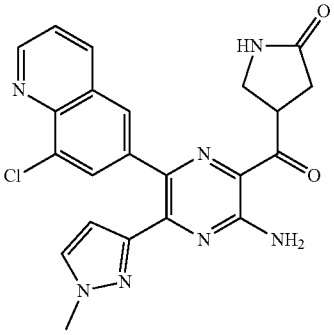 [SMILES: Cn1ccc(-c2nc(N)c(C(=O)C3CNC(=O)C3)nc2-c2cc(Cl)c3ncccc3c2)n1] |

TABLE 2-continued

| Compound No. | Structure |
|---|---|
| 2.009 | 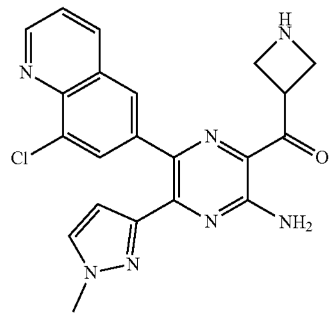 [SMILES: Cn1ccc(-c2nc(N)c(C(=O)C3CNC3)nc2-c2cc(Cl)c3ncccc3c2)n1] |
| 2.010 | 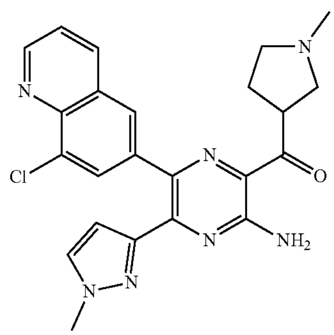 [SMILES: CN1CCC(C(=O)c2nc(-c3cc(Cl)c4ncccc4c3)c(-c3ccn(C)n3)nc2N)C1] |
| 2.011 | 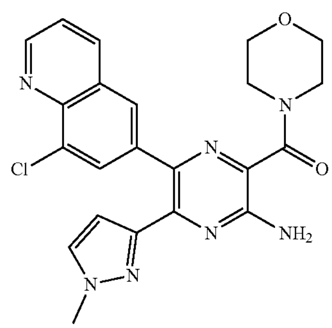 [SMILES: Cn1ccc(-c2nc(N)c(C(=O)N3CCOCC3)nc2-c2cc(Cl)c3ncccc3c2)n1] |
| 2.012 | 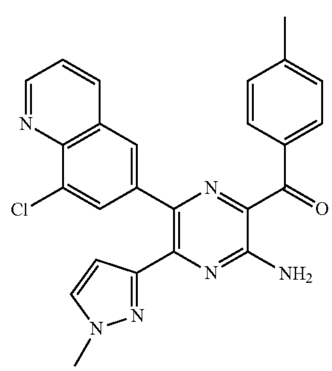 [SMILES: Cc1ccc(C(=O)c2nc(-c3cc(Cl)c4ncccc4c3)c(-c3ccn(C)n3)nc2N)cc1] |

TABLE 2-continued

| Compound No. | Structure |
|---|---|
| 2.013 | 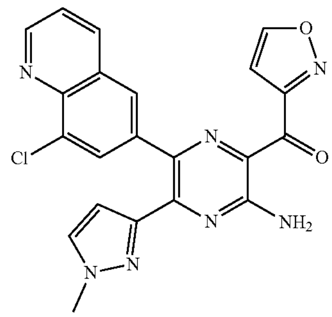 [SMILES: Cn1ccc(-c2nc(N)c(C(=O)c3ccon3)nc2-c2cc(Cl)c3ncccc3c2)n1] |
| 2.014 | 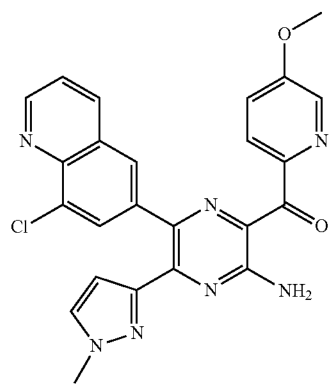 [SMILES: COc1ccc(C(=O)c2nc(-c3cc(Cl)c4ncccc4c3)c(-c3ccn(C)n3)nc2N)nc1] |
| 2.015 | 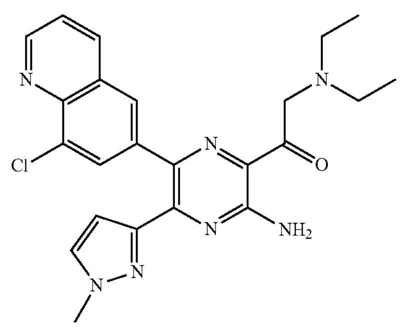 [SMILES: CCN(CC)CC(=O)c1nc(-c2cc(Cl)c3ncccc3c2)c(-c2ccn(C)n2)nc1N] |
| 2.016 | 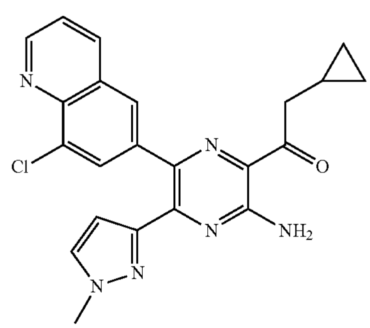 [SMILES: Cn1ccc(-c2nc(N)c(C(=O)CC3CC3)nc2-c2cc(Cl)c3ncccc3c2)n1] |

TABLE 2-continued
| Compound No. | Structure |
|---|---|
| 2.017 | 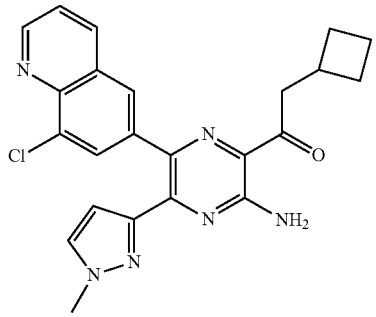 [SMILES: Cn1ccc(-c2nc(N)c(C(=O)CC3CCC3)nc2-c2cc(Cl)c3ncccc3c2)n1] |
| 2.018 | 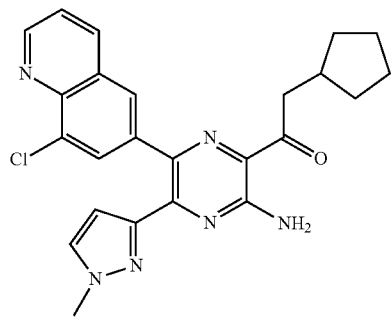 [SMILES: Cn1ccc(-c2nc(N)c(C(=O)CC3CCCC3)nc2-c2cc(Cl)c3ncccc3c2)n1] |
| 2.019 | 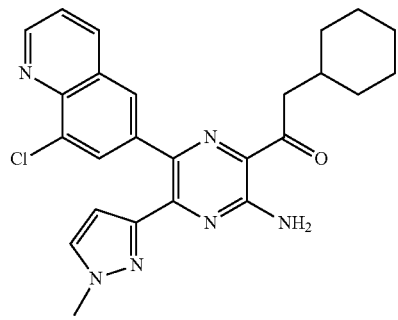 [SMILES: Cn1ccc(-c2nc(N)c(C(=O)CC3CCCCC3)nc2-c2cc(Cl)c3ncccc3c2)n1] |
| 2.020 | 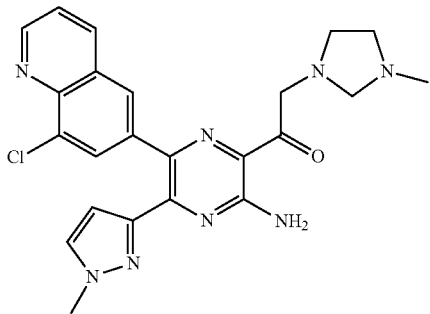 [SMILES: CN1CCN(CC(=O)c2nc(-c3cc(Cl)c4ncccc4c3)c(-c3ccn(C)n3)nc2N)C1] |

TABLE 2-continued
| Compound No. | Structure |
|---|---|
| 2.021 | 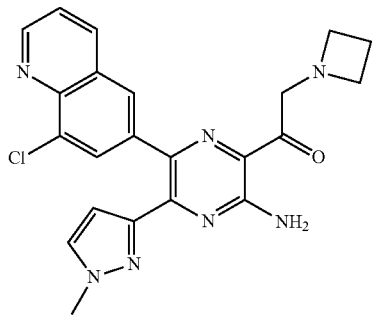 [SMILES: Cn1ccc(-c2nc(N)c(C(=O)CN3CCC3)nc2-c2cc(Cl)c3ncccc3c2)n1] |
| 2.022 | 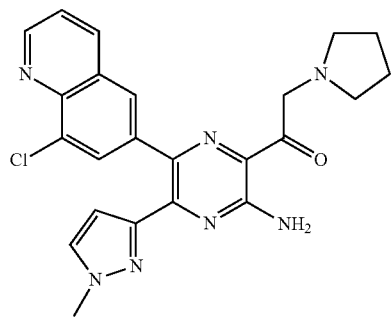 |
| 2.023 | 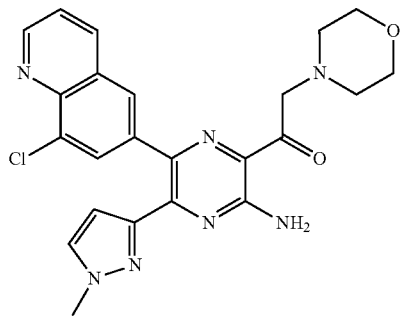 [SMILES: Cn1ccc(-c2nc(N)c(C(=O)CN3CCOCC3)nc2-c2cc(Cl)c3ncccc3c2)n1] |
| 2.024 | 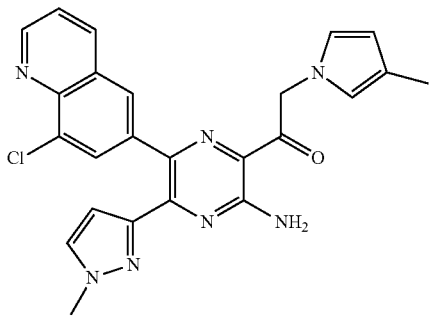 [SMILES: Cc1ccn(CC(=O)c2nc(-c3cc(Cl)c4ncccc4c3)c(-c3ccn(C)n3)nc2N)c1] |

TABLE 2-continued

| Compound No. | Structure |
| --- | --- |
| 2.025 | 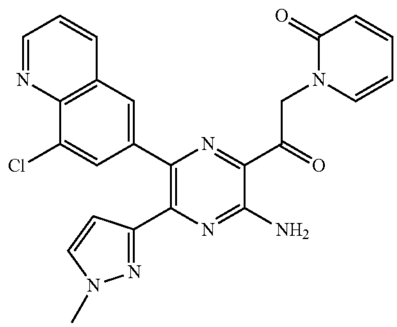 [SMILES: Cn1ccc(-c2nc(N)c(C(=O)Cn3ccccc3=O)nc2-c2cc(Cl)c3ncccc3c2)n1] |
| 2.026 | 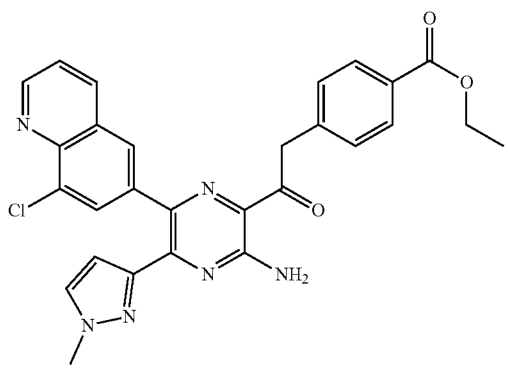 [SMILES: CCOC(=O)c1ccc(CC(=O)c2nc(-c3cc(Cl)c4ncccc4c3)c(-c3ccn(C)n3)nc2N)cc1] |
| 2.027 | 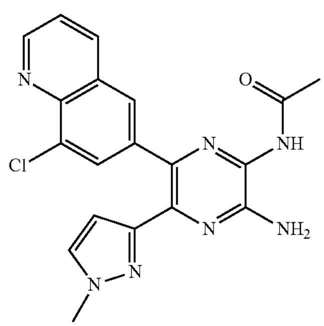 [SMILES: CC(=O)Nc1nc(-c2cc(Cl)c3ncccc3c2)c(-c2ccn(C)n2)nc1N] |
| 2.028 | 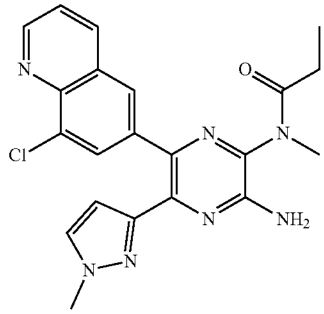 [SMILES: CCC(=O)N(C)c1nc(-c2cc(Cl)c3ncccc3c2)c(-c2ccn(C)n2)nc1N] |

TABLE 2-continued
| Compound No. | Structure |
|---|---|
| 2.029 | 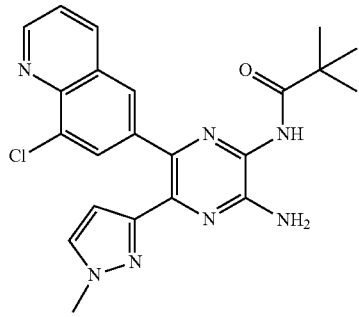 [SMILES: Cn1ccc(-c2nc(N)c(NC(=O)C(C)(C)C)nc2-c2cc(Cl)c3ncccc3c2)n1] |
| 2.030 | 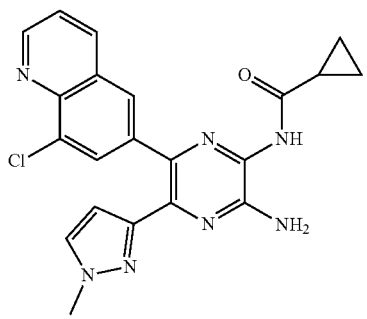 [SMILES: Cn1ccc(-c2nc(N)c(NC(=O)C3CC3)nc2-c2cc(Cl)c3ncccc3c2)n1] |
| 2.031 | 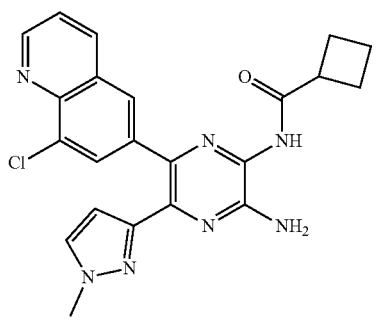 [SMILES: Cn1ccc(-c2nc(N)c(NC(=O)C3CCC3)nc2-c2cc(Cl)c3ncccc3c2)n1] |
| 2.032 | 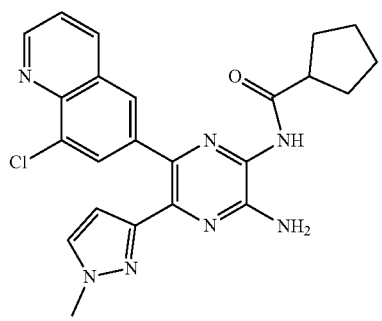 [SMILES: Cn1ccc(-c2nc(N)c(NC(=O)C3CCCC3)nc2-c2cc(Cl)c3ncccc3c2)n1] |

TABLE 2-continued
| Compound No. | Structure |
|---|---|
| 2.033 | 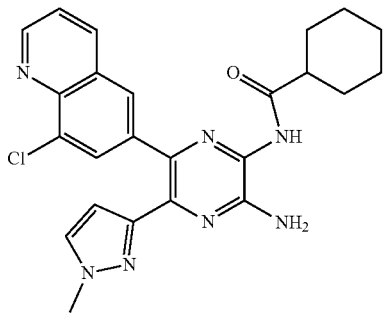 [SMILES: Cn1ccc(-c2nc(N)c(NC(=O)C3CCCCC3)nc2-c2cc(Cl)c3ncccc3c2)n1] |
| 2.034 | 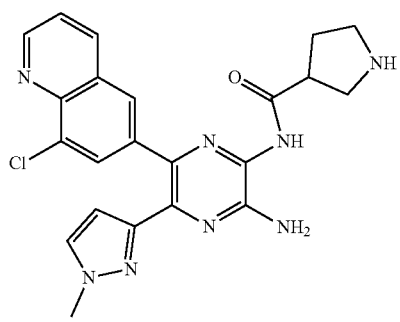 [SMILES: Cn1ccc(-c2nc(N)c(NC(=O)C3CCNC3)nc2-c2cc(Cl)c3ncccc3c2)n1] |
| 2.035 | 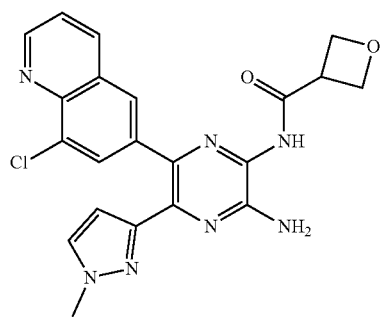 [SMILES: Cn1ccc(-c2nc(N)c(NC(=O)C3COC3)nc2-c2cc(Cl)c3ncccc3c2)n1] |
| 2.036 | 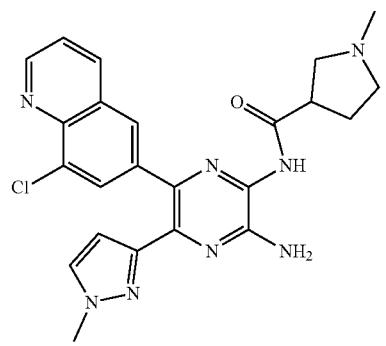 [SMILES: CN1CCC(C(=O)Nc2nc(-c3cc(Cl)c4ncccc4c3)c(-c3ccn(C)n3)nc2N)C1] |

TABLE 2-continued
| Compound No. | Structure |
|---|---|
| 2.037 | 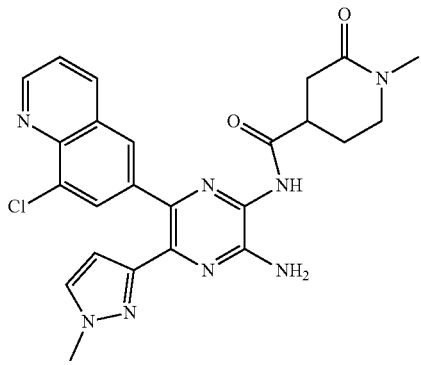 [SMILES: CN1CCC(C(=O)Nc2nc(-c3cc(Cl)c4ncccc4c3)c(-c3ccn(C)n3)nc2N)CC1=O] |
| 2.038 | 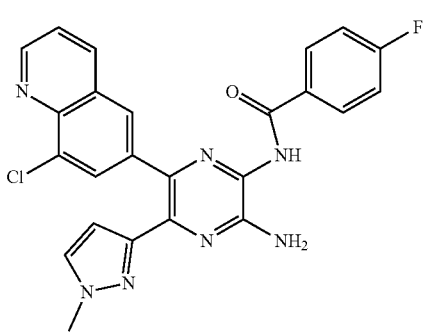 [SMILES: Cn1ccc(-c2nc(N)c(NC(=O)c3ccc(F)cc3)nc2-c2cc(Cl)c3ncccc3c2)n1] |
| 2.039 | 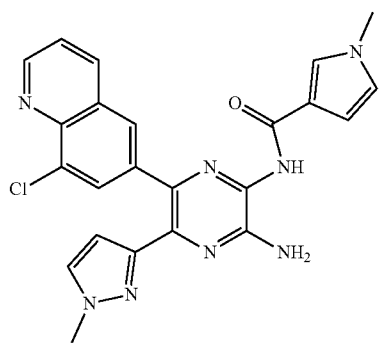 [SMILES: Cn1ccc(C(=O)Nc2nc(-c3cc(Cl)c4ncccc4c3)c(-c3ccn(C)n3)nc2N)c1] |
| 2.040 | 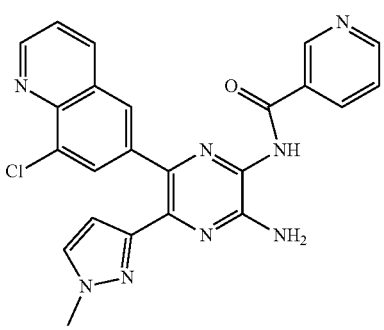 [SMILES: Cn1ccc(-c2nc(N)c(NC(=O)c3cccnc3)nc2-c2cc(Cl)c3ncccc3c2)n1] |

TABLE 2-continued

| Compound No. | Structure |
|---|---|
| 2.041 | (structure) |
| 2.042 | (structure) |
| 2.043 | (structure) |
| 2.044 | (structure) |

TABLE 2-continued

| Compound No. | Structure |
|---|---|
| 2.045 | (8-chloroquinolin-6-yl)/(1-methylpyrazol-3-yl)-substituted aminopyrazine with 2-cyclohexylacetamide |
| 2.046 | (8-chloroquinolin-6-yl)/(1-methylpyrazol-3-yl)-substituted aminopyrazine with 2-(3-methylimidazolidin-1-yl)acetamide |
| 2.047 | (8-chloroquinolin-6-yl)/(1-methylpyrazol-3-yl)-substituted aminopyrazine with 2-(3-hydroxyazetidin-1-yl)acetamide |
| 2.048 | (8-chloroquinolin-6-yl)/(1-methylpyrazol-3-yl)-substituted aminopyrazine with 2-(2-oxopyrrolidin-1-yl)acetamide |

TABLE 2-continued
| Compound No. | Structure |
|---|---|
| 2.049 | 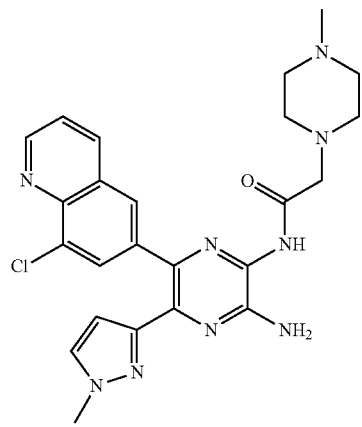 [SMILES: CN1CCN(CC(=O)Nc2nc(-c3cc(Cl)c4ncccc4c3)c(-c3ccn(C)n3)nc2N)CC1] |
| 2.050 | 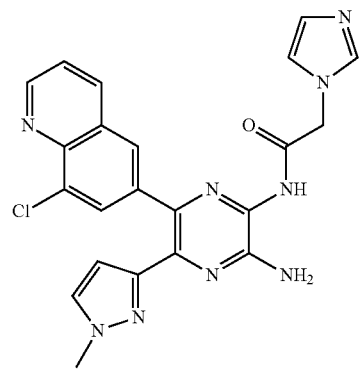 [SMILES: Cn1ccc(-c2nc(N)c(NC(=O)Cn3ccnc3)nc2-c2cc(Cl)c3ncccc3c2)n1] |
| 2.051 | 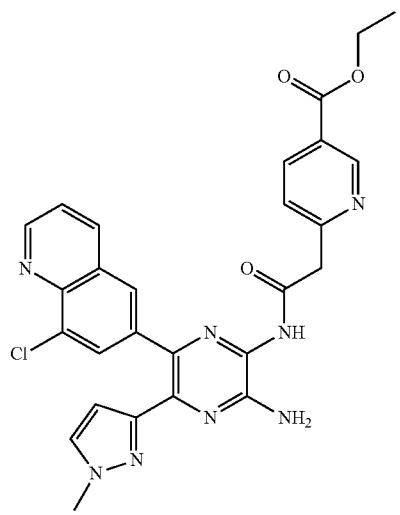 [SMILES: CCOC(=O)c1ccc(CC(=O)Nc2nc(-c3cc(Cl)c4ncccc4c3)c(-c3ccn(C)n3)nc2N)nc1] |

TABLE 2-continued

| Compound No. | Structure |
|---|---|
| 2.052 | (structure) |
| 2.053 | (structure) |
| 2.054 | (structure) |
| 2.055 | (structure) |

TABLE 2-continued
| Compound No. | Structure |
| --- | --- |
| 2.056 | 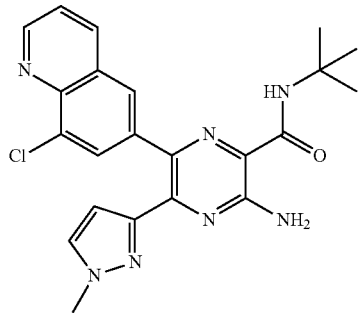 [SMILES: Cn1ccc(-c2nc(N)c(C(=O)NC(C)(C)C)nc2-c2cc(Cl)c3ncccc3c2)n1] |
| 2.057 | 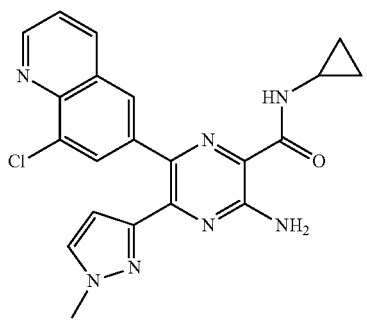 [SMILES: Cn1ccc(-c2nc(N)c(C(=O)NC3CC3)nc2-c2cc(Cl)c3ncccc3c2)n1] |
| 2.058 | 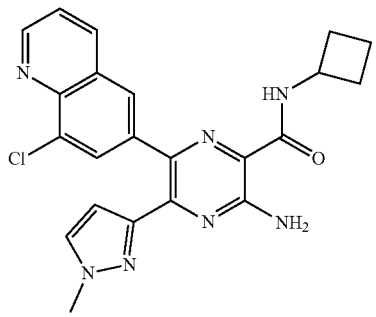 [SMILES: Cn1ccc(-c2nc(N)c(C(=O)NC3CCC3)nc2-c2cc(Cl)c3ncccc3c2)n1] |
| 2.059 | 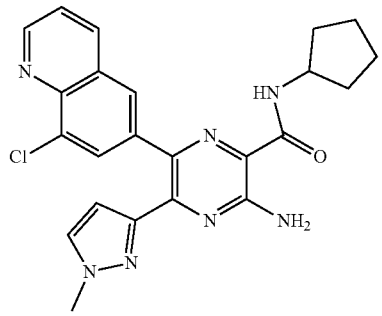 [SMILES: Cn1ccc(-c2nc(N)c(C(=O)NC3CCCC3)nc2-c2cc(Cl)c3ncccc3c2)n1] |

татье TABLE 2-continued
| Compound No. | Structure |
|---|---|
| 2.060 | 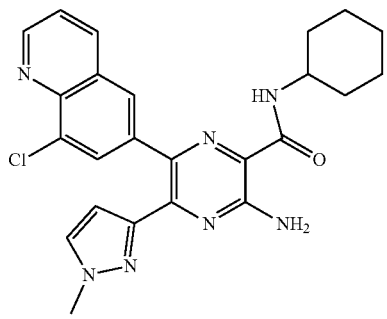 [SMILES: Cn1ccc(-c2nc(N)c(C(=O)NC3CCCCC3)nc2-c2cc(Cl)c3ncccc3c2)n1] |
| 2.061 | 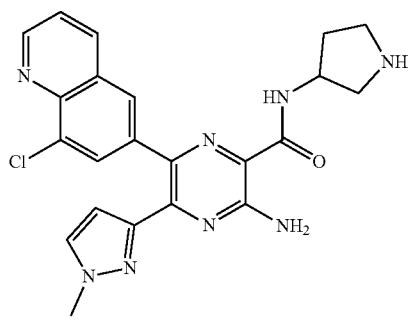 [SMILES: Cn1ccc(-c2nc(N)c(C(=O)NC3CCNC3)nc2-c2cc(Cl)c3ncccc3c2)n1] |
| 2.062 | 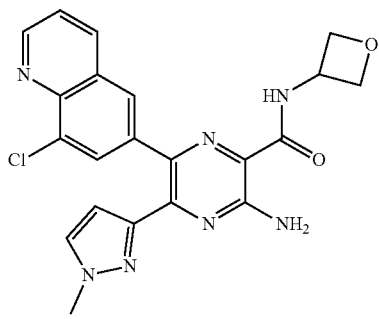 [SMILES: Cn1ccc(-c2nc(N)c(C(=O)NC3COC3)nc2-c2cc(Cl)c3ncccc3c2)n1] |
| 2.063 | 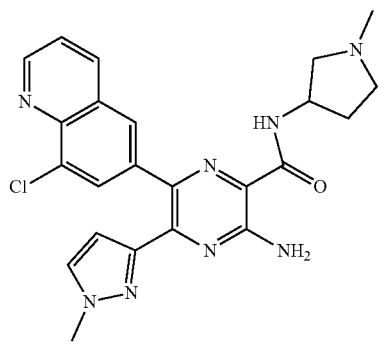 [SMILES: CN1CCC(NC(=O)c2nc(-c3cc(Cl)c4ncccc4c3)c(-c3ccn(C)n3)nc2N)C1] |

TABLE 2-continued
| Compound No. | Structure |
|---|---|
| 2.064 | 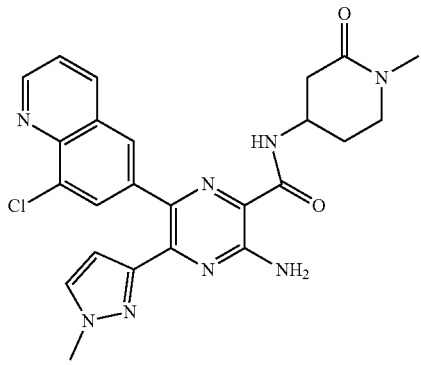 [SMILES: CN1CCC(NC(=O)c2nc(-c3cc(Cl)c4ncccc4c3)c(-c3ccn(C)n3)nc2N)CC1=O] |
| 2.065 | 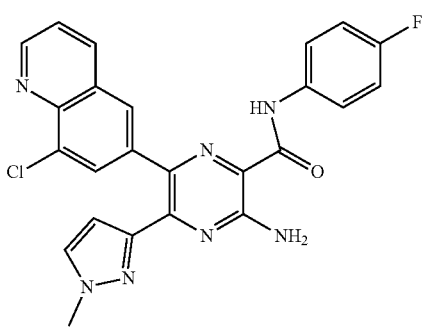 [SMILES: Cn1ccc(-c2nc(N)c(C(=O)Nc3ccc(F)cc3)nc2-c2cc(Cl)c3ncccc3c2)n1] |
| 2.066 | 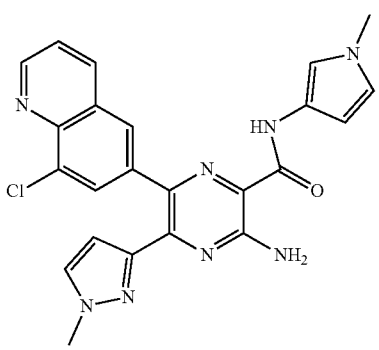 [SMILES: Cn1ccc(NC(=O)c2nc(-c3cc(Cl)c4ncccc4c3)c(-c3ccn(C)n3)nc2N)c1] |
| 2.067 | 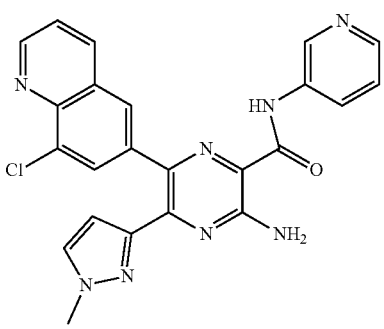 [SMILES: Cn1ccc(-c2nc(N)c(C(=O)Nc3cccnc3)nc2-c2cc(Cl)c3ncccc3c2)n1] |

TABLE 2-continued

| Compound No. | Structure |
|---|---|
| 2.068 | 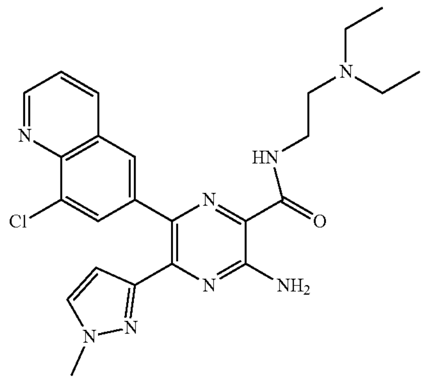 [SMILES: CCN(CC)CCNC(=O)c1nc(-c2cc(Cl)c3ncccc3c2)c(-c2ccn(C)n2)nc1N] |
| 2.069 | 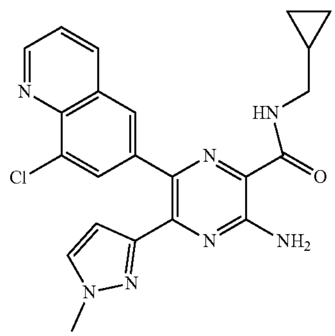 [SMILES: Cn1ccc(-c2nc(N)c(C(=O)NCC3CC3)nc2-c2cc(Cl)c3ncccc3c2)n1] |
| 2.070 | 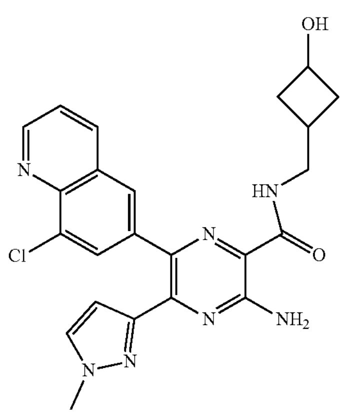 [SMILES: Cn1ccc(-c2nc(N)c(C(=O)NCC3CC(O)C3)nc2-c2cc(Cl)c3ncccc3c2)n1] |
| 2.071 | 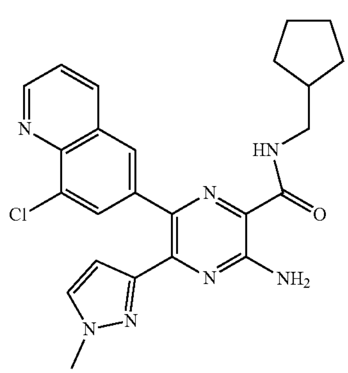 [SMILES: Cn1ccc(-c2nc(N)c(C(=O)NCC3CCCC3)nc2-c2cc(Cl)c3ncccc3c2)n1] |

TABLE 2-continued

| Compound No. | Structure |
|---|---|
| 2.072 | 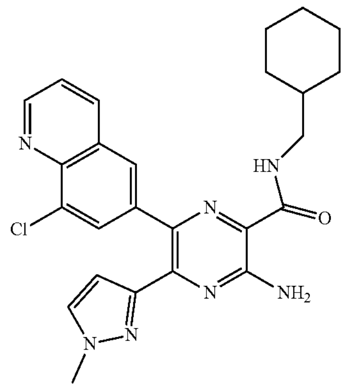 [SMILES: Cn1ccc(-c2nc(N)c(C(=O)NCC3CCCCC3)nc2-c2cc(Cl)c3ncccc3c2)n1] |
| 2.073 | 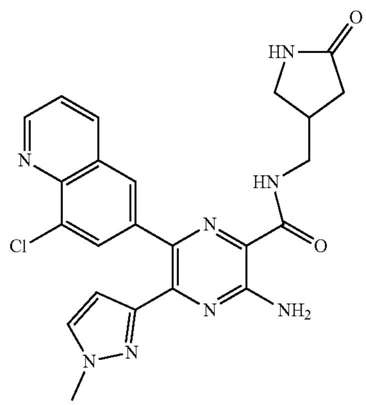 [SMILES: Cn1ccc(-c2nc(N)c(C(=O)NCC3CNC(=O)C3)nc2-c2cc(Cl)c3ncccc3c2)n1] |
| 2.074 | 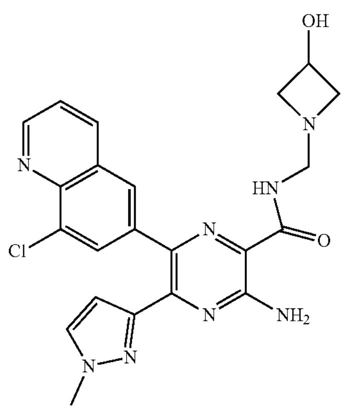 [SMILES: Cn1ccc(-c2nc(N)c(C(=O)NCN3CC(O)C3)nc2-c2cc(Cl)c3ncccc3c2)n1] |
| 2.075 | 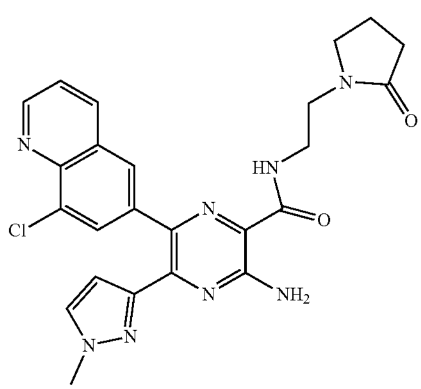 [SMILES: Cn1ccc(-c2nc(N)c(C(=O)NCCN3CCCC3=O)nc2-c2cc(Cl)c3ncccc3c2)n1] |

TABLE 2-continued
| Compound No. | Structure |
|---|---|
| 2.076 | 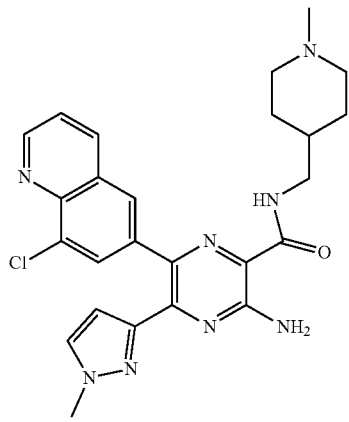 [SMILES: CN1CCC(CNC(=O)c2nc(-c3cc(Cl)c4ncccc4c3)c(-c3ccn(C)n3)nc2N)CC1] |
| 2.077 | 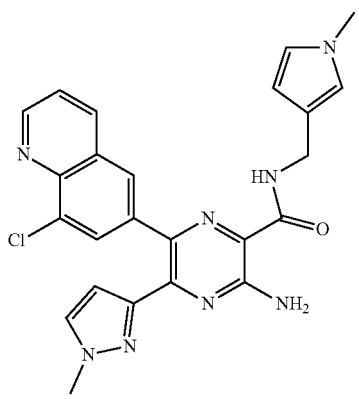 [SMILES: Cn1ccc(CNC(=O)c2nc(-c3cc(Cl)c4ncccc4c3)c(-c3ccn(C)n3)nc2N)c1] |
| 2.078 | 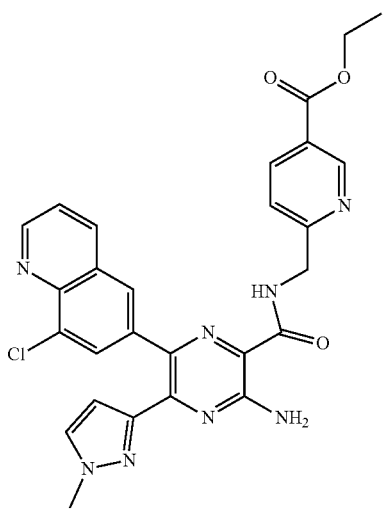 [SMILES: CCOC(=O)c1ccc(CNC(=O)c2nc(-c3cc(Cl)c4ncccc4c3)c(-c3ccn(C)n3)nc2N)nc1] |

TABLE 2-continued

| Compound No. | Structure |
|---|---|
| 2.079 | 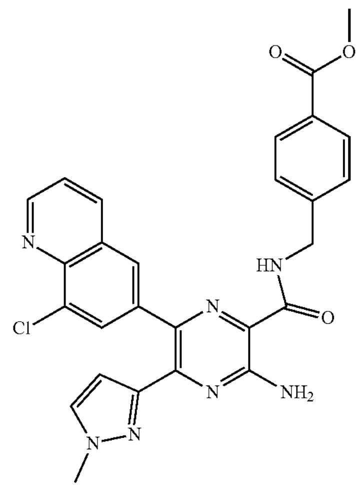 [SMILES: COC(=O)c1ccc(CNC(=O)c2nc(-c3cc(Cl)c4ncccc4c3)c(-c3ccn(C)n3)nc2N)cc1] |
| 2.080 | 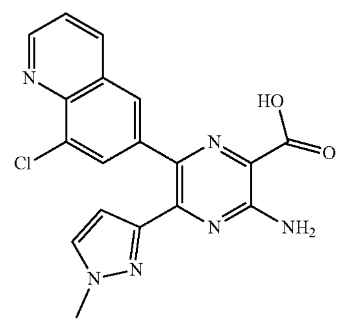 [SMILES: Cn1ccc(-c2nc(N)c(C(=O)O)nc2-c2cc(Cl)c3ncccc3c2)n1] |
| 2.081 | 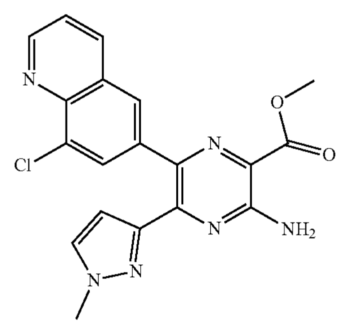 [SMILES: COC(=O)c1nc(-c2cc(Cl)c3ncccc3c2)c(-c2ccn(C)n2)nc1N] |
| 2.082 | 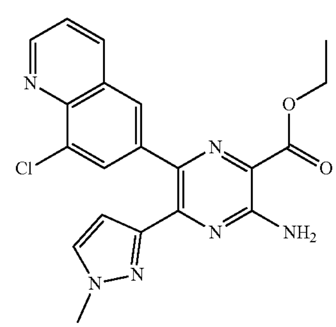 |

TABLE 2-continued

| Compound No. | Structure |
|---|---|
| 2.083 | *tert-butyl 3-amino-6-(8-chloroquinolin-6-yl)-5-(1-methyl-1H-pyrazol-3-yl)pyrazine-2-carboxylate* |
| 2.084 | *cyclopropyl 3-amino-6-(8-chloroquinolin-6-yl)-5-(1-methyl-1H-pyrazol-3-yl)pyrazine-2-carboxylate* |
| 2.085 | *cyclobutyl 3-amino-6-(8-chloroquinolin-6-yl)-5-(1-methyl-1H-pyrazol-3-yl)pyrazine-2-carboxylate* |
| 2.086 | *cyclopentyl 3-amino-6-(8-chloroquinolin-6-yl)-5-(1-methyl-1H-pyrazol-3-yl)pyrazine-2-carboxylate* |
| 2.087 | *cyclohexyl 3-amino-6-(8-chloroquinolin-6-yl)-5-(1-methyl-1H-pyrazol-3-yl)pyrazine-2-carboxylate* |

TABLE 2-continued
| Compound No. | Structure |
|---|---|
| 2.088 | 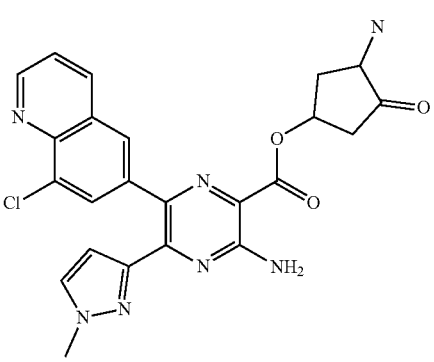 [SMILES: Cn1ccc(-c2nc(N)c(C(=O)OC3CC(=O)C(N)C3)nc2-c2cc(Cl)c3ncccc3c2)n1] |
| 2.089 | 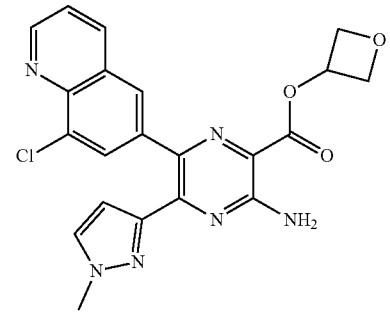 [SMILES: Cn1ccc(-c2nc(N)c(C(=O)OC3COC3)nc2-c2cc(Cl)c3ncccc3c2)n1] |
| 2.090 | 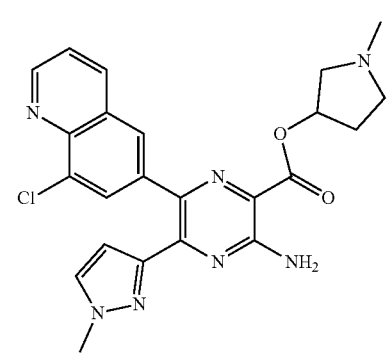 [SMILES: CN1CCC(OC(=O)c2nc(-c3cc(Cl)c4ncccc4c3)c(-c3ccn(C)n3)nc2N)C1] |
| 2.091 | 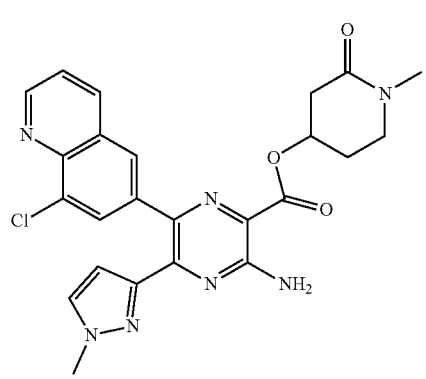 [SMILES: CN1CCC(OC(=O)c2nc(-c3cc(Cl)c4ncccc4c3)c(-c3ccn(C)n3)nc2N)CC1=O] |

TABLE 2-continued
| Compound No. | Structure |
|---|---|
| 2.092 | 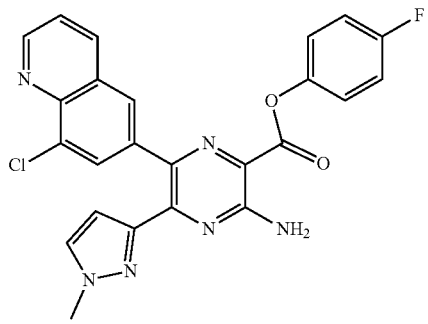 [SMILES: Cn1ccc(-c2nc(N)c(C(=O)Oc3ccc(F)cc3)nc2-c2cc(Cl)c3ncccc3c2)n1] |
| 2.093 | 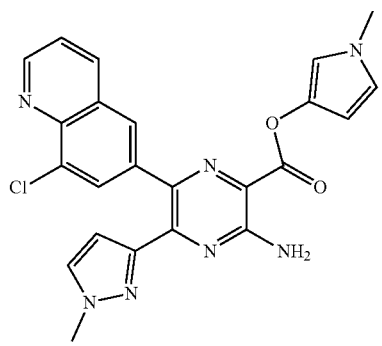 [SMILES: Cn1ccc(OC(=O)c2nc(-c3cc(Cl)c4ncccc4c3)c(-c3ccn(C)n3)nc2N)c1] |
| 2.094 | 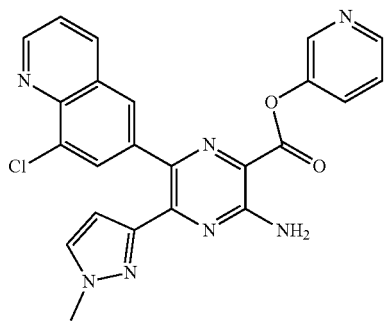 [SMILES: Cn1ccc(-c2nc(N)c(C(=O)Oc3cccnc3)nc2-c2cc(Cl)c3ncccc3c2)n1] |
| 2.095 | 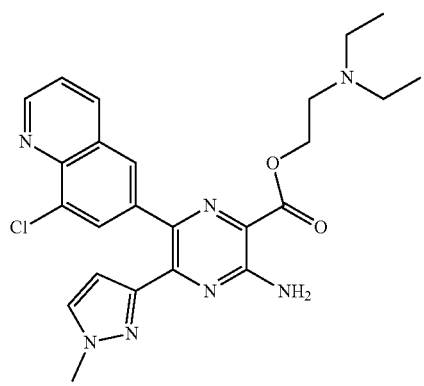 [SMILES: CCN(CC)CCOC(=O)c1nc(-c2cc(Cl)c3ncccc3c2)c(-c2ccn(C)n2)nc1N] |

TABLE 2-continued
| Compound No. | Structure |
|---|---|
| 2.096 | 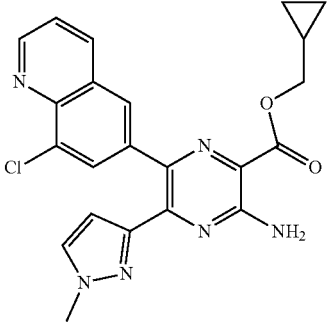 [SMILES: Cn1ccc(-c2nc(N)c(C(=O)OCC3CC3)nc2-c2cc(Cl)c3ncccc3c2)n1] |
| 2.097 | 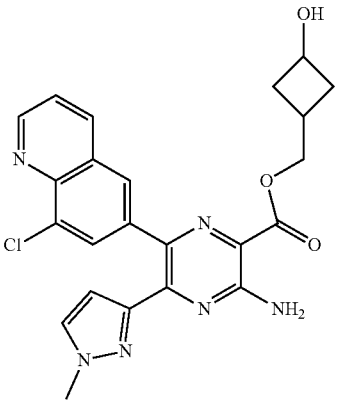 [SMILES: Cn1ccc(-c2nc(N)c(C(=O)OCC3CC(O)C3)nc2-c2cc(Cl)c3ncccc3c2)n1] |
| 2.098 | 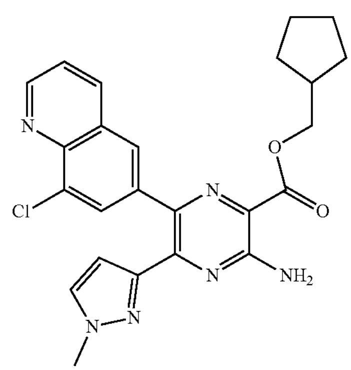 [SMILES: Cn1ccc(-c2nc(N)c(C(=O)OCC3CCCC3)nc2-c2cc(Cl)c3ncccc3c2)n1] |
| 2.099 | 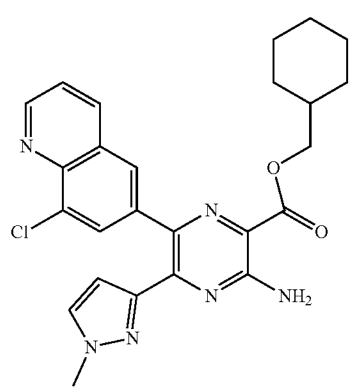 [SMILES: Cn1ccc(-c2nc(N)c(C(=O)OCC3CCCCC3)nc2-c2cc(Cl)c3ncccc3c2)n1] |

TABLE 2-continued
| Compound No. | Structure |
|---|---|
| 2.100 | 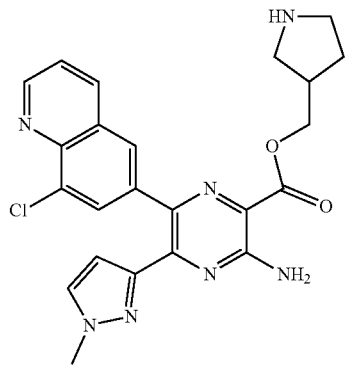 [SMILES: Cn1ccc(-c2nc(N)c(C(=O)OCC3CCNC3)nc2-c2cc(Cl)c3ncccc3c2)n1] |
| 2.101 | 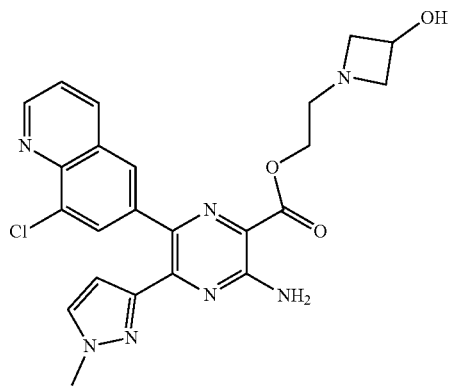 [SMILES: Cn1ccc(-c2nc(N)c(C(=O)OCCN3CC(O)C3)nc2-c2cc(Cl)c3ncccc3c2)n1] |
| 2.102 | 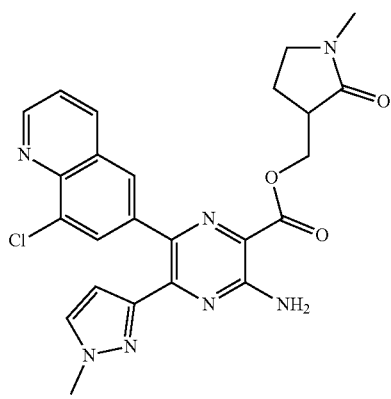 [SMILES: CN1CCC(COC(=O)c2nc(-c3cc(Cl)c4ncccc4c3)c(-c3ccn(C)n3)nc2N)C1=O] |
| 2.103 | 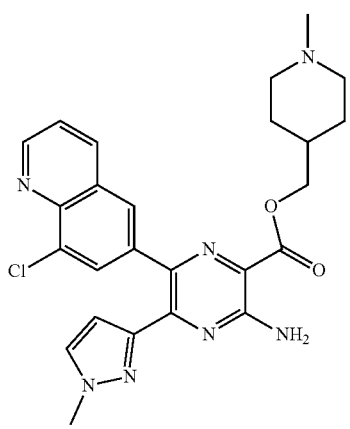 [SMILES: CN1CCC(COC(=O)c2nc(-c3cc(Cl)c4ncccc4c3)c(-c3ccn(C)n3)nc2N)CC1] |

TABLE 2-continued

| Compound No. | Structure |
|---|---|
| 2.104 | 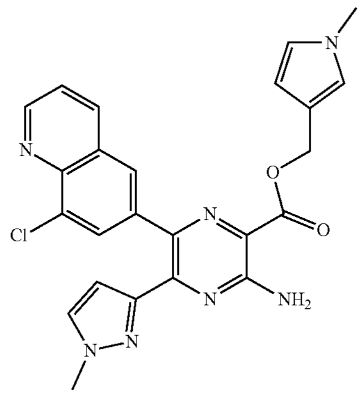 [SMILES: Cn1ccc(COC(=O)c2nc(-c3cc(Cl)c4ncccc4c3)c(-c3ccn(C)n3)nc2N)c1] |
| 2.105 | 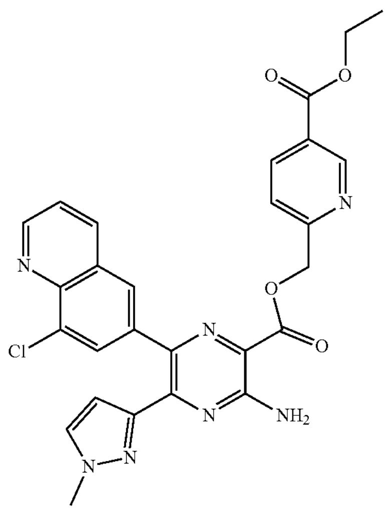 [SMILES: CCOC(=O)c1ccc(COC(=O)c2nc(-c3cc(Cl)c4ncccc4c3)c(-c3ccn(C)n3)nc2N)nc1] |
| 2.106 | 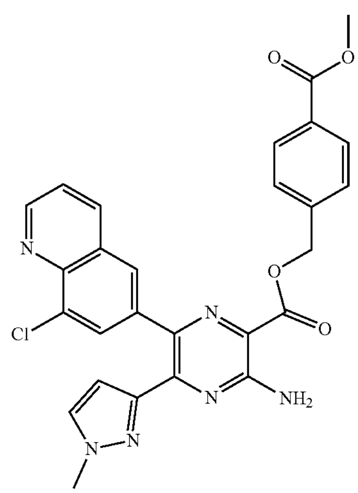 [SMILES: COC(=O)c1ccc(COC(=O)c2nc(-c3cc(Cl)c4ncccc4c3)c(-c3ccn(C)n3)nc2N)cc1] |

TABLE 2-continued

| Compound No. | Structure |
|---|---|
| 2.107 | (8-chloroquinolin-6-yl, 1-methylpyrazol-3-yl, aminopyrazine, N-methylurea) |
| 2.108 | (8-chloroquinolin-6-yl, 1-methylpyrazol-3-yl, aminopyrazine, N-ethyl-N'-methylurea) |
| 2.109 | (8-chloroquinolin-6-yl, 1-methylpyrazol-3-yl, aminopyrazine, N-tert-butylurea) |
| 2.110 | (8-chloroquinolin-6-yl, 1-methylpyrazol-3-yl, aminopyrazine, N-cyclopropylurea) |

TABLE 2-continued

| Compound No. | Structure |
|---|---|
| 2.111 | 8-chloroquinolin-6-yl / 1-methylpyrazol-3-yl / pyrazine with amino and cyclobutyl-urea substituents |
| 2.112 | 8-chloroquinolin-6-yl / 1-methylpyrazol-3-yl / pyrazine with amino and cyclopentyl-urea substituents |
| 2.113 | 8-chloroquinolin-6-yl / 1-methylpyrazol-3-yl / pyrazine with amino and cyclohexyl-urea substituents |
| 2.114 | 8-chloroquinolin-6-yl / 1-methylpyrazol-3-yl / pyrazine with amino and (2-oxopiperidin-4-yl)-urea substituents |

TABLE 2-continued

| Compound No. | Structure |
|---|---|
| 2.115 | 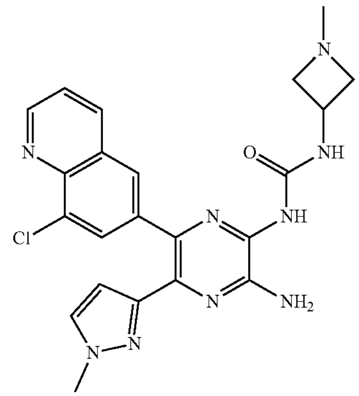 [SMILES: CN1CC(NC(=O)Nc2nc(-c3cc(Cl)c4ncccc4c3)c(-c3ccn(C)n3)nc2N)C1] |
| 2.116 | 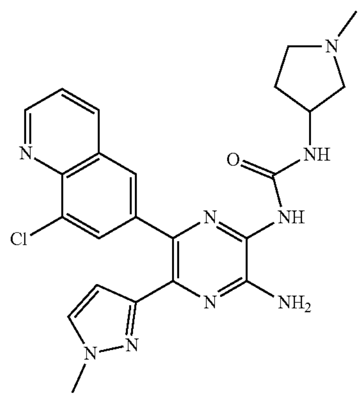 [SMILES: CN1CCC(NC(=O)Nc2nc(-c3cc(Cl)c4ncccc4c3)c(-c3ccn(C)n3)nc2N)C1] |
| 2.117 | 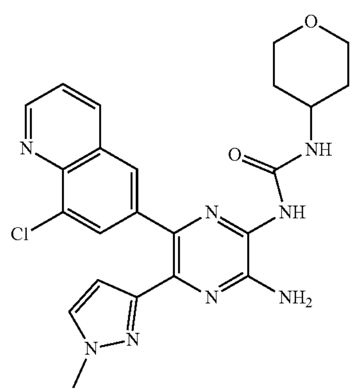 [SMILES: Cn1ccc(-c2nc(N)c(NC(=O)NC3CCOCC3)nc2-c2cc(Cl)c3ncccc3c2)n1] |
| 2.118 | 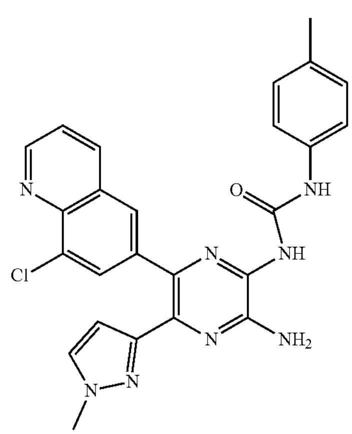 [SMILES: Cc1ccc(NC(=O)Nc2nc(-c3cc(Cl)c4ncccc4c3)c(-c3ccn(C)n3)nc2N)cc1] |

TABLE 2-continued
| Compound No. | Structure |
|---|---|
| 2.119 | 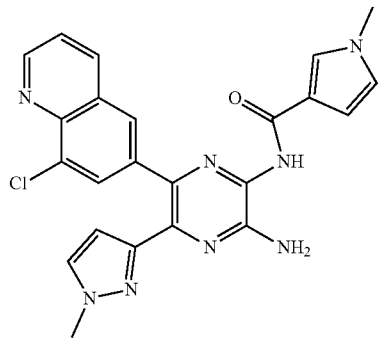 [SMILES: Cn1ccc(C(=O)Nc2nc(-c3cc(Cl)c4ncccc4c3)c(-c3ccn(C)n3)nc2N)c1] |
| 2.120 | 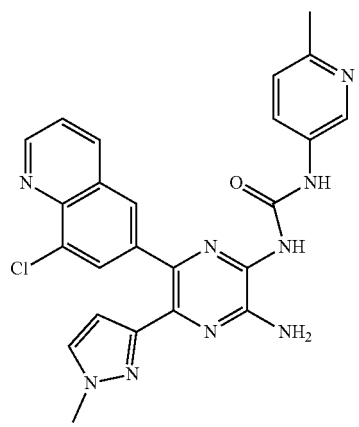 [SMILES: Cc1ccc(NC(=O)Nc2nc(-c3cc(Cl)c4ncccc4c3)c(-c3ccn(C)n3)nc2N)cn1] |
| 2.121 | 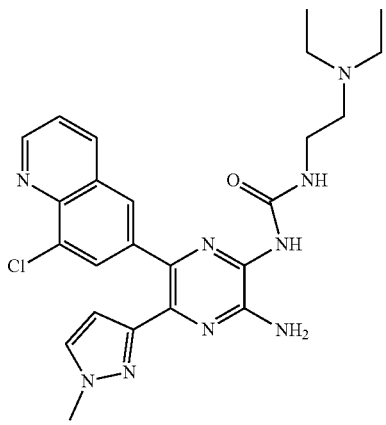 [SMILES: CCN(CC)CCNC(=O)Nc1nc(-c2cc(Cl)c3ncccc3c2)c(-c2ccn(C)n2)nc1N] |
| 2.122 | 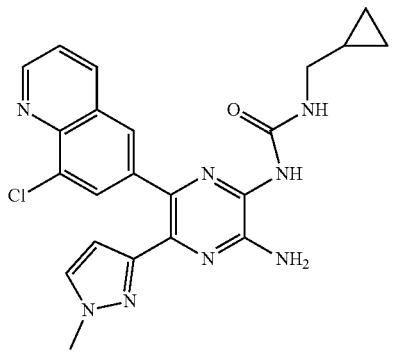 [SMILES: Cn1ccc(-c2nc(N)c(NC(=O)NCC3CC3)nc2-c2cc(Cl)c3ncccc3c2)n1] |

TABLE 2-continued

| Compound No. | Structure |
|---|---|
| 2.123 | 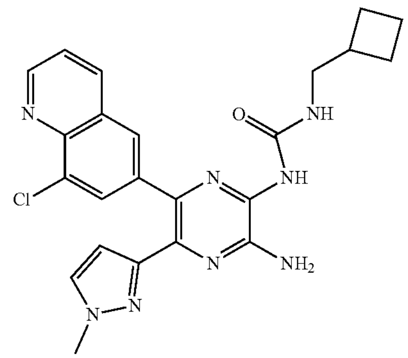 [SMILES: Cn1ccc(-c2nc(N)c(NC(=O)NCC3CCC3)nc2-c2cc(Cl)c3ncccc3c2)n1] |
| 2.124 | 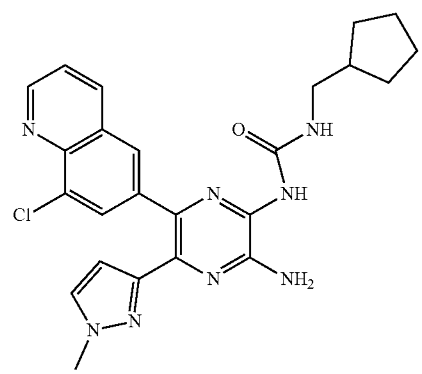 [SMILES: Cn1ccc(-c2nc(N)c(NC(=O)NCC3CCCC3)nc2-c2cc(Cl)c3ncccc3c2)n1] |
| 2.125 | 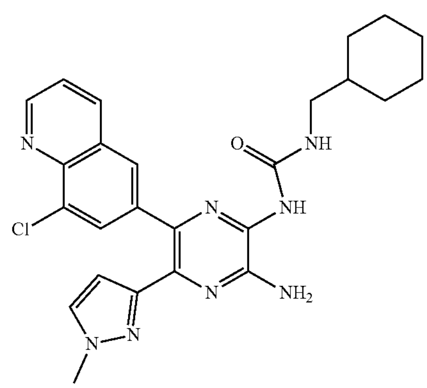 [SMILES: Cn1ccc(-c2nc(N)c(NC(=O)NCC3CCCCC3)nc2-c2cc(Cl)c3ncccc3c2)n1] |
| 2.126 | 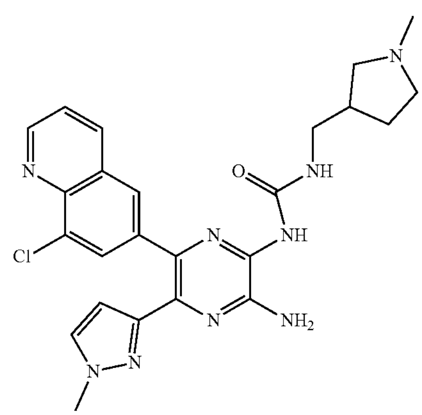 [SMILES: CN1CCC(CNC(=O)Nc2nc(-c3cc(Cl)c4ncccc4c3)c(-c3ccn(C)n3)nc2N)C1] |

TABLE 2-continued
| Compound No. | Structure |
|---|---|
| 2.127 | 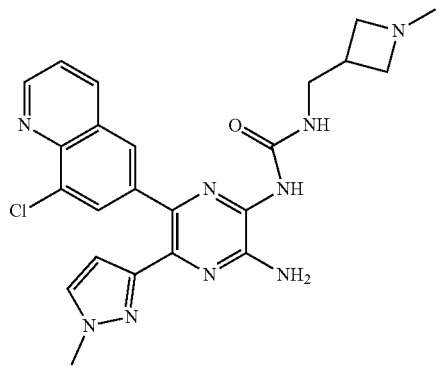 [SMILES: CN1CC(CNC(=O)Nc2nc(-c3cc(Cl)c4ncccc4c3)c(-c3ccn(C)n3)nc2N)C1] |
| 2.128 | 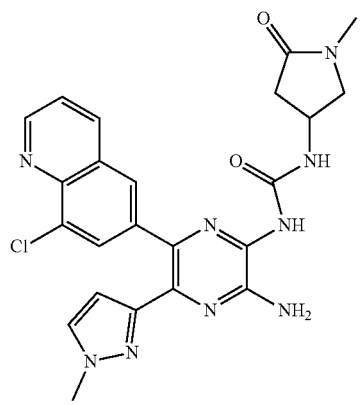 [SMILES: CN1CC(NC(=O)Nc2nc(-c3cc(Cl)c4ncccc4c3)c(-c3ccn(C)n3)nc2N)CC1=O] |
| 2.129 | 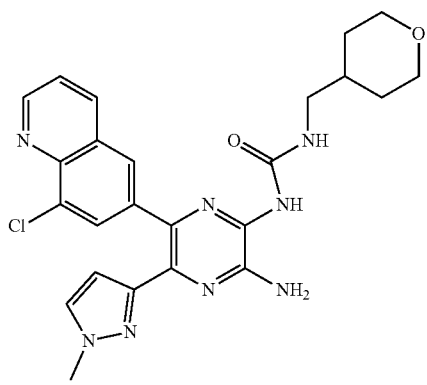 [SMILES: Cn1ccc(-c2nc(N)c(NC(=O)NCC3CCOCC3)nc2-c2cc(Cl)c3ncccc3c2)n1] |
| 2.130 | 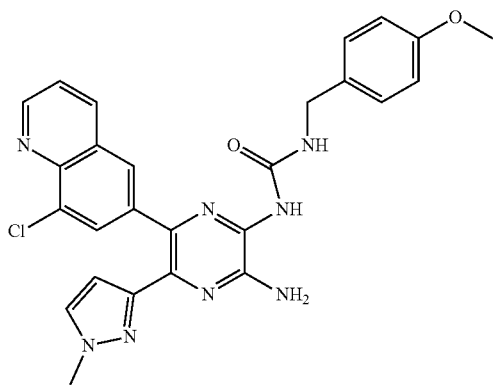 [SMILES: COc1ccc(CNC(=O)Nc2nc(-c3cc(Cl)c4ncccc4c3)c(-c3ccn(C)n3)nc2N)cc1] |

TABLE 2-continued

| Compound No. | Structure |
|---|---|
| 2.131 | 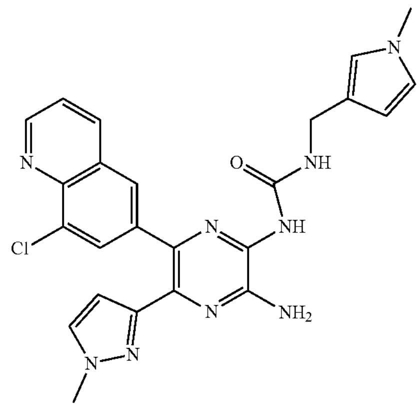 [SMILES: Cn1ccc(CNC(=O)Nc2nc(-c3cc(Cl)c4ncccc4c3)c(-c3ccn(C)n3)nc2N)c1] |
| 2.132 | 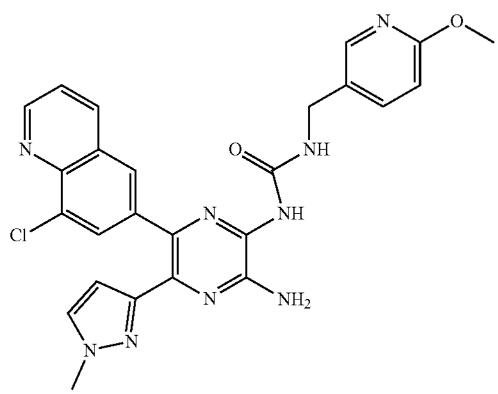 [SMILES: COc1ccc(CNC(=O)Nc2nc(-c3cc(Cl)c4ncccc4c3)c(-c3ccn(C)n3)nc2N)cn1] |
| 2.133 | 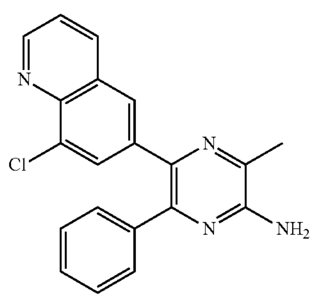 |
| 2.134 | 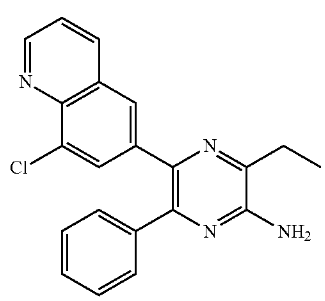 [SMILES: CCc1nc(-c2cc(Cl)c3ncccc3c2)c(-c2ccccc2)nc1N] |

TABLE 2-continued

| Compound No. | Structure |
|---|---|
| 2.135 | 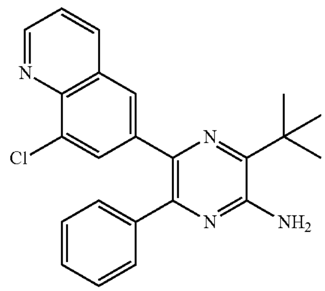 [SMILES: CC(C)(C)c1nc(-c2cc(Cl)c3ncccc3c2)c(-c2ccccc2)nc1N] |
| 2.136 | 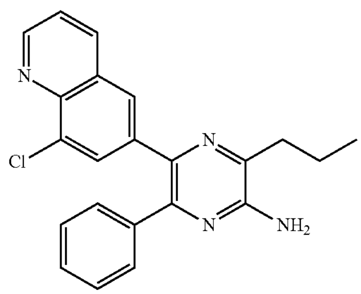 [SMILES: CCCc1nc(-c2cc(Cl)c3ncccc3c2)c(-c2ccccc2)nc1N] |
| 2.137 | 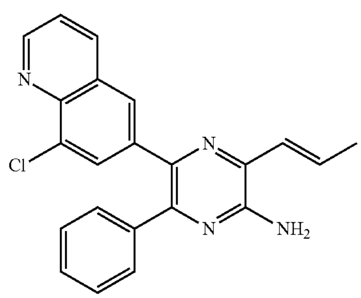 [SMILES: C/C=C/c1nc(-c2cc(Cl)c3ncccc3c2)c(-c2ccccc2)nc1N] |
| 2.138 | 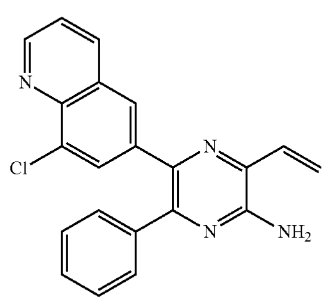 [SMILES: C=Cc1nc(-c2cc(Cl)c3ncccc3c2)c(-c2ccccc2)nc1N] |
| 2.139 | 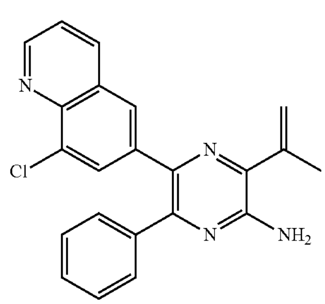 [SMILES: C=C(C)c1nc(-c2cc(Cl)c3ncccc3c2)c(-c2ccccc2)nc1N] |

TABLE 2-continued

| Compound No. | Structure |
|---|---|
| 2.140 | 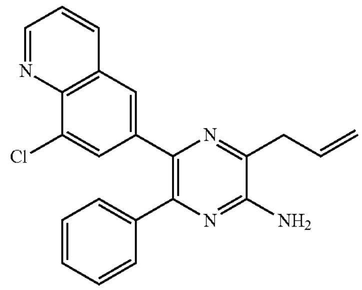 [SMILES: C=CCc1nc(-c2cc(Cl)c3ncccc3c2)c(-c2ccccc2)nc1N] |
| 2.141 | 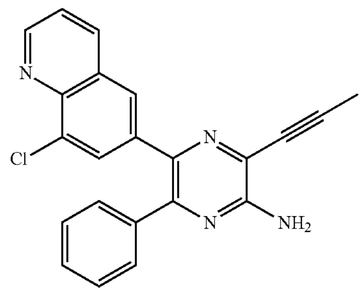 [SMILES: CC#Cc1nc(-c2cc(Cl)c3ncccc3c2)c(-c2ccccc2)nc1N] |
| 2.142 | 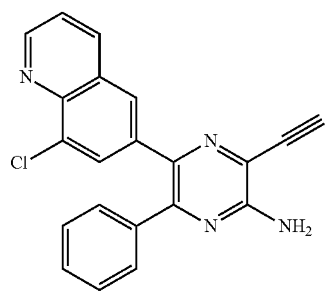 [SMILES: C#Cc1nc(-c2cc(Cl)c3ncccc3c2)c(-c2ccccc2)nc1N] |
| 2.143 | 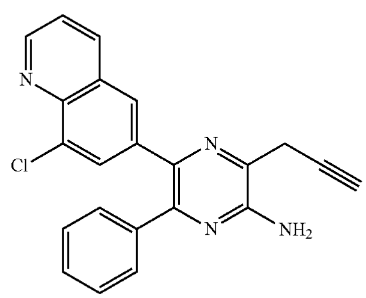 [SMILES: C#CCc1nc(-c2cc(Cl)c3ncccc3c2)c(-c2ccccc2)nc1N] |
| 2.144 | 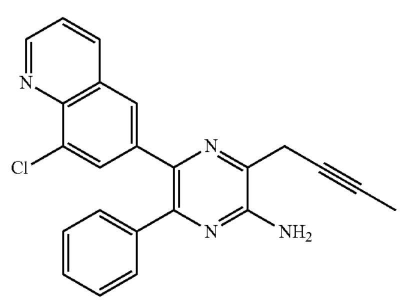 [SMILES: CC#CCc1nc(-c2cc(Cl)c3ncccc3c2)c(-c2ccccc2)nc1N] |

TABLE 2-continued

| Compound No. | Structure |
|---|---|
| 2.145 | *8-chloroquinolin-6-yl, 3-phenyl, 6-phenyl, 2-amino pyrazine* |
| 2.146 | *8-chloroquinolin-6-yl, 3-(naphthalen-2-yl), 6-phenyl, 2-amino pyrazine* |
| 2.147 | *8-chloroquinolin-6-yl, 3-cyclopropyl, 6-phenyl, 2-amino pyrazine* |
| 2.148 | *8-chloroquinolin-6-yl, 3-cyclobutyl, 6-phenyl, 2-amino pyrazine* |
| 2.149 | *8-chloroquinolin-6-yl, 3-cyclopentyl, 6-phenyl, 2-amino pyrazine* |

TABLE 2-continued

| Compound No. | Structure |
|---|---|
| 2.150 | (structure) |
| 2.151 | (structure) |
| 2.152 | (structure) |
| 2.153 | (structure) |
| 2.154 | (structure) |

TABLE 2-continued

| Compound No. | Structure |
|---|---|
| 2.155 | 8-chloroquinolin-6-yl, 4-hydroxypiperidin-1-yl, phenyl, NH₂-substituted pyrazine |
| 2.156 | 8-chloroquinolin-6-yl, F, phenyl, NH₂-substituted pyrazine |
| 2.157 | 8-chloroquinolin-6-yl, Cl, phenyl, NH₂-substituted pyrazine |
| 2.158 | 8-chloroquinolin-6-yl, Br, phenyl, NH₂-substituted pyrazine |
| 2.159 | 8-chloroquinolin-6-yl, CF₃, phenyl, NH₂-substituted pyrazine |

TABLE 2-continued

| Compound No. | Structure |
|---|---|
| 2.160 | 8-chloroquinolin-6-yl / trifluoromethoxy / phenyl / amino pyrazine |
| 2.161 | 8-chloroquinolin-6-yl / hydroxy / phenyl / amino pyrazine |
| 2.162 | 8-chloroquinolin-6-yl / methoxy / phenyl / amino pyrazine |
| 2.163 | 8-chloroquinolin-6-yl / ethoxy / phenyl / amino pyrazine |
| 2.164 | 8-chloroquinolin-6-yl / isopropoxy / phenyl / amino pyrazine |

TABLE 2-continued

| Compound No. | Structure |
|---|---|
| 2.165 | 8-chloroquinolin-6-yl, cyclopropyloxy, phenyl, amino-pyrazine |
| 2.166 | 8-chloroquinolin-6-yl, cyclobutyloxy, phenyl, amino-pyrazine |
| 2.167 | 8-chloroquinolin-6-yl, cyclopentyloxy, phenyl, amino-pyrazine |
| 2.168 | 8-chloroquinolin-6-yl, cyclohexyloxy, phenyl, amino-pyrazine |
| 2.169 | 8-chloroquinolin-6-yl, (1-methyl-2-oxopyrrolidin-4-yl)oxy, phenyl, amino-pyrazine |

TABLE 2-continued

| Compound No. | Structure |
|---|---|
| 2.170 | 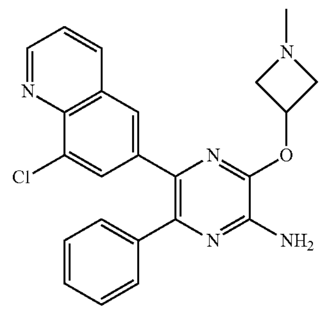 [SMILES: CN1CC(Oc2nc(-c3cc(Cl)c4ncccc4c3)c(-c3ccccc3)nc2N)C1] |
| 2.171 | 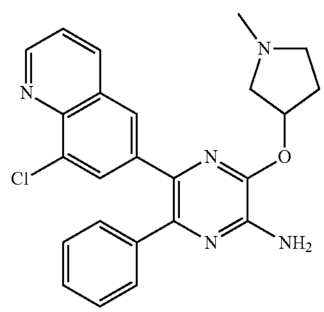 [SMILES: CN1CCC(Oc2nc(-c3cc(Cl)c4ncccc4c3)c(-c3ccccc3)nc2N)C1] |
| 2.172 | 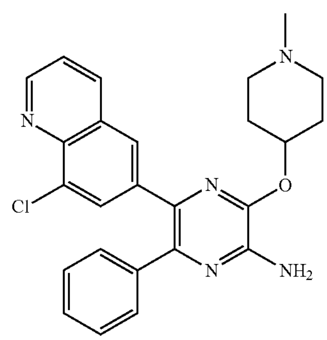 [SMILES: CN1CCC(Oc2nc(-c3cc(Cl)c4ncccc4c3)c(-c3ccccc3)nc2N)CC1] |
| 2.173 | 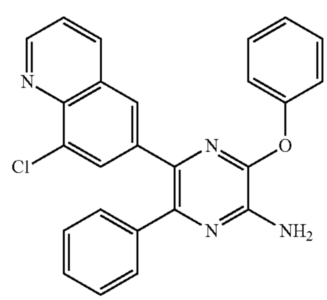 [SMILES: Nc1nc(-c2ccccc2)c(-c2cc(Cl)c3ncccc3c2)nc1Oc1ccccc1] |
| 2.174 | 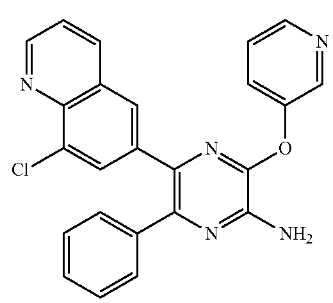 [SMILES: Nc1nc(-c2ccccc2)c(-c2cc(Cl)c3ncccc3c2)nc1Oc1cccnc1] |

TABLE 2-continued

| Compound No. | Structure |
|---|---|
| 2.175 | 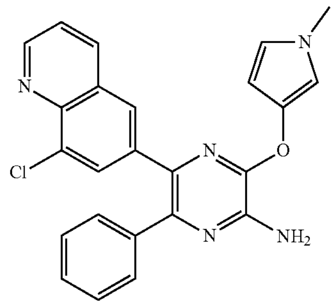 [SMILES: Cn1ccc(Oc2nc(-c3cc(Cl)c4ncccc4c3)c(-c3ccccc3)nc2N)c1] |
| 2.176 | 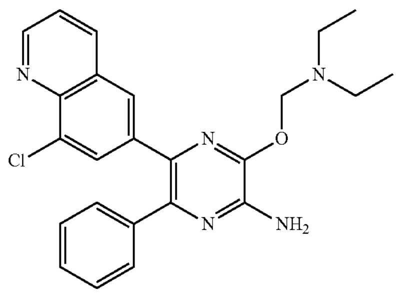 [SMILES: CCN(CC)COc1nc(-c2cc(Cl)c3ncccc3c2)c(-c2ccccc2)nc1N] |
| 2.177 | 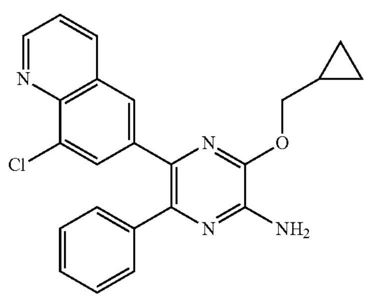 [SMILES: Nc1nc(-c2ccccc2)c(-c2cc(Cl)c3ncccc3c2)nc1OCC1CC1] |
| 2.178 | 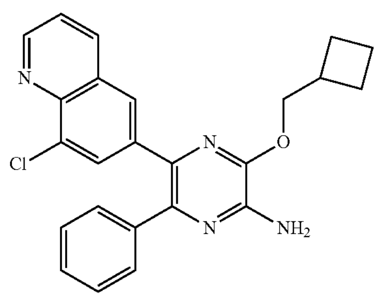 |
| 2.179 | 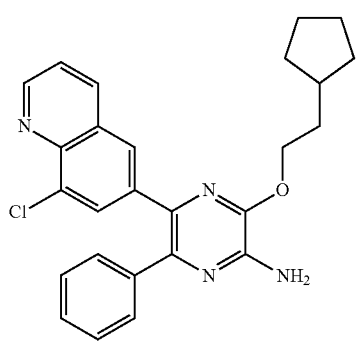 [SMILES: Nc1nc(-c2ccccc2)c(-c2cc(Cl)c3ncccc3c2)nc1OCCC1CCCC1] |

TABLE 2-continued

| Compound No. | Structure |
|---|---|
| 2.180 | *(8-chloroquinolin-6-yl)-3-(cyclohexylmethoxy)-6-phenylpyrazin-2-amine)* |
| 2.181 | *(8-chloroquinolin-6-yl)-3-((1-methyl-5-oxopyrrolidin-3-yl)methoxy)-6-phenylpyrazin-2-amine)* |
| 2.182 | *(8-chloroquinolin-6-yl)-3-((1-methylazetidin-3-yl)methoxy)-6-phenylpyrazin-2-amine)* |
| 2.183 | *(8-chloroquinolin-6-yl)-6-phenyl-3-(2-(pyrrolidin-1-yl)ethoxy)pyrazin-2-amine)* |
| 2.184 | *(8-chloroquinolin-6-yl)-3-((1-methylpiperidin-4-yl)methoxy)-6-phenylpyrazin-2-amine)* |

TABLE 2-continued
| Compound No. | Structure |
|---|---|
| 2.185 | 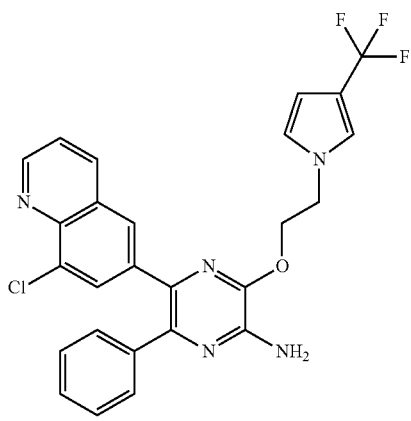 [SMILES: Nc1nc(-c2ccccc2)c(-c2cc(Cl)c3ncccc3c2)nc1OCCn1ccc(C(F)(F)F)c1] |
| 2.186 | 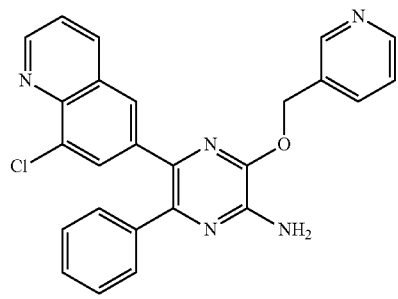 [SMILES: Nc1nc(-c2ccccc2)c(-c2cc(Cl)c3ncccc3c2)nc1OCc1cccnc1] |
| 2.187 | 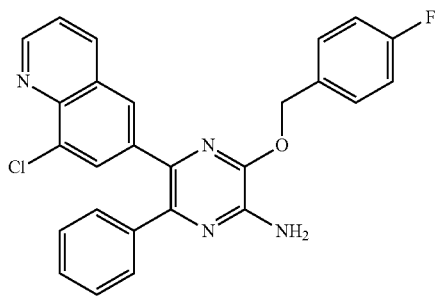 |
| 2.188 | 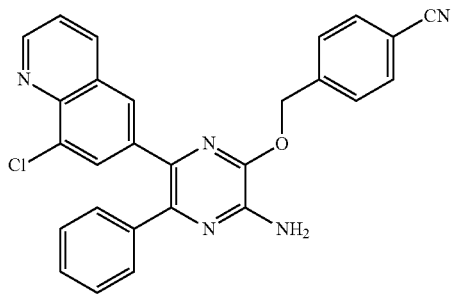 [SMILES: N#Cc1ccc(COc2nc(-c3cc(Cl)c4ncccc4c3)c(-c3ccccc3)nc2N)cc1] |

TABLE 2-continued
| Compound No. | Structure |
|---|---|
| 2.189 | 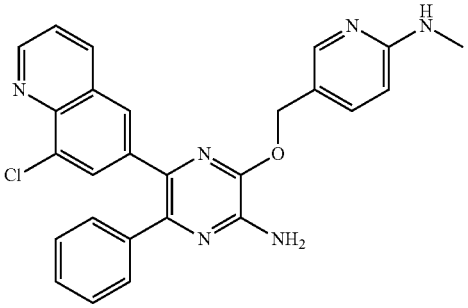 |
| 2.190 | 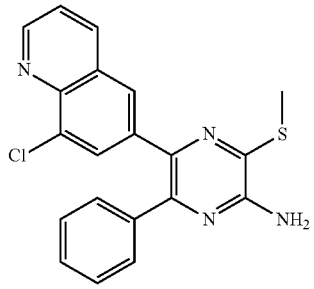 [SMILES: CSc1nc(-c2cc(Cl)c3ncccc3c2)c(-c2ccccc2)nc1N] |
| 2.191 | 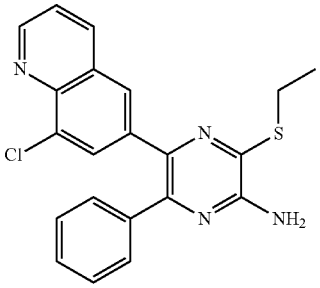 [SMILES: CCSc1nc(-c2cc(Cl)c3ncccc3c2)c(-c2ccccc2)nc1N] |
| 2.192 | 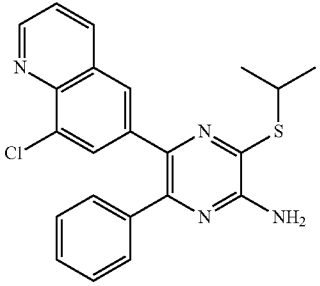 [SMILES: CC(C)Sc1nc(-c2cc(Cl)c3ncccc3c2)c(-c2ccccc2)nc1N] |
| 2.193 | 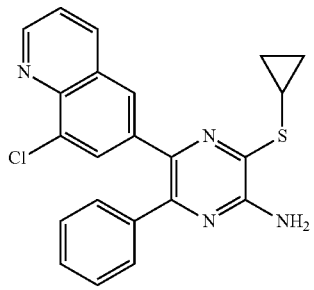 [SMILES: Nc1nc(-c2ccccc2)c(-c2cc(Cl)c3ncccc3c2)nc1SC1CC1] |

TABLE 2-continued

| Compound No. | Structure |
|---|---|
| 2.194 | 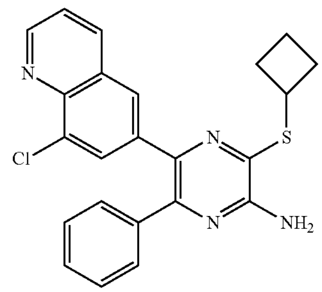 [SMILES: Nc1nc(-c2ccccc2)c(-c2cc(Cl)c3ncccc3c2)nc1SC1CCC1] |
| 2.195 | 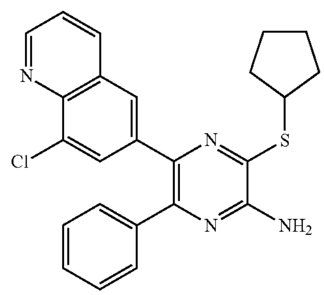 [SMILES: Nc1nc(-c2ccccc2)c(-c2cc(Cl)c3ncccc3c2)nc1SC1CCCC1] |
| 2.196 | 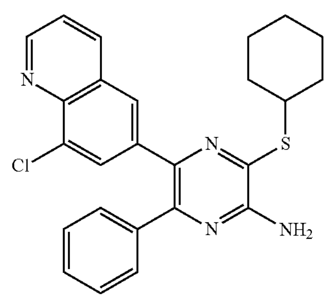 [SMILES: Nc1nc(-c2ccccc2)c(-c2cc(Cl)c3ncccc3c2)nc1SC1CCCCC1] |
| 2.197 | 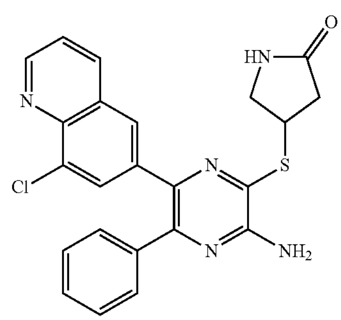 [SMILES: Nc1nc(-c2ccccc2)c(-c2cc(Cl)c3ncccc3c2)nc1SC1CNC(=O)C1] |
| 2.198 | 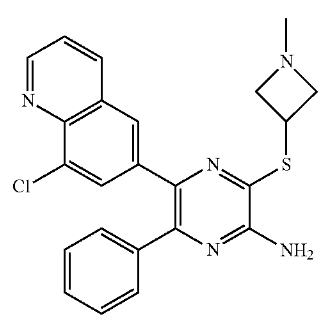 [SMILES: CN1CC(Sc2nc(-c3cc(Cl)c4ncccc4c3)c(-c3ccccc3)nc2N)C1] |

TABLE 2-continued
| Compound No. | Structure |
|---|---|
| 2.199 | 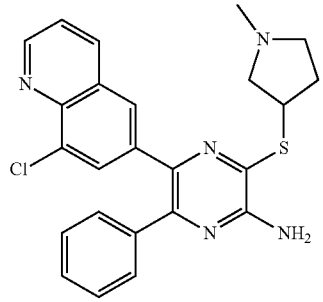 [SMILES: CN1CCC(Sc2nc(-c3cc(Cl)c4ncccc4c3)c(-c3ccccc3)nc2N)C1] |
| 2.200 | 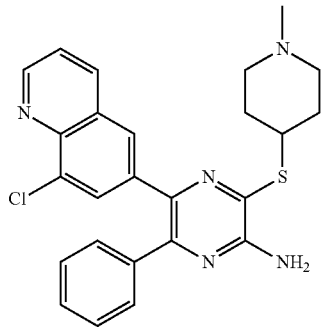 [SMILES: CN1CCC(Sc2nc(-c3cc(Cl)c4ncccc4c3)c(-c3ccccc3)nc2N)CC1] |
| 2.201 | 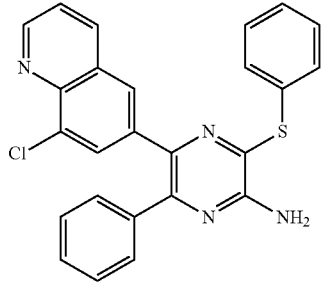 [SMILES: Nc1nc(-c2ccccc2)c(-c2cc(Cl)c3ncccc3c2)nc1Sc1ccccc1] |
| 2.202 | 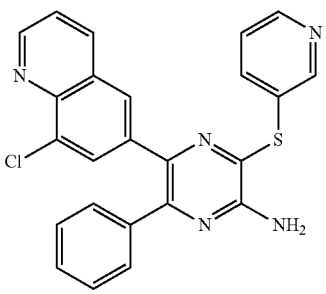 [SMILES: Nc1nc(-c2ccccc2)c(-c2cc(Cl)c3ncccc3c2)nc1Sc1cccnc1] |
| 2.203 | 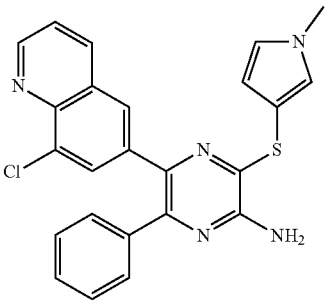 [SMILES: Cn1ccc(Sc2nc(-c3cc(Cl)c4ncccc4c3)c(-c3ccccc3)nc2N)c1] |

TABLE 2-continued
| Compound No. | Structure |
|---|---|
| 2.204 | 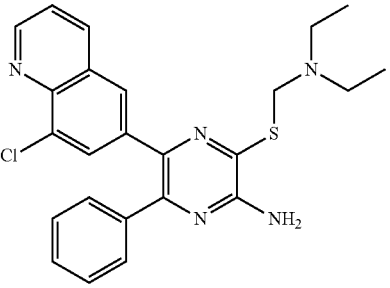 [SMILES: CCN(CC)CSc1nc(-c2cc(Cl)c3ncccc3c2)c(-c2ccccc2)nc1N] |
| 2.205 | 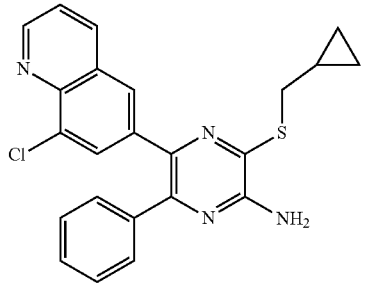 [SMILES: Nc1nc(-c2ccccc2)c(-c2cc(Cl)c3ncccc3c2)nc1SCC1CC1] |
| 2.206 | 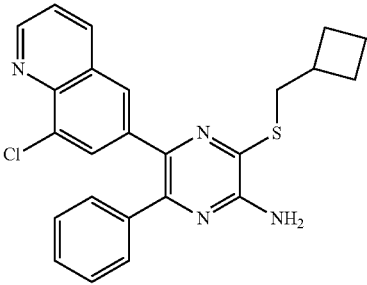 |
| 2.207 | 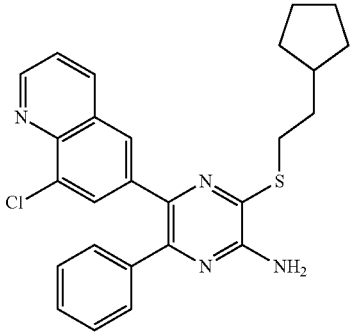 [SMILES: Nc1nc(-c2ccccc2)c(-c2cc(Cl)c3ncccc3c2)nc1SCCC1CCCC1] |
| 2.208 | 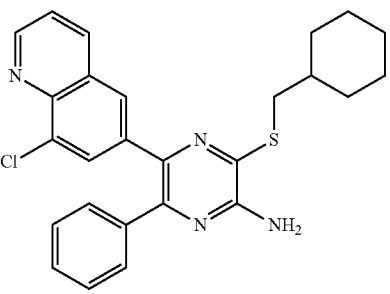 [SMILES: Nc1nc(-c2ccccc2)c(-c2cc(Cl)c3ncccc3c2)nc1SCC1CCCCC1] |

TABLE 2-continued
| Compound No. | Structure |
|---|---|
| 2.209 | 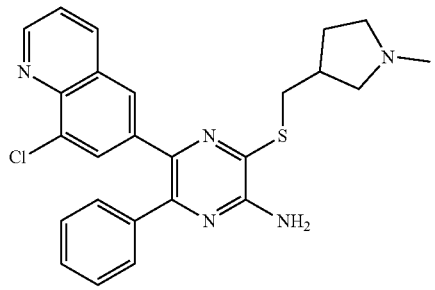 [SMILES: CN1CCC(CSc2nc(-c3cc(Cl)c4ncccc4c3)c(-c3ccccc3)nc2N)C1] |
| 2.210 | 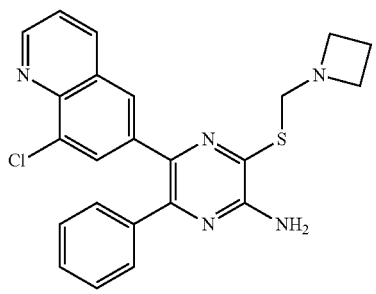 [SMILES: Nc1nc(-c2ccccc2)c(-c2cc(Cl)c3ncccc3c2)nc1SCN1CCC1] |
| 2.211 | 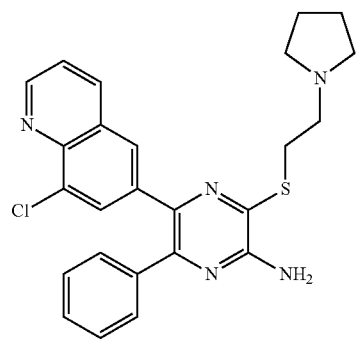 [SMILES: Nc1nc(-c2ccccc2)c(-c2cc(Cl)c3ncccc3c2)nc1SCCN1CCCC1] |
| 2.212 | 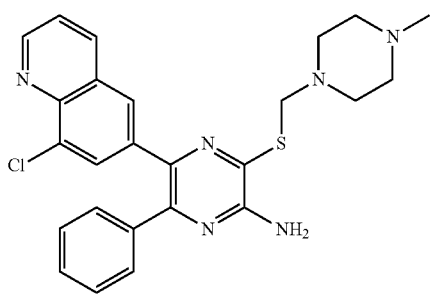 [SMILES: CN1CCN(CSc2nc(-c3cc(Cl)c4ncccc4c3)c(-c3ccccc3)nc2N)CC1] |

TABLE 2-continued
| Compound No. | Structure |
|---|---|
| 2.213 | 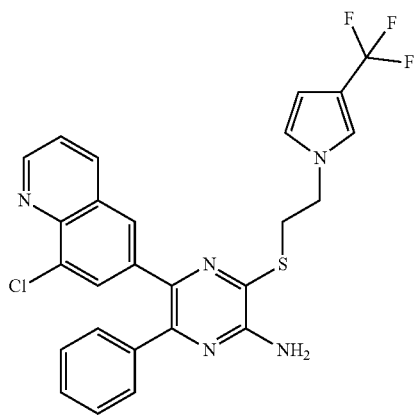 [SMILES: Nc1nc(-c2ccccc2)c(-c2cc(Cl)c3ncccc3c2)nc1SCCn1ccc(C(F)(F)F)c1] |
| 2.214 | 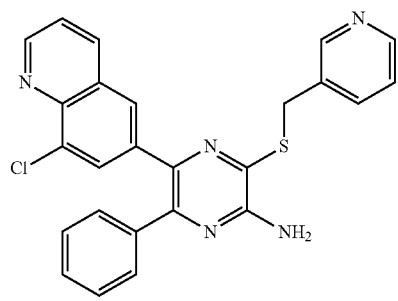 [SMILES: Nc1nc(-c2ccccc2)c(-c2cc(Cl)c3ncccc3c2)nc1SCc1cccnc1] |
| 2.215 | 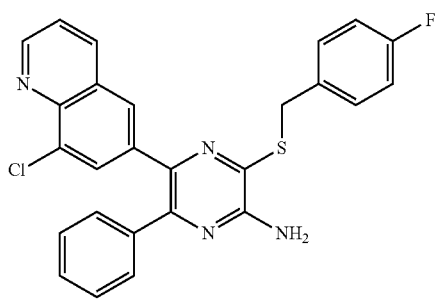 [SMILES: Nc1nc(-c2ccccc2)c(-c2cc(Cl)c3ncccc3c2)nc1SCc1ccc(F)cc1] |
| 2.216 | 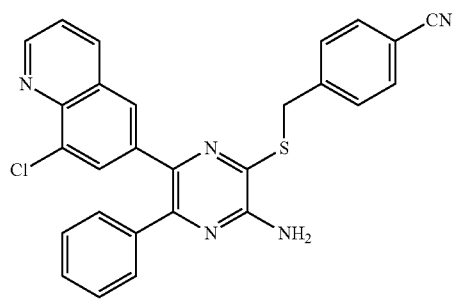 |

TABLE 2-continued

| Compound No. | Structure |
|---|---|
| 2.217 | 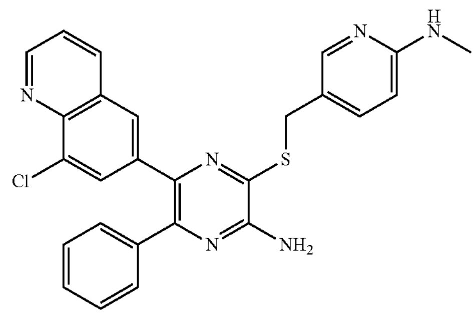 |
| 2.218 | 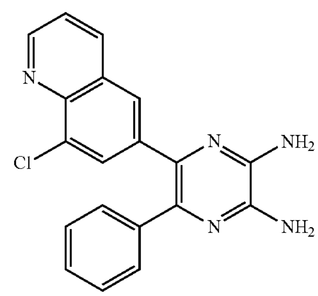 [SMILES: Nc1nc(-c2ccccc2)c(-c2cc(Cl)c3ncccc3c2)nc1N] |
| 2.219 | 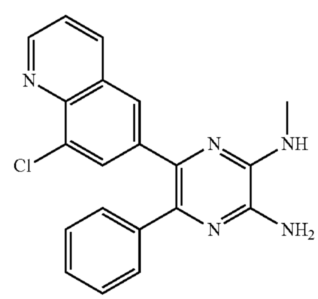 [SMILES: CNc1nc(-c2cc(Cl)c3ncccc3c2)c(-c2ccccc2)nc1N] |
| 2.220 | 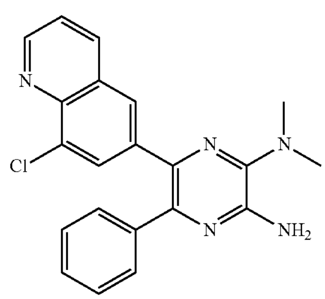 [SMILES: CN(C)c1nc(-c2cc(Cl)c3ncccc3c2)c(-c2ccccc2)nc1N] |
| 2.221 | 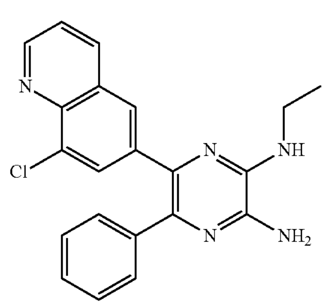 [SMILES: CCNc1nc(-c2cc(Cl)c3ncccc3c2)c(-c2ccccc2)nc1N] |

TABLE 2-continued
| Compound No. | Structure |
|---|---|
| 2.222 | 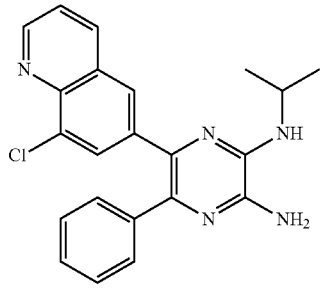 [SMILES: CC(C)Nc1nc(-c2cc(Cl)c3ncccc3c2)c(-c2ccccc2)nc1N] |
| 2.223 | 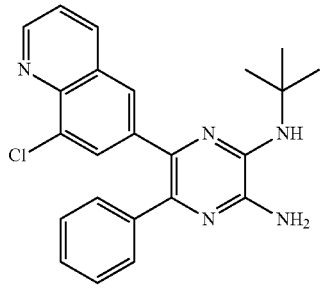 [SMILES: CC(C)(C)Nc1nc(-c2cc(Cl)c3ncccc3c2)c(-c2ccccc2)nc1N] |
| 2.224 | 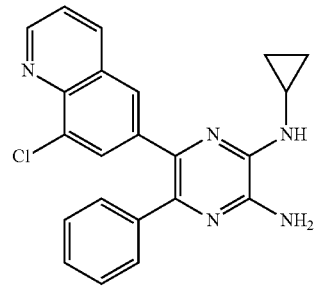 [SMILES: Nc1nc(-c2ccccc2)c(-c2cc(Cl)c3ncccc3c2)nc1NC1CC1] |
| 2.225 | 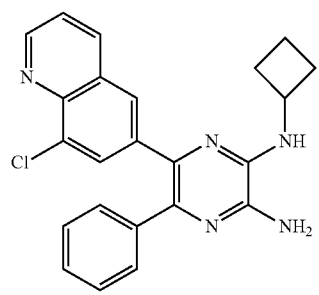 [SMILES: Nc1nc(-c2ccccc2)c(-c2cc(Cl)c3ncccc3c2)nc1NC1CCC1] |
| 2.226 | 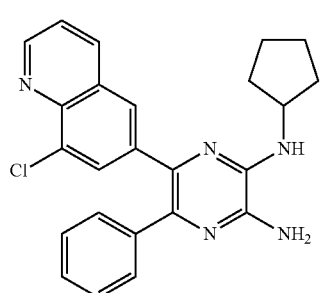 |

US 11,028,058 B2
TABLE 2-continued
| Compound No. | Structure |
|---|---|
| 2.227 | 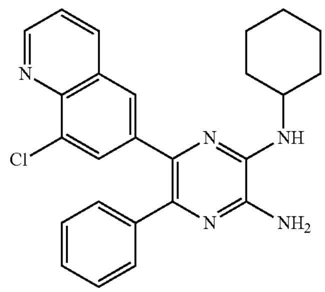 [SMILES: Nc1nc(-c2ccccc2)c(-c2cc(Cl)c3ncccc3c2)nc1NC1CCCCC1] |
| 2.228 | 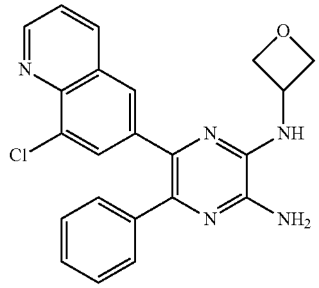 [SMILES: Nc1nc(-c2ccccc2)c(-c2cc(Cl)c3ncccc3c2)nc1NC1COC1] |
| 2.229 | 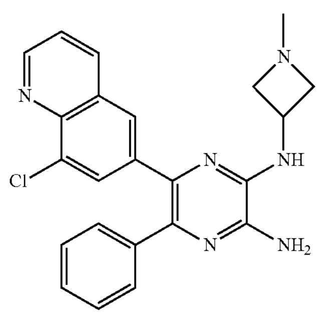 [SMILES: CN1CC(Nc2nc(-c3cc(Cl)c4ncccc4c3)c(-c3ccccc3)nc2N)C1] |
| 2.230 | 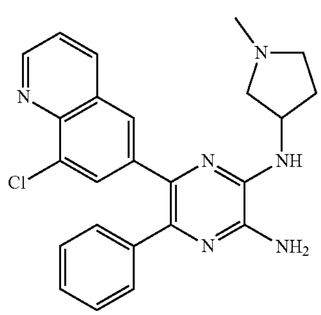 [SMILES: CN1CCC(Nc2nc(-c3cc(Cl)c4ncccc4c3)c(-c3ccccc3)nc2N)C1] |
| 2.231 | 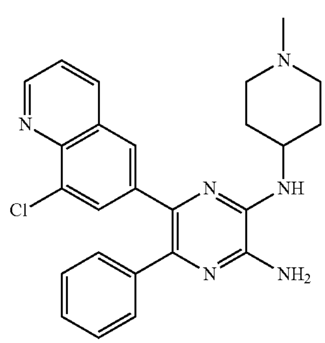 [SMILES: CN1CCC(Nc2nc(-c3cc(Cl)c4ncccc4c3)c(-c3ccccc3)nc2N)CC1] |

TABLE 2-continued
| Compound No. | Structure |
|---|---|
| 2.232 | 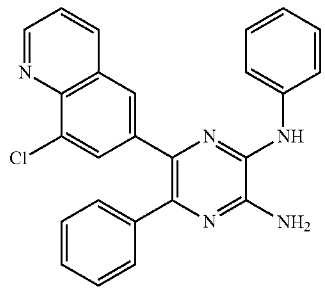 [SMILES: Nc1nc(-c2ccccc2)c(-c2cc(Cl)c3ncccc3c2)nc1Nc1ccccc1] |
| 2.233 | 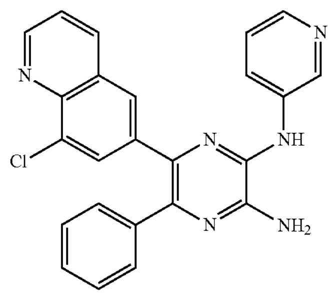 [SMILES: Nc1nc(-c2ccccc2)c(-c2cc(Cl)c3ncccc3c2)nc1Nc1cccnc1] |
| 2.234 | 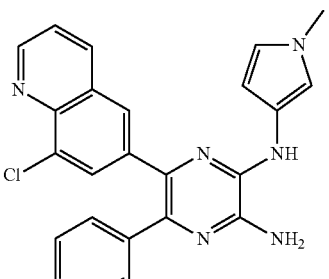 |
| 2.235 | 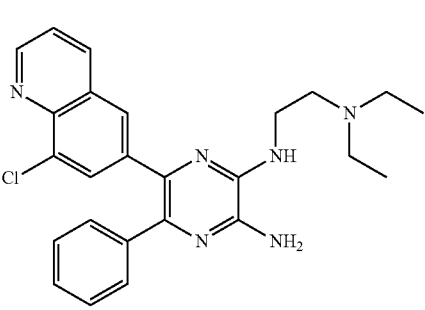 [SMILES: CCN(CC)CCNc1nc(-c2cc(Cl)c3ncccc3c2)c(-c2ccccc2)nc1N] |
| 2.236 | 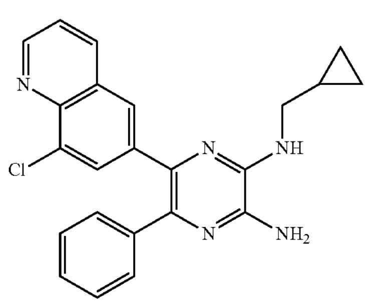 [SMILES: Nc1nc(-c2ccccc2)c(-c2cc(Cl)c3ncccc3c2)nc1NCC1CC1] |

TABLE 2-continued
| Compound No. | Structure |
|---|---|
| 2.237 | 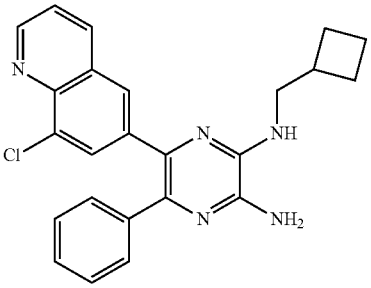 [SMILES: Nc1nc(-c2ccccc2)c(-c2cc(Cl)c3ncccc3c2)nc1NCC1CCC1] |
| 2.238 | 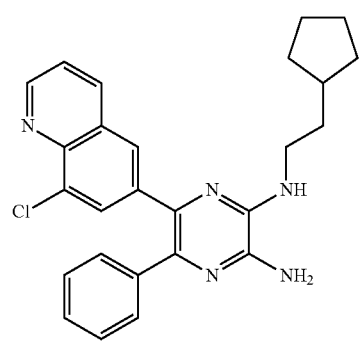 |
| 2.239 | 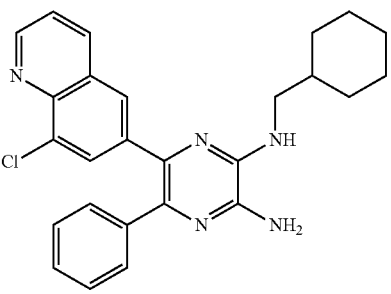 |
| 2.240 | 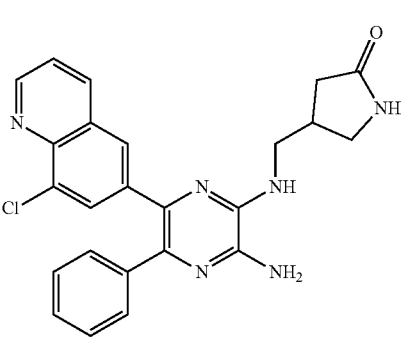 [SMILES: Nc1nc(-c2ccccc2)c(-c2cc(Cl)c3ncccc3c2)nc1NCC1CNC(=O)C1] |
| 2.241 | 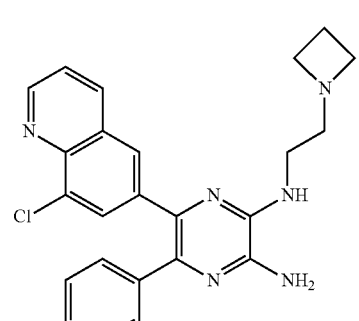 |

TABLE 2-continued
| Compound No. | Structure |
|---|---|
| 2.242 | 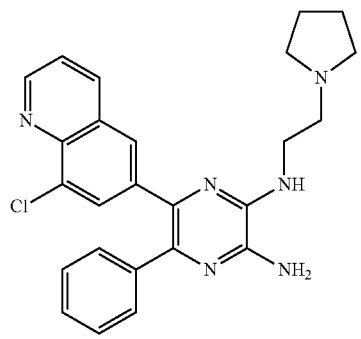 [SMILES: Nc1nc(-c2ccccc2)c(-c2cc(Cl)c3ncccc3c2)nc1NCCN1CCCC1] |
| 2.243 | 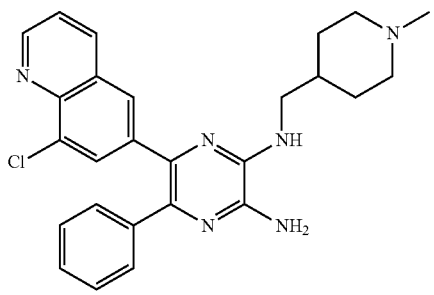 [SMILES: CN1CCC(CNc2nc(-c3cc(Cl)c4ncccc4c3)c(-c3ccccc3)nc2N)CC1] |
| 2.244 | 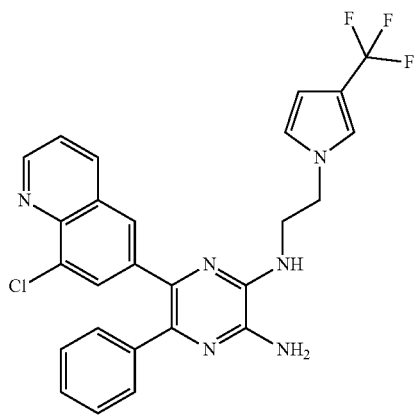 [SMILES: Nc1nc(-c2ccccc2)c(-c2cc(Cl)c3ncccc3c2)nc1NCCn1ccc(C(F)(F)F)c1] |
| 2.245 | 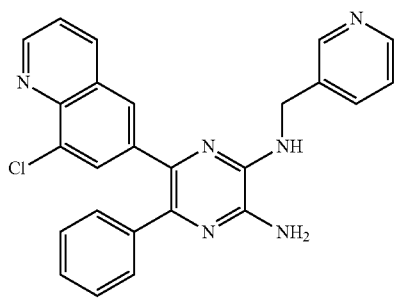 |

TABLE 2-continued

| Compound No. | Structure |
|---|---|
| 2.246 | (structure: 8-chloroquinolin-6-yl, phenyl, NH-CH2-(4-fluorophenyl), NH2 substituted pyrazine) |
| 2.247 | (structure: 8-chloroquinolin-6-yl, phenyl, NH-CH2-(4-cyanophenyl), NH2 substituted pyrazine) |
| 2.248 | (structure: 8-chloroquinolin-6-yl, phenyl, NH-CH2-(6-(methylamino)pyridin-3-yl), NH2 substituted pyrazine) |
| 2.249 | (structure: 8-chloroquinolin-6-yl, phenyl, acetyl, NH2 substituted pyrazine) |
| 2.250 | (structure: 8-chloroquinolin-6-yl, phenyl, propanoyl, NH2 substituted pyrazine) |

TABLE 2-continued

| Compound No. | Structure |
|---|---|
| 2.251 | (8-chloroquinolin-6-yl, phenyl, cyclopropyl carbonyl, amino pyrazine) |
| 2.252 | (8-chloroquinolin-6-yl, phenyl, cyclobutyl carbonyl, amino pyrazine) |
| 2.253 | (8-chloroquinolin-6-yl, phenyl, cyclopentyl carbonyl, amino pyrazine) |
| 2.254 | (8-chloroquinolin-6-yl, phenyl, cyclohexyl carbonyl, amino pyrazine) |
| 2.255 | (8-chloroquinolin-6-yl, phenyl, pyrrolidin-3-yl carbonyl, amino pyrazine) |

TABLE 2-continued

| Compound No. | Structure |
|---|---|
| 2.256 | (structure) |
| 2.257 | (structure) |
| 2.258 | (structure) |
| 2.259 | (structure) |
| 2.260 | (structure) |

TABLE 2-continued
| Compound No. | Structure |
|---|---|
| 2.261 | 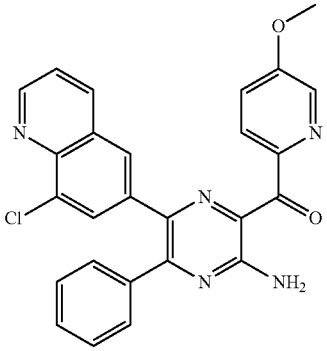 [SMILES: COc1ccc(C(=O)c2nc(-c3cc(Cl)c4ncccc4c3)c(-c3ccccc3)nc2N)nc1] |
| 2.262 | 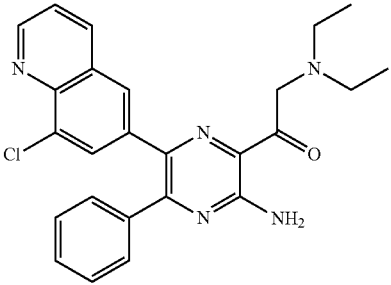 |
| 2.263 | 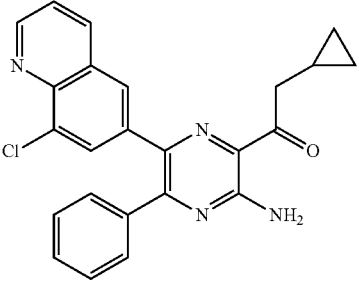 |
| 2.264 | 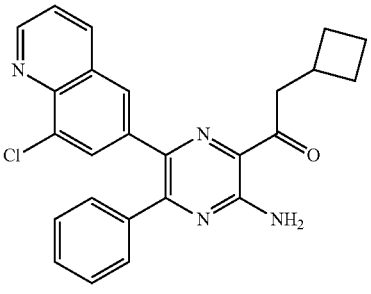 [SMILES: Nc1nc(-c2ccccc2)c(-c2cc(Cl)c3ncccc3c2)nc1C(=O)CC1CCC1] |
| 2.265 | 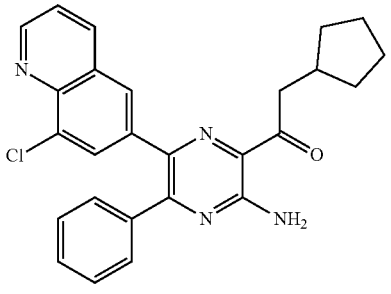 [SMILES: Nc1nc(-c2ccccc2)c(-c2cc(Cl)c3ncccc3c2)nc1C(=O)CC1CCCC1] |

TABLE 2-continued

| Compound No. | Structure |
|---|---|
| 2.266 | 8-chloroquinolin-6-yl, phenyl, 3-amino-pyrazine with 2-cyclohexyl-1-oxoethyl substituent |
| 2.267 | 8-chloroquinolin-6-yl, phenyl, 3-amino-pyrazine with 2-(3-methylimidazolidin-1-yl)-1-oxoethyl substituent |
| 2.268 | 8-chloroquinolin-6-yl, phenyl, 3-amino-pyrazine with 2-(azetidin-1-yl)-1-oxoethyl substituent |
| 2.269 | 8-chloroquinolin-6-yl, phenyl, 3-amino-pyrazine with 2-(pyrrolidin-1-yl)-1-oxoethyl substituent |
| 2.270 | 8-chloroquinolin-6-yl, methyl, 3-amino-pyrazine with 2-morpholino-1-oxoethyl substituent |

TABLE 2-continued

| Compound No. | Structure |
|---|---|
| 2.271 | 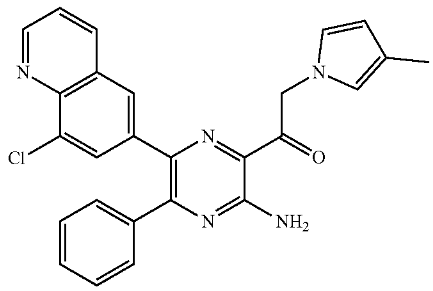 [SMILES: Cc1ccn(CC(=O)c2nc(-c3cc(Cl)c4ncccc4c3)c(-c3ccccc3)nc2N)c1] |
| 2.272 | 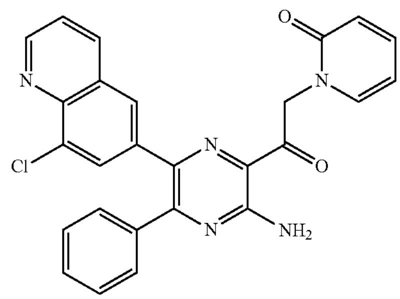 [SMILES: Nc1nc(-c2ccccc2)c(-c2cc(Cl)c3ncccc3c2)nc1C(=O)Cn1ccccc1=O] |
| 2.273 | 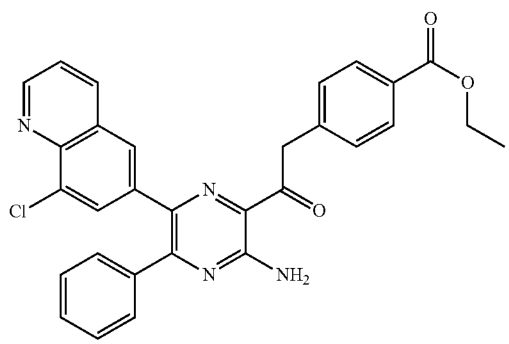 [SMILES: CCOC(=O)c1ccc(CC(=O)c2nc(-c3cc(Cl)c4ncccc4c3)c(-c3ccccc3)nc2N)cc1] |
| 2.274 | 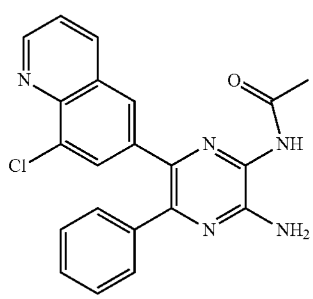 [SMILES: CC(=O)Nc1nc(-c2cc(Cl)c3ncccc3c2)c(-c2ccccc2)nc1N] |
| 2.275 | 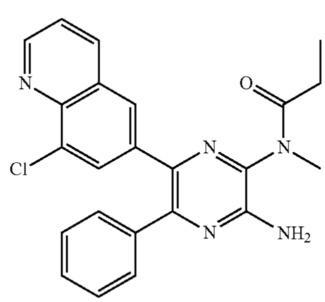 [SMILES: CCC(=O)N(C)c1nc(-c2cc(Cl)c3ncccc3c2)c(-c2ccccc2)nc1N] |

TABLE 2-continued
| Compound No. | Structure |
|---|---|
| 2.276 | 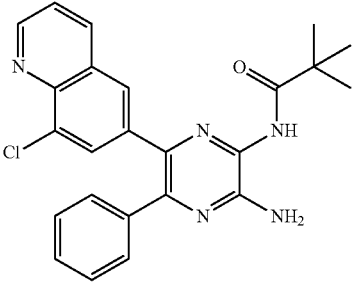 [SMILES: CC(C)(C)C(=O)Nc1nc(-c2cc(Cl)c3ncccc3c2)c(-c2ccccc2)nc1N] |
| 2.277 | 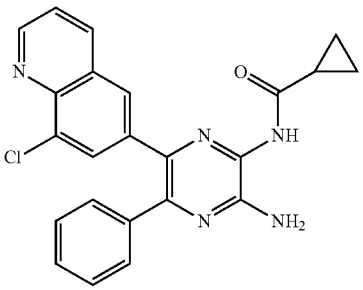 [SMILES: Nc1nc(-c2ccccc2)c(-c2cc(Cl)c3ncccc3c2)nc1NC(=O)C1CC1] |
| 2.278 | 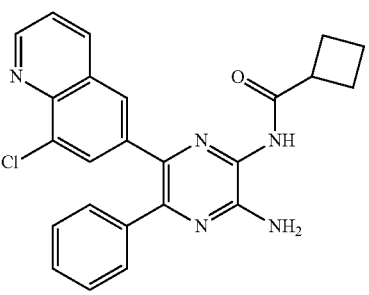 [SMILES: Nc1nc(-c2ccccc2)c(-c2cc(Cl)c3ncccc3c2)nc1NC(=O)C1CCC1] |
| 2.279 | 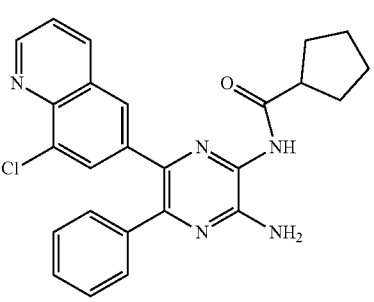 [SMILES: Nc1nc(-c2ccccc2)c(-c2cc(Cl)c3ncccc3c2)nc1NC(=O)C1CCCC1] |
| 2.280 | 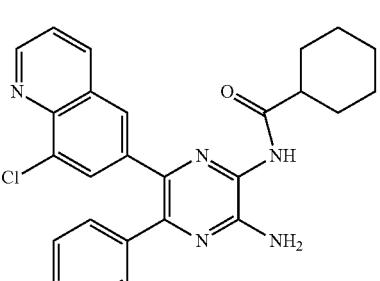 |

TABLE 2-continued

| Compound No. | Structure |
|---|---|
| 2.281 | 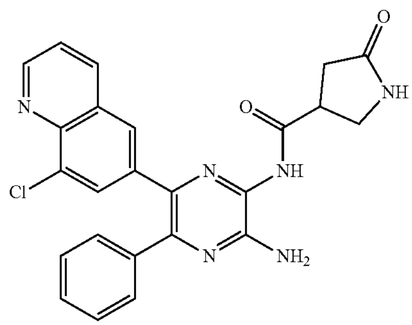 [SMILES: Nc1nc(-c2ccccc2)c(-c2cc(Cl)c3ncccc3c2)nc1NC(=O)C1CNC(=O)C1] |
| 2.282 | 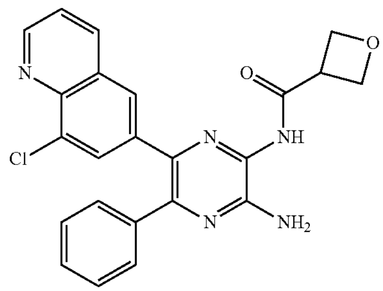 [SMILES: Nc1nc(-c2ccccc2)c(-c2cc(Cl)c3ncccc3c2)nc1NC(=O)C1COC1] |
| 2.283 | 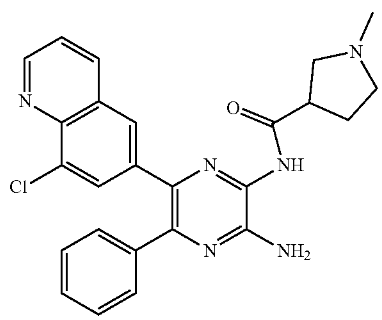 [SMILES: CN1CCC(C(=O)Nc2nc(-c3cc(Cl)c4ncccc4c3)c(-c3ccccc3)nc2N)C1] |
| 2.284 | 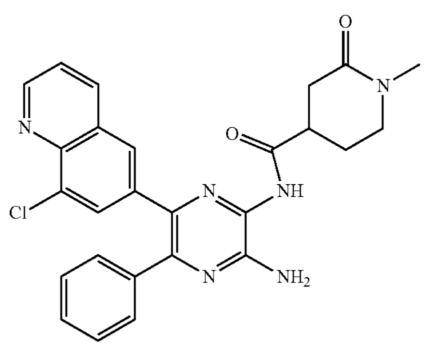 [SMILES: CN1CCC(C(=O)Nc2nc(-c3cc(Cl)c4ncccc4c3)c(-c3ccccc3)nc2N)CC1=O] |
| 2.285 | 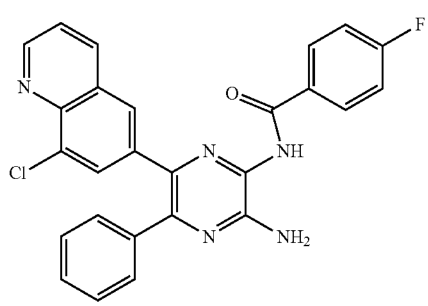 [SMILES: Nc1nc(-c2ccccc2)c(-c2cc(Cl)c3ncccc3c2)nc1NC(=O)c1ccc(F)cc1] |

TABLE 2-continued
| Compound No. | Structure |
|---|---|
| 2.286 | 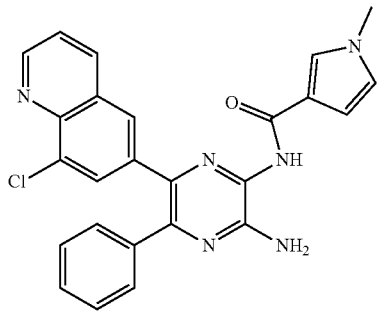 [SMILES: Cn1ccc(C(=O)Nc2nc(-c3cc(Cl)c4ncccc4c3)c(-c3ccccc3)nc2N)c1] |
| 2.287 | 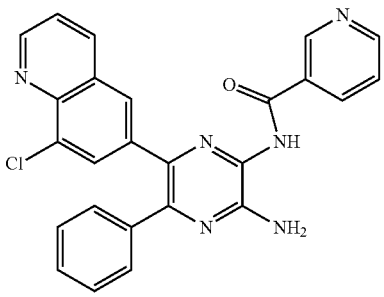 [SMILES: Nc1nc(-c2ccccc2)c(-c2cc(Cl)c3ncccc3c2)nc1NC(=O)c1cccnc1] |
| 2.288 | 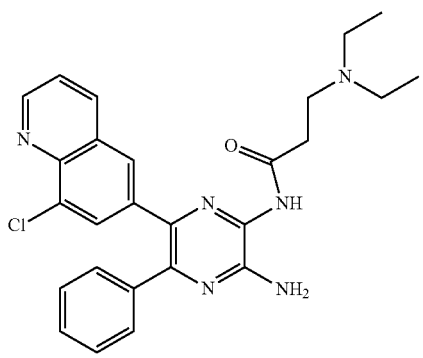 [SMILES: CCN(CC)CCC(=O)Nc1nc(-c2cc(Cl)c3ncccc3c2)c(-c2ccccc2)nc1N] |
| 2.289 | 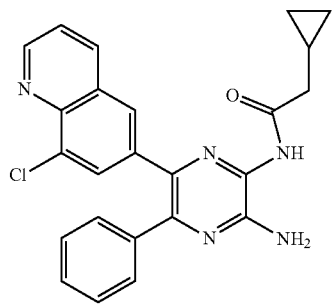 [SMILES: Nc1nc(-c2ccccc2)c(-c2cc(Cl)c3ncccc3c2)nc1NC(=O)CC1CC1] |

TABLE 2-continued
| Compound No. | Structure |
|---|---|
| 2.290 | 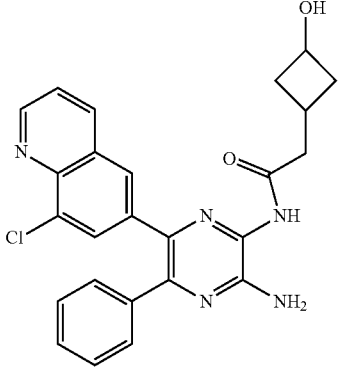 [SMILES: Nc1nc(-c2ccccc2)c(-c2cc(Cl)c3ncccc3c2)nc1NC(=O)CC1CC(O)C1] |
| 2.291 | 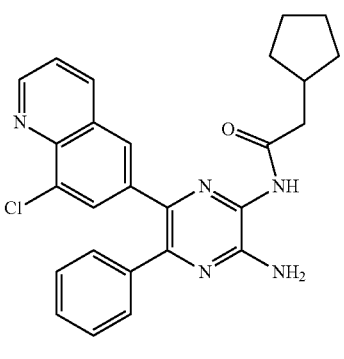 [SMILES: Nc1nc(-c2ccccc2)c(-c2cc(Cl)c3ncccc3c2)nc1NC(=O)CC1CCCC1] |
| 2.292 | 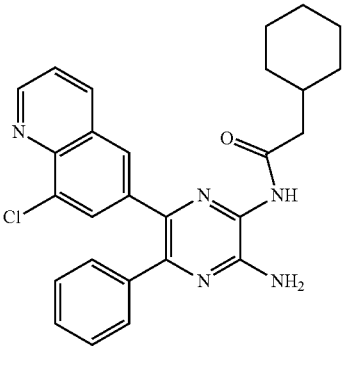 [SMILES: Nc1nc(-c2ccccc2)c(-c2cc(Cl)c3ncccc3c2)nc1NC(=O)CC1CCCCC1] |
| 2.293 | 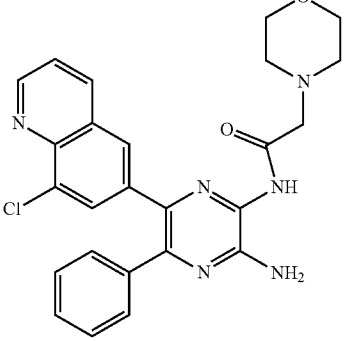 |

TABLE 2-continued
| Compound No. | Structure |
|---|---|
| 2.294 | 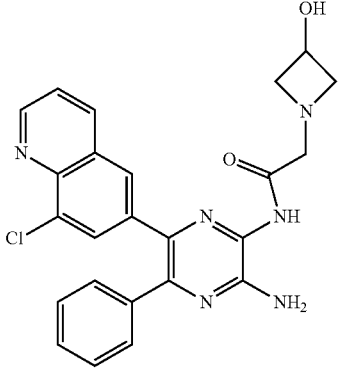 [SMILES: Nc1nc(-c2ccccc2)c(-c2cc(Cl)c3ncccc3c2)nc1NC(=O)CN1CC(O)C1] |
| 2.295 | 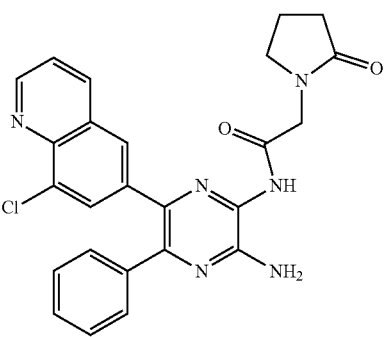 [SMILES: Nc1nc(-c2ccccc2)c(-c2cc(Cl)c3ncccc3c2)nc1NC(=O)CN1CCCC1=O] |
| 2.296 | 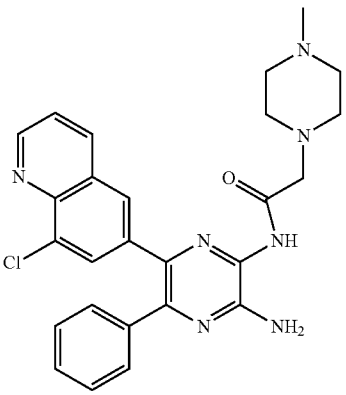 [SMILES: CN1CCN(CC(=O)Nc2nc(-c3cc(Cl)c4ncccc4c3)c(-c3ccccc3)nc2N)CC1] |
| 2.297 | 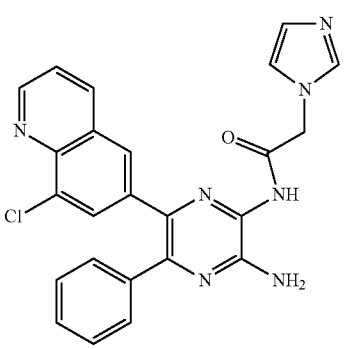 [SMILES: Nc1nc(-c2ccccc2)c(-c2cc(Cl)c3ncccc3c2)nc1NC(=O)Cn1ccnc1] |

TABLE 2-continued

| Compound No. | Structure |
| --- | --- |
| 2.298 | 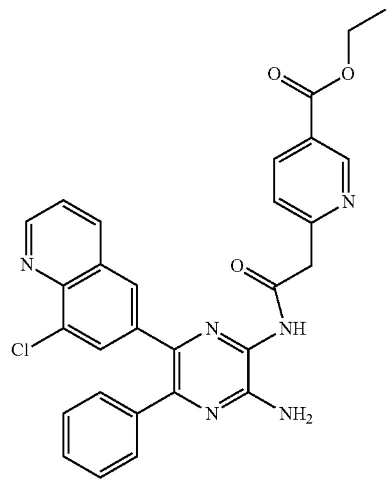 [SMILES: CCOC(=O)c1ccc(CC(=O)Nc2nc(-c3cc(Cl)c4ncccc4c3)c(-c3ccccc3)nc2N)nc1] |
| 2.299 | 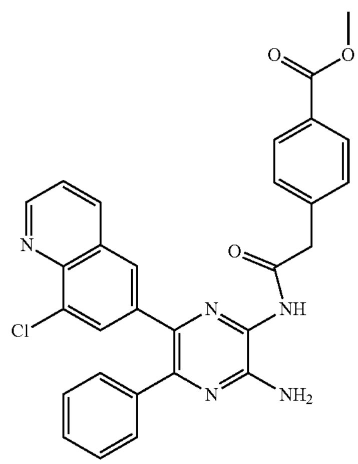 [SMILES: COC(=O)c1ccc(CC(=O)Nc2nc(-c3cc(Cl)c4ncccc4c3)c(-c3ccccc3)nc2N)cc1] |
| 2.300 | 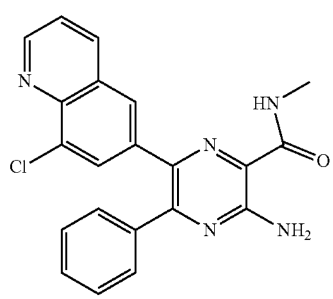 [SMILES: CNC(=O)c1nc(-c2cc(Cl)c3ncccc3c2)c(-c2ccccc2)nc1N] |
| 2.301 | 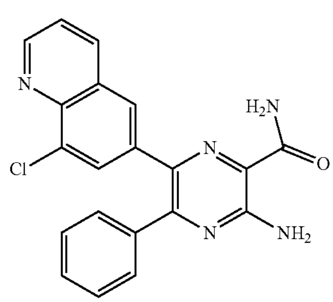 [SMILES: NC(=O)c1nc(-c2cc(Cl)c3ncccc3c2)c(-c2ccccc2)nc1N] |

TABLE 2-continued

| Compound No. | Structure |
|---|---|
| 2.302 | (8-chloroquinolin-6-yl / phenyl / 3-amino-pyrazine-2-carboxamide, N-ethyl) |
| 2.303 | (8-chloroquinolin-6-yl / phenyl / 3-amino-pyrazine-2-carboxamide, N-tert-butyl) |
| 2.304 | (8-chloroquinolin-6-yl / phenyl / 3-amino-pyrazine-2-carboxamide, N-cyclopropyl) |
| 2.305 | (8-chloroquinolin-6-yl / phenyl / 3-amino-pyrazine-2-carboxamide, N-cyclobutyl) |
| 2.306 | (8-chloroquinolin-6-yl / phenyl / 3-amino-pyrazine-2-carboxamide, N-cyclopentyl) |

TABLE 2-continued
| Compound No. | Structure |
|---|---|
| 2.307 | 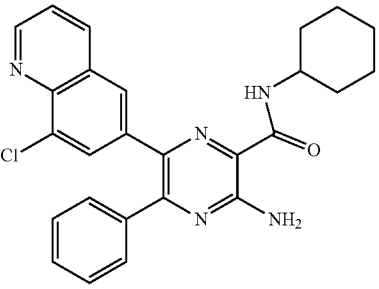 [SMILES: Nc1nc(-c2ccccc2)c(-c2cc(Cl)c3ncccc3c2)nc1C(=O)NC1CCCCC1] |
| 2.308 | 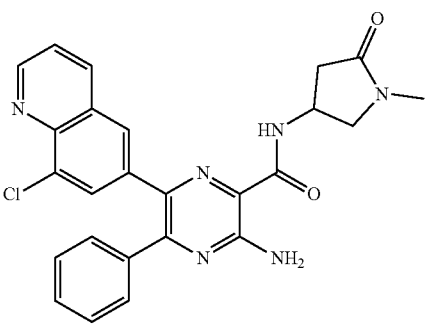 [SMILES: CN1CC(NC(=O)c2nc(-c3cc(Cl)c4ncccc4c3)c(-c3ccccc3)nc2N)CC1=O] |
| 2.309 | 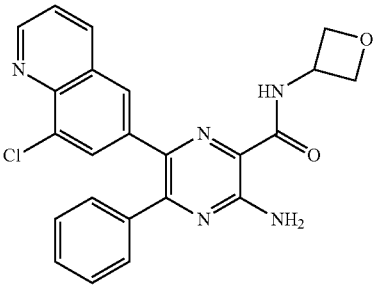 [SMILES: Nc1nc(-c2ccccc2)c(-c2cc(Cl)c3ncccc3c2)nc1C(=O)NC1COC1] |
| 2.310 | 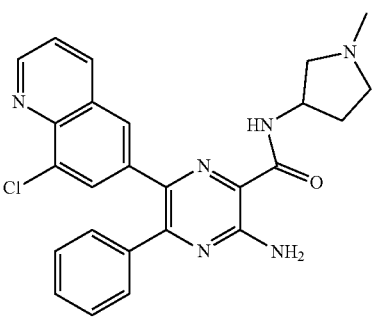 [SMILES: CN1CCC(NC(=O)c2nc(-c3cc(Cl)c4ncccc4c3)c(-c3ccccc3)nc2N)C1] |
| 2.311 | 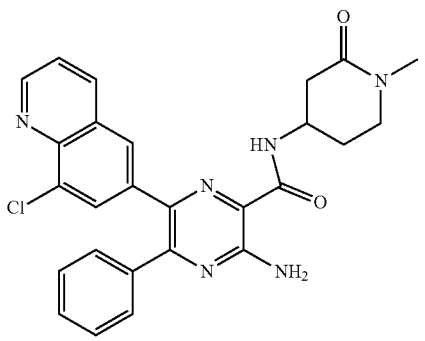 [SMILES: CN1CCC(NC(=O)c2nc(-c3cc(Cl)c4ncccc4c3)c(-c3ccccc3)nc2N)CC1=O] |

TABLE 2-continued
| Compound No. | Structure |
|---|---|
| 2.312 | 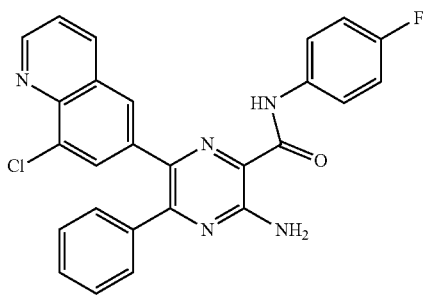 [SMILES: Nc1nc(-c2ccccc2)c(-c2cc(Cl)c3ncccc3c2)nc1C(=O)Nc1ccc(F)cc1] |
| 2.313 | 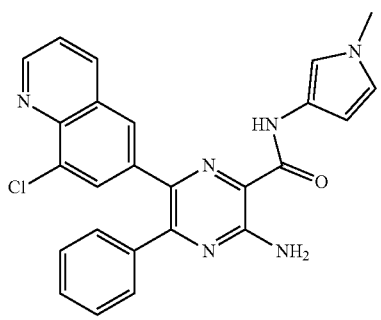 [SMILES: Cn1ccc(NC(=O)c2nc(-c3cc(Cl)c4ncccc4c3)c(-c3ccccc3)nc2N)c1] |
| 2.314 | 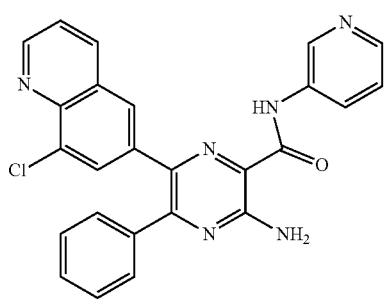 [SMILES: Nc1nc(-c2ccccc2)c(-c2cc(Cl)c3ncccc3c2)nc1C(=O)Nc1cccnc1] |
| 2.315 | 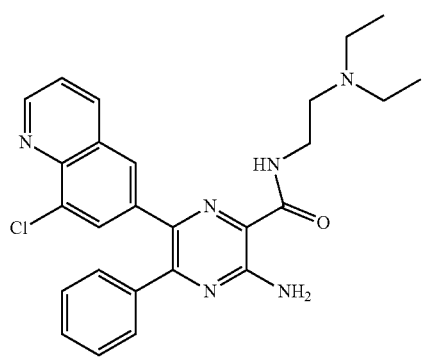 [SMILES: CCN(CC)CCNC(=O)c1nc(-c2cc(Cl)c3ncccc3c2)c(-c2ccccc2)nc1N] |

TABLE 2-continued
| Compound No. | Structure |
|---|---|
| 2.316 | 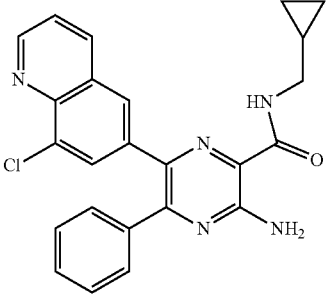 [SMILES: Nc1nc(-c2ccccc2)c(-c2cc(Cl)c3ncccc3c2)nc1C(=O)NCC1CC1] |
| 2.317 | 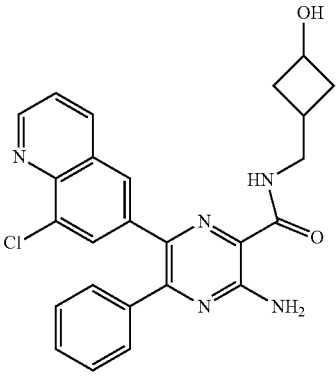 [SMILES: Nc1nc(-c2ccccc2)c(-c2cc(Cl)c3ncccc3c2)nc1C(=O)NCC1CC(O)C1] |
| 2.318 | 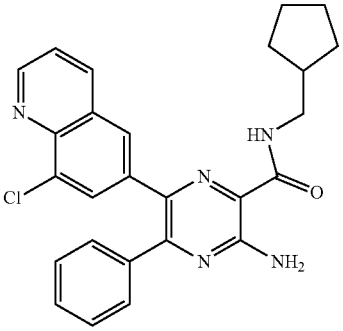 [SMILES: Nc1nc(-c2ccccc2)c(-c2cc(Cl)c3ncccc3c2)nc1C(=O)NCC1CCCC1] |
| 2.319 | 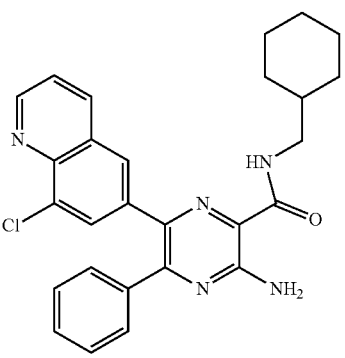 [SMILES: Nc1nc(-c2ccccc2)c(-c2cc(Cl)c3ncccc3c2)nc1C(=O)NCC1CCCCC1] |

TABLE 2-continued
| Compound No. | Structure |
|---|---|
| 2.320 | 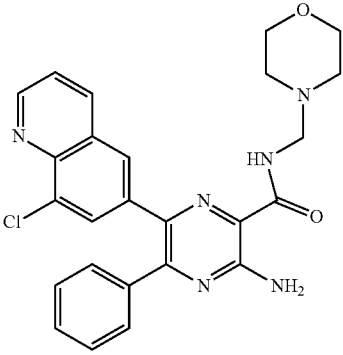 [SMILES: Nc1nc(-c2ccccc2)c(-c2cc(Cl)c3ncccc3c2)nc1C(=O)NCN1CCOCC1] |
| 2.321 | 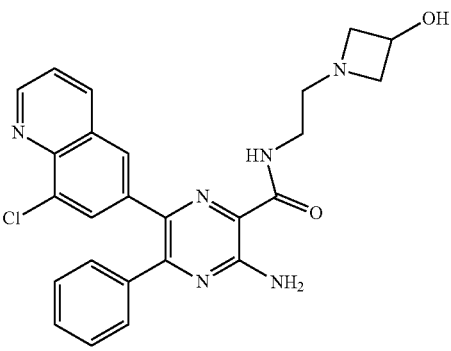 [SMILES: Nc1nc(-c2ccccc2)c(-c2cc(Cl)c3ncccc3c2)nc1C(=O)NCCN1CC(O)C1] |
| 2.322 | 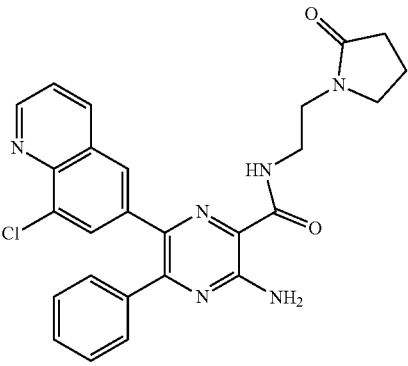 [SMILES: Nc1nc(-c2ccccc2)c(-c2cc(Cl)c3ncccc3c2)nc1C(=O)NCCN1CCCC1=O] |
| 2.323 | 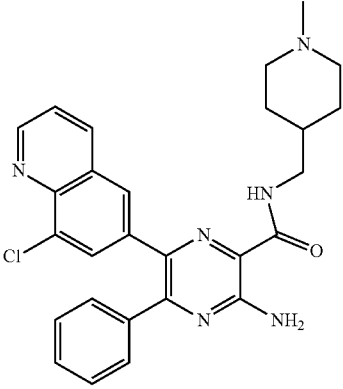 [SMILES: CN1CCC(CNC(=O)c2nc(-c3cc(Cl)c4ncccc4c3)c(-c3ccccc3)nc2N)CC1] |

TABLE 2-continued
| Compound No. | Structure |
|---|---|
| 2.324 | 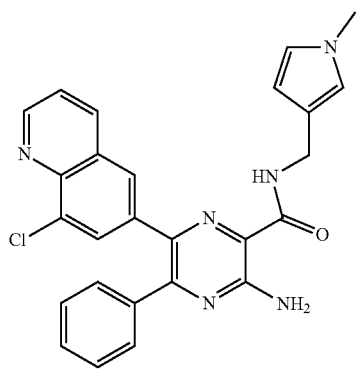 [SMILES: Cn1ccc(CNC(=O)c2nc(-c3cc(Cl)c4ncccc4c3)c(-c3ccccc3)nc2N)c1] |
| 2.325 | 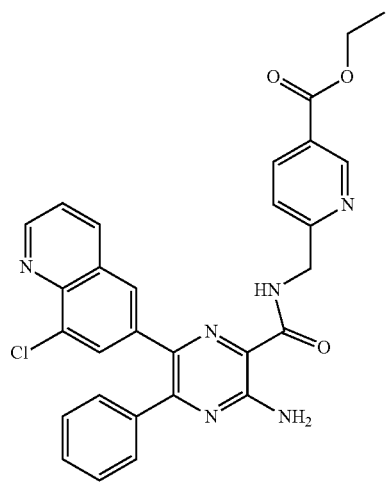 [SMILES: CCOC(=O)c1ccc(CNC(=O)c2nc(-c3cc(Cl)c4ncccc4c3)c(-c3ccccc3)nc2N)nc1] |
| 2.326 | 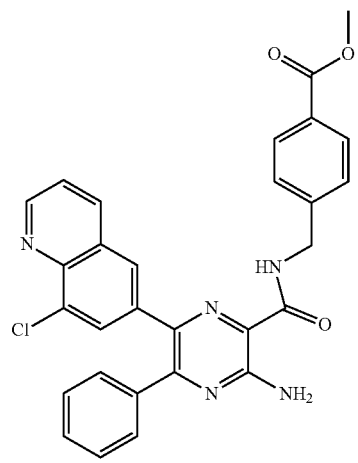 [SMILES: COC(=O)c1ccc(CNC(=O)c2nc(-c3cc(Cl)c4ncccc4c3)c(-c3ccccc3)nc2N)cc1] |

TABLE 2-continued
| Compound No. | Structure |
|---|---|
| 2.327 | 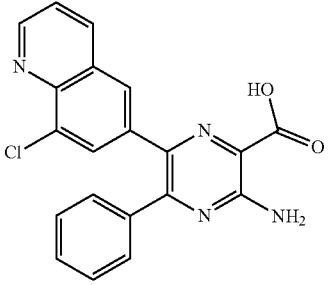 [SMILES: Nc1nc(-c2ccccc2)c(-c2cc(Cl)c3ncccc3c2)nc1C(=O)O] |
| 2.328 | 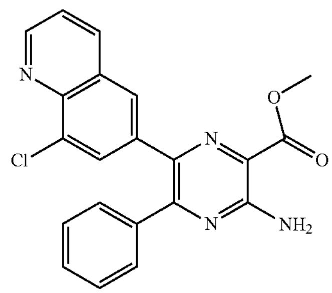 [SMILES: COC(=O)c1nc(-c2cc(Cl)c3ncccc3c2)c(-c2ccccc2)nc1N] |
| 2.329 | 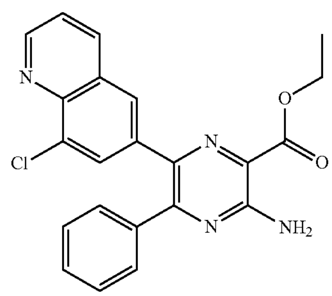 [SMILES: CCOC(=O)c1nc(-c2cc(Cl)c3ncccc3c2)c(-c2ccccc2)nc1N] |
| 2.330 | 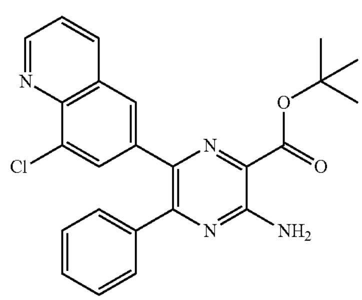 [SMILES: CC(C)(C)OC(=O)c1nc(-c2cc(Cl)c3ncccc3c2)c(-c2ccccc2)nc1N] |
| 2.331 | 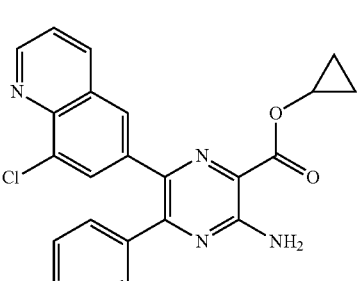 |

TABLE 2-continued

| Compound No. | Structure |
|---|---|
| 2.332 | 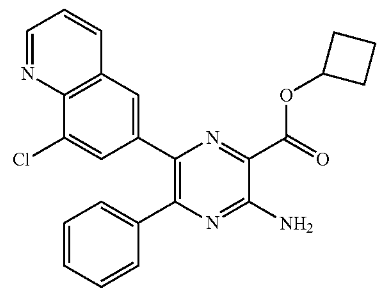 [SMILES: Nc1nc(-c2ccccc2)c(-c2cc(Cl)c3ncccc3c2)nc1C(=O)OC1CCC1] |
| 2.333 | 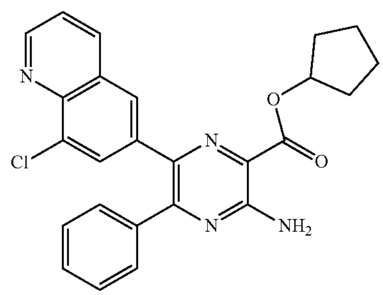 [SMILES: Nc1nc(-c2ccccc2)c(-c2cc(Cl)c3ncccc3c2)nc1C(=O)OC1CCCC1] |
| 2.334 | 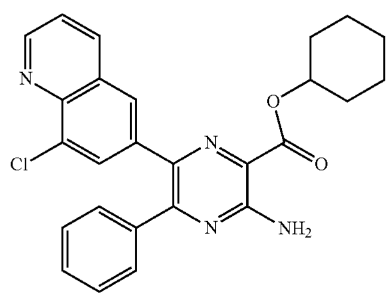 [SMILES: Nc1nc(-c2ccccc2)c(-c2cc(Cl)c3ncccc3c2)nc1C(=O)OC1CCCCC1] |
| 2.335 | 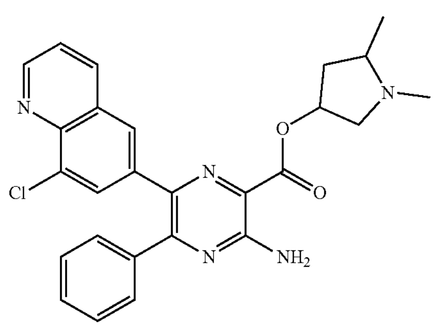 [SMILES: CC1CC(OC(=O)c2nc(-c3cc(Cl)c4ncccc4c3)c(-c3ccccc3)nc2N)CN1C] |
| 2.336 | 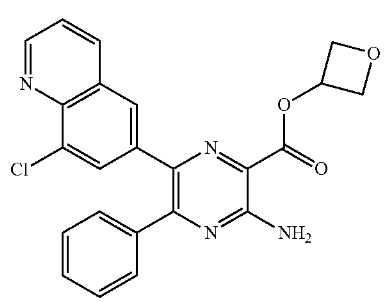 [SMILES: Nc1nc(-c2ccccc2)c(-c2cc(Cl)c3ncccc3c2)nc1C(=O)OC1COC1] |

TABLE 2-continued

| Compound No. | Structure |
| --- | --- |
| 2.337 | 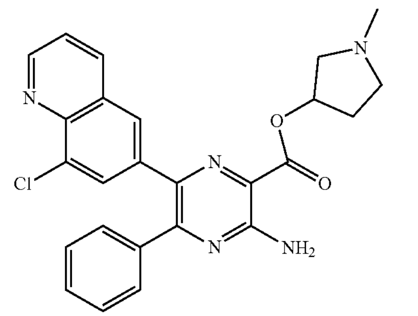 [SMILES: CN1CCC(OC(=O)c2nc(-c3cc(Cl)c4ncccc4c3)c(-c3ccccc3)nc2N)C1] |
| 2.338 | 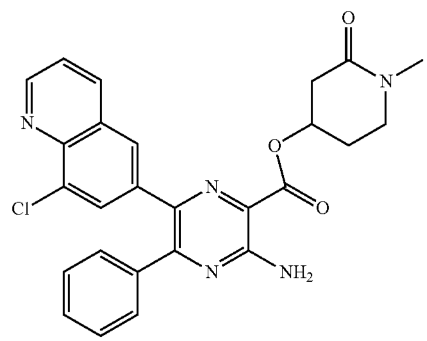 [SMILES: CN1CCC(OC(=O)c2nc(-c3cc(Cl)c4ncccc4c3)c(-c3ccccc3)nc2N)CC1=O] |
| 2.339 | 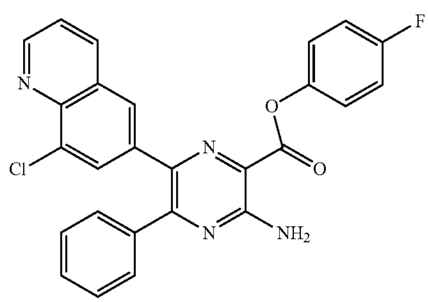 [SMILES: Nc1nc(-c2ccccc2)c(-c2cc(Cl)c3ncccc3c2)nc1C(=O)Oc1ccc(F)cc1] |
| 2.340 | 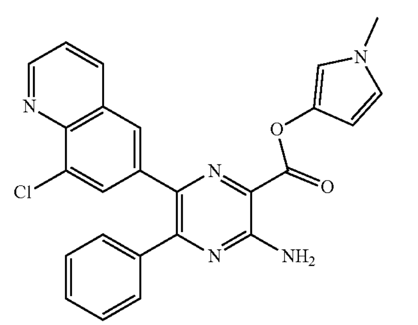 [SMILES: Cn1ccc(OC(=O)c2nc(-c3cc(Cl)c4ncccc4c3)c(-c3ccccc3)nc2N)c1] |
| 2.341 | 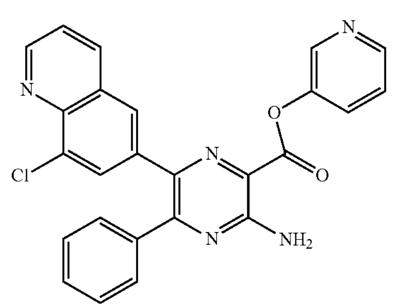 [SMILES: Nc1nc(-c2ccccc2)c(-c2cc(Cl)c3ncccc3c2)nc1C(=O)Oc1cccnc1] |

TABLE 2-continued
| Compound No. | Structure |
|---|---|
| 2.342 | 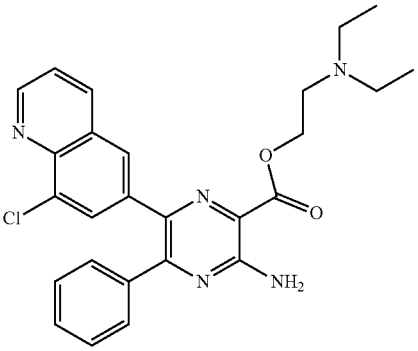 [SMILES: CCN(CC)CCOC(=O)c1nc(-c2cc(Cl)c3ncccc3c2)c(-c2ccccc2)nc1N] |
| 2.343 | 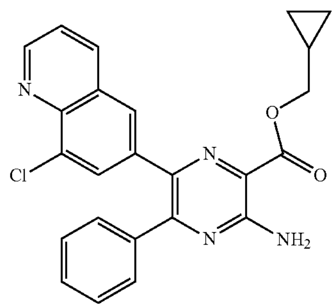 [SMILES: Nc1nc(-c2ccccc2)c(-c2cc(Cl)c3ncccc3c2)nc1C(=O)OCC1CC1] |
| 2.344 | 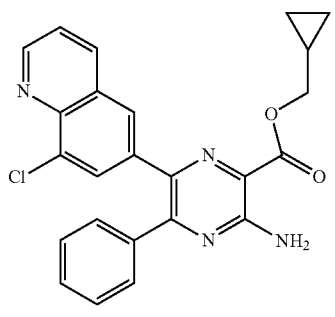 |
| 2.345 | 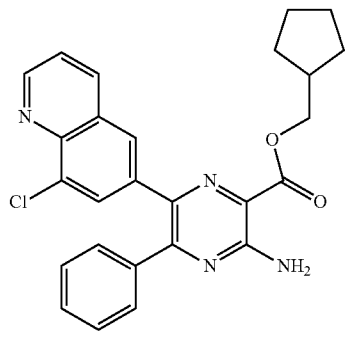 [SMILES: Nc1nc(-c2ccccc2)c(-c2cc(Cl)c3ncccc3c2)nc1C(=O)OCC1CCCC1] |

TABLE 2-continued
| Compound No. | Structure |
|---|---|
| 2.346 | 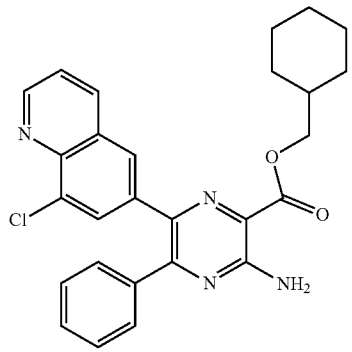 [SMILES: Nc1nc(-c2ccccc2)c(-c2cc(Cl)c3ncccc3c2)nc1C(=O)OCC1CCCCC1] |
| 2.347 | 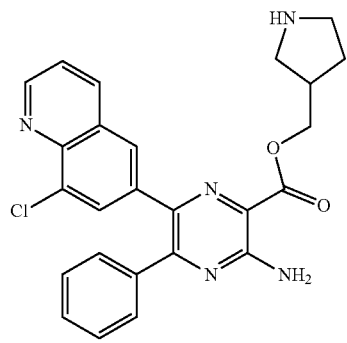 [SMILES: Nc1nc(-c2ccccc2)c(-c2cc(Cl)c3ncccc3c2)nc1C(=O)OCC1CCNC1] |
| 2.348 | 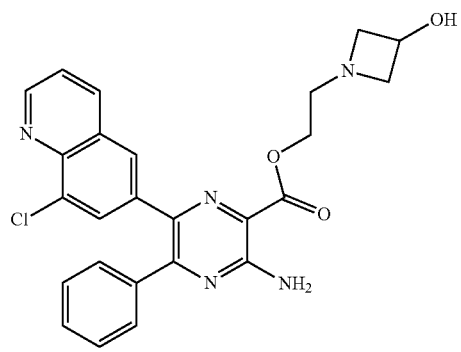 [SMILES: Nc1nc(-c2ccccc2)c(-c2cc(Cl)c3ncccc3c2)nc1C(=O)OCCN1CC(O)C1] |
| 2.349 | 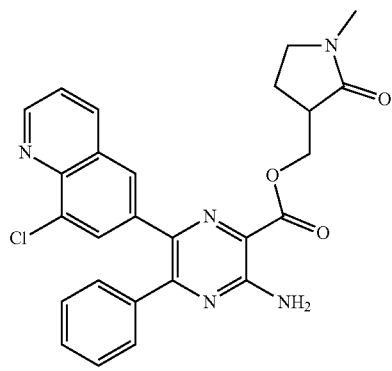 [SMILES: CN1CCC(COC(=O)c2nc(-c3cc(Cl)c4ncccc4c3)c(-c3ccccc3)nc2N)C1=O] |

TABLE 2-continued
| Compound No. | Structure |
|---|---|
| 2.350 | 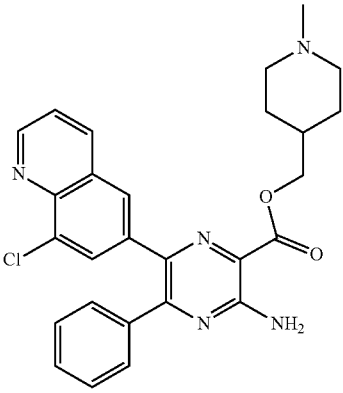 [SMILES: CN1CCC(COC(=O)c2nc(-c3cc(Cl)c4ncccc4c3)c(-c3ccccc3)nc2N)CC1] |
| 2.351 | 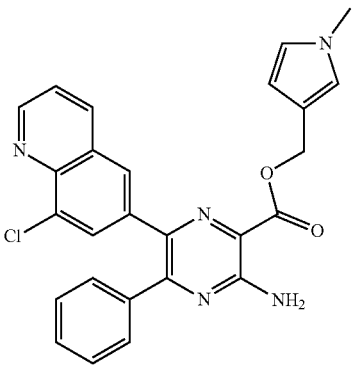 [SMILES: Cn1ccc(COC(=O)c2nc(-c3cc(Cl)c4ncccc4c3)c(-c3ccccc3)nc2N)c1] |
| 2.352 | 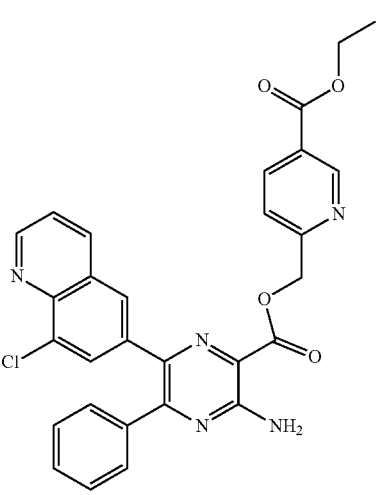 [SMILES: CCOC(=O)c1ccc(COC(=O)c2nc(-c3cc(Cl)c4ncccc4c3)c(-c3ccccc3)nc2N)nc1] |

TABLE 2-continued
| Compound No. | Structure |
|---|---|
| 2.353 | 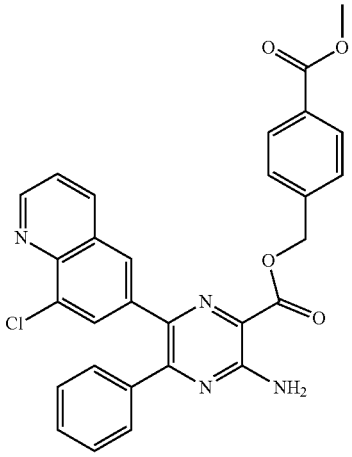 [SMILES: COC(=O)c1ccc(COC(=O)c2nc(-c3cc(Cl)c4ncccc4c3)c(-c3ccccc3)nc2N)cc1] |
| 2.354 | 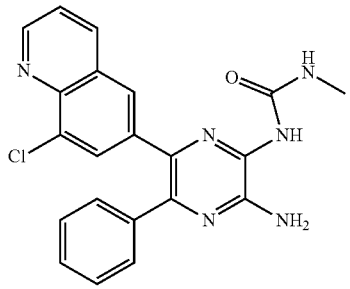 [SMILES: CNC(=O)Nc1nc(-c2cc(Cl)c3ncccc3c2)c(-c2ccccc2)nc1N] |
| 2.355 | 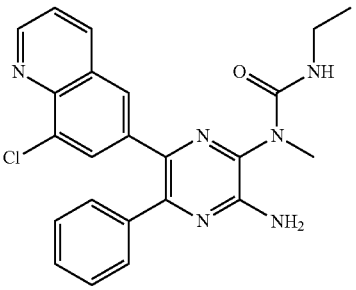 [SMILES: CCNC(=O)N(C)c1nc(-c2cc(Cl)c3ncccc3c2)c(-c2ccccc2)nc1N] |
| 2.356 | 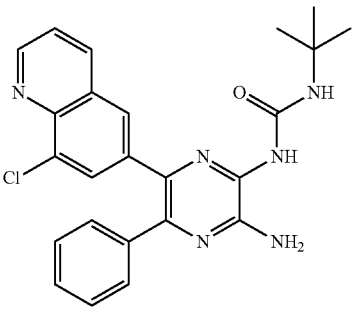 [SMILES: CC(C)(C)NC(=O)Nc1nc(-c2cc(Cl)c3ncccc3c2)c(-c2ccccc2)nc1N] |

TABLE 2-continued
| Compound No. | Structure |
|---|---|
| 2.357 | 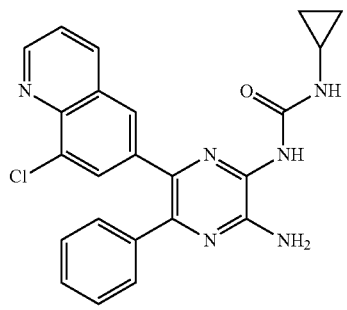 [SMILES: Nc1nc(-c2ccccc2)c(-c2cc(Cl)c3ncccc3c2)nc1NC(=O)NC1CC1] |
| 2.358 | 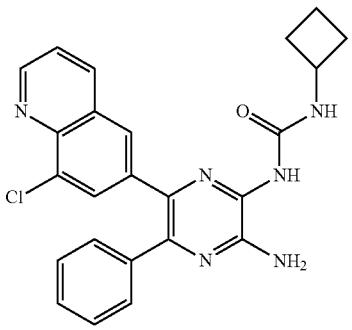 [SMILES: Nc1nc(-c2ccccc2)c(-c2cc(Cl)c3ncccc3c2)nc1NC(=O)NC1CCC1] |
| 2.359 | 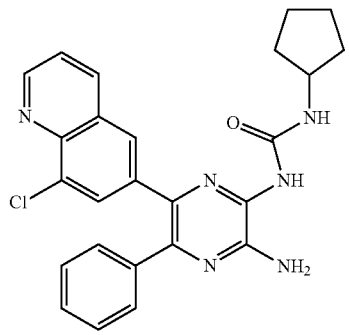 [SMILES: Nc1nc(-c2ccccc2)c(-c2cc(Cl)c3ncccc3c2)nc1NC(=O)NC1CCCC1] |
| 2.360 | 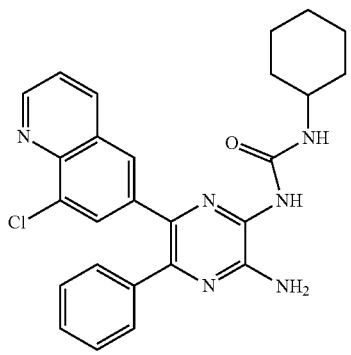 [SMILES: Nc1nc(-c2ccccc2)c(-c2cc(Cl)c3ncccc3c2)nc1NC(=O)NC1CCCCC1] |

TABLE 2-continued
| Compound No. | Structure |
|---|---|
| 2.361 | 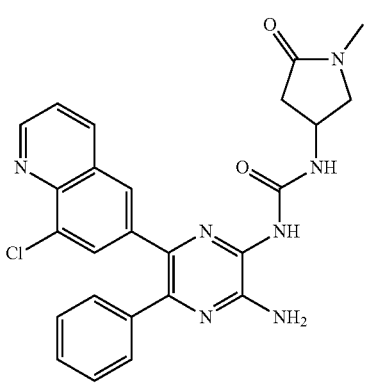 [SMILES: CN1CC(NC(=O)Nc2nc(-c3cc(Cl)c4ncccc4c3)c(-c3ccccc3)nc2N)CC1=O] |
| 2.362 | 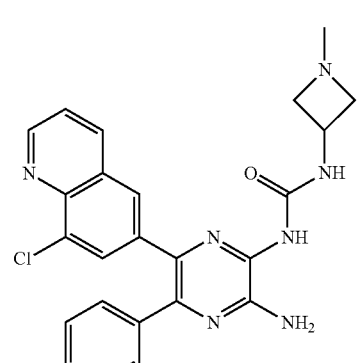 |
| 2.363 | 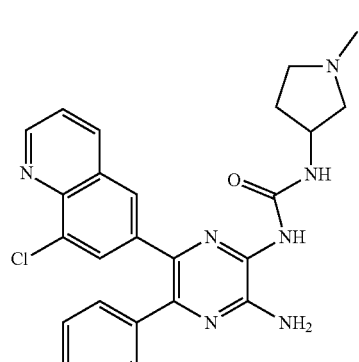 |
| 2.364 | 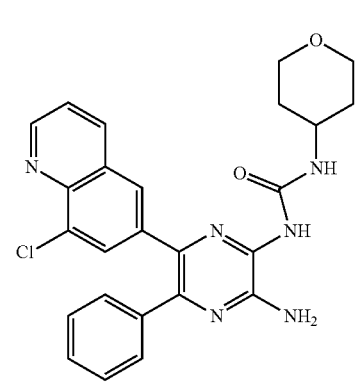 [SMILES: Nc1nc(-c2ccccc2)c(-c2cc(Cl)c3ncccc3c2)nc1NC(=O)NC1CCOCC1] |

TABLE 2-continued
| Compound No. | Structure |
|---|---|
| 2.365 | 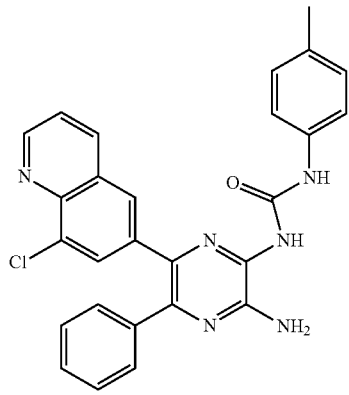 [SMILES: Cc1ccc(NC(=O)Nc2nc(-c3cc(Cl)c4ncccc4c3)c(-c3ccccc3)nc2N)cc1] |
| 2.366 | 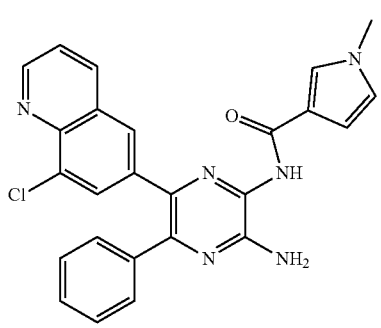 [SMILES: Cn1ccc(C(=O)Nc2nc(-c3cc(Cl)c4ncccc4c3)c(-c3ccccc3)nc2N)c1] |
| 2.367 | 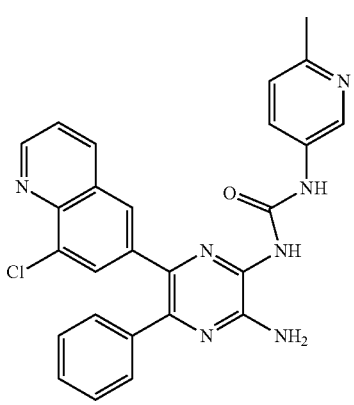 [SMILES: Cc1ccc(NC(=O)Nc2nc(-c3cc(Cl)c4ncccc4c3)c(-c3ccccc3)nc2N)cn1] |
| 2.368 | 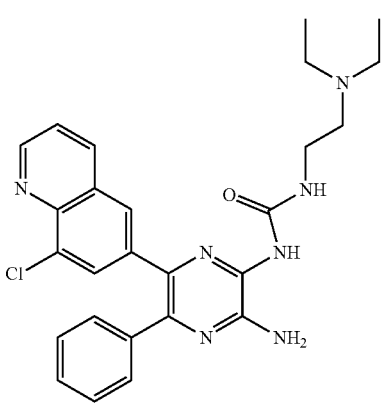 [SMILES: CCN(CC)CCNC(=O)Nc1nc(-c2cc(Cl)c3ncccc3c2)c(-c2ccccc2)nc1N] |

TABLE 2-continued
| Compound No. | Structure |
|---|---|
| 2.369 | 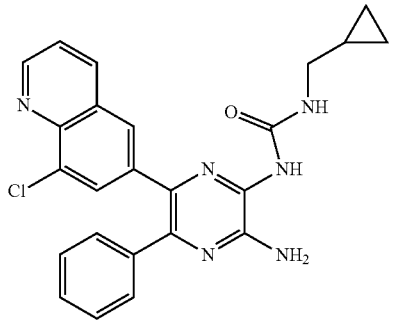 [SMILES: Nc1nc(-c2ccccc2)c(-c2cc(Cl)c3ncccc3c2)nc1NC(=O)NCC1CC1] |
| 2.370 | 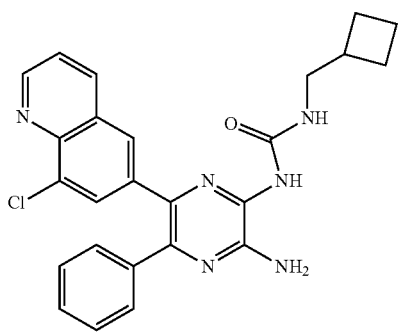 [SMILES: Nc1nc(-c2ccccc2)c(-c2cc(Cl)c3ncccc3c2)nc1NC(=O)NCC1CCC1] |
| 2.371 | 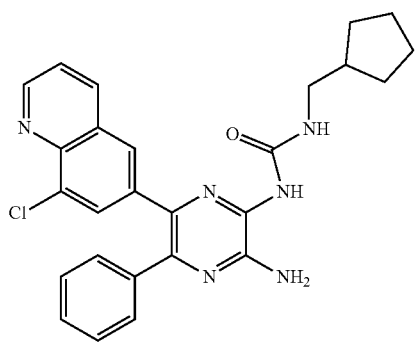 [SMILES: Nc1nc(-c2ccccc2)c(-c2cc(Cl)c3ncccc3c2)nc1NC(=O)NCC1CCCC1] |
| 2.372 | 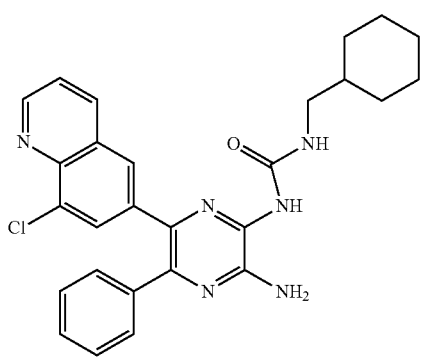 [SMILES: Nc1nc(-c2ccccc2)c(-c2cc(Cl)c3ncccc3c2)nc1NC(=O)NCC1CCCCC1] |

TABLE 2-continued
| Compound No. | Structure |
|---|---|
| 2.373 | 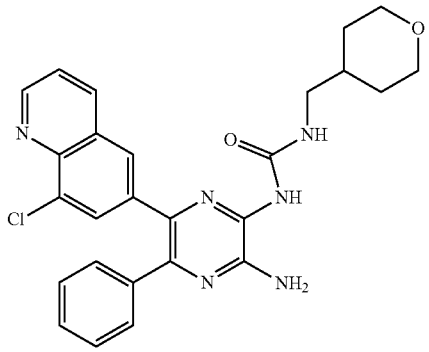 [SMILES: Nc1nc(-c2ccccc2)c(-c2cc(Cl)c3ncccc3c2)nc1NC(=O)NCC1CCOCC1] |
| 2.374 | 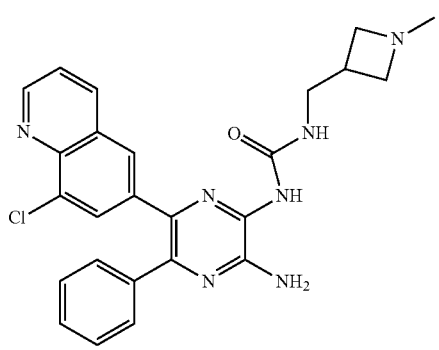 [SMILES: CN1CC(CNC(=O)Nc2nc(-c3cc(Cl)c4ncccc4c3)c(-c3ccccc3)nc2N)C1] |
| 2.375 | 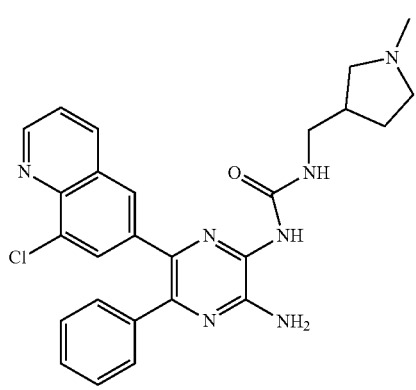 [SMILES: CN1CCC(CNC(=O)Nc2nc(-c3cc(Cl)c4ncccc4c3)c(-c3ccccc3)nc2N)C1] |
| 2.376 | 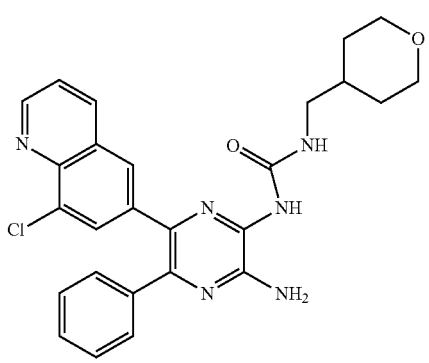 [SMILES: Nc1nc(-c2ccccc2)c(-c2cc(Cl)c3ncccc3c2)nc1NC(=O)NCC1CCOCC1] |

TABLE 2-continued
| Compound No. | Structure |
|---|---|
| 2.377 | 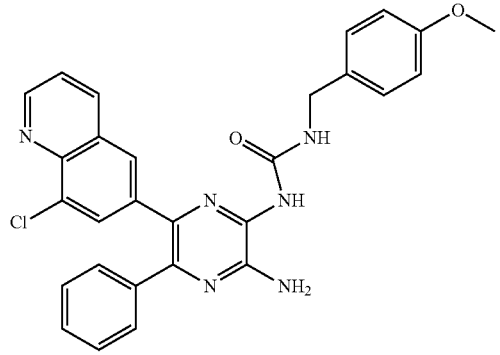 |
| 2.378 | 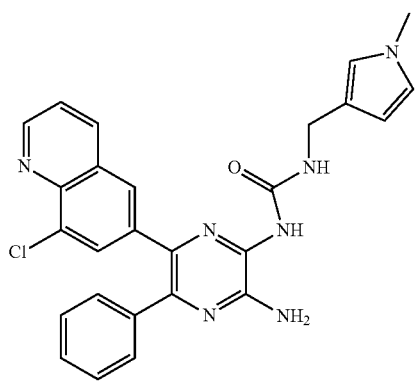 [SMILES: Cn1ccc(CNC(=O)Nc2nc(-c3cc(Cl)c4ncccc4c3)c(-c3ccccc3)nc2N)c1] |
| 2.379 | 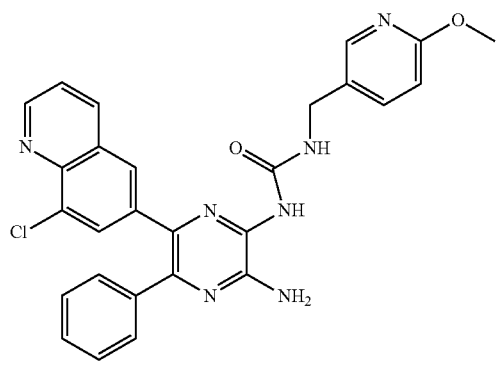 [SMILES: COc1ccc(CNC(=O)Nc2nc(-c3cc(Cl)c4ncccc4c3)c(-c3ccccc3)nc2N)cn1] |
| 2.380 | 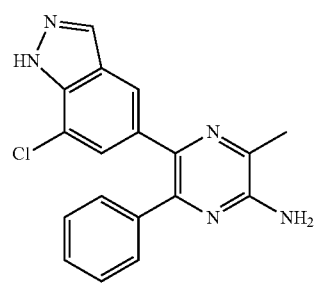 [SMILES: Cc1nc(-c2cc(Cl)c3[nH]ncc3c2)c(-c2ccccc2)nc1N] |

TABLE 2-continued

| Compound No. | Structure |
|---|---|
| 2.381 | 5-(7-chloro-1H-indazol-5-yl)-3-ethyl-6-phenylpyrazin-2-amine |
| 2.382 | 3-tert-butyl-5-(7-chloro-1H-indazol-5-yl)-6-phenylpyrazin-2-amine |
| 2.383 | 5-(7-chloro-1H-indazol-5-yl)-6-phenyl-3-propylpyrazin-2-amine |
| 2.384 | 5-(7-chloro-1H-indazol-5-yl)-6-phenyl-3-(prop-1-en-1-yl)pyrazin-2-amine |
| 2.385 | 5-(7-chloro-1H-indazol-5-yl)-6-phenyl-3-vinylpyrazin-2-amine |

TABLE 2-continued

| Compound No. | Structure |
|---|---|
| 2.386 | 7-chloro-1H-indazol-5-yl / isopropenyl / phenyl / aminopyrazine |
| 2.387 | 7-chloro-1H-indazol-5-yl / allyl / phenyl / aminopyrazine |
| 2.388 | 7-chloro-1H-indazol-5-yl / propynyl / phenyl / aminopyrazine |
| 2.389 | 7-chloro-1H-indazol-5-yl / ethynyl / phenyl / aminopyrazine |
| 2.390 | 7-chloro-1H-indazol-5-yl / propargyl / phenyl / aminopyrazine |

TABLE 2-continued

| Compound No. | Structure |
| --- | --- |
| 2.391 | 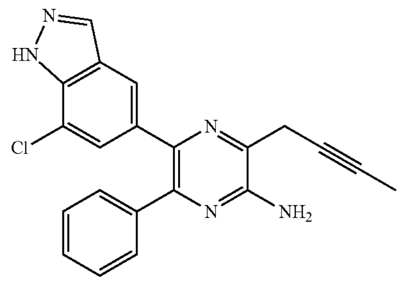 [SMILES: CC#CCc1nc(-c2cc(Cl)c3[nH]ncc3c2)c(-c2ccccc2)nc1N] |
| 2.392 | 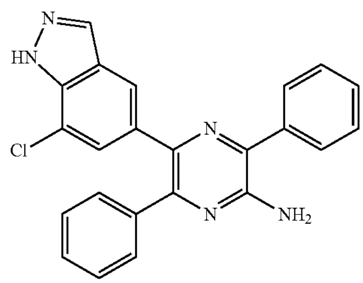 [SMILES: Nc1nc(-c2ccccc2)c(-c2cc(Cl)c3[nH]ncc3c2)nc1-c1ccccc1] |
| 2.393 | 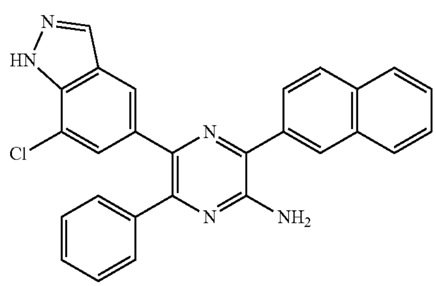 [SMILES: Nc1nc(-c2ccccc2)c(-c2cc(Cl)c3[nH]ncc3c2)nc1-c1ccc2ccccc2c1] |
| 2.394 | 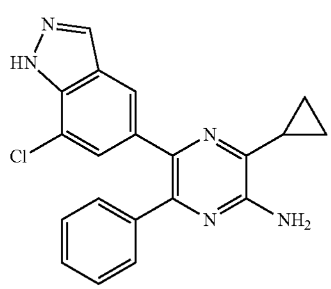 [SMILES: Nc1nc(-c2ccccc2)c(-c2cc(Cl)c3[nH]ncc3c2)nc1C1CC1] |
| 2.395 | 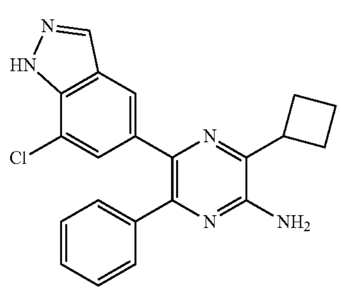 [SMILES: Nc1nc(-c2ccccc2)c(-c2cc(Cl)c3[nH]ncc3c2)nc1C1CCC1] |

TABLE 2-continued
| Compound No. | Structure |
|---|---|
| 2.396 | 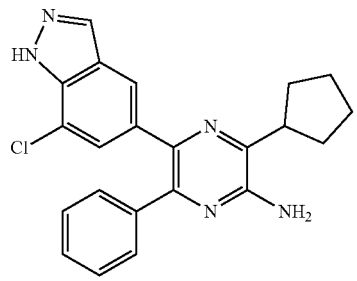 [SMILES: Nc1nc(-c2ccccc2)c(-c2cc(Cl)c3[nH]ncc3c2)nc1C1CCCC1] |
| 2.397 | 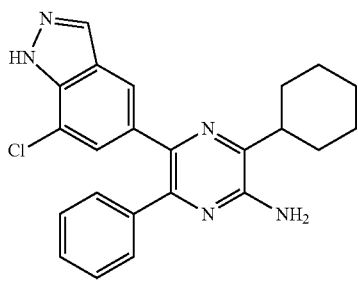 [SMILES: Nc1nc(-c2ccccc2)c(-c2cc(Cl)c3[nH]ncc3c2)nc1C1CCCCC1] |
| 2.398 | 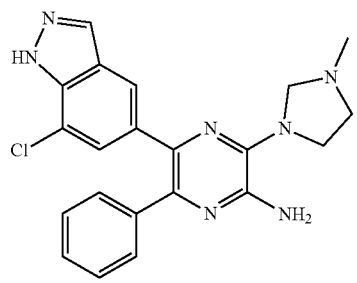 [SMILES: CN1CCN(c2nc(-c3cc(Cl)c4[nH]ncc4c3)c(-c3ccccc3)nc2N)C1] |
| 2.399 | 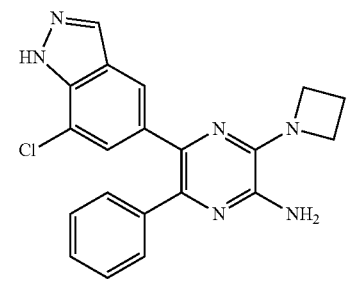 [SMILES: Nc1nc(-c2ccccc2)c(-c2cc(Cl)c3[nH]ncc3c2)nc1N1CCC1] |
| 2.400 | 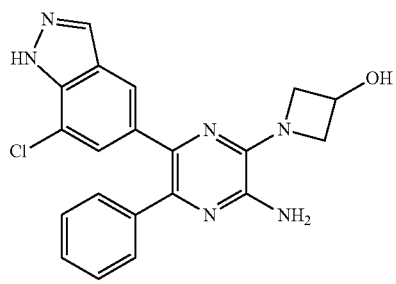 [SMILES: Nc1nc(-c2ccccc2)c(-c2cc(Cl)c3[nH]ncc3c2)nc1N1CC(O)C1] |

TABLE 2-continued

| Compound No. | Structure |
|---|---|
| 2.401 | 7-chloro-1H-indazol-5-yl pyrazine with pyrrolidine, phenyl, and NH₂ substituents |
| 2.402 | 7-chloro-1H-indazol-5-yl pyrazine with 4-hydroxypiperidine, phenyl, and NH₂ substituents |
| 2.403 | 7-chloro-1H-indazol-5-yl pyrazine with F, phenyl, and NH₂ substituents |
| 2.404 | 7-chloro-1H-indazol-5-yl pyrazine with Cl, phenyl, and NH₂ substituents |
| 2.405 | 7-chloro-1H-indazol-5-yl pyrazine with Br, phenyl, and NH₂ substituents |

TABLE 2-continued

| Compound No. | Structure |
|---|---|
| 2.406 | 7-chloro-1H-indazol-5-yl / 3-amino-6-phenyl-5-(trifluoromethyl)pyrazin-2-yl |
| 2.407 | 7-chloro-1H-indazol-5-yl / 3-amino-6-phenyl-5-(trifluoromethoxy)pyrazin-2-yl |
| 2.408 | 7-chloro-1H-indazol-5-yl / 5-amino-3-hydroxy-6-phenylpyrazin-2-yl |
| 2.409 | 7-chloro-1H-indazol-5-yl / 3-amino-6-methoxy-5-phenylpyrazin-2-yl |
| 2.410 | 7-chloro-1H-indazol-5-yl / 3-amino-6-ethoxy-5-phenylpyrazin-2-yl |

TABLE 2-continued

| Compound No. | Structure |
|---|---|
| 2.411 | 5-(7-chloro-1H-indazol-5-yl)-3-isopropoxy-6-phenylpyrazin-2-amine |
| 2.412 | 5-(7-chloro-1H-indazol-5-yl)-3-cyclopropoxy-6-phenylpyrazin-2-amine |
| 2.413 | 5-(7-chloro-1H-indazol-5-yl)-3-cyclobutoxy-6-phenylpyrazin-2-amine |
| 2.414 | 5-(7-chloro-1H-indazol-5-yl)-3-cyclopentyloxy-6-phenylpyrazin-2-amine |
| 2.415 | 5-(7-chloro-1H-indazol-5-yl)-3-cyclohexyloxy-6-phenylpyrazin-2-amine |

TABLE 2-continued
| Compound No. | Structure |
|---|---|
| 2.416 | 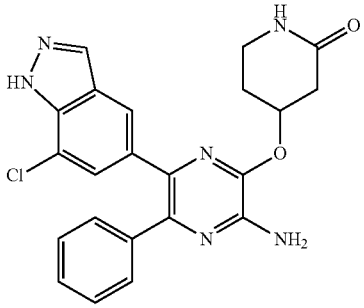 [SMILES: Nc1nc(-c2ccccc2)c(-c2cc(Cl)c3[nH]ncc3c2)nc1OC1CCNC(=O)C1] |
| 2.417 | 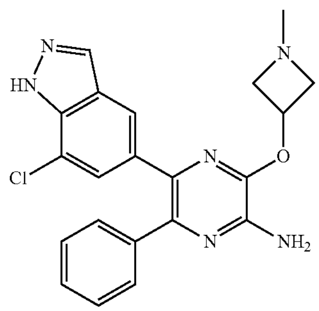 [SMILES: CN1CC(Oc2nc(-c3cc(Cl)c4[nH]ncc4c3)c(-c3ccccc3)nc2N)C1] |
| 2.418 | 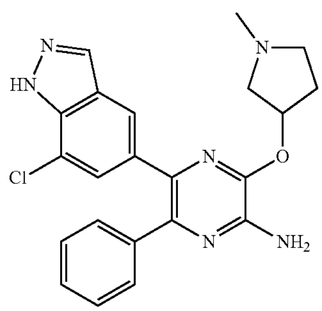 [SMILES: CN1CCC(Oc2nc(-c3cc(Cl)c4[nH]ncc4c3)c(-c3ccccc3)nc2N)C1] |
| 2.419 | 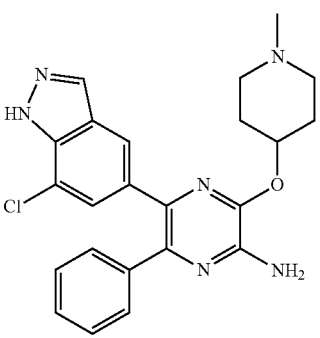 [SMILES: CN1CCC(Oc2nc(-c3cc(Cl)c4[nH]ncc4c3)c(-c3ccccc3)nc2N)CC1] |
| 2.420 | 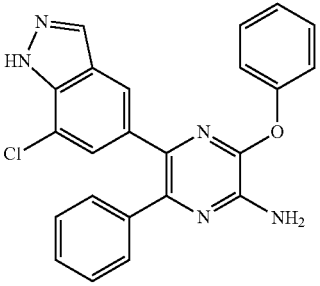 [SMILES: Nc1nc(-c2ccccc2)c(-c2cc(Cl)c3[nH]ncc3c2)nc1Oc1ccccc1] |

TABLE 2-continued

| Compound No. | Structure |
|---|---|
| 2.421 | 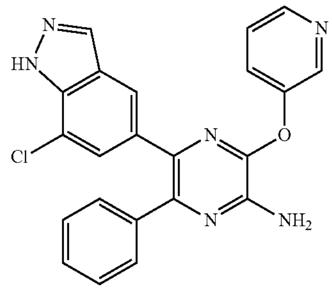 [SMILES: Nc1nc(-c2ccccc2)c(-c2cc(Cl)c3[nH]ncc3c2)nc1Oc1cccnc1] |
| 2.422 | 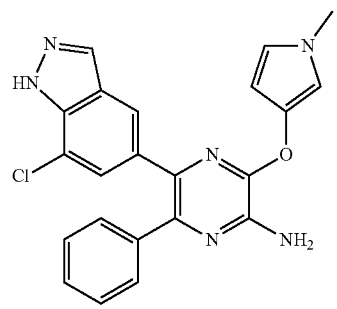 [SMILES: Cn1ccc(Oc2nc(-c3cc(Cl)c4[nH]ncc4c3)c(-c3ccccc3)nc2N)c1] |
| 2.423 | 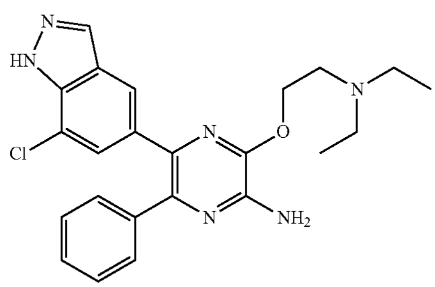 [SMILES: CCN(CC)CCOc1nc(-c2cc(Cl)c3[nH]ncc3c2)c(-c2ccccc2)nc1N] |
| 2.424 | 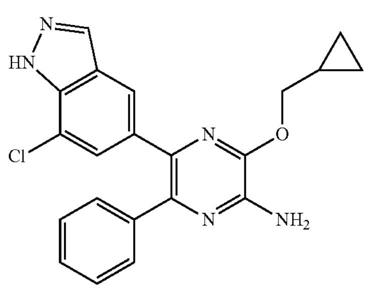 [SMILES: Nc1nc(-c2ccccc2)c(-c2cc(Cl)c3[nH]ncc3c2)nc1OCC1CC1] |
| 2.425 | 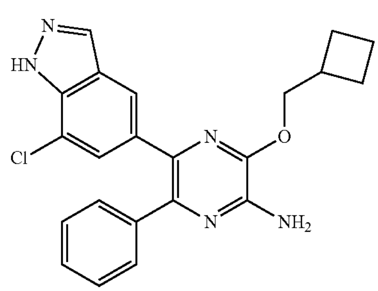 [SMILES: Nc1nc(-c2ccccc2)c(-c2cc(Cl)c3[nH]ncc3c2)nc1OCC1CCC1] |

TABLE 2-continued

| Compound No. | Structure |
|---|---|
| 2.426 | 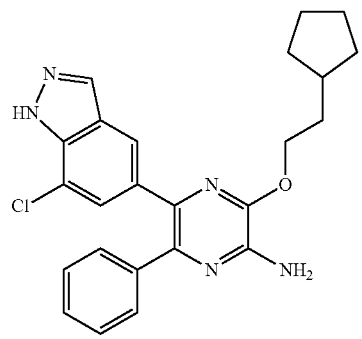 [SMILES: Nc1nc(-c2ccccc2)c(-c2cc(Cl)c3[nH]ncc3c2)nc1OCCC1CCCC1] |
| 2.427 | 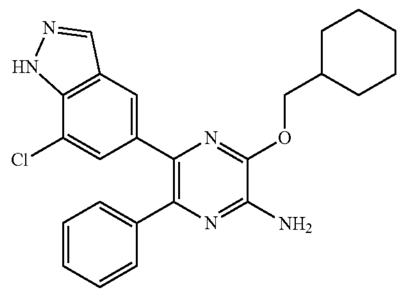 [SMILES: Nc1nc(-c2ccccc2)c(-c2cc(Cl)c3[nH]ncc3c2)nc1OCC1CCCCC1] |
| 2.428 | 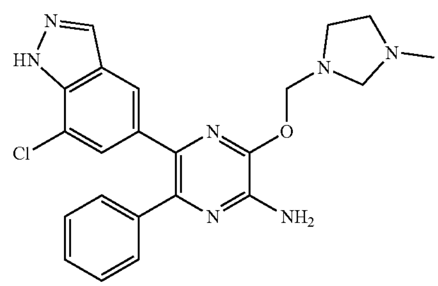 [SMILES: CN1CCN(COc2nc(-c3cc(Cl)c4[nH]ncc4c3)c(-c3ccccc3)nc2N)C1] |
| 2.429 | 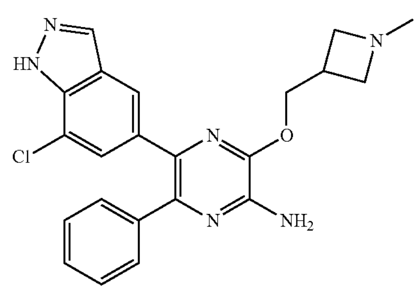 [SMILES: CN1CC(COc2nc(-c3cc(Cl)c4[nH]ncc4c3)c(-c3ccccc3)nc2N)C1] |
| 2.430 | 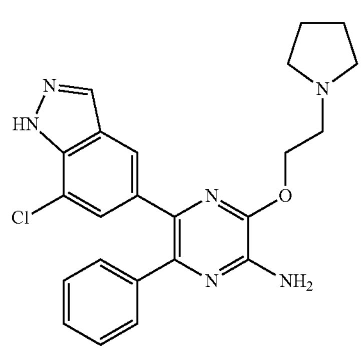 [SMILES: Nc1nc(-c2ccccc2)c(-c2cc(Cl)c3[nH]ncc3c2)nc1OCCN1CCCC1] |

TABLE 2-continued

| Compound No. | Structure |
|---|---|
| 2.431 | 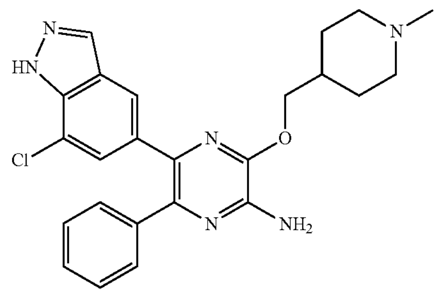 |
| 2.432 | 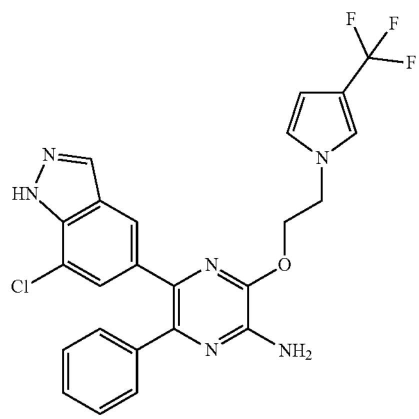 [SMILES: Nc1nc(-c2ccccc2)c(-c2cc(Cl)c3[nH]ncc3c2)nc1OCCn1ccc(C(F)(F)F)c1] |
| 2.433 | 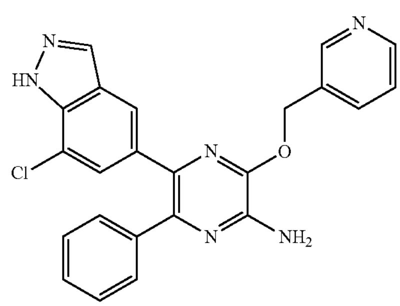 [SMILES: Nc1nc(-c2ccccc2)c(-c2cc(Cl)c3[nH]ncc3c2)nc1OCc1cccnc1] |
| 2.434 | 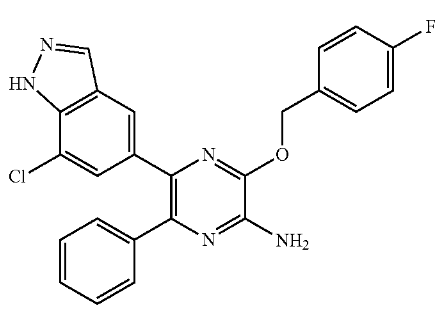 [SMILES: Nc1nc(-c2ccccc2)c(-c2cc(Cl)c3[nH]ncc3c2)nc1OCc1ccc(F)cc1] |

TABLE 2-continued
| Compound No. | Structure |
|---|---|
| 2.435 | 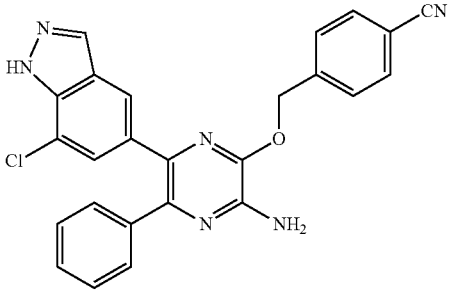 [SMILES: N#Cc1ccc(COc2nc(-c3cc(Cl)c4[nH]ncc4c3)c(-c3ccccc3)nc2N)cc1] |
| 2.436 | 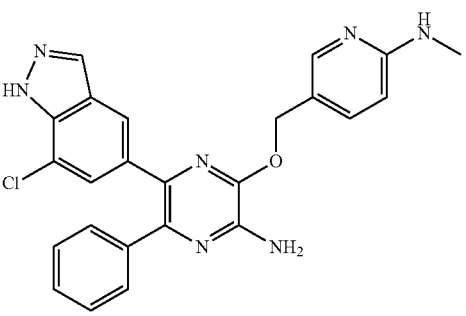 [SMILES: CNc1ccc(COc2nc(-c3cc(Cl)c4[nH]ncc4c3)c(-c3ccccc3)nc2N)cn1] |
| 2.437 | 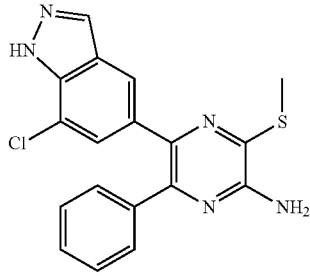 |
| 2.438 | 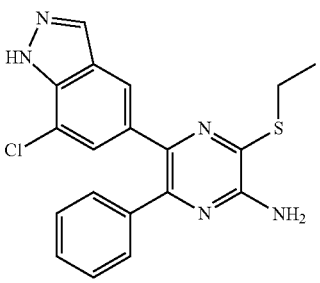 |
| 2.439 | 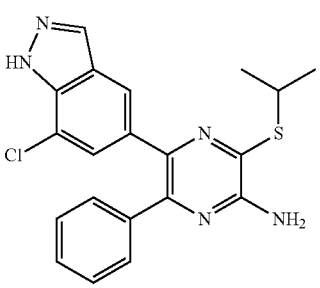 |

TABLE 2-continued
| Compound No. | Structure |
|---|---|
| 2.440 | 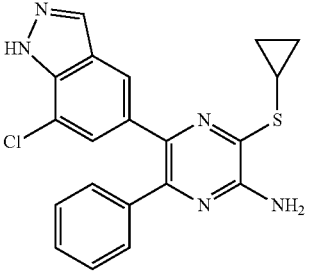 |
| 2.441 | 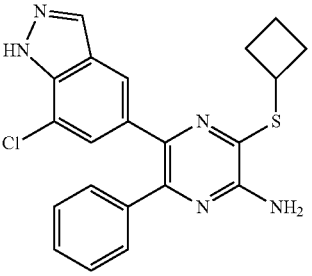 [SMILES: Nc1nc(-c2ccccc2)c(-c2cc(Cl)c3[nH]ncc3c2)nc1SC1CCC1] |
| 2.442 | 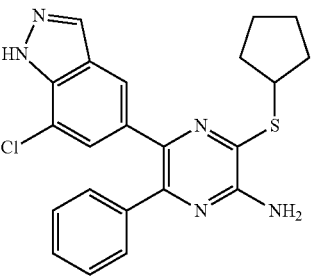 [SMILES: Nc1nc(-c2ccccc2)c(-c2cc(Cl)c3[nH]ncc3c2)nc1SC1CCCC1] |
| 2.443 | 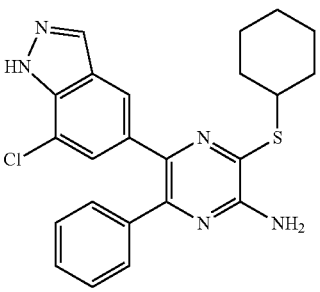 |
| 2.444 | 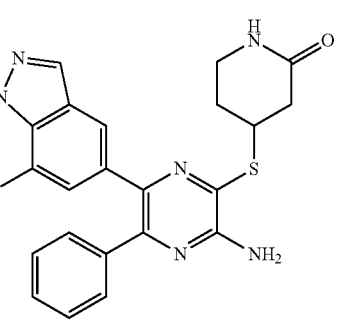 |

TABLE 2-continued
| Compound No. | Structure |
|---|---|
| 2.445 | 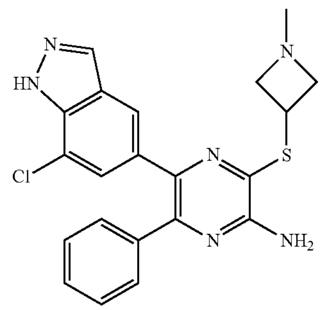 |
| 2.446 | 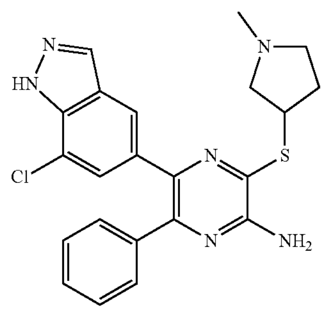 [SMILES: CN1CCC(Sc2nc(-c3cc(Cl)c4[nH]ncc4c3)c(-c3ccccc3)nc2N)C1] |
| 2.447 | 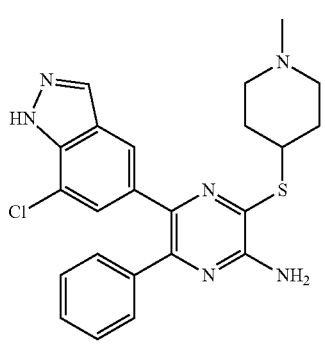 |
| 2.448 | 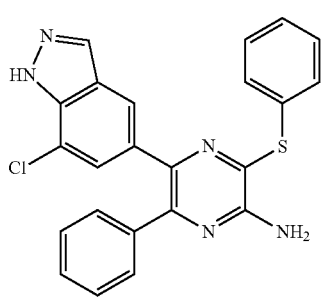 |
| 2.449 | 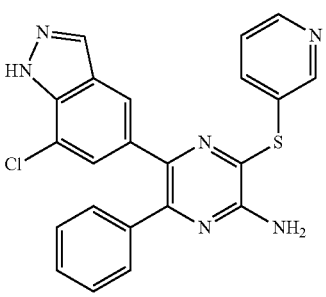 |

TABLE 2-continued

| Compound No. | Structure |
|---|---|
| 2.450 | 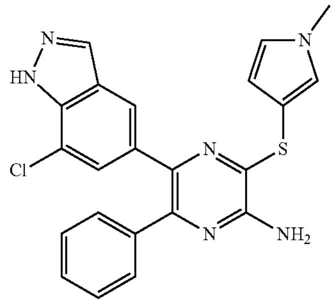 [SMILES: Cn1ccc(Sc2nc(-c3cc(Cl)c4[nH]ncc4c3)c(-c3ccccc3)nc2N)c1] |
| 2.451 | 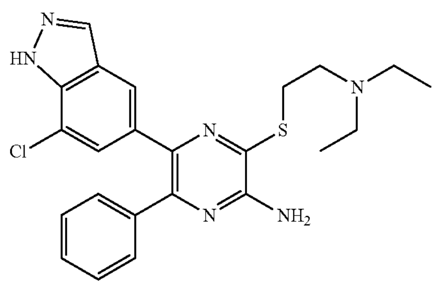 |
| 2.452 | 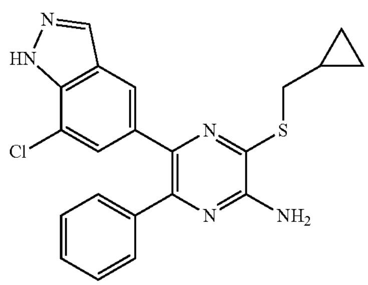 [SMILES: Nc1nc(-c2ccccc2)c(-c2cc(Cl)c3[nH]ncc3c2)nc1SCC1CC1] |
| 2.453 | 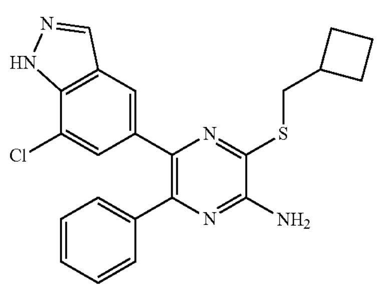 |
| 2.454 | 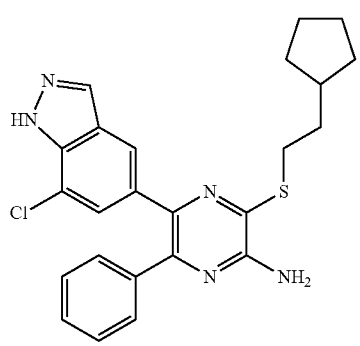 [SMILES: Nc1nc(-c2ccccc2)c(-c2cc(Cl)c3[nH]ncc3c2)nc1SCCC1CCCC1] |

TABLE 2-continued
| Compound No. | Structure |
|---|---|
| 2.455 | 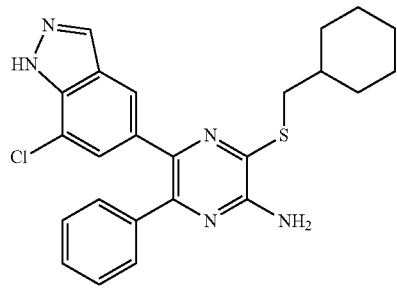 |
| 2.456 | 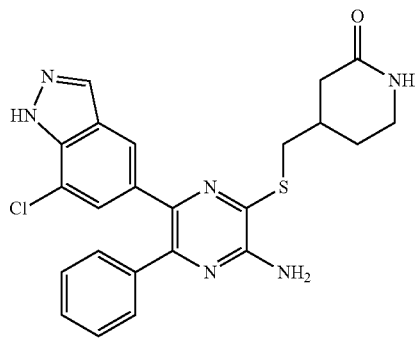 [SMILES: Nc1nc(-c2ccccc2)c(-c2cc(Cl)c3[nH]ncc3c2)nc1SCC1CCNC(=O)C1] |
| 2.457 | |
| 2.458 | |
| 2.459 | 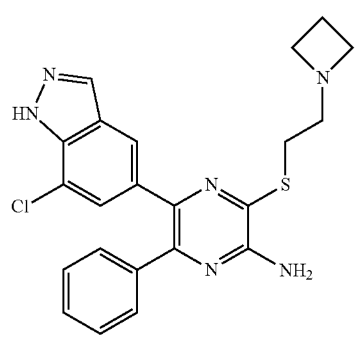 [SMILES: Nc1nc(-c2ccccc2)c(-c2cc(Cl)c3[nH]ncc3c2)nc1SCCN1CCC1] |
| 2.460 | 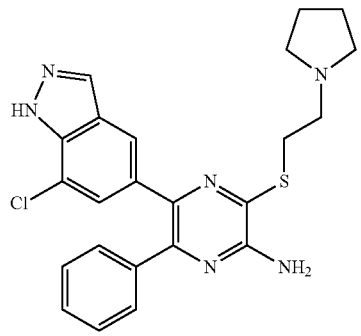 |

TABLE 2-continued
| Compound No. | Structure |
|---|---|
| 2.461 | 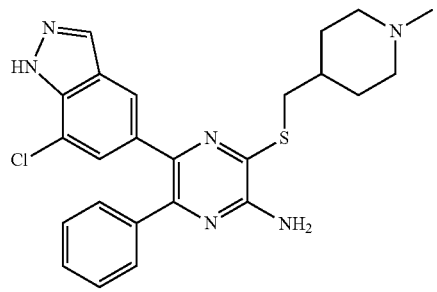 [SMILES: CN1CCC(CSc2nc(-c3cc(Cl)c4[nH]ncc4c3)c(-c3ccccc3)nc2N)CC1] |
| 2.462 | 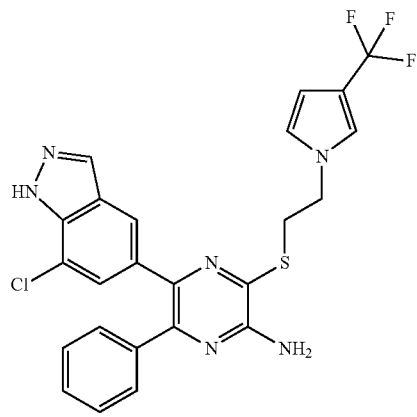 [SMILES: Nc1nc(-c2ccccc2)c(-c2cc(Cl)c3[nH]ncc3c2)nc1SCCn1ccc(C(F)(F)F)c1] |
| 2.463 | 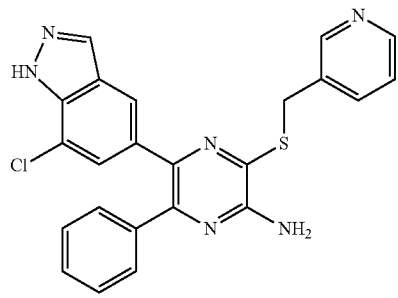 [SMILES: Nc1nc(-c2ccccc2)c(-c2cc(Cl)c3[nH]ncc3c2)nc1SCc1cccnc1] |
| 2.464 | 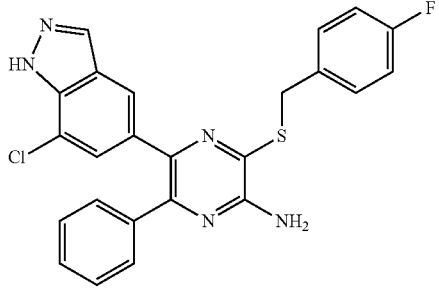 [SMILES: Nc1nc(-c2ccccc2)c(-c2cc(Cl)c3[nH]ncc3c2)nc1SCc1ccc(F)cc1] |

TABLE 2-continued

| Compound No. | Structure |
|---|---|
| 2.465 | (structure) |
| 2.466 | (structure) |
| 2.467 | (structure) |
| 2.468 | (structure) |
| 2.469 | (structure) |

TABLE 2-continued

| Compound No. | Structure |
|---|---|
| 2.470 | (7-chloro-1H-indazol-5-yl, phenyl, NHEt, NH₂ pyrazine) |
| 2.471 | (7-chloro-1H-indazol-5-yl, phenyl, NH-iPr, NH₂ pyrazine) |
| 2.472 | (7-chloro-1H-indazol-5-yl, phenyl, NH-tBu, NH₂ pyrazine) |
| 2.473 | (7-chloro-1H-indazol-5-yl, phenyl, NH-cyclopropyl, NH₂ pyrazine) |
| 2.474 | (7-chloro-1H-indazol-5-yl, phenyl, NH-cyclobutyl, NH₂ pyrazine) |

TABLE 2-continued

| Compound No. | Structure |
|---|---|
| 2.475 | 5-(7-chloro-1H-indazol-5-yl)-N3-cyclopentyl-6-phenylpyrazine-2,3-diamine |
| 2.476 | 5-(7-chloro-1H-indazol-5-yl)-N3-cyclohexyl-6-phenylpyrazine-2,3-diamine |
| 2.477 | 4-((3-amino-6-(7-chloro-1H-indazol-5-yl)-5-phenylpyrazin-2-yl)amino)-1-methylpyrrolidin-2-one |
| 2.478 | 5-(7-chloro-1H-indazol-5-yl)-N3-(1-methylazetidin-3-yl)-6-phenylpyrazine-2,3-diamine |
| 2.479 | 5-(7-chloro-1H-indazol-5-yl)-N3-(1-methylpyrrolidin-3-yl)-6-phenylpyrazine-2,3-diamine |

TABLE 2-continued
| Compound No. | Structure |
|---|---|
| 2.480 | 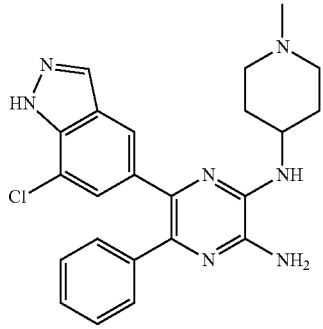 [SMILES: CN1CCC(Nc2nc(-c3cc(Cl)c4[nH]ncc4c3)c(-c3ccccc3)nc2N)CC1] |
| 2.481 | 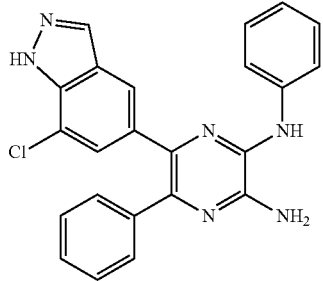 [SMILES: Nc1nc(-c2ccccc2)c(-c2cc(Cl)c3[nH]ncc3c2)nc1Nc1ccccc1] |
| 2.482 | 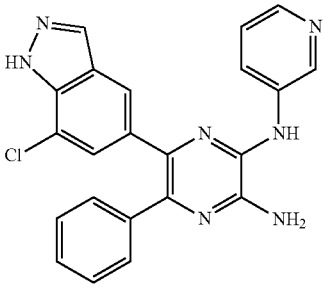 [SMILES: Nc1nc(-c2ccccc2)c(-c2cc(Cl)c3[nH]ncc3c2)nc1Nc1cccnc1] |
| 2.483 | 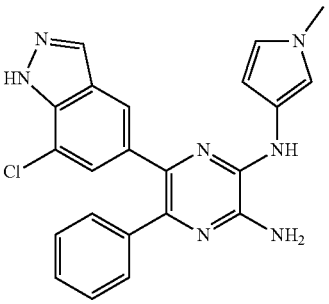 [SMILES: Cn1ccc(Nc2nc(-c3cc(Cl)c4[nH]ncc4c3)c(-c3ccccc3)nc2N)c1] |
| 2.484 | 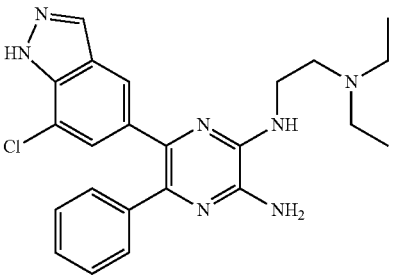 [SMILES: CCN(CC)CCNc1nc(-c2cc(Cl)c3[nH]ncc3c2)c(-c2ccccc2)nc1N] |

TABLE 2-continued
| Compound No. | Structure |
|---|---|
| 2.485 | 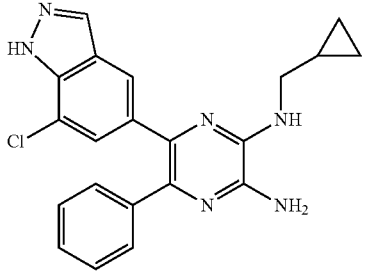 [SMILES: Nc1nc(-c2ccccc2)c(-c2cc(Cl)c3[nH]ncc3c2)nc1NCC1CC1] |
| 2.486 | 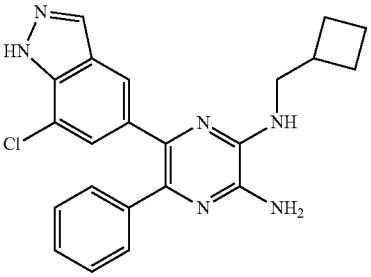 [SMILES: Nc1nc(-c2ccccc2)c(-c2cc(Cl)c3[nH]ncc3c2)nc1NCC1CCC1] |
| 2.487 | 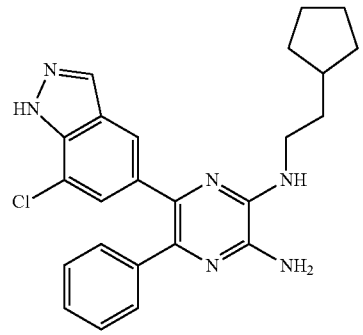 [SMILES: Nc1nc(-c2ccccc2)c(-c2cc(Cl)c3[nH]ncc3c2)nc1NCCC1CCCC1] |
| 2.488 | 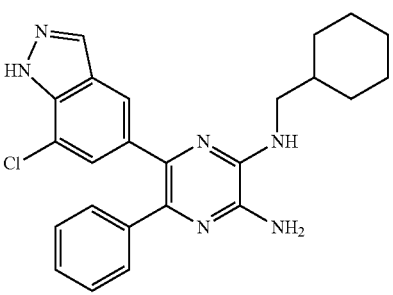 [SMILES: Nc1nc(-c2ccccc2)c(-c2cc(Cl)c3[nH]ncc3c2)nc1NCC1CCCCC1] |
| 2.489 | 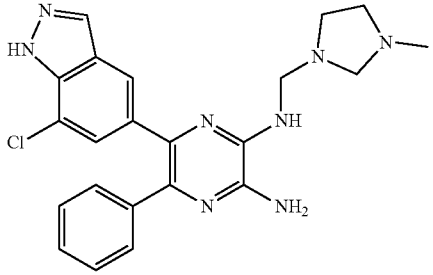 [SMILES: CN1CCN(CNc2nc(-c3cc(Cl)c4[nH]ncc4c3)c(-c3ccccc3)nc2N)C1] |

TABLE 2-continued
| Compound No. | Structure |
|---|---|
| 2.490 | 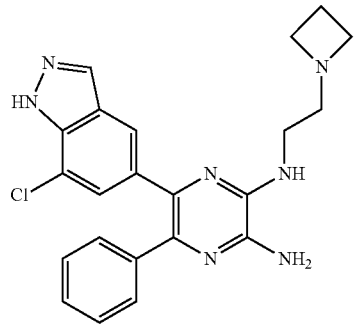 [SMILES: Nc1nc(-c2ccccc2)c(-c2cc(Cl)c3[nH]ncc3c2)nc1NCCN1CCC1] |
| 2.491 | 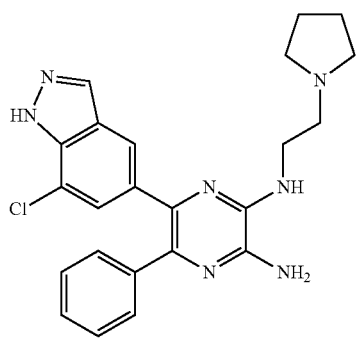 |
| 2.492 | 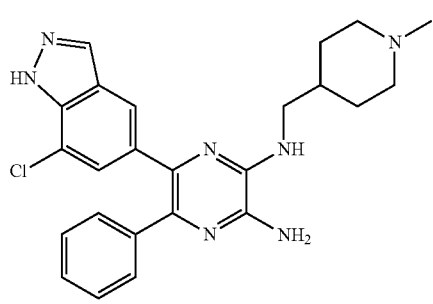 [SMILES: CN1CCC(CNc2nc(-c3cc(Cl)c4[nH]ncc4c3)c(-c3ccccc3)nc2N)CC1] |
| 2.493 | 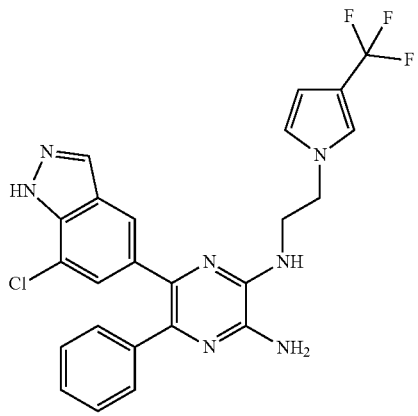 [SMILES: Nc1nc(-c2ccccc2)c(-c2cc(Cl)c3[nH]ncc3c2)nc1NCCn1ccc(C(F)(F)F)c1] |

TABLE 2-continued
| Compound No. | Structure |
|---|---|
| 2.494 | 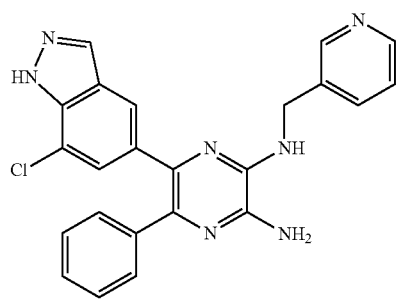 [SMILES: Nc1nc(-c2ccccc2)c(-c2cc(Cl)c3[nH]ncc3c2)nc1NCc1cccnc1] |
| 2.495 | 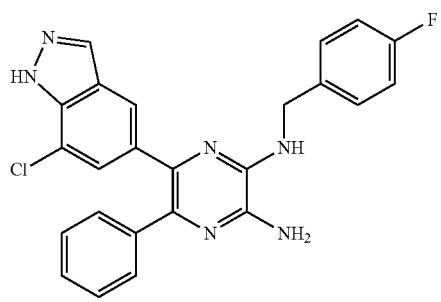 [SMILES: Nc1nc(-c2ccccc2)c(-c2cc(Cl)c3[nH]ncc3c2)nc1NCc1ccc(F)cc1] |
| 2.496 | 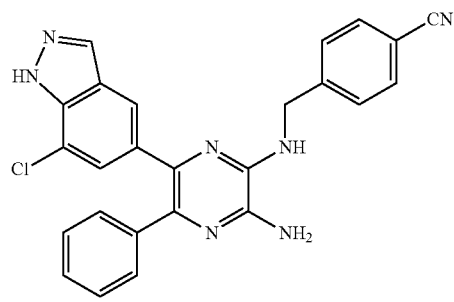 |
| 2.497 | 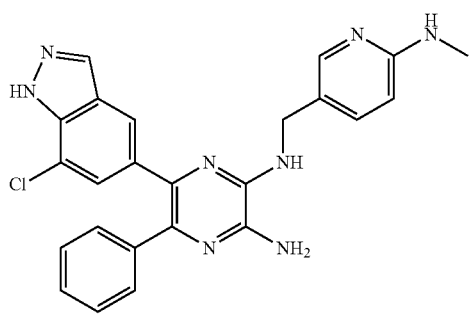 [SMILES: CNc1ccc(CNc2nc(-c3cc(Cl)c4[nH]ncc4c3)c(-c3ccccc3)nc2N)cn1] |
| 2.498 | 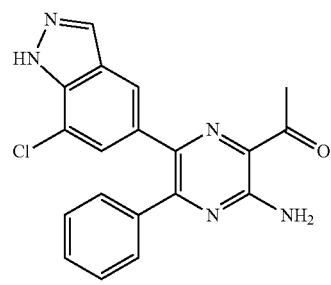 [SMILES: CC(=O)c1nc(-c2cc(Cl)c3[nH]ncc3c2)c(-c2ccccc2)nc1N] |

TABLE 2-continued

| Compound No. | Structure |
|---|---|
| 2.499 | 5-(7-chloro-1H-indazol-5-yl)-3-amino-6-phenyl-2-propanoyl-pyrazine |
| 2.500 | 5-(7-chloro-1H-indazol-5-yl)-3-amino-2-(cyclopropanecarbonyl)-6-phenyl-pyrazine |
| 2.501 | 5-(7-chloro-1H-indazol-5-yl)-3-amino-2-(cyclobutanecarbonyl)-6-phenyl-pyrazine |
| 2.502 | 5-(7-chloro-1H-indazol-5-yl)-3-amino-2-(cyclopentanecarbonyl)-6-phenyl-pyrazine |
| 2.503 | 5-(7-chloro-1H-indazol-5-yl)-3-amino-2-(cyclohexanecarbonyl)-6-phenyl-pyrazine |

TABLE 2-continued

| Compound No. | Structure |
|---|---|
| 2.504 | 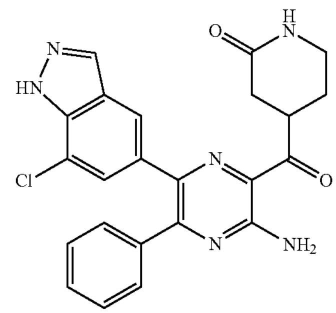 [SMILES: Nc1nc(-c2ccccc2)c(-c2cc(Cl)c3[nH]ncc3c2)nc1C(=O)C1CCNC(=O)C1] |
| 2.505 | 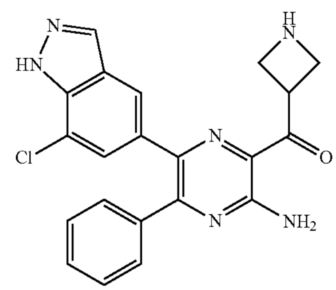 [SMILES: Nc1nc(-c2ccccc2)c(-c2cc(Cl)c3[nH]ncc3c2)nc1C(=O)C1CNC1] |
| 2.506 | 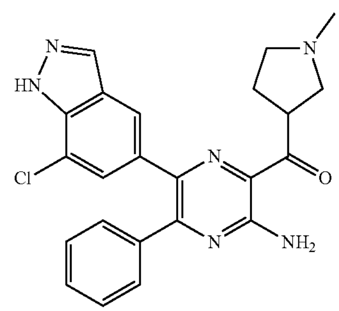 [SMILES: CN1CCC(C(=O)c2nc(-c3cc(Cl)c4[nH]ncc4c3)c(-c3ccccc3)nc2N)C1] |
| 2.507 | 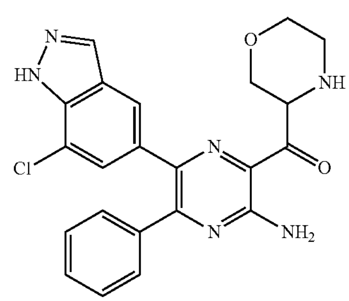 [SMILES: Nc1nc(-c2ccccc2)c(-c2cc(Cl)c3[nH]ncc3c2)nc1C(=O)C1COCCN1] |
| 2.508 | 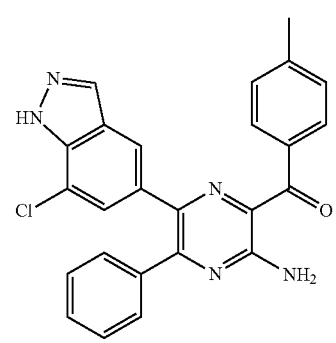 [SMILES: Cc1ccc(C(=O)c2nc(-c3cc(Cl)c4[nH]ncc4c3)c(-c3ccccc3)nc2N)cc1] |

TABLE 2-continued

| Compound No. | Structure |
|---|---|
| 2.509 | 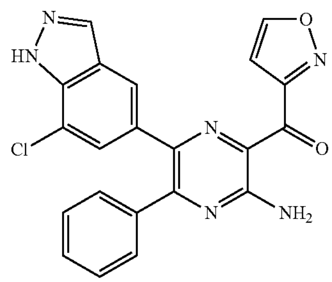 [SMILES: Nc1nc(-c2ccccc2)c(-c2cc(Cl)c3[nH]ncc3c2)nc1C(=O)c1ccon1] |
| 2.510 | 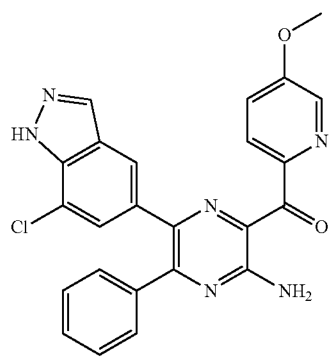 [SMILES: COc1ccc(C(=O)c2nc(-c3cc(Cl)c4[nH]ncc4c3)c(-c3ccccc3)nc2N)nc1] |
| 2.511 | 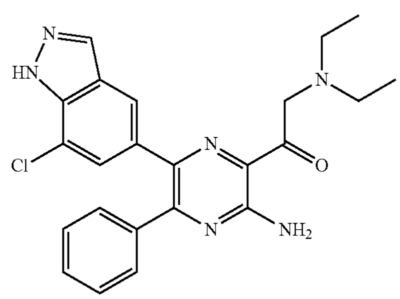 [SMILES: CCN(CC)CC(=O)c1nc(-c2cc(Cl)c3[nH]ncc3c2)c(-c2ccccc2)nc1N] |
| 2.512 | 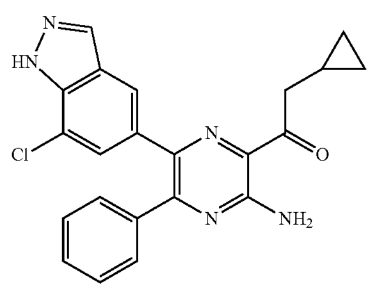 [SMILES: Nc1nc(-c2ccccc2)c(-c2cc(Cl)c3[nH]ncc3c2)nc1C(=O)CC1CC1] |
| 2.513 | 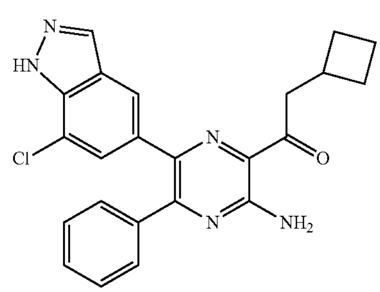 |

TABLE 2-continued
| Compound No. | Structure |
|---|---|
| 2.514 | 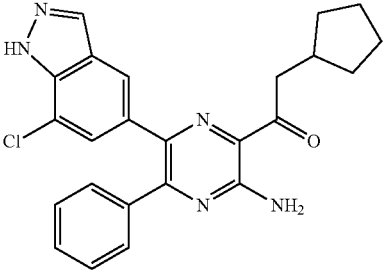 |
| 2.515 | 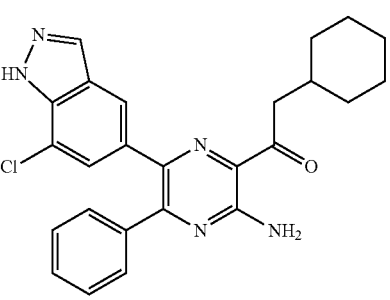 [SMILES: Nc1nc(-c2ccccc2)c(-c2cc(Cl)c3[nH]ncc3c2)nc1C(=O)CC1CCCCC1] |
| 2.516 | 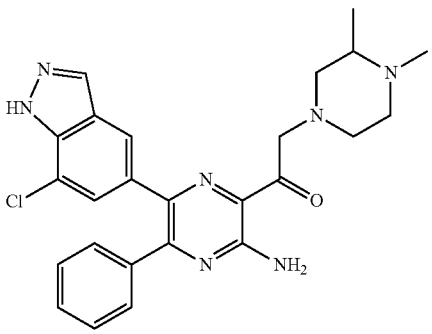 [SMILES: CC1CN(CC(=O)c2nc(-c3cc(Cl)c4[nH]ncc4c3)c(-c3ccccc3)nc2N)CCN1C] |
| 2.517 | 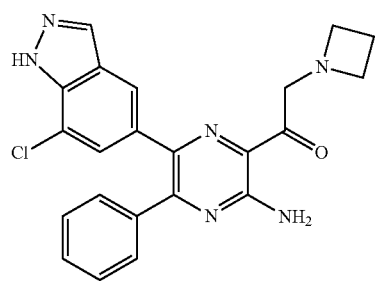 |
| 2.518 | 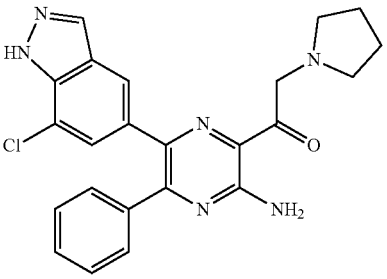 [SMILES: Nc1nc(-c2ccccc2)c(-c2cc(Cl)c3[nH]ncc3c2)nc1C(=O)CN1CCCC1] |

TABLE 2-continued
| Compound No. | Structure |
|---|---|
| 2.519 | 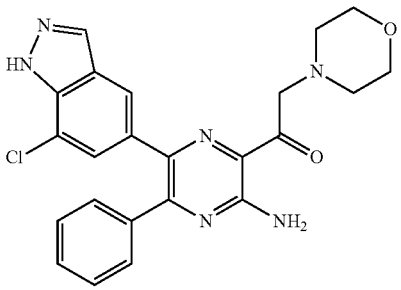 [SMILES: Nc1nc(-c2ccccc2)c(-c2cc(Cl)c3[nH]ncc3c2)nc1C(=O)CN1CCOCC1] |
| 2.520 | 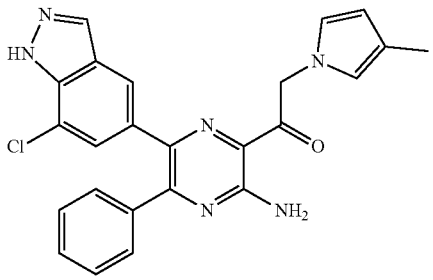 [SMILES: Cc1ccn(CC(=O)c2nc(-c3cc(Cl)c4[nH]ncc4c3)c(-c3ccccc3)nc2N)c1] |
| 2.521 | 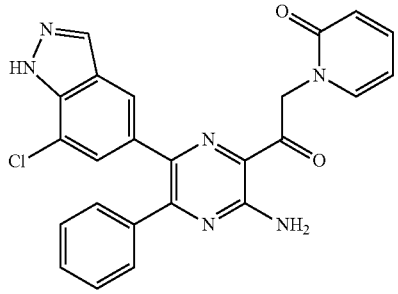 [SMILES: Nc1nc(-c2ccccc2)c(-c2cc(Cl)c3[nH]ncc3c2)nc1C(=O)Cn1ccccc1=O] |
| 2.522 | 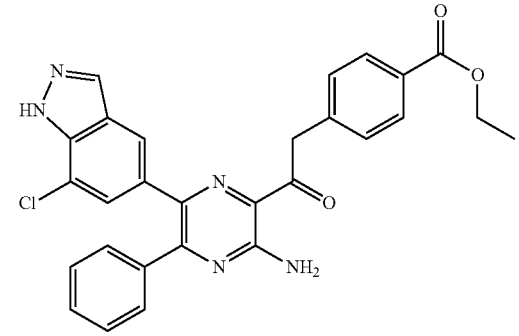 [SMILES: CCOC(=O)c1ccc(CC(=O)c2nc(-c3cc(Cl)c4[nH]ncc4c3)c(-c3ccccc3)nc2N)cc1] |
| 2.523 | 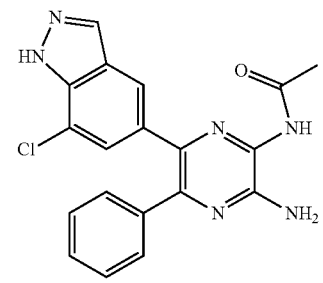 [SMILES: CC(=O)Nc1nc(-c2cc(Cl)c3[nH]ncc3c2)c(-c2ccccc2)nc1N] |

TABLE 2-continued
| Compound No. | Structure |
|---|---|
| 2.524 | 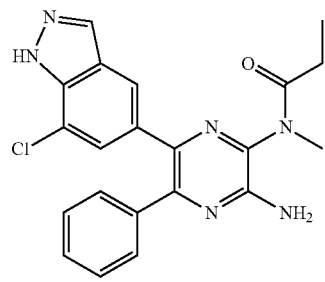 [SMILES: CCC(=O)N(C)c1nc(-c2cc(Cl)c3[nH]ncc3c2)c(-c2ccccc2)nc1N] |
| 2.525 | 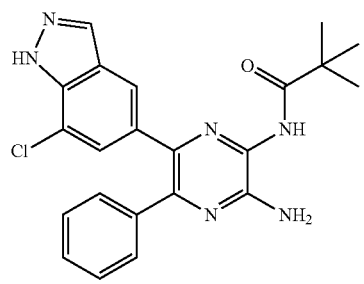 [SMILES: CC(C)(C)C(=O)Nc1nc(-c2cc(Cl)c3[nH]ncc3c2)c(-c2ccccc2)nc1N] |
| 2.526 | 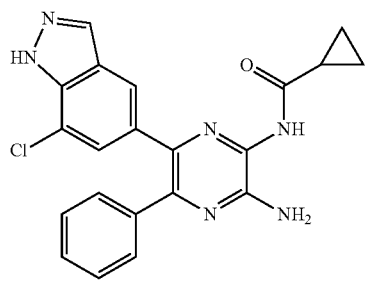 [SMILES: Nc1nc(-c2ccccc2)c(-c2cc(Cl)c3[nH]ncc3c2)nc1NC(=O)C1CC1] |
| 2.527 | 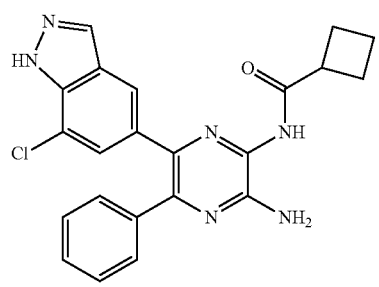 [SMILES: Nc1nc(-c2ccccc2)c(-c2cc(Cl)c3[nH]ncc3c2)nc1NC(=O)C1CCC1] |
| 2.528 | 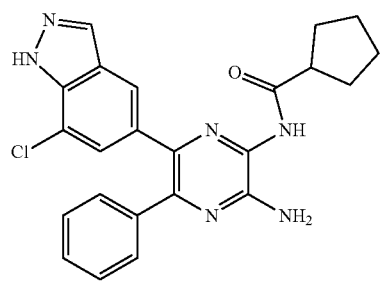 [SMILES: Nc1nc(-c2ccccc2)c(-c2cc(Cl)c3[nH]ncc3c2)nc1NC(=O)C1CCCC1] |

TABLE 2-continued
| Compound No. | Structure |
|---|---|
| 2.529 | 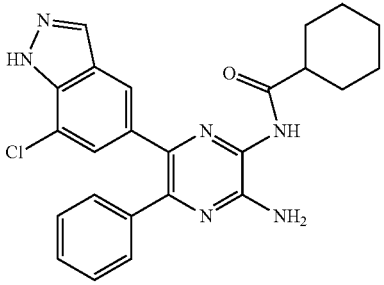 [SMILES: Nc1nc(-c2ccccc2)c(-c2cc(Cl)c3[nH]ncc3c2)nc1NC(=O)C1CCCCC1] |
| 2.530 | 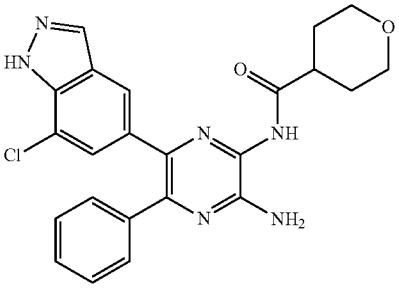 [SMILES: Nc1nc(-c2ccccc2)c(-c2cc(Cl)c3[nH]ncc3c2)nc1NC(=O)C1CCOCC1] |
| 2.531 | 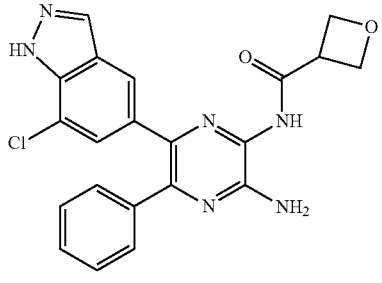 [SMILES: Nc1nc(-c2ccccc2)c(-c2cc(Cl)c3[nH]ncc3c2)nc1NC(=O)C1COC1] |
| 2.532 | 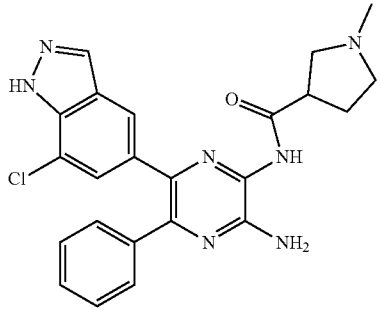 [SMILES: CN1CCC(C(=O)Nc2nc(-c3cc(Cl)c4[nH]ncc4c3)c(-c3ccccc3)nc2N)C1] |
| 2.533 | 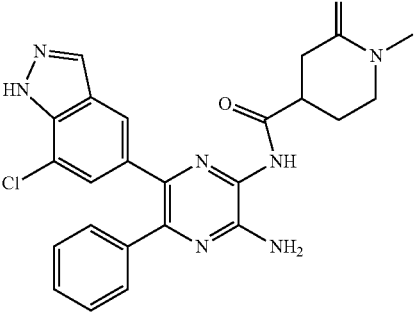 |

TABLE 2-continued
| Compound No. | Structure |
|---|---|
| 2.534 | 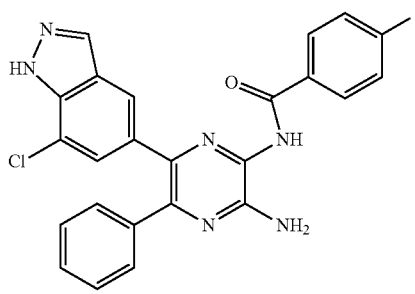 |
| 2.535 | 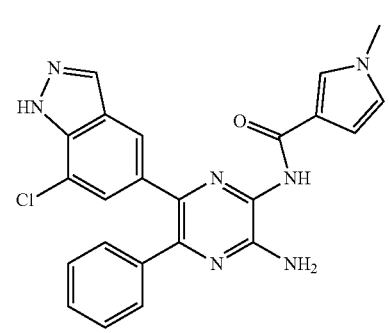 [SMILES: Cn1ccc(C(=O)Nc2nc(-c3cc(Cl)c4[nH]ncc4c3)c(-c3ccccc3)nc2N)c1] |
| 2.536 | 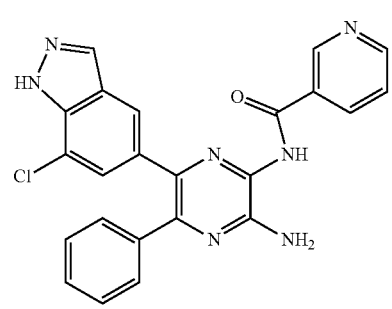 [SMILES: Nc1nc(-c2ccccc2)c(-c2cc(Cl)c3[nH]ncc3c2)nc1NC(=O)c1cccnc1] |
| 2.537 | 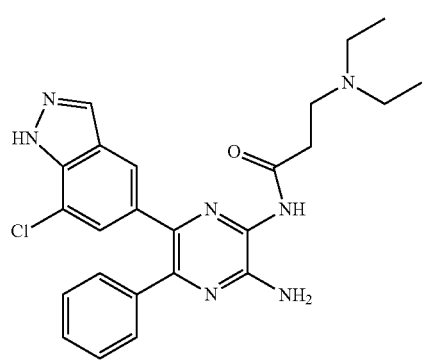 [SMILES: CCN(CC)CCC(=O)Nc1nc(-c2cc(Cl)c3[nH]ncc3c2)c(-c2ccccc2)nc1N] |
| 2.538 | 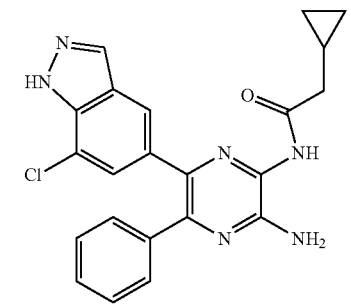 [SMILES: Nc1nc(-c2ccccc2)c(-c2cc(Cl)c3[nH]ncc3c2)nc1NC(=O)CC1CC1] |

TABLE 2-continued

| Compound No. | Structure |
| --- | --- |
| 2.539 | 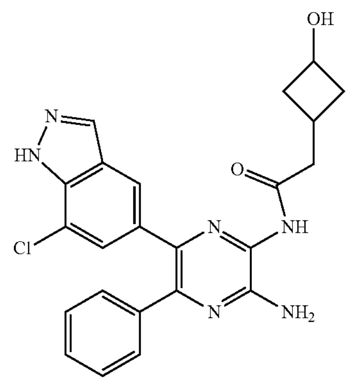 [SMILES: Nc1nc(-c2ccccc2)c(-c2cc(Cl)c3[nH]ncc3c2)nc1NC(=O)CC1CC(O)C1] |
| 2.540 | 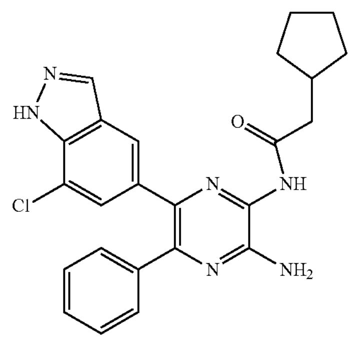 [SMILES: Nc1nc(-c2ccccc2)c(-c2cc(Cl)c3[nH]ncc3c2)nc1NC(=O)CC1CCCC1] |
| 2.541 | 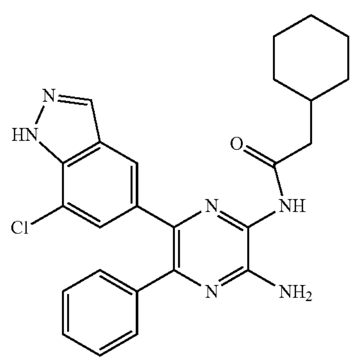 [SMILES: Nc1nc(-c2ccccc2)c(-c2cc(Cl)c3[nH]ncc3c2)nc1NC(=O)CC1CCCCC1] |
| 2.542 | 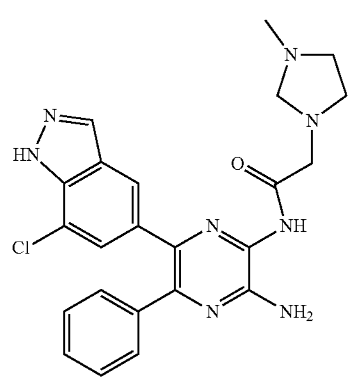 [SMILES: CN1CCN(CC(=O)Nc2nc(-c3cc(Cl)c4[nH]ncc4c3)c(-c3ccccc3)nc2N)C1] |

TABLE 2-continued
| Compound No. | Structure |
|---|---|
| 2.543 | 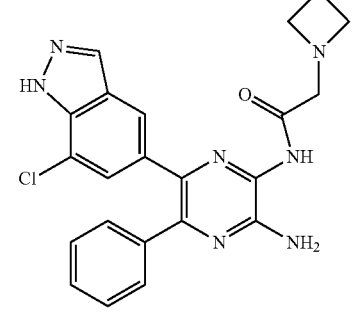 |
| 2.544 | 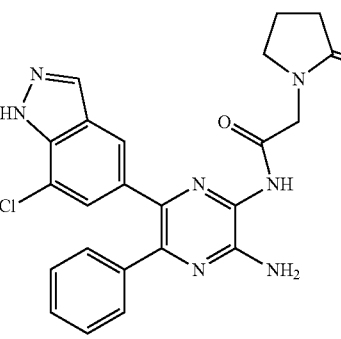 |
| 2.545 | 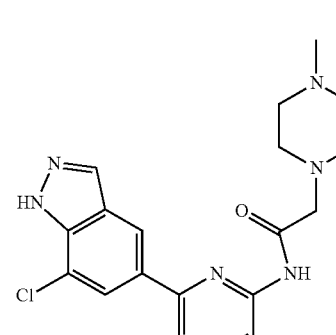 |
| 2.546 | 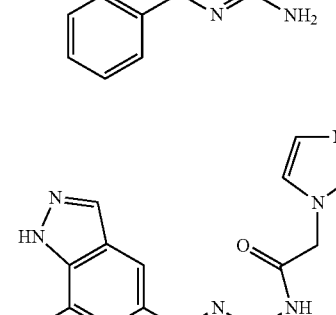 |

TABLE 2-continued

| Compound No. | Structure |
|---|---|
| 2.547 | 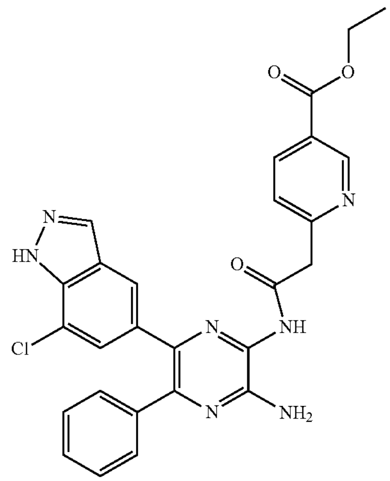 [SMILES: CCOC(=O)c1ccc(CC(=O)Nc2nc(-c3cc(Cl)c4[nH]ncc4c3)c(-c3ccccc3)nc2N)nc1] |
| 2.548 | 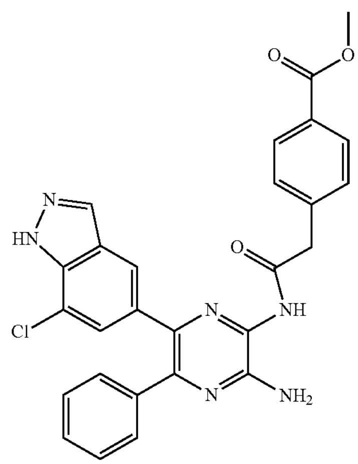 [SMILES: COC(=O)c1ccc(CC(=O)Nc2nc(-c3cc(Cl)c4[nH]ncc4c3)c(-c3ccccc3)nc2N)cc1] |
| 2.549 | 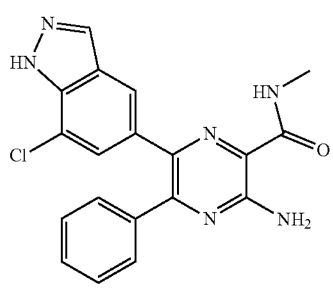 [SMILES: CNC(=O)c1nc(-c2cc(Cl)c3[nH]ncc3c2)c(-c2ccccc2)nc1N] |
| 2.550 | 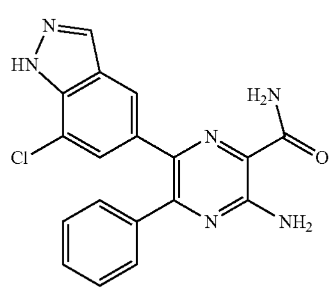 [SMILES: NC(=O)c1nc(-c2cc(Cl)c3[nH]ncc3c2)c(-c2ccccc2)nc1N] |

TABLE 2-continued

| Compound No. | Structure |
|---|---|
| 2.551 | 3-amino-6-(7-chloro-1H-indazol-5-yl)-N-ethyl-5-phenylpyrazine-2-carboxamide |
| 2.552 | 3-amino-N-tert-butyl-6-(7-chloro-1H-indazol-5-yl)-5-phenylpyrazine-2-carboxamide |
| 2.553 | 3-amino-6-(7-chloro-1H-indazol-5-yl)-N-cyclopropyl-5-phenylpyrazine-2-carboxamide |
| 2.554 | 3-amino-6-(7-chloro-1H-indazol-5-yl)-N-cyclobutyl-5-phenylpyrazine-2-carboxamide |
| 2.555 | 3-amino-6-(7-chloro-1H-indazol-5-yl)-N-cyclopentyl-5-phenylpyrazine-2-carboxamide |

TABLE 2-continued
| Compound No. | Structure |
|---|---|
| 2.556 | 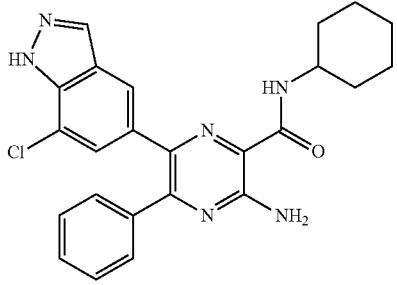 [SMILES: Nc1nc(-c2ccccc2)c(-c2cc(Cl)c3[nH]ncc3c2)nc1C(=O)NC1CCCCC1] |
| 2.557 | 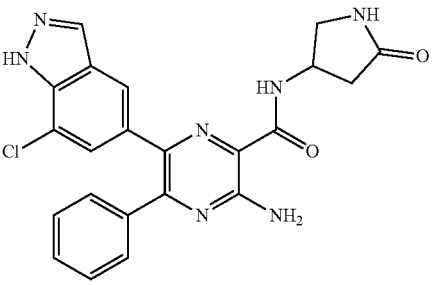 [SMILES: Nc1nc(-c2ccccc2)c(-c2cc(Cl)c3[nH]ncc3c2)nc1C(=O)NC1CNC(=O)C1] |
| 2.558 | 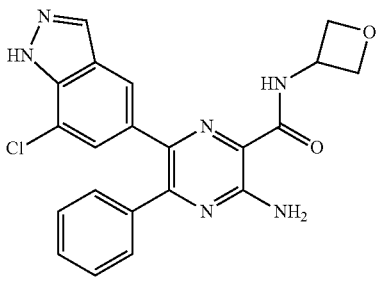 [SMILES: Nc1nc(-c2ccccc2)c(-c2cc(Cl)c3[nH]ncc3c2)nc1C(=O)NC1COC1] |
| 2.559 | 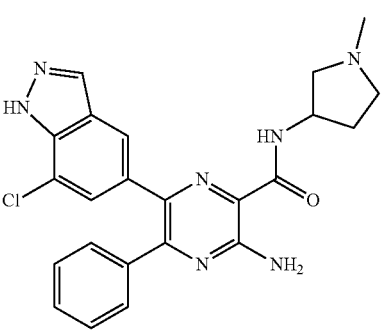 [SMILES: CN1CCC(NC(=O)c2nc(-c3cc(Cl)c4[nH]ncc4c3)c(-c3ccccc3)nc2N)C1] |
| 2.560 | 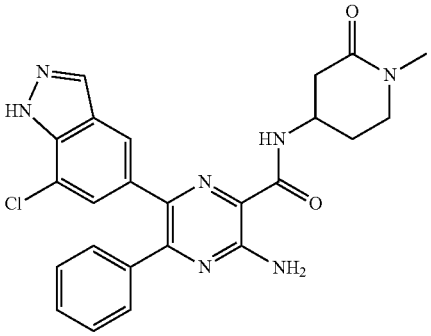 [SMILES: CN1CCC(NC(=O)c2nc(-c3cc(Cl)c4[nH]ncc4c3)c(-c3ccccc3)nc2N)CC1=O] |

TABLE 2-continued
| Compound No. | Structure |
|---|---|
| 2.561 | 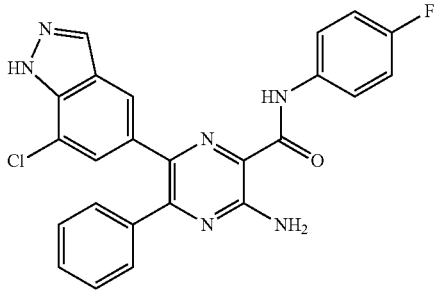 [SMILES: Nc1nc(-c2ccccc2)c(-c2cc(Cl)c3[nH]ncc3c2)nc1C(=O)Nc1ccc(F)cc1] |
| 2.562 | 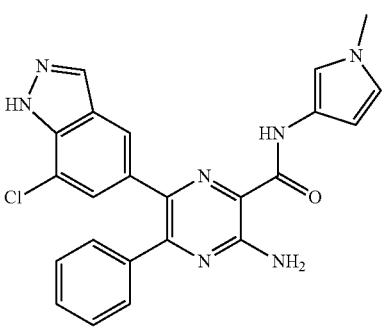 [SMILES: Cn1ccc(NC(=O)c2nc(-c3cc(Cl)c4[nH]ncc4c3)c(-c3ccccc3)nc2N)c1] |
| 2.563 | 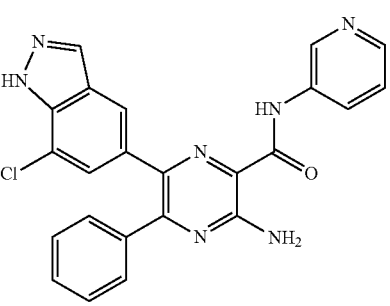 [SMILES: Nc1nc(-c2ccccc2)c(-c2cc(Cl)c3[nH]ncc3c2)nc1C(=O)Nc1cccnc1] |
| 2.564 | 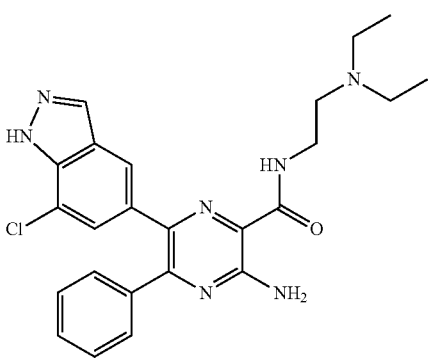 [SMILES: CCN(CC)CCNC(=O)c1nc(-c2cc(Cl)c3[nH]ncc3c2)c(-c2ccccc2)nc1N] |
| 2.565 | 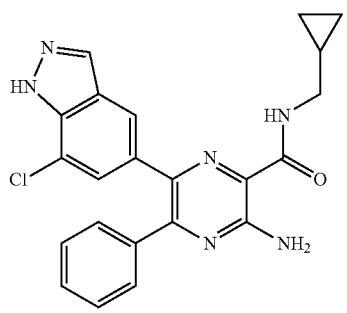 [SMILES: Nc1nc(-c2ccccc2)c(-c2cc(Cl)c3[nH]ncc3c2)nc1C(=O)NCC1CC1] |

TABLE 2-continued
| Compound No. | Structure |
|---|---|
| 2.566 | 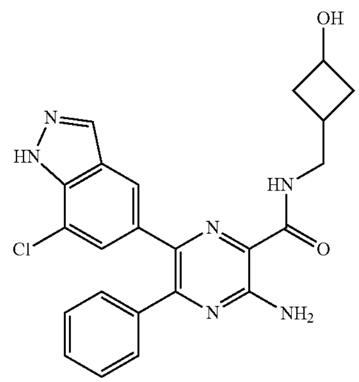 [SMILES: Nc1nc(-c2ccccc2)c(-c2cc(Cl)c3[nH]ncc3c2)nc1C(=O)NCC1CC(O)C1] |
| 2.567 | 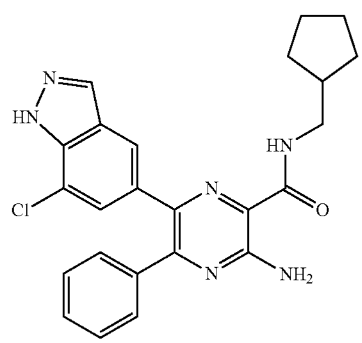 [SMILES: Nc1nc(-c2ccccc2)c(-c2cc(Cl)c3[nH]ncc3c2)nc1C(=O)NCC1CCCC1] |
| 2.568 | 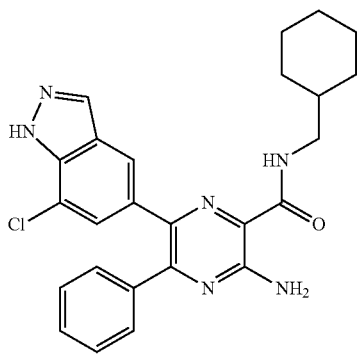 [SMILES: Nc1nc(-c2ccccc2)c(-c2cc(Cl)c3[nH]ncc3c2)nc1C(=O)NCC1CCCCC1] |
| 2.569 | 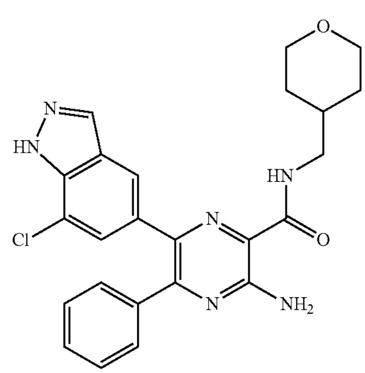 [SMILES: Nc1nc(-c2ccccc2)c(-c2cc(Cl)c3[nH]ncc3c2)nc1C(=O)NCC1CCOCC1] |

TABLE 2-continued
| Compound No. | Structure |
|---|---|
| 2.570 | 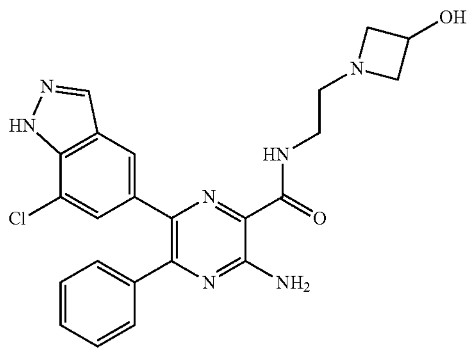 [SMILES: Nc1nc(-c2ccccc2)c(-c2cc(Cl)c3[nH]ncc3c2)nc1C(=O)NCCN1CC(O)C1] |
| 2.571 | 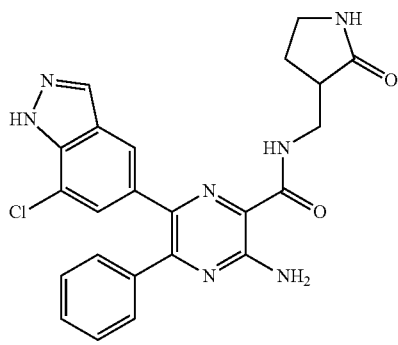 [SMILES: Nc1nc(-c2ccccc2)c(-c2cc(Cl)c3[nH]ncc3c2)nc1C(=O)NCC1CCNC1=O] |
| 2.572 | 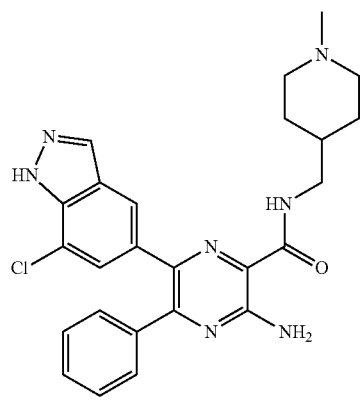 [SMILES: CN1CCC(CNC(=O)c2nc(-c3cc(Cl)c4[nH]ncc4c3)c(-c3ccccc3)nc2N)CC1] |
| 2.573 | 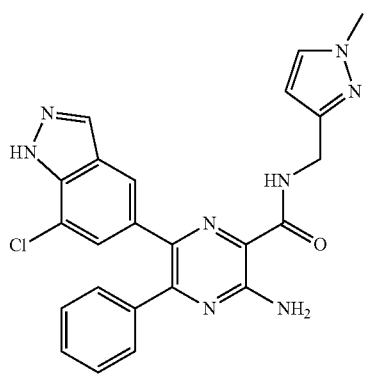 [SMILES: Cn1ccc(CNC(=O)c2nc(-c3cc(Cl)c4[nH]ncc4c3)c(-c3ccccc3)nc2N)n1] |

TABLE 2-continued

| Compound No. | Structure |
|---|---|
| 2.574 | 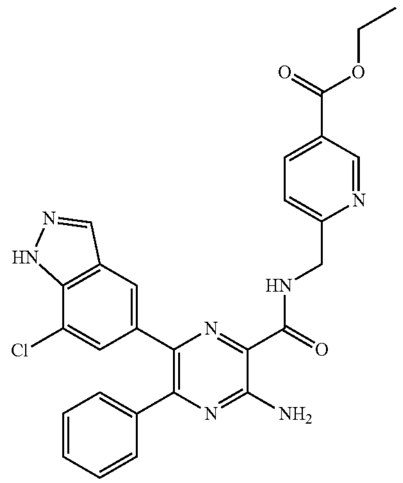 [SMILES: CCOC(=O)c1ccc(CNC(=O)c2nc(-c3cc(Cl)c4[nH]ncc4c3)c(-c3ccccc3)nc2N)nc1] |
| 2.575 | 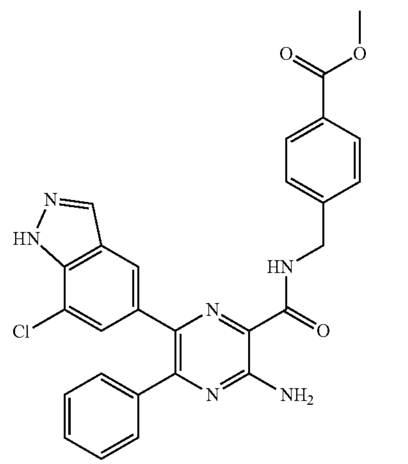 [SMILES: COC(=O)c1ccc(CNC(=O)c2nc(-c3cc(Cl)c4[nH]ncc4c3)c(-c3ccccc3)nc2N)cc1] |
| 2.576 | 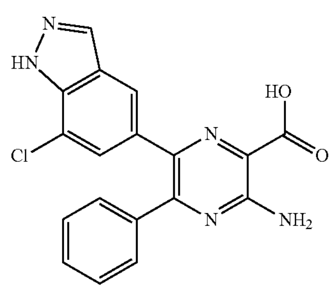 [SMILES: Nc1nc(-c2ccccc2)c(-c2cc(Cl)c3[nH]ncc3c2)nc1C(=O)O] |
| 2.577 | 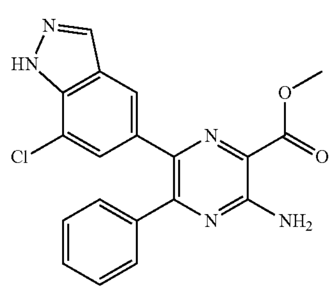 [SMILES: COC(=O)c1nc(-c2cc(Cl)c3[nH]ncc3c2)c(-c2ccccc2)nc1N] |

TABLE 2-continued

| Compound No. | Structure |
|---|---|
| 2.578 | ethyl 3-amino-6-(7-chloro-1H-indazol-5-yl)-5-phenylpyrazine-2-carboxylate |
| 2.579 | tert-butyl 3-amino-6-(7-chloro-1H-indazol-5-yl)-5-phenylpyrazine-2-carboxylate |
| 2.580 | cyclopropyl 3-amino-6-(7-chloro-1H-indazol-5-yl)-5-phenylpyrazine-2-carboxylate |
| 2.581 | cyclobutyl 3-amino-6-(7-chloro-1H-indazol-5-yl)-5-phenylpyrazine-2-carboxylate |
| 2.582 | cyclopentyl 3-amino-6-(7-chloro-1H-indazol-5-yl)-5-phenylpyrazine-2-carboxylate |

TABLE 2-continued
| Compound No. | Structure |
|---|---|
| 2.583 | 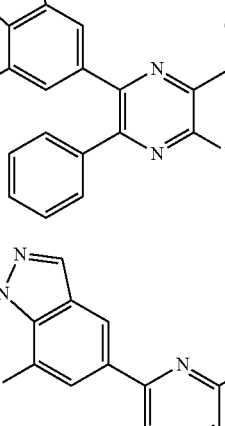 |
| 2.584 | 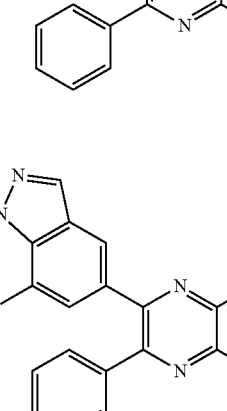 |
| 2.585 | 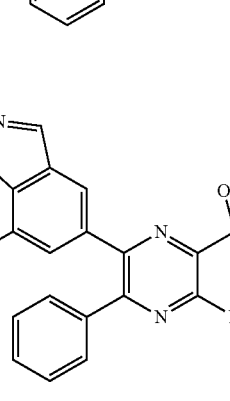 |
| 2.586 | 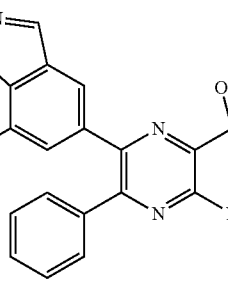 |
| 2.587 | 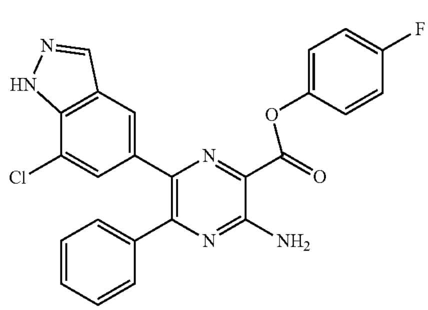 [SMILES: Nc1nc(-c2ccccc2)c(-c2cc(Cl)c3[nH]ncc3c2)nc1C(=O)Oc1ccc(F)cc1] |

TABLE 2-continued
| Compound No. | Structure |
|---|---|
| 2.588 | 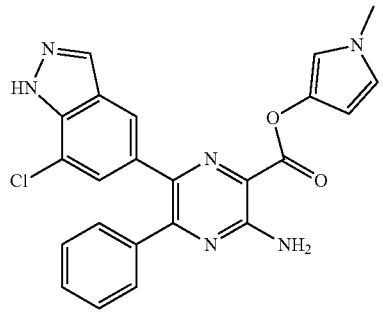 [SMILES: Cn1ccc(OC(=O)c2nc(-c3cc(Cl)c4[nH]ncc4c3)c(-c3ccccc3)nc2N)c1] |
| 2.589 | 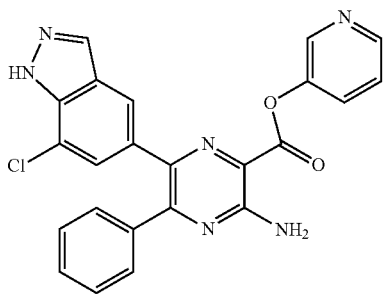 [SMILES: Nc1nc(-c2ccccc2)c(-c2cc(Cl)c3[nH]ncc3c2)nc1C(=O)Oc1cccnc1] |
| 2.590 | 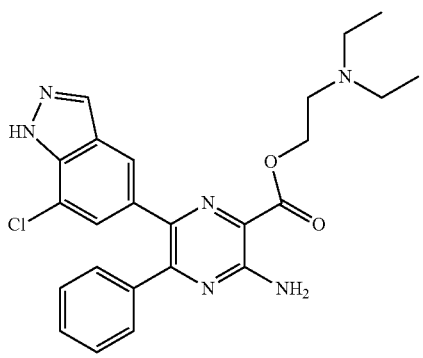 [SMILES: CCN(CC)CCOC(=O)c1nc(-c2cc(Cl)c3[nH]ncc3c2)c(-c2ccccc2)nc1N] |
| 2.591 | 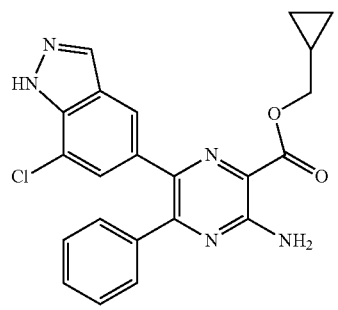 [SMILES: Nc1nc(-c2ccccc2)c(-c2cc(Cl)c3[nH]ncc3c2)nc1C(=O)OCC1CC1] |

US 11,028,058 B2
TABLE 2-continued
| Compound No. | Structure |
|---|---|
| 2.592 | 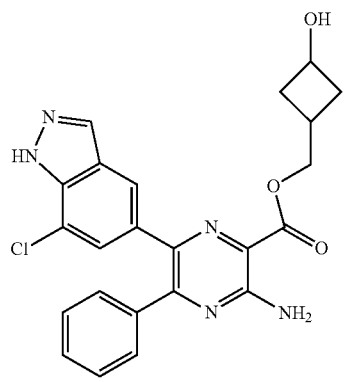 [SMILES: Nc1nc(-c2ccccc2)c(-c2cc(Cl)c3[nH]ncc3c2)nc1C(=O)OCC1CC(O)C1] |
| 2.593 | 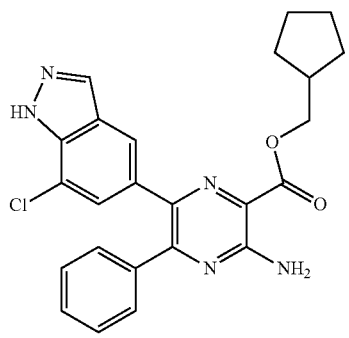 [SMILES: Nc1nc(-c2ccccc2)c(-c2cc(Cl)c3[nH]ncc3c2)nc1C(=O)OCC1CCCC1] |
| 2.594 | 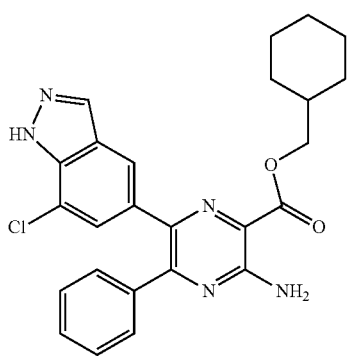 [SMILES: Nc1nc(-c2ccccc2)c(-c2cc(Cl)c3[nH]ncc3c2)nc1C(=O)OCC1CCCCC1] |
| 2.595 | 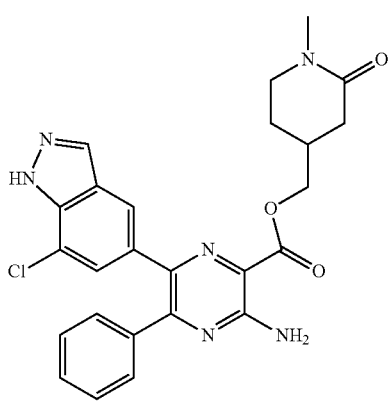 [SMILES: CN1CCC(COC(=O)c2nc(-c3cc(Cl)c4[nH]ncc4c3)c(-c3ccccc3)nc2N)CC1=O] |

TABLE 2-continued

| Compound No. | Structure |
| --- | --- |
| 2.596 | 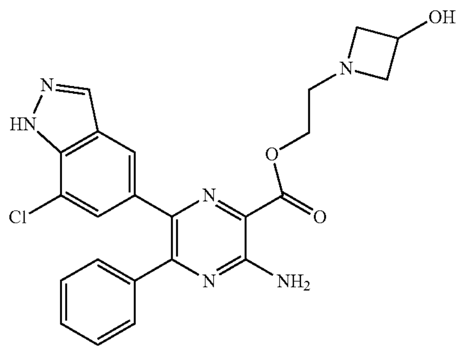 [SMILES: Nc1nc(-c2ccccc2)c(-c2cc(Cl)c3[nH]ncc3c2)nc1C(=O)OCCN1CC(O)C1] |
| 2.597 | 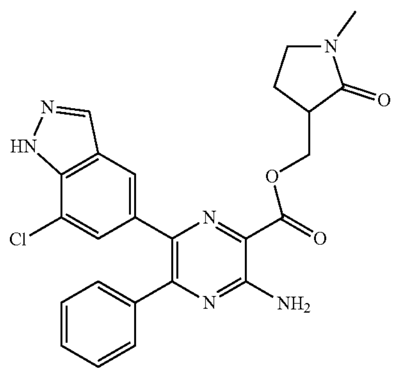 [SMILES: CN1CCC(COC(=O)c2nc(-c3cc(Cl)c4[nH]ncc4c3)c(-c3ccccc3)nc2N)C1=O] |
| 2.598 | 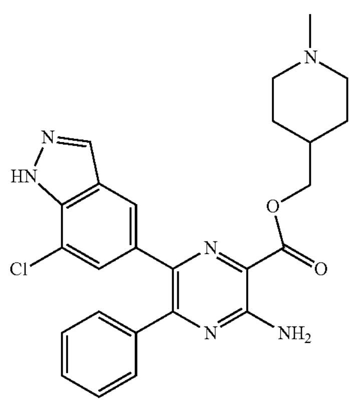 [SMILES: CN1CCC(COC(=O)c2nc(-c3cc(Cl)c4[nH]ncc4c3)c(-c3ccccc3)nc2N)CC1] |
| 2.599 | 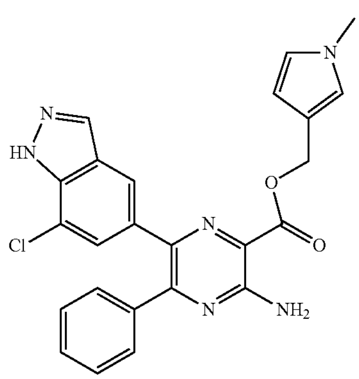 [SMILES: Cn1ccc(COC(=O)c2nc(-c3cc(Cl)c4[nH]ncc4c3)c(-c3ccccc3)nc2N)c1] |

TABLE 2-continued

| Compound No. | Structure |
|---|---|
| 2.600 | 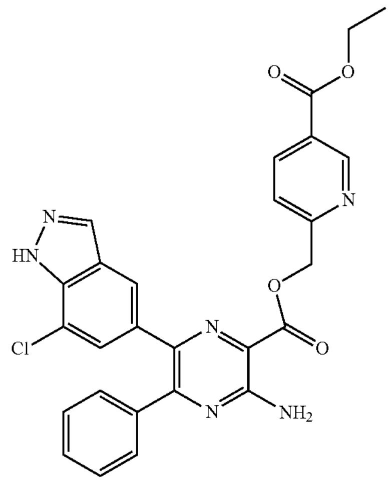 [SMILES: CCOC(=O)c1ccc(COC(=O)c2nc(-c3cc(Cl)c4[nH]ncc4c3)c(-c3ccccc3)nc2N)nc1] |
| 2.601 | 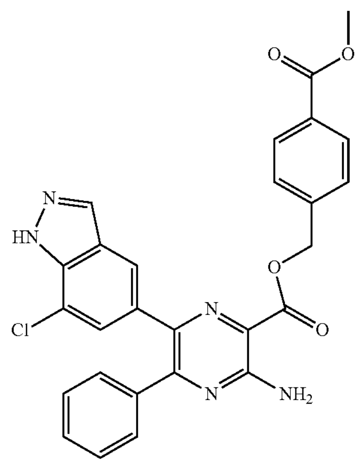 [SMILES: COC(=O)c1ccc(COC(=O)c2nc(-c3cc(Cl)c4[nH]ncc4c3)c(-c3ccccc3)nc2N)cc1] |
| 2.602 | 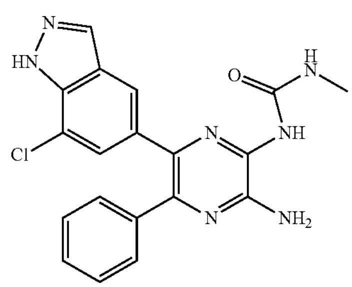 [SMILES: CNC(=O)Nc1nc(-c2cc(Cl)c3[nH]ncc3c2)c(-c2ccccc2)nc1N] |
| 2.603 | 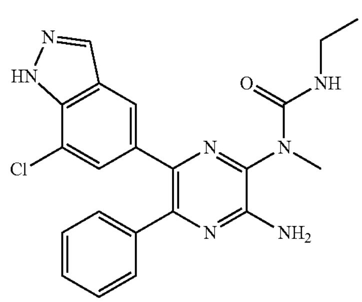 [SMILES: CCNC(=O)N(C)c1nc(-c2cc(Cl)c3[nH]ncc3c2)c(-c2ccccc2)nc1N] |

TABLE 2-continued
| Compound No. | Structure |
|---|---|
| 2.604 | 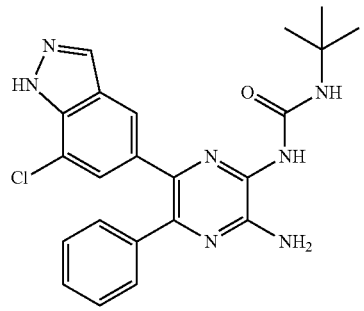 [SMILES: CC(C)(C)NC(=O)Nc1nc(-c2cc(Cl)c3[nH]ncc3c2)c(-c2ccccc2)nc1N] |
| 2.605 | 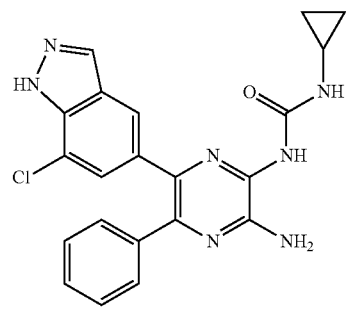 [SMILES: Nc1nc(-c2ccccc2)c(-c2cc(Cl)c3[nH]ncc3c2)nc1NC(=O)NC1CC1] |
| 2.606 | 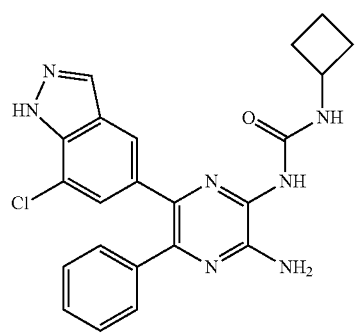 [SMILES: Nc1nc(-c2ccccc2)c(-c2cc(Cl)c3[nH]ncc3c2)nc1NC(=O)NC1CCC1] |
| 2.607 | 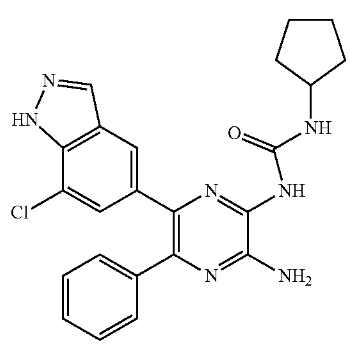 [SMILES: Nc1nc(-c2ccccc2)c(-c2cc(Cl)c3[nH]ncc3c2)nc1NC(=O)NC1CCCC1] |

TABLE 2-continued

| Compound No. | Structure |
|---|---|
| 2.608 | *7-chloro-1H-indazol-5-yl / phenyl / aminopyrazine with N-cyclohexyl urea substituent* |
| 2.609 | *7-chloro-1H-indazol-5-yl / phenyl / aminopyrazine with N-(tetrahydropyran-4-yl) urea substituent* |
| 2.610 | *7-chloro-1H-indazol-5-yl / phenyl / aminopyrazine with N-(1-methylazetidin-3-yl) urea substituent* |
| 2.611 | *7-chloro-1H-indazol-5-yl / phenyl / aminopyrazine with N-(1-methylpyrrolidin-3-yl) urea substituent* |

TABLE 2-continued

| Compound No. | Structure |
|---|---|
| 26.12 | 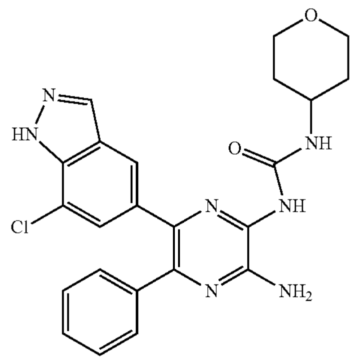 [SMILES: Nc1nc(-c2ccccc2)c(-c2cc(Cl)c3[nH]ncc3c2)nc1NC(=O)NC1CCOCC1] |
| 2.613 | 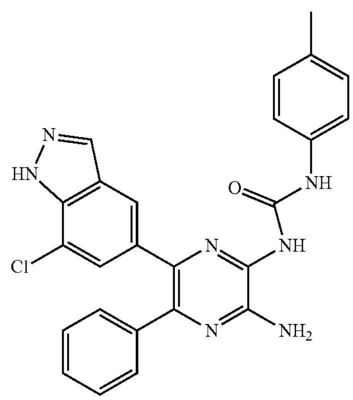 [SMILES: Cc1ccc(NC(=O)Nc2nc(-c3cc(Cl)c4[nH]ncc4c3)c(-c3ccccc3)nc2N)cc1] |
| 2.614 | 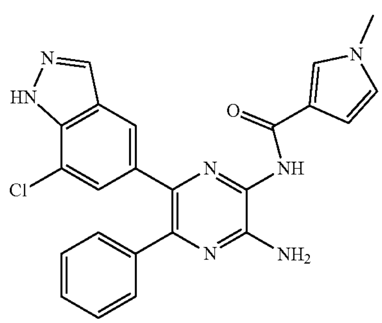 [SMILES: Cn1ccc(C(=O)Nc2nc(-c3cc(Cl)c4[nH]ncc4c3)c(-c3ccccc3)nc2N)c1] |
| 2.615 | 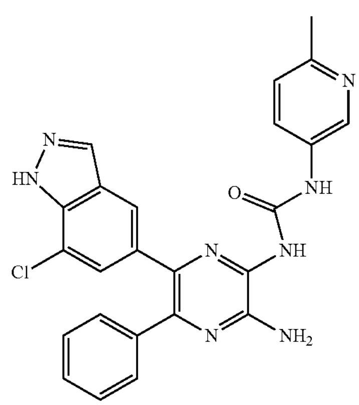 [SMILES: Cc1ccc(NC(=O)Nc2nc(-c3cc(Cl)c4[nH]ncc4c3)c(-c3ccccc3)nc2N)cn1] |

TABLE 2-continued
| Compound No. | Structure |
|---|---|
| 2.616 | 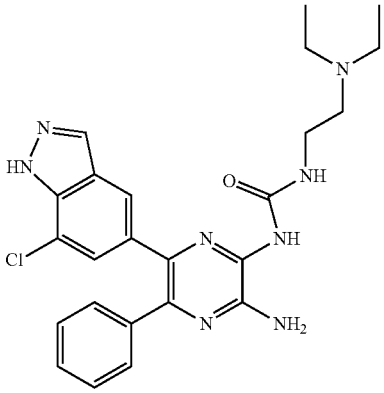 [SMILES: CCN(CC)CCNC(=O)Nc1nc(-c2cc(Cl)c3[nH]ncc3c2)c(-c2ccccc2)nc1N] |
| 2.617 | 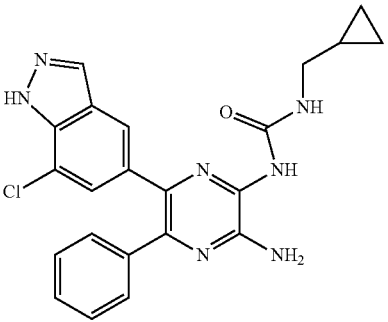 [SMILES: Nc1nc(-c2ccccc2)c(-c2cc(Cl)c3[nH]ncc3c2)nc1NC(=O)NCC1CC1] |
| 2.618 | 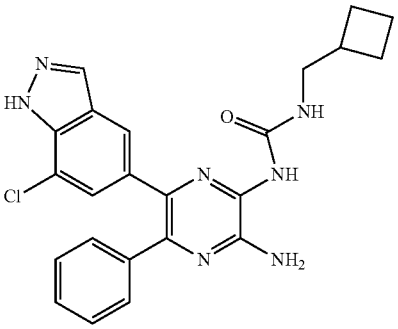 [SMILES: Nc1nc(-c2ccccc2)c(-c2cc(Cl)c3[nH]ncc3c2)nc1NC(=O)NCC1CCC1] |
| 2.619 | 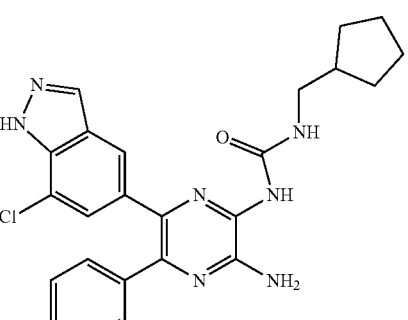 |

TABLE 2-continued
| Compound No. | Structure |
|---|---|
| 2.620 | 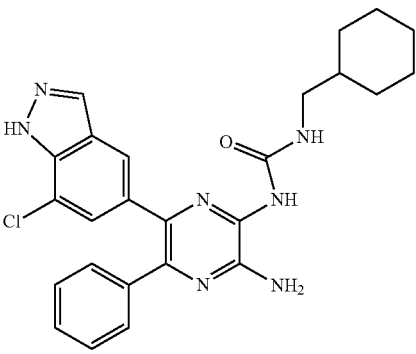 [SMILES: Nc1nc(-c2ccccc2)c(-c2cc(Cl)c3[nH]ncc3c2)nc1NC(=O)NCC1CCCCC1] |
| 2.621 | 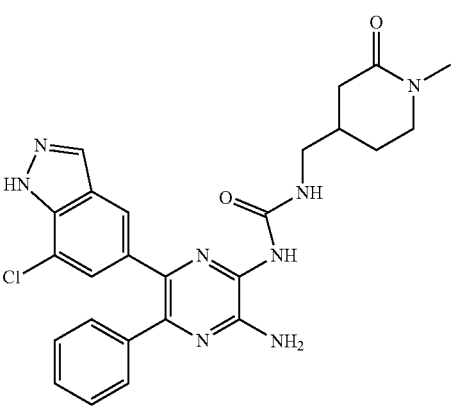 [SMILES: CN1CCC(CNC(=O)Nc2nc(-c3cc(Cl)c4[nH]ncc4c3)c(-c3ccccc3)nc2N)CC1=O] |
| 2.622 | 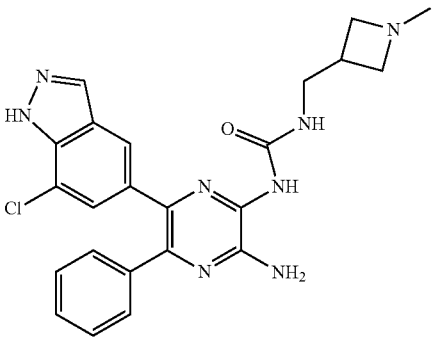 [SMILES: CN1CC(CNC(=O)Nc2nc(-c3cc(Cl)c4[nH]ncc4c3)c(-c3ccccc3)nc2N)C1] |
| 2.623 | 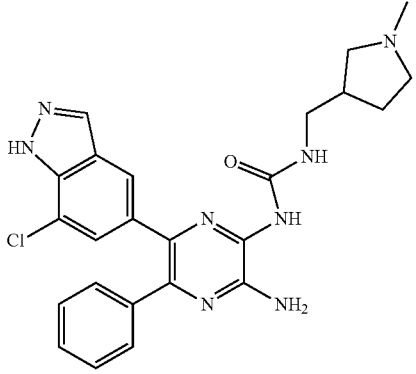 [SMILES: CN1CCC(CNC(=O)Nc2nc(-c3cc(Cl)c4[nH]ncc4c3)c(-c3ccccc3)nc2N)C1] |

TABLE 2-continued
| Compound No. | Structure |
|---|---|
| 2.624 | 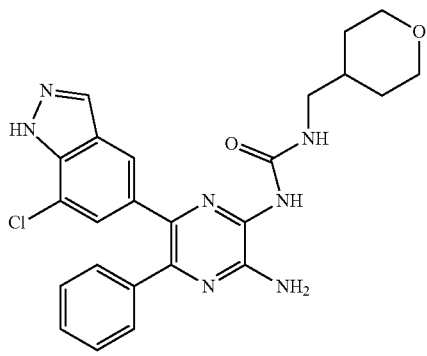 [SMILES: Nc1nc(-c2ccccc2)c(-c2cc(Cl)c3[nH]ncc3c2)nc1NC(=O)NCC1CCOCC1] |
| 2.625 | 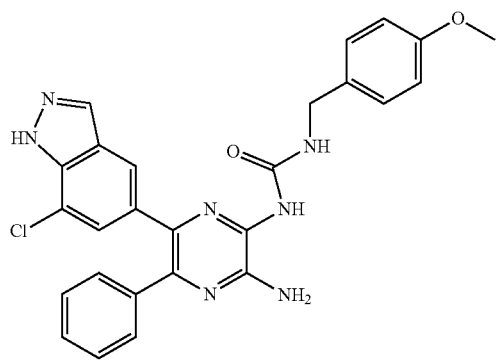 [SMILES: COc1ccc(CNC(=O)Nc2nc(-c3cc(Cl)c4[nH]ncc4c3)c(-c3ccccc3)nc2N)cc1] |
| 2.626 | 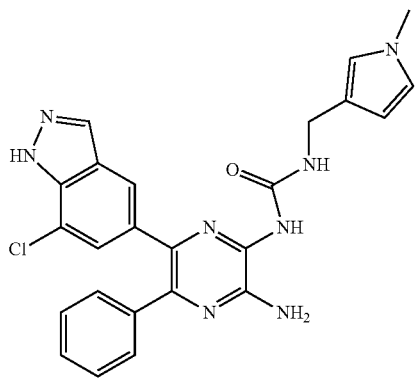 [SMILES: Cn1ccc(CNC(=O)Nc2nc(-c3cc(Cl)c4[nH]ncc4c3)c(-c3ccccc3)nc2N)c1] |
| 2.627 | 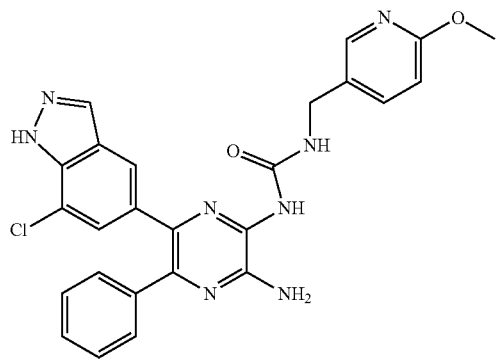 |

TABLE 2-continued

| Compound No. | Structure |
|---|---|
| 2.628 | 7-chloro-1H-indazol-5-yl / phenyl / pyrazine-CN / NH-ethyl |
| 2.629 | 7-chloro-1H-indazol-5-yl / phenyl / pyrazine-CN / NH-isopropyl |
| 2.630 | 7-chloro-1H-indazol-5-yl / phenyl / pyrazine-CN / NH-tert-butyl |
| 2.631 | 7-chloro-1H-indazol-5-yl / phenyl / pyrazine-CN / NH-(but-2-en-1-yl) |
| 2.632 | 7-chloro-1H-indazol-5-yl / phenyl / pyrazine-CN / NH-(prop-2-yn-1-yl) |

TABLE 2-continued

| Compound No. | Structure |
|---|---|
| 2.633 | 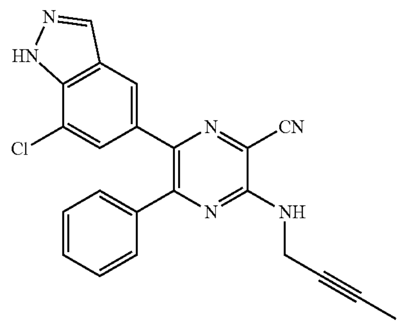 |
| 2.634 | 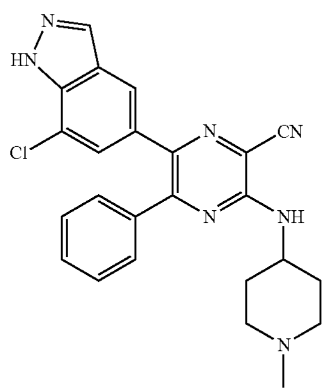 [SMILES: CN1CCC(Nc2nc(-c3ccccc3)c(-c3cc(Cl)c4[nH]ncc4c3)nc2C#N)CC1] |
| 2.635 | 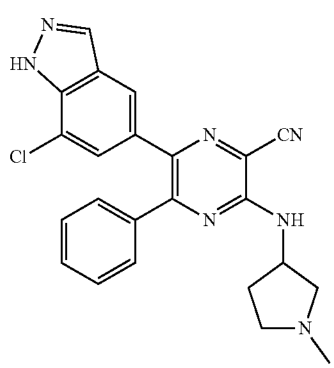 |
| 2.636 | 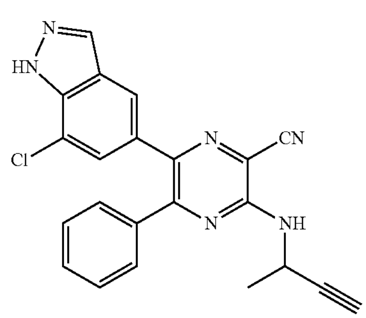 [SMILES: C#CC(C)Nc1nc(-c2ccccc2)c(-c2cc(Cl)c3[nH]ncc3c2)nc1C#N] |

TABLE 2-continued
| Compound No. | Structure |
|---|---|
| 2.637 | 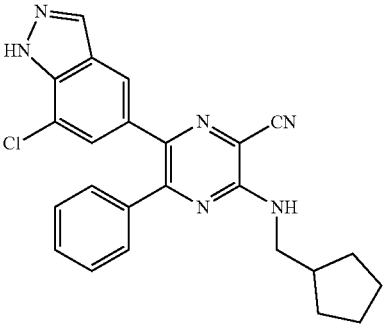 [SMILES: N#Cc1nc(-c2cc(Cl)c3[nH]ncc3c2)c(-c2ccccc2)nc1NCC1CCCC1] |
| 2.638 | 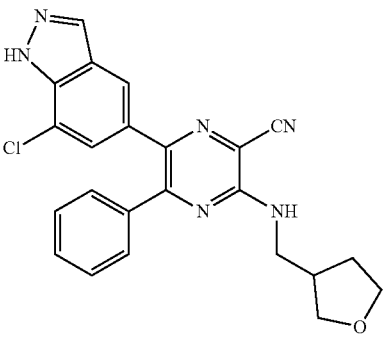 [SMILES: N#Cc1nc(-c2cc(Cl)c3[nH]ncc3c2)c(-c2ccccc2)nc1NCC1CCOC1] |
| 2.639 | 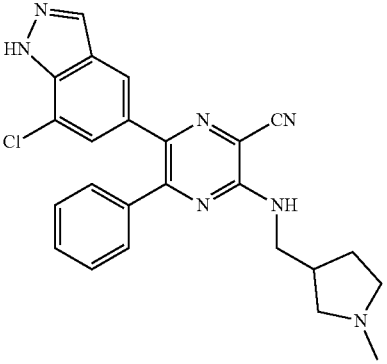 [SMILES: CN1CCC(CNc2nc(-c3ccccc3)c(-c3cc(Cl)c4[nH]ncc4c3)nc2C#N)C1] |
| 2.640 | 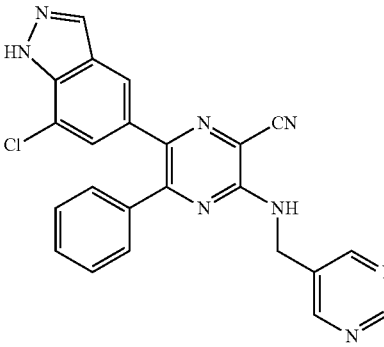 |

TABLE 2-continued
| Compound No. | Structure |
|---|---|
| 2.641 | 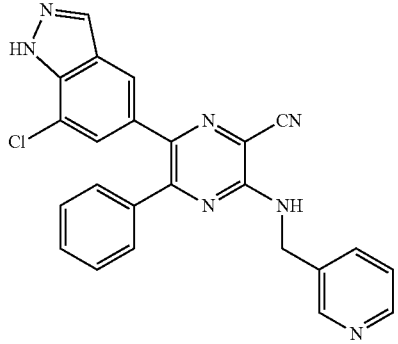 [SMILES: N#Cc1nc(-c2cc(Cl)c3[nH]ncc3c2)c(-c2ccccc2)nc1NCc1cccnc1] |
| 2.642 | 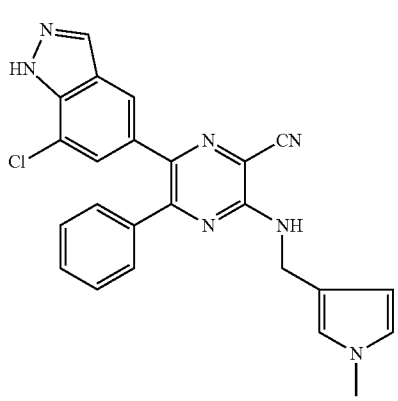 |
| 2.643 | 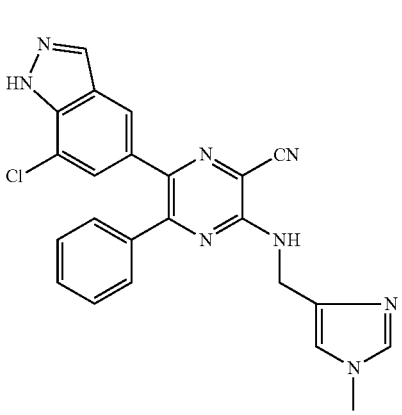 [SMILES: Cn1cnc(CNc2nc(-c3ccccc3)c(-c3cc(Cl)c4[nH]ncc4c3)nc2C#N)c1] |
| 2.644 | 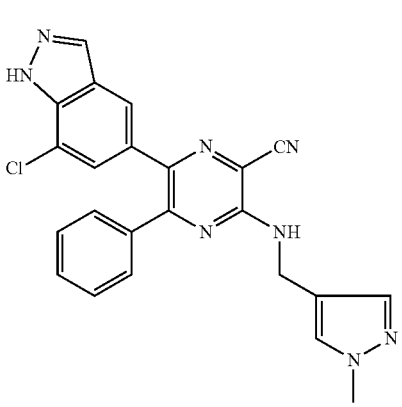 |

TABLE 2-continued
| Compound No. | Structure |
|---|---|
| 2.645 | 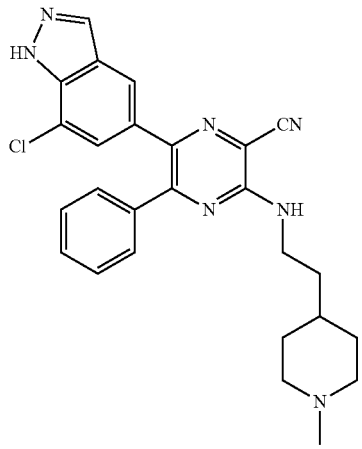 [SMILES: CN1CCC(CCNc2nc(-c3ccccc3)c(-c3cc(Cl)c4[nH]ncc4c3)nc2C#N)CC1] |
| 2.646 | 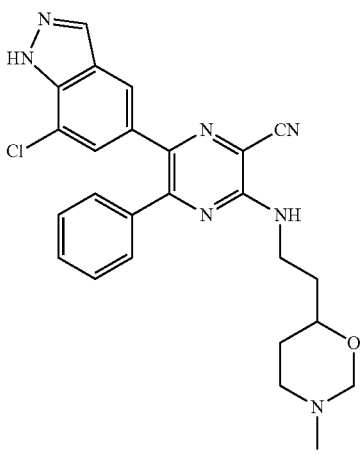 [SMILES: CN1CCC(CCNc2nc(-c3ccccc3)c(-c3cc(Cl)c4[nH]ncc4c3)nc2C#N)OC1] |
| 2.647 | 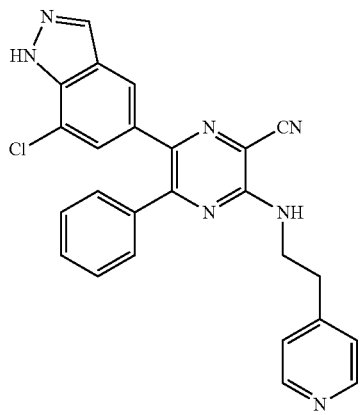 [SMILES: N#Cc1nc(-c2cc(Cl)c3[nH]ncc3c2)c(-c2ccccc2)nc1NCCc1ccncc1] |

TABLE 2-continued

| Compound No. | Structure |
|---|---|
| 2.648 | 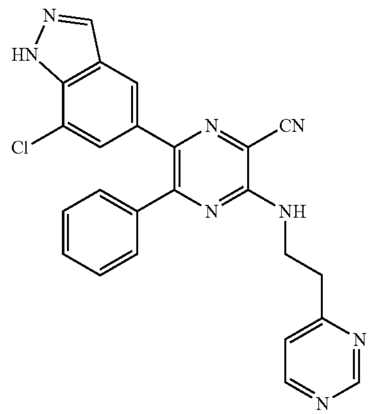 [SMILES: N#Cc1nc(-c2cc(Cl)c3[nH]ncc3c2)c(-c2ccccc2)nc1NCCc1ccncn1] |
| 2.649 | 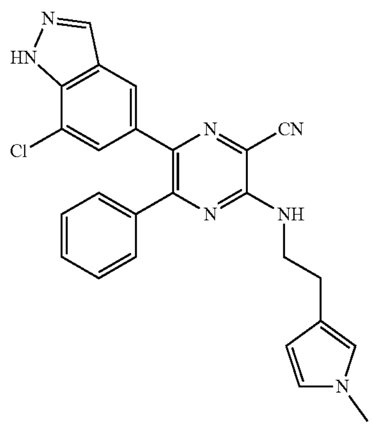 [SMILES: Cn1ccc(CCNc2nc(-c3ccccc3)c(-c3cc(Cl)c4[nH]ncc4c3)nc2C#N)c1] |
| 2.650 | 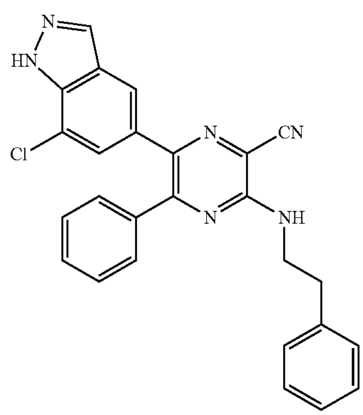 [SMILES: N#Cc1nc(-c2cc(Cl)c3[nH]ncc3c2)c(-c2ccccc2)nc1NCCc1ccccc1] |
| 2.651 | 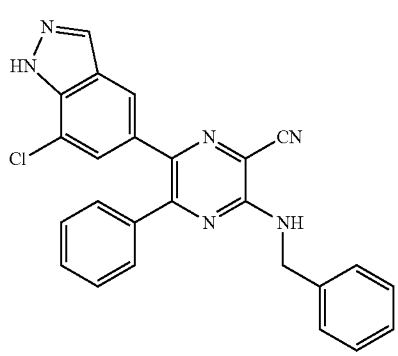 [SMILES: N#Cc1nc(-c2cc(Cl)c3[nH]ncc3c2)c(-c2ccccc2)nc1NCc1ccccc1] |

TABLE 2-continued
| Compound No. | Structure |
| --- | --- |
| 2.652 | 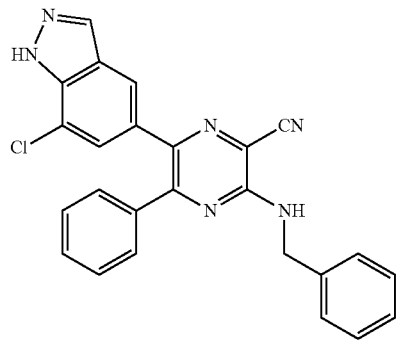 [SMILES: N#Cc1nc(-c2cc(Cl)c3[nH]ncc3c2)c(-c2ccccc2)nc1NCc1ccccc1] |
| 2.653 | 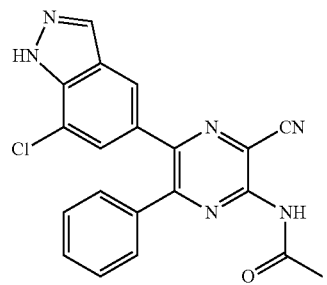 [SMILES: CC(=O)Nc1nc(-c2ccccc2)c(-c2cc(Cl)c3[nH]ncc3c2)nc1C#N] |
| 2.654 | 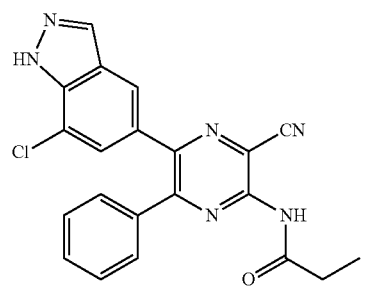 |
| 2.655 | 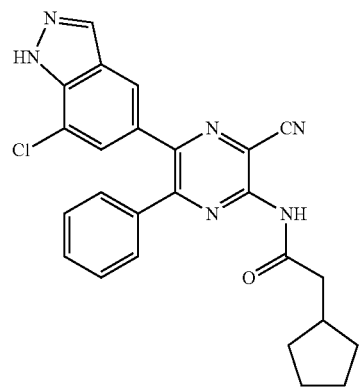 |

TABLE 2-continued

| Compound No. | Structure |
|---|---|
| 2.656 | 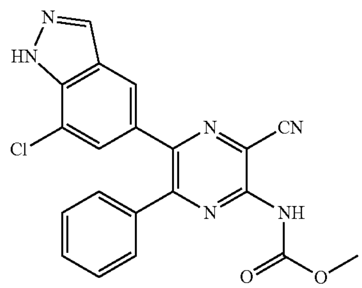 [SMILES: CCC(=O)Nc1nc(-c2ccccc2)c(-c2cc(Cl)c3[nH]ncc3c2)nc1C#N] |
| 2.657 | 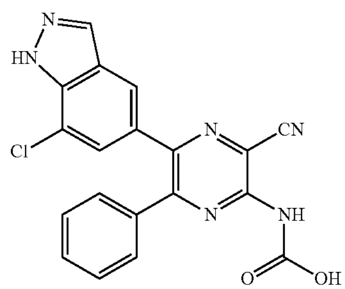 [SMILES: N#Cc1nc(-c2cc(Cl)c3[nH]ncc3c2)c(-c2ccccc2)nc1NC(=O)O] |
| 2.658 | 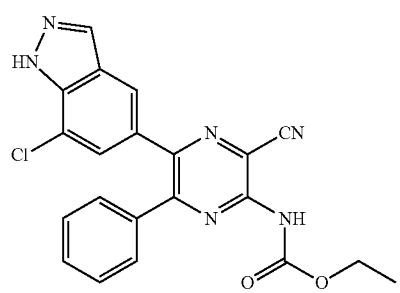 [SMILES: CCOC(=O)Nc1nc(-c2ccccc2)c(-c2cc(Cl)c3[nH]ncc3c2)nc1C#N] |
| 2.659 | 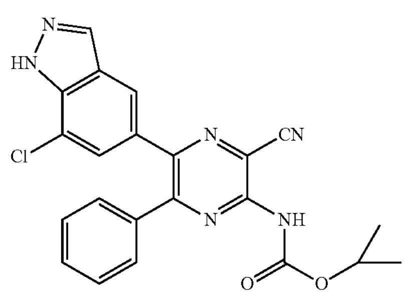 [SMILES: CC(C)OC(=O)Nc1nc(-c2ccccc2)c(-c2cc(Cl)c3[nH]ncc3c2)nc1C#N] |
| 2.660 | 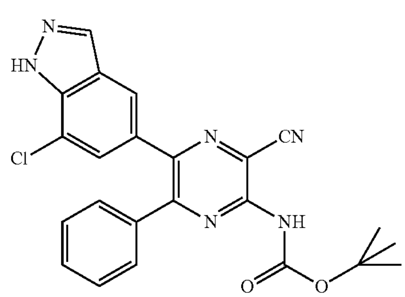 |

TABLE 2-continued
| Compound No. | Structure |
|---|---|
| 2.661 | 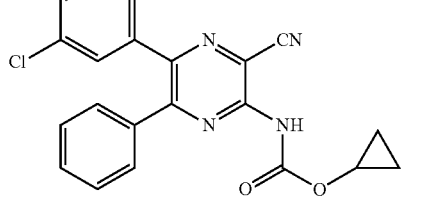 |
| 2.662 | 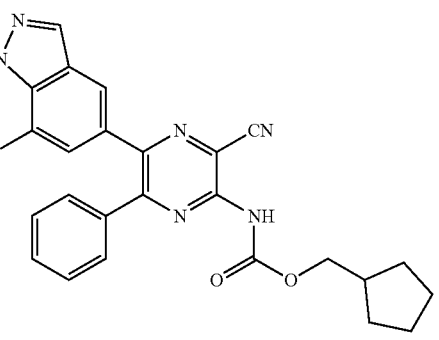 |
| 2.663 | 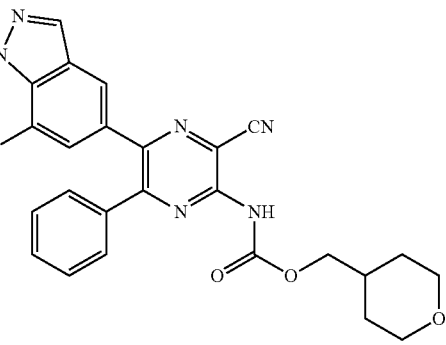 |
| 2.664 | 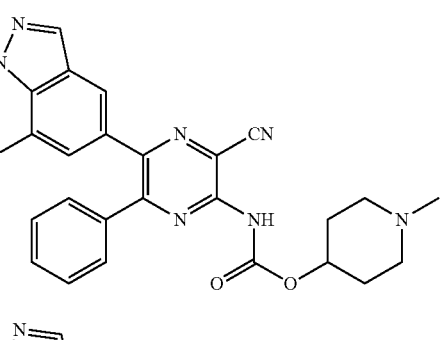 |
| 2.665 | 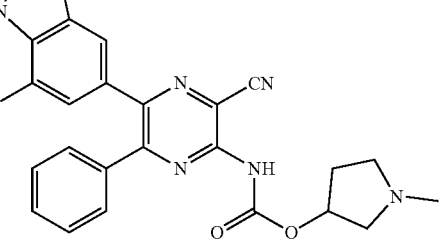 |

TABLE 2-continued

| Compound No. | Structure |
|---|---|
| 2.666 | (structure) |
| 2.667 | (structure) |
| 2.668 | (structure) |
| 2.669 | (structure) |
| 2.670 | (structure) |

TABLE 2-continued

| Compound No. | Structure |
|---|---|
| 2.671 | 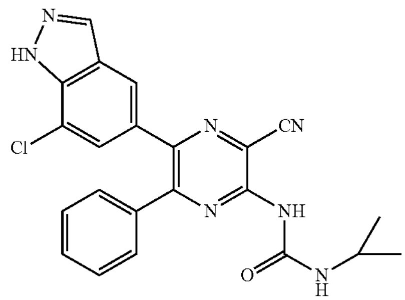 |
| 2.672 | 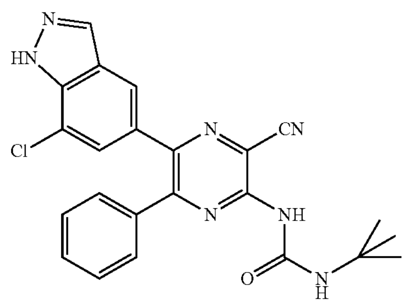 [SMILES: CC(C)(C)NC(=O)Nc1nc(-c2ccccc2)c(-c2cc(Cl)c3[nH]ncc3c2)nc1C#N] |
| 2.673 | 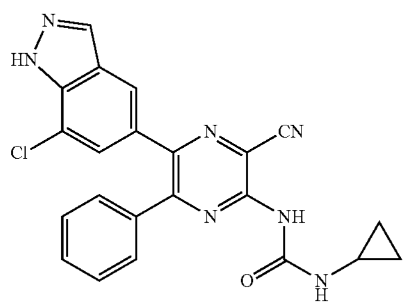 [SMILES: N#Cc1nc(-c2cc(Cl)c3[nH]ncc3c2)c(-c2ccccc2)nc1NC(=O)NC1CC1] |
| 2.674 | 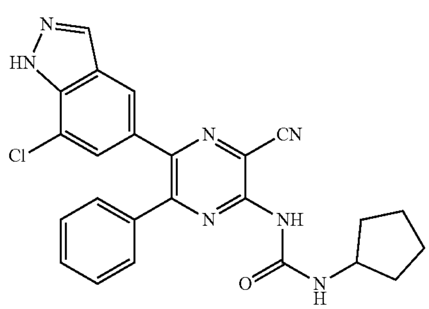 [SMILES: N#Cc1nc(-c2cc(Cl)c3[nH]ncc3c2)c(-c2ccccc2)nc1NC(=O)NC1CCCC1] |
| 2.675 | 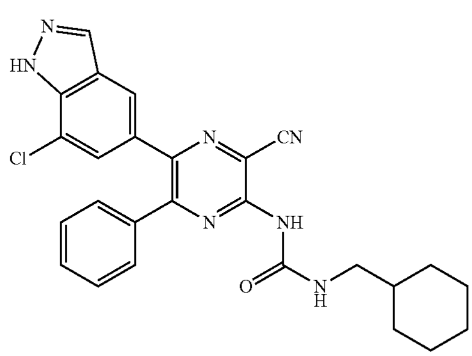 [SMILES: N#Cc1nc(-c2cc(Cl)c3[nH]ncc3c2)c(-c2ccccc2)nc1NC(=O)NCC1CCCCC1] |

TABLE 2-continued

| Compound No. | Structure |
|---|---|
| 2.676 | (7-chloro-1H-indazol-5-yl), phenyl, CN-pyrazine with NH-C(O)-NH-CH2-(1-methylazetidin-3-yl) substituent |
| 2.677 | (7-chloro-1H-indazol-5-yl), phenyl, CN-pyrazine with NH-C(O)-NH-(1-methylpiperidin-4-yl) substituent |
| 2.678 | (7-chloro-1H-indazol-5-yl), phenyl, CN-pyrazine with NH-C(O)-NH-benzyl substituent |
| 2.679 | (7-chloro-1H-indazol-5-yl), phenyl, CN-pyrazine with NH-C(O)-NH-CH2-(pyridin-3-yl) substituent |
| 2.680 | (7-chloro-1H-indazol-5-yl), phenyl, CN-pyrazine with NH-C(O)-NH-CH2-(2-methylpyrimidin-5-yl) substituent |

TABLE 2-continued
| Compound No. | Structure |
|---|---|
| 2.681 | 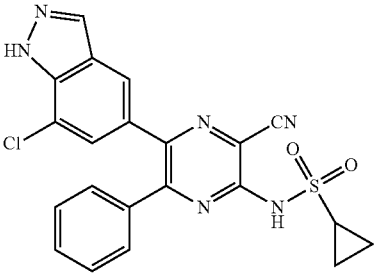 [SMILES: N#Cc1nc(-c2cc(Cl)c3[nH]ncc3c2)c(-c2ccccc2)nc1NS(=O)(=O)C1CC1] |
| 2.682 | 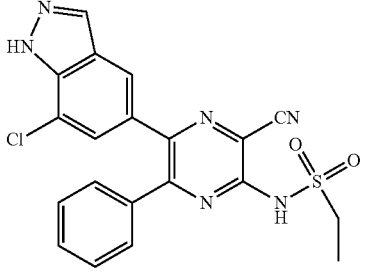 [SMILES: CCS(=O)(=O)Nc1nc(-c2ccccc2)c(-c2cc(Cl)c3[nH]ncc3c2)nc1C#N] |
| 2.683 | 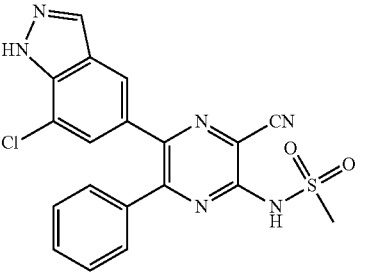 |
| 2.684 | 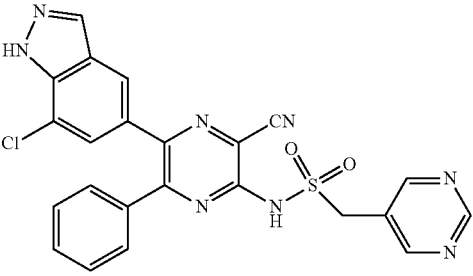 [SMILES: N#Cc1nc(-c2cc(Cl)c3[nH]ncc3c2)c(-c2ccccc2)nc1NS(=O)(=O)Cc1cncnc1] |
| 2.685 | 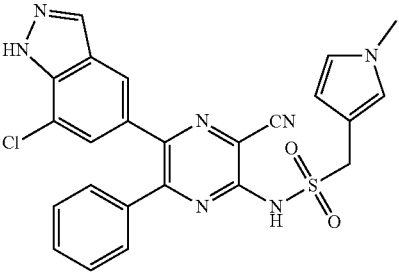 [SMILES: Cn1ccc(CS(=O)(=O)Nc2nc(-c3ccccc3)c(-c3cc(Cl)c4[nH]ncc4c3)nc2C#N)c1] |

TABLE 2-continued
| Compound No. | Structure |
|---|---|
| 2.686 | 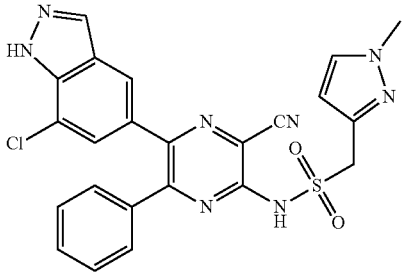 [SMILES: Cn1ccc(CS(=O)(=O)Nc2nc(-c3ccccc3)c(-c3cc(Cl)c4[nH]ncc4c3)nc2C#N)n1] |
| 2.687 | 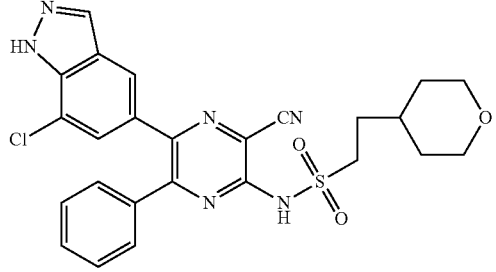 |
| 2.688 | 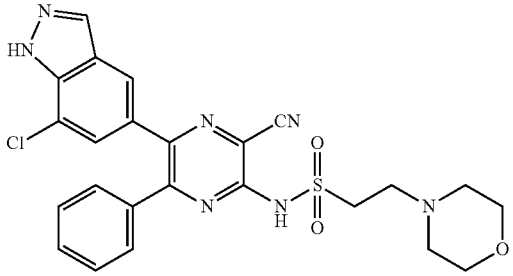 [SMILES: N#Cc1nc(-c2cc(Cl)c3[nH]ncc3c2)c(-c2ccccc2)nc1NS(=O)(=O)CCN1CCOCC1] |
| 2.689 | 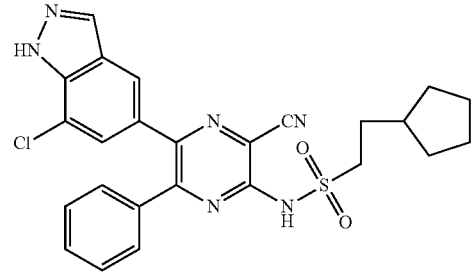 [SMILES: N#Cc1nc(-c2cc(Cl)c3[nH]ncc3c2)c(-c2ccccc2)nc1NS(=O)(=O)CCC1CCCC1] |
| 2.690 | 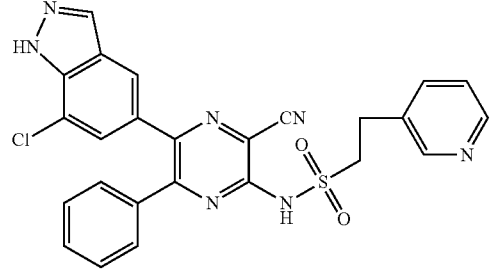 [SMILES: N#Cc1nc(-c2cc(Cl)c3[nH]ncc3c2)c(-c2ccccc2)nc1NS(=O)(=O)CCc1cccnc1] |

TABLE 2-continued

| Compound No. | Structure |
|---|---|
| 2.691 | 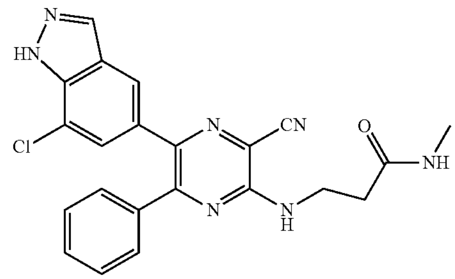 [SMILES: CNC(=O)CCNc1nc(-c2ccccc2)c(-c2cc(Cl)c3[nH]ncc3c2)nc1C#N] |
| 2.692 | 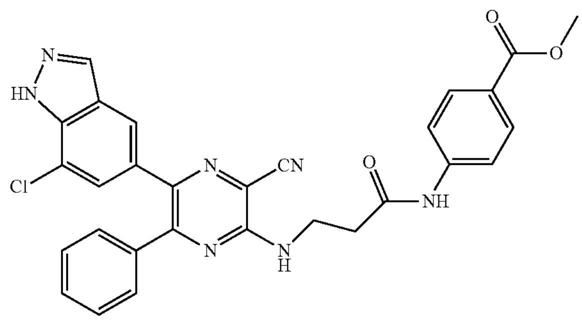 [SMILES: COC(=O)c1ccc(NC(=O)CCNc2nc(-c3ccccc3)c(-c3cc(Cl)c4[nH]ncc4c3)nc2C#N)cc1] |
| 2.693 | 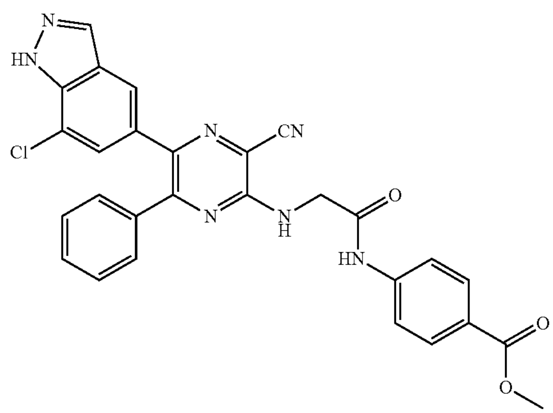 [SMILES: COC(=O)c1ccc(NC(=O)CNc2nc(-c3ccccc3)c(-c3cc(Cl)c4[nH]ncc4c3)nc2C#N)cc1] |
| 2.694 | 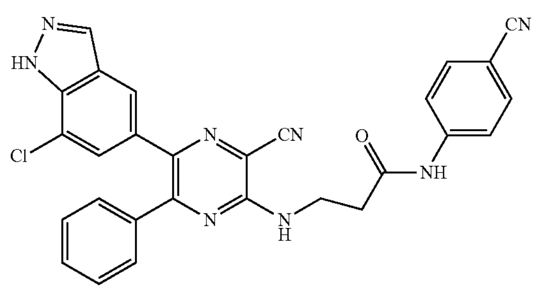 |
| 2.695 | 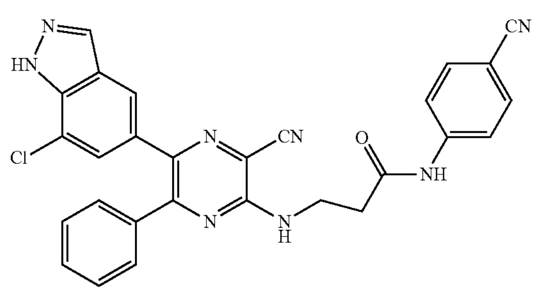 [SMILES: N#Cc1ccc(NC(=O)CCNc2nc(-c3ccccc3)c(-c3cc(Cl)c4[nH]ncc4c3)nc2C#N)cc1] |

TABLE 2-continued

| Compound No. | Structure |
|---|---|
| 2.696 | (7-chloro-1H-indazol-5-yl / phenyl / pyrazine-CN / NH-(CH₂)₃-NH-(6-cyanopyridin-3-yl)) |
| 2.697 | (7-chloro-1H-indazol-5-yl / phenyl / pyrazine-CN / NH-(CH₂)₃-NH-cyclopropyl) |
| 2.698 | (7-chloro-1H-indazol-5-yl / 1-methyl-1H-pyrazol-3-yl / pyrazine-CN / NH-ethyl) |
| 2.699 | (7-chloro-1H-indazol-5-yl / 1-methyl-1H-pyrazol-3-yl / pyrazine-CN / NH-isopropyl) |
| 2.700 | (7-chloro-1H-indazol-5-yl / 1-methyl-1H-pyrazol-3-yl / pyrazine-CN / NH-tert-butyl) |

TABLE 2-continued

| Compound No. | Structure |
|---|---|
| 2.701 | 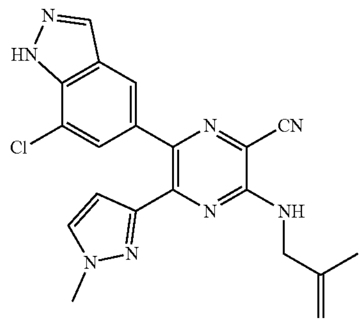 [SMILES: C=C(C)CNc1nc(-c2ccn(C)n2)c(-c2cc(Cl)c3[nH]ncc3c2)nc1C#N] |
| 2.702 | 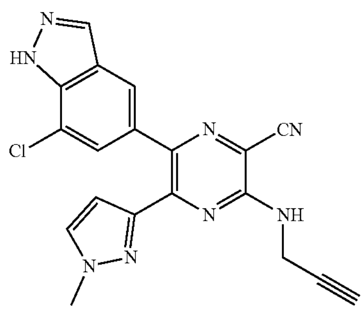 [SMILES: C#CCNc1nc(-c2ccn(C)n2)c(-c2cc(Cl)c3[nH]ncc3c2)nc1C#N] |
| 2.703 | 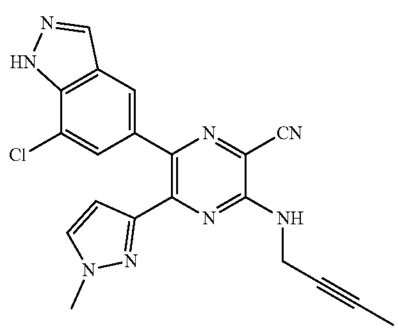 [SMILES: CC#CCNc1nc(-c2ccn(C)n2)c(-c2cc(Cl)c3[nH]ncc3c2)nc1C#N] |
| 2.704 | 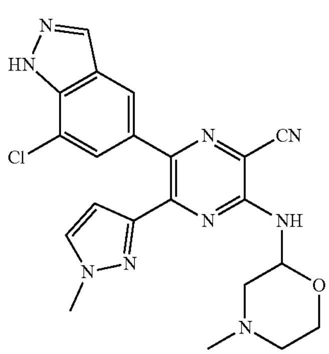 [SMILES: CN1CCOC(Nc2nc(-c3ccn(C)n3)c(-c3cc(Cl)c4[nH]ncc4c3)nc2C#N)C1] |

TABLE 2-continued

| Compound No. | Structure |
|---|---|
| 2.705 | 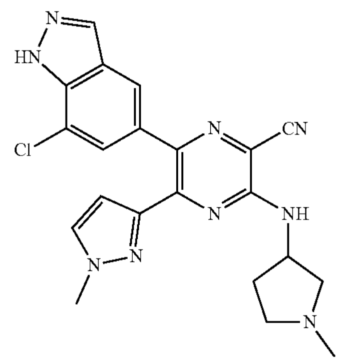 [SMILES: CN1CCC(Nc2nc(-c3ccn(C)n3)c(-c3cc(Cl)c4[nH]ncc4c3)nc2C#N)C1] |
| 2.706 | 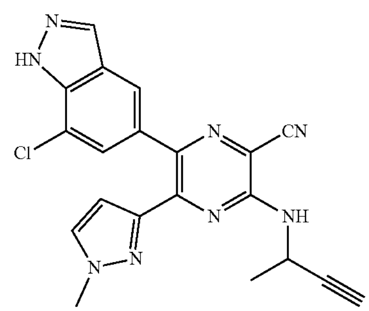 [SMILES: C#CC(C)Nc1nc(-c2ccn(C)n2)c(-c2cc(Cl)c3[nH]ncc3c2)nc1C#N] |
| 2.707 | 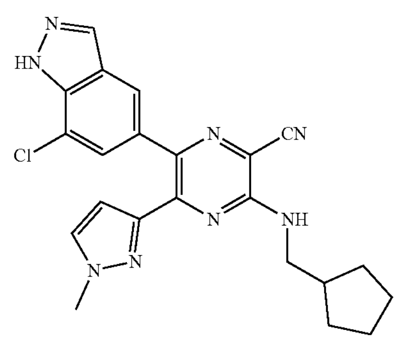 [SMILES: Cn1ccc(-c2nc(NCC3CCCC3)c(C#N)nc2-c2cc(Cl)c3[nH]ncc3c2)n1] |
| 2.708 | 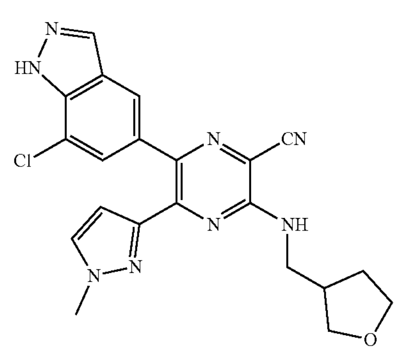 [SMILES: Cn1ccc(-c2nc(NCC3CCOC3)c(C#N)nc2-c2cc(Cl)c3[nH]ncc3c2)n1] |

TABLE 2-continued
| Compound No. | Structure |
|---|---|
| 2.709 | 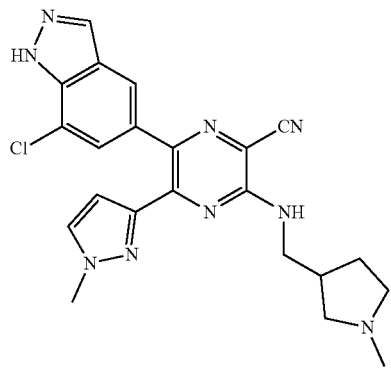 [SMILES: CN1CCC(CNc2nc(-c3ccn(C)n3)c(-c3cc(Cl)c4[nH]ncc4c3)nc2C#N)C1] |
| 2.710 | 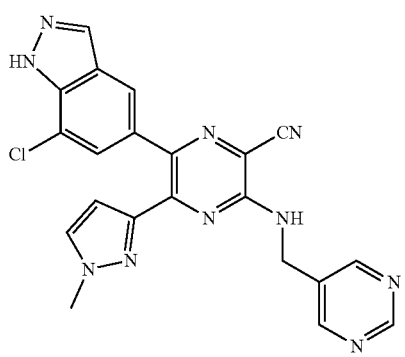 [SMILES: Cn1ccc(-c2nc(NCc3cncnc3)c(C#N)nc2-c2cc(Cl)c3[nH]ncc3c2)n1] |
| 2.711 | 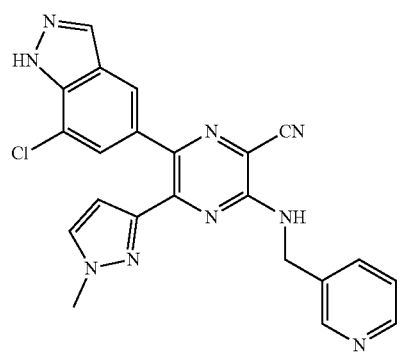 [SMILES: Cn1ccc(-c2nc(NCc3cccnc3)c(C#N)nc2-c2cc(Cl)c3[nH]ncc3c2)n1] |
| 2.712 | 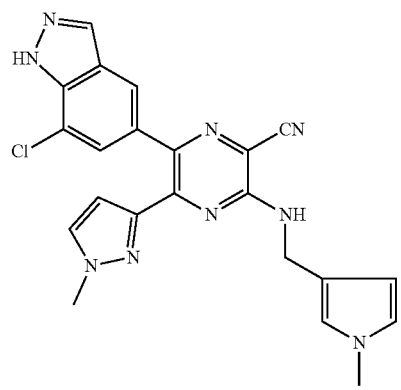 [SMILES: Cn1ccc(CNc2nc(-c3ccn(C)n3)c(-c3cc(Cl)c4[nH]ncc4c3)nc2C#N)c1] |

TABLE 2-continued
| Compound No. | Structure |
|---|---|
| 2.713 | 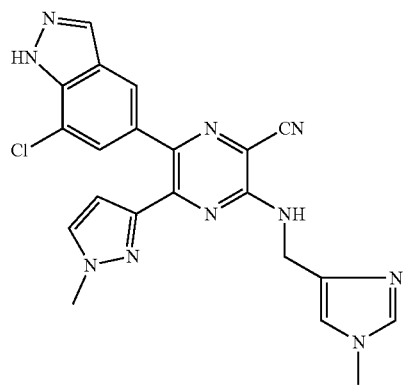 [SMILES: Cn1cnc(CNc2nc(-c3ccn(C)n3)c(-c3cc(Cl)c4[nH]ncc4c3)nc2C#N)c1] |
| 2.714 | 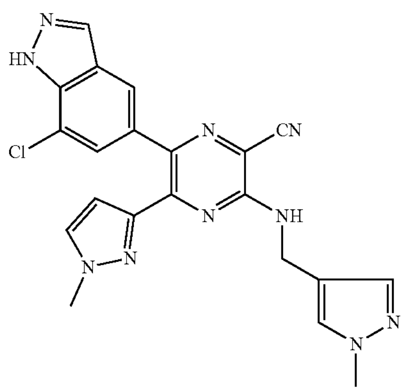 [SMILES: Cn1cc(CNc2nc(-c3ccn(C)n3)c(-c3cc(Cl)c4[nH]ncc4c3)nc2C#N)cn1] |
| 2.715 | 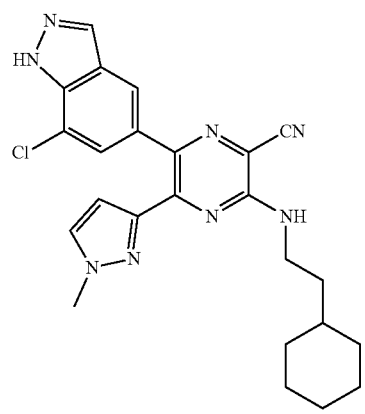 [SMILES: Cn1ccc(-c2nc(NCCC3CCCCC3)c(C#N)nc2-c2cc(Cl)c3[nH]ncc3c2)n1] |

TABLE 2-continued

| Compound No. | Structure |
|---|---|
| 2.716 | 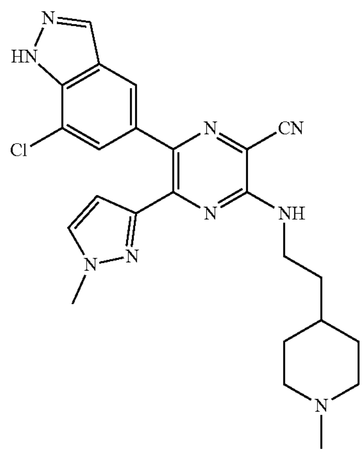 [SMILES: CN1CCC(CCNc2nc(-c3ccn(C)n3)c(-c3cc(Cl)c4[nH]ncc4c3)nc2C#N)CC1] |
| 2.717 | 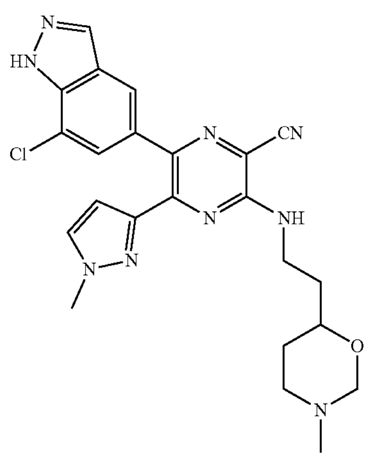 [SMILES: CN1CCC(CCNc2nc(-c3ccn(C)n3)c(-c3cc(Cl)c4[nH]ncc4c3)nc2C#N)OC1] |
| 2.718 | 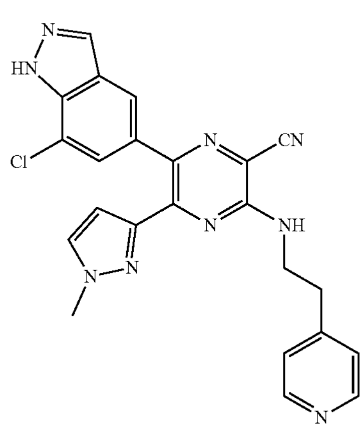 [SMILES: Cn1ccc(-c2nc(NCCc3ccncc3)c(C#N)nc2-c2cc(Cl)c3[nH]ncc3c2)n1] |

TABLE 2-continued

| Compound No. | Structure |
|---|---|
| 2.719 | 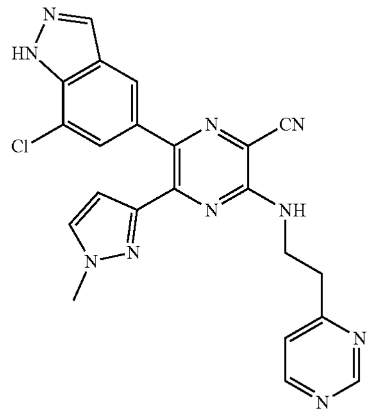 [SMILES: Cn1ccc(-c2nc(NCCc3ccncn3)c(C#N)nc2-c2cc(Cl)c3[nH]ncc3c2)n1] |
| 2.720 | 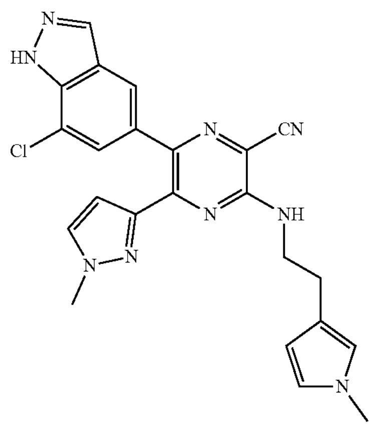 [SMILES: Cn1ccc(CCNc2nc(-c3ccn(C)n3)c(-c3cc(Cl)c4[nH]ncc4c3)nc2C#N)c1] |
| 2.721 | 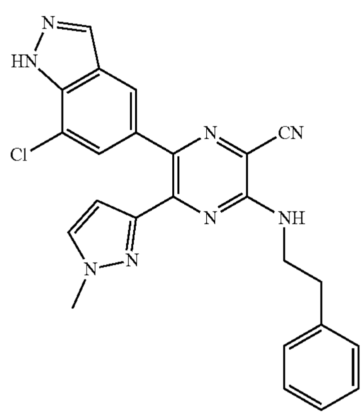 [SMILES: Cn1ccc(-c2nc(NCCc3ccccc3)c(C#N)nc2-c2cc(Cl)c3[nH]ncc3c2)n1] |
| 2.722 | 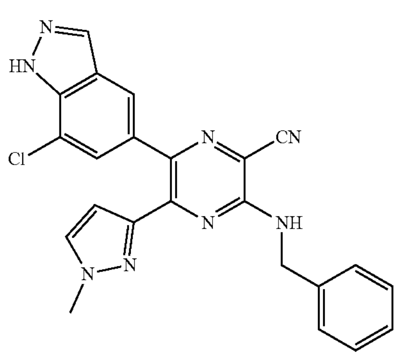 [SMILES: Cn1ccc(-c2nc(NCc3ccccc3)c(C#N)nc2-c2cc(Cl)c3[nH]ncc3c2)n1] |

TABLE 2-continued

| Compound No. | Structure |
|---|---|
| 2.723 | 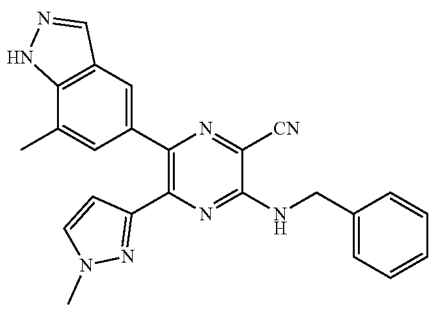 [SMILES: Cc1cc(-c2nc(C#N)c(NCc3ccccc3)nc2-c2ccn(C)n2)cc2cn[nH]c12] |
| 2.724 | 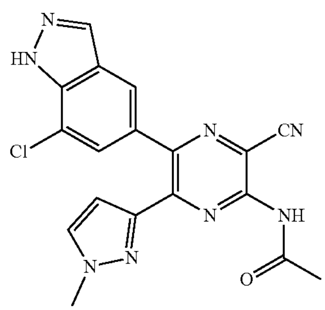 [SMILES: CC(=O)Nc1nc(-c2ccn(C)n2)c(-c2cc(Cl)c3[nH]ncc3c2)nc1C#N] |
| 2.725 | 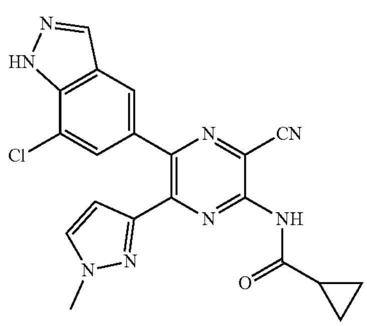 [SMILES: Cn1ccc(-c2nc(NC(=O)C3CC3)c(C#N)nc2-c2cc(Cl)c3[nH]ncc3c2)n1] |
| 2.726 | 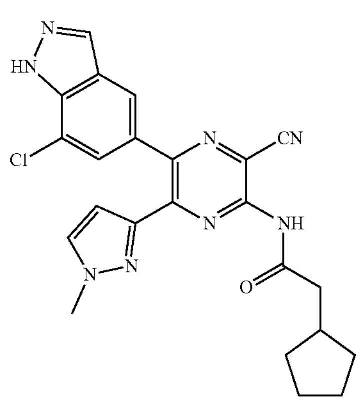 [SMILES: Cn1ccc(-c2nc(NC(=O)CC3CCCC3)c(C#N)nc2-c2cc(Cl)c3[nH]ncc3c2)n1] |

TABLE 2-continued

| Compound No. | Structure |
|---|---|
| 2.727 | 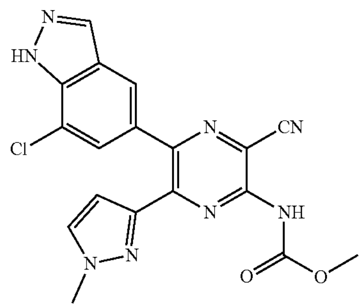 [SMILES: COC(=O)Nc1nc(-c2ccn(C)n2)c(-c2cc(Cl)c3[nH]ncc3c2)nc1C#N] |
| 2.728 | 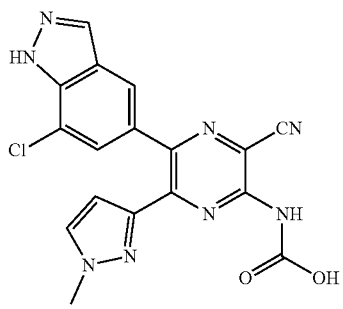 [SMILES: Cn1ccc(-c2nc(NC(=O)O)c(C#N)nc2-c2cc(Cl)c3[nH]ncc3c2)n1] |
| 2.729 | 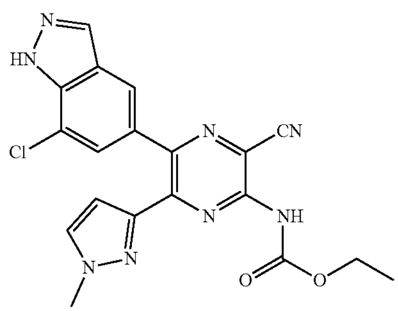 [SMILES: CCOC(=O)Nc1nc(-c2ccn(C)n2)c(-c2cc(Cl)c3[nH]ncc3c2)nc1C#N] |
| 2.730 | 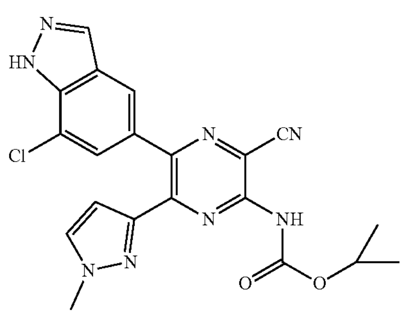 [SMILES: CC(C)OC(=O)Nc1nc(-c2ccn(C)n2)c(-c2cc(Cl)c3[nH]ncc3c2)nc1C#N] |
| 2.731 | 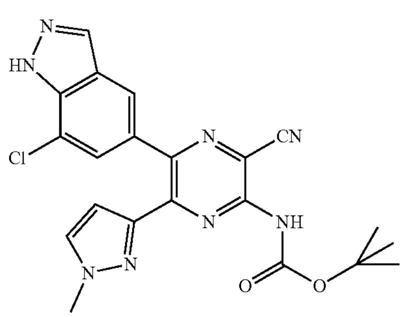 [SMILES: Cn1ccc(-c2nc(NC(=O)OC(C)(C)C)c(C#N)nc2-c2cc(Cl)c3[nH]ncc3c2)n1] |

TABLE 2-continued

| Compound No. | Structure |
|---|---|
| 2.732 | 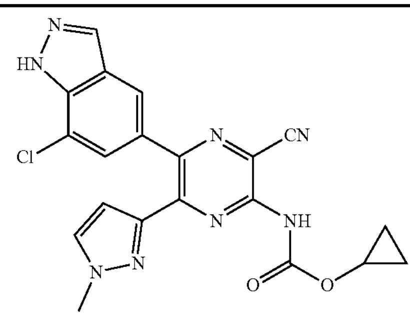 |
| 2.733 | 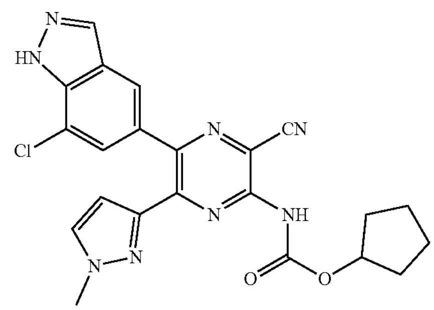 [SMILES: Cn1ccc(-c2nc(NC(=O)OC3CCCC3)c(C#N)nc2-c2cc(Cl)c3[nH]ncc3c2)n1] |
| 2.734 | 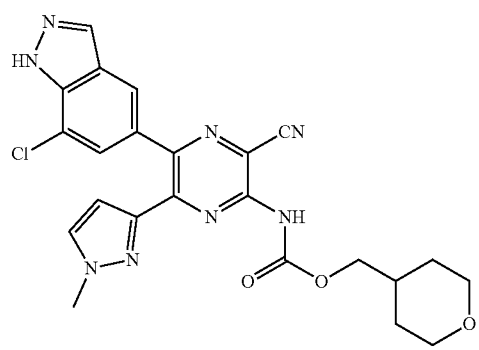 [SMILES: Cn1ccc(-c2nc(NC(=O)OCC3CCOCC3)c(C#N)nc2-c2cc(Cl)c3[nH]ncc3c2)n1] |
| 2.735 | 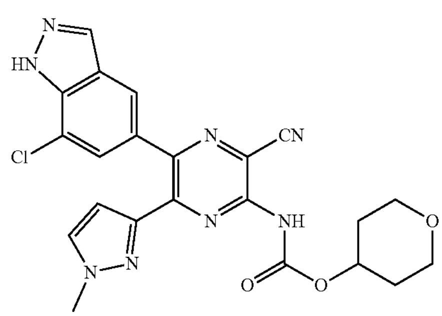 [SMILES: Cn1ccc(-c2nc(NC(=O)OC3CCOCC3)c(C#N)nc2-c2cc(Cl)c3[nH]ncc3c2)n1] |
| 2.736 | 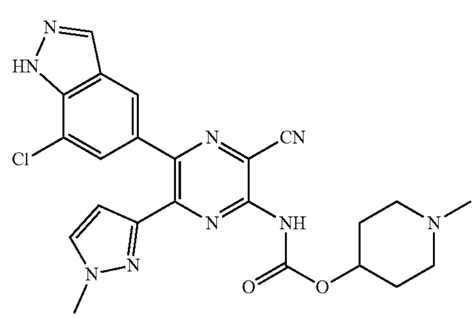 [SMILES: CN1CCC(OC(=O)Nc2nc(-c3ccn(C)n3)c(-c3cc(Cl)c4[nH]ncc4c3)nc2C#N)CC1] |

TABLE 2-continued

| Compound No. | Structure |
|---|---|
| 2.737 | (structure) |
| 2.738 | (structure) |
| 2.739 | (structure) |
| 2.740 | (structure) |
| 2.741 | (structure) |

TABLE 2-continued

| Compound No. | Structure |
|---|---|
| 2.742 | (structure: 7-chloro-1H-indazol-5-yl and 1-methylpyrazol-3-yl substituted cyanopyrazine with isopropyl urea) |
| 2.743 | (structure: 7-chloro-1H-indazol-5-yl and 1-methylpyrazol-3-yl substituted cyanopyrazine with tert-butyl urea) |
| 2.744 | (structure: 7-chloro-1H-indazol-5-yl and 1-methylpyrazol-3-yl substituted cyanopyrazine with cyclopropyl urea) |
| 2.745 | (structure: 7-chloro-1H-indazol-5-yl and 1-methylpyrazol-3-yl substituted cyanopyrazine with cyclopentyl urea) |
| 2.746 | (structure: 7-chloro-1H-indazol-5-yl and 1-methylpyrazol-3-yl substituted cyanopyrazine with cyclohexylmethyl urea) |

TABLE 2-continued

| Compound No. | Structure |
|---|---|
| 2.747 | 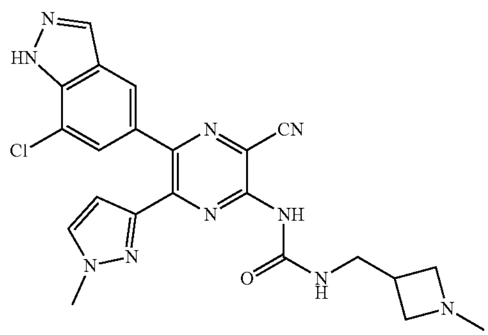 [SMILES: CN1CC(CNC(=O)Nc2nc(-c3ccn(C)n3)c(-c3cc(Cl)c4[nH]ncc4c3)nc2C#N)C1] |
| 2.748 | 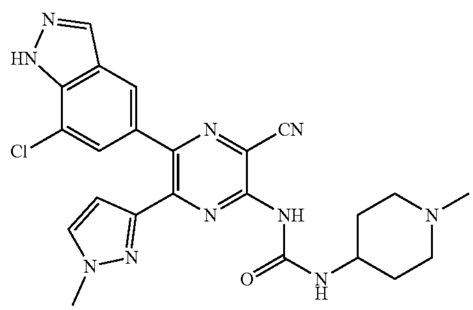 [SMILES: CN1CCC(NC(=O)Nc2nc(-c3ccn(C)n3)c(-c3cc(Cl)c4[nH]ncc4c3)nc2C#N)CC1] |
| 2.749 | 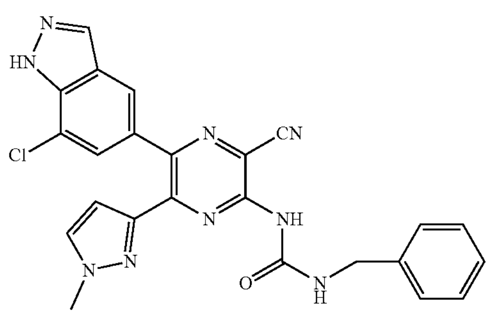 |
| 2.750 | 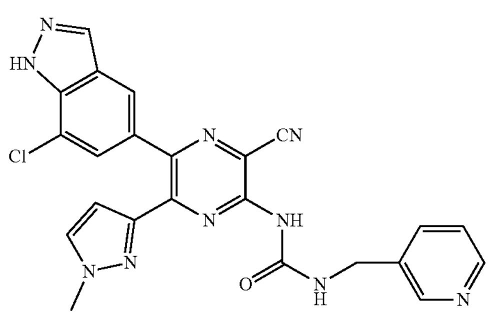 [SMILES: Cn1ccc(-c2nc(NC(=O)NCc3cccnc3)c(C#N)nc2-c2cc(Cl)c3[nH]ncc3c2)n1] |
| 2.751 | 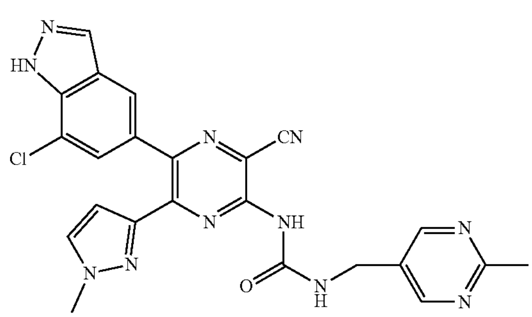 [SMILES: Cc1ncc(CNC(=O)Nc2nc(-c3ccn(C)n3)c(-c3cc(Cl)c4[nH]ncc4c3)nc2C#N)cn1] |

TABLE 2-continued
| Compound No. | Structure |
|---|---|
| 2.752 | 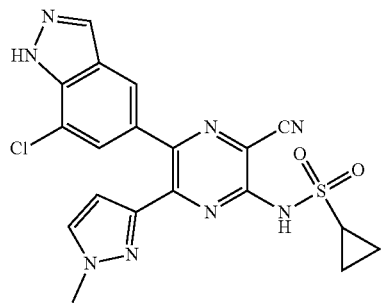 [SMILES: Cn1ccc(-c2nc(NS(=O)(=O)C3CC3)c(C#N)nc2-c2cc(Cl)c3[nH]ncc3c2)n1] |
| 2.753 | 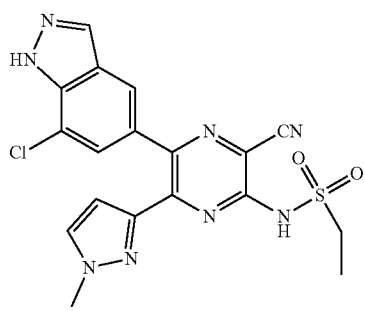 [SMILES: CCS(=O)(=O)Nc1nc(-c2ccn(C)n2)c(-c2cc(Cl)c3[nH]ncc3c2)nc1C#N] |
| 2.754 | 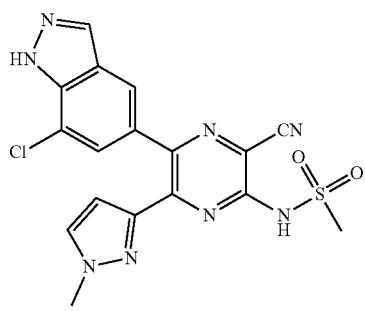 [SMILES: Cn1ccc(-c2nc(NS(C)(=O)=O)c(C#N)nc2-c2cc(Cl)c3[nH]ncc3c2)n1] |
| 2.755 | 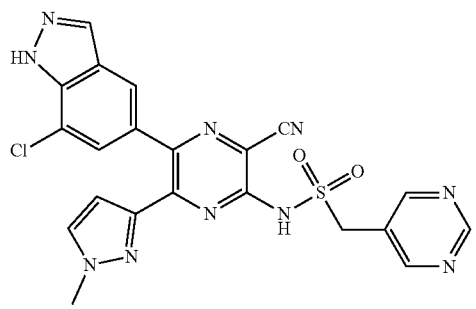 [SMILES: Cn1ccc(-c2nc(NS(=O)(=O)Cc3cncnc3)c(C#N)nc2-c2cc(Cl)c3[nH]ncc3c2)n1] |
| 2.756 | 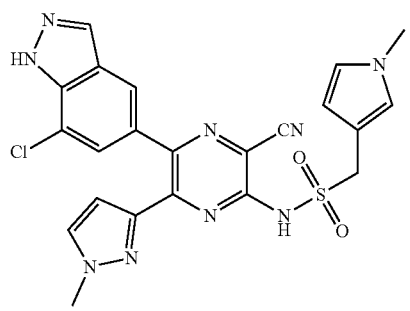 [SMILES: Cn1ccc(CS(=O)(=O)Nc2nc(-c3ccn(C)n3)c(-c3cc(Cl)c4[nH]ncc4c3)nc2C#N)c1] |

TABLE 2-continued
| Compound No. | Structure |
|---|---|
| 2.757 | 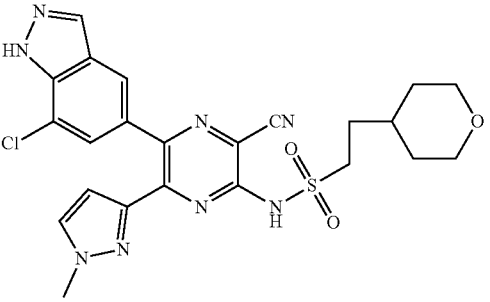 [SMILES: Cn1ccc(-c2nc(NS(=O)(=O)CCC3CCOCC3)c(C#N)nc2-c2cc(Cl)c3[nH]ncc3c2)n1] |
| 2.758 | 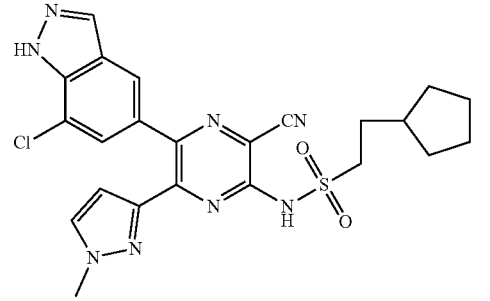 [SMILES: Cn1ccc(-c2nc(NS(=O)(=O)CCC3CCCC3)c(C#N)nc2-c2cc(Cl)c3[nH]ncc3c2)n1] |
| 2.759 | 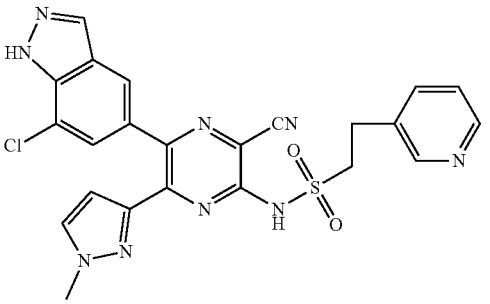 [SMILES: Cn1ccc(-c2nc(NS(=O)(=O)CCc3cccnc3)c(C#N)nc2-c2cc(Cl)c3[nH]ncc3c2)n1] |
| 2.760 | 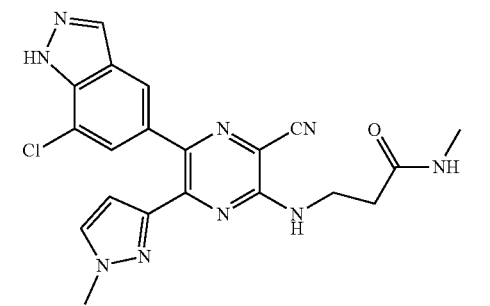 [SMILES: CNC(=O)CCNc1nc(-c2ccn(C)n2)c(-c2cc(Cl)c3[nH]ncc3c2)nc1C#N] |
| 2.761 | 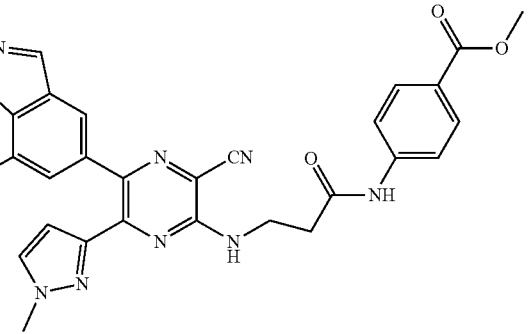 |

TABLE 2-continued
| Compound No. | Structure |
|---|---|
| 2.762 | 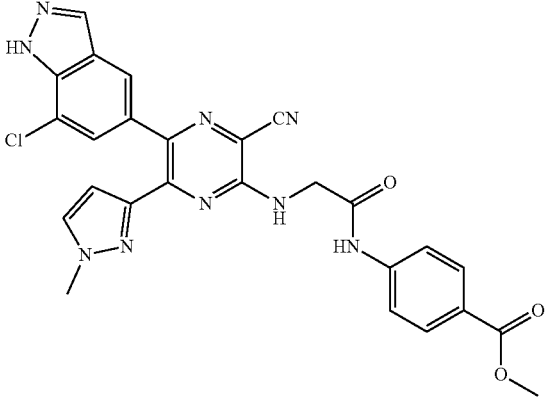 [SMILES: COC(=O)c1ccc(NC(=O)CNc2nc(-c3ccn(C)n3)c(-c3cc(Cl)c4[nH]ncc4c3)nc2C#N)cc1] |
| 2.763 | 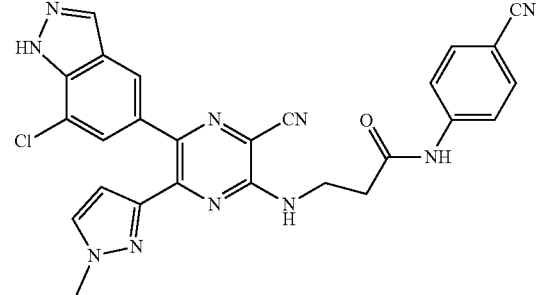 [SMILES: Cn1ccc(-c2nc(NCCC(=O)Nc3ccc(C#N)cc3)c(C#N)nc2-c2cc(Cl)c3[nH]ncc3c2)n1] |
| 2.764 | 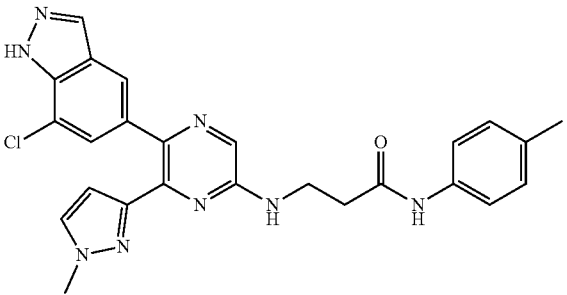 [SMILES: Cc1ccc(NC(=O)CCNc2cnc(-c3cc(Cl)c4[nH]ncc4c3)c(-c3ccn(C)n3)n2)cc1] |
| 2.765 | 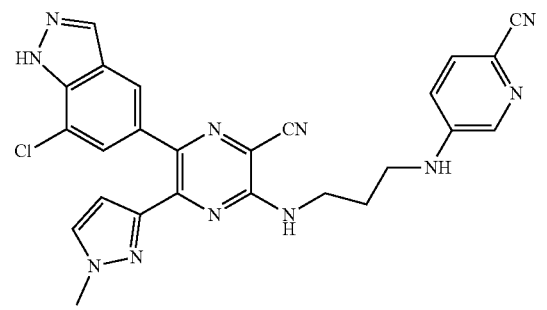 [SMILES: Cn1ccc(-c2nc(NCCCNc3ccc(C#N)nc3)c(C#N)nc2-c2cc(Cl)c3[nH]ncc3c2)n1] |

TABLE 2-continued

| Compound No. | Structure |
| --- | --- |
| 2.766 | 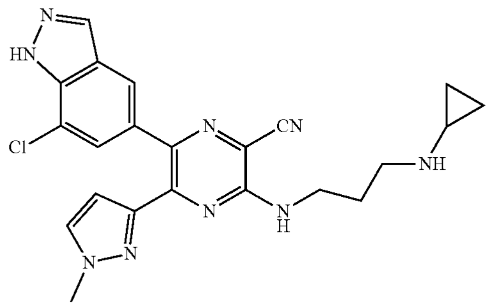 [SMILES: Cn1ccc(-c2nc(NCCCNC3CC3)c(C#N)nc2-c2cc(Cl)c3[nH]ncc3c2)n1] |
| 2.767 | 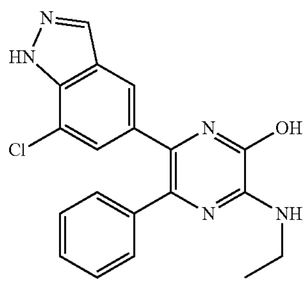 [SMILES: CCNc1nc(-c2ccccc2)c(-c2cc(Cl)c3[nH]ncc3c2)nc1O] |
| 2.768 | 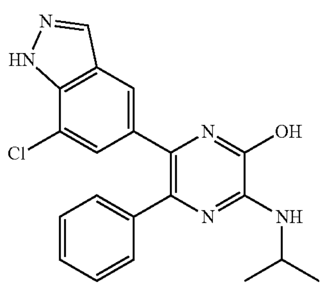 |
| 2.769 | 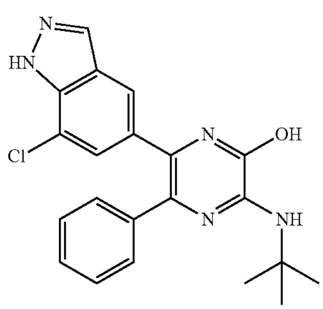 [SMILES: CC(C)(C)Nc1nc(-c2ccccc2)c(-c2cc(Cl)c3[nH]ncc3c2)nc1O] |
| 2.770 | 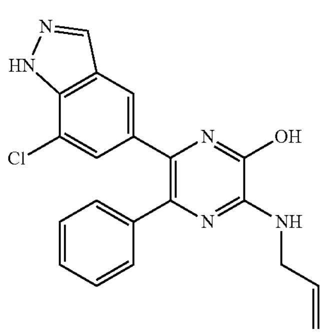 [SMILES: C=CCNc1nc(-c2ccccc2)c(-c2cc(Cl)c3[nH]ncc3c2)nc1O] |

TABLE 2-continued

| Compound No. | Structure |
|---|---|
| 2.771 | (7-chloro-1H-indazol-5-yl, phenyl, OH, NH-CH2-C≡CH substituted pyrazine) |
| 2.772 | (7-chloro-1H-indazol-5-yl, phenyl, OH, NH-CH2-C≡C-CH3 substituted pyrazine) |
| 2.773 | (7-chloro-1H-indazol-5-yl, phenyl, OH, NH-(1-methylpiperidin-4-yl) substituted pyrazine) |
| 2.774 | (7-chloro-1H-indazol-5-yl, phenyl, OH, NH-(1-methylpyrrolidin-3-yl) substituted pyrazine) |

TABLE 2-continued

| Compound No. | Structure |
|---|---|
| 2.775 | 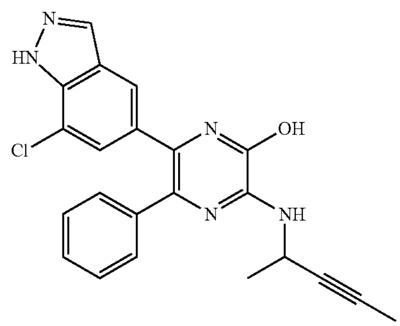 [SMILES: CC#CC(C)Nc1nc(-c2ccccc2)c(-c2cc(Cl)c3[nH]ncc3c2)nc1O] |
| 2.776 | 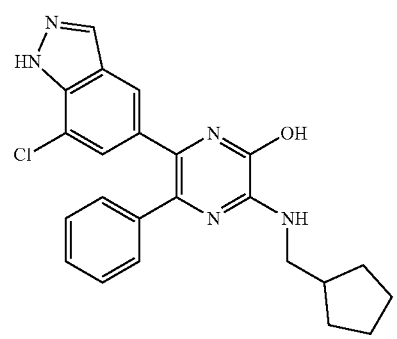 [SMILES: Oc1nc(-c2cc(Cl)c3[nH]ncc3c2)c(-c2ccccc2)nc1NCC1CCCC1] |
| 2.777 | 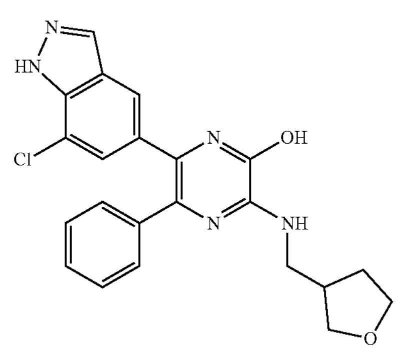 |
| 2.778 | 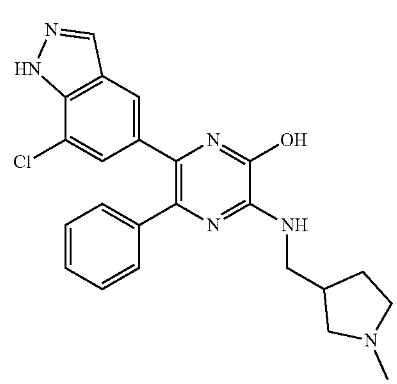 |

TABLE 2-continued
| Compound No. | Structure |
|---|---|
| 2.779 | 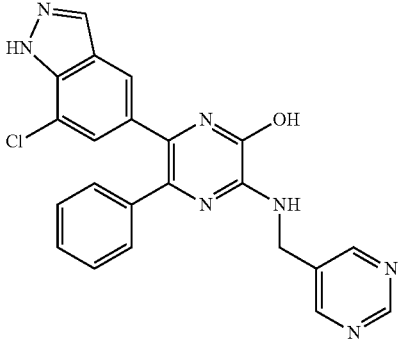 [SMILES: Oc1nc(-c2cc(Cl)c3[nH]ncc3c2)c(-c2ccccc2)nc1NCc1cncnc1] |
| 2.780 | 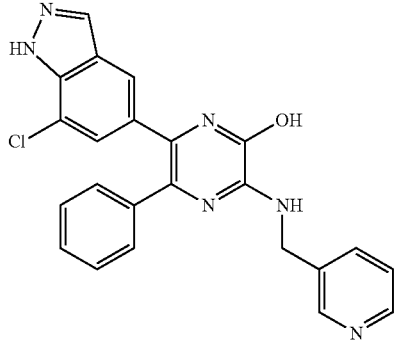 [SMILES: Oc1nc(-c2cc(Cl)c3[nH]ncc3c2)c(-c2ccccc2)nc1NCc1cccnc1] |
| 2.781 | 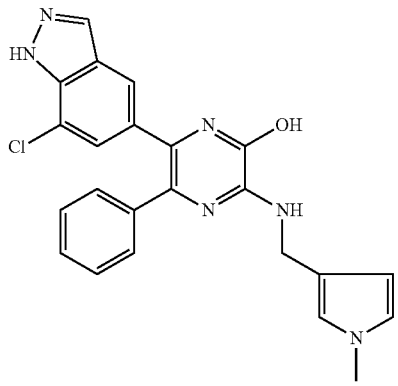 [SMILES: Cn1ccc(CNc2nc(-c3ccccc3)c(-c3cc(Cl)c4[nH]ncc4c3)nc2O)c1] |
| 2.782 | 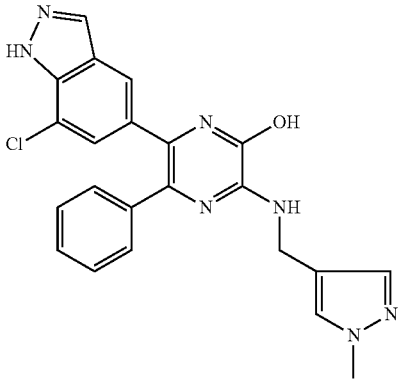 |

TABLE 2-continued
| Compound No. | Structure |
|---|---|
| 2.783 | 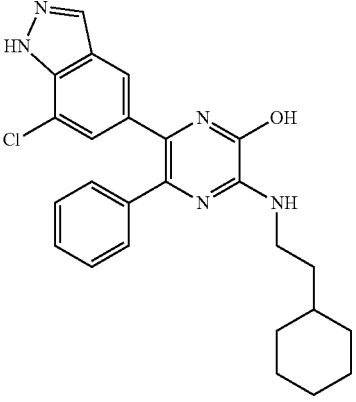 [SMILES: Oc1nc(-c2cc(Cl)c3[nH]ncc3c2)c(-c2ccccc2)nc1NCCC1CCCCC1] |
| 2.784 | 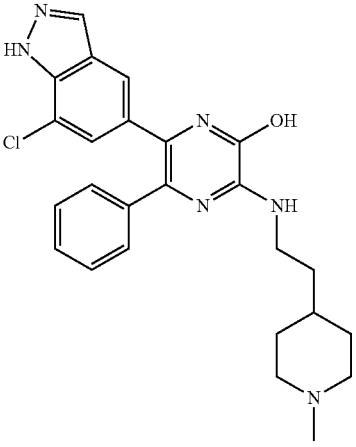 |
| 2.785 | 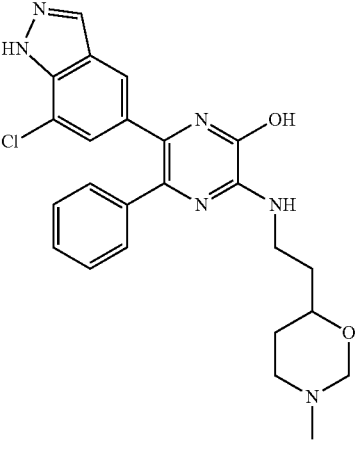 [SMILES: CN1CCC(CCNc2nc(-c3ccccc3)c(-c3cc(Cl)c4[nH]ncc4c3)nc2O)OC1] |

TABLE 2-continued

| Compound No. | Structure |
|---|---|
| 2.786 | 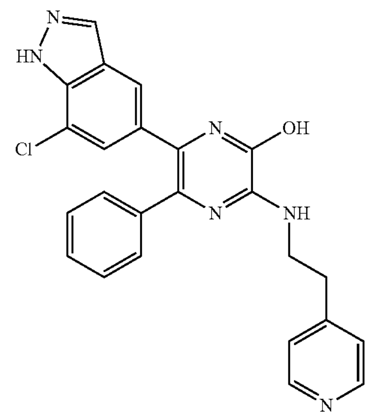 |
| 2.787 | 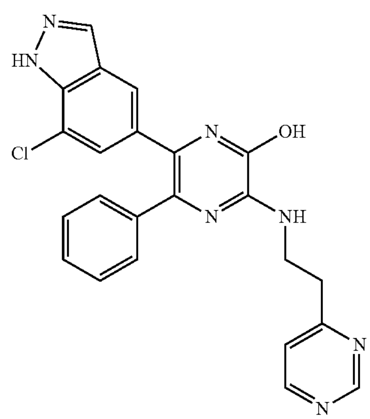 |
| 2.788 | 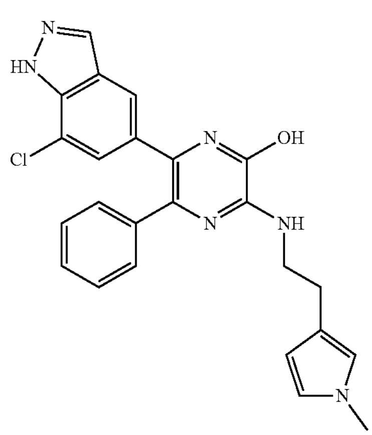 |

TABLE 2-continued
| Compound No. | Structure |
|---|---|
| 2.789 | 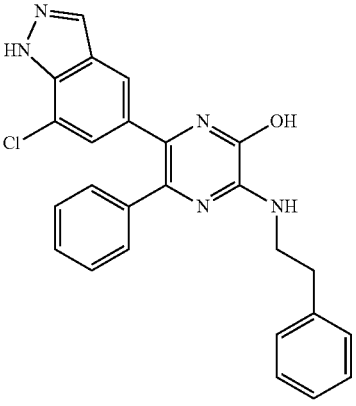 [SMILES: Oc1nc(-c2cc(Cl)c3[nH]ncc3c2)c(-c2ccccc2)nc1NCCc1ccccc1] |
| 2.790 | 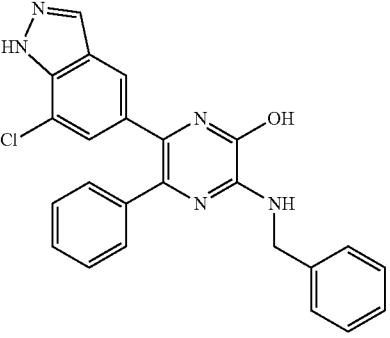 [SMILES: Oc1nc(-c2cc(Cl)c3[nH]ncc3c2)c(-c2ccccc2)nc1NCc1ccccc1] |
| 2.791 | 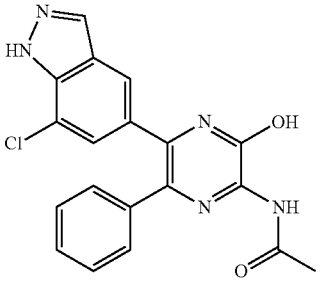 [SMILES: CC(=O)Nc1nc(-c2ccccc2)c(-c2cc(Cl)c3[nH]ncc3c2)nc1O] |
| 2.792 | 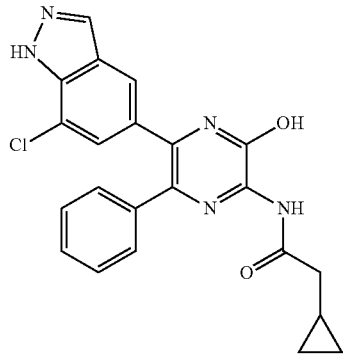 [SMILES: O=C(CC1CC1)Nc1nc(-c2ccccc2)c(-c2cc(Cl)c3[nH]ncc3c2)nc1O] |

TABLE 2-continued

| Compound No. | Structure |
|---|---|
| 2.793 | (7-chloro-1H-indazol-5-yl, phenyl, hydroxy pyrazine with NH-C(O)-cyclopentyl) |
| 2.794 | (7-chloro-1H-indazol-5-yl, phenyl, hydroxy pyrazine with NH-C(O)-O-methyl) |
| 2.795 | (7-chloro-1H-indazol-5-yl, phenyl, hydroxy pyrazine with NH-C(O)-OH) |
| 2.796 | (7-chloro-1H-indazol-5-yl, phenyl, hydroxy pyrazine with NH-C(O)-O-ethyl) |
| 2.797 | (7-chloro-1H-indazol-5-yl, phenyl, hydroxy pyrazine with NH-C(O)-O-isopropyl) |

TABLE 2-continued

| Compound No. | Structure |
|---|---|
| 2.798 | 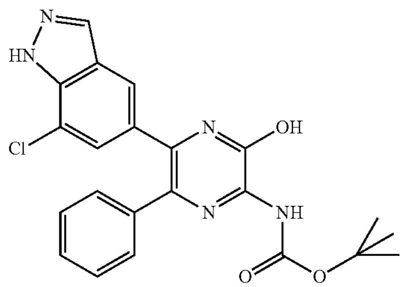 [SMILES: CC(C)(C)OC(=O)Nc1nc(-c2ccccc2)c(-c2cc(Cl)c3[nH]ncc3c2)nc1O] |
| 2.799 | 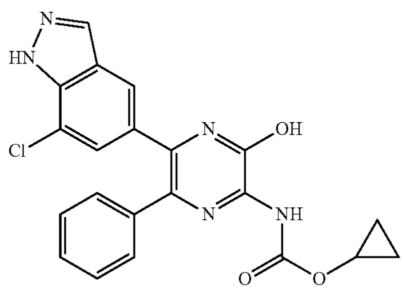 [SMILES: O=C(Nc1nc(-c2ccccc2)c(-c2cc(Cl)c3[nH]ncc3c2)nc1O)OC1CC1] |
| 2.800 | 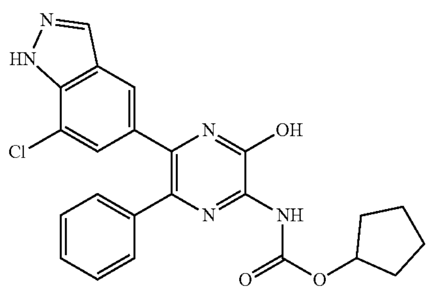 [SMILES: O=C(Nc1nc(-c2ccccc2)c(-c2cc(Cl)c3[nH]ncc3c2)nc1O)OC1CCCC1] |
| 2.801 | 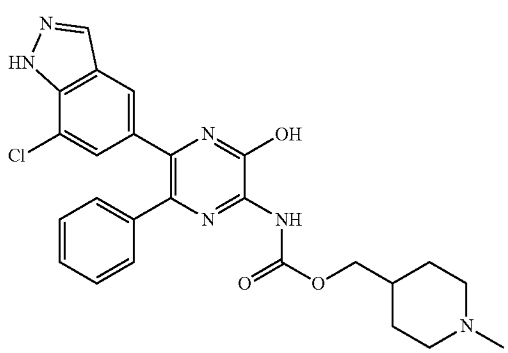 [SMILES: CN1CCC(COC(=O)Nc2nc(-c3ccccc3)c(-c3cc(Cl)c4[nH]ncc4c3)nc2O)CC1] |
| 2.802 | 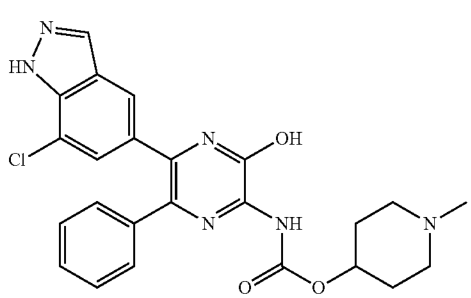 |

TABLE 2-continued
| Compound No. | Structure |
|---|---|
| 2.803 | 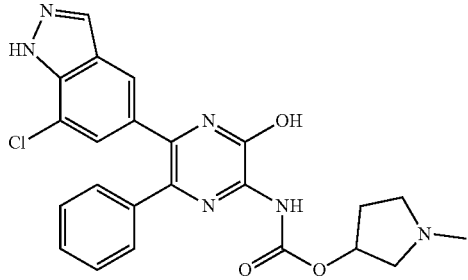 [SMILES: CN1CCC(OC(=O)Nc2nc(-c3ccccc3)c(-c3cc(Cl)c4[nH]ncc4c3)nc2O)C1] |
| 2.804 | 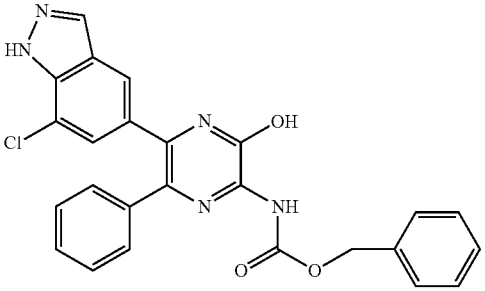 |
| 2.805 | 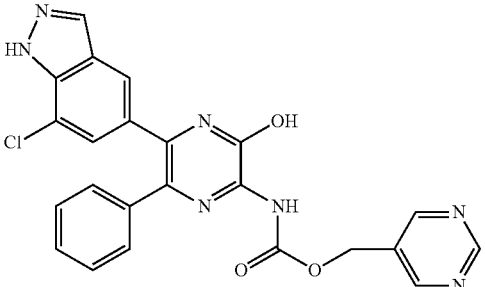 |
| 2.806 | 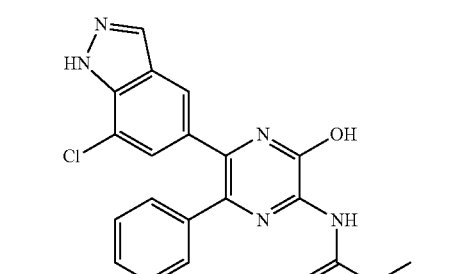 |
| 2.807 | 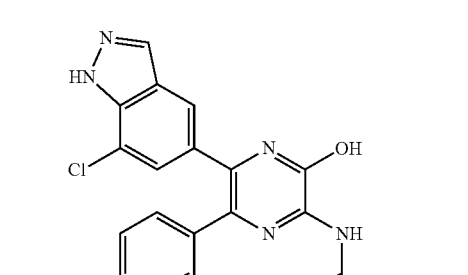 |

TABLE 2-continued

| Compound No. | Structure |
|---|---|
| 2.808 | 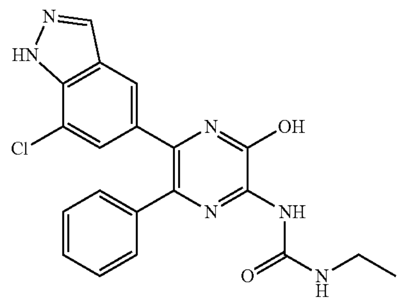 [SMILES: CCNC(=O)Nc1nc(-c2ccccc2)c(-c2cc(Cl)c3[nH]ncc3c2)nc1O] |
| 2.809 | 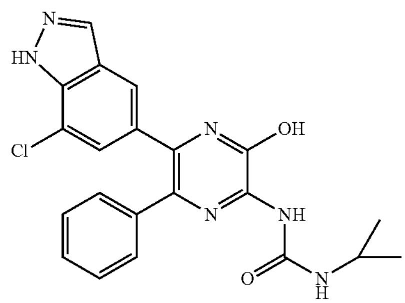 [SMILES: CC(C)NC(=O)Nc1nc(-c2ccccc2)c(-c2cc(Cl)c3[nH]ncc3c2)nc1O] |
| 2.810 | 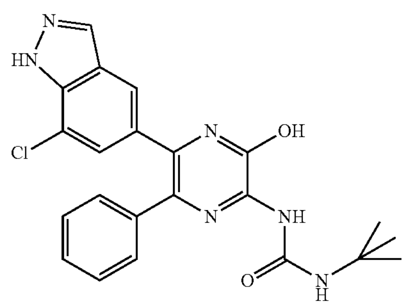 |
| 2.811 | 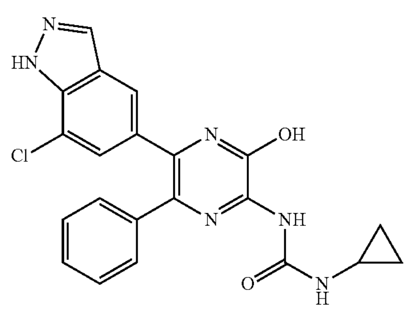 |
| 2.812 | 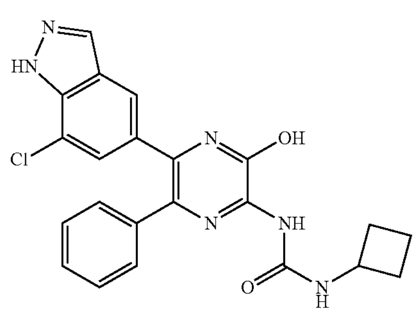 [SMILES: O=C(Nc1nc(-c2ccccc2)c(-c2cc(Cl)c3[nH]ncc3c2)nc1O)NC1CCC1] |

TABLE 2-continued

| Compound No. | Structure |
|---|---|
| 2.813 | 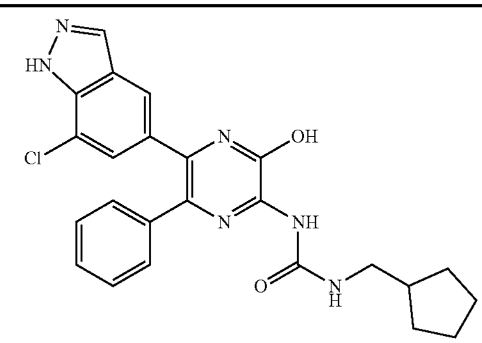 |
| 2.814 | 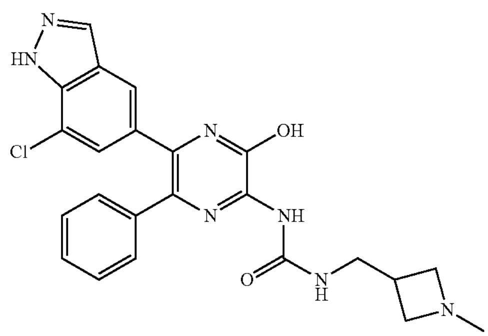 [SMILES: CN1CC(CNC(=O)Nc2nc(-c3ccccc3)c(-c3cc(Cl)c4[nH]ncc4c3)nc2O)C1] |
| 2.815 | 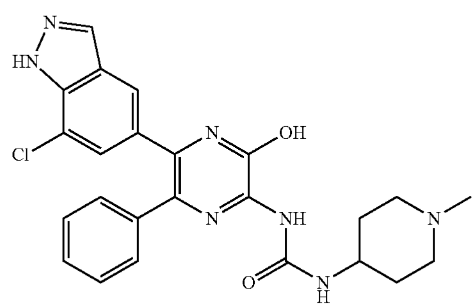 |
| 2.816 | 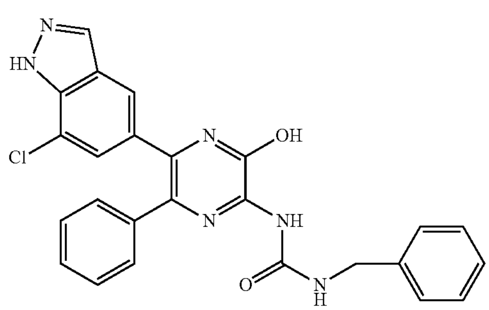 |
| 2.817 | 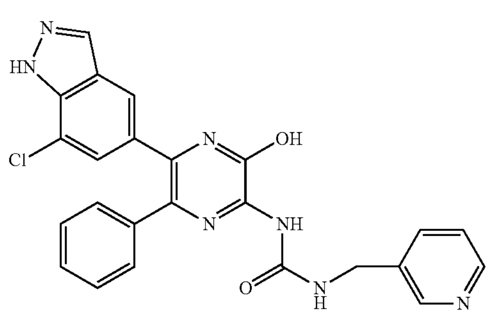 [SMILES: O=C(NCc1cccnc1)Nc1nc(-c2ccccc2)c(-c2cc(Cl)c3[nH]ncc3c2)nc1O] |

TABLE 2-continued
| Compound No. | Structure |
|---|---|
| 2.818 | 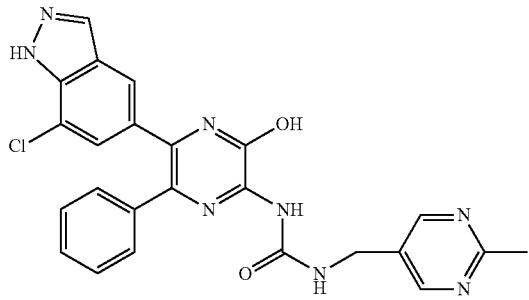 |
| 2.819 | 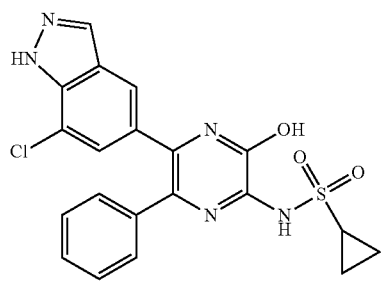 |
| 2.820 | 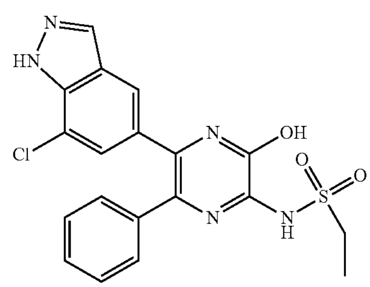 [SMILES: CCS(=O)(=O)Nc1nc(-c2ccccc2)c(-c2cc(Cl)c3[nH]ncc3c2)nc1O] |
| 2.821 | 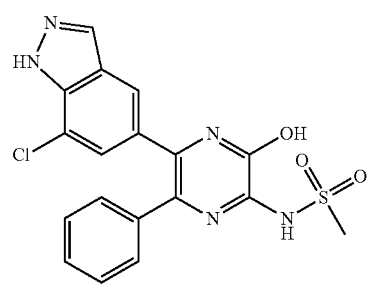 [SMILES: CS(=O)(=O)Nc1nc(-c2ccccc2)c(-c2cc(Cl)c3[nH]ncc3c2)nc1O] |
| 2.822 | 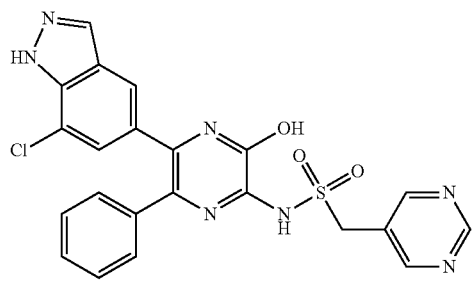 [SMILES: O=S(=O)(Cc1cncnc1)Nc1nc(-c2ccccc2)c(-c2cc(Cl)c3[nH]ncc3c2)nc1O] |

TABLE 2-continued
| Compound No. | Structure |
|---|---|
| 2.823 | 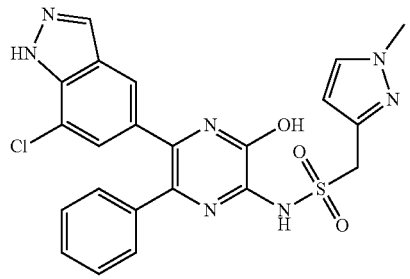 |
| 2.824 | 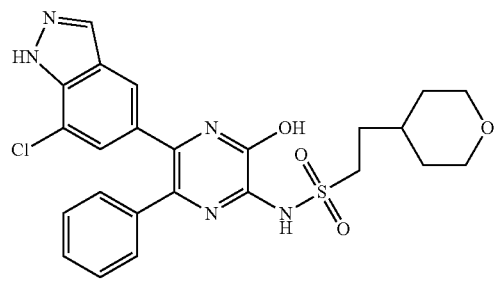 [SMILES: O=S(=O)(CCC1CCOCC1)Nc1nc(-c2ccccc2)c(-c2cc(Cl)c3[nH]ncc3c2)nc1O] |
| 2.825 | 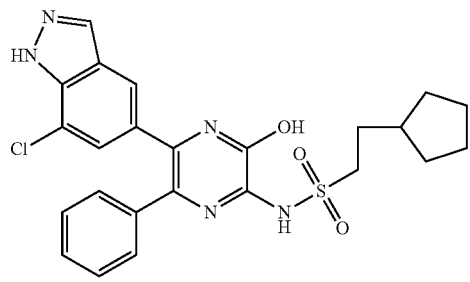 |
| 2.826 | 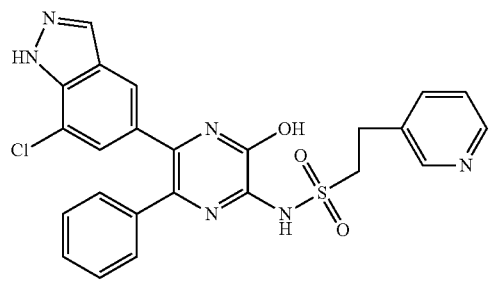 [SMILES: O=S(=O)(CCc1cccnc1)Nc1nc(-c2ccccc2)c(-c2cc(Cl)c3[nH]ncc3c2)nc1O] |
| 2.827 | 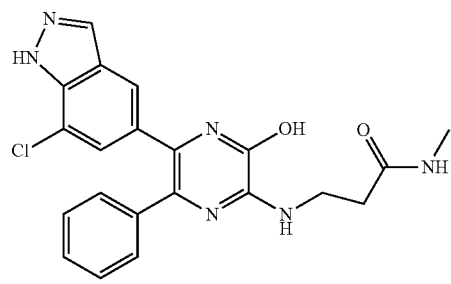 [SMILES: CNC(=O)CCNc1nc(-c2ccccc2)c(-c2cc(Cl)c3[nH]ncc3c2)nc1O] |

TABLE 2-continued

| Compound No. | Structure |
|---|---|
| 2.828 | 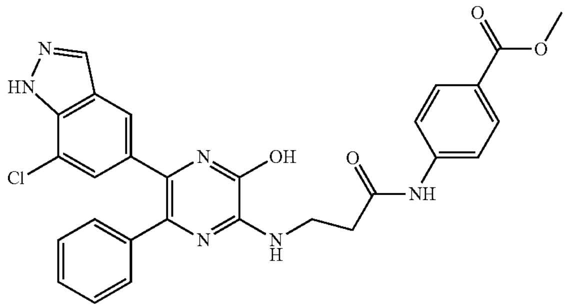 [SMILES: COC(=O)c1ccc(NC(=O)CCNc2nc(-c3ccccc3)c(-c3cc(Cl)c4[nH]ncc4c3)nc2O)cc1] |
| 2.829 | 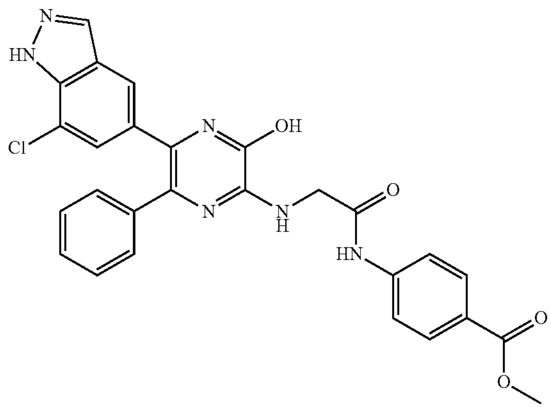 |
| 2.830 | 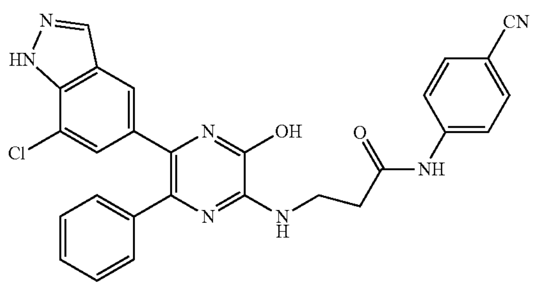 |
| 2.831 | 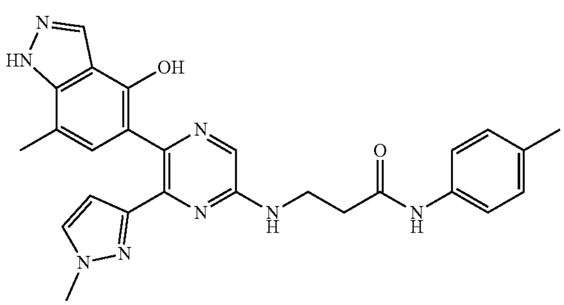 |
| 2.832 | 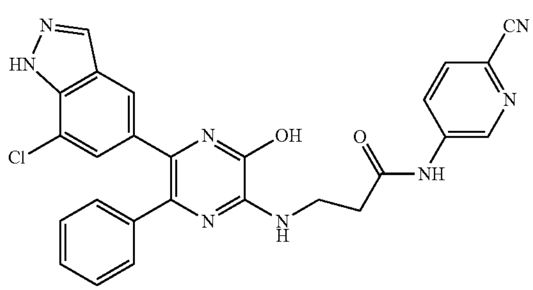 [SMILES: N#Cc1ccc(NC(=O)CCNc2nc(-c3ccccc3)c(-c3cc(Cl)c4[nH]ncc4c3)nc2O)cn1] |

TABLE 2-continued

| Compound No. | Structure |
|---|---|
| 2.833 | 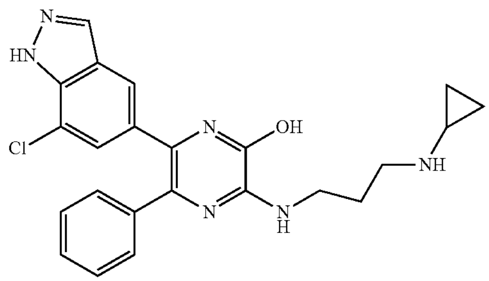 |
| 2.834 | 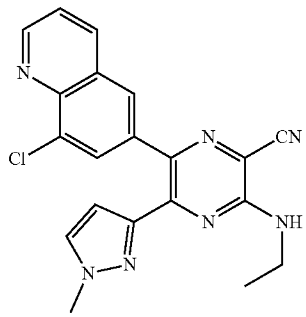 [SMILES: CCNc1nc(-c2ccn(C)n2)c(-c2cc(Cl)c3ncccc3c2)nc1C#N] |
| 2.835 | 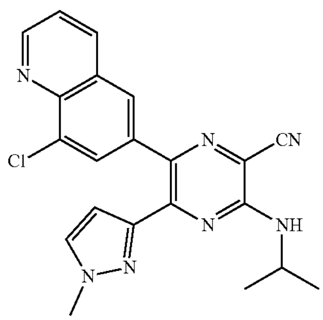 [SMILES: CC(C)Nc1nc(-c2ccn(C)n2)c(-c2cc(Cl)c3ncccc3c2)nc1C#N] |
| 2.836 | 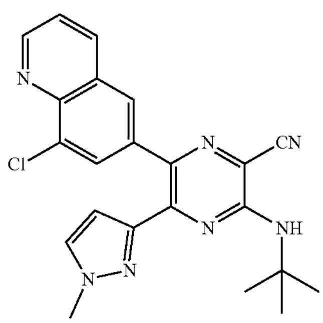 [SMILES: Cn1ccc(-c2nc(NC(C)(C)C)c(C#N)nc2-c2cc(Cl)c3ncccc3c2)n1] |
| 2.837 | 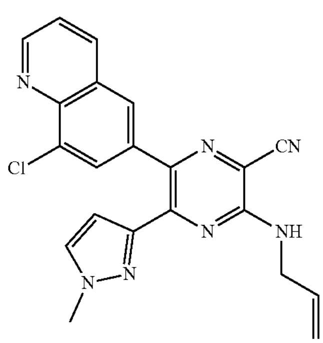 [SMILES: C=CCNc1nc(-c2ccn(C)n2)c(-c2cc(Cl)c3ncccc3c2)nc1C#N] |

TABLE 2-continued
| Compound No. | Structure |
|---|---|
| 2.838 | 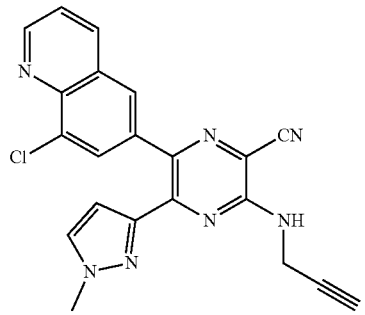 [SMILES: C#CCNc1nc(-c2ccn(C)n2)c(-c2cc(Cl)c3ncccc3c2)nc1C#N] |
| 2.839 | 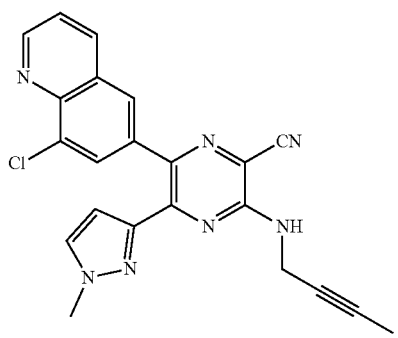 [SMILES: CC#CCNc1nc(-c2ccn(C)n2)c(-c2cc(Cl)c3ncccc3c2)nc1C#N] |
| 2.840 | 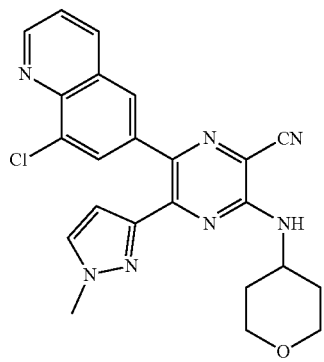 [SMILES: Cn1ccc(-c2nc(NC3CCOCC3)c(C#N)nc2-c2cc(Cl)c3ncccc3c2)n1] |
| 2.841 | 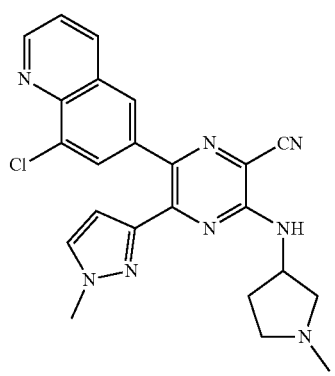 [SMILES: CN1CCC(Nc2nc(-c3ccn(C)n3)c(-c3cc(Cl)c4ncccc4c3)nc2C#N)C1] |

TABLE 2-continued
| Compound No. | Structure |
|---|---|
| 2.842 | 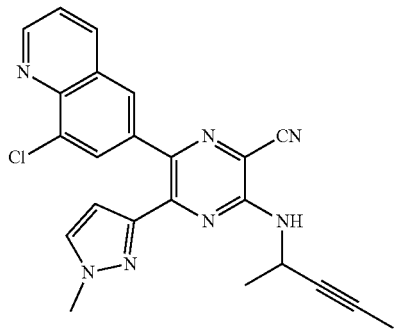 |
| 2.843 | 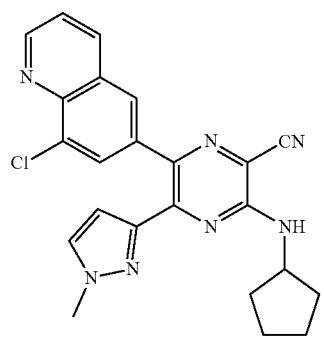 [SMILES: Cn1ccc(-c2nc(NC3CCCC3)c(C#N)nc2-c2cc(Cl)c3ncccc3c2)n1] |
| 2.844 | 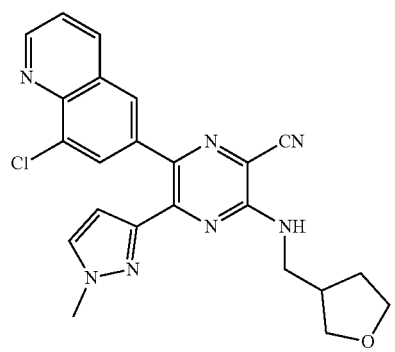 [SMILES: Cn1ccc(-c2nc(NCC3CCOC3)c(C#N)nc2-c2cc(Cl)c3ncccc3c2)n1] |
| 2.845 | 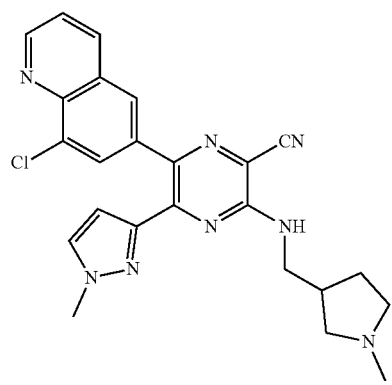 [SMILES: CN1CCC(CNc2nc(-c3ccn(C)n3)c(-c3cc(Cl)c4ncccc4c3)nc2C#N)C1] |

TABLE 2-continued

| Compound No. | Structure |
|---|---|
| 2.846 | 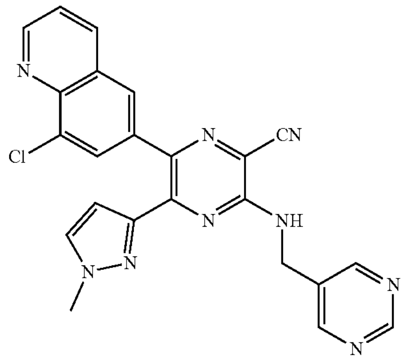 [SMILES: Cn1ccc(-c2nc(NCc3cncnc3)c(C#N)nc2-c2cc(Cl)c3ncccc3c2)n1] |
| 2.847 | 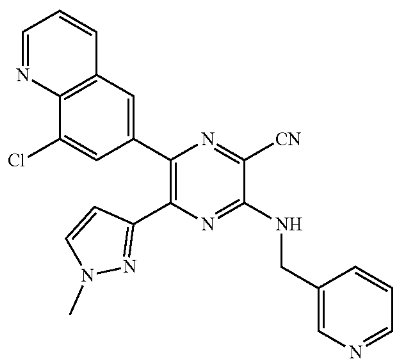 [SMILES: Cn1ccc(-c2nc(NCc3cccnc3)c(C#N)nc2-c2cc(Cl)c3ncccc3c2)n1] |
| 2.848 | 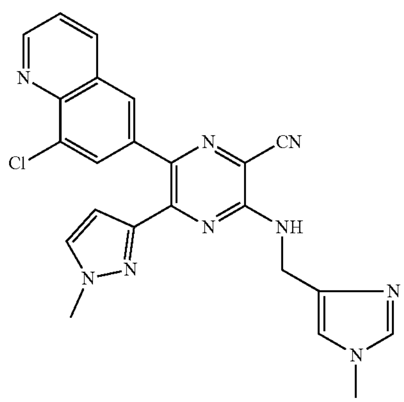 [SMILES: Cn1cnc(CNc2nc(-c3ccn(C)n3)c(-c3cc(Cl)c4ncccc4c3)nc2C#N)c1] |
| 2.849 | 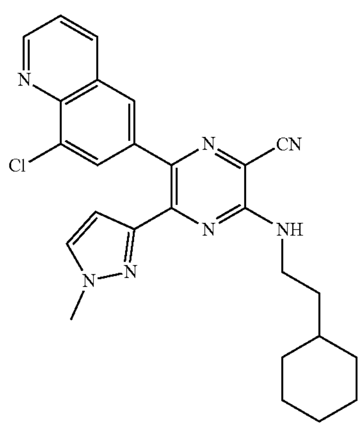 [SMILES: Cn1ccc(-c2nc(NCCC3CCCCC3)c(C#N)nc2-c2cc(Cl)c3ncccc3c2)n1] |

TABLE 2-continued
| Compound No. | Structure |
|---|---|
| 2.850 | 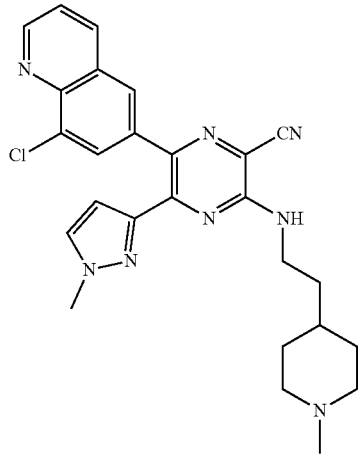 [SMILES: CN1CCC(CCNc2nc(-c3ccn(C)n3)c(-c3cc(Cl)c4ncccc4c3)nc2C#N)CC1] |
| 2.851 | 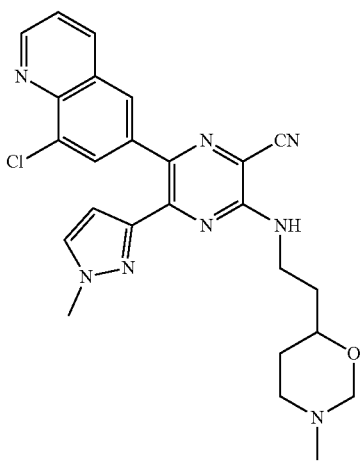 [SMILES: CN1CCC(CCNc2nc(-c3ccn(C)n3)c(-c3cc(Cl)c4ncccc4c3)nc2C#N)OC1] |
| 2.852 | 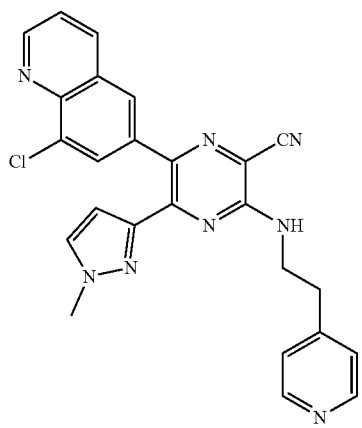 [SMILES: Cn1ccc(-c2nc(NCCc3ccncc3)c(C#N)nc2-c2cc(Cl)c3ncccc3c2)n1] |

TABLE 2-continued
| Compound No. | Structure |
|---|---|
| 2.853 | 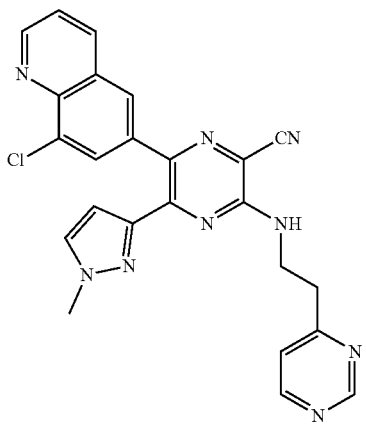 [SMILES: Cn1ccc(-c2nc(NCCc3ccncn3)c(C#N)nc2-c2cc(Cl)c3ncccc3c2)n1] |
| 2.854 | 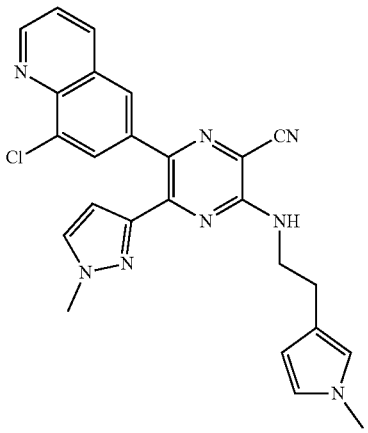 [SMILES: Cn1ccc(CCNc2nc(-c3ccn(C)n3)c(-c3cc(Cl)c4ncccc4c3)nc2C#N)c1] |
| 2.855 | 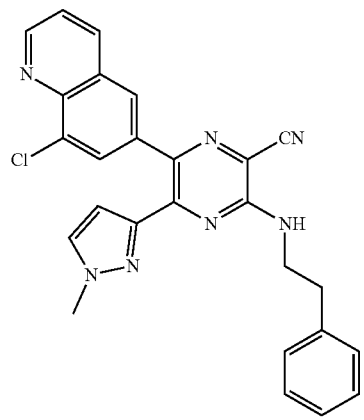 [SMILES: Cn1ccc(-c2nc(NCCc3ccccc3)c(C#N)nc2-c2cc(Cl)c3ncccc3c2)n1] |

TABLE 2-continued

| Compound No. | Structure |
|---|---|
| 2.856 | 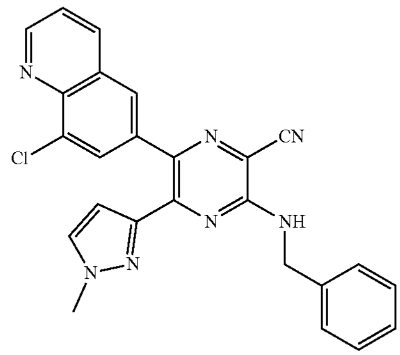 [SMILES: Cn1ccc(-c2nc(NCc3ccccc3)c(C#N)nc2-c2cc(Cl)c3ncccc3c2)n1] |
| 2.857 | 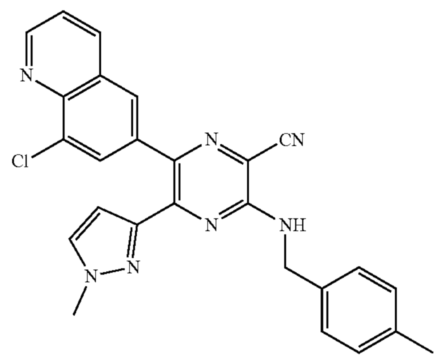 [SMILES: Cc1ccc(CNc2nc(-c3ccn(C)n3)c(-c3cc(Cl)c4ncccc4c3)nc2C#N)cc1] |
| 2.858 | 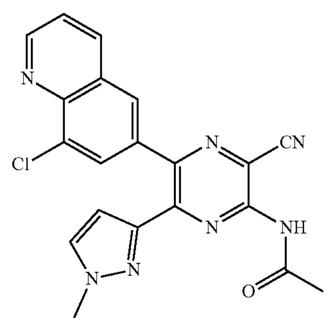 |
| 2.859 | 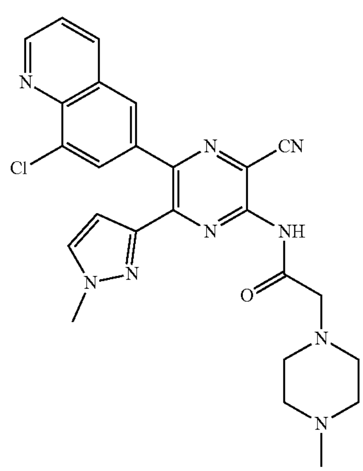 [SMILES: CN1CCN(CC(=O)Nc2nc(-c3ccn(C)n3)c(-c3cc(Cl)c4ncccc4c3)nc2C#N)CC1] |

TABLE 2-continued
| Compound No. | Structure |
|---|---|
| 2.860 | 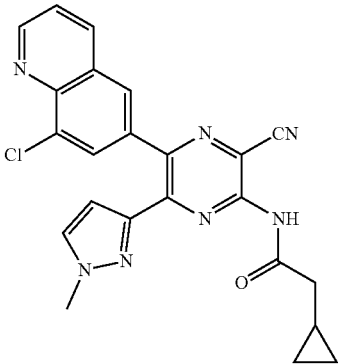 [SMILES: Cn1ccc(-c2nc(NC(=O)CC3CC3)c(C#N)nc2-c2cc(Cl)c3ncccc3c2)n1] |
| 2.861 | 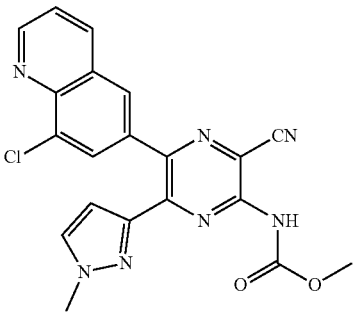 [SMILES: COC(=O)Nc1nc(-c2ccn(C)n2)c(-c2cc(Cl)c3ncccc3c2)nc1C#N] |
| 2.862 | 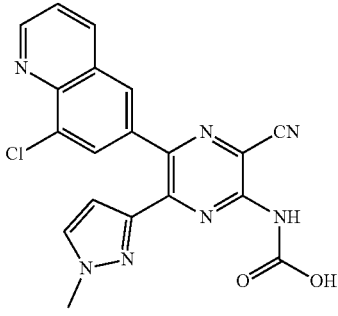 [SMILES: Cn1ccc(-c2nc(NC(=O)O)c(C#N)nc2-c2cc(Cl)c3ncccc3c2)n1] |
| 2.863 | 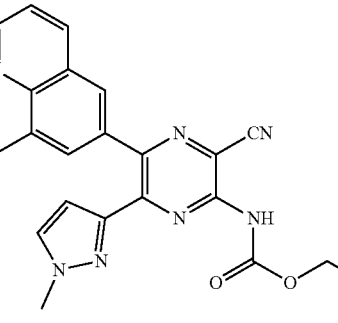 |

TABLE 2-continued
| Compound No. | Structure |
|---|---|
| 2.864 | 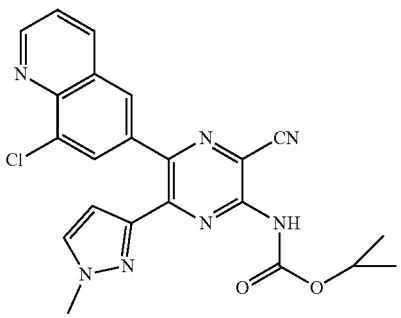 [SMILES: CC(C)OC(=O)Nc1nc(-c2ccn(C)n2)c(-c2cc(Cl)c3ncccc3c2)nc1C#N] |
| 2.865 | 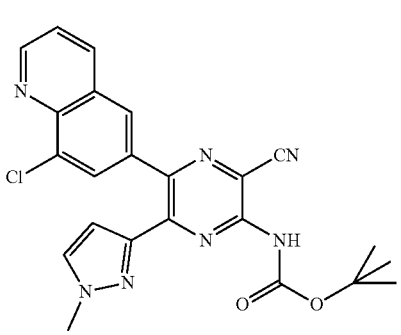 [SMILES: Cn1ccc(-c2nc(NC(=O)OC(C)(C)C)c(C#N)nc2-c2cc(Cl)c3ncccc3c2)n1] |
| 2.866 | 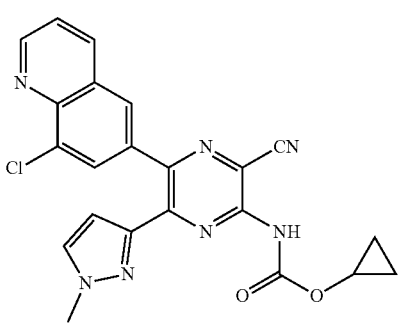 |
| 2.867 | 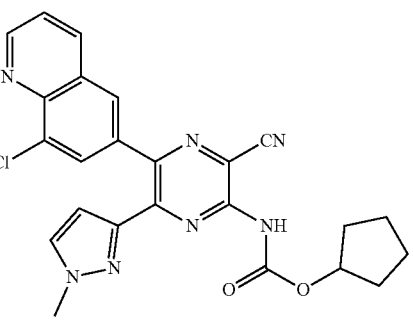 |

TABLE 2-continued

| Compound No. | Structure |
|---|---|
| 2.868 | 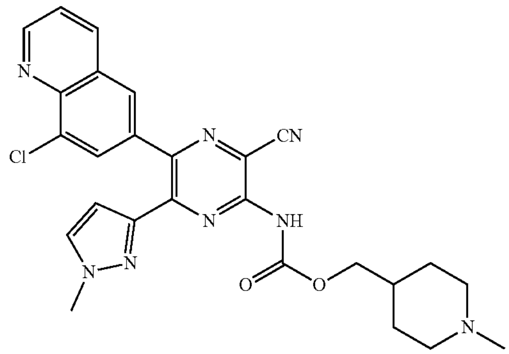 [SMILES: CN1CCC(COC(=O)Nc2nc(-c3ccn(C)n3)c(-c3cc(Cl)c4ncccc4c3)nc2C#N)CC1] |
| 2.869 | 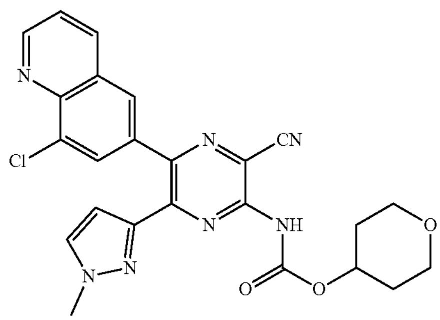 [SMILES: Cn1ccc(-c2nc(NC(=O)OC3CCOCC3)c(C#N)nc2-c2cc(Cl)c3ncccc3c2)n1] |
| 2.870 | 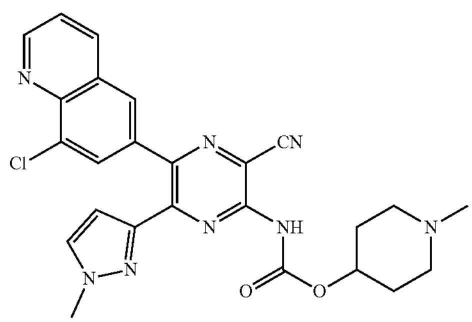 [SMILES: CN1CCC(OC(=O)Nc2nc(-c3ccn(C)n3)c(-c3cc(Cl)c4ncccc4c3)nc2C#N)CC1] |
| 2.871 | 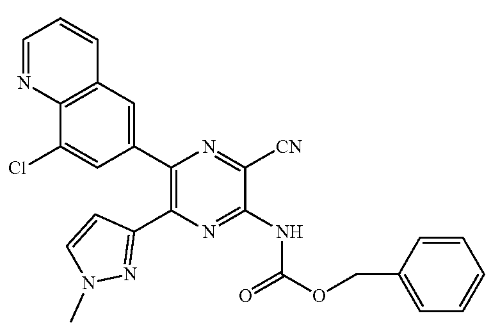 [SMILES: Cn1ccc(-c2nc(NC(=O)OCc3ccccc3)c(C#N)nc2-c2cc(Cl)c3ncccc3c2)n1] |

TABLE 2-continued

| Compound No. | Structure |
|---|---|
| 2.872 | 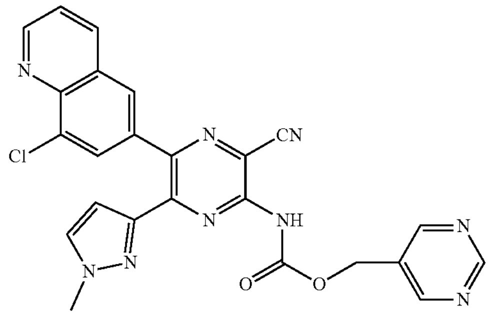 [SMILES: Cn1ccc(-c2nc(NC(=O)OCc3cncnc3)c(C#N)nc2-c2cc(Cl)c3ncccc3c2)n1] |
| 2.873 | 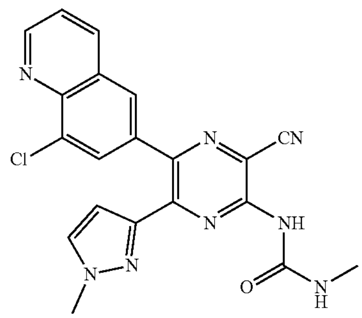 [SMILES: CNC(=O)Nc1nc(-c2ccn(C)n2)c(-c2cc(Cl)c3ncccc3c2)nc1C#N] |
| 2.874 | 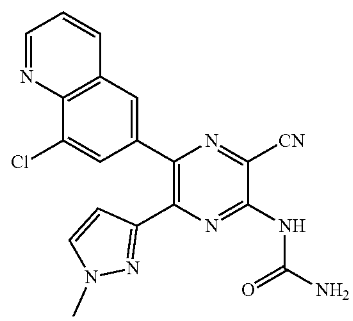 [SMILES: Cn1ccc(-c2nc(NC(N)=O)c(C#N)nc2-c2cc(Cl)c3ncccc3c2)n1] |
| 2.875 | 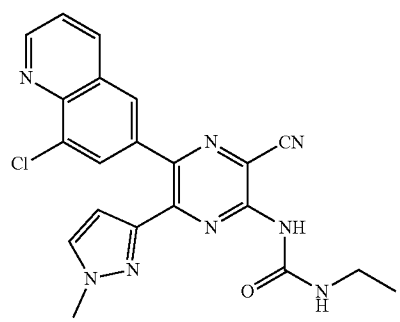 [SMILES: CCNC(=O)Nc1nc(-c2ccn(C)n2)c(-c2cc(Cl)c3ncccc3c2)nc1C#N] |
| 2.876 | 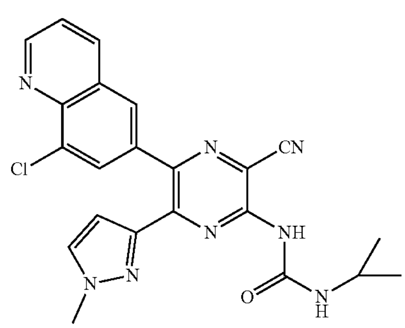 [SMILES: CC(C)NC(=O)Nc1nc(-c2ccn(C)n2)c(-c2cc(Cl)c3ncccc3c2)nc1C#N] |

TABLE 2-continued
| Compound No. | Structure |
|---|---|
| 2.877 | 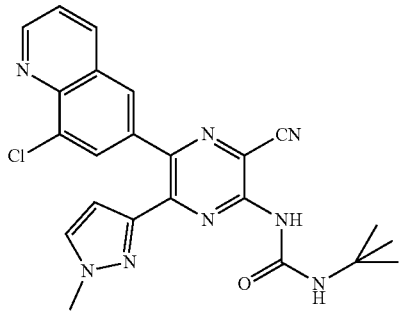 [SMILES: Cn1ccc(-c2nc(NC(=O)NC(C)(C)C)c(C#N)nc2-c2cc(Cl)c3ncccc3c2)n1] |
| 2.878 | 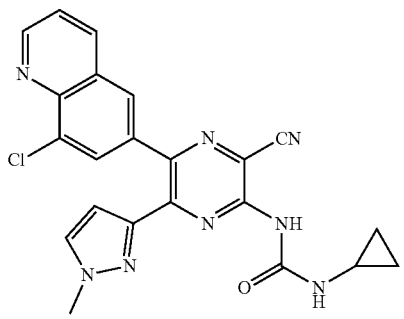 [SMILES: Cn1ccc(-c2nc(NC(=O)NC3CC3)c(C#N)nc2-c2cc(Cl)c3ncccc3c2)n1] |
| 2.879 | 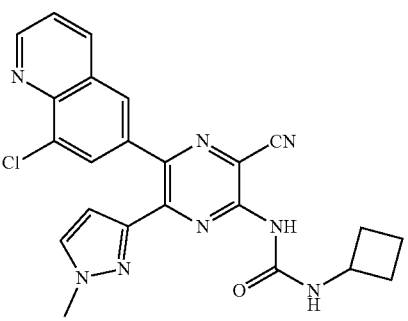 [SMILES: Cn1ccc(-c2nc(NC(=O)NC3CCC3)c(C#N)nc2-c2cc(Cl)c3ncccc3c2)n1] |
| 2.880 | 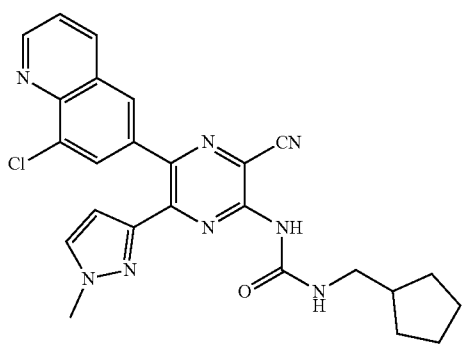 [SMILES: Cn1ccc(-c2nc(NC(=O)NCC3CCCC3)c(C#N)nc2-c2cc(Cl)c3ncccc3c2)n1] |

TABLE 2-continued

| Compound No. | Structure |
| --- | --- |
| 2.881 | 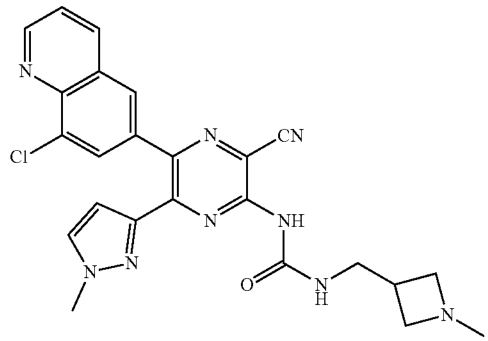 [SMILES: CN1CC(CNC(=O)Nc2nc(-c3ccn(C)n3)c(-c3cc(Cl)c4ncccc4c3)nc2C#N)C1] |
| 2.882 | 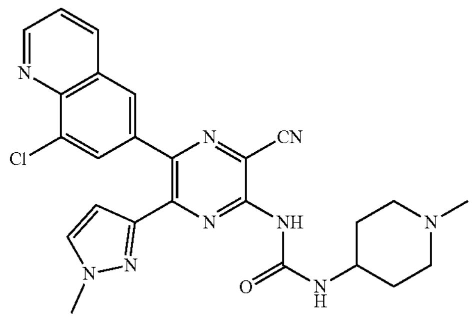 [SMILES: CN1CCC(NC(=O)Nc2nc(-c3ccn(C)n3)c(-c3cc(Cl)c4ncccc4c3)nc2C#N)CC1] |
| 2.883 | 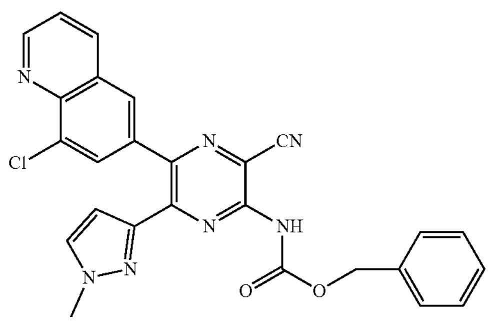 [SMILES: Cn1ccc(-c2nc(NC(=O)OCc3ccccc3)c(C#N)nc2-c2cc(Cl)c3ncccc3c2)n1] |
| 2.884 | 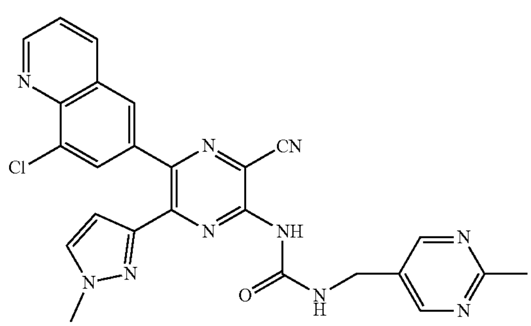 [SMILES: Cc1ncc(CNC(=O)Nc2nc(-c3ccn(C)n3)c(-c3cc(Cl)c4ncccc4c3)nc2C#N)cn1] |

TABLE 2-continued

| Compound No. | Structure |
|---|---|
| 2.885 | 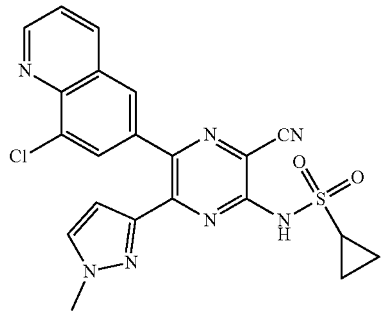 [SMILES: Cn1ccc(-c2nc(NS(=O)(=O)C3CC3)c(C#N)nc2-c2cc(Cl)c3ncccc3c2)n1] |
| 2.886 | 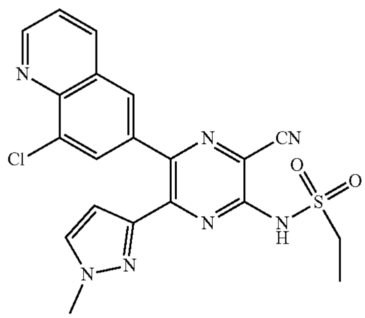 [SMILES: CCS(=O)(=O)Nc1nc(-c2ccn(C)n2)c(-c2cc(Cl)c3ncccc3c2)nc1C#N] |
| 2.887 | 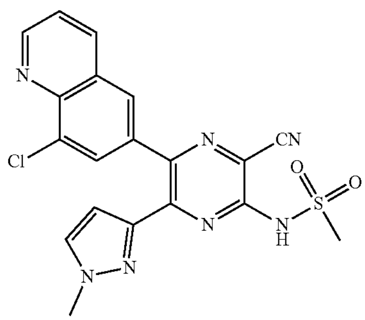 [SMILES: Cn1ccc(-c2nc(NS(C)(=O)=O)c(C#N)nc2-c2cc(Cl)c3ncccc3c2)n1] |
| 2.888 | 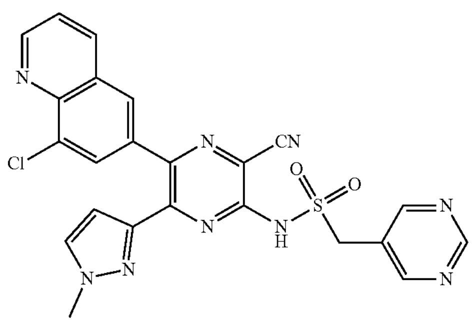 [SMILES: Cn1ccc(-c2nc(NS(=O)(=O)Cc3cncnc3)c(C#N)nc2-c2cc(Cl)c3ncccc3c2)n1] |
| 2.889 | 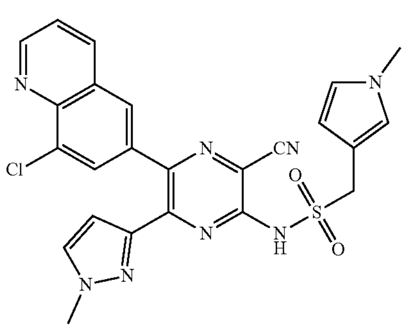 [SMILES: Cn1ccc(CS(=O)(=O)Nc2nc(-c3ccn(C)n3)c(-c3cc(Cl)c4ncccc4c3)nc2C#N)c1] |

TABLE 2-continued
| Compound No. | Structure |
|---|---|
| 2.890 | 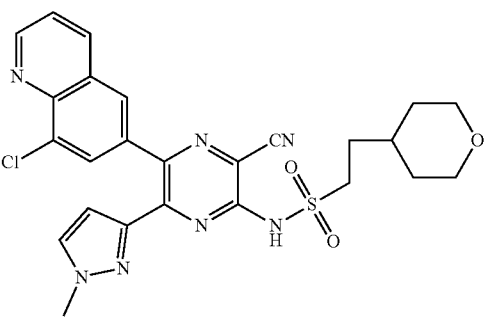 [SMILES: Cn1ccc(-c2nc(NS(=O)(=O)CCC3CCOCC3)c(C#N)nc2-c2cc(Cl)c3ncccc3c2)n1] |
| 2.891 | 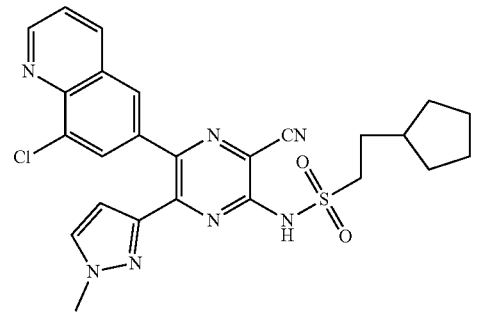 [SMILES: Cn1ccc(-c2nc(NS(=O)(=O)CCC3CCCC3)c(C#N)nc2-c2cc(Cl)c3ncccc3c2)n1] |
| 2.892 | 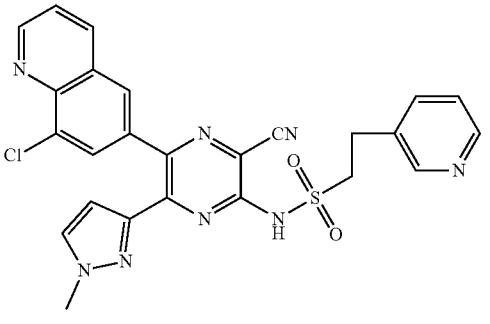 [SMILES: Cn1ccc(-c2nc(NS(=O)(=O)CCc3cccnc3)c(C#N)nc2-c2cc(Cl)c3ncccc3c2)n1] |
| 2.893 | 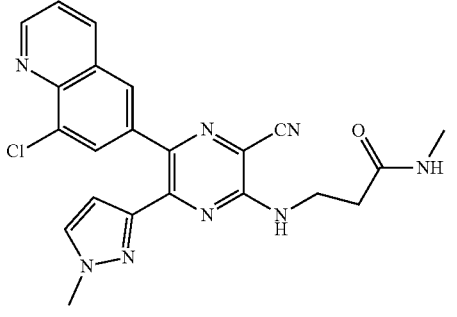 [SMILES: CNC(=O)CCNc1nc(-c2ccn(C)n2)c(-c2cc(Cl)c3ncccc3c2)nc1C#N] |

TABLE 2-continued

| Compound No. | Structure |
|---|---|
| 2.894 | 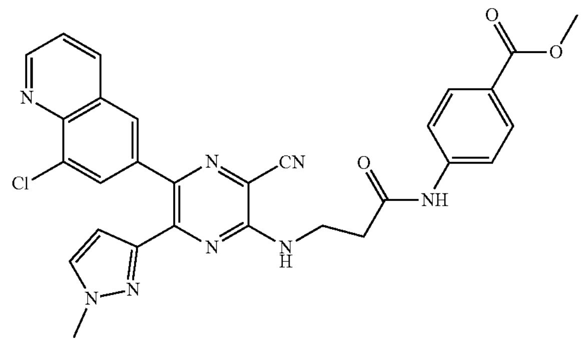 [SMILES: COC(=O)c1ccc(NC(=O)CCNc2nc(-c3ccn(C)n3)c(-c3cc(Cl)c4ncccc4c3)nc2C#N)cc1] |
| 2.895 | 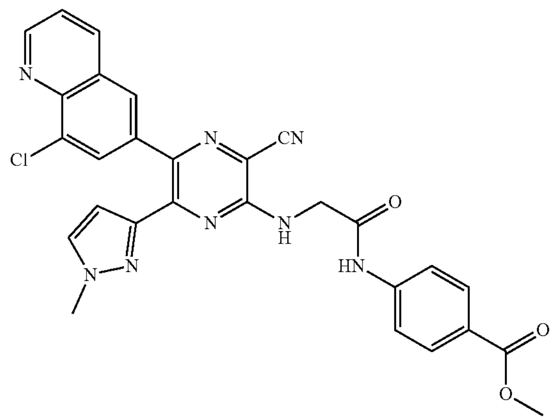 [SMILES: COC(=O)c1ccc(NC(=O)CNc2nc(-c3ccn(C)n3)c(-c3cc(Cl)c4ncccc4c3)nc2C#N)cc1] |
| 2.896 | 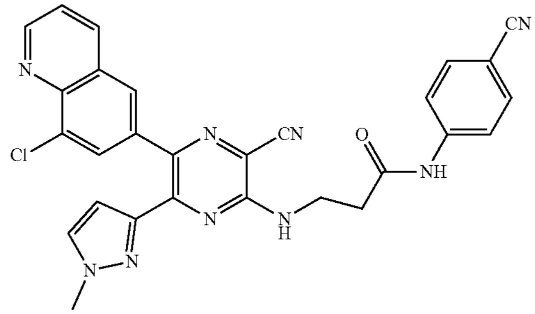 [SMILES: Cn1ccc(-c2nc(NCCC(=O)Nc3ccc(C#N)cc3)c(C#N)nc2-c2cc(Cl)c3ncccc3c2)n1] |
| 2.897 | 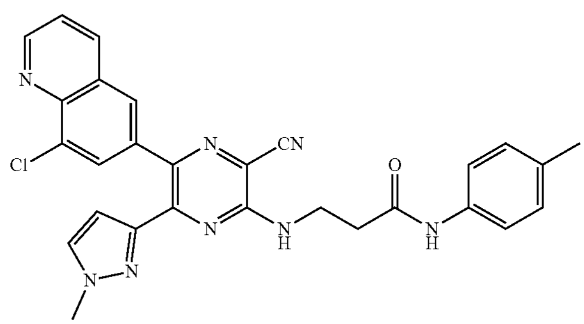 [SMILES: Cc1ccc(NC(=O)CCNc2nc(-c3ccn(C)n3)c(-c3cc(Cl)c4ncccc4c3)nc2C#N)cc1] |

TABLE 2-continued

| Compound No. | Structure |
|---|---|
| 2.898 | (structure) |
| 2.899 | (structure) |

In some embodiments, provided herein are compounds described in Table 2, including pharmaceutically acceptable salts thereof, and uses thereof. Isomers of compounds of Table 2 are also provided, as are compositions comprising a compound, or any isomer thereof, in any ratio, including racemic mixtures. Isotopic varients of the compounds are also provided.

The embodiments and variations described herein are suitable for compounds of any formulae detailed herein, where applicable.

Representative examples of compounds detailed herein, including intermediates and final compounds according to the present disclosure are depicted herein. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described. The structure or name is intended to embrace all possible stereoisomers of a compound depicted, and each unique stereoisomer has a compound number bearing a suffix "a", "b", etc. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (I) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^{2}H$, $^{3}H$, $^{11}C$, $^{13}C$, $^{14}C$, $^{13}N$, $^{15}O$, $^{17}O$, $^{32}P$, $^{35}S$, $^{18}F$, $^{36}Cl$. Certain isotope labeled compounds (e.g. $^{3}H$ and $^{14}C$) are useful in compound or substrate tissue distribution study. Incorporation of heavier isotopes such as deuterium ($^{2}H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Articles of manufacture comprising a compound described herein, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

In some embodiments, compounds of the formula (I) may be synthesized according to Scheme 1. In some embodiments, compounds of the formula (I) may be synthesized according to Scheme 1, 2, 3, 4, 5, or 6.

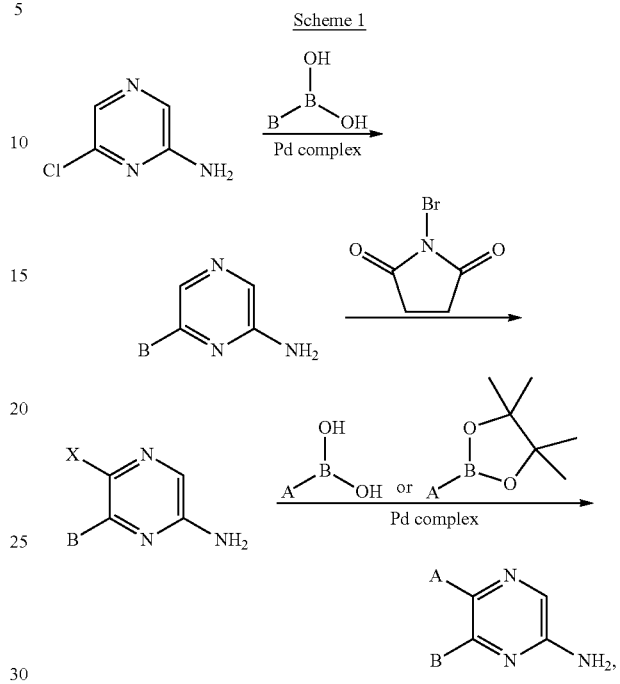

wherein A and B are as defined for formula (I), or any variation thereof detailed herein; and X is a leaving group (e.g., alkoxy or halogen).

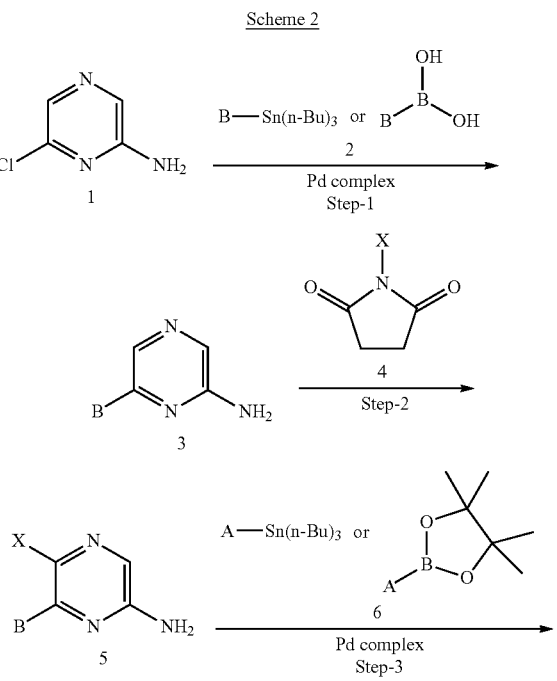

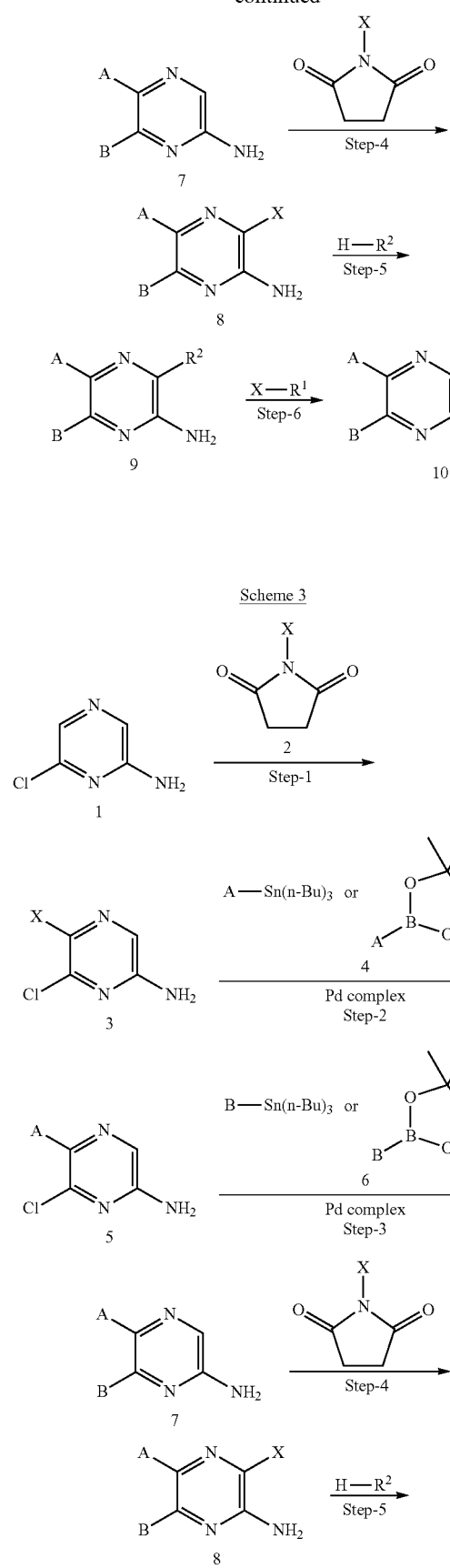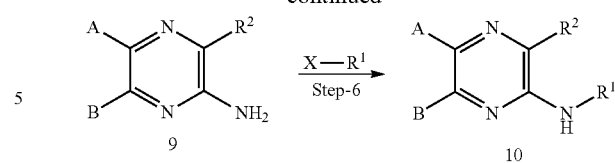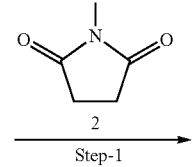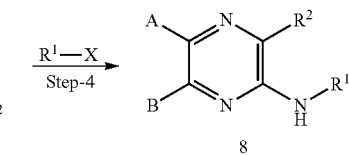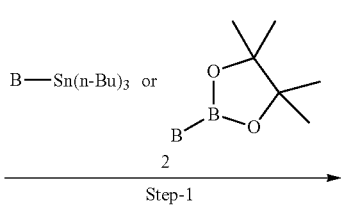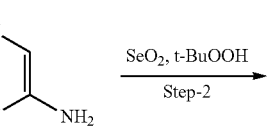

939
-continued
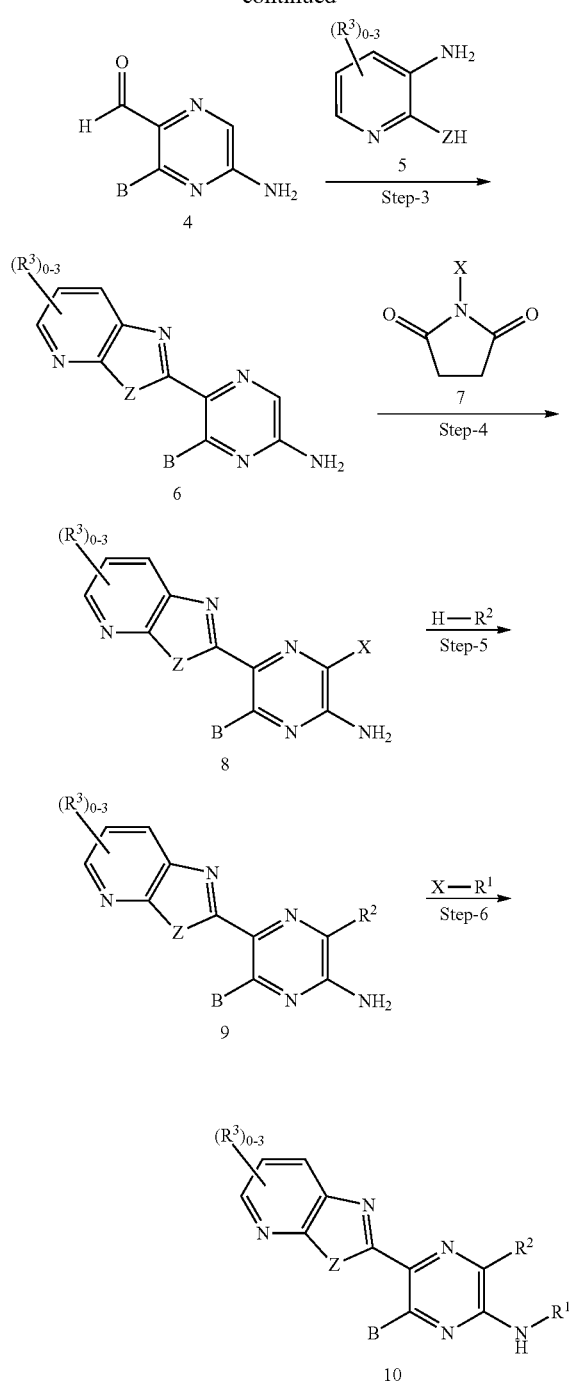
940
-continued
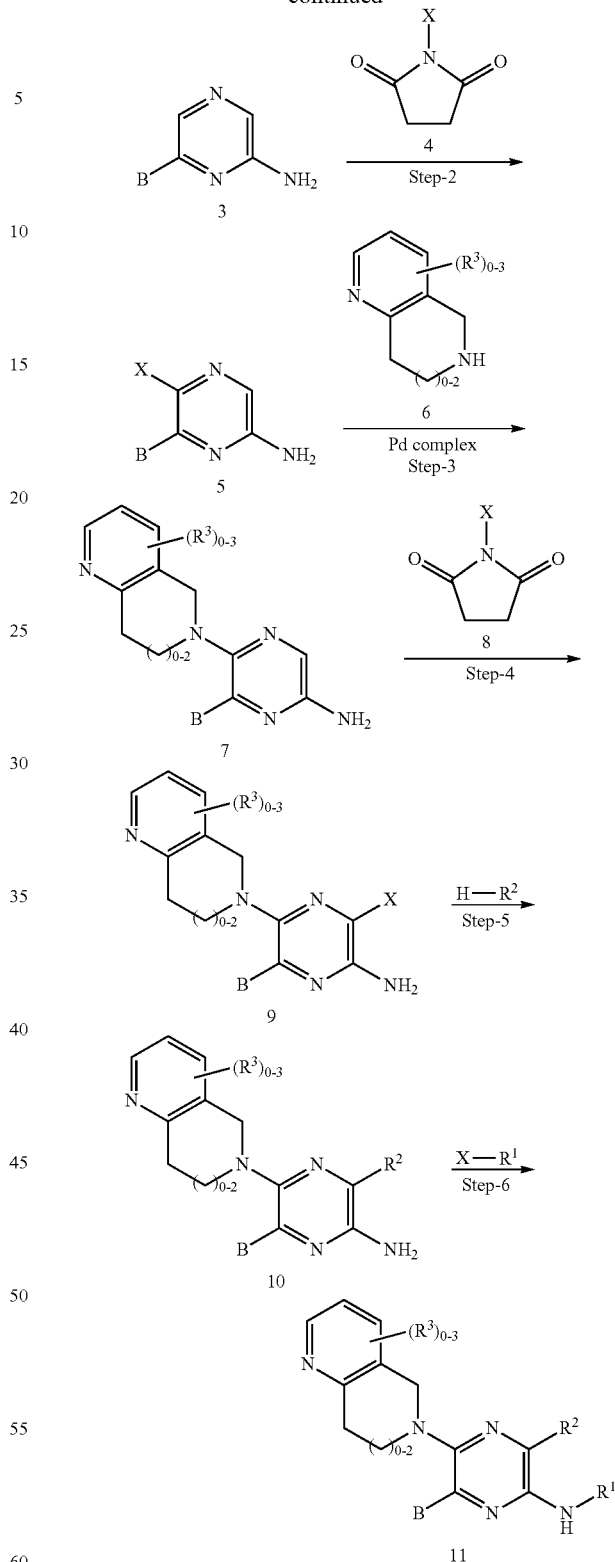
Scheme 6
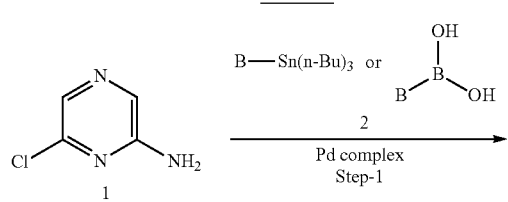
wherein A, B, R¹, R² and R³ are as defined for formula (I), or any variation thereof detailed herein; X is a leaving group (e.g., alkoxy or halogen) and Z is a heteroatom selected from O, S or NH. R³ groups may be the same or different, and which may be present on either one ring or both rings.

It is understood that General Synthetic Schemes 1-6 and present synthetic routes involving steps clearly familiar to those skilled in the art, wherein the substituents described in compounds of formula (I) herein can be varied with a choice of appropriate starting materials and reagents utilized in the steps presented.

Pharmaceutical Compositions and Formulations

Pharmaceutical compositions of any of the compounds detailed herein are embraced by this disclosure. Thus, the present disclosure includes pharmaceutical compositions comprising a compound as detailed herein or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound or salt thereof and a pharmaceutically acceptable carrier or excipient. In another variation, a composition of substantially pure compound is provided.

Methods of Use

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease in an individual comprising administering an effective amount of a compound of formula (I) or any embodiment, variation or aspect thereof (collectively, a compound of formula (I) or the present compounds or the compounds detailed or described herein) or a pharmaceutically acceptable salt thereof, to the individual. In some embodiments, provided herein is a method of treating a disease mediated by a G protein coupled receptor signaling pathway in an individual comprising administering an effective amount of a compound of formula (I), or a pharmaceutically acceptable salt thereof, to the individual. In some embodiments, the disease is mediated by a class A G protein coupled receptor. In some embodiments, the disease is mediated by a class B G protein coupled receptor. In some embodiments, the disease is mediated by a class C G protein coupled receptor. In some embodiments, the G protein coupled receptor is a purinergic G protein receptor. In some embodiments, the G protein coupled receptor is an adenosine receptor, such as any of the $A_1$, $A_{2A}$, $A_{2B}$, and $A_3$ receptors.

The present compounds or salts thereof are believed to be effective for treating a variety of diseases and disorders. For example, in some embodiments, the present compositions may be used to treat a proliferative disease, such as cancer. In some embodiments the cancer is a solid tumor. In some embodiments the cancer is any of adult and pediatric oncology, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer, including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

In some embodiments, the present compounds or salts thereof are used in treatment of tumors which produce high levels of ATP and/or adenosine. For example, in some embodiments the extracellular concentration of adenosine is 10-20 times higher in the tumor compared to adjacent tissue. In some embodiments, the present compounds or salts thereof are used in treatment of tumors that express high levels of an ectonucleotidase. In some embodiments, the ectonucleotidase is CD39. In some embodiments, the ectonucleotidase is CD73.

Also provided herein is a method of enhancing an immune response in an individual in need thereof comprising administering an effective amount of a compound of formula (I), or a pharmaceutically acceptable salt thereof, to the individual. Adenosine receptors are known to play an immunosuppressive role in cancer biology. High levels of adenosine present in the tumor microenvironment bind to adenosine receptors on immune cells to provide an immunosuppressive microenvironment. Specifically, binding of adenosine to the $A_{2A}$ receptor provides an immunosuppressive signal that inhibits T cell proliferation, cytokine production and cytotoxicity. The $A_{2A}$ receptor signaling has been implicated in adenosine-mediated inhibition of NK cell cytotoxicity, NKT cell cytokine production and CD40L upregulation. Therefore, use of an $A_{2A}$ receptor antagonist, such as those provided herein, may reverse the immunosuppressive effect of adenosine on immune cells. In some embodiments, the immune response is enhanced by a compound of formula (I) or a salt thereof enhancing activity of natural killer (NK) cells. In some embodiments, the present compounds or salts thereof increase NK cell-meditated cytotoxicity. In some embodiments, the immune response is enhanced by enhancing the activity of CD8+ T cells. In some embodiments, the present compounds or salts thereof cause an inflammatory response in the tumor microenvironment.

The present disclosure further provides a method of increasing the activity of a natural killer cell in an individual comprising administering an effective amount of a compound of formula (I), or a pharmaceutically acceptable salt thereof, to the individual. In some of these embodiments, the present compounds or salts thereof increase NK cell-meditated cytotoxicity. In some embodiments, a compound of formula (I) or a salt thereof increases the number of NK cells.

A compound of formula (I) or a salt thereof may be useful for modulating the activity of G protein receptor coupled signaling pathway proteins. In some embodiments, a compound of formula (I) or a salt thereof activates a G protein receptor coupled signaling pathway protein (i.e. is an agonist of a G protein receptor). In some embodiments, a compound of formula (I) or a salt thereof inhibits a G protein receptor coupled signaling pathway protein (i.e., is a G protein receptor antagonist). In some embodiments, a compound of formula (I) or a salt thereof is an adenosine receptor antagonist. In some embodiments, a compound of formula (I) or a salt thereof is an antagonist of any of the $A_1$, $A_{2A}$, $A_{2B}$, and $A_3$ receptors.

Accordingly, also provided herein is a method of modulating the activity of an $A_{2A}$ receptor in an individual comprising administering an effective amount of a compound of formula (I), or a pharmaceutically acceptable salt thereof to an individual. In some embodiments a compound of formula (I) or a salt thereof is an $A_{2A}$ receptor antagonist. In some embodiments, a compound of formula (I) or a salt thereof reduces $A_{2A}$ receptor signaling by at least 10%, 20%, 30%, 40%, 50%, 60%, 70%, 80%, 90%, 91%, 92%, 93%, 94%, 95%, 96%, 97%, 98%, or 99%. In some embodiments, a compound of formula (I) or a salt thereof reduces $A_{2A}$ receptor signaling by 40-99%, 50-99%, 60-99%, 70-99%, 80-99%, 90-99%, or 95-99%. In some of these embodiments, a compound of formula (I) or a salt thereof binds to the $A_{2A}$ receptor with an $IC_{50}$ of less than 1 µM, less than 900 nM, less than 800 nM, less than 700 nM, less than 600 nM, less than 500 nM, less than 400 nM, less than 300 nM, less than 200 nM, less than 100 nM, less than 10 nM, less than 1 nM or less than 100 pM. In some embodiments, [compound x] binds to the $A_{2A}$ receptor with an $IC_{50}$ of 500 nM to 100 pM, 400 nM to 100 pM, 300 nM to 100 pM, 200 nM to 100 pM, or 100 nM to 100 pM.

Also provided herein is a method of modulating the activity of an $A_{2B}$ receptor in an individual comprising administering an effective amount of a compound of formula (I), or a pharmaceutically acceptable salt thereof to an individual. In some embodiments a compound of formula (I) or a salt thereof is an $A_{2B}$ receptor antagonist. In some embodiments, a compound of formula (I) or a salt thereof reduces $A_{2B}$ receptor signaling by at least 10%, 20%, 30%, 40%, 50%, 60%, 70%, 80%, 90%, 91%, 92%, 93%, 94%, 95%, 96%, 97%, 98%, or 99%. In some embodiments, a compound of formula (I) or a salt thereof reduces $A_{2B}$ receptor signaling by 40-99%, 50-99%, 60-99%, 70-99%, 80-99%, 90-99%, or 95-99%. In some of these embodiments, a compound of formula (I) or a salt thereof binds to the $A_{2B}$ receptor with an $IC_{50}$ of less than 1 µM, less than 900 nM, less than 800 nM, less than 700 nM, less than 600 nM, less than 500 nM, less than 400 nM, less than 300 nM, less than 200 nM, less than 100 nM, less than 10 nM, less than 1 nM or less than 100 pM. In some embodiments, a compound of formula (I) or a salt thereof binds to the $A_{2B}$ receptor with an $IC_{50}$ of 500 nM to 100 pM, 400 nM to 100 pM, 300 nM to 100 pM, 200 nM to 100 pM, or 100 nM to 100 pM.

Also provided herein is a method of modulating the activity of an $A_3$ receptor in an individual comprising administering an effective amount of a compound of formula (I), or a pharmaceutically acceptable salt thereof to an individual. In some embodiments a compound of formula (I) or a salt thereof is an $A_3$ receptor antagonist. In some embodiments, a compound of formula (I) or a salt thereof reduces $A_3$ receptor signaling by at least 10%, 20%, 30%, 40%, 50%, 60%, 70%, 80%, 90%, 91%, 92%, 93%, 94%, 95%, 96%, 97%, 98%, or 99%. In some embodiments, a compound of formula (I) or a salt thereof reduces $A_3$ receptor signaling by 40-99%, 50-99%, 60-99%, 70-99%, 80-99%, 90-99%, or 95-99%. In some of these embodiments, a compound of formula (I) or a salt thereof binds to the $A_3$ receptor with an $IC_{50}$ of less than 1 µM, less than 900 nM, less than 800 nM, less than 700 nM, less than 600 nM, less than 500 nM, less than 400 nM, less than 300 nM, less than 200 nM, less than 100 nM, less than 10 nM, less than 1 nM or less than 100 pM. In some embodiments, a compound of formula (I) or a salt thereof binds to the $A_3$ receptor with an $IC_{50}$ of 500 nM to 100 pM, 400 nM to 100 pM, 300 nM to 100 pM, 200 nM to 100 pM, or 100 nM to 100 pM.

In some embodiments, the present invention comprises a method of inhibiting tumor metastasis in an individual in need thereof comprising administering a compound of formula (I), or a pharmaceutically acceptable salt thereof, to the individual. In some embodiments, the metastasis is to the lung, liver, lymph node, bone, adrenal gland, brain, peritoneum, muscle, or vagina. In some embodiments, a compound of formula (I) or a salt thereof inhibits metastasis of melanoma cells. In some embodiments, the present disclosure includes a method of delaying tumor metastasis comprising administering a compound of formula (I), or a pharmaceutically acceptable salt thereof, to the individual. In some of these embodiments, the time to metastatic is delayed by 1 month, 2 months 3 months, 4 months, 5 months, 6 months, 12 months, or more, upon treatment with the compounds of the present invention.

In some embodiments, a compound of formula (I) or a salt thereof is used to treat an individual having a proliferative disease, such as cancer as described herein. In some embodiments, the individual is at risk of developing a proliferative disease, such as cancer. In some of these embodiments, the individual is determined to be at risk of developing cancer based upon one or more risk factors. In some of these embodiments, the risk factor is a family history and/or gene associated with cancer. In some embodiments, the individual has a cancer that expresses a high level of a nucleotide metabolizing enzyme. In some embodiments, the nucleotide metabolizing enzyme is a nucleotidase, such as CD73 (ecto-5'-nucleotidase, Ecto5'NTase). In some of these embodiments, the individual has a cancer that expresses a high level of a nucleotidase, such as CD73. In any of these embodiments, the nucleotide metabolizing enzyme is an ecto-nucleotidase. In some embodiments, the ecto-nucleotidase degrades adenosine monophosphate. In some embodiments, the nucleotide metabolizing enzyme is CD39 (ecto-nucleoside triphosphate diphosphohydrolase 1, E-NTPDase1). In some of these embodiments, the individual has a cancer that expresses a high level of CD39. In some embodiments, the individual has a cancer that expresses a high level of an adenosine receptor, such as the $A_{2A}$ receptor.

Combination Therapy

As provided herein, the presently disclosed compounds or a salt thereof may activate the immune system by modulating the activity of a G protein coupled receptor signaling pathway, for example acting as an $A_{2A}$ receptor antagonist, which results in significant anti-tumor effects. Accordingly, the present compounds or a salt thereof may be used in combination with other anti-cancer agents to enhance tumor immunotherapy. In some embodiments, provided herein is a method of treating a disease mediated by a G protein coupled receptor signaling pathway in an individual comprising administering an effective amount of a compound of formula (I), or a pharmaceutically acceptable salt thereof, and an additional therapeutic agent to the individual. In some embodiments, the disease mediated by a G protein coupled receptor signaling pathway is a proliferative disease such as cancer.

In some embodiments, the additional therapeutic agent is a cancer immunotherapy. In some embodiments, the additional therapeutic agent is an immunostimulatory agent. In some embodiments, the additional therapeutic agent targets a checkpoint protein. In some embodiments, the additional therapeutic agent is effective to stimulate, enhance or improve an immune response against a tumor.

In another aspect, provided herein is a combination therapy in which a compound of formula (I) is coadministered (which may be separately or simultaneously) with one or more additional agents that are effective in stimulating immune responses to thereby further enhance, stimulate or upregulate immune responses in a subject. For example, provided is a method for stimulating an immune response in a subject comprising administering to the subject a compound of formula (I) or a salt thereof and one or more immunostimulatory antibodies, such as an anti-PD-1 antibody, an anti-PD-L1 antibody and/or an anti-CTLA-4 antibody, such that an immune response is stimulated in the subject, for example to inhibit tumor growth. In one embodiment, the subject is administered a compound of formula (I) or a salt thereof and an anti-PD-1 antibody. In another embodiment, provided is a method for stimulating an immune response in a subject comprising administering to the subject a compound of formula (I) or a salt thereof and one or more immunostimulatory antibodies or immunotherapy like Chimeric antigen receptor (CAR) T-cell therapy; immunostimulatory antibodies such as an anti-PD-1 antibody, an anti-PD-L1 antibody and/or an anti-CTLA-4 antibody, such that an immune response is stimulated in the subject, for example to inhibit tumor growth. In another embodiment, the subject is administered a compound of formula (I) or a salt thereof and an anti-PD-L1 antibody. In yet another embodiment, the subject is administered a compound of formula (I) or a salt thereof and an anti-CTLA-4 antibody. In another embodiment, the immunostimulatory antibody (e.g., anti-PD-1, anti-PD-L1 and/or anti-CTLA-4 antibody) is a human antibody. Alternatively, the immunostimulatory antibody can be, for example, a chimeric or humanized antibody (e.g., prepared from a mouse anti-PD-1, anti-PD-L1 and/or anti-CTLA-4 antibody). In another embodiment, the subject is administered a compound of formula (I) or a salt thereof and CAR T-cells (genetically modified T cells).

In one embodiment, the present disclosure provides a method for treating a proliferative disease (e.g., cancer), comprising administering a compound of formula (I) or a salt thereof and an anti-PD-1 antibody to a subject. In further embodiments, a compound of formula (I) or a salt thereof is administered at a subtherapeutic dose, the anti-PD-1 antibody is administered at a subtherapeutic dose, or both are administered at a subtherapeutic dose. In another embodiment, the present disclosure provides a method for altering an adverse event associated with treatment of a hyperproliferative disease with an immunostimulatory agent, comprising administering a compound of formula (I) or a salt thereof and a subtherapeutic dose of anti-PD-1 antibody to a subject. In certain embodiments, the subject is human. In certain embodiments, the anti-PD-1 antibody is a human sequence monoclonal antibody In one embodiment, the present invention provides a method for treating a hyperproliferative disease (e.g., cancer), comprising administering a compound of formula (I) or a salt thereof and an anti-PD-L1 antibody to a subject. In further embodiments, a compound of formula (I) or a salt thereof is administered at a subtherapeutic dose, the anti-PD-L1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering a compound of formula (I) or a salt thereof and a subtherapeutic dose of anti-PD-L1 antibody to a subject. In certain embodiments, the subject is human. In certain embodiments, the anti-PD-L1 antibody is a human sequence monoclonal antibody.

In certain embodiments, the combination of therapeutic agents discussed herein can be administered concurrently as a single composition in a pharmaceutically acceptable carrier, or concurrently as separate compositions each in a pharmaceutically acceptable carrier. In another embodiment, the combination of therapeutic agents can be administered sequentially. For example, an anti-CTLA-4 antibody and a compound of formula (I) or a salt thereof can be administered sequentially, such as anti-CTLA-4 antibody being administered first and a compound of formula (I) or a salt thereof second, or a compound of formula (I) or a salt thereof being administered first and anti-CTLA-4 antibody second. Additionally or alternatively, an anti-PD-1 antibody and a compound of formula (I) or a salt thereof can be administered sequentially, such as anti-PD-1 antibody being administered first and a compound of formula (I) or a salt thereof second, or a compound of formula (I) or a salt thereof being administered first and anti-PD-1 antibody second. Additionally or alternatively, an anti-PD-L1 antibody and a compound of formula (I) or a salt thereof can be administered sequentially, such as anti-PD-L1 antibody being administered first and a compound of formula (I) or a salt thereof second, or a compound of formula (I) or a salt thereof being administered first and anti-PD-L1 antibody second.

Furthermore, if more than one dose of the combination therapy is administered sequentially, the order of the sequential administration can be reversed or kept in the same order at each time point of administration, sequential administrations can be combined with concurrent administrations, or any combination thereof.

Optionally, the combination of a compound of formula (I) or a salt thereof can be further combined with an immunogenic agent, such as cancerous cells, purified tumor antigens (including recombinant proteins, peptides, and carbohydrate molecules), cells, and cells transfected with genes encoding immune stimulating cytokines.

A compound of formula (I) or a salt thereof can also be further combined with standard cancer treatments. For example, a compound of formula (I) or a salt thereof can be effectively combined with chemotherapeutic regimes. In these instances, it is possible to reduce the dose of other chemotherapeutic reagent administered with the combination of the instant disclosure (Mokyr et al. (1998) *Cancer Research* 58: 5301-5304). Other combination therapies with a compound of formula (I) or a salt thereof include radiation, surgery, or hormone deprivation. Angiogenesis inhibitors can also be combined with a compound of formula (I) or a salt thereof. Inhibition of angiogenesis leads to tumor cell death, which can be a source of tumor antigen fed into host antigen presentation pathways.

In another example, a compound of formula (I) or a salt thereof can be used in conjunction with anti-neoplastic antibodies. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or a compound of formula (I) or a salt thereof. In an exemplary embodiment, a treatment of a hyperproliferative disease (e.g., a cancer tumor) can include an anti-cancer antibody in combination with a compound of formula (I) or a salt thereof and anti-CTLA-4 and/or anti-PD-1 and/or anti-PD-L1 antibodies, concurrently or sequentially or any combination thereof, which can potentiate anti-tumor immune responses by the host. Other antibodies that can be used to activate host immune responsiveness can be further used in combination with a compound of formula (I) or a salt thereof.

In some embodiments, a compound of formula (I) or a salt thereof can be combined with an anti-CD73 therapy, such as an anti-CD73 antibody.

In some embodiments, a compound of formula (I) or a salt thereof can be combined with an anti-CD39 therapy, such as an anti-CD39 antibody.

In yet further embodiments, a compound of formula (I) or a salt thereof is administered in combination another G protein receptor antagonist, such as an adenosine $A_1$ and/or $A_3$ antagonist.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal. A compound provided herein can be administered frequently at low doses, known as 'metronomic therapy,' or as part of a maintenance therapy using compound alone or in combination with one or more additional drugs. Metronomic therapy or maintenance therapy can comprise administration of a compound provided herein in cycles. Metronomic therapy or maintenance therapy can comprise intra-tumoral administration of a compound provided herein.

In one aspect, the invention provides a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal.

The invention also provides compositions (including pharmaceutical compositions) as described herein for the use in treating, preventing, and/or delaying the onset and/or development of cancer and other methods described herein. In certain embodiments, the composition comprises a pharmaceutical formulation which is present in a unit dosage form.

Also provided are articles of manufacture comprising a compound of the disclosure or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed.

Kits

The present disclosure further provides kits for carrying out the methods of the invention, which comprises one or more compounds described herein or a composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein (e.g., hypertension) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting.

EXAMPLES

Synthetic Examples

Example S1. Synthesis of 4-(5-amino-3-phenylpyrazin-2-chlorophenol (Compound No. 1.1)

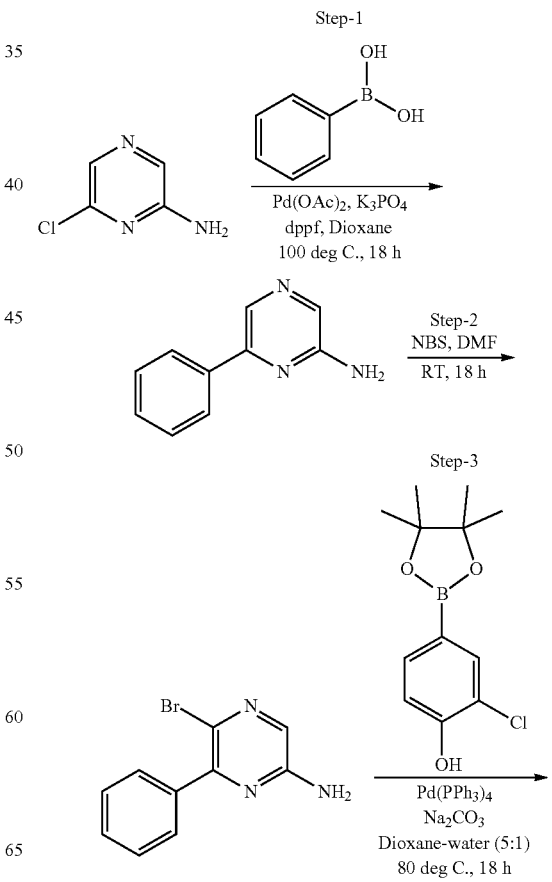

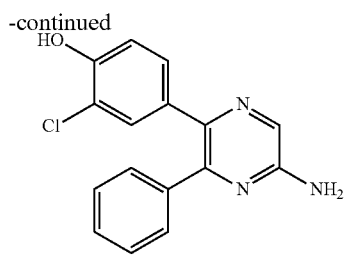

Step-1 Synthesis of 6-phenylpyrazin-2-amine

To a solution of 6-chloropyrazin-2-amine (1.00 g, 7.75 mmol, 1 eq.) in 1,4-dioxane (30 mL) was added phenylboronic acid (1.42 g, 11.62 mmol, 1.5 eq.), $K_3PO_4$ (3.286 g, 15.50 mmol, 2 eq.), $Pd(OA_C)_2$ (0.086 g, 0.38 mmol, 0.05 eq.), 1,1'-bis(diphenylphosphino)ferrocene (0.214 g, 0.38 mmol, 0.05 eq.). The reaction mixture was deoxygenated using $N_2$ atmosphere and the reaction mixture was heated at 100° C. overnight. The reaction was monitored by TLC and LCMS and found to be complete after 18 h. The reaction mixture was cooled to RT, filtered through Celite-bed and washed with ethyl acetate (2×20 mL). The reaction mixture was diluted with water (50 mL) and extracted with ethyl acetate (2×50 mL). The separated organic layer was dried over sodium sulfate and concentrated under reduced pressure. The crude product was purified by CombiFlash on silica gel using $CH_3OH$—$CH_2Cl_2$ system as eluent to afford 1.10 g (63%) of 6-phenylpyrazin-2-amine. LC/MS: 172 $[M+1]^+$.

Step-2: Synthesis of 5-bromo-6-phenylpyrazin-2-amine

To a solution of 6-phenylpyrazin-2-amine (0.150 g, 0.877 mmol, 1 eq.) in DMF (3 mL) was added N-bromosuccinimide (0.156 g, 0.877 mmol, 1 eq.) and the reaction mixture was stirred at RT for 1 h. The reaction was monitored by TLC and NMR. After completion, the reaction mixture was diluted with water (50 mL) and extracted by ethyl acetate (2×20 mL). Combined organic layer was washed with water (5×20 mL) followed by brine and dried over anhydrous sodium sulfate. The solvent was evaporated under reduced pressure to get the crude product which was purified by CombiFlash on silica gel using EtOAc-Hexane system as eluent to afford 100 mg (46%) of 5-bromo-6-phenylpyrazin-2-amine. LC/MS: 251 $[M+1]^+$.

Step-3: Synthesis of 4-(5-amino-3-phenylpyrazin-2-yl)-2-chlorophenol

To a solution of 5-bromo-6-phenylpyrazin-2-amine (100 mg, 0.4 mmol, 1 eq.) in 1,4-dioxane-water (6 mL, 5:1) was added 2-chloro-4-(4,4,5,5-tetramethyl-1,3,2-dioxaborolan-2-yl)phenol[1] (121 mg, 0.48 mmol, 1.2 eq.), $Na_2CO_3$ (84 mg, 0.8 mmol, 2 eq.), $Pd(PPh_3)_4$ (23 mg, 0.02 mmol, 0.05 eq.). The reaction mixture was deoxygenated using $N_2$ atmosphere and the reaction mixture was allowed to stir at 80° C. overnight. The reaction was monitored by NMR and LCMS and found to be complete after 18 h. The reaction mixture was cooled to RT, diluted with water (50 mL) and extracted with EtOAc (3×50 mL). Combined organic layer was washed with brine (50 mL) and dried over sodium sulfate. Removal of solvent under reduced pressure gave crude which was purified by SFC to afford 20 mg (17%) of 4-(5-amino-3-phenylpyrazin-2-yl)-2-chlorophenol LC/MS: 298 $[M+1]^+$. $^1H$ NMR (400 MHz, DMSO-$d_6$) δ 7.90 (s, 1H), 7.45 (s, 4H), 7.20 (s, 1H), 6.90 (d, 1H), 7.78 (d, 1H), 6.58 (s, 2H).

Reference: WO2014/209034 A1.

Example S2. Synthesis of 4-(5-amino-3-phenylpyrazin-2-yl)-2,6-dichlorophenol (Compound No. 1.2)

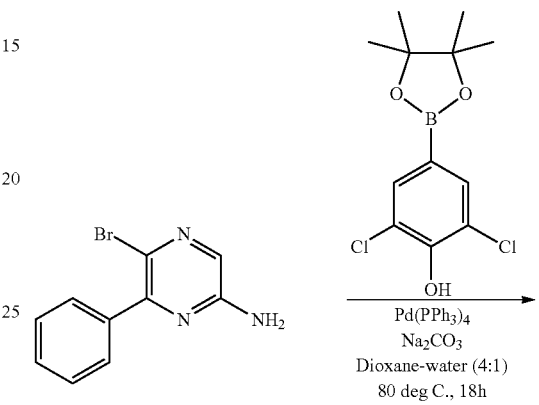

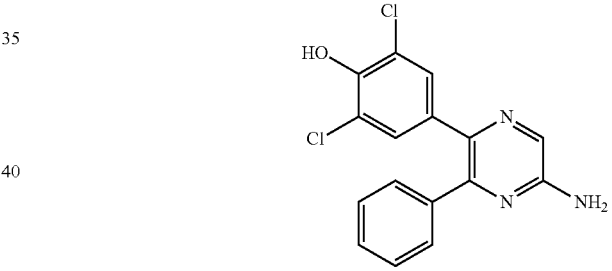

To a solution of 5-bromo-6-phenylpyrazin-2-amine (100 mg, 0.40 mmol, 1 eq.) in 1,4-dioxane-water (10 mL, 4:1) was added 2,6-dichloro-4-(4,4,5,5-tetramethyl-1,3,2-dioxaborolan-2-yl)phenol (174 mg, 0.48 mmol, 1.2 eq.), $Cs_2CO_3$ (391 mg, 1.20 mmol, 3.0 eq.), $PdCl_2(dppf)CH_2Cl_2$ complex (32 mg, 0.04 mmol, 0.05 eq.). The reaction mixture was deoxygenated using $N_2$ atmosphere and the reaction mixture was allowed to stir at 80° C. overnight. The progress of reaction was monitored by TLC and LCMS and found to be complete after 18 h. The reaction mixture was cooled to RT, diluted with water (50 mL) and extracted using ethyl acetate (3×50 mL). Combined organic layer was washed with brine (50 mL) and dried over sodium sulfate. Removal of solvent under reduced pressure gave crude which was purified by SFC to afford 15 mg (11 of 4-(5-amino-3-phenylpyrazin-2-yl)-2,6-dichlorophenol. LCMS: 332 $[M+1]^+$. $^1H$ NMR (400 MHz, DMSO-$d_6$) δ 6.28 (s, 2H), 6.64 (s, 1H), 7.10 (s, 2H), 7.38 (s, 4H), 7.90 (s, 1H).

Example S3. Synthesis of N-(5-(3-chloro-4-hydroxyphenyl)-6-phenylpyrazin-2-yl)acetamide (Compound No. 1.3)

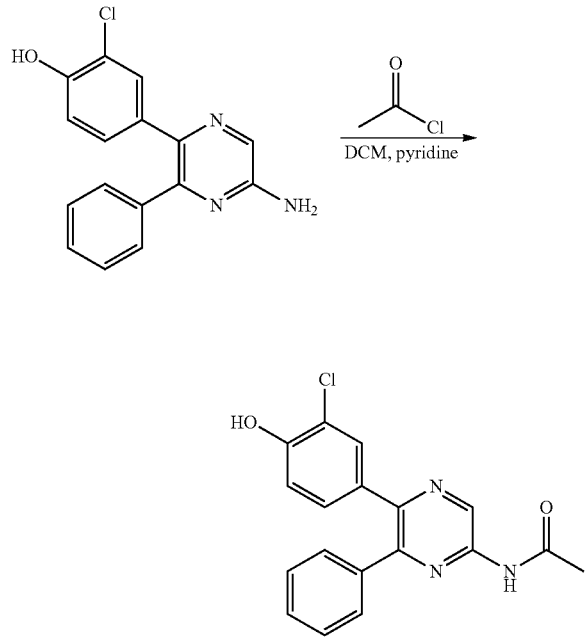

To a solution of 4-(5-amino-3-phenylpyrazin-2-yl)-2-chlorophenol (200 mg, 0.67 mmol, 1.0 eq) in $CH_2Cl_2$ (20 mL) was added pyridine (79 mg, 1.01 mmol, 1.5 eq) and acetyl chloride (78 mg, 1.01 mmol, 1.5 eq). The reaction mixture was allowed to stir at room temperature overnight. Progress of reaction was monitored by TLC and LCMS and found to be complete after for 18 h. The reaction mixture was diluted with water (20 mL) and extracted with ethyl acetate (3×30 mL). The combined organic layer was washed with brine (30 mL) and dried over sodium sulfate. Removal of solvent under reduced pressure gave crude which was purified by reversed phase column chromatography to afford 10 mg (4%) of N-(5-(3-chloro-4-hydroxyphenyl)-6-phenylpyrazin-2-yl)acetamide.

LCMS: 340 [M+1]$^+$.

Example S4. Synthesis of 5-(1H-indol-5-yl)-6-phenylpyrazin-2-amine (Compound No 1.4)

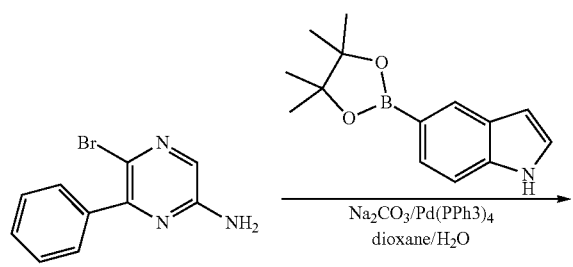

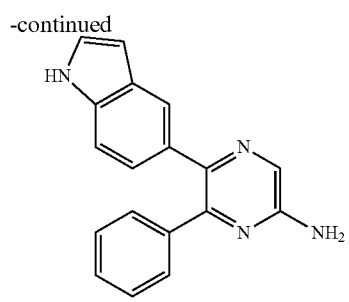

To a solution of 5-bromo-6-phenylpyrazin-2-amine (100 mg, 0.4 mmol, 1 eq.) in 1,4 dioxane (5 mL): water (1 mL) was added 5-(4,4,5,5-tetramethyl-1,3,2-dioxaborolan-2-yl)-1H-indole (77 mg, 0.48 mmol, 1.2 eq.), $Na_2CO_3$ (84 mg, 0.8 mmol, 2 eq.), Pd(PPh3)$_4$ (23 mg, 0.02 mmol, 0.05 eq.). The reaction mixture was deoxygenated using $N_2$ atmosphere and the reaction mixture was heated at 80° C. for 18 h. The reaction was monitored by NMR and LCMS. The reaction mixture was diluted with water (50 mL) and extracted using ethyl acetate (2×50 mL). The separated organic layer was dried over sodium sulfate and concentrated under reduced pressure. The crude product was purified by Supercritical Fluid Chromatography to afford 5-(6-amino-3-pyridyl)-6-phenyl-pyrazin-2-amine (20 mg, 17.8%) as white solid.

LCMS: 287.1 (M+1)$^+$.

$^1$HNMR (400 MHz, DMSO-d$_6$) 11.00 s (1H), 7.98 s (1H), 7.62 s (1H), 7.59-7.18 m (7H), 6.95d (1H), 6.40 d (2H), 6.35 s (1H).

Example S5. Synthesis of 4-(5-amino-3-phenylpyrazin-2-yl)-2-tert-butylphenol. (Compound No. 1.6)

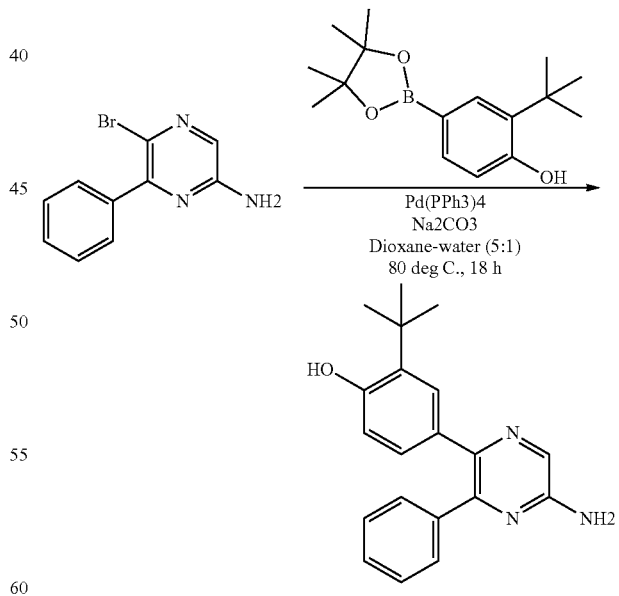

To a solution of 5-bromo-6-phenylpyrazin-2-amine (100 mg, 0.4 mmol, 1 eq.) in 1,4-dioxane-water (6 mL, 5:1) was added 2-tert-butyl-4-(4,4,5,5-tetramethyl-1,3,2-dioxaborolan-2-yl)phenol (132 mg, 0.48 mmol, 1.2 eq.), $Na_2CO_3$ (84 mg, 0.8 mmol, 2 eq.), (PdCl$_2$(PPh$_3$)$_2$ (14 mg, 0.02 mmol, 0.05 eq.). The reaction mixture was deoxygenated with $N_2$ and the reaction mixture was stirred at 80° C. overnight. The reaction was monitored by NMR and LCMS and found to be complete after 18 h. The reaction mixture was cooled to RT, diluted with water (50 mL) and extracted with ethyl acetate (2×50 mL). Combined organic layer was washed with brine (20 mL) and dried over sodium sulfate. Removal of solvent under reduced pressure gave crude which was purified by SFC to afford 4-(5-amino-3-phenyl-pyrazin-2-yl)-2-tert-butyl-phenol (20 mg, 15.7%) as white solid.

LCMS: 320.2 [M+1]+. 1HNMR (400 MHz, DMSO-d6) 9.36 (s, 1H), 7.95 (s, 1H), 7.40-7.23 (m, 5H), 7.15 (d, 1H), 6.80 (s, 1H), 6.63 (d, 1H), 6.40 (s, 2H), 1.03 (s, 9H).

Example S6. Synthesis of 4-(5-amino-3-phenylpyrazin-2-yl)phenol. (Compound No. 1.7)

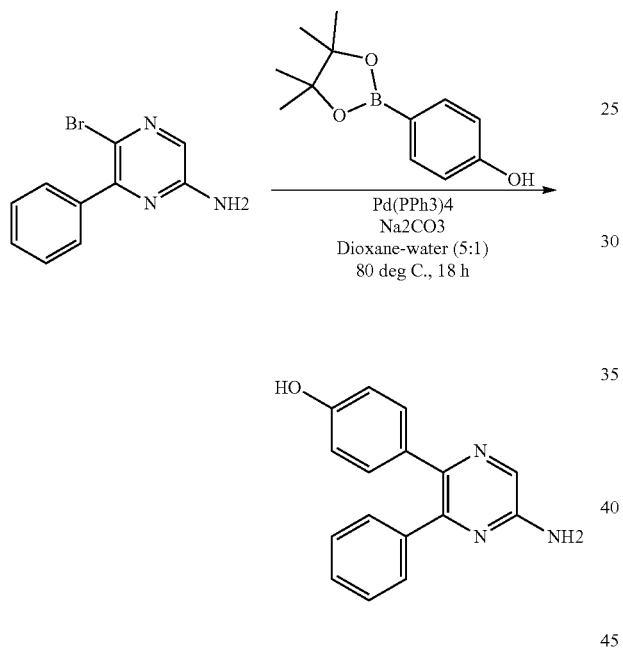

To a solution of 5-bromo-6-phenylpyrazin-2-amine (100 mg, 0.4 mmol, 1 eq.) in 1,4-dioxane-water (6 mL, 5:1) was added 4-(4,4,5,5-tetramethyl-1,3,2-dioxaborolan-2-yl)phenol (105.6 mg, 0.48 mmol, 1.2 eq.), $Na_2CO_3$ (84 mg, 0.8 mmol, 2 eq.), $PdCl_2(PPh_3)_2$ (15 mg, 0.02 mmol, 0.05 eq.). The reaction mixture was deoxygenated with $N_2$ and the reaction mixture was stirred at 80° C. overnight. The reaction was monitored by NMR and LCMS and found to be complete after 18 h. The reaction mixture was cooled to RT, diluted with water (50 mL) and extracted with ethyl acetate (2×50 mL). Combined organic layer was washed with brine (20 mL) and dried over sodium sulfate. Removal of solvent under reduced pressure gave crude which was purified by SFC to afford 4-(5-amino-3-phenyl-pyrazin-2-yl) phenol (35 mg, 33.33%) as white solid.

LCMS: 264.1 [M+1]+. 1H NMR (400 MHz, DMSO-d6): δ 9.40 (brs, 1H), 7.98 (s, 1H), 7.40-7.20 (m, 5H), 7.00 (d, 2H), 6.60 (d, 2H), 6.20 (s, 1H).

Example S7. Synthesis of 4-(5-amino-3-(furan-2-yl)pyrazin-2-yl)-2-chlorophenol. (Compound No. 1.8)

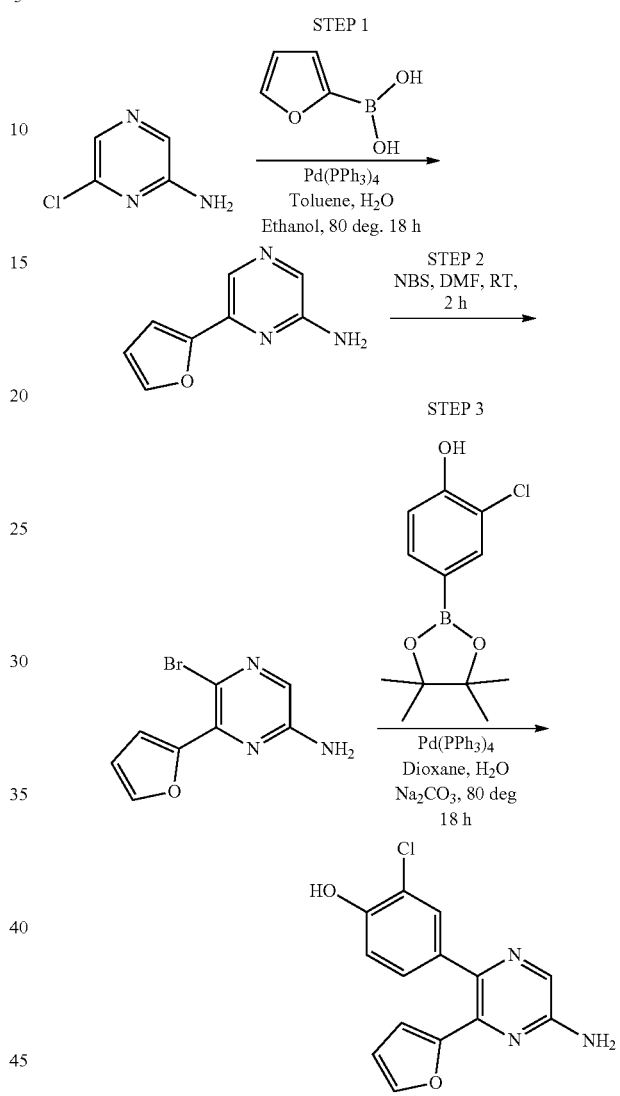

Step-1 Synthesis of 6-(furan-2-yl)pyrazin-2-amine

To a solution of 6-chloropyrazin-2-amine (1.00 g, 7.75 mmol, 1 eq.) in a solution of toluene and ethanol (20 mL, 1:1) was added furan-2-ylboronic acid (0.955 g, 8.52 mmol, 1.1 eq.), $Na_2CO_3$ (1.479 g, 13.95 mmol, 1.8 eq.) in $H_2O$ (10 mL), $Pd(PPh_3)_4$ (0.223 g, 0.193 mmol, 0.025 eq.). The reaction mixture was deoxygenated using $N_2$ atmosphere and the reaction mixture was heated at 100° C. for 18 h. The reaction was monitored by NMR. The reaction mixture was filtered through Celite with wash of ethyl acetate (2×20 mL). The reaction mixture was diluted with water (50 mL) and extracted using ethyl acetate (2×50 mL). The separated organic layer was dried over sodium sulfate and concentrated under reduced pressure. The crude product was purified by CombiFlash on silica gel to afford 1.00 g (80%) of 6-(furan-2-yl)pyrazin-2-amine.

Step-2 Synthesis of
5-bromo-6-(furan-2-yl)pyrazin-2-amine

To a solution of 6-(furan-2-yl)pyrazin-2-amine (0.200 g, 1.24 mmol, 1 eq.) in DMF (4 mL) was added N-bromosuccinimide (0.222 g, 1.24 mmol, 1 eq.). The reaction mixture was stirred at room temperature for 2 h. The reaction was monitored by TLC and NMR. The reaction mixture was diluted with water (50 mL) and extracted by ethyl acetate (2×20 mL). The organic layer was separated, washed with water (5×20 mL) followed by brine and dried over anhydrous sodium sulfate. The solvent was evaporated under reduced pressure to get the crude product. The crude product was purified by CombiFlash on silica gel to afford 70 mg (30%) of 5-bromo-6-(furan-2-yl)pyrazin-2-amine.

Step-3 Synthesis of 4-(5-amino-3-(furan-2-yl)pyrazin-2-yl)-2-chlorophenol

To a solution of 5-bromo-6-(furan-2-yl)pyrazin-2-amine (70 mg, 0.29 mmol, 1 eq.) in a solution of 1,4-dioxane and water (7 mL, 6:1) was added 2-chloro-4-(4,4,5,5-tetramethyl-1,3,2-dioxaborolan-2-yl)phenol (89 mg, 0.35 mmol, 1.2 eq.), Na$_2$CO$_3$ (62 mg, 0.585 mmol, 2 eq.), Pd(PPh$_3$)$_4$ (8 mg, 0.007 mmol, 0.025 eq.). The reaction mixture was deoxygenated using N$_2$ atmosphere and the reaction mixture was heated at 80° C. for 18 h. The reaction was monitored by NMR and LCMS. The reaction mixture was diluted with water (50 mL) and extracted using ethyl acetate (2×50 mL). The separated organic layer was dried over sodium sulfate and concentrated under reduced pressure. The crude product was purified by SFC to afford 30 mg (36%) of 4-(5-amino-3-(furan-2-yl)pyrazin-2-yl)-2-chlorophenol.

LCMS: 288 [M+1]$^+$ $^1$H NMR (400 MHz, CD$_3$OD) δ 6.42 (d, 1H), 6.50 (d, 1H), 6.60-6.64 (m, 2H), 6.90 (d, 1H), 7.00-7.02 (d, 1H), 7.20 (d, 1H), 6.60-6.62 (s, 1H), 7.85 (s, 1H), 10.20 (bs, 1H).

Example S8. Synthesis of 5-(2-methyl-1H-benzo[d]imidazol-5-yl)-6-phenylpyrazin-2-amine (compound 1.9)

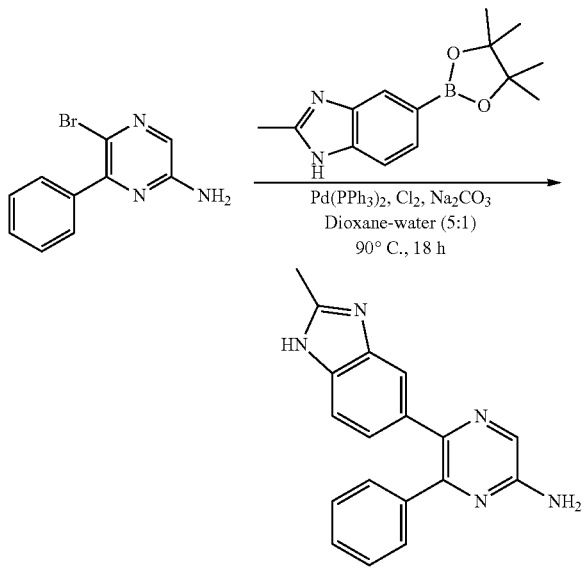

To a solution of 5-bromo-6-phenylpyrazin-2-amine (100 mg, 0.4 mmol, 1 eq.) in 1,4-dioxane-water (6 mL, 5:1) was added 2-methyl-5-(4,4,5,5-tetramethyl-1,3,2-dioxaborolan-2-yl)-1H-benzo[d]imidazole (124 mg, 0.48 mmol, 1.2 eq.), Na$_2$CO$_3$ (84 mg, 0.8 mmol, 2 eq.) and PdCl$_2$(PPh$_3$)$_2$ (14 mg, 0.02 mmol, 0.05 eq.). The reaction mixture was deoxygenated with N$_2$ and the reaction mixture was stirred at 90° C. overnight. The reaction was monitored by NMR and LCMS and found to be complete after 18 h. The reaction mixture was cooled to RT, diluted with water (50 mL) and extracted with ethyl acetate (2×50 mL). Combined organic layers were washed with brine (20 mL) and dried over sodium sulfate. Removal of solvent under reduced pressure gave crude which was purified by SFC to afford the desired product as white solid. (20 mg 16.6%)

LCMS: 302.0 [M+1]$^+$

1H NMR (400 MHz, DMSO-d6) δ 12.08 (d, J=18.42 Hz, 1H), 7.94 (s, 1H), 7.30-7.25 (m, 6H), 6.96-7.10 (m, 1H), 6.49 (d, J=9.65 Hz, 2H), 2.43 (s, 3H)

Example S9. Synthesis of 5-(1H-benzo[d]imidazol-6-yl)-6-phenylpyrazin-2-amine. (Compound No. 1.10)

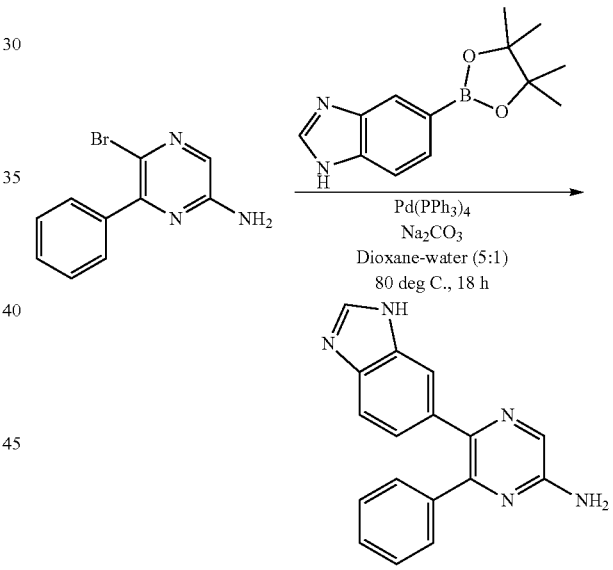

To a solution of 5-bromo-6-phenylpyrazin-2-amine (100 mg, 0.4 mmol, 1 eq.) in 1,4-dioxane-water (6 mL, 5:1) was added 5-(4,4,5,5-tetramethyl-1,3,2-dioxaborolan-2-yl)-1H-benzimidazole (124 mg, 0.48 mmol, 1.2 eq.), Na$_2$CO$_3$ (84 mg, 0.8 mmol, 2 eq.), (PdCl$_2$(PPh$_3$)$_2$ (14 mg, 0.02 mmol, 0.05 eq.). The reaction mixture was deoxygenated with N$_2$ and the reaction mixture was stirred at 80° C. overnight. The reaction was monitored by NMR and LCMS and found to be complete after 18 h. The reaction mixture was cooled to RT, diluted with water (50 mL) and extracted with ethyl acetate (2×50 mL). Combined organic layer was washed with brine (20 mL) and dried over sodium sulfate. Removal of solvent under reduced pressure gave crude which was purified by Reverse phase column chromatography to afford 5-(3H-benzimidazol-5-yl)-6-phenyl-pyrazin-2-amine (20 mg, 18.18%) as white solid.

LCMS: 288.1 [M+1]⁺. ¹HNMR (400 MHz, DMSO-d₆) 12.40 (s, 1H), 8.18 (s, 1H), 8.00 (s, 1H), 7.65 (s, 1H), 7.40-7.20 (m, 5H), 7.00 (s, 1H), 6.50 (s, 2H).

Example S10. Synthesis of 5-(5-amino-3-phenylpyrazin-2-yl)-2-hydroxybenzonitrile. Compound No. 1.11)

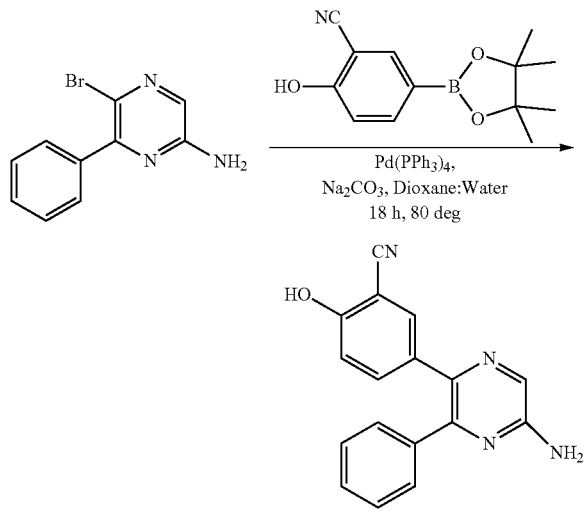 [SMILES: Nc1cnc(Br)c(-c2ccccc2)n1 ; CC1(C)OB(c2ccc(O)c(C#N)c2)OC1(C)C ; N#Cc1cc(-c2ncc(N)nc2-c2ccccc2)ccc1O]

To a solution of 4-benzyl-5-bromopyrimidin-2-amine (100 mg, 0.40 mmol, 1 eq.) in 1,4-dioxane-water (10 mL, 5:1) was added 2-hydroxy-5-(4,4,5,5-tetramethyl-1,3,2-dioxaborolan-2-yl)benzonitrile (107 mg, 0.44 mmol, 1.2 eq.), Na₂CO₃ (84 mg, 0.80 mmol, 2.0 eq.), Pd(PPh₃)₄ (11 mg, 0.01 mmol, 0.025 eq.). The reaction mixture was deoxygenated using N₂ atmosphere and the reaction mixture was heated at 90° C. for 18 h. The reaction was monitored by NMR and LCMS. The reaction mixture was diluted with water (50 mL) and extracted using ethyl acetate (2 X⁵⁰ mL). The separated organic layer was dried over sodium sulfate and concentrated under reduced pressure. The crude product was purified by CombiFlash on silica gel to afford 10 mg (11%) of 5-(5-amino-3-phenylpyrazin-2-yl)-2-hydroxybenzonitrile.

LCMS: 289 [M+1]⁺. ¹H NMR (400 MHz, CD₃OD) δ 6.80 (d, 1H), 7.32-7.50 (m, 7H), 8.20 (s, 1H).

Example S11. Synthesis of 6-phenyl-5-(quinolin-6-yl)pyrazin-2-amine. (Compound No. 1.12)

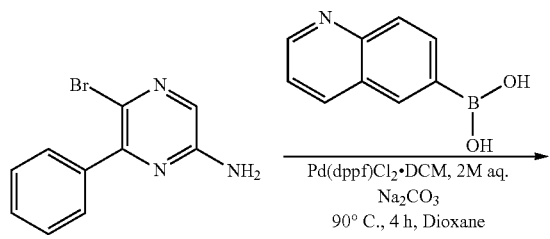

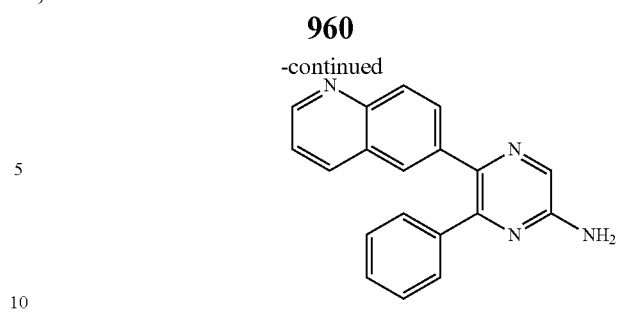

To a stirred solution of quinolin-6-ylboronic acid (0.100 g, 0.57 mmol, 1.2 equiv) and 5-bromo-6-phenylpyrazin-2-amine (0.120 g, 0.48 mmol, 1.0 equiv) in dioxane (3 mL) was added 2M aqueous Na₂CO₃ (0.101 g, 0.96 mmol, 2.0 equiv, 0.5 mL). The reaction was purged with N₂ for 5 min. To this reaction mixture was added Pd(dppf)Cl₂.DCM (0.020 g, 5 mol %) and N₂ was purged again for 5 more mins. The reaction mixture was heated at 90° C. for 4 h. The reaction mixture was allowed to cool to RT and extracted using ethyl acetate (2×35 mL). The combined organic layers were washed (brine), dried (anhydrous Na₂SO₄) and concentrated under vacuum to get the solid residue which was purified by normal phase silica gel flash column chromatography to get the desired product as off white solid (0.030 g, 21%)

LCMS: 299 (M+1)⁺. ¹H NMR (400 MHz, DMSO-d₆) δ 8.84 (d, J=2.93 Hz, 1H), 8.22 (d, J=8.31 Hz, 1H), 8.01 (s, 1H), 7.92 (s, 1H), 7.80 (d, J=8.80 Hz, 1H), 7.42-7.60 (m, 2H), 7.20-7.41 (m, 4H), 6.73 (s, 2H).

Example S12. Synthesis of 5-(7-chloro-1H-benzo[d]imidazol-5-yl)-6-phenylpyrazin-2-amine (Compound No. 1.13)

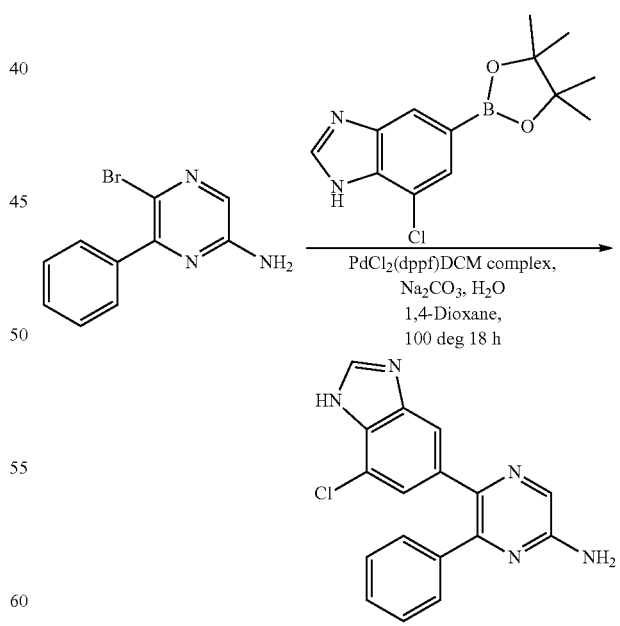

To a solution of 5-bromo-6-phenylpyrazin-2-amine (120 mg, 0.48 mmol, 1 eq.) in 1,4-dioxane (8 mL): water (2 mL) was added 7-chloro-5-(4,4,5,5-tetramethyl-1,3,2-dioxaborolan-2-yl)-1H-benzo[d]imidazole (146 mg, 0.52 mmol, 1.2 eq.), Na₂CO₃ (101 mg, 0.96 mmol, 2 eq.), PdCl₂(dppf)

•DCM complex (19 mg, 0.024 mmol, 0.05 eq.). The reaction mixture was deoxygenated using $N_2$ atmosphere and the reaction mixture was heated at 80° C. for 18 h. The reaction was monitored by NMR and LCMS. The reaction mixture was diluted with water (30 mL) and extracted using ethyl acetate (2×50 mL). The separated organic layer was dried over sodium sulfate and concentrated under reduced pressure. The crude product was purified by reverse phase column chromatography to afford 15 mg (8%) of 5-(7-chloro-1 benzo[d]imidazol-5-yl)-6-phenylpyrazin-2-amine.

LCMS: 322 [M+1]+. 1H NMR (400 MHz, DMSO) δ 6.60-6.80 (bs, 2H) 7.22-7.38 (m, 6H), 7.40 (s, 1H), 7.98 (s, 1H), 8.68 (bs, 1H).

Example S13. Synthesis of 3-bromo-6-phenyl-5-(quinolin-6-yl)pyrazin-2-amine. (Compound No. 1.14)

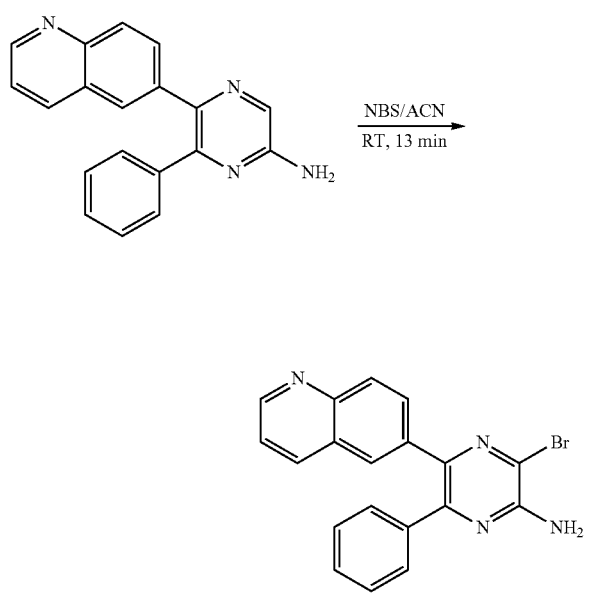

To a solution of 6-phenyl-5-(quinolin-6-yl)pyrazin-2-amine (20 mg, 0.068 mmol, 1 eq.) in acetonitrile (12 mL) at room temperature was added N-bromosuccinimide (12 mg, 0.068 mmol, 1 eq.) portion wise and the reaction mixture was allowed to stir at room temperature. Progress of reaction was monitored by TLC and was found to be complete after 13 minutes. Reaction mixture was diluted with water and extracted with ethyl acetate (3×20 mL). Combined organic layer was washed with water (3×20 mL) and dried over anhydrous sodium sulfate. Removal of solvent gave crude which was purified by reversed phase HPLC to give 10 mg (40%) 3-bromo-6-phenyl-5-(quinolin-6-yl)pyrazin-2-amine.

LCMS: 377 [M+1]+. 1H NMR (400 MHz, DMSO-d6) δ 7.05 (brs, 2H), 7.25-7.40 (m, 5H), 7.45-7.55 (m, 2H), 7.62 (d, 1H), 7.97 (s, 1H), 8.30 (d, 1H), 8.87 (s, 1H).

Example S14. Synthesis of 6-(4-fluorophenyl)-5-(quinolin-6-yl)pyrazin-2-amine. (Compound No. 1.15)

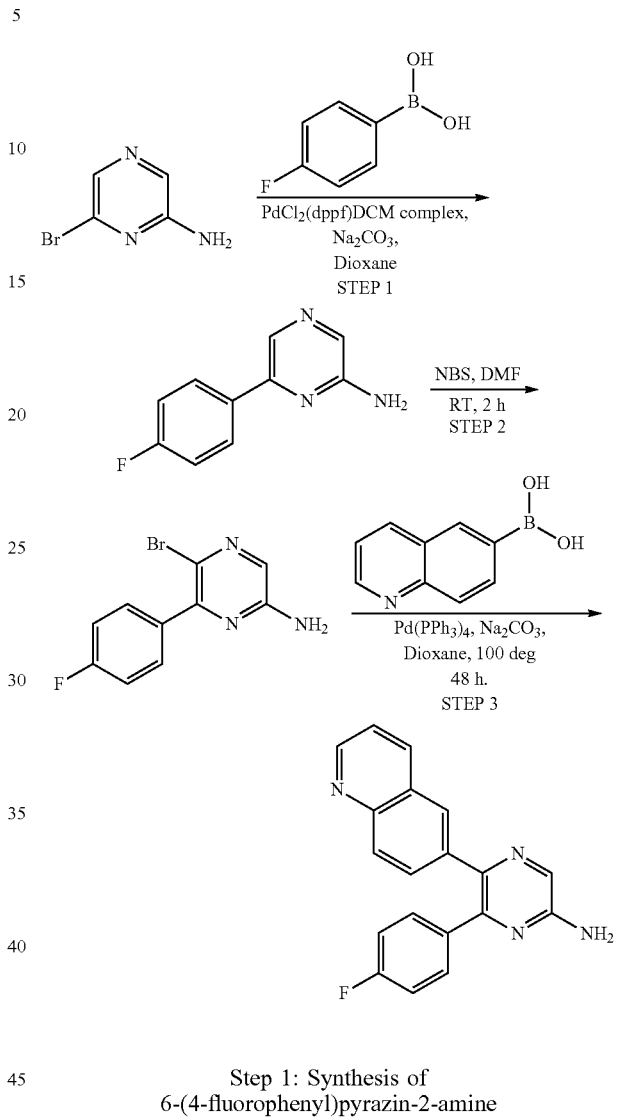

Step 1: Synthesis of 6-(4-fluorophenyl)pyrazin-2-amine

To a solution of 6-bromopyrazin-2-amine (1.00 g, 5.780 mmol, 1 eq.) in 1,4 dioxane (20 mL) was added 4-fluorophenylboronic acid (1.213 g, 8.67 mmol, 1.5 eq.), $Na_2CO_3$ (1.225 g, 11.56 mmol, 2 eq.) and $PdCl_2$(dppf)•DCM complex (0.235 g, 0.289 mmol, 0.05 eq.). The reaction mixture was deoxygenated using $N_2$ atmosphere and the reaction mixture was heated at 100° C. for 48 h. The reaction was monitored by NMR. The reaction mixture was filtered through Celite with wash of ethyl acetate (2×50 mL). The reaction mixture was diluted with water (50 mL) and extracted using ethyl acetate (2×50 mL). The separated organic layer was dried over sodium sulfate and concentrated under reduced pressure. The crude product was purified by Combi-Flash column chromatography to afford 550 mg (50%) of 6-(4-fluorophenyl)pyrazin-2-amine.

Step 2: Synthesis of 5-bromo-6-(4-fluorophenyl)pyrazin-2-amine

To a solution of 6-(4-fluorophenyl)pyrazin-2-amine (0.530 g, 2.80 mmol, 1 eq.) in mixture of DMF (5 mL) was added N-bromosuccinimide (0.549 g, 3.08 mmol, 1 eq.). The reaction mixture was stirred at room temperature for 1 h. The reaction was monitored by TLC and NMR. The reaction was diluted with water (50 mL) and extracted by ethyl acetate (2×50 mL). The organic layer was separated, washed water (5×50 mL) and brine and dried over anhydrous sodium sulfate. The solvent was evaporated under reduced pressure to get the crude product. The crude product was purified by Combi-Flash column chromatography to afford 250 mg (32%) of 5-bromo-6-(4-fluorophenyl)pyrazin-2-amine.

Step 3: Synthesis of 6-(4-fluorophenyl)-5-(quinolin-6-yl)pyrazin-2-amine

To a solution of 5-bromo-6-(4-fluorophenyl)pyrazin-2-amine (100 mg, 0.37 mmol, 1 eq.) in 1,4 dioxane (8 mL): water (2 mL) was added quinolin-6-ylboronic acid (77 mg, 0.44 mmol, 1.2 eq.), $Na_2CO_3$ (79 mg, 0.74 mmol, 2 eq), $Pd(PPh_3)_4$ (21 mg, 0.018 mmol, 0.05 eq.). The reaction mixture was deoxygenated using $N_2$ atmosphere and the reaction mixture was heated at 100° C. for 48 h. The reaction was monitored by TLC and LCMS. The reaction mixture was diluted with water (20 mL) and extracted using ethyl acetate (2×50 mL). The separated organic layer was dried over sodium sulfate and concentrated under reduced pressure. The crude product was purified by supercritical fluid chromatography to afford 45 mg (38%) of 6-(4-fluorophenyl)-5-(quinolin-6-yl)pyrazin-2-amine.

LCMS: 317 $[M+1]^+$. $^1$H NMR (400 MHz, DMSO-$d_6$) δ 6.58 (bs, 2H), 7.30 (t, 2H), 7.60 (q, 1H), 8.02-8.20 (m, 4H), 8.40-8.50 (m, 2H), 8.60 (s, 1H), 8.98 (bs, 1H).

Example S15. Synthesis of 6-phenyl-5-quinoxalin-6-yl-pyrazin-2-amine. (Compound No. 1.16)

Step 1: Synthesis of quinoxalin-6-ylboronic acid

To a solution of 6-bromoquinoxaline (500 mg, 2.39 mmol, 1 eq.) in 1,4-dioxane (10 mL) was added 5-(4,4,5,5-Bis(pinacolato)diboron (729 mg, 2.87 mmol, 1.2 eq.), KOAc (469 mg, 4.78 mmol, 2 eq.), and $PdCl_2dppf$•DCM complex (195 mg, 0.23 mmol, 0.1 eq.). The reaction mixture was deoxygenated with $N_2$ allowed stir at 80° C. for 18 h. The reaction mixture was cooled to RT, diluted with water (50 mL) and extracted with ethyl acetate (2×50 mL). Combined organic layer was washed with brine (20 mL) and dried over sodium sulfate. Removal of solvent under reduced pressure gave crude which was purified by normal phase Combi-flash column chromatography (0-100% EtOAC-Hexane) to afford quinoxalin-6-ylboronic acid (350 mg, 85%) as brown oil.

LCMS: 175 $[M+1]^+$

Step 2: Synthesis of 6-phenyl-5-quinoxalin-6-yl-pyrazin-2-amine

To a solution of 5-bromo-6-phenyl-pyrazin-2-amine (100 mg, 0.40 mmol, 1 eq.) in DME-water (2 mL) was added quinoxalin-6-yl boronic acid (69.6 mg, 0.40 mmol, 1 eq.), $Na_2CO_3$ (106 mg, 1.0 mmol, 2.5 eq.), and $Pd(PPh_3)_4$ (13.86 mg, 0.01 mmol, 0.03 eq.). The reaction mixture was deoxygenated with $N_2$ and allowed stir at 120° C. for 30 min under Microwave irradiation. The reaction was monitored by LCMS and found to be complete after 30 min. The reaction mixture was cooled to RT, diluted with water (20 mL) and extracted with ethyl acetate (2×50 mL). Combined organic layer was washed with brine (20 mL) and dried over sodium sulfate. Removal of solvent under reduced pressure gave crude which was purified by reversed phase column chromatography to afford 6-phenyl-5-quinoxalin-6-yl-pyrazin-2-amine (10 mg, 8%) as a white solid.

LCMS: 300 $[M+1]^+$. $^1$H NMR (400 MHz, DMSO-$d_6$): δ 8.56 (s, 2H), 8.00 (s, 1H), 7.98-7.80 (m, 2H), 7.65 (m, 1H), 7.40-7.20 (m, 5H), 6.80 (s, 2H).

Example S16. Synthesis of 5-(8-chloroquinolin-6-yl)-6-phenylpyrazin-2-amine. (Compound No. 1.17)

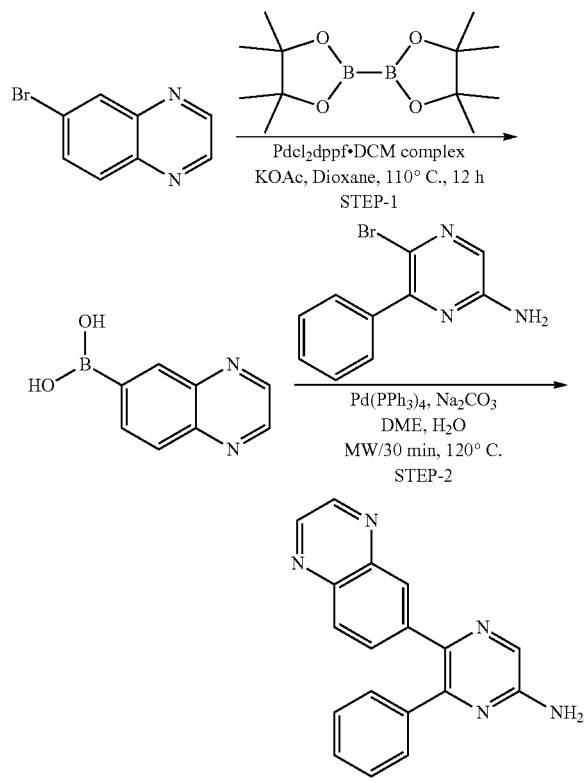

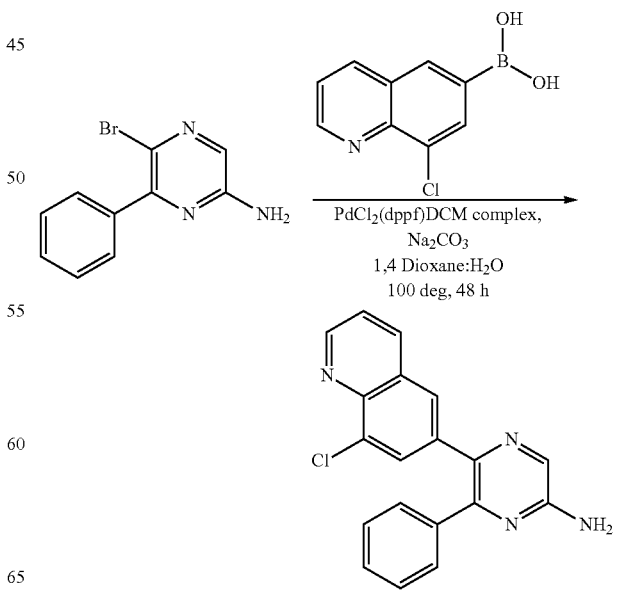

To a solution of 5-bromo-6-phenylpyrazin-2-amine (100 mg, 0.4 mmol, 1 eq.) in 1,4 dioxane (5 mL): water (1 mL) was added 8-chloroquinolin-6-ylboronic acid (99 mg, 0.48 mmol, 1.2 eq.), $Na_2CO_3$ (84 mg, 0.8 mmol, 2 eq.), and $PdCl_2$(dppf)•DCM (16 mg, 0.02 mmol, 0.05 eq.). The reaction mixture was deoxygenated using $N_2$ atmosphere and the reaction mixture was heated at 80° C. for 18 h. The reaction was monitored by NMR and LCMS. The reaction mixture was diluted with water (50 mL) and extracted using ethyl acetate (2×50 mL). The separated organic layer was dried over sodium sulfate and concentrated under reduced pressure. The crude product was purified by Supercritical Fluid Chromatography to afford 10 mg of 5-(8-chloroquinolin-6-yl)-6-phenylpyrazin-2-amine, LCMS: 333 [M+1]$^+$. $^1$H NMR (400 MHz, DMSO-d$_6$) δ 7.30-7.40 (m, 5H), 7.60 (m, 1H), 7.70 (s, 1H), 7.88 (s, 1H), 8.00 (s, 1H), 8.30 (d, 1H), 8.98 (d, 1H).

Example S17. Synthesis of 5-(benzo[d]oxazol-5-yl)-6-phenylpyrazin-2-amine. (Compound No. 1.18)

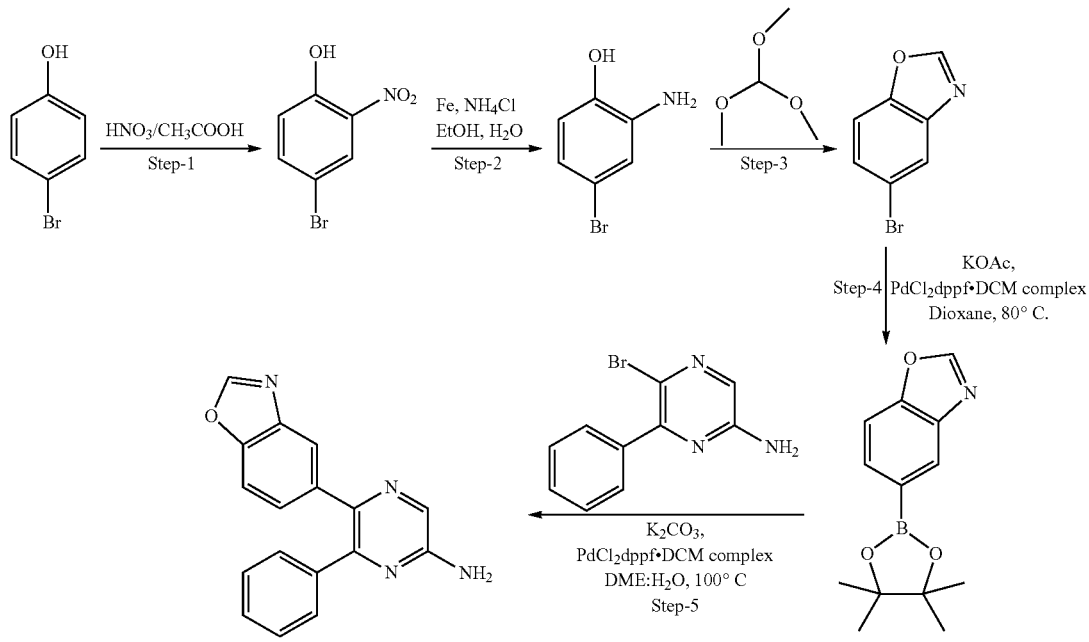

Step 1: Synthesis of 4-bromo-2-nitrophenol

To a solution of 6-bromophenol (5 g, 28.90 mmol, 1 eq.) in acetic acid (10 mL) was added nitric acid (1 mL) drop wise. Reaction mixture was stirred at RT for 5 min. Progress of the reaction was monitored by LCMS and TLC. The reaction mixture was poured over ice, resulting in solid precipitates which were filtered and dried under vacuum to afford 4-bromo-2-nitrophenol (6 g, 95.23%) as yellow solid. LCMS: 175 [M+1]$^+$ Step 2: Synthesis of 2-amino-4-bromophenol To a solution of 4-bromo-2-nitrophenol (3 g, 13.76 mmol, 1 eq.) in ethanol:water (50 mL, 9:1) was added ammonium chloride (2.1 g, 41.28 mmol, 3 eq.) and Iron powder(2.3 g, 41.28 mmol). The reaction was stirred at 90° C. for 2 h. Progress of the reaction was monitored by LCMS. The reaction mixture was cooled to RT, evaporated under reduced pressure to remove the solvent, diluted with water (20 mL) and extracted with ethyl acetate (2×50 mL). The combined organic layer was washed with brine (20 mL) and dried over anhydrous sodium sulfate. Removal of solvent under reduced pressure gave crude material which was purified by flash chromatography to obtain the 2-amino-4-bromophenol (2 g, 80%) as brown solid.

LCMS: 188, 190 [M+1]$^+$

Step 3: Synthesis of 5-bromobenzo[d]oxazole

A solution 2-amino-4-bromophenol (1.5, 7.90 mmol, 1 eq.) in methylorthoformate (10 mL) was stirred at 150° C. for 6 h. Progress of the reaction was monitored by LCMS. The reaction mixture was cooled to RT, evaporated under reduced pressure to remove the solvent; diluted with water (20 mL) and extracted with ethyl acetate (2×50 mL). The combined organic layer was washed with brine (20 mL) and dried over anhydrous sodium sulfate. Removal of solvent under reduced pressure gave crude material which was purified by flash chromatography to obtain the 5-bromobenzo[d]oxazole (1.2 g, 80.0%) as yellow solid.

$^1$HNMR (400 MHz, DMSO-d$_6$) 8.80 (s, 1H), 8.00 (s, 1H), 7.80 (d, 1H), 7.60 (d, 1H).

Step 4: Synthesis of 5-(4,4,5,5-tetramethyl-1,3,2-dioxaborolan-2-yl)benzo[d]oxazole To a solution of 5-bromobenzo[d]oxazole (1.2 g, 6.06 mmol, 1 eq.) in DMF (10 mL) was added 5-(4,4,5,5-Bis(pinacolato)diboron (1.68 g, 1.66 mmol, 1.1 eq.), KOAc (1.7 g, 18.09 mmol, 3 eq.), and $PdCl_2$(dppf)•DCM complex (247 mg, 0.23 mmol, 0.05 eq.). The reaction mixture was deoxygenated with $N_2$ and the reaction mixture was stirred at 80° C. for 18 h. The progress of the reaction was monitored by LCMS. The reaction mixture was cooled to RT, diluted with water (50 mL) and extracted with ethyl acetate (2×50 mL). Combined organic layer was washed with brine (20 mL) and dried over sodium sulfate. Removal of solvent under reduced pressure gave crude which was purified by flash chromatography(0-100% Hexane-EtOAc) to afford 5-(4,4,5,5-tetramethyl-1,3,2-dioxaborolan-2-yl)benzo[d]oxazole (0.900 g, 60%) as off white solid. LCMS: 245, 247 [M+1]+

Step 5: Synthesis of 5-(benzo[d]oxazol-5-yl)-6-phenylpyrazin-2-amine

To a solution of 5-bromo-6-phenylpyrazin-2-amine (100 mg, 0.40 mmol, 1 eq) in dioxane-water (5:1 mL) was added 5-(4,4,5,5-tetramethyl-1,3,2-dioxaborolan-2-yl)benzo[d]oxazole (122 mg, 0.48 mmol, 1.2 eq), Na$_2$CO$_3$ (84.8 mg, 0.80 mmol, 2.0 eq), and PdCl$_2$(dppf)•DCM complex (16.32 mg, 0.02 mmol, 0.05 eq.). The reaction mixture was deoxygenated with N$_2$ and stirred at 100° C. for 12 h. The progress of the reaction was monitored by LCMS. The reaction mixture was cooled to RT, diluted with water (20 mL) and extracted with ethyl acetate (2×50 mL). Combined organic layer was washed with brine (20 mL) and dried over anhydrous sodium sulfate. Removal of solvent under reduced pressure gave crude material which was purified by reversed-phase column chromatography to afford 5-(benzo[d]oxazol-5-yl)-6-phenylpyrazin-2-amine (10 mg, 9.00%) as an off white solid.

LCMS: 289.1 (M+1). $^1$HNMR (400 MHz, DMSO-d$_6$) 8.70 (s, 1H), 8.50 (s, 1H), 7.72-7.56 (m, 2H), 7.40-7.20 (m, 6H), 6.60 (s, 2H).

Example S18A. Synthesis of 3-amino-5-phenyl-6-(quinolin-6-yl)pyrazine-2-carbonitrile (Compound No. 1.19)

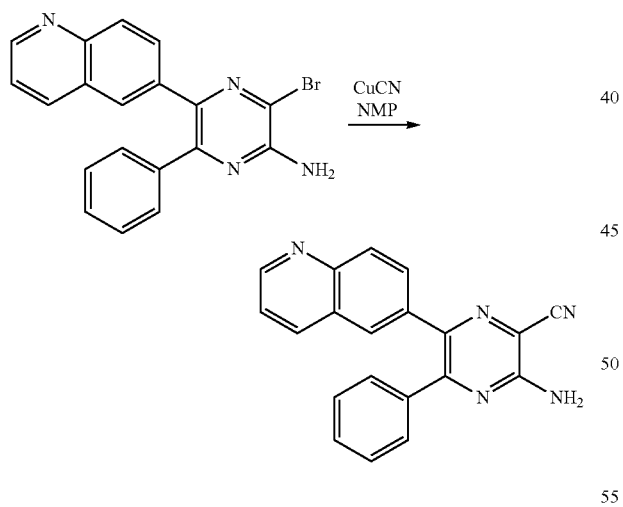

To a stirred solution of 6-phenyl-5-(quinolin-6-yl)pyrazin-2-amine (0.220 g, 0.58 mmol, 1.0 eq) in NMP (1.5 mL) was added cuprous cyanide (0.155 g, 1.74 mmol, 3.0 eq). The reaction mixture was allowed to stir at 170° C. for 1 h. The progress of the reaction was monitored by LCMS. The reaction mixture was allowed to cool to RT and extracted using ethyl acetate (3×50 mL). The combined organic layers were washed (brine), dried (anhydrous Na$_2$SO$_4$) and concentrated under vacuum to get the solid which was purified by normal phase column chromatography to get the desired product as an off white solid (0.020 g, 10%).

LCMS: 324 (M+1)$^+$. $^1$H NMR (400 MHz, METHANOL-d$_4$) δ 8.83 (d, J=3.07 Hz, 1H), 8.25 (d, J=7.45 Hz, 1H), 7.95 (d, J=2.19 Hz, 1H), 7.88 (d, J=8.77 Hz, 1H), 7.65 (dd, J=2.19, 8.77 Hz, 1H), 7.52 (dd, J=4.38, 8.33 Hz, 1H), 7.40-7.47 (m, 2H), 7.36 (d, J=7.45 Hz, 1H), 7.22-7.32 (m, 2H).

Example S18B. Alternative synthesis of 3-amino-5-phenyl-6-(quinolin-6-yl)pyrazine-2-carbonitrile. (Compound No. 1.19)

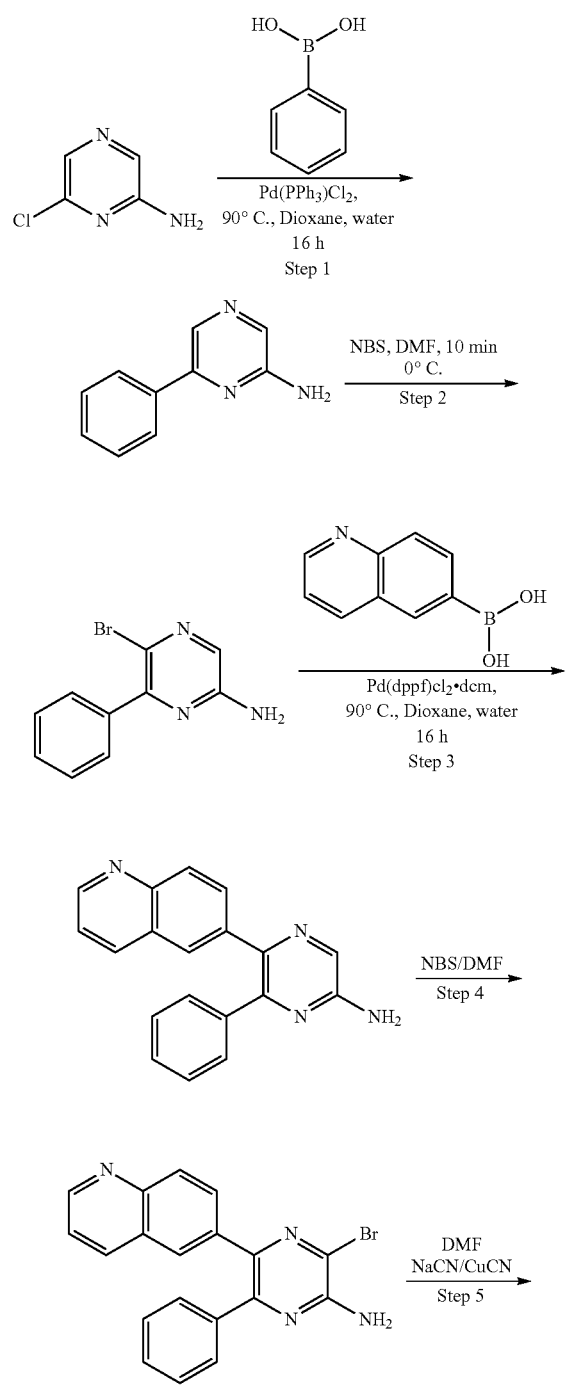

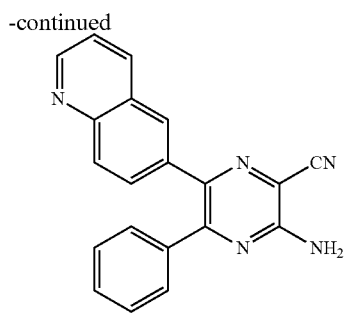

Step 1: Synthesis of 6-phenylpyrazin-2-amine: To a stirred solution of 6-chloropyrazin-2-amine (50 g, 0.3861 mol) in dioxane:water (400 mL; 100 mL) was added benzeneboronic acid (56.4 g, 0.46 mol). The reaction mixture was purged with nitrogen for 20 min then charged Na$_2$CO$_3$ (70.6 g, 0.57 mol) and Pd(PPh$_3$)Cl$_2$ (13.5 g, 0.01930 mol). The reaction mixture was again purged with nitrogen. The reaction mixture was stirred at RT for 10 min followed by heating at 90° C. for 16 h. The reaction was monitored by TLC & LCMS. The reaction mixture was filter through celite and distilled. The reaction was diluted with water and extracted with ethyl acetate (3×200 mL). The combined organic layers were washed (brine), dried (anhydrous Na$_2$SO$_4$) & concentrated under vacuum to get the solid which was purified by column chromatography over silica gel (100-200 mesh) [Ethyl acetate: Hexane (3:7) as eluent] to get the desired product (55 g, 83%).

LCMS: 172 [M+1]$^+$. $^1$H NMR (400 MHz, CHLOROFORM-d) δ 8.38 (s, 1H), 7.83-7.99 (m, 3H), 7.40-7.49 (m, 3H), 4.82 (br. s., 2H)

Step 2: Synthesis of 5-bromo-6-phenylpyrazin-2-amine: To a stirred solution of 6-phenylpyrazin-2-amine (48 g, 0.2803 mol) in DMF was added NBS (49.9 g, 0.28 mol) at 0° c. under nitrogen atmosphere. The reaction mixture was stirred at RT for 16 h. The reaction was monitored by TLC & LCMS. The reaction was diluted with water and extracted with ethyl acetate (3×100 mL). The combined organic layers were washed (brine), dried (anhydrous Na$_2$SO$_4$) & concentrated under vacuum to get the solid which was purified by column chromatography silica gel (100-200 mesh) [Ethyl acetate: Hexane (1:4) as eluent] to get the desired product (38 g, 55%).

LCMS: 252 [M+2]$^+$. $^1$H NMR (400 MHz, DMSO-d$_6$) δ 7.68 (s, 1H), 7.55-7.64 (m, 2H), 7.40-7.51 (m, 3H), 6.75 (br. s., 2H)

Step 3: synthesis of 6-phenyl-5-(quinolin-6-yl)pyrazin-2-amine: To a stirred solution of 5-bromo-6-phenylpyrazin-2-amine (38 g, 0.1519 mol) in dioxane:water (320 mL; 80 mL) was added quinolin-6-ylboronic acid (46.4 g, 0.18 mol). The reaction mixture was purged with nitrogen for 20 min then charged with Na$_2$CO$_3$ (32.2 g, 0.3038 mol) and Pd(dppf)Cl$_2$ (6.19 g, 0.007 mol). The reaction mixture was again purged with nitrogen. The reaction mixture was stirred at RT for 10 min followed by heating at 90° C. for 16 h. The reaction was monitored by TLC & LCMS. The reaction mixture was filtered through celite and distilled. The reaction was diluted with water and extracted with ethyl acetate (3×200 mL). The combined organic layers were washed (brine), dried (anhydrous Na$_2$SO$_4$) & concentrated under vacuum to get the solid which was purified by column chromatography over basic alumina [Ethyl acetate: Hexane (3:7) as eluent] to get the desired product (31 g, 68%).

LCMS: 299 [M+1]$^+$. $^1$H NMR (400 MHz, DMSO-d6) δ 8.83 (d, J=3.07 Hz, 1H), 8.21 (d, J=7.89 Hz, 1H), 8.02 (s, 1H), 7.93 (s, 1H), 7.80 (d, J=8.33 Hz, 1H), 7.41-7.64 (m, 2H), 7.16-7.40 (m, 5H), 6.73 (s, 2H)

Step 4: synthesis of 3-bromo-6-phenyl-5-(quinolin-6-yl)pyrazin-2-amine: To a stirred solution of 6-phenyl-5-(quinolin-6-yl) pyrazin-2-amine (21 g, 0.07 mol) in DMF was added NBS (12.5 g, 0.07 mol) at 0° c. under nitrogen atmosphere. The reaction mixture was stir at RT for 16 h. The reaction was monitored by TLC & LCMS. The reaction was diluted with water and extracted with ethyl acetate (3×30 mL). The combined organic layers were washed (brine), dried (anhydrous Na$_2$SO$_4$) & concentrated under vacuum to get the solid which was purified by column chromatography over basic alumina [Ethyl acetate: Hexane (3:7) as eluent] to get the desired product (18 g, 69%).

LCMS: 377 [M+1]$^+$. $^1$H NMR (400 MHz, CHLOROFORM-d) δ 8.88 (br. s., 1H), 8.11-7.96 (m, 3H), 7.60-7.26 (m, 7H), 5.23 (br. s., 2H).

Step 5: Synthesis of 3-amino-5-phenyl-6-(quinolin-6-yl)pyrazine-2-carbonitrile: To a stirred solution of NaCN (1.56 g, 0.03 mol) and CuCN (5.7 g, 0.06 mol) in dry DMF (150 mL) was added 3-bromo-6-phenyl-5-(quinolin-6-yl)pyrazin-2-amine (12.0 g, 0.03 mol) at 120° C. The reaction mixture was stirred at 145° C. for 12 h. The reaction was monitored by TLC & LCMS. The reaction was distilled. The crude product was poured in ice-water the solid precipitate out. The reaction mixture pH was adjusted with aqueous ammonia and extracted with ethyl acetate (3×100 mL). The combined organic layers were washed (brine), dried (anhydrous Na$_2$SO$_4$) & concentrated under vacuum to get the solid which was purified by column chromatography using basic alumina [Ethyl acetate: Hexane (1:1) as eluent] to get the desired product (3.8 g, 34%). LCMS: 354 [M+1]$^+$. $^1$H NMR (400 MHz, DMSO-d$_6$) δ 8.88 (d, J=2.63 Hz, 1H), 8.29 (d, J=7.89 Hz, 1H), 7.99 (s, 1H), 7.84 (d, J=8.77 Hz, 1H), 7.58 (br. s., 2H), 7.47-7.54 (m, 2H), 7.35-7.42 (m, 3H), 7.27-7.34 (m, 2H)

Example S19. Synthesis of 6-(5-methylfuran-2-yl)-5-(quinolin-6-yl)pyrazin-2-amine. (Compound No. 1.20)

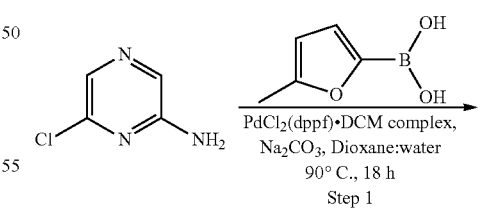

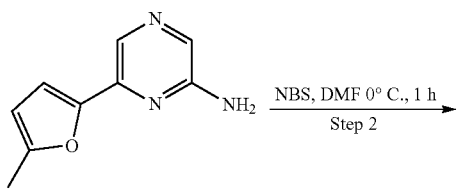

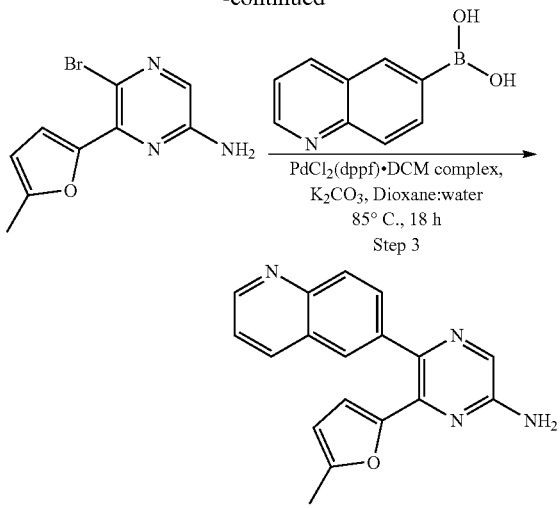

and PdCl$_2$(dppf)•DCM complex (16 mg, 0.019 mmol, 0.05 eq.). The reaction mixture was deoxygenated using N$_2$ atmosphere and the reaction mixture was heated at 100° C. for 18 h. The reaction was monitored by NMR and LCMS. The reaction mixture was diluted with water (50 mL) and extracted using ethyl acetate (2×50 mL). The separated organic layer was dried over anhydrous sodium sulfate and concentrated under reduced pressure. The crude product was purified by supercritical fluid chromatography to afford 6-(5-methylfuran-2-yl)-5-(quinolin-6-yl)pyrazin-2-amine (0.020 g, 16.80%).

LCMS: 303 [M+1]$^+$. $^1$H NMR (400 MHz, DMSO-d$_6$) δ 2.03 (s, 3H), 6.12 (s, 1H), 6.20 (s, 1H), 6.70 (bs, 2H), 7.50 (d, 1H), 7.64 (d, 1H), 7.90 (s, 1H), 7.99 (d, 1H), 8.00 (s, 1H), 8.38 (d, 1H), 8.90 (d, 1H).

Example S20. Synthesis of 5-(8-chloroquinolin-6-yl)-6-(5-methylfuran-2-yl)pyrazin-2-amine (Compound No. 1.21)

Step 1: Synthesis of 6-(5-methylfuran-2-yl)pyrazin-2-amine

To a solution of 6-chloropyrazin-2-amine (1.00 g, 7.75 mmol, 1 eq.) in 1,4-dioxane (20 mL) was added 5-methylfuran-2-ylboronic acid (1.074 g, 8.52 mmol, 1.1 eq.), Na$_2$CO$_3$ (1.23 g, 11.62 mmol, 1.5 eq.), and PdCl$_2$(dppf) •DCM complex (0.316 g, 0.38 mmol, 0.05 eq.). The reaction mixture was deoxygenated using N$_2$ atmosphere and the reaction mixture was heated at 90° C. for 18 h. The progress of the reaction was monitored by LCMS. The reaction mixture was filtered through Celite and washed with ethyl acetate (2×20 mL). The filtrate was diluted with water (50 mL) and extracted using ethyl acetate (2×50 mL). The separated organic layer was dried over sodium sulfate and concentrated under reduced pressure. The crude product was purified by flash column chromatography to afford 6-(5-methylfuran-2-yl)pyrazin-2-amine (0.600 g, 43%). LCMS: 176 [M+1]$^+$

Step 2: Synthesis of 5-bromo-6-(5-methylfuran-2-yl)pyrazin-2-amine

To a solution of 6-(5-methylfuran-2-yl)pyrazin-2-amine (300 mg, 1.69 mmol, 1 eq.) in DMF (5 mL) was added NBS (301 mg, 1.69 mmol, 1 eq.) portion-wise at 0° C. The reaction mixture was stirred at 0° C. for 1 h. The reaction was monitored by TLC and NMR. The reaction was diluted with water (50 mL) and extracted by ethyl acetate (2×20 mL). The organic layer was separated, washed with water (5×20 mL) and brine and dried over anhydrous sodium sulfate. The solvent was evaporated under reduced pressure to get the crude product. The crude product was purified by flash column chromatography to afford 5-bromo-6-(5-methylfuran-2-yl)pyrazin-2-amine (0.100 g, 22%).

LCMS: 254 [M+1]$^+$

Step 3: Synthesis of 6-(5-methylfuran-2-yl)-5-(quinolin-6-yl)pyrazin-2-amine To a solution of 5-bromo-6-(5-methylfuran-2-yl)pyrazin-2-amine (100 mg, 0.39 mmol, 1 eq.) in 1,4-dioxane (8 mL): water (1 mL) was added quinolin-6-ylboronic acid (74 mg, 0.43 mmol, 1.2 eq.), K$_2$CO$_3$ (81 mg, 0.59 mmol, 1.5 eq.),

Step-1: Synthesis of 6-chloro-5-iodopyrazin-2-amine

To a stirred solution of 2-amino-6-chloropyrazine (2.0 g, 1.0 eq., 15.50 mmol) in acetonitrile (20 mL) was added NIS (3.46 g, 1.0 eq., 15.50 mmol) at 0° C. The reaction was allowed to stir at RT. Progress of the reaction was monitored by TLC and LCMS. After completion of the reaction the solvent was evaporated under vacuum and the solid was extracted using ethyl acetate (3×100 mL). The combined organic layers were washed (brine), dried (anhydrous Na$_2$SO$_4$) and concentrated under vacuum to get the solid which was purified by normal phase column chromatography to get the desired product (1.7 g, 42%).

LCMS: 256 [M+1]$^+$

Step-2: Synthesis of 6-chloro-5-(8-chloroquinolin-6-yl)pyrazin-2-amine

To a stirred solution of 6-chloro-5-iodopyrazin-2-amine (0.500 g, 1.95 mmol, 1.0 eq.) and (8-chloroquinolin-6-yl)boronic acid (0.487 g, 2.3 mmol, 1.2 eq.) in 1,4-dioxane (4.0 mL) was added sodium carbonate (0.307 g, 2.9 mmol, 1.5 eq.) and 1 mL of water. The reaction mixture was purged with nitrogen and Pd(dppf)Cl$_2$•DCM complex (0.084 g, 0.05 eq.) was added. The reaction mixture was again purged with nitrogen and heated at 85° C. for 16 h. Progress of the reaction was monitored by TLC and LCMS. Reaction mixture was allowed to cool to RT and extracted using ethyl acetate (3×50 mL). The combined organic layers were washed (brine), dried (anhydrous Na$_2$SO$_4$) and concentrated under vacuum to get the solid which was purified by normal phase column chromatography to get the desired product (0.140 g, 25%).

LCMS: 291 [M+1]$^+$

Step-3: Synthesis of 5-(8-chloroquinolin-6-yl)-6-(5-methylfuran-2-yl)pyrazin-2-amine To a stirred solution of 6-chloro-5-(8-chloroquinolin-6-yl)pyrazin-2-amine (0.100 g, 0.34 mmol, 1.0 eq.) and (5-methylfuran-2-yl)boronic acid (0.051 g, 0.41 mmol, 1.2 eq.) in 1,4-dioxane (3.0 mL) was added sodium carbonate (0.054 g, 0.54 mmol, 1.5 eq.) and 1 mL of water. The reaction mixture was purged with nitrogen and Pd(dppf)Cl$_2$•DCM complex (0.014 g, 0.05 eq.) was added. The reaction mixture was again purged with nitrogen and heated at 85° C. for 16 h. Progress of the reaction was monitored by TLC and LCMS. Reaction mixture was allowed to cool to RT and extracted using ethyl acetate (3×25 mL). The combined organic layers were washed (brine), dried (anhydrous Na$_2$SO$_4$) and concentrated under vacuum to get the solid which was purified by normal phase column chromatography to get the desired product (0.025 g, 14%). LCMS: 337 [M+1]$^+$. $^1$H NMR (400 MHz, DMSO-d$_6$) δ 9.00 (br. s., 1H), 8.45 (d, J=7.89 Hz, 1H), 8.01 (br. s., 1H), 7.90 (s, 1H), 7.83 (br. s., 1H), 7.65 (br. s., 1H), 6.80 (br. s., 2H), 6.38 (br. s., 1H), 6.14 (br. s., 1H), 2.08 (s, 3H).

Example S21. Synthesis of 6-(1H-pyrazol-1-yl)-5-(quinolin-6-yl)pyrazin-2-amine (Compound No. 1.22)

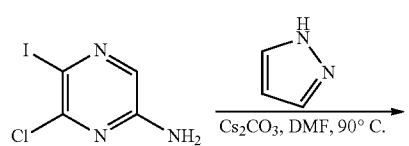

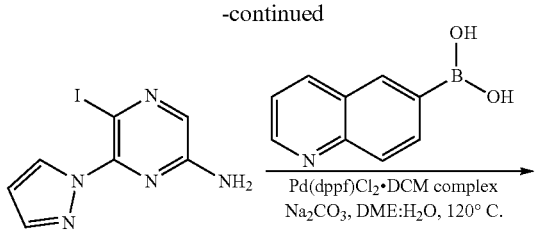

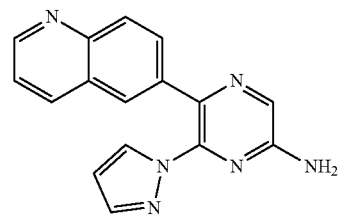

Step 1: Synthesis of 5-iodo-6-(1H-pyrazol-1-yl)pyrazin-2-amine

To a solution of 6-chloro-5-iodopyrazin-2-amine (300 mg, 1.2 mmol, 1 eq.) in DMF (8 mL) was added pyrazole (159 mg, 2.3 mmol, 2.0 eq.) and Cs$_2$CO$_3$ (1.148 g, 3.5 mmol, 3.0 eq.). The reaction mixture was allowed to heat at 90° C. for 18 h. The progress of the reaction was monitored by TLC and LCMS. The reaction mixture was diluted with water (30 mL) and extracted using ethyl acetate (2×50 mL). The separated organic layer was dried over sodium sulfate and concentrated under reduced pressure. The crude product was purified by reverse phase column chromatography to afford the desired product (120 mg, 35%).

LCMS: 288 [M+1]$^+$

Step 2: Synthesis of 6-(1H-pyrazol-1-yl)-5-(quinolin-6-yl)pyrazin-2-amine

To a solution of 5-iodo-6-(1H-pyrazol-1-yl)pyrazin-2-amine (0.100 g, 0.34 mmol, 1 eq.) in DME (4.0 mL) was added boronic acid (0.071 g, 0.41 mmol, 1.2 eq.), Na$_2$CO$_3$ (0.047 g, 0.45 mmol, 1.3 eq.) and PdCl$_2$(dppf)•DCM complex (0.014 g, 0.017 mmol, 0.05 eq.). The reaction mixture was deoxygenated using N$_2$ atmosphere and the reaction mixture was heated at 120° C. for 1.5 h under microwave irradiation. The reaction was monitored by TLC and LCMS. The reaction mixture was filtered through Celite. The filtrate was extracted with ethyl acetate (2×25 mL). The separated organic layer was dried over anhydrous sodium sulphate and concentrated under reduced pressure. The crude product was purified by reverse phase column chromatography to afford desired product (13 mg, 13%).

LCMS 289 [M+1]$^+$. $^1$H NMR (400 MHz, DMSO-d6) δ 8.84 (d, J=2.63 Hz, 1H), 8.23 (d, J=8.33 Hz, 1H), 8.12 (s, 1H), 8.07 (d, J=2.19 Hz, 1H), 7.74-7.84 (m, 2H), 7.56 (s, 1H), 7.49 (dd, J=4.17, 8.11 Hz, 1H), 7.30 (d, J=7.02 Hz, 1H), 7.07 (s, 1H), 6.47 (br. s., 1H).

Example S22. Synthesis of 3-amino-5-phenyl-6-(quinolin-6-yl)pyrazin-2-ol (Compound No. 1.241)

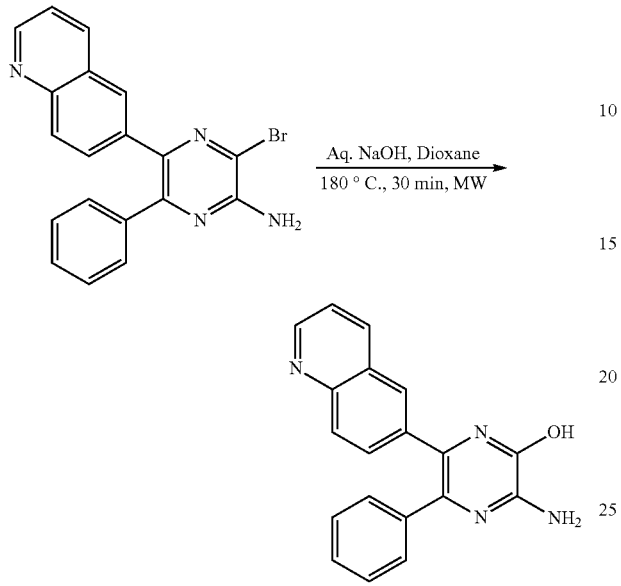

To a stirred solution of 3-bromo-6-phenyl-5-(quinolin-6-yl)pyrazin-2-amine (0.050 g, 0.13 mmol, 1.0 eq) in dioxane (1 mL) was added 10% aqueous NaOH solution (1 mL). The resulting reaction mixture was heated at 180° C. for 30 min under microwave irradiation. The reaction mixture was allowed to cool to RT. The solvent was evaporated under vacuum to get the solid which was purified by reversed phase column chromatography to get the desired product as yellowish green solid (0.018 g, 45%).

LCMS: 315 (M+1)$^+$. $^1$H NMR: (400 MHz, DMSO-d$_6$) δ 11.96 (br. s., 1H), 8.88 (s, 1H), 8.28 (d, J=7.45 Hz, 1H), 7.93 (br. s., 1H), 7.82 (d, J=8.77 Hz, 1H), 7.52 (d, J=3.95 Hz, 1H), 7.40 (d, J=9.21 Hz, 1H), 6.99-7.28 (m, 5H), 6.84 (br. s., 2H).

Example S23. Synthesis of 5-(7-chloro-1H-benzimidazol-5-yl)-6-(5-methylfuran-2-yl)pyrazin-2-amine (Compound No. 1.45)

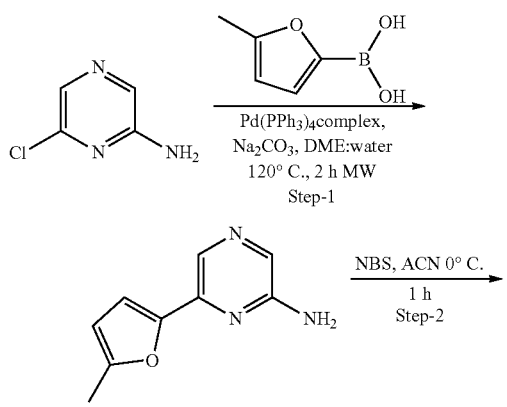

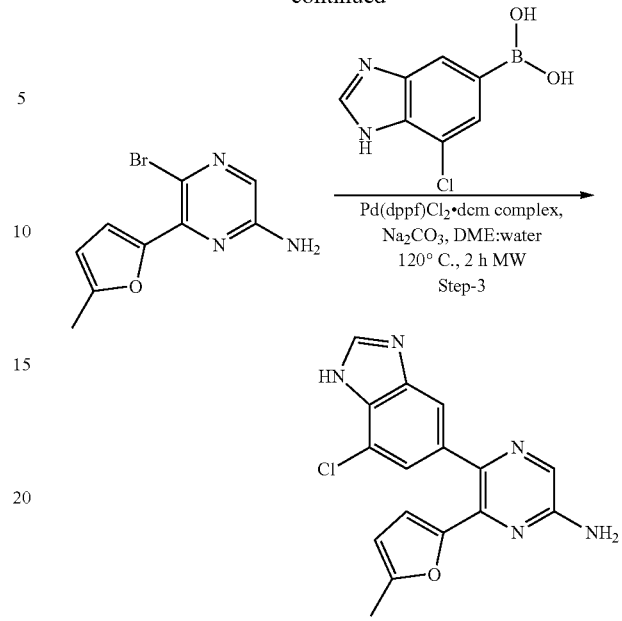

Step-1: Synthesis of 6-(5-methylfuran-2-yl)pyrazin-2-amine: 6-chloropyrazin-2-amine (1.0 g, 7.7 mmol, 1.0 eq.) and (5-methylfuran-2-yl)boronic acid (1.2 g, 9.3 mmol, 1.2 eq) was dissolved in DME:water (10.0 mL, 8:2). The reaction mixture was deoxygenated using nitrogen followed by addition of Pd(PPh$_3$)$_4$ complex (0.045 g, 0.04 mmol, 0.05 eq.) and sodium carbonate (1.6 g, 15.4 mmol, 2.5 eq.). The reaction mixture was again purged with nitrogen and heated at 150° C. for 2 h under microwave irradiation. Progress of the reaction was monitored by TLC and LCMS. Reaction mixture was allowed to cool to RT and quenched by adding water and extracted using ethyl acetate (3×100 mL) The combined organic layers were washed (brine), dried (anhydrous Na$_2$SO$_4$) and concentrated under vacuum to get the solid which was purified by silica gel column chromatography to get the desired product (0.350 g, 24%)

LCMS: 176 [M+1]$^+$

Step-2: Synthesis of 5-bromo-6-(5-methylfuran-2-yl) pyrazin-2-amine: To a stirred solution of 6-(5-methylfuran-2-yl)pyrazin-2-amine (0.7 g, 3.9 mmol, 1.0 eq.) in ACN (3.0 mL) was added N-bromosuccinimide (0.7 g, 3.9 mmol, 1.0 eq.) portionwise at 0° C. Progress of the reaction was monitored by TLC and LCMS. The reaction mixture was quenched by adding cold water and extracted using ethyl acetate (3×50 mL). The combined organic layers were washed with brine, dried with anhydrous Na$_2$SO$_4$ and concentrated under vacuum to get the solid which was purified by normal phase column chromatography to get the desired product (0.140 g, 14%)

LCMS: 254 [M+1]$^+$

Step-3: Synthesis of 5-(7-chloro-1H-benzimidazol-5-yl)-6-(5-methylfuran-2-yl)pyrazin-2-amine: 5-bromo-6-(5-methylfuran-2-yl)pyrazin-2-amine (0.140 g, 0.27 mmol, 1.0 eq.) and (7-chloro-1H-benzo[d]imidazol-5-yl)boronic acid (0.140 g, 0.35 mmol, 1.3 eq.) was dissolved in DME:water (10.0 mL, 8:2). The reaction mixture was deoxygenated using nitrogen followed by addition of Pd(dppf)Cl$_2$.DCM complex (0.022 g, 5 mol %) and sodium carbonate (0.088 g, 0.41 mmol, 1.5 eq.). The reaction mixture was again purged with nitrogen and allowed to heat at 120° C. for 2 h using microwave irradiation. Progress of the reaction was monitored by TLC and LCMS. Reaction mixture was allowed to cool to RT and quenched by adding water and extracted using ethyl acetate (3×30 mL) The combined organic layers were washed with brine, dried with anhydrous $Na_2SO_4$ and concentrated under vacuum to get the solid which was purified by reversed phase column chromatography to afford the desired product (4.9 mg, 6%)

LCMS: 326 [M+1]+. 1H NMR: (400 MHz, DMSO-$d_6$) δ 12.78 (s, 1H), 8.31 (s, 1H), 7.84 (s, 1H), 7.45 (br. s., 1H), 7.19 (br. s., 1H), 6.64 (br. s., 2H), 6.07 (br. s., 2H), 1.91-2.20 (m, 3H).

Example S24. Synthesis of 5-(naphthalen-2-yl)-6-phenylpyrazin-2-amine (Compound No. 1.185)

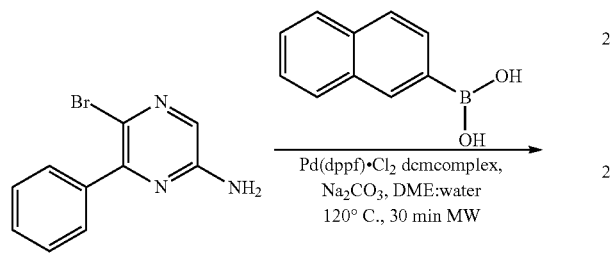

To a stirred solution of 5-bromo-6-phenylpyrazin-2-amine (0.100 g, 0.39 mmol, 1.0 eq.)) in DME:water (5.0 mL, 4:1) was added naphthalen-2-ylboronic acid (0.089 g, 0.51 mmol, 1.3 eq.). The reaction mixture was deoxygenated using nitrogen gas, and Pd(dppf)$Cl_2$ DCM complex (0.016 g, 0.05 eq. 0.019 mmol) was added. The reaction mixture was again purged with nitrogen and heated at 120° C. for 2 h under microwave irradiation. Progress of the reaction was monitored by TLC and LCMS. Reaction mixture was allowed to cool to RT and quenched by adding water and extracted using ethyl acetate (3×30 mL) The combined organic layers were washed (brine), dried (anhydrous $Na_2SO_4$) and concentrated under vacuum to get the solid which was purified by normal phase column chromatography to get the desired product (0.05 g, 43.10%)

LCMS: 298 [M+1]+. 1H NMR: (400 MHz, DMSO-$d_6$) δ 6.66 (s, 2H) 7.17-7.33 (m, 4H) 7.35 (br. s., 2H) 7.40-7.50 (m, 2H) 7.64-7.79 (m, 2H) 7.82 (br. s., 1H) 7.87 (s, 1H) 8.00 (s, 1H).

Example S25. Synthesis of 5-(1H-indazol-5-yl)-6-phenylpyrazin-2-amine (Compound No. 1.270)

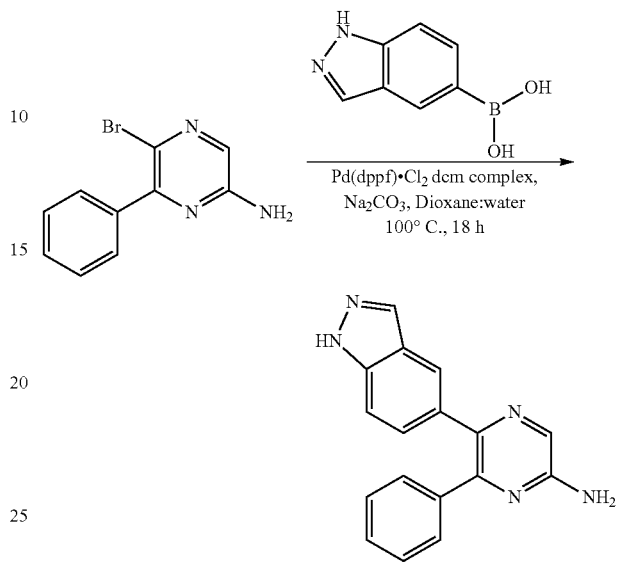

To a stirred solution of 5-bromo-6-phenylpyrazin-2-amine (0.1 g, 0.4 mmol, 1.0 eq.) and (1H-indazol-5-yl) boronic acid (0.127 g, 0.44 mmol, 1.1 eq.) in dioxane (4 mL) was added $Na_2CO_3$ (0.085 g, 0.8 mmol, 2.0 eq.) and 1 mL water. The reaction was purged with $N_2$ for 5 min. To this reaction mixture was added with Pd(dppf)$Cl_2$.DCM complex (0.016 g, 5 mol %) and $N_2$ was purged again for another 5 min. The reaction mixture was heated at 100° C. for 18 h. The reaction mixture was allowed to cool to RT and extracted using ethyl acetate (3×35 mL). The combined organic layers were washed (brine), dried (anhydrous $Na_2SO_4$) and concentrated under vacuum to get the solid residue which was purified by reversed phase column chromatography to get the desired product as off white solid (0.02 g, 17%)

LCMS: 288 [M+1]+. 1H NMR: (400 MHz, DMSO-$d_6$) δ 13.01 (br. s., 1H), 7.96 (d, J=5.26 Hz, 2H), 7.64 (s, 1H), 7.28-7.43 (m, 3H), 7.10-7.28 (m, 4H), 6.54 (br. s., 2H).

Example S26. Synthesis of 5-(8-chloroquinolin-6-yl)-6-(3-methyl-1H-pyrazol-1-yl)pyrazin-2-amine (Compound No. 1.271)

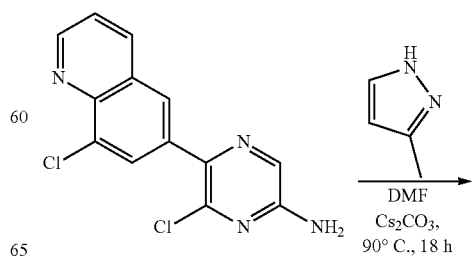

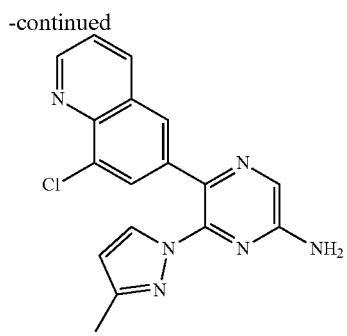

To a stirred solution of 5-(8-chloroquinolin-6-yl)-6-(3-methyl-1H-pyrazol-1-yl)pyrazin-2-amine (120 mg, 0.41 mmol, 1 eq.) in DMF (2 mL), was added 3-methyl-1H-pyrazole (169 mg, 2.06 mmol, 5 eq.) and Cs$_2$CO$_3$ (671 mg, 2.06 mmol, 5 eq.). Resulting mixture was heated at 90° C. for 18 h. Progress of the reaction was monitored by TLC and LCMS. On completion of the reaction, reaction mixture was diluted with water (30 mL) and extracted with ethyl acetate (50 mL×2). Combined organic layer was washed with water (100 mL×2), dried with anhydrous Na$_2$SO$_4$ and concentrated under vacuum to get the solid residue which was purified by reversed phase column chromatography to get the desired product 5-(8-chloroquinolin-6-yl)-6-(3-methyl-1H-pyrazol-1-yl)pyrazin-2-amine (16 mg, 11%).

LCMS: 337 [M+1]$^+$. $^1$H NMR: (400 MHz, DMSO-d$_6$) δ 2.08 (s, 3H) 6.31 (d, J=2.19 Hz, 1H) 7.20 (s, 2H) 7.61 (s, 1H) 7.81 (dd, J=8.11, 4.17 Hz, 1H) 7.93 (s, 1H) 8.10 (d, J=2.19 Hz, 1H) 8.18 (s, 1H) 8.90 (d, J=8.77 Hz, 1H) 9.01 (d, J=3.07 Hz, 1H)

Example S27. Synthesis of 6-(5-methylthiophen-2-yl)-5-(quinolin-6-yl)pyrazin-2-amine (Compound No. 1.210)

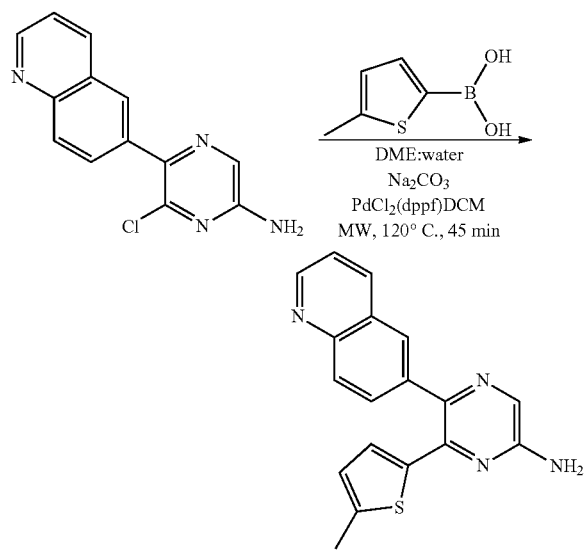

To a stirred solution of 5-(8-chloroquinolin-6-yl)-6-(3-methyl-1H-pyrazol-1-yl)pyrazin-2-amine (120 mg, 0.46 mmol, 1.0 eq.) and 5-methyl-2-thiopheneboronic acid (79 mg, 0.56 mmol, 1.2 eq.) in dioxane (6 mL) and water (0.5 mL), was added Na$_2$CO$_3$ (173 mg, 0.69 mmol, 1.5 eq.). The reaction was purged with N$_2$ for 5 min. To this reaction mixture was added Pd(dppf)Cl$_2$.DCM complex (18 mg, 0.02 mmol) and N$_2$ was purged again for another 5 min. The reaction mixture was irradiated at 120° C. for 45 min using microwave. Progress of the reaction was monitored by TLC and LCMS. On completion of the reaction, reaction mixture was filtered through layer of celite and washed with ethyl acetate. Organic layer was washed with water (50 mL×2) and dried with anhydrous Na$_2$SO$_4$ and concentrated under vacuum to get the solid residue which was purified by reversed phase column chromatography to get the desired product 6-(5-methylthiophen-2-yl)-5-(quinolin-6-yl)pyrazin-2-amine (14 mg, 9%) as an off white solid.

LCMS: 319 [M+1]$^+$. $^1$H NMR: (400 MHz, DMSO-d$_6$) δ 8.91 (br. s., 1H), 8.37 (br. s., 1H), 8.07 (br. s., 1H), 7.99 (d, J=8.33 Hz, 1H), 7.86 (br. s., 1H), 7.72 (br. s., 1H), 7.54 (br. s., 1H), 6.67 (br. s., 2H), 6.52 (br. s., 1H), 6.40 (br. s., 1H), 2.40 (br.s., 3H)

Example S28. Synthesis of 3-amino-5-phenyl-6-(quinolin-6-yl) pyrazine-2-carboxylic acid (Compound No. 1.238)

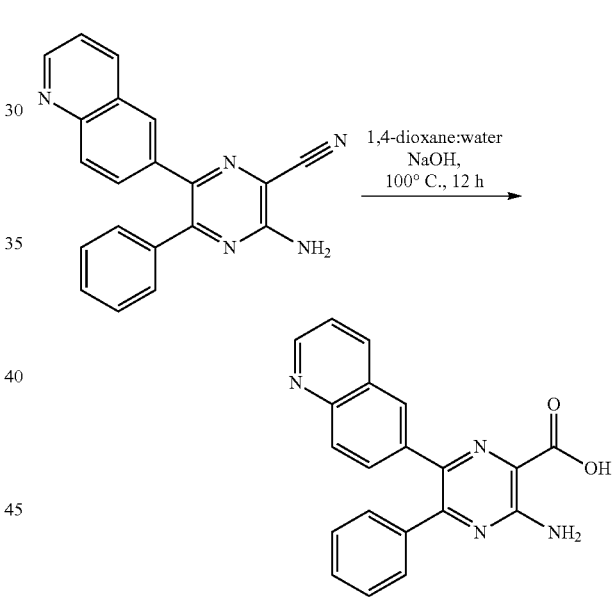

A stirred solution of 3-amino-5-phenyl-6-(quinolin-6-yl) pyrazine-2-carbonitrile (100 mg, 0.30 mmol, 1 eq.) in 1,4-dioxane (5 mL) and aqueous NaOH (61 mg dissolved in 5 mL water) was heated at 100° C. for 12 h. Progress of reaction was monitored by LCMS. On completion of the reaction, the reaction mixture was concentrated under vacuum to get the solid residue which was diluted with water (15 mL) and acidified with 3N HCl solution (10 mL), and extracted with ethyl acetate (50 mL×2). Organic layer was washed with water (100 mL×2), dried over anhydrous Na$_2$SO$_4$ and concentrated under vacuum to get the solid residue which was purified by reversed phase column chromatography to get the desired product (8 mg, 7.5%).

LCMS: 343 [M+1]$^+$. $^1$H NMR: (400 MHz, DMSO-d$_6$) δ 7.18-7.31 (m, 4H) 7.31-7.39 (m, 2H) 7.43-7.50 (m, 2H) 7.53 (d, J=8.77 Hz, 1H) 7.78 (d, J=8.77 Hz, 1H) 7.96 (br. s., 1H) 8.22 (d, J=7.45 Hz, 1H) 8.83 (br. s., 1H).

Example S29. Synthesis of 3-amino-5-phenyl-6-(quinolin-6-yl)pyrazine-2-carboxamide (Compound No. 1.272)

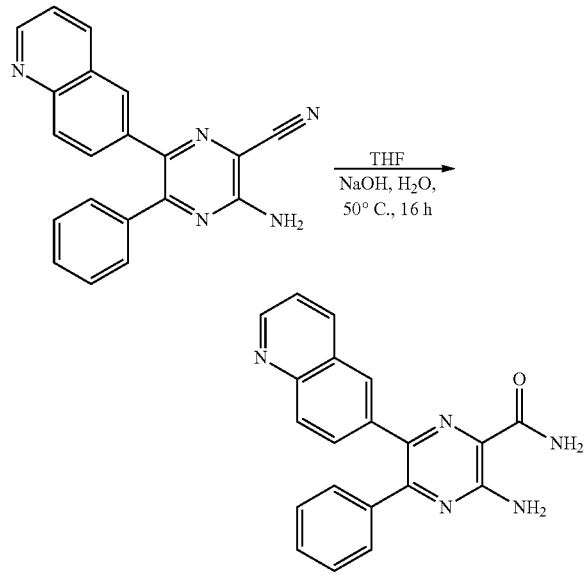

To a stirred solution of 3-amino-5-phenyl-6-(quinolin-6-yl)pyrazine-2-carbonitrile (100 mg, 0.307 mmol, 1 eq.) in THF (5 mL), was added aq. solution of NaOH (5 mL, 10%). Resulting mixture was heated at 50° C. for 16 h. Progress of reaction was monitored by LCMS. On completion of reaction, reaction mixture was concentrated under vacuum to obtain a solid residue which was diluted with water (15 mL), was extracted with ethyl acetate (50 mL×2). Organic layer was washed with water (50 mL×2), dried over anhydrous Na$_2$SO$_4$ and concentrated under vacuum to get the solid residue which was purified by reversed phase column chromatography to get the desired 3-amino-5-phenyl-6-(quinolin-6-yl)pyrazine-2-carboxamide (19 mg, 18%).

LCMS: 342 [M+1]$^+$. $^1$H NMR: (400 MHz, DMSO-d$_6$) δ 7.22-7.46 (m, 5H) 7.50 (dd, J=8.11, 4.17 Hz, 1H) 7.63 (dd, J=8.77, 1.75 Hz, 1H) 7.74 (br. s., 1H) 7.81 (d, J=8.77 Hz, 1H) 8.13 (s, 1H) 8.16-8.26 (m, 2H) 8.86 (d, J=2.63 Hz, 1H).

Example S30. Synthesis of 3-amino-N-((6-methylpyridin-2-yl)methyl)-5-phenyl-6-(quinolin-6-yl)pyrazine-2-carboxamide (Compound No. 1.273)

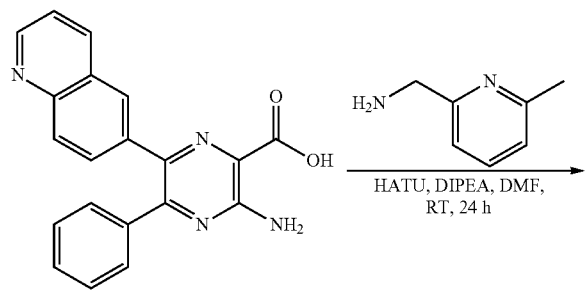

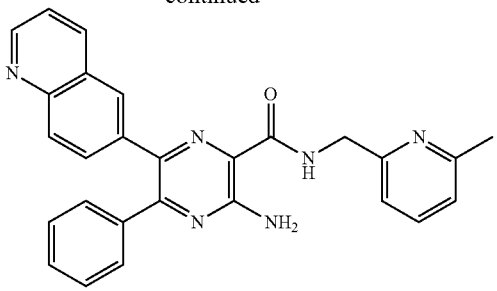

To a stirred solution of 3-amino-5-phenyl-6-(quinolin-6-yl)pyrazine-2-carboxylic acid (0.110 g, 0.32 mmol, 1 eq.) and (6-methylpyridin-2-yl)methanamine in DMF (2 mL), was added HATU (0.182 g, 0.48 mmol, 1.5 eq.) and DIPEA (0.124 g, 0.96 mmol, 3.0 eq.). The reaction mixture was allowed to stir at RT for 24 h. Progress of reaction was monitored by TLC and LCMS. On completion of the reaction, the reaction mixture was diluted with water (15 mL) and extracted with ethyl acetate (50 mL×2). Combined organic layer was washed with water (50 mL×2), dried over anhydrous Na$_2$SO$_4$ and concentrated under vacuum to get the solid residue which was purified by reversed phase column chromatography to get the desired 3-amino-N-((6-methylpyridin-2-yl)methyl)-5-phenyl-6-(quinolin-6-yl)pyrazine-2-carboxamide (10 mg, 7%).

LCMS: 447 [M+1]$^+$. $^1$H NMR: (400 MHz, DMSO-d$_6$) δ 9.45 (br. s., 1H), 8.86 (br. s., 1H), 8.21 (d, J=8.77 Hz, 1H), 8.06 (br. s., 1H), 7.86 (d, J=9.21 Hz, 2H), 7.59-7.79 (m, 4H), 7.51 (br. s., 2H), 7.24-7.47 (m, 6H), 7.08-7.20 (m, 2H), 4.60 (d, J=5.70 Hz, 3H).

Example S31. Synthesis of 3-amino-6-(1H-indazol-5-yl)-5-phenylpyrazine-2-carbonitrile (Compound No. 1.274)

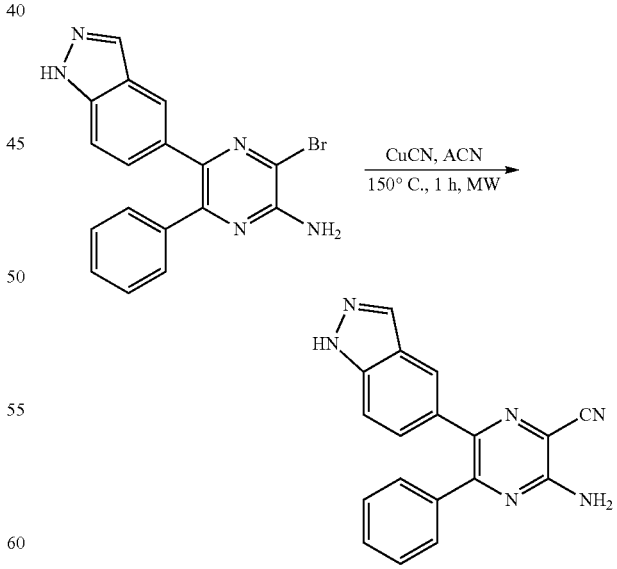

To a stirred solution of 3-bromo-5-(1H-indazol-5-yl)-6-phenylpyrazin-2-amine (0.080 g, 0.21 mmol, 1.0 eq.) in ACN (5 mL) was added cuprous cyanide (0.058 g, 0.65 mmol, 3.0 eq.). The reaction mixture was allowed to stir at 150° C. for 1 h under microwave irradiation. The reaction mixture was allowed to cool to RT, diluted with aqueous ammonia (5 mL) and extracted using ethyl acetate (3×25 mL). The combined organic layers were washed with brine, dried over anhydrous $Na_2SO_4$ and concentrated under vacuum to get the solid which was purified by reversed phase column chromatography to get the desired product as an off white solid (0.010 g, 15%).

LCMS: 313 [M+1]+. 1H NMR: (400 MHz, DMSO-$d_6$) δ 13.07 (br. s., 1H), 8.00 (br. s., 1H), 7.67 (s, 1H), 7.24-7.45 (m, 8H), 7.17 (d, J=8.77 Hz, 1H).

Example S32. Synthesis of 3-morpholino-6-phenyl-5-(quinolin-6-yl)pyrazin-2-amine (Compound No. 1.275)

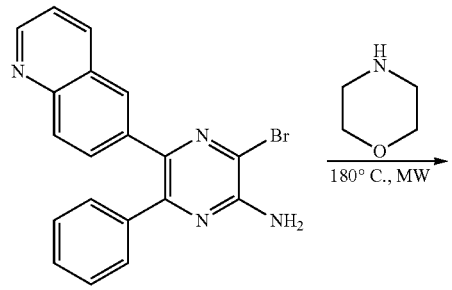

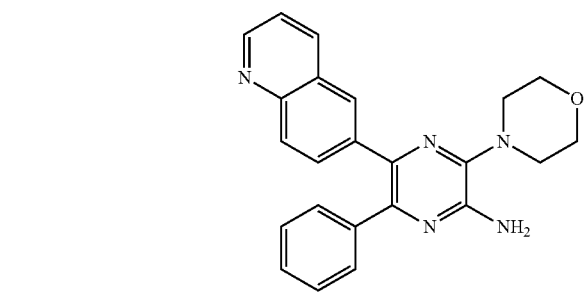

Mixture of 3-bromo-6-phenyl-5-(quinolin-6-yl)pyrazin-2-amine (0.100 g, 0.26 mmol, 1.0 eq.) and morpholine (0.226 g, 2.6 mmol, 10.0 eq.) was heated at 180° C., for 1 h using microwave irradiation. The reaction mixture was allowed to cool to RT. The solvent was evaporated under vacuum to get the solid which was purified by normal phase column chromatography to get the desired product as off white solid (0.055 g, 56%).

LCMS: 384 [M+1]+. 1H NMR: (400 MHz, DMSO-$d_6$) δ 8.83 (d, J=3.07 Hz, 1H), 8.19 (d, J=8.33 Hz, 1H), 7.92 (s, 1H), 7.80 (d, J=8.77 Hz, 1H), 7.59 (d, J=7.45 Hz, 1H), 7.46 (dd, J=4.17, 8.11 Hz, 1H), 7.29-7.38 (m, 2H), 7.18-7.29 (m, 3H), 6.35 (br. s., 2H), 3.82 (br. s., 4H), 3.12-3.25 (m, 4H).

Example S33. Synthesis of 3-morpholino-6-phenyl-5-(quinolin-6-yl)pyrazin-2-amine (Compound No. 1.276)

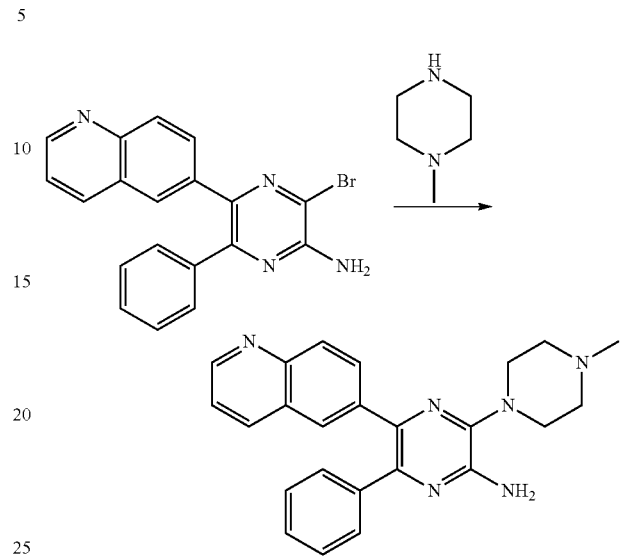

Mixture of 3-bromo-6-phenyl-5-(quinolin-6-yl)pyrazin-2-amine (0.150 g, 0.39 mmol, 1.0 eq.) and 1-methylpiperazine (0.390 g, 3.9 mmol, 10.0 eq.) was heated at 180° C. for 30 min using microwave irradiation. The reaction mixture was allowed to cool to RT. The solvent was evaporated under vacuum to get the solid which was purified by normal phase column chromatography to get the desired product as off white solid (0.060 g, 39%).

LCMS: 397 [M+1]+. 1H NMR: (400 MHz, DMSO-$d_6$) δ 8.83 (d, J=3.07 Hz, 1H), 8.19 (d, J=7.89 Hz, 1H), 8.14 (s, 1H), 7.90 (s, 1H), 7.81 (d, J=8.33 Hz, 1H), 7.59 (d, J=8.33 Hz, 1H), 7.46 (dd, J=3.95, 7.89 Hz, 1H), 7.29-7.37 (m, 2H), 7.26 (br. s., 3H), 6.23 (br. s., 2H), 3.24 (br. s., 3H), 2.57-2.69 (m, 4H), 2.31 (br. s., 4H).

Example S34. Synthesis of 6-[3-(pyridin-2-yl)pyrazin-2-yl]quinolone (Compound No. 1.25)

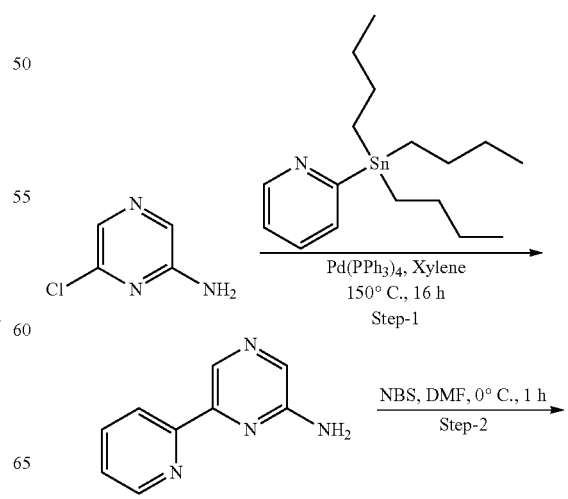

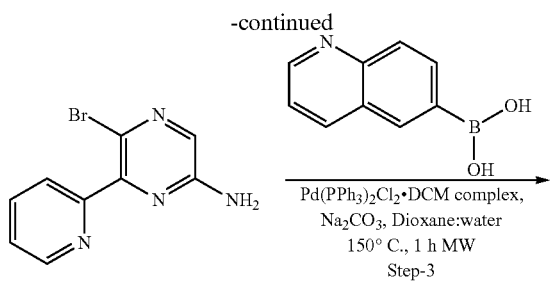

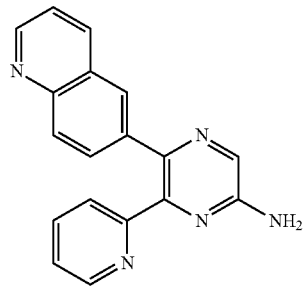

Step-1: Synthesis of 6-(pyridin-2-yl)pyrazin-2-amine: To a stirred solution of 6-chloropyrazin-2-amine (0.500 g, 3.85 mmol, 1.0 eq.) in xylene (20.0 mL) was added 2-(tributylstannyl)pyridine reagent (1.42 g, 3.85 mmol, 1.0 eq.). The reaction mixture was deoxygenated using $N_2$ gas and Pd(PPh$_3$)$_4$ (0.223 g, 0.05 eq. 0.192 mmol) was added. The reaction mixture was again purged with $N_2$ and allowed to heat at 150° C. for 16 h in seal tube. Progress of the reaction was monitored by TLC and LCMS. Reaction mixture was allowed to cool to RT and quenched by adding aq. NaOH and extracted using ethyl acetate (3×100 mL). The combined organic layers were washed with brine, dried over anhydrous $Na_2SO_4$ and concentrated under vacuum to get the solid which was purified by normal phase column chromatography to get the desired product (0.400 g, 60%).

LCMS: 173 [M+1]$^+$

Step-2: Synthesis of 5-bromo-6-(pyridin-2-yl)pyrazin-2-amine: To a stirred solution of 6-(pyridin-2-yl)pyrazin-2-amine (0.400 g, 2.32 mmol, 1.0 eq.) in DMF (5.0 mL) was added N-bromosuccinimide (0.413 g, 2.32 mmol, 1.0 eq.) portionwise at 0° C. Progress of the reaction was monitored by TLC and LCMS. The reaction was quenched by adding cold water and extracted using ethyl acetate (3×50 mL). The combined organic layers were washed with brine, dried (anhydrous $Na_2SO_4$) and concentrated under vacuum to get the solid which was purified by normal phase column chromatography to afford the desired product (0.100 g, 17%).

LCMS: 250 [M+1]$^+$

Step-3: Synthesis of 6-(pyridin-2-yl)-5-(quinolin-6-yl)pyrazin-2-amine: To a stirred solution of 5-bromo-6-(pyridin-2-yl)pyrazin-2-amine (0.100 g, 0.398 mmol, 1.0 eq.) and quinolin-6-ylboronic acid (0.103 g, 0.59 mmol, 1.5 eq.) in 1,4-dioxane (4.0 mL) was added sodium carbonate (0.105 g, 0.95 mmol, 2.5 eq.) and 1 mL of water. The reaction mixture was deoxygenated using nitrogen gas, and Pd(dppf)Cl$_2$.DCM complex (0.016 g, 0.019 mmol, 0.05 eq.) was added. The reaction mixture was again purged with nitrogen and allowed to heat at 120° C. for 1 h under microwave irradiation. Progress of the reaction was monitored by TLC and LCMS. Reaction mixture was allowed to cool to RT and quenched by adding water and extracted using ethyl acetate (3×100 mL). The combined organic layers were washed with brine, dried over anhydrous $Na_2SO_4$ and concentrated under vacuum to get the solid which was purified by normal phase column chromatography to get the desired product (0.010 g, 9%).

LCMS: 300 [M+1]$^+$. $^1$H NMR: (400 MHz, DMSO-d$_6$) δ 8.82 (d, J=2.63 Hz, 1H), 8.34 (d, J=4.38 Hz, 1H), 8.08 (s, 1H) 8.20 (d, J=7.89 Hz, 1H), 7.81-7.88 (m, 2H), 7.76 (d, J=8.77 Hz, 1H), 7.65 (d, J=7.45 Hz, 1H), 7.36-7.50 (m, 2H), 7.22-7.36 (m, 1H), 6.77 (br. s., 2H).

Example S35. Synthesis of 3-amino-6-(benzo[d]thiazol-6-yl)-5-phenylpyrazine-2-carbonitrile (Compound No. 1.192)

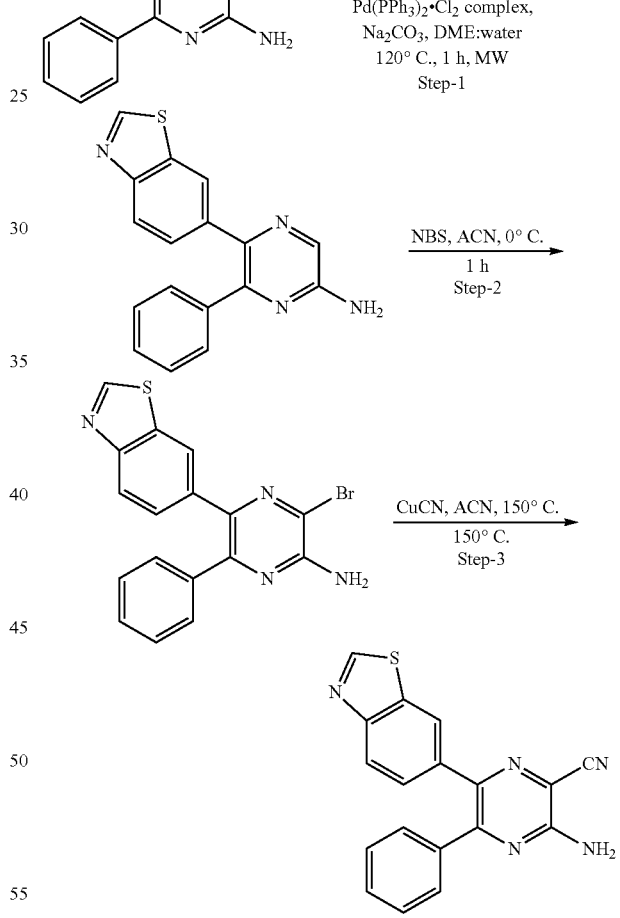

Step-1: Synthesis of 5-(benzo[d]thiazol-6-yl)-6-phenylpyrazin-2-amine: To a stirred solution of 5-bromo-6-phenylpyrazin-2-amine (0.500 g, 2.0 mmol, 1.0 eq.) and benzo[d]thiazol-6-ylboronic acid (0.467 g, 2.6 mmol, 1.3 eq.) in DME (8.0 mL) was added sodium carbonate (0.532 g, 4.99 mmol, 2.5 eq.) and 2 mL of water. The reaction mixture was deoxygenated using nitrogen gas Then Pd(PPh$_3$)$_2$.Cl$_2$ complex (0.081 g, 0.05 eq. 0.1 mmol) was added. The reaction mixture was again purged with nitrogen and allowed to heat at 120° C. for 1 h under microwave irradiation. Progress of the reaction was monitored by TLC and LCMS. Reaction mixture was allowed to cool to RT and quenched by adding water and extracted using ethyl acetate (3×100 mL). The combined organic layers were washed with brine, dried over anhydrous Na$_2$SO$_4$ and concentrated under vacuum to get the solid which was purified by normal phase column chromatography to get the desired product (0.140 g, 23.02%).

LCMS: 305 [M+1]$^+$

Step-2: Synthesis of 5-(1,3-benzothiazol-6-yl)-3-bromo-6-phenylpyrazin-2-amine: To a stirred solution of 5-(benzo[d]thiazol-6-yl)-6-phenylpyrazin-2-amine (0.140 g, 0.36 mmol, 1.0 eq.) in ACN (2.0 mL) was added N-bromosuccinimide (0.065 g, 0.36 mmol, 1.0 eq.) portionwise at 0° C. Progress of the reaction was monitored by TLC and LCMS. The reaction was quenched by adding cold water and extracted using ethyl acetate (3×50 mL). The combined organic layers were washed with brine, dried with anhydrous Na$_2$SO$_4$ and concentrated under vacuum to get the solid which was purified by normal phase column chromatography to get the desired product (0.140 g, 79.54%).

LCMS: 383 [M+1]$^+$

Step-3: Synthesis of 3-amino-6-(benzo[d]thiazol-6-yl)-5-phenylpyrazine-2-carbonitrile: To a stirred solution of 5-(1,3-benzothiazol-6-yl)-3-bromo-6-phenylpyrazin-2-amine (0.140 g, 0.36 mmol, 1.0 eq.) in ACN (2 mL) was added CuCN (0.100 g, 1.09 mmol, 3.0 eq.). Reaction was stirred at 150° C. for 1 h under microwave irradiation. Progress of the reaction was monitored by TLC and LCMS. The reaction mixture was then filtered and the filtrate was concentrated under reduced pressure to obtain the crude, which was then purified by reversed phase preparative chromatography to get the desired product (0.015 g, 12%)

LCMS: 330[M+1]$^+$. $^1$H NMR: (400 MHz, DMSO-d$_6$) δ 9.39 (s, 1H), 8.09-8.19 (m, 1H), 7.92 (d, J=8.33 Hz, 1H), 7.54 (s, 2H), 7.35-7.43 (m, 3H), 7.11-7.35 (m, 3H).

Example S36. Synthesis of 3-amino-6-(7-chloro-1H-benzimidazol-5-yl)-5-phenylpyrazine-2-carbonitrile (Compound No. 1.277)

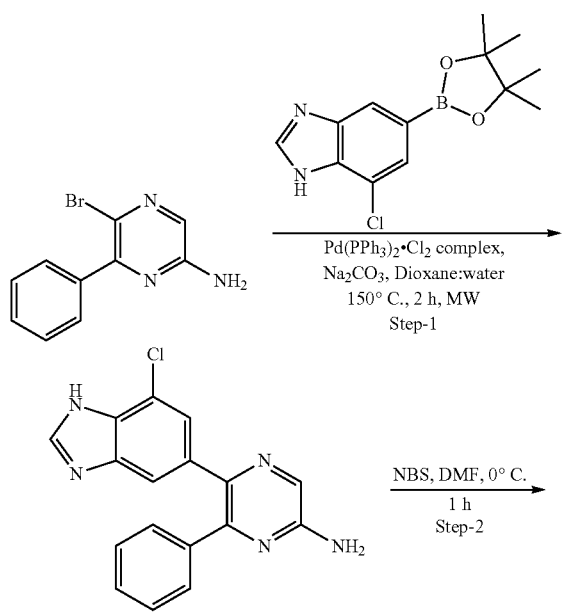

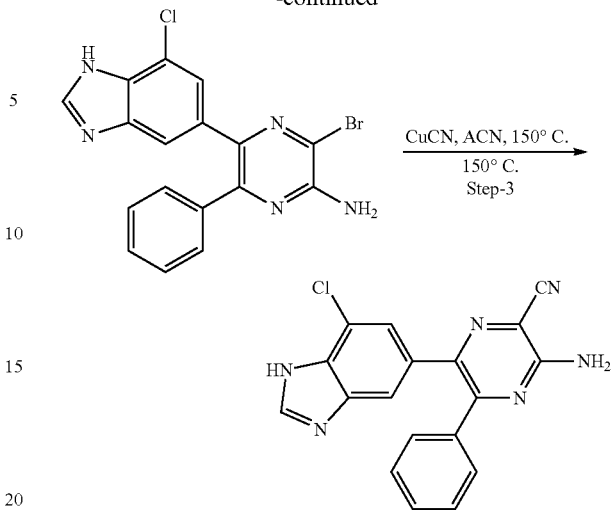

Step-1: Synthesis of 5-(7-chloro-1H-benzimidazol-5-yl)-6-phenylpyrazin-2-amine: To a stirred solution of 5-bromo-6-phenylpyrazin-2-amine (0.500 g, 1.99 mmol, 1.0 eq.) and 7-chloro-5-(4,4,5,5-tetramethyl-1,3,2-dioxaborolan-2-yl)-1H-benzo[d]imidazole (0.72 g, 2.59 mmol, 1.3 eq.) in 1,4-dioxane (6.0 mL) was added sodium carbonate (0.529 g, 4.99 mmol, 2.5 eq.) and 1.5 mL of water. The reaction mixture was deoxygenated using N$_2$ and Pd(PPh$_3$)$_2$Cl$_2$.DCM complex (0.081 g, 0.099 mmol, 0.05 eq.) was added. The reaction mixture was again purged with N$_2$ and allowed to heat at 150° C. for 2 h using microwave irradiation. Progress of the reaction was monitored by TLC and LCMS. Reaction mixture was allowed to cool to RT and quenched by adding water and extracted using ethyl acetate (3×100 mL). The combined organic layers were washed with brine, dried over anhydrous Na$_2$SO$_4$ and concentrated under vacuum to get the solid which was purified by normal phase column chromatography to get the desired product (0.160 g, 24.88%)

LCMS: 322 [M+1]$^+$

Step-2: Synthesis of 3-bromo-5-(7-chloro-1H-benzimidazol-5-yl)-6-phenylpyrazin-2-amine: To a stirred solution of 5-(7-chloro-1H-benzimidazol-5-yl)-6-phenylpyrazin-2-amine (0.160 g, 0.497 mmol, 1.0 eq.) in DMF (3.0 mL) was added N-bromosuccinimide (0.088 g, 0.49 mmol, 1.0 eq.) portionwise at 0° C. Progress of the reaction was monitored by TLC and LCMS. The reaction was stirred for 1 h at same temperature and quenched with cold water. The mixture was extracted using ethyl acetate (3×50 mL). The combined organic layers were washed with brine, dried over anhydrous Na$_2$SO$_4$ and concentrated under vacuum to get the solid product (0.150 g, 75%).

LCMS: 400 [M+1]$^+$

Step-3: Synthesis of 3-amino-6-(7-chloro-1H-benzimidazol-5-yl)-5-phenylpyrazine-2-carbonitrile: To a stirred solution of 3-bromo-5-(7-chloro-1H-benzimidazol-5-yl)-6-phenylpyrazin-2-amine (0.150 g, 0.374 mmol, 1.0 eq.) in ACN (3.0 mL) was added CuCN (0.100 g, 1.12 mmol, 3.0 eq.). Reaction was stirred at 150° C. for 1 h under microwave irradiation. Progress of the reaction was monitored by TLC and LCMS. Reaction was filtered and concentrated under reduced pressure to get the crude product which was purified by reversed phase column chromatography to get the desired product (0.003 g, 2%).

LCMS: 347 [M+1]⁺. ¹H NMR: (400 MHz, DMSO-d₆) δ 8.28 (s, 1H), 7.49 (br. s., 2H), 7.29-7.43 (m, 5H), 7.16-7.20 (s, 1H), 6.66 (br. s., 2H).

Example S37. Synthesis of 6-(1-methyl-1H-pyrazol-3-yl)-5-(quinolin-6-yl)pyrazin-2-amine (Compound No. 1.278)

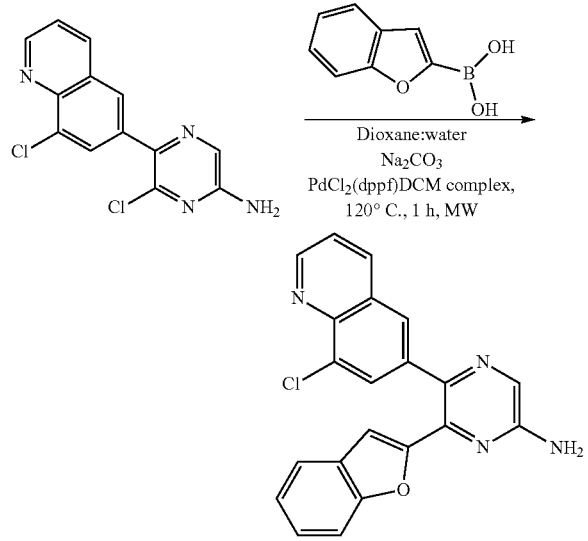

To a stirred solution of 6-chloro-5-(quinolin-6-yl)pyrazin-2-amine (150 mg, 0.52 mmol, 1.0 eq.) and benzofuran-3-ylboronic acid (125 mg, 0.64 mmol, 1.1 eq.) in dioxane (4 mL) and water (1 mL), was added Na₂CO₃ (109 mg, 1.03 mmol, 2.0 eq.). The reaction was purged with N₂ for 5 min. To this reaction mixture was added Pd(dppf)Cl₂.DCM complex (21 mg, 5 mol %) and N₂ was purged again for another 5 min. The reaction mixture was heated at 120° C. for 1 h under microwave irradiation. Progress of the reaction was monitored by TLC and LCMS. On completion of the reaction, the reaction mixture was extracted with ethyl acetate (35 mL×3). Combined organic layer was washed with water (50 mL×2), dried over anhydrous Na₂SO₄ and concentrated under vacuum to get the solid residue which was purified by normal phase column chromatography to get the desired product (25 mg, 13%) as an off white solid.

LCMS: 373 [M+1]⁺. ¹H NMR: (400 MHz, DMSO-d₆) δ 8.93 (dd, J=1.53, 4.17 Hz, 1H), 8.26 (d, J=7.02 Hz, 1H), 7.96-8.05 (m, 1H), 7.87 (d, J=1.75 Hz, 1H), 7.72 (dd, J=1.53, 4.60 Hz, 2H), 7.46-7.60 (m, 2H), 7.26 (dd, J=1.53, 8.55 Hz, 1H), 6.93 (d, J=1.32 Hz, 1H), 6.80 (s, 2H)

Example S38. Synthesis of 3-amino-6-(benzo[d]oxazol-6-yl)-5-phenylpyrazine-2-carbonitrile (Compound No. 1.193)

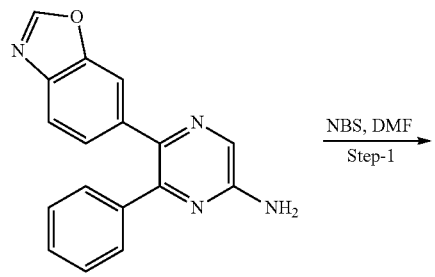

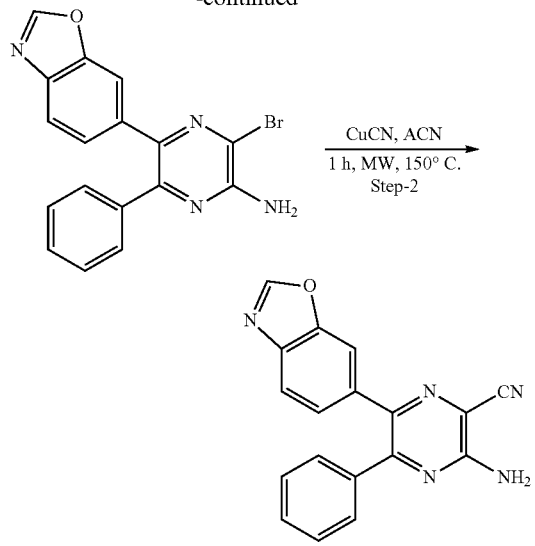

Step 1. Synthesis of 5-(benzo[d]oxazol-6-yl)-3-bromo-6-phenylpyrazin-2-amine: To a solution of 6-(3-methyl-1H-pyrazol-1-yl)-5-(quinolin-6-yl)pyrazin-2-amine (200 mg, 0.69 mmol, 1 eq.) in ACN (2 mL) at 0° C. was added N-bromosuccinimide (123 mg, 0.69 mmol, 1 eq.) portion wise and the reaction mixture was allowed to stir at the same temperature for 1 h. Following this, the reaction mixture was poured over ice-water to afford the solid precipitate which was filtered under vacuum and washed with excess water. The solid was vacuum dried to yield the desired product as off white solid (0.200 g, 79%)

Step 2. Synthesis of 3-amino-6-(8-chloroquinolin-6-yl)-5-(3-methyl-1H-pyrazol-1-yl)pyrazine-2-carbonitrile: To a stirred solution of 5-(benzo[d]oxazol-6-yl)-3-bromo-6-phenylpyrazin-2-amine (0.100 g, 0.27 mmol, 1.0 eq.) in ACN (3 mL) was added cuprous cyanide (0.073 g, 0.88 mmol, 3.0 eq.). The reaction mixture was allowed to stir at 150° C. for 1 h under microwave irradiation. The progress of the reaction was monitored by TLC and LCMS. The reaction mixture was allowed to cool to RT and extracted with ethyl acetate (3×30 mL). The combined organic layers were washed with brine, dried over anhydrous Na₂SO₄ and concentrated under vacuum to get the solid which was purified by reversed phase column chromatography to afford the desired product as an off white solid (0.010 g, 12%).

LCMS: 314 [M+1]⁺. ¹H NMR: (400 MHz, DMSO-d₆) δ 8.74 (s, 1H), 7.61-7.70 (m, 2H), 7.54 (s, 2H), 7.22-7.41 (m, 6H).

Example S39. Synthesis of 5-(benzo[d]oxazol-6-yl)-6-phenylpyrazin-2-amine (Compound No. 1.35)

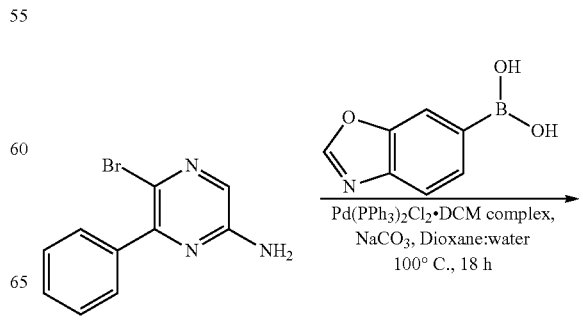

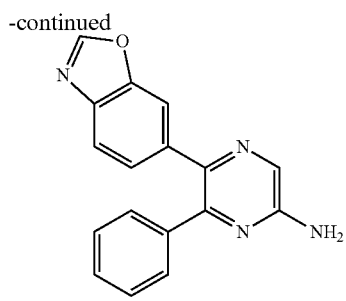

To a stirred solution of 5-bromo-6-phenylpyrazin-2-amine (0.500 g, 2.0 mmol, 1.0 eq.) and benzo[d]oxazol-6-ylboronic acid (0.429 g, 2.5 mmol, 1.3 eq.) in dioxane (8 mL) was added $Na_2CO_3$ (0.317 g, 3 mmol, 1.5 eq.) and 2 mL water. The reaction was purged with $N_2$ for 5 min. To this reaction mixture was added Pd(dppf)$Cl_2$·DCM complex (0.08 g, 5 mol %) and $N_2$ was purged again for another 5 min. The reaction mixture was heated at 100° C. for 18 h. The reaction mixture was allowed to cool to RT and extracted using ethyl acetate (2×100 mL). The combined organic layers were washed with brine, dried over anhydrous $Na_2SO_4$ and concentrated under vacuum to get the solid residue which was purified by normal phase flash column chromatography to afford the desired product as off white solid (0.250 g, 43%)

LCMS: 289 [M+1]$^+$. $^1$H NMR: (400 MHz, DMSO-d$_6$) δ 9.34 (s, 1H), 8.08 (s, 1H), 7.98 (s, 1H), 7.88 (d, J=8.77 Hz, 1H), 7.23-7.38 (m, 6H), 6.68 (s, 2H).

Example S40. Synthesis of 5-(quinolin-6-yl)-6-(1,3-thiazol-2-yl)pyrazin-2-amine (Compound No. 1.279)

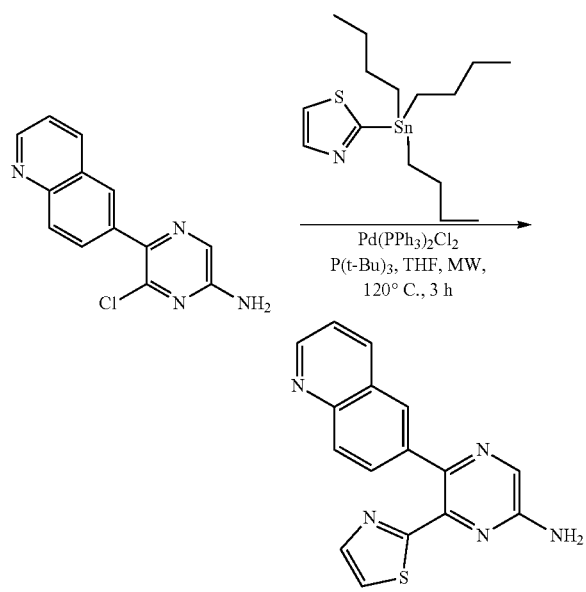

To a stirred solution of 6-chloro-5-(quinolin-6-yl)pyrazin-2-amine (150 mg, 0.58 mmol, 1 eq.) in THF (5 mL) was added 2-(tributylstannyl)thiazole (436 mg, 1.16 mmol). The reaction was purged with $N_2$ for 5 min. To this reaction mixture was added Pd(dppf)$Cl_2$ (3.5 mg, 5 mol %) and p(t-Bu)$_3$ (23 mg, 0.2 eq.). The reaction was purged with $N_2$ for another 5 min. Resulting mixture was heated at 120° C. for 3 h. Progress of the reaction was monitored by LCMS. On completion of the reaction, the reaction mixture was quenched with NaOH solution (10 mL) and diluted with water (15 mL) followed by extraction with ethyl acetate (50 mL×2). Combined organic layers were washed with water (50 mL×2), dried over anhydrous $Na_2SO_4$ and concentrated under vacuum to get the solid residue which was purified by reversed phase column chromatography to get the desired product (8 mg, 4%).

LCMS: 305 [M+1]$^+$. $^1$H NMR: (400 MHz, DMSO-d$_6$) δ 8.88 (d, J=3.07 Hz, 1H), 8.50 (br. s., 1H), 8.33 (d, J=7.02 Hz, 1H), 8.08 (s, 1H), 8.03 (s, 1H), 7.89 (d, J=8.33 Hz, 1H), 7.62-7.70 (m, 1H), 7.51 (dd, J=8.33, 4.38 Hz, 1H), 6.95 (s, 2H).

Example S41. Synthesis of 6-phenyl-5-(1,2,3,4-tetrahydroquinolin-6-yl)pyrazin-2-amine (Compound No. 1.186)

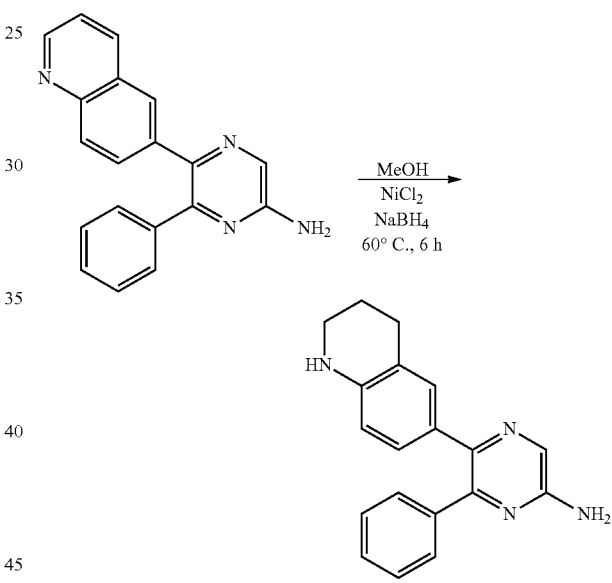

To a stirred solution of 6-phenyl-5-(quinolin-6-yl)pyrazin-2-amine (100 mg, 0.33 mmol, 1 eq.) in methanol (10 mL), was added NiCl$_2$ (22 mg, 0.16 mmol, 0.5 eq.). Reaction mixture was stirred for 10 min at RT followed by portion wise addition of NaBH$_4$ (90 mg, 2.64 mmol). Resulting reaction mixture was heated at 60° C. for 6 h. Progress of reaction was monitored by TLC and LCMS. On completion of the reaction, the reaction mixture was filtered through layer of celite and concentrated under reduce pressure. The obtained residue was diluted with water (50 mL) and extracted with ethyl acetate (50 mL×3). Combined organic layers were washed with water (50 mL), dried over anhydrous $Na_2SO_4$ and concentrated under reduce pressure to obtain solid residue which was purified by flash chromatography to get the desired product (18 mg, 18%).

LCMS: 302 [M+1]$^+$. $^1$H NMR: (400 MHz, DMSO-d$_6$) δ 7.86 (s, 1H), 7.20-7.40 (m, 4H), 6.86 (s, 1H), 6.60 (d, J=8.33 Hz, 1H), 6.32 (s, 2H), 6.18 (d, J=8.33 Hz, 1H), 5.66 (br. s., 1H), 3.14 (br. m., 2H), 2.58 (br. m., 2H), 1.74 (br. m., 2H)

Example S42. Synthesis of 5-(8-chloroquinolin-6-yl)-6-(3-methyl-1H-pyrazol-1-yl)pyrazin-2-amine (Compound No. 1.280)

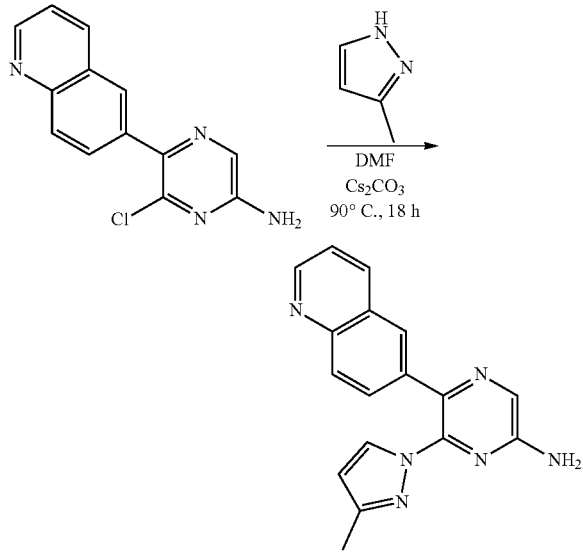

To a stirred solution of 6-chloro-5-(quinolin-6-yl)pyrazin-2-amine (300 mg, 1.16 mmol, 1 eq.) in DMF (2 mL), was added 3-methyl-1H-pyrazole (478 mg, 5.83 mmol, 5 eq.) and Cs₂CO₃ (1.9 g, 5.83 mmol, 5 eq.). Resulting mixture was heated at 90° C. for 18 h. Progress of the reaction was monitored by TLC and LCMS. On completion of the reaction, the reaction mixture was diluted with water (30 mL) and extracted with ethyl acetate (50 mL×3). Organic layer was washed with water (100 mL×3), dried over anhydrous Na₂SO₄ and concentrated under vacuum to get the solid residue which was purified by reversed phase column chromatography to get the desired product (100 mg, 33%).

LCMS: 303 [M+1]⁺. ¹H NMR: (400 MHz, DMSO-d₆) δ 8.92 (d, J=3.95 Hz, 1H), 8.41 (d, J=8.33 Hz, 1H), 8.09 (s, 1H), 7.82-7.93 (m, 3H), 7.60 (dd, J=4.38, 8.33 Hz, 1H), 7.36 (d, J=9.21 Hz, 1H), 7.06 (br. s., 2H), 6.26 (d, J=2.19 Hz, 1H), 2.06 (s, 3H).

Example S43. Synthesis of 5-(benzo[d]thiazol-6-yl)-6-phenylpyrazin-2-amine (Compound No. 1.36)

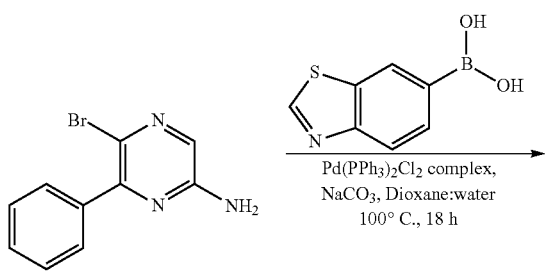

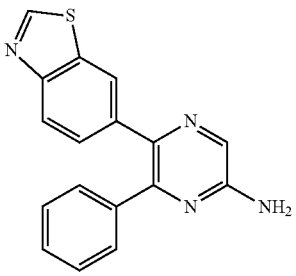

To a stirred solution of 5-bromo-6-phenylpyrazin-2-amine (0.125 g, 0.5 mmol, 1.0 eq.) and 8-chloro-6 benzo[d]thiazol-6-ylboronic acid (0.116 g, 0.65 mmol, 1.3 eq.) in dioxane (4 mL) was added Na₂CO₃ (0.106 g, 1 mmol, 2.0 eq.) and 1 mL of water. The reaction was purged with N₂ for 5 min. To this reaction mixture was added Pd(dppf)Cl₂.DCM complex (0.02 g, 5 mol %) and N₂ was purged again for another 5 min. The reaction mixture was heated at 100° C. for 18 h. The reaction mixture was allowed to cool to RT and extracted using ethyl acetate (2×35 mL). The combined organic layers were washed with brine, dried over anhydrous Na₂SO₄ and concentrated under vacuum to get the solid residue which was purified by normal phase flash column chromatography to get the desired product as off white solid (0.02 g, 13%)

LCMS: 305 [M+1]⁺. ¹H NMR: (400 MHz, DMSO-d₆) δ 9.34 (s, 1H), 8.08 (s, 1H), 7.98 (s, 1H), 7.88 (d, J=8.77 Hz, 1H), 7.23-7.38 (m, 6H), 6.68 (s, 2H).

Example S44. Synthesis of 3-amino-5-(5-methylfuran-2-yl)-6-(quinolin-6-yl)pyrazine-2-carbonitrile (Compound No. 1.281)

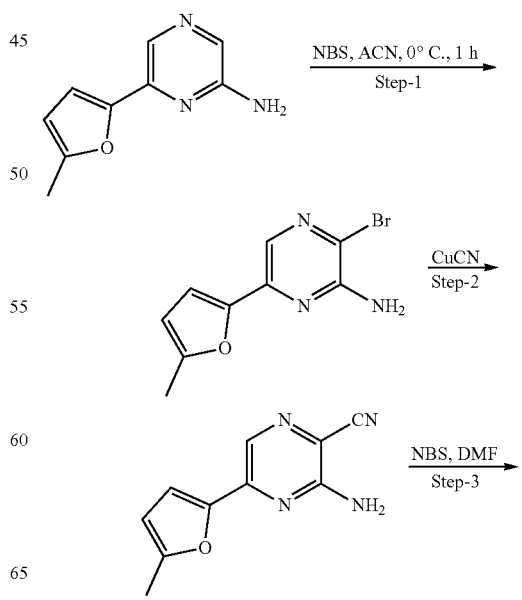

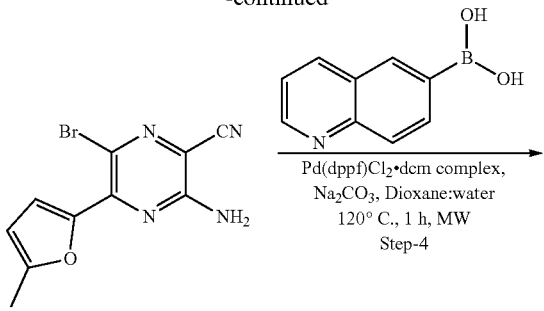

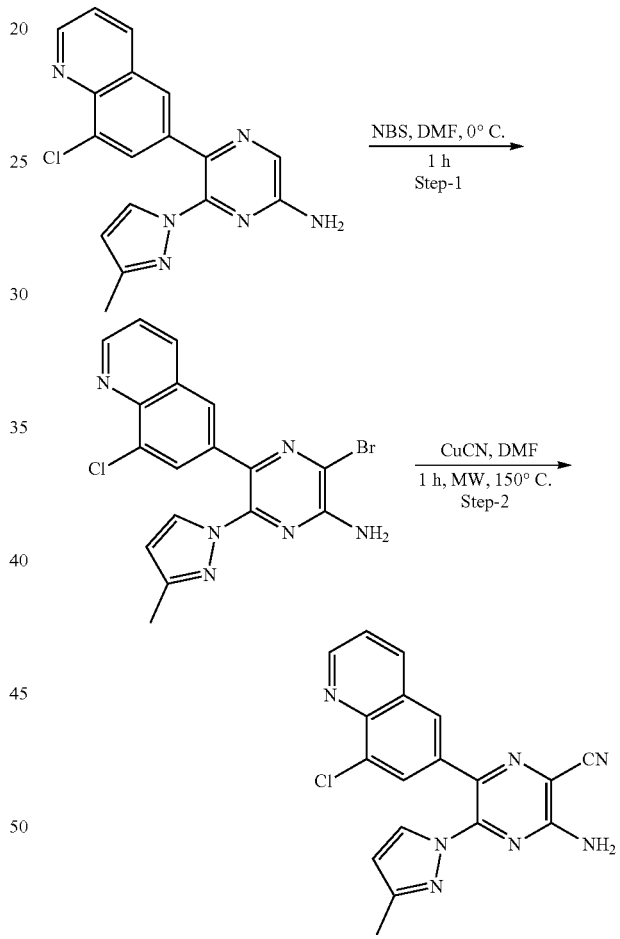

Step-1: Synthesis of 3-bromo-6-(5-methylfuran-2-yl)pyrazin-2-amine: To a stirred solution of 6-(5-methylfuran-2-yl)pyrazin-2-amine (0.7 g, 3.9 mmol, 1.0 eq.) in ACN (3.0 mL) was added N-bromosuccinimide (0.7 g, 3.9 mmol, 1.0 eq.) portionwise at 0° C. Progress of the reaction was monitored by TLC and LCMS. The reaction was quenched by adding cold water and extracted using ethyl acetate (3×50 mL) The combined organic layers were washed with brine, dried over anhydrous $Na_2SO_4$ and concentrated under vacuum to get the solid which was purified by normal phase column chromatography to afford the desired product (0.140 g, 14%)

LCMS: 254 [M+1]$^+$

Step-2: Synthesis of 3-amino-5-(5-methylfuran-2-yl)pyrazine-2-carbonitrile: To a stirred solution of 3-bromo-6-(5-methylfuran-2-yl)pyrazin-2-amine (0.508 g, 2.0 mmol, 1.0 eq.) in ACN (10.0 mL) was added CuCN (0.528 g, 5.9 mmol, 3.0 eq.). Reaction was stirred at 150° C. for 1.5 h under microwave irradiation. Progress of the reaction was monitored by TLC and LCMS. The reaction was filtered and concentrated under reduced pressure to afford the desired product (0.400 g, 99%).

LCMS: 201 [M+1]$^+$

Step-3: Synthesis of 3-amino-6-bromo-5-(5-methylfuran-2-yl)pyrazine-2-carbonitrile: To a stirred solution of 3-amino-5-(5-methylfuran-2-yl)pyrazine-2-carbonitrile (0.40 g, 2.00 mmol, 1.0 eq.) in DMF (5.0 mL) was added N-bromosuccinimide (0.373 g, 2.09 mmol, 1.0 eq.) slowly at 0° C. Progress of the reaction was monitored by TLC and LCMS. The reaction was quenched by adding cold water and the precipitate obtained was filtered and vacuum dried to afford the desired product (0.38 g, 68%).

LCMS: 279 [M+1]$^+$

Step 4: Synthesis of 3-amino-5-(5-methylfuran-2-yl)-6-(quinolin-6-yl)pyrazine-2-carbonitrile: To a stirred solution of 3-amino-6-bromo-5-(5-methylfuran-2-yl)pyrazine-2-carbonitrile (0.100 g, 0.35 mmol, 1.0 eq.) and quinolin-6-ylboronic acid (0.080 g, 0.46 mmol, 1.3 eq.) in dioxane (4 mL) was added $Na_2CO_3$ (0.056 g, 0.53 mmol, 1.5 eq.) and 1 mL water. The reaction was purged with $N_2$ for 5 min. To this reaction mixture was added Pd(dppf)Cl$_2$·DCM complex (0.02 g, 5 mol %) and $N_2$ was purged again for another 5 min. The reaction mixture was heated at 100° C. for 18 h. The reaction mixture was allowed to cool to RT and extracted using ethyl acetate (2×35 mL). The combined organic layers were washed with brine, dried over anhydrous $Na_2SO_4$ and concentrated under vacuum to get the solid residue which was purified by normal phase flash column chromatography to afford the desired product as off white solid (0.042 g, 37%)

LCMS: 328[M+1]$^+$. $^1$H NMR: (400 MHz, DMSO-d$_6$) δ 8.95 (d, J=3.81 Hz, 1H), 8.42 (d, J=7.63 Hz, 1H), 8.00-8.13 (m, 2H), 7.72 (d, J=8.90 Hz, 1H), 7.55-7.60 (m, 1H), 7.50 (s, 2H), 6.21 (d, J=2.54 Hz, 1H), 6.14 (br. s., 1H), 2.15 (s, 3H).

Example S45. Synthesis of 3-amino-6-(8-chloroquinolin-6-yl)-5-(3-methyl-1H-pyrazol-1-yl)pyrazine-2-carbonitrile (Compound No. 1.292)

Step 1. Synthesis of 3-bromo-5-(8-chloroquinolin-6-yl)-6-(3-methyl-1H-pyrazol-1-yl)pyrazin-2-amine: To a solution of 6-(3-methyl-1H-pyrazol-1-yl)-5-(quinolin-6-yl)pyrazin-2-amine (220 mg, 0.72 mmol, 1 eq.) in DMF (5 mL) at room temperature was added N-bromosuccinimide (123 mg, 0.72 mmol, 1 eq.) portion wise and the reaction mixture was allowed to stir at room temperature for 1 h. The reaction was poured over ice-water to obtain the solid precipitate which was filtered under vacuum and washed with excess water. The solid was vacuum dried to afford the desired product as off white solid (0.200 g, 67%)

LCMS: 415 [M+1]$^+$.

Step 2. Synthesis of 3-amino-6-(8-chloroquinolin-6-yl)-5-(3-methyl-1H-pyrazol-1-yl)pyrazine-2-carbonitrile: To a stirred solution of 6-phenyl-5-(quinolin-6-yl)pyrazin-2-amine (0.220 g, 0.26 mmol, 1.0 eq.) in DMF (3 mL) was added cuprous cyanide (0.155 g, 0.78 mmol, 3.0 eq.). The reaction mixture was allowed to stir at 150° C. for 1 h under microwave irradiation. The progress of the reaction was monitored by LCMS. The reaction mixture was allowed to cool to RT and extracted using ethyl acetate (3×50 mL). The combined organic layers were washed with brine, dried over anhydrous Na$_2$SO$_4$ and concentrated under vacuum to get the solid which was purified by reversed phase column chromatography to get the desired product as an off white solid (0.020 g, 23%).

LCMS: 362 [M+1]$^+$. $^1$H NMR: (400 MHz, DMSO-d$_6$) δ 9.00 (br. s., 1H), 8.47 (d, J=7.45 Hz, 1H), 8.11 (d, J=2.63 Hz, 1H), 7.97 (s, 1H), 7.84 (br. s., 2H), 7.65 (dd, J=3.95, 7.89 Hz, 1H), 7.53 (s, 1H), 6.39 (s, 1H), 1.99 (s, 3H).

Example S46. Synthesis of 3-amino-5-(5-methylthiophen-2-yl)-6-(quinolin-6-yl)pyrazine-2-carbonitrile (Compound No. 1.282)

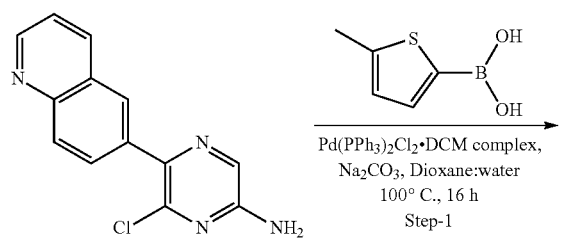

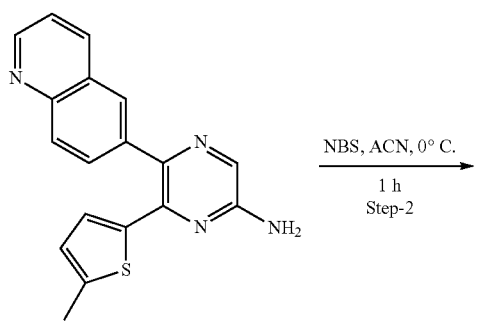

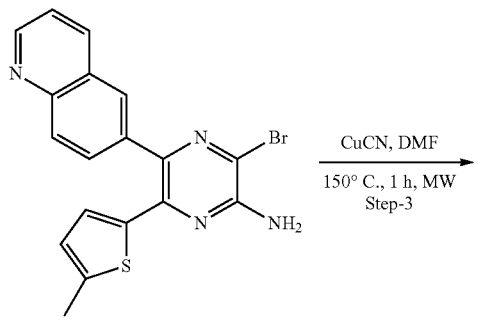

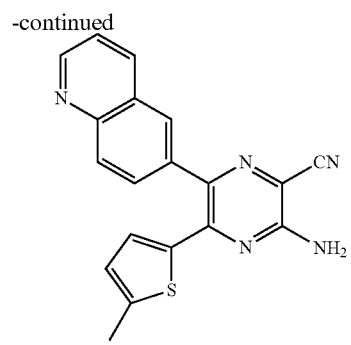

Step-1 Synthesis of 6-(5-methylthiophen-2-yl)-5-(quinolin-6-yl)pyrazin-2-amine: 6-chloro-5-(quinolin-6-yl)pyrazin-2-amine (1.0 g, 3.8 mmol, 1.0 eq.) and (5-methylthiophen-2-yl)boronic acid (0.842 g, 5.7 mmol, 1.5 eq.) was dissolved in dioxane:water (8.0 mL, 3:1). The reaction mixture was deoxygenated using nitrogen followed by addition of Pd(dppf)Cl$_2$·DCM complex (0.02 g, 5 mol %) and sodium carbonate (0.816 g, 7.7 mmol, 2.0 eq.). The reaction mixture was again purged with nitrogen and allowed to heat at 100° C. for 16 h. Progress of the reaction was monitored by TLC and LCMS. Reaction mixture was allowed to cool to RT and quenched by adding water and extracted using ethyl acetate (3×100 mL) The combined organic layers were washed with brine, dried over anhydrous Na$_2$SO$_4$ and concentrated under vacuum to get the solid which was purified by silica gel column chromatography to afford the desired product (0.480 g, 40%).

LCMS: 319 [M+1]$^+$.

Step-2: Synthesis of 3-bromo-6-(5-methylthiophen-2-yl)-5-(quinolin-6-yl)pyrazin-2-amine: To a stirred solution of 6-(5-methylthiophen-2-yl)-5-(quinolin-6-yl)pyrazin-2-amine (0.180 g, 0.56 mmol, 1.0 eq.) in DMF (3.0 mL) was added N-bromosuccinimide (0.100 g, 0.56 mmol, 1.0 eq.) portionwise at 0° C. Progress of the reaction was monitored by TLC and LCMS. Then quenched by adding cold water and extracted using ethyl acetate (3×50 mL) The combined organic layers were washed with brine, dried over anhydrous Na$_2$SO$_4$ and concentrated under vacuum to get the solid which was purified by normal phase column chromatography to afford the desired product (0.140 g, 63%).

LCMS: 397 [M+1]$^+$.

Step-3: Synthesis of 3-amino-5-(5-methylthiophen-2-yl)-6-(quinolin-6-yl)pyrazine-2-carbonitrile: To a stirred solution of 3-bromo-6-(5-methylthiophen-2-yl)-5-(quinolin-6-yl)pyrazin-2-amine (0.140 g, 0.35 mmol, 1.0 eq.) in DMF (3.0 mL) was added CuCN (0.095 g, 1.1 mmol, 3.0 eq.). Reaction was stirred at 150° C. for 1 h under microwave irradiation. Progress of the reaction was monitored by TLC and LCMS. Reaction was allowed to cool to RT and aqueous ammonia was added to adjust the pH to 7-8. The mixture was extracted using ethyl acetate (3×50 mL). The combined organic layers were washed with brine, dried over anhydrous Na$_2$SO$_4$ and concentrated under vacuum to obtain the solid which was purified by normal phase column chromatography to afford the desired product (0.012 g, 10%).

LCMS: 344 [M+1]$^+$. $^1$H NMR: (400 MHz, DMSO-d$_6$) δ 8.96 (d, J=2.54 Hz, 1H), 8.43 (d, J=7.63 Hz, 1H), 8.14 (s, 1H), 8.05 (d, J=8.90 Hz, 1H), 7.75 (d, J=8.90 Hz, 1H), 7.59 (dd, J=4.45, 8.27 Hz, 1H), 7.44 (s, 2H), 6.60 (d, J=3.81 Hz, 1H), 6.50 (d, J=3.81 Hz, 1H), 2.40 (s, 3H).

Example S47. Synthesis of 3-amino-5-phenyl-6-(quinazolin-6-yl)pyrazine-2-carbonitrile (Compound No. 1.283)

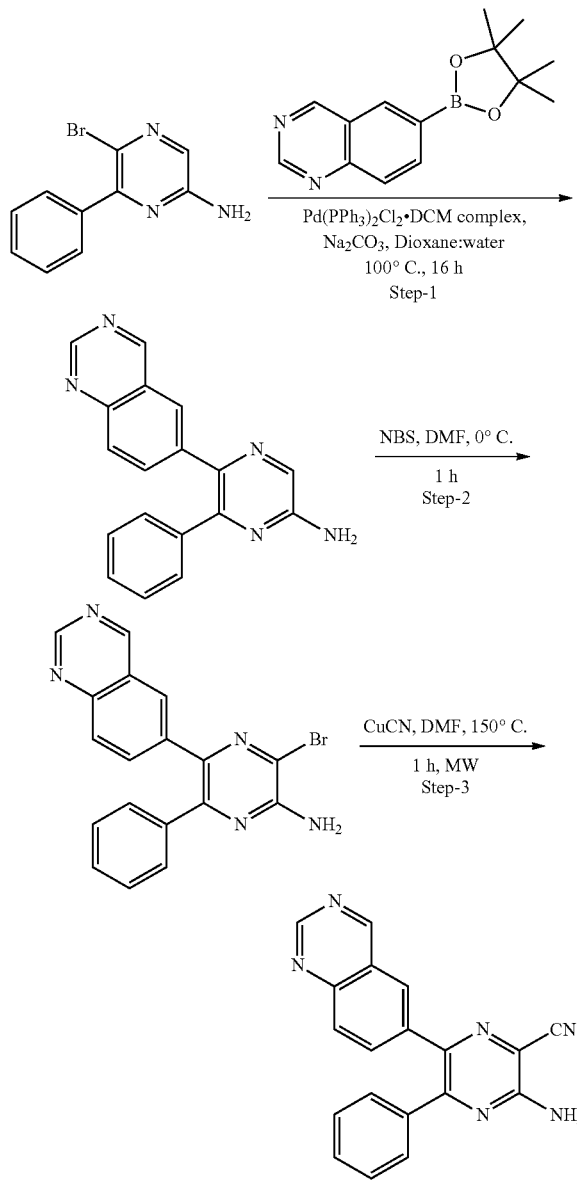

Step-1: Synthesis of 6-phenyl-5-(quinazolin-6-yl)pyrazin-2-amine: To a stirred solution of 5-bromo-6-phenylpyrazin-2-amine (0.400 g, 1.59 mmol, 1.0 eq.) and 6-(4,4,5,5-tetramethyl-1,3,2-dioxaborolan-2-yl)quinazoline (0.491 g, 1.91 mmol, 1.2 eq.) in 1,4-dioxane (4.0 mL) was added sodium carbonate (0.423 g, 3.9 mmol, 2.5 eq.) and 1 mL water. The reaction mixture was deoxygenated using nitrogen gas and Pd(PPh$_3$)$_2$Cl$_2$·DCM complex (0.065 g, 5 mol %) was added. The reaction mixture was again purged with nitrogen and allowed to heat at 100° C. for 16 h. Progress of the reaction was monitored by TLC and LCMS. Reaction mixture was allowed to cool to RT and quenched by adding water and extracted using ethyl acetate (3×50 mL). The combined organic layers were washed with brine, dried over anhydrous Na$_2$SO$_4$ and concentrated under vacuum to obtain the solid which was purified by normal phase column chromatography to afford the desired product (0.205 g, 41%).

LCMS: 300 [M+1]$^+$.

Step-2: Synthesis of 3-bromo-6-phenyl-5-(quinazolin-6-yl)pyrazin-2-amine: To a stirred solution of 6-phenyl-5-(quinazolin-6-yl)pyrazin-2-amine (0.200 g, 0.67 mmol, 1.0 eq.) in DMF (3.0 mL) was added N-bromosuccinimide (0.118 g, 0.67 mmol, 1.0 eq.) portionwise at 0° C. Progress of the reaction was monitored by TLC and LCMS. Reaction mixture was diluted with cold water and the obtained precipitate was filtered under vacuum, washed with excess water and vacuum dried to afford the desired product (0.200 g, 79%).

LCMS: 378 [M+1]$^+$.

Step-3: Synthesis of 3-amino-5-phenyl-6-(quinazolin-6-yl)pyrazine-2-carbonitrile: To a stirred solution of 3-bromo-6-phenyl-5-(quinazolin-6-yl)pyrazin-2-amine (0.200 g, 0.52 mmol, 1.0 eq.) in DMF (3.0 mL) was added CuCN (0.142 g, 1.58 mmol, 3.0 eq.). Reaction was stirred at 150° C. for 1 h under microwave irradiation. Progress of the reaction was monitored by TLC and LCMS. Reaction was allowed to cool to RT and aqueous ammonia was added to adjust the pH to 7-8. The mixture was extracted using ethyl acetate (3×35 mL). The combined organic layers were washed with brine, dried over anhydrous Na$_2$SO$_4$ and concentrated under vacuum to get the solid which was purified by normal phase column chromatography to afford the desired product (0.014 g, 9%).

LCMS: 325 [M+1]$^+$. $^1$H NMR: (400 MHz, DMSO-d$_6$) δ 9.56 (s, 1H), 9.28 (s, 1H), 8.20 (s, 1H), 7.84 (d, J=8.77 Hz, 1H), 7.70-7.78 (m, 1H), 7.65 (s, 2H), 7.27-7.44 (m, 5H).

Example S48. Synthesis of N-(3-cyano-6-phenyl-5-(quinolin-6-yl)pyrazin-2-yl)acetamide (Compound No. 1.284)

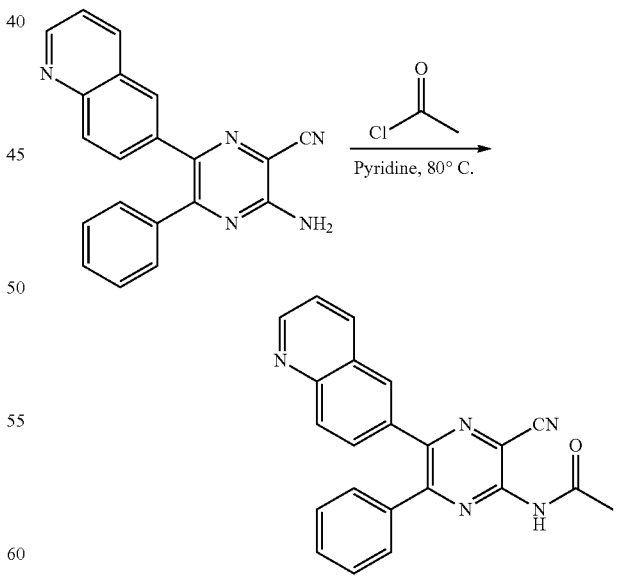

To a stirred solution of 3-amino-5-phenyl-6-(quinolin-6-yl)pyrazine-2-carbonitrile (100 mg, 0.31 mmol) in pyridine (4 mL) was added acetyl chloride (0.06 mL, 0.93 mmol) at 0° C. under N$_2$. The reaction mixture was stirred at RT for 30 min followed by heating at 80° C. for 12 h. The reaction was monitored by TLC and LCMS. The reaction was diluted with water and extracted with ethyl acetate (3×30 mL). The combined organic layers were washed with brine, dried over anhydrous $Na_2SO_4$ and concentrated under vacuum to obtain the solid which was purified by preparative thin layer chromatography to afford the desired product (18 mg, 16%).

LCMS: 366 [M+1]$^+$. $^1$H NMR: (400 MHz, DMSO-$d_6$) δ 11.36 (s, 1H), 8.94 (d, J=3.81 Hz, 1H), 8.38 (d, J=7.63 Hz, 1H), 8.22 (s, 1H), 7.92 (d, J=8.90 Hz, 1H), 7.65 (d, J=7.63 Hz, 1H), 7.56 (dd, J=4.45, 8.27 Hz, 1H), 7.50 (d, J=6.36 Hz, 2H), 7.31-7.47 (m, 3H), 2.23 (s, 3H).

Example S49. Synthesis of 6-(1-methyl-1H-pyrazol-3-yl)-5-(quinolin-6-yl)pyrazin-2-amine (Compound No. 1.285)

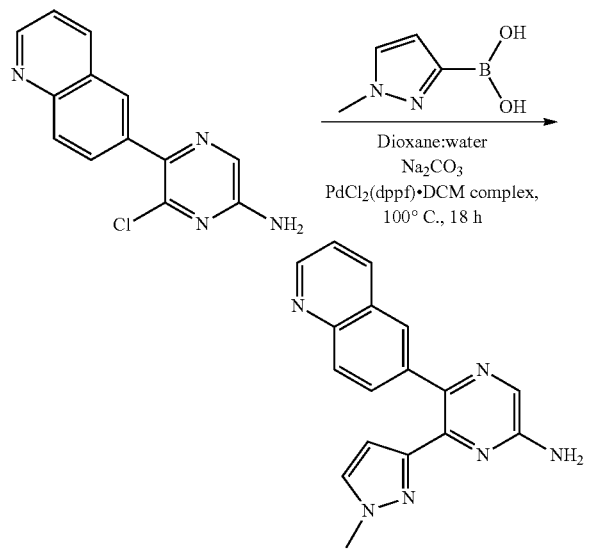

To a stirred solution of 6-chloro-5-(quinolin-6-yl)pyrazin-2-amine (150 mg, 0.58 mmol, 1.0 eq.) and (1-methyl-1H-pyrazol-3-yl)boronic acid (81 mg, 0.64 mmol, 1.1 eq.) in dioxane (5 mL) and water (1 mL), was added $Na_2CO_3$ (122 mg, 1.16 mmol, 2.0 eq.). The reaction was purged with $N_2$ for 5 min. To this reaction mixture was added Pd(dppf)Cl$_2$'DCM complex (24 mg, 5 mol %) and $N_2$ was purged again for another 5 min. The reaction mixture was heated at 100° C. for 18 h. progress of reaction was monitored by TLC and LCMS. On completion of the reaction, the reaction mixture was extracted with ethyl acetate (35 mL×3). Combined organic layer was washed with water (50 mL×2), dried over anhydrous $Na_2SO_4$ and concentrated under vacuum to get the solid residue which was purified by reversed phase column chromatography to afford the desired product 6-(1-methyl-1H-pyrazol-3-yl)-5-(quinolin-6-yl)pyrazin-2-amine (14 mg, 9%) as an off white solid.

LCMS: 303 [M+1]$^+$. $^1$H NMR: (400 MHz, DMSO-$d_6$) δ 8.85 (d, J=2.63 Hz, 1H), 8.30 (d, J=7.89 Hz, 1H), 7.92-8.03 (m, 2H), 7.84 (d, J=8.77 Hz, 1H), 7.55-7.64 (m, 2H), 7.49 (dd, J=4.39, 8.33 Hz, 1H), 6.65 (s, 2H), 6.12 (d, J=2.19 Hz, 1H), 3.71 (s, 3H).

Example S50. Synthesis of 5-(benzo[d]thiazol-6-yl)-6-(3-methyl-1H-pyrazol-1-yl)pyrazin-2-amine (Compound No. 1.286)

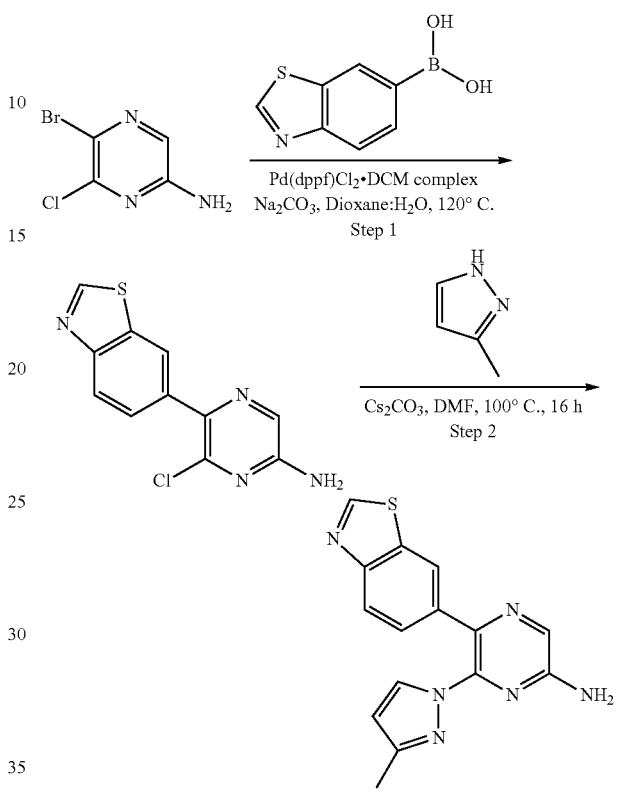

Step 1: Synthesis of 5-iodo-6-(1H-pyrazol-1-yl)pyrazin-2-amine: To a solution of 5-bromo-6-chloropyrazin-2-amine (0.600 g, 2.8 mmol, 1 eq.) and benzo[d]thiazol-6-ylboronic acid (0.412 g, 2.3 mmol, 0.8 eq.) in dioxane (8 mL) and water (2 mL) was added $Na_2CO_3$ (0.549 g, 5.18 mmol, 2 eq.). The reaction was purged with $N_2$ and PdCl$_2$(dppf)•DCM complex (0.117 g, 5 mol %). The reaction mixture was deoxygenated using $N_2$ atmosphere and the reaction mixture was heated at 100° C. for 16 h under microwave irradiation. The reaction was monitored by TLC and LCMS. The reaction mixture was diluted with water and extracted with ethyl acetate (3×100 mL). The separated organic layer was dried over anhydrous sodium sulphate and concentrated under reduced pressure. The crude product was purified by normal phase column chromatography to afford desired product (0.210 g, 28%).

LCMS: 263 [M+1]$^+$.

Step 2: synthesis of 5-(benzo[d]thiazol-6-yl)-6-(3-methyl-1H-pyrazol-1-yl)pyrazin-2-amine: To a solution of 5-bromo-6-chloropyrazin-2-amine (200 mg, 0.98 mmol, 1 eq.) in DMF (3 mL) was added 3-methyl pyrazole (312 mg, 3.8 mmol, 5.0 eq.) and $Cs_2CO_3$ (1.24 g, 3.8 mmol, 5.0 eq.). The reaction mixture was allowed to heat at 100° C. for 16 h. The progress of the reaction was monitored by TLC and LCMS. The reaction mixture was diluted with water (30 mL) and extracted using ethyl acetate (2×50 mL). The separated organic layer was dried over sodium sulfate and concentrated under reduced pressure. The crude product was purified by normal phase column chromatography to afford the desired product (16 mg, 54%). LCMS: 309 [M+1]$^+$. $^1$H NMR: (400 MHz, DMSO-d$_6$) δ 9.35 (s, 1H), 8.06 (s, 1H), 7.96 (d, J=1.32 Hz, 1H), 7.90 (d, J=8.77 Hz, 1H), 7.81 (d, J=2.19 Hz, 1H), 7.13 (dd, J=1.75, 8.77 Hz, 1H), 6.98 (s, 2H), 6.23 (d, J=2.19 Hz, 1H), 2.08 (s, 3H).

Example S51. Synthesis of 5-(1H-indazol-5-yl)-6-(3-methyl-1H-pyrazol-1-yl)pyrazin-2-amine (Compound No. 1.287)

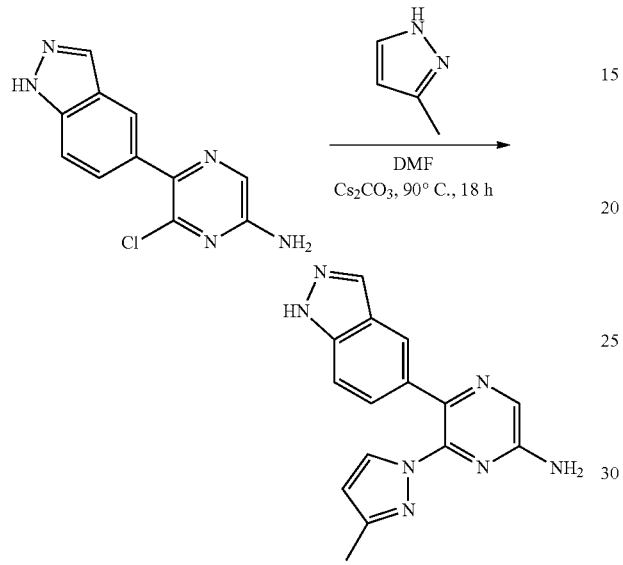

To a stirred solution of 6-chloro-5-(1H-indazol-5-yl)pyrazin-2-amine (85 mg, 0.35 mmol, 1 eq.) in DMF (2 mL), was added 3-methyl-1H-pyrazole (143 mg, 1.75 mmol, 5 eq.) and Cs$_2$CO$_3$ (570 mg, 1.75 mmol, 5 eq.). The resulting reaction mixture was heated at 90° C. for 18 h. Progress of the reaction was monitored by TLC and LCMS. On completion of reaction, reaction mixture was diluted with water (30 mL) and extracted with ethyl acetate (35 mL×3). Combined organic layer was washed with water (50 mL×3), dried over anhydrous Na$_2$SO$_4$ and concentrated under vacuum to obtain the solid residue which was purified by reversed phase column chromatography to afford the desired product (5 mg, 35%).

LCMS: 292 [M+1]$^+$. $^1$H NMR: (400 MHz, DMSO-d$_6$) δ 13.01 (br. s., 1H), 8.04 (s, 1H), 8.00 (s, 1H), 7.69 (d, J=2.19 Hz, 1H), 7.55 (s, 1H), 7.36 (d, J=8.77 Hz, 1H), 7.05 (d, J=9.21 Hz, 1H), 6.83 (s, 2H), 6.18 (d, J=2.19 Hz, 1H), 2.11 (s, 3H).

Example S52. Synthesis of 6-(2-methylthiazol-5-yl)-5-(quinolin-6-yl)pyrazin-2-amine (Compound No. 1.288)

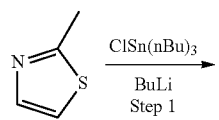

Step 1: Synthesis of 2-methyl-5-(tributylstannyl)thiazole: To a stirred solution of 2-methylthiazole (1 g, 0.01 mol, 1 eq.) in THF (25 mL) was added n-butyl lithium (1.6 M, 6.9 ml, 0.011 mol, 1.1 eq.) at −78° C. under N$_2$. The reaction mixture was stirred at the same for 30 min then charged tri butyl tin chloride (3.2 mL, 0.012 mol, 1.2 eq.) then the reaction mixture was stirred at −78° c. for 1 h and 16 h at room temperature. The reaction was monitored by TLC and LCMS. The reaction was diluted aq. NaHCO$_3$ and extracted with diethyl ether (3×25 mL). The combined organic layers were washed with brine, dried over anhydrous Na$_2$SO$_4$ and concentrated under vacuum to obtain the solid which was purified by normal phase column chromatography to afford the desired product as an off white solid (2.1 g, 54%).

LCMS: 390 [M+1]$^+$.

Step 2: Synthesis of 6-(2-methylthiazol-5-yl)-5-(quinolin-6-yl)pyrazin-2-amine: To a stirred solution of 6-chloro-5-(quinolin-6-yl)pyrazin-2-amine (0.200 g, 0.78 mol, 1.0 eq.) and 2-methyl-5-(tributylstannyl)thiazole (0.911 g, 2.34 mol, 3 eq.) in xylene (5 mL) and DMF (1 mL) was added Pd(PPh$_3$)$_4$ (0.090 g, 10 mol %) under N$_2$. The reaction mixture was heated at 150° C. for 48 h. The reaction mixture was allowed to cool to RT and charged with water extracted using ethyl acetate (2×35 mL). The combined organic layers were washed with brine, dried over anhydrous Na$_2$SO$_4$ and concentrated under vacuum to get the solid residue which was purified by reversed phase column chromatography to get the desired product (20 mg, 8%).

LCMS: 320 [M+1]$^+$. $^1$H NMR: (400 MHz, DMSO-d6) δ 8.93 (d, J=3.51 Hz, 1H), 8.39 (d, J=7.89 Hz, 1H), 8.08 (s, 1H), 8.02 (d, J=8.77 Hz, 1H), 7.93 (s, 1H), 7.73 (d, J=7.45 Hz, 1H), 7.56 (dd, J=4.17, 8.55 Hz, 1H), 7.11 (s, 1H), 6.79 (s, 2H), 2.56 (s, 3H).

Example S53. Synthesis of 5-(1H-indazol-5-yl)-6-phenylpyrazin-2-amine (Compound No. 1.289)

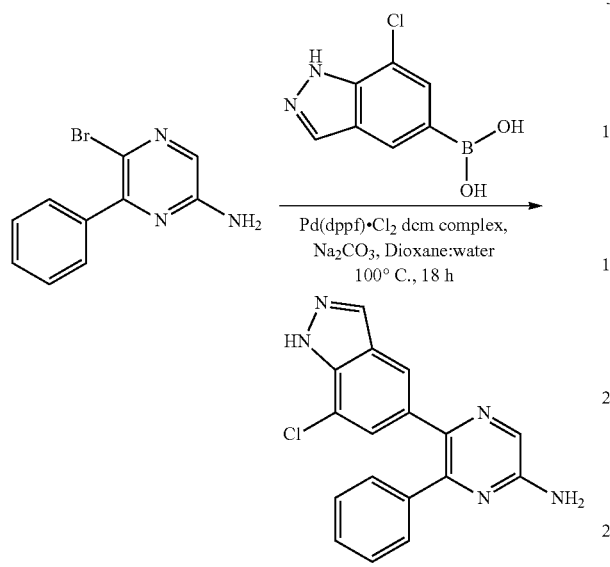

To a stirred solution of 5-bromo-6-phenylpyrazin-2-amine (0.120 g, 0.48 mmol, 1.0 eq.) and (7-chloro-1H-indazol-5-yl)boronic acid (0.104 g, 0.53 mmol, 1.1 eq.) in dioxane (4 mL) was added $Na_2CO_3$ (0.102 g, 0.96 mmol, 2.0 eq.) and 1 mL water. The reaction was purged with $N_2$ for 5 min. To this reaction mixture was added with Pd(dppf)$Cl_2$.DCM complex (0.020 g, 5 mol %) and $N_2$ was purged again for another 5 min. The reaction mixture was heated at 100° C. for 18 h. The reaction mixture was allowed to cool to RT and extracted using ethyl acetate (3×35 mL). The combined organic layers were washed with brine, dried over anhydrous $Na_2SO_4$ and concentrated under vacuum to obtain the solid residue which was purified by reversed phase column chromatography to get the desired product as off white solid (0.008 g, 5%).

LCMS: 322 [M+1]$^+$. $^1$H NMR: (400 MHz, DMSO-$d_6$) δ 13.54 (br. s., 1H), 8.07 (br. s., 1H), 7.95 (s, 1H), 7.54 (br. s., 1H), 7.30 (d, J=9.65 Hz, 6H), 6.63 (br. s., 2H).

Example S54. Synthesis of 3-amino-5-(3-methyl-1H-pyrazol-1-yl)-6-(quinolin-6-yl)pyrazine-2-carbonitrile (Compound No. 1.290)

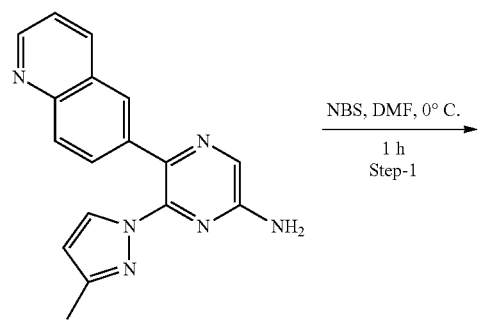

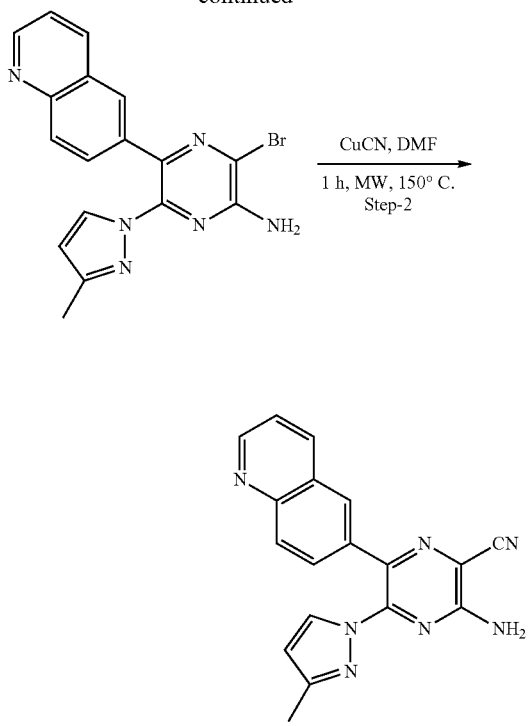

Step 1. Synthesis of 3-bromo-6-(3-methyl-1H-pyrazol-1-yl)-5-(quinolin-6-yl)pyrazin-2-amine: To a solution of 6-(3-methyl-1H-pyrazol-1-yl)-5-(quinolin-6-yl)pyrazin-2-amine (220 mg, 0.72 mmol, 1 eq.) in DMF (5 mL) at room temperature was added N-bromosuccinimide (123 mg, 0.72 mmol, 1 eq.) portion wise and the reaction mixture was allowed to stir at room temperature for 1 h. The reaction was poured over ice-water to get the solid precipitate which was filtered under vacuum and washed with excess water. The solid was vacuum dried to afford the desired product as off white solid (0.200 g, 73%).

LCMS: 381 [M+1]$^+$.

Step 2. Synthesis of 3-amino-5-(3-methyl-1H-pyrazol-1-yl)-6-(quinolin-6-yl)pyrazine-2-carbonitrile: To a stirred solution of 6-phenyl-5-(quinolin-6-yl)pyrazin-2-amine (0.220 g, 0.26 mmol, 1.0 eq.) in DMF (3 mL) was added cuprous cyanide (0.155 g, 0.78 mmol, 3.0 eq.). The reaction mixture was allowed to stir at 150° C. for 1 h under microwave irradiation. The progress of the reaction was monitored by LCMS. The reaction mixture was allowed to cool to RT and extracted using ethyl acetate (3×50 mL). The combined organic layers were washed with brine, dried over anhydrous $Na_2SO_4$ and concentrated under vacuum to obtain the solid which was purified by normal phase column chromatography to afford the desired product as an off white solid (0.020 g, 23%).

LCMS: 328 [M+1]$^+$ 0.1H NMR: (400 MHz, DMSO-d6) δ 8.89 (d, J=3.07 Hz, 1H), 8.36 (d, J=7.45 Hz, 1H), 8.01 (d, J=2.63 Hz, 1H), 7.96 (s, 1H), 7.86 (d, J=8.77 Hz, 1H), 7.79 (br. s., 2H), 7.53 (dd, J=3.95, 8.33 Hz, 1H), 7.38 (d, J=7.45 Hz, 1H), 6.33 (d, J=2.19 Hz, 1H), 1.99 (s, 3H).

Example S55. Synthesis of 6-(3,5-dimethyl-1H-pyrazol-1-yl)-5-(quinolin-6-yl)pyrazin-2-amine (Compound No. 1.291)

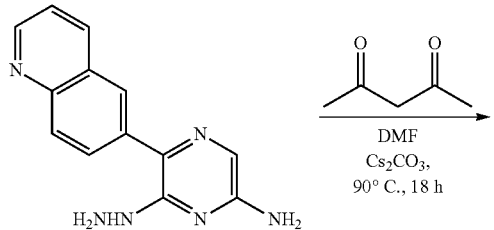

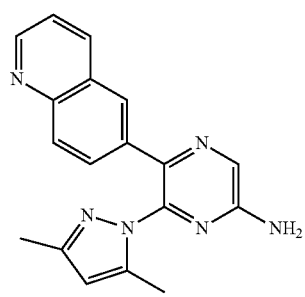

A mixture of 6-hydrazinyl-5-(quinolin-6-yl)pyrazin-2-amine (0.120 g, 0.48 mmol, 1.0 eq.), acetylacetone (0.071 g, 0.71 mmol, 1.5 eq.), ethanol (4 mL) and concentrated sulfuric acid (0.02 mL) was heated at reflux for 18 h. After cooling the mixture to ambient temperature, the reaction was quenched by adding saturated aqueous sodium hydrogen carbonate. The organic layer was extracted with ethyl acetate (3×30 mL), washed with water and brine, dried over anhydrous sodium sulfate, filtered, and concentrated in vacuum. The residue was purified by reversed column chromatography to afford the desired product (35 mg, 23%).

LCMS: 317 [M+1]$^+$. $^1$H NMR: (400 MHz, DMSO-d$_6$) δ 8.84 (dd, J=1.53, 4.17 Hz, 1H), 8.12-8.26 (m, 2H), 7.84 (d, J=8.77 Hz, 1H), 7.66 (d, J=1.32 Hz, 1H), 7.49 (dd, J=4.38, 8.33 Hz, 1H), 7.36 (dd, J=1.97, 8.99 Hz, 1H), 7.05 (s, 2H), 5.98 (s, 1H), 2.12 (s, 3H), 1.89 (s, 3H).

Example S56. Synthesis of 6-(1H-pyrazol-3-yl)-5-(quinolin-6-yl)pyrazin-2-amine (Compound No. 1.293)

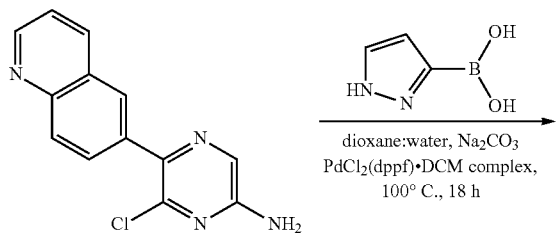

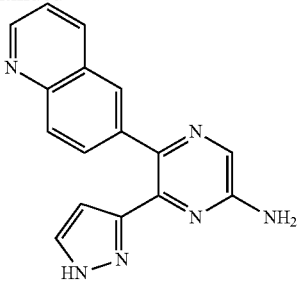

To a stirred solution of 6-chloro-5-(quinolin-6-yl)pyrazin-2-amine (100 mg, 0.39 mmol, 1.0 eq.) and (1H-pyrazol-3-yl)boronic acid (81 mg, 0.47 mmol, 1.2 eq.) in dioxane (3 mL) and water (0.5 mL), was added Na$_2$CO$_3$ (83 mg, 0.78 mmol, 2.0 eq.). The reaction was purged with N$_2$ for 5 min. To this reaction mixture was added Pd(dppf)Cl$_2$.DCM complex (16 mg, 5 mol %) and N$_2$ was purged again for another 5 min. The reaction mixture was heated at 100° C. for 18 h. Progress of reaction was monitored by TLC and LCMS. On completion of the reaction, the reaction mixture was extracted with ethyl acetate (35 mL×3). Combined organic layers were washed with water (20 mL×2), dried over anhydrous Na$_2$SO$_4$ and concentrated under vacuum to obtain the solid residue which was purified by reversed phase column chromatography to afford the desired product (10 mg, 9%) as an off white solid.

LCMS: 289 [M+1]$^+$, $^1$H NMR: (400 MHz, DMSO-d$_6$) δ12.59 (s, 1H), 8.86 (br. s., 1H), 8.29 (d, J=7.45 Hz, 1H), 7.95 (s, 2H), 7.86 (d, J=8.33 Hz, 2H), 7.58 (d, J=8.33 Hz, 2H), 7.50 (br. s., 1H), 6.64 (br. s., 2H).

Example S57. Synthesis of 6-(3,5-dimethyl-1H-pyrazol-4-yl)-5-(quinolin-6-yl)pyrazin-2-amine (Compound No. 1.294)

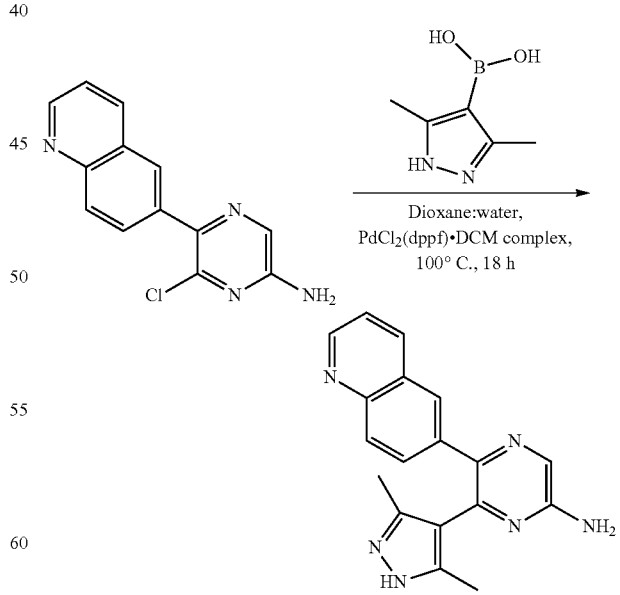

To a stirred solution of 6-chloro-5-(quinolin-6-yl)pyrazin-2-amine (100 mg, 0.39 mmol, 1.0 eq.) and (3,5-dimethyl-1H-pyrazol-4-yl)boronic acid (104 mg, 0.47 mmol, 1.2 eq.) in dioxane (3 mL) and water (0.5 mL), was added Na$_2$CO$_3$ (83 mg, 0.78 mmol, 2.0 eq.). The reaction was purged with N$_2$ for 5 min. To this reaction mixture was added Pd(dppf)Cl$_2$.DCM complex (16 mg, 5 mol %) and N$_2$ was purged again for another 5 min. The reaction mixture was heated at 100° C. for 16 h. progress of reaction was monitored by TLC and LCMS. On completion of the reaction, the reaction mixture was extracted with ethyl acetate (35 mL×3). Combined organic layer was washed with water (20 mL×2), dried over anhydrous Na$_2$SO$_4$ and concentrated under vacuum to obtain the solid residue which was purified by reversed phase column chromatography to afford the desired product (20 mg, 16%) as an off white solid.

LCMS: 317 [M+1]$^+$. $^1$H NMR: (400 MHz, DMSO-d$_6$) δ8.89 (d, J=3.95 Hz, 1H), 8.38 (d, J=8.33 Hz, 1H), 8.02 (s, 1H), 7.96 (s, 1H), 7.85 (d, J=8.77 Hz, 1H), 7.63 (d, J=9.21 Hz, 1H), 7.55 (dd, J=4.38, 7.89 Hz, 1H), 6.63 (br. s., 2H), 1.80 (s, 6H).

Example S58. Synthesis of 5-(7-chloro-1H-indazol-5-yl)-6-(3-methyl-1H-pyrazol-1-yl)pyrazin-2-amine (Compound No. 1.295)

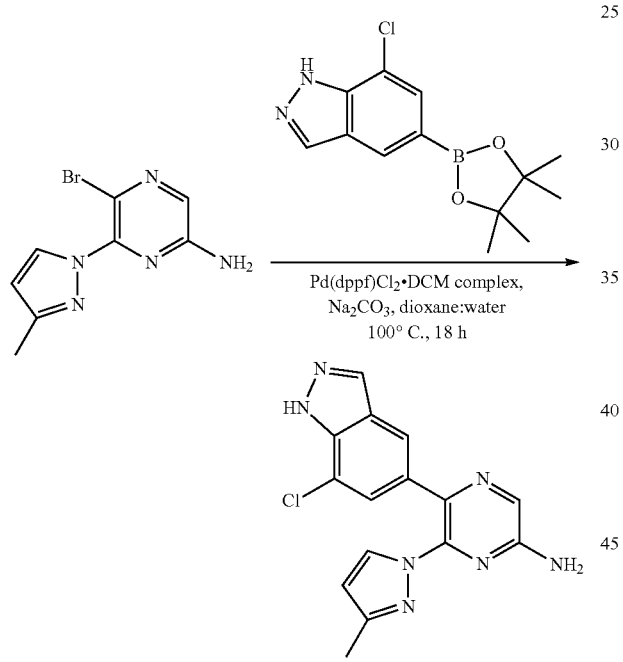

To a stirred solution of 5-bromo-6-(3-methyl-1H-pyrazol-1-yl)pyrazin-2-amine (0.150 g, 0.60 mmol, 1.0 eq.) and 7-chloro-5-(4,4,5,5-tetramethyl-1,3,2-dioxaborolan-2-yl)-1H-indazole (0.198 g, 0.71 mmol, 1.2 eq.) in dioxane (4 mL) was added Na$_2$CO$_3$ (0.127 g, 1.2 mmol, 2.0 eq.) and 1 mL water. The reaction was purged with N$_2$ for 5 min. To this reaction mixture was added with Pd(dppf)Cl$_2$.DCM complex (0.024 g, 5 mol %) and N$_2$ was purged again for another 5 min. The reaction mixture was heated at 100° C. for 18 h. The reaction mixture was allowed to cool to RT and extracted using ethyl acetate (3×35 mL). The combined organic layers were washed with brine, dried over anhydrous Na$_2$SO$_4$ and concentrated under vacuum to obtain the solid residue which was purified by normal phase column chromatography to afford the desired product as off white solid (0.035 g, 8%).

LCMS: 326 [M+1]$^+$. $^1$H NMR: (400 MHz, DMSO-d$_6$) δ 13.54 (br. s., 1H), 8.13 (s, 1H), 8.04 (s, 1H), 7.81 (br. s., 1H), 7.50 (s, 1H), 7.04 (s, 1H), 6.93 (br. s., 2H), 6.24 (br. s., 1H), 2.10 (s, 3H).

Example S59. Synthesis of 6-(3-methyl-1H-pyrazol-1-yl)-5-(8-methylquinolin-6-yl)pyrazin-2-amine (Compound No. 1.296)

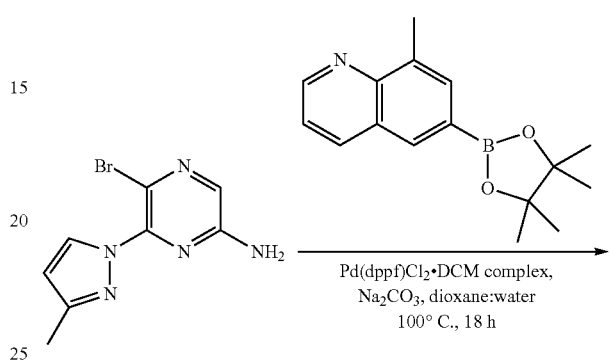

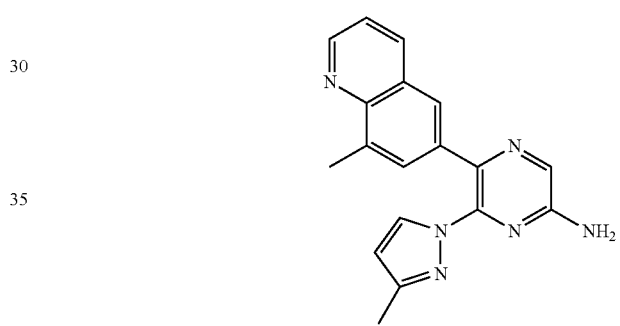

To a stirred solution of 5-bromo-6-(3-methyl-1H-pyrazol-1-yl)pyrazin-2-amine (0.150 g, 0.60 mmol, 1.0 eq.) and 8-methyl-6-(4,4,5,5-tetramethyl-1,3,2-dioxaborolan-2-yl)quinoline (0.175 g, 0.65 mmol, 1.1 eq.) in dioxane (4 mL) was added Na$_2$CO$_3$ (0.127 g, 1.2 mmol, 2.0 eq.) and 1 mL water. The reaction was purged with N$_2$ for 5 min. To this reaction mixture was added with Pd(dppf)Cl$_2$.DCM complex (0.024 g, 5 mol %) and N$_2$ was purged again for another 5 min. The reaction mixture was heated at 100° C. for 18 h. The reaction mixture was allowed to cool to RT and extracted using ethyl acetate (3×35 mL). The combined organic layers were washed with brine, dried over anhydrous Na$_2$SO$_4$ and concentrated under vacuum to obtain the solid residue which was purified by normal phase column chromatography to afford the desired product as off white solid (0.035 g, 19%).

LCMS: 361 [M+1]$^+$. $^1$H NMR: (400 MHz, DMSO-d$_6$) δ 8.86 (d, J=2.63 Hz, 1H), 8.18 (d, J=7.89 Hz, 1H), 8.09 (s, 1H), 7.81 (s, 1H), 7.56 (s, 1H), 7.48 (dd, J=4.17, 8.11 Hz, 1H), 7.21 (s, 1H), 7.01 (br. s., 2H), 6.25 (s, 1H), 2.59 (s, 3H), 2.10 (s, 3H).

Example S60. Synthesis of 5-(8-chloroquinolin-6-yl)-6-(1-methyl-1H-pyrazol-3-yl)pyrazin-2-amine (Compound No. 1.297)

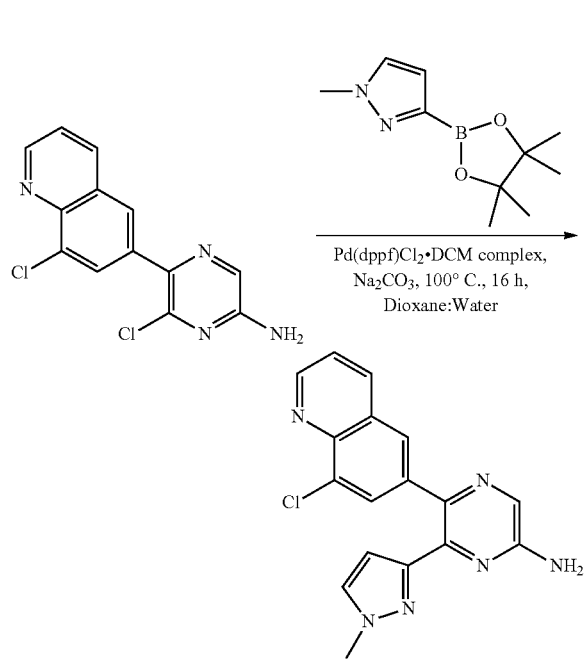

To a stirred solution of 6-chloro-5-(8-chloroquinolin-6-yl)pyrazin-2-amine (0.460 g, 1.57 mmol, 1.0 eq.) and 1-methyl-3-(4,4,5,5-tetramethyl-1,3,2-dioxaborolan-2-yl)-1H-pyrazole (0.394 g, 1.89 mmol, 1.2 eq.) in dioxane (10 mL) was added Na$_2$CO$_3$ (0.334 g, 3.15 mmol, 2.0 eq.) and 2 mL water. Then reaction was purged with N$_2$ for about 5 min. To this reaction mixture was added Pd(dppf)Cl$_2$.DCM complex (0.129 g, 10 mol %) and N$_2$ was purged again for another 5 min. Then reaction mixture was heated at 100° C. for 16 h, allowed to cool to RT and extracted using ethyl acetate (3×50 mL). The combined organic layers were washed with brine, dried over anhydrous Na$_2$SO$_4$ and concentrated under vacuum to obtain the solid residue which was purified by reversed phase column chromatography to afford the desired product as yellow solid (0.005 g, 1%).

LCMS: 337[M+1]$^+$. $^1$H NMR: (400 MHz, DMSO-d$_6$) δ 8.97 (d, J=2.63 Hz, 1H), 8.39 (d, J=7.89 Hz, 1H), 7.97 (s, 2H), 7.76 (s, 1H), 7.66 (br. s., 1H), 7.61 (dd, J=4.17, 8.11 Hz, 1H), 6.72 (s, 2H), 6.26 (br. s., 1H), 3.71 (s, 3H).

Example S61. Synthesis of 6-(pyrrolidin-1-yl)-5-(quinolin-6-yl)pyrazin-2-amine (Compound No. 1.298)

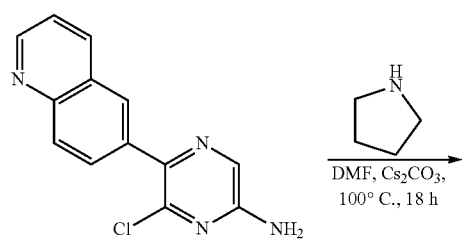

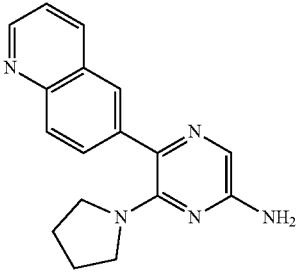

To a stirred solution of 6-chloro-5-(quinolin-6-yl)pyrazin-2-amine (128 mg, 0.5 mmol, 1 eq.) in DMF (2 mL), was added pyrrolidine (177 mg, 2.5 mmol, 5 eq.) and Cs$_2$CO$_3$ (0.815 g, 2.5 mmol, 5 eq.). Resulting mixture was heated at 100° C. for 18 h. Progress of the reaction was monitored by TLC and LCMS. On completion of the reaction, the reaction mixture was diluted with water (30 mL) and extracted with ethyl acetate (50 mL×3). Organic layer was washed with water (100 mL×3), dried (anhydrous Na$_2$SO$_4$) and concentrated under vacuum to get the solid residue which was purified by normal phase column chromatography to afford the desired product as off white solid (100 mg, 33%).

LCMS: 292 [M+1]$^+$. $^1$H NMR: (400 MHz, DMSO-d$_6$) δ 8.86 (br. s., 1H), 8.42 (d, J=7.89 Hz, 1H), 7.83-8.04 (m, 3H), 7.48-7.59 (m, 1H), 7.40 (s, 1H), 6.18 (br. s., 2H), 3.09 (br. s., 4H), 1.72 (br. s., 4H).

Example S62. Synthesis of 5-(1H-indazol-5-yl)-6-(1-methyl-1H-pyrazol-3-yl)pyrazin-2-amine (Compound No. 1.299)

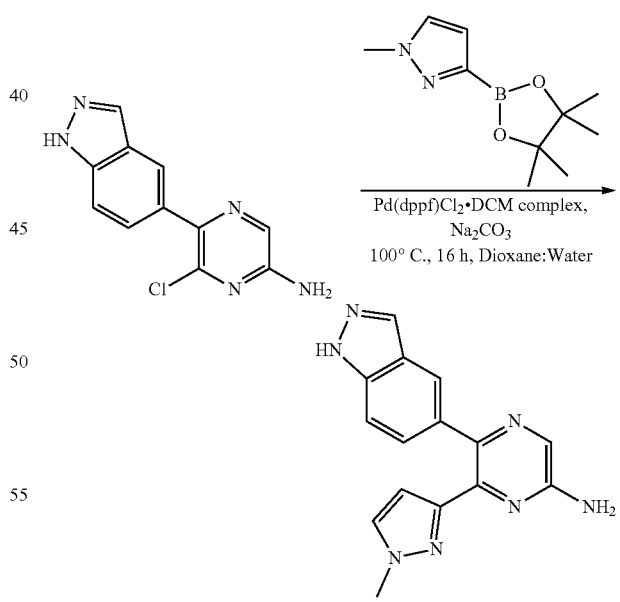

To a stirred solution of 6-chloro-5-(1H-indazol-5-yl)pyrazin-2-amine (0.150 g, 0.61 mmol, 1.0 eq.) and 1-methyl-3-(4,4,5,5-tetramethyl-1,3,2-dioxaborolan-2-yl)-1H-pyrazole (0.152 g, 0.73 mmol, 1.2 eq.) in dioxane (10 mL) was added Na$_2$CO$_3$ (0.129 g, 1.22 mmol, 2.0 eq.) and 2 mL water. Then reaction was purged with N$_2$ for about 5 min. To this reaction mixture was added Pd(dppf)Cl$_2$.DCM complex (0.025 g, 5 mol %) and N₂ was purged again for another 5 min. The reaction mixture was heated at 100° C. for 16 h. After that reaction mixture was allowed to cool to RT and extracted using ethyl acetate (3×50 mL). The combined organic layers were washed (brine), dried (anhydrous Na₂SO₄) and concentrated under vacuum to get the solid residue which was purified by reversed phase column chromatography to afford the desired product as off white solid (0.010 g, 6%).

LCMS: 292.2 [M+1]⁺. ¹H NMR: (400 MHz, DMSO-d₆) δ 13.01 (br. s., 1H), 8.01 (s, 1H), 7.90 (s, 1H), 7.69 (s, 1H), 7.53 (d, J=1.75 Hz, 1H), 7.40 (d, J=8.77 Hz, 1H), 7.25 (d, J=8.77 Hz, 1H), 6.48 (s, 2H), 5.89 (d, J=2.19 Hz, 1H), 3.74 (s, 3H).

Example S63. Synthesis of 5-(7-methyl-1H-indazol-5-yl)-6-(3-methyl-1H-pyrazol-1-yl)pyrazin-2-amine (Compound No. 1.300)

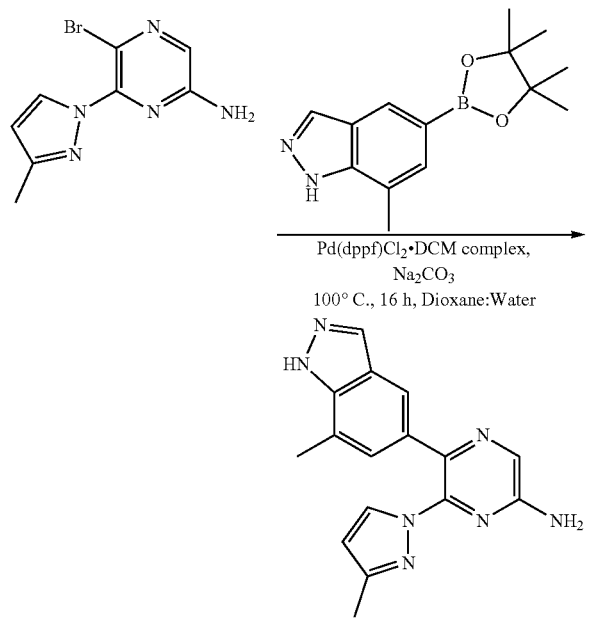

To a stirred solution of 5-bromo-6-(3-methyl-1H-pyrazol-1-yl)pyrazin-2-amine (0.100 g, 0.39 mmol, 1.0 eq.) and 7-methyl-5-(4,4,5,5-tetramethyl-1,3,2-dioxaborolan-2-yl)-1H-indazole (0.121 g, 0.47 mmol, 1.2 eq.) in dioxane (10 mL) was added Na₂CO₃ (0.083 g, 0.78 mmol, 2.0 eq.) and 2 mL water. The reaction was purged with N₂ for about 5 min and Pd(dppf)Cl₂.DCM complex (0.016 g, 5 mol %) was added. Reaction was purged with N₂ for another 5 min and was heated at 100° C. for 16 h. Following this, reaction mixture was allowed to cool to RT and extracted using ethyl acetate (3×50 mL). The combined organic layers were washed with brine, dried anhydrous Na₂SO₄ and concentrated under vacuum to obtain the solid residue which was purified by reversed phase column chromatography to afford the desired product as off white solid (0.012 g, 10%).

LCMS: 306.2 [M+1]⁺. ¹H NMR: (400 MHz, DMSO-d₆) δ 13.04 (br. s., 1H), 8.04 (s, 1H), 7.96 (s, 1H), 7.66 (br. s., 1H), 7.28 (s, 1H), 6.87 (br. s., 1H), 6.83 (br. s., 2H), 6.17 (br. s., 1H), 2.41 (s, 3H), 2.12 (s, 3H).

Example S64. Synthesis of 1-(6-amino-3-(quinolin-6-yl)pyrazin-2-yl)pyrrolidin-2-one (Compound No. 1.301)

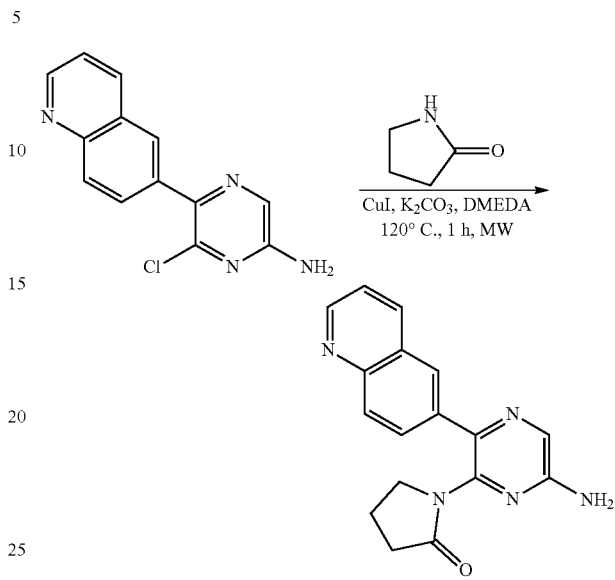

To a stirred solution of 6-chloro-5-(quinolin-6-yl)pyrazin-2-amine (128 mg, 0.5 mmol, 1 eq.) in DMF (2 mL), was added pyrrolidin-2-one (64 mg, 0.75 mmol, 1.5 eq.), CuI (19 mg, 0.1 mmol, 0.2 eq.) and DMEDA (17 mg, 0.2 mmol, 0.4 eq.). The reaction mixture was deoxygenated using N₂ and was allowed to heat at 120° C. for 1 h under microwave irradiation. Reaction was allowed to cool to RT and extracted with ethyl acetate (50 mL×3). Combined organic layers were washed with brine (20 mL×3), dried over anhydrous Na₂SO₄ and concentrated under vacuum to obtain the solid residue which was purified by reversed phase column chromatography to afford the desired product as off white solid (15 mg, 10%).

LCMS: 306 [M+1]⁺. ¹H NMR: (400 MHz, DMSO-d₆) δ 8.86 (s, 1H), 8.39 (d, J=7.89 Hz, 1H), 8.09 (br. s., 1H), 7.93-8.01 (m, 2H), 7.90 (d, J=7.02 Hz, 1H), 7.52 (dd, J=4.17, 8.11 Hz, 1H), 6.79 (br. s., 2H), 3.92 (d, J=6.58 Hz, 2H), 2.18 (d, J=6.58 Hz, 2H), 2.04-2.14 (m, 2H).

Example S65. Synthesis of 5-(7-chloro-1H-benzo[d]imidazol-5-yl)-6-(3-methyl-1H-pyrazol-1-yl)pyrazin-2-amine (Compound No. 1.302)

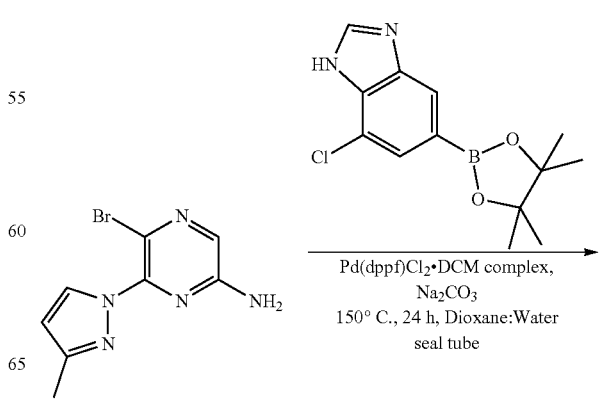

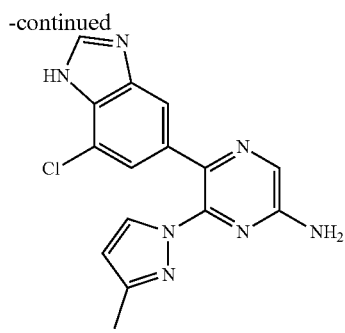

To a stirred solution of 5-bromo-6-(3-methyl-1H-pyrazol-1-yl)pyrazin-2-amine (0.5 g, 1.96 mmol, 1.0 eq.) and 7-chloro-5-(4,4,5,5-tetramethyl-1,3,2-dioxaborolan-2-yl)-1H-benzo[d]imidazole (0.657 g, 2.36 mmol, 1.2 eq.) in dioxane (20 mL) was added $Na_2CO_3$ (0.415 g, 3.92 mmol, 2.0 eq.) and 4 mL water. The reaction was purged with $N_2$ for about 5 min and Pd(dppf)Cl$_2$·DCM complex (0.080 g, 5 mol %) was added. Reaction was purged with $N_2$ for another 5 min and was heated at 150° C. for 24 h in a sealed tube. Following this, reaction mixture was allowed to cool to RT and extracted using ethyl acetate (3×50 mL). The combined organic layer was washed brine, dried over anhydrous $Na_2SO_4$ and concentrated under vacuum to obtain the solid residue which was purified by reversed phase column chromatography to afford the desired product as off white solid (0.026 g, 4.05%).

LCMS: 326.2 [M+1]$^+$. $^1$H NMR: (400 MHz, DMSO-d$_6$) δ 12.72 (br. s., 1H), 8.26 (s, 1H), 8.05 (s, 1H), 7.76 (d, J=1.75 Hz, 1H), 7.22 (br. s., 1H), 6.93 (br. s., 3H), 6.23 (s, 1H), 2.12 (s, 3H).

Example S66. Synthesis of 5-(8-chloroquinolin-6-yl)-6-(4-methyl-1H-pyrazol-1-yl)pyrazin-2-amine (Compound No. 1.303)

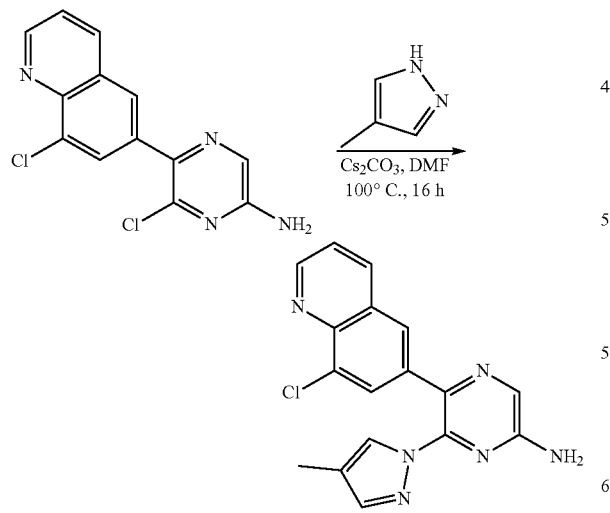

To a stirred solution of 6-chloro-5-(8-chloroquinolin-6-yl)pyrazin-2-amine (120 mg, 0.41 mmol, 1 eq.) in DMF (5 mL), was added 4-methyl-1H-pyrazole (84 mg, 1.03 mmol, 2.5 eq.) and $Cs_2CO_3$ (335 mg, 1.03 mmol, 2.5 eq.). Resulting mixture was heated at 100° C. for 16 h. Progress of reaction was monitored by TLC and LCMS. On completion of the reaction, the reaction mixture was diluted with water (30 mL) and extracted with ethyl acetate (50 mL×2). Combined organic layers were washed with water (100 mL×2), dried over anhydrous $Na_2SO_4$ and concentrated under vacuum to obtain the solid residue which was purified by normal phase column chromatography to afford the desired product as pale yellow solid (60 mg, 43%).

LCMS: 337.2 [M+1]$^+$. $^1$H NMR: (400 MHz, DMSO-d$_6$) δ 8.96 (d, J=3.51 Hz, 1H), 8.36 (d, J=7.45 Hz, 1H), 8.07 (s, 1H), 7.94 (s, 1H), 7.80 (s, 1H), 7.61 (dd, J=4.17, 8.11 Hz, 1H), 7.41 (d, J=9.65 Hz, 2H), 7.09 (s, 2H), 2.08 (s, 3H).

Example S67. Synthesis of 5-(7-chloro-1H-indazol-5-yl)-6-(1-methyl-1H-pyrazol-3-yl)pyrazin-2-amine (Compound No. 1.304)

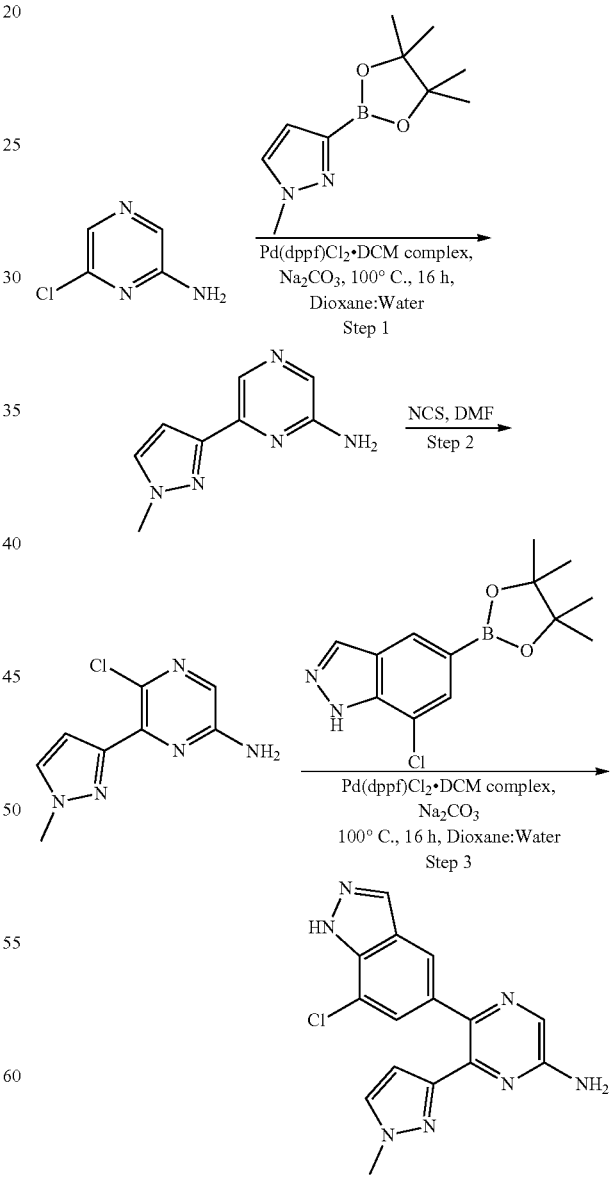

Step 1: Synthesis of 6-(1-methyl-1H-pyrazol-3-yl)pyrazin-2-amine: To a stirred solution of 6-chloropyrazin- 2-amine (1 g, 7.72 mmol, 1.0 eq.) and 1-methyl-3-(4,4,5,5-tetramethyl-1,3,2-dioxaborolan-2-yl)-1H-pyrazole (1.76 g, 8.49 mmol, 1.1 eq.) in dioxane (40 mL) was added Na$_2$CO$_3$ (1.63 g, 15.4 mmol, 2.0 eq.) and 8 mL of water. The reaction mixture was purged with N$_2$ for about 5 min and Pd(dppf)Cl$_2$.DCM complex (0.315 g, 5 mol %) was added. Reaction mixture was re-purged with N$_2$ and heated at 100° C. for 16 h. Following this, reaction was allowed to cool to RT and extracted using ethyl acetate (3×150 mL). The combined organic layers were washed with brine, dried over anhydrous Na$_2$SO$_4$ and concentrated under vacuum to obtain the solid residue which was purified by normal phase column chromatography to afford the desired product as brown solid (0.380 g, 28%).

LCMS: 176 [M+1]$^+$.

RT and extracted using ethyl acetate (3×50 mL). The combined organic layers were washed with brine, dried over anhydrous Na$_2$SO$_4$ and concentrated under vacuum to obtain the solid residue which was purified by reversed phase column chromatography to afford the desired product as off white solid (0.039 g, 20%).

LCMS: 326 [M+1]$^+$. $^1$H NMR: (400 MHz, DMSO-d$_6$) δ 13.53 (br. s., 1H), 8.14 (s, 1H), 7.90 (s, 1H), 7.65 (s, 1H), 7.59 (d, J=2.19 Hz, 1H), 7.33 (s, 1H), 6.57 (s, 2H), 6.06 (d, J=2.19 Hz, 1H), 3.73 (s, 3H).

Example S68. Synthesis of 5-(4-chlorobenzo[d]thiazol-6-yl)-6-(1-methyl-1H-pyrazol-3-yl)pyrazin-2-amine (Compound No. 1.305)

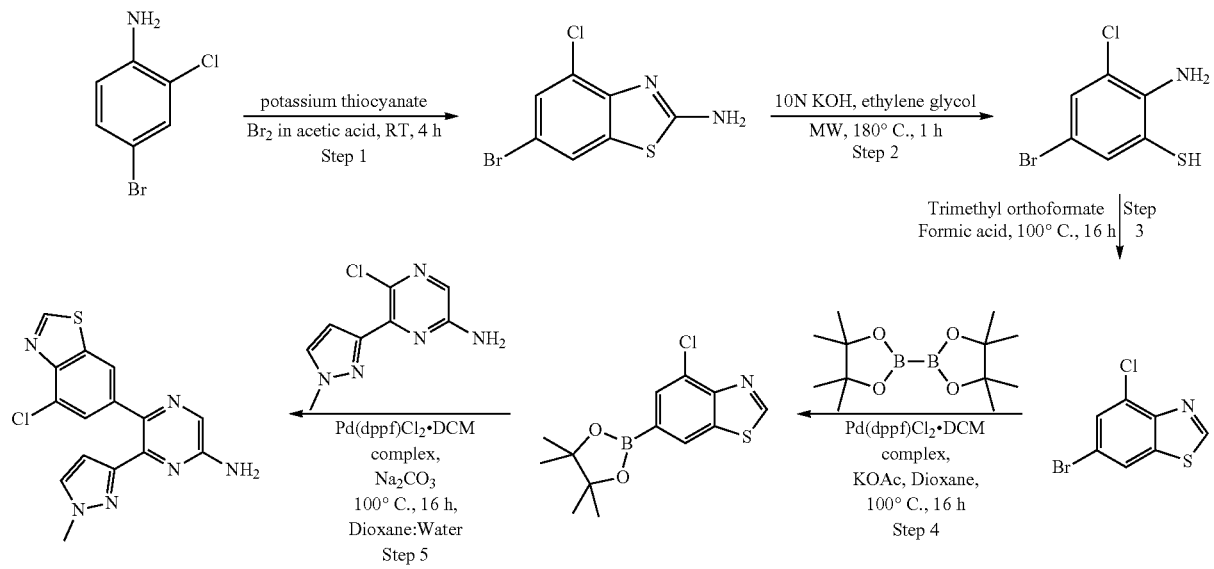

Step 2: Synthesis of 5-chloro-6-(1-methyl-1H-pyrazol-3-yl)pyrazin-2-amine: To a solution of 6-(1-methyl-1H-pyrazol-3-yl)pyrazin-2-amine (0.380 g, 2.16 mmol, 1 eq.) in DMF (10 mL) was added N-chlorosuccinimide (0.289 g, 2.16 mmol, 1 eq.) and the reaction mixture was stirred at 60° C. for 16 h. The reaction was monitored by TLC and LCMS. After completion, the reaction mixture was diluted with water (50 mL) and extracted by ethyl acetate (2×100 mL). Combined organic layer was washed with water (5×30 mL) followed by brine and dried over anhydrous sodium sulfate. The solvent was evaporated under reduced pressure to get the crude product which was purified by normal phase column chromatography to afford the desired product as yellow solid (165 mg, 36%).

LCMS: 210 [M+1]$^+$.

Step 3: Synthesis of 5-(7-chloro-1H-indazol-5-yl)-6-(1-methyl-1H-pyrazol-3-yl)pyrazin-2-amine: To a stirred solution of 5-chloro-6-(1-methyl-1H-pyrazol-3-yl)pyrazin-2-amine (0.125 g, 0.59 mmol, 1.0 eq.) and 7-chloro-5-(4,4,5,5-tetramethyl-1,3,2-dioxaborolan-2-yl)-1H-indazole (0.182 g, 0.65 mmol, 1.1 eq.) in dioxane (10 mL) was added Na$_2$CO$_3$ (0.126 g, 1.192 mmol, 2.0 eq.) and 2 mL water. The reaction mixture was purged with N$_2$ for about 5 min and Pd(dppf)Cl$_2$.DCM complex (0.024 g, 5 mol %) was added. Reaction mixture was re-purged with N$_2$ and heated at 100° C. for 16 h. Following this, reaction was allowed to cool to Step 1: Synthesis of 6-bromo-4-chlorobenzo[d]thiazol-2-amine: To a solution of 4-bromo-2-chloroaniline (2.5 g, 12.11 mmol, 1 eq.) in acetic acid (25 ml) was added at RT potassium thiocyanate (4.7 g, 48.4 mmol, 4.0 eq). To this mixture was added a solution of bromine (1.25 ml, 24.22 mmol, 2 eq.) in acetic acid (5 ml) drop-wise for 15 min and allowed to stir at RT for 4 h. The reaction mixture was neutralized with aqueous sodium hydroxide solution and product was precipitated out as solid and filtered to get residue. Residue was further purified using pentane and diethyl ether wash to get desired compound as pale yellow solid (2 g, 62.6%).

LCMS: 263 [M+1]$^+$.

Step 2: synthesis of 2-amino-5-bromo-3-chlorobenzenethiol: To the stirred solution of 6-bromo-4-chlorobenzo[d]thiazol-2-amine (0.5 g, 1.89 mmol, 1 eq.) in ethylene glycol (3 ml) was added 10 N KOH solution (3.77 ml, 37.9 mmol, 20.0 eq.) and the reaction mixture was microwave irradiated at 180° C. for 1 h. Reaction mixture was neutralized using 1N HCl solution and product was precipitated out as solid which was filtered to get residue. The obtained residue was further dissolved in methanol, filtered & concentrated under reduced pressure to get desired product as yellow viscous compound (350 mg, 77.4%).

LCMS: 238 [M+1]$^+$

Step 3: Synthesis of 6-bromo-4-chlorobenzo[d]thiazole: To the stirred solution of 2-amino-5-bromo-3-chlorobenzenethiol (0.250 g, 1.048 mmol, 1 eq.) in formic acid (5 ml) was added trimethyl orthoformate (0.346 ml, 3.14 mmol, 3.0 eq.) and the reaction mixture was allowed to stir at 100° C. for 16 h. The reaction mixture was allowed to cool to RT, neutralized using 10% sodium hydroxide solution and extracted using ethyl acetate (3×150 mL). The combined organic layers were washed (brine), dried (anhydrous $Na_2SO_4$) and concentrated under vacuum to get the solid residue which was purified by normal phase column chromatography to get the desired product as off white solid (0.110 g, 42.3%).

LCMS: 247 [M+1]$^+$

Step 4: 4-chloro-6-(4,4,5,5-tetramethyl-1,3,2-dioxaborolan-2-yl)benzo[d]thiazole: To the stirred solution of 6-bromo-4-chlorobenzo[d]thiazole (0.130 g, 0.523 mmol, 1 eq.) and 4,4,4',4',5,5,5',5'-octamethyl-2,2'-bi(1,3,2-dioxaborolane) (0.199 g, 0.784 mmol, 1.5 eq.) in 10 mL of dioxane was added potassium acetate (0.154 g, 1.56 mmol, 3.0 eq.). The reaction mixture was purged with $N_2$ for about 5 min and Pd(dppf)Cl$_2$.DCM complex (0.021 g, 5 mol %) was added. Reaction mixture was re-purged with $N_2$ and heated at 100° C. for 16 h. Following this reaction mixture was allowed to cool to RT and filtered through celite bed and washed with ethyl acetate (200 mL). The obtained organic layer was concentrated under reduced pressure to get desired product which was used as such for next step without further purification.

LCMS: 296 [M+1]$^+$

Step 5 Synthesis of 5-(4-chlorobenzo[d]thiazol-6-yl)-6-(1-methyl-1H-pyrazol-3-yl)pyrazin-2-amine: To a stirred solution of 5-chloro-6-(1-methyl-1H-pyrazol-3-yl)pyrazin-2-amine (0.120 g, 0.572 mmol, 1.0 eq.) and 4-chloro-6-(4,4,5,5-tetramethyl-1,3,2-dioxaborolan-2-yl)benzo[d]thiazole (0.186 g, 0.629 mmol, 1.1 eq.) in dioxane (10 mL) was added $Na_2CO_3$ (0.121 g, 1.14 mmol, 2.0 eq.) and 2 mL water. Then reaction was purged with $N_2$ for about 5 min and Pd(dppf)Cl$_2$.DCM complex (0.0233 g, 5 mol %) was added. The reaction was re-purged again for another 5 min and was heated at 100° C. for 16 h. Following this, reaction mixture was allowed to cool to RT and extracted using ethyl acetate (3×50 mL). The combined organic layer was washed with brine, dried over anhydrous $Na_2SO_4$ and concentrated under vacuum to obtain the solid residue which was purified by reversed phase column chromatography to afford the desired product as pale yellow solid (0.020 g, 10%).

LCMS: 343 [M+1]$^+$. $^1$H NMR: (400 MHz, DMSO-d$_6$) δ 9.43 (s, 1H), 8.08 (s, 1H), 7.93 (s, 1H), 7.64 (br. s., 1H), 7.47 (s, 1H), 6.70 (br. s., 2H), 6.21 (br. s., 1H), 3.71 (s, 3H).

Example S69. Synthesis of 5-(8-chloroquinolin-6-yl)-6-(3-(trifluoromethyl)-1H-pyrazol-1-yl)pyrazin-2-amine (Compound No 1.306)

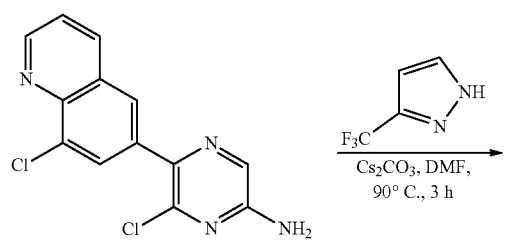

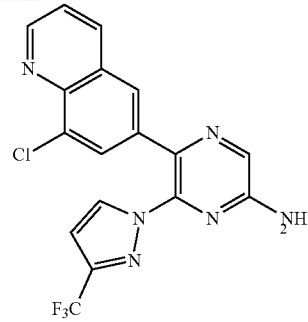

To a stirred solution of 3-(trifluoromethyl)-1H-pyrazole (0.154 g, 1.13 mmol, 2.2 eq.) in DMF (1 mL) was added $Cs_2CO_3$ (0.504 g, 1.55 mmol, 3 eq.) and the mixture was stirred at RT for 30 min. To this mixture 6-chloro-5-(8-chloroquinolin-6-yl)pyrazin-2-amine (0.150, 0.52 mmol, 1.0 eq.) was added and the resultant mixture was heated at 90° C. for 3 h. The progress of the reaction was monitored by TLC. Upon completion, the mixture was diluted with water (40 mL), extracted with EtOAc (2×100 mL). The combined organic layers were washed with water (40 mL), brine (40 mL), dried over $Na_2SO_4$, filtered & concentrated under reduced pressure to afford a crude residue which was purified by reversed phase chromatography to afford the desired product as an off-white solid (100 mg, 50%).

LCMS: 391 [M+1]$^+$. $^1$H NMR (400 MHz, DMSO-d$_6$) δ 8.91 (dd, J=1.53, 4.17 Hz, 1H), 8.27 (dd, J=1.75, 8.33 Hz, 1H), 8.15-8.21 (m, 2H), 7.68 (d, J=1.75 Hz, 1H), 7.56-7.64 (m, 2H), 6.80 (d, J=2.63 Hz, 1H).

Example S70. Synthesis of 5-(8-chloroquinolin-6-yl)-6-(1-cyclopropyl-1H-pyrazol-3-yl)pyrazin-2-amine (Compound No. 1.307)

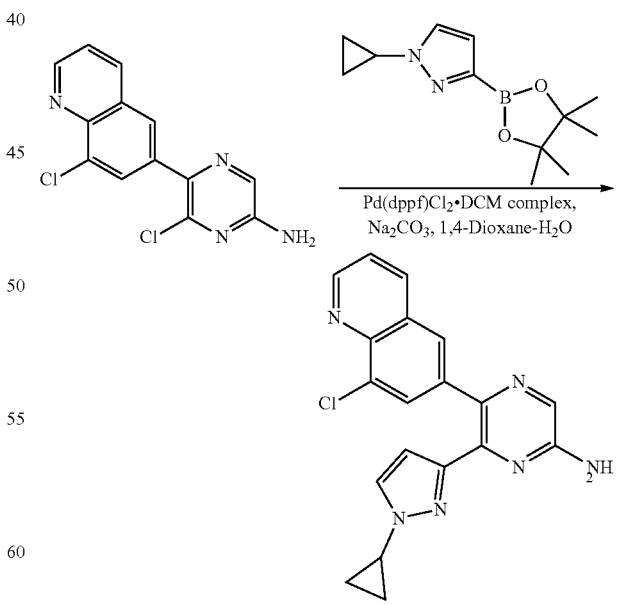

To a stirred solution of 6-chloro-5-(8-chloroquinolin-6-yl)pyrazin-2-amine (0.025 g, 0.086 mmol, 1.0 eq) in 1,4-Dioxane:Water (2:1, 1.5 mL) was added 1-cyclopropyl-3-(4,4,5,5-tetramethyl-1,3,2-dioxaborolan-2-yl)-1H-pyrazole (0.030 g, 0.129 mmol, 1.5 eq), sodium carbonate (0.027 g, 0.258 mmol, 3.0 eq) at RT and the resulting mixture was degassed under nitrogen for 20 min. Pd(dppf)Cl$_2$.DCM complex (0.006 g, 0.0086 mmol, 0.1 eq) and then added to the mixture and the mixture was further degassed under nitrogen for 10 min. The resultant mixture was heated at 110° C. for 16 h. The progress of reaction was monitored by TLC. Upon completion, the reaction mixture was diluted with water (50 mL), extracted with EtOAc (2×100 mL). The combined organic layers were washed with water (50 mL), brine (50 mL), dried over Na$_2$SO$_4$, filtered and concentrated under reduced pressure to afford a crude residue which was purified by SFC to afford the desired product as an off-white solid (5 mg, 16%).

LCMS: 363 [M+1]$^+$. $^1$H NMR: (400 MHz, MeOD) δ 8.92 (d, J=2.63 Hz, 1H), 8.36 (d, J=7.02 Hz, 1H), 8.02 (s, 1H), 7.92 (s, 1H), 7.76 (d, J=1.75 Hz, 1H), 7.56-7.68 (m, 2H), 6.32 (d, J=2.19 Hz, 1H), 3.56 (br. s., 1H), 0.78-0.93 (m, 4H).

Example S71. Synthesis of 1-(6-amino-3-(8-chloro-quinolin-6-yl)pyrazin-2-yl)pyridin-2(1H)-one (Compound No. 1.308)

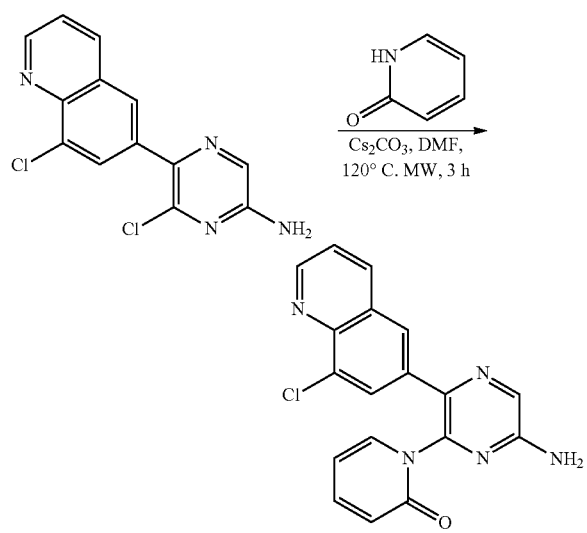

To a stirred solution of pyridin-2(1H)-one (0.122 g, 1.3 mmol, 2.2 eq.) in DMF (1 mL) was added Cs$_2$CO$_3$ (0.672 g, 2.06 mmol, 4 eq.) and the mixture was stirred at RT for 15 min. To this mixture 6-chloro-5-(8-chloroquinolin-6-yl) pyrazin-2-amine (0.150, 0.517 mmol, 1.0 eq.) was added and the resultant mixture was irradiated under MW irradiation at 120° C. for 3 h. The progress of reaction was monitored by TLC. Upon completion, the mixture was diluted with water (40 mL), extracted with EtOAc (2×100 mL). The combined organic layers were washed with water (40 mL), brine (40 mL), dried over Na$_2$SO$_4$, filtered & concentrated under reduced pressure to afford a crude residue which was purified by reversed phase chromatography to afford the desired product as an off-white solid (17 mg, 9%).

LCMS: 350 [M+1]$^+$. $^1$H NMR: (400 MHz, DMSO-d$_6$) δ 8.90 (dd, J=1.53, 4.17 Hz, 1H), 8.55 (d, J=1.75 Hz, 1H), 8.48 (d, J=1.75 Hz, 1H), 8.41 (dd, J=1.75, 8.33 Hz, 1H), 8.25 (d, J=3.51 Hz, 1H), 7.88-7.92 (m, 2H), 7.60 (dd, J=4.39, 8.33 Hz, 1H), 7.19-7.28 (m, 2H).

Example S72. Synthesis of 3-amino-6-(8-chloroquinolin-6-yl)-5-(1-methyl-1H-pyrazol-3-yl)pyrazine-2-carbonitrile (Compound No. 1.309)

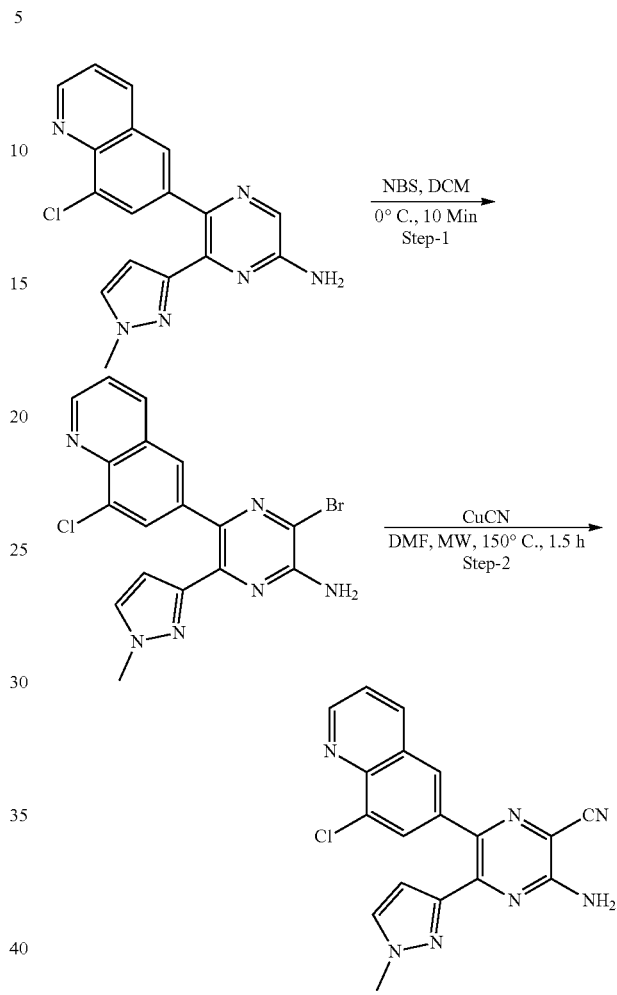

Step-1: Synthesis of 3-bromo-5-(8-chloroquinolin-6-yl)-6-(1-methyl-1H-pyrazol-3-yl)pyrazin-2-amine: To a stirred solution of 5-(8-chloroquinolin-6-yl)-6-(1-methyl-1H-pyrazol-3-yl)pyrazin-2-amine (0.350 g, 1.04 mmol, 1.0 eq.) in DCM (20 mL) was added N-Bromosuccinimide (0.194 g, 1.09 mmol, 1.05 eq.) portion wise at 0° C. and the mixture was allowed to stir at the same temperature for 10 min. The progress of reaction was monitored by TLC. Upon completion, the reaction mixture was diluted with water (15 mL), extracted with DCM (2×50 mL). The combined organic layers were washed with water (15 mL), brine (15 mL), dried over Na$_2$SO$_4$, filtered & concentrated under reduced pressure to afford the desired product as an off brown solid (0.400 g, 83%).

LCMS: 415 [M+1]$^+$.

Step-2: Synthesis of 3-amino-6-(8-chloroquinolin-6-yl)-5-(1-methyl-1H-pyrazol-3-yl)pyrazine-2-carbonitrile: To ethyl 4-(2-(2-methoxyethyl)hydrazinyl)-2-(methylthio)pyrimidine-5-carboxylate (0.200 g, 0.48 mmol, 1 eq.) in DMF (4 mL) was added copper cyanide (0.129 g, 1.44 mmol, 3 eq.) at RT and the resultant mixture was irradiated under MW irradiation at 150° C. for 90 min. The progress of reaction was monitored by TLC. Upon completion, ice cold water (15 mL) was added to the mixture to obtain a precipitate which was filtered over Buchner funnel to afford crude residue. The crude obtained was purified by reversed phase chromatography to afford the desired product as an off-white solid (0.005 g, 2.8%).

LCMS: 362 [M+H]+. 1H NMR: (400 MHz, DMSO-d6) δ 8.95 (br. s., 1H), 8.39 (d, J=7.45 Hz, 1H), 7.99 (br. s., 1H), 7.87 (br. s., 1H), 7.63 (d, J=4.38 Hz, 1H), 7.55 (br. s., 1H), 6.37 (br. s., 1H), 3.78 (br. s., 3H).

Example S73. Synthesis of 3-amino-6-(8-chloroqui-nolin-6-yl)-5-(1-methyl-1H-pyrazol-3-yl)pyrazin-2-ol (Compound No. 1.310)

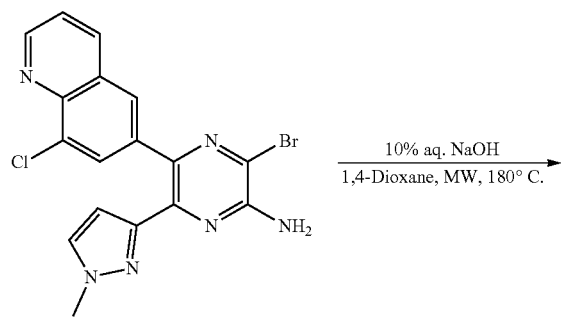

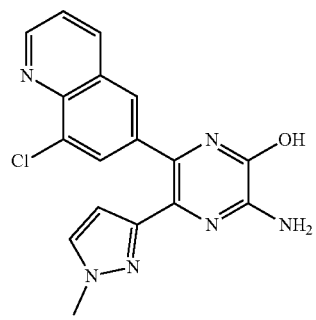

To ethyl 4-(2-(2-methoxyethyl)hydrazinyl)-2-(methyl-thio)pyrimidine-5-carboxylate (0.070 g, 0.17 mmol, 1 eq) in 1,4-Dioxane (1.2 mL) was added 10% aq. NaOH solution (1.2 mL) and the mixture was irradiated under MW irradiation at 180° C. for 40 min. The progress of reaction was monitored by TLC. Upon completion, the mixture was concentrated under reduced pressure. To the residue obtained was added ice cold water (15 ml) to obtain a precipitate which was filtered over Buchner funnel to obtain a crude which was purified by reversed phase chromatography to afford desired product as an off-white solid (0.010 g, 17%).

LCMS: 353 [M+H]+. 1H NMR: (400 MHz, DMSO-d6) δ 8.96 (d, J=3.51 Hz, 1H), 8.40 (d, J=8.77 Hz, 1H), 7.92 (s, 1H), 7.74 (s, 1H), 7.64 (dd, J=4.38, 8.33 Hz, 1H), 7.41 (s, 1H), 5.91 (d, J=2.19 Hz, 1H), 3.78 (s, 3H).

Example S74. Synthesis of 3-amino-6-(8-chloroqui-nolin-6-yl)-5-(1-methyl-1H-pyrazol-3-yl)pyrazine-2-carboxamide (Compound No. 1.311)

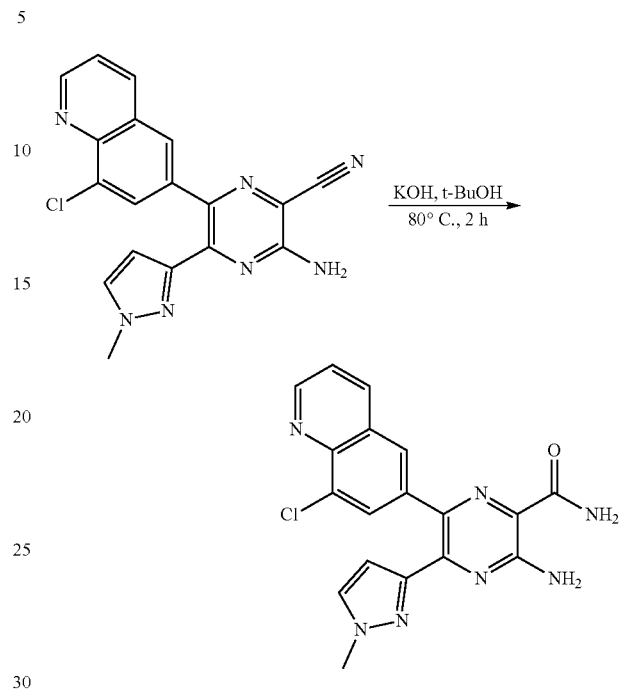

To a stirred solution of 3-amino-6-(8-chloroquinolin-6-yl)-5-(1-methyl-1H-pyrazol-3-yl)pyrazine-2-carbonitrile (0.120 g, 0.33 mmol, 1 eq) in t-BuOH (6 mL) was added potassium hydroxide (0.055 g, 0.99 mmol, 3 eq) and the mixture was heated at 80° C. for 2 h. The progress of reaction was monitored by TLC. Upon completion, the mixture was concentrated under reduced pressure. To the residue obtained was added ice cold water (15 mL) to obtain a precipitate which was filtered over Buchner funnel to obtain a crude which was purified by reversed phase chromatography to afford 3-amino-6-(8-chloroquinolin-6-yl)-5-(1-methyl-1H-pyrazol-3-yl)pyrazine-2-carboxamide (0.004 g, 3%) as an off yellow solid.

LCMS: 380 [M+H]+, 1H NMR: (400 MHz, DMSO-d6) δ 8.94 (d, J=3.95 Hz, 1H), 8.40 (d, J=8.33 Hz, 1H), 8.06 (s, 1H), 7.94 (s, 1H), 7.63 (d, J=3.95 Hz, 1H), 7.56 (br. s., 1H), 6.32 (br. s., 1H), 3.81 (s, 3H).

Example S75. Synthesis of 5-(8-chloroquinolin-6-yl)-3-methoxy-6-(1-methyl-1H-pyrazol-3-yl)pyrazin-2-amine (Compound No. 1.312)

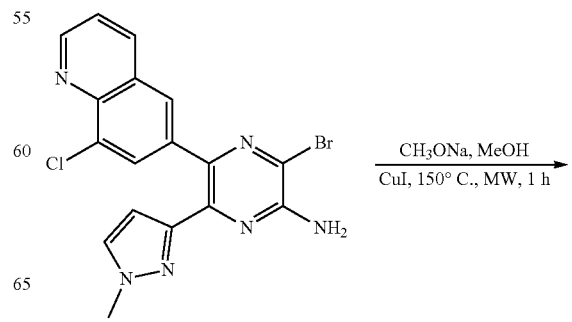

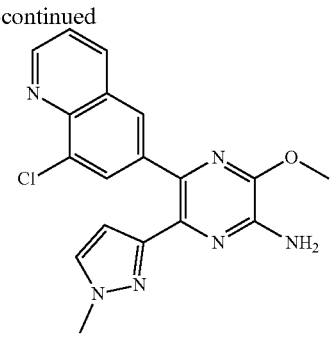

To ethyl 4-(2-(2-methoxyethyl)hydrazinyl)-2-(methylthio)pyrimidine-5-carboxylate (0.15 g, 0.361 mmol, 1 eq) in methanol (4 mL) were successively added sodium methoxide (0.097 g, 1.80 mmol, 5 eq) and CuI (0.034 g, 0.18 mmol, 0.5 eq) at RT and the mixture was irradiated under MW irradiation at 150° C. for 60 min. The progress of reaction was monitored by TLC. Upon completion, the mixture was concentrated under reduced pressure. To the residue obtained was added ice cold water (15 mL) to obtain a precipitate which was filtered over Buchner funnel to obtain a crude which was purified by reversed phase chromatography to afford 5-(8-chloroquinolin-6-yl)-3-methoxy-6-(1-methyl-1H-pyrazol-3-yl)pyrazin-2-amine (0.009 g, 6.81%) as an off-white solid.

LCMS: 367 [M+H]$^+$, $^1$H NMR: (400 MHz, DMSO-d$_6$) δ 8.90 (br. s., 1H), 8.32 (d, J=7.02 Hz, 1H), 7.95 (br. s., 1H), 7.90 (br. s., 1H), 7.52-7.62 (m, 2H), 6.10 (br. s., 1H), 4.13 (s, 3H), 3.84 (br. s., 3H).

Example S76. Synthesis of 3-amino-6-(8-chloroquinolin-6-yl)-5-(3-methyl-1H-pyrazol-1-yl)pyrazin-2-ol (Compound No. 1.313)

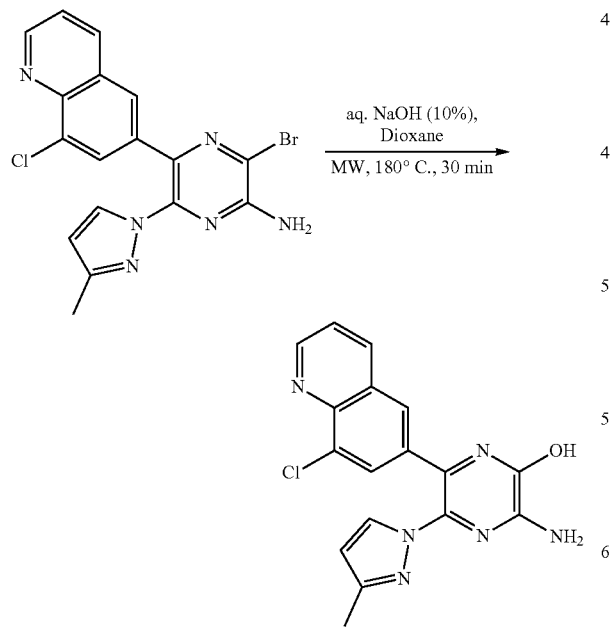

To a stirred solution of 3-bromo-5-(8-chloroquinolin-6-yl)-6-(3-methyl-1H-pyrazol-1-yl)pyrazin-2-amine (0.05 g, 0.12 mmol, 1.0 eq.) in dioxane (1 mL) was added aqueous NaOH solution (1 mL, 2.5 mmol, 20.0 eq.). Following this reaction mixture was microwave irradiated for 30 min at 180° C. The reaction was monitored by TLC and LCMS. After completion of reaction, reaction mixture was concentrated under reduced pressure to get desired product as solid residue which was purified by reversed phase column chromatography to get the desired product as off white solid (0.005 g, 12%).

LCMS: 353 [M+1]$^+$, $^1$H NMR (400 MHz, DMSO-d$_6$) δ 12.22 (br. s., 1H), 8.97 (d, J=2.63 Hz, 1H), 8.31 (d, J=7.45 Hz, 1H), 7.77 (br. s., 1H), 7.62 (dd, J=4.17, 8.11 Hz, 1H), 7.55 (s, 1H), 7.33 (s, 1H), 7.10 (br. s., 2H), 6.09 (s, 1H), 2.12 (s, 3H)

Example S77. Synthesis of 5-(8-fluoroquinolin-6-yl)-6-(1-methyl-1H-pyrazol-3-yl)pyrazin-2-amine (Compound No. 1.314)

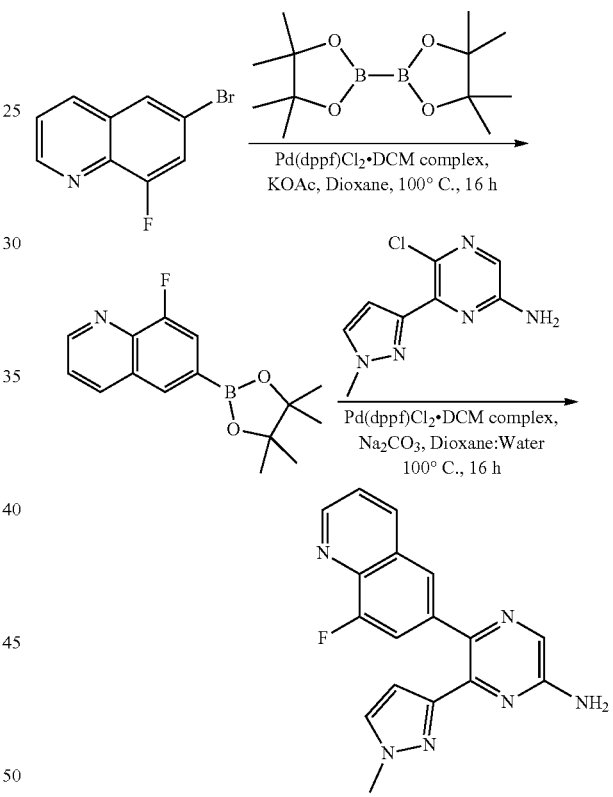

Step 1: Synthesis of 8-fluoro-6-(4,4,5,5-tetramethyl-1,3,2-dioxaborolan-2-yl)quinoline: To the stirred solution of 6-bromo-8-fluoroquinoline (0.2 g, 0.88 mmol, 1 eq.) and 4,4,4',4',5,5,5',5'-octamethyl-2,2'-bi(1,3,2-dioxaborolane) (0.336 g, 1.327 mmol, 1.5 eq.) in 10 mL of dioxane was added potassium acetate (0.260 g, 2.65 mmol, 3.0 eq.). The reaction mixture was purged with N$_2$ for about 5 min and Pd(dppf)Cl$_2$.DCM complex (0.036 g, 5 mol %) was added. Reaction mixture was re-purged with N$_2$ and heated at 100° C. for 16 h. Following this reaction mixture was allowed to cool to RT and filtered through celite bed and washed with ethyl acetate (200 mL). The organic layer was concentrated under reduced pressure to get desired product which was used as such for next step without further purification.

LCMS: 274 [M+1]$^+$

Step 2: Synthesis of 5-(8-fluoroquinolin-6-yl)-6-(1-methyl-1H-pyrazol-3-yl)pyrazin-2-amine: To a stirred solution of 5-chloro-6-(1-methyl-1H-pyrazol-3-yl)pyrazin-2-amine (0.120 g, 0.572 mmol, 1.0 eq.) and 8-fluoro-6-(4,4,5,5-tetramethyl-1,3,2-dioxaborolan-2-yl)quinoline (0.187 g, 0.686 mmol, 1.2 eq.) in dioxane (10 mL) was added $Na_2CO_3$ (0.121 g, 1.144 mmol, 2.0 eq.) and 2 mL water. The reaction was purged with $N_2$ for about 5 min and Pd(dppf)$Cl_2$.DCM complex (0.023 g, 5 mol %) was added. Reaction was purged with $N_2$ for another 5 min and was heated at 100° C. for 16 h. Following this, reaction mixture was allowed to cool to RT and extracted using ethyl acetate (3×50 mL). The combined organic layers were washed (brine), dried (anhydrous $Na_2SO_4$) and concentrated under vacuum to get the solid residue which was purified by reversed phase column chromatography to get the desired product as off white solid (0.003 g, 1%).

LCMS: 321 [M+1]$^+$. $^1$H NMR (400 MHz, DMSO-d$_6$) δ 8.90 (dd, J=1.53, 4.17 Hz, 1H), 8.38 (d, J=8.33 Hz, 1H), 7.97 (s, 1H), 7.84 (s, 1H), 7.65 (d, J=1.75 Hz, 1H), 7.60 (dd, J=4.17, 8.55 Hz, 1H), 7.36 (dd, J=1.53, 12.50 Hz, 1H), 6.76 (br. s., 2H), 6.22 (d, J=2.19 Hz, 1H), 3.72 (s, 3H).

Example S78. Synthesis of 6-(5-amino-3-(1-methyl-1H-pyrazol-3-yl)pyrazin-2-yl)isoquinolin-1-ol (Compound No. 1.315)

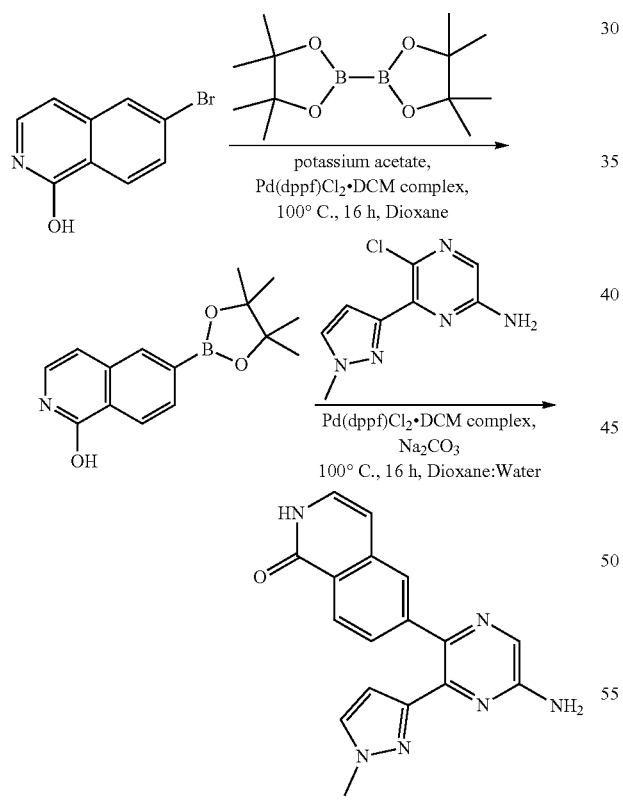

Step 1: synthesis of 6-(4,4,5,5-tetramethyl-1,3,2-dioxaborolan-2-yl)isoquinolin-1-ol: To the stirred solution of 6-bromoisoquinolin-1-ol (0.2 g, 0.89 mmol, 1 eq.) and 4,4,4',4',5,5,5',5'-octamethyl-2,2'-bi(1,3,2-dioxaborolane) (0.339 g, 1.33 mmol, 1.5 eq.) in 10 mL of dioxane was added potassium acetate(0.26 g, 2.67 mmol, 3.0 eq.). The reaction mixture was purged with $N_2$ for about 5 min and Pd(dppf)$Cl_2$.DCM complex (0.036 g, 5 mol %) was added. Reaction mixture was re-purged with $N_2$ and heated at 100° C. for 16 h. Following this reaction mixture was allowed to cool to RT and filtered through celite bed and washed with ethyl acetate (200 mL). The obtained organic layer was concentrated under reduced pressure to get desired product which was used as such for next step without further purification.

LCMS: 272 [M+1]$^+$,

Step 2: Synthesis of 6-(5-amino-3-(1-methyl-1H-pyrazol-3-yl)pyrazin-2-yl)isoquinolin-1-ol: To a stirred solution of 5-chloro-6-(1-methyl-1H-pyrazol-3-yl)pyrazin-2-amine (0.120 g, 0.572 mmol, 1.0 eq.) and 6-(4,4,5,5-tetramethyl-1,3,2-dioxaborolan-2-yl)isoquinolin-1-ol (0.186 g, 0.686 mmol, 1.2 eq.) in dioxane (10 mL) was added $Na_2CO_3$ (0.121 g, 1.144 mmol, 2.0 eq.) and 2 mL water. The reaction was purged with $N_2$ for about 5 min and Pd(dppf)$Cl_2$'DCM complex (0.023 g, 5 mol %) was added. Reaction was purged with $N_2$ for another 5 min and was heated at 100° C. for 16 h. Following this, reaction mixture was allowed to cool to RT and extracted using ethyl acetate (3×50 mL). The combined organic layers were washed (brine), dried (anhydrous $Na_2SO_4$) and concentrated under vacuum to get the solid residue which was purified by reversed phase column chromatography to get the desired product as off white solid (0.002 g, 1%).

LCMS: 319 [M+1]$^+$. $^1$H NMR (400 MHz, DMSO-d$_6$) δ 11.16 (br. s., 1H), 7.99 (d, J=7.89 Hz, 1H), 7.93 (s, 1H), 7.64 (s, 1H), 7.60 (d, J=2.19 Hz, 1H), 7.29 (d, J=9.65 Hz, 1H), 7.11 (br. s., 1H), 6.68 (br. s., 2H), 6.48 (d, J=7.45 Hz, 1H), 6.11 (d, J=1.75 Hz, 1H), 3.72 (s, 3H).

Example S79. Synthesis of 3-bromo-5-(8-chloroquinolin-6-yl)-6-(3-methyl-1H-pyrazol-1-yl)pyrazin-2-amine (Compound No. 1.316)

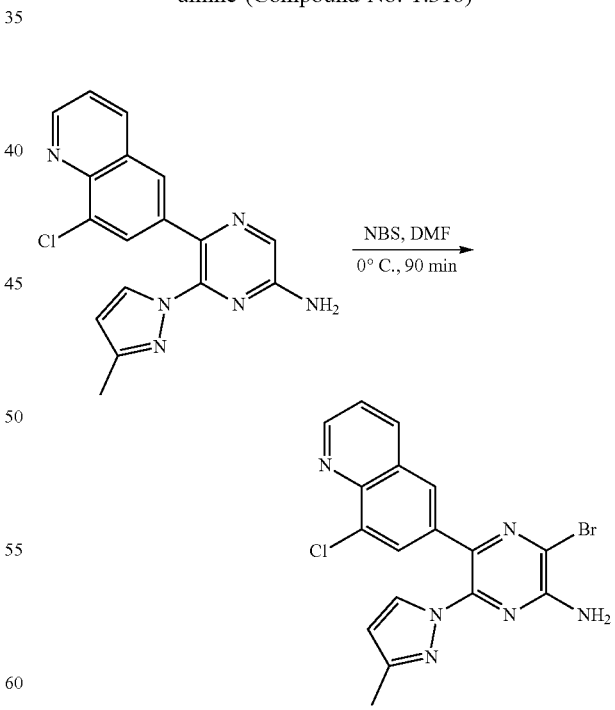

To a solution of 5-(8-chloroquinolin-6-yl)-6-(3-methyl-1H-pyrazol-1-yl)pyrazin-2-amine (0.38 g, 1.13 mmol, 1 eq.) in DMF (15 mL) was added N-bromosuccinimide (0.20 g, 1.13 mmol, 1 eq.) and the reaction mixture was stirred at 0° C. for 90 min. The reaction was monitored by TLC and LCMS. After completion of the reaction, ice was poured into reaction mixture to afford the precipitate which was filtered and washed with water (100 mL). Further purification was done using normal phase column chromatography to afford desired product as off white solid (0.006 g, 1%).

LCMS: 415 [M+1]$^+$. $^1$H NMR (400 MHz, DMSO-d$_6$) δ 8.98 (dd, J=1.53, 4.17 Hz, 1H), 8.42 (d, J=7.02 Hz, 1H), 7.95 (d, J=2.19 Hz, 1H), 7.85 (d, J=1.75 Hz, 1H), 7.63 (dd, J=4.39, 8.33 Hz, 1H), 7.39 (br. s., 2H), 7.34 (d, J=1.75 Hz, 1H), 6.33 (d, J=2.19 Hz, 1H), 2.08 (s, 3H).

Example S80. Synthesis of 3-amino-6-(8-chloroquinolin-6-yl)-5-(3-methyl-1H-pyrazol-1-yl)pyrazine-2-carboxamide (Compound No. 1.317)

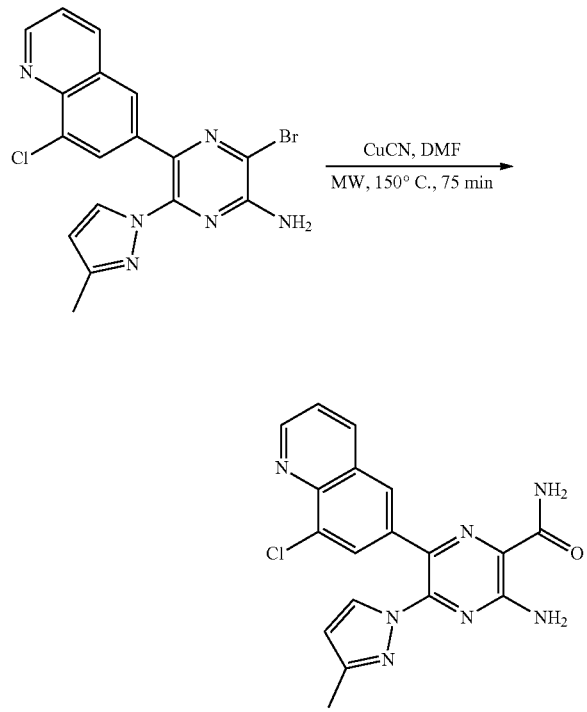 [SMILES: Cc1ccn(-c2nc(N)c(Br)nc2-c2cc(Cl)c3ncccc3c2)n1 ; Cc1ccn(-c2nc(N)c(C(N)=O)nc2-c2cc(Cl)c3ncccc3c2)n1]

To a solution of 3-bromo-5-(8-chloroquinolin-6-yl)-6-(3-methyl-1H-pyrazol-1-yl)pyrazin-2-amine (0.42 g, 1.01 mmol, 1 eq.) in DMF (7 mL) was added copper cyanide (0.27 g, 3.03 mmol, 3 eq.). Following this reaction mixture was microwave irradiated for 75 min at 150° C. Following this, reaction was allowed to cool to RT, and was diluted with water (5 mL) and extracted using ethyl acetate (3×30 mL) The combined organic layers were washed (brine), dried (anhydrous Na$_2$SO$_4$) and concentrated under vacuum to get solid residue which was purified by normal phase column chromatography to afford desired product as off white solid (0.003 g, 1%).

LCMS: 380 [M+1]$^+$. $^1$H NMR (400 MHz, DMSO-d$_6$) δ 8.98 (d, J=2.63 Hz, 1H), 8.30-8.35 (m, 2H), 8.07 (dd, J=2.19, 6.58 Hz, 2H), 7.80 (br. s., 1H), 7.61-7.65 (m, 2H), 6.37 (d, J=2.63 Hz, 1H), 2.05 (s, 3H).

Example S81. Synthesis of 5-(8-chloroquinolin-6-yl)-6-(2-methylthiazol-5-yl)pyrazin-2-amine (Compound No. 1.318)

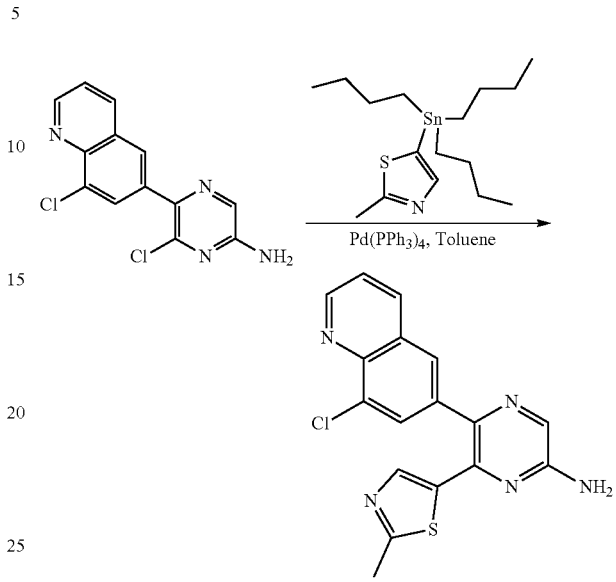

To a stirred solution of 6-chloro-5-(8-chloroquinolin-6-yl)pyrazin-2-amine (0.450 g, 1.55 mmol, 1.0 eq) in toluene (5 mL) was added 2-methyl-5-(tributylstannyl)thiazole (1.32 g, 3.41 mmol, 2.2 eq) at RT & the resulting mixture was degassed under nitrogen for 20 min. Pd(PPh$_3$)$_4$ (0.179 g, 0.55 mmol, 0.1 eq.) and then added to the mixture and the mixture was further degassed under nitrogen for 10 min. The resultant mixture was heated at 110° C. for 16 h. The progress of reaction was monitored by TLC. Upon completion, the reaction mixture was diluted with water (200 mL), extracted with EtOAc (2×200 mL). The combined organic layers were washed with water (200 mL), brine (100 mL), dried over Na$_2$SO$_4$, filtered and concentrated under reduced pressure to afford a crude residue which was purified by silica gel column chromatography (20% KF/silica mixture) compound eluting at 3% MeOH/DCM to obtain 0.350 g of the desired product (~90% pure). 70 mg of the product obtained was further purified by SFC to afford the desired product as an off-white solid (0.021 g, 25%).

LCMS: 354 [M+H]$^+$ $^1$H NMR: (400 MHz, MeOD) δ 8.99 (d, J=2.63 Hz, 1H), 8.42 (d, J=8.33 Hz, 1H), 8.03 (d, J=1.75 Hz, 1H), 7.97 (d, J=1.75 Hz, 1H), 7.94 (s, 1H), 7.66 (dd, J=3.95, 8.33 Hz, 1H), 7.26 (s, 1H), 2.61 (s, 3H).

Example S82. Synthesis of 5-(8-chloroquinolin-6-yl)-6-(1-ethyl-1H-pyrazol-3-yl)pyrazin-2-amine (Compound No. 1.319)

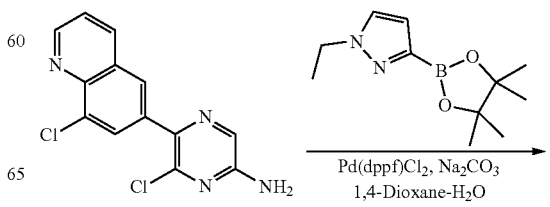

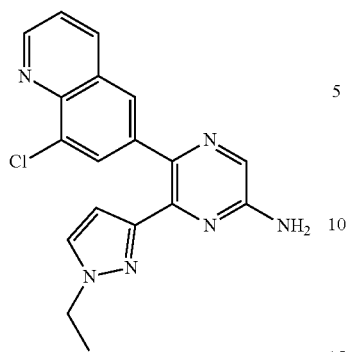

To a stirred solution of 6-chloro-5-(8-chloroquinolin-6-yl)pyrazin-2-amine (0.05 g, 0.172 mmol, 1.0 eq.) in 1,4-Dioxane:Water (4:1, 5 mL) was added 1-ethyl-3-(4,4,5,5-tetramethyl-1,3,2-dioxaborolan-2-yl)-1H-pyrazole (0.057 g, 0.258 mmol, 1.5 eq.), sodium carbonate (0.055 g, 0.517 mmol, 3.0 eq.) at RT and the resulting mixture was degassed under nitrogen for 20 min. Pd(dppf)Cl$_2$.DCM complex (0.013 g, 1.102 mmol, 0.017 eq.) and then added to the mixture and the mixture was further degassed under nitrogen for 10 min. The resultant mixture was heated at 110° C. for 16 h. The progress of reaction was monitored by TLC. Upon completion, the reaction mixture was diluted with water (50 mL), extracted with EtOAc (2×100 mL). The combined organic layers were washed with water (50 mL), brine (50 mL), dried over Na$_2$SO$_4$, filtered and concentrated under reduced pressure to afford a crude residue which was purified by SFC to afford the desired product (0.005 g, 8%) as an off-white solid.

LCMS: 351 [M+1]$^+$. $^1$H NMR: (400 MHz, MeOD) δ 8.91 (d, J=2.63 Hz, 1H), 8.34 (s, 1H), 8.03 (s, 1H), 7.93 (s, 1H), 7.80 (s, 1H), 7.54-7.65 (m, 2H), 6.30 (d, J=1.75 Hz, 1H), 4.07 (d, J=7.02 Hz, 2H), 1.26 (t, J=7.45 Hz, 3H).

Example S83. Synthesis of 5-(8-chloroquinolin-6-yl)-6-(5-methylthiazol-2-yl)pyrazin-2-amine (Compound 1.395)

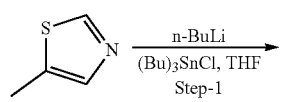

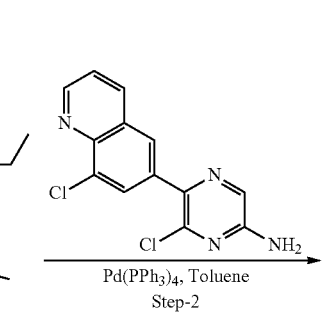

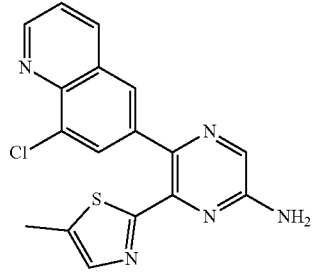

Step-1: Synthesis of 5-(8-chloroquinolin-6-yl)-6-(5-methylthiazol-2-yl)pyrazin-2-amine: To a stirred solution of 5-methylthiazole (1.0 g, 10.0 mmol, 1.0 eq) in THF (10 mL) was added n-BuLi (7.0 mL, 11.0 mmol, 1.1 eq) at −78° C. and the mixture was stirred at −78° C. for 30 min. tri-Butyl tin chloride (4.0 ml, 12.0 mmol, and 1.2 eq) was then added to the mixture at −78° C. and the resultant mixture was stirred at RT for 2 h. The progress of reaction was monitored by $^1$H NMR. Upon completion, the reaction mixture was quenched with saturated ammonium chloride solution (100 mL), extracted with EtOAc (200 mL×2). The combined organic layers were washed with water (200 mL), brine (100 mL), dried over Na$_2$SO$_4$, filtered and concentrated under reduced pressure to afford 5-methyl-2-(tributylstannyl)thiazole (1.5 g, 38%) as an viscous liquid which was taken to next step without further purification.

$^1$H NMR (400 MHz, CDCl$_3$) δ 7.73 (s, 1H), 2.49 (s, 3H), 1.48-1.64 (m, 9H), 1.25-1.37 (m, 12H), 1.10-1.21 (m, 6H).

Step-2: Synthesis of 5-(8-chloroquinolin-6-yl)-6-(5-methylthiazol-2-yl)pyrazin-2-amine: To a stirred solution of 6-chloro-5-(8-chloroquinolin-6-yl)pyrazin-2-amine (0.100 g, 0.34 mmol, 1.0 eq) in toluene (5 mL) was added 5-methyl-2-(tributylstannyl)thiazole (0.300 g, 0.75 mmol, 2.2 eq) at RT and the resulting mixture was degassed under nitrogen for 20 min. To this reaction mixture Pd(PPh$_3$)$_4$ (0.040 g, 0.034 mmol, 0.1 eq) was added and the mixture was further degassed under nitrogen for 10 min. The resultant mixture was heated at 110° C. for 16 h. The progress of reaction was monitored by TLC. Upon completion, the reaction mixture was diluted with water (60 mL), extracted with EtOAc (150 mL×2). The combined organic layers were washed with water (50 mL), brine (50 mL), dried over Na$_2$SO$_4$, filtered and concentrated under reduced pressure to afford a crude residue which was purified by reversed phase chromatography to afford 5-(8-chloroquinolin-6-yl)-6-(5-methylthiazol-2-yl)pyrazin-2-amine (8.5 mg, 7%) as an off-white solid.

LCMS: 354 [M+H]$^+$. $^1$H NMR (400 MHz, MeOD) δ 8.93 (d, J=3.07 Hz, 1H), 8.38 (d, J=8.77 Hz, 1H), 8.04 (s, 1H), 7.96 (s, 1H), 7.91 (d, J=1.75 Hz, 1H), 7.62 (dd, J=4.17, 8.55 Hz, 1H), 7.30 (s, 1H), 2.49 (s, 3H).

Example S84. Synthesis of 3-(6-amino-3-(8-chloroquinolin-6-yl)pyrazin-2-yl)-1-methylpyridin-2(1H)-one (Compound No. 1.329)

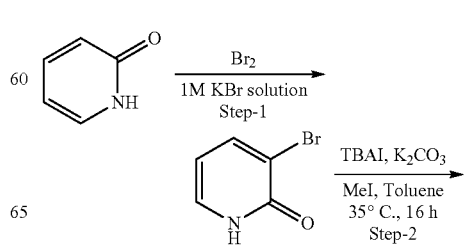

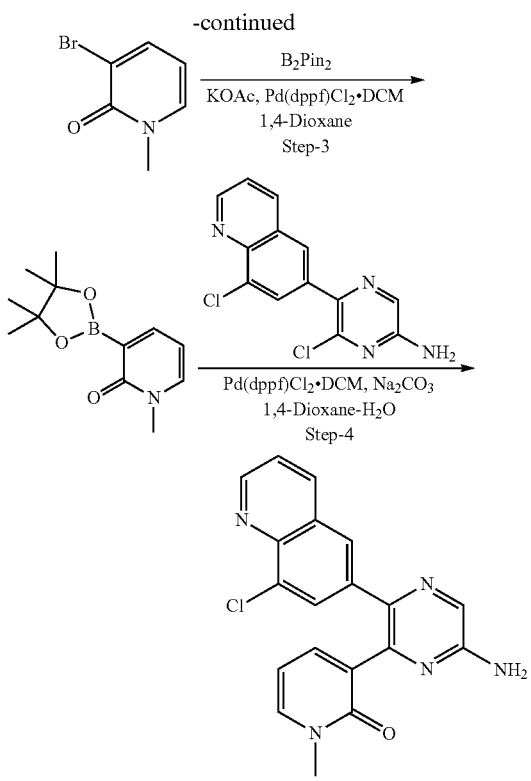

Step-1: Synthesis of 3-bromopyridin-2(1H)-one: To a stirred solution of pyridin-2(1H)-one (1.0 g, 10 mmol, 1.0 eq.) in 1M aq. KBr solution (10 mL) was added bromine (0.840 g, 10 mmol, 1 eq), 1M aq KBr (20 ml) at 0° C. dropwise and the mixture was stirred at RT for 16 h. The progress of reaction was monitored by TLC. Upon completion, the reaction mixture was diluted with water (100 mL), extracted with EtOAc (300 mL×2). The combined organic layers were washed with water (50 mL), brine (50 mL), dried over $Na_2SO_4$, filtered & concentrated under reduced pressure to afford a crude residue which was purified by column chromatography (Eluent—10% MeOH/DCM) to afford 3-bromopyridin-2(1H)-one (0.700 g, 38%) as an off white solid.

LCMS: 174 $[M+H]^+$

Step-2: Synthesis of 3-bromo-1-methylpyridin-2(1H)-one: To a stirred solution of 3-bromopyridin-2(1H)-one (0.700 g, 7.36 mmol, 1.0 eq) in toluene (10 mL) were successively added potassium carbonate (2.5 g, 36.8 mmol, 2.5 eq) and TBAI (0.272 g, 0.736 mmol, 0.05 eq) at RT and the mixture was stirred at RT for 15 min. Methyl iodide (2.50 mL, 73.60 mmol, 5.5 eq) was then added to the mixture and the resultant mixture was heated at 70° C. for 16 h. The progress of reaction was monitored by TLC. Upon completion, the mixture was diluted with water (80 mL) and extracted with EtOAc (200 mL×2). The combined organic layers were washed with water (50 mL), brine (50 mL), dried over $Na_2SO_4$, filtered and concentrated under reduced pressure to afford a crude residue which was purified by column chromatography over silica gel (elutent—5% MeOH/DCM) to afford 3-bromo-1-methylpyridin-2(1H)-one (0.300 g, 39.68%) as a white solid.

LCMS 188 $[M+H]^+$

Step-3: Synthesis of 1-methyl-3-(4,4,5,5-tetramethyl-1,3,2-dioxaborolan-2-yl)pyridin-2(1H)-one: To a stirred solution of 3-bromo-1-methylpyridin-2(1H)-one (0.300 g, 1.59 mmol, 1.0 eq) in 1,4-Dioxane (150 mL) was added bis(pinacolato)diboron (0.670 g, 2.39 mmol, 1.5 eq), potassium acetate (0.470 g, 4.78 mmol, 3.0 eq) at RT and the resulting mixture was degassed under nitrogen for 30 min, Pd(dppf) $Cl_2$.DCM complex (0.065 g, 0.079 mmole, 0.05 eq) was then added to the mixture and the mixture was further degassed under nitrogen for 15 min. The resultant mixture was then heated at 110° C. for 16 h. The progress of the reaction was monitored by TLC. Upon completion, the reaction mixture was diluted with water (50 mL), extracted with EtOAc (250 mL×2). The combined organic layers were washed with water (40 mL), brine (40 mL), dried over $Na_2SO_4$, filtered and concentrated under reduced pressure to afford a crude residue which was purified by silica gel chromatography (Eluent—30% EtOAc/Hexane) to afford 1-methyl-3-(4,4,5,5-tetramethyl-1,3,2-dioxaborolan-2-yl)pyridin-2(1H)-one (0.250 g, 66%) as a light brown viscous solid.

$^1$H NMR (400 MHz, CDCl3) δ 7.85 (s, 1H), 7.37 (dd, J=2.41, 6.80 Hz, 1H), 6.13 (t, J=6.58 Hz, 1H), 3.51 (s, 3H), 1.28-1.35 (m, 12H).

Step-4: Synthesis of 3-(6-amino-3-(8-chloroquinolin-6-yl)pyrazin-2-yl)-1-methylpyridin-2(1H)-one: To a stirred solution of 6-chloro-5-(8-chloroquinolin-6-yl)pyrazin-2-amine (0.050 g, 0.17 mmol, 1.0 eq) in 1,4-Dioxane-water (4:1, 6 mL) was added 1-methyl-3-(4,4,5,5-tetramethyl-1,3,2-dioxaborolan-2-yl)pyridin-2(1H)-one (0.060 g, 0.25 mmol, 1.1 eq), sodium carbonate (0.054 g, 0.51 mmol, 3.0 eq) at RT and the resulting mixture was degassed under nitrogen for 30 min. Pd(dppf)$Cl_2$.DCM (0.012 g, 0.017 mmole, 0.1 eq) was then added to the mixture and the mixture was further degassed under nitrogen for 15 min. The resultant mixture was heated at 110° C. for 16 h. The progress of the reaction was monitored by TLC. Upon completion, the reaction mixture was diluted with water (25 mL), extracted with EtOAc (100 mL×2). The combined organic layers were washed with water (25 mL), brine (25 mL), dried over $Na_2SO_4$, filtered and concentrated under reduced pressure to afford a crude residue which was purified by reversed phase column chromatography to afford 3-(6-amino-3-(8-chloroquinolin-6-yl)pyrazin-2-yl)-1-methylpyridin-2(1H)-one (6.6 mg, 10.6%) as a white solid.

LCMS: 364 $[M+H]^+$. $^1$H NMR (400 MHz, MeOD) δ 8.89 (d, J=3.07 Hz, 1H), 8.27 (d, J=6.58 Hz, 1H), 8.07 (s, 1H), 8.00 (s, 1H), 7.85 (d, J=1.75 Hz, 1H), 7.70 (d, J=6.58 Hz, 1H), 7.51-7.61 (m, 2H), 6.44 (t, J=6.80 Hz, 1H), 3.39 (s, 3H).

Example S85. Synthesis of 3-bromo-5-(8-chloroquinolin-6-yl)-6-(1-methyl-1H-pyrazol-3-yl)pyrazin-2-amine. (Compound No. 1.324)

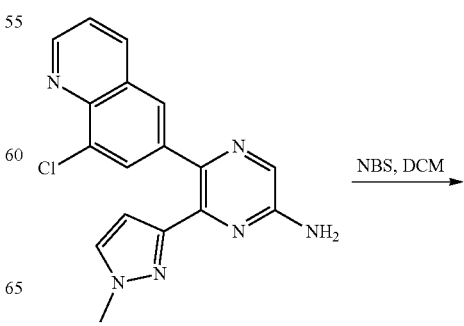

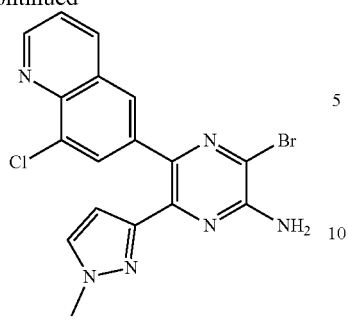

To a stirred solution of ethyl 4-(2-(tert-butoxycarbonyl)-2-(2-methoxyethyl)hydrazinyl)-2-(methylthio)pyrimidine-5-carboxylate (0.350 g, 1.041 mmol, 1.0 eq.) in 20 mL of DCM was successively added N-bromosuccinamide (0.194 g, 1.093 mmole, 1.05 eq.) portion-wise at 0° C. and allowed to stir at same temperature for 10 min. The progress of the reaction was monitored by TLC. Upon completion, the reaction mixture was diluted with water (15 mL), extracted with DCM (2×50 mL). The combined organic layers were washed with water (15 mL), with brine (15 mL), dried over Na$_2$SO$_4$, concentrated under reduced pressure afford ethyl 4-(2-(2-methoxyethyl)hydrazinyl)-2-(methylthio)pyrimidine-5-carboxylate (0.400 g, 82.99%) as off brown solid.

LCMS 415 [M+H]$^+$. $^1$H NMR (400 MHz, MeOD) δ 8.92 (d, J=2.63 Hz, 1H), 8.35 (d, J=8.33 Hz, 1H), 7.95 (s, 1H), 7.84 (s, 1H), 7.61 (d, J=4.38 Hz, 1H), 7.54 (s, 1H), 6.24 (d, J=2.19 Hz, 1H), 3.82 (s, 3H).

Example S86. Synthesis of 3-amino-6-(8-chloroquinolin-6-yl)-5-(2-methylthiazol-5-yl)pyrazine-2-carbonitrile (Compound No. 1.402)

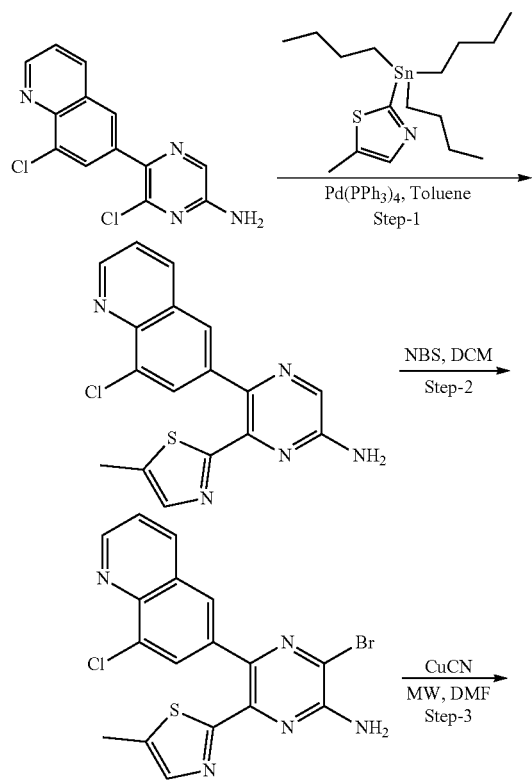

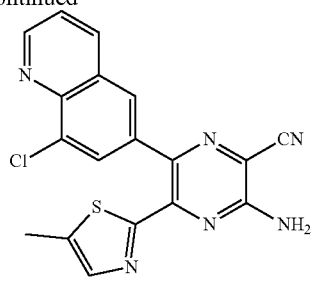

Step-1: Synthesis of 5-(8-chloroquinolin-6-yl)-6-(2-methylthiazol-5-yl)pyrazin-2-amine: To a stirred solution of 6-chloro-5-(8-chloroquinolin-6-yl)pyrazin-2-amine (0.450 g, 1.55 mmol, 1.0 eq) in toluene (5 mL) was added 5-methyl-2-(tributylstannyl)thiazole (1.32 g, 3.41 mmol, 2.2 eq) at RT and the mixture was degassed under nitrogen for 20 min. To this mixture Pd(PPh$_3$)$_4$ (0.179 g, 0.55 mmol, 0.1 eq) was added and the mixture was further degassed under nitrogen for 10 min. The resultant mixture was heated at 110° C. for 16 h. The progress of reaction was monitored by TLC. Upon completion, the reaction mixture was diluted with water (200 mL), extracted with EtOAc (200 mL×2). The combined organic layers were washed with water (200 mL), brine (100 mL), dried over Na$_2$SO$_4$, filtered and concentrated under reduced pressure to afford a crude residue which was purified by silica gel column chromatography (20% KF/silica mixture) (Eluent—3% MeOH/DCM) to obtain 5-(8-chloroquinolin-6-yl)-6-(2-methylthiazol-5-yl)pyrazin-2-amine (0.350 g, light brown solid, ~90% pure).

LCMS 354 [M+H]$^+$

Step-2: Synthesis of 3-bromo-5-(8-chloroquinolin-6-yl)-6-(5-methylthiazol-2-yl)pyrazin-2-amine: To a stirred solution of 5-(8-chloroquinolin-6-yl)-6-(2-methylthiazol-5-yl)pyrazin-2-amine (0.450 g, 1.274 mmol, 1.0 eq.) in DCM (20 mL) was added N-Bromosuccinimide (0.239 g, 1.338 mmole, 1.05 eq.) portion wise at 0° C. and the mixture was allowed to stir at the same temperature for 30 min. The progress of reaction was monitored by TLC. Upon completion, the reaction mixture was diluted with water (15 mL), extracted with DCM (50 mL×2). The combined organic layers were washed with water (15 mL), brine (15 mL), dried over Na$_2$SO$_4$, filtered & concentrated under reduced pressure to afford 3-bromo-5-(8-chloroquinolin-6-yl)-6-(5-methylthiazol-2-yl)pyrazin-2-amine (0.430 g, 78.18%) as a brown solid.

LCMS: 432 [M+H]$^+$

Step-3: Synthesis of 3-amino-6-(8-chloroquinolin-6-yl)-5-(2-methylthiazol-5-yl)pyrazine-2-carbonitrile: To stirred solution of 3-bromo-5-(8-chloroquinolin-6-yl)-6-(5-methylthiazol-2-yl)pyrazin-2-amine (0.150 g, 0.344 mmol, 1 eq) in DMF (4 mL) was added copper cyanide (0.093 g, 1.040 mmol, 3 eq) at RT and the mixture was irradiated under MW irradiation at 150° C. for 90 min. The progress of the reaction was monitored by TLC. Upon completion, ice cold water (15 mL) was added to the mixture to obtain a precipitate which was filtered over Buchner funnel to afford crude residue. The crude obtained was purified by reversed phase column chromatography to afford 3-amino-6-(8-chloroquinolin-6-yl)-5-(2-methylthiazol-5-yl)pyrazine-2-carbonitrile (11.5 mg, 8%) as an off white solid.

LCMS: 379 [M+H]$^+$. $^1$H NMR (400 MHz, MeOD) δ 8.52 (d, J=7.89 Hz, 1H), 8.15 (s, 1H), 8.02 (s, 1H), 7.65 (br. s., 1H), 7.28 (s, 1H), 2.60 (s, 2H).

Example S87. Synthesis of 6-(5-amino-3-(1-methyl-1H-pyrazol-3-yl)pyrazin-2-yl)quinolin-2(1H)-one (Compound No. 1.353)

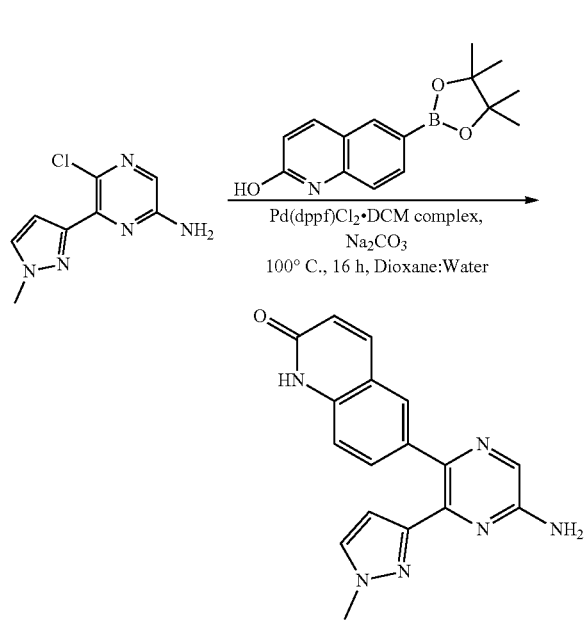

To a stirred solution of 5-chloro-6-(1-methyl-1H-pyrazol-3-yl)pyrazin-2-amine (0.120 g, 0.572 mmol, 1.0 eq.) and 6-(4,4,5,5-tetramethyl-1,3,2-dioxaborolan-2-yl)isoquinolin-1-ol (0.186 g, 0.686 mmol, 1.2 eq.) in dioxane (10 mL) was added Na$_2$CO$_3$ (0.121 g, 1.14 mmol, 2.0 eq.) and 2 mL water. Then reaction was purged with N$_2$ for about 5 min and Pd(dppf)Cl$_2$·DCM complex (0.023 g, 5 mol %) was added. The reaction was re-purged with N$_2$ for another 5 min and was allowed to heat at 100° C. for 16 h. Following this, reaction mixture was allowed to cool to RT and extracted using ethyl acetate (3×50 mL). The combined organic layers were washed (brine), dried (anhydrous Na$_2$SO$_4$) and concentrated under vacuum to get the solid residue which was purified by reversed phase column chromatography to get the desired product as off white solid (0.015 g, 8.24%).

LCMS: 319.2 [M+1]$^+$. $^1$H NMR (400 MHz, DMSO-d$_6$) δ 11.74 (br. s., 1H), 7.90 (s, 1H), 7.85 (d, J=9.65 Hz, 1H), 7.66 (d, J=1.75 Hz, 1H), 7.59 (d, J=1.75 Hz, 1H), 7.34 (d, J=8.33 Hz, 1H), 7.14 (d, J=8.33 Hz, 1H), 6.55 (s, 2H), 6.46 (d, J=9.65 Hz, 1H), 6.04 (d, J=2.19 Hz, 1H), 3.74 (s, 3H).

Example S88. Synthesis of 6-(5-amino-3-phenylpyrazin-2-yl)isoquinolin-1(2H)-one. (Compound No. 1.327)

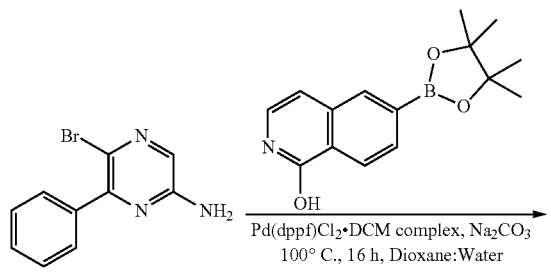

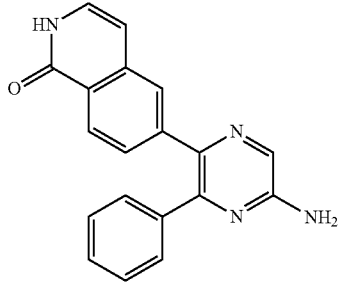

To a stirred solution of 5-bromo-6-phenylpyrazin-2-amine (0.120 g, 0.479 mmol, 1.0 eq.) and 6-(4,4,5,5-tetramethyl-1,3,2-dioxaborolan-2-yl)isoquinolin-1-ol (0.156 g, 0.575 mmol, 1.2 eq.) in dioxane (10 mL) was added Na$_2$CO$_3$ (0.101 g, 0.958 mmol, 2.0 eq.) and 2 mL water. Then reaction was purged with N$_2$ for about 5 min and Pd(dppf)Cl$_2$.DCM complex (0.019 g, 5 mol %) was added. The reaction was re-purged with N$_2$ for another 5 min and was allowed to heat at 100° C. for 16 h. Following this, reaction mixture was allowed to cool to RT and extracted using ethyl acetate (3×50 mL). The combined organic layer was washed (brine), dried (anhydrous Na$_2$SO$_4$) and concentrated under vacuum to get the solid residue which was purified by reversed phase column chromatography to get the desired product as off white solid (0.002 g, 1.33%).

LCMS: 315.3 [M+1]$^+$. $^1$H NMR (400 MHz, DMSO-d$_6$) δ 11.18 (br. s., 1H), 7.99 (s, 1H), 7.93 (d, J=8.33 Hz, 1H), 7.59 (s, 1H), 7.25-7.35 (m, 5H), 7.21 (d, J=9.21 Hz, 1H), 7.08-7.12 (m, 1H), 6.76 (s, 2H), 6.40 (d, J=7.45 Hz, 1H).

Example S89. Synthesis of 3-amino-5-phenyl-6-(quinolin-6-yl)pyrazine-2-carbonitrile (Compound No. 1.19)

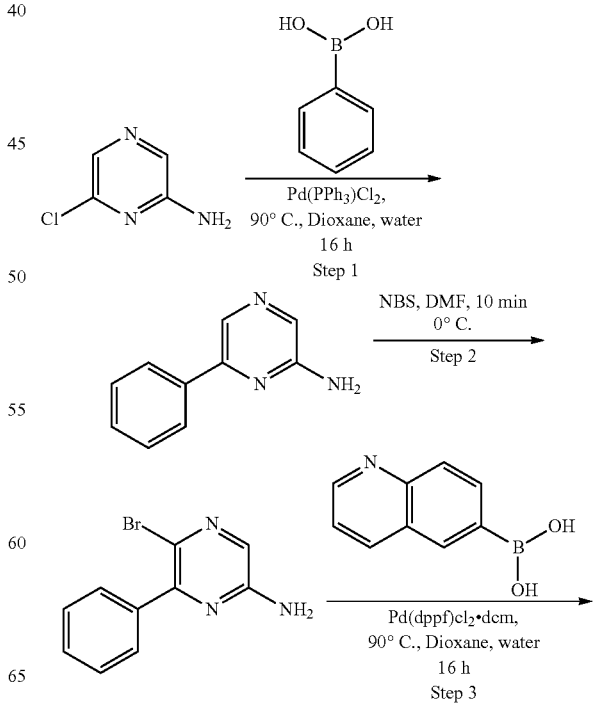

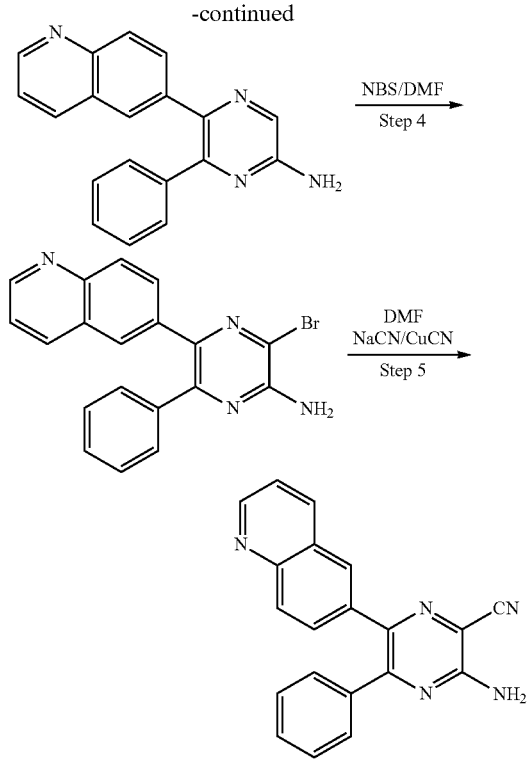

Step 1: Synthesis of 6-phenylpyrazin-2-amine: To a stirred solution of 6-chloropyrazin-2-amine (50 g, 0.3861 mol) in dioxane:water (400 mL; 100 mL) was added benzeneboronic acid (56.4 g, 0.46 mol). The reaction mixture was purged with nitrogen for 20 min then charged Na$_2$CO$_3$ (70.6 g, 0.57 mol) and Pd(PPh$_3$)Cl$_2$ (13.5 g, 0.01930 mol). The reaction mixture was again purged with nitrogen. The reaction mixture was stirred at RT for 10 min followed by heating at 90° C. for 16 h. The reaction was monitored by TLC & LCMS. The reaction mixture was filter through celite and distilled. The reaction was diluted with water and extracted with ethyl acetate (3×200 mL). The combined organic layers were washed (brine), dried (anhydrous Na$_2$SO$_4$) & concentrated under vacuum to get the solid which was purified by column chromatography over silica gel (100-200 mesh) [Ethyl acetate: Hexane (3:7) as eluent] to get the desired product (55 g, 83%).

LCMS: 172 [M+1]$^+$. $^1$H NMR (400 MHz, CHLOROFORM-d) δ 8.38 (s, 1H), 7.83-7.99 (m, 3H), 7.40-7.49 (m, 3H), 4.82 (br. s., 2H)

Step 2: Synthesis of 5-bromo-6-phenylpyrazin-2-amine: To a stirred solution of 6-phenylpyrazin-2-amine (48 g, 0.2803 mol) in DMF was added NBS (49.9 g, 0.28 mol) at 0° c. under nitrogen atmosphere. The reaction mixture was stirred at RT for 16 h. The reaction was monitored by TLC & LCMS. The reaction was diluted with water and extracted with ethyl acetate (3×100 mL). The combined organic layers were washed (brine), dried (anhydrous Na$_2$SO$_4$) & concentrated under vacuum to get the solid which was purified by column chromatography silica gel (100-200 mesh) [Ethyl acetate: Hexane (1:4) as eluent] to get the desired product (38 g, 55%).

LCMS: 252 [M+2]$^+$. $^1$H NMR (400 MHz, DMSO-d$_6$) δ 7.68 (s, 1H), 7.55-7.64 (m, 2H), 7.40-7.51 (m, 3H), 6.75 (br. s., 2H)

Step 3: synthesis of 6-phenyl-5-(quinolin-6-yl)pyrazin-2-amine: To a stirred solution of 5-bromo-6-phenylpyrazin-2-amine (38 g, 0.1519 mol) in dioxane:water (320 mL; 80 mL) was added quinolin-6-ylboronic acid (46.4 g, 0.18 mol). The reaction mixture was purged with nitrogen for 20 min then charged with Na$_2$CO$_3$ (32.2 g, 0.3038 mol) and Pd(dppf)Cl$_2$ (6.19 g, 0.007 mol). The reaction mixture was again purged with nitrogen. The reaction mixture was stirred at RT for 10 min followed by heating at 90° C. for 16 h. The reaction was monitored by TLC & LCMS. The reaction mixture was filtered through celite and distilled. The reaction was diluted with water and extracted with ethyl acetate (3×200 mL). The combined organic layers were washed (brine), dried (anhydrous Na$_2$SO$_4$) & concentrated under vacuum to get the solid which was purified by column chromatography over basic alumina [Ethyl acetate: Hexane (3:7) as eluent] to get the desired product (31 g, 68%).

LCMS: 299 [M+1]$^+$. $^1$H NMR (400 MHz, DMSO-d6) δ 8.83 (d, J=3.07 Hz, 1H), 8.21 (d, J=7.89 Hz, 1H), 8.02 (s, 1H), 7.93 (s, 1H), 7.80 (d, J=8.33 Hz, 1H), 7.41-7.64 (m, 2H), 7.16-7.40 (m, 5H), 6.73 (s, 2H)

Step 4: synthesis of 3-bromo-6-phenyl-5-(quinolin-6-yl)pyrazin-2-amine: To a stirred solution of 6-phenyl-5-(quinolin-6-yl) pyrazin-2-amine (21 g, 0.07 mol) in DMF was added NBS (12.5 g, 0.07 mol) at 0° c. under nitrogen atmosphere. The reaction mixture was stir at RT for 16 h. The reaction was monitored by TLC & LCMS. The reaction was diluted with water and extracted with ethyl acetate (3×30 mL). The combined organic layers were washed (brine), dried (anhydrous Na$_2$SO$_4$) & concentrated under vacuum to get the solid which was purified by column chromatography over basic alumina [Ethyl acetate: Hexane (3:7) as eluent] to get the desired product (18 g, 69%).

LCMS: 377 [M+1]$^+$. $^1$H NMR (400 MHz, CHLOROFORM-d) δ 8.88 (br. s., 1H), 8.11-7.96 (m, 3H), 7.60-7.26 (m, 7H), 5.23 (br. s., 2H).

Step 5: Synthesis of 3-amino-5-phenyl-6-(quinolin-6-yl)pyrazine-2-carbonitrile: To a stirred solution of NaCN (1.56 g, 0.03 mol) and CuCN (5.7 g, 0.06 mol) in dry DMF (150 mL) was added 3-bromo-6-phenyl-5-(quinolin-6-yl) pyrazin-2-amine (12.0 g, 0.03 mol) at 120° C. The reaction mixture was stirred at 145° C. for 12 h. The reaction was monitored by TLC & LCMS. The reaction was distilled. The crude product was poured in ice-water the solid precipitate out. The reaction mixture pH was adjusted with aqueous ammonia and extracted with ethyl acetate (3×100 mL). The combined organic layers were washed (brine), dried (anhydrous Na$_2$SO$_4$) & concentrated under vacuum to get the solid which was purified by column chromatography using basic alumina [Ethyl acetate: Hexane (1:1) as eluent] to get the desired product (3.8 g, 34%).

LCMS: 354 [M+1]$^+$. $^1$H NMR (400 MHz, DMSO-d$_6$) δ 8.88 (d, J=2.63 Hz, 1H), 8.29 (d, J=7.89 Hz, 1H), 7.99 (s, 1H), 7.84 (d, J=8.77 Hz, 1H), 7.58 (br. s., 2H), 7.47-7.54 (m, 2H), 7.35-7.42 (m, 3H), 7.27-7.34 (m, 2H)

BIOLOGICAL EXAMPLES

Example B1. Radioligand Binding Competition Assay

Binding of selected compounds to the adenosine $A_{2A}$, $A_1$, $A_{2B}$, and $A_3$ receptors was tested using a binding competition assay.

The general protocol for the radioligand binding competition assay was as follows. Competition binding was performed in duplicate in the wells of a 96 well plate (Master Block, Greiner, 786201) containing binding buffer (optimized for each receptor), membrane extracts (amount of protein/well optimized for each receptor), radiotracer (final concentration optimized for each receptor), and test compound. Nonspecific binding was determined by co-incubation with 200-fold excess of cold competitor. The samples were incubated in a final volume of 0.1 mL at 25° C. for 60 minutes and then filtered over filter plates. Filters were washed six times with 0.5 mL of ice-cold washing buffer (optimized for each receptor) and 50 µL of Microscint 20 (Packard) were added on each filter. The filter plates were sealed, incubated 15 min on an orbital shaker and scintillation counted with a TopCount for 30 sec/filter.

For the $A_{2A}$ adenosine receptor radioligand binding assay, the following modifications were made to the general protocol. GF/C filters (Perkin Elmer, 6005174), presoaked in 0.01% Brij for 2 h at room temperature were used. Filters were washed six times with 0.5 mL of ice-cold washing buffer (50 mM Tris pH 7.4) and 50 µL of Microscint 20 (Packard) was added in each well. The plates were then incubated for 15 min on an orbital shaker and then counted with a TopCount™ for 1 min/well. Another radioligand binding assay was used to evaluate the binding affinity for the adenosine $A_{2A}$ receptor assay was performed in duplicate in the wells of a 384 plate. Assay buffer contained DPBS 500 mM, $MgCl_2$ 0.1 mM, and 1% DMSO. Membrane-bead suspension was prepared by mixing 25.98 µL of human adenosine $A_{2A}$ membrane preparation (Perkin Elmer, RBHA2AM400UA) at 33.4 µg/mL, 28 µL of ADA at 20 µg/mL, and 932 µL of SPA beads at 3.33 mg/mL) and incubated the mixture for 20 min at room temperature. Mixed 20 µL of radiotracer ($^3$H-SCH 58261) at 15 nM to each well containing test articles at various concentrations and centrifuge the plate at 1000 rpm for 1 minute. Added 30 µL of the membraine-bead suspension to each well. Sealed the plates and incubated for 1 hr at room temperature with vigorous mixing on a plate mixer. Plates were read on Microbeta$^2$ (Perkin Elmer, 2450-0010).

For the adenosine $A_1$ radioligand binding competition assay, a similar procedure was used except that the following reagents were used: CHO-K1-A1 cell membranes; binding buffer comprising HEPES 25 mM pH 7.4, $MgCl_2$ 5 mM, $CaCl_2$ 1 mM, NaCl 100 mM, saponin 10 µg/mL; wash buffer comprising HEPES 25 mM pH 7.4, $MgCl_2$ 5 mM, $CaCl_2$ 1 mM, NaCl 100 mM; Unifilter GF/B—treated for 2 h with 0.5% PEI was the filter; and 1.6 nM of $^3$H-DPCPX was the tracer.

Similarly, the following reagents were used for the adenosine $A_{2B}$ radioligand binding competition assay: HEK-293-$A_{2B}$ cell membranes, 20 µg/well, preincubated 30 min at RT with 25 µg/mL Adenosine Deaminase; a binding buffer comprising HEPES 10 mM pH 7.4, EDTA 1 mM, 0.5% BSA; a wash buffer comprising HEPES 10 mM pH 7.4, EDTA 1 mM; a Unifilter GF/C—treated for 2 h with 0.5% PEI; and 10 nM $^3$H-DPCPX as the tracer.

For the adenosine $A_3$ radioligand binding competition assay, the following reagents were used:

CHO-K1-A3 cell membranes, 1.5 µg/well; a binding buffer comprising HEPES 25 mM pH 7.4, $MgCl_2$ 5 mM, $CaCl_2$ 1 mM, 0.5% BSA; a wash buffer comprising HEPES 25 mM pH 7.4, $MgCl_2$ 5 mM, $CaCl_2$ 1 mM; a Unifilter GF/C—treated for 2 h with 0.5% BS; and 0.4 nM of $^{125}$I-AB-MECA as the tracer.

The results of the binding assay are shown in Tables B1-1 and B1-2 and are shown as percent residual binding at a given concentration. Percent of residual binding means binding of a compound in the presence of competitor normalized to the amount of binding in the absence of competitor. The compounds tested showed a range of binding to the adenosine receptors tested. For example, compound 1 strongly bound to adenosine $A_{2A}$ receptor (30% residual binding at a concentration of 100 nM), $A_1$ receptor (−3% residual binding at 300 nM) and $A_{2B}$, (−9% residual binding at 300 nM) but weakly bound to $A_3$ receptor (96% residual binding at 300 nM).

TABLE B1-1

| Compound No. | $A_{2A}$ radioligand binding competition assay % residual binding @ 3000/1000/300/100 nM | Radioligand binding competition assay % residual binding @ 300 nM ($A_1/A_{2B}/A_3$) | $A_{2A}$ binding $IC_{50}$ (nM) |
|---|---|---|---|
| 1.1 | ND/12/ND/30 | −3/−9/96 | 57 |
| 1.2 | ND/ND/ND/62 | ND | ND |
| 1.3 | ND/ND/ND/57 | ND | ND |
| 1.7 | ND/ND/100/ND | ND | ND |
| 1.8 | ND/ND/39/ND | ND | ND |
| 1.10 | 39/64/70/77 | ND | ND |
| 1.11 | ND/ND/126/ND | ND | ND |
| 1.12 | 12/12/66/ND | ND | ND |
| 1.13 | 18/17/69/83 | ND | ND |
| 1.14 | 12/29/48/76 | ND | ND |
| 1.15 | 104/ND/ND/ND | ND | ND |
| 1.16 | 80/ND/ND/ND | ND | ND |
| 1.17 | 8/ND/ND/ND | ND | ND |
| 1.18 | 100/ND/ND/ND | ND | ND |
| 1.19 | 4/ND/ND/ND | ND | ND |
| 1.20 | 3/ND/ND/ND | ND | ND |
| 1.21 | 5/ND/ND/ND | ND | ND |
| 1.22 | 39/ND/ND/ND | ND | ND |

ND = Not determined

TABLE B1-2

| Compound No. | A2a binding IC50 (nM) | A2a binding % inh @ 3000 nM | A2a binding % inh @ 1000/100/10/1 nM |
|---|---|---|---|
| 1.241 | ND | 86 | ND |
| 1.45 | ND | 91 | ND |
| 1.185 | ND | 20 | ND |
| 1.270 | ND | 100 | ND |
| 1.271 | 2.1 | ND | ND |
| 1.210 | ND | 100 | ND |
| 1.238 | ND | 11 | ND |
| 1.272 | ND | 80 | ND |
| 1.273 | ND | 100 | ND |
| 1.274 | ND | 80 | ND |
| 1.275 | ND | 11 | ND |
| 1.276 | ND | 24 | ND |
| 1.25 | ND | 48 | ND |
| 1.192 | ND | 89 | ND |
| 1.277 | ND | 83 | ND |
| 1.278 | ND | 95 | ND |
| 1.193 | ND | 83 | ND |
| 1.35 | ND | 64 | ND |
| 1.279 | ND | 58 | ND |
| 1.186 | ND | 30 | ND |
| 1.280 | ND | 75 | ND |
| 1.36 | ND | 81 | ND |
| 1.281 | ND | ND | 80/88/78/ND |
| 1.292 | 2.4 | ND | ND/95/93/50 |
| 1.282 | ND | ND | 79/82/74/ND |
| 1.283 | ND | ND | 95/83/63/ND |
| 1.284 | ND | ND | 83/76/32/ND |
| 1.285 | ND | ND | 90/76/56/ND |
| 1.286 | ND | ND | 86/96/87/40 |
| 1.287 | ND | ND | 80/90/77/42 |
| 1.288 | 55.5 | ND | 84/86/83/42 |
| 1.289 | ND | ND | 95/87/75/41 |

TABLE B1-2-continued

| Compound No. | A2a binding IC50 (nM) | A2a binding % inh @ 3000 nM | A2a binding % inh @ 1000/100/10/1 nM |
|---|---|---|---|
| 1.290 | 3.3 | ND | 89/89/85/57 |
| 1.291 | ND | ND | ND/0/0/0 |
| 1.293 | ND | ND | ND/31/32/28 |
| 1.295 | 5.5 | ND | ND |
| 1.297 | 17 | ND | ND |
| 1.304 | 9 | ND | ND |
| 1.308 | >10000 | ND | ND |
| 1.309 | 1.6 | ND | ND |
| 1.315 | 101 | ND | ND |
| 1.318 | 9.4 | ND | ND |

ND = Not determined

Example B2. cAMP Assay

The functional activity of compounds was tested using one of the two assays to detect the present of cAMP. Activation of G-protein coupled receptors (such as $A_{2A}$) results in activation of adenylcyclase which converts ATP into cAMP which is used as a downstream signaling molecule. Therefore, molecules which act as GPCR (or specifically $A_{2A}$ receptor) antagonists cause a decrease in intracellular cAMP concentration.

Both assays used HEK-293 cells expressing human recombinant adenosine $A_{2A}$ receptor were grown prior to the test in media without antibiotic. Assay 1 (Table B2-1): The cells were detached by gentle flushing with PBS-EDTA (5 mM EDTA), recovered by centrifugation and suspended in assay buffer (KRH: 5 mM KCl, 1.25 mM $MgSO_4$, 124 mM NaCl, 25 mM HEPES, 13.3 mM Glucose, 1.25 mM $KH_2PO_4$, 1.45 mM $CaCl_2$, 0.5 g/L BSA, supplemented with Rolipram).

12 μL of cells were mixed with 6 μL of the test compound at increasing concentrations and then incubated for 10 min. Thereafter 6 μL of the reference agonist was added at a final concentration corresponding to the historical $EC_{80}$. The plates were then incubated for 30 min at room temperature. After addition of the lysis buffer and 1 hour incubation, cAMP concentrations were estimated, according to the manufacturer specification, with the HTRF® kit.

Assay 2 (Table B2-2): 100 nL of test articles at 100× of final concentration were transferred to assay plate by Echo. Cells were washed twice with 5 mL of PBS 10 μL of cells were mixed with 5 mL PBS. After aspirating the PBS and adding 1.5 mL versine, cells were incubated at 37° C. for 2-5 min. After centrifugation, 4 mL of medium was added and adjusted cell density to 5,000 cells/well with Stimulation Buffer. 10 μL of cells were aliquoted to the assay plate, centrifuged at 1000 rpm for 1 minute, and incubated for 60 minutes at room temperature. 5 μL 4×Eu-cAMP tracer solution and 5 μL 4×Ulight™-anti-cAMP solution were added to assay plate, followed by centrifugation and 60-minute incubation at room temperature. Plates were read on EnVision.

As shown in Tables B2-1 and B2-2, many of the compounds disclosed herein strongly reduced intracellular levels of cAMP. For example, compound 1.1 reduced cAMP levels by 97% compared to untreated cells.

TABLE B2-1

| Compound No. | A2a cAMP (% inh @ 100 nM) | A2a cAMP $IC_{50}$ (nM) |
|---|---|---|
| 1.1 | 97 | 6 |
| 1.2 | 100 | ND |
| 1.3 | 100 | ND |
| 1.4 | 1.4 | ND |
| 1.6 | 47 | ND |
| 1.7 | 100 | ND |
| 1.8 | 100 | ND |
| 1.9 | 49 | ND |
| 1.10 | 100 | ND |
| 1.11 | 100 | ND |
| 1.12 | 94 | ND |
| 1.13 | 51 | ND |
| 1.14 | 100 | ND |
| 1.15 | 0 | ND |
| 1.16 | 0 | ND |
| 1.17 | 99 | ND |
| 1.18 | 14 | ND |
| 1.19 | 100 | ND |
| 1.20 | 81 | ND |
| 1.21 | 100 | ND |
| 1.22 | 24 | ND |

ND = Not determined

TABLE B2-2

| Compound No. | A2a cAMP IC50 (nM) | A2a cAMP % inh @ 100 nM |
|---|---|---|
| 1.241 | ND | 80 |
| 1.45 | ND | 100 |
| 1.185 | ND | 9 |
| 1.270 | ND | 100 |
| 1.271 | 50 | ND |
| 1.210 | ND | 100 |
| 1.238 | ND | 7 |
| 1.272 | ND | 96 |
| 1.273 | 12 | ND |
| 1.274 | ND | 60 |
| 1.275 | ND | 0 |
| 1.276 | ND | 0 |
| 1.25 | ND | 6 |
| 1.192 | ND | 93 |
| 1.277 | ND | 44 |
| 1.278 | 303.8 | ND |
| 1.193 | ND | 87 |
| 1.35 | ND | 22 |
| 1.279 | ND | 9 |
| 1.186 | ND | 12 |
| 1.280 | ND | 51 |
| 1.36 | ND | 77 |
| 1.285 | ND | 34 |
| 1.286 | ND | 20 |
| 1.287 | ND | 16 |
| 1.288 | 1054 | ND |
| 1.290 | 35.7 | ND |
| 1.294 | >10000 | ND |
| 1.295 | 33 | ND |
| 1.296 | 130 | ND |
| 1.297 | 47.9 | ND |
| 1.298 | >10000 | ND |
| 1.299 | 1250 | ND |
| 1.300 | 119.9 | ND |
| 1.301 | >10000 | ND |
| 1.302 | 867 | ND |
| 1.303 | 573 | ND |
| 1.304 | 40 | ND |
| 1.305 | 96 | ND |
| 1.306 | 120 | ND |
| 1.307 | 8477 | ND |
| 1.308 | >10000 | ND |
| 1.309 | 13.1 | ND |
| 1.310 | 127 | ND |
| 1.311 | 279.3 | ND |

TABLE B2-2-continued

| Compound No. | A2a cAMP IC50 (nM) | A2a cAMP % inh @ 100 nM |
|---|---|---|
| 1.312 | 251 | ND |
| 1.313 | 1550 | ND |
| 1.314 | 1536 | ND |
| 1.315 | 1397 | ND |
| 1.316 | 40.1 | ND |
| 1.317 | 279.5 | ND |
| 1.318 | 199.6 | ND |
| 1.319 | 1927 | ND |
| 1.395 | 562.8 | ND |
| 1.329 | >10000 | ND |
| 1.324 | 12.5 | ND |
| 1.402 | 260.1 | ND |
| 1.353 | >10000 | ND |
| 1.327 | 172.6 | ND |

ND = Not determined

Example B3 GTPγ$^{35}$S Scintillation Proximity Assay for $A_{2A}$ Receptor

A scintillation proximity assay (SPA) was used to determine the kinetic profile of the binding of candidate molecule compound 1.1 to the $A_{2A}$ receptor.

For antagonist testing, membranes extracts were prepared from HEK-293 cells expressing recombinant human $A_{2A}$ receptor, were mixed with GDP (volume:volume) and were incubated in assay buffer comprising 20 mM HEPES pH 7.4; 100 mM NaCl, 10 µg/mL saponin, 5 mM MgCl$_2$ for at least 15 min on ice. In parallel, GTPγ[$^{35}$S] was mixed with the beads (volume:volume) just before starting the reaction. The following reagents were successively added in the wells of an Optiplate (Perkin Elmer): 25 µL of test compound or reference ligand, 25 µL of the membranes: GDP mix, 25 µL of reference agonist at historical EC$_{80}$ and 25 µL of GTPγ [$^{35}$S] (PerkinElmer NEG030X), diluted in assay buffer to give 0.1 nM. The plate was incubated at room temperature for 1 hour. Then, 20 µL of IGEPAL was added for 30 minutes at room temperature. Following this incubation, 20 µL of beads (PVT-anti rabbit (PerkinElmer, RPNQ0016)), diluted in assay buffer at 50 mg/mL (0.5 mg/10 µL) and 20 µL of an Anti-GαS/olf antibody were added for a final incubation of 3 hours at room temperature. Then, the plates were centrifuged for 10 min at 2000 rpm, incubated at room temperature for 1 hour and counted for 1 min/well with a PerkinElmer TopCount reader.

TABLE B3

| Compound No. | $A_{2A}$ γGTP assay (% Inh Avg) @ 100 nM |
|---|---|
| 1.1 | 82 |

Example B4 Functional T Cell Assay

Figure 2:
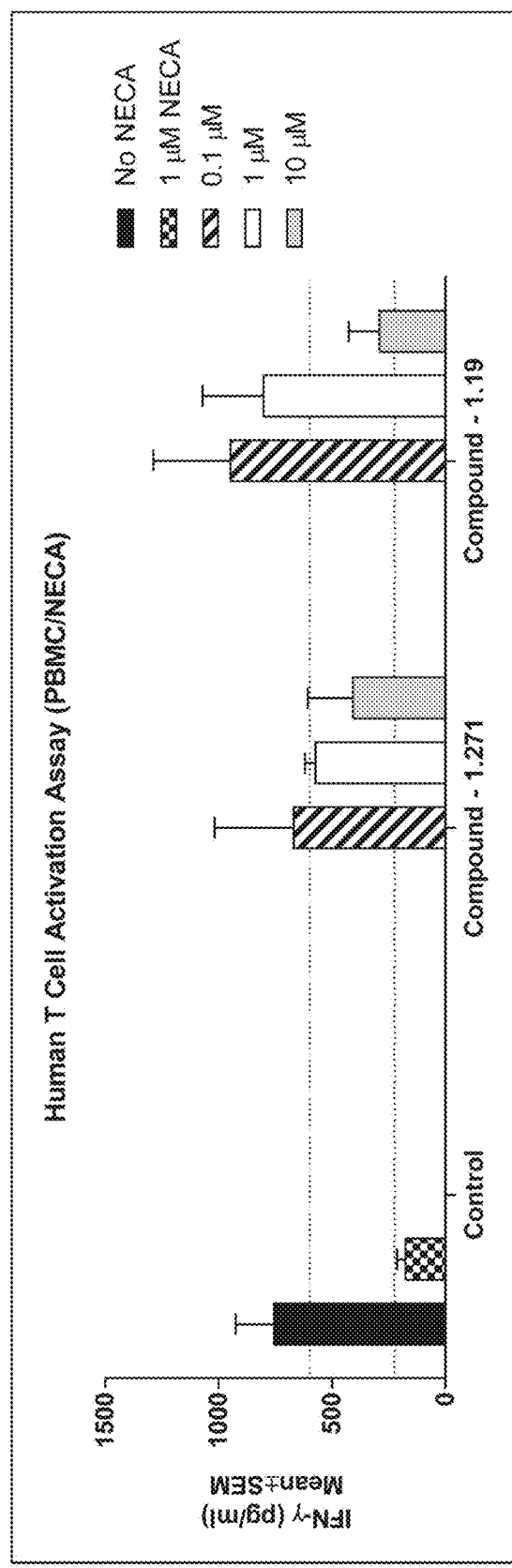
FIG. 2 shows the effects of certain compounds on IFN-γ production in activated human PBMCs.

Human T Cell Activation Assay: Fresh human blood was diluted with the same volume of PBS and the buffy coat containing peripheral blood mononuclear cells (PBMCs) were prepared and resuspend in culture medium at a density of 2×10$^6$/mL. 2×10$^5$ PBMCs (in 100 µL) were plated to each well of 96-well flat bottom plate. 25 µL of 8× final concentration of 10-fold serial diluted compounds were added to indicated wells and incubate for 30 mins in 37° C./5% CO2. Beads included in T cell activation/expansion kit (Miltenyi biotec Cat #130-091-441) at a bead-to-cell ratio of 1:6 in 50 µL were added to all well with the final concentration of DMSO at 0.1% and final volume at 200 µL. 60 µL of supernatant post 24 hr and 48 hr incubation was collected for TNF-α and IFN-γ concentration evaluation using TNF-α ELISA ready-set-go kit (eBioscience, Cat #88-7346-77) and IFN-γ ELISA ready-set-go kit (eBioscience, Cat #88-7316-77), respectively. FIG. 1 and FIG. 2 show that the compounds of invention reversed NECA-mediated suppression of TNF-α and IFN-γ secretion in activated human T cells in vitro.

Example B5 cAMP Assay

In a 96-well plate coated with anti-CD3 antibody, CD8$^+$ T-cells (1×10$^5$) were cultured alone, with 3 µM of NECA, or in the presence of 1 µM of compound of the interest with or without 3 µM of NECA. The cells were incubated for 30 min at 37° C. and 5% CO2, and the reaction was stopped by addition of 200 µL, 0.1 M hydrochloric acid. cAMP levels were determined by an ELISA kit.

Example B6 Anti-Tumor Activities in Immuno-Oncology Mouse Models

The anti-tumor activities of test articles will be evaluated in selective mouse models (e.g., syngeneic model, xenograft model, or PDX) as a monotherapy or combination therapies. Using MC-38 syngeneic model as an example: female C57BL/6 mice are inoculated subcutaneously at right flank with MC-38 cells for tumor development. Five days after tumor inoculation, mice with tumor size ranging from 40-85 mm$^3$ are selected and assigned into sub-groups using stratified randomization with 10 mice per group based upon their tumor volumes. Mice receive pre-defined treatments include vehicle, test article at various doses alone, test article at various doses plus other anti-cancer therapy, and other anti-cancer therapy control. Body weight and tumor sizes are measured three times per week during the treatment. Tumor volume will be expressed in mm$^3$ using the formula: V=0.5 a×b$^2$ where a and b are the long and short diameters of the tumor, respectively. The tumor sizes are used for the calculations of both tumor growth inhibition (TGI) and T/C values. When an individual animal reaches to the termination endpoint (e.g., with TV>1000 mm$^3$), the mouse are euthanized. The time from inoculation to the termination are deemed as its survival time. Survival curve are plotted by Kaplan-Meier method. At the end of study, plasma and tumor samples are collected to explore biomarkers.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

What is claimed is:

1. A compound of the formula (I):

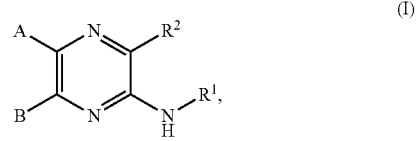

or a tautomer or stereoisomer thereof, or a pharmaceutically acceptable salt of any of the foregoing, wherein:

A is 4-hydroxyphenyl optionally further substituted by $R^3$, 4-hydroxy-2-pyridyl optionally further substituted by $R^4$, a naphthyl substituted by $R^4$, a 9- or 10-membered bicyclic heterocyclyl optionally substituted by $R^4$, or a 10-membered bicyclic heteroaryl optionally substituted by $R^4$;

B is a phenyl optionally substituted by $R^3$, $C_3$-$C_6$ cycloalkyl optionally substituted by $R^4$, 3- to 6-membered heterocyclyl optionally substituted by $R^4$ or a 5- to 10-membered heteroaryl optionally substituted by $R^4$;

$R^1$ is a hydrogen, $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, 5- to 10-membered heteroaryl, —($C_1$-$C_3$ alkylene)($C_3$-$C_6$ cycloalkyl), —($C_1$-$C_3$ alkylene)(3-6-membered heterocyclyl), —($C_1$-$C_3$ alkylene)(5-6-membered heteroaryl), —($C_1$-$C_3$ alkylene)($C_6$ aryl), —C(O)$R^{1a}$, —C(O)O$R^{1a}$, —C(O)N$R^{1b}R^{1c}$, —N$R^{1b}R^{1c}$, —S(O)$_2R^{1a}$, —($C_1$-$C_3$ alkylene)C(O)N$R^{1b}R^{1c}$, —($C_1$-$C_3$ alkylene)C(O)$R^{1a}$ or —($C_1$-$C_3$ alkylene)N$R^{1b}R^{1c}$, wherein the $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, 5- to 10-membered heteroaryl, —($C_1$-$C_3$ alkylene)($C_3$-$C_6$ cycloalkyl), —($C_1$-$C_3$ alkylene)(3-6-membered heterocyclyl), —($C_1$-$C_3$ alkylene)(5-6-membered heteroaryl), and —($C_1$-$C_3$ alkylene)($C_6$ aryl) of $R^1$ are independently optionally substituted by R4;

each $R^{1a}$ is independently hydrogen, $C_1$-$C_6$ alkyl, $C_3$-$C_6$ cycloalkyl, 3-6-membered heterocyclyl, $C_6$ aryl, 5-6-membered heteroaryl, —($C_1$-$C_3$ alkylene)($C_3$-$C_6$ cycloalkyl), —($C_1$-$C_3$ alkylene)(3-6-membered heterocyclyl), —($C_1$-$C_3$ alkylene)($C_6$ aryl) or —($C_1$-$C_3$ alkylene)(5-6-membered heteroaryl), wherein each of which is optionally substituted by methyl, ethyl, halogen, oxo, —CF$_3$, —OH, —OCH$_3$, —CN, —C(O)OCH$_3$, —C(O)O$C_2H_5$, —NH$_2$ or —NHCH$_3$;

each $R^{1b}$ and $R^{1c}$ is independently hydrogen, $C_1$-$C_6$ alkyl, $C_3$-$C_6$ cycloalkyl, 3-6-membered heterocyclyl, $C_6$ aryl, 5-6-membered heteroaryl, —($C_1$-$C_3$ alkylene)($C_3$-$C_6$ cycloalkyl), —($C_1$-$C_3$ alkylene)(3-6-membered heterocyclyl), —($C_1$-$C_3$ alkylene)($C_6$ aryl) or —($C_1$-$C_3$ alkylene)(5-6-membered heteroaryl), wherein each of which is optionally substituted by methyl, ethyl, halogen, oxo, —CF$_3$, —OH, —OCH$_3$, —CN, —C(O)OCH$_3$, —C(O)O$C_2H_5$, —NH$_2$ or —NHCH$_3$;

or $R^{1b}$ and $R^{1c}$ are taken together with the nitrogen atom to which they are attached to form a 3- to 6-membered heterocyclyl;

$R^2$ is hydrogen, $C_1$-$C_6$ alkyl, $C_2$-$C_6$ alkenyl, $C_2$-$C_6$ alkynyl, $C_6$-$C_{14}$ aryl, $C_5$-$C_{14}$ heteroaryl, $C_3$-$C_6$ cycloalkyl, 3- to 6-membered heterocyclyl, —CN, halogen, —O$R^{2a}$, —S$R^{2a}$, —N$R^{2b}R^{2c}$, —C(O)$R^{2a}$, —N$R^{2b}$C(O)$R^{2c}$, —N$R^{2a}$C(O)N$R^{2b}R^{2c}$, —C(O)O$R^{2a}$, —C(O)ON$R^{2b}R^{2c}$ or —C(O)N$R^{2b}R^{2c}$, wherein the $C_1$-$C_6$ alkyl, $C_2$-$C_6$ alkenyl, $C_2$-$C_6$ alkynyl, $C_6$-$C_{14}$ aryl, $C_3$-$C_6$ cycloalkyl and 3- to 6-membered heterocyclyl of $R^2$ are independently optionally substituted by $R^4$;

each $R^{2a}$ is independently hydrogen, $C_1$-$C_6$ alkyl, $C_3$-$C_6$ cycloalkyl, 3- to 6-membered heterocyclyl, $C_6$-aryl, 5- to 6-membered heteroaryl, —($C_1$-$C_3$ alkylene)N($C_2H_5$)$_2$, —($C_1$-$C_3$ alkylene)($C_3$-$C_6$ cycloalkyl), —($C_1$-$C_3$ alkylene)(3-6-membered heterocyclyl), —($C_1$-$C_3$ alkylene)(5-6-membered heteroaryl) or —($C_1$-$C_3$ alkylene)($C_6$ aryl), wherein each of which is optionally substituted by methyl, ethyl, halogen, oxo, —CF$_3$, —OH, —OCH$_3$, —CN, —C(O)OCH$_3$, —C(O)O$C_2H_5$, —NH$_2$ or —NHCH$_3$;

each $R^{2b}$ and $R^{2c}$ is independently hydrogen, $C_1$-$C_6$ alkyl, $C_3$-$C_6$ cycloalkyl, 3- to 6-membered heterocyclyl, $C_6$-aryl, 5- to 6-membered heteroaryl, —($C_1$-$C_3$ alkylene)N($C_2H_5$)$_2$, —($C_1$-$C_3$ alkylene)($C_3$-$C_6$ cycloalkyl), —($C_1$-$C_3$ alkylene)(3-6-membered heterocyclyl), —($C_1$-$C_3$ alkylene)(5-6-membered heteroaryl) or —($C_1$-$C_3$ alkylene)($C_6$ aryl), wherein each of which is optionally substituted by methyl, ethyl, halogen, oxo, —CF$_3$, —OH, —OCH$_3$, —CN, —C(O)OCH$_3$, —C(O)O$C_2H_5$, —NH$_2$ or —NHCH$_3$;

or $R^{2b}$ and $R^{2'}$ are taken together with the nitrogen atom to which they are attached to form a 3- to 6-membered heterocyclyl;

each $R^3$ is independently $C_1$-$C_6$ alkyl, $C_2$-$C_6$ alkenyl, $C_2$-$C_6$ alkynyl, halogen, —CN, —O$R^5$, —S$R^5$, —N$R^6R^7$, —NO$_2$, —C=NH(O$R^5$), —C(O)$R^5$, —OC(O)$R^5$, —C(O)O$R^5$, —C(O)N$R^6R^7$, —OC(O)N$R^6R^7$, —N$R^5$C(O)O$R^6$, —N$R^5$C(O)N$R^6R^7$, —S(O)$R^5$, —S(O)$_2R^5$, —N$R^5$S(O)$R^6$, —C(O)N$R^5$S(O)$R^6$, —N$R^5$S(O)$_2R^6$, —C(O)N$R^5$S(O)$_2R^6$, —S(O)N$R^6R^7$, —S(O)$_2$N$R^6R^7$, —P(O)(O$R^6$)(O$R^7$), $C_3$-$C_6$ cycloalkyl, 3-12-membered heterocyclyl, 5- to 10-membered heteroaryl, $C_6$-$C_{14}$ aryl, —($C_1$-$C_3$ alkylene)CN, —($C_1$-$C_3$ alkylene)O$R^5$, —($C_1$-$C_3$ alkylene)S$R^5$, —($C_1$-$C_3$ alkylene)N$R^6R^7$, —($C_1$-$C_3$ alkylene)CF$_3$, —($C_1$-$C_3$ alkylene)NO$_2$, —C=NH(O$R^5$), —($C_1$-$C_3$ alkylene)C(O)$R^5$, —($C_1$-$C_3$ alkylene)OC(O)$R^5$, —($C_1$-$C_3$ alkylene)C(O)O$R^5$, —($C_1$-$C_3$ alkylene)C(O)N$R^6R^7$, —($C_1$-$C_3$ alkylene)OC(O)N$R^6R^7$, —($C_1$-$C_3$ alkylene)N$R^5$C(O)$R^6$, —($C_1$-$C_3$ alkylene)N$R^5$C(O)O$R^6$, —($C_1$-$C_3$ alkylene)N$R^5$C(O)N$R^6R^7$, —($C_1$-$C_3$ alkylene)S(O)$R^5$, —($C_1$-$C_3$ alkylene)S(O)$_2R^5$, —($C_1$-$C_3$ alkylene)N$R^5$S(O)$R^6$, —C(O)(($C_1$-$C_3$ alkylene)N$R^5$S(O)$R^6$, —($C_1$-$C_3$ alkylene)N$R^5$S(O)$_2R^6$, —($C_1$-$C_3$ alkylene)C(O)N$R^5$S(O)$_2R^6$, —($C_1$-$C_3$ alkylene)S(O)N$R^6R^7$, —($C_1$-$C_3$ alkylene)S(O)$_2$N$R^6R^7$, —($C_1$-$C_3$ alkylene)P(O)(O$R^6$)(O$R^7$), —($C_1$-$C_3$ alkylene)($C_3$-$C_6$ cycloalkyl), —($C_1$-$C_3$ alkylene)(3-12-membered heterocyclyl), —($C_1$-$C_3$ alkylene)(5-10-membered heteroaryl) or —($C_1$-$C_3$ alkylene)($C_6$-$C_{14}$ aryl), wherein each $R^3$ is independently optionally substituted by halogen, oxo, —O$R^8$, —N$R^8R^9$, —C(O)$R^8$, —CN, —S(O)$R^8$, —S(O)$_2R^8$, —P(O)(O$R^8$)(O$R^9$), —($C_1$-$C_3$ alkylene)O$R^8$, —($C_1$-$C_3$ alkylene)N$R^8R^9$, —($C_1$-$C_3$ alkylene)C(O)$R^8$, —($C_1$-$C_3$ alkylene)S(O)$R^8$, —($C_1$-$C_3$ alkylene)S(O)$_2R^8$, —($C_1$-$C_3$ alkylene)P(O)(O$R^8$)(O$R^9$), $C_3$-$C_8$ cycloalkyl, or $C_1$-$C_6$ alkyl optionally substituted by oxo, —OH or halogen;

each $R^4$ is independently oxo or $R^3$;

$R^5$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6-membered heterocyclyl of $R^5$ are independently optionally substituted by halogen, oxo, —CN, —O$R^9$, —N$R^9R^{10}$, —P(O)(O$R^9$)(O$R^{10}$), phenyl optionally substituted by halogen, or $C_1$-$C_6$ alkyl optionally substituted by halogen, —OH or oxo;

$R^6$ and $R^7$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl, —($C_1$-$C_3$ alkylene)($C_6$ aryl) or 3-6 membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl, —($C_1$-$C_3$ alkylene)($C_6$ aryl) and 3-6 membered heterocyclyl of $R^6$ and $R^7$ are independently optionally substituted by halogen, oxo, —CN, —$OR^9$, —$NR^9R^{10}$ or $C_1$-$C_6$ alkyl optionally substituted by halogen, —OH or oxo;

or $R^6$ and $R^7$ are taken together with the atom to which they attached to form a 3-6 membered heterocyclyl optionally substituted by halogen, oxo, —$OR^9$, —$NR^9R^{10}$ or $C_1$-$C_6$ alkyl optionally substituted by halogen, oxo or —OH;

$R^8$ and $R^9$ in $R^3$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or $R^8$ and $R^9$ in $R^3$ are taken together with the atom to which they attached to form a 3-6 membered heterocyclyl optionally substituted by halogen, oxo or $C_1$-$C_6$ alkyl optionally substituted by halogen or oxo; and $R^9$ and $R^{10}$ in $R^5$, $R^6$ and $R^7$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or $R^9$ and $R^{10}$ in $R^5$, $R^6$ and $R^7$ are taken together with the atom to which they attached to form a 3-6 membered heterocyclyl optionally substituted by halogen, oxo or $C_1$-$C_6$ alkyl optionally substituted by oxo or halogen.

2. The compound of claim 1, or a tautomer or stereoisomer thereof, or a pharmaceutically acceptable salt of any of the foregoing, wherein:

A is 4-hydroxyphenyl optionally further substituted by $R^3$, 4-hydroxy-2-pyridyl optionally further substituted by $R^4$, or a 10-membered bicyclic heteroaryl optionally substituted by $R^4$;

B is a phenyl optionally substituted by $R^3$, or 5- to 6-membered heteroaryl optionally substituted by $R^4$;

$R^1$ is a hydrogen, $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, —$C(O)R^{1a}$, —$C(O)OR^{1a}$, —$C(O)NR^{1b}R^{1c}$, or —$NR^{1b}R^{1c}$, wherein the $C_1$-$C_6$ alkyl, $C_2$-$C_6$ alkenyl, $C_2$-$C_6$ alkynyl, $C_3$-$C_6$ cycloalkyl and 3- to 6-membered heterocyclyl of $R^1$ are independently optionally substituted by $R^4$;

each $R^{1a}$ is independently hydrogen, $C_1$-$C_6$ alkyl, or $C_3$-$C_6$ cycloalkyl;

each $R^{1b}$ and $R^{1c}$ is independently hydrogen, $C_1$-$C_6$ alkyl, or $C_3$-$C_6$ cycloalkyl;

or $R^{1b}$ and $R^{1c}$ are taken together with the nitrogen atom to which they are attached to form a 3- to 6-membered heterocyclyl;

$R^2$ is hydrogen, $C_1$-$C_6$ alkyl, $C_2$-$C_6$ alkenyl, $C_2$-$C_6$ alkynyl, $C_6$-$C_{14}$ aryl, —CN, halogen, —$OR^{2a}$, —$NR^{2b}R^{2"}$, —$C(O)R^{2a}$, —$C(O)OR^{2a}$, or —$C(O)NR^{2b}R^{2'}$, wherein the $C_1$-$C_6$ alkyl, $C_2$-$C_6$ alkenyl, $C_2$-$C_6$ alkynyl and $C_6$-$C_{14}$ aryl of $R^2$ are independently optionally substituted by $R^4$;

each $R^{2a}$ is independently hydrogen, $C_1$-$C_6$ alkyl, or $C_3$-$C_6$ cycloalkyl;

each $R^{2b}$ and $R^{2c}$ is independently hydrogen, $C_1$-$C_6$ alkyl, or $C_3$-$C_6$ cycloalkyl;

or $R^{2b}$ and $R^{2c}$ are taken together with the nitrogen atom to which they are attached to form a 3- to 6-membered heterocyclyl;

each $R^3$ is independently $C_1$-$C_6$ alkyl, $C_2$-$C_6$ alkenyl, $C_2$-$C_6$ alkynyl, halogen, —CN, —$OR^5$, —$SR^5$, —$NR^6R^7$, —$NO_2$, —C=$NH(OR^5)$, —$C(O)R^5$, —$OC(O)R^5$, —$C(O)OR^5$, —$C(O)NR^6R^7$, —$OC(O)NR^6R^7$, —$NR^5C(O)R^6$, —$NR^5C(O)OR^6$, —$NR^5C(O)NR^6R^7$, —$S(O)R^5$, —$S(O)_2R^5$, —$NR^5S(O)R^6$, —$C(O)NR^5S(O)R^6$, —$NR^5S(O)_2R^6$, —$C(O)NR^5S(O)_2R^6$, —$S(O)NR^6R^7$, —$S(O)_2NR^6R^7$, —$P(O)(OR^6)(OR^7)$, $C_3$-$C_6$ cycloalkyl, 3-12-membered heterocyclyl, 5- to 10-membered heteroaryl, $C_6$-$C_{14}$ aryl, —($C_1$-$C_3$ alkylene)CN, —($C_1$-$C_3$ alkylene)$OR^5$, —($C_1$-$C_3$ alkylene)$SR^5$, —($C_1$-$C_3$ alkylene)$NR^6R^7$, —($C_1$-$C_3$ alkylene)$CF_3$, —($C_1$-$C_3$ alkylene)$NO_2$, —C=$NH(OR^5)$, —($C_1$-$C_3$ alkylene)$C(O)R^5$, —($C_1$-$C_3$ alkylene)$OC(O)R^5$, —($C_1$-$C_3$ alkylene)$C(O)OR^5$, —($C_1$-$C_3$ alkylene)$C(O)NR^6R^7$, —($C_1$-$C_3$ alkylene)$OC(O)NR^6R^7$, —($C_1$-$C_3$ alkylene)$NR^5C(O)R^6$, —($C_1$-$C_3$ alkylene)$NR^5C(O)OR^6$, —($C_1$-$C_3$ alkylene)$NR^5C(O)NR^6R^7$, —($C_1$-$C_3$ alkylene)$S(O)R^5$, —($C_1$-$C_3$ alkylene)$S(O)_2R^5$, —($C_1$-$C_3$ alkylene)$NR^5S(O)R^6$, —$C(O)$($C_1$-$C_3$ alkylene)$NR^5S(O)R^6$, —($C_1$-$C_3$ alkylene)$NR^5S(O)_2R^6$, —($C_1$-$C_3$ alkylene)$C(O)NR^5S(O)_2R^6$, —($C_1$-$C_3$ alkylene)$S(O)NR^6R^7$, —($C_1$-$C_3$ alkylene)$S(O)_2NR^6R^7$, —($C_1$-$C_3$ alkylene)$P(O)(OR^6)(OR^7)$, —($C_1$-$C_3$ alkylene)($C_3$-$C_6$ cycloalkyl), —($C_1$-$C_3$ alkylene)(3-12-membered heterocyclyl), —($C_1$-$C_3$ alkylene)(5-10-membered heteroaryl) or —($C_1$-$C_3$ alkylene)($C_6$-$C_{14}$ aryl), wherein each $R^3$ is independently optionally substituted by halogen, oxo, —$OR^8$, —$NR^8R^9$, —$C(O)R^8$, —CN, —$S(O)R^8$, —$S(O)_2R^8$, —$P(O)(OR^8)(OR^9)$, —($C_1$-$C_3$ alkylene)$OR^8$, —($C_1$-$C_3$ alkylene)$NR^8R^9$, —($C_1$-$C_3$ alkylene)$C(O)R^8$, —($C_1$-$C_3$ alkylene)$S(O)R^8$, —($C_1$-$C_3$ alkylene)$S(O)_2R^8$, —($C_1$-$C_3$ alkylene)$P(O)(OR^8)(OR^9)$, $C_3$-$C_8$ cycloalkyl, or $C_1$-$C_6$ alkyl optionally substituted by oxo, —OH or halogen;

each $R^4$ is independently oxo or $R^3$;

$R^5$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6-membered heterocyclyl of $R^5$ are independently optionally substituted by halogen, oxo, —CN, —$OR^9$, —$NR^9R^{10}$, —$P(O)(OR^9)(OR^{10})$, phenyl optionally substituted by halogen, or $C_1$-$C_6$ alkyl optionally substituted by halogen, —OH or oxo;

$R^6$ and $R^7$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl or 3-6 membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl and 3-6 membered heterocyclyl of $R^6$ and $R^7$ are independently optionally substituted by halogen, oxo, —CN, —$OR^9$, —$NR^9R^{10}$ or $C_1$-$C_6$ alkyl optionally substituted by halogen, —OH or oxo;

or $R^6$ and $R^7$ are taken together with the atom to which they attached to form a 3-6 membered heterocyclyl optionally substituted by halogen, oxo, —$OR^9$, —$NR^9R^{10}$ or $C_1$-$C_6$ alkyl optionally substituted by halogen, oxo or —OH;

R[8] and R[9] are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or R[8] and R[9] are taken together with the atom to which they attached to form a 3-6 membered heterocyclyl optionally substituted by halogen, oxo or $C_1$-$C_6$ alkyl optionally substituted by halogen or oxo; and R[9] and R[10] are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or R[9] and R[10] are taken together with the atom to which they attached to form a 3-6 membered heterocyclyl optionally substituted by halogen, oxo or $C_1$-$C_6$ alkyl optionally substituted by oxo or halogen.

3. The compound of claim 1, or a tautomer or stereoisomer thereof, or a pharmaceutically acceptable salt of any of the foregoing, wherein R[1] is hydrogen or —C(O)R[1a].

4. The compound of claim 3, or a tautomer or stereoisomer thereof, or a pharmaceutically acceptable salt of any of the foregoing, wherein R[1] is hydrogen.

5. The compound of claim 3, or a tautomer or stereoisomer thereof, or a pharmaceutically acceptable salt of any of the foregoing, wherein R[1] is —C(O)R[1a] and R[1a] is $C_1$-$C_6$ alkyl.

6. The compound of claim 1, or a tautomer or stereoisomer thereof, or a pharmaceutically acceptable salt of any of the foregoing, wherein R[2] is hydrogen, $C_1$-$C_6$ alkyl, —CN, halogen, —OR[2a].

7. The compound of claim 6, or a tautomer or stereoisomer thereof, or a pharmaceutically acceptable salt of any of the foregoing, wherein R[2] is hydrogen.

8. The compound of claim 6, or a tautomer or stereoisomer thereof, or a pharmaceutically acceptable salt of any of the foregoing, wherein R[2] is $C_1$-$C_6$ alkyl.

9. The compound of claim 6, or a tautomer or stereoisomer thereof, or a pharmaceutically acceptable salt of any of the foregoing, wherein R[2] is CN or halogen.

10. The compound of claim 6, or a tautomer or stereoisomer thereof, or a pharmaceutically acceptable salt of any of the foregoing, wherein R[2] is —OR[2a] and R[2a] is $C_1$-$C_6$ alkyl.

11. The compound of claim 1, or a tautomer or stereoisomer thereof, or a pharmaceutically acceptable salt of any of the foregoing, wherein A is 4-hydroxyphenyl optionally further substituted by R[3] or 4-hydroxy-2-pyridyl optionally further substituted by R[4].

12. The compound of claim 11, or a tautomer or stereoisomer thereof, or a pharmaceutically acceptable salt of any of the foregoing, wherein A is 4-hydroxyphenyl optionally further substituted by R[3].

13. The compound of claim 11, or a tautomer or stereoisomer thereof, or a pharmaceutically acceptable salt of any of the foregoing, wherein A is 4-hydroxy-2-pyridyl optionally further substituted by R[4].

14. The compound of claim 1, or a tautomer or stereoisomer thereof, or a pharmaceutically acceptable salt of any of the foregoing, wherein A is a 10-membered bicyclic heteroaryl optionally substituted by R[4].

15. The compound of claim 1, or a tautomer or stereoisomer thereof, or a pharmaceutically acceptable salt of any of the foregoing, wherein the A is selected from the group consisting of quinolinyl, isoquinolinyl, quinoxalinyl, quinazolinyl, cinnolinyl, and naphthyridinyl, each of which is optionally substituted by R[4].

16. The compound of claim 15, or a tautomer or stereoisomer thereof, or a pharmaceutically acceptable salt of any of the foregoing, wherein R[4] is R[3] and each R[3] is independently selected from the group consisting of halogen, —CN, —OR[5], —SR[5], —NR[6]R[7], —NO$_2$, —C(O)R[5], —C(O)OR[5], —C(O)NR[6]R[7], —C(O)NR[5]S(O)$_2$R[6], —OC(O)R[5], —OC(O)NR[6]R[7], —NR[5]C(O)R[6], —NR[5]C(O)NR[6]R[7], —S(O)R[5], —S(O)$_2$R[5], $C_3$-$C_6$ cycloalkyl and $C_1$-$C_6$ alkyl optionally substituted by halogen.

17. The compound of claim 16, or a tautomer or stereoisomer thereof, or a pharmaceutically acceptable salt of any of the foregoing, wherein each R[3] is independently selected from the group consisting of halogen, —OR[5] and $C_1$-$C_6$ alkyl optionally substituted by halogen.

18. The compound of claim 1, or a tautomer or stereoisomer thereof, or a pharmaceutically acceptable salt of any of the foregoing, wherein A is selected from the group consisting of:

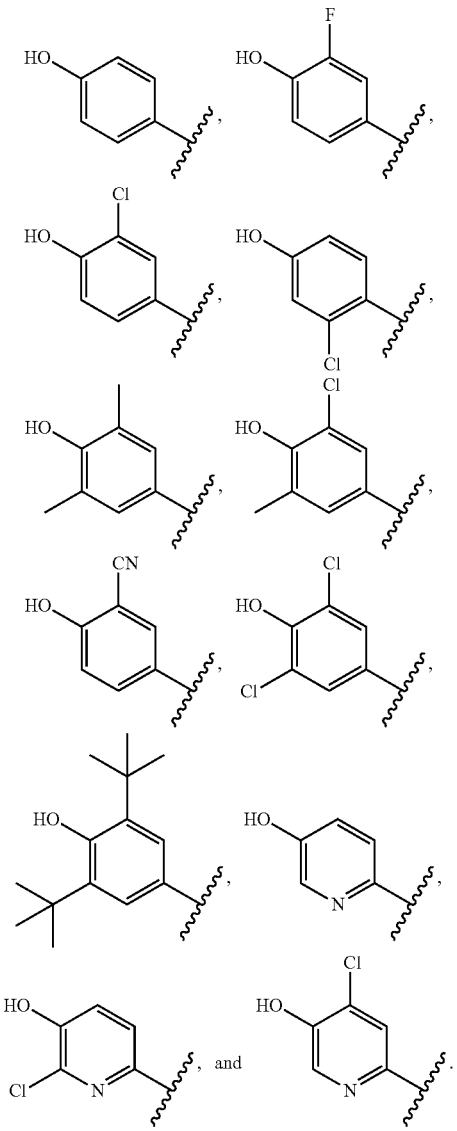

19. The compound of claim 1, or a tautomer or stereoisomer thereof, or a pharmaceutically acceptable salt of any of the foregoing, wherein A is selected from the group consisting of:

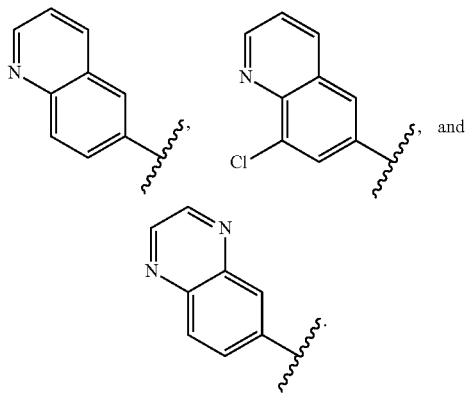

20. The compound of claim 1, or a tautomer or stereoisomer thereof, or a pharmaceutically acceptable salt of any of the foregoing, wherein B is a phenyl optionally substituted by R³.

21. The compound of claim 1, or a tautomer or stereoisomer thereof, or a pharmaceutically acceptable salt of any of the foregoing, wherein B is a 5- to 6-membered heteroaryl optionally substituted by R⁴.

22. The compound of claim 21, or a tautomer or stereoisomer thereof, or a pharmaceutically acceptable salt of any of the foregoing, wherein the B is a 5-membered heteroaryl selected from the group consisting of furanyl, oxazolyl, thiophenyl, pyrazolyl, isoxazolyl, 1,3,4-oxadiazolyl, imidazolyl, thiazolyl, isothiazolyl, triazolyl, 1,3,4-thiadiazolyl and tetrazolyl, which is optionally substituted by R⁴.

23. The compound of claim 21, or a tautomer or stereoisomer thereof, or a pharmaceutically acceptable salt of any of the foregoing, wherein the B is a 6-membered heteroaryl selected from the group consisting of pyridyl and pyrimidinyl, which is optionally substituted by R⁴.

24. The compound of claim 21, or a tautomer or stereoisomer thereof, or a pharmaceutically acceptable salt of any of the foregoing, wherein R⁴ is R³ and R³ is selected from the group consisting of halogen, —OR⁵, —NR⁶R⁷, —C(O)R⁵, $C_3$-$C_6$ cycloalkyl and $C_1$-$C_6$ alkyl optionally substituted by halogen.

25. The compound of claim 24, or a tautomer or stereoisomer thereof, or a pharmaceutically acceptable salt of any of the foregoing, wherein R³ is selected from the group consisting of halogen and $C_1$-$C_6$ alkyl optionally substituted by halogen.

26. The compound of claim 1, or a tautomer or stereoisomer thereof, or a pharmaceutically acceptable salt of any of the foregoing, wherein B is selected from the group consisting of:

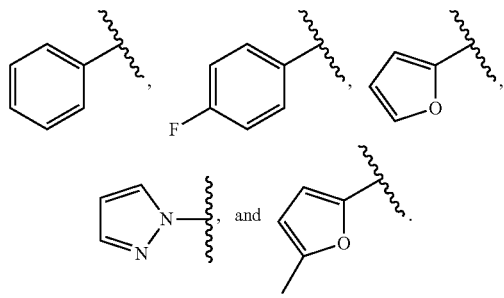

27. The compound of claim 1, wherein the compound is of the formula (II):

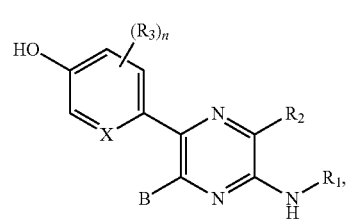

or a tautomer or stereoisomer thereof, or a pharmaceutically acceptable salt of any of the foregoing, wherein R¹, R² and B are as defined for formula (I);
X is N or CH;
each R³ is independently halogen, —CN, —OR⁵, —SR⁵, —NR⁶R⁷, —NO₂, —C(O)R⁵, —C(O)OR⁵, —C(O)NR⁶R⁷, —C(O)NR⁵S(O)₂R⁶, —OC(O)R⁵, —OC(O)NR⁶R⁷, —NR⁵C(O)R⁶, —NR⁵C(O)NR⁶R⁷, —S(O)R⁵, —S(O)₂R⁵, $C_3$-$C_6$ cycloalkyl, or $C_1$-$C_6$ alkyl optionally substituted by halogen;
each R⁵ is independently hydrogen, $C_1$-$C_6$ alkyl, or $C_3$-$C_6$ cycloalkyl;
R⁶ and R⁷ are each independently hydrogen, $C_1$-$C_6$ alkyl, or $C_3$-$C_6$ cycloalkyl;
or R⁶ and R⁷ are taken together with the atom to which they attached to form a 3-6 membered heterocyclyl; and
n is 0, 1, 2 or 3.

28. The compound of claim 27, or a tautomer or stereoisomer thereof, or a pharmaceutically acceptable salt of any of the foregoing, wherein R³ is selected from the group consisting of halogen, —OR⁵ and $C_1$-$C_6$ alkyl optionally substituted by halogen.

29. The compound of claim 1, wherein the compound is of the formula (IVc):

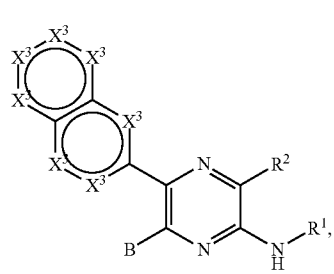

or a tautomer or stereoisomer thereof, or a pharmaceutically acceptable salt of any of the foregoing, wherein R¹, R² and B are as defined for formula (I);
each X³ is independently CR⁴, CH or N;
each R⁴ is independently halogen, —CN, —OR⁵, —SR⁵, —NR⁶R⁷, —NO₂, —C(O)R⁵, —C(O)OR⁵, —C(O)NR⁶R⁷, —C(O)NR⁵S(O)₂R⁶, —OC(O)R⁵, —OC(O)NR⁶R⁷, —NR⁵C(O)R⁶, —NR⁵C(O)NR⁶R⁷, —S(O)R⁵, —S(O)₂R⁵, $C_3$-$C_6$ cycloalkyl, or $C_1$-$C_6$ alkyl optionally substituted by halogen;
where each R⁵ is independently hydrogen, $C_1$-$C_6$ alkyl, or $C_3$-$C_6$ cycloalkyl; and
R⁶ and R⁷ are each independently hydrogen, $C_1$-$C_6$ alkyl, or $C_3$-$C_6$ cycloalkyl;

or $R^6$ and $R^7$ are taken together with the atom to which they attached to form a 3-6 membered heterocyclyl.

30. The compound of claim 29, or a tautomer or stereoisomer thereof, or a pharmaceutically acceptable salt of any of the foregoing, wherein $R^4$ is selected from the group consisting of halogen, —$OR^5$ and $C_1$-$C_6$ alkyl optionally substituted by halogen.

31. The compound of claim 29, or a tautomer or stereoisomer thereof, or a pharmaceutically acceptable salt of any of the foregoing, wherein one of $X^3$ is N, and the remaining $X^3$ are each $CR^4$.

32. The compound of claim 29, or a tautomer or stereoisomer thereof, or a pharmaceutically acceptable salt of any of the foregoing, wherein two of $X^3$ are N, and the remaining $X^3$ are each $CR^4$.

33. A compound selected from the group consisting of

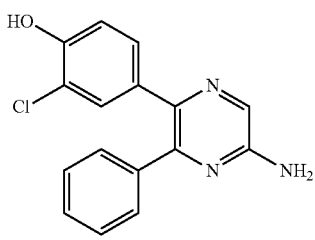

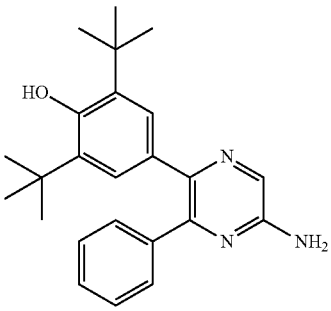

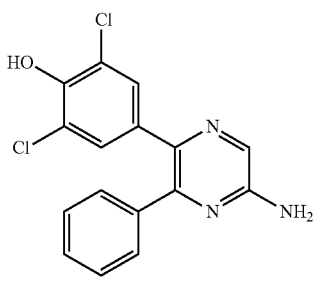

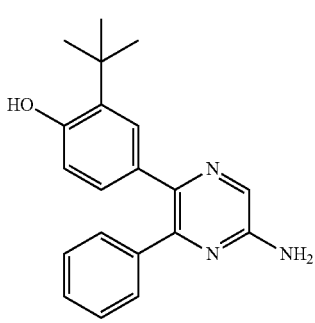

-continued

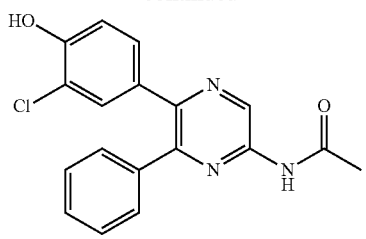

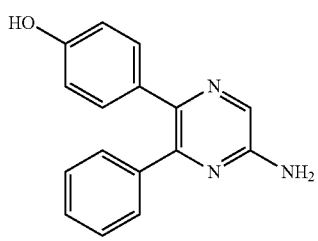

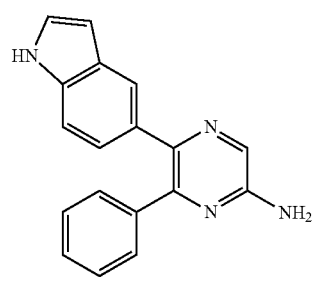

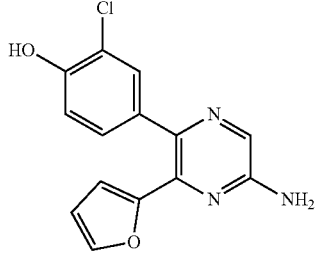

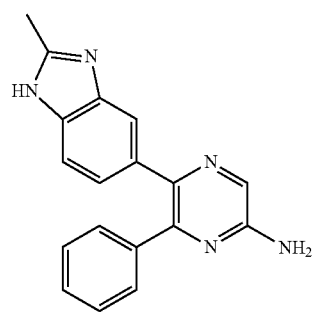

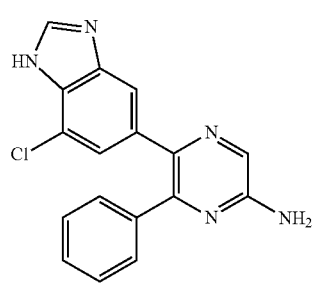

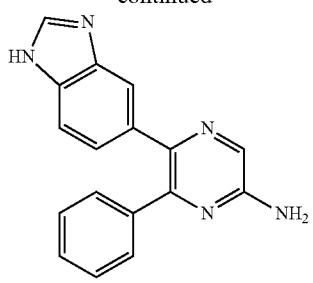
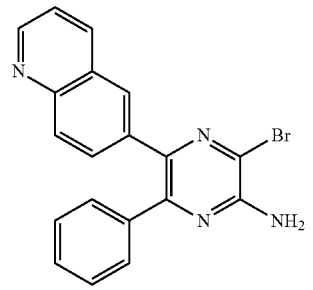
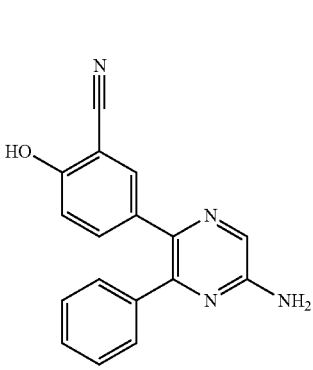
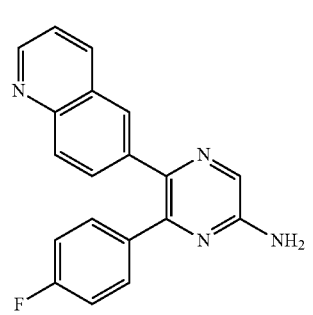
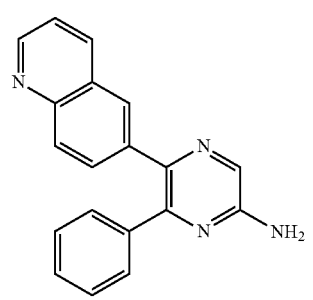
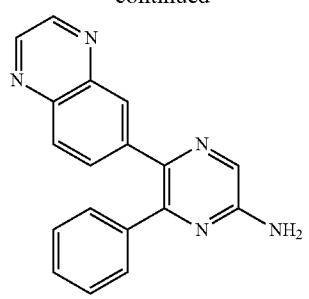
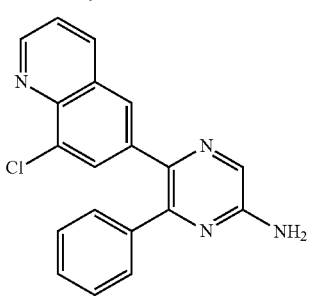
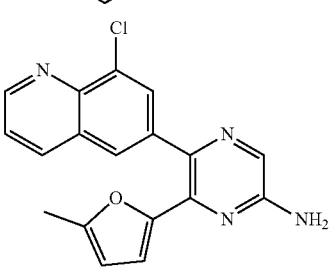
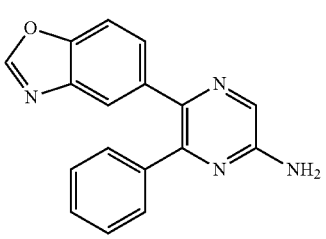
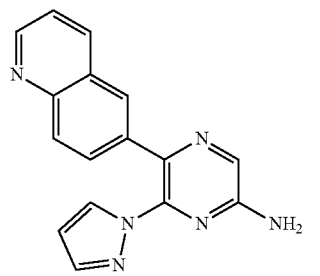
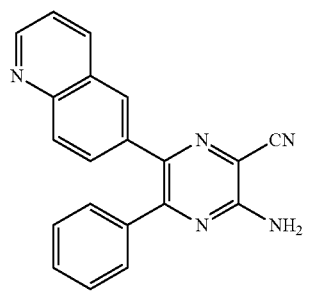

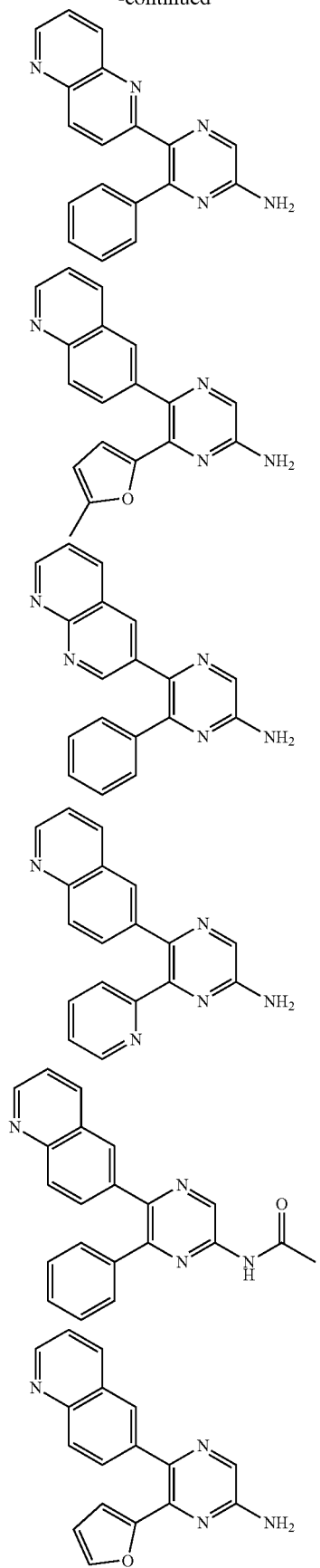
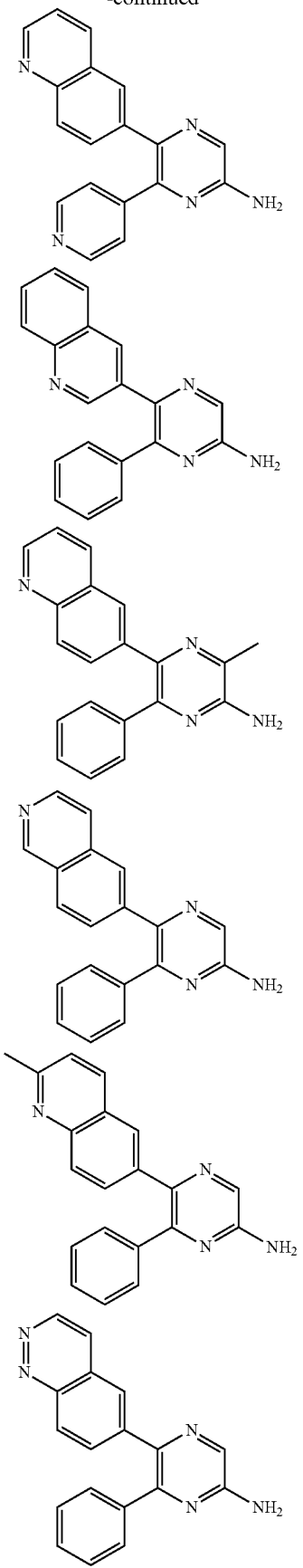

-continued
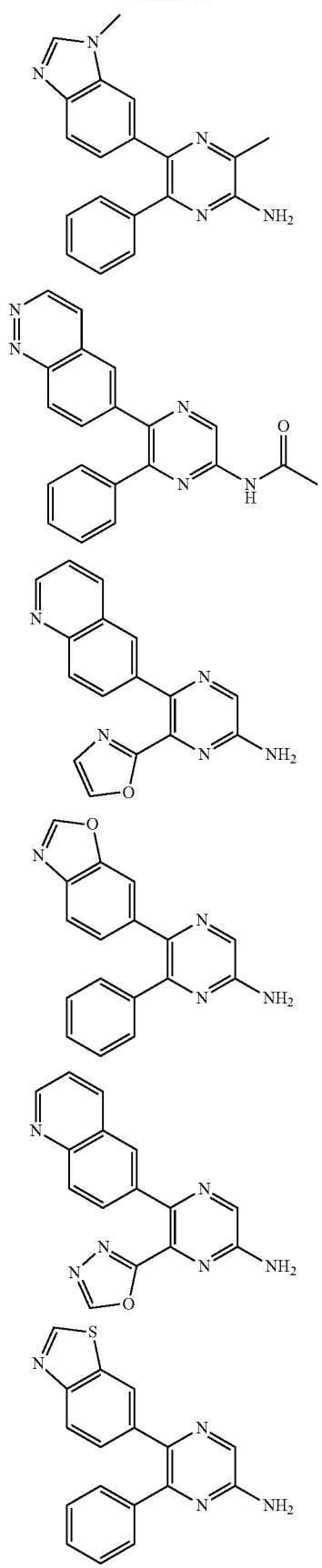
-continued
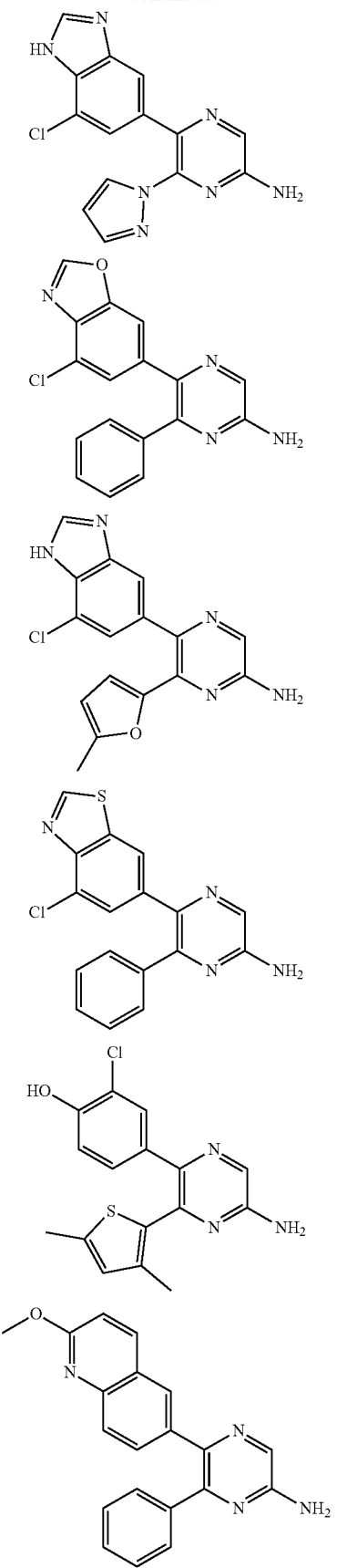

1063
-continued
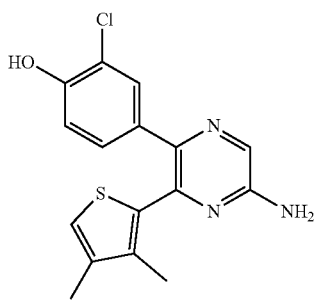
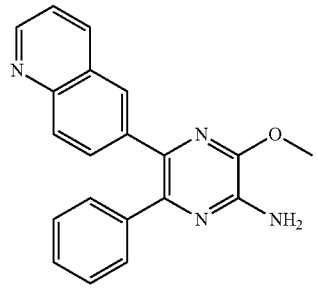
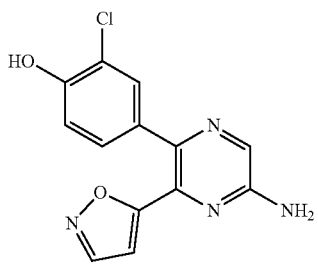
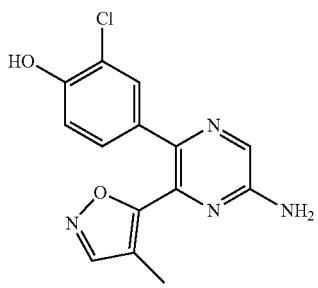
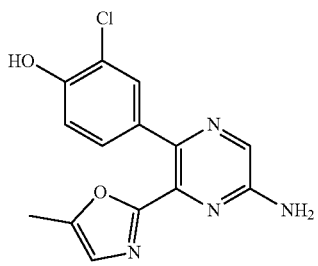
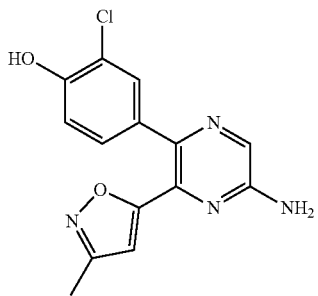
1064
-continued
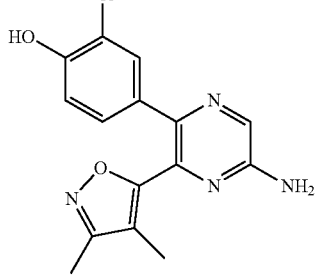
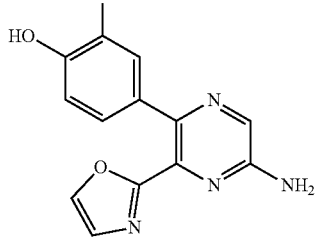
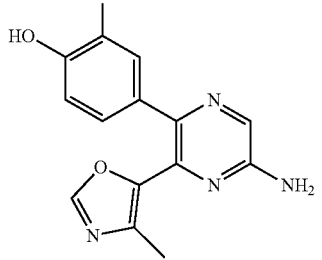

1065
-continued
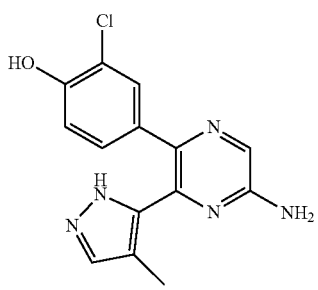
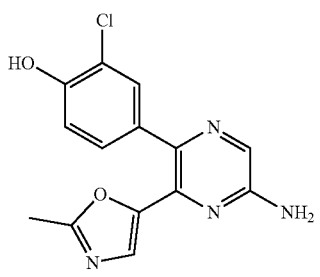
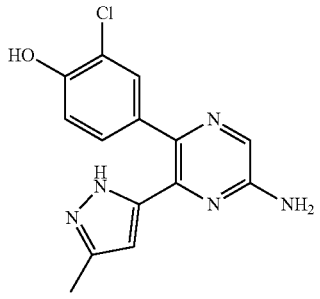
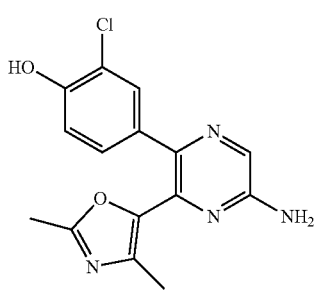
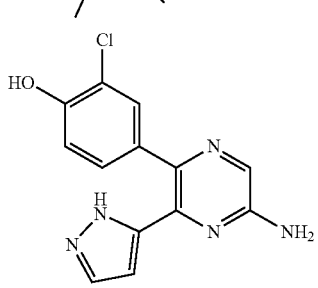
1066
-continued
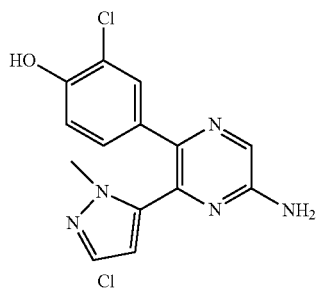
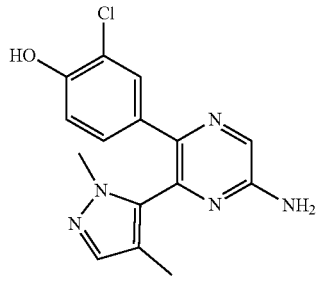
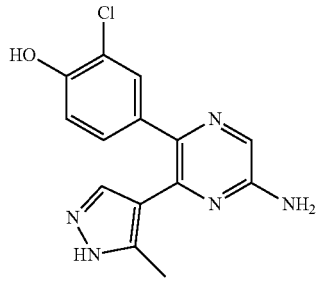
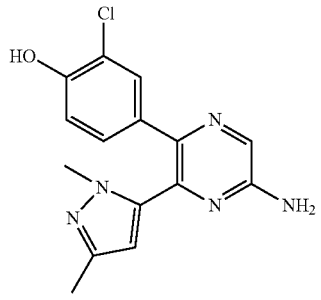
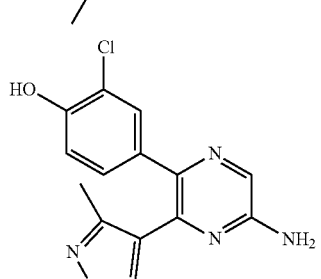
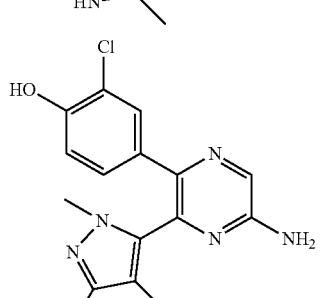

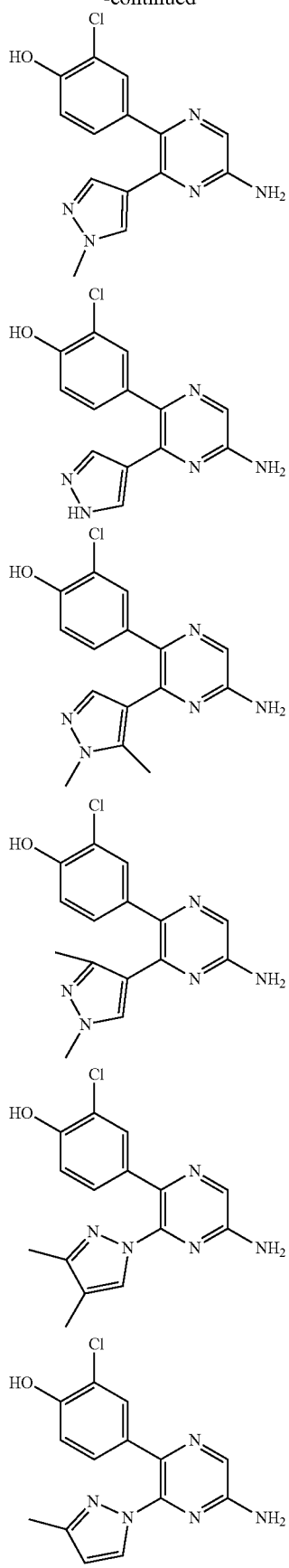
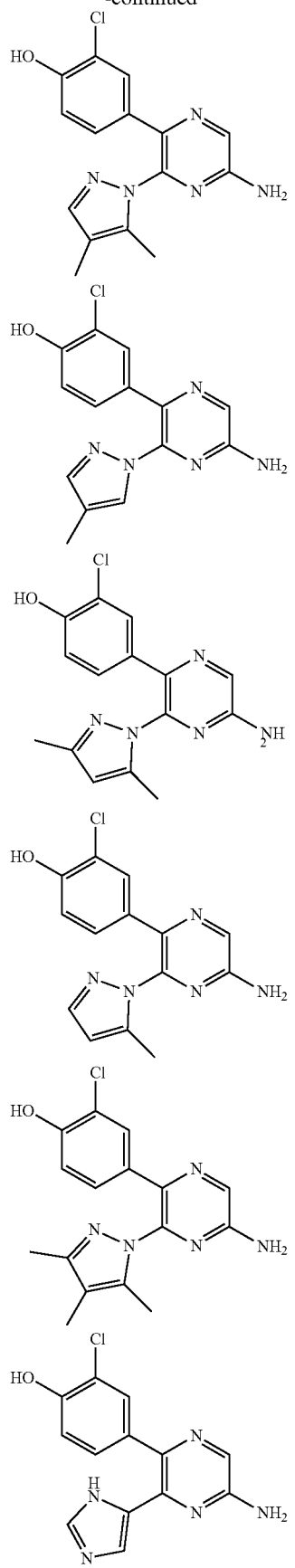

1069
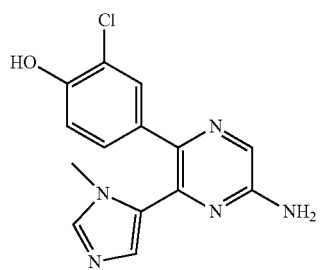
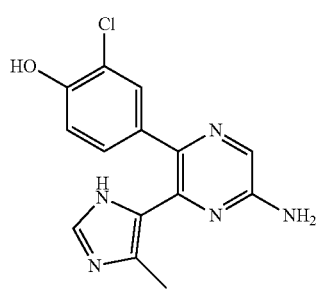
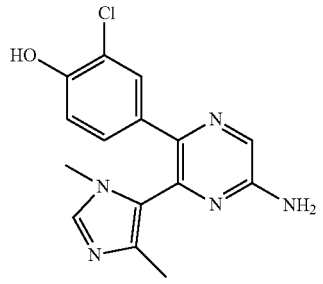
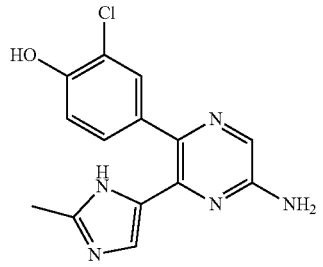
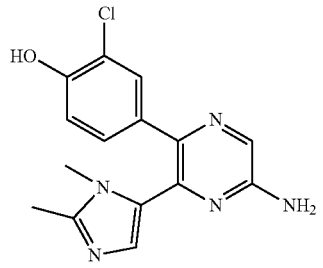
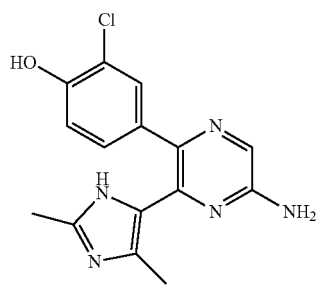
1070
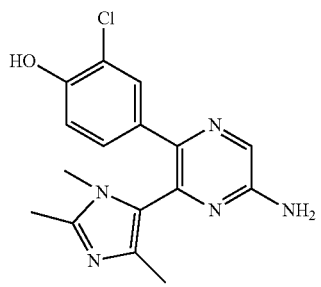
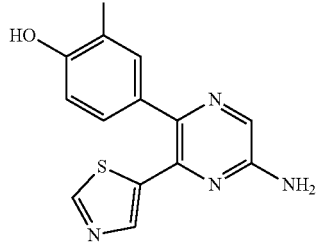
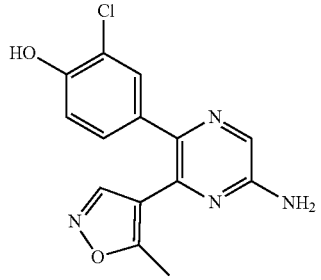
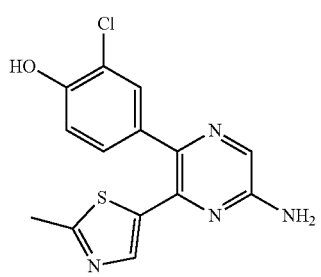
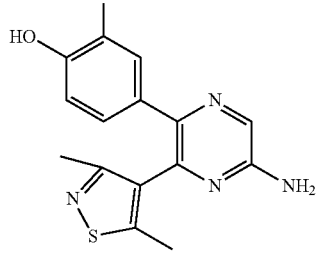
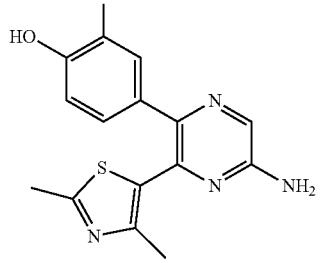

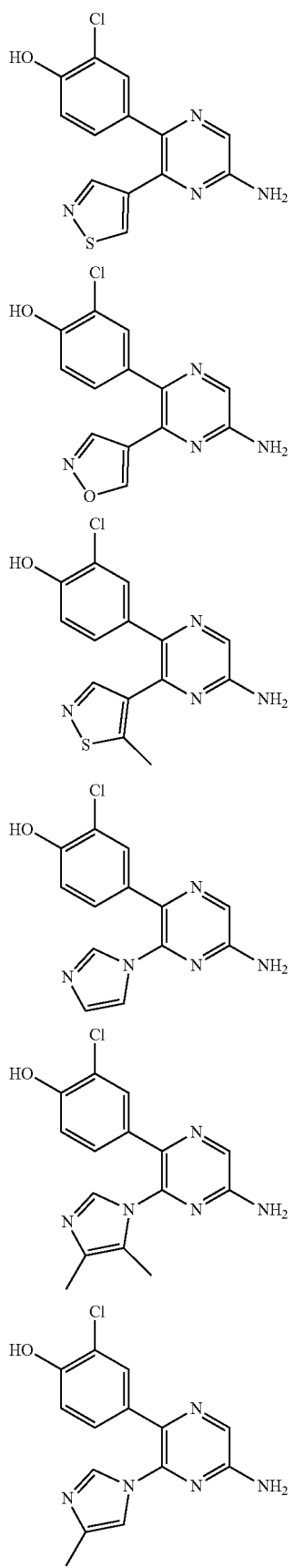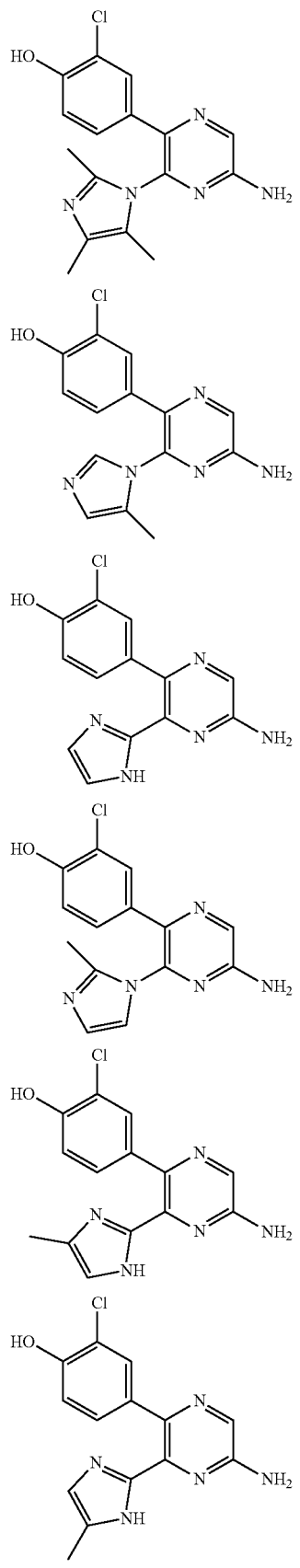

-continued
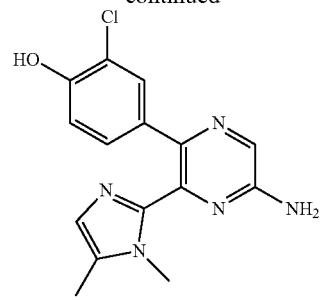
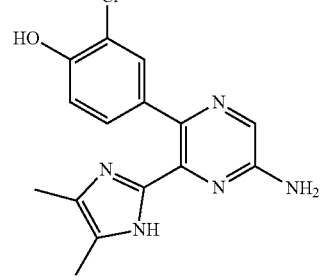
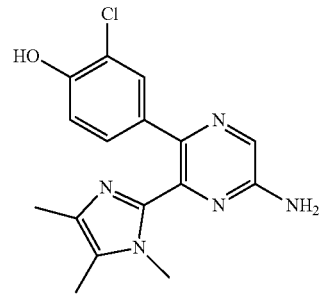
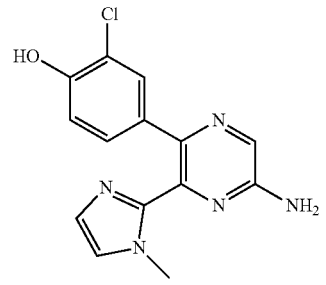
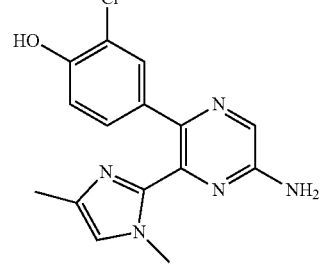
-continued
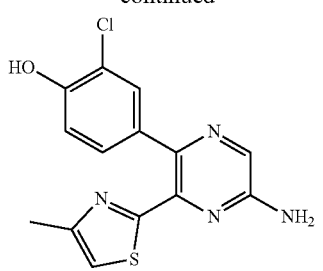
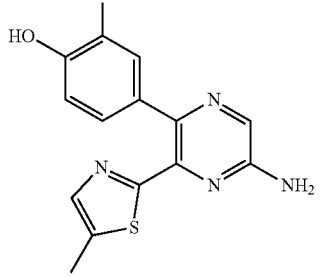
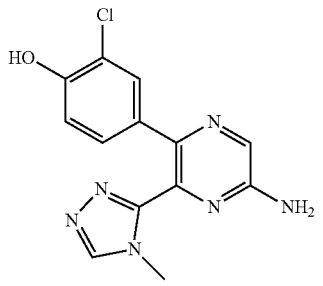
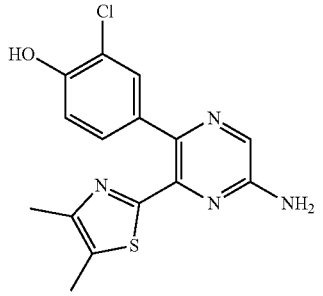
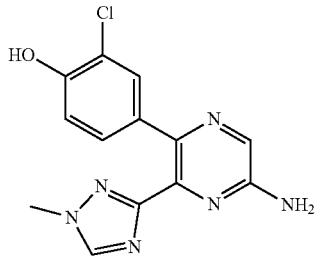
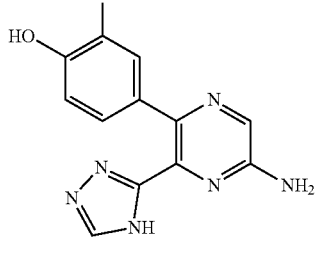

1075
-continued
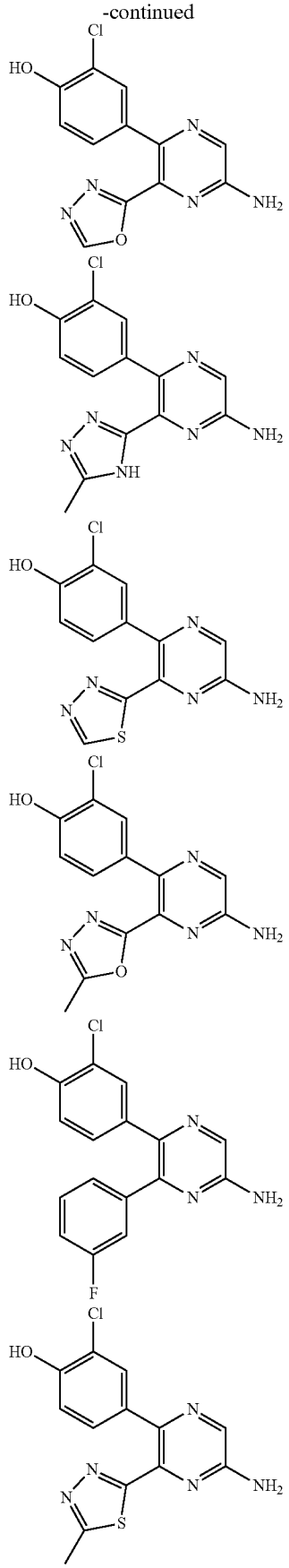
1076
-continued
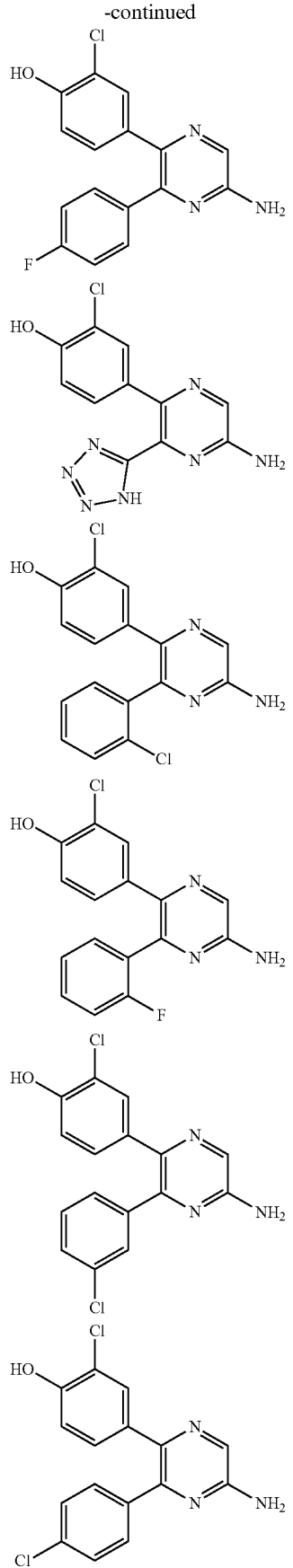

1077
-continued
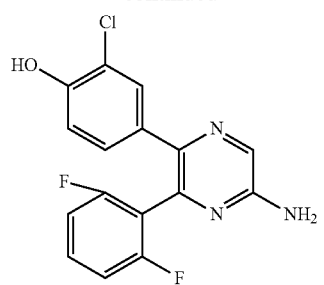
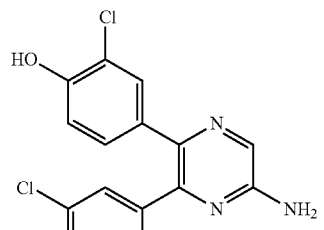
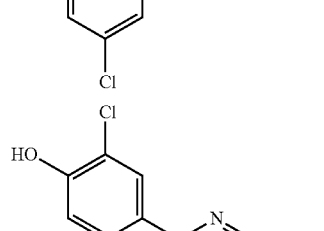
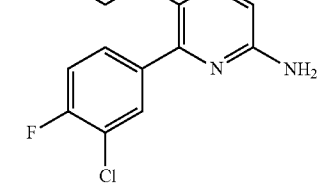
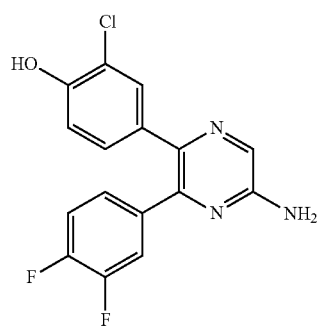
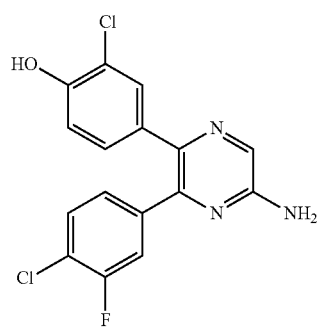
1078
-continued
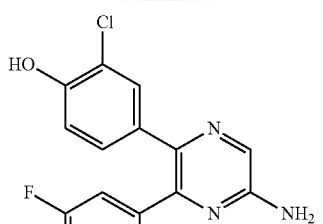
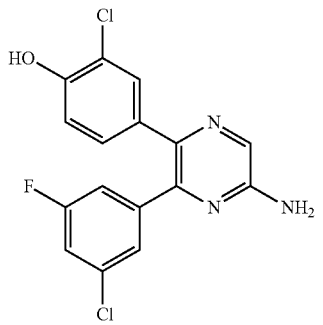
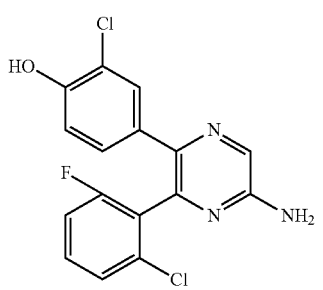
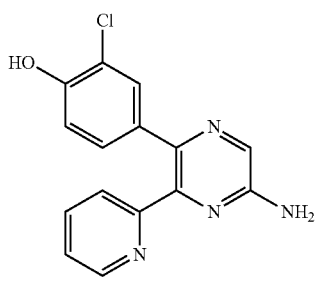
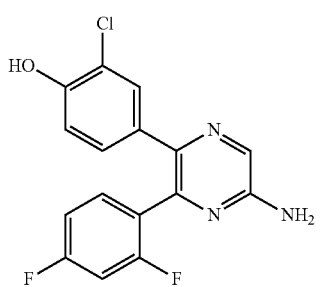

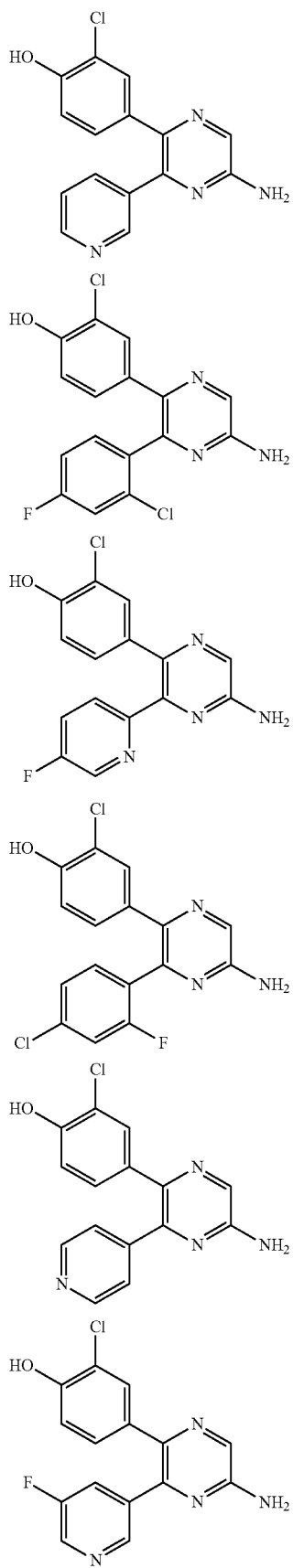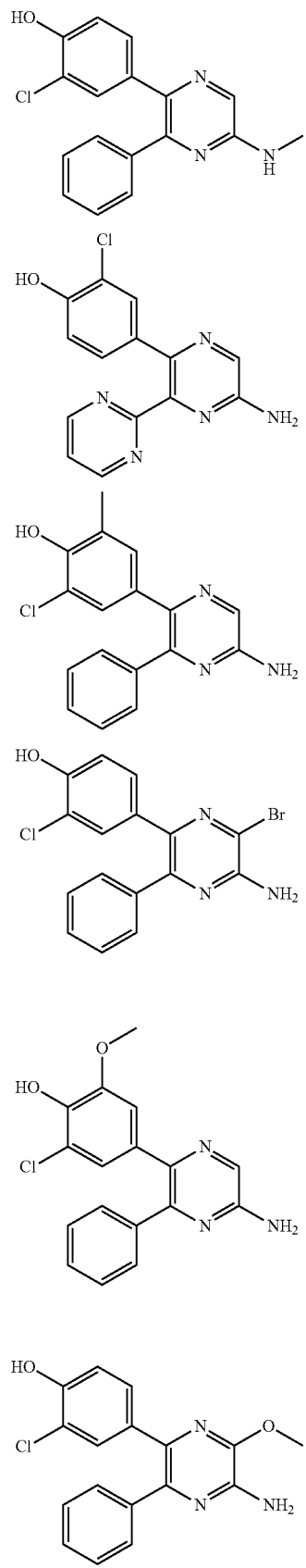

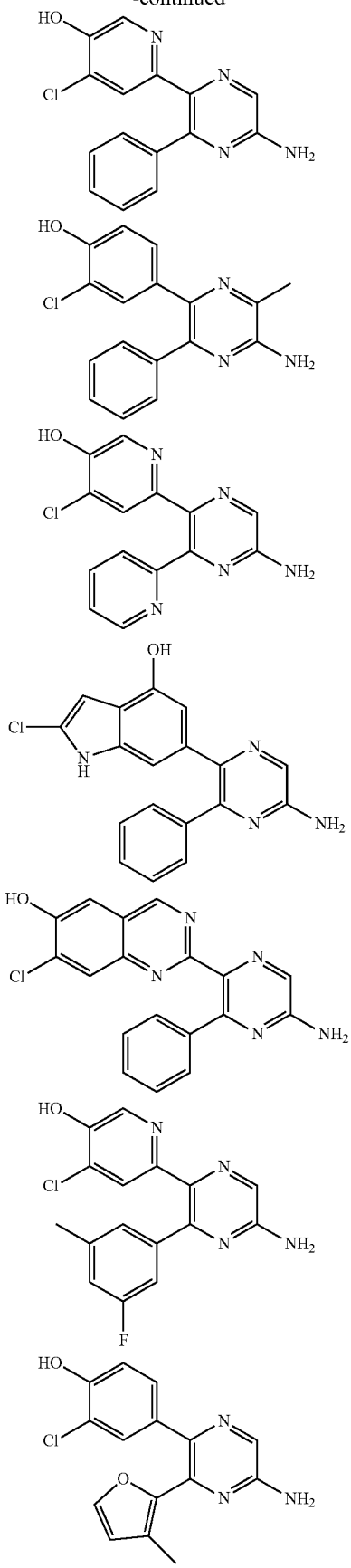
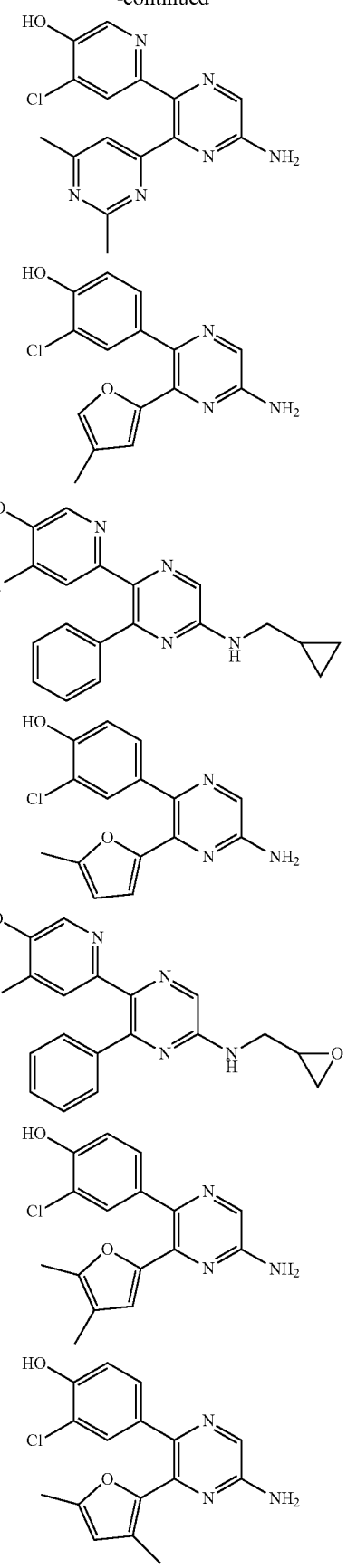

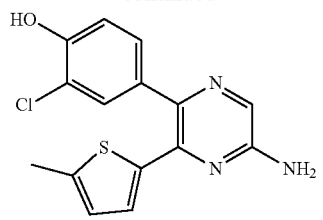
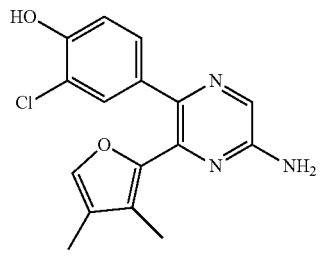
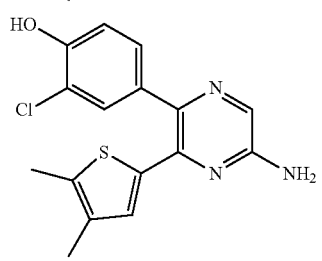
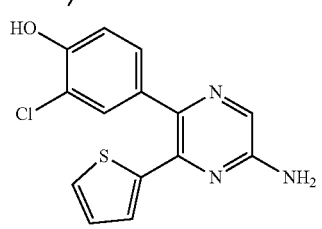
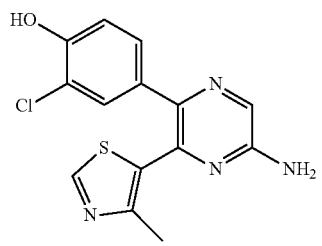
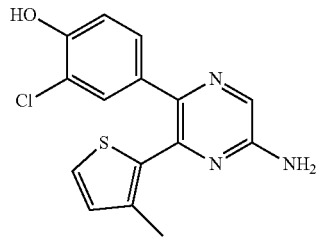
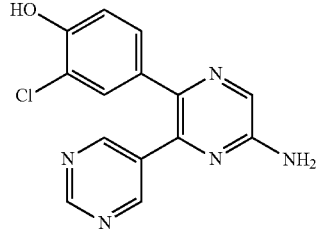
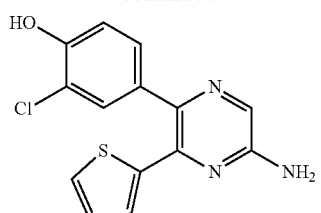
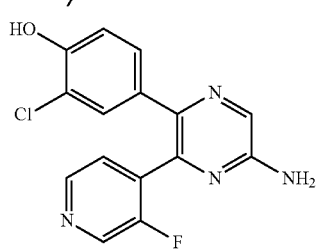
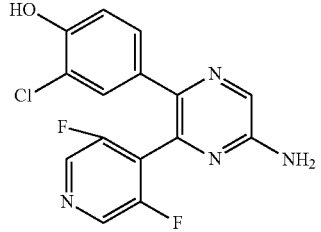
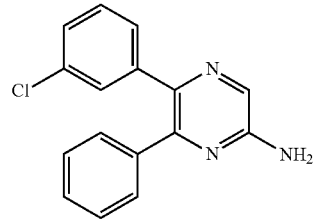
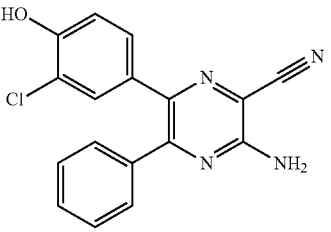
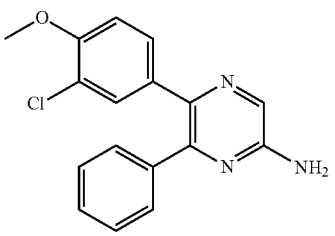
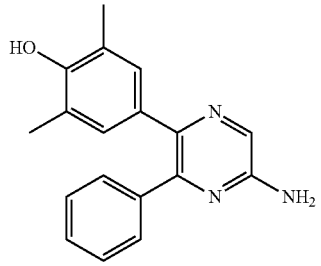

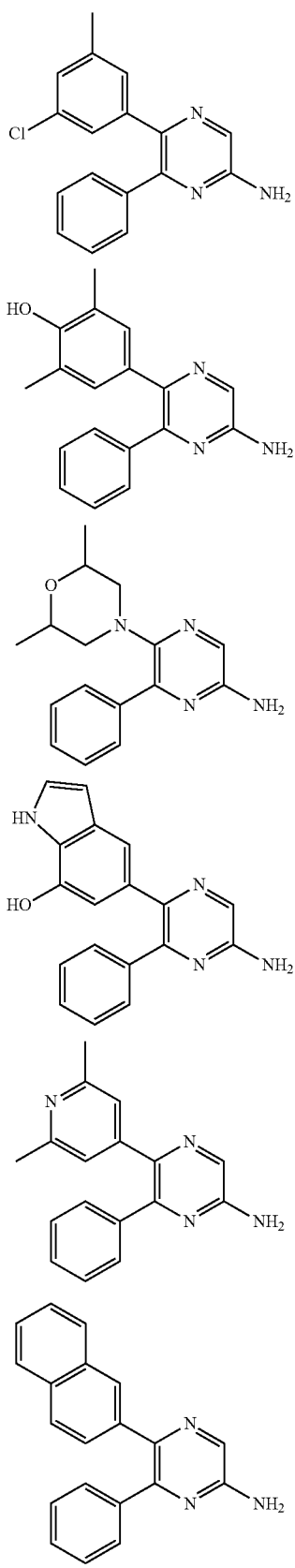
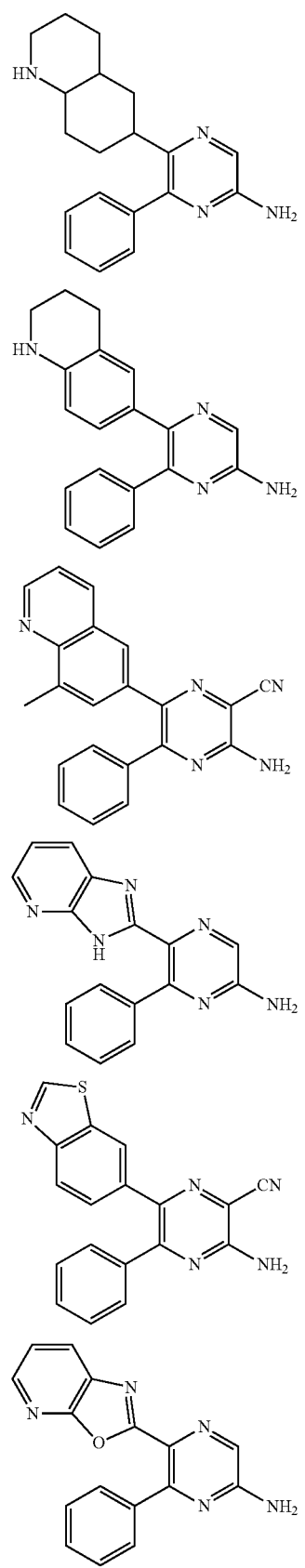

1087
-continued
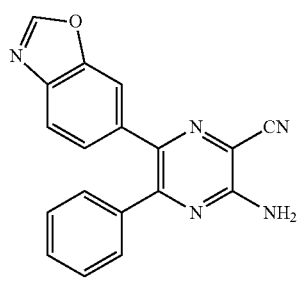
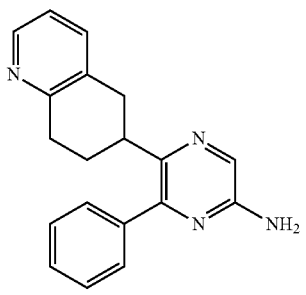
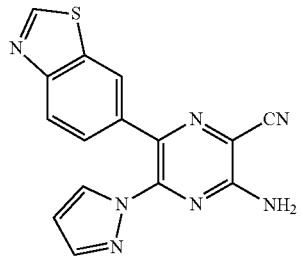
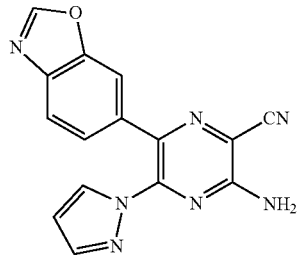
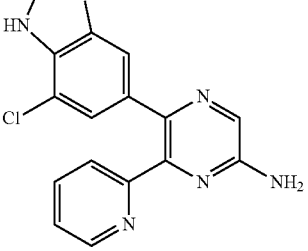
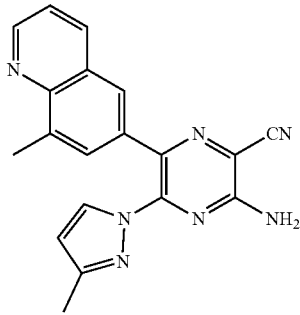
1088
-continued
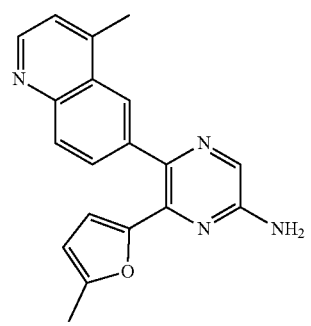
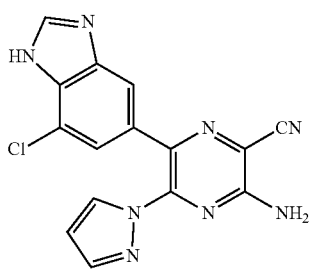
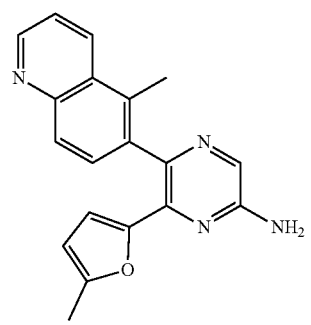
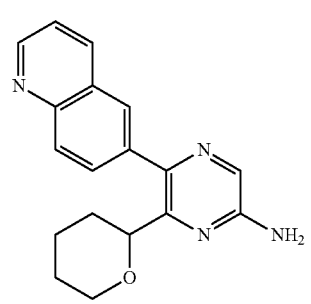
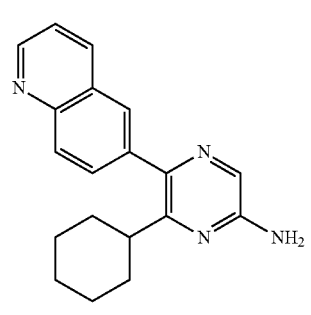

1089
-continued
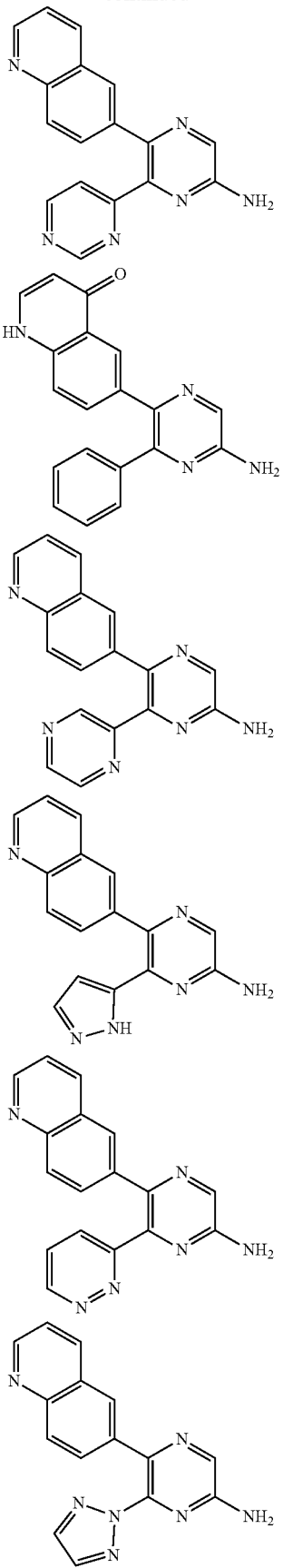
1090
-continued
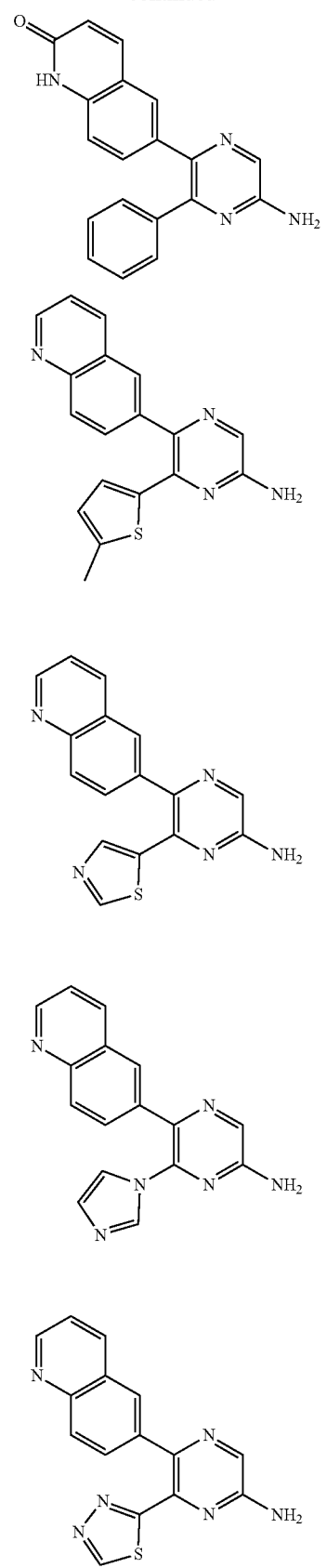

1091
-continued
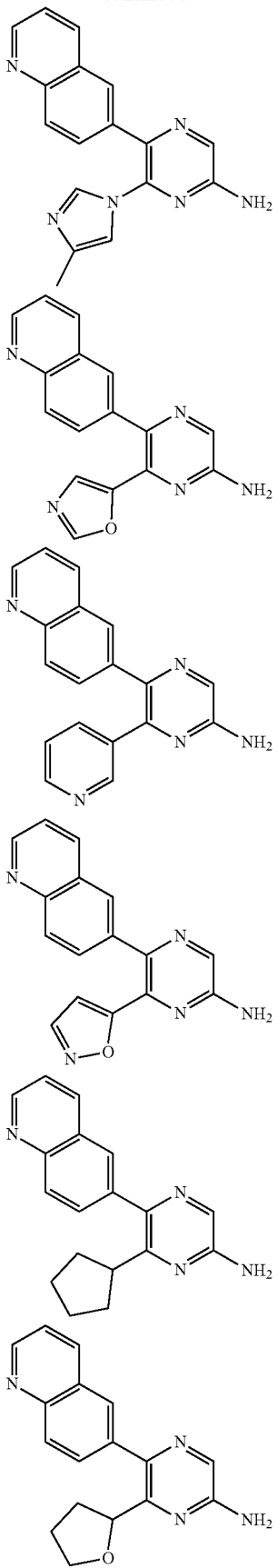
1092
-continued
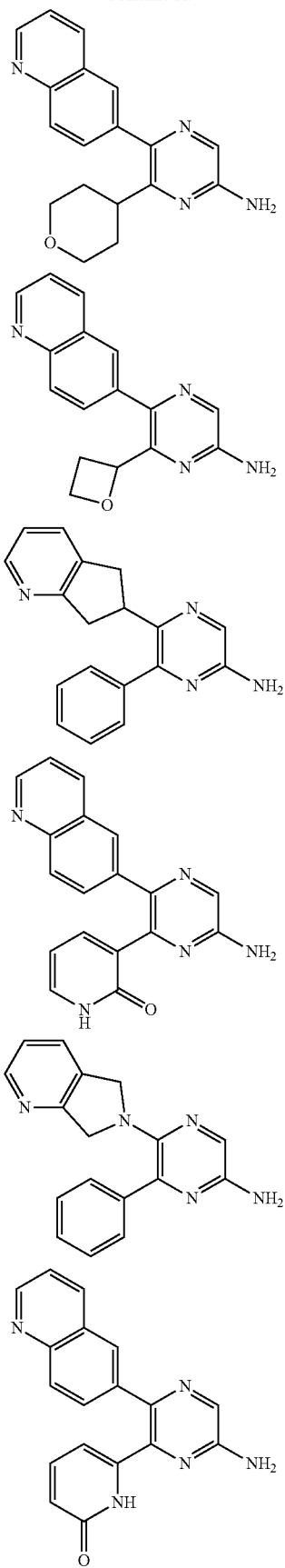

1093
-continued
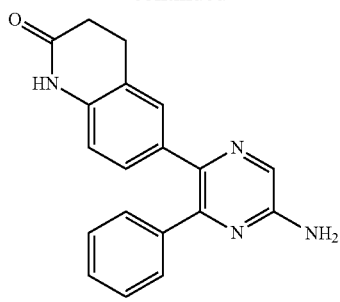
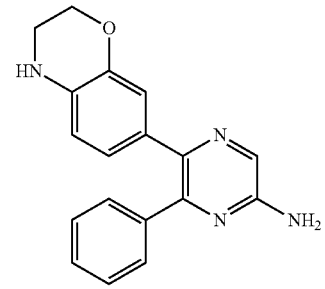
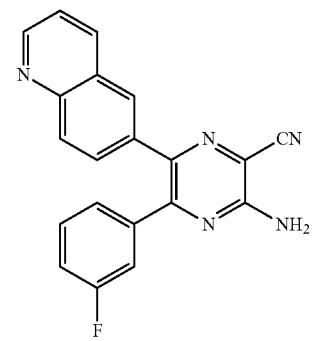
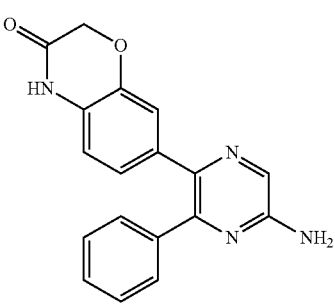
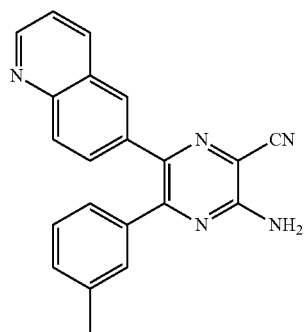
1094
-continued
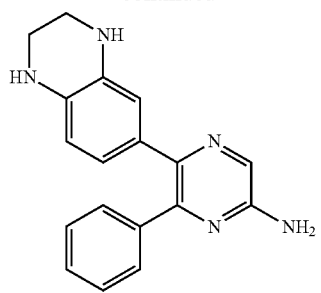
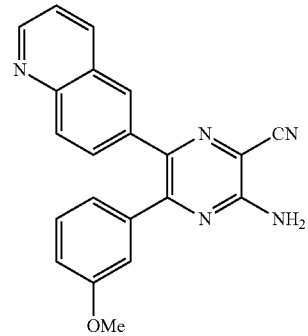
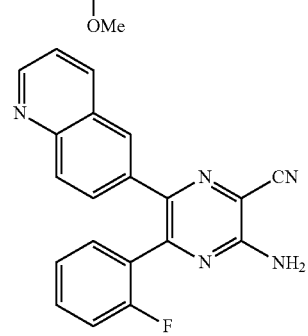
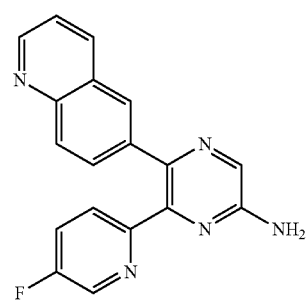
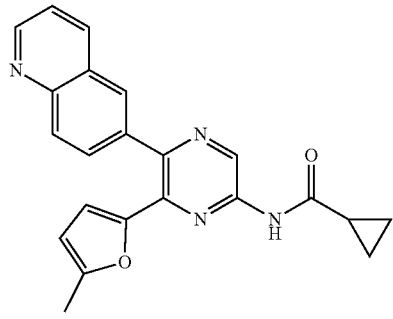

-continued
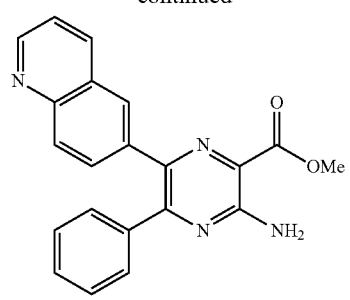
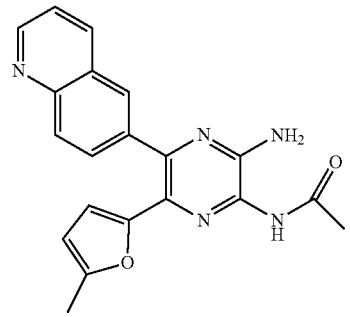
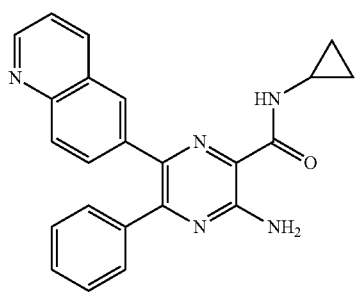
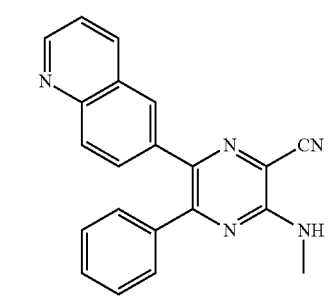
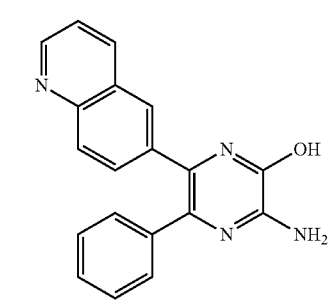
-continued
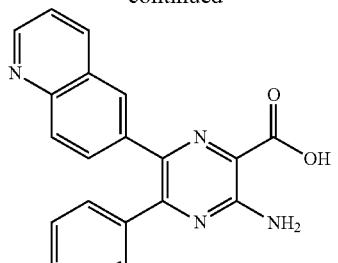
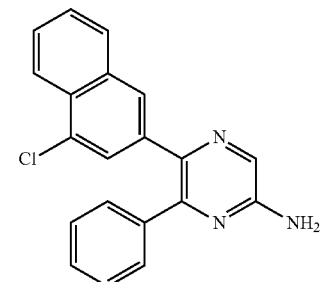
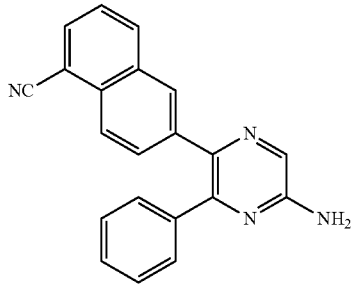
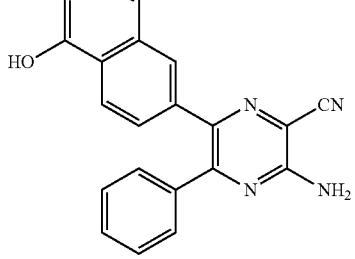
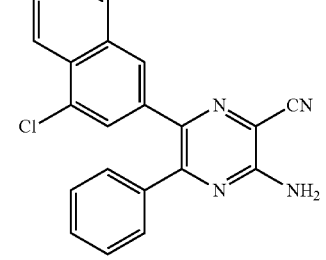
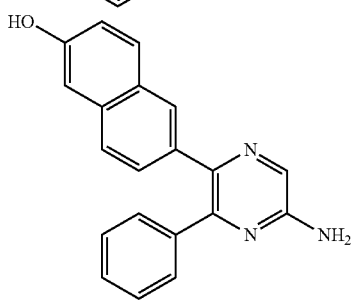

1097
-continued
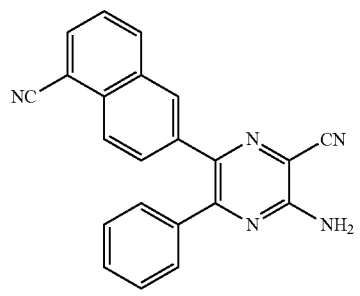
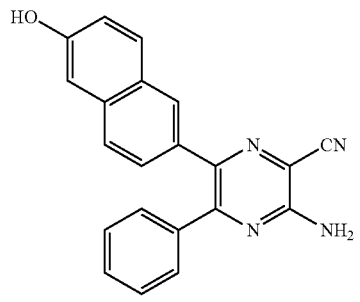
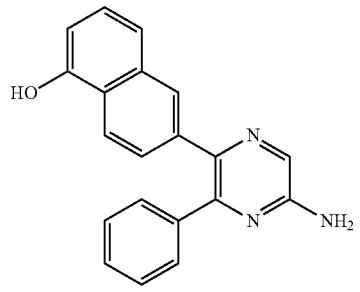
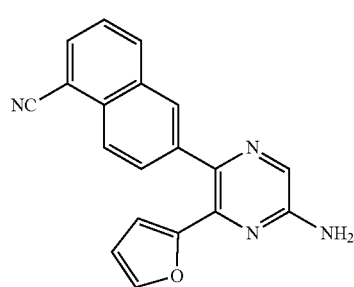
1098
-continued
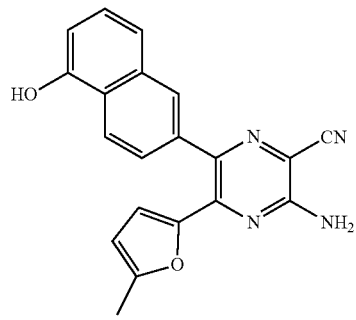
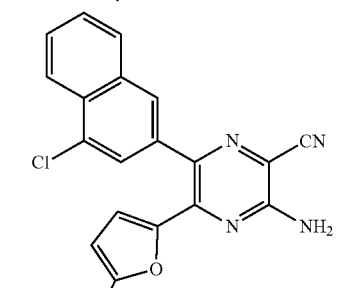
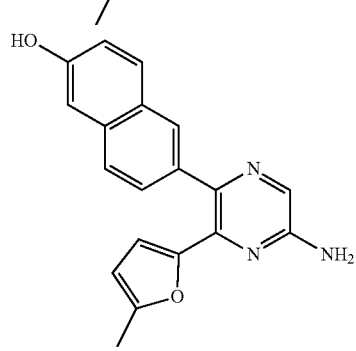
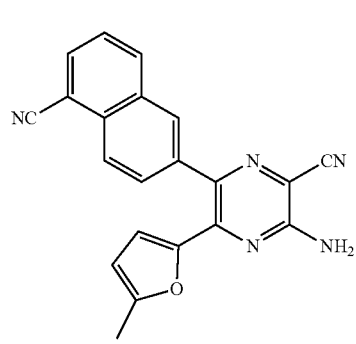
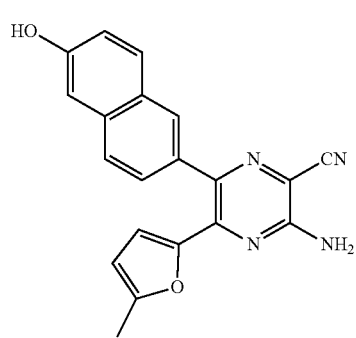

1099
-continued
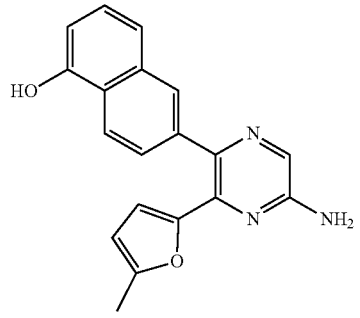
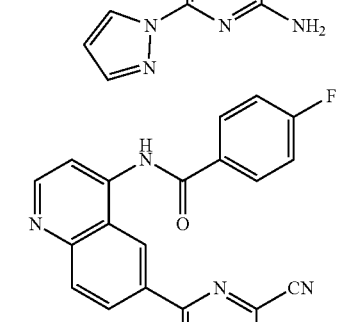

1100
-continued
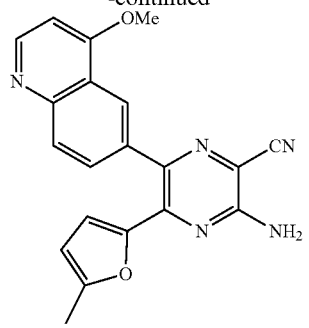
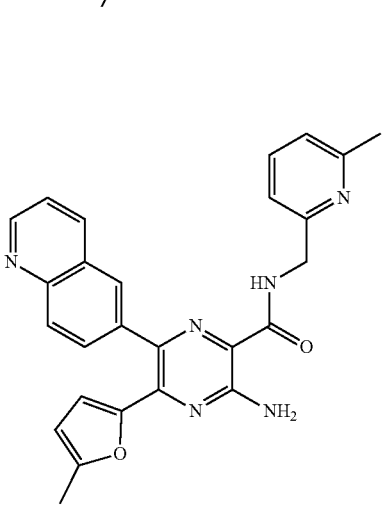
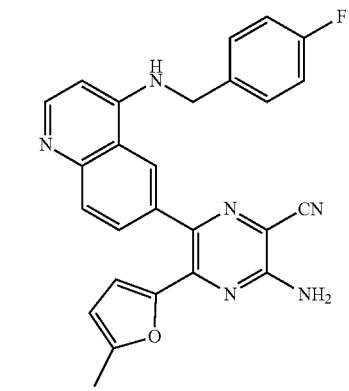
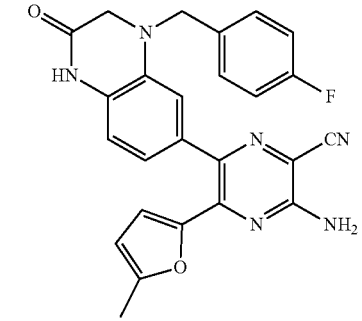

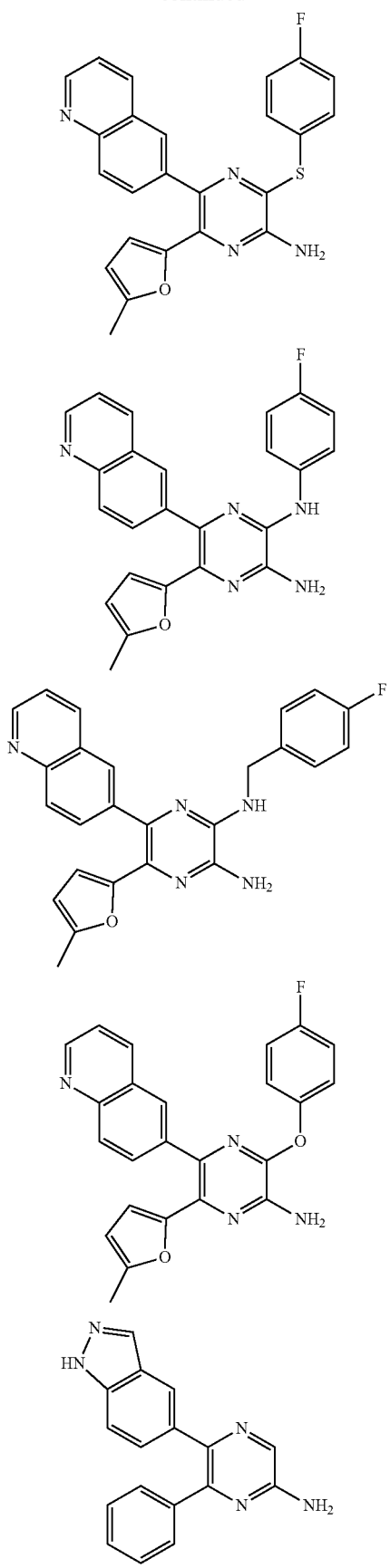
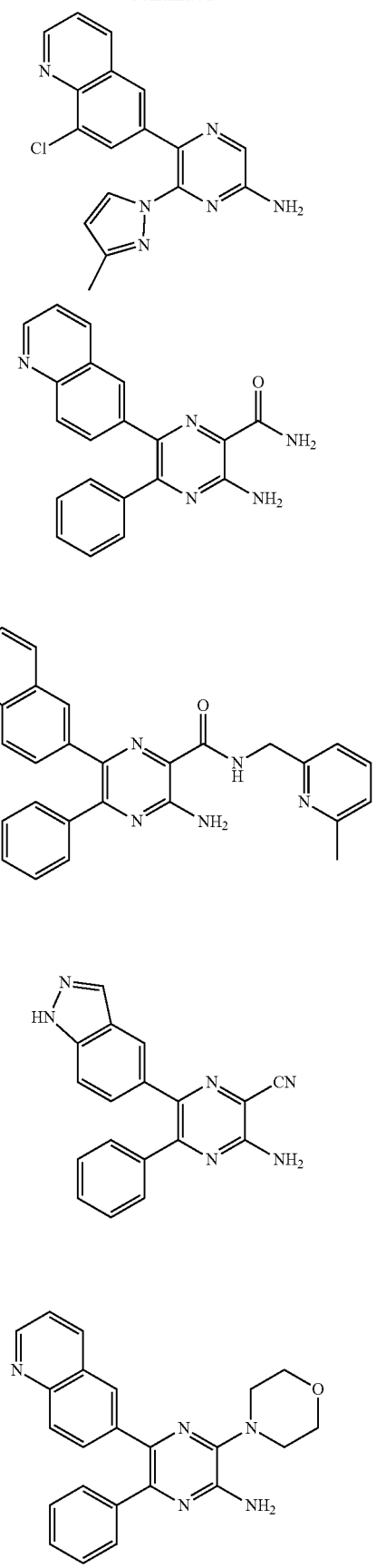

1103
-continued
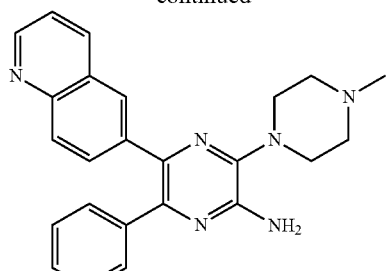
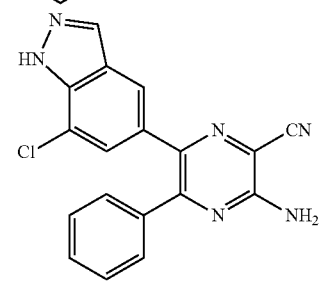
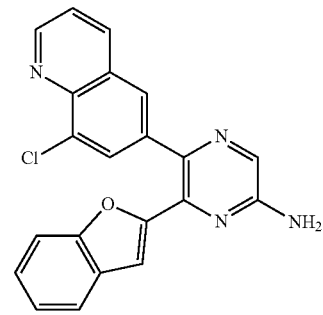
1104
-continued
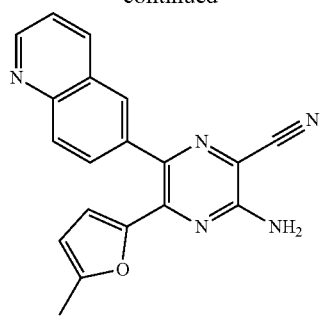
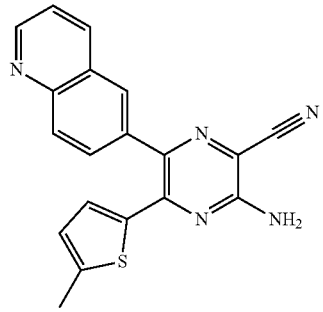
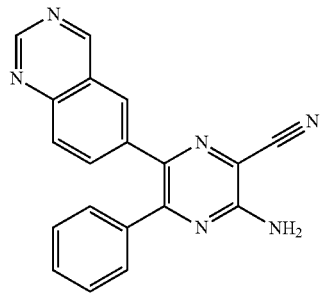
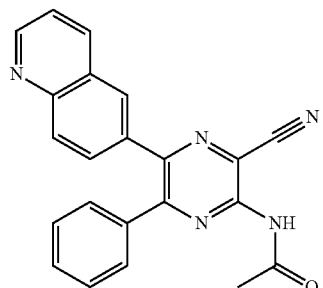
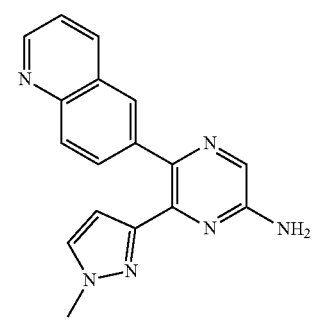

1105
-continued
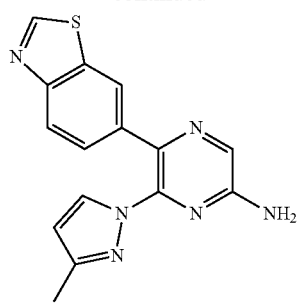
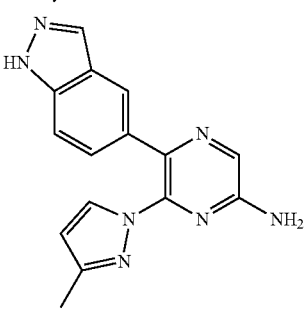
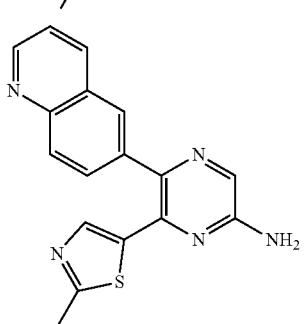

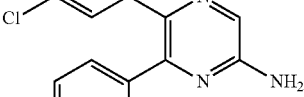

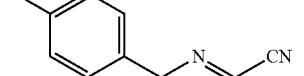
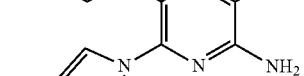
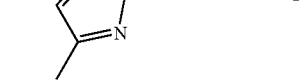
1106
-continued
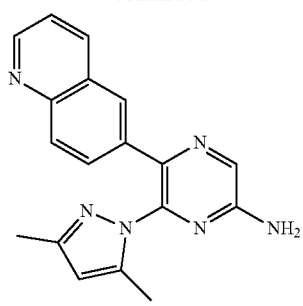
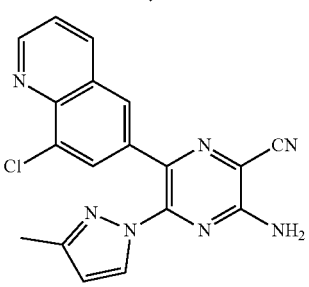
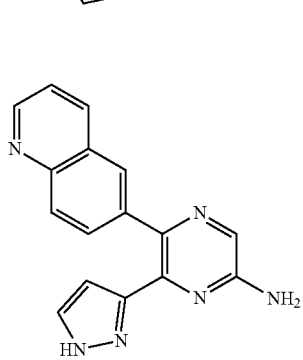
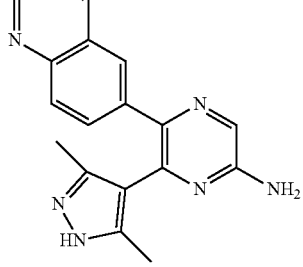
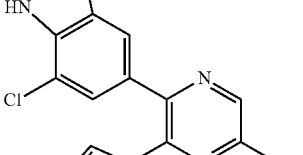
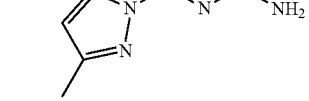

1107
-continued
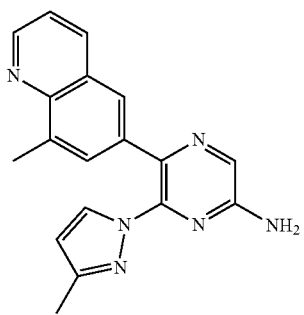
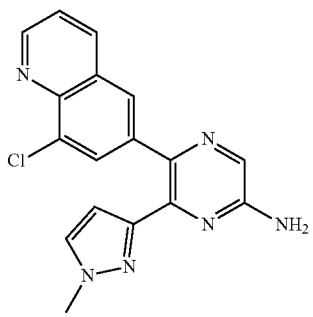
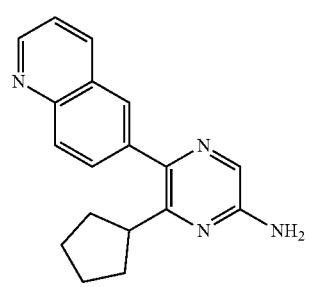
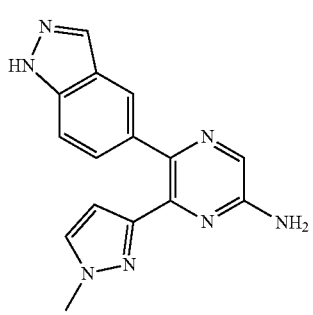
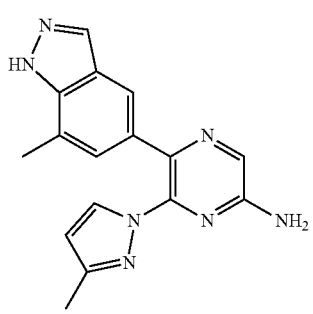 [SMILES: Cc1ccn(-c2nc(N)cnc2-c2cc(Cl)c3[nH]ncc3c2)n1]
1108
-continued
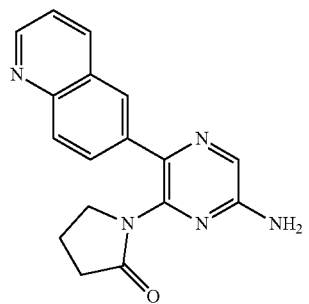
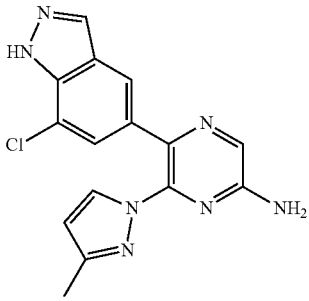
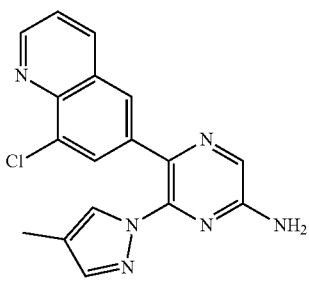
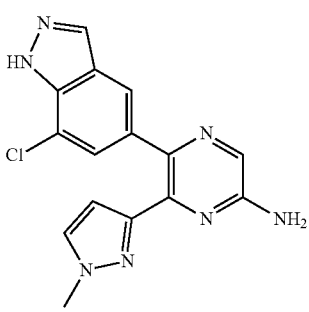
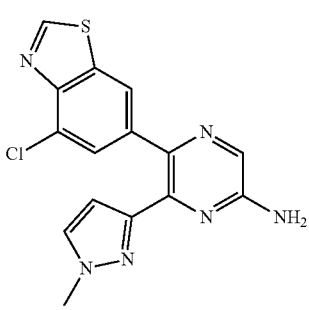

1109
-continued
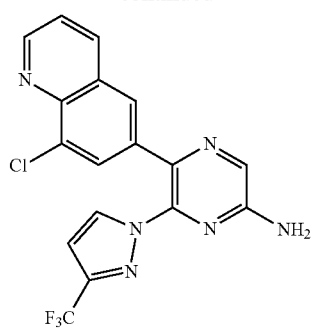
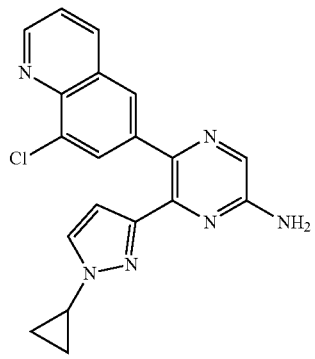
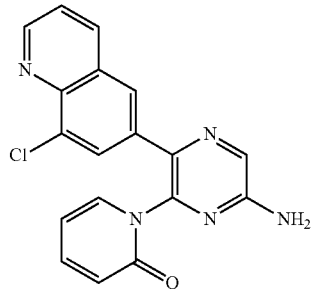
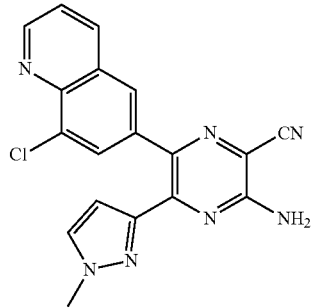
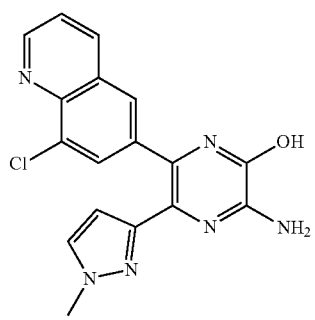
1110
-continued
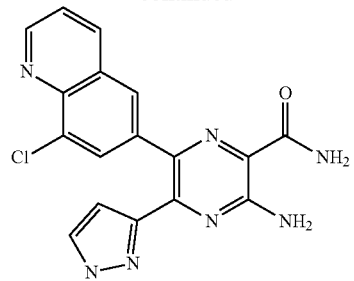
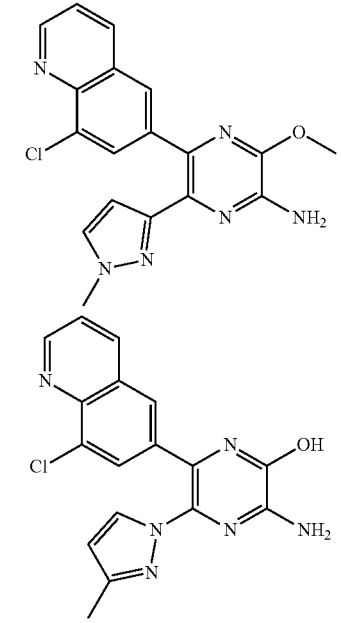
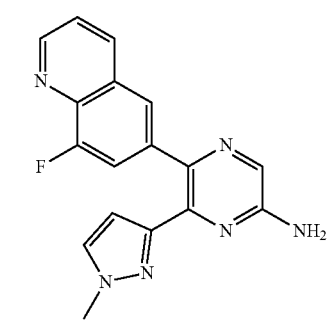
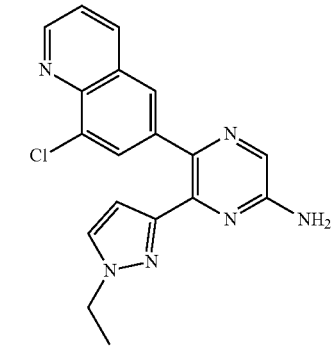

| 1111 -continued | 1112 -continued |
|---|---|
| 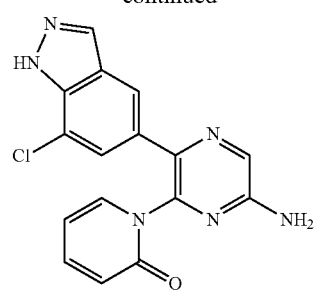 | 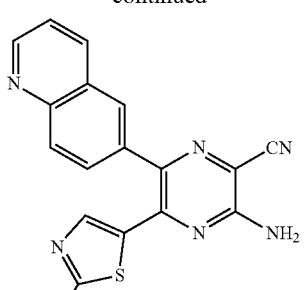 |
| 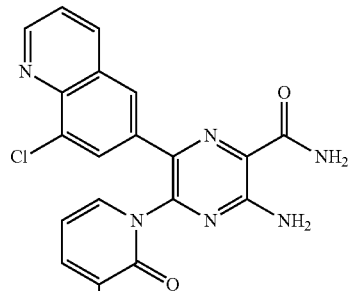 | 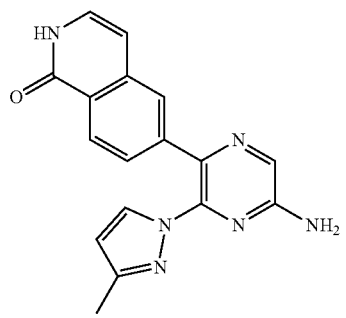 |
| 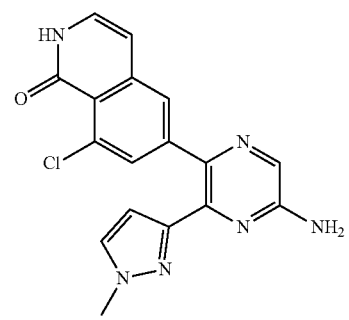 | 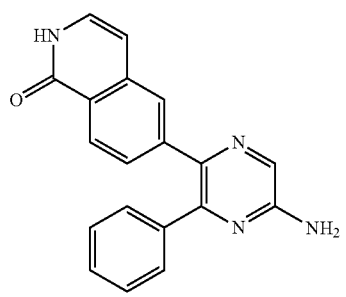 |
| 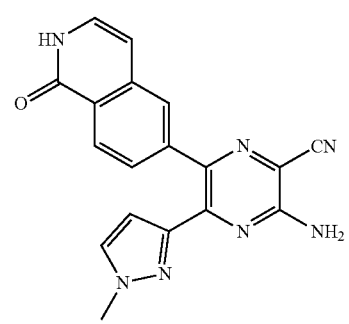 | 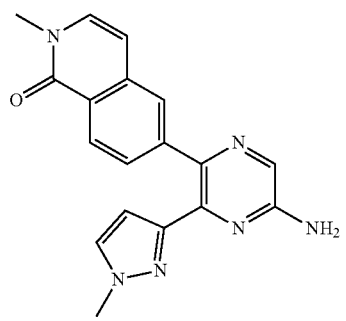 |
| 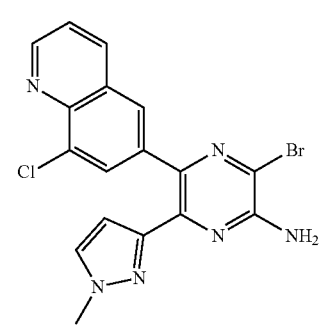 | 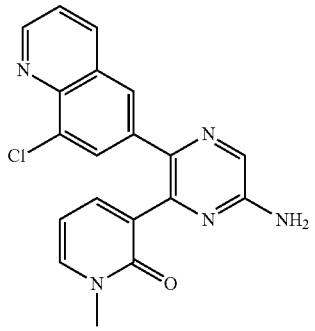 |

1113
-continued
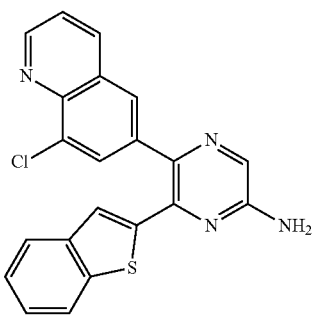
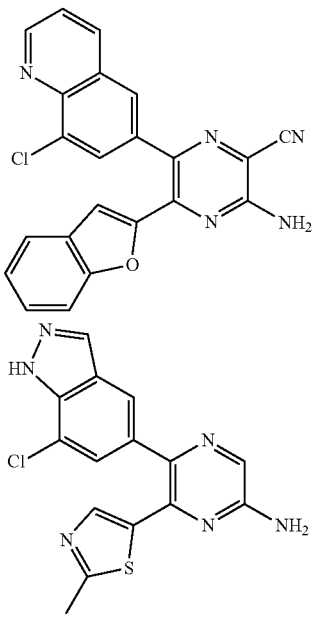
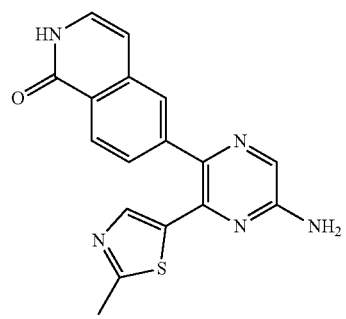
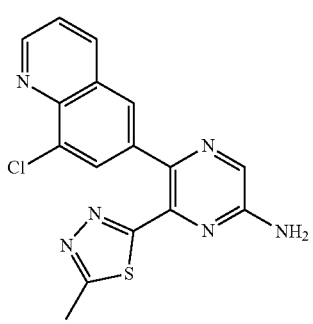
1114
-continued
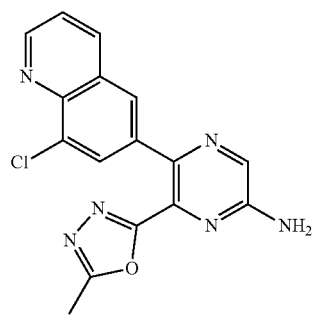
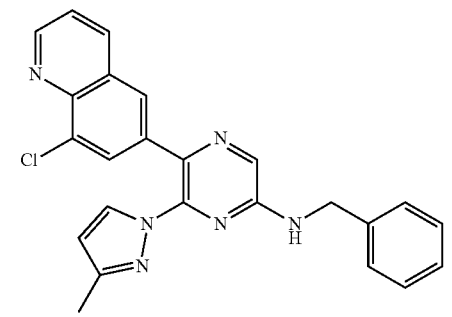
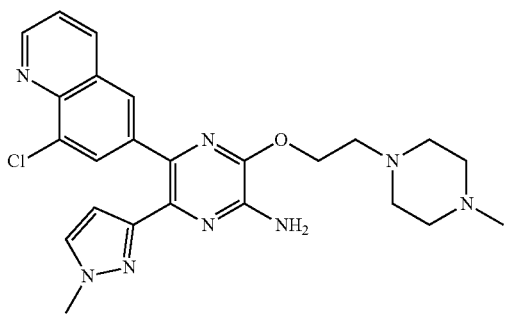
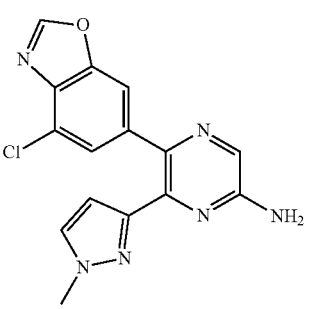
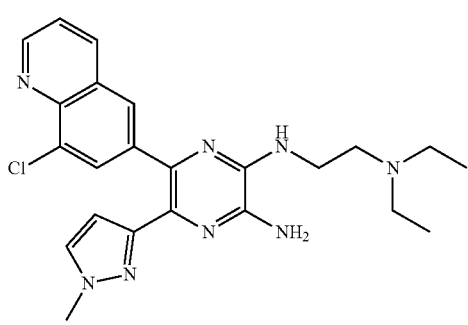

1115
-continued
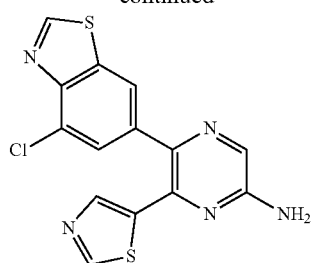
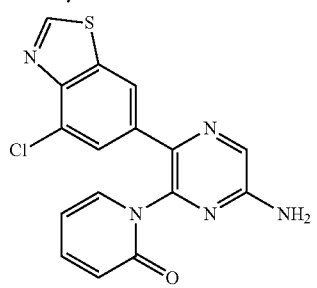
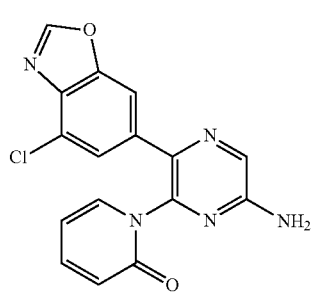
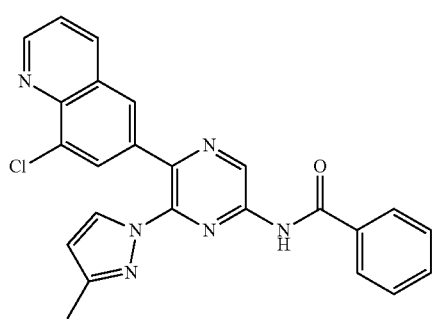
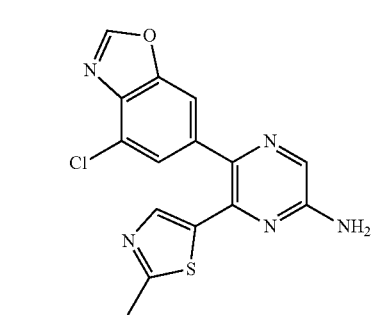
1116
-continued
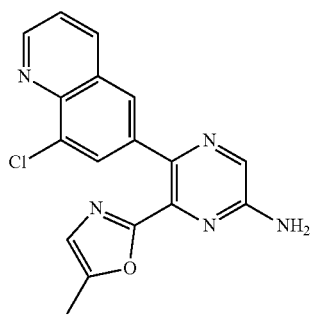
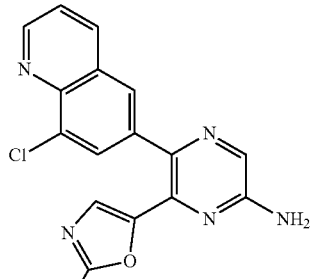
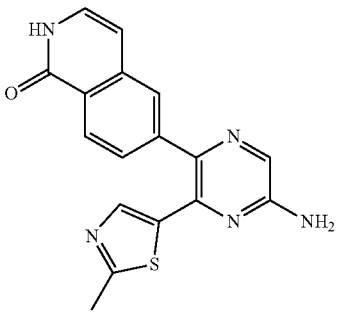
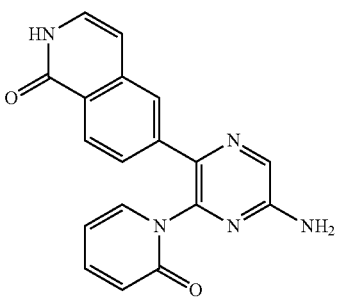
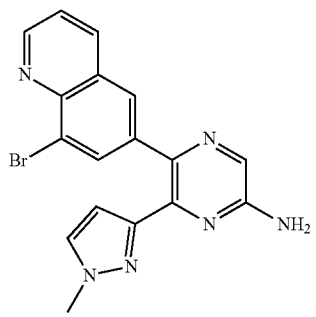

1117
-continued
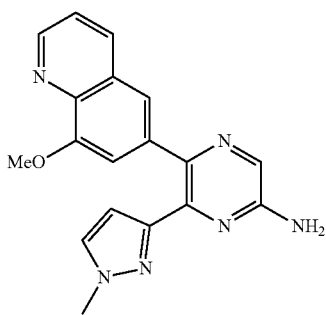
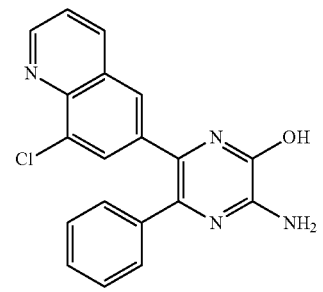
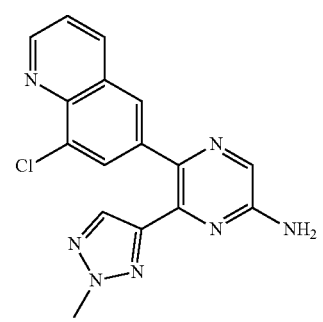
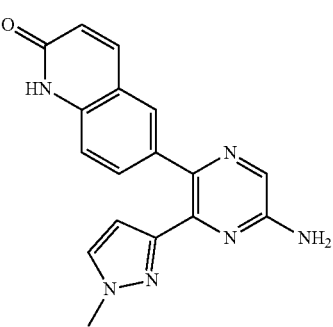
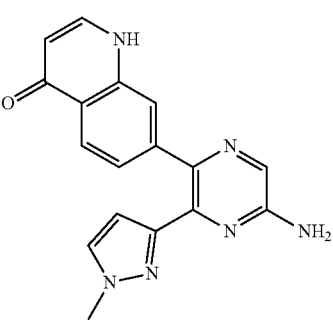
1118
-continued
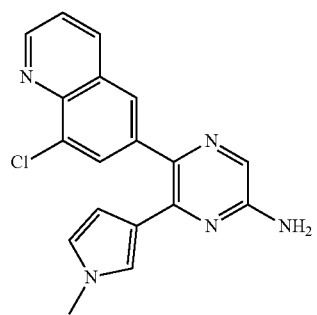
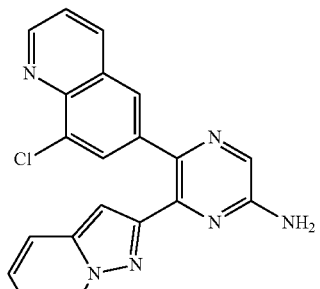
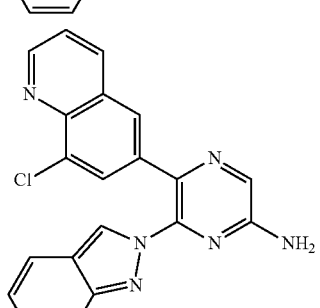
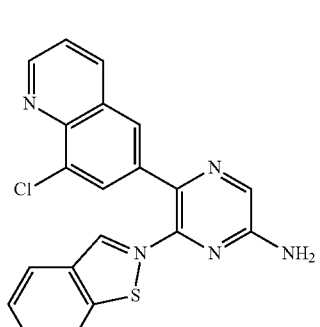
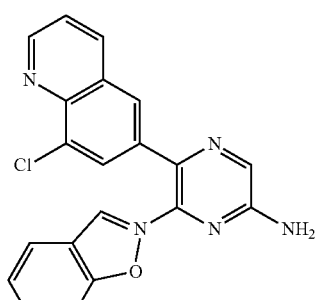

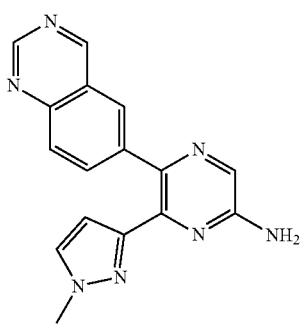
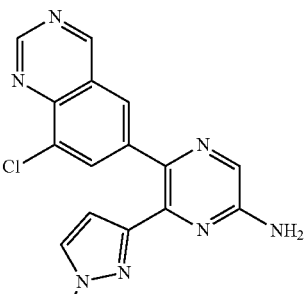
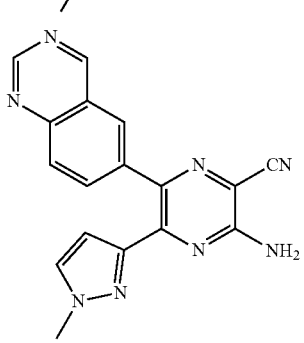
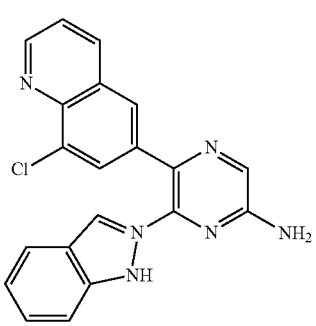
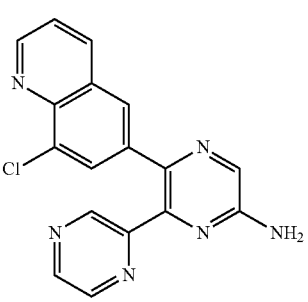
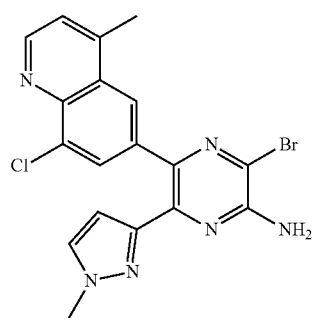
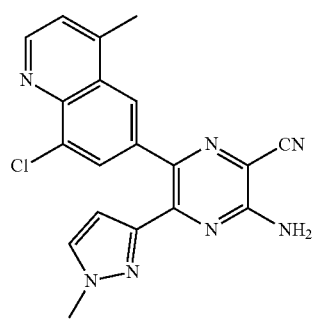
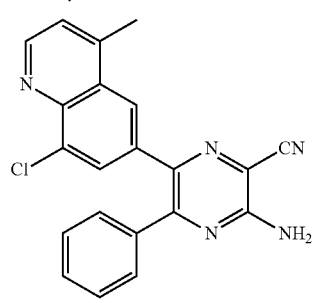
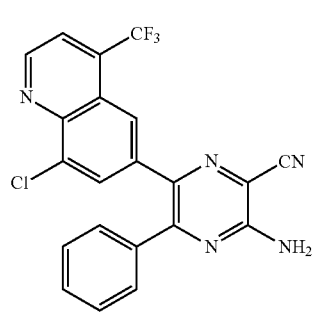
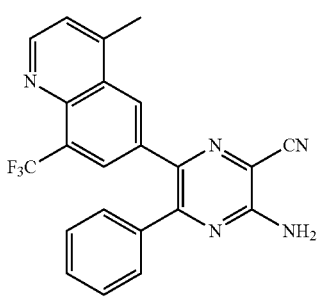

1121
-continued
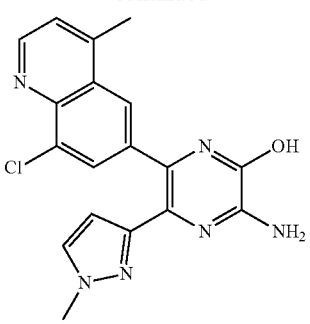
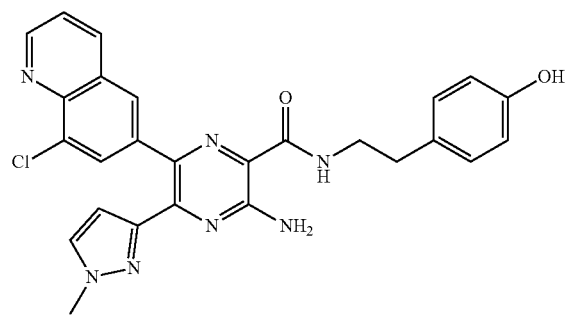
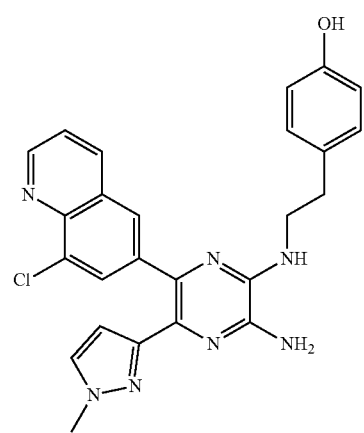
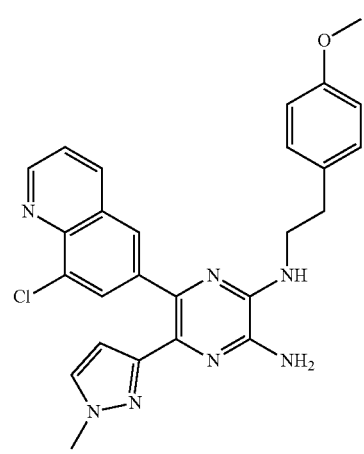
1122
-continued
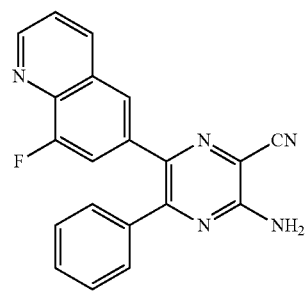
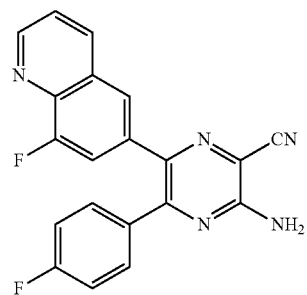
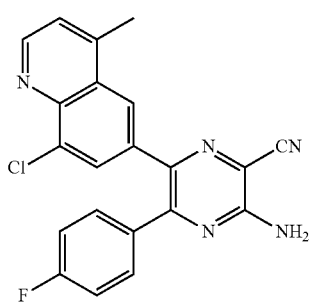
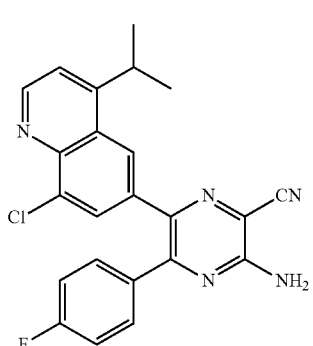
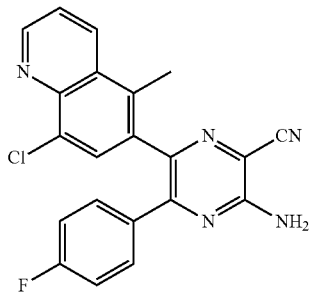

1123
-continued
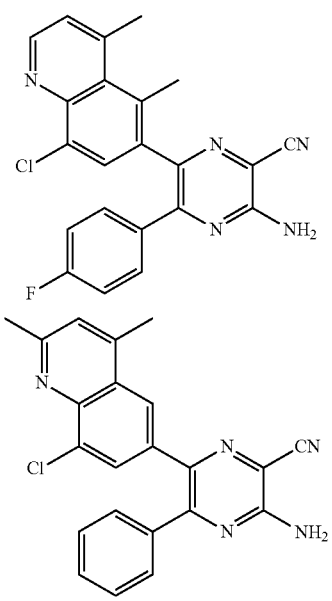
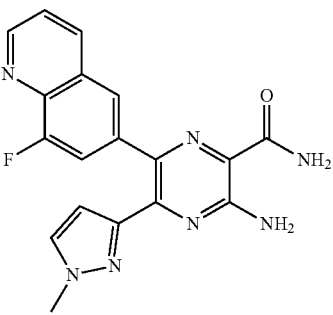
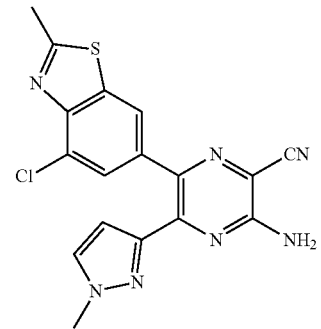
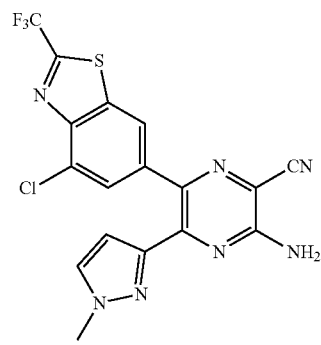
1124
-continued
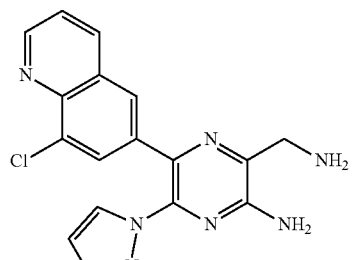
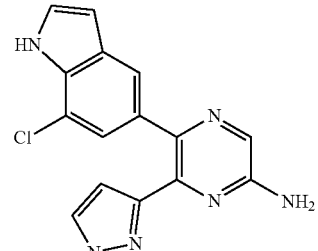
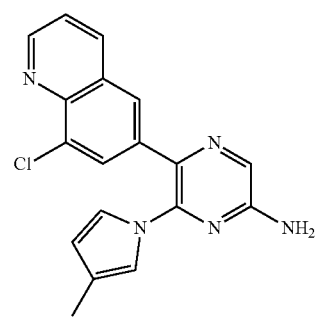
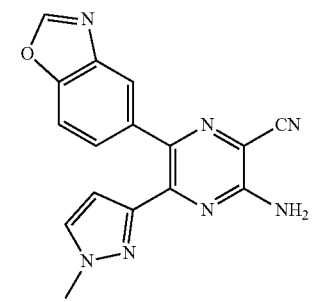
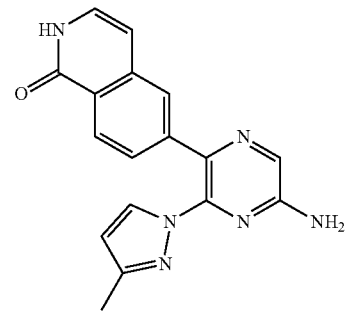

1125
-continued
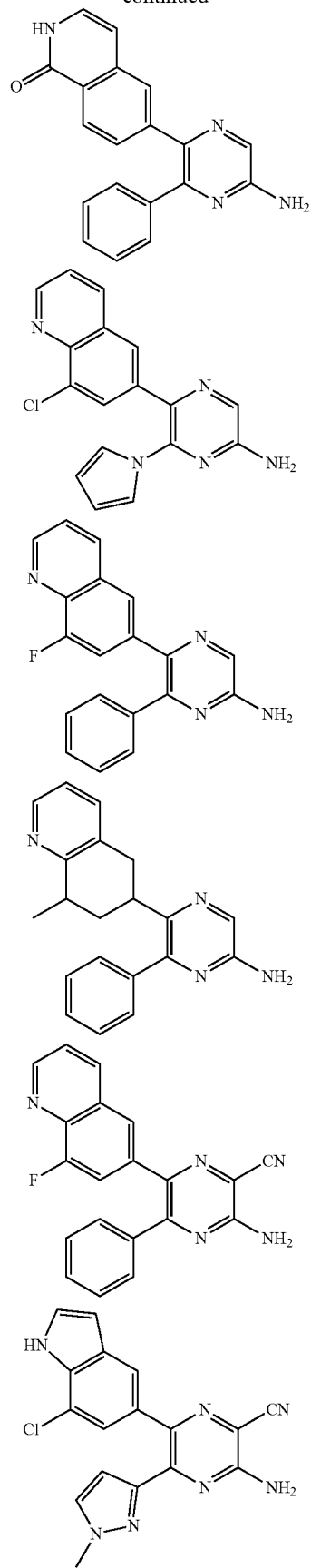
1126
-continued
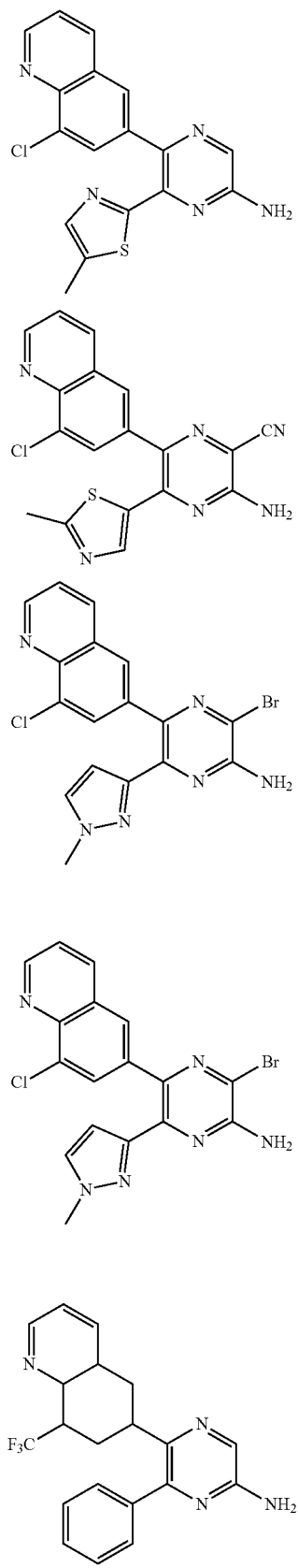

1127
-continued
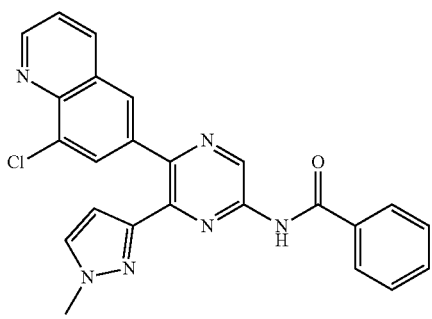
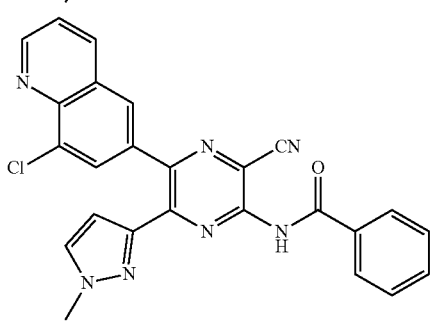
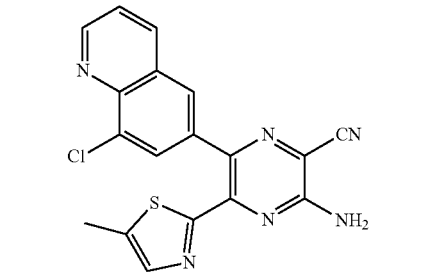
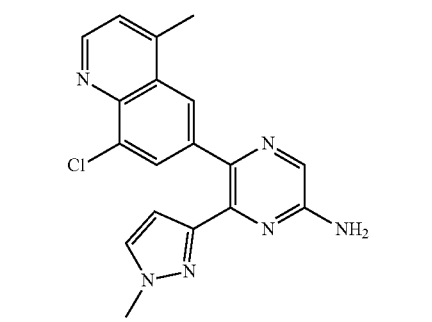
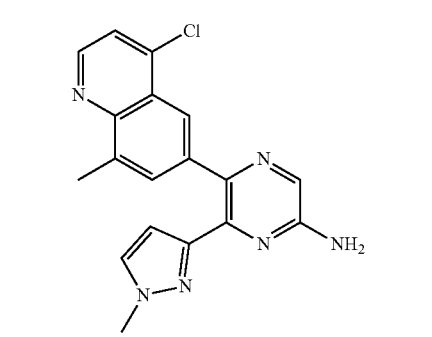
1128
-continued
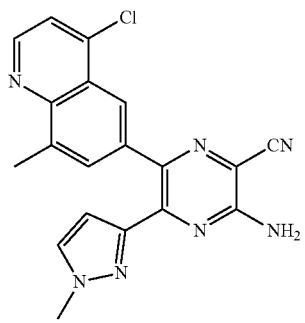
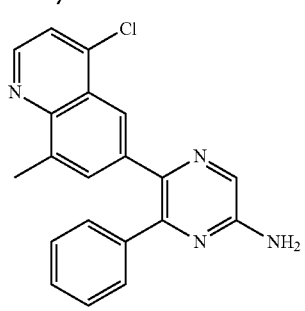
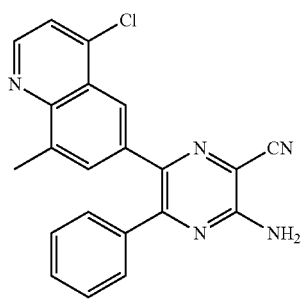
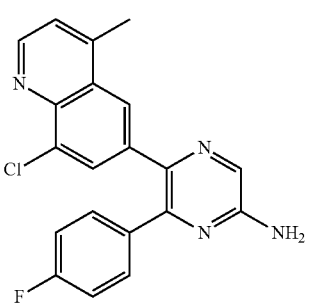
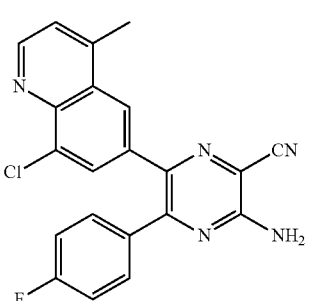

1129
-continued
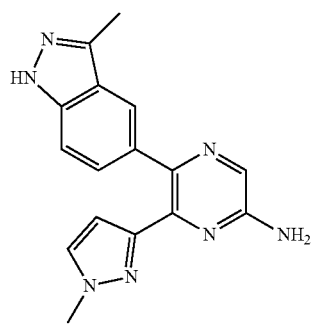
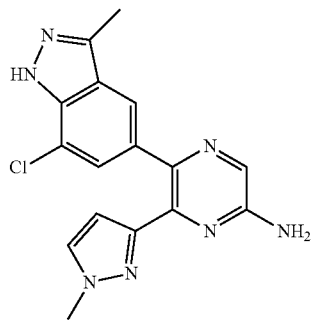
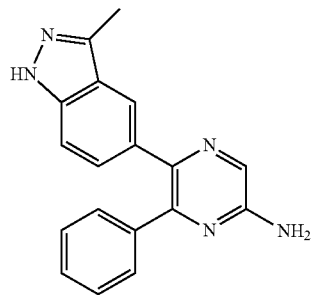
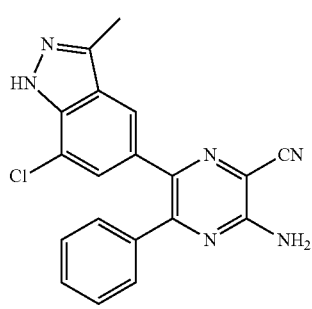
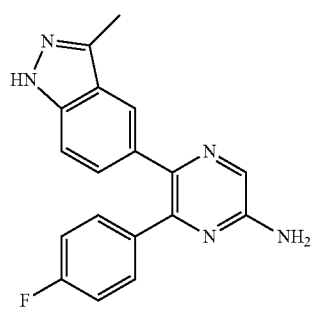
1130
-continued
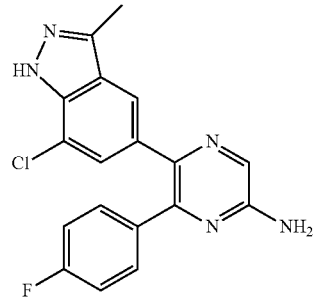
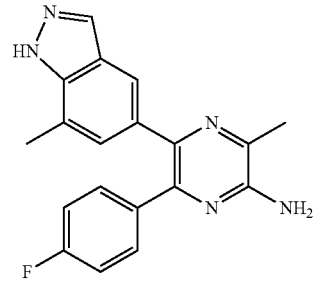
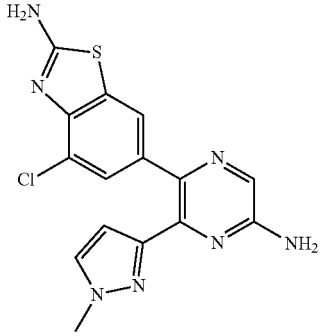
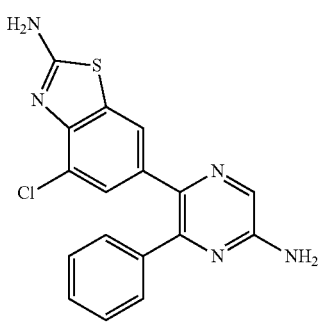
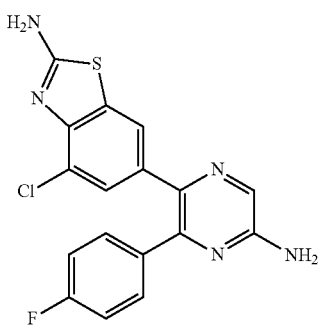

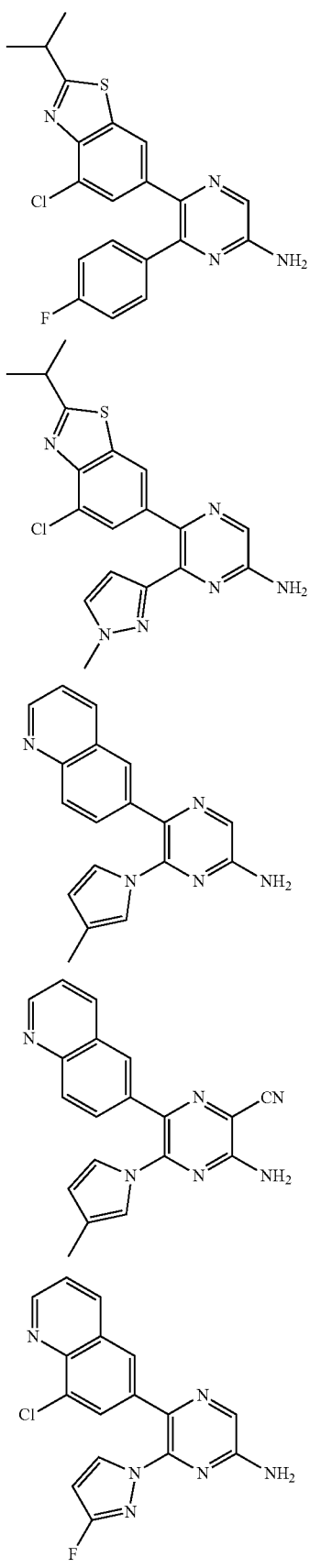
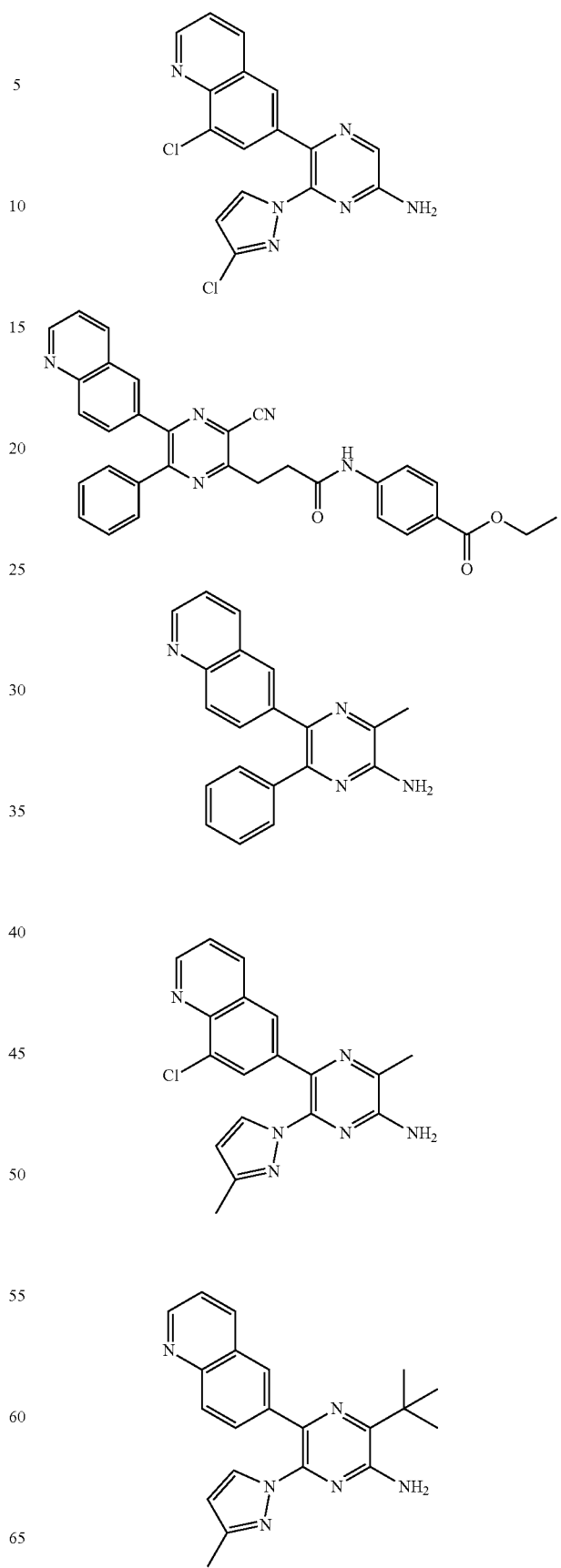

1133
-continued
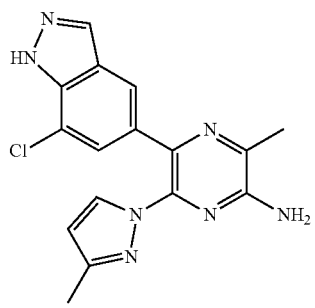
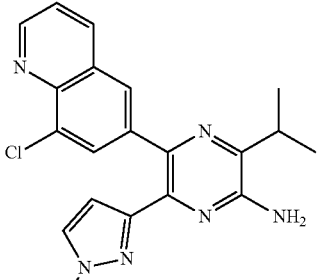
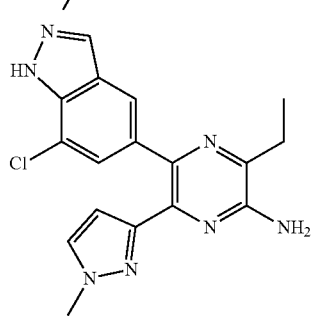
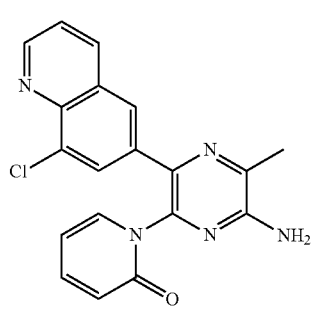
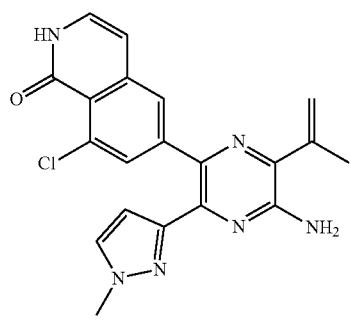
1134
-continued
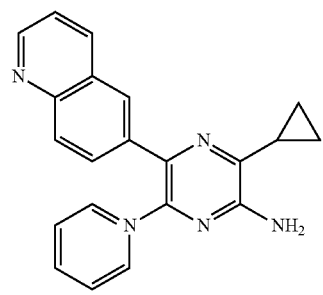
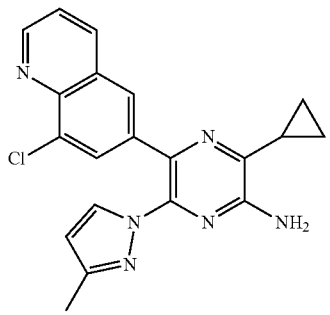
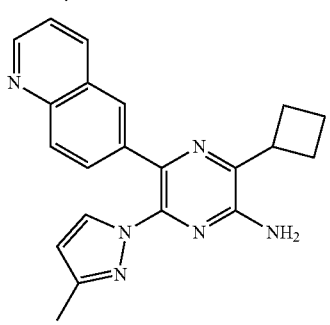
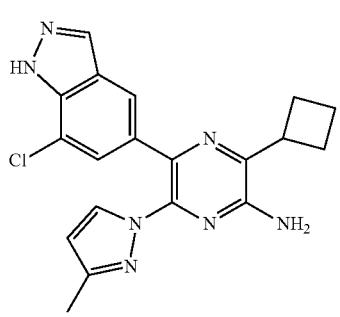
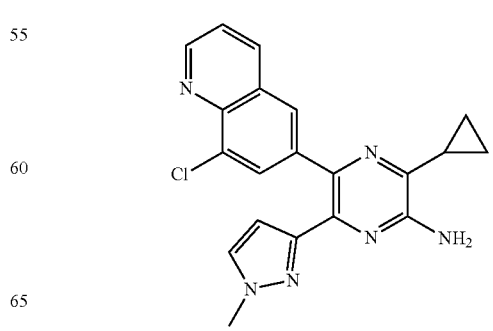

1135
-continued
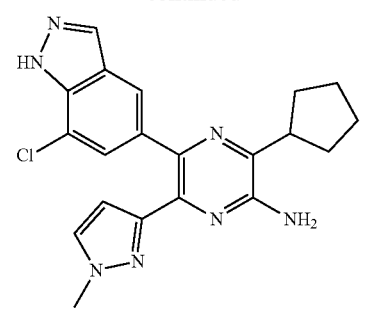
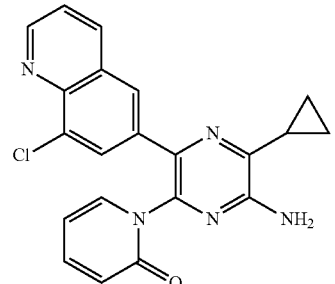
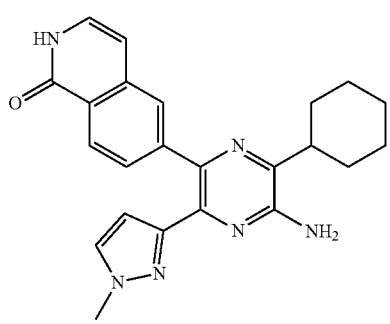
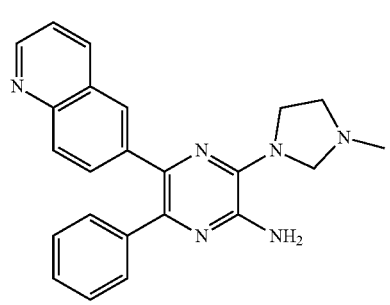

1136
-continued
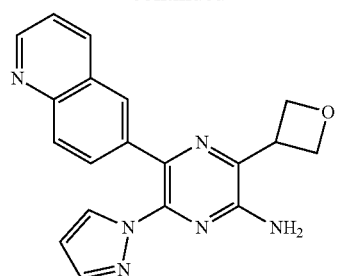
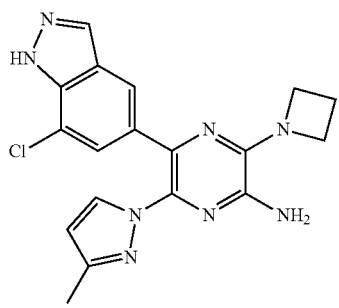
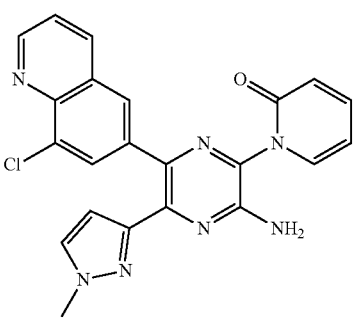
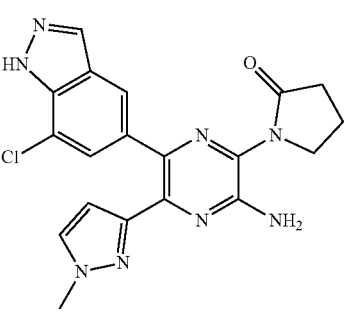
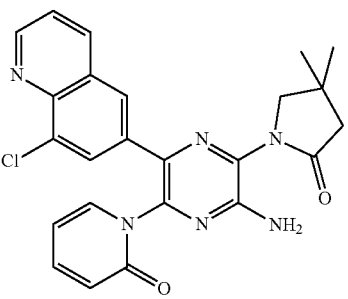

1137
-continued
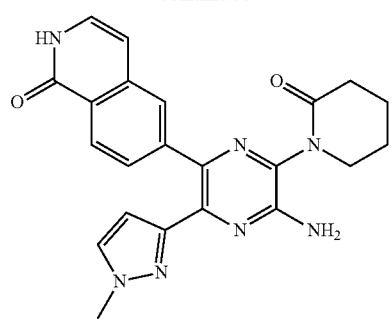
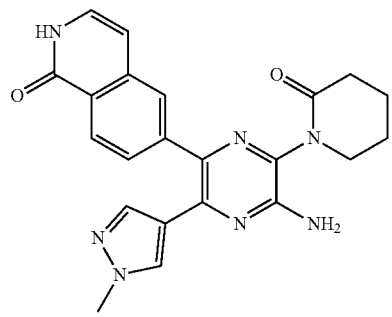
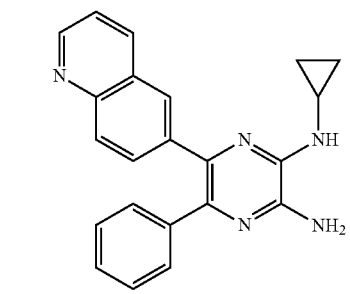
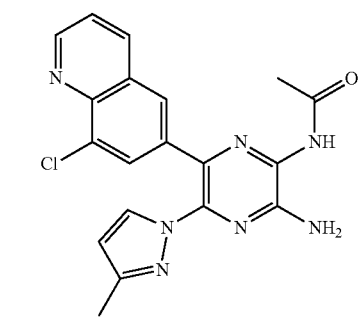
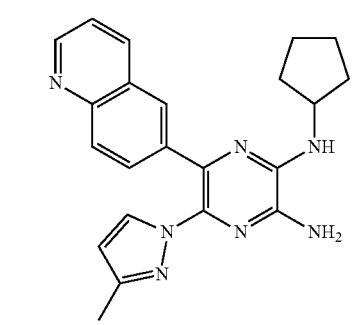
1138
-continued
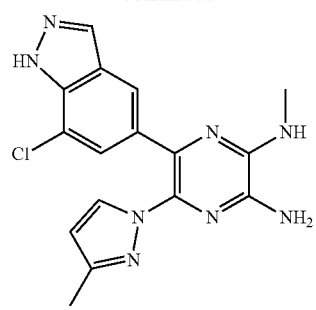
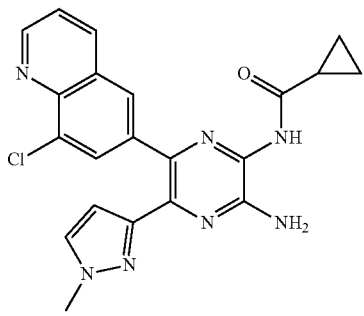
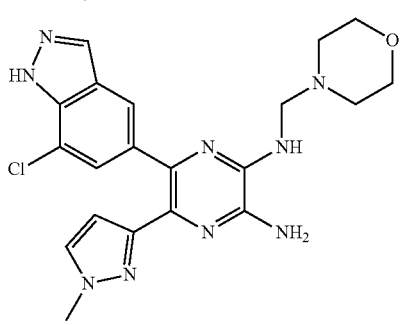
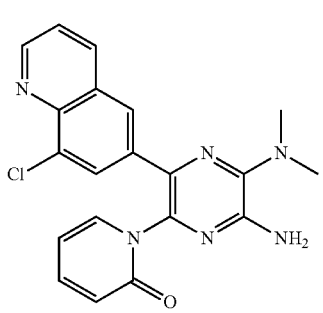
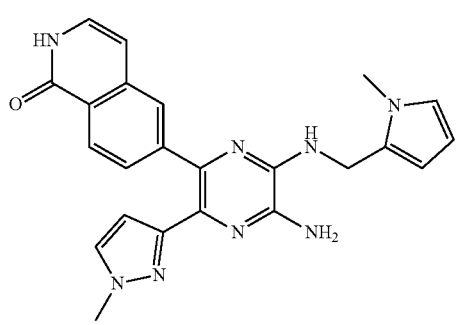

1139
-continued
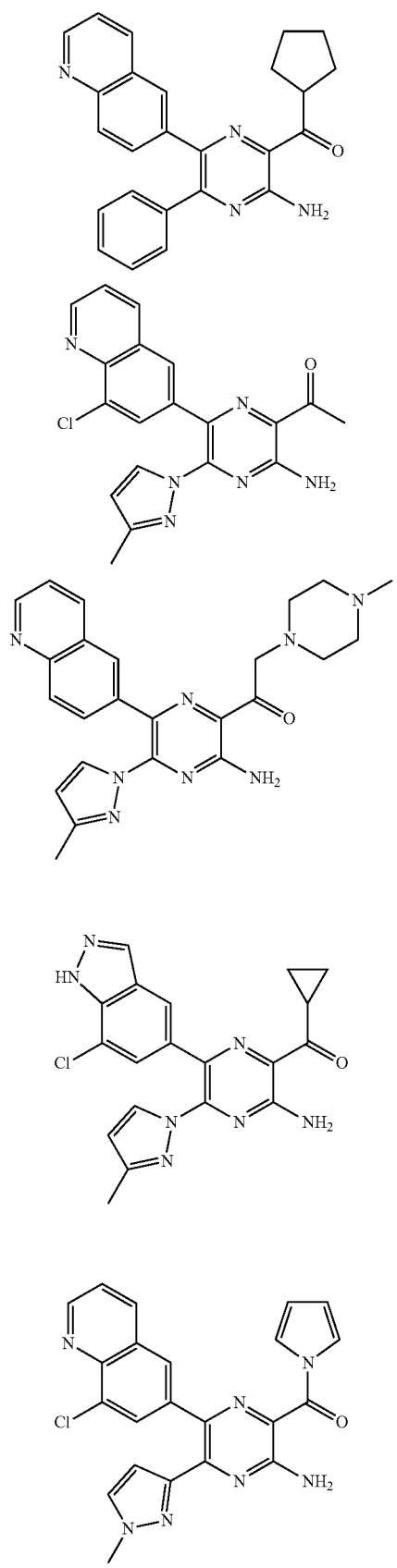
1140
-continued
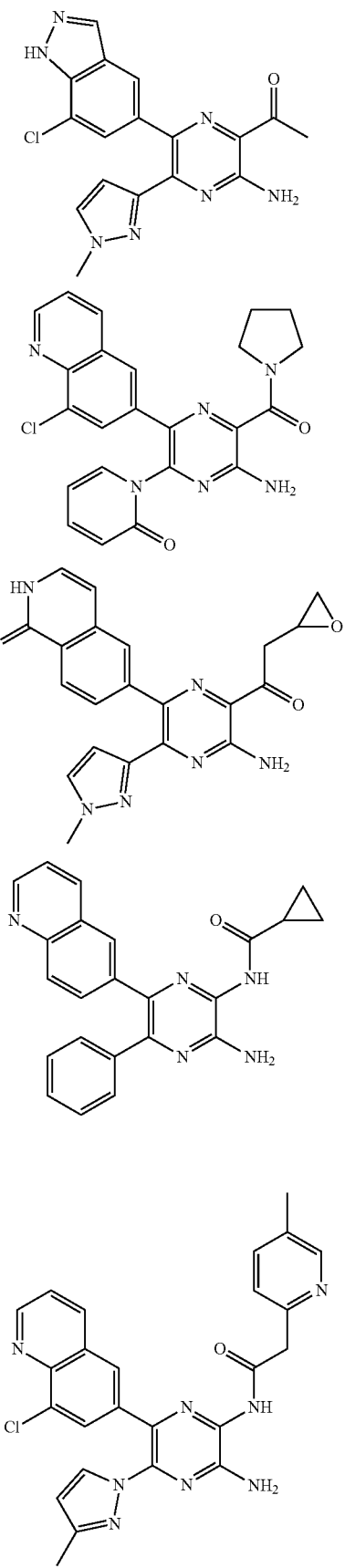

1141
-continued
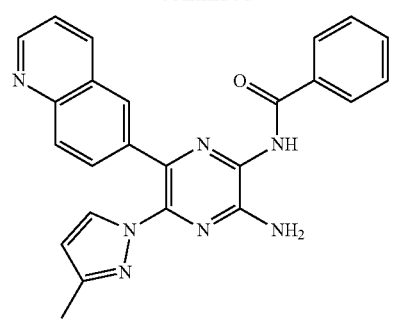
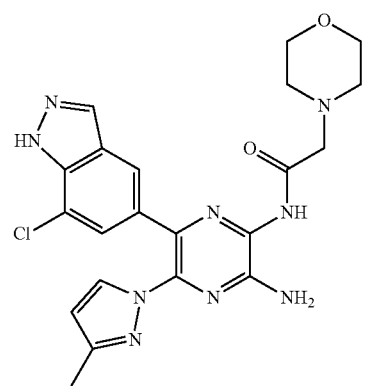
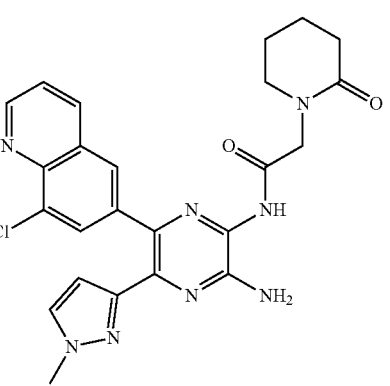
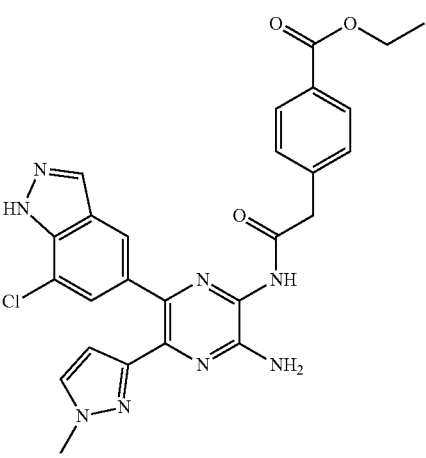
1142
-continued
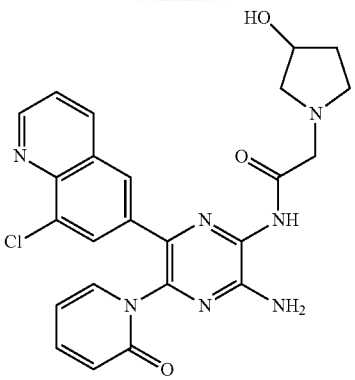
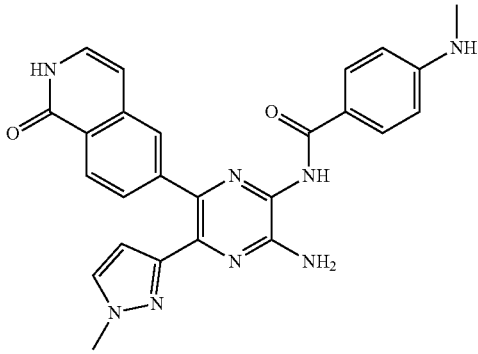
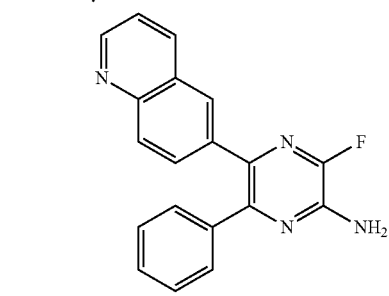
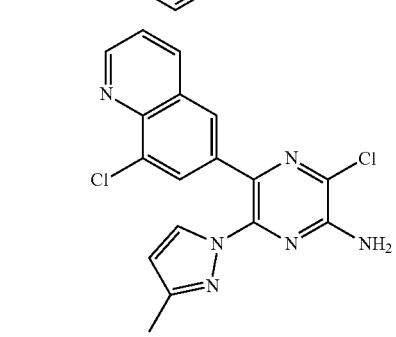
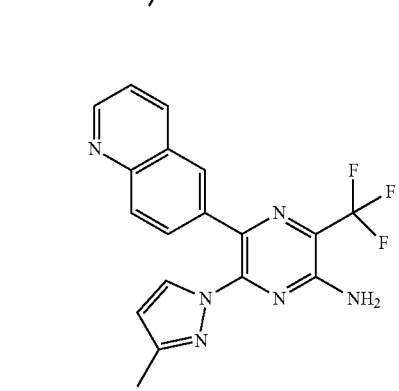

1143
-continued
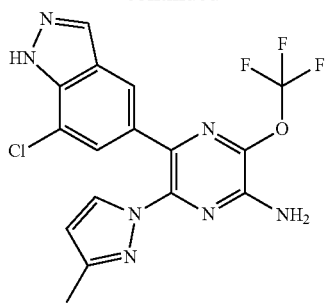
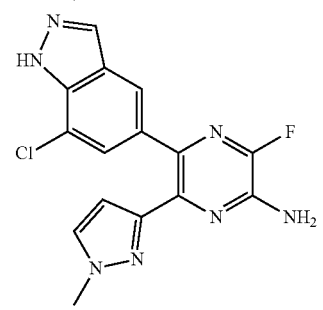
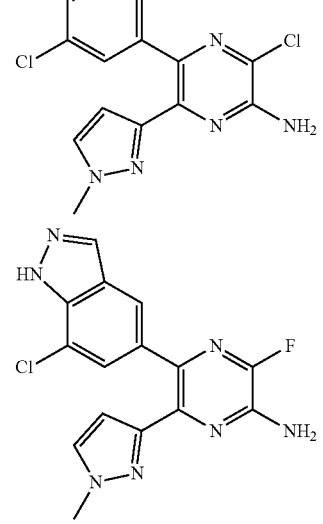
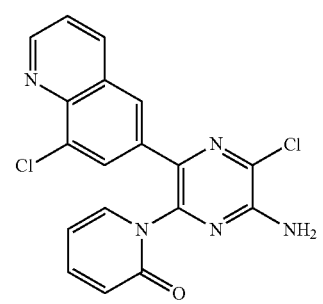
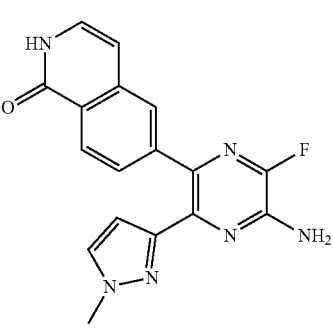
1144
-continued
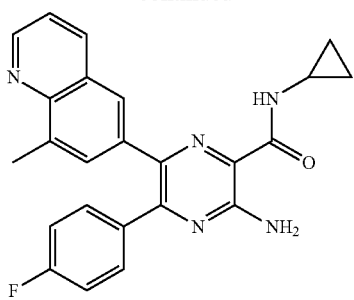
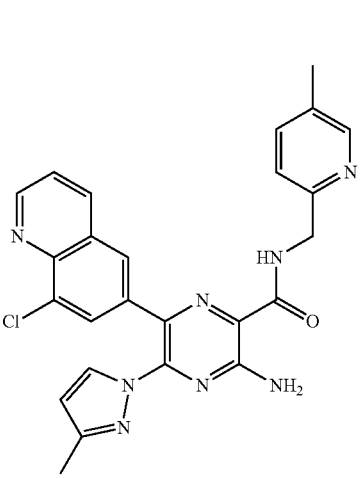
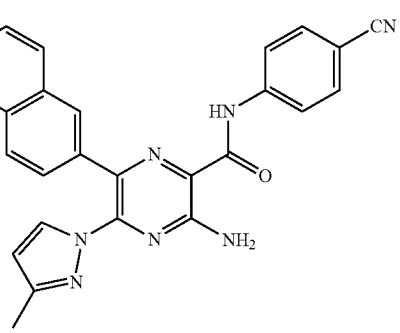
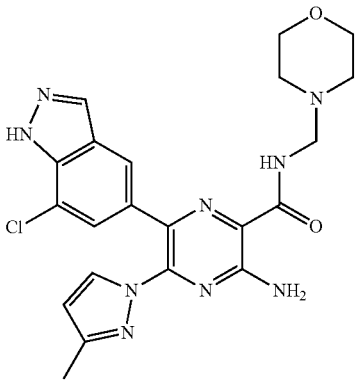

1145
-continued
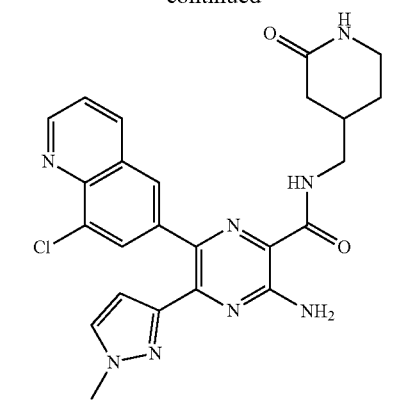
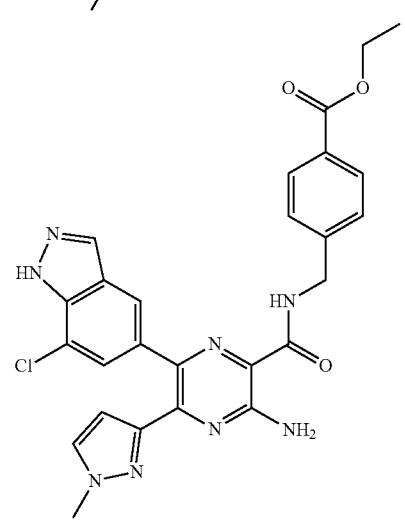
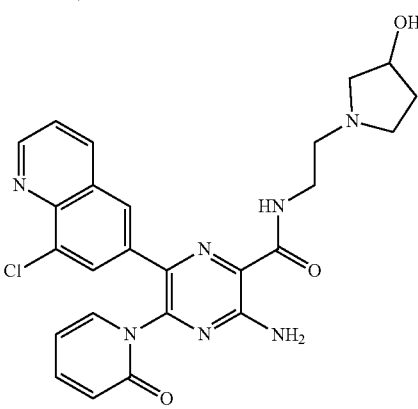
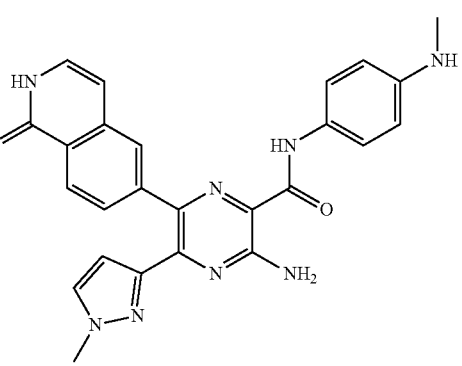
1146
-continued
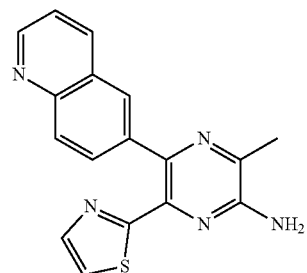
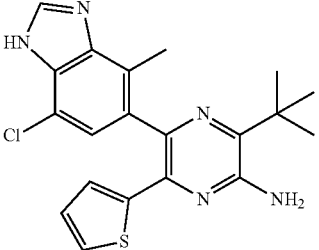
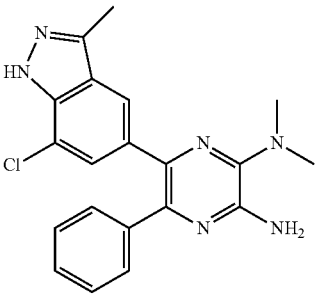
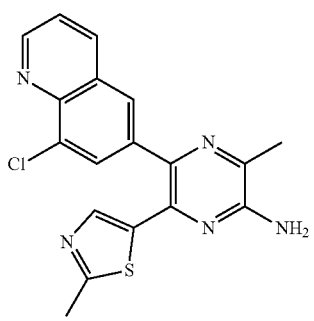
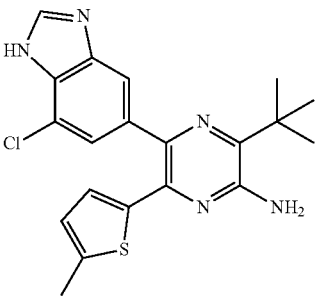

1147
-continued
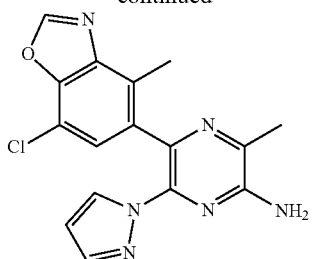
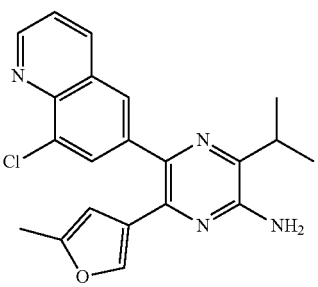
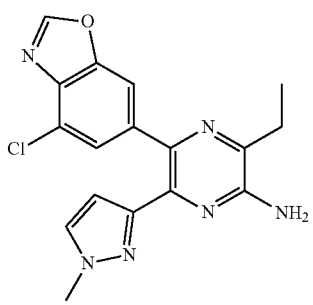
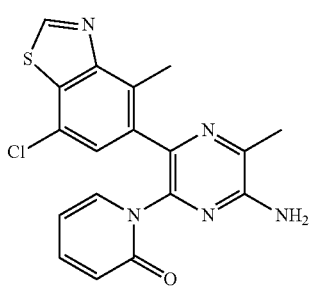
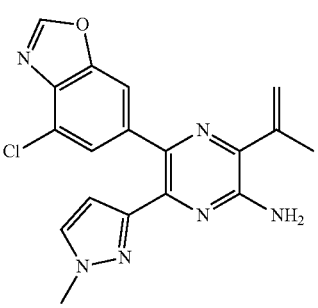
1148
-continued
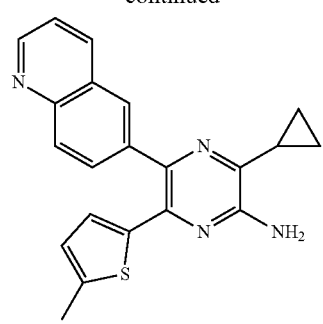
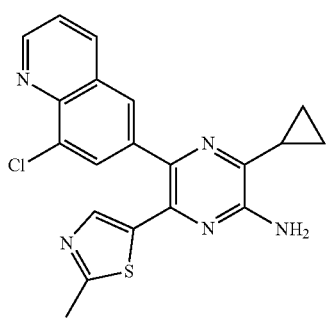
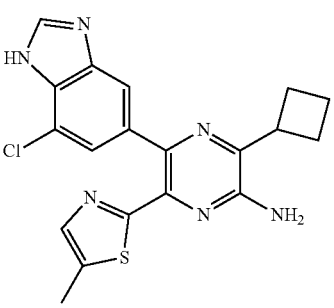
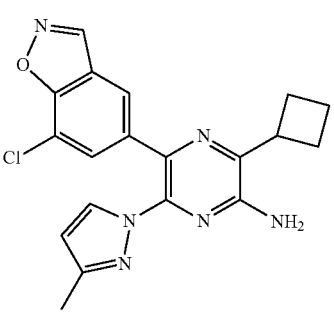
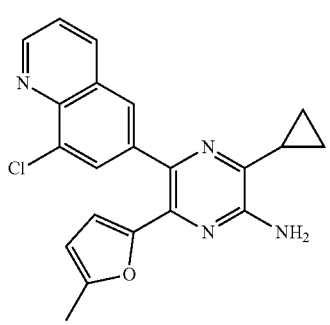

1149
-continued
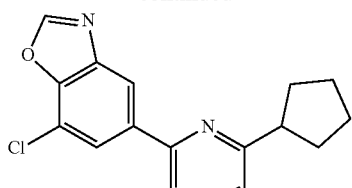
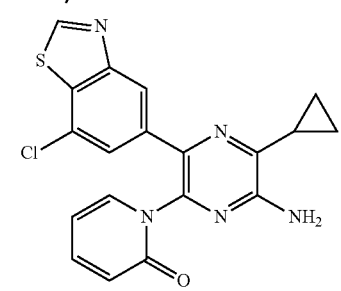
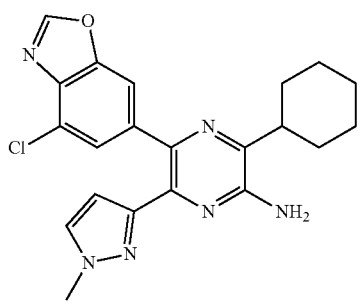
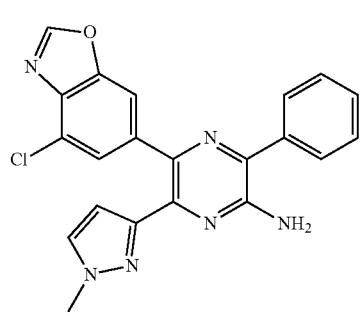
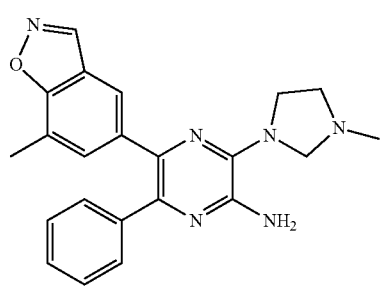
1150
-continued
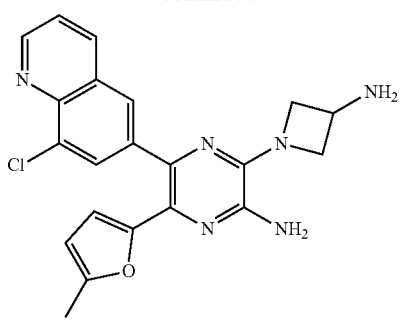
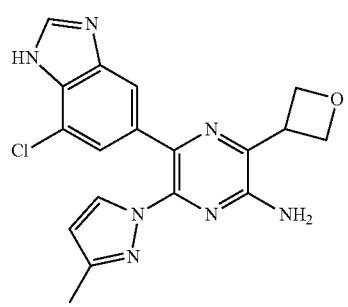
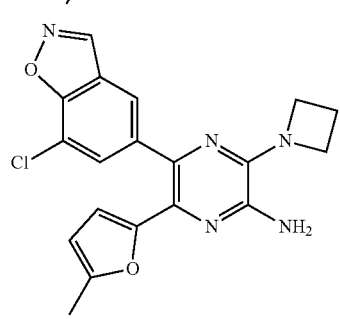
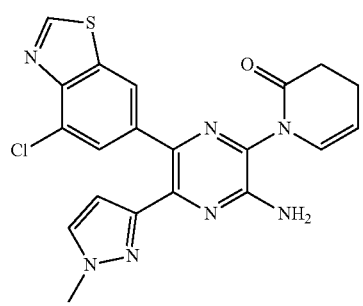
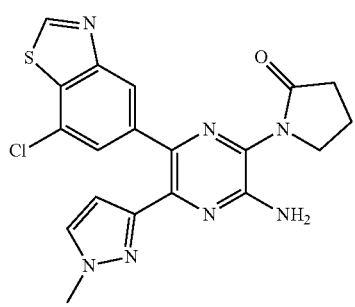

1151
-continued
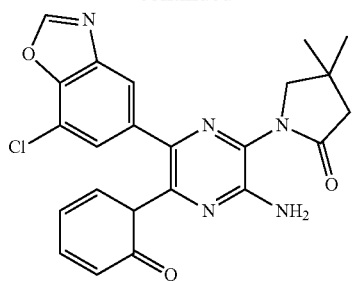
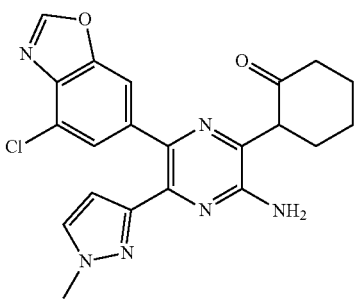
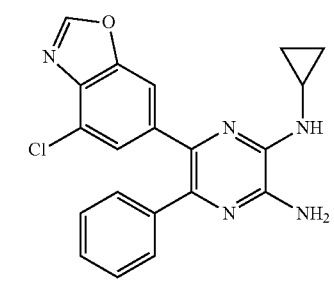
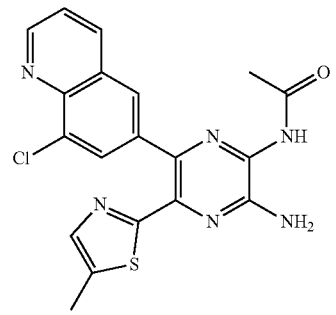
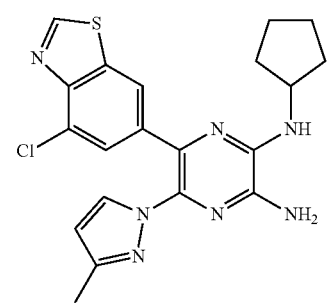
1152
-continued
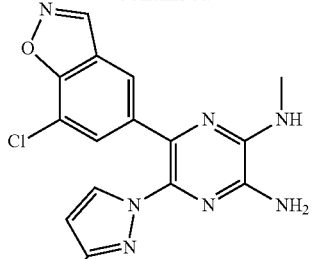
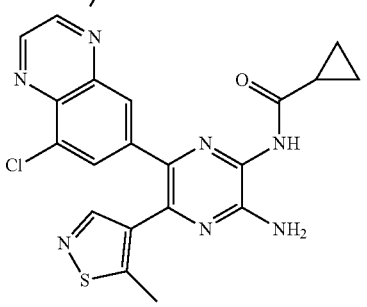
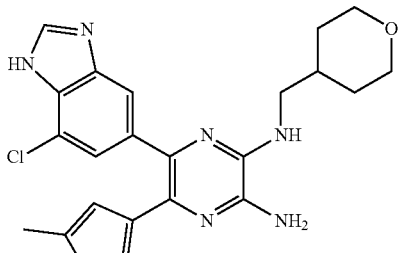
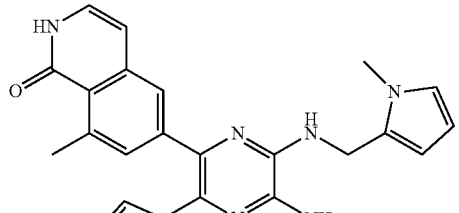
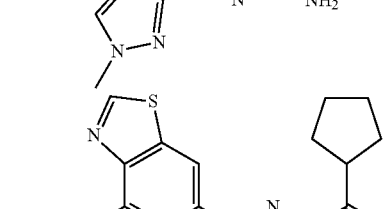
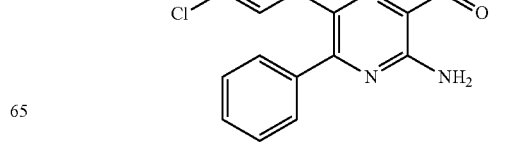

1153
-continued
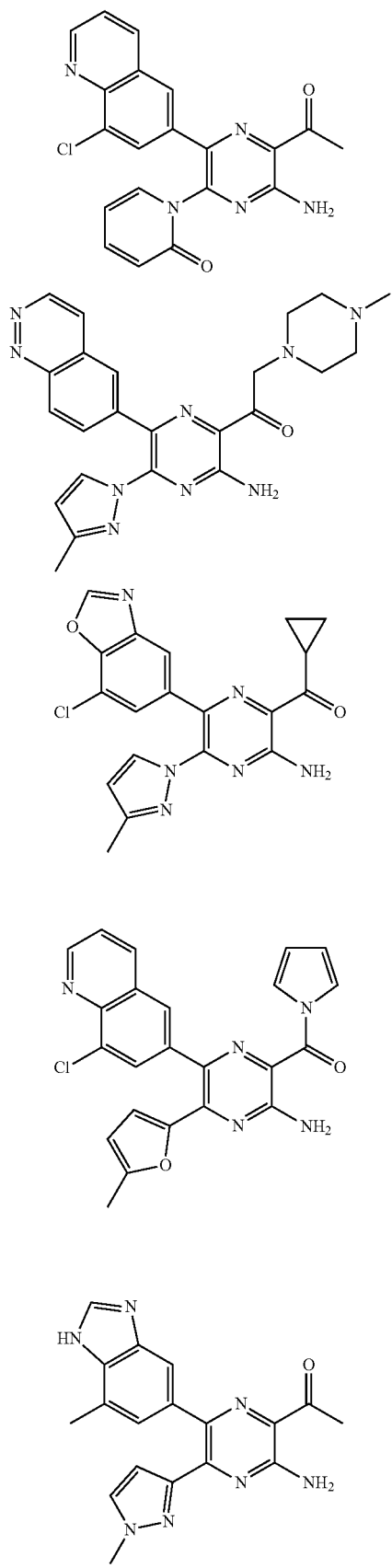
1154
-continued
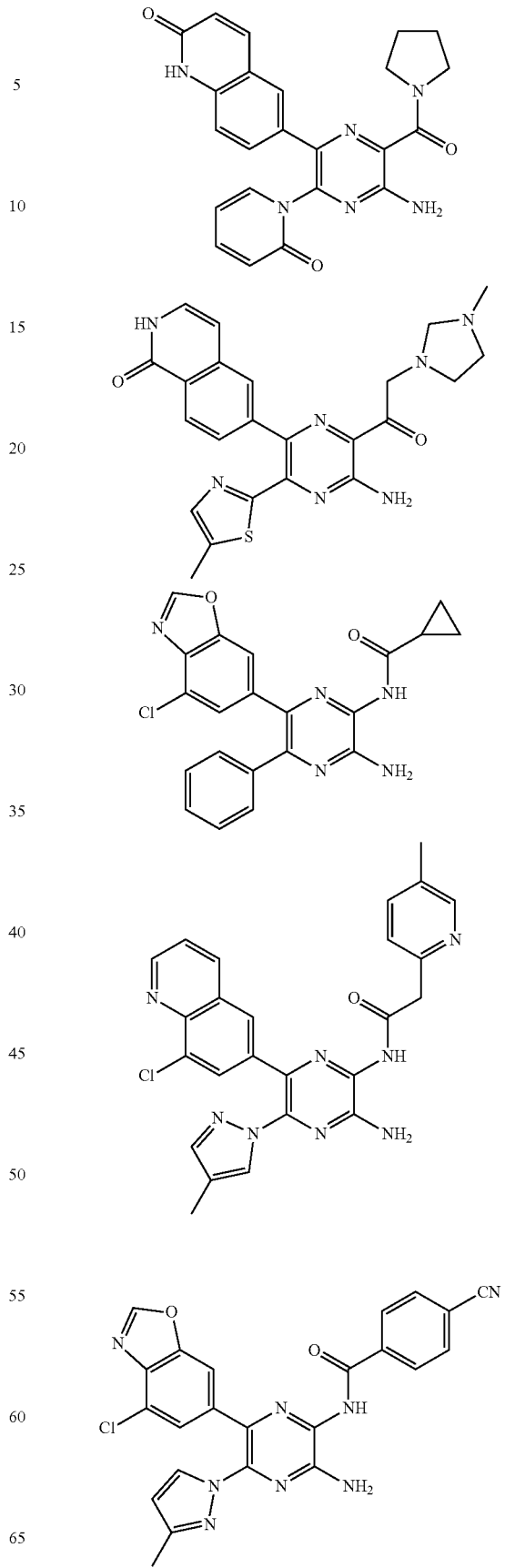

1155
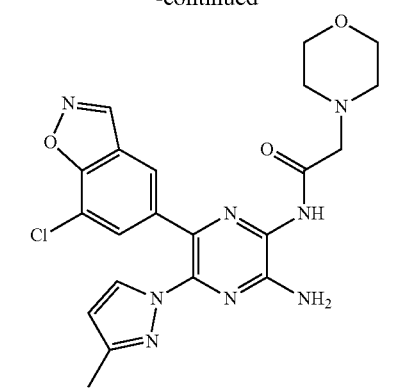
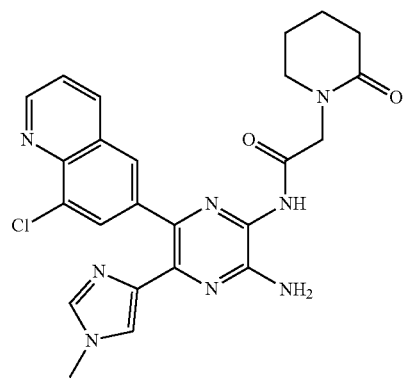
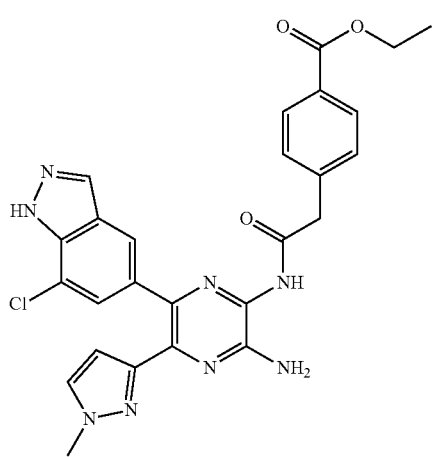
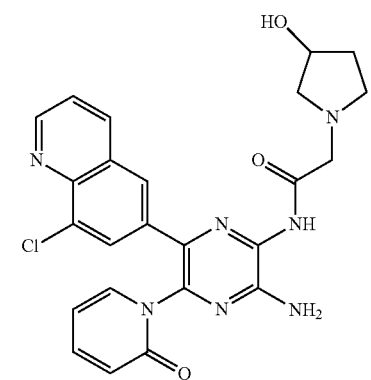
1156
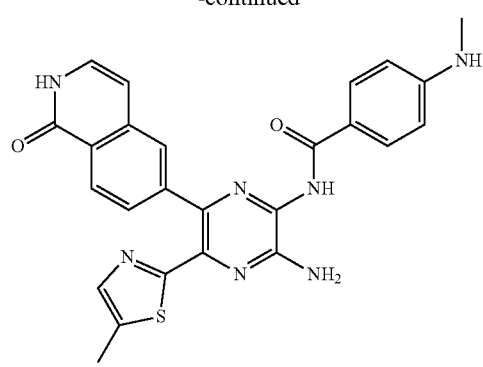
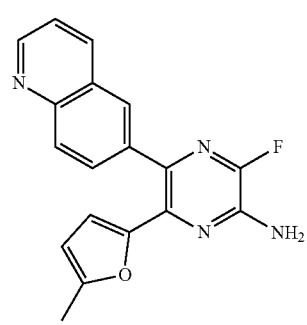
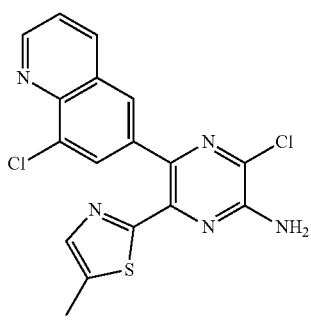
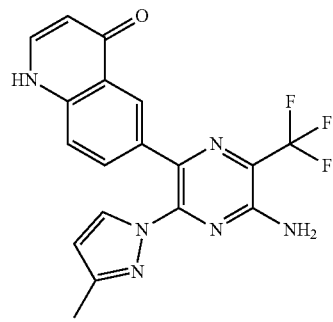
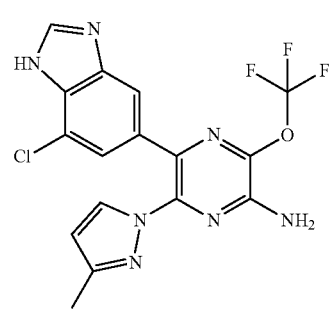

1157
-continued
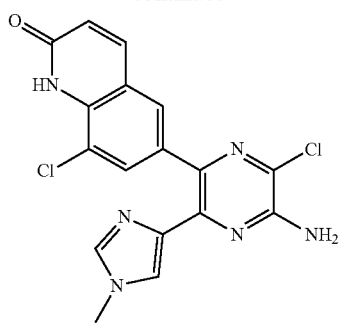
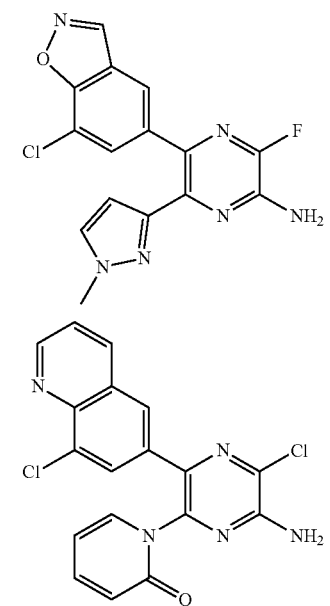
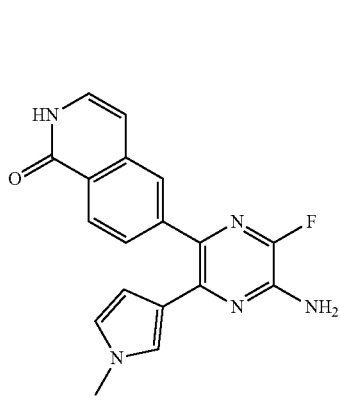
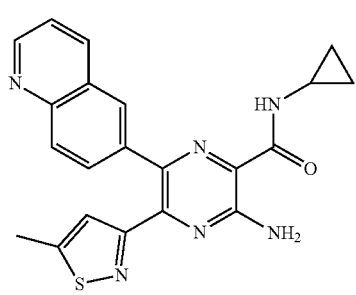
1158
-continued
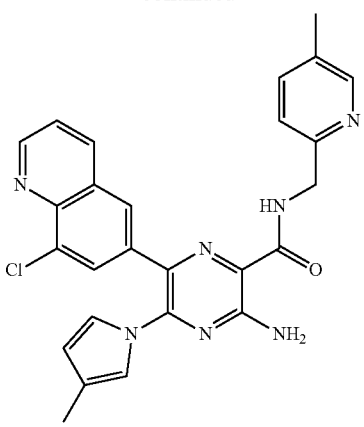
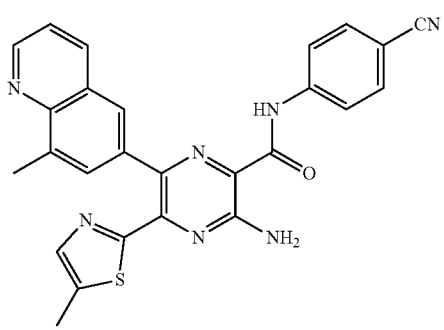
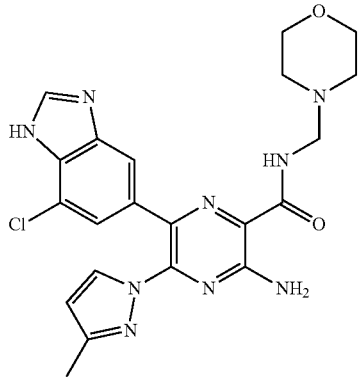
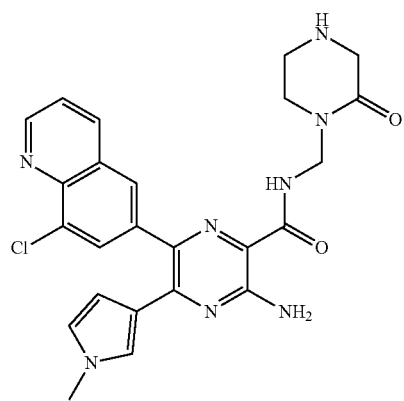

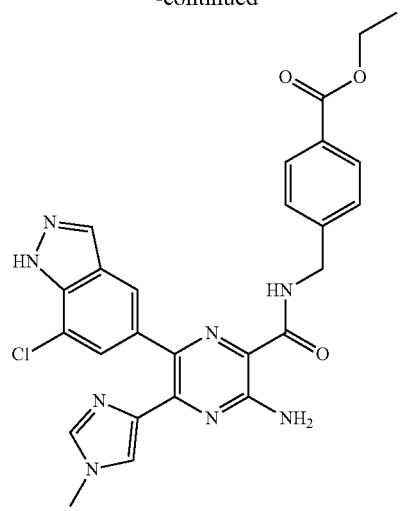
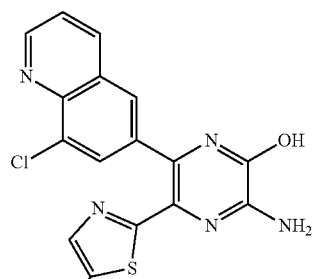
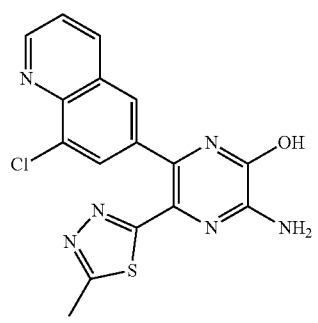
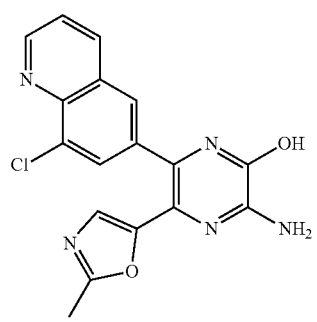
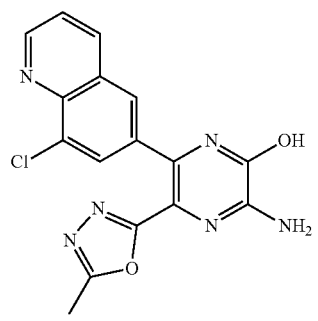
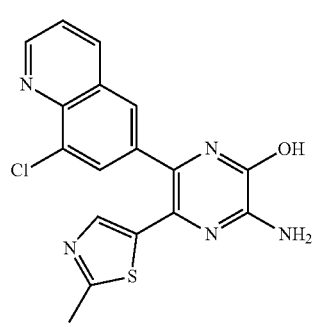

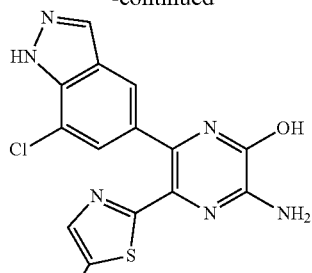
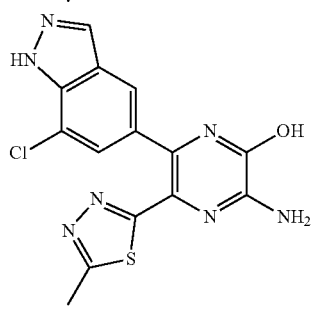
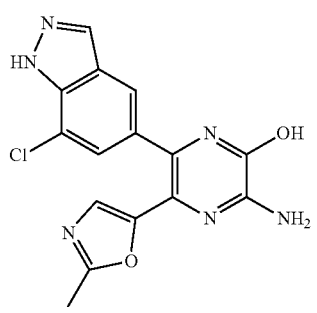
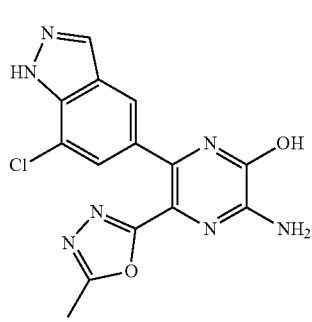
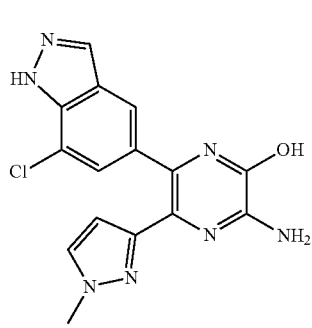
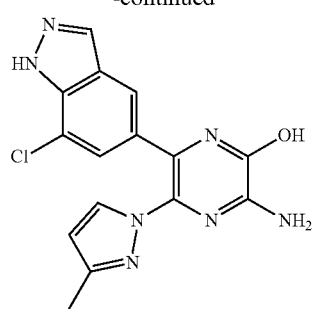
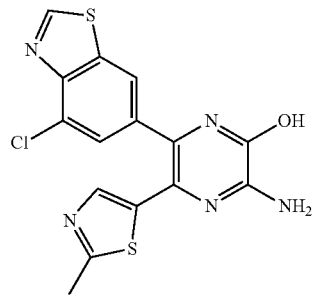
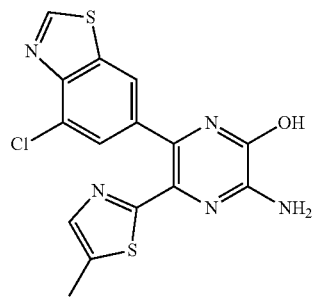
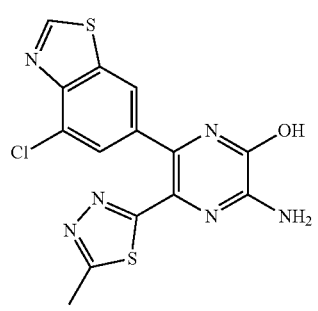
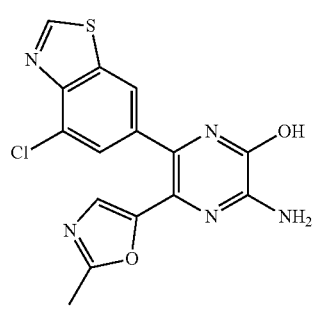

-continued
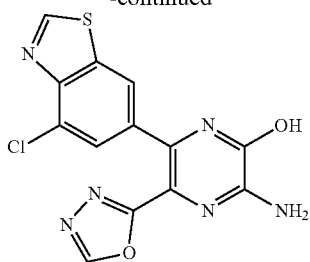
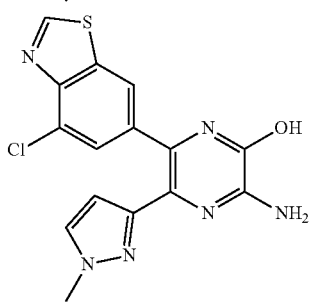
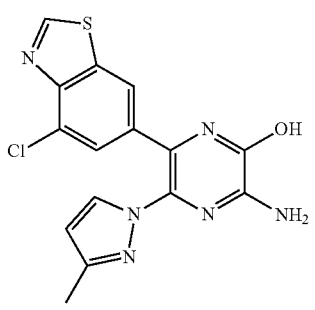
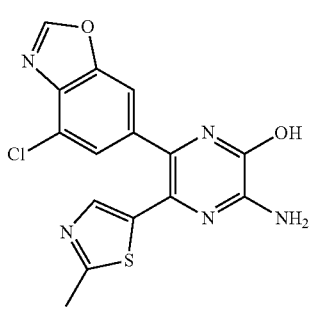
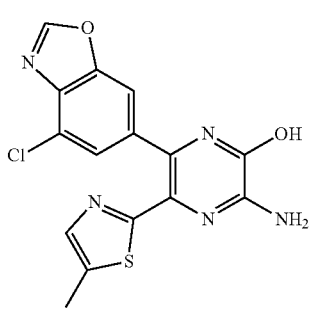
-continued
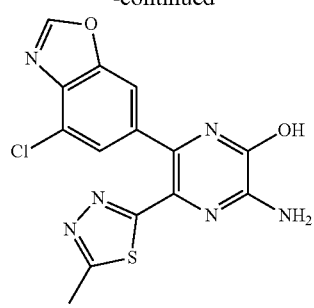
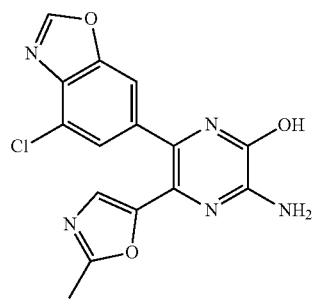
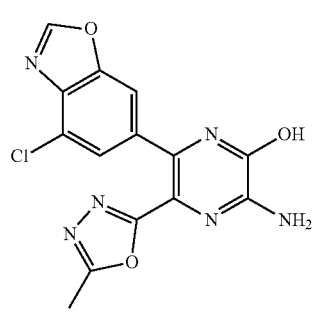
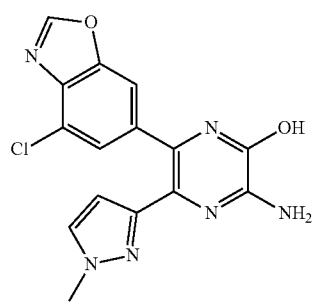
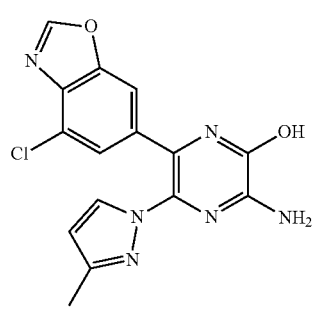

1165
-continued
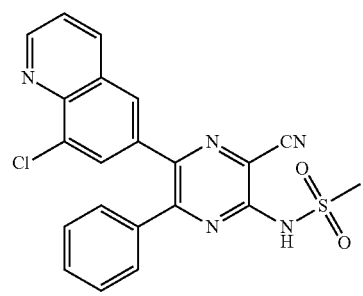
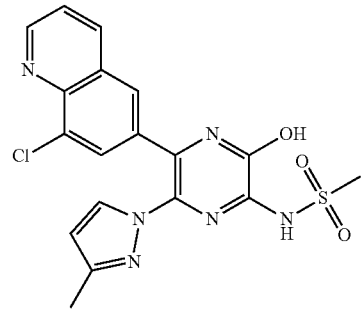
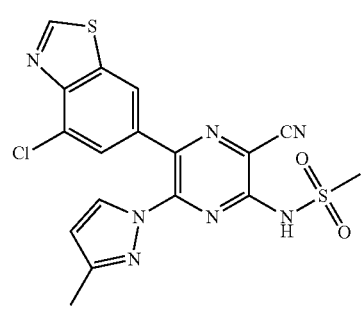
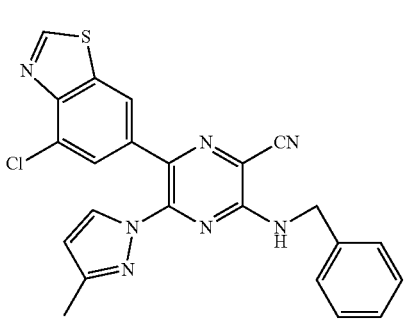
1166
-continued
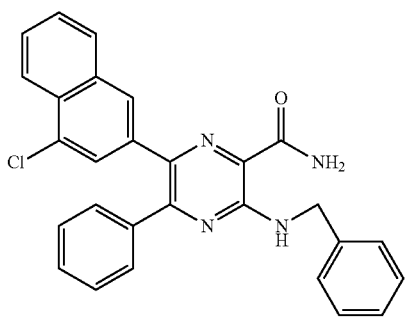
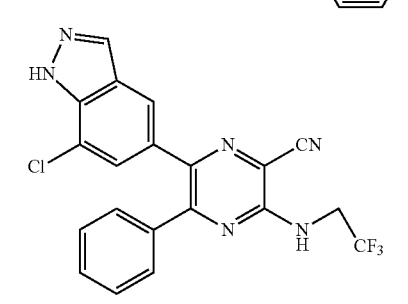
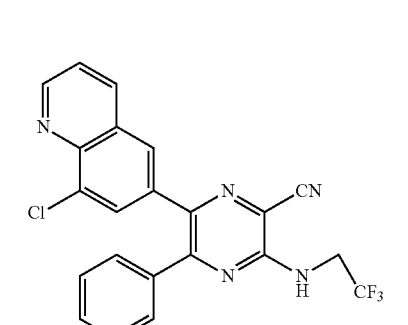
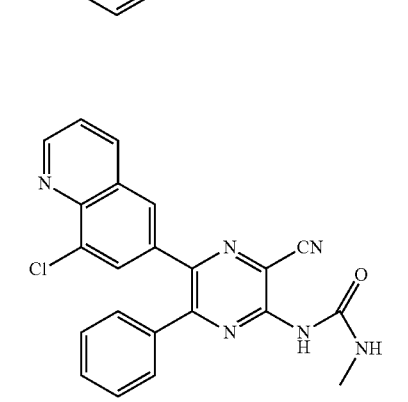
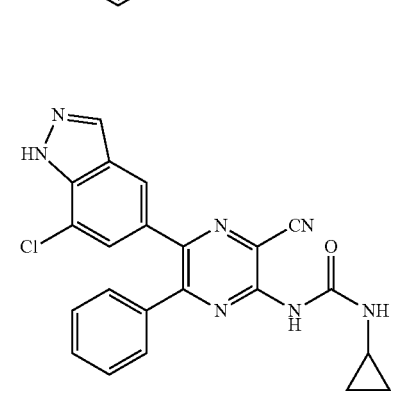

1167
-continued
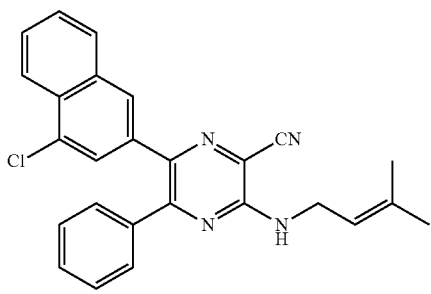
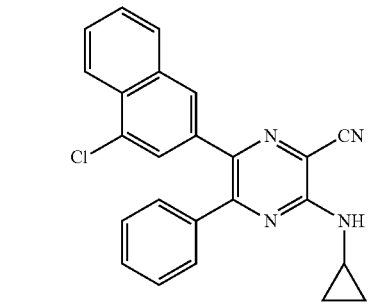
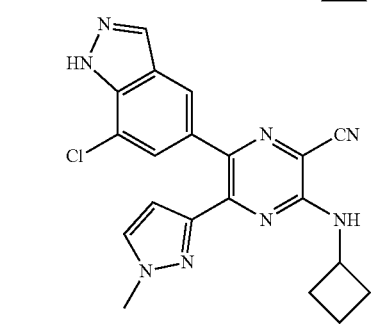
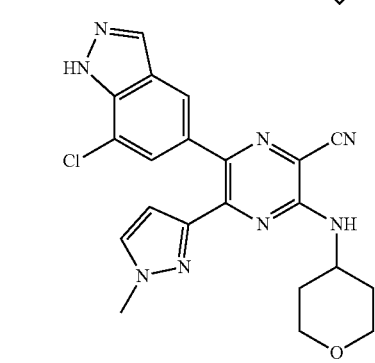
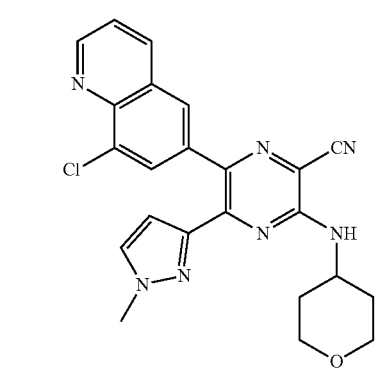
1168
-continued
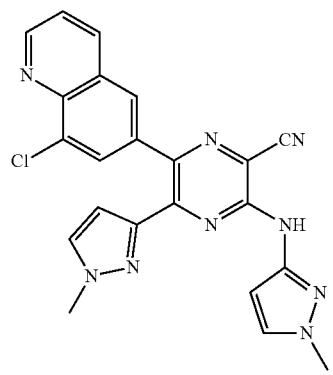
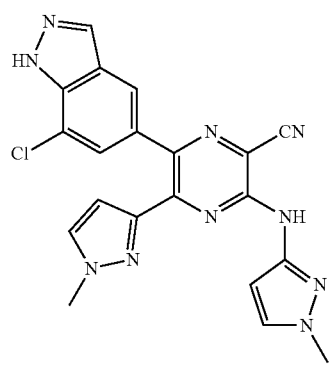
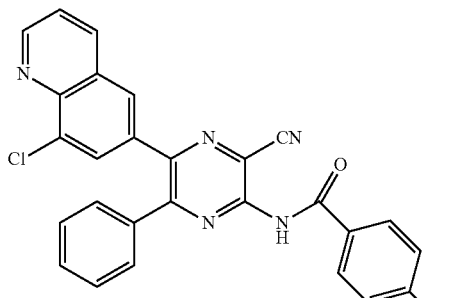
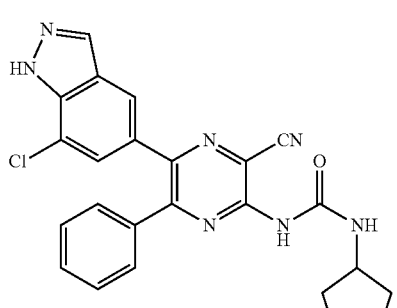
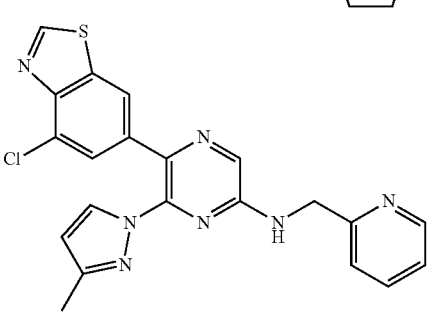

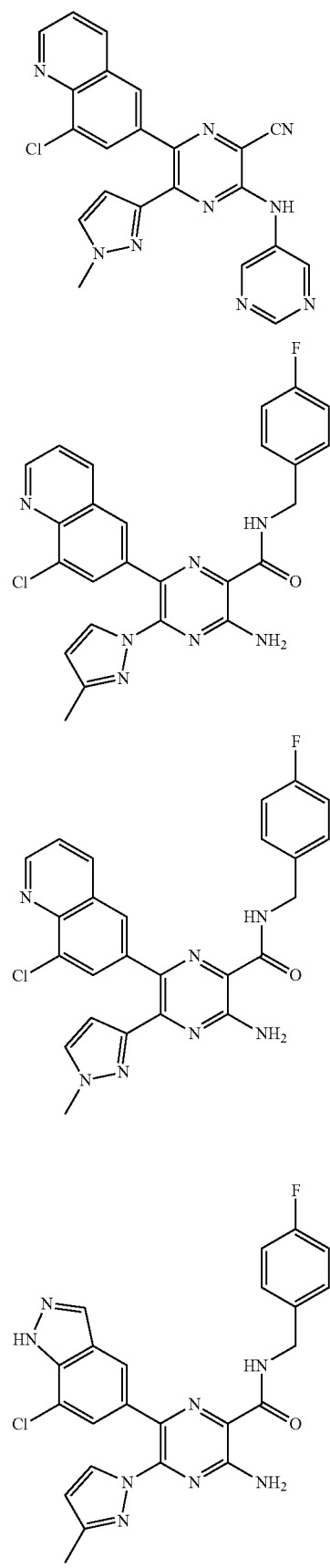
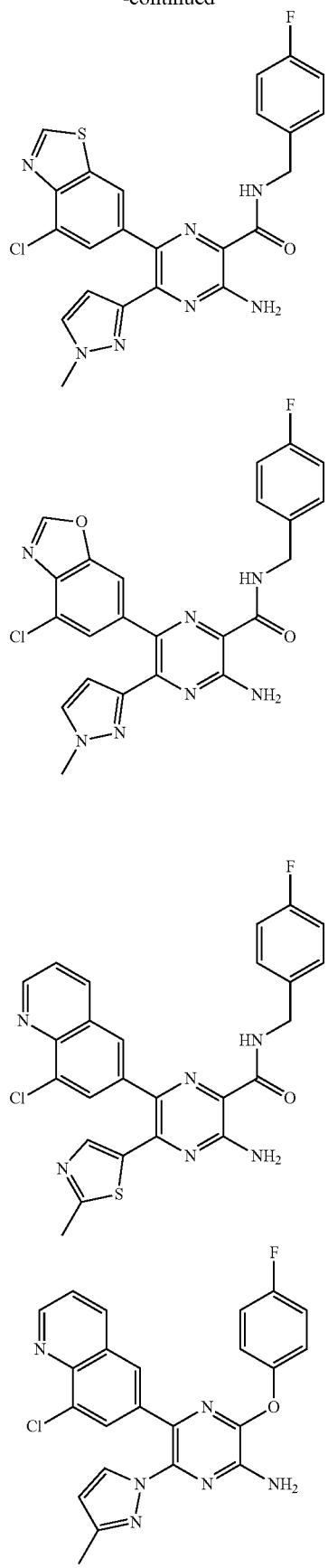

-continued
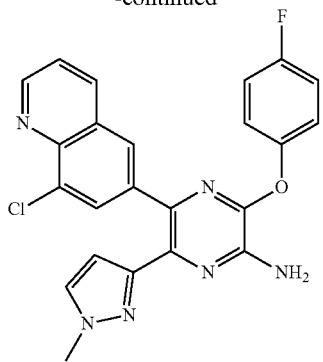
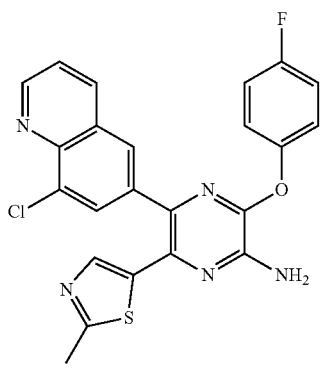
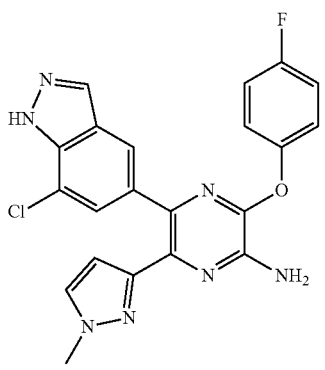
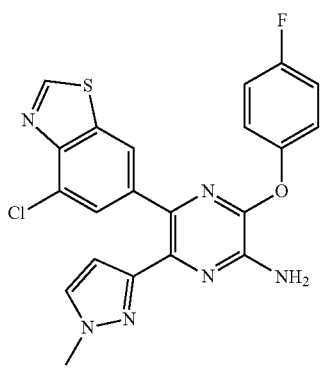
-continued
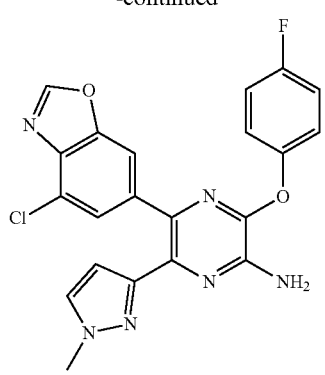
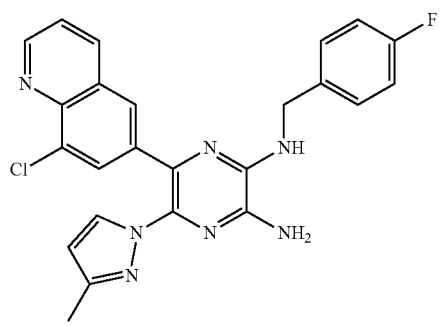
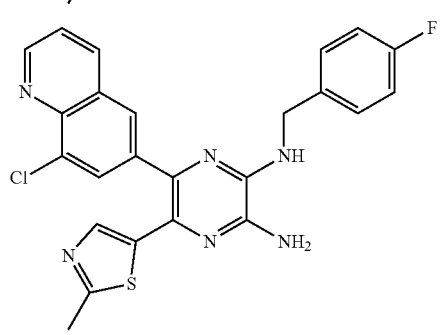

1173
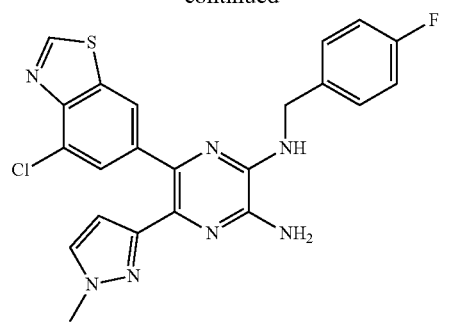
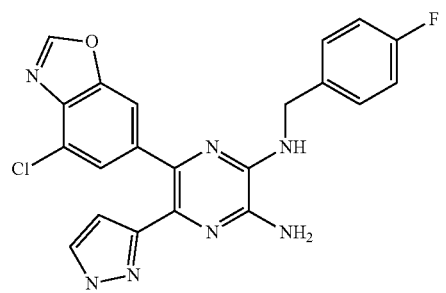
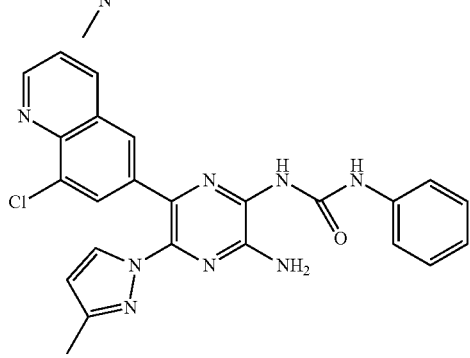
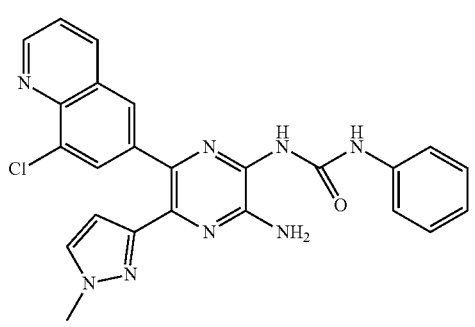
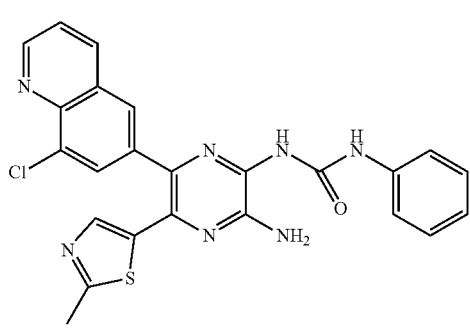
1174
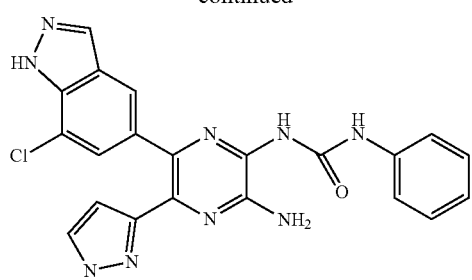
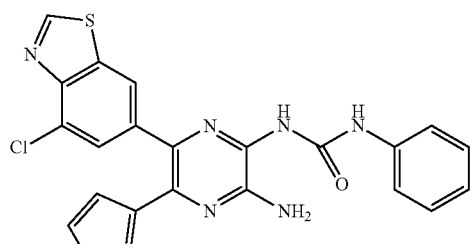
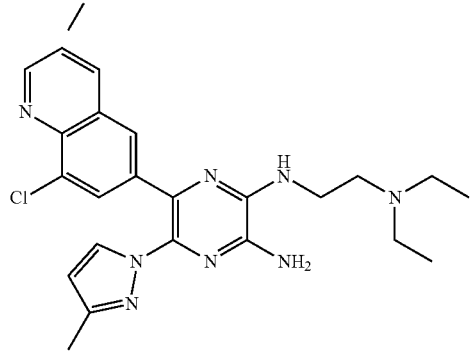
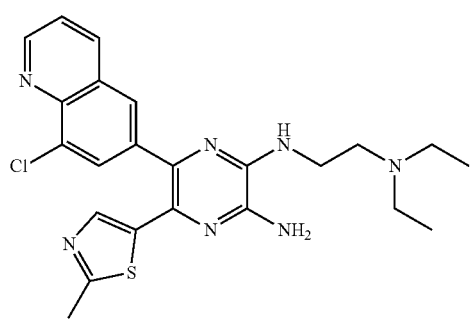
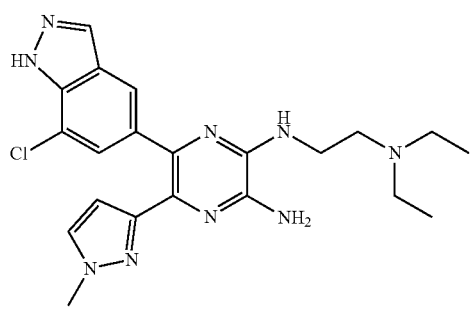

1175
-continued
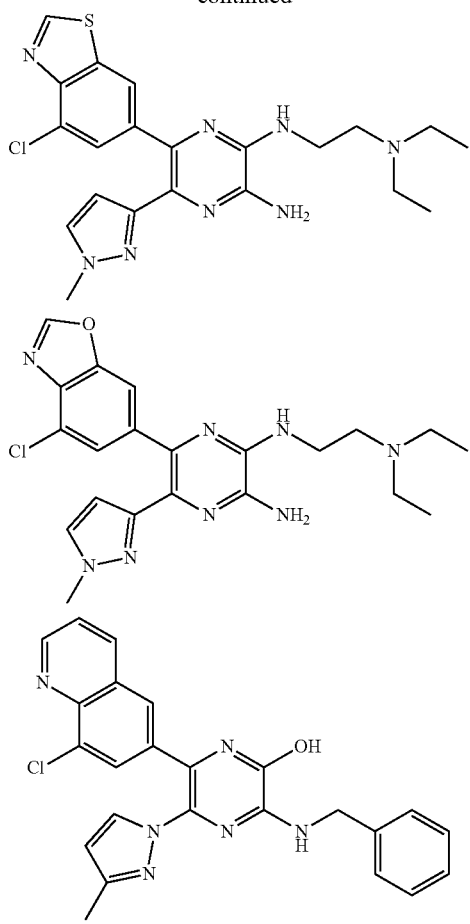
1176
-continued
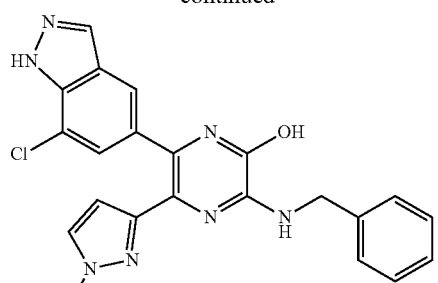
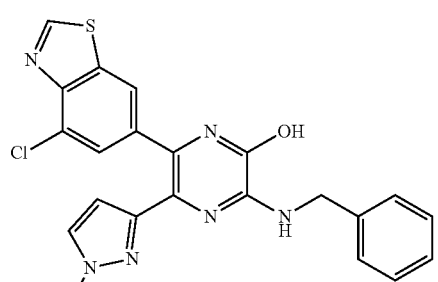
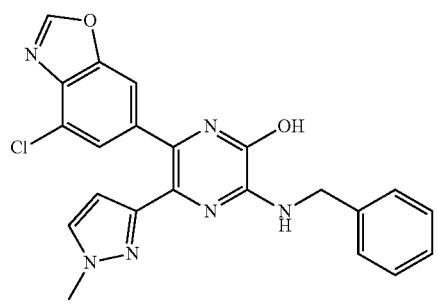
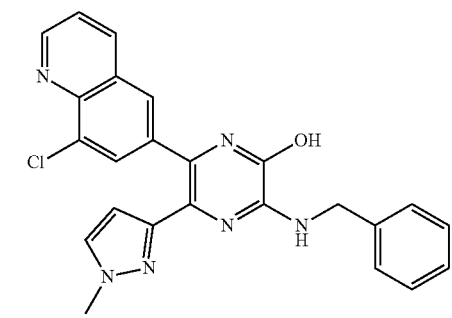
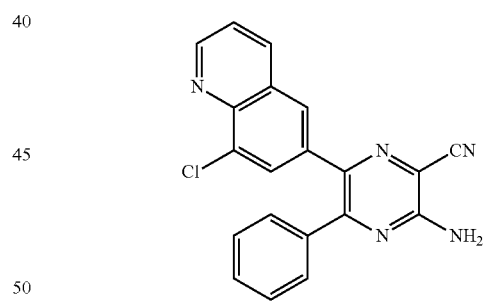
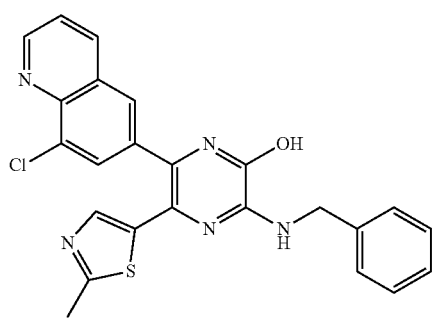
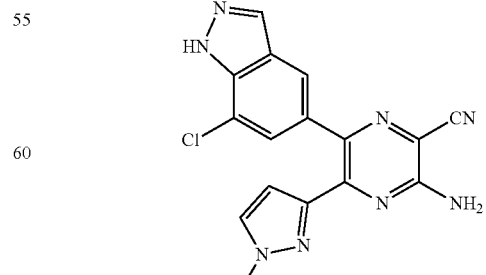

1177
-continued
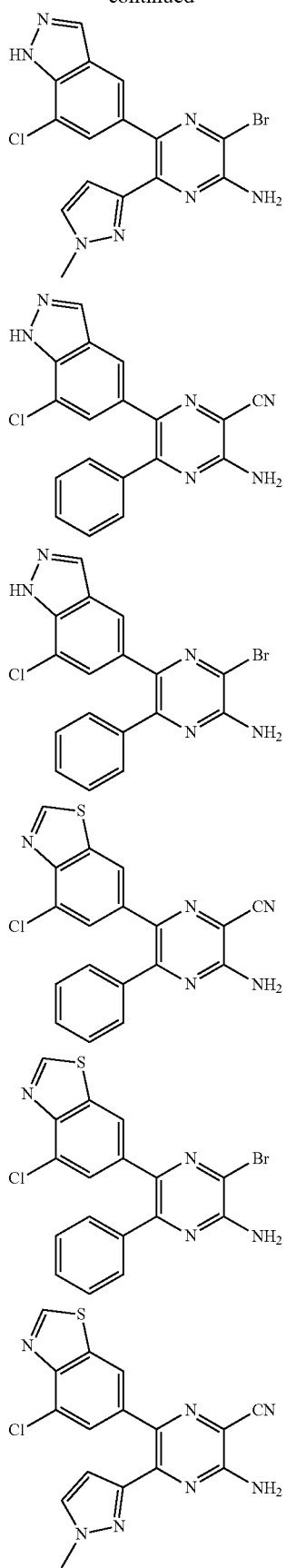
1178
-continued
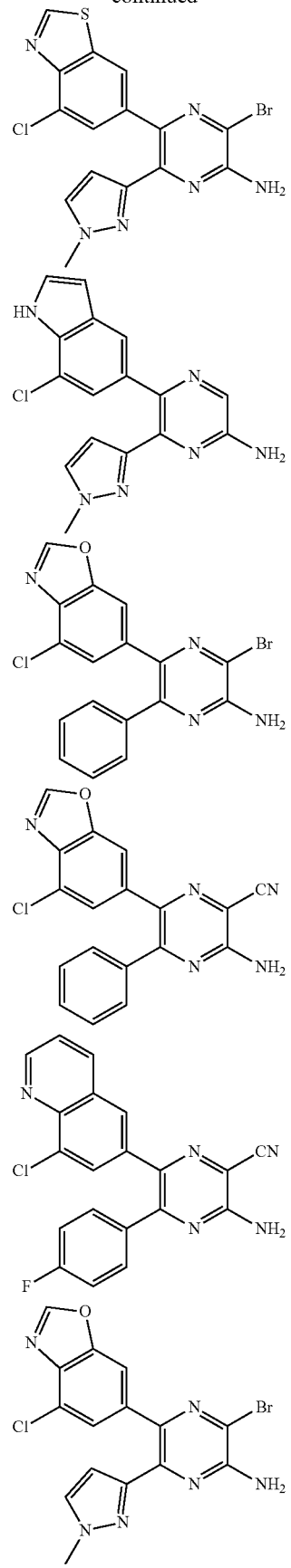

1179
-continued
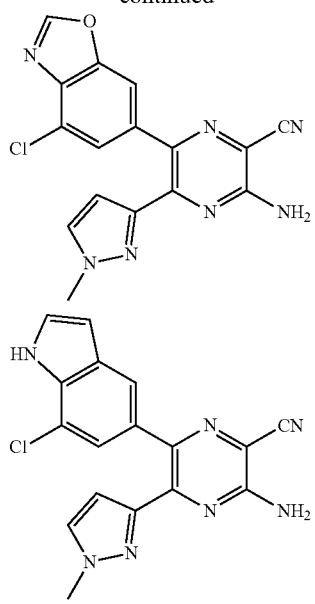
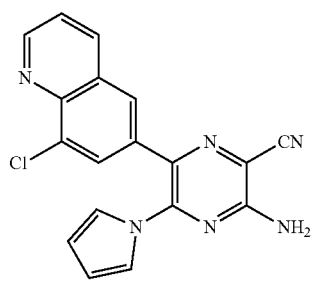
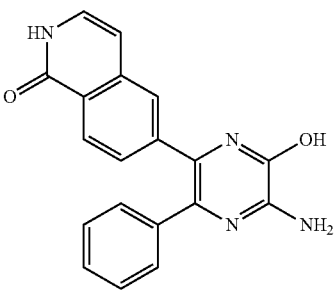
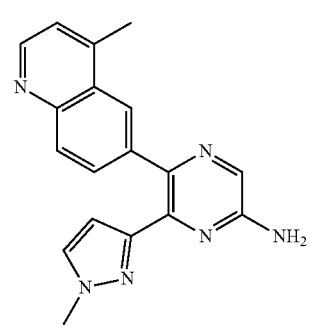
1180
-continued
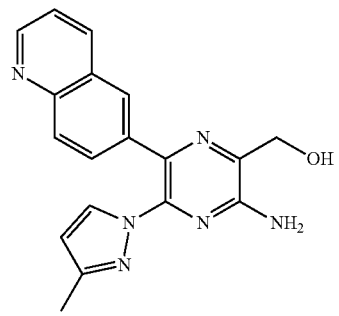
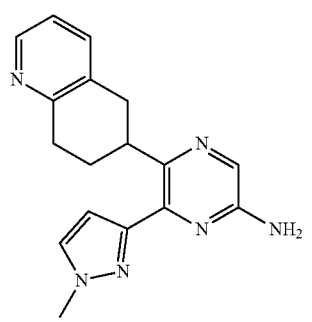
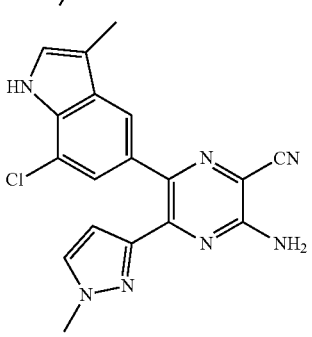
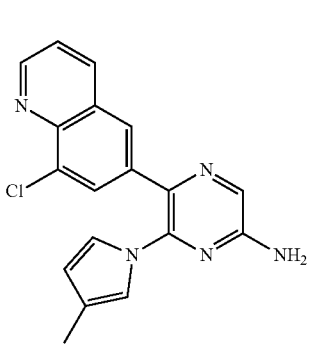
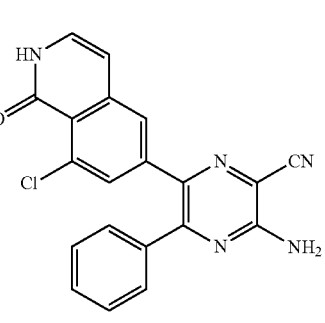

1181
-continued
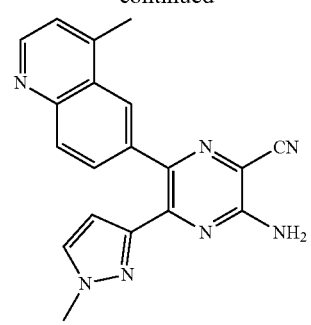
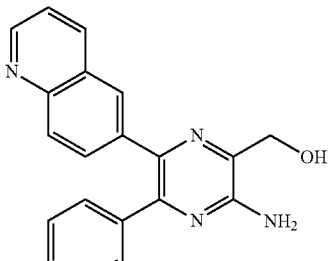
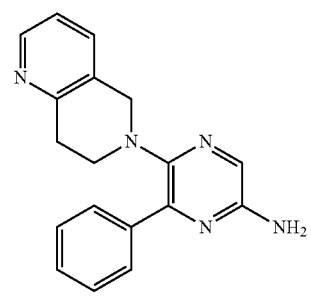
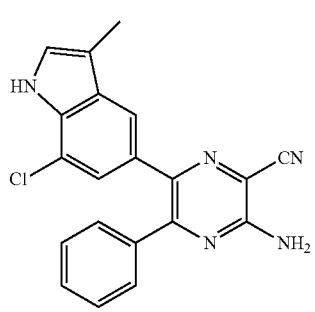
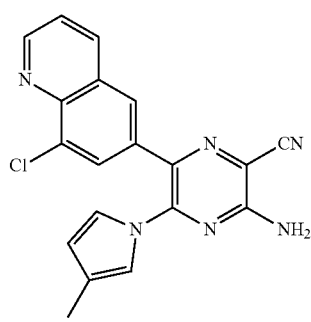
1182
-continued
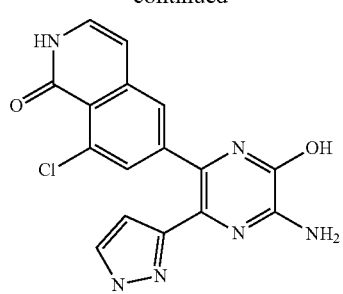
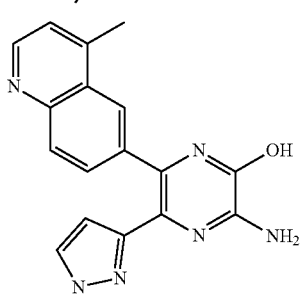
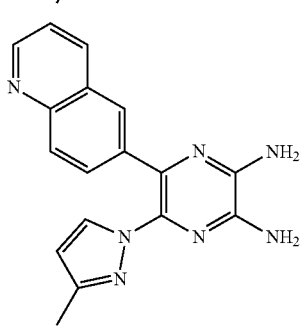
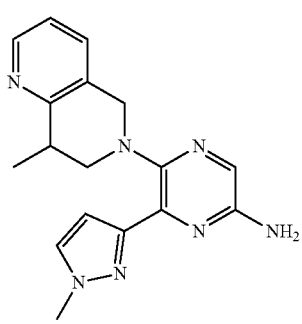
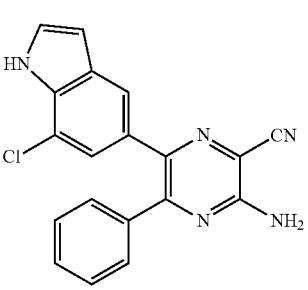

1183
-continued
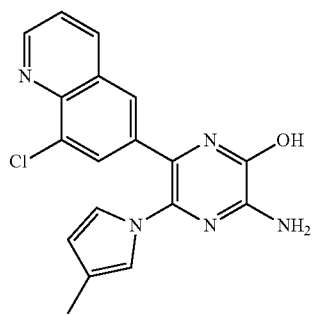
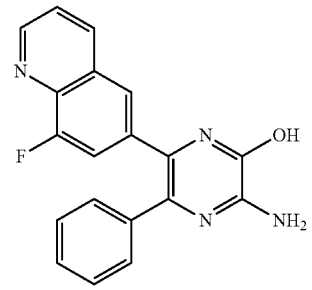
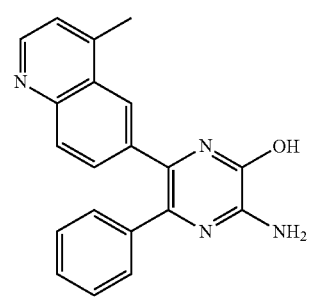
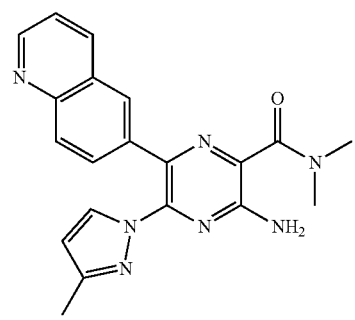
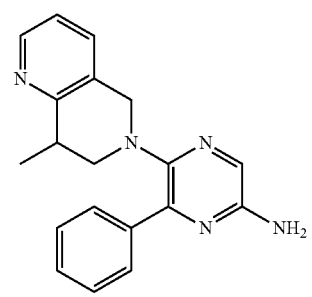
1184
-continued
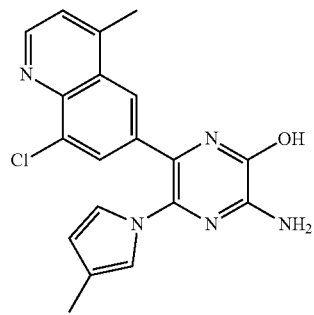
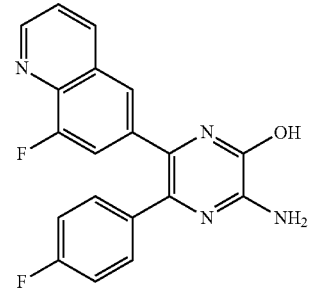
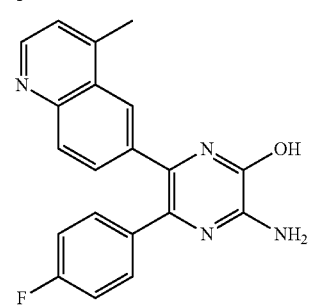
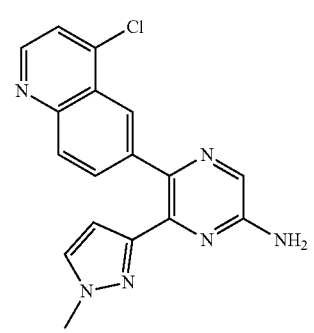
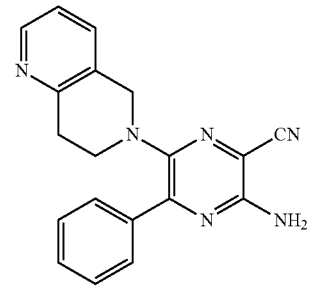

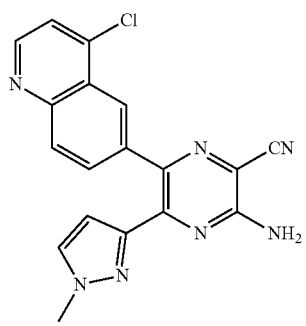
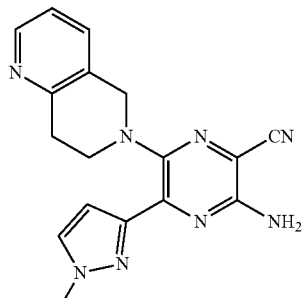
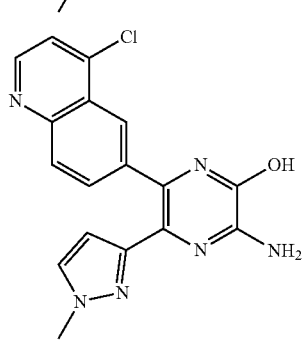
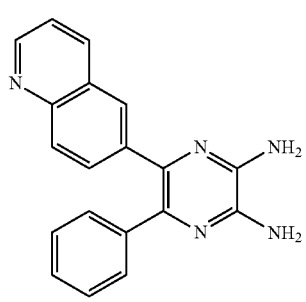
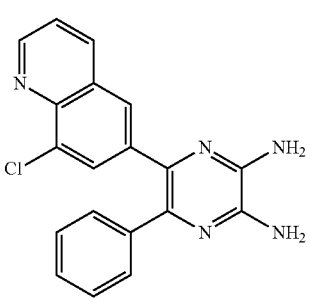
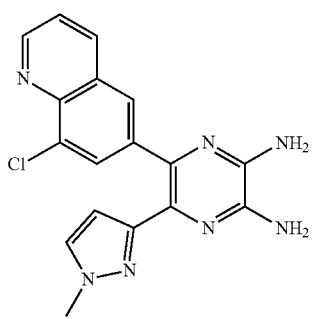
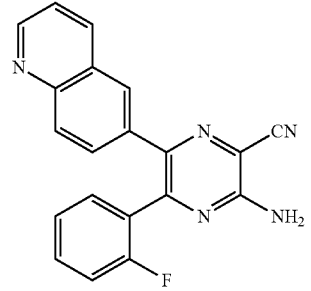
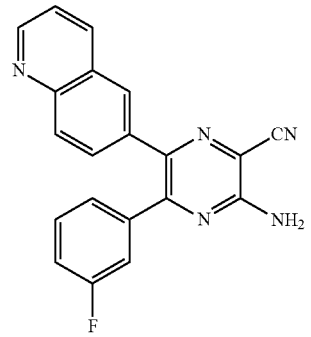
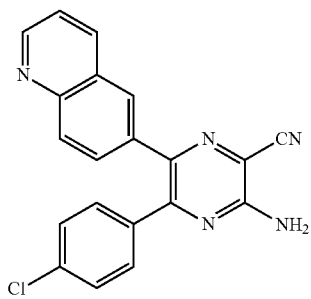
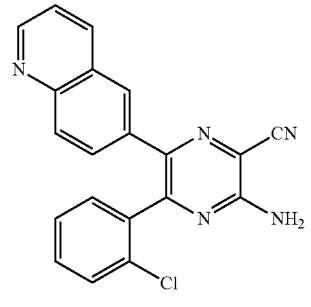

1187
-continued
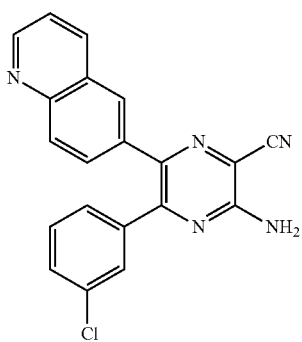
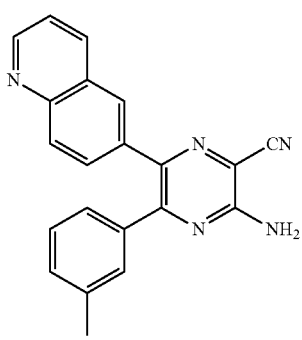
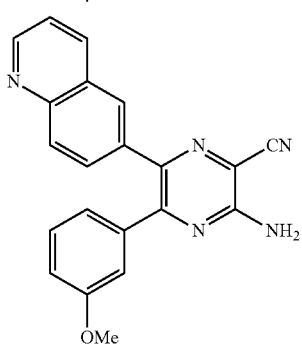
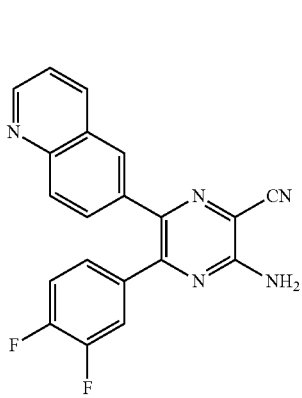
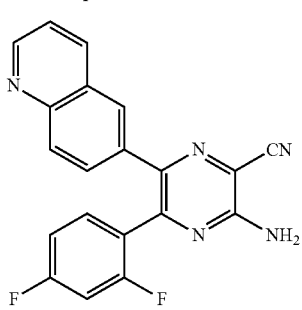
1188
-continued
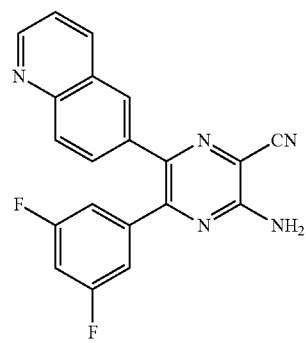
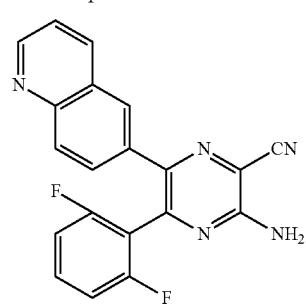
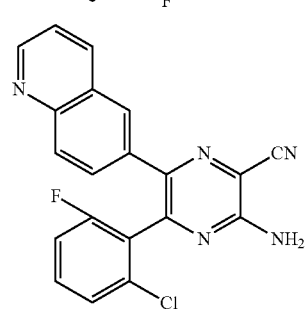
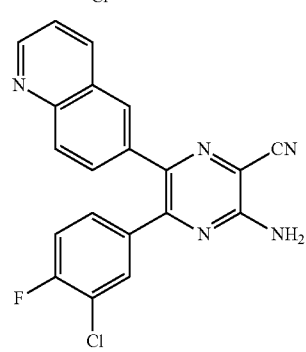

1189
-continued
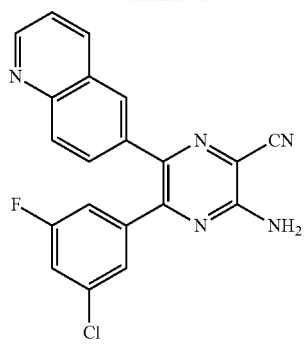
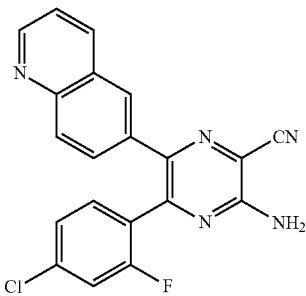
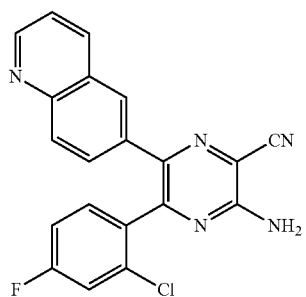
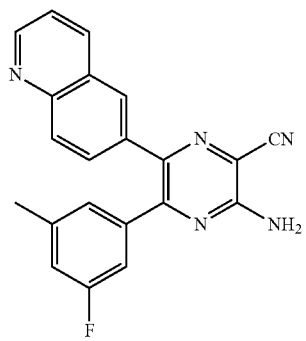
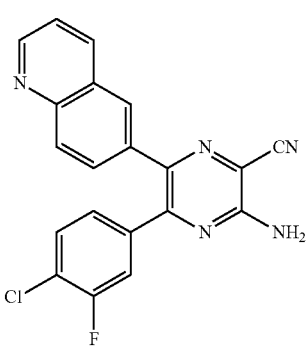
1190
-continued
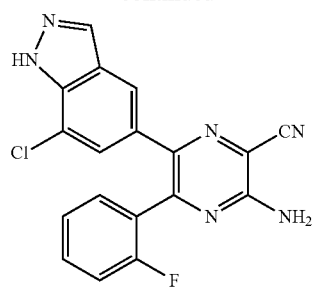
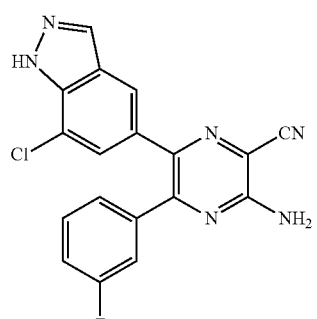
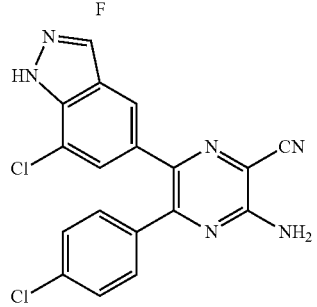
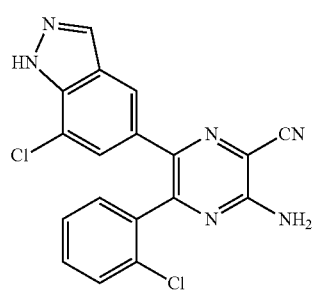
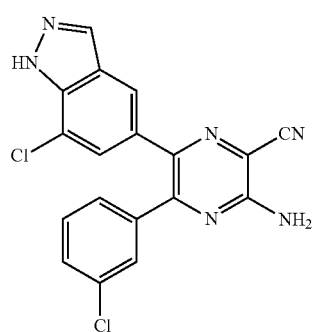

1191
-continued
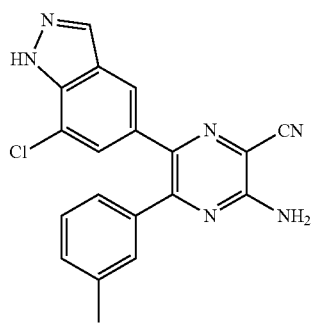
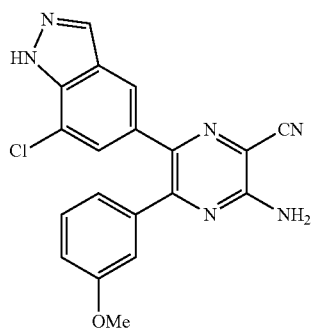
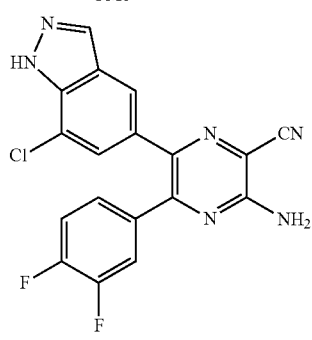
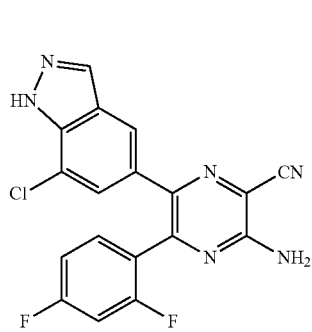
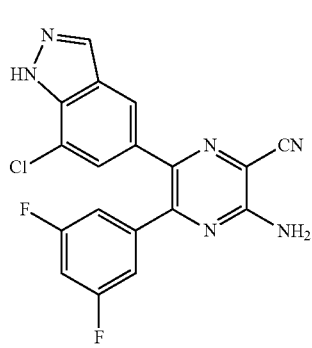
1192
-continued
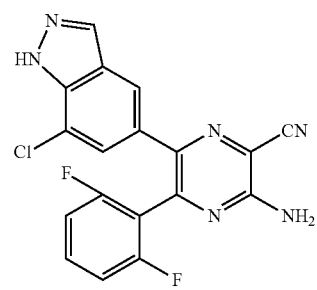
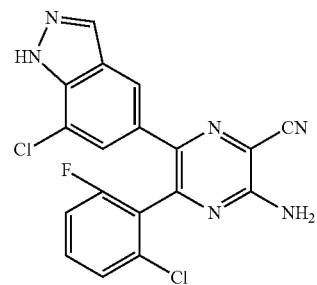
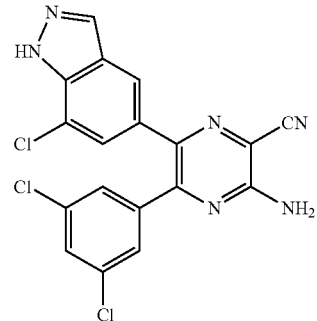
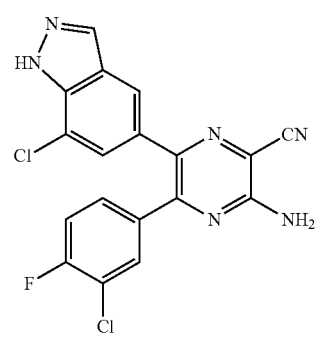
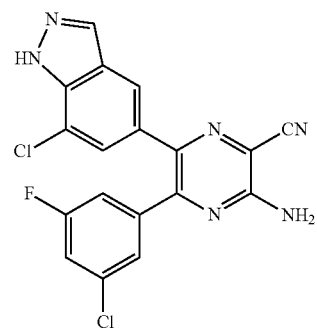

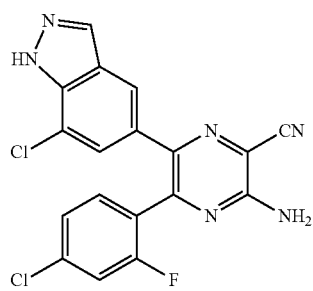
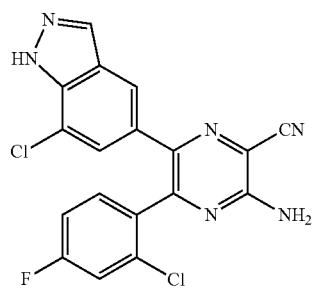
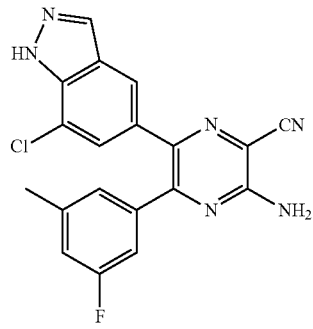
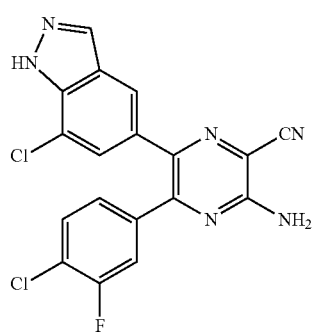
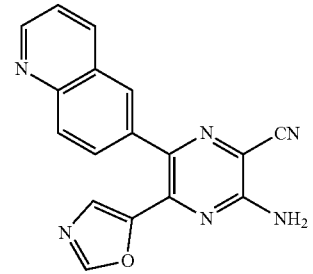
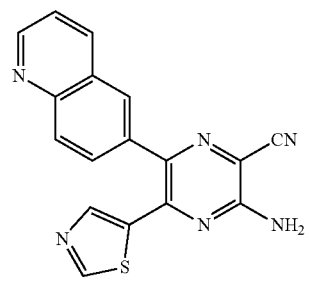
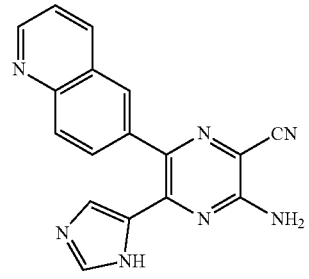
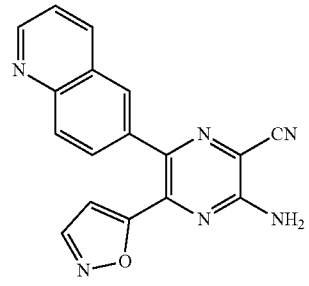
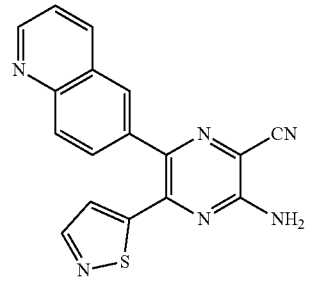
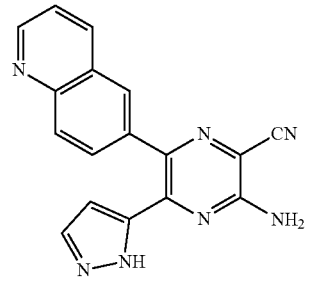
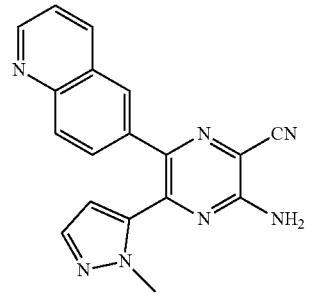

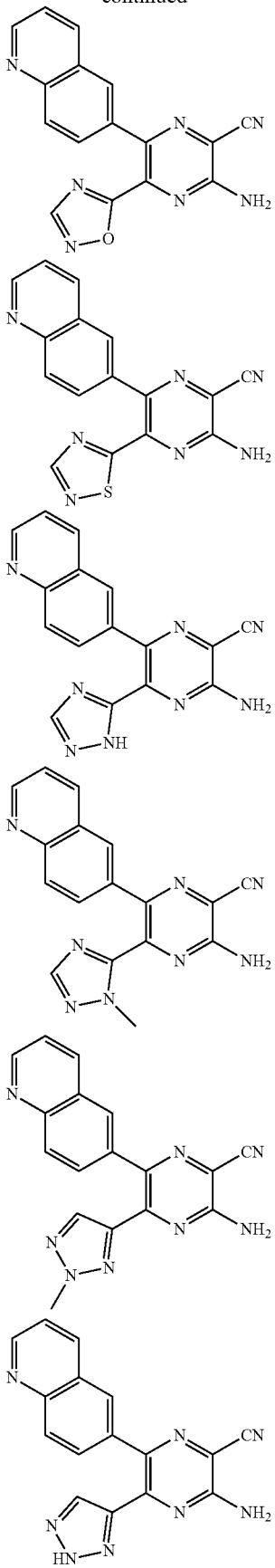
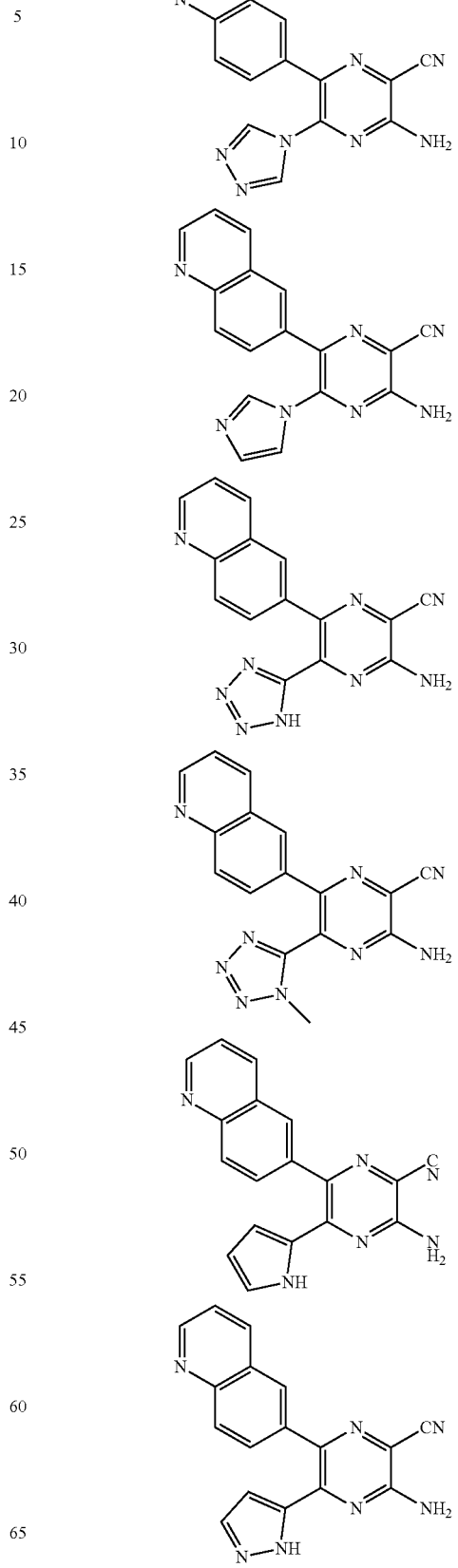

-continued
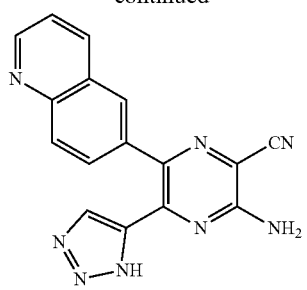
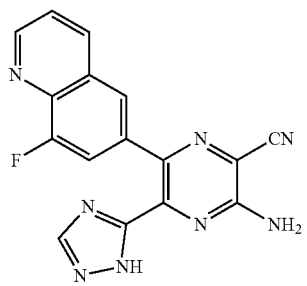
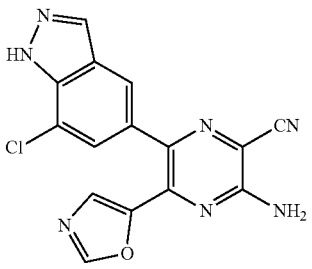
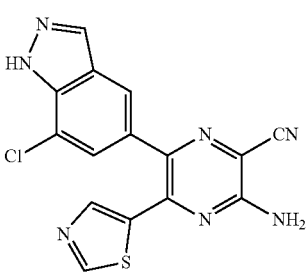
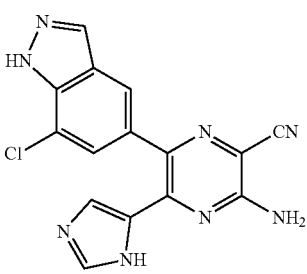
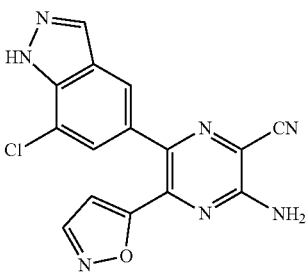
-continued
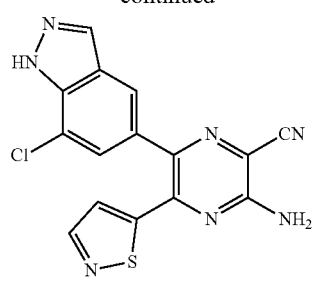
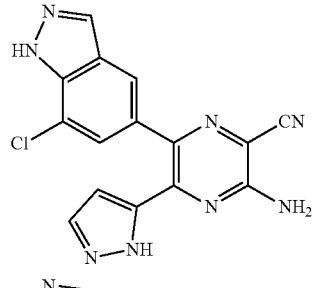
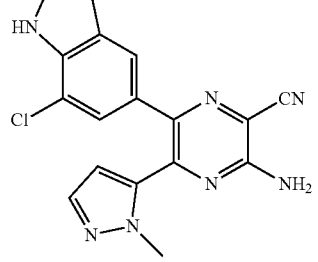
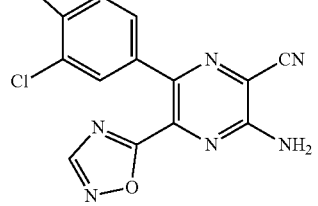
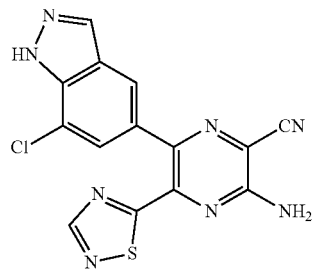
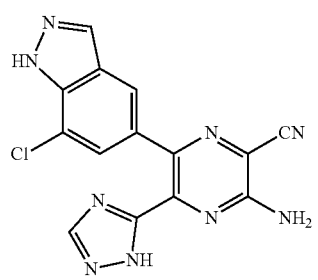

1199
-continued
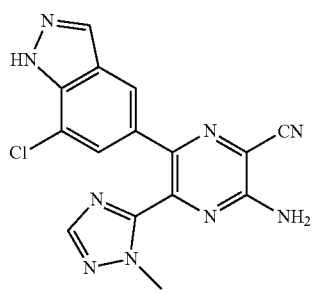
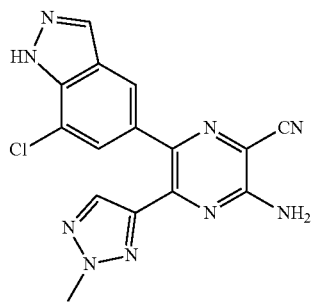
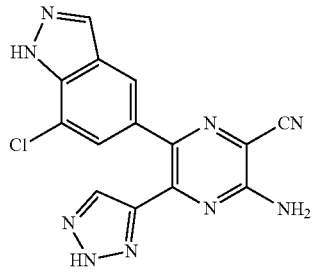
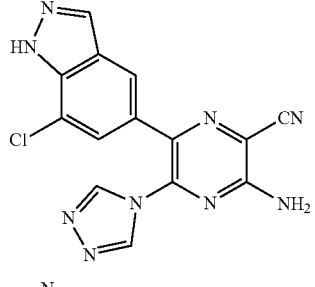
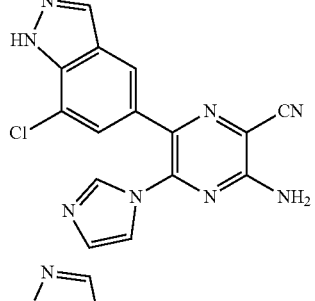
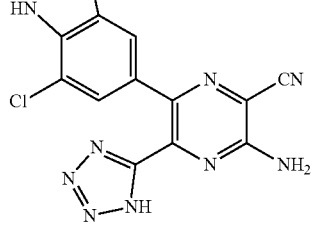
1200
-continued
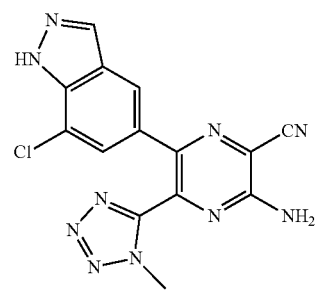
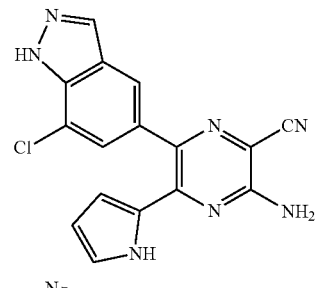
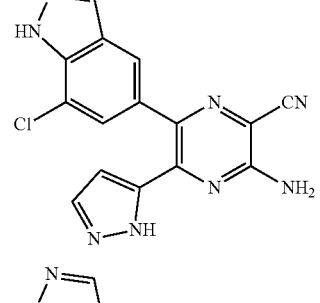
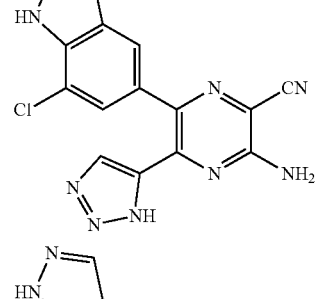
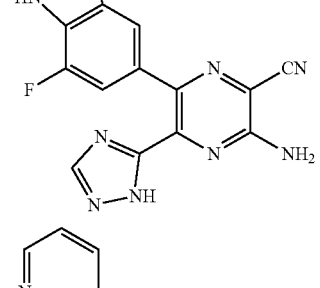
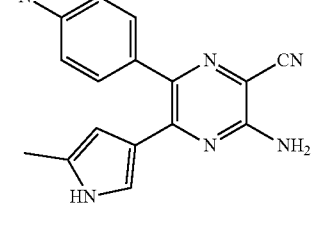

1201
-continued
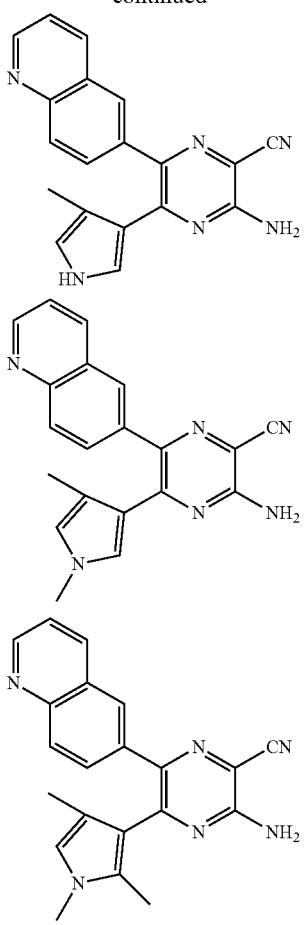
1202
-continued
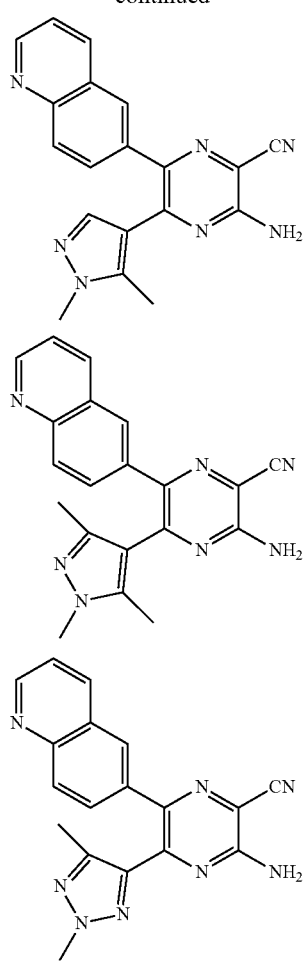
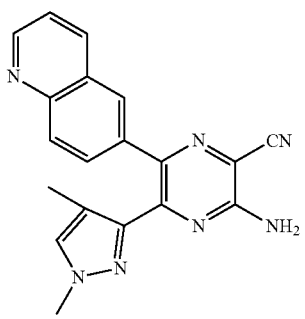
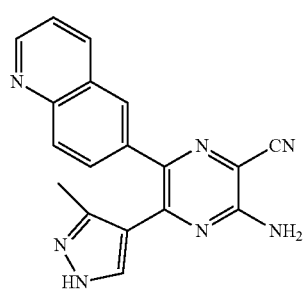
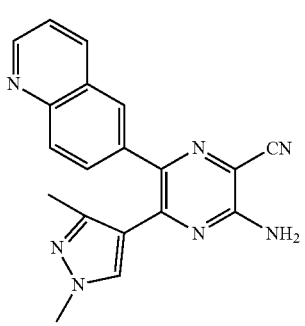
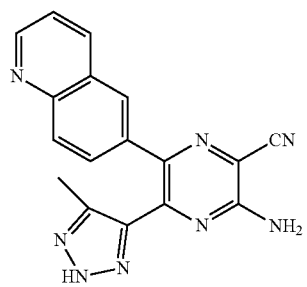

1203
-continued
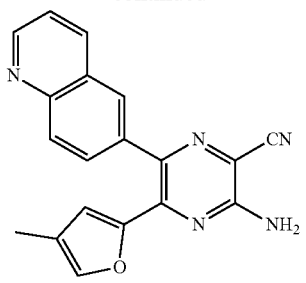
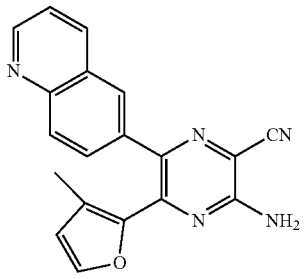
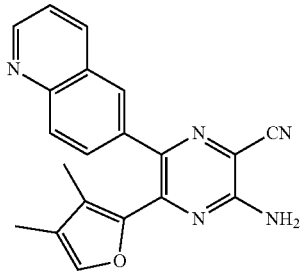
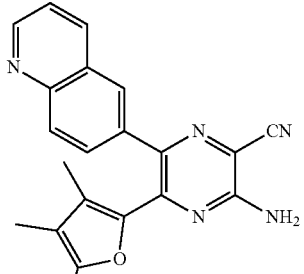
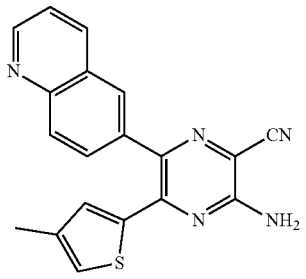
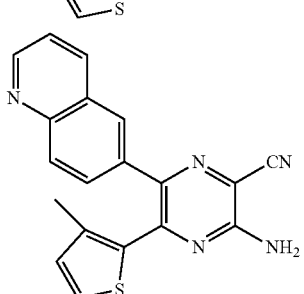
1204
-continued
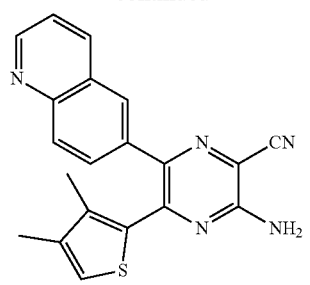
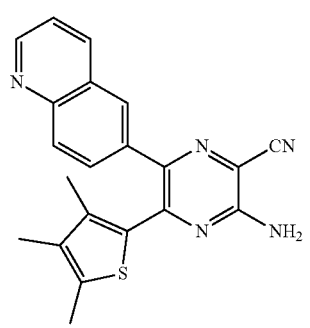
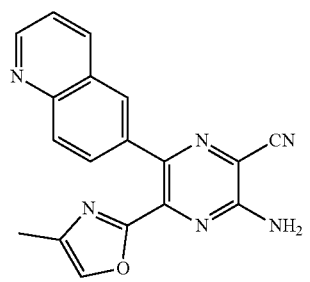
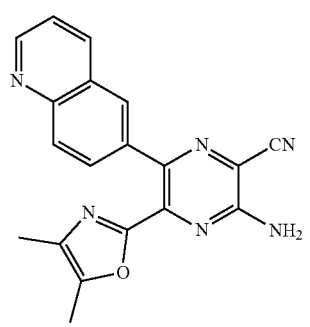
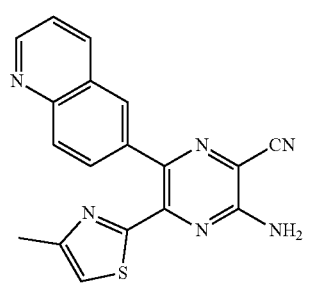

1205
-continued
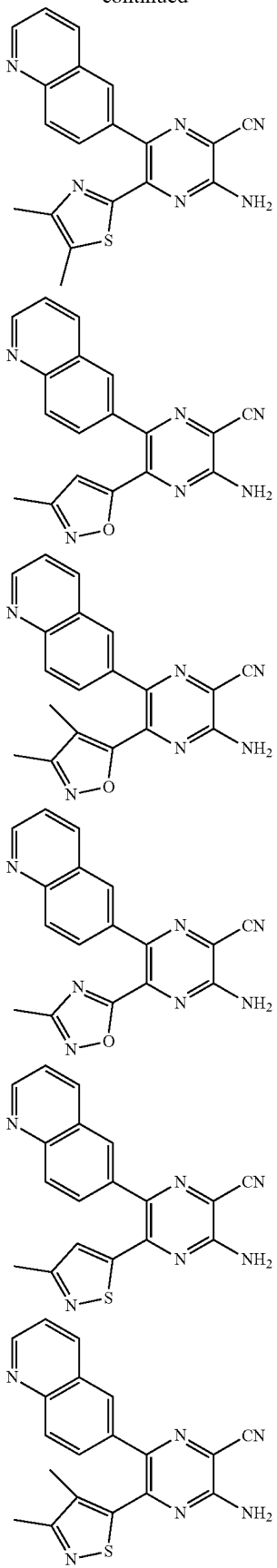
1206
-continued
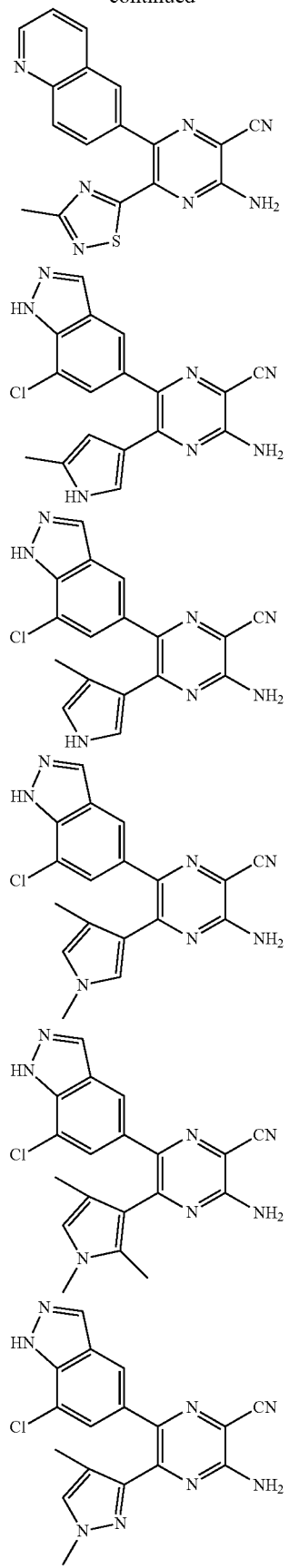

1207
-continued
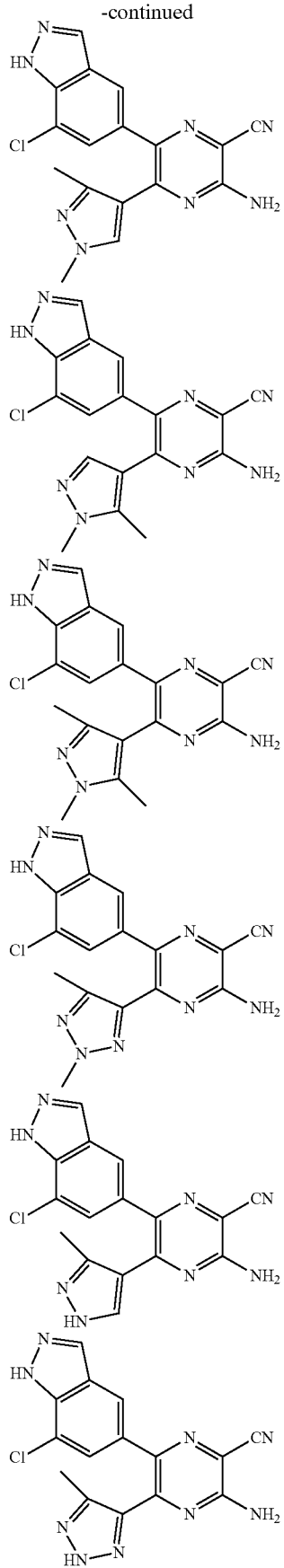
1208
-continued
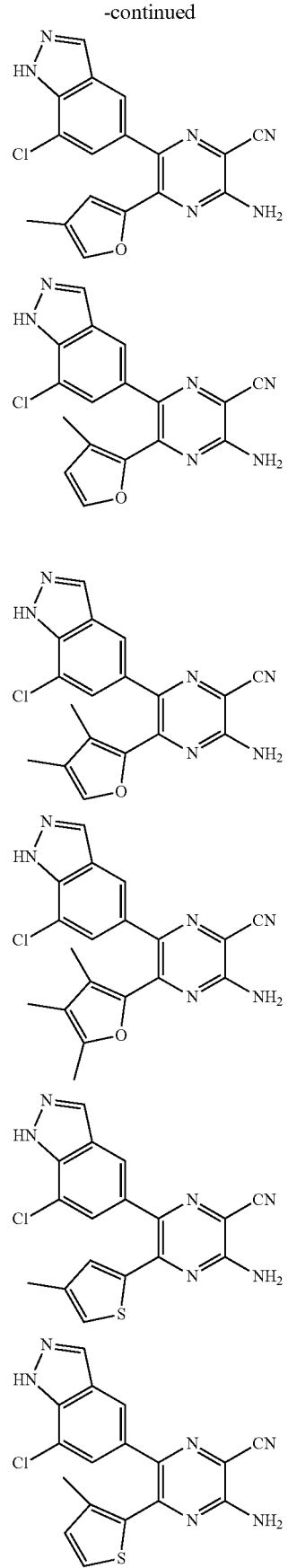

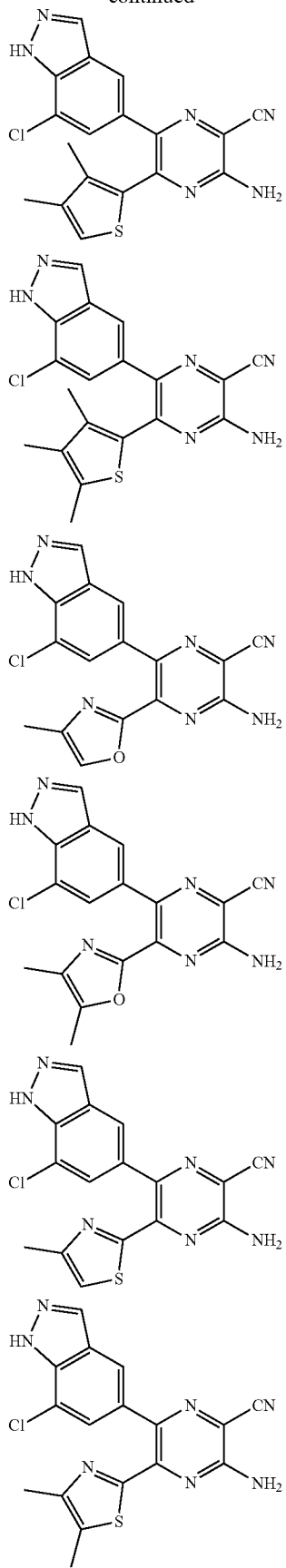
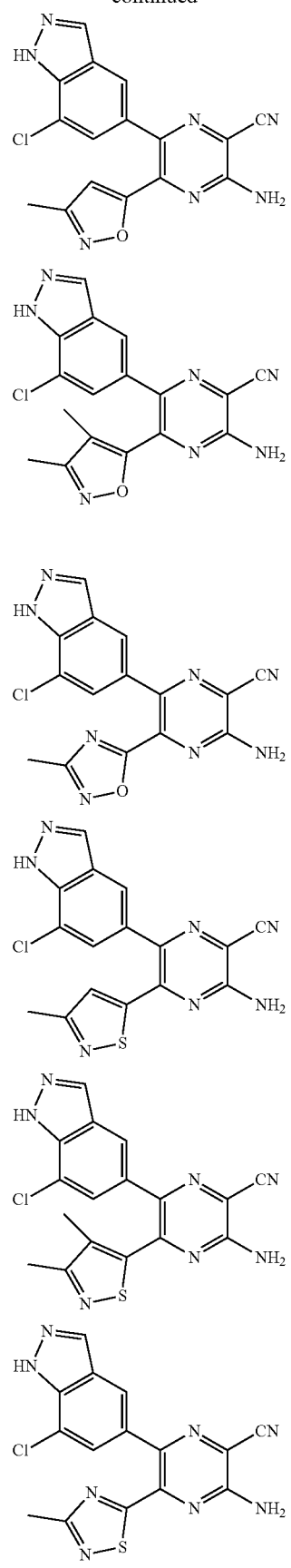

1211
-continued
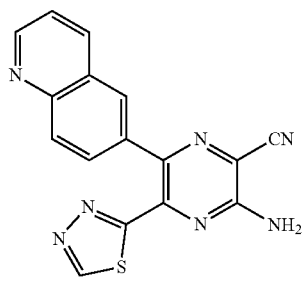
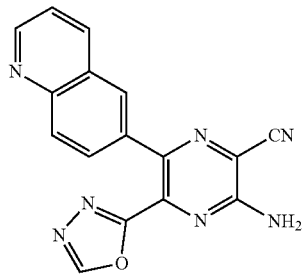
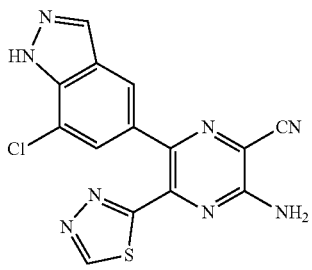
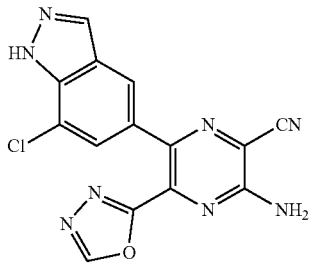
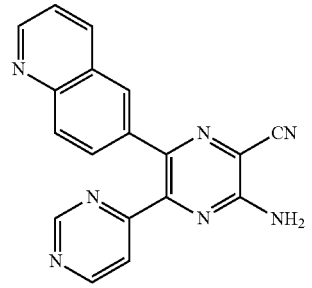
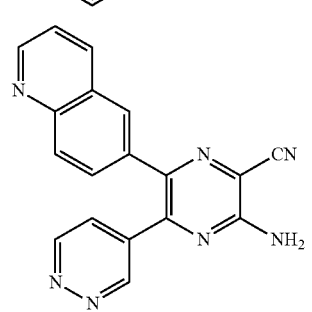
1212
-continued
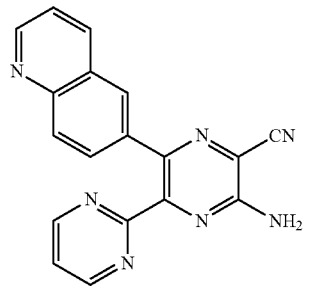
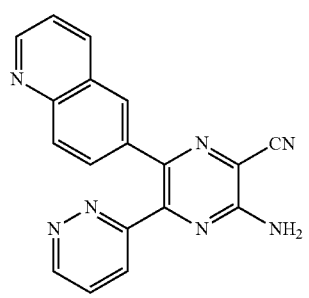
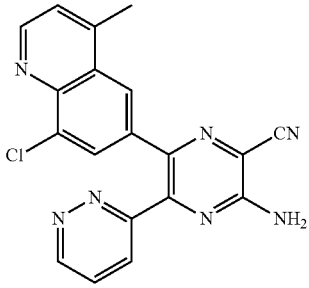
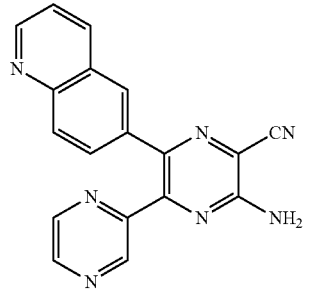
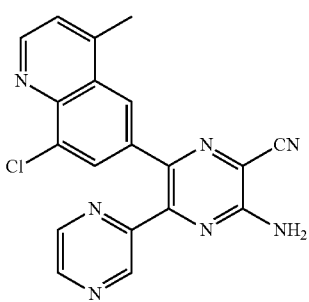

1213
-continued
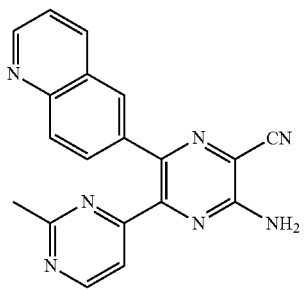
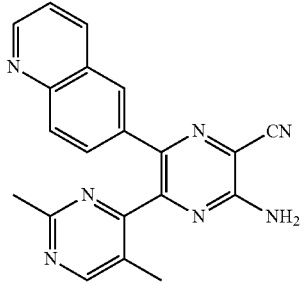
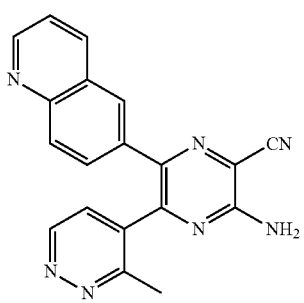
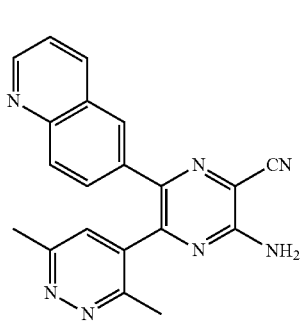
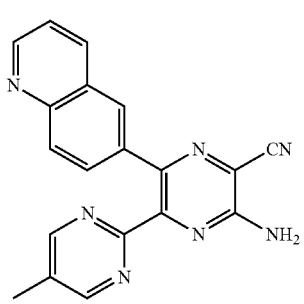
1214
-continued
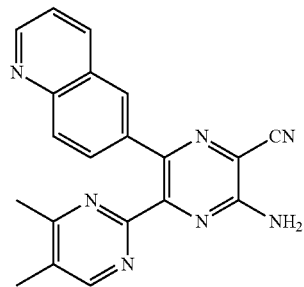
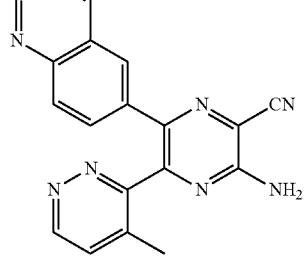
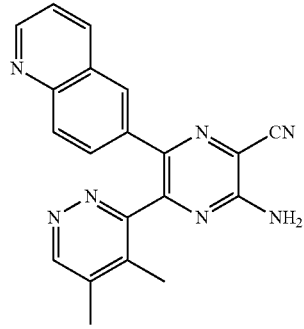
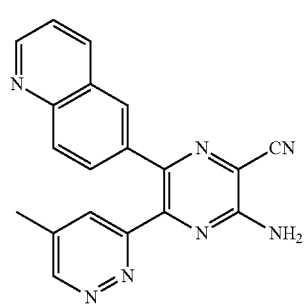
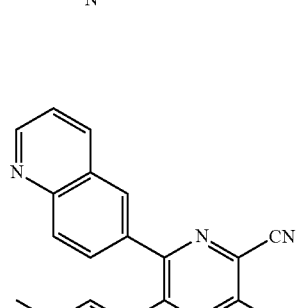

1215
-continued
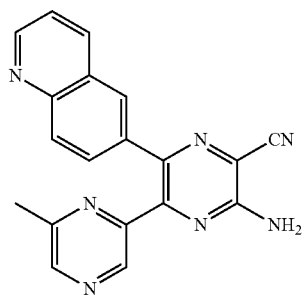
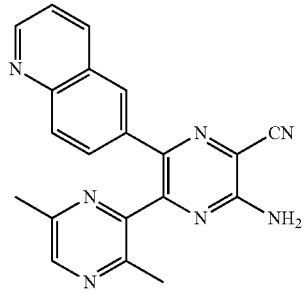
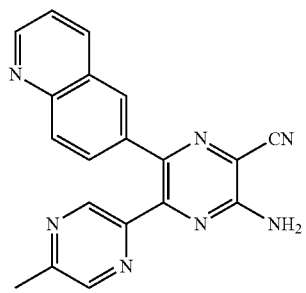
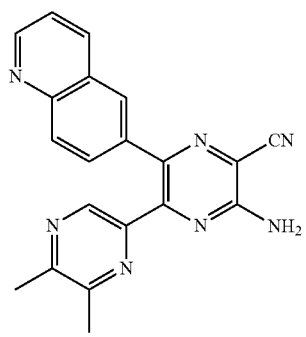
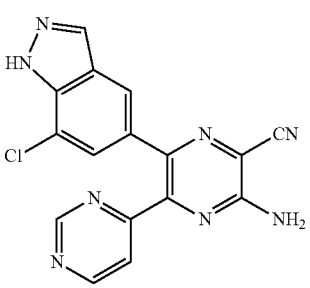
1216
-continued
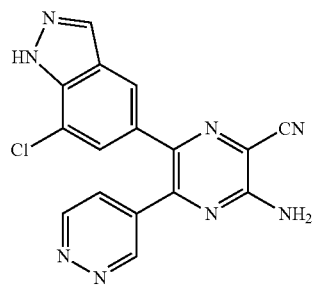
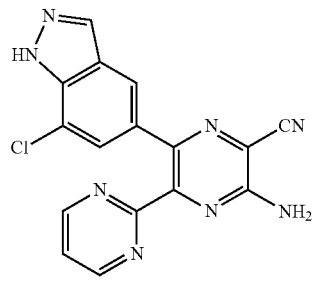
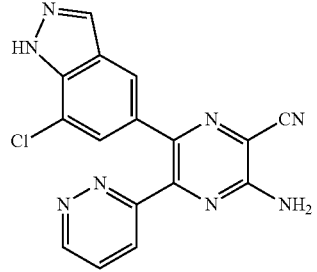
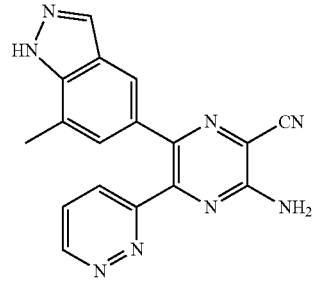
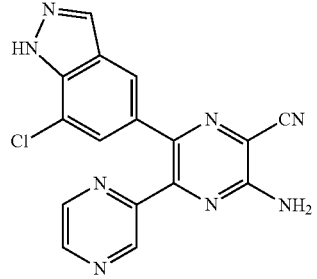
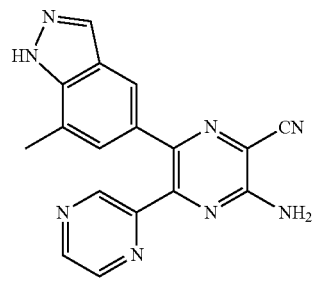

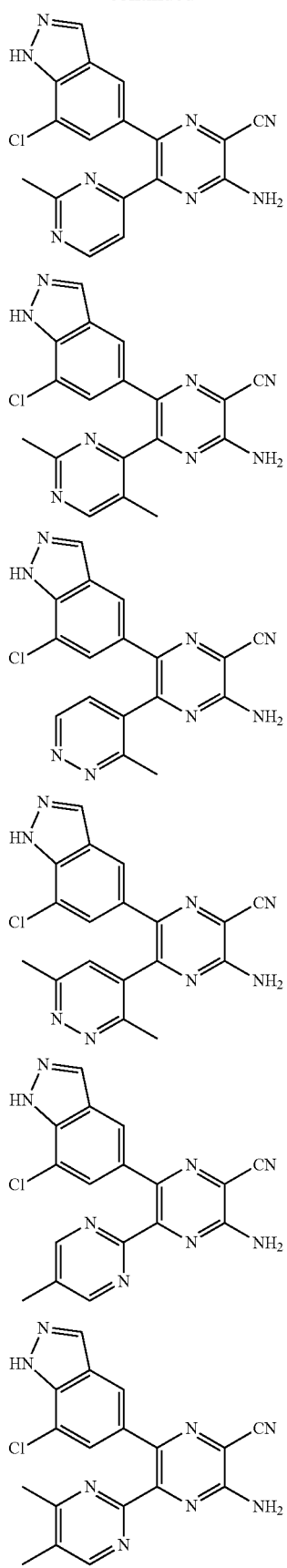
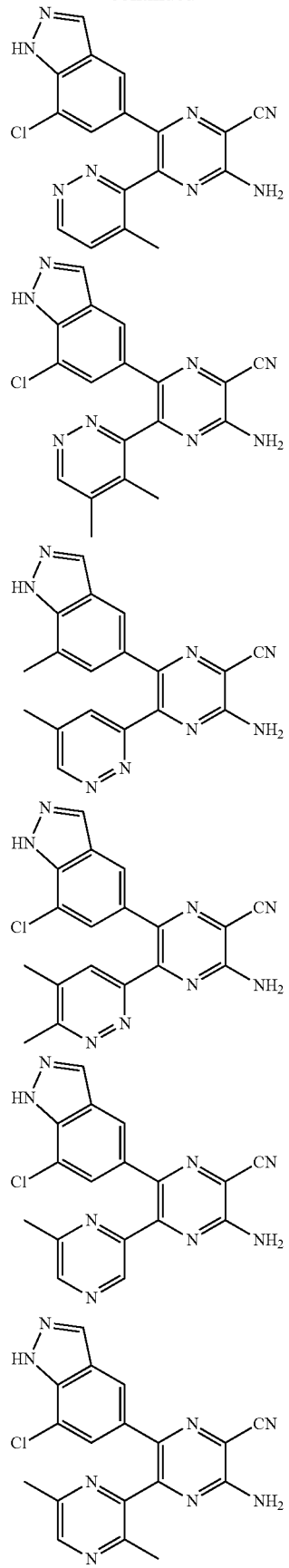

1219
-continued
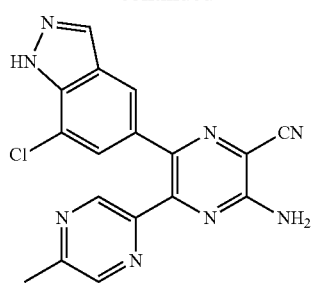
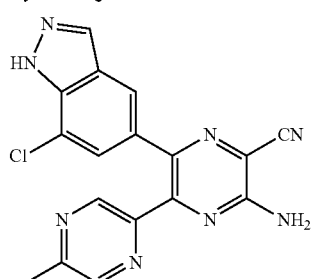
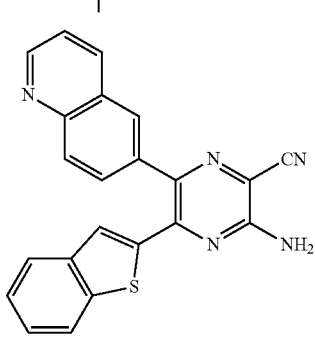
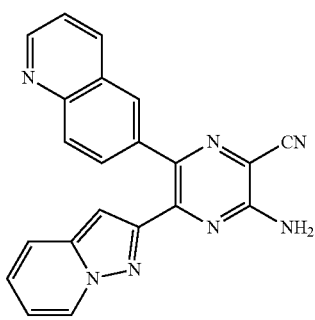
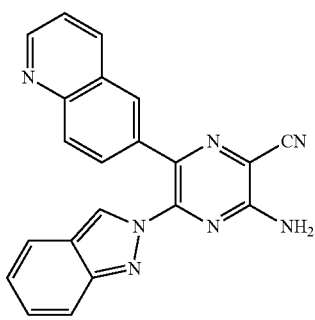
1220
-continued
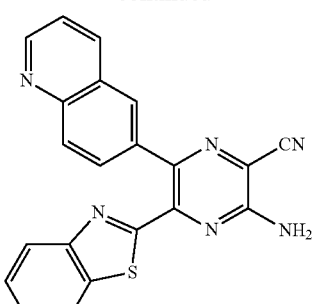
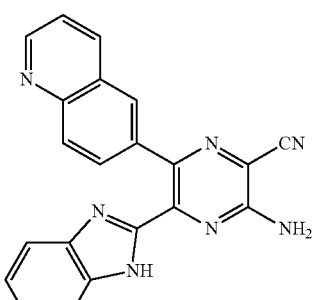
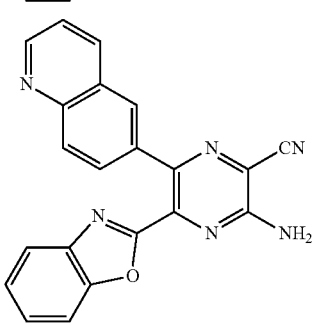
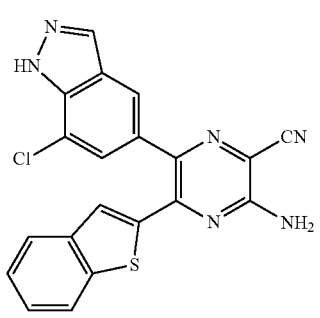
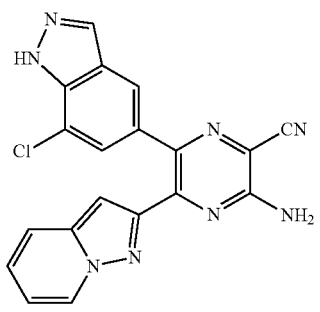

1221
-continued
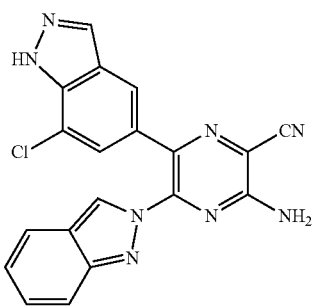
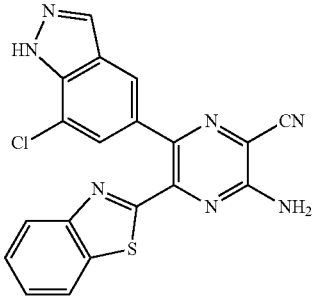
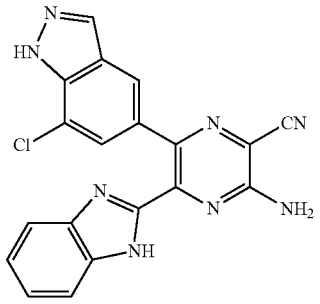
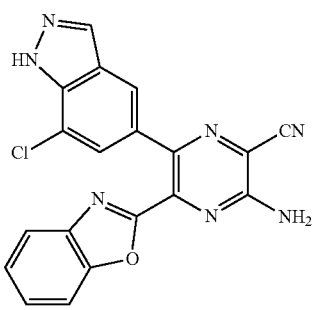
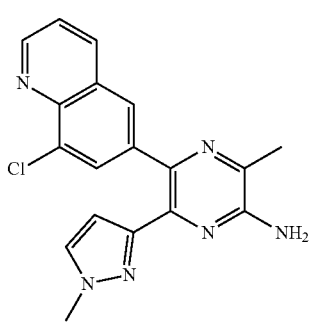
1222
-continued
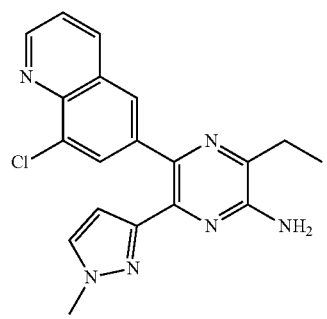
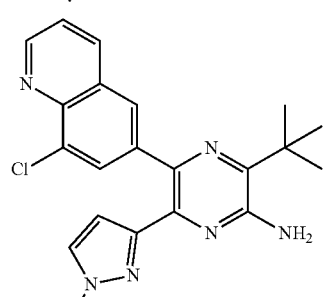
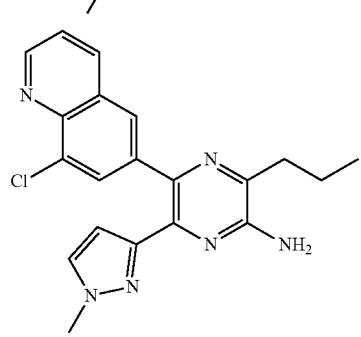
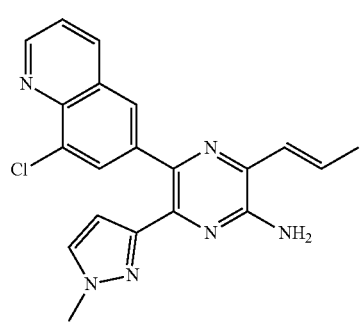
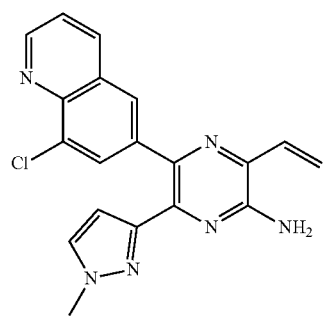

1223
-continued
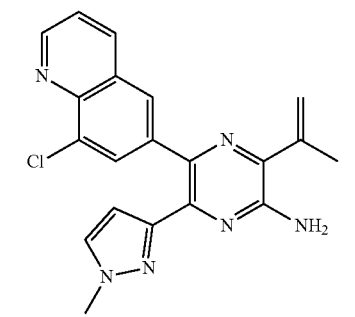
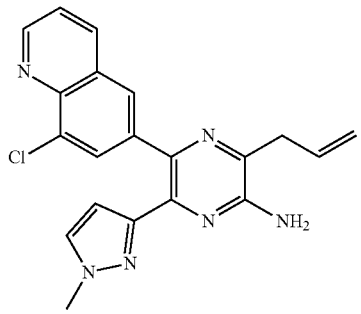
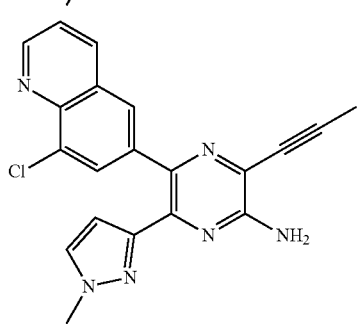
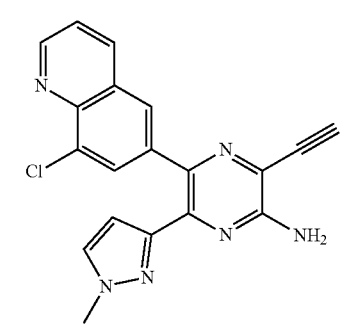
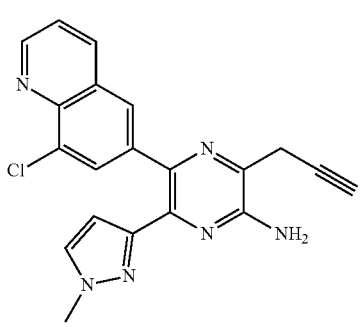
1224
-continued
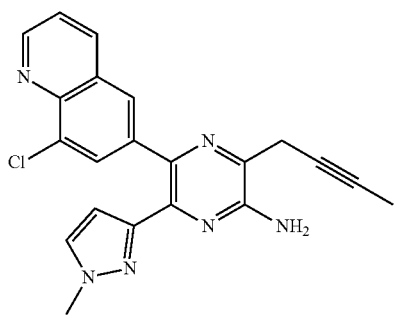
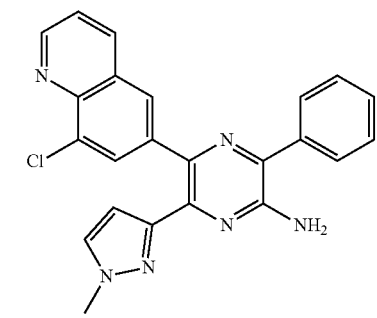
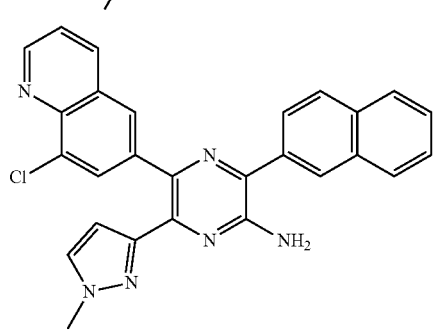
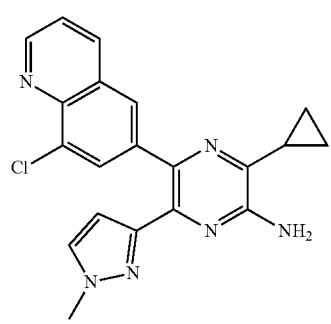
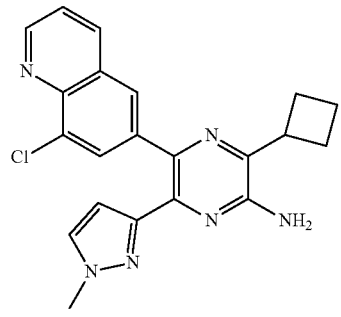

| 1225 -continued | 1226 -continued |
|---|---|
| 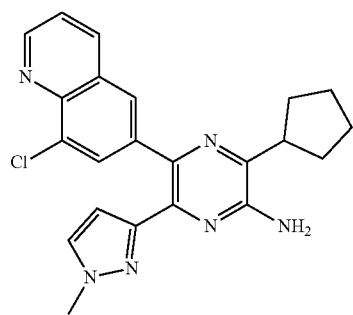 | 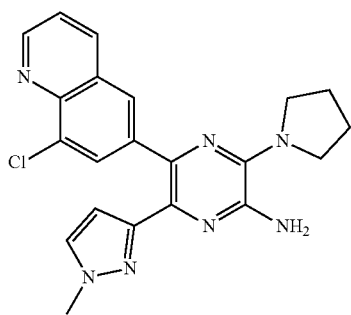 |
| 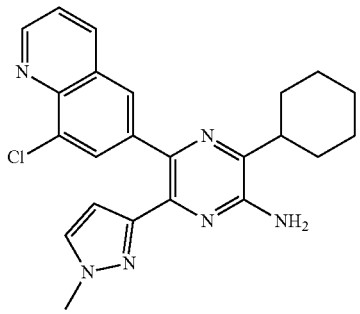 | 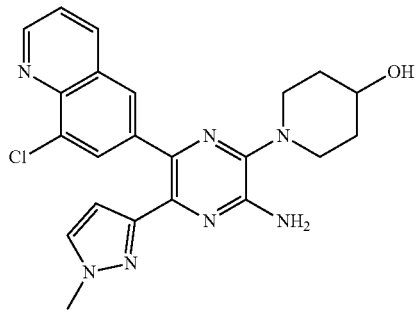 |
| 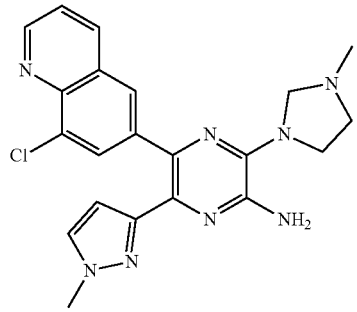 | 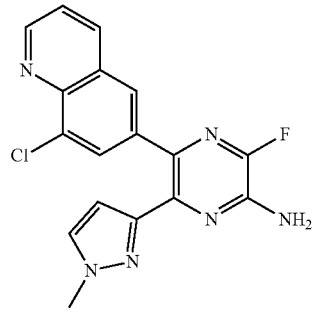 |
| 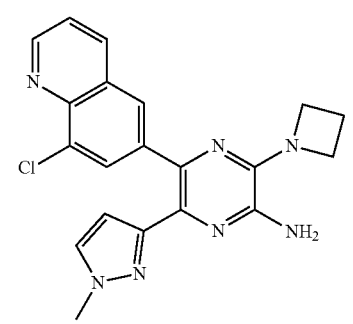 | 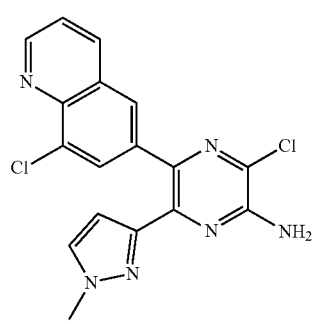 |
| 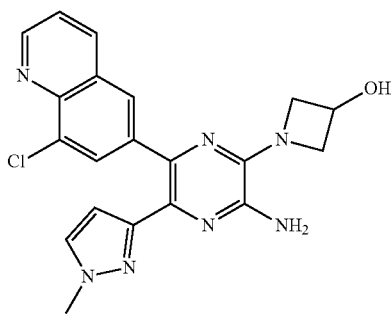 | 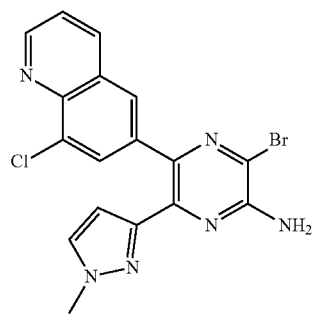 |

1227
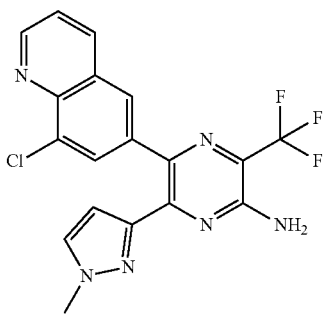
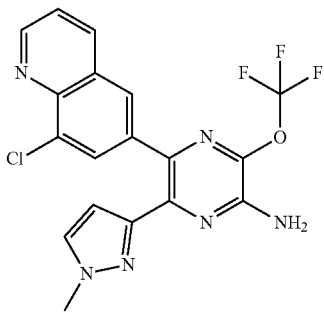
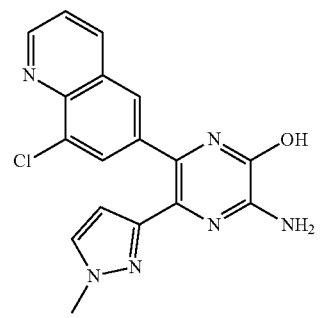
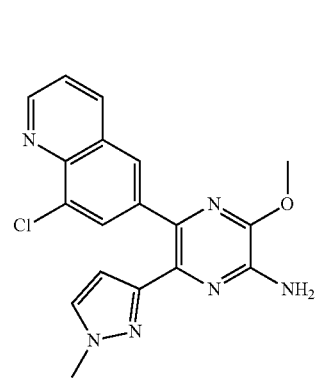
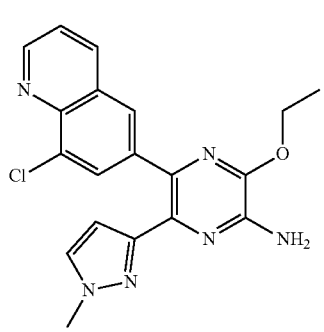
1228
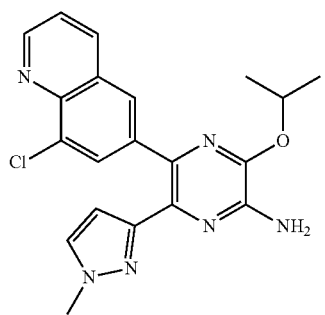
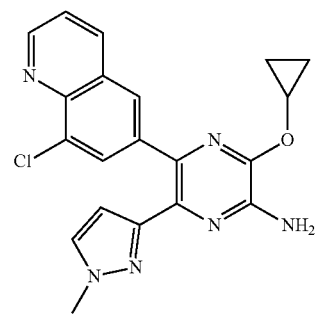
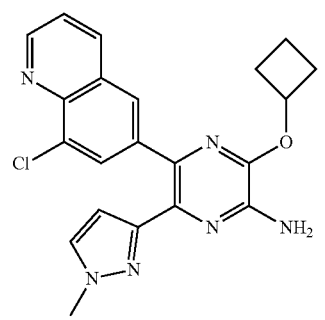
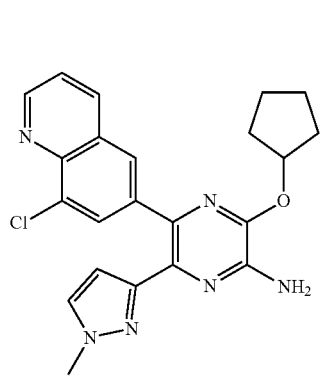
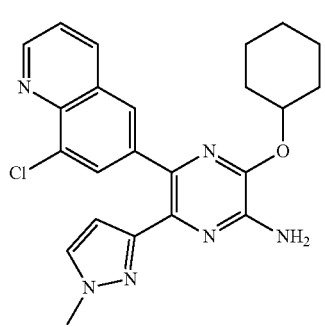

1229
-continued
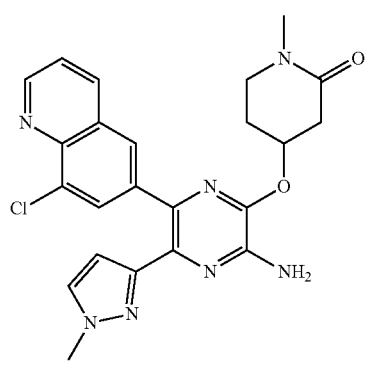
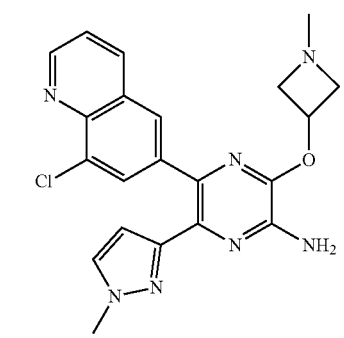
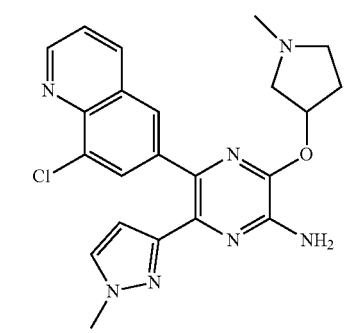
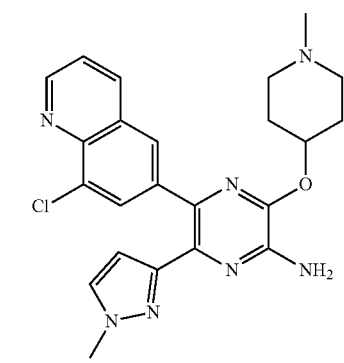
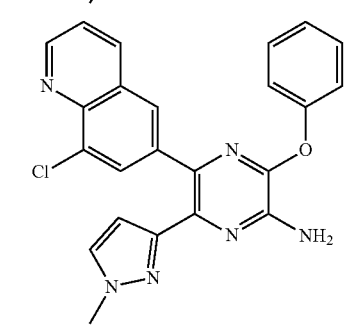
1230
-continued
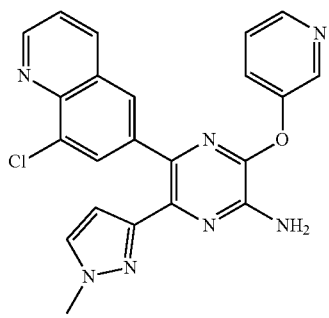
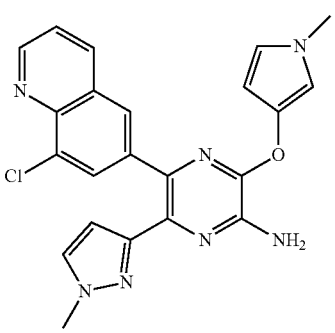
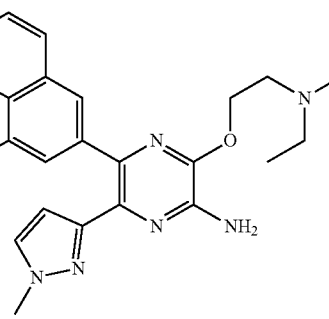
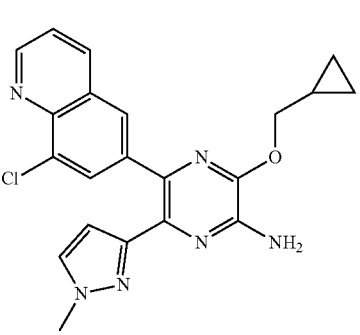
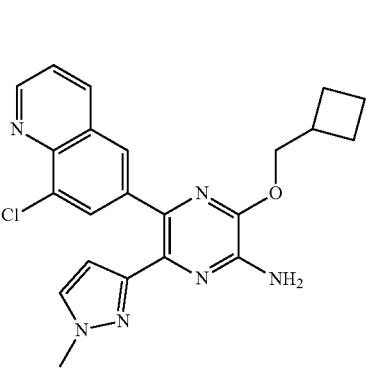

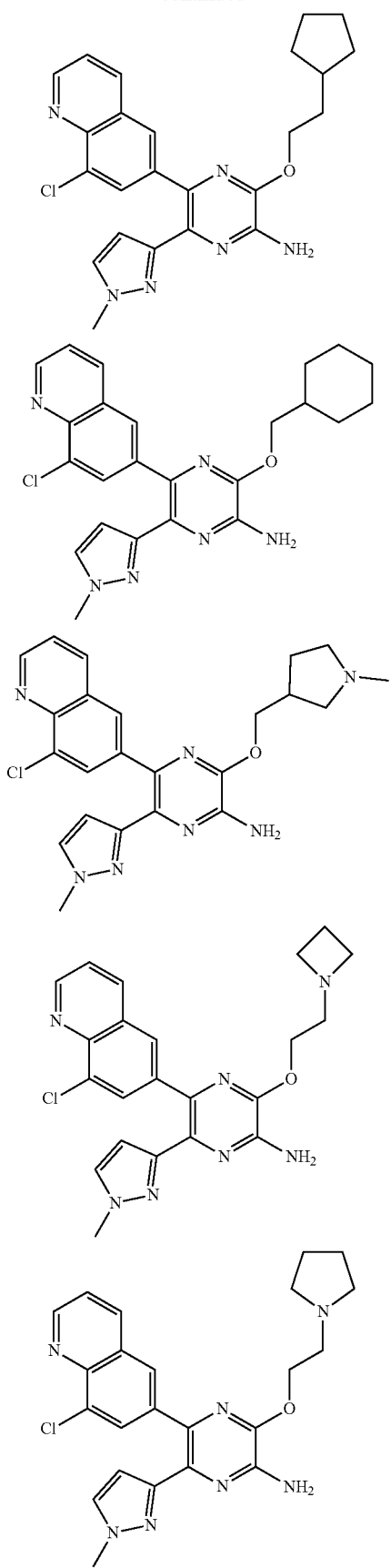
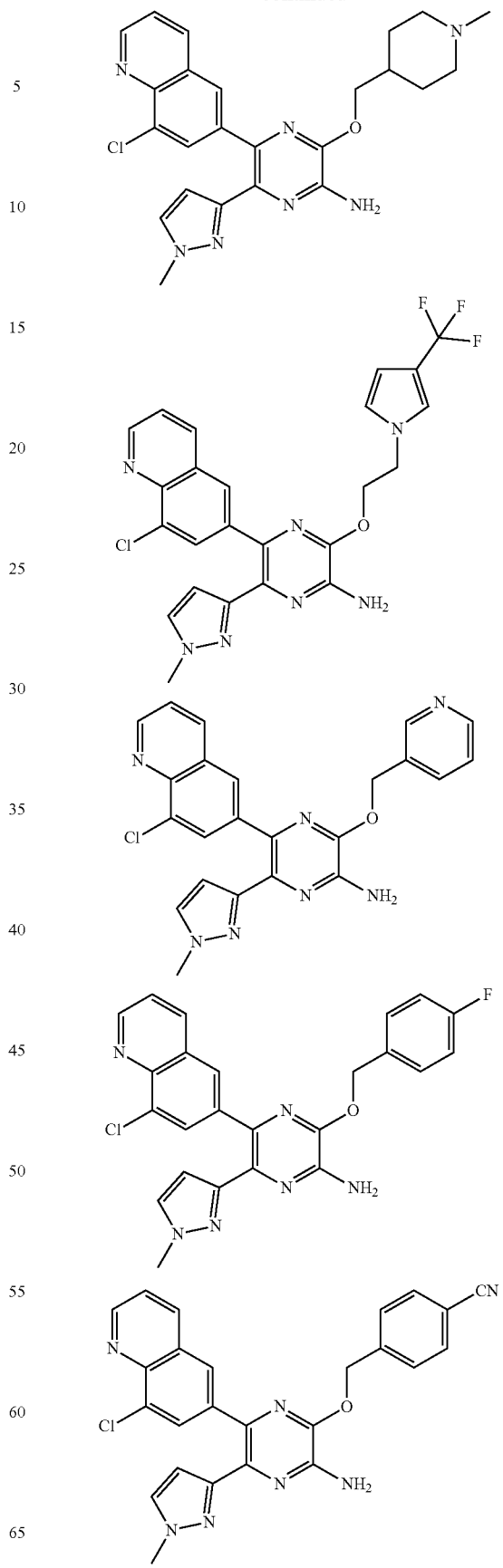

1233
-continued
1234
-continued
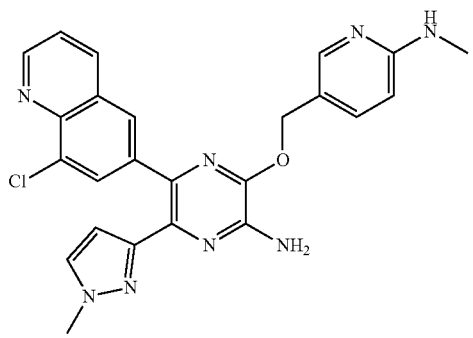

1235
-continued
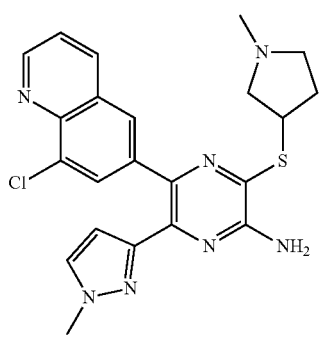
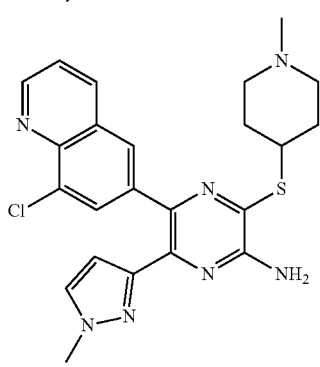
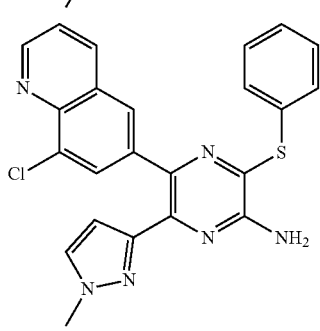
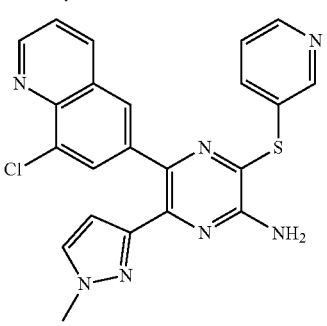
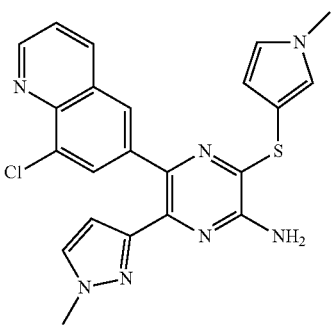
1236
-continued
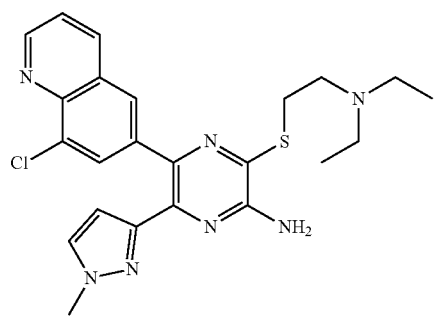
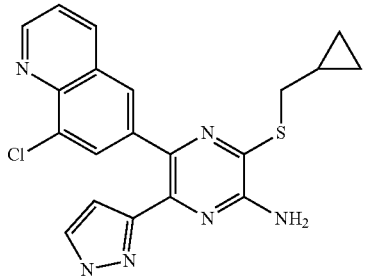
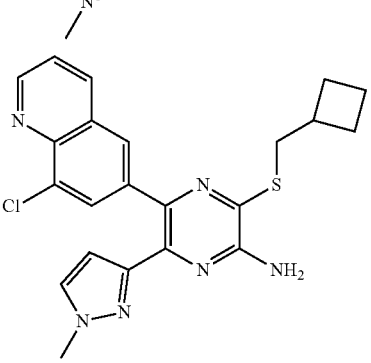
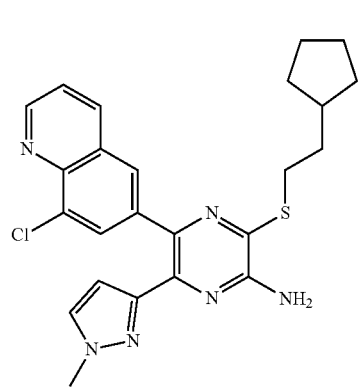
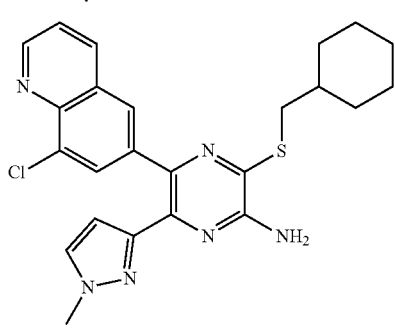

1237
-continued
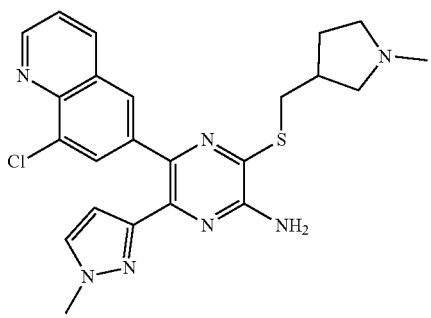
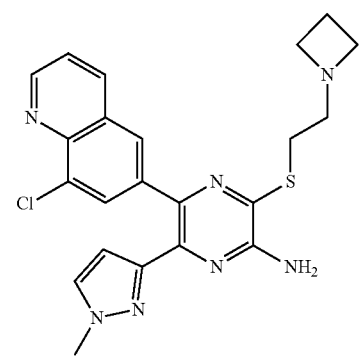
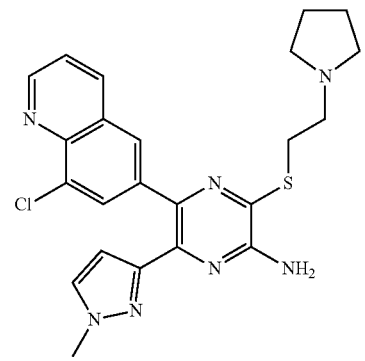
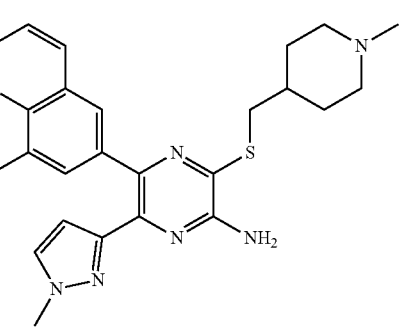
1238
-continued
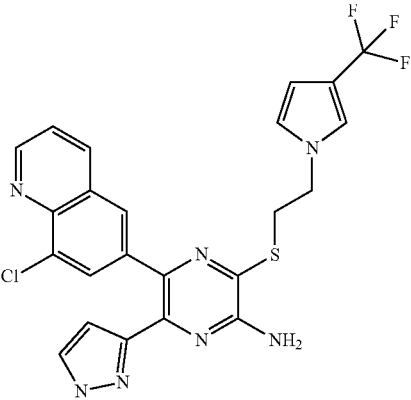
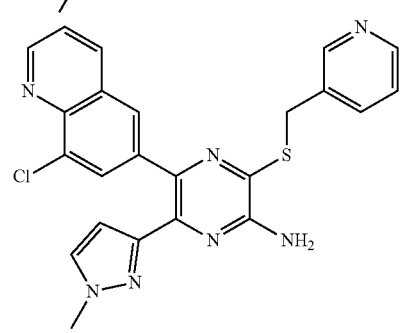
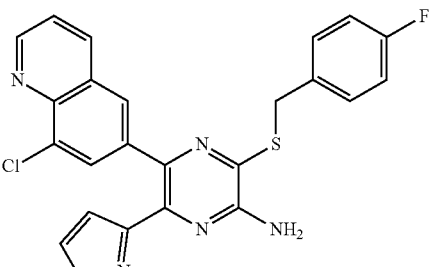
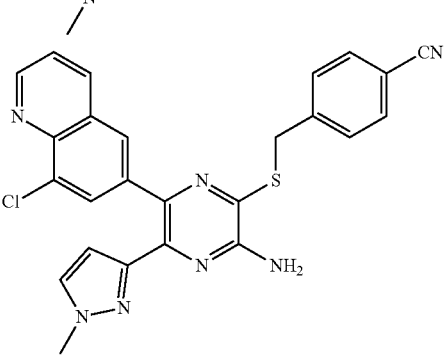
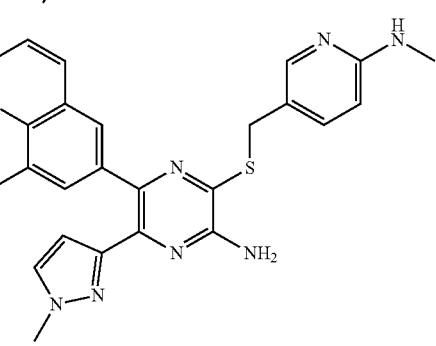

1239
-continued
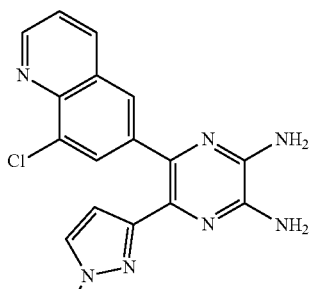
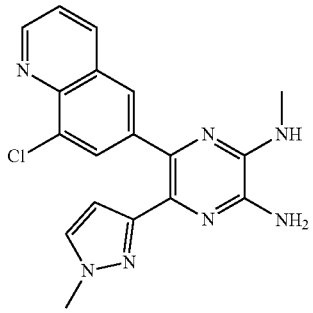
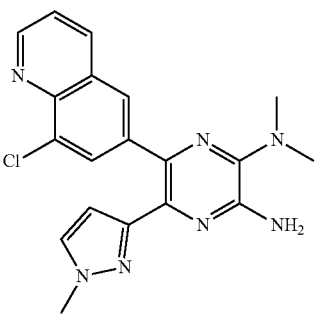
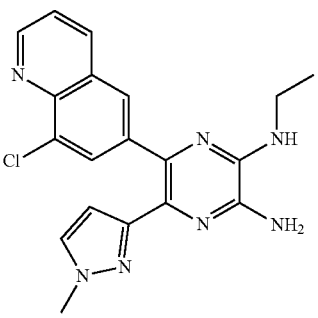
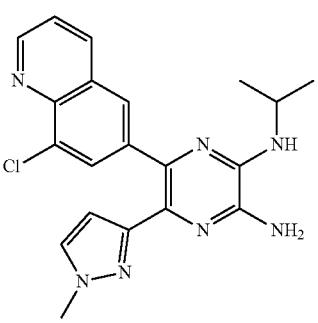
1240
-continued
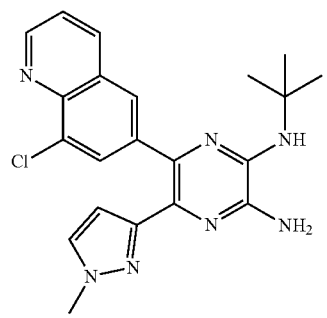
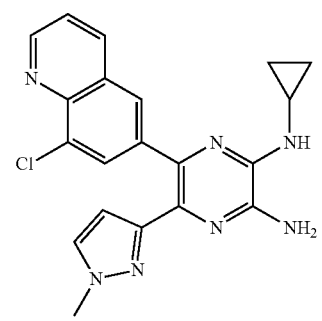
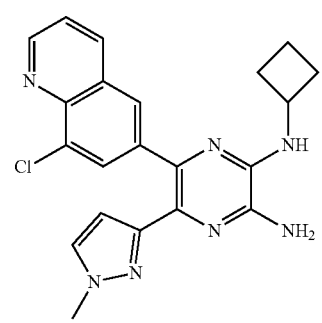
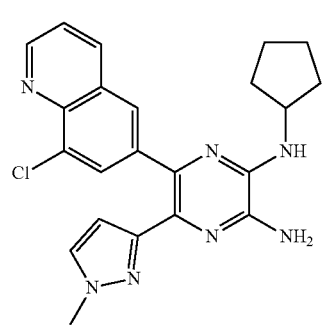
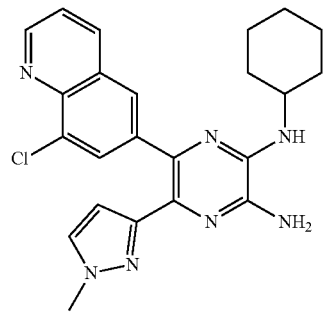

1241
-continued
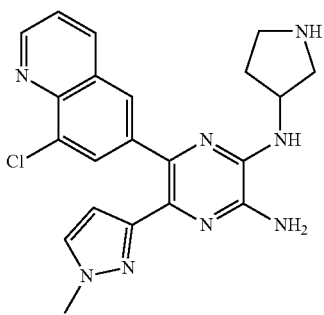
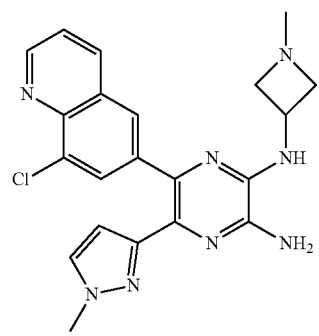
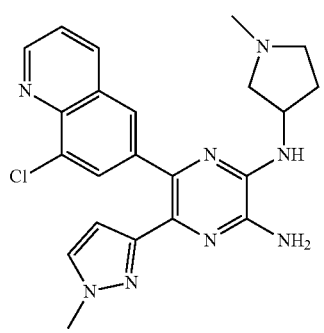
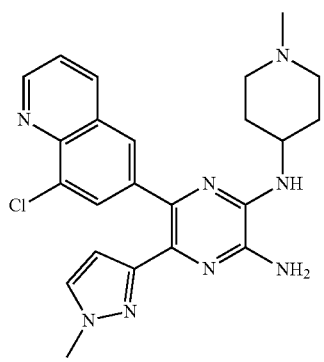
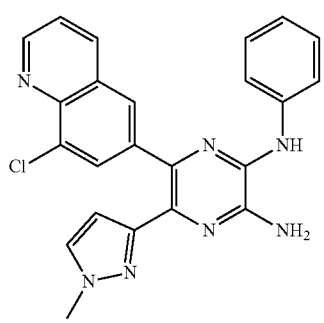
1242
-continued
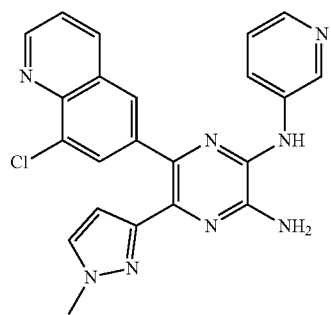
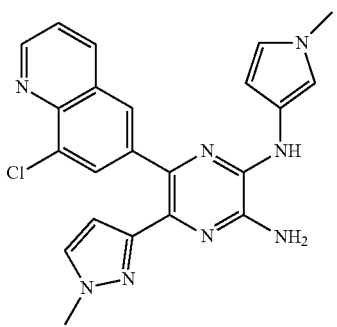
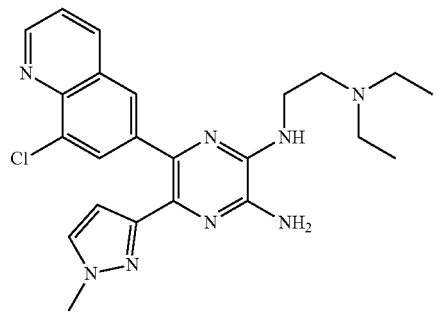
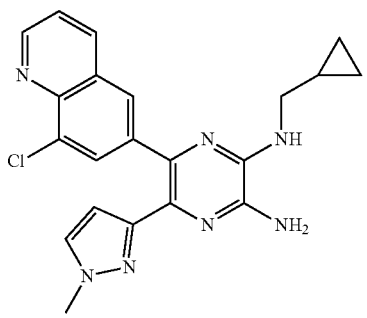
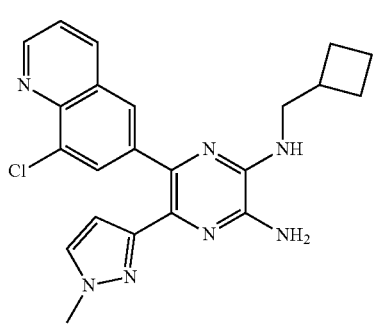

1243
-continued
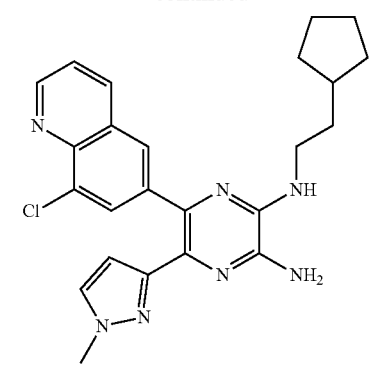
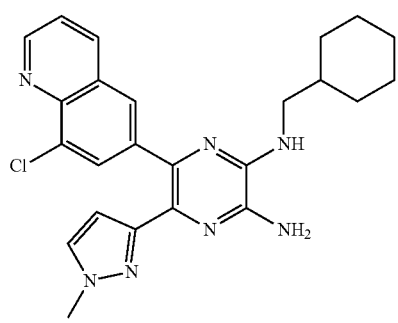
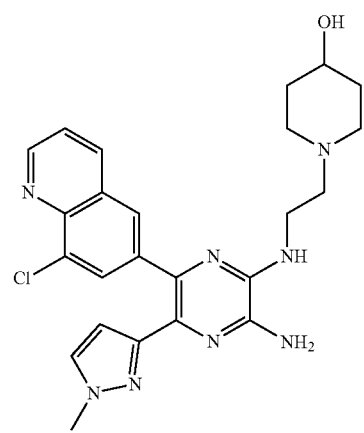
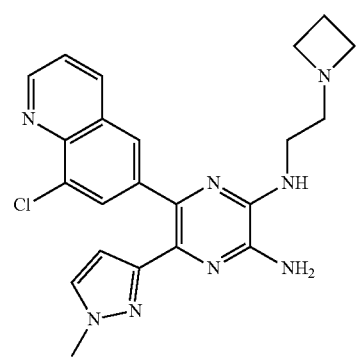
1244
-continued
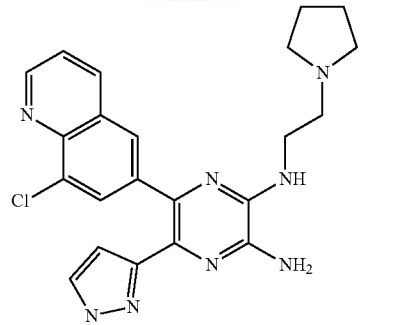
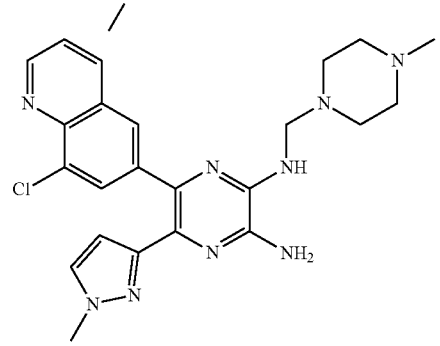
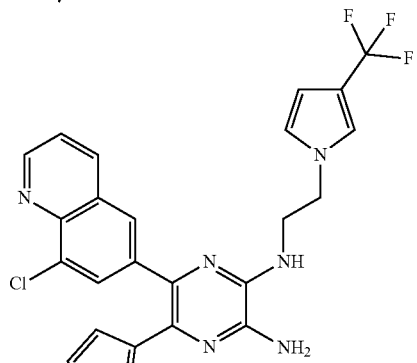
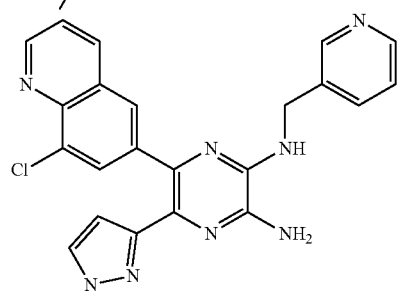
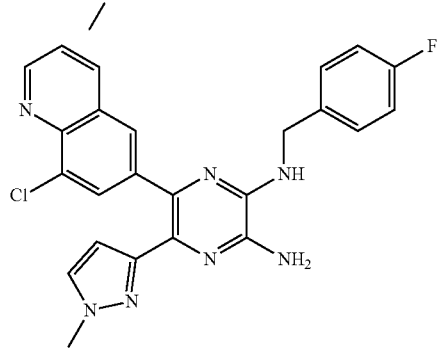

1245
-continued
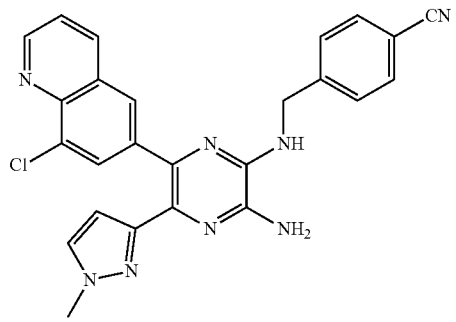
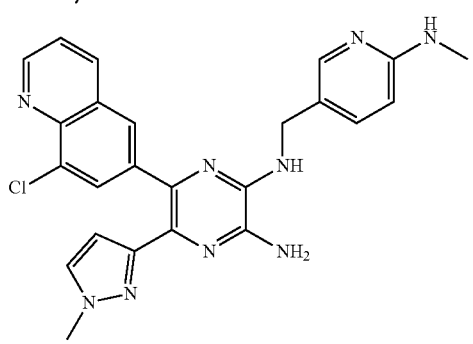
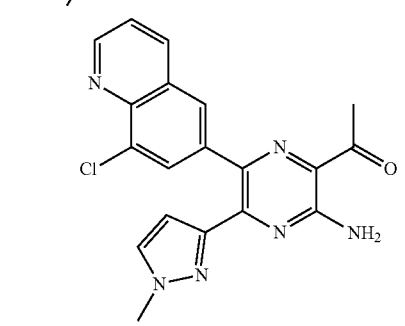
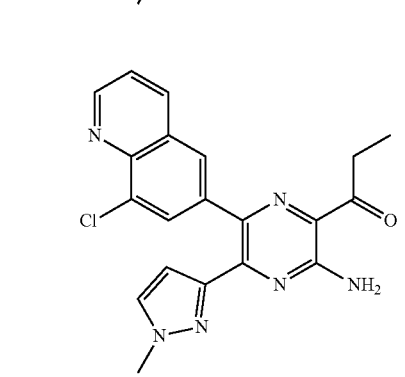
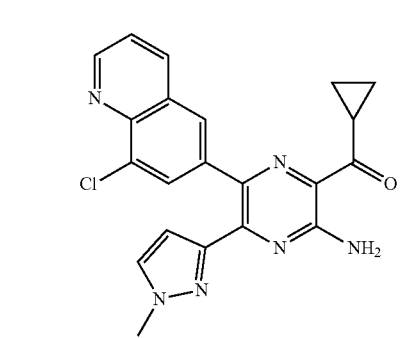
1246
-continued
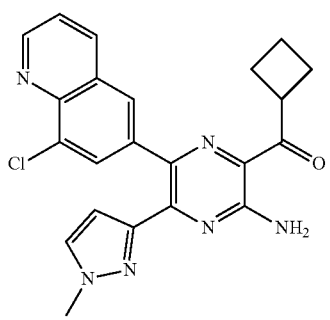
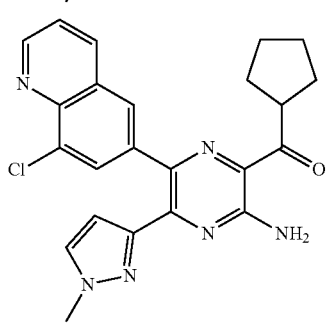
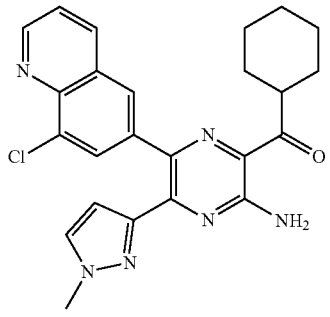
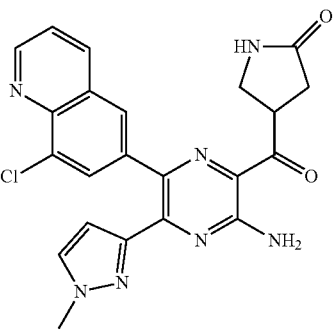
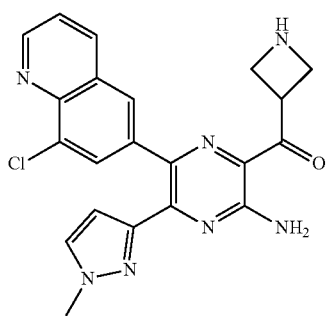

1247
-continued
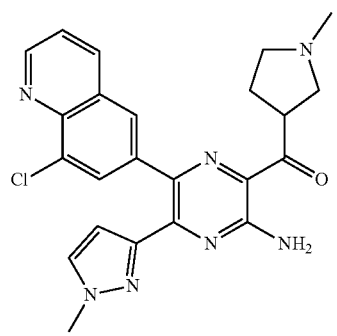
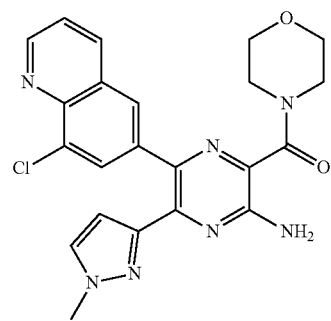
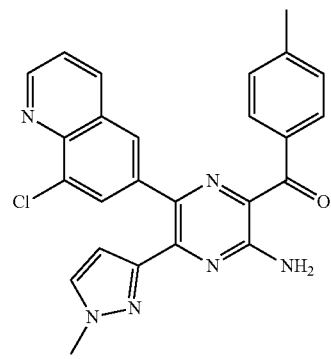
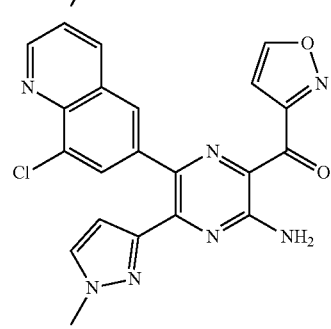
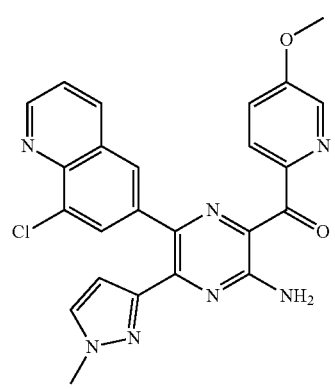
1248
-continued
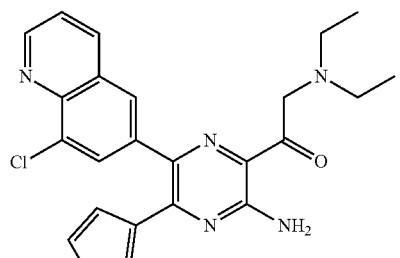
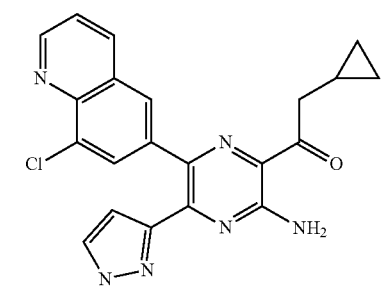
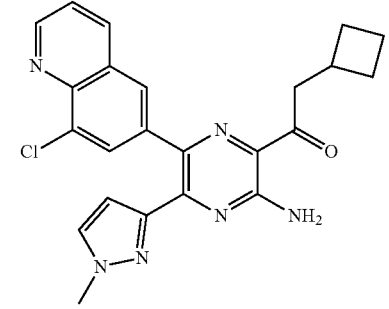
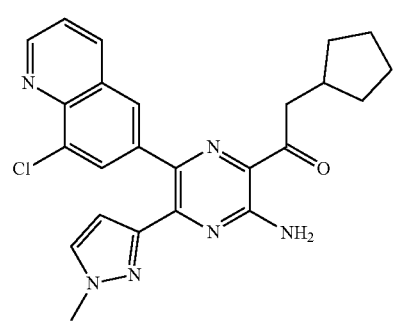
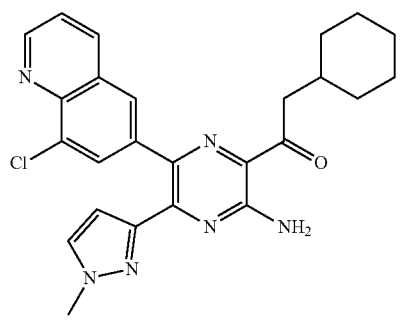

1249
-continued
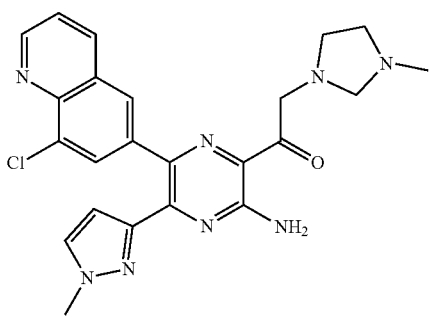
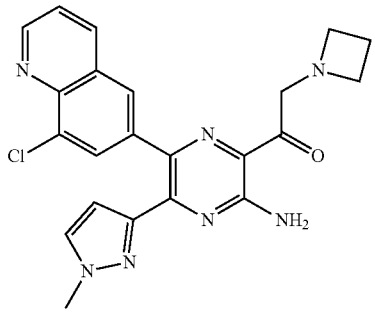
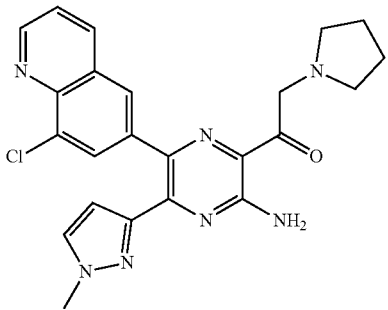
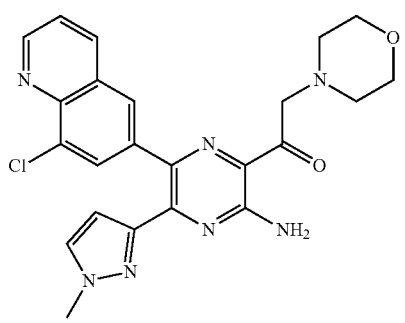
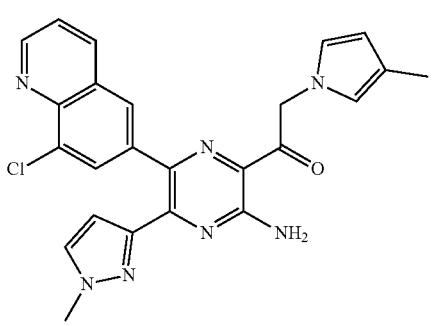
1250
-continued
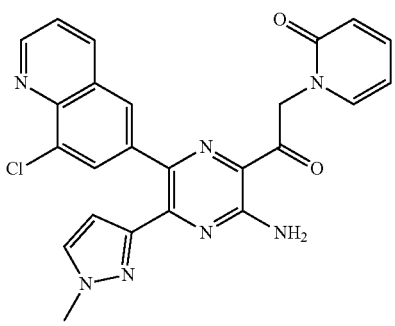
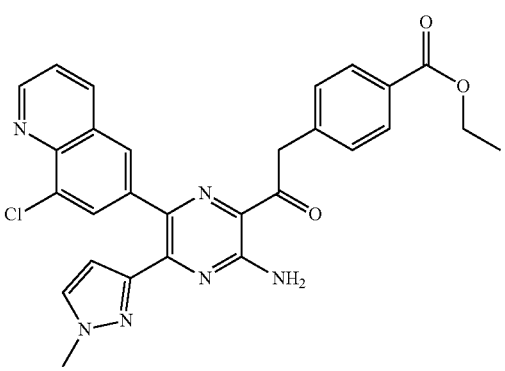
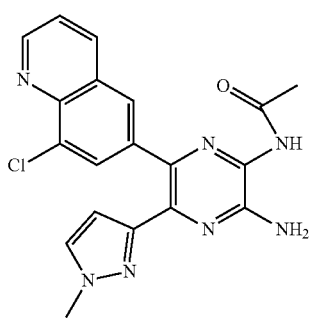
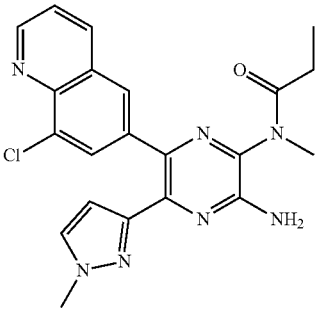
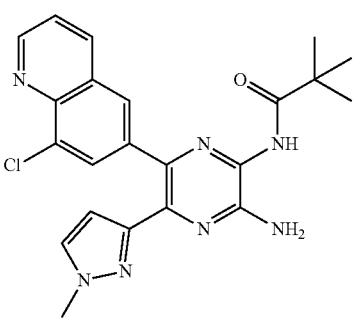

1251
-continued
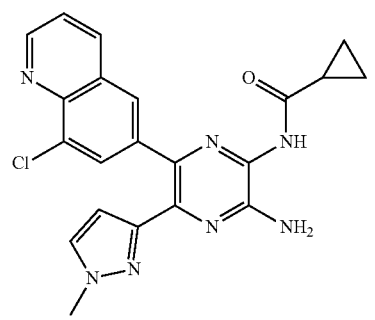
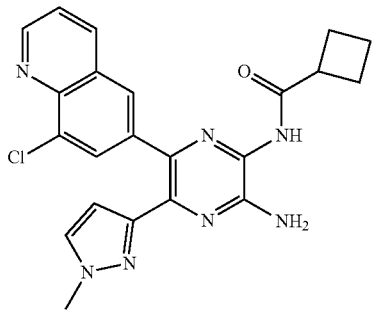
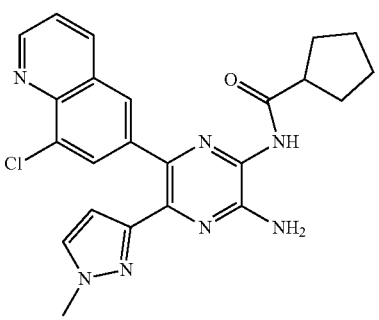
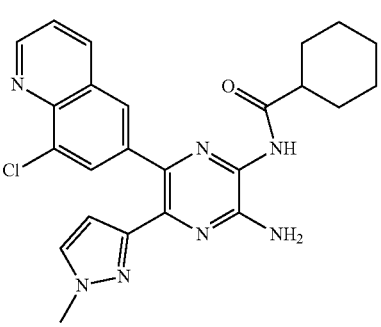
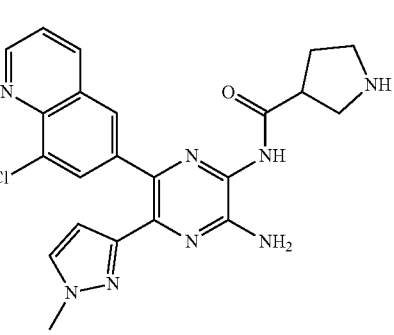
1252
-continued
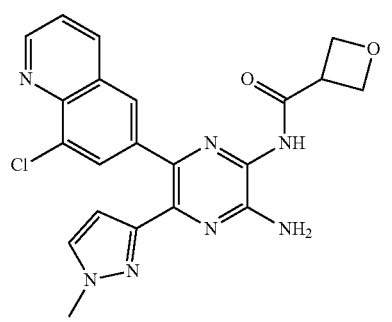
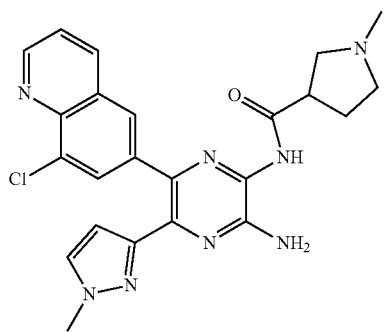
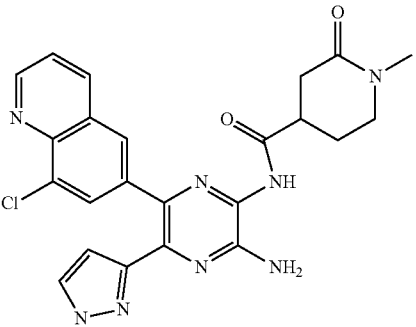
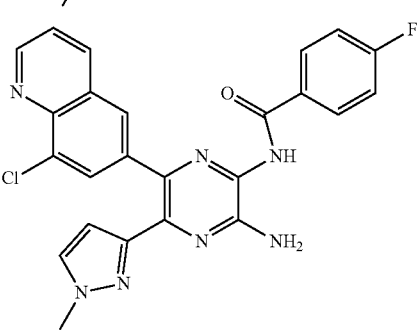
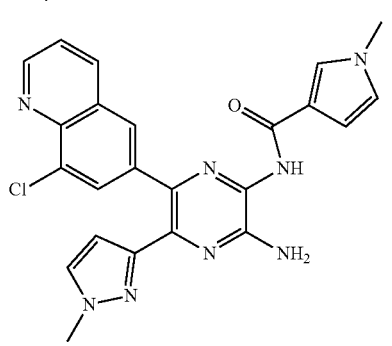

1253
-continued
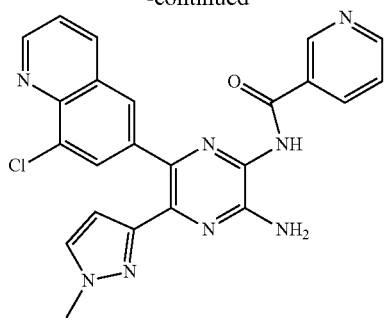
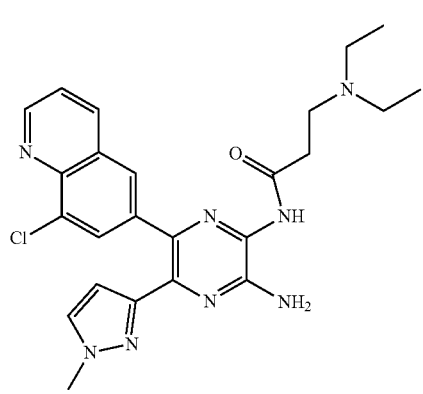
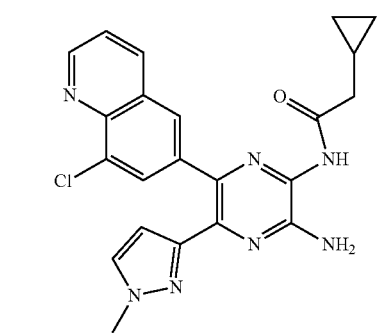
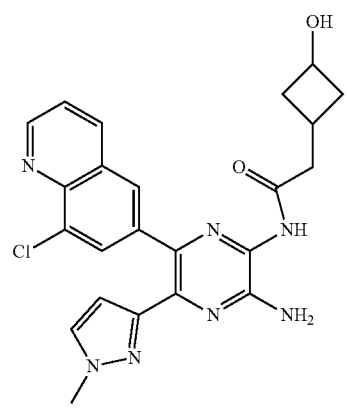
1254
-continued
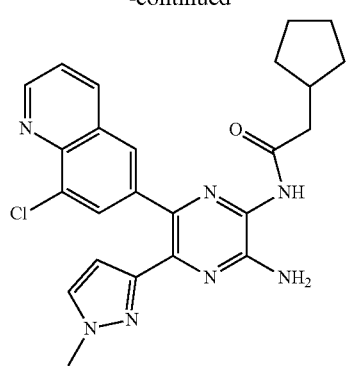
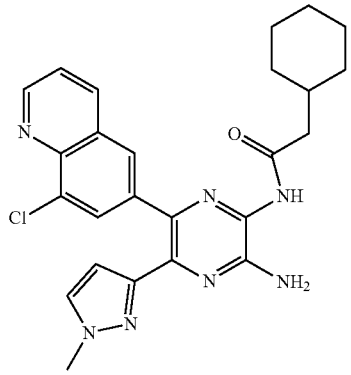
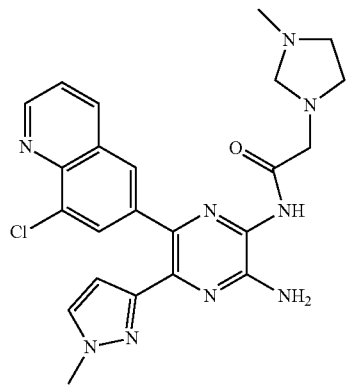
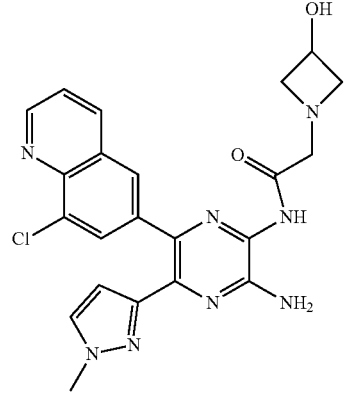

1255
-continued
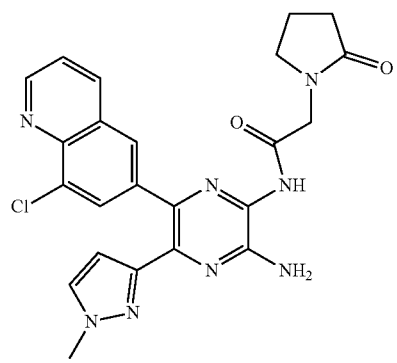
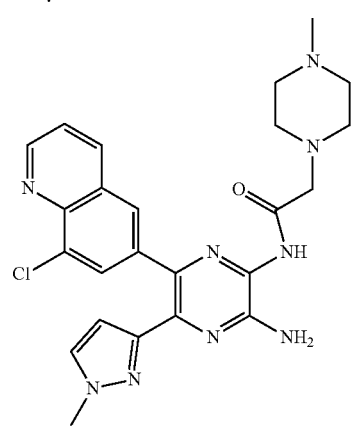
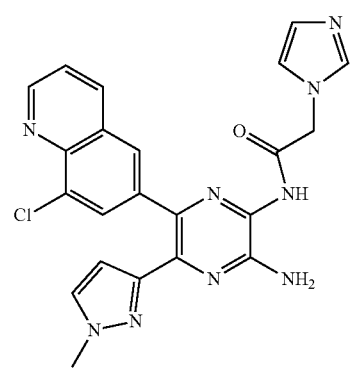
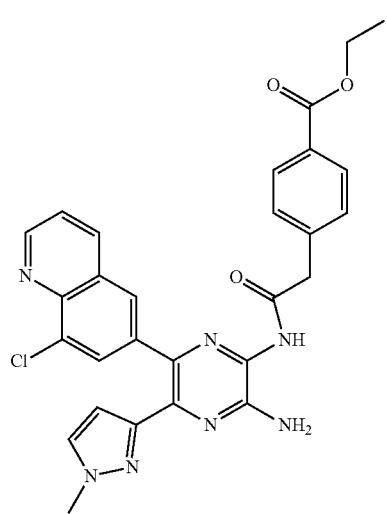
1256
-continued
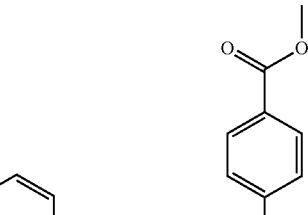
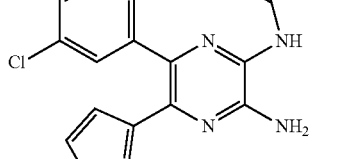
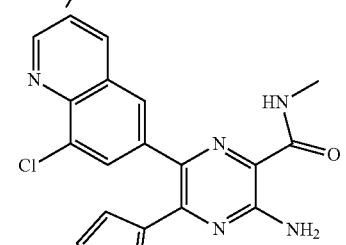
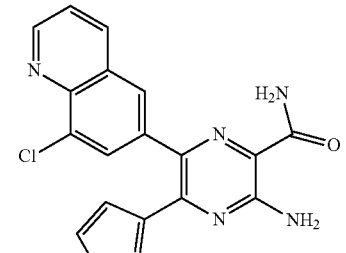
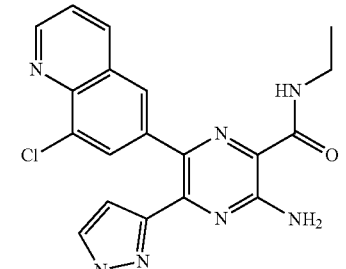
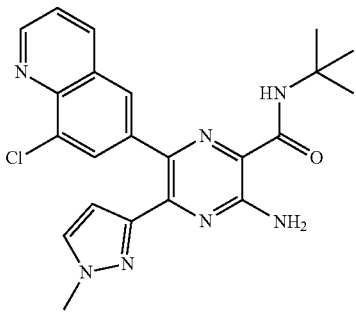

1257
-continued
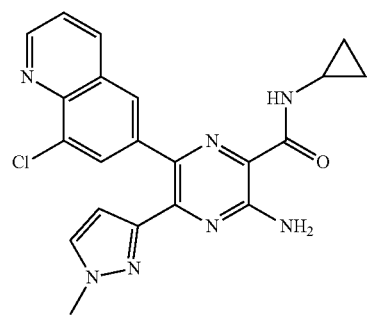
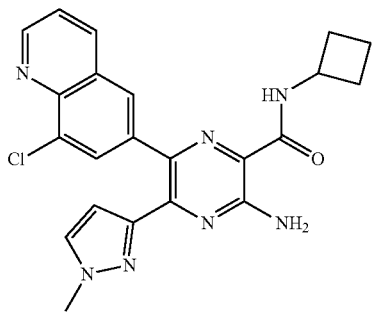
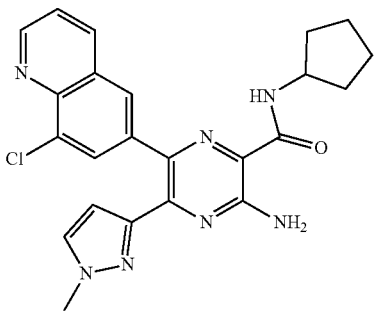
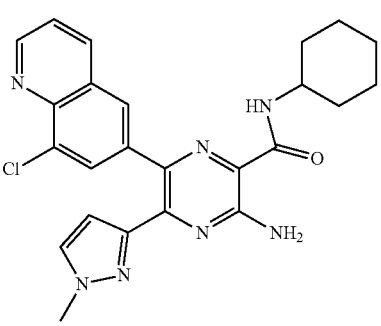
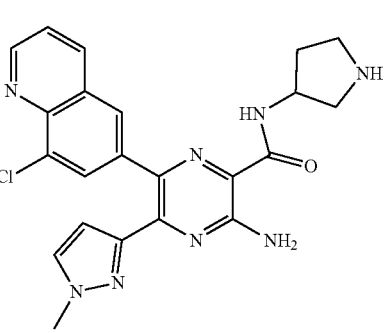
1258
-continued
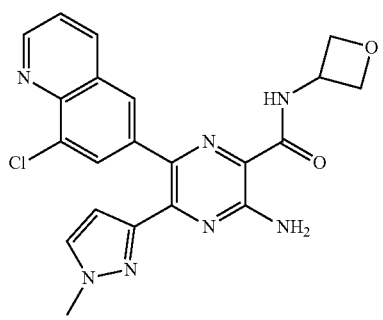
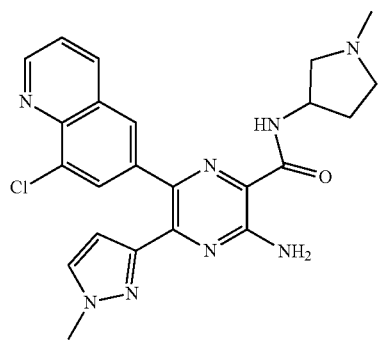
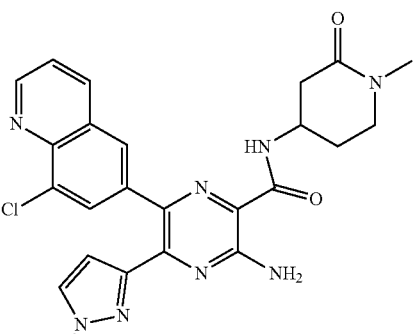
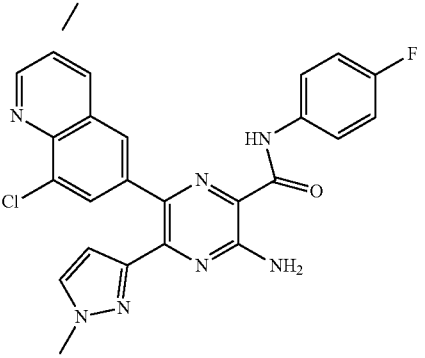
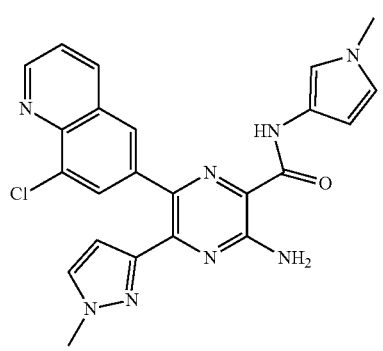

1259
-continued
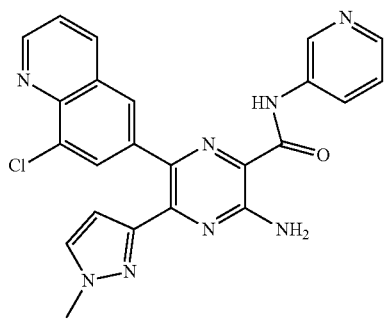
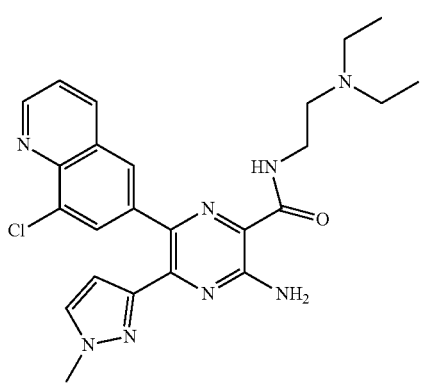
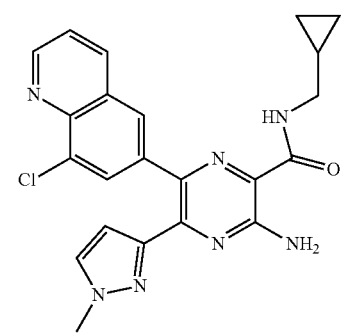
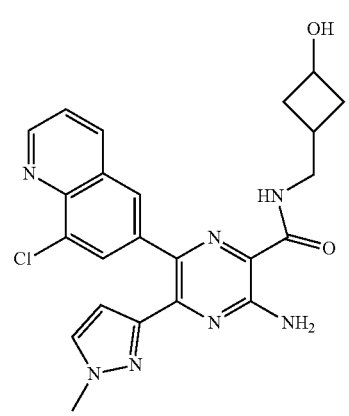
1260
-continued
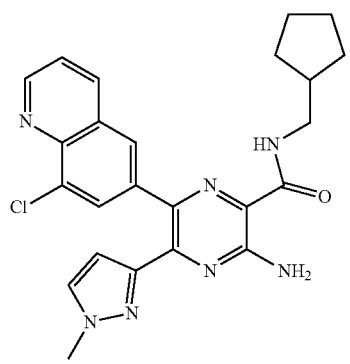
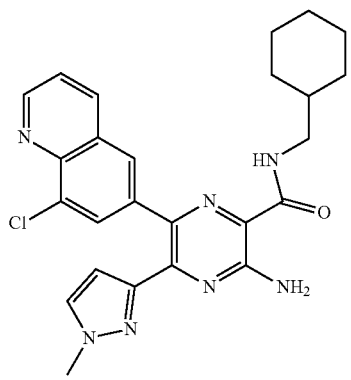
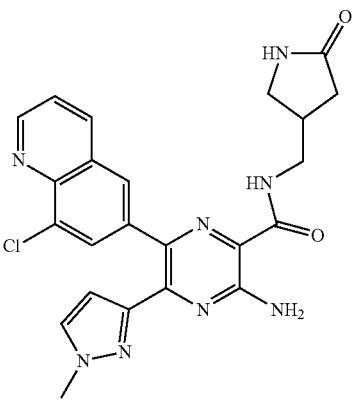
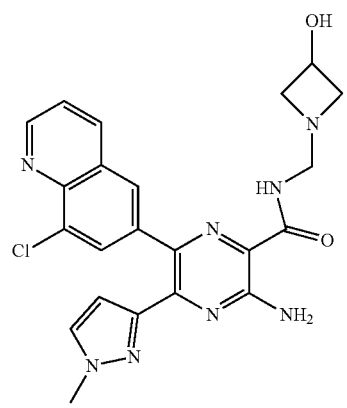

1261
-continued
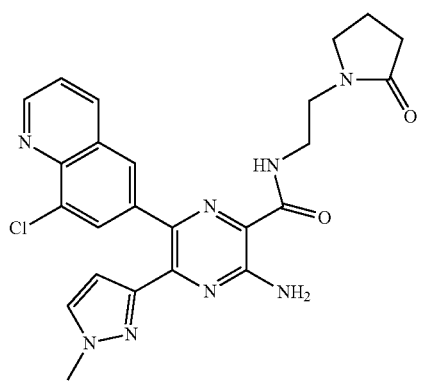
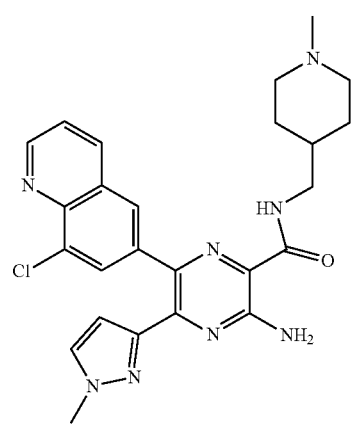
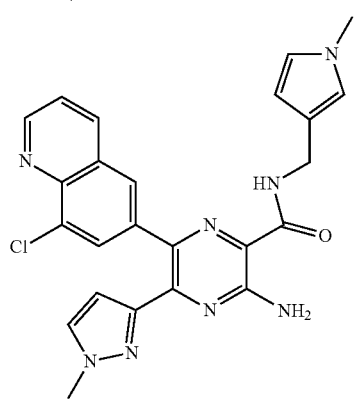
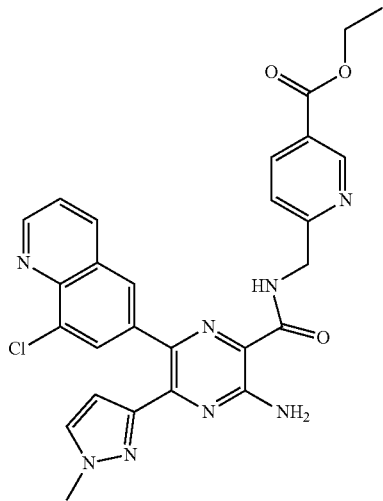
1262
-continued
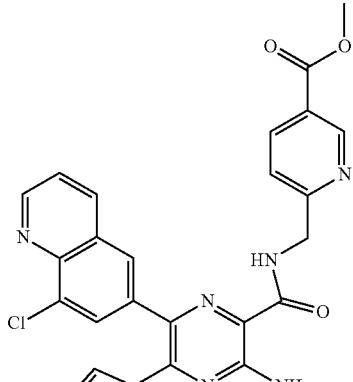
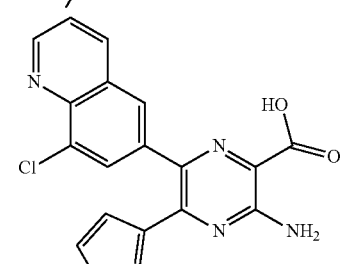
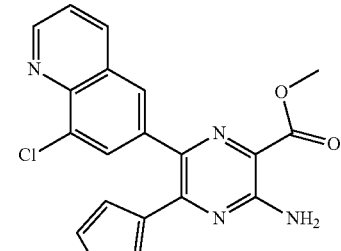
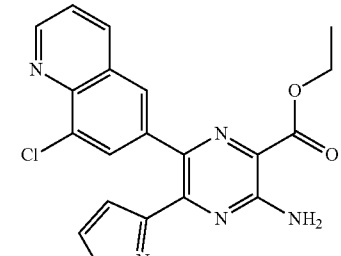
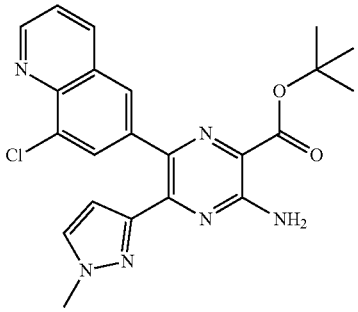

1263
-continued
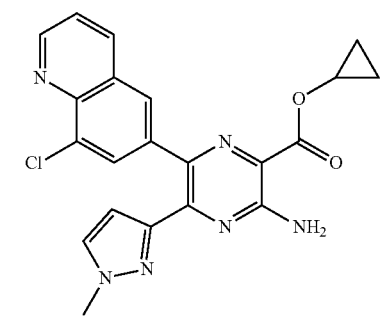
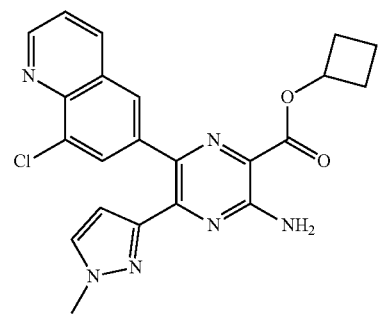
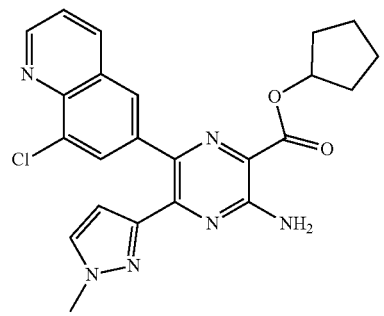
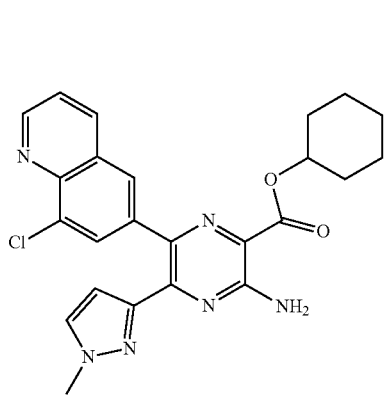
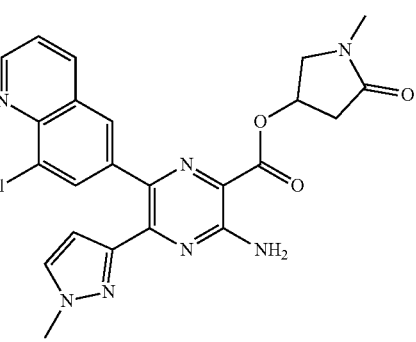
1264
-continued
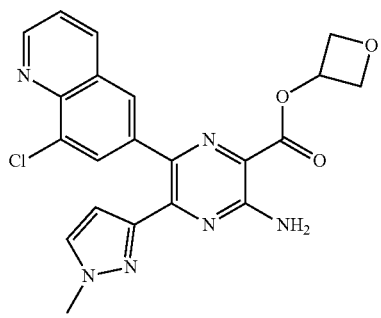
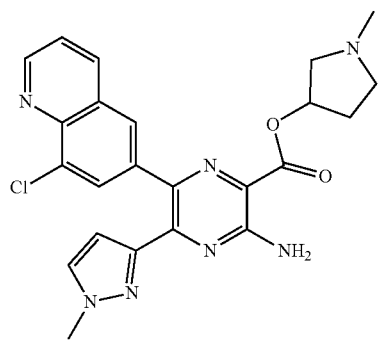
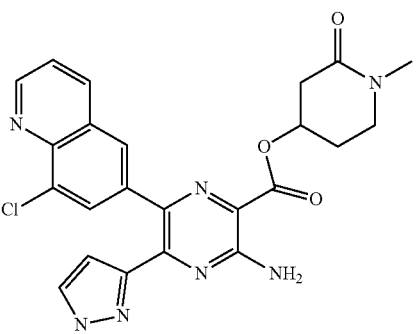
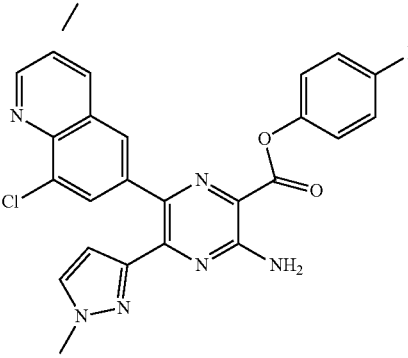
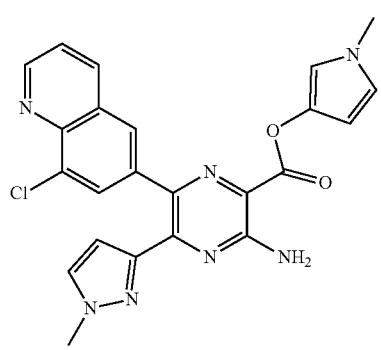

1265
-continued
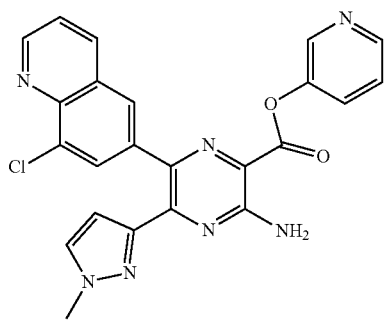
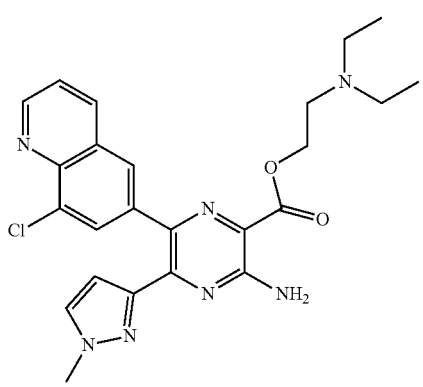
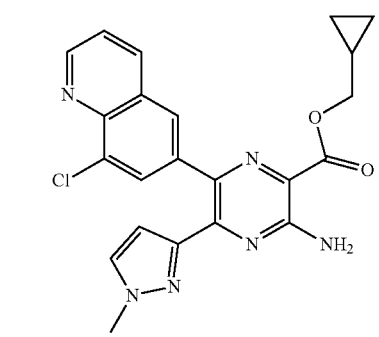
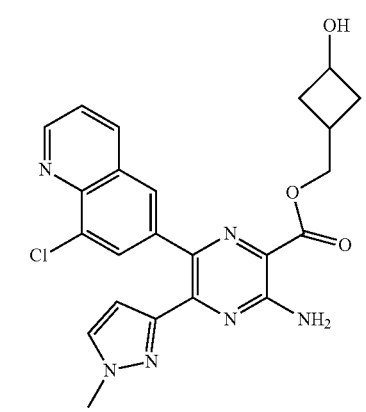
1266
-continued
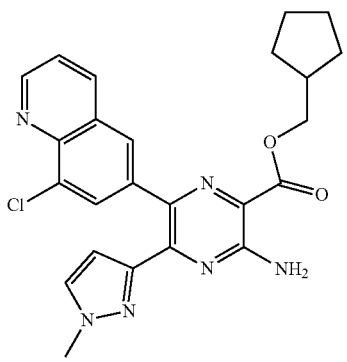
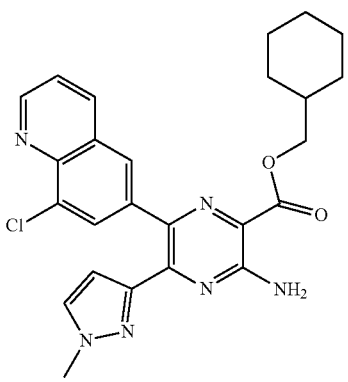
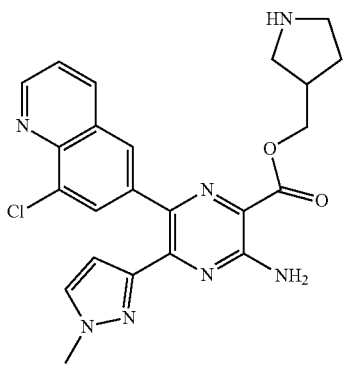
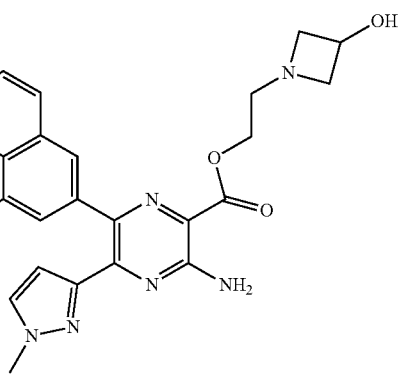

1267
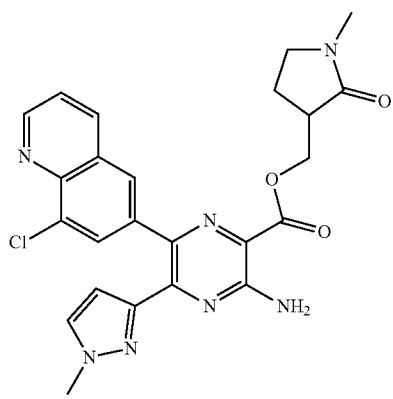
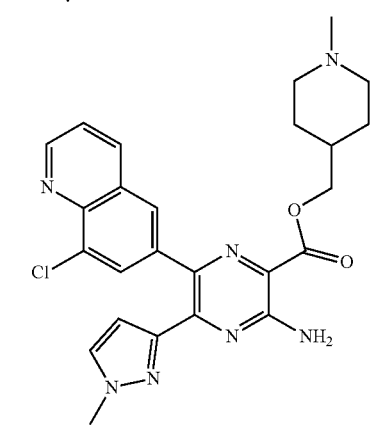
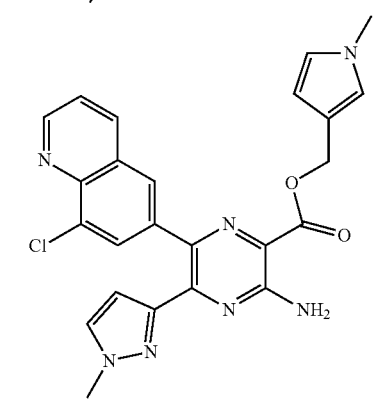
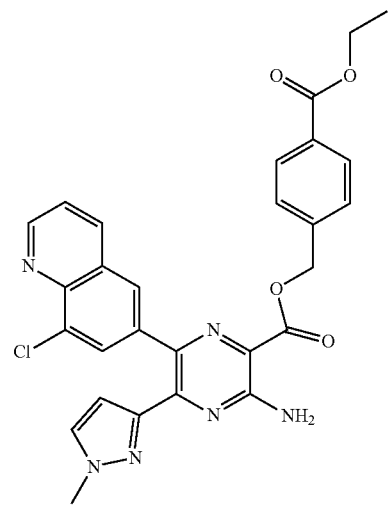
1268
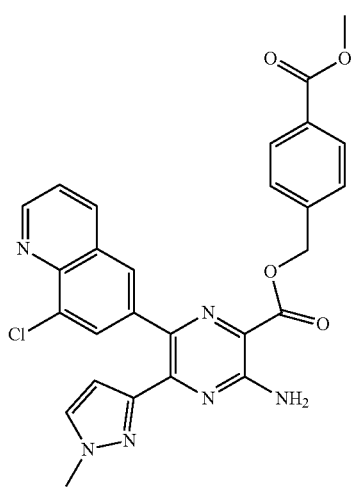
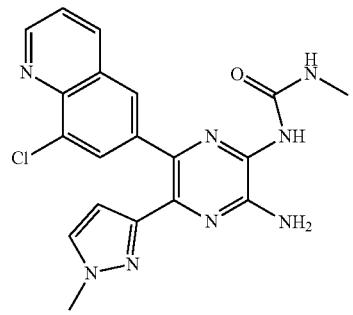
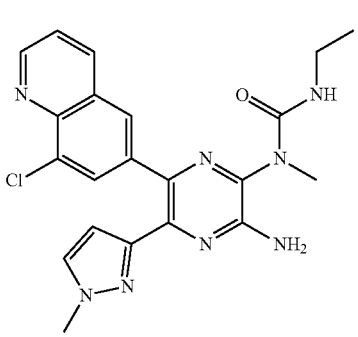
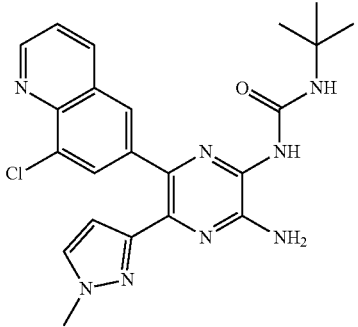

1269
-continued
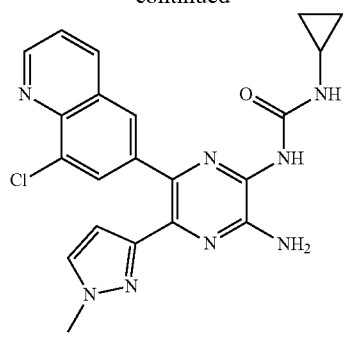
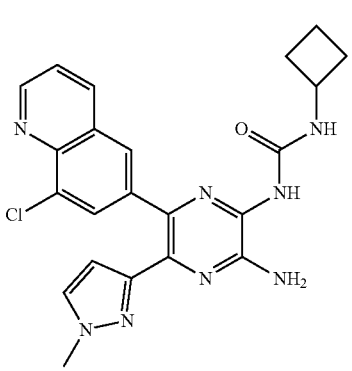
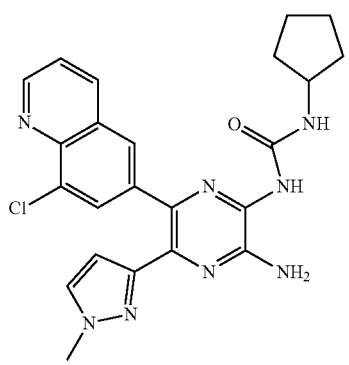
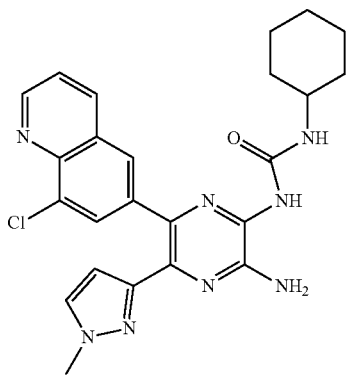
1270
-continued
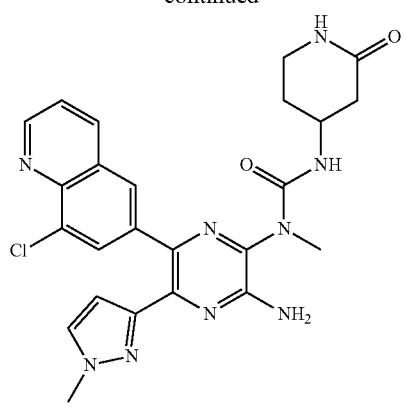
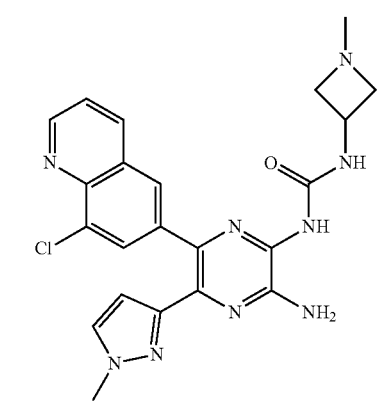
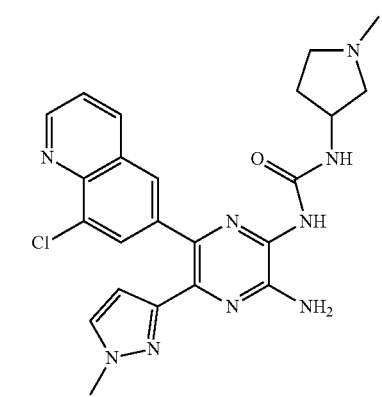
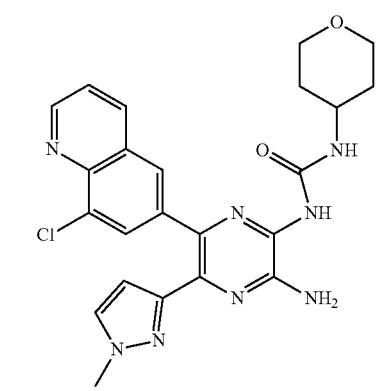

1271
-continued
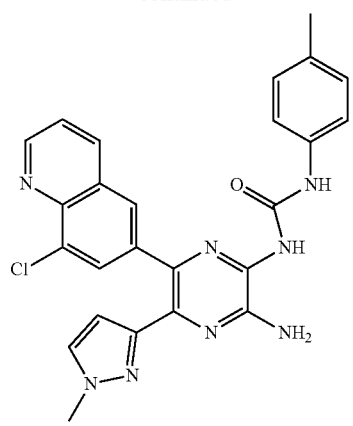
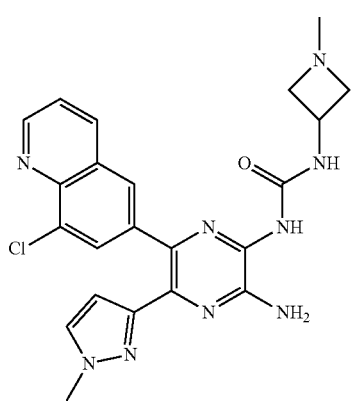
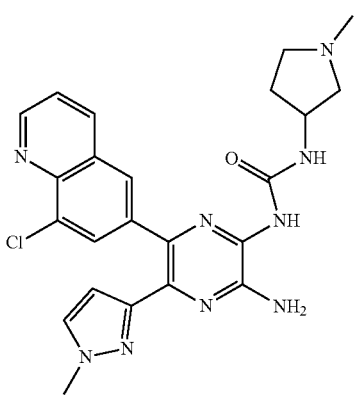
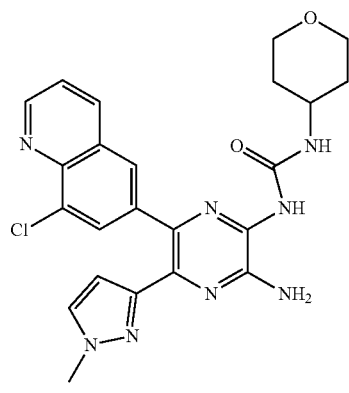
1272
-continued
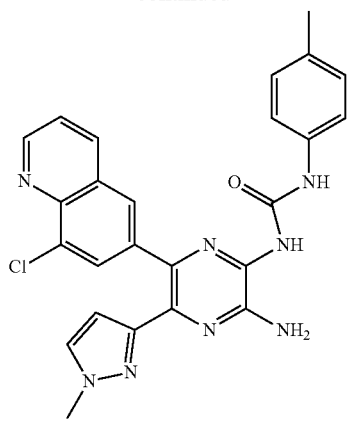
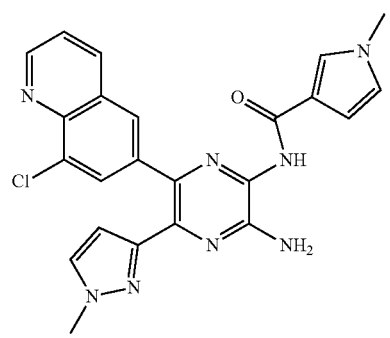
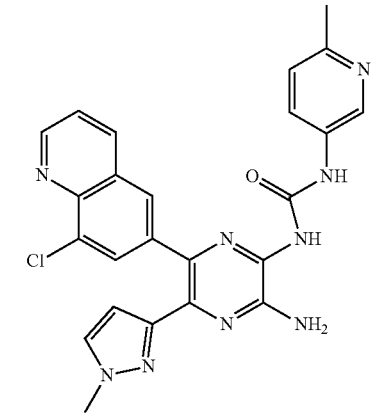
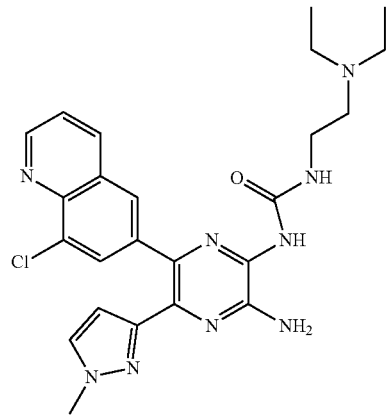

1273 -continued
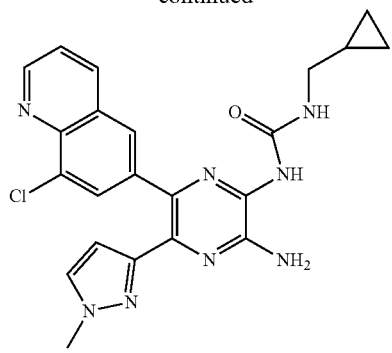
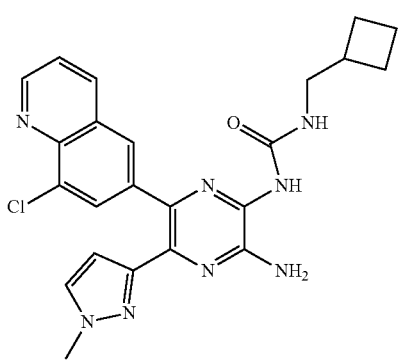
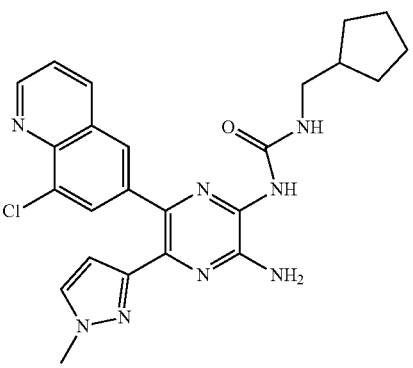
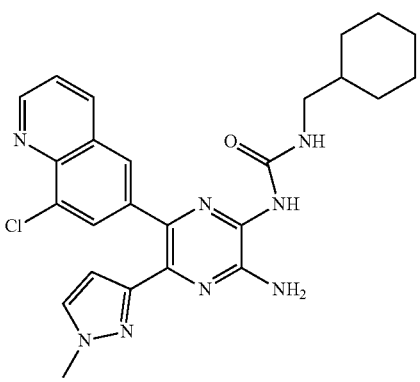
1274 -continued
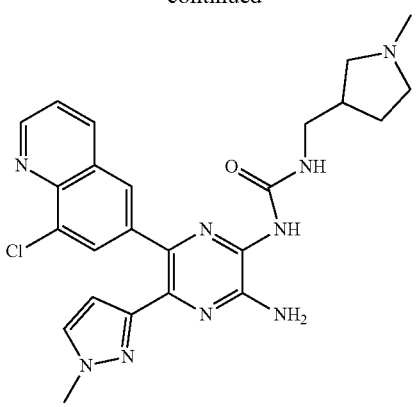
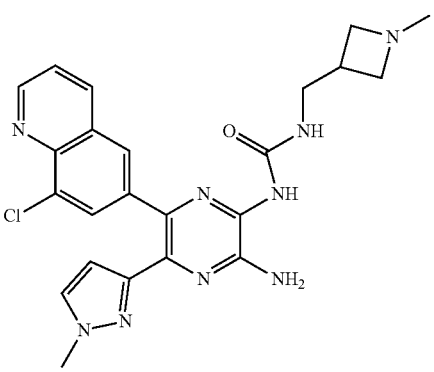
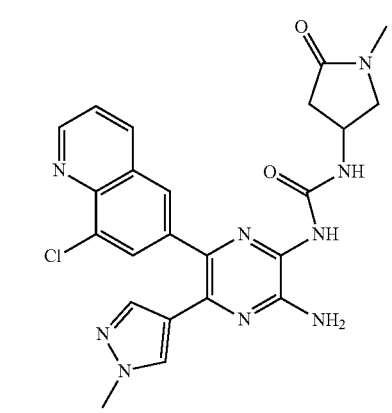
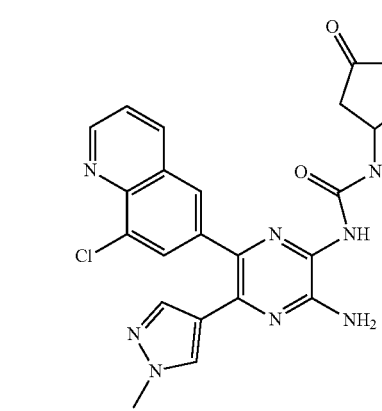

1275
-continued
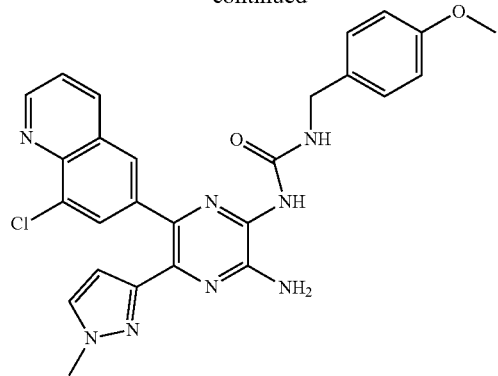
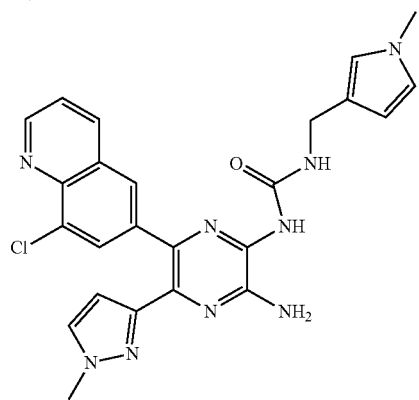
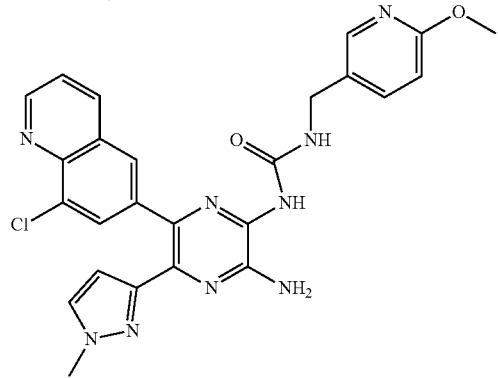
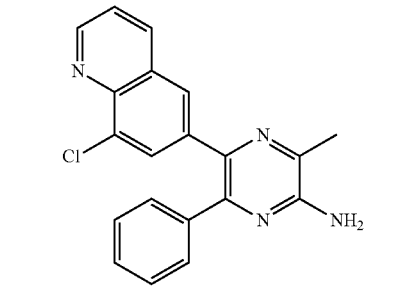
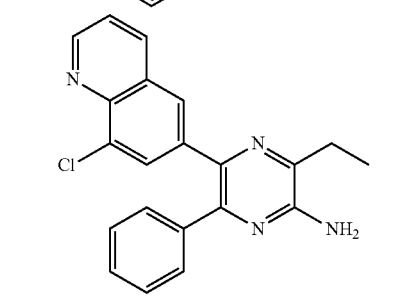
1276
-continued
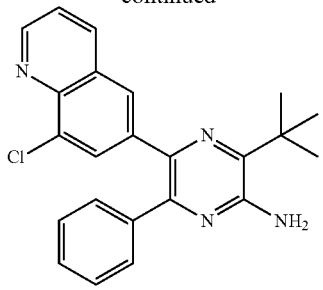
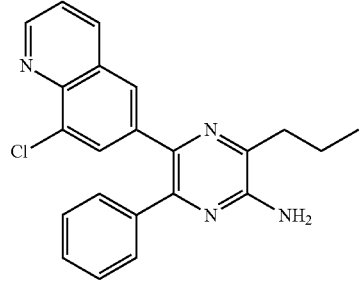
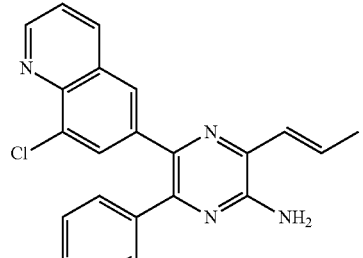
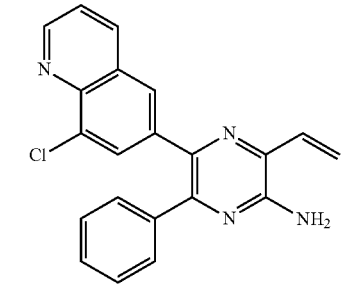
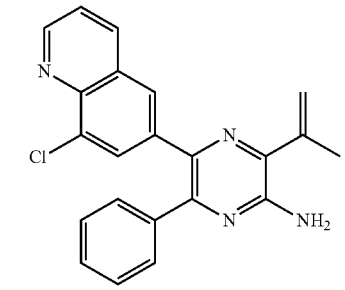
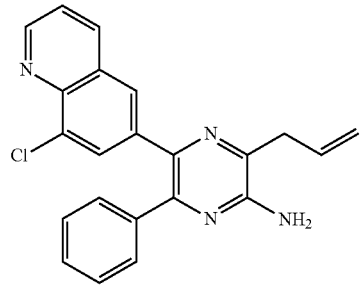

1277
-continued
1278
-continued
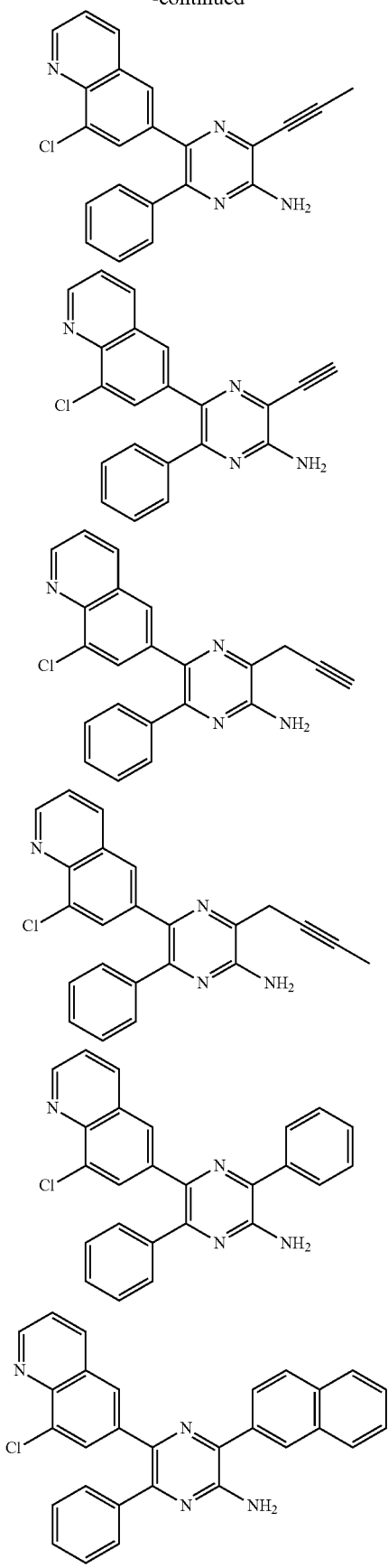
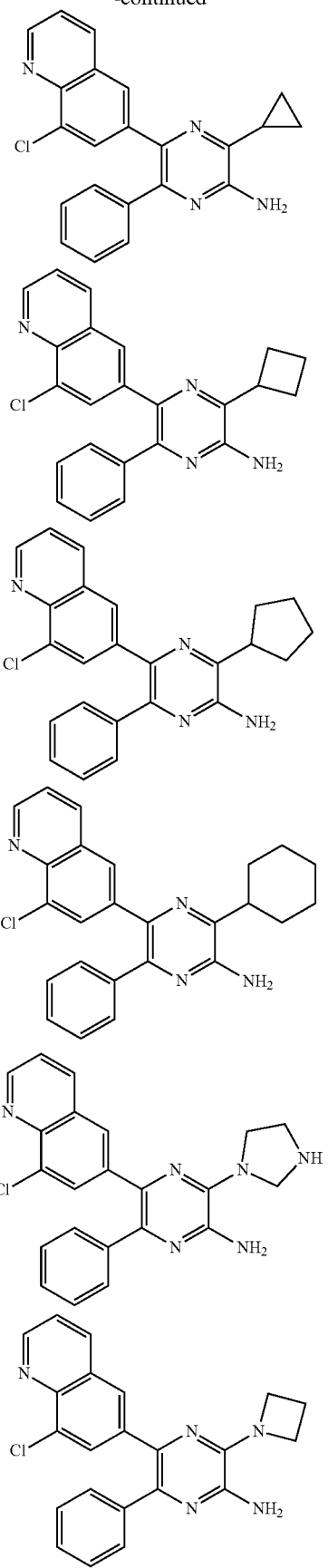

1279
-continued
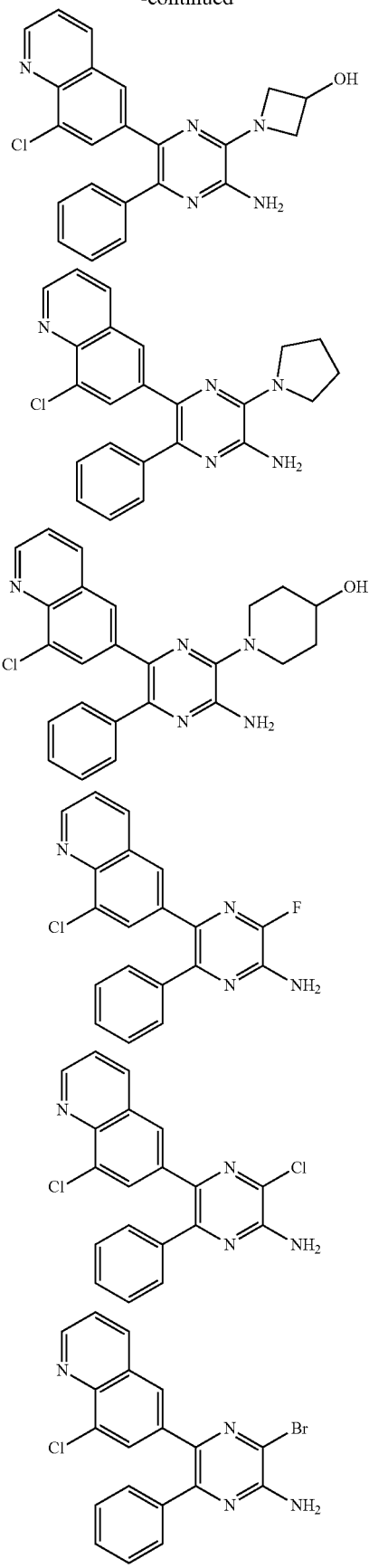
1280
-continued
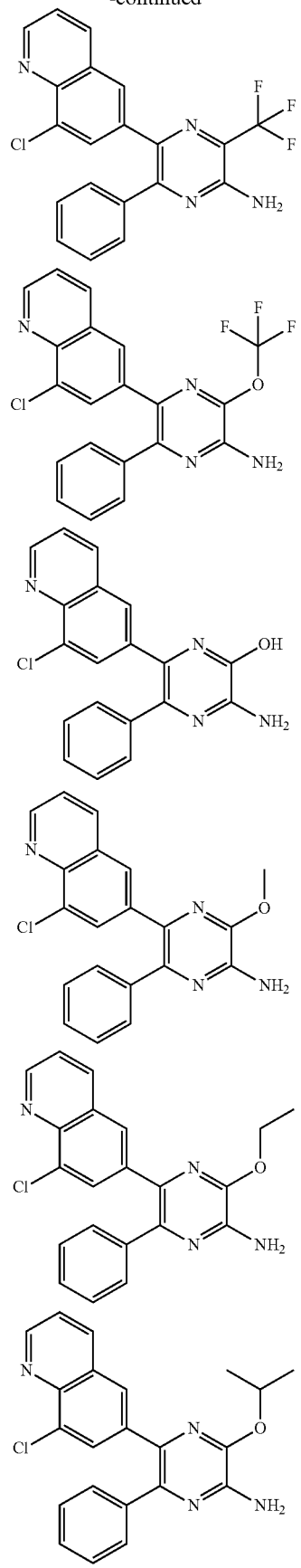

1281
-continued
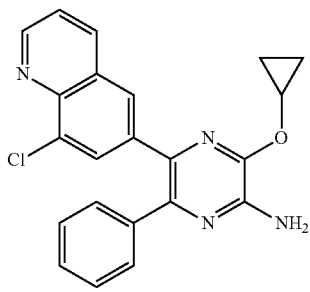
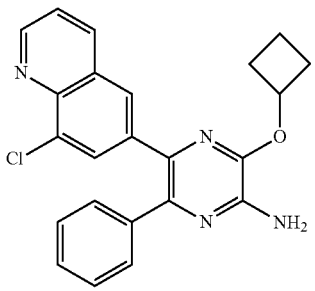
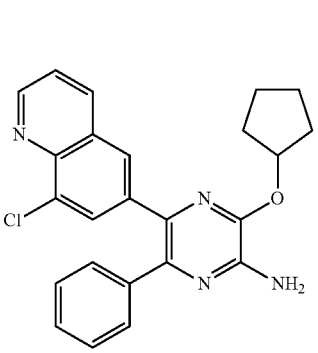
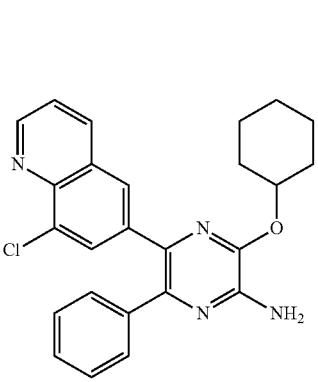
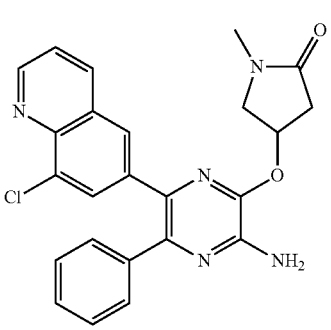
1282
-continued
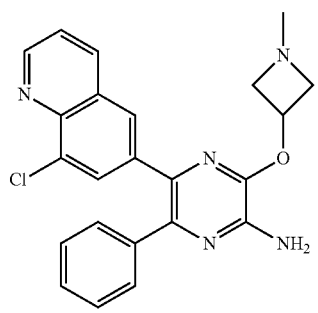
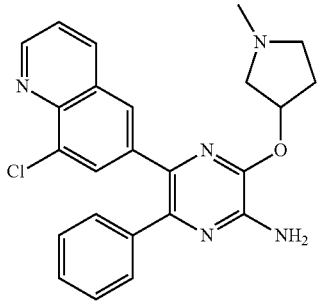
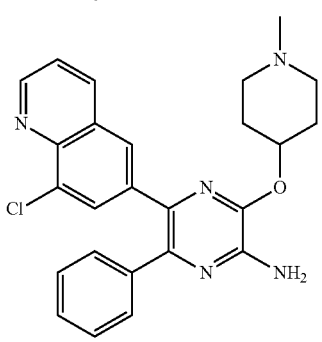
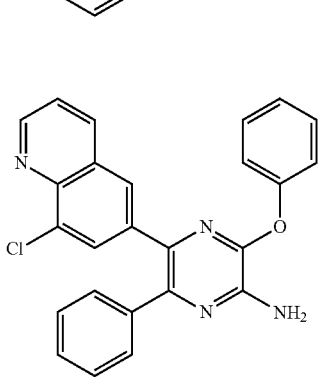
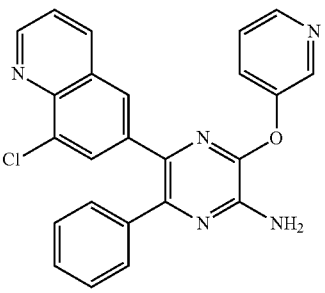

1283
-continued
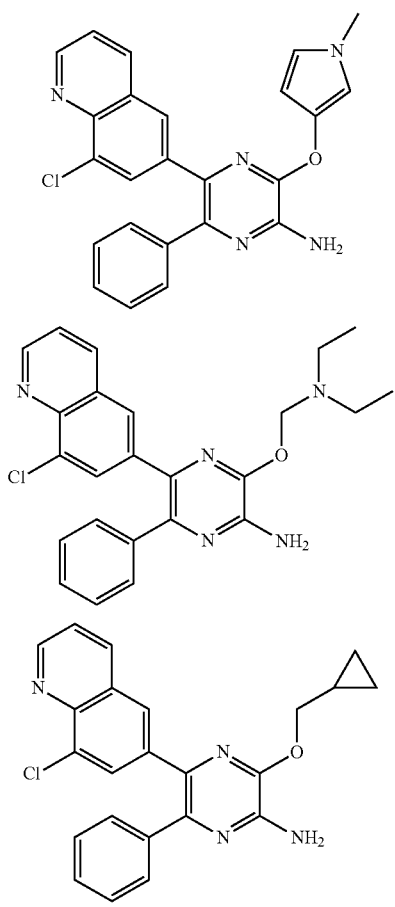
1284
-continued
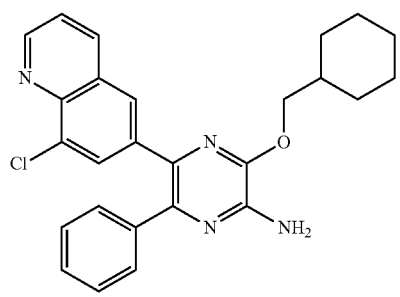
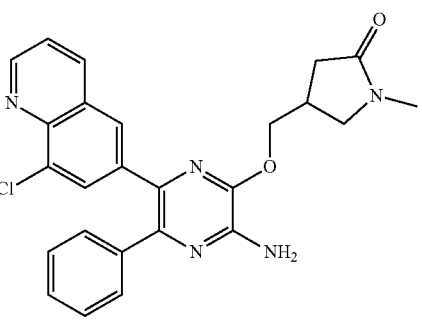
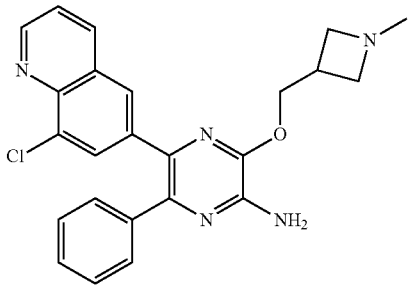
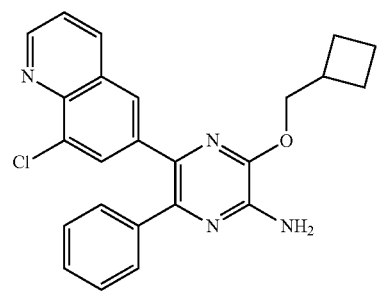
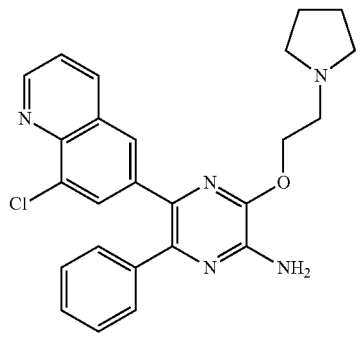
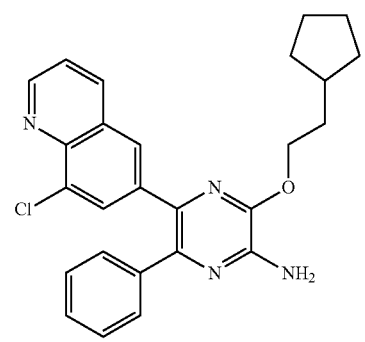
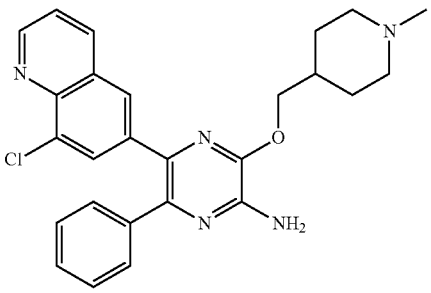

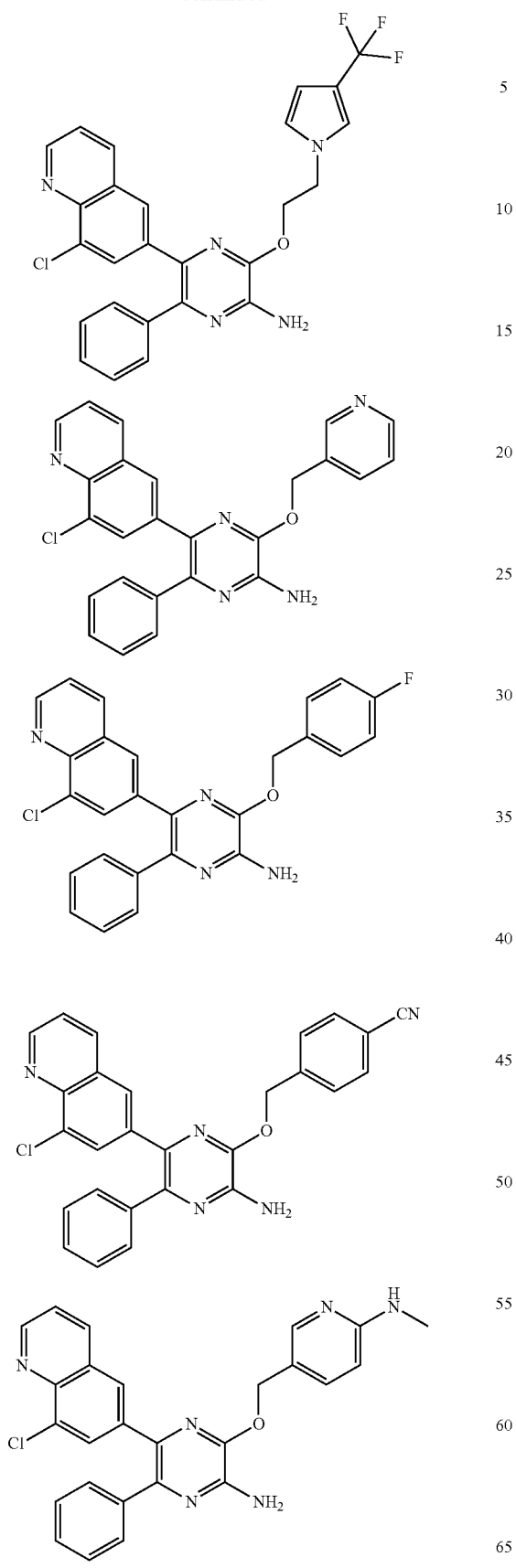
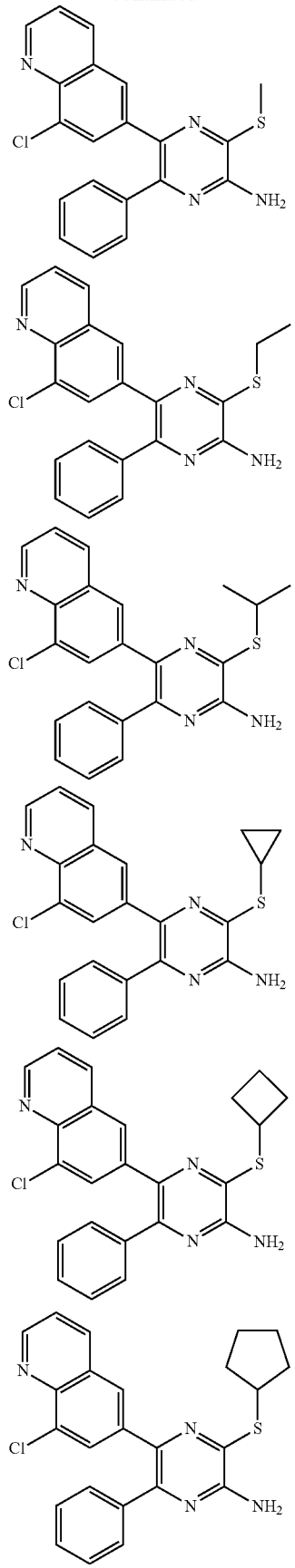

1287
-continued
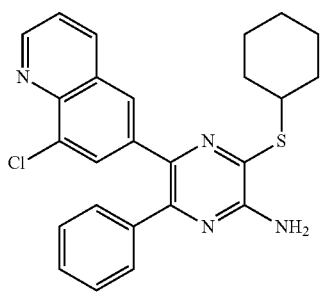
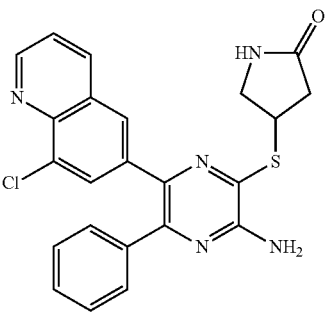
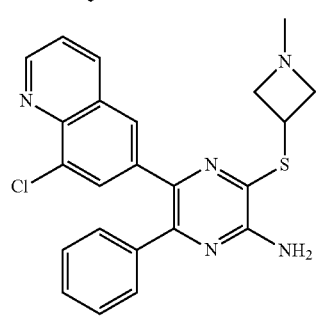
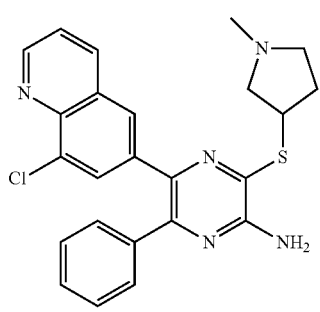
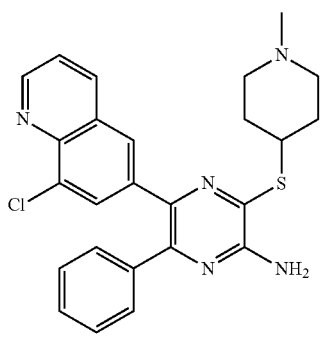
1288
-continued
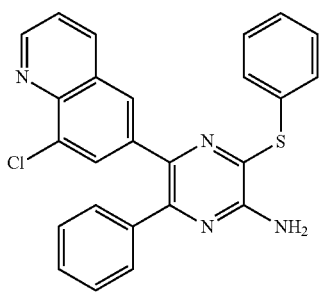
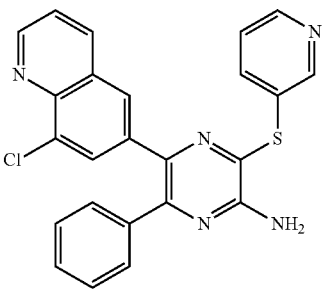
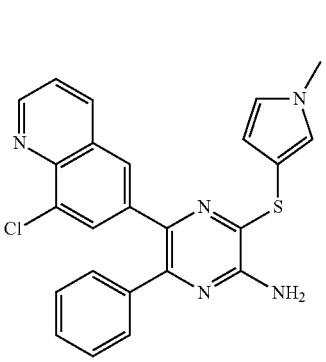
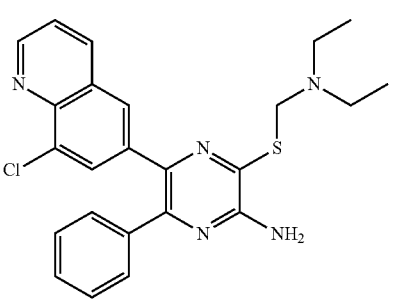
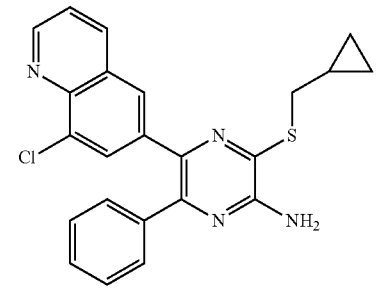

1289
-continued
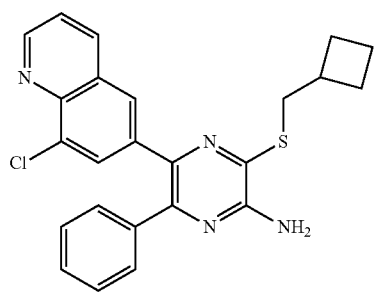
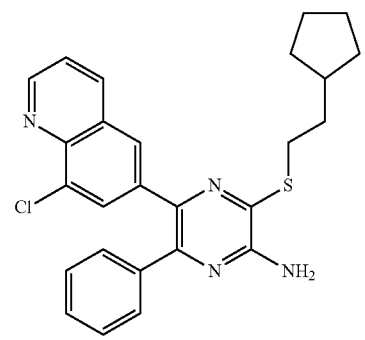
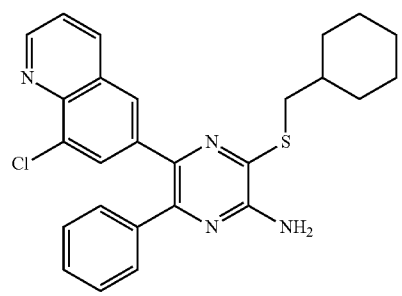
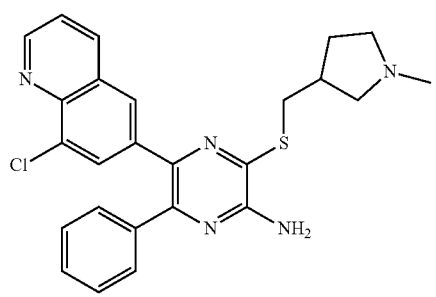
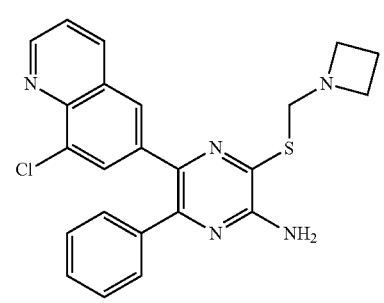
1290
-continued
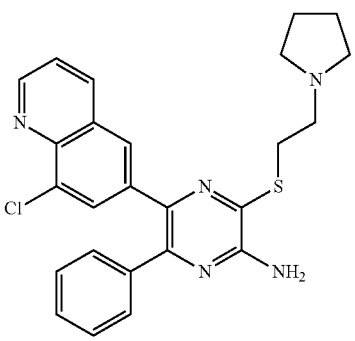
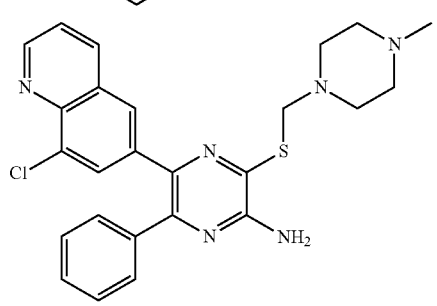
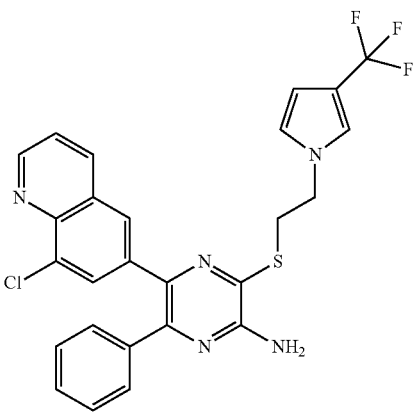
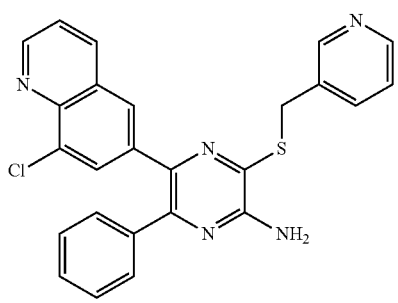
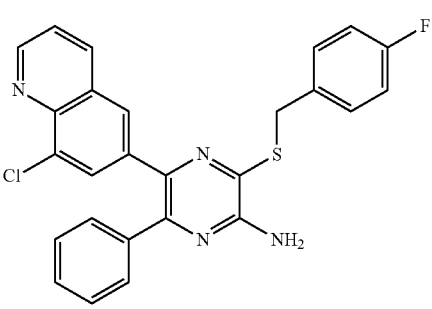

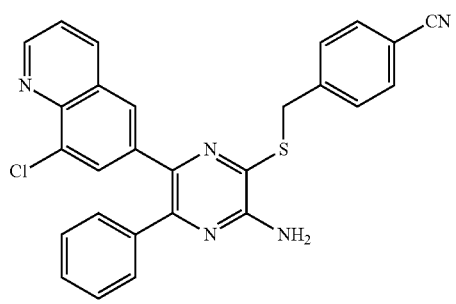
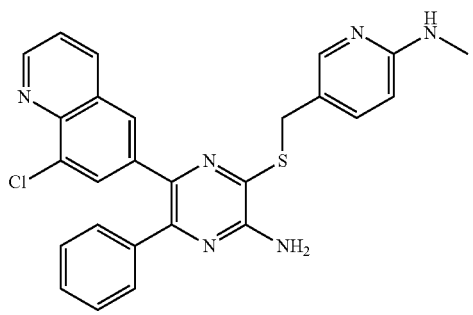
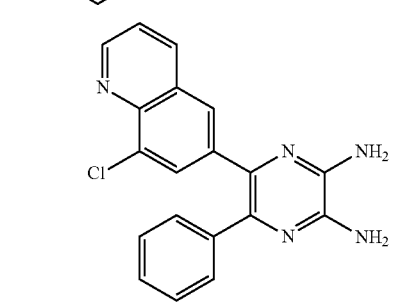
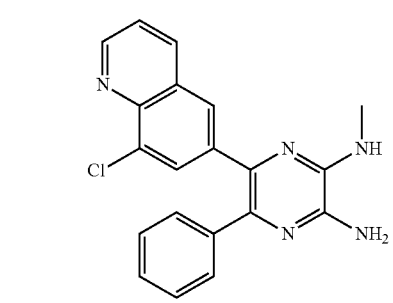
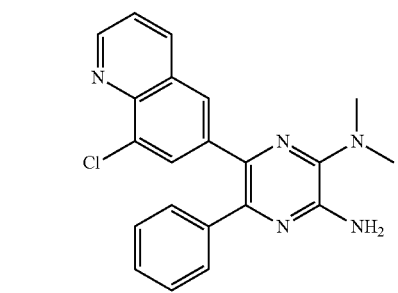
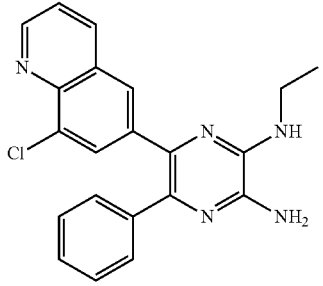
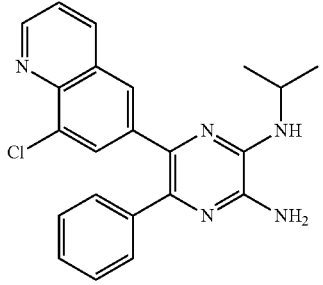
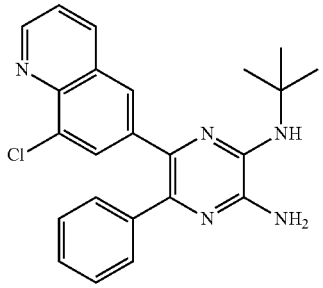
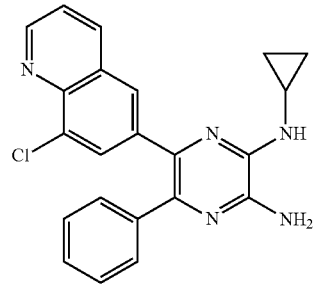
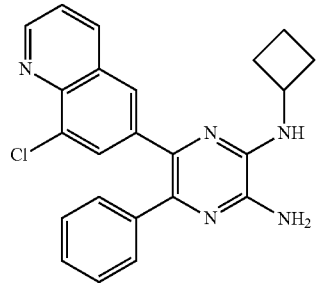
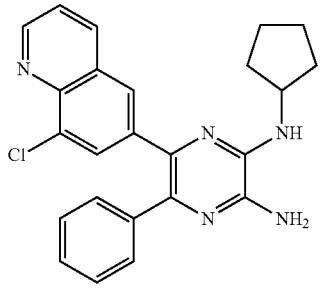

1293
-continued
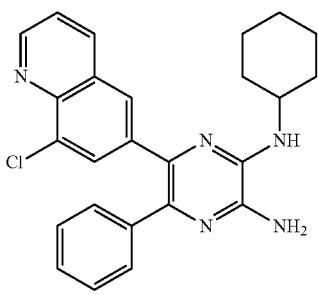
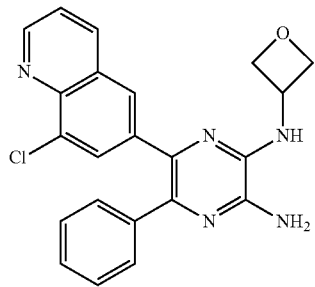
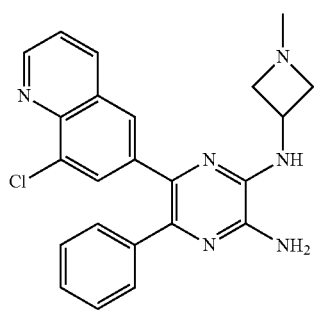
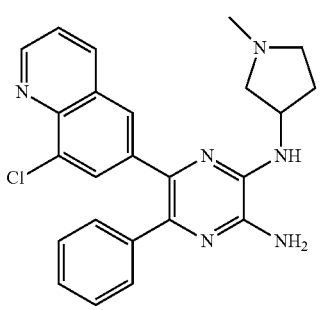
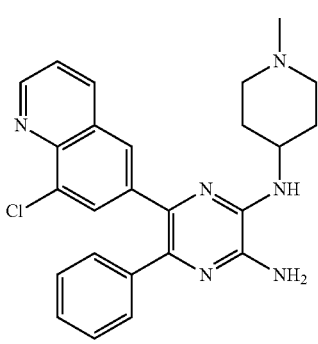
1294
-continued
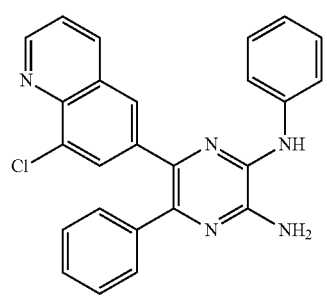
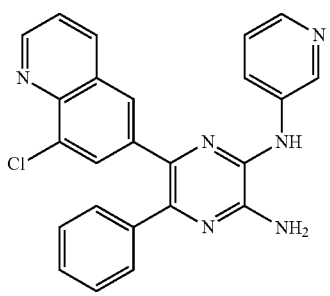
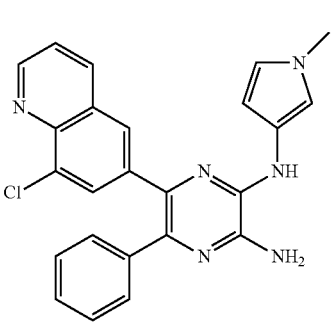
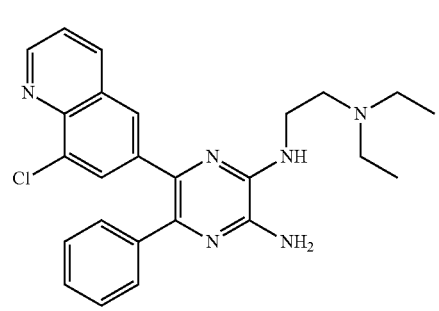
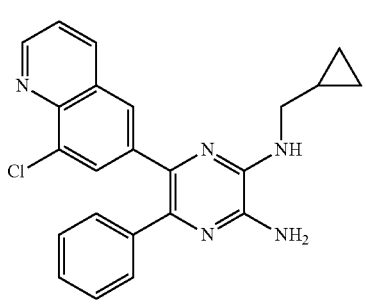

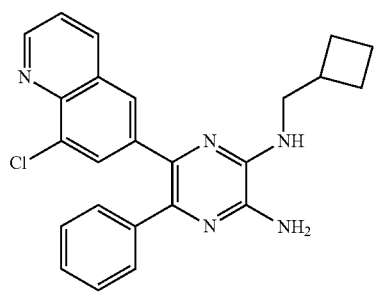
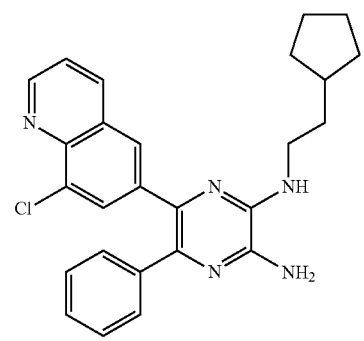
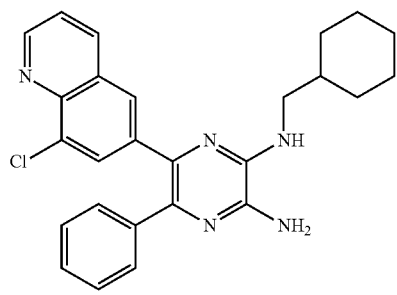
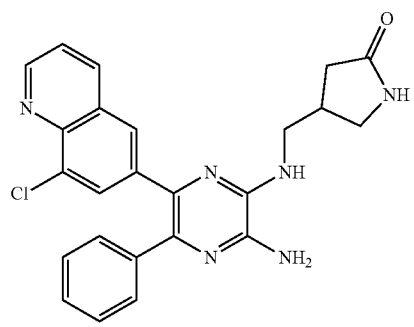
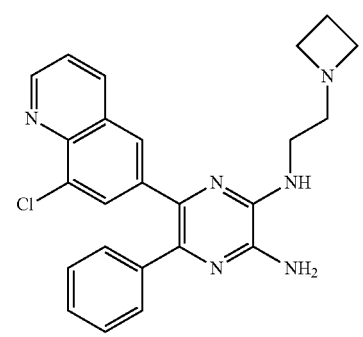
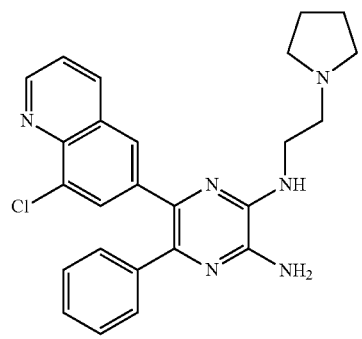
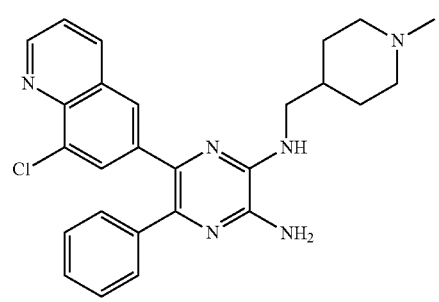
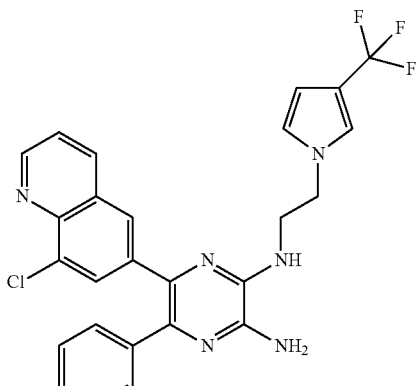
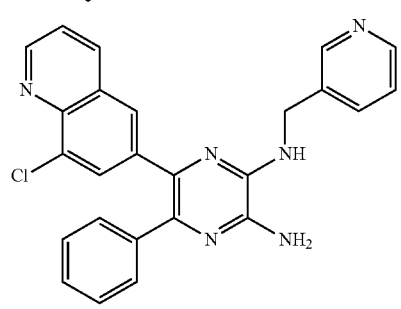
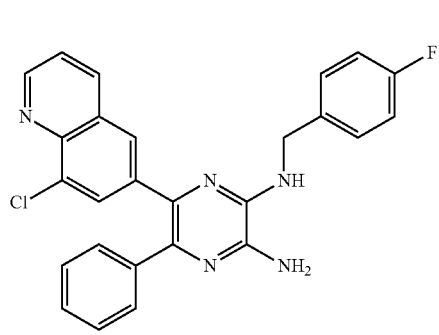

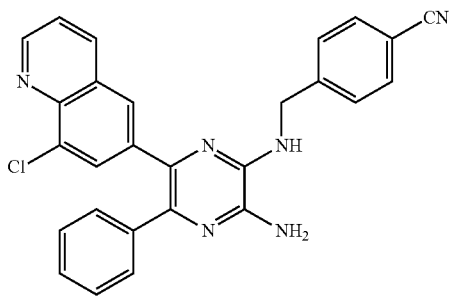
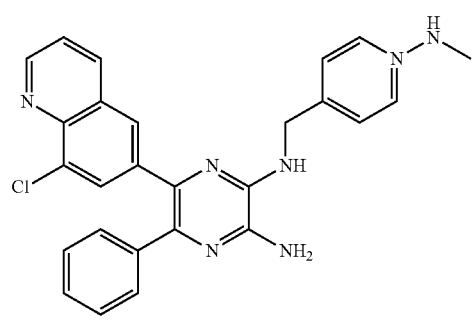
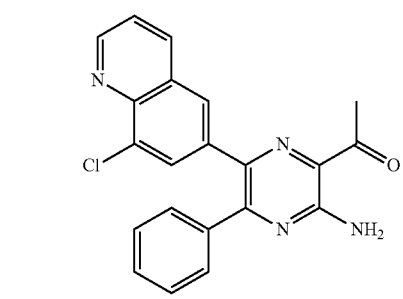
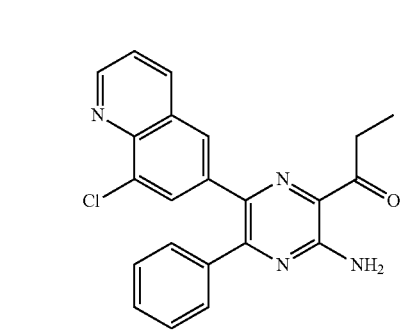
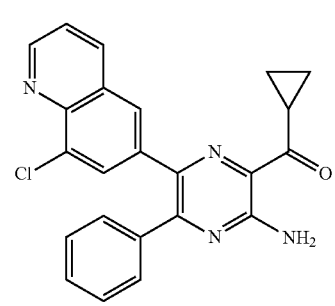
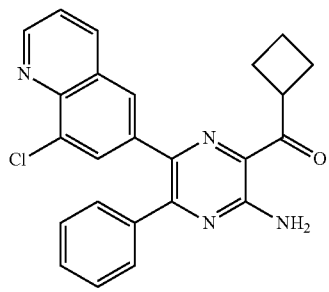
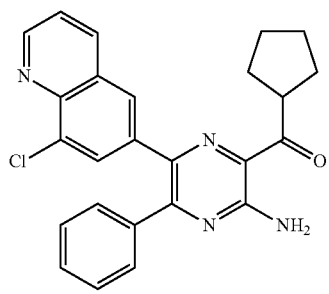
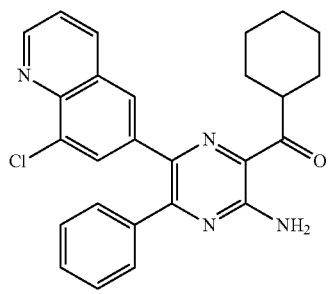
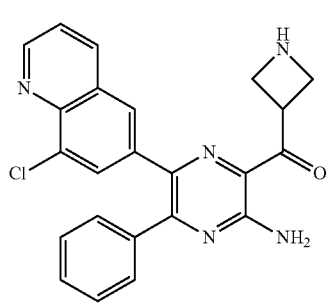
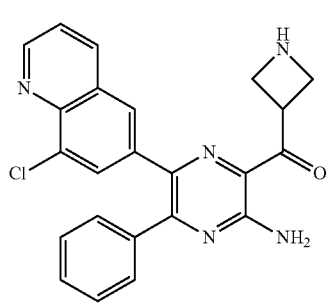

1299
-continued
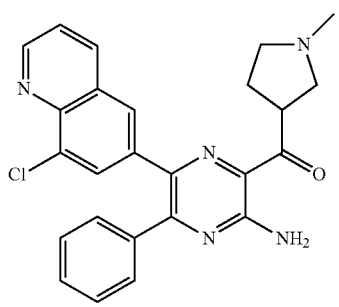
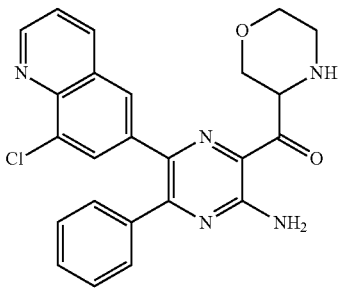
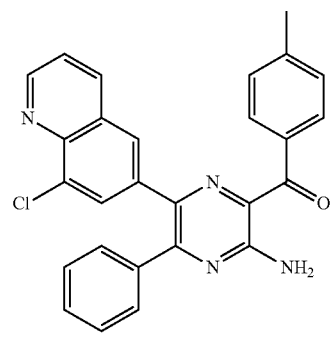
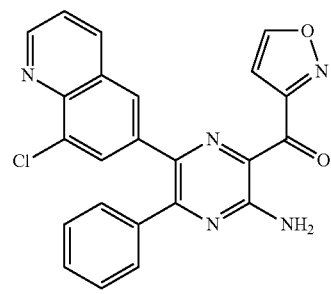
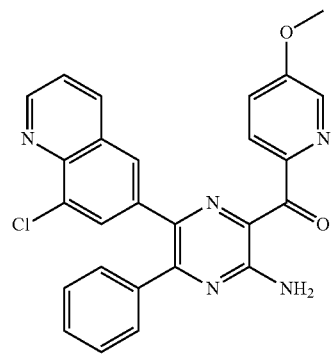
1300
-continued
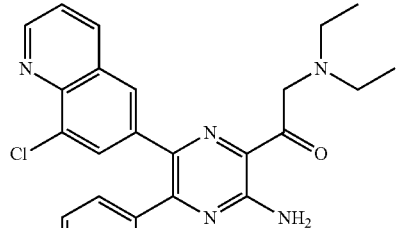
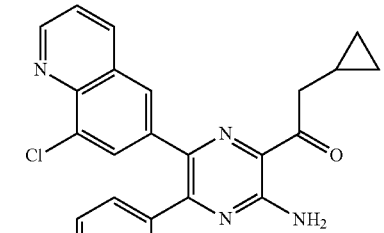
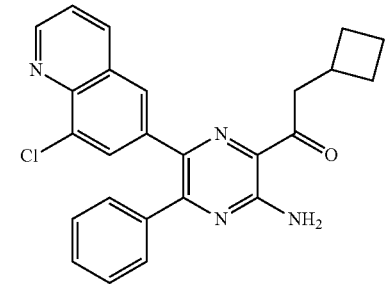
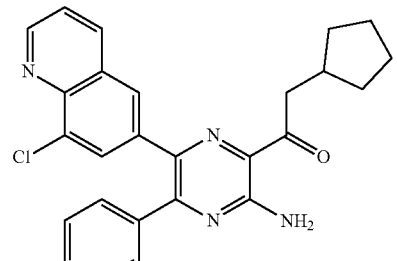
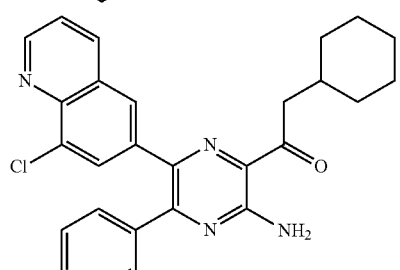
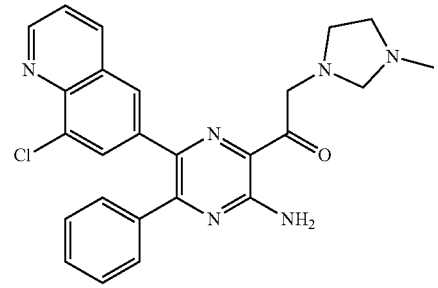

| 1301 | 1302 |
|---|---|
| -continued | -continued |
| 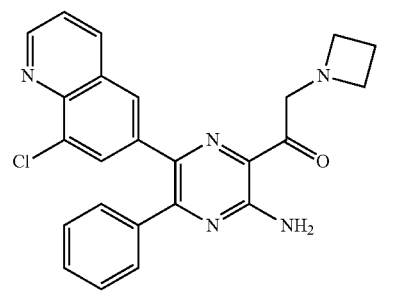 | 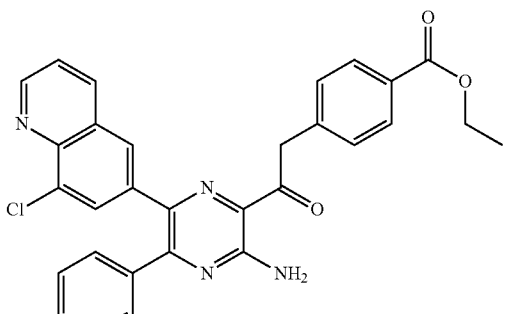 |
| 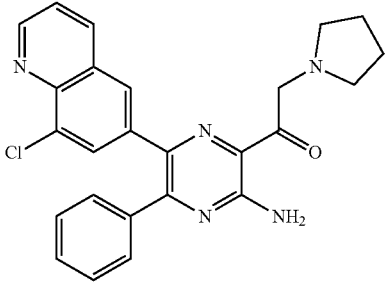 | 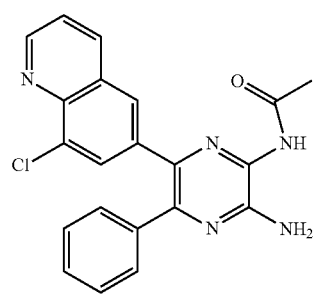 |
| 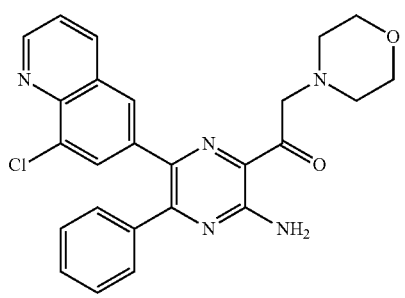 | 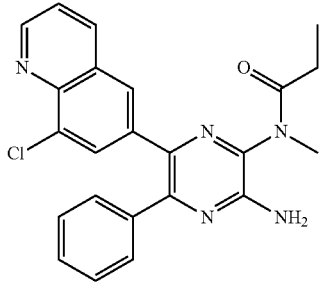 |
| 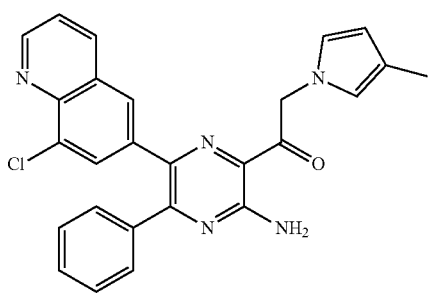 | 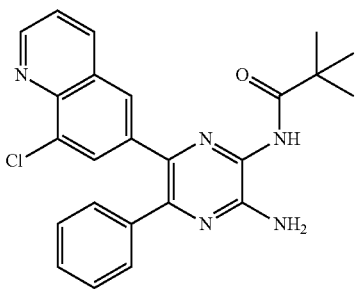 |
| 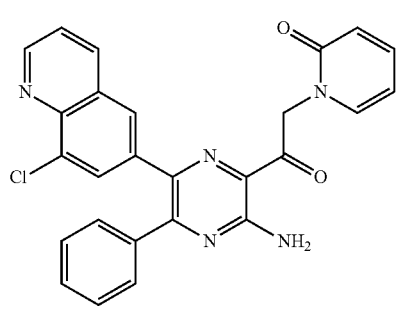 | 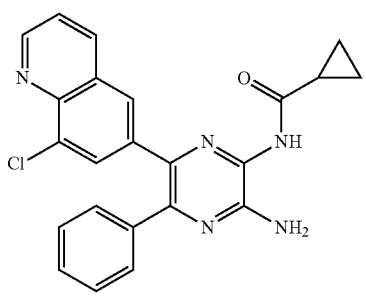 |

1303
-continued
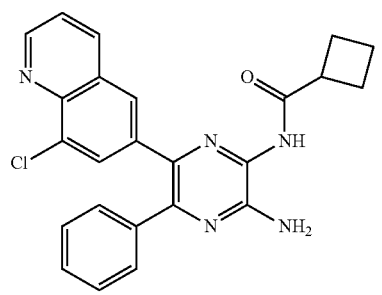
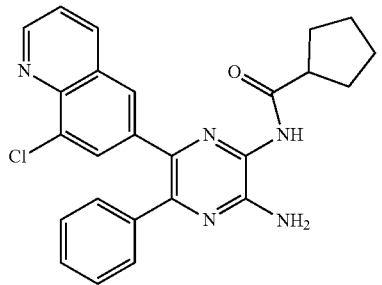
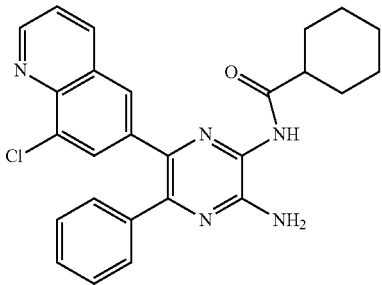
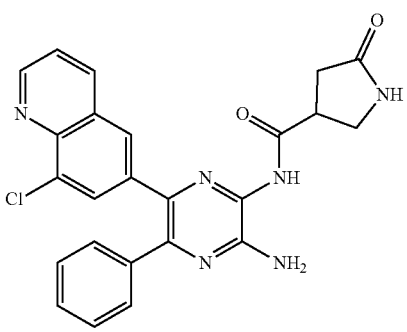
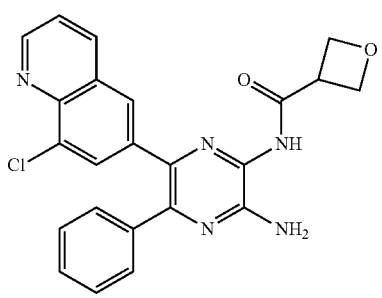
1304
-continued
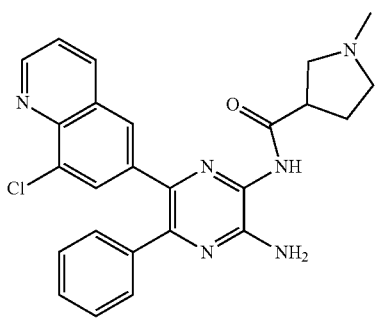
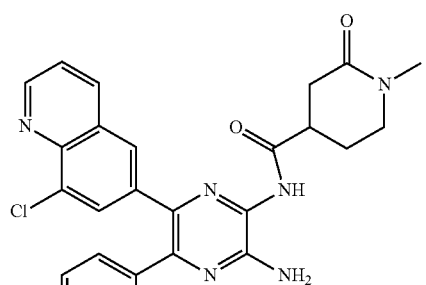
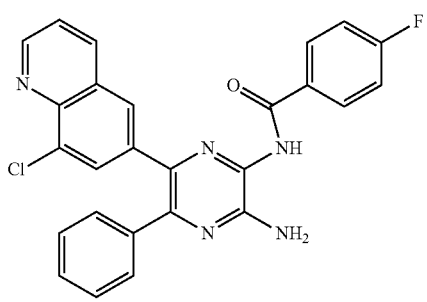
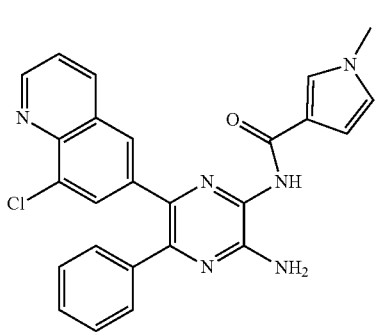
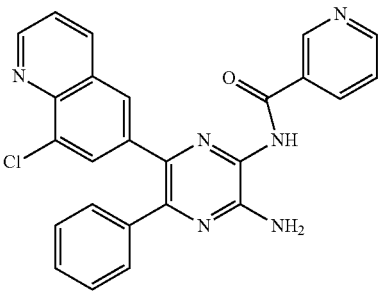

1305
-continued
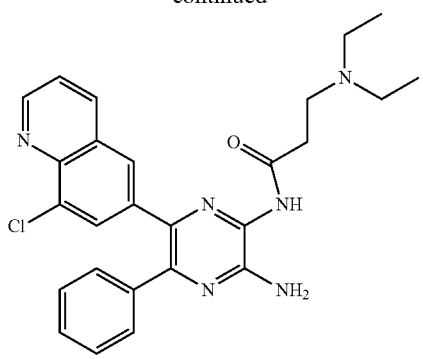
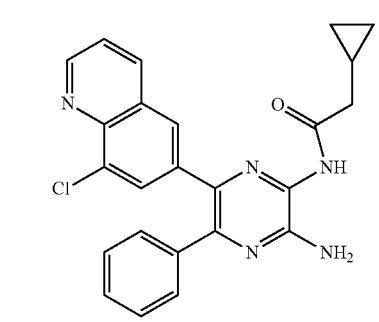
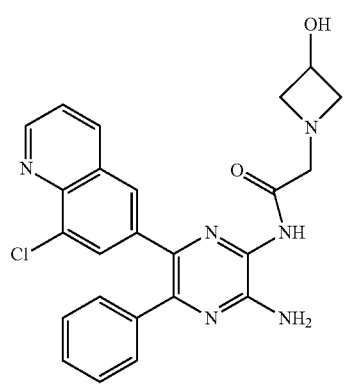
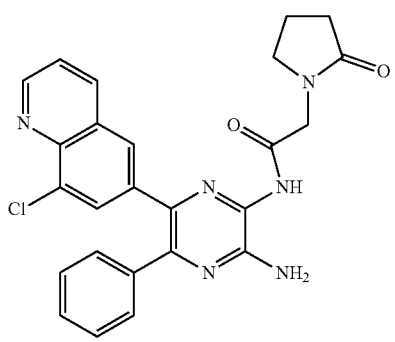
1306
-continued
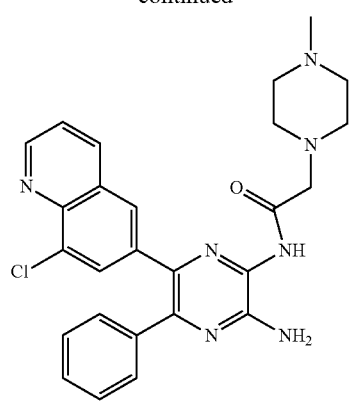
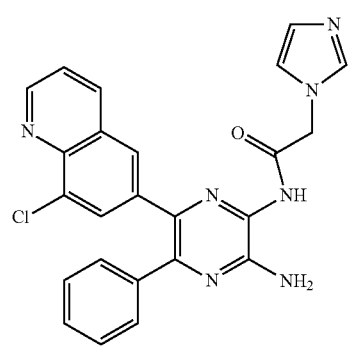
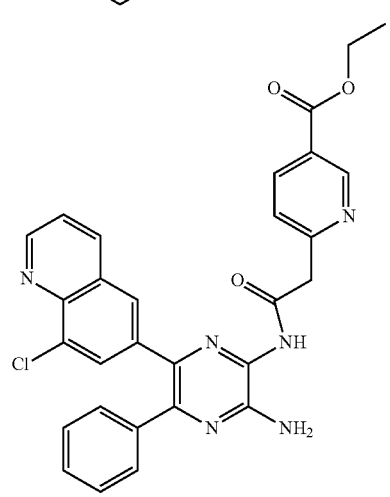
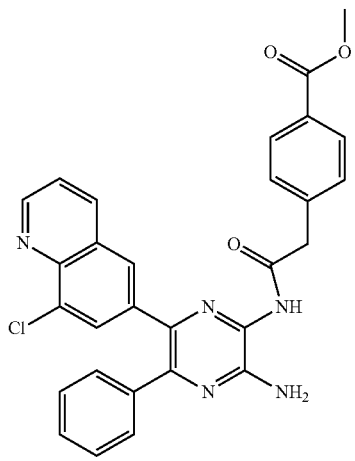

1307
-continued
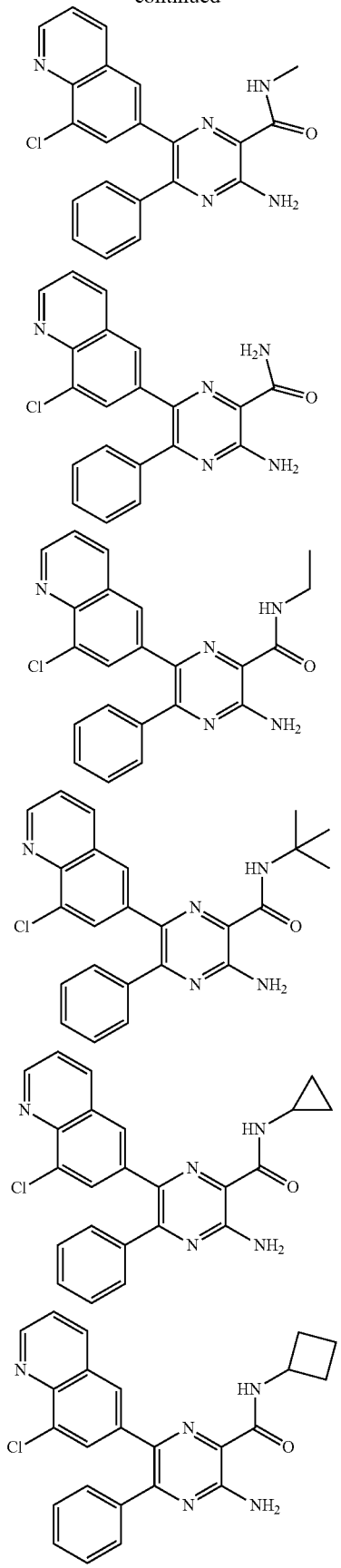
1308
-continued
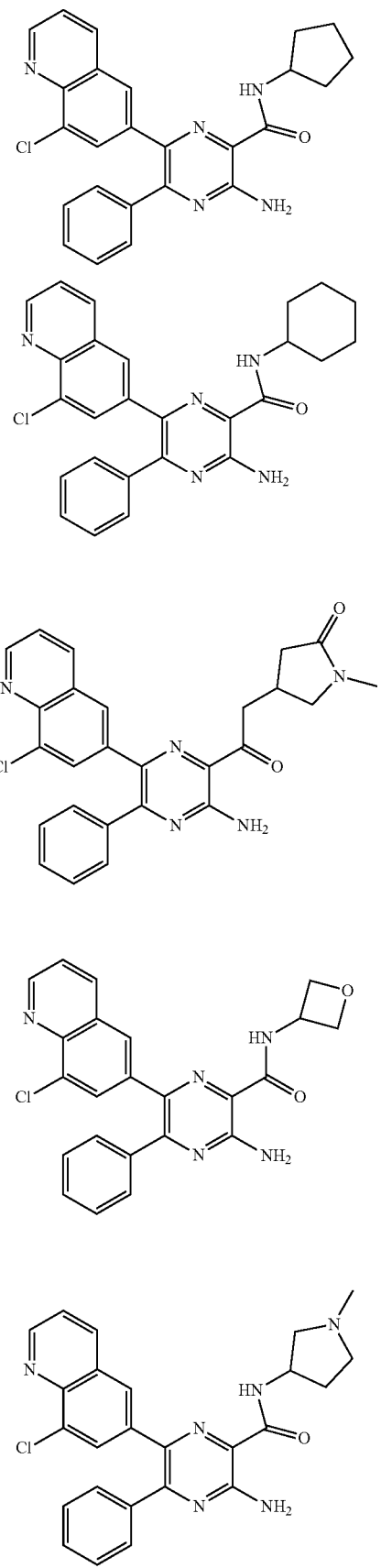

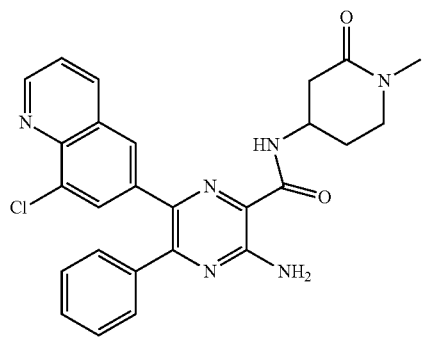
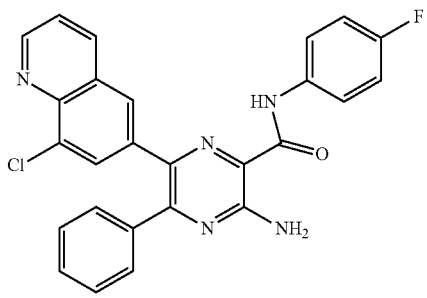
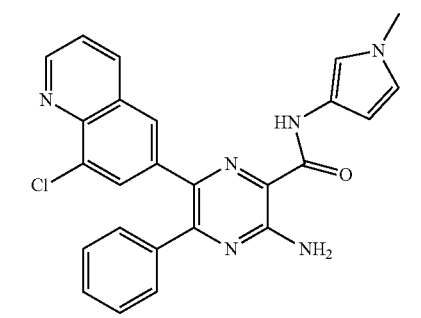
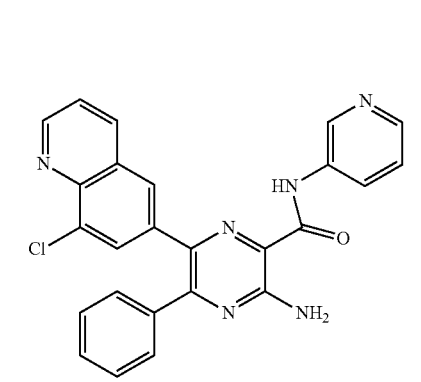
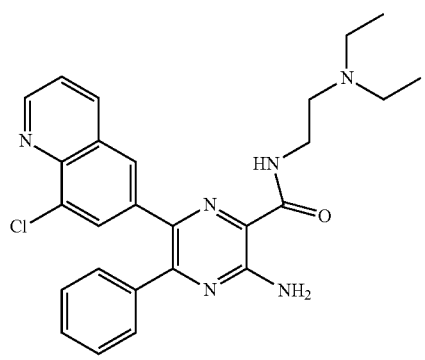
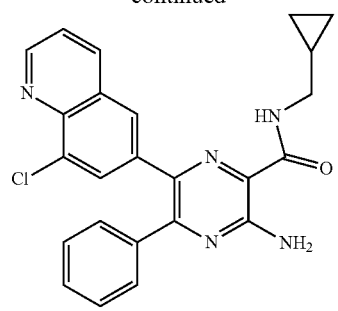
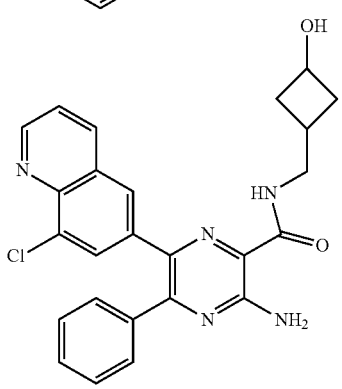
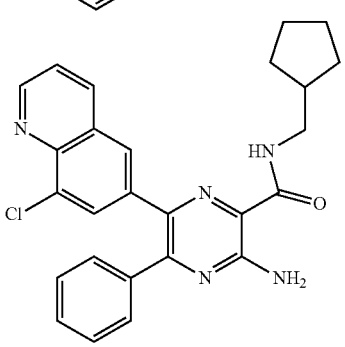
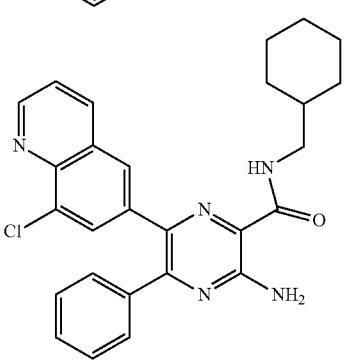
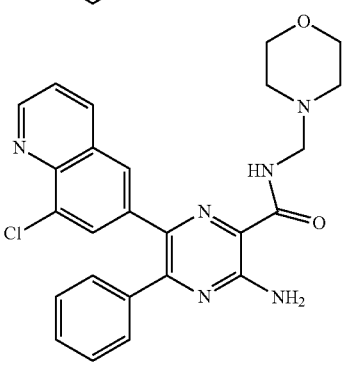

1311
-continued
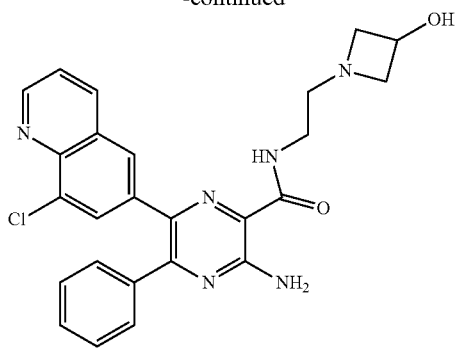
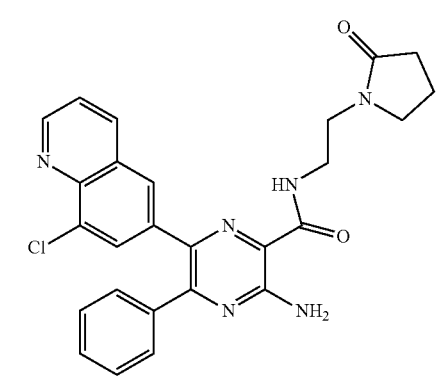
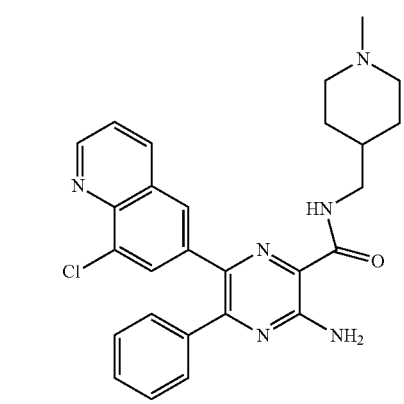
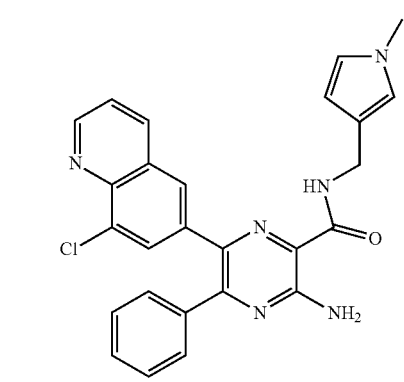
1312
-continued
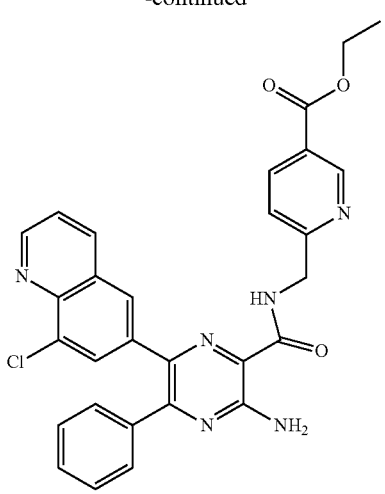
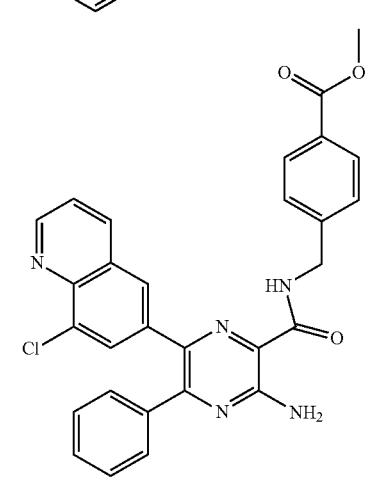
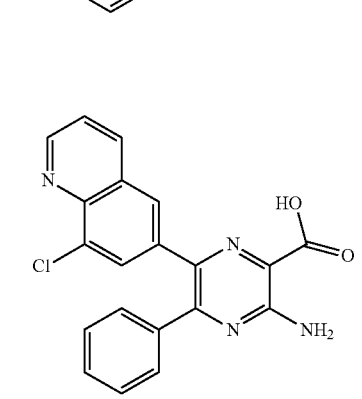
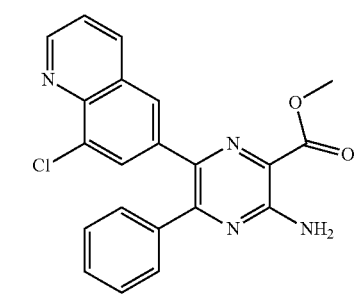

1313
-continued
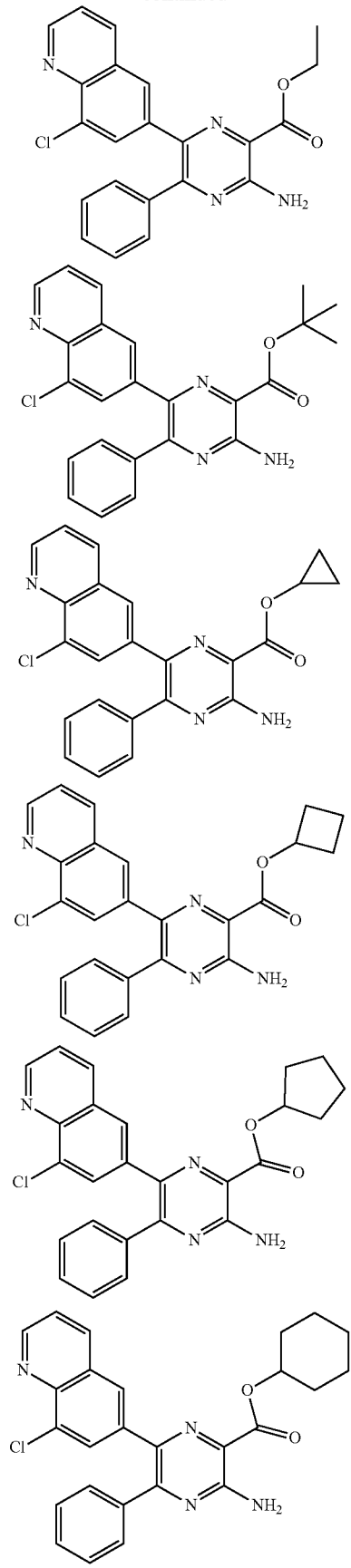
1314
-continued
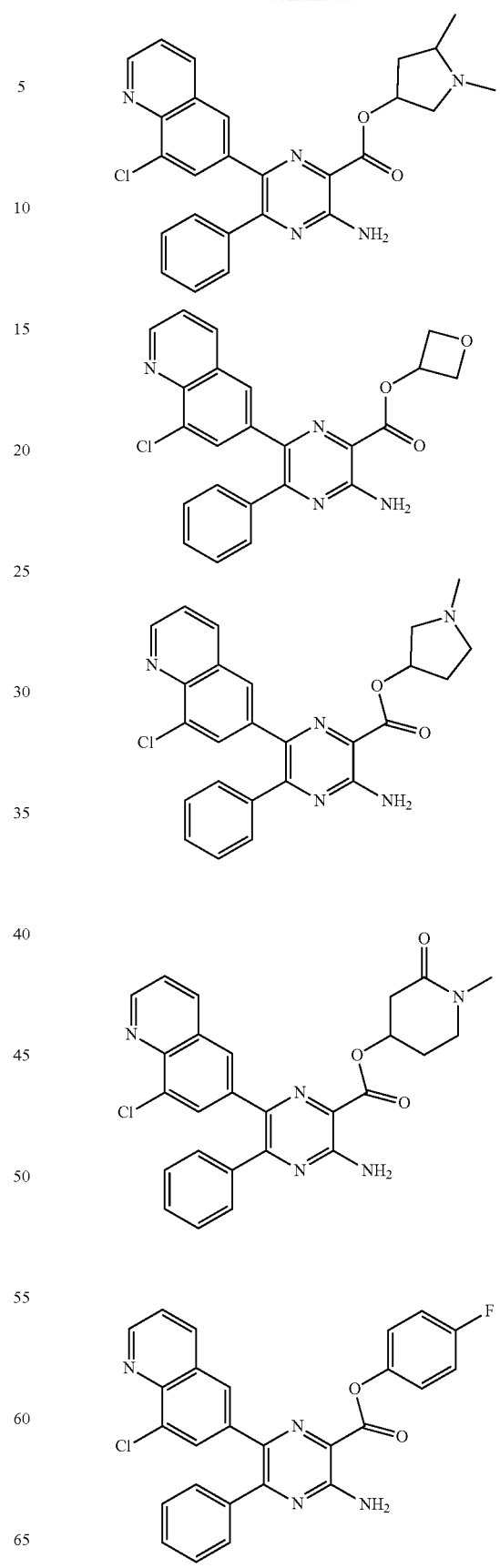

1315
-continued
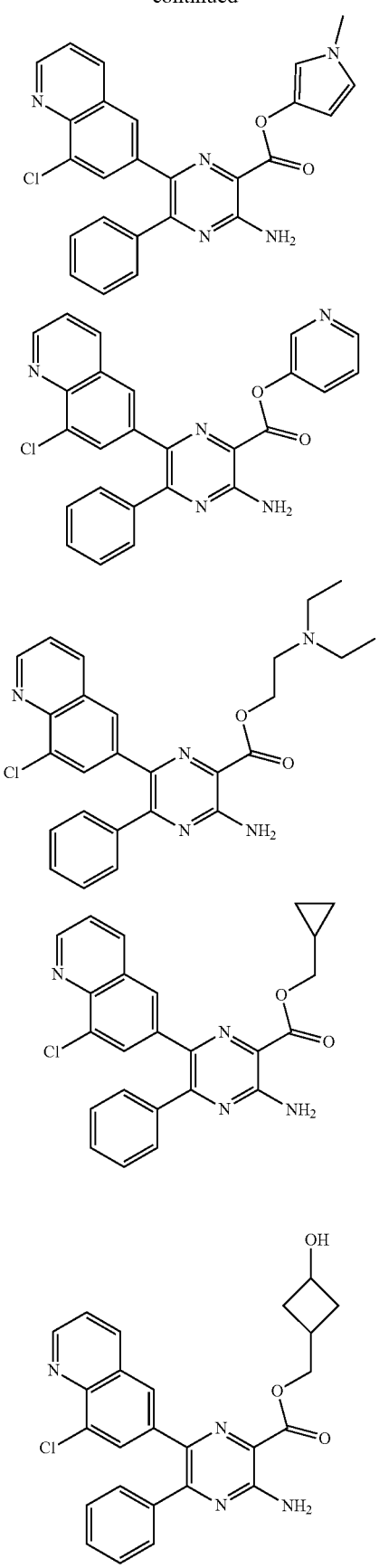
1316
-continued
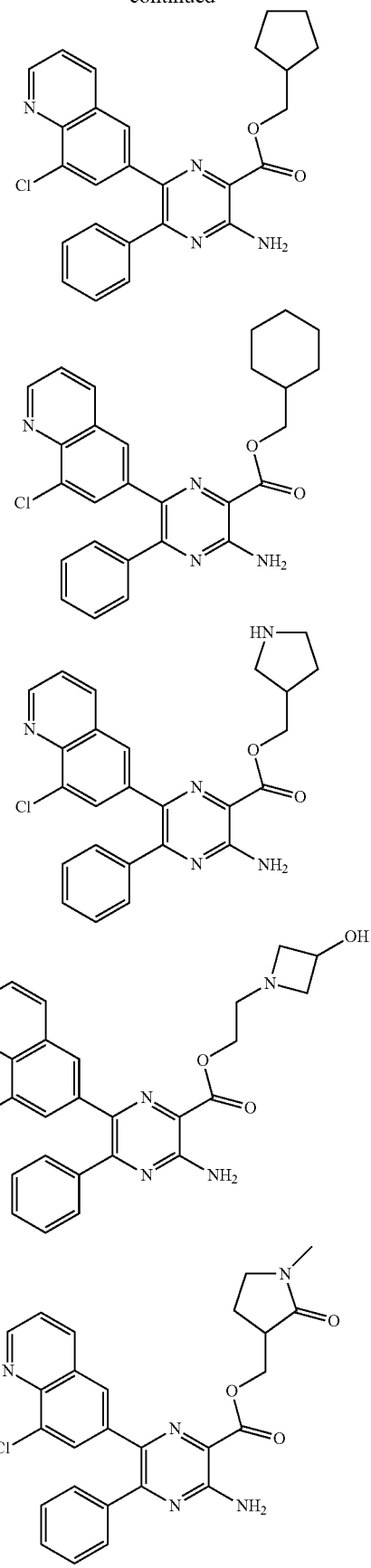

1317
-continued
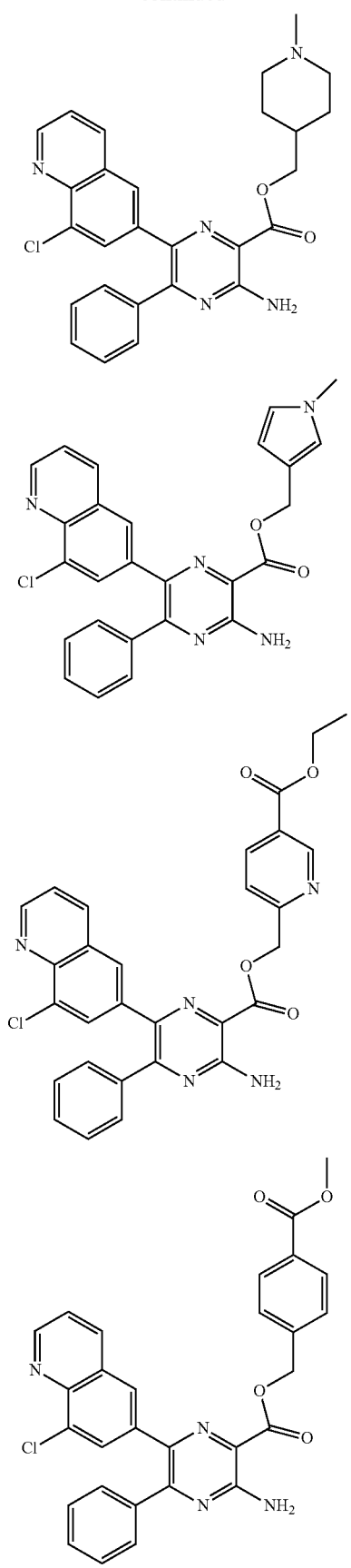
1318
-continued
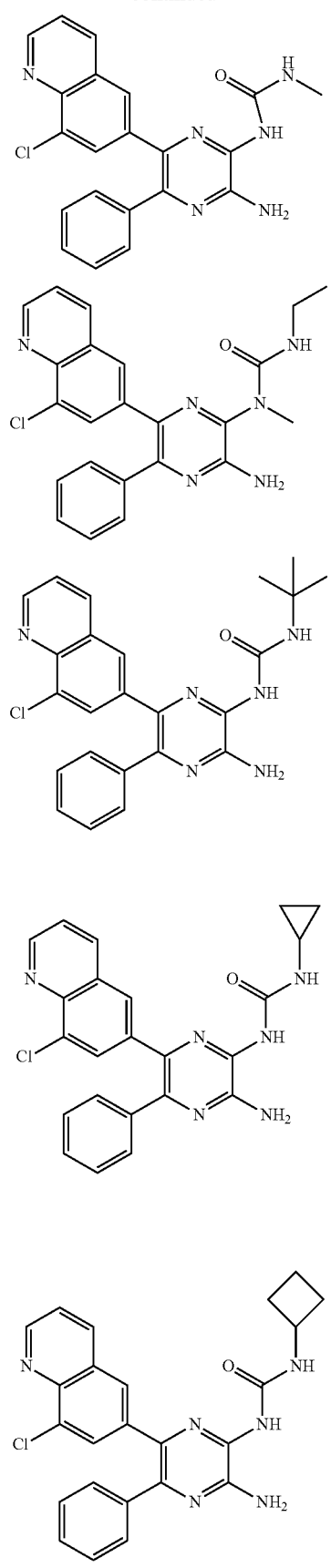

1319
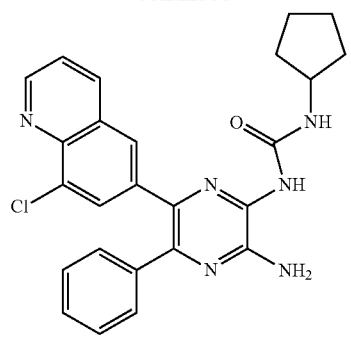
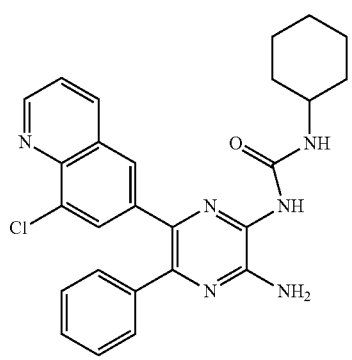
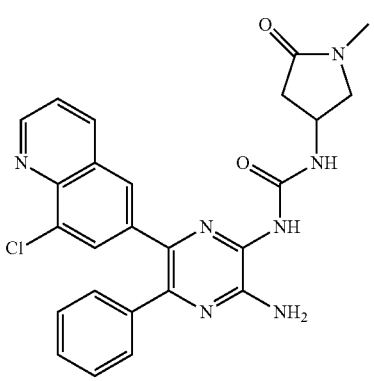
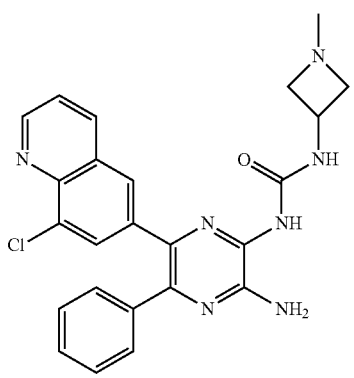
1320
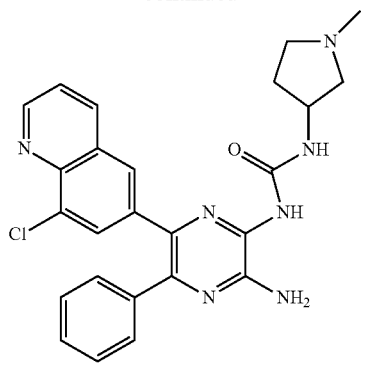
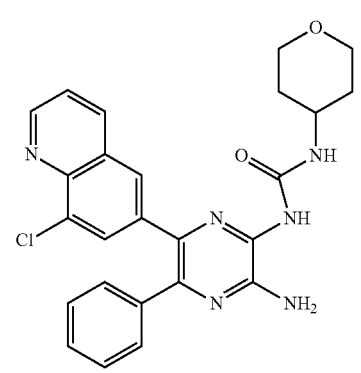
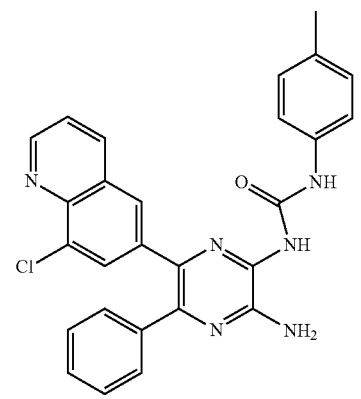
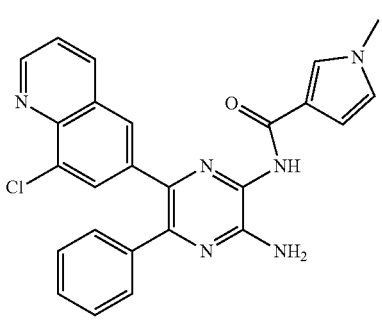

1321
-continued
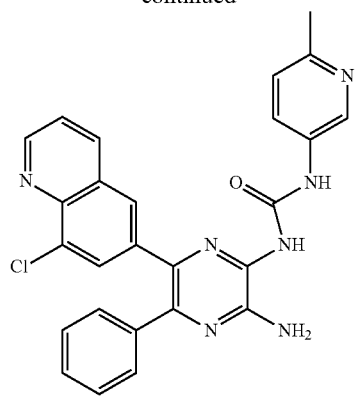
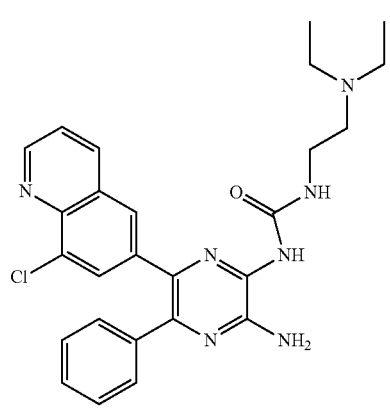
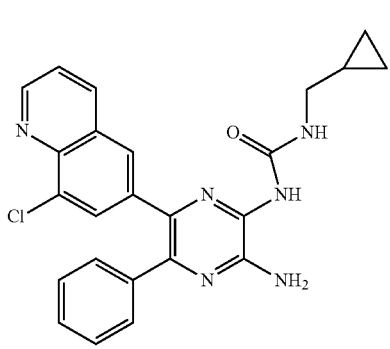
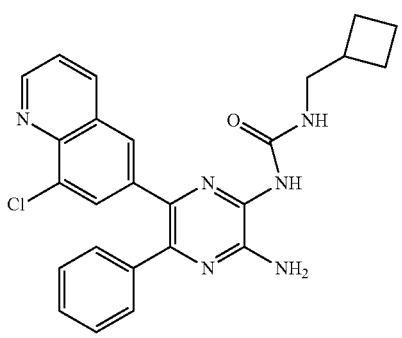
1322
-continued
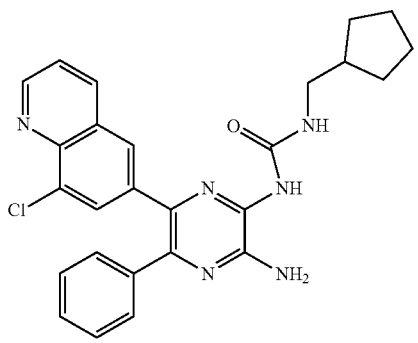
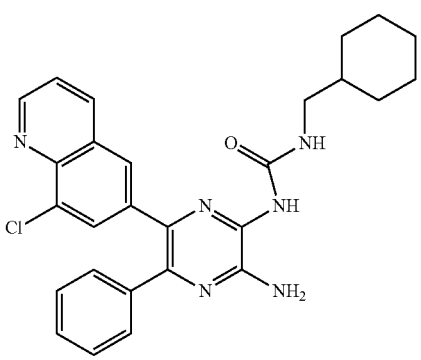
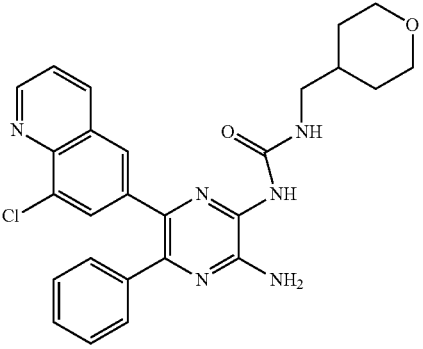
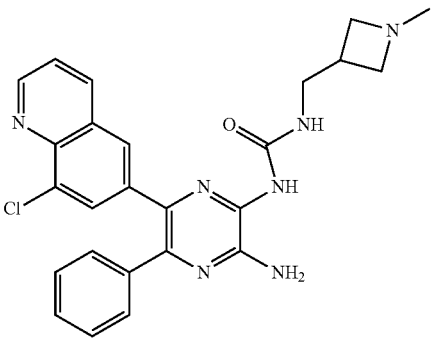

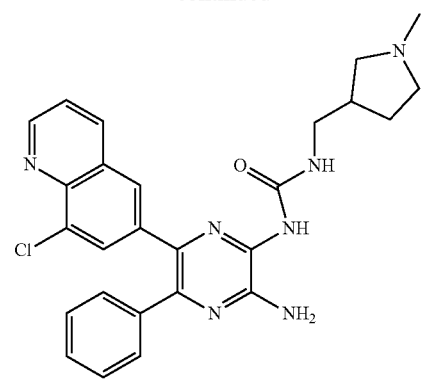
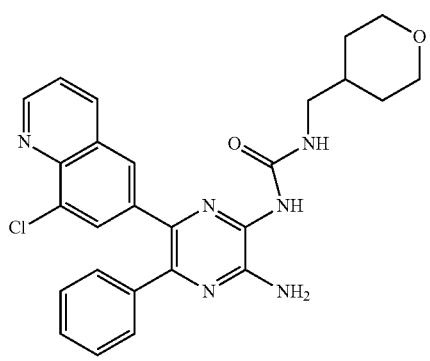
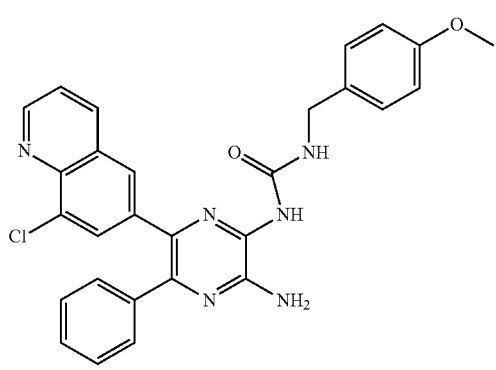
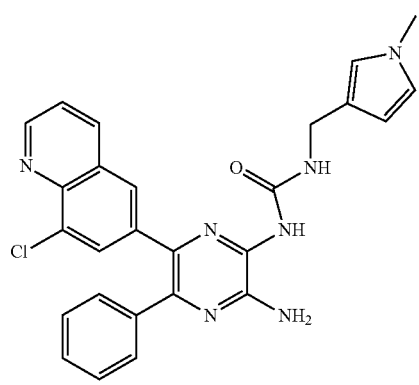
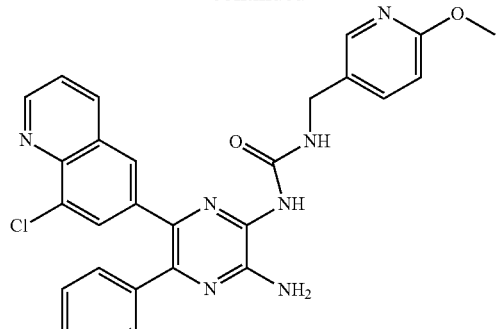
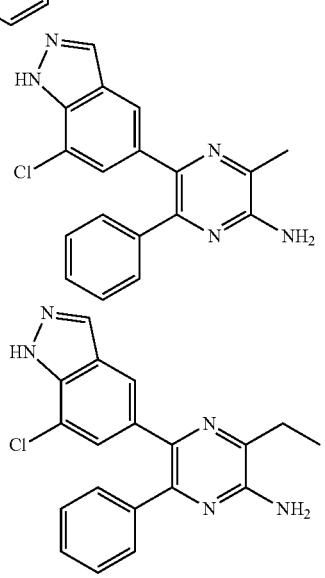
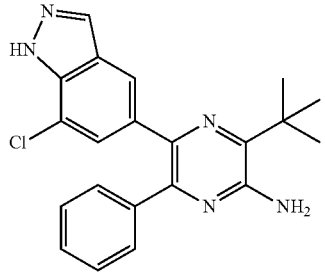
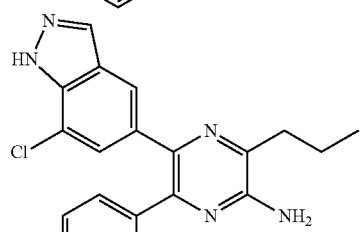
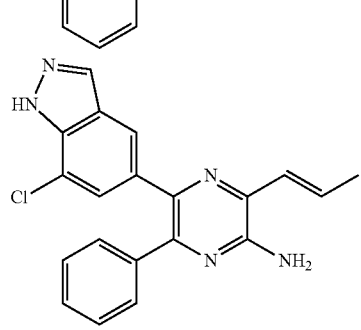

1325
-continued
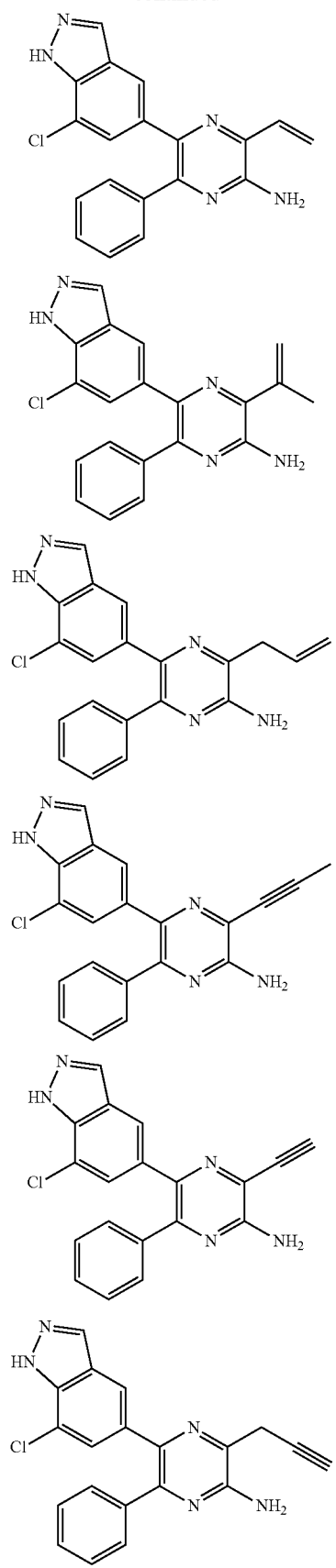
1326
-continued
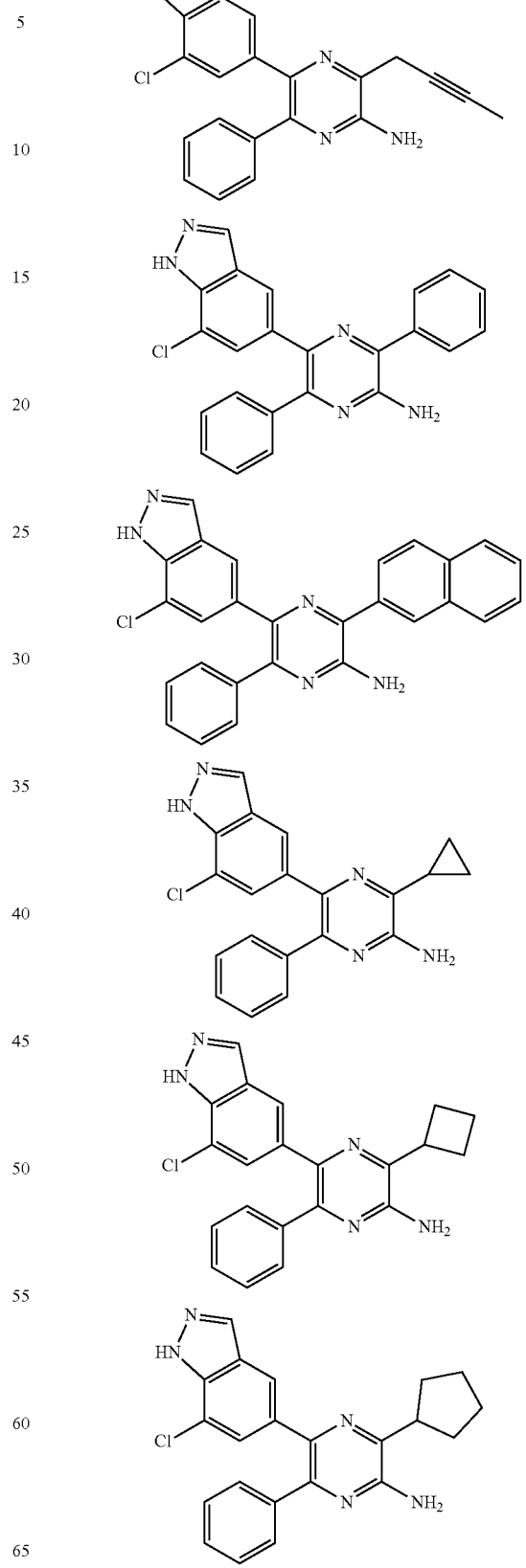

1327
-continued
1328
-continued
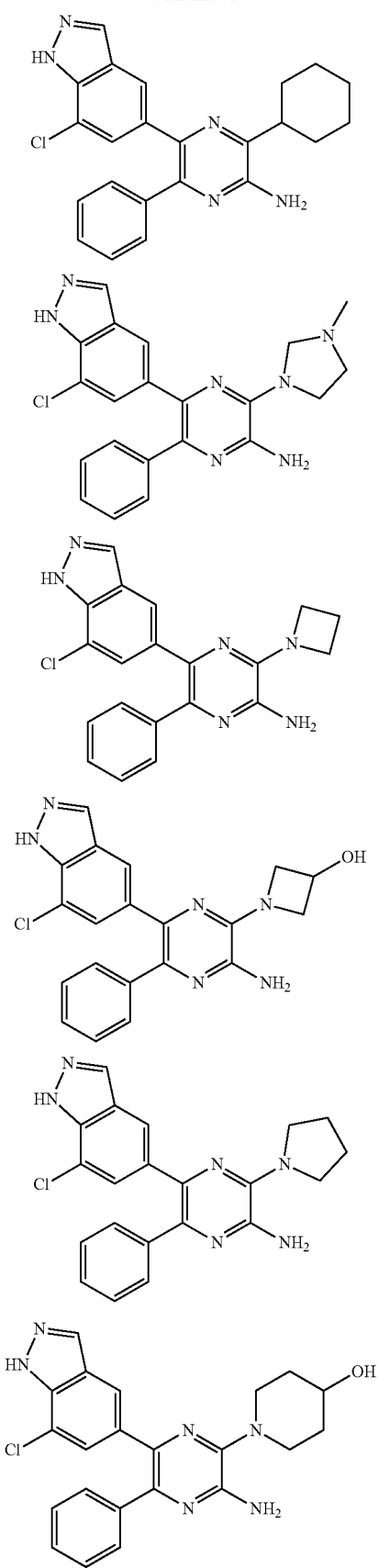
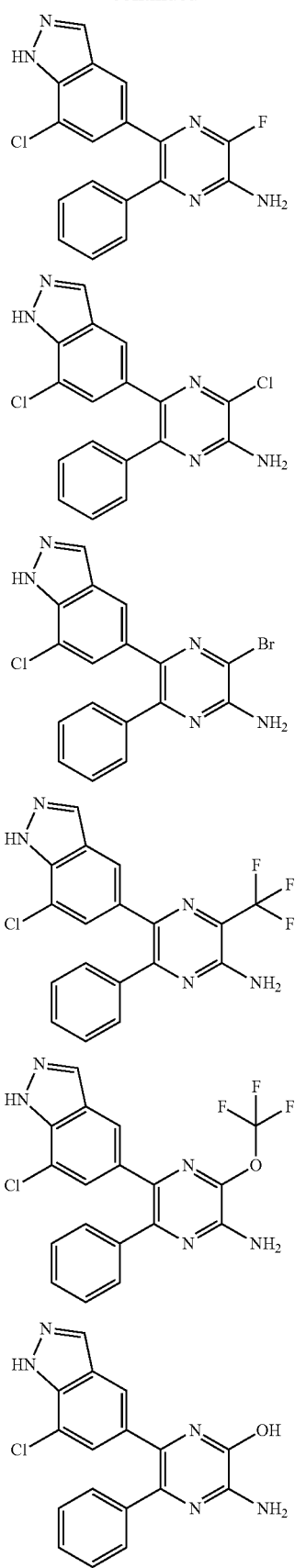

1329
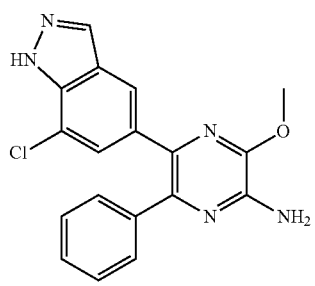
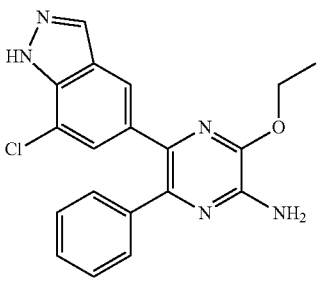
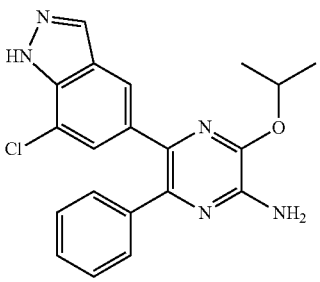
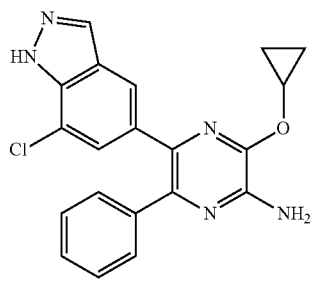
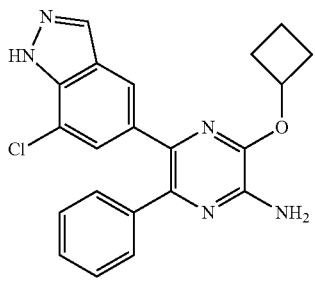
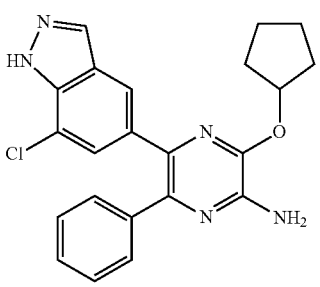
1330
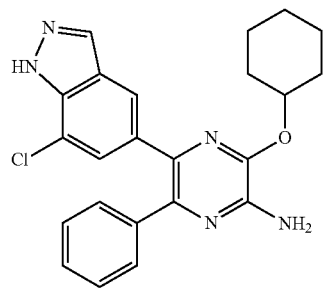
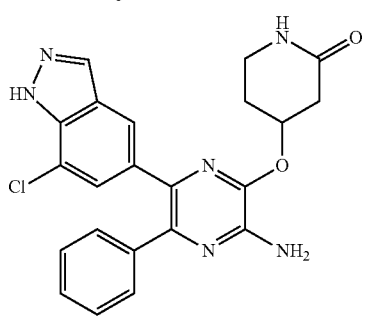
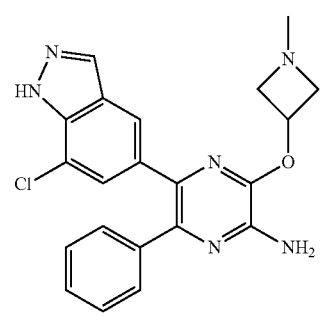
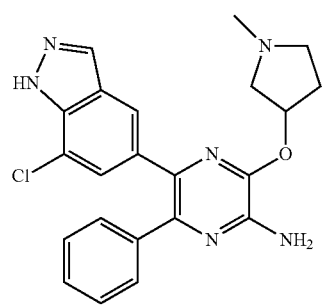
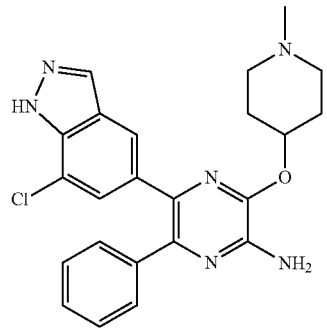

1331
-continued
1332
-continued
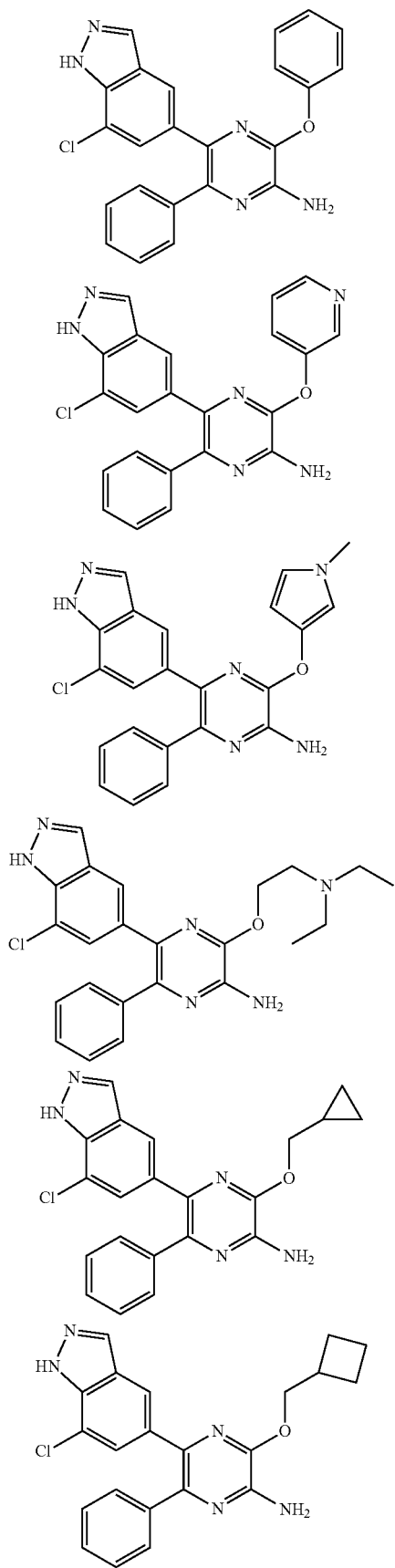
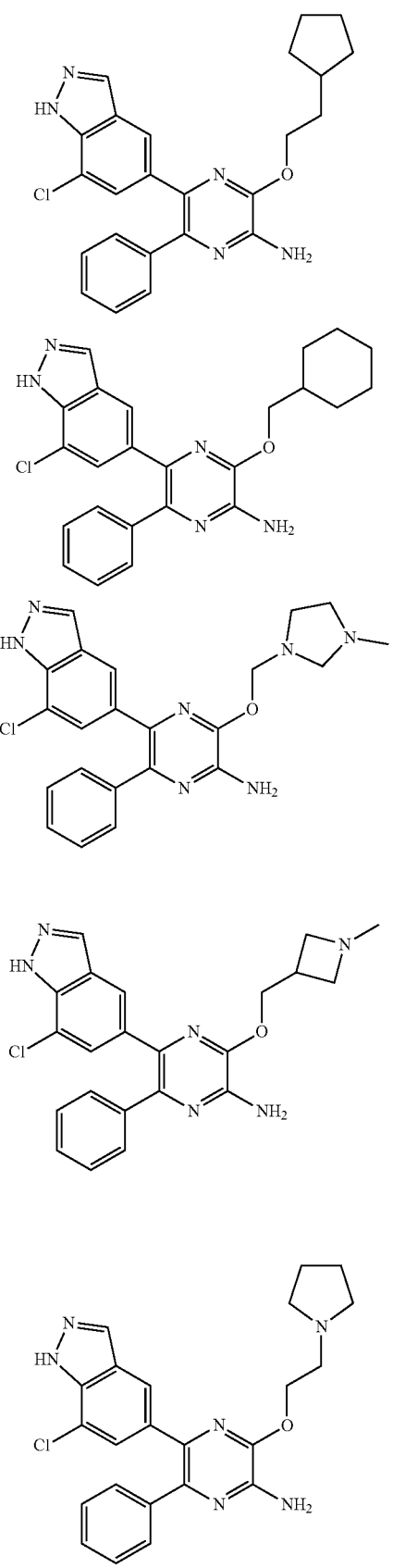

1333
-continued
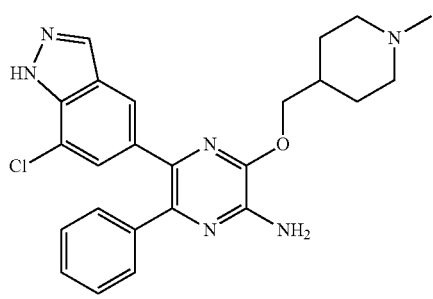
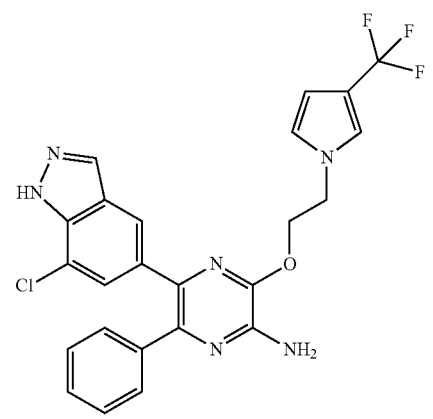
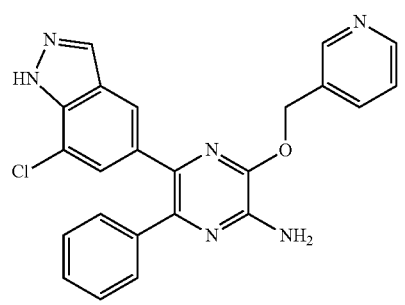
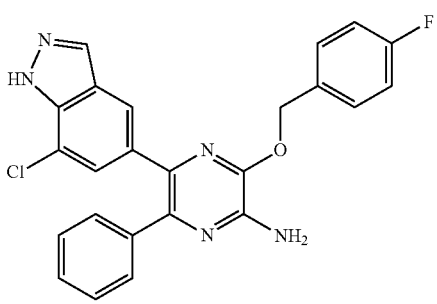
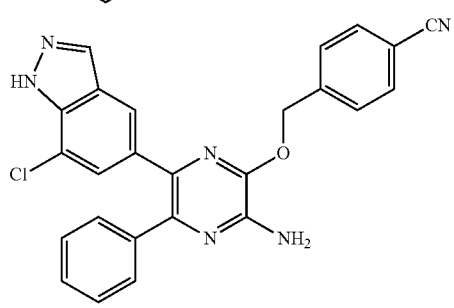
1334
-continued
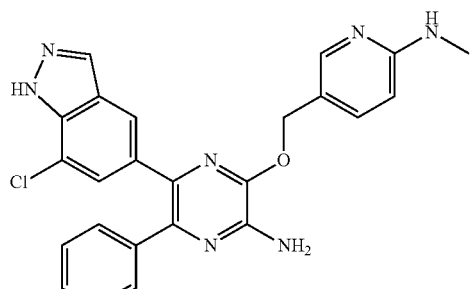
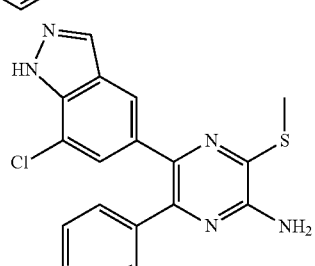
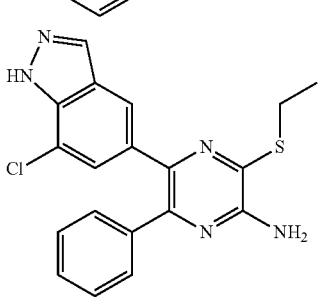
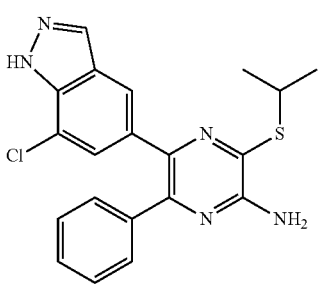
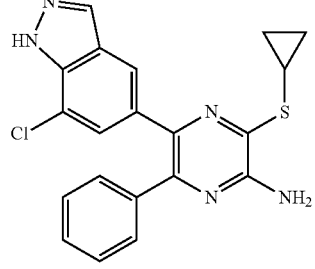
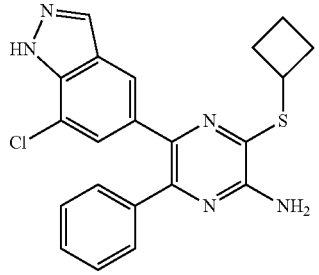

1335
-continued
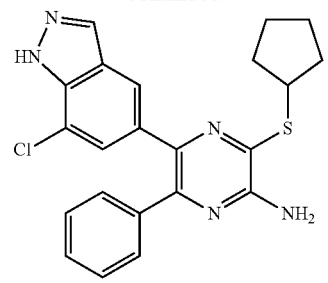
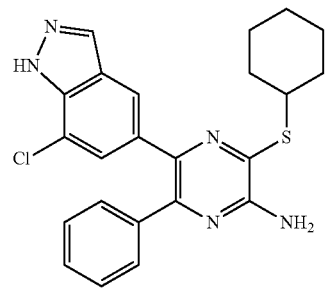
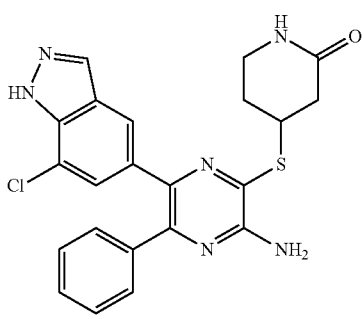
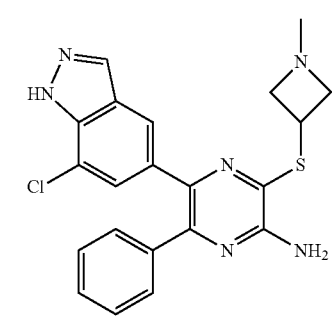
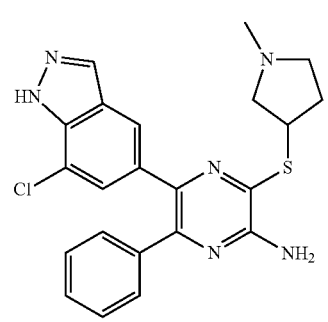
1336
-continued
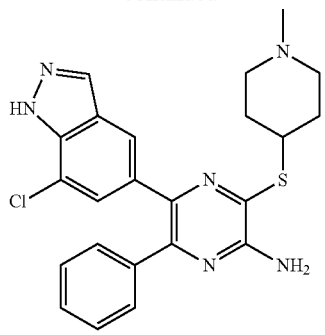
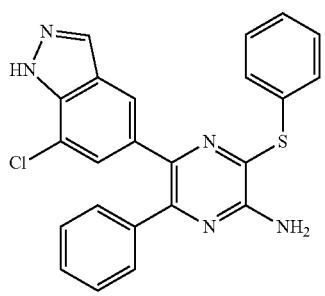
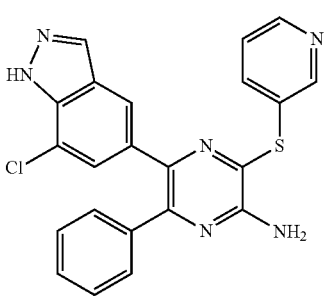
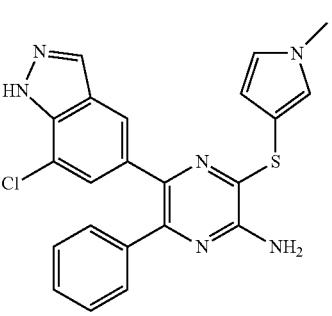
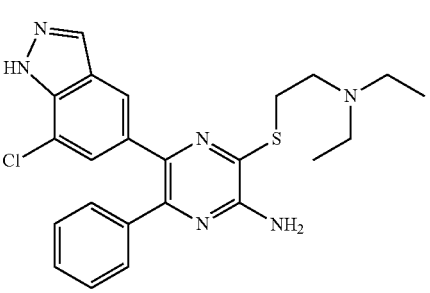

1337
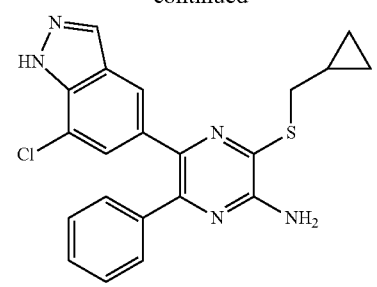
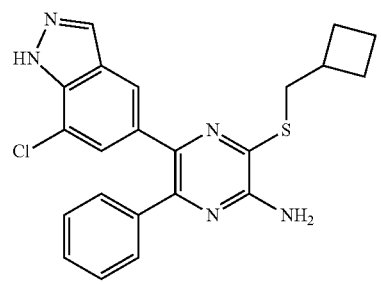
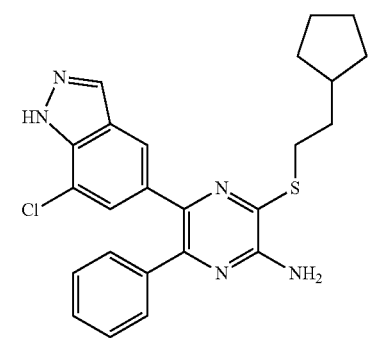
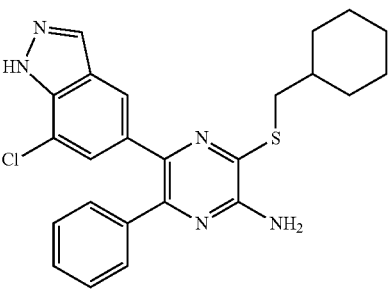
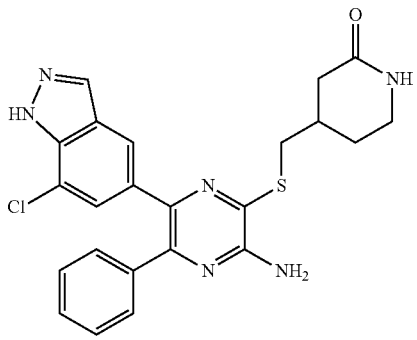
1338
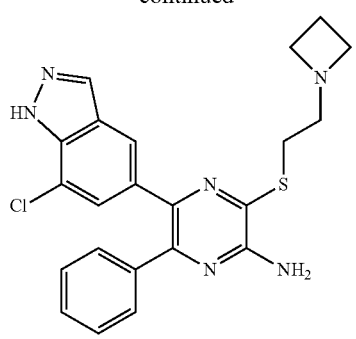
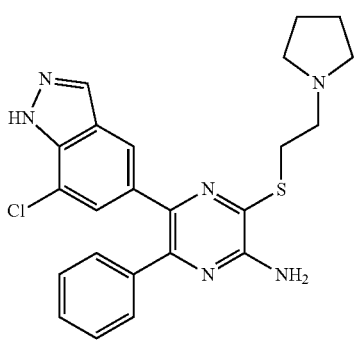
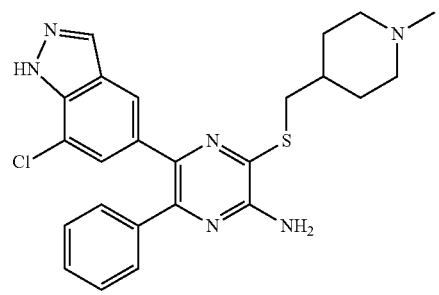
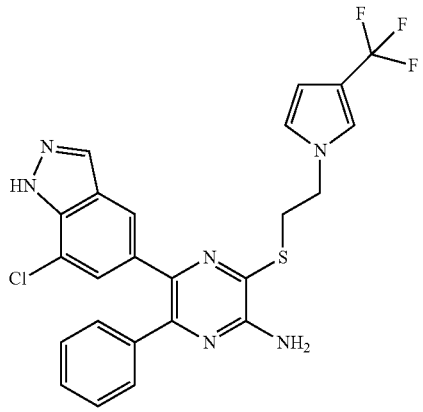
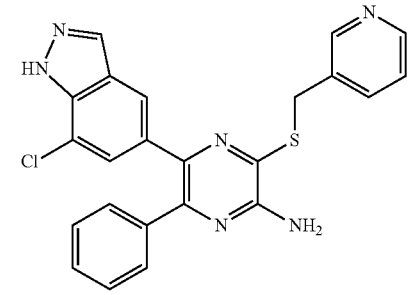

1339
-continued
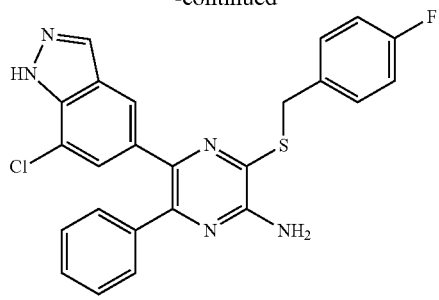
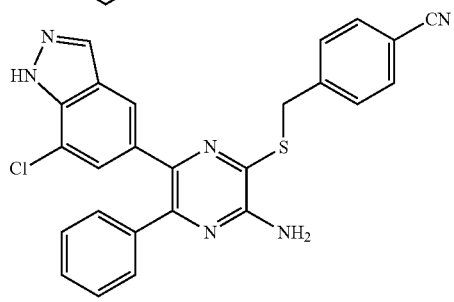
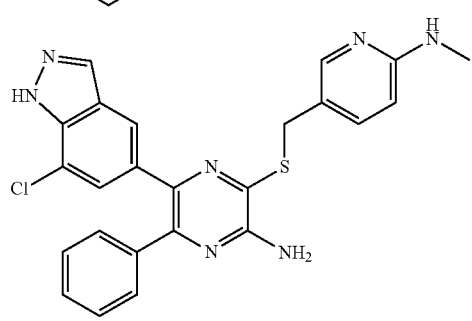
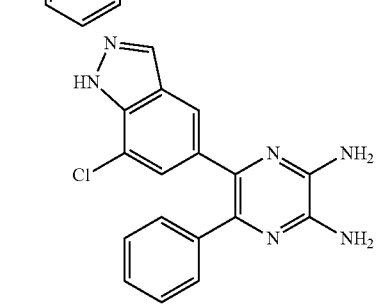
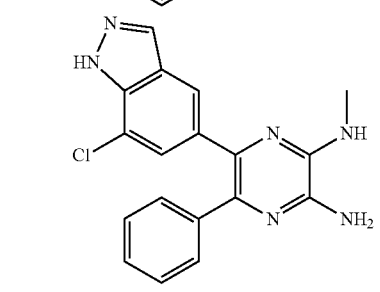
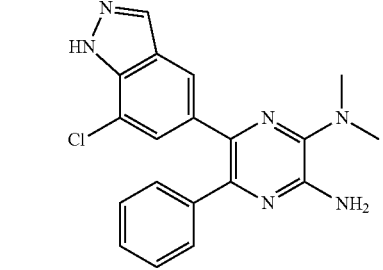
1340
-continued
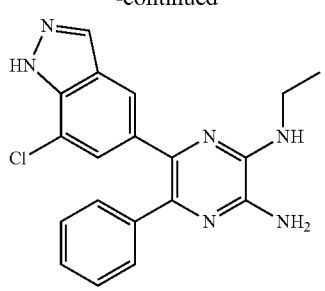
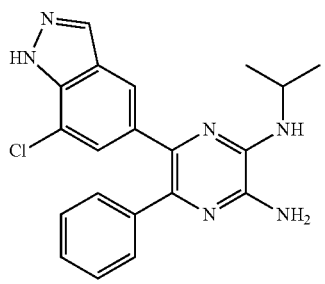
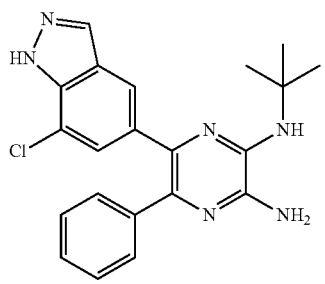
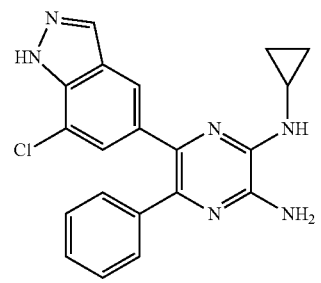
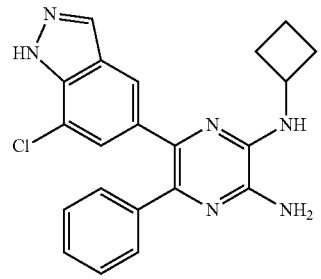
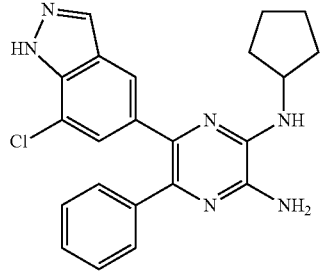

1341
-continued
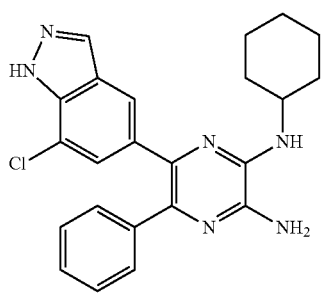
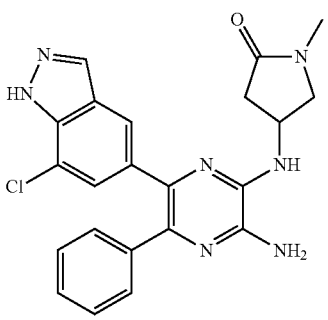
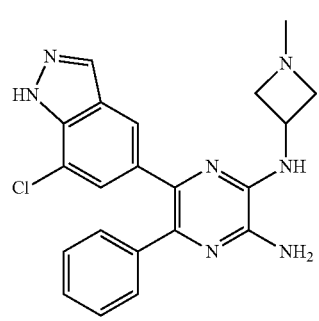
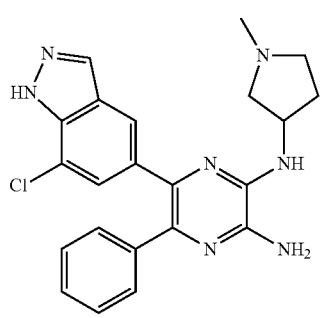
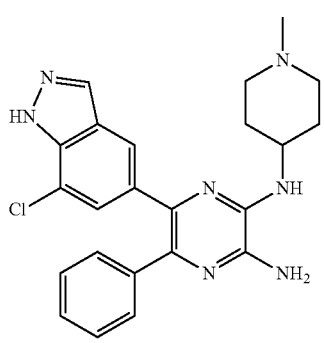
1342
-continued
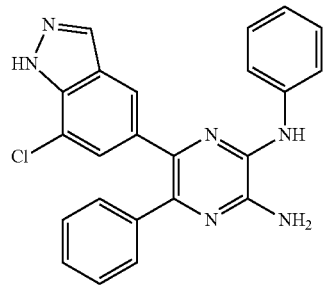
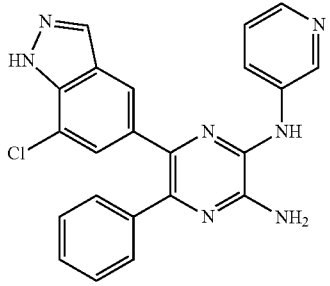
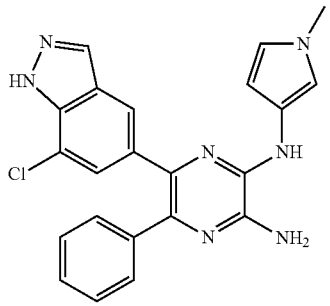
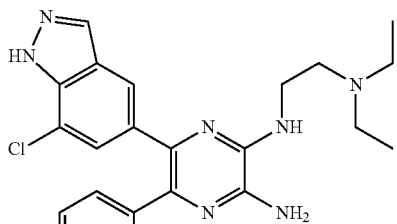
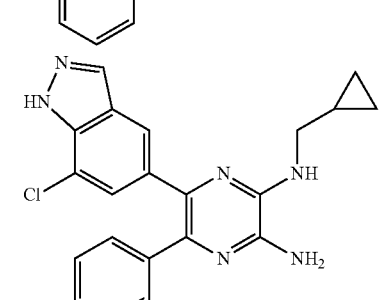
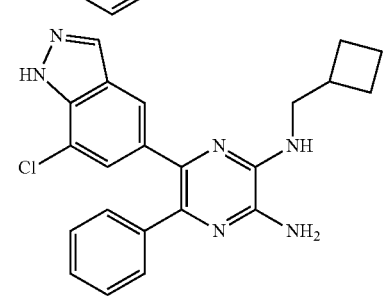

1343
-continued
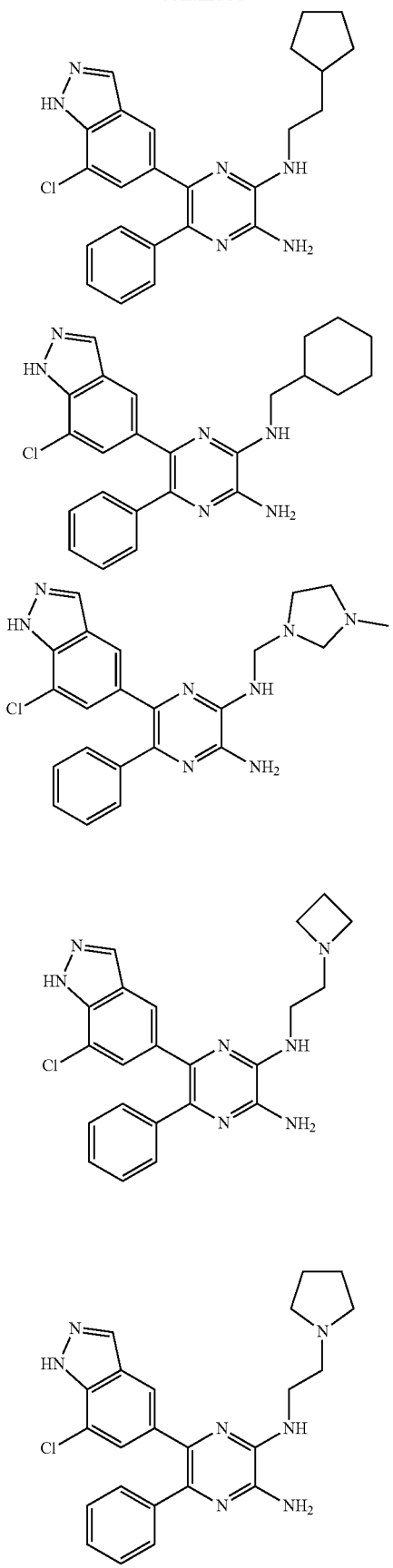
1344
-continued
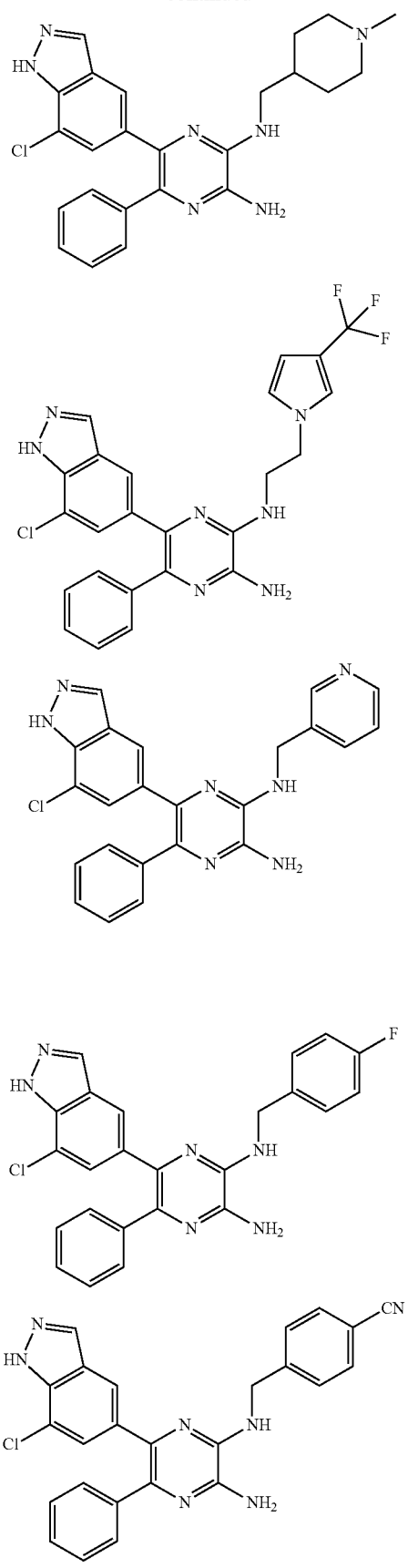

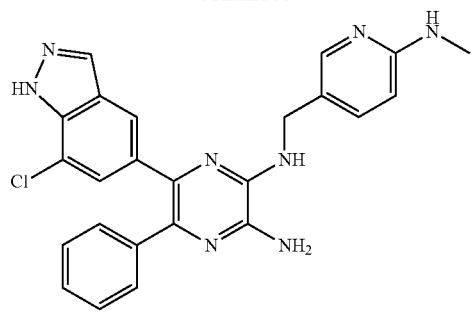
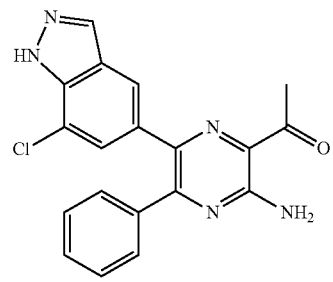
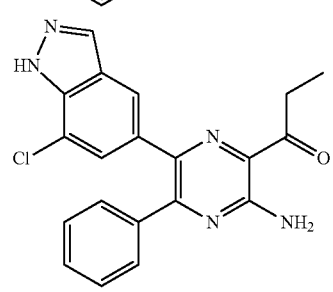
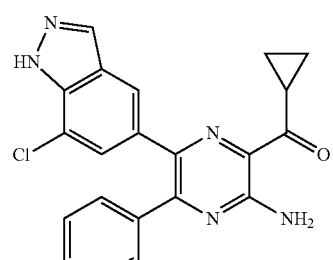
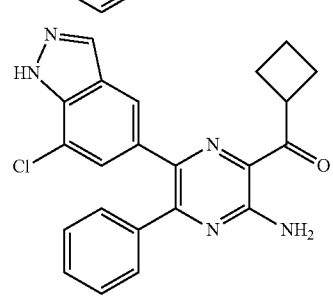
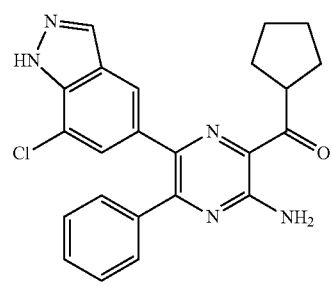
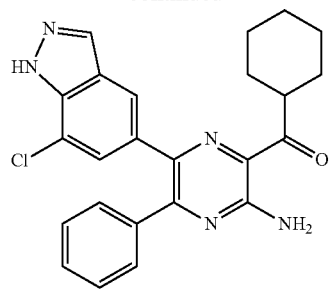
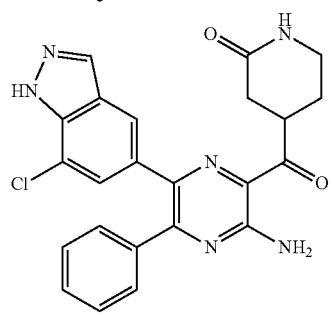
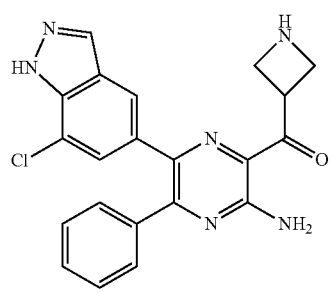
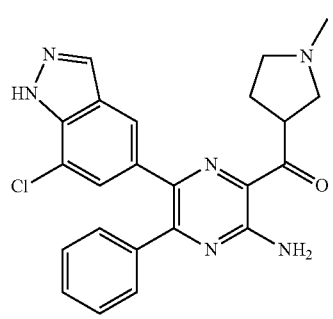
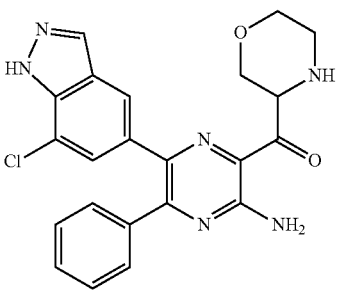

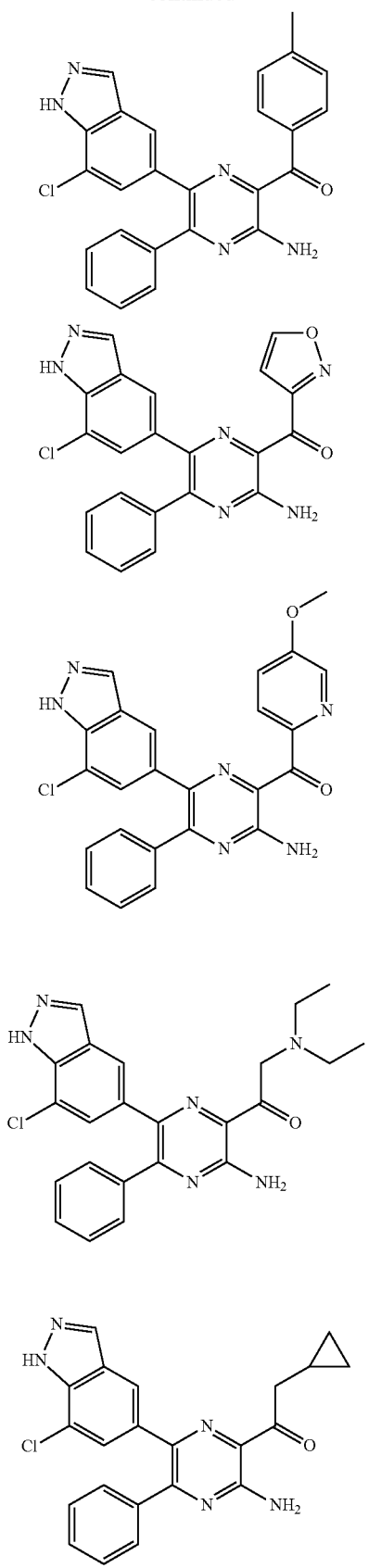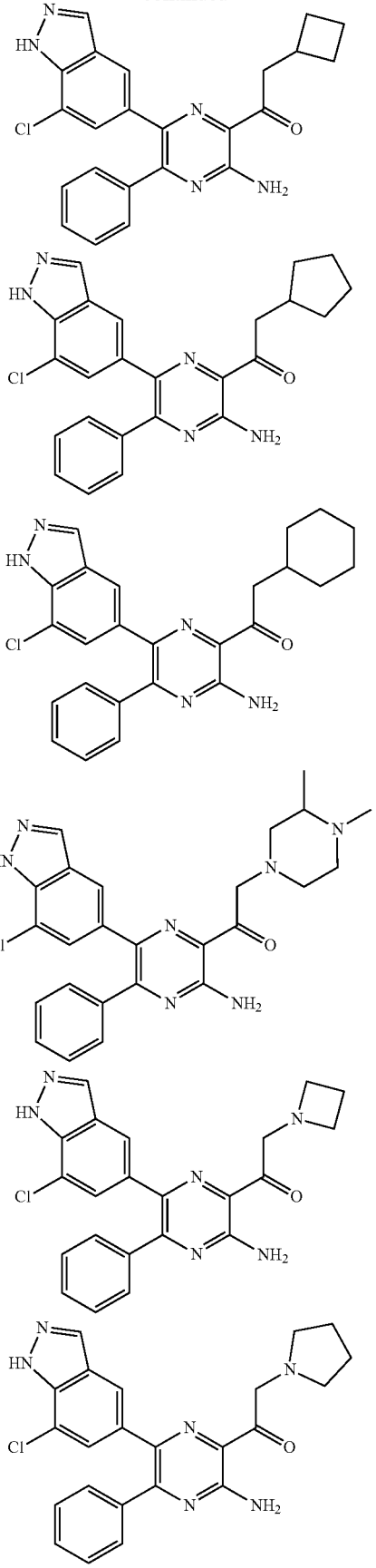

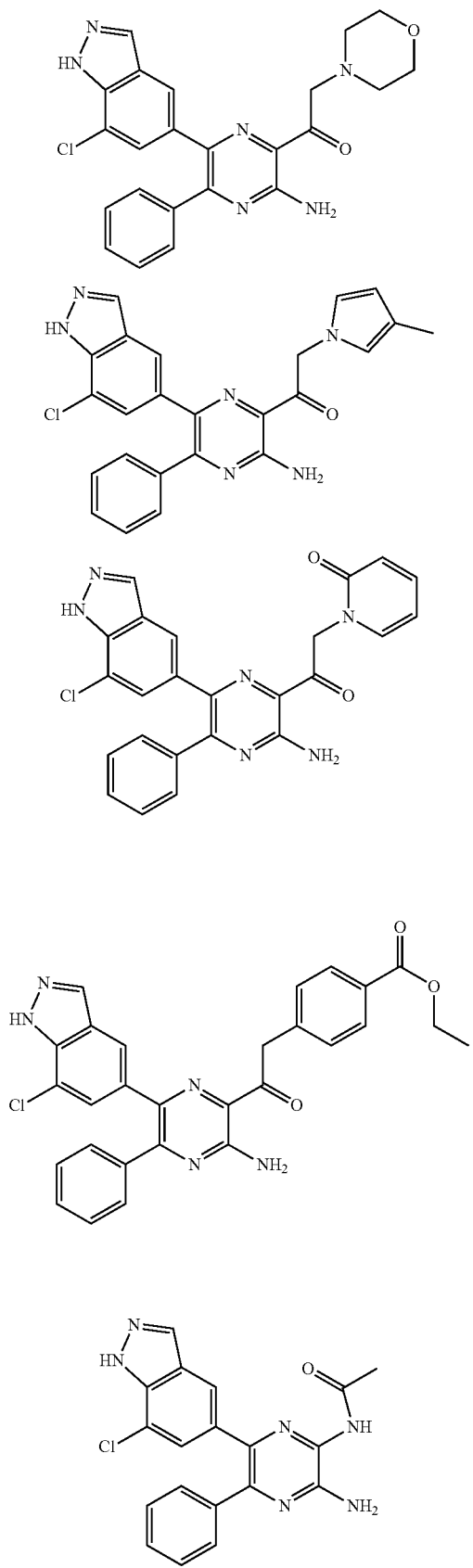
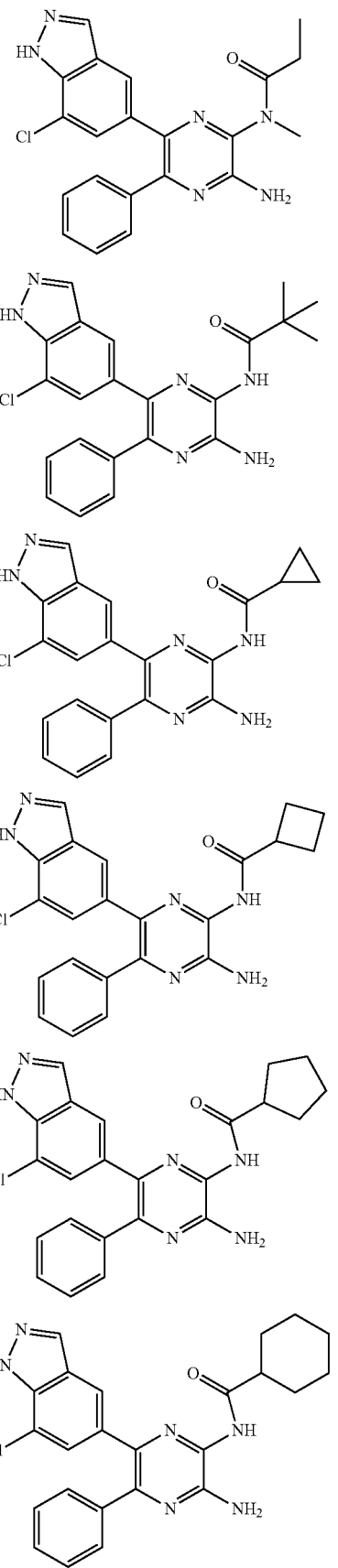

1351
-continued
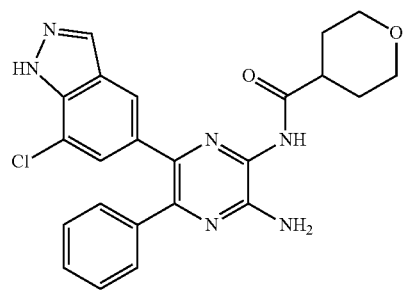
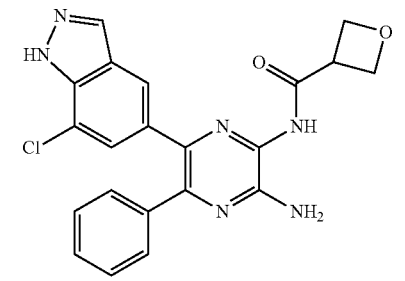
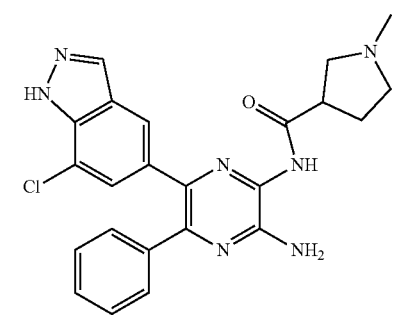
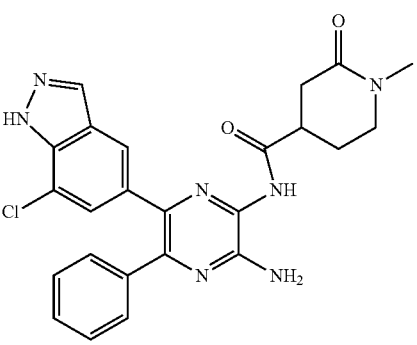
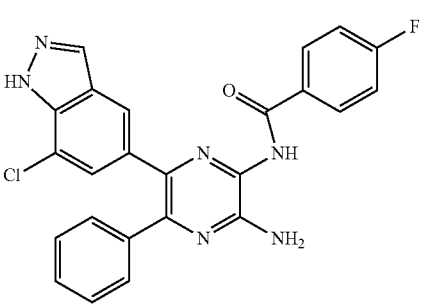
1352
-continued
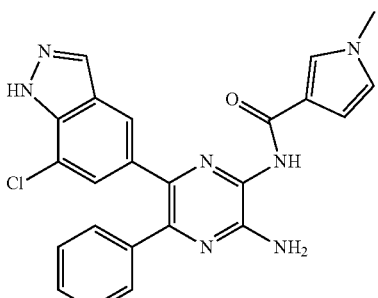
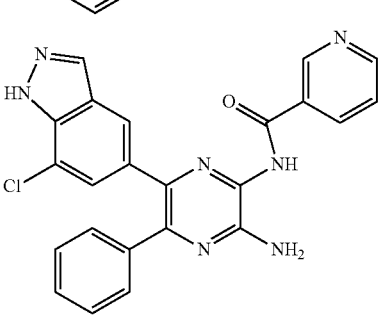
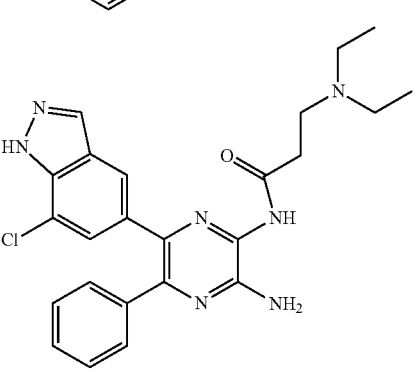
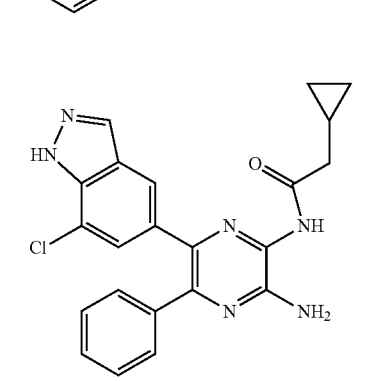
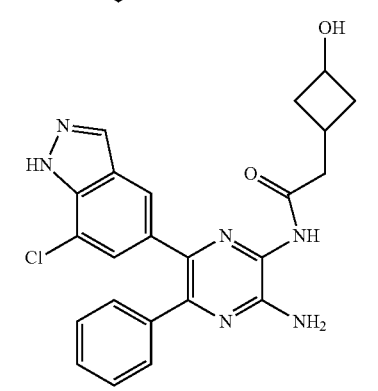

1353
-continued
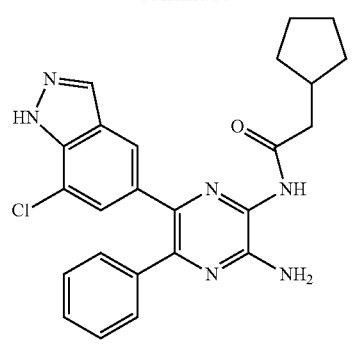
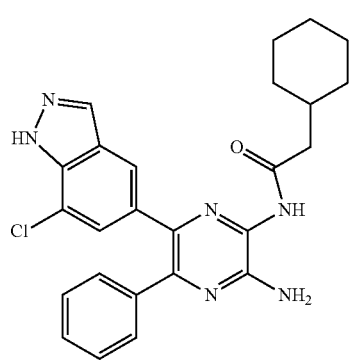
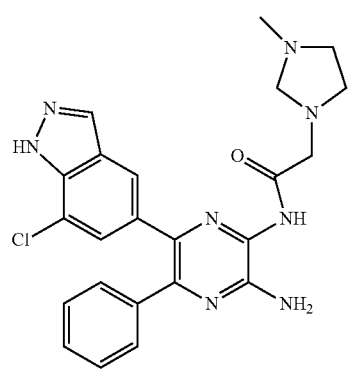
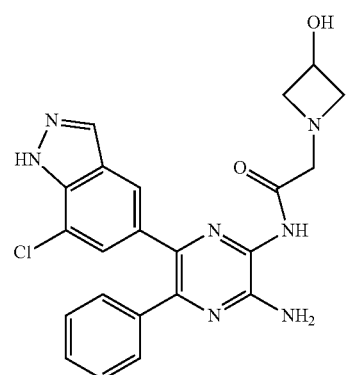
1354
-continued
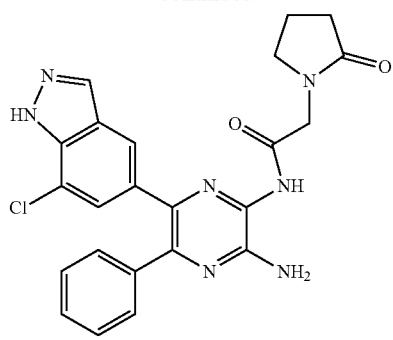
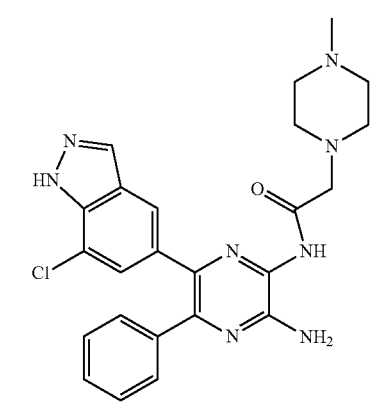
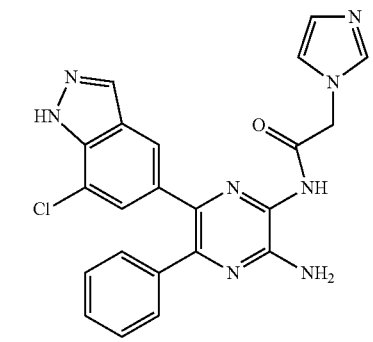
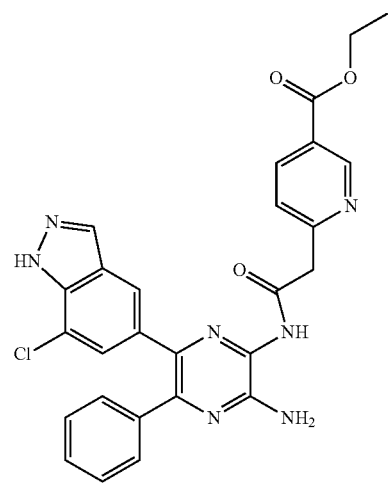

1355
-continued
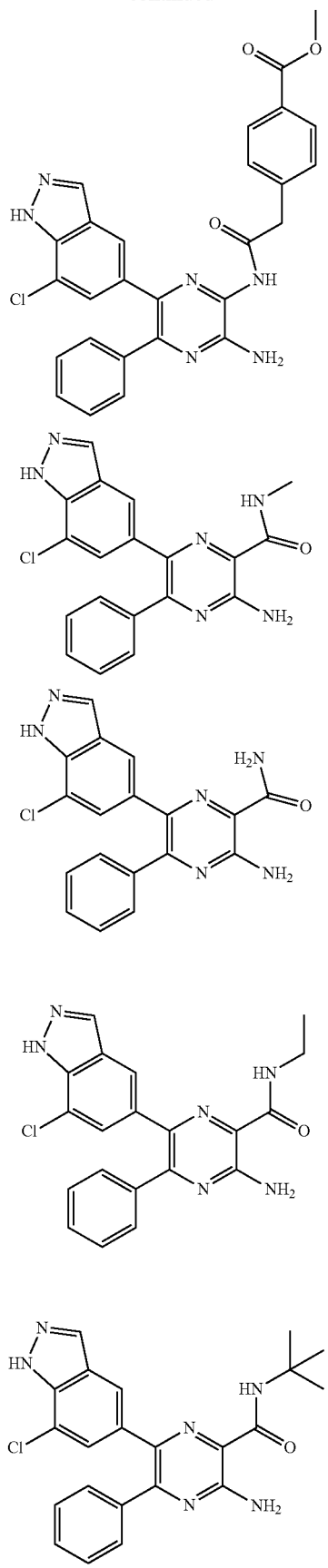
1356
-continued
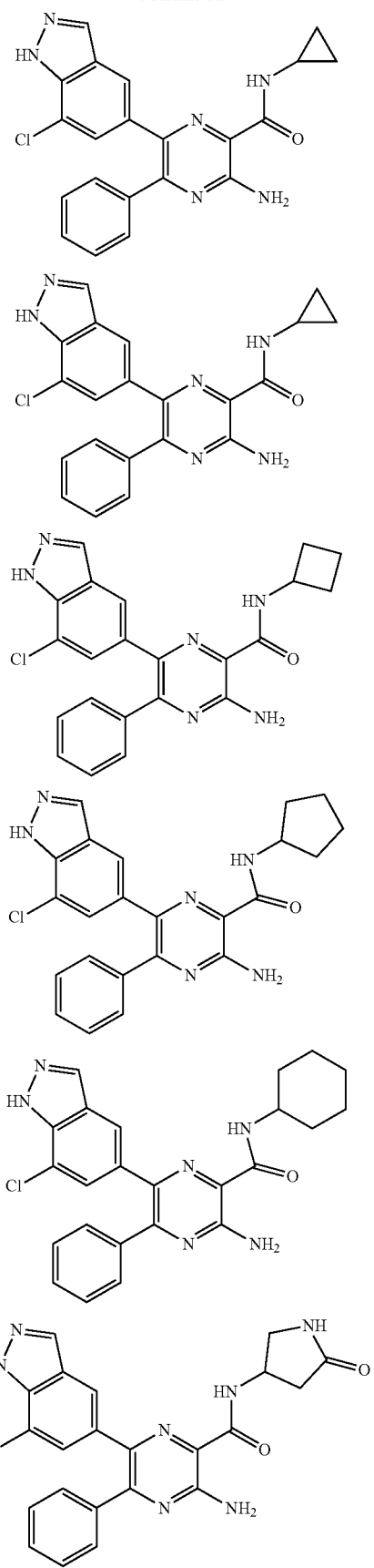

1357
-continued
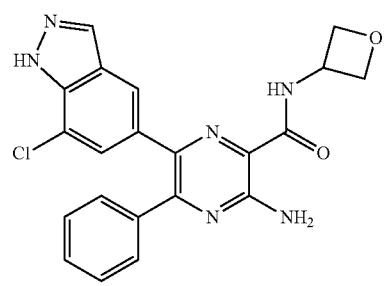
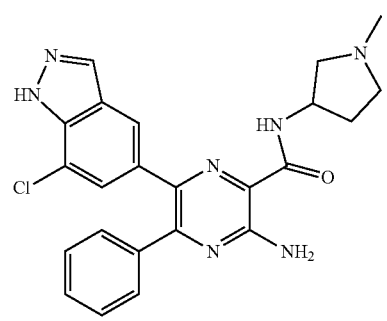
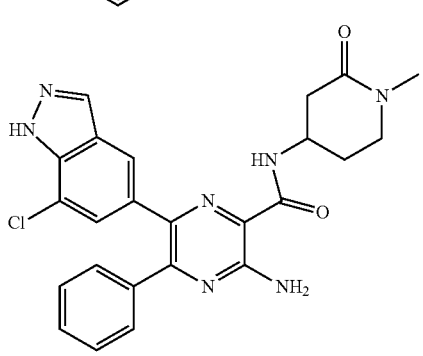
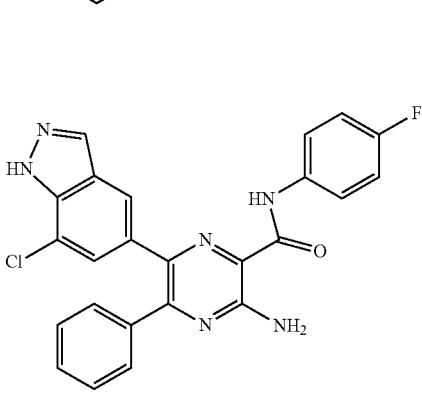
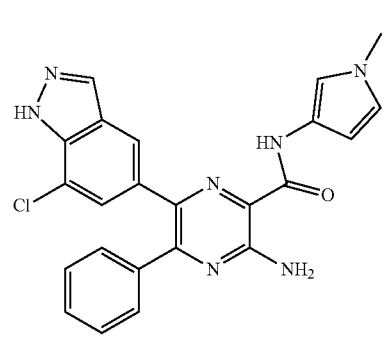
1358
-continued
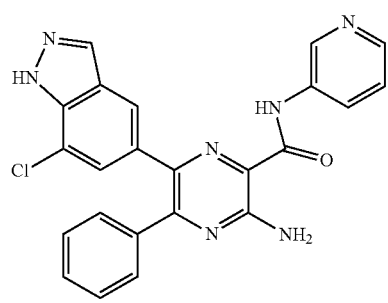
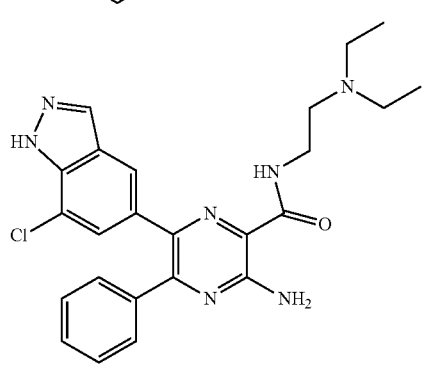
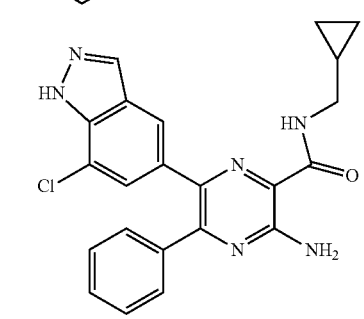
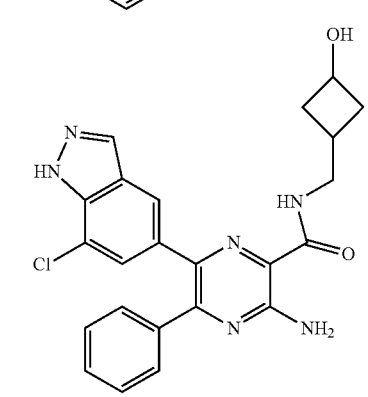
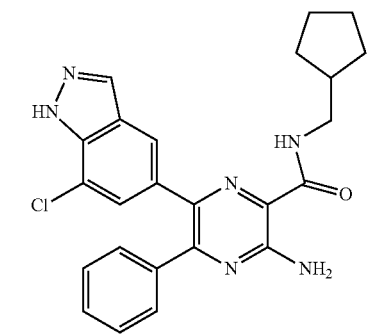

-continued
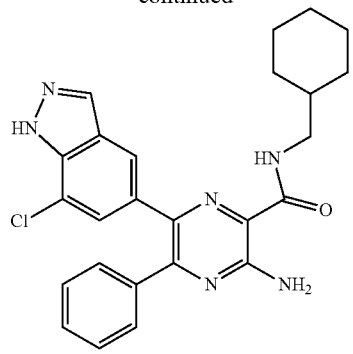
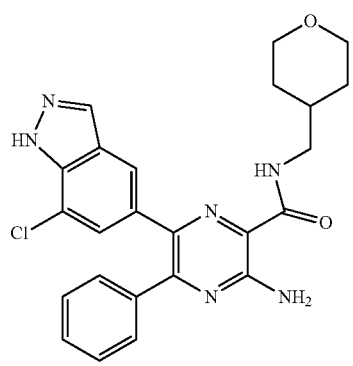
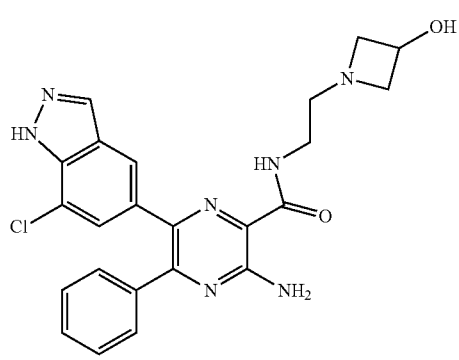
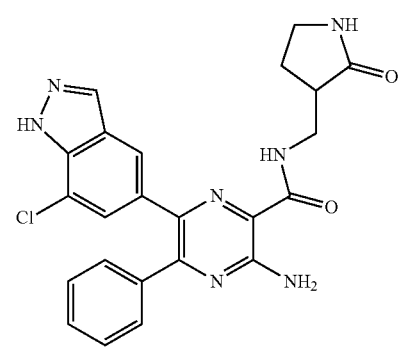
-continued
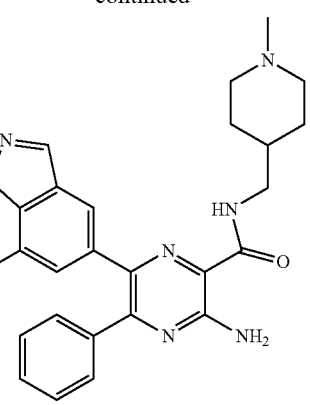
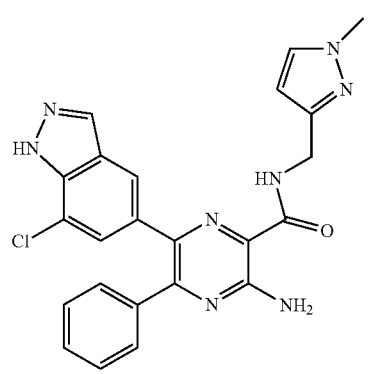
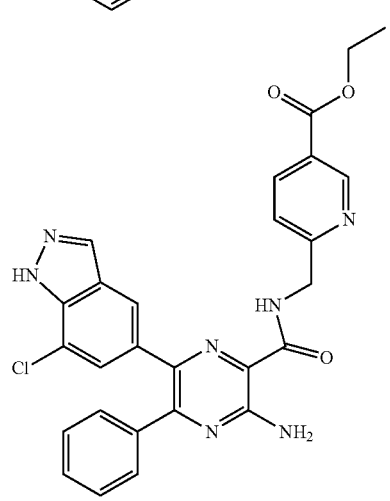
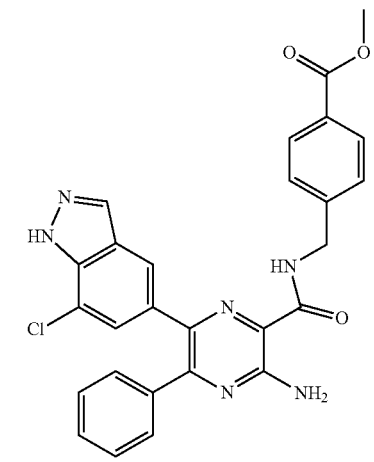

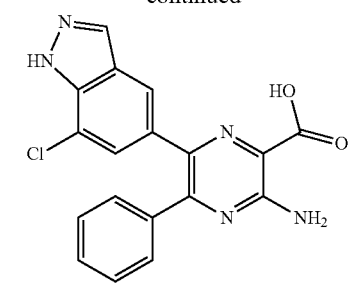
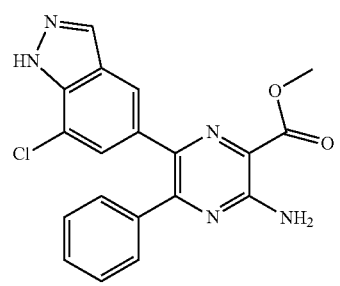
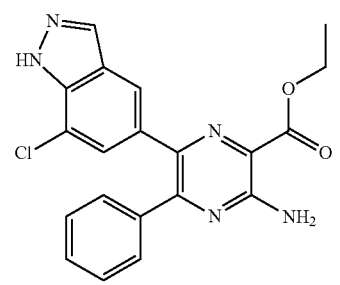
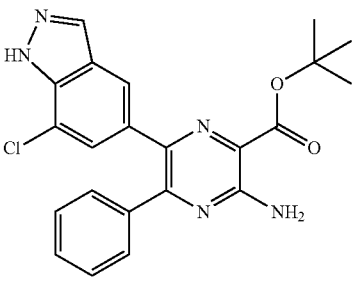
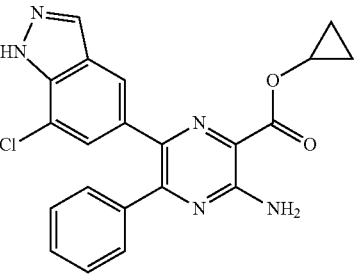
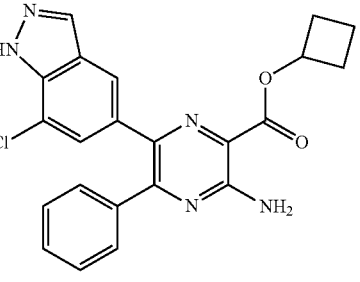
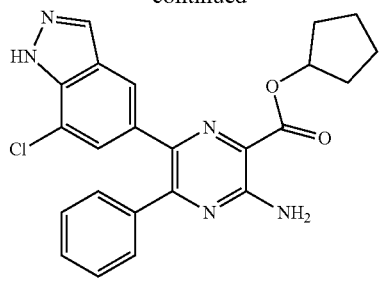
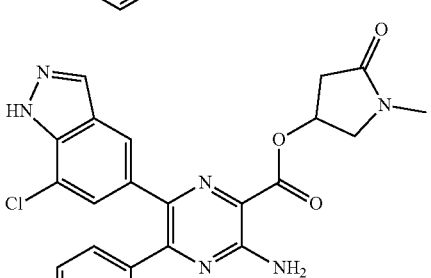
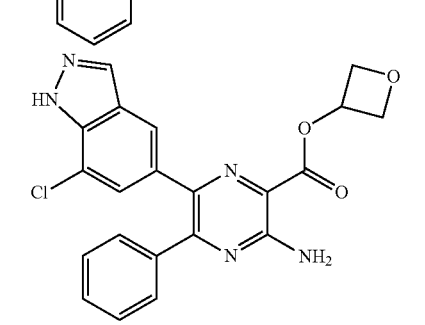
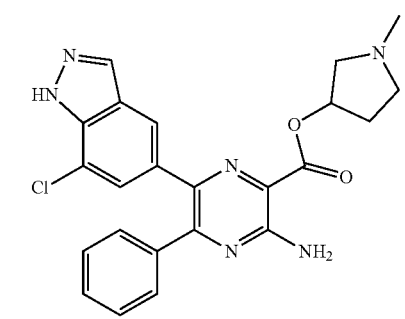
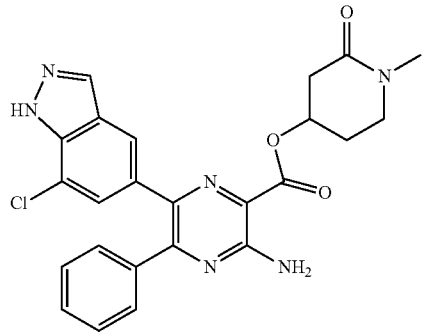

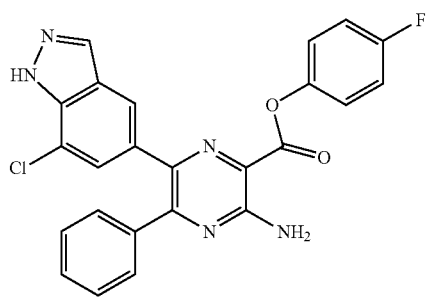
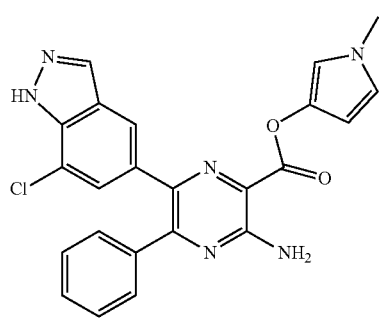
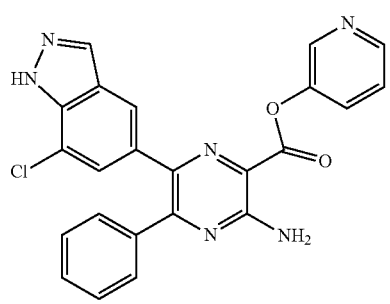
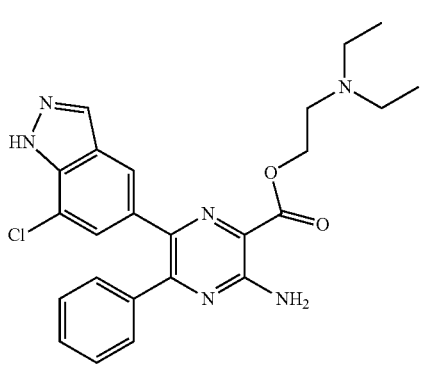
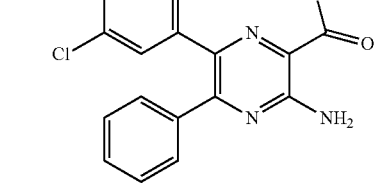
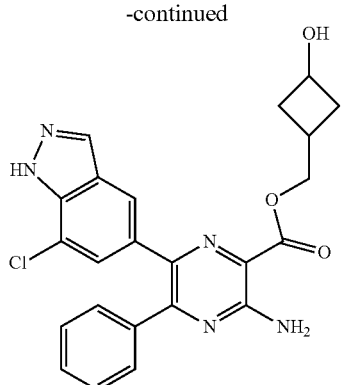
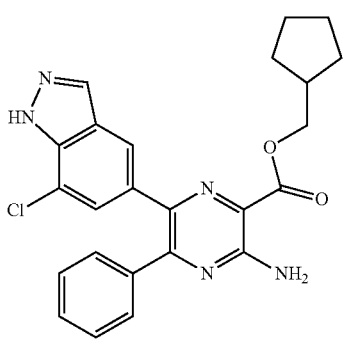
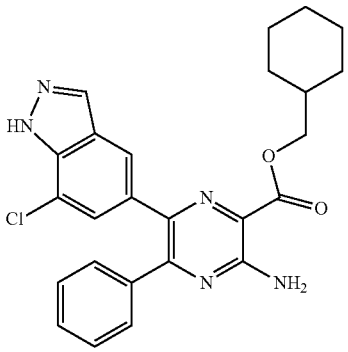
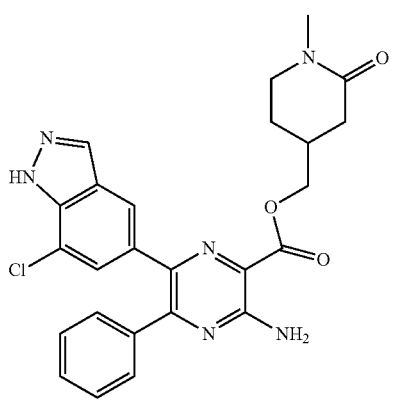

1365
-continued
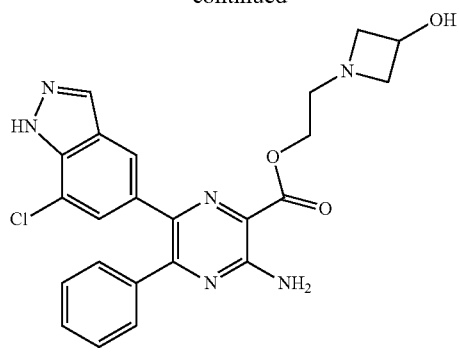
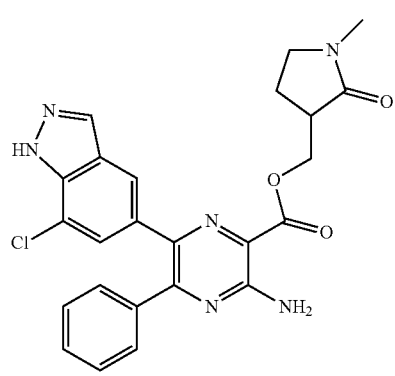
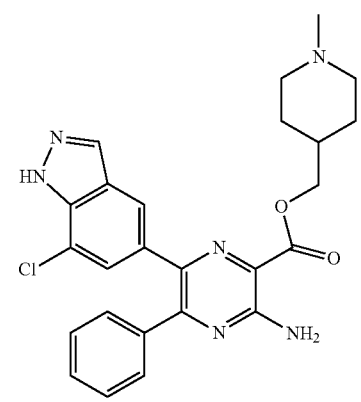
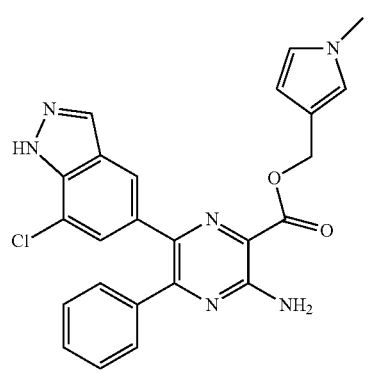
1366
-continued
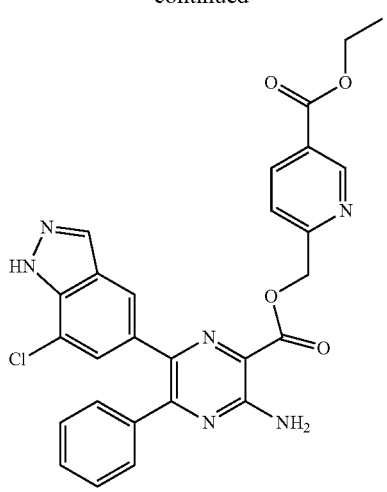
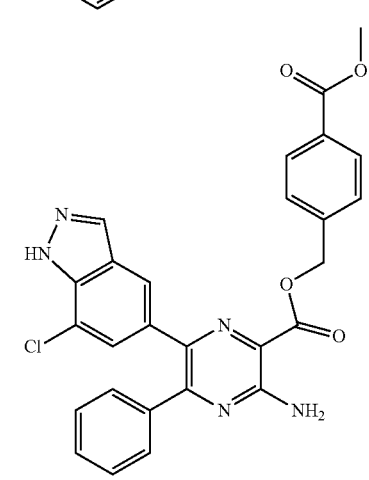
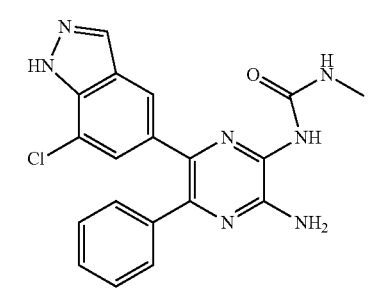
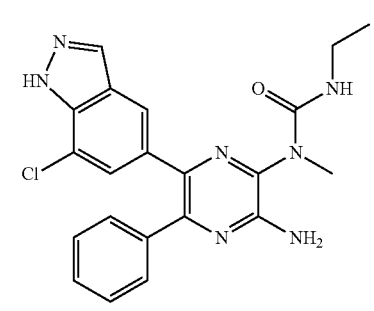

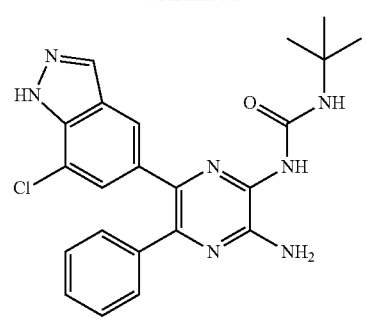
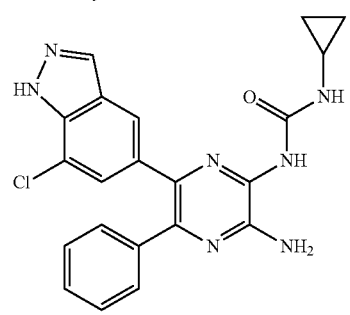
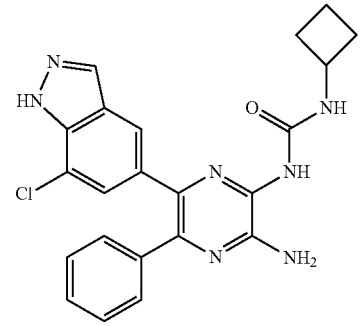
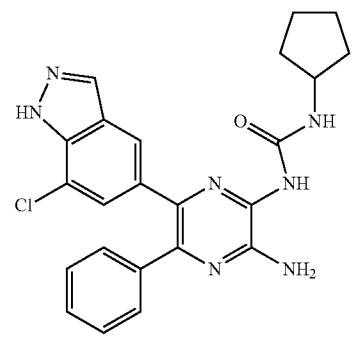
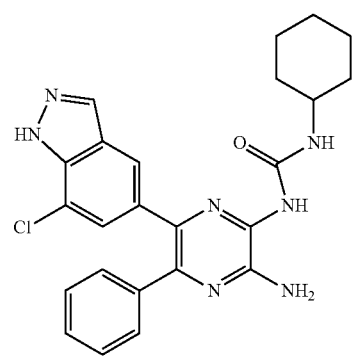
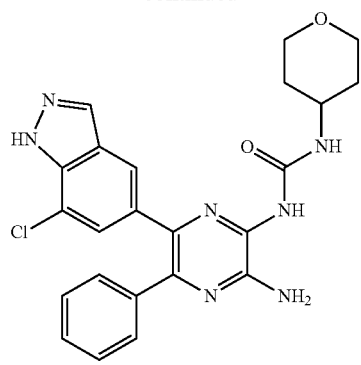
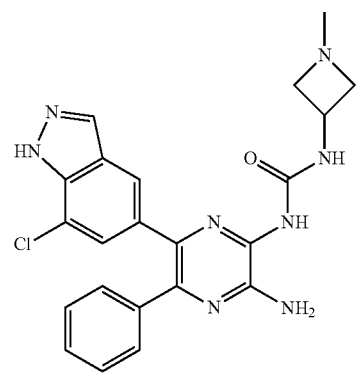
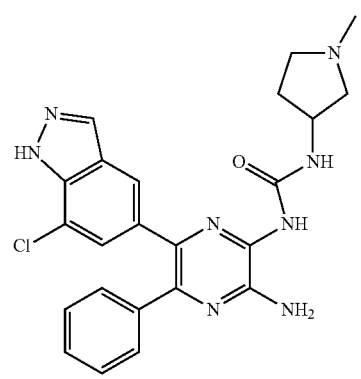
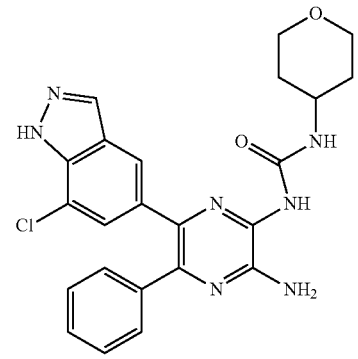

1369
-continued
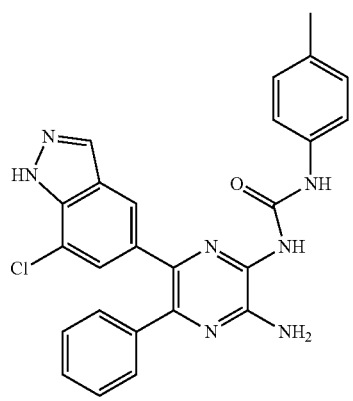
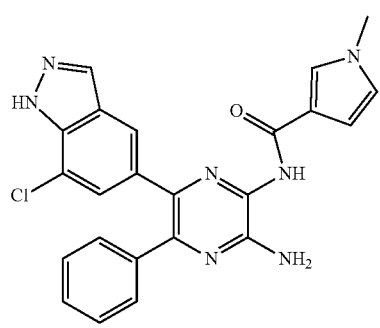
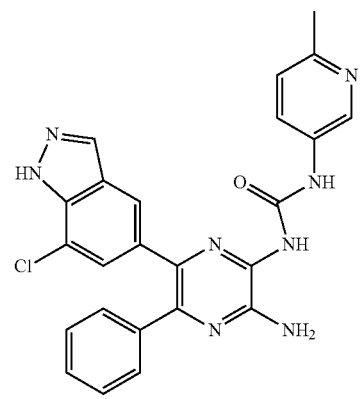
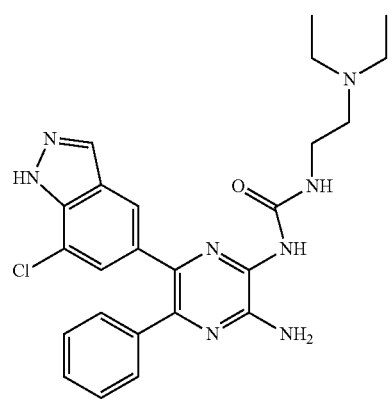
1370
-continued
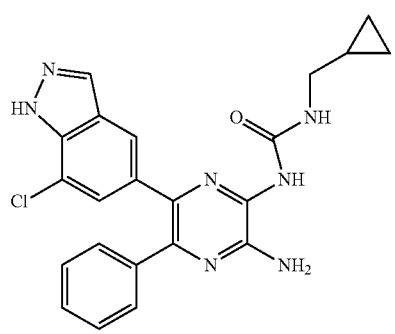
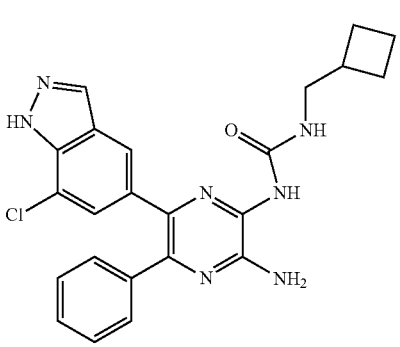
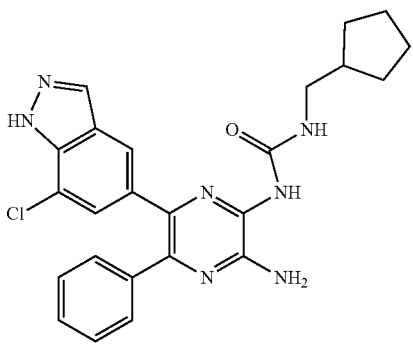
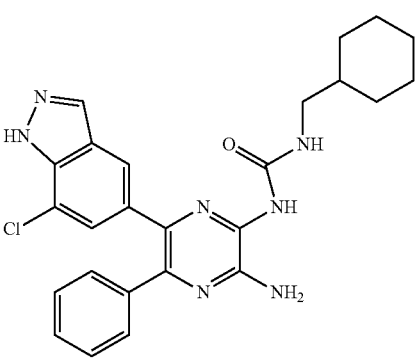

1371
-continued
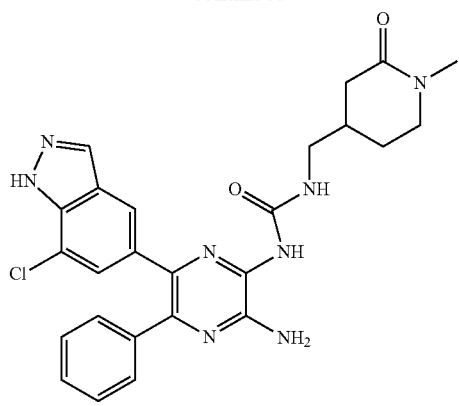
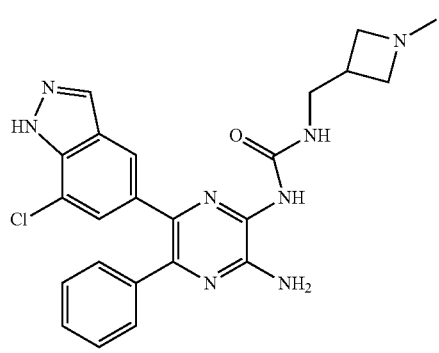
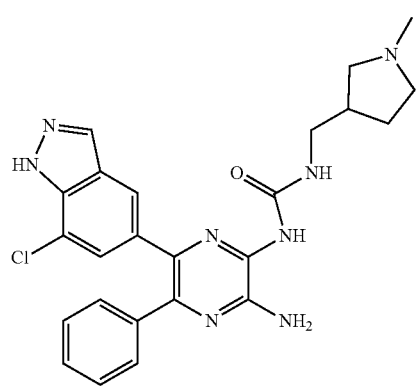
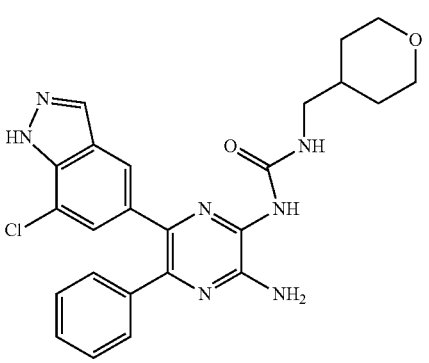
1372
-continued
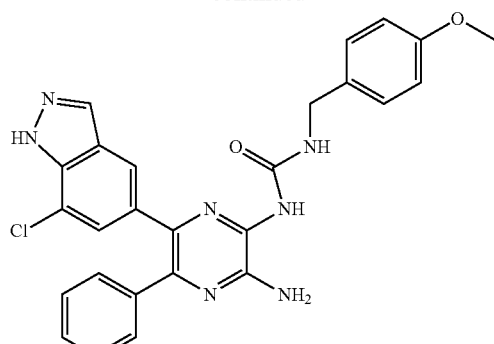
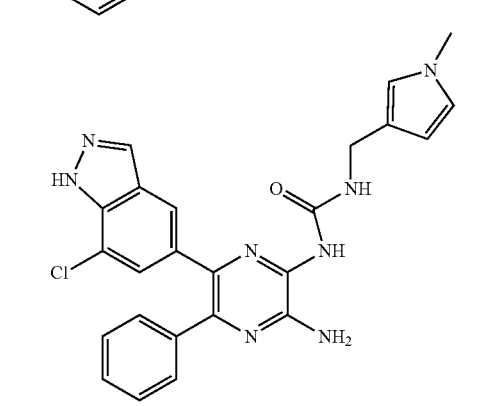
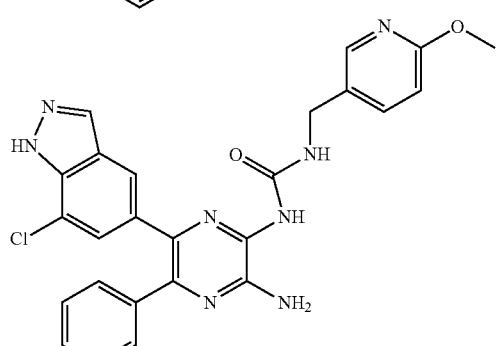
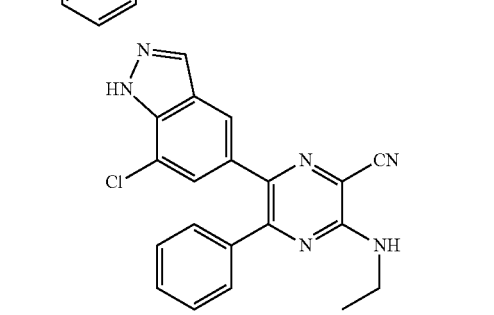
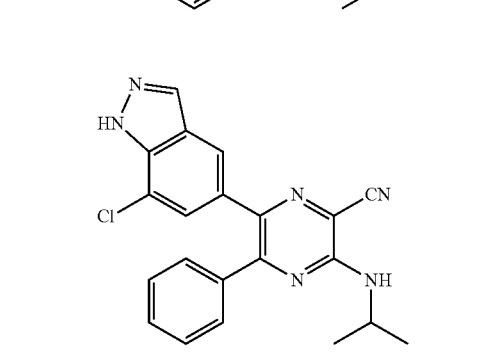

1373
-continued
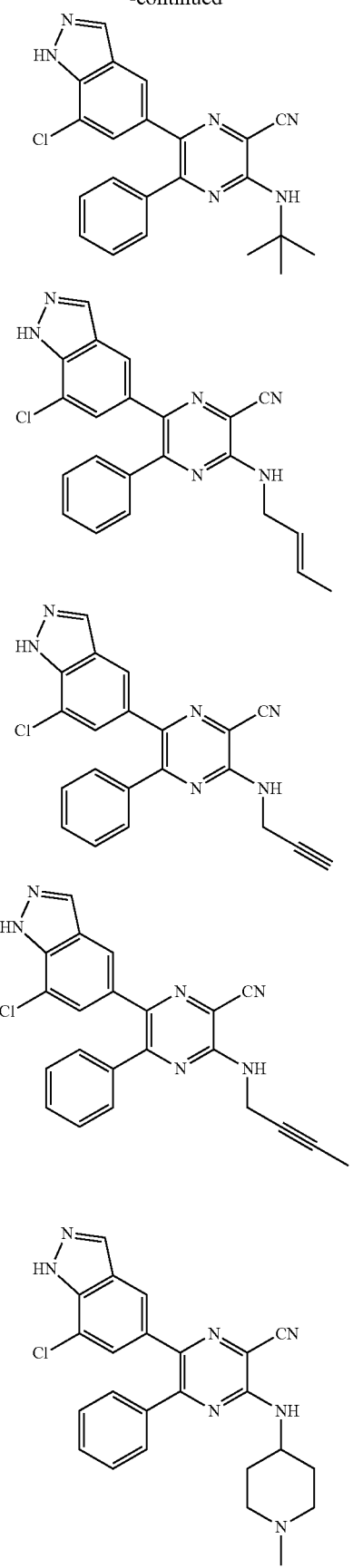
1374
-continued
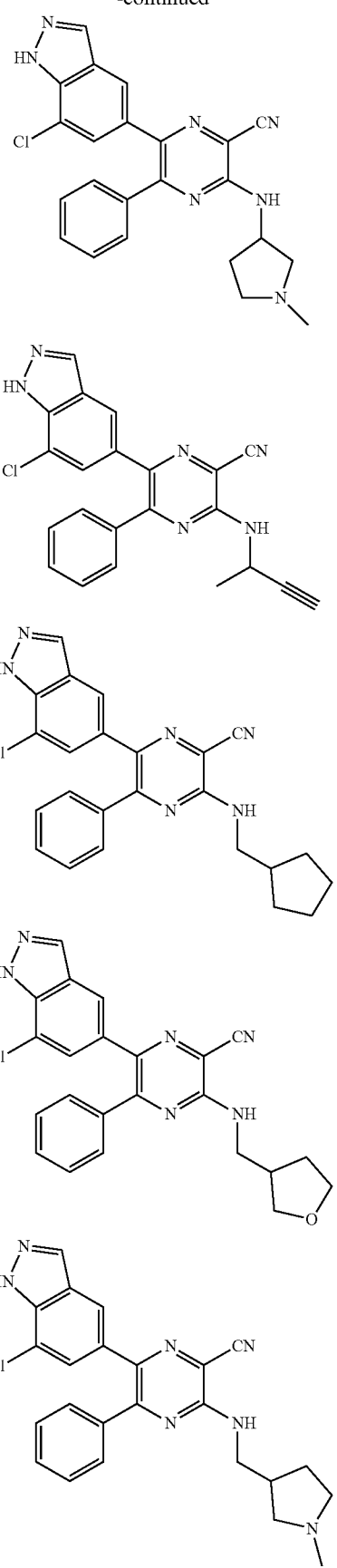

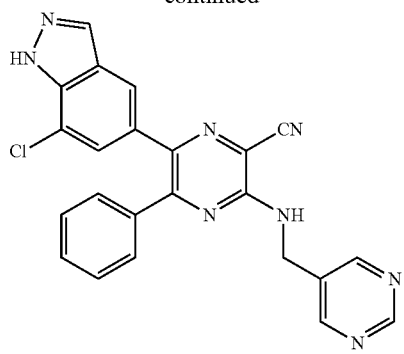
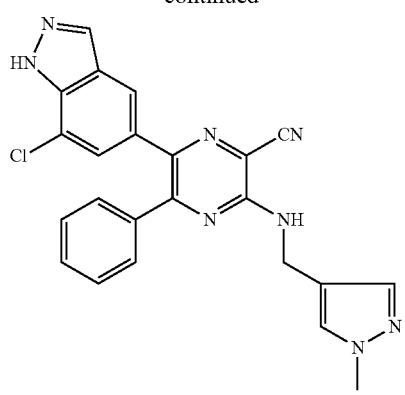

1377
-continued
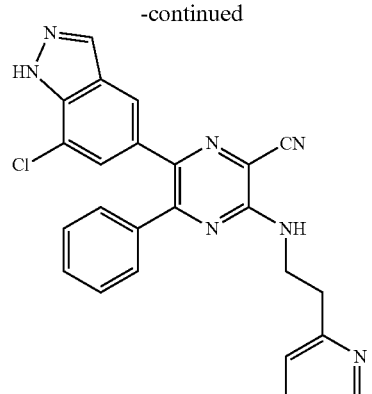
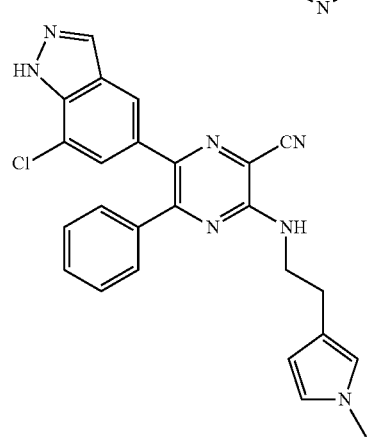
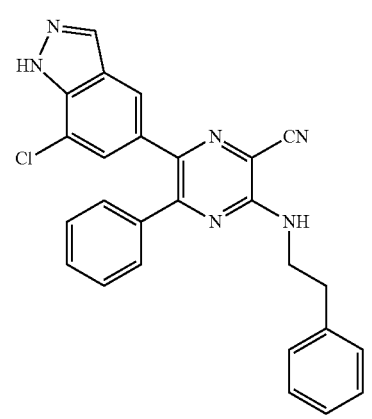
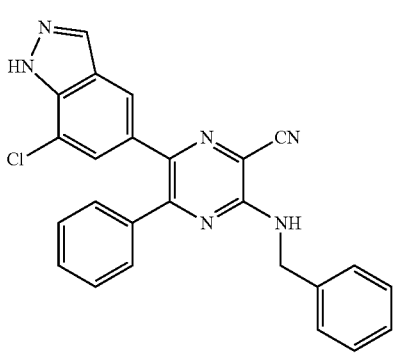
1378
-continued
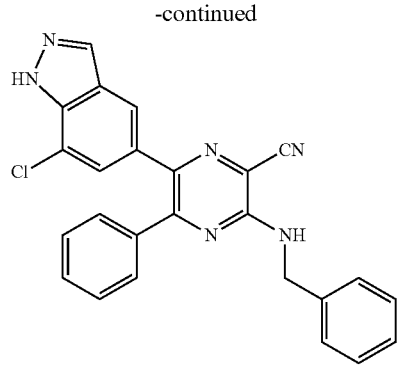
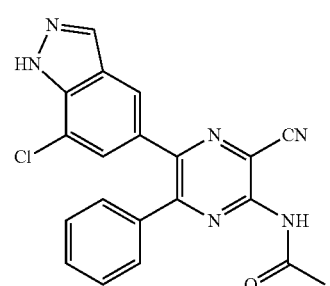
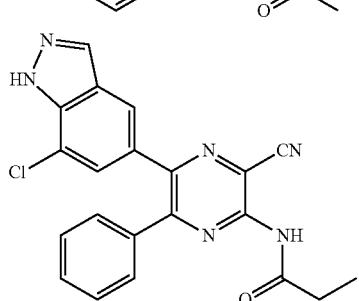
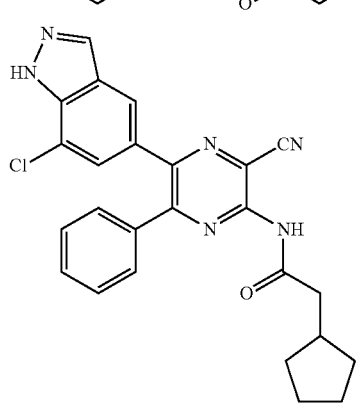
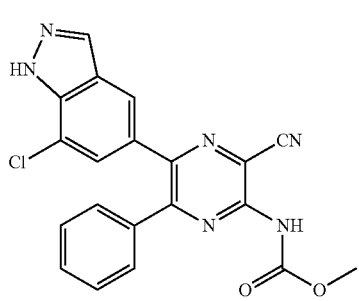

1379
-continued
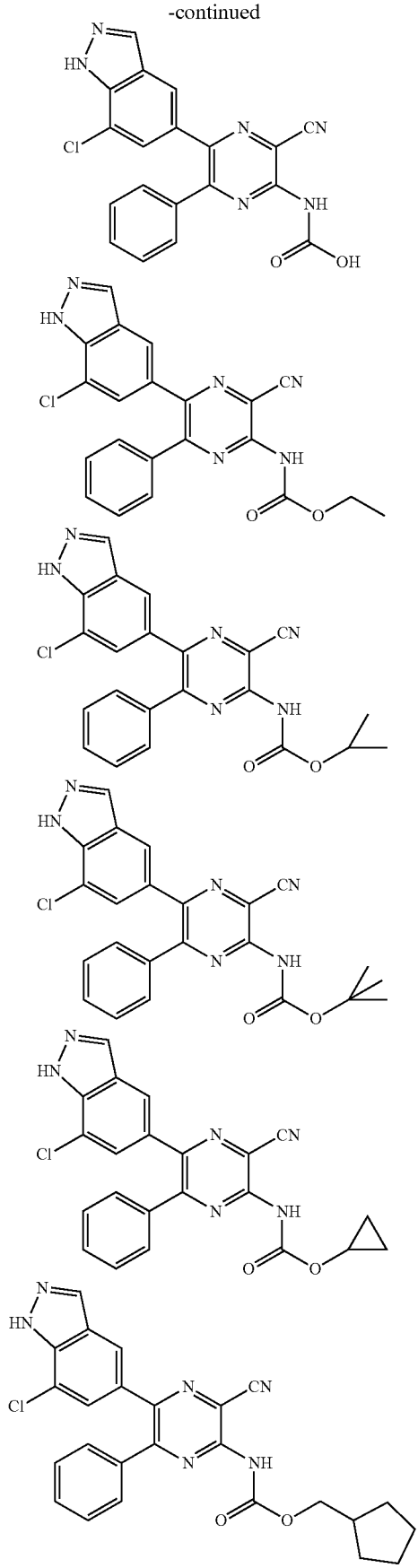
1380
-continued
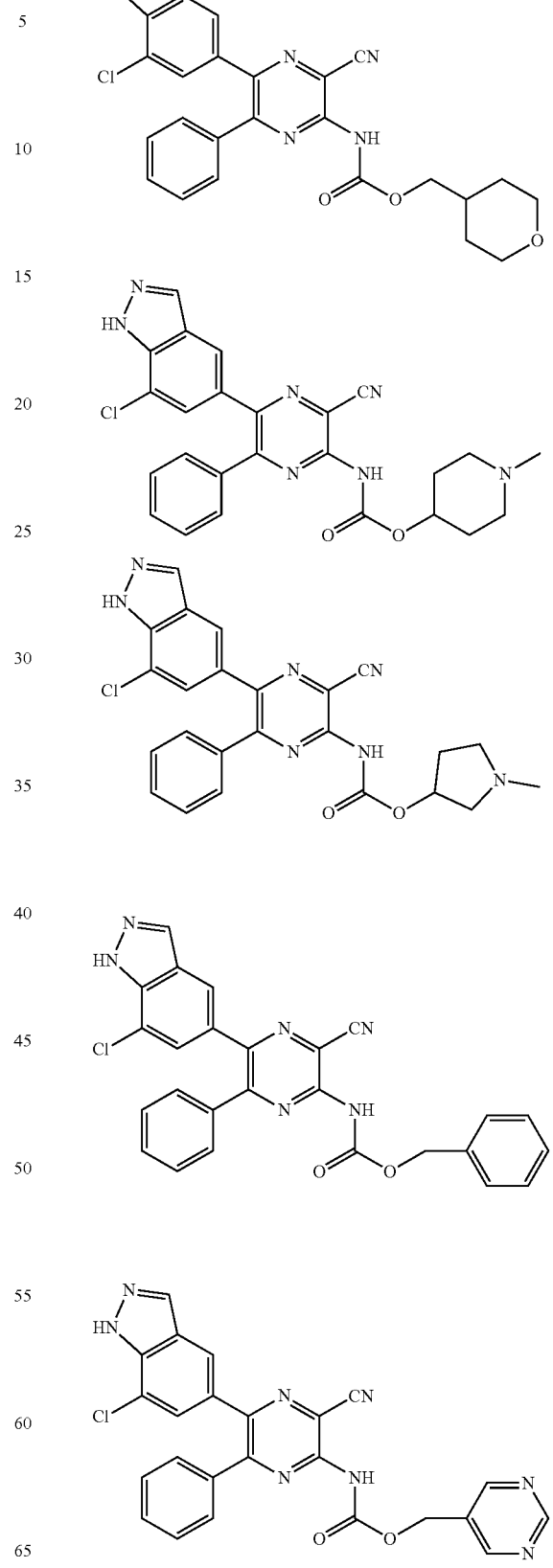

1381
-continued
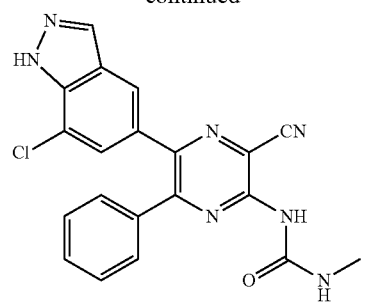
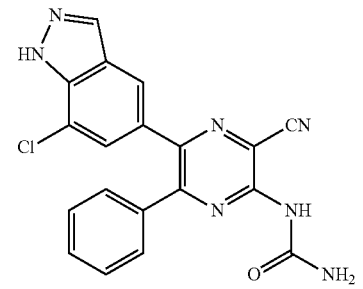
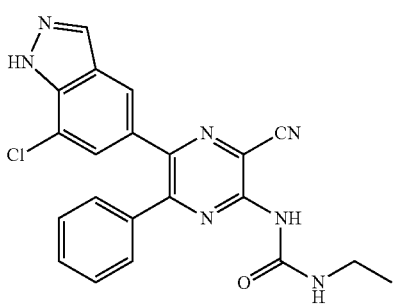
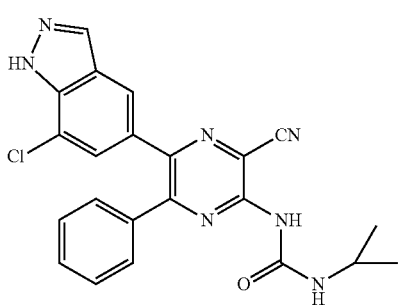
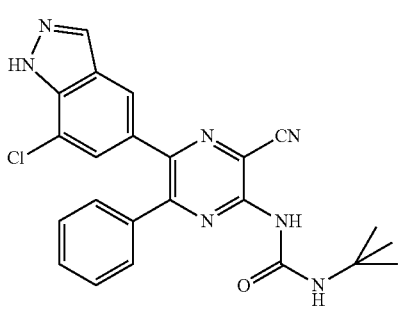
1382
-continued
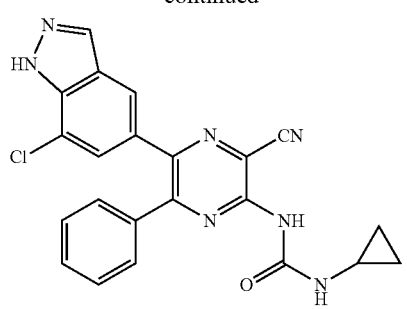
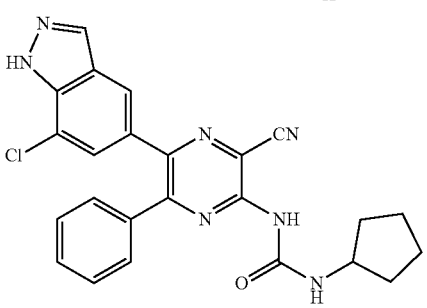
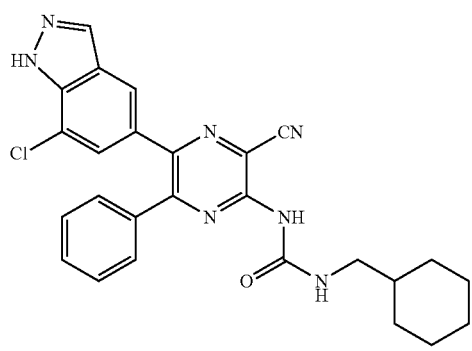
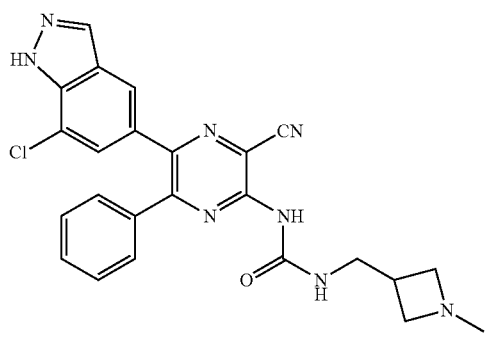
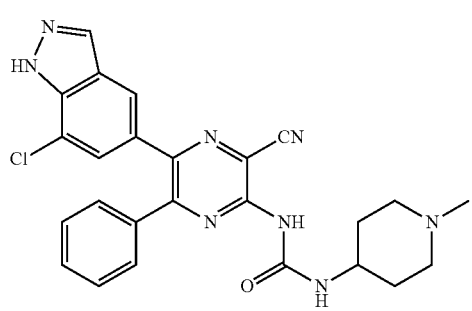

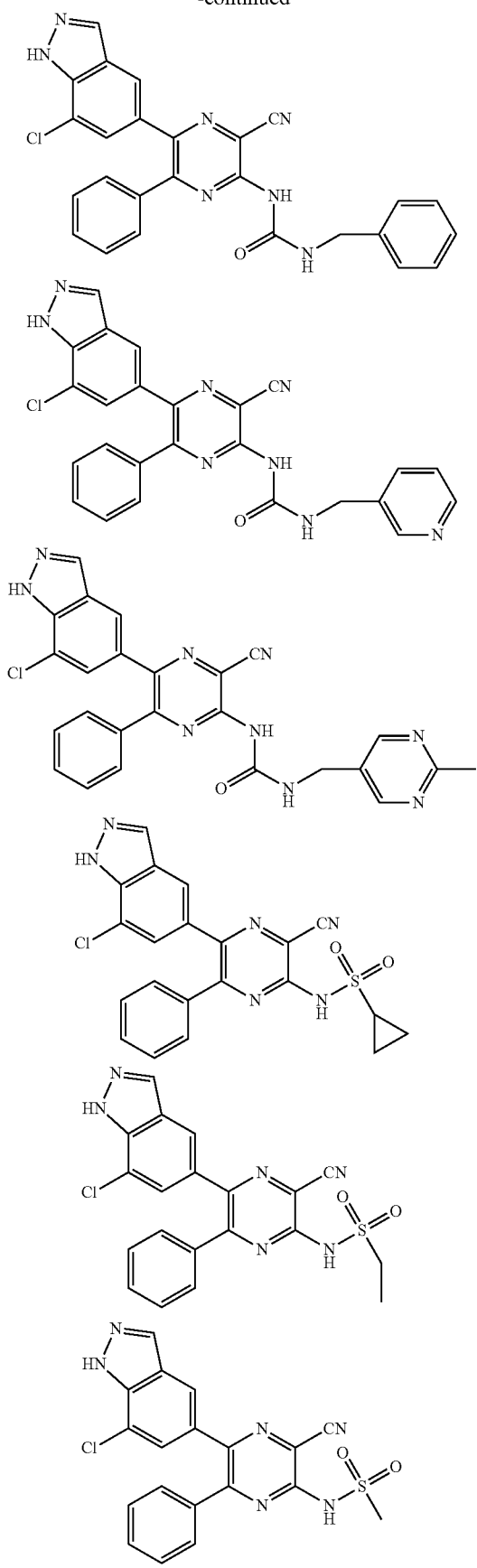
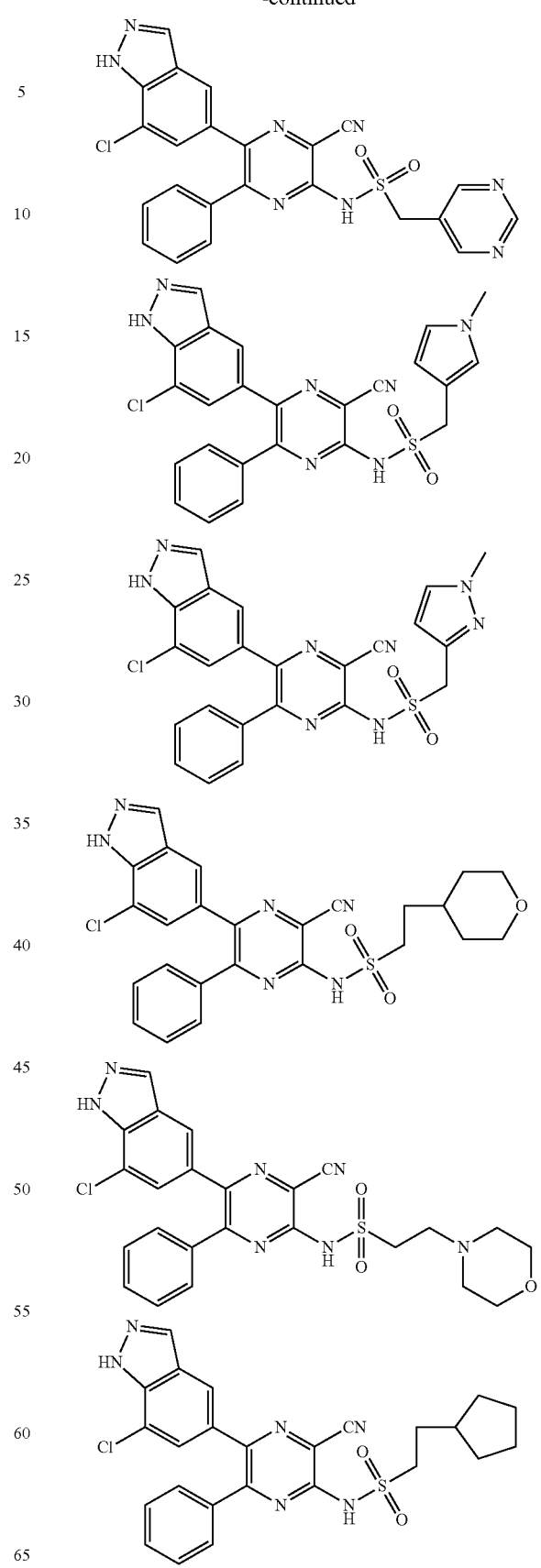

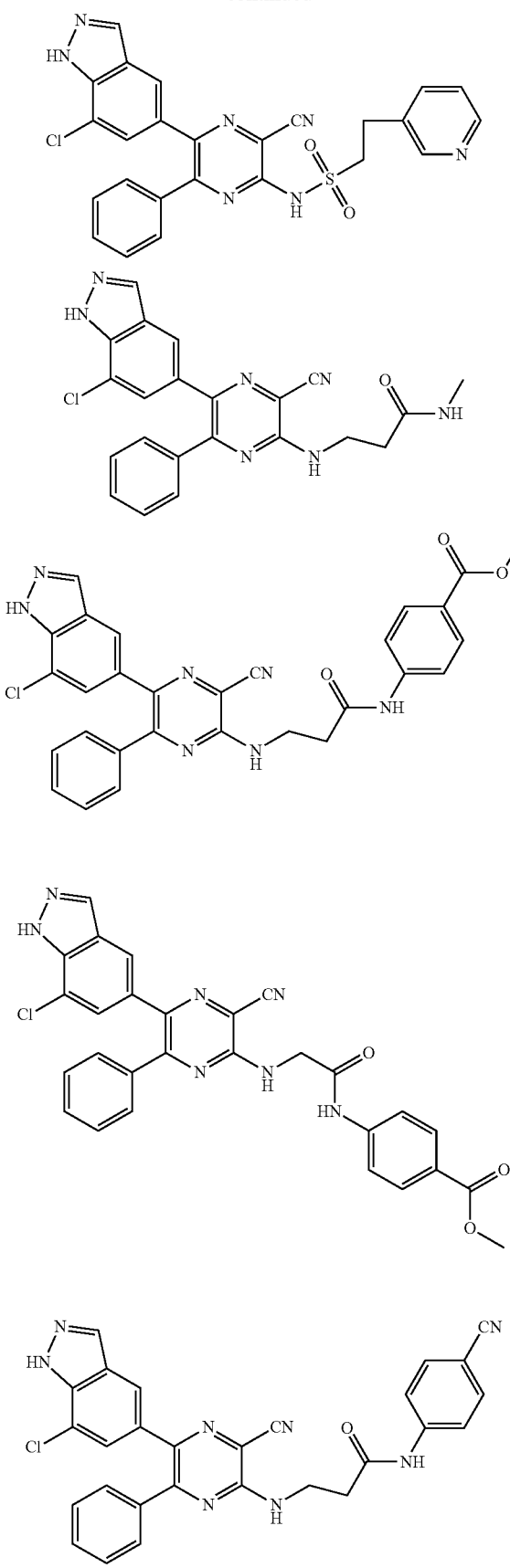
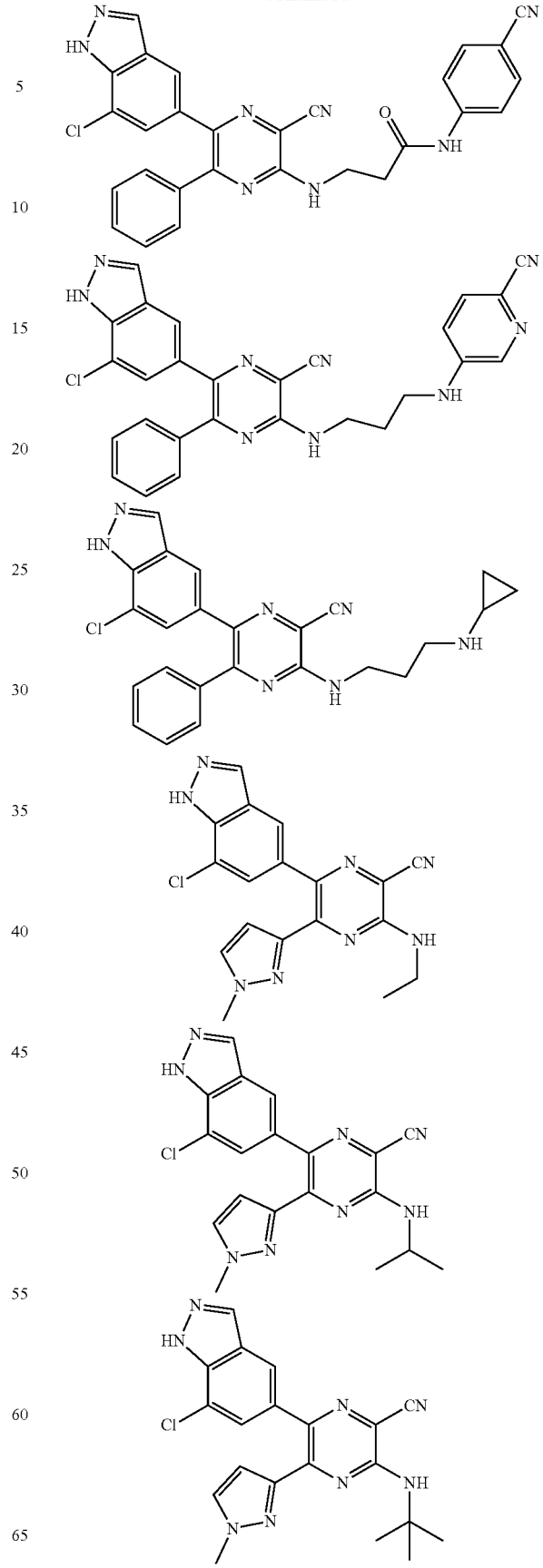

1387
-continued
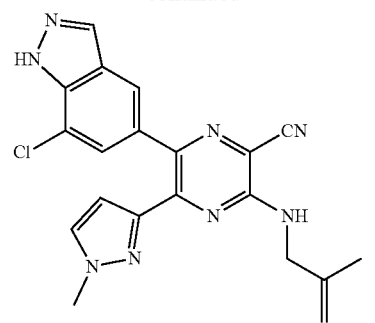
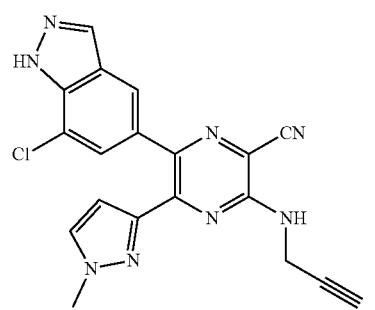
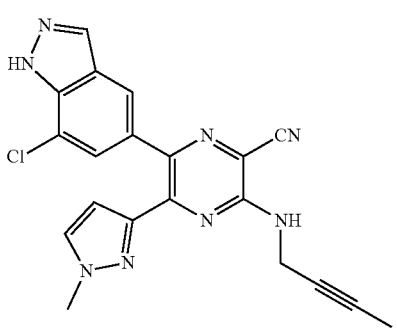
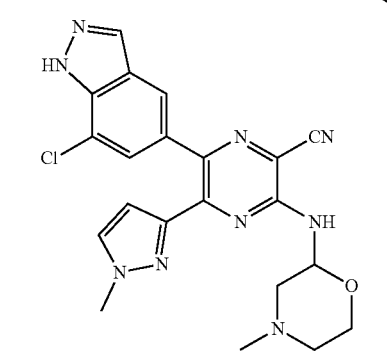
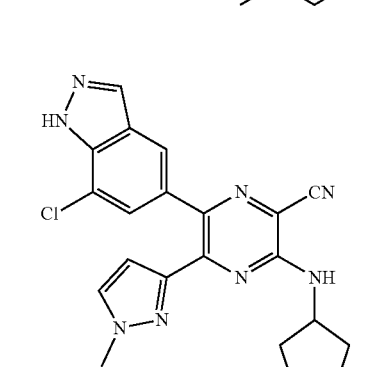
1388
-continued
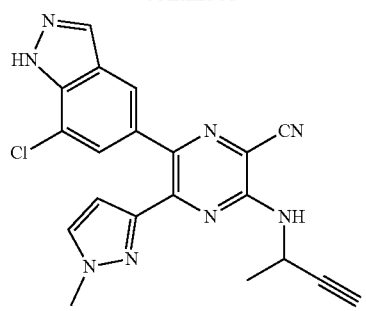
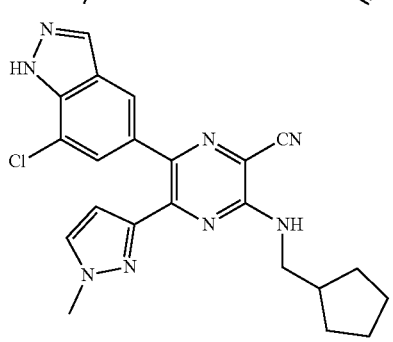
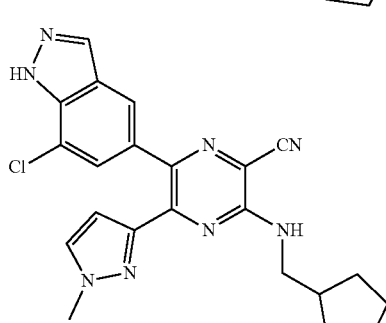
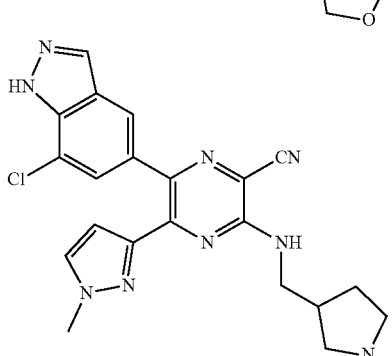
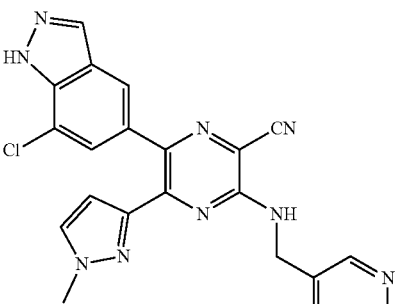

1389
-continued
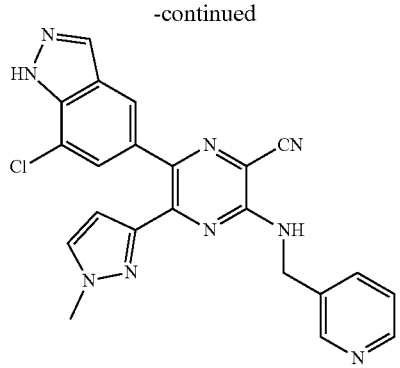
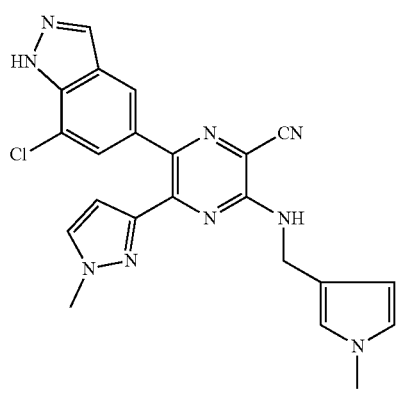
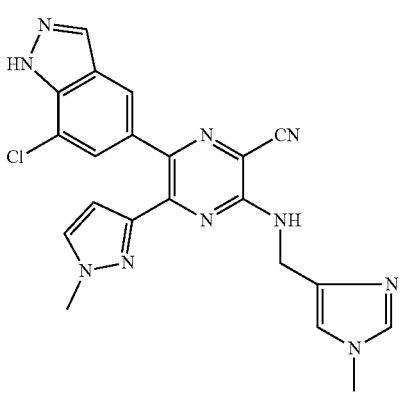
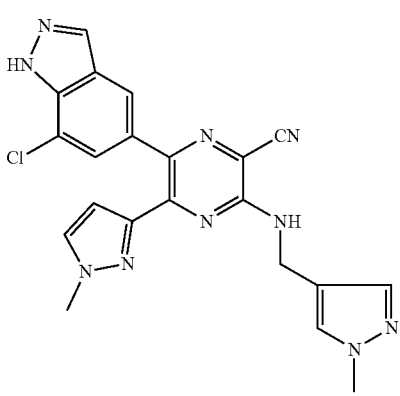
1390
-continued
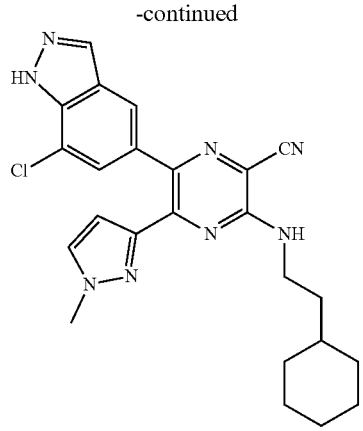
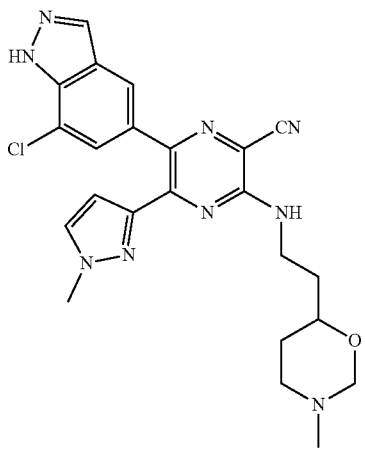

1391
-continued
1392
-continued
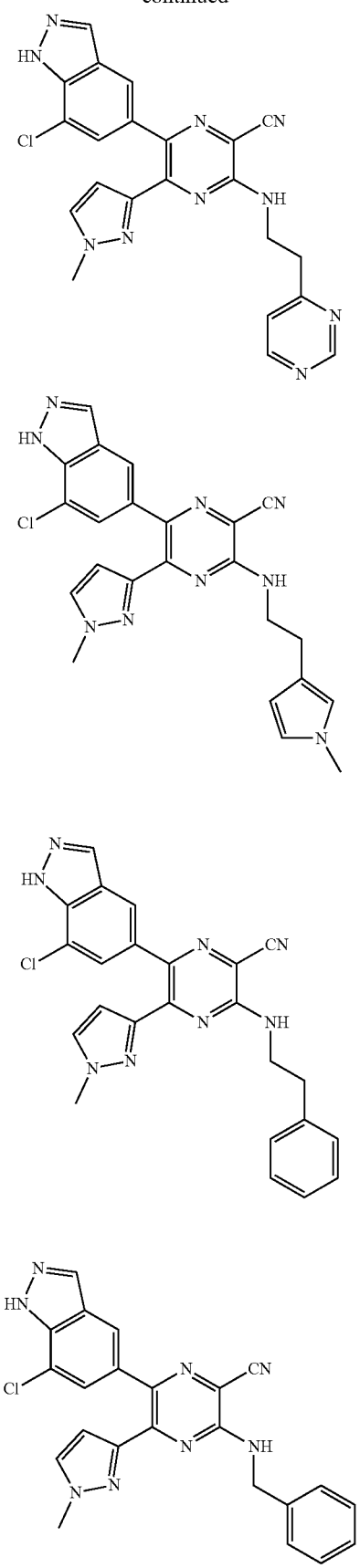
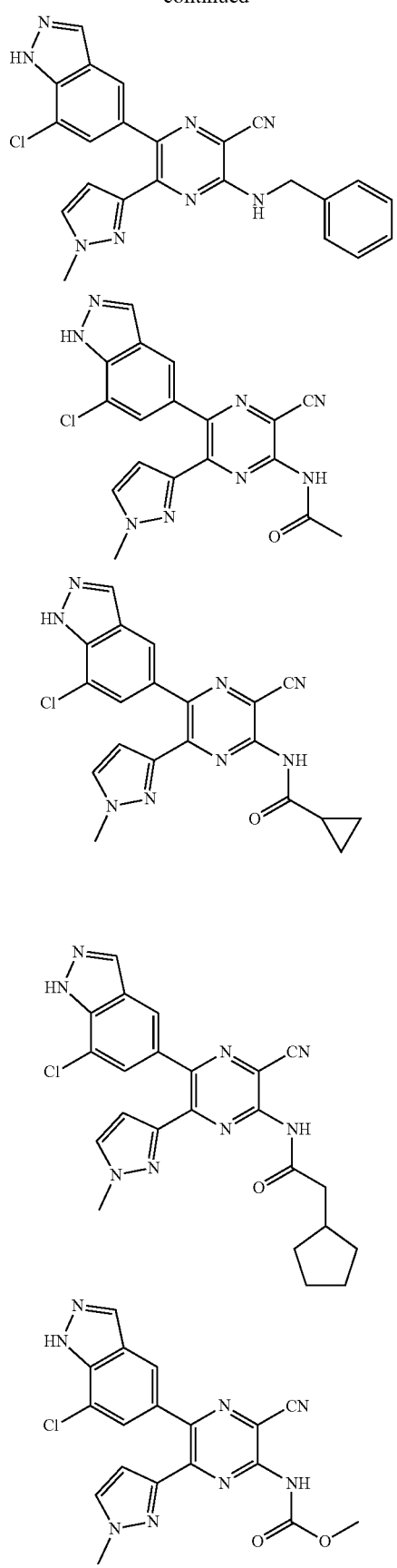

1393
-continued
1394
-continued
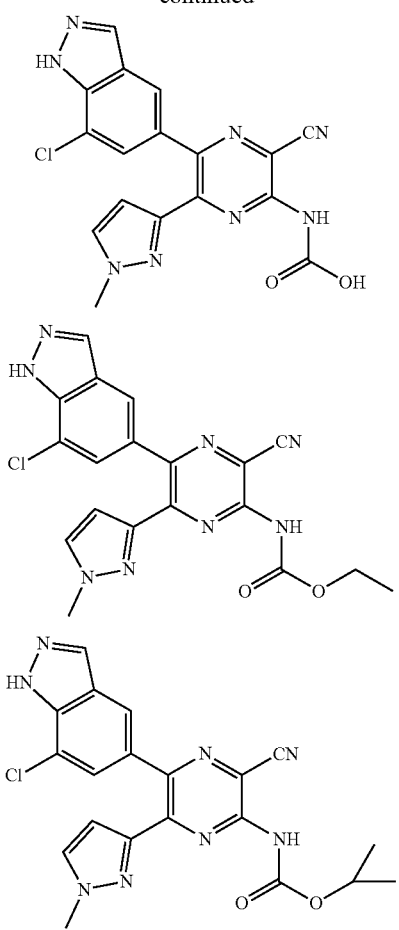
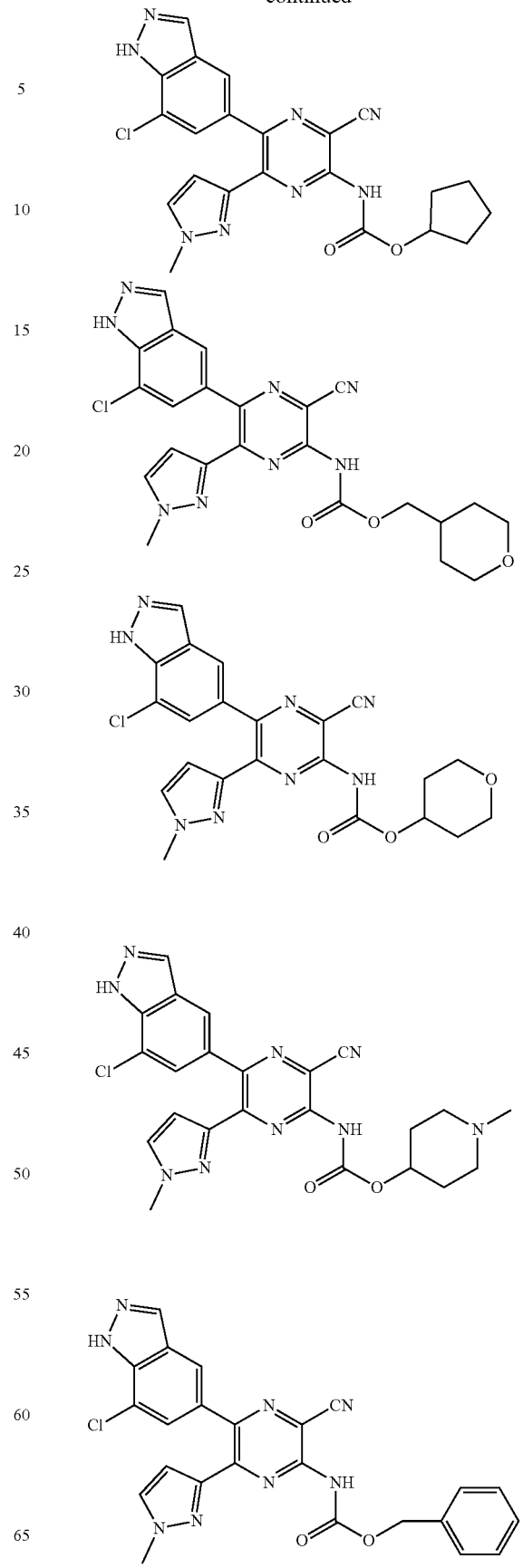

1395
-continued
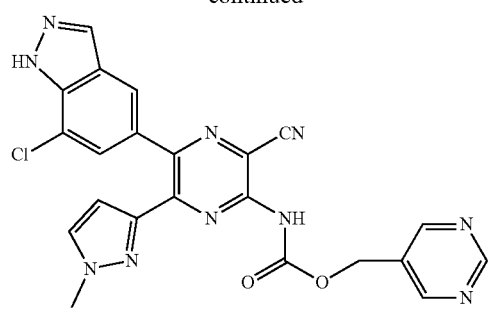
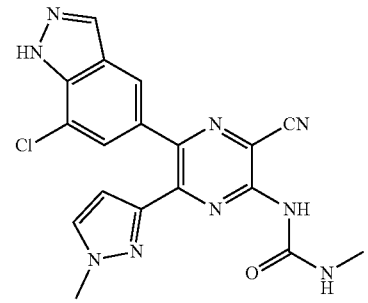
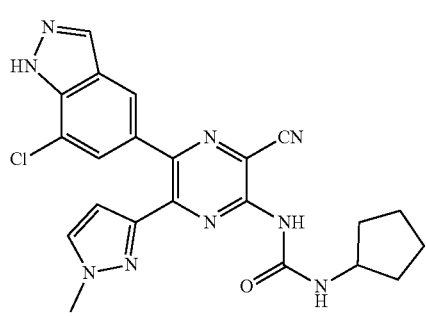
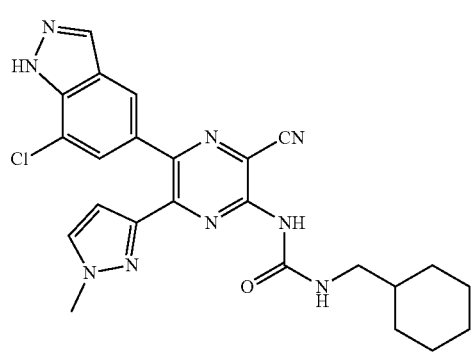
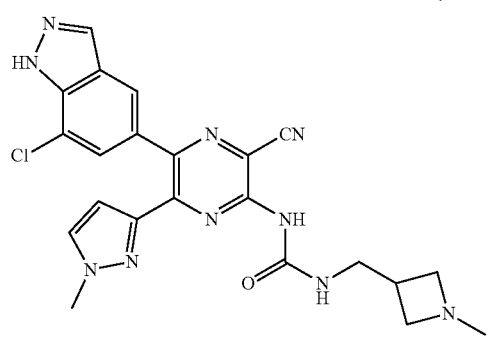
1396
-continued
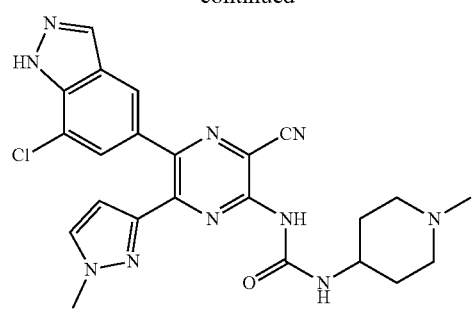
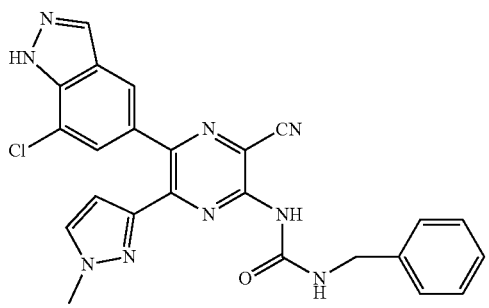
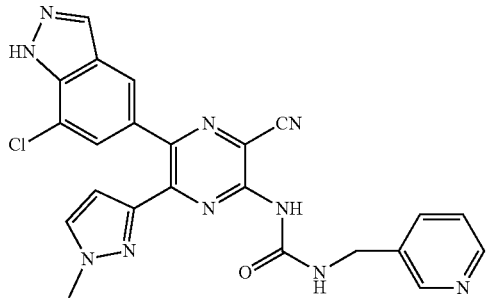
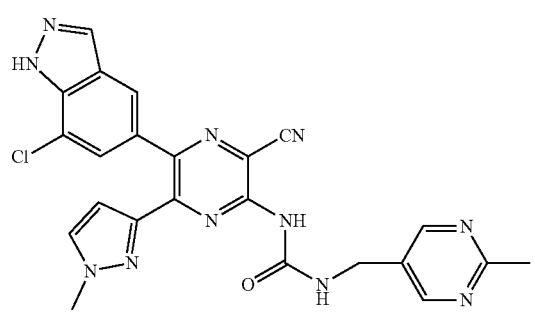
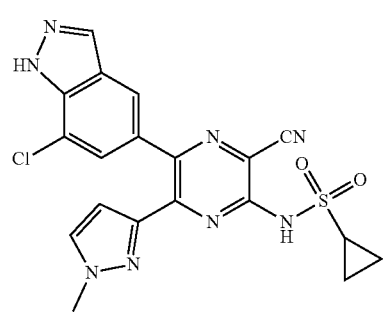

1397
-continued
1398
-continued
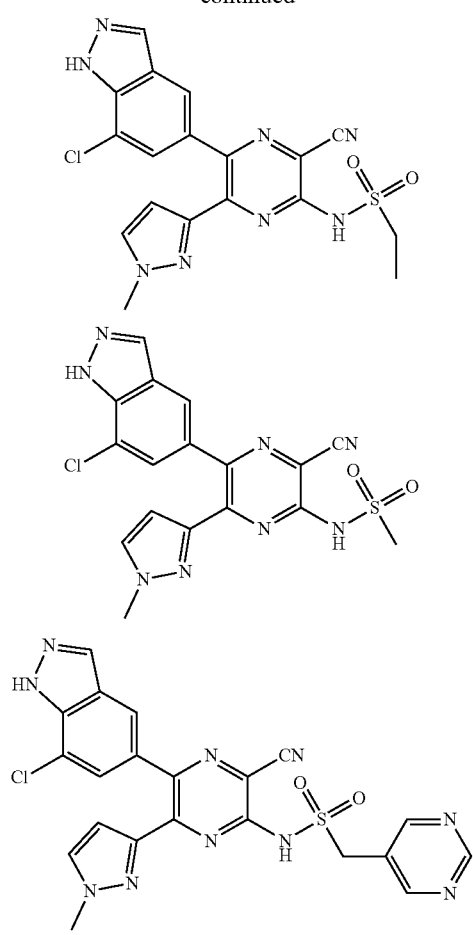
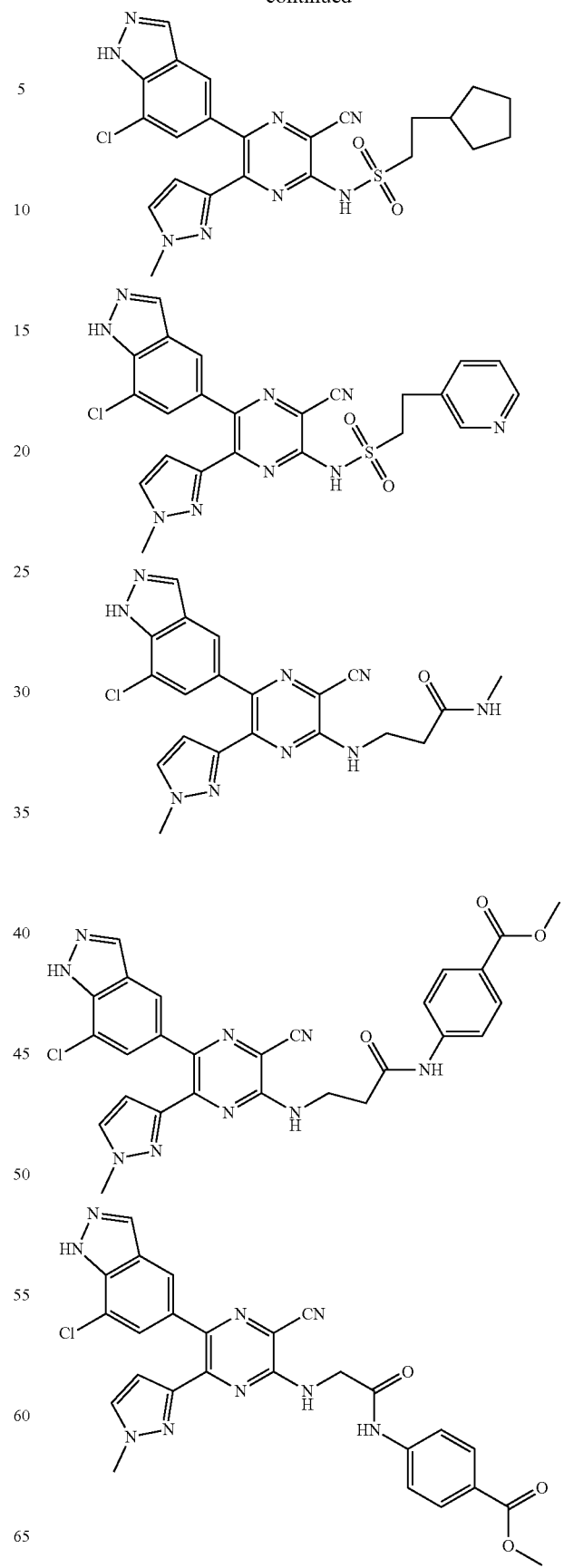

1399
-continued
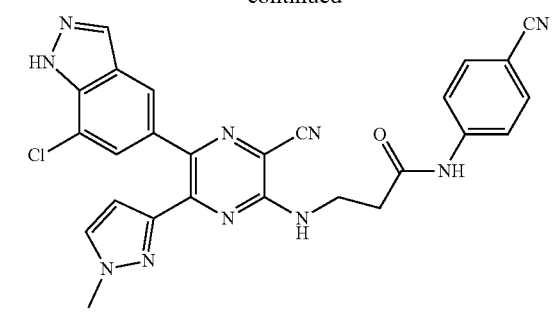
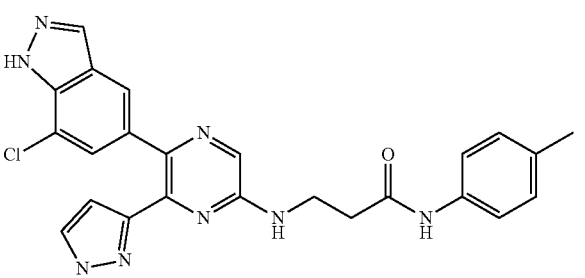
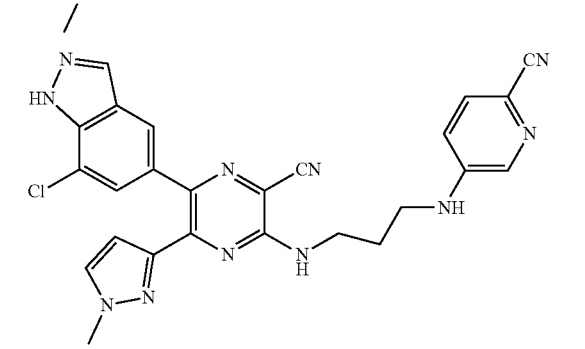
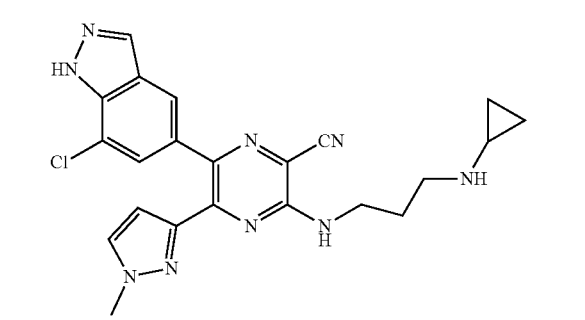
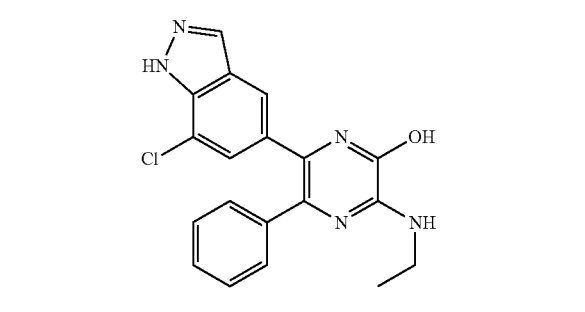
1400
-continued
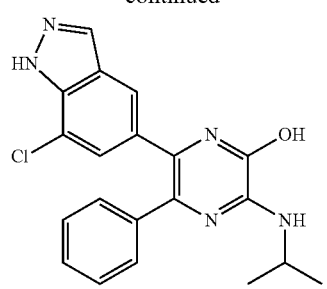
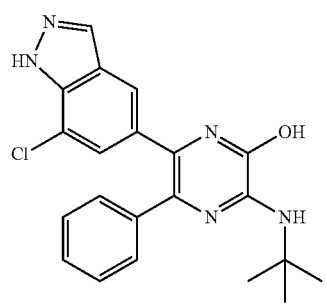
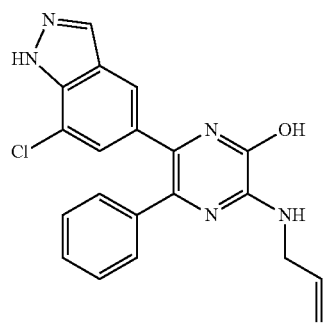
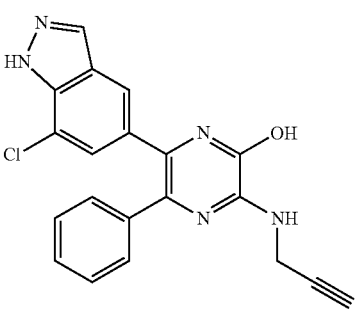
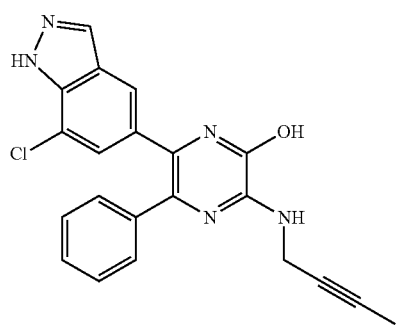

1401
-continued
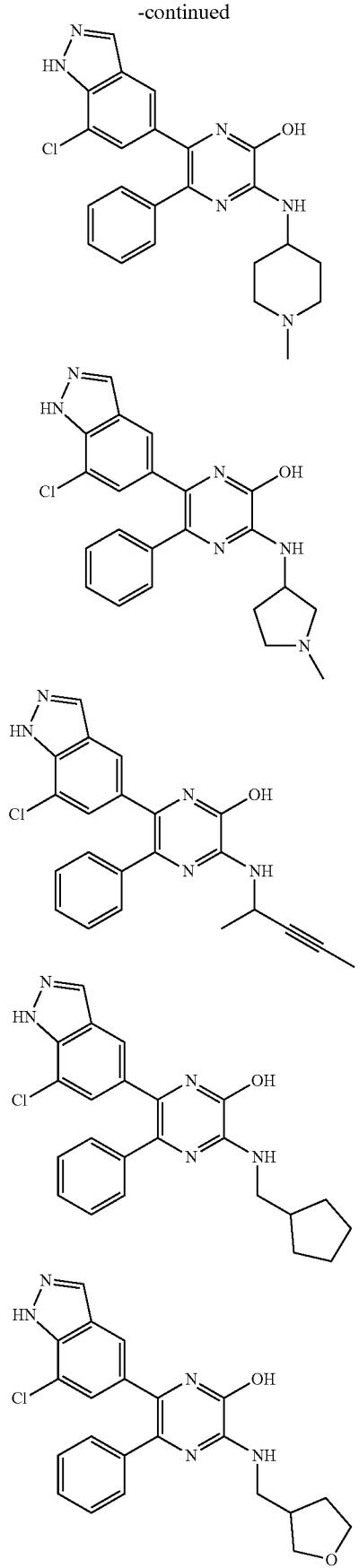
1402
-continued
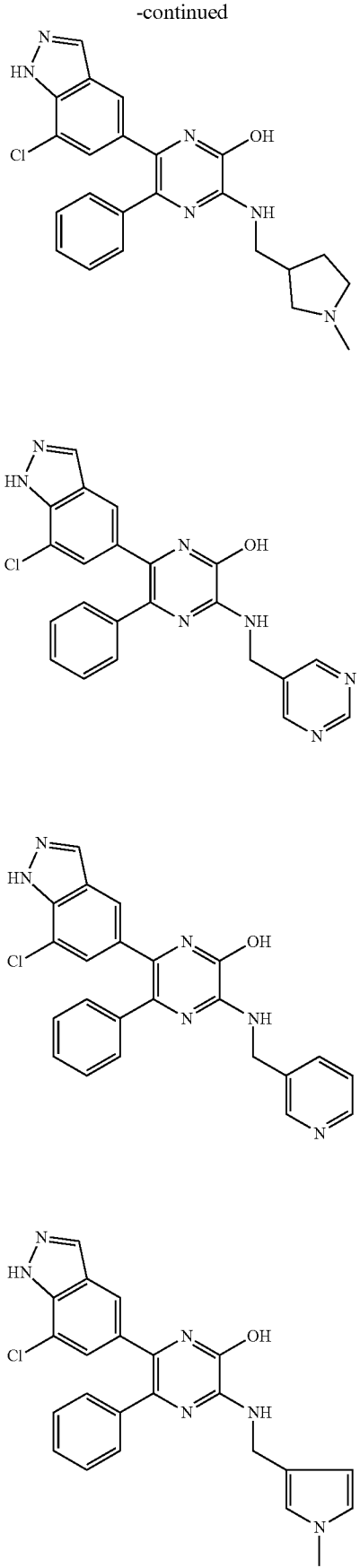

1403
-continued
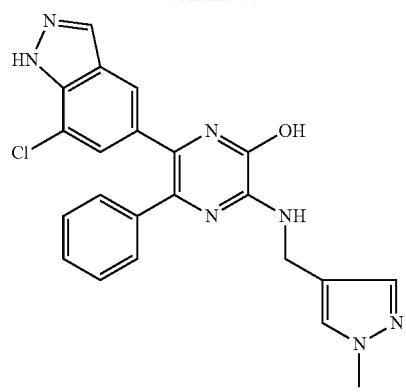
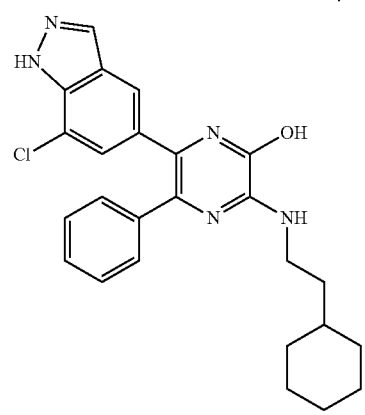
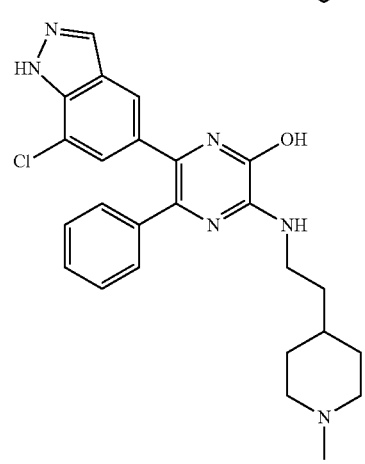
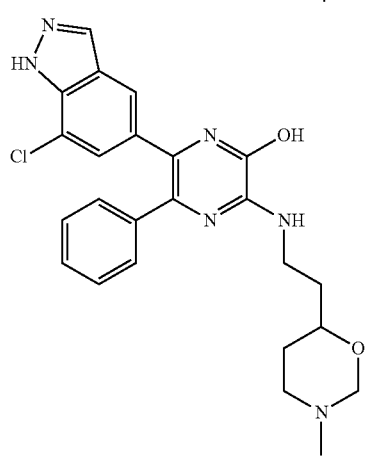
1404
-continued
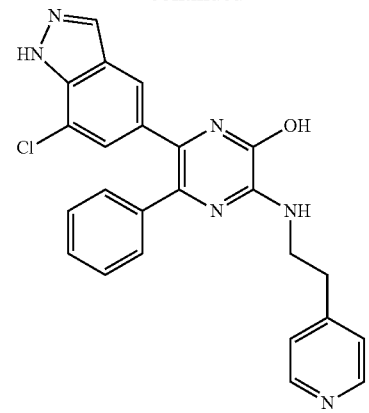
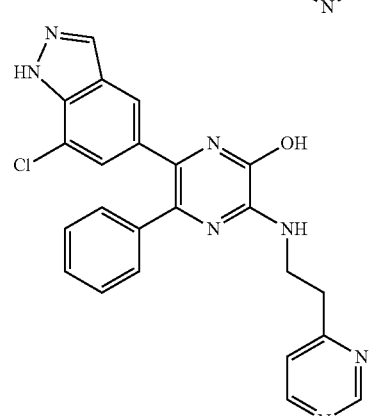
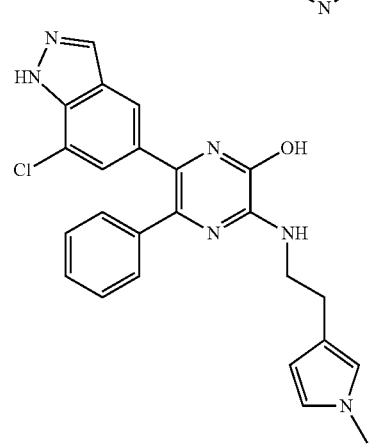
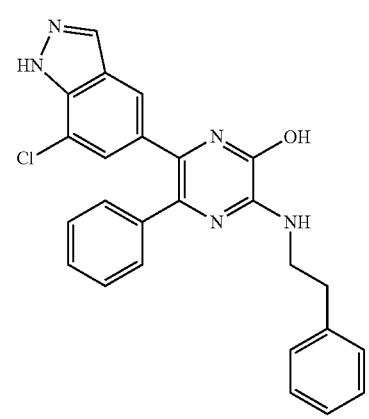

1405
-continued
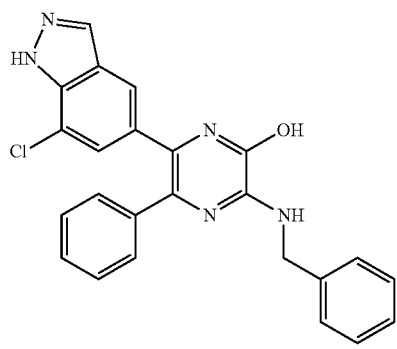
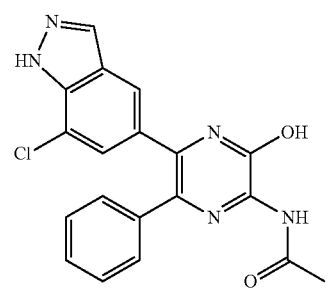
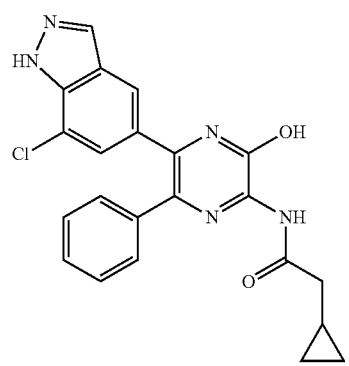
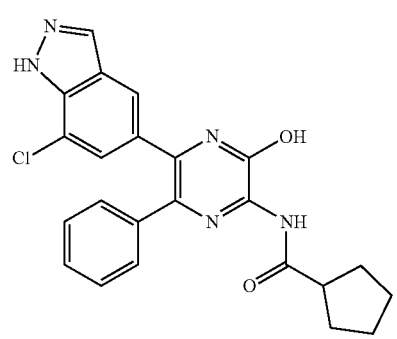
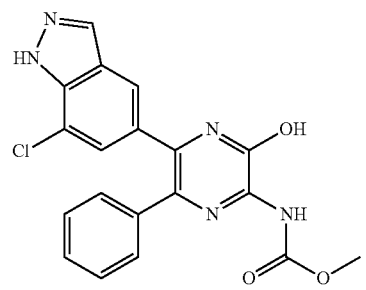
1406
-continued
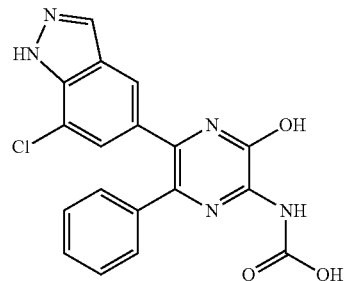
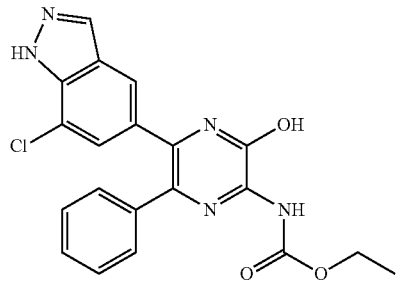
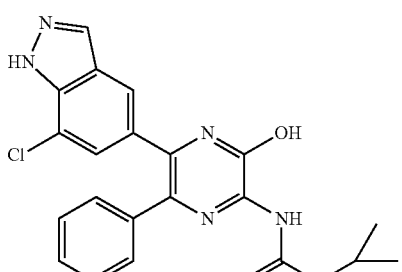
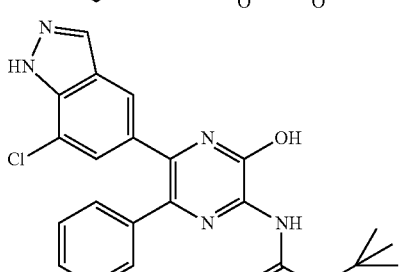
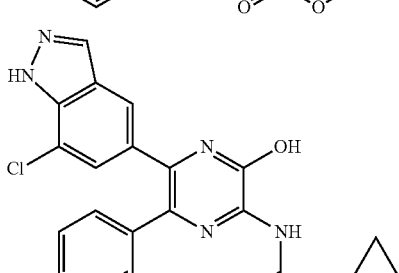
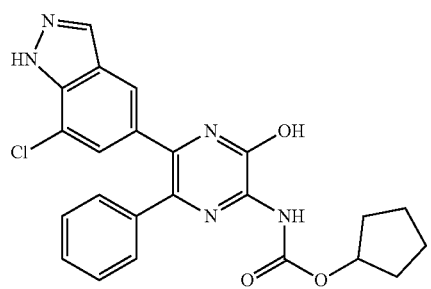

1407
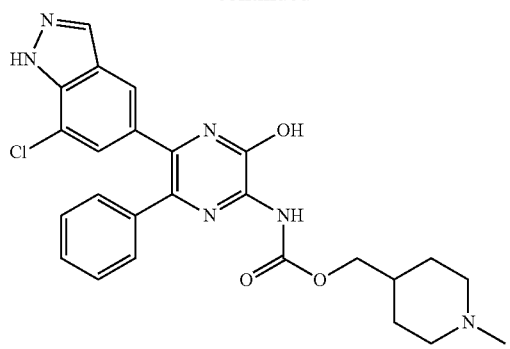
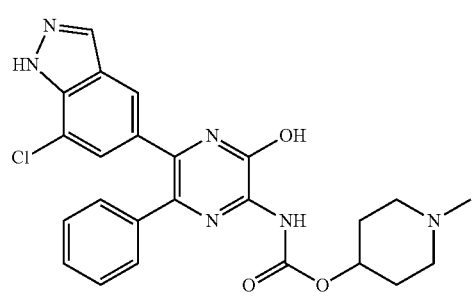
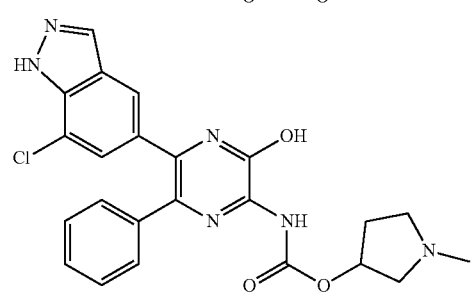
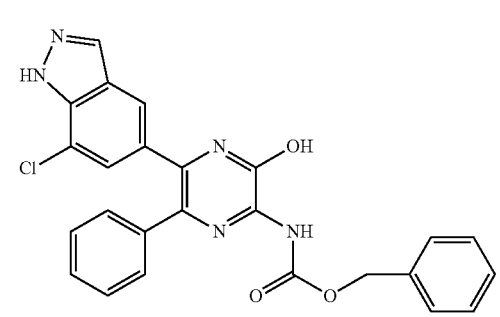
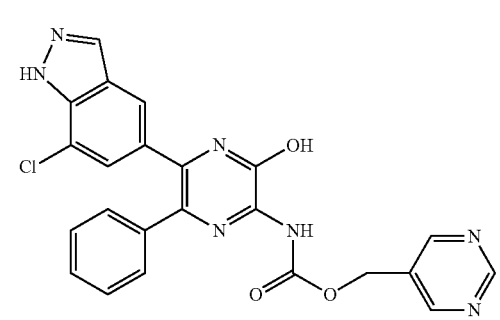
1408
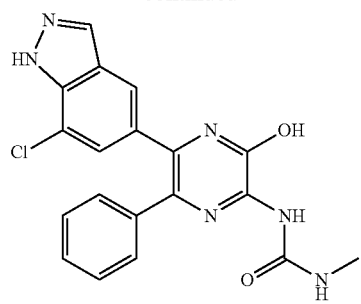
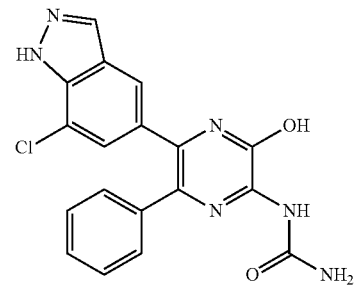
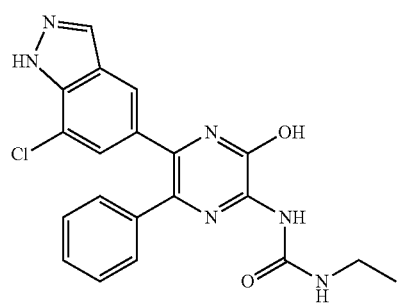
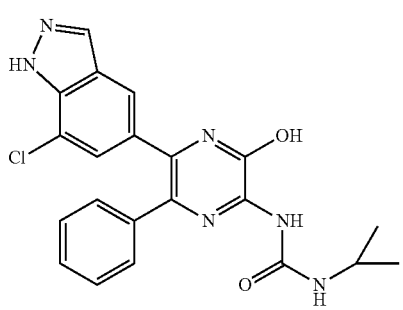
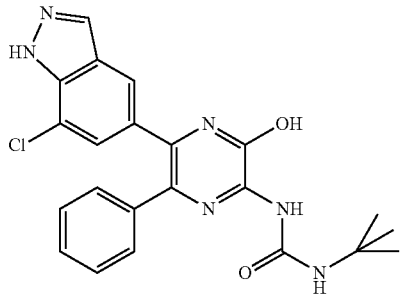

1409
-continued
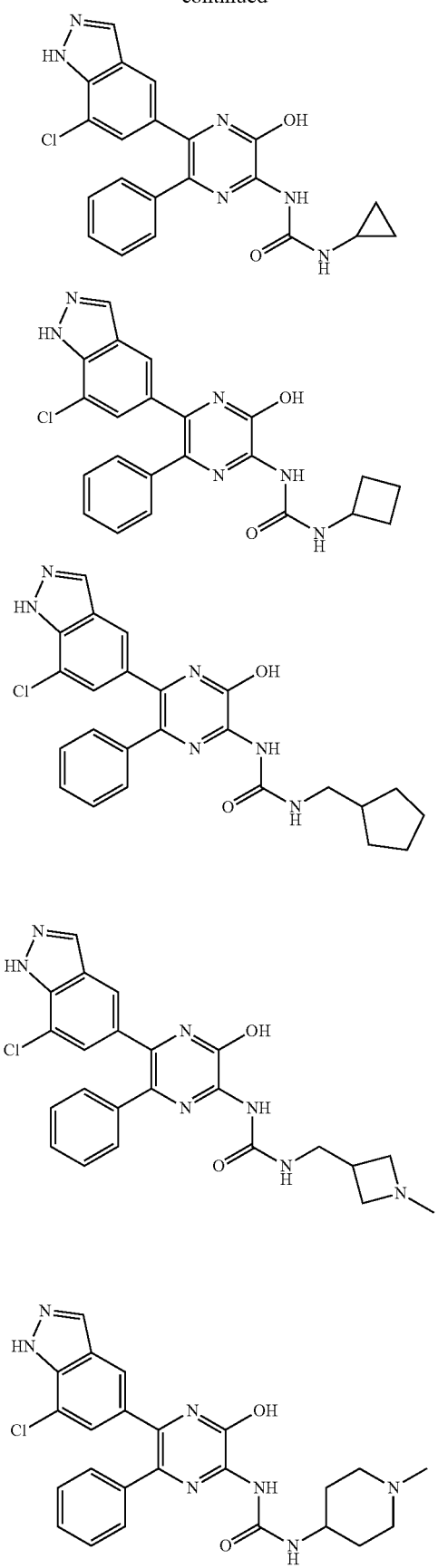
1410
-continued
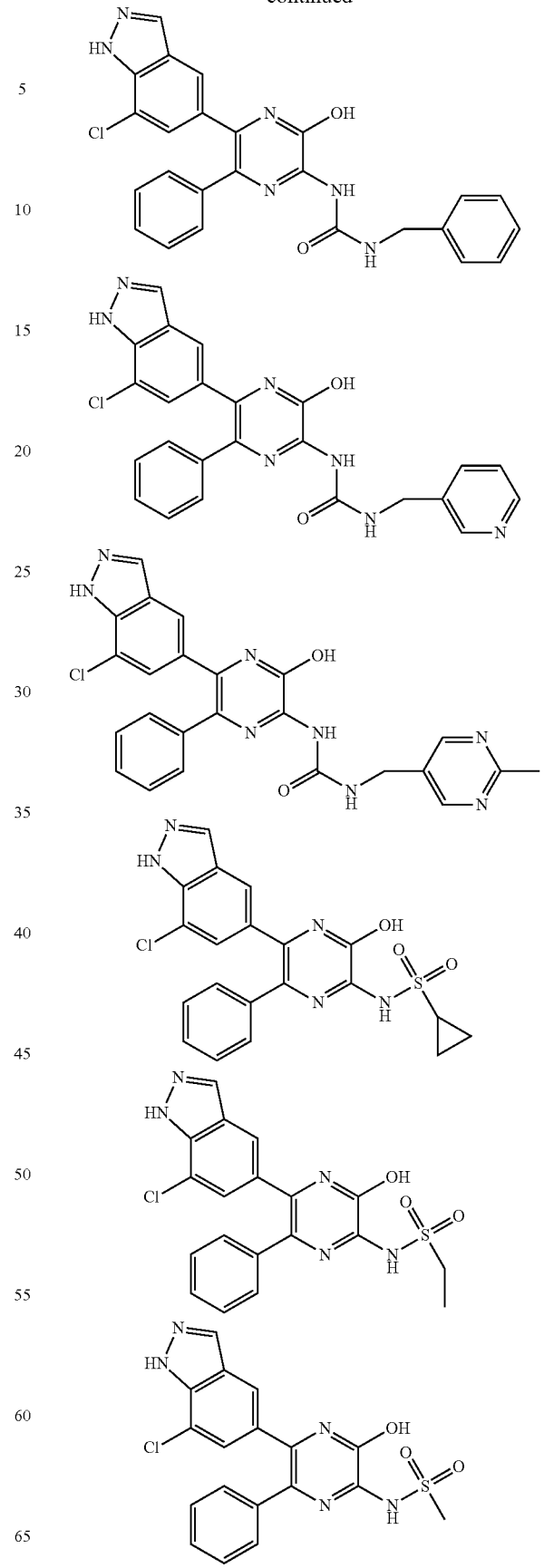

1411
-continued
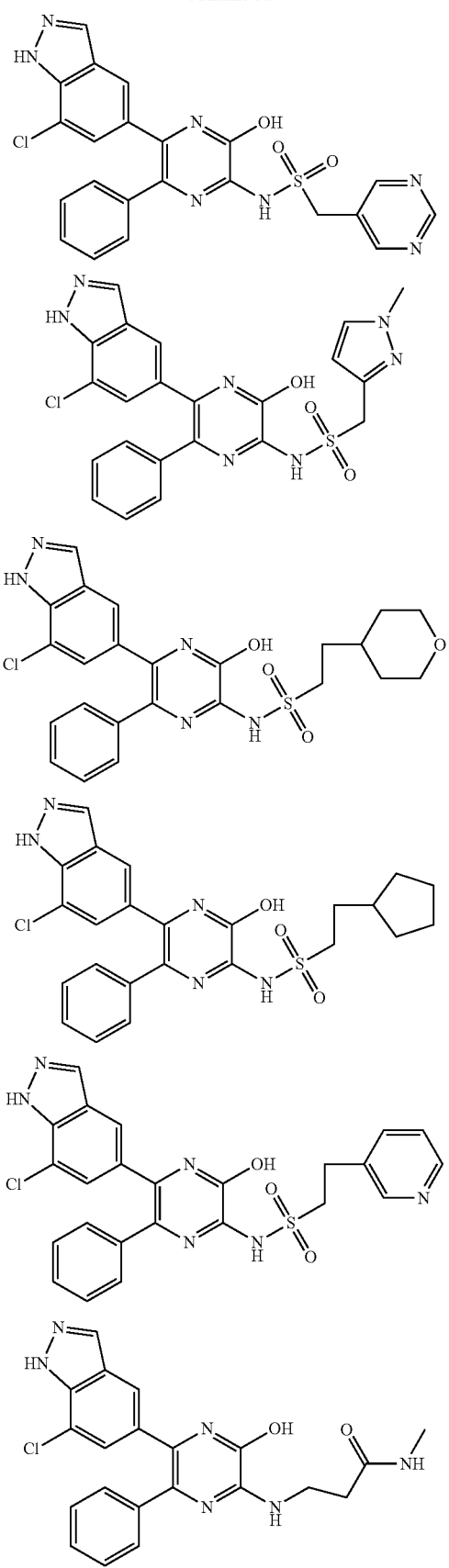
1412
-continued
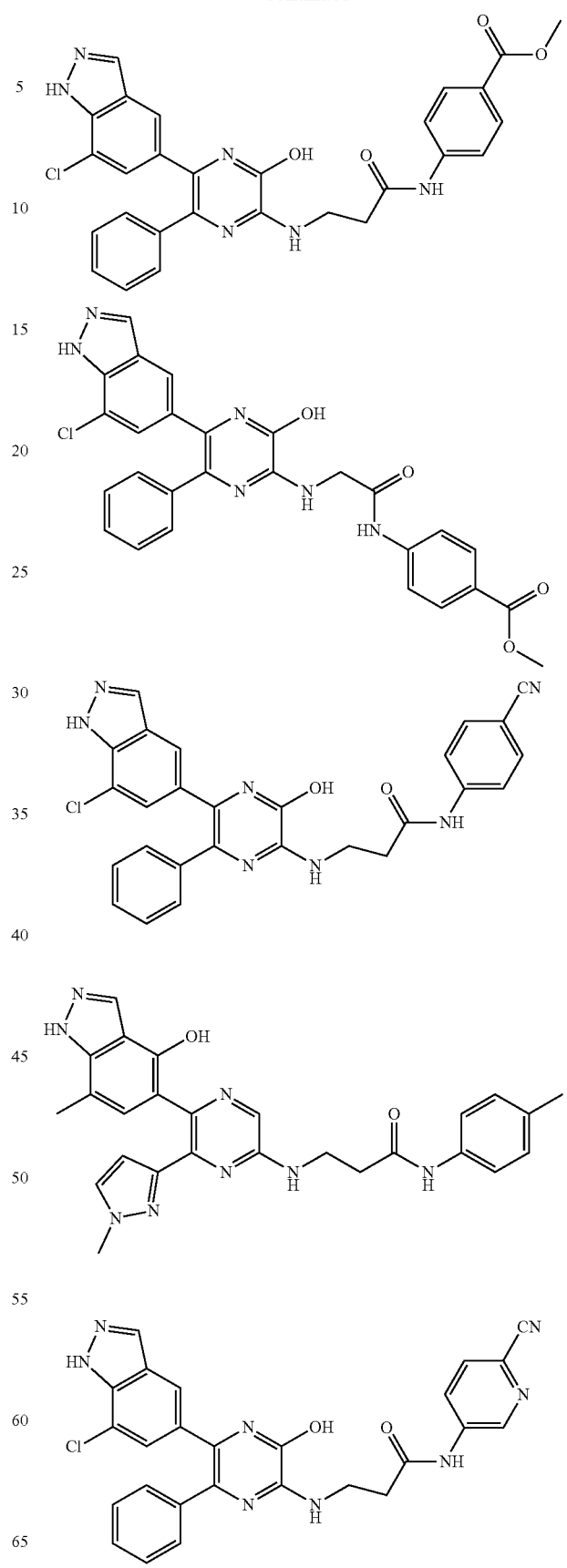

1413
-continued
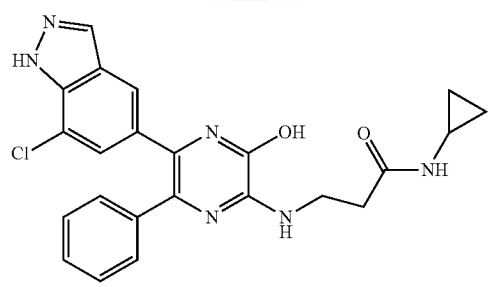
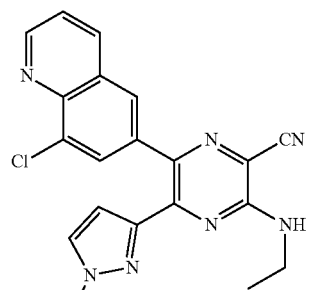
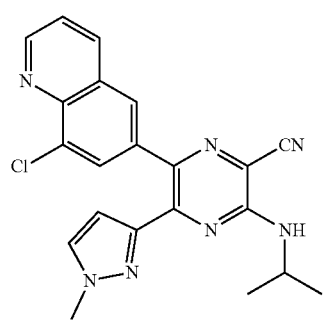
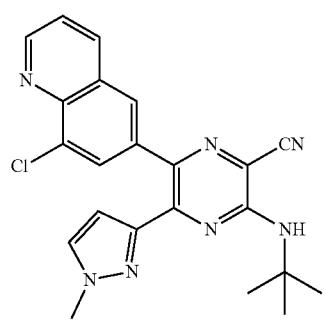
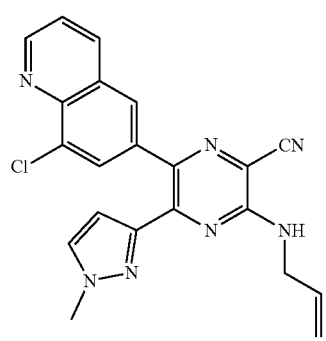
1414
-continued
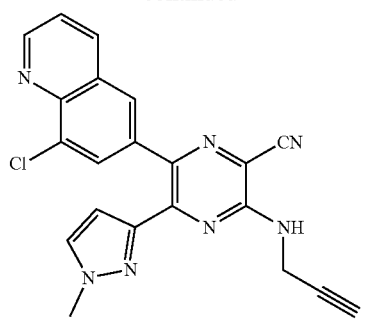
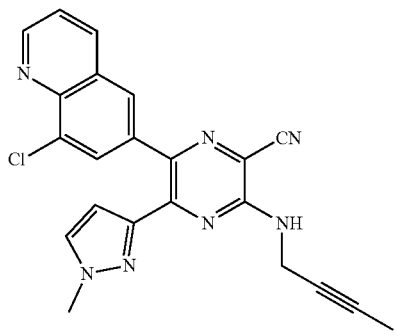
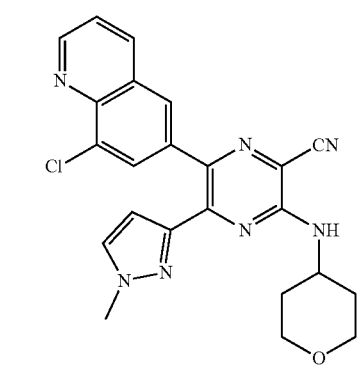
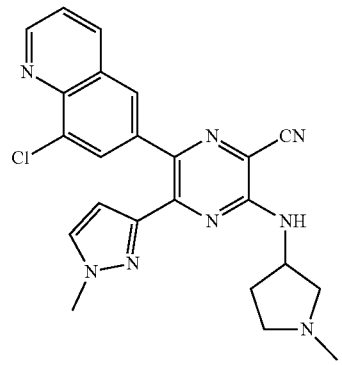
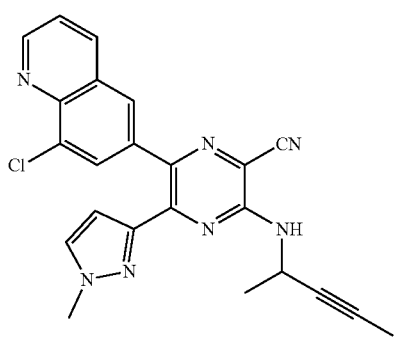

1415
-continued
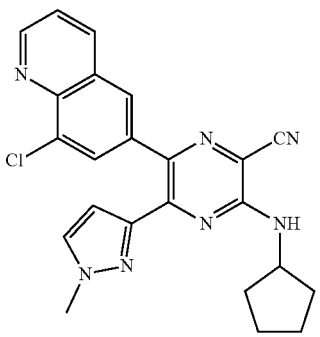
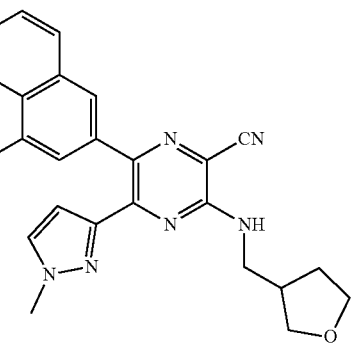
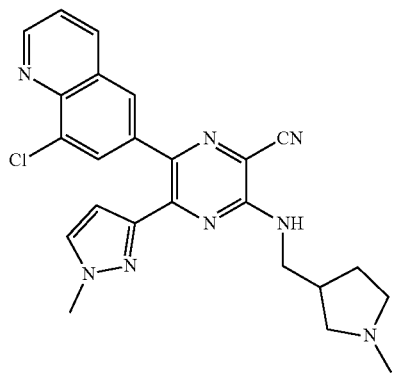
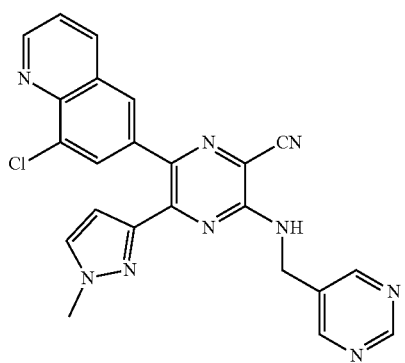
1416
-continued
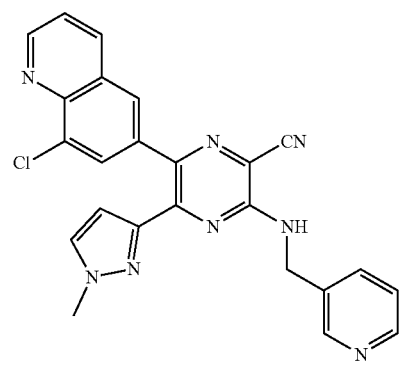
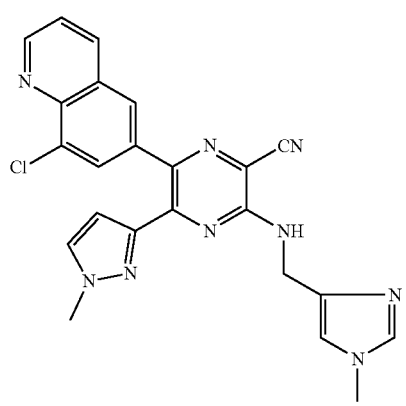
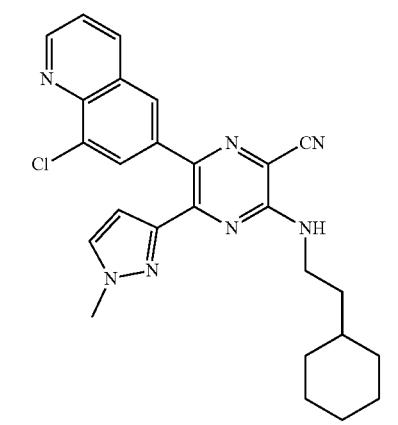
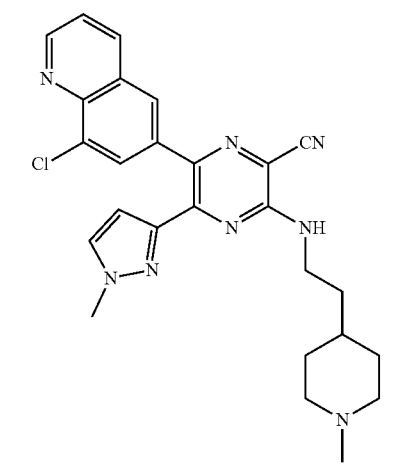

| 1417 -continued | 1418 -continued |
|---|---|
| 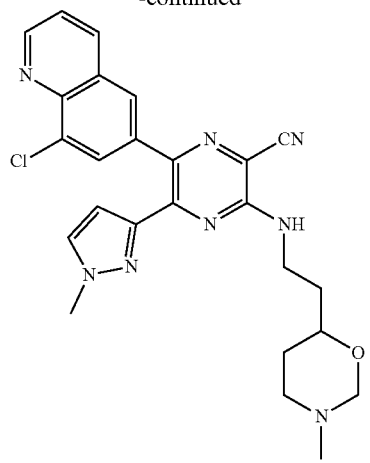 | 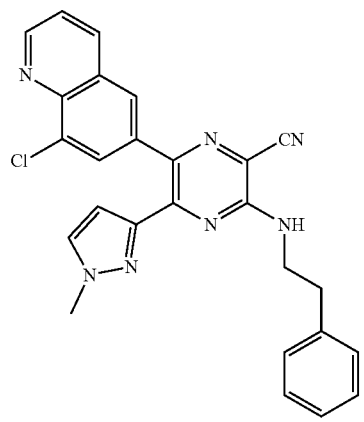 |
| 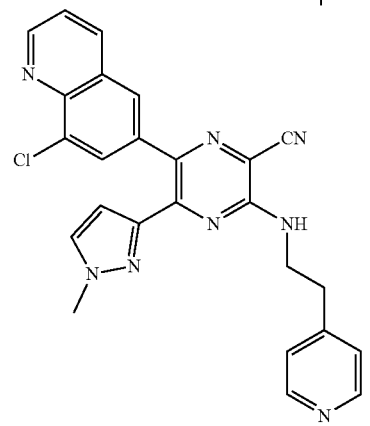 | 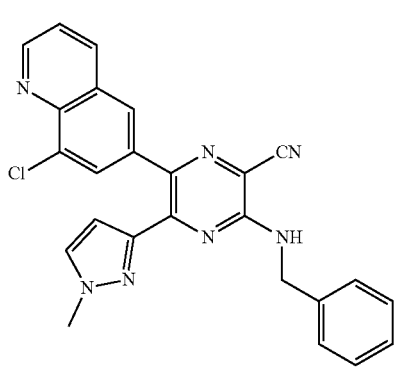 |
| 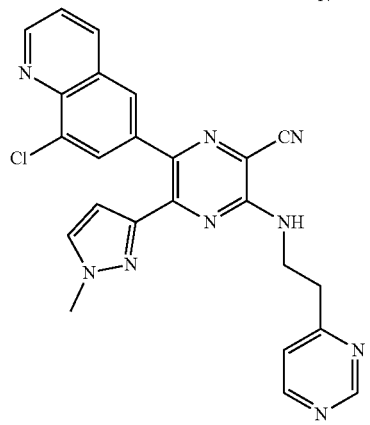 | 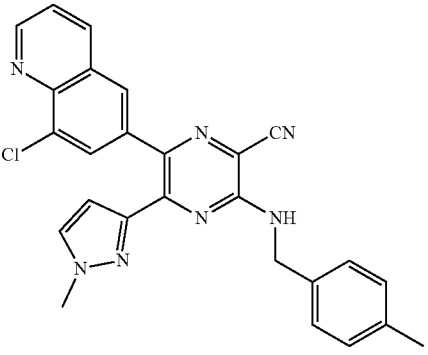 |
| 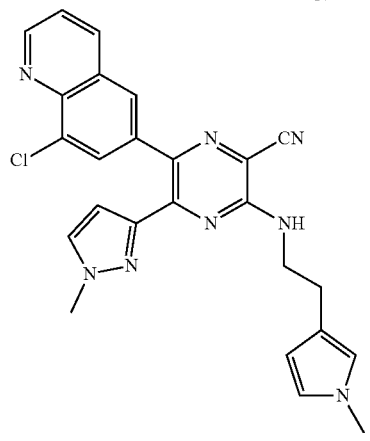 | 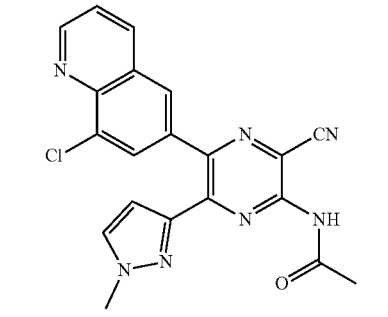 |

1419
-continued
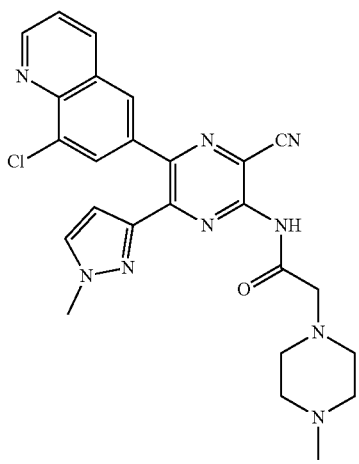
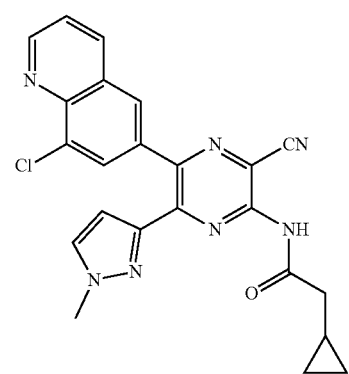
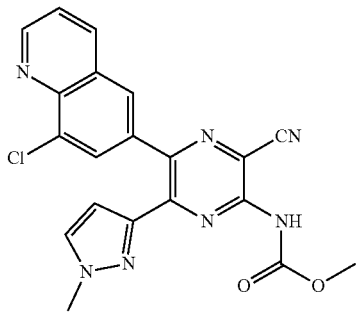
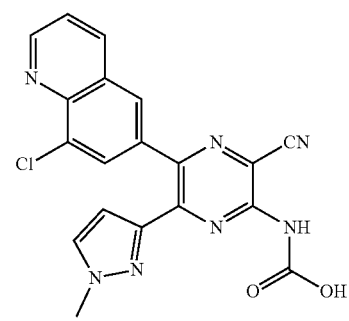
1420
-continued
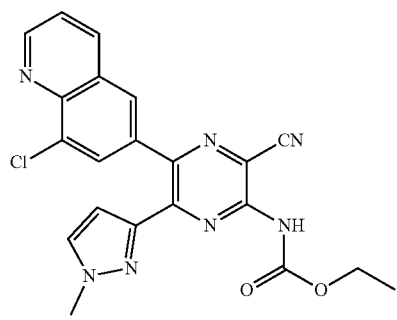
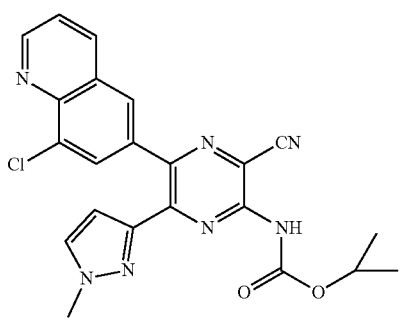
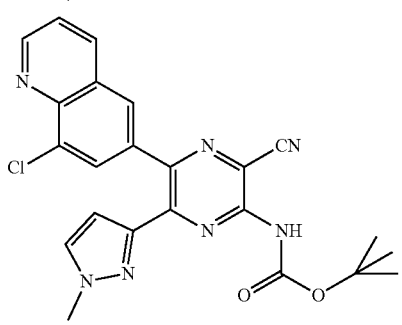
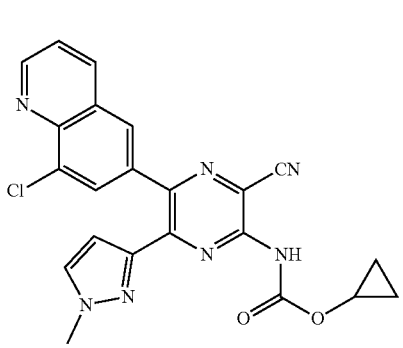
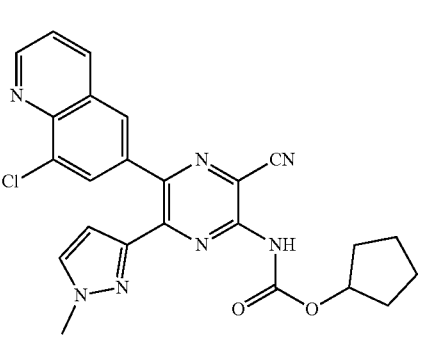

1421
-continued
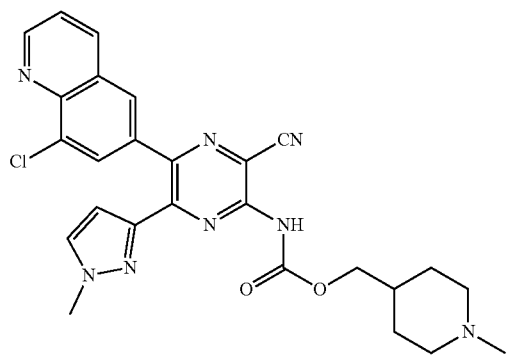
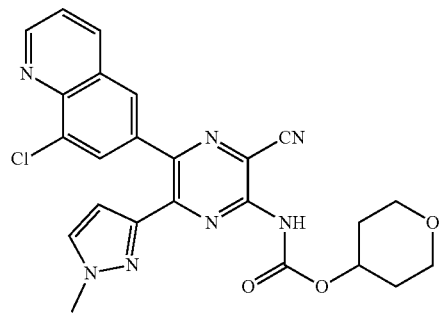
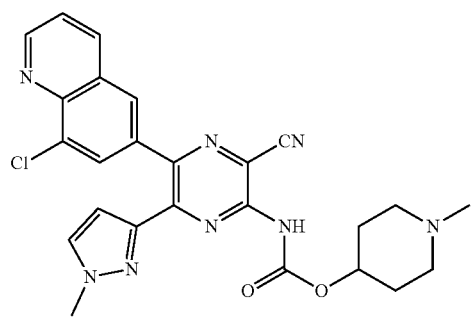
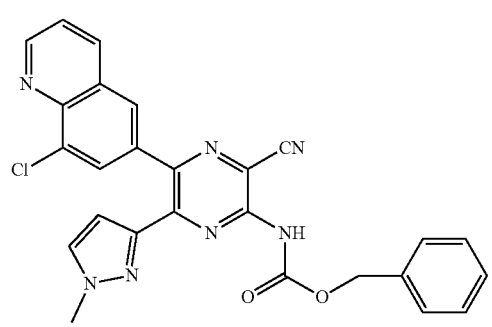
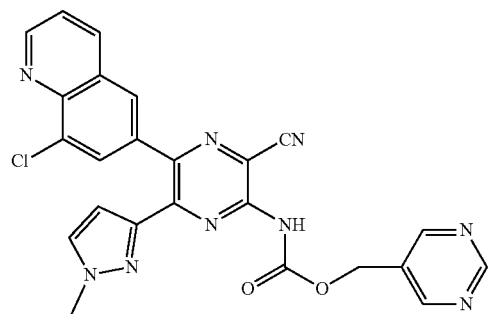
1422
-continued
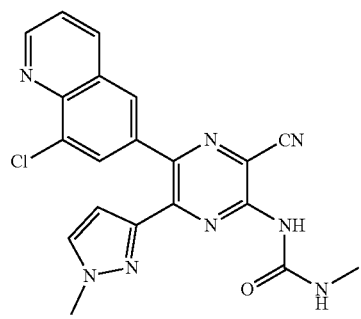
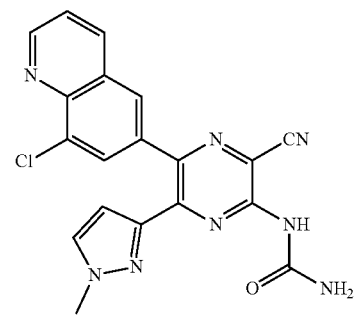
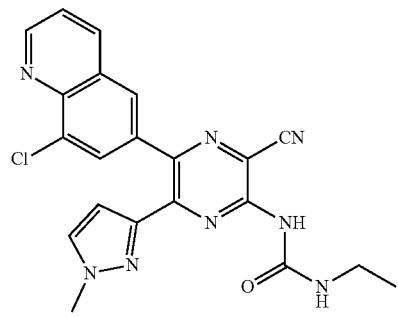
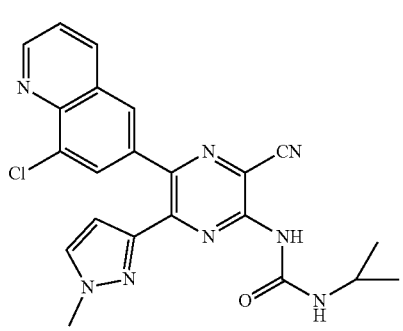
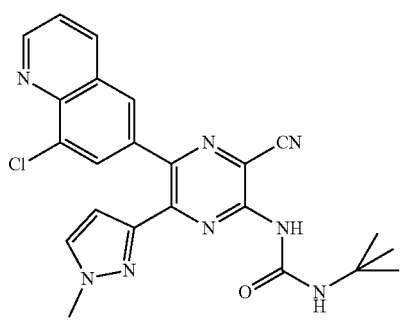

1423
-continued
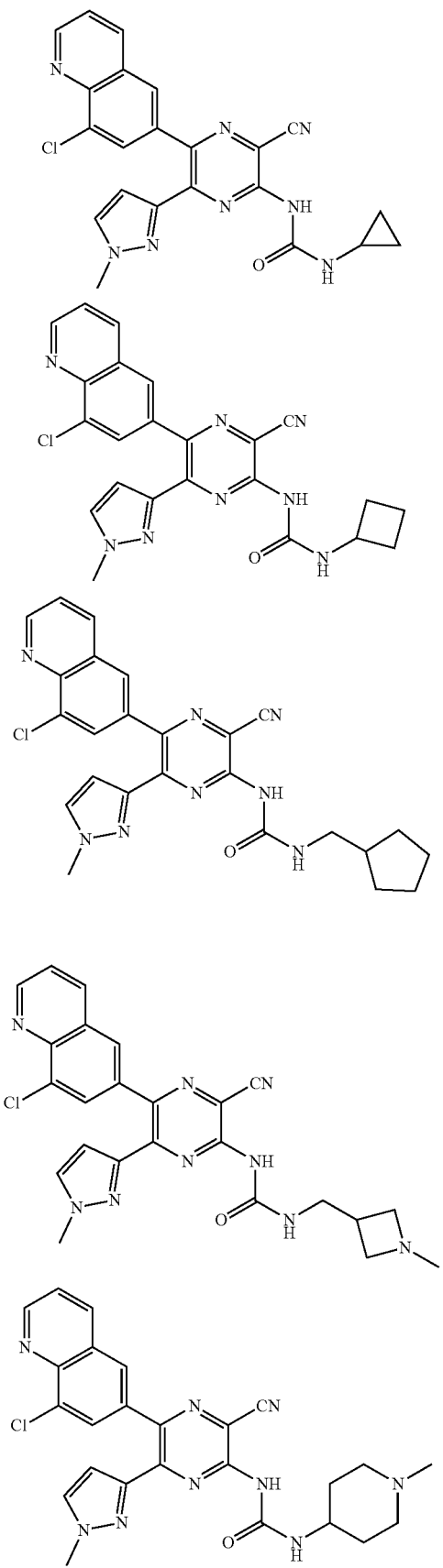
1424
-continued
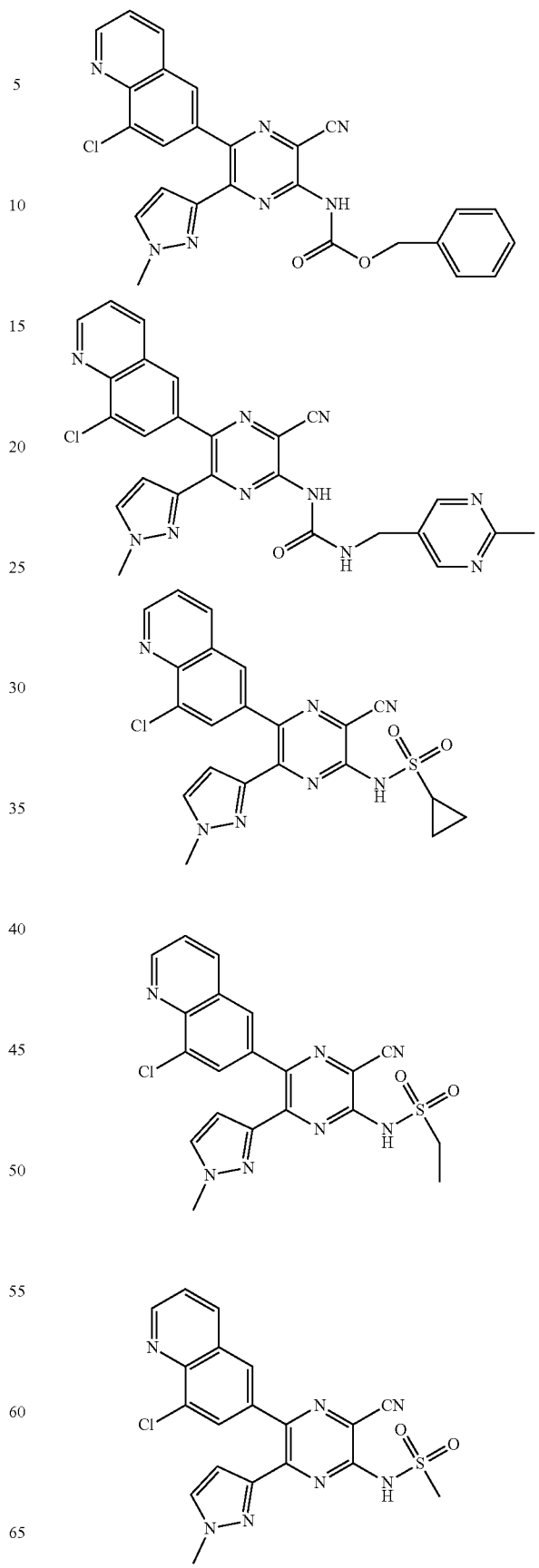

1425
-continued
1426
-continued
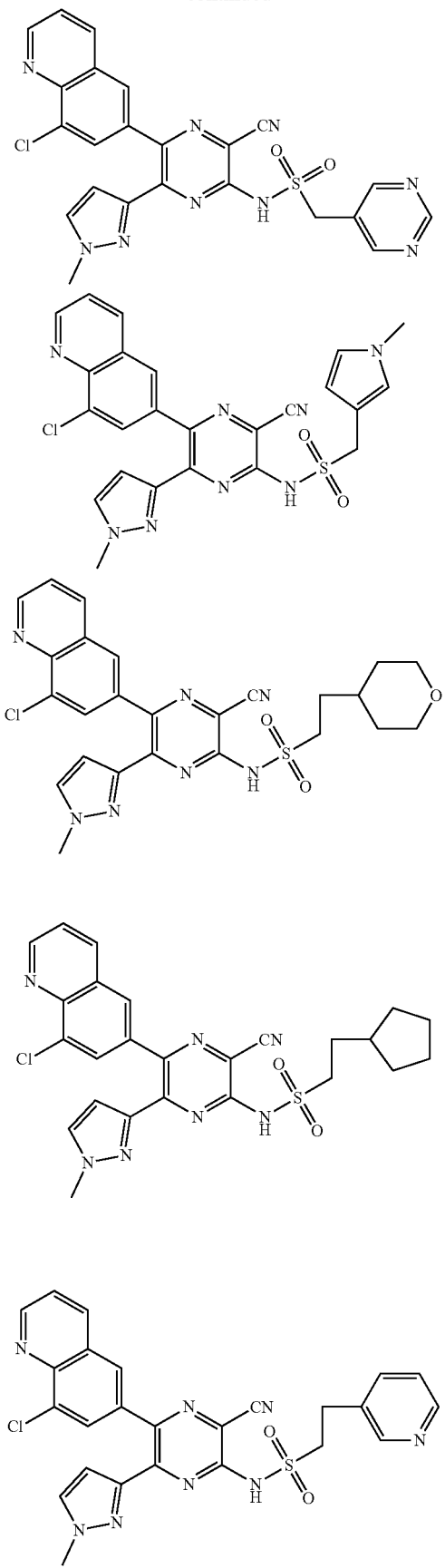
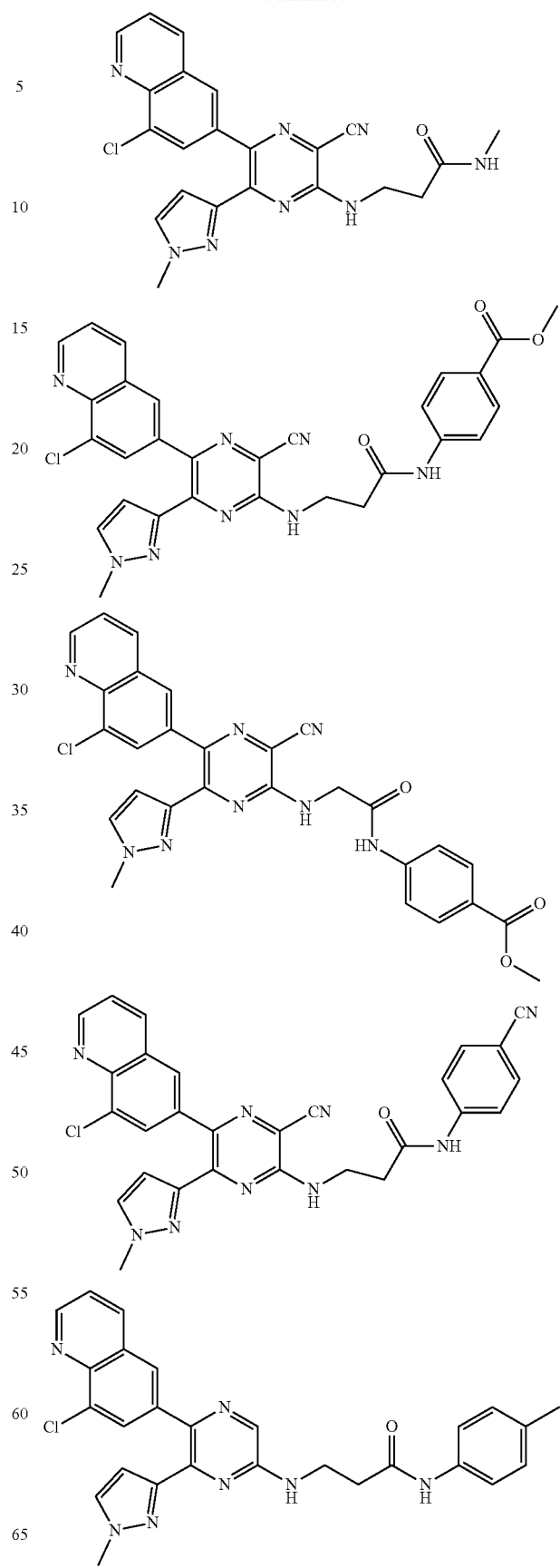

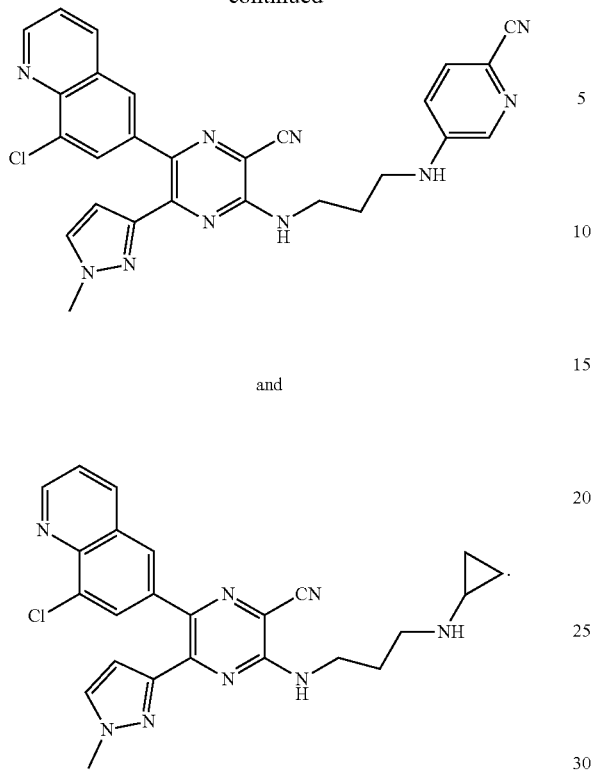

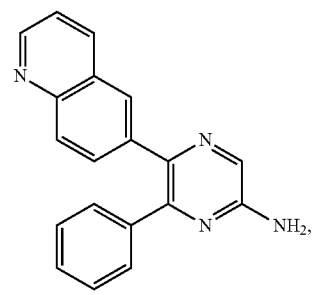
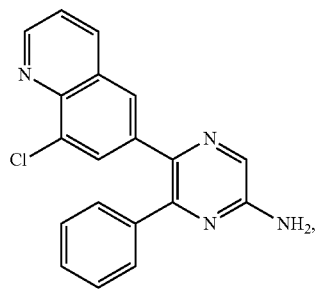
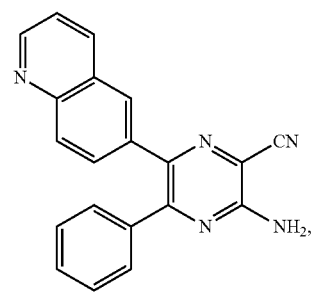
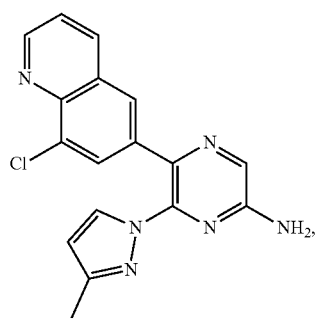
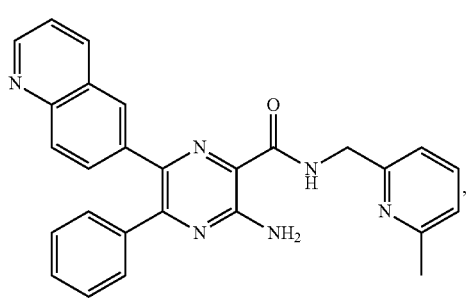

or a tautomer or stereoisomer thereof, or a pharmaceutically acceptable salt of any of the foregoing.

34. The compound of claim 33, or a pharmaceutically acceptable salt thereof.

35. A pharmaceutical composition comprising a compound of claim 1, or a tautomer or stereoisomer thereof, or a pharmaceutically acceptable salt of any of the foregoing, and a pharmaceutically acceptable carrier.

36. A method of treating disease mediated by an adenosine signaling pathway in an individual in need thereof comprising administering to the individual a therapeutically effective amount of a compound of claim 1, or a tautomer or stereoisomer thereof, or a pharmaceutically acceptable salt of any of the foregoing.

37. A method of treating cancer in an individual in need thereof comprising administering to the individual a therapeutically effective amount of a compound of claim 1, or a tautomer or stereoisomer thereof, or a pharmaceutically acceptable salt of any of the foregoing.

38. A method of inhibiting an adenosine receptor of subtype A2A, A2B or A3 in a cell, comprising administering a compound of claim 1, or a tautomer or stereoisomer thereof, or a pharmaceutically acceptable salt of any of the foregoing, to the cell.

39. The method of claim 38, wherein the adenosine receptor is of subtype A2A.

40. A kit comprising a compound of claim 1, or a tautomer or stereoisomer thereof, or a pharmaceutically acceptable salt of any of the foregoing.

41. The compound of claim 33, or a pharmaceutically acceptable salt thereof, wherein the compound is selected from the group consisting of:

1429
-continued

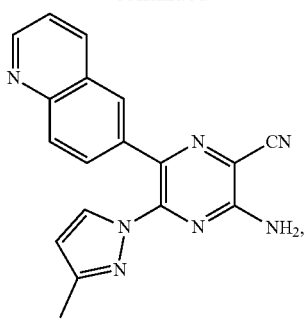

and

1430
-continued

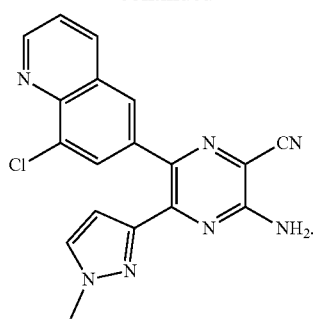 [SMILES: Cn1ccc(-c2nc(N)c(C#N)nc2-c2cc(Cl)c3ncccc3c2)n1]

42. The compound of claim 41, or a pharmaceutically acceptable salt thereof, wherein the compound is

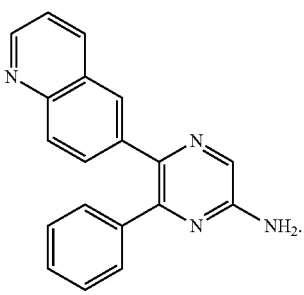

43. The compound of claim 41, or a pharmaceutically acceptable salt thereof, wherein the compound is

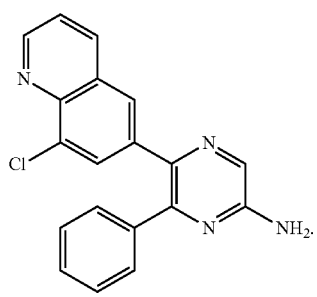

44. The compound of claim 41, or a pharmaceutically acceptable salt thereof, wherein the compound is

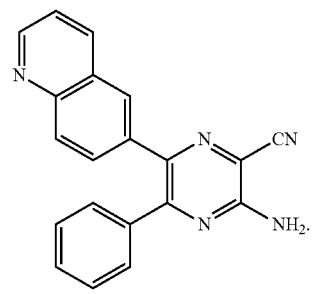

45. The compound of claim 41, or a pharmaceutically acceptable salt thereof, wherein the compound is

46. The compound of claim 41, or a pharmaceutically acceptable salt thereof, wherein the compound is

47. The compound of claim 41, or a pharmaceutically acceptable salt thereof, wherein the compound is

48. The compound of claim 41, or a pharmaceutically acceptable salt thereof, wherein the compound is

49. The compound of claim 41, or a pharmaceutically acceptable salt thereof, wherein the compound is

50. The compound of claim 41, or a pharmaceutically acceptable salt thereof, wherein the compound is

51. The compound of claim 41, or a pharmaceutically acceptable salt thereof, wherein the compound is

52. The compound of claim 41, or a pharmaceutically acceptable salt thereof, wherein the compound is

* * * * *